US012521393B2

(12) United States Patent
Chen et al.

(10) Patent No.: US 12,521,393 B2
(45) Date of Patent: Jan. 13, 2026

(54) CYTOTOXICITY TARGETING CHIMERAS FOR CCR2-EXPRESSING CELLS

(71) Applicant: GLAXOSMITHKLINE INTELLECTUAL PROPERTY DEVELOPMENT LIMITED, Brentford (GB)

(72) Inventors: Peiling Chen, Collegeville, PA (US); Jason W. Dodson, Collegeville, PA (US); Beth A. Knapp-Reed, Collegeville, PA (US); Craig Leach, Collegeville, PA (US); Yuehu Li, Collegeville, PA (US); Joseph Paul Marino, Jr., Collegeville, PA (US); Matthew Robert Sender, Collegeville, PA (US); Brandon Turunen, Collegeville, PA (US); Guosen Ye, Collegeville, PA (US); Cunyu Zhang, Collegeville, PA (US)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

(21) Appl. No.: 18/437,813

(22) Filed: Feb. 9, 2024

(65) Prior Publication Data

US 2024/0325392 A1 Oct. 3, 2024

Related U.S. Application Data

(63) Continuation of application No. PCT/IB2022/057561, filed on Aug. 12, 2022.

(Continued)

(51) Int. Cl.
*A61K 31/517* (2006.01)
*A61K 39/00* (2006.01)

(Continued)

(52) U.S. Cl.
CPC ............ *A61K 31/517* (2013.01); *A61P 35/00* (2018.01); *C07D 401/14* (2013.01); *C07K 16/16* (2013.01);

(Continued)

(58) Field of Classification Search
CPC . A61K 31/517; A61K 2039/505; A61P 35/00; C07D 401/14; C07K 16/16; C07K 2317/565
See application file for complete search history.

(56) References Cited

U.S. PATENT DOCUMENTS

| | | | |
|---|---|---|---|
| 6,869,606 | B1 | 3/2005 | Newman et al. |
| 8,008,448 | B2 | 8/2011 | Park et al. |

(Continued)

FOREIGN PATENT DOCUMENTS

| | | | |
|---|---|---|---|
| WO | WO-2000047212 | A1 | 8/2000 |
| WO | WO-2008014361 | A2 | 1/2008 |

(Continued)

OTHER PUBLICATIONS

Kim H, Yoon S, Chung J. In vitro and in vivo application of anti-cotinine antibody and cotinine-conjugated compounds. BMB Rep. Mar. 2014;47(3):130-4. doi: 10.5483/bmbrep.2014.47.3.006. PMID: 24499668; PMCID: PMC4163880. (Year: 2014).*

(Continued)

*Primary Examiner* — Clinton A Brooks
*Assistant Examiner* — Izabela Schmidt
(74) *Attorney, Agent, or Firm* — Dechert LLP

(57) ABSTRACT

The present disclosure relates to heterobifunctional molecules, referred to as cytotoxicity targeting chimeras (Continued)

(CyTaCs) or antibody recruiting molecules (ARMs) that are able to simultaneously bind a target cell-surface protein as well as an exogenous antibody protein. The present disclosure also relates to agents capable of binding to a receptor on a surface of a pathogenic cell and inducing the depletion of the pathogenic cell in a subject for use in the treatment of cancer, inflammatory diseases, autoimmune diseases, viral infection, or bacterial infection.

29 Claims, 13 Drawing Sheets

Specification includes a Sequence Listing.

Related U.S. Application Data

(60) Provisional application No. 63/233,166, filed on Aug. 13, 2021.

(51) Int. Cl.

| | |
|---|---|
| ***A61P 35/00*** | (2006.01) |
| ***C07D 401/14*** | (2006.01) |
| ***C07K 16/16*** | (2006.01) |

(52) U.S. Cl.

CPC .. *A61K 2039/505* (2013.01); *C07K 2317/565* (2013.01)

(56) References Cited

U.S. PATENT DOCUMENTS

| | | | | |
|---|---|---|---|---|
| 9,867,886 | B2 | 1/2018 | Chung et al. | |
| 2003/0190676 | A1 | 10/2003 | Barbas et al. | |
| 2008/0014361 | A1 | 1/2008 | Johannessen | |
| 2008/0226650 | A1 | 9/2008 | Park et al. | |
| 2009/0092578 | A1 | 4/2009 | Su et al. | |
| 2012/0034295 | A1 | 2/2012 | Spiegel et al. | |
| 2014/0056926 | A1 | 2/2014 | Chung et al. | |
| 2018/0256744 | A1 | 9/2018 | Choi et al. | |
| 2019/0336489 | A1* | 11/2019 | Bailey | A61K 31/506 |

FOREIGN PATENT DOCUMENTS

| | | | | |
|---|---|---|---|---|
| WO | WO-2010093706 | A2 | 8/2010 | |
| WO | WO-2015014442 | A1 | 2/2015 | |
| WO | WO-2016205176 | A1 * | 12/2016 | A61K 47/6803 |
| WO | WO-2018009916 | A1 * | 1/2018 | A61K 39/39 |
| WO | WO-2018026997 | A1 | 2/2018 | |
| WO | WO-2018134731 | A1 | 7/2018 | |
| WO | WO-2023017483 | A1 | 2/2023 | |
| WO | WO-2023017484 | A1 | 2/2023 | |
| WO | WO-2023161874 | A1 | 8/2023 | |
| WO | WO-2023161881 | A1 | 8/2023 | |

OTHER PUBLICATIONS

Yang et al., ACS Med. Chem. Lett. Dec. 2021, 969-975, published May 25, 2021 (Year: 202).*

Troup RI, Fallan C, Baud MGJ. Current strategies for the design of PROTAC linkers: a critical review. Explor Target Antitumor Ther. 2020;1:273-312 (Year: 2020).*

Cherney, R.J. et al., "BMS-813160: A Potent CCR2 and CCR5 Dual Antagonist Selected as a Clinical Candidate," *ACS Medicinal Chemistry Letters*, 12:1753-1758 (2021).

Ishida, T. et al., "CXC Chemokine Receptor 3 and CC Chemokine Receptor 4 Expression in T-Cell and NK-Cell Lymphomas with Special Reference to Clinicopathological Significance for Peripheral T-Cell Lymphoma, Unspecified," *Clinical Cancer Research*, 10(16):5494-5500 (2004).

Somovilla-Crespo, B. et al., "Anti-CCR7 therapy exerts a potent anti-tumor activity in a xenograft model of human mantle cell lymphoma," *Journal of Hematology & Oncology*, 6(89):1-14 (2013).

Struthers, M. and Pasternak, A., "CCR2 Antagonists," *Current Topics in Medicinal Chemistry*, 10(13):1278-1298 (2010).

Vela, M. et al., "Chemokine receptor-specific antibodies in cancer immunotherapy: achievements and challenges," *Frontiers in Immunology*, 6(12): 1-15 (2015).

Yang, M.G. et al. "Discovery of BMS-753426: A Potent Orally Bioavailable Antagonist of CC Chemokine Receptor 2," *ACS Medicinal Chemistry Letters*, 12:969-975 (2021).

International Search Report for international application PCT/IB2018/050260, dated Apr. 13, 2018 (4 pages).

International Search Report for international application PCT/IB2022/057561, dated Nov. 15, 2022 (5 pages).

International Search Report for international application PCT/IB2022/057562, dated Nov. 17, 2022 (5 pages).

International Search Report for international application PCT/IB2023/051743, dated May 26, 2023 (4 pages).

International Search Report for international application PCT/IB2023/051750, dated Apr. 25, 2023 (6 pages).

International Preliminary Report on Patentability for international application PCT/IB2018/050260, dated Jul. 23, 2019 (7 pages).

International Preliminary Report on Patentability for international application PCT/IB2022/057561, dated Feb. 13, 2024 (8 pages).

International Preliminary Report on Patentability for international application PCT/IB2022/057562, dated Feb. 13, 2024 (10 pages).

International Preliminary Report on Patentability for international application PCT/IB2023/051743, dated Aug. 27, 2024 (5 pages).

International Preliminary Report on Patentability for international application PCT/IB2023/051750, dated Aug. 27, 2024 (6 pages).

Written Opinion for International Application No. PCT/IB2022/057561 (7 pages).

Hao et al. in *Cell Communication and Signaling* (2020) vol. 18(82), pp. 1-13.

Lu et al. in *J. Cellular Biochemistry* (2007) vol. 101, pp. 676-685.

* cited by examiner

Healthy donor- PBMC depletion

Bladder Cancer Patient- PBMC Depletion

CYTOTOXICITY TARGETING CHIMERAS FOR CCR2-EXPRESSING CELLS

CROSS REFERENCE TO RELATED APPLICATIONS

This application is a continuation of International (PCT) Patent Application Serial No. PCT/IB2022/057561, filed Aug. 12, 2022, which claims the benefit of and priority to U.S. Provisional Patent Application Ser. No. 63/233,166, filed Aug. 13, 2021; the contents of each of which are hereby incorporated by reference.

REFERENCE TO AN ELECTRONIC SEQUENCE LISTING

This application contains a Sequence Listing which has been submitted electronically via Patent Center in XML format and is hereby incorporated by reference in its entirety. Said XML copy, created on Aug. 11, 2022, is named 054624-09-5005-WO.xml and is 15,358 bytes in size.

FIELD OF THE DISCLOSURE

The present disclosure relates to heterobifunctional molecules, referred to as cytotoxicity targeting chimeras (CyTaCs) or antibody recruiting molecules (ARMs) that are able to simultaneously bind a target cell-surface protein as well as an exogenous antibody protein. The present disclosure also relates to agents capable of binding to a receptor on a surface of a pathogenic cell and inducing the depletion of the pathogenic cell in a subject for use in the treatment of cancer, inflammatory diseases, autoimmune diseases, viral infection, or bacterial infection.

BACKGROUND

Cell-surface proteins and their ligands play key roles in a range of inflammatory, infectious, and autoimmune diseases as well tumor initiation, growth and metastasis. Antibody-based therapeutics have promising properties as drug candidates for these indications due to their selectivity for pathogenic cell-surface targets and their ability to direct immune surveillance to target-expressing tissues or cells to induce depletion of the pathogenic cells. Examples of such depletion mechanisms include antibody-dependent cellular cytotoxicity (ADCC), antibody-dependent cellular phagocytosis (ADCP), and complement-dependant cytotocity (CDC). However, antibody-based therapeutics often suffer from a lack of bioavailability, high cost, thermal instability, and difficult manufacturing due to their size, complexity and peptide based structures. Conversely, small molecule therapeutics often provide affordability, stability, and the convenience of oral dosing, but may suffer from poor selectivity and off-target effects, while also lacking the immune control of therapeutic antibodies.

Accordingly, a need exists for improved therapeutic approaches that target pathogenic cells for use in the treatment of disease. Such compositions and related methods are provided in the present disclosure.

SUMMARY

In one aspect, the present disclosure provides a heterobifunctional molecule referred to as a cytoxicity targeting chimera (CyTaC) or an antibody recruiting molecule (ARM), wherein the ARM comprises a moiety that binds a target cell-surface protein on a cell and a moiety that binds an exogenous antibody. In a further aspect, the ARM comprises a divalent linker that links the target-binding moiety to the antibody-binding moiety. In a further aspect, the target-binding moiety is a C-C chemokine receptor type 2 (CCR2)-binding moiety. In a further aspect, the exogenous antibody is an anti-cotinine antibody, or antigen-binding fragment thereof.

In a further aspect, the ARM is a compound of Formula (I):

(I)

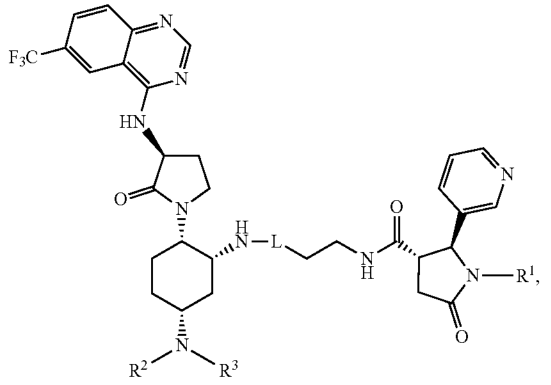

or a pharmaceutically acceptable salt thereof, wherein:

$R^1$ is $C_{1-4}$ alkyl or $C_{3-6}$ cycloalkyl;

$R^2$ is hydrogen or $C_{1-4}$ alkyl;

$R^3$ is hydrogen or $C_{1-4}$ alkyl; and

L is a divalent linker as described herein.

In one aspect, the present disclosure provides a method of treating and/or preventing a disease or disorder in a patient in need thereof, comprising: administering to the patient a compound of Formula (I) as disclosed herein and an anti-cotinine antibody, or antigen-binding fragment thereof.

In one aspect, the present disclosure provides a method of increasing antibody-dependent cell cytotoxicity (ADCC) of CCR2-expressing cells comprising: contacting the cells with a compound of Formula (I) as disclosed herein and an anti-cotinine antibody, or antigen-binding fragment thereof.

In one aspect, the present disclosure provides a method of depleting CCR2-expressing cells comprising: contacting the cells with a compound of Formula (I) as disclosed herein and an anti-cotinine antibody, or antigen-binding fragment thereof.

In one aspect, the present disclosure provides a compound of Formula (I) as disclosed herein for use in therapy. In a further aspect, the present disclosure provides a combination comprising a compound of Formula (I) as disclosed herein and an anti-cotinine antibody, or antigen-binding fragment thereof, for use in therapy.

In one aspect, the present disclosure provides a combination comprising a compound of Formula (I) as disclosed herein and an anti-cotinine antibody, or antigen-binding fragment thereof, for use in the treatment of a disease or disorder.

In one aspect, the present disclosure provides use of a compound of Formula (I) as disclosed herein in the manufacture of a medicament for the treatment of a disease or disorder. In a further aspect, the present disclosure provides use of a combination comprising a compound of Formula (I)

as disclosed herein and an anti-cotinine antibody, or antigen-binding fragment thereof, in the manufacture of a medicament for the treatment of a disease or disorder.

In one aspect, the present disclosure provides a combination comprising a compound of Formula (I) as disclosed herein and an anti-cotinine antibody, or antigen-binding fragment thereof.

BRIEF DESCRIPTION OF THE FIGURES

FIG. 1A shows tumor volume of tumor bearing mice treated with ARM compound in the presence of anti-cotinine antibody at various concentrations of ARM and antibody over time as described in Example 204; FIG. 1B shows blood drug concentration of the ARM compound at various time points post-dosing in mice (see FIG. 1A for legend key); and FIG. 1C shows % depletion of CCR2 expressing cells as determined by flow cytometry.

FIG. 2A shows tumor growth in the presence of CD4 and CD8 T cells; FIG. 2B shows tumor growth with depletion of CD4 and CD8 T cells; the results demonstrate that tumor growth inhibition of the antibody/ARM compound is dependent upon the presence of CD4 and CD8 T cells.

FIG. 3A shows blood concentration of small molecule ARM compound at various timepoints following administration (each time point representative of three animals tested, except for the 168 hour timepoint which is representative of 6 animals tested); FIG. 3B shows percent depletion of CCR2+ expressing cells (see FIG. 3A for legend); the results demonstrate that PK and PD are unchanged by co-dosing vs sequential dosing of the anti-cotinine antibody and small molecule ARM compound.

FIG. 6A shows blood concentration of small molecule ARM compound at various timepoints following administration; FIG. 6B shows percentage depletion of CCR2 expressing cells as determined by flow cytometry (see FIG. 6A for key).

FIG. 7A shows the blood concentration of small molecule ARM compound after administration of (S)-cotinine at the indicated time point; FIG. 7B shows depletion of target expressing cells.

FIG. 8A shows the flow cytometry data demonstrating depletion of CCR2+ cells upon treatment with ARM compound (Example 36) in the presence of anti-cotinine antibody; FIG. 8B shows the percentage of CD8+ T cells divided; CD8+ T cell expansion was observed in 2 of 3 donor samples in which robust CCR2+ cell depletion was observed.

FIG. 9A shows amount of compound of Example 1 detected in blood following dosing of compound and anti-cotinine antibody; FIG. 9B shows depletion of target expressing cells as determined by flow cytometry.

FIG. 10A shows that the percentage of CD8+ T cells increased and the percentage of mMDSCs decreased upon treatment with ARM compound+antibody as compared to treatment with the ARM compound alone; FIG. 10B shows percent survival of tumor bearing mice treated with ARM compound alone or in the presence of anti-cotinine antibody.

FIG. 11A shows depletion in PBMCs from a healthy donor; FIG. 11B shows depletion in PBMCs from a bladder cancer patient; the data demonstrates that CCR2 expression is primarily restricted to target cells of interest for selective depletion (MDSCs) and that the CCR2 expressing target cells are selectively depleted in the presence of anti-cotinine antibody+ARM compound (right panel), but not in the presence of ARM compound alone (left panel).

DETAILED DESCRIPTION

Figure 1A:
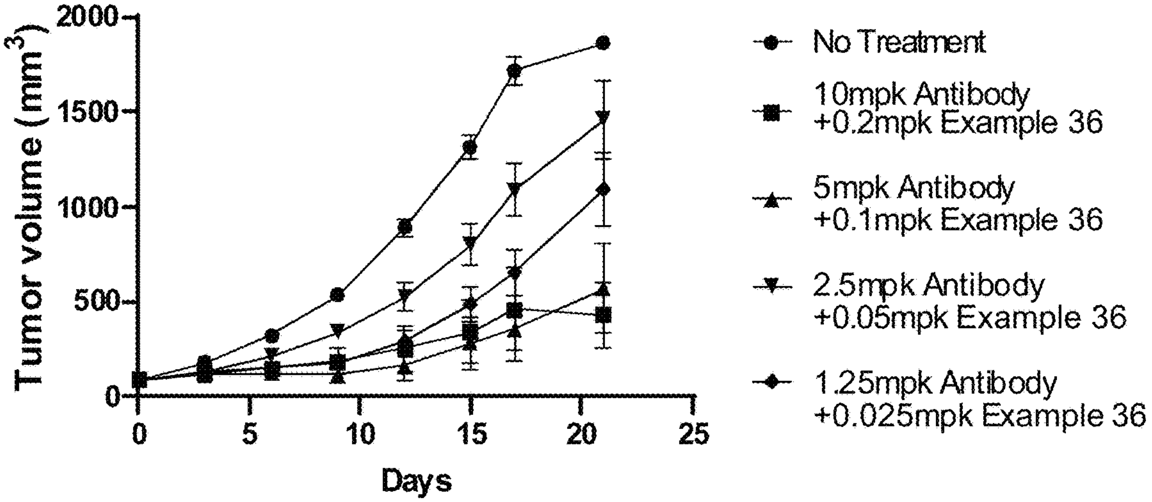
FIGS. 1A-1C: Analysis of MC38 tumor bearing mice (Human CCR2 knock-in C57 mice) dosed with ARM compound (compound of Example 36) in the presence of anti-cotinine antibody as described in Example 204.
Figure 1B:
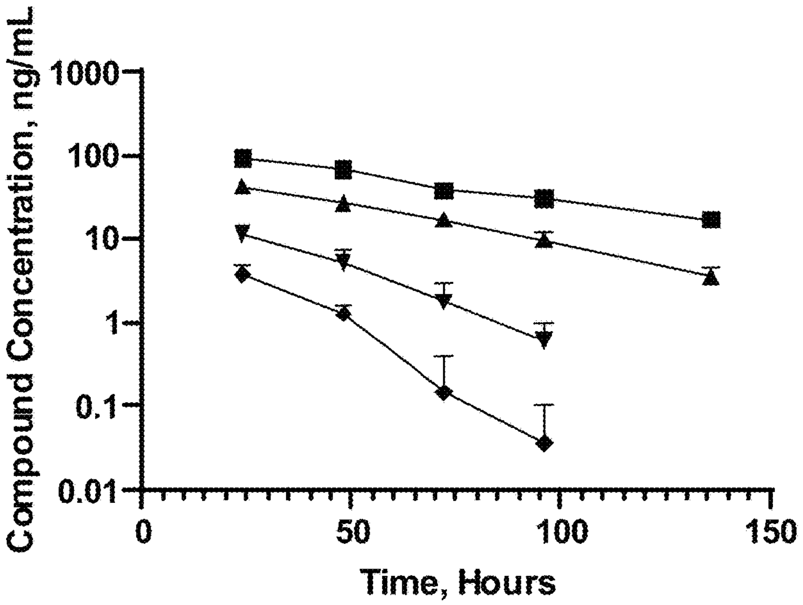
Figure 1C:
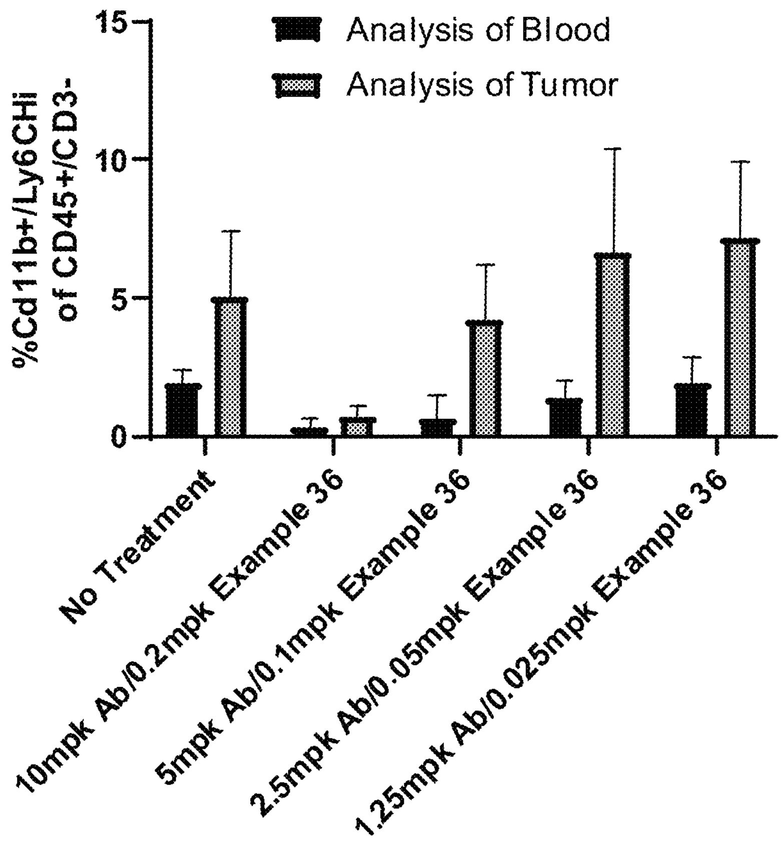

In one aspect, the present disclosure provides a compound of Formula (I):

(I)

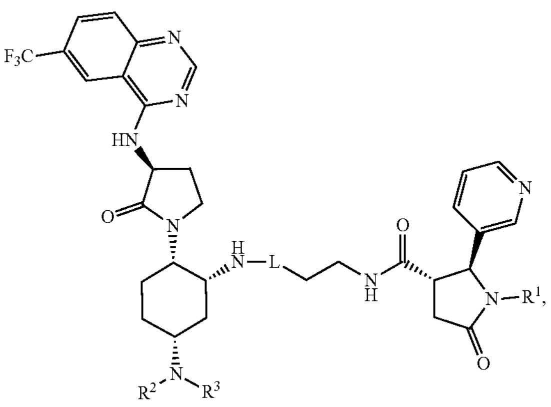

or a pharmaceutically acceptable salt thereof, wherein:

$R^1$ is $C_{1-4}$ alkyl or $C_{3-6}$ cycloalkyl;

$R^2$ is hydrogen or $C_{1-4}$ alkyl;

$R^3$ is hydrogen or $C_{1-4}$ alkyl; and

L is a divalent linker of Formula (L-a), (L-b), (L-c), (L-d), (L-e), (L-f), (L-g), (L-h), (L-i), (L-j), (L-k), (L-m), (L-n-i), (L-n-ii), (L-n-iii), or (L-n-iv).

In one embodiment of the disclosure L is a divalent linker of Formula (L-a):

(L-a)

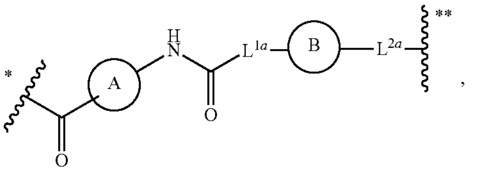

or a stereoisomer thereof, wherein:

Ring A and Ring B are each independently $C_{4-6}$ cycloalkylene;

$L^{1a}$ is $C_{3-5}$ linear alkylene, wherein 1 or 2 methylene units are replaced with —O— or —$NR^a$—;

each $R^a$ is independently hydrogen or $C_{1-3}$ alkyl; and $L^{2a}$ is —O—, —NHC(O)—, or —$CH_2$—O—;

wherein

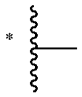

represents a covalent bond to the NH group of Formula (I), and

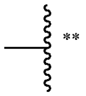

represents a covalent bond to the methylene group of Formula (I).

In another embodiment, Ring A and Ring B of Formula (L-a) are each independently

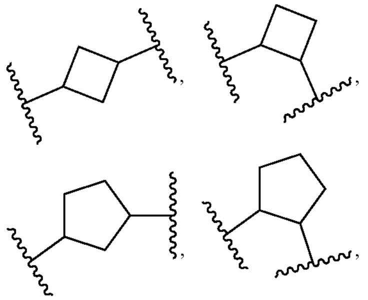

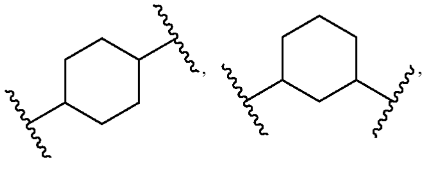

or

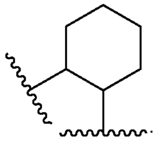

In another embodiment, L is a divalent linker of Formula (L-a-i):

(L-a-i)

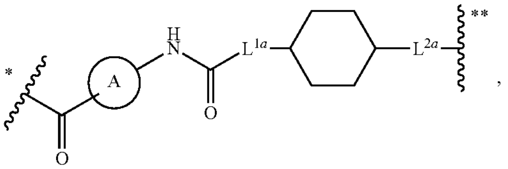

or a stereoisomer thereof, wherein:

Ring A is $C_{4-6}$ cycloalkylene;

$L^{1a}$ is $C_{3-5}$ linear alkylene, wherein 1 or 2 methylene units are replaced with —O— or —$NR^a$—;

each $R^a$ is independently hydrogen or $C_{1-3}$ alkyl; and $L^{2a}$ is —O—, —NHC(O)—, or —$CH_2$—O—;

wherein

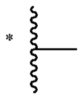

represents a covalent bond to the NH group of Formula (I), and

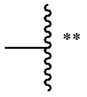

represents a covalent bond to the methylene group of Formula (I).

In another embodiment, Ring A of Formula (L-a-i) is

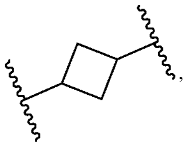 , 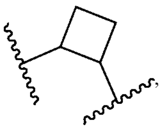 ,

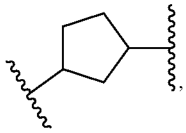 , 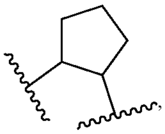 ,

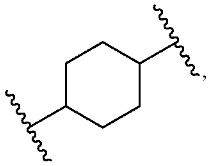 , 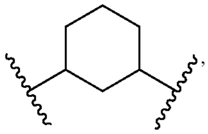 , or

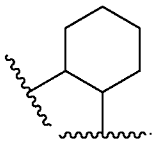 .

In another embodiment, L is a divalent linker of Formula (L-a-ii):

(L-a-ii)

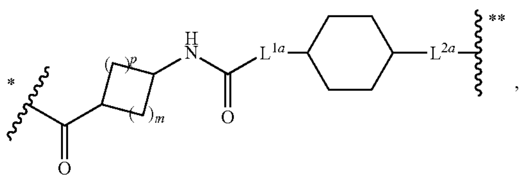 , or a stereoisomer thereof, wherein:

$L^{1a}$ is $C_{3-5}$ linear alkylene, wherein 1 or 2 methylene units are replaced with —O— or —$NR^a$—;

each $R^a$ is independently hydrogen or $C_{1-3}$ alkyl;

$L^{2a}$ is —O—, —NHC(O)—, or —$CH_2$—O—;

p is 1 or 2; and m is 1 or 2;

wherein

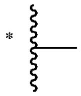

represents a covalent bond to the NH group of Formula (I), and

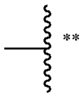

represents a covalent bond to the methylene group of Formula (I).

In another embodiment, L of Formula (L-a), (L-a-i), or (L-a-ii) is selected from

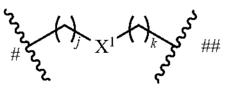 or 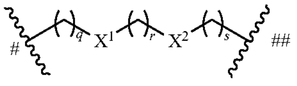 , wherein:

j is 1,2,3, or 4;

k is 0, 1, 2, or 3;

the sum of j and k is 2, 3, or 4;

g is 1 or 2;

r is 1 or 2;

s is 0 or 1;

the sum of q, r, and s is 2 or 3;

$X^1$ and $X^2$ are independently —O— or $NR^a$; and each $R^a$ is independently hydrogen or $C_{1-3}$ alkyl;

wherein

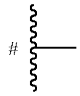

represents a covalent bond to the C(O) group of Formula (L-a), (L-a-i), or (L-a-ii), and

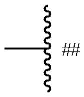

represents a covalent bond to Ring B of Formula (L-a) or to the cyclohexylene group of Formula (L-a-i) or (L-a-ii).

In another embodiment, L of Formula (L-a), (L-a-i), or (L-a-ii) is selected from —$(CH_2)_2O$—, —$(CH_2)_3O$—, —$(CH_2)_4O$—, —$(CH_2)_2OCH_2$—, —$(CH_2)_3OCH_2$—, —$(CH_2)_2O(CH_2)_2$—, —$CH_2OCH_2$—, —$CH_2O(CH_2)_2$—, —$CH_2O(CH_2)_3$—, —$CH_2OCH_2O$—, or —$CH_2OCH_2OCH_2$—. In another embodiment, $L^{1a}$ of Formula (L-a), (L-a-i), or (L-a-ii) is selected from $—(CH_2)_2O—$, $—(CH_2)_3O—$, $—(CH_2)_2OCH_2—$, or $—(CH_2)_3OCH_2—$. In another embodiment, L of Formula (L-a), (L-a-i), or (L-a-ii) is selected from $—(CH_2)_2NR^a—$, $—(CH_2)_3NR^a—$, $—(CH_2)_4NR^a—$, $—(CH_2)_2NR^aCH_2—$, $—(CH_2)_3NR^aCH_2—$, $—(CH_2)_2NR^a(CH_2)_2—$, $—CH_2NR^aCH_2—$, $—CH_2NR^a(CH_2)_2—$, $—CH_2NR^a(CH_2)_3—$, $—CH_2NR^aCH_2NR^a—$, or $—CH_2NR^aCH_2NR^aCH_2—$, wherein each $R^a$ is independently hydrogen or $C_{1-3}$ alkyl. In another embodiment, L of Formula (L-a), (L-a-i), or (L-a-ii) is selected from $—(CH_2)_2NR^a—$, $—(CH_2)_3NR^a—$, $—(CH_2)_2NR^aCH_2—$, or $—(CH_2)_3NR^aCH_2—$, wherein $R^a$ is hydrogen or $C_{1-3}$ alkyl. In another embodiment, L of Formula (L-a), (L-a-i), or (L-a-ii) is selected from $—(CH_2)_2NH—$, $—(CH_2)_3NH—$, $—(CH_2)_4NH—$, $—(CH_2)_2NHCH_2—$, $—(CH_2)_3NHCH_2—$, $—(CH_2)_2NH(CH_2)_2—$, $—CH_2NHCH_2—$, $—CH_2NH(CH_2)_2—$, $—CH_2NH(CH_2)_3—$, $—CH_2NHCH_2NH—$, or $—CH_2NHCH_2NHCH_2—$. In another embodiment, L of Formula (L-a), (L-a-i), or (L-a-ii) is selected from $—(CH_2)_2NH—$, $—(CH_2)_3NH—$, $—(CH_2)_2NHCH_2—$, or $—(CH_2)_3NHCH_2—$. In another embodiment, L of Formula (L-a), (L-a-i), or (L-a-ii) is selected from $—CH_2OCH_2NR^a—$, $—CH_2NR^aCH_2O—$, $—CH_2OCH_2NR^aCH_2—$, $—CH_2NR^aCH_2OCH_2—$, wherein $R^a$ is independently hydrogen or $C_{1-3}$ alkyl. In another embodiment, L of Formula (L-a), (L-a-i), or (L-a-ii) is selected from $—CH_2OCH_2NH—$, $—CH_2NHCH_2O—$, $—CH_2OCH_2NHCH_2—$, $—CH_2NHCH_2OCH_2—$.

In another embodiment, L is a divalent linker of Formula (L-a-iii):

(L-a-iii)

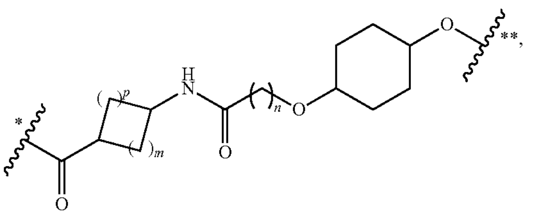

or a stereoisomer thereof, wherein:

p is 1 or 2;

m is 1 or 2; and n is 1, 2, or 3;

wherein

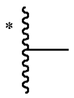

represents a covalent bond to the NH group of Formula (I), and

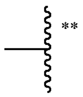

represents a covalent bond to the methylene group of Formula (I).

In another embodiment, L is a divalent linker of Formula (L-a) selected from the group consisting of:

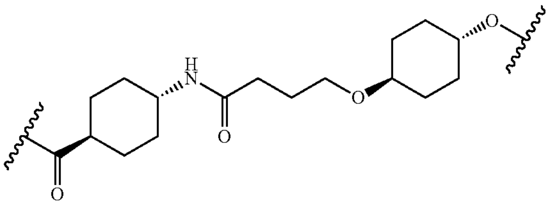

,

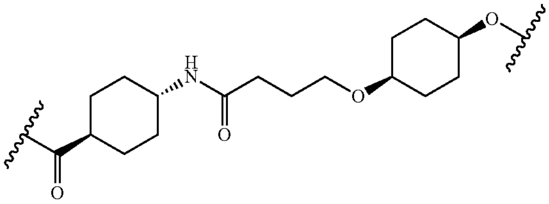

,

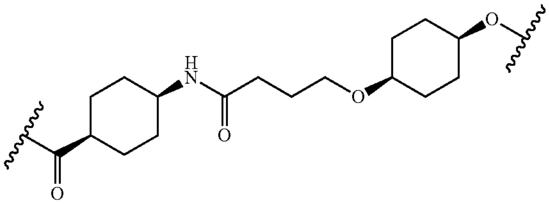

,

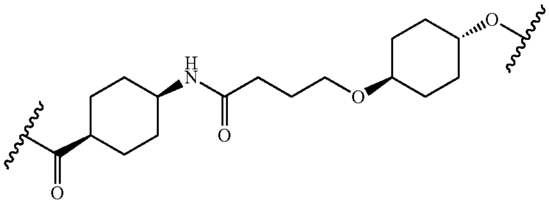

,

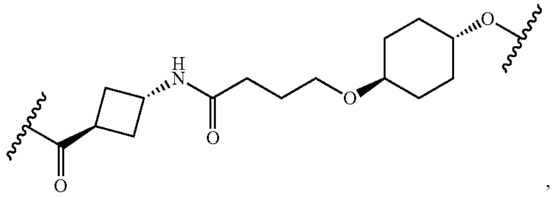

,

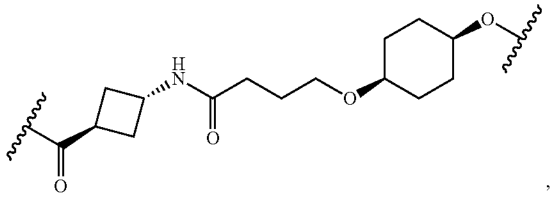

,

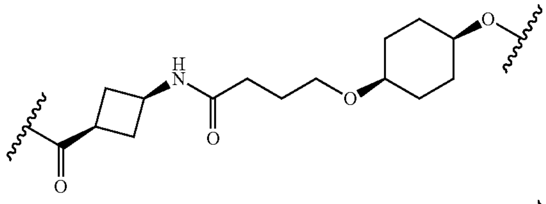

,

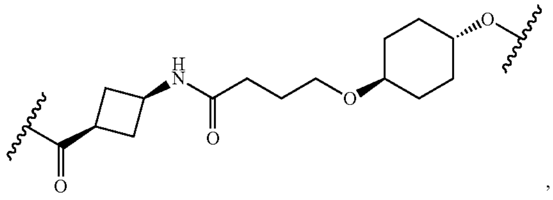

,

-continued
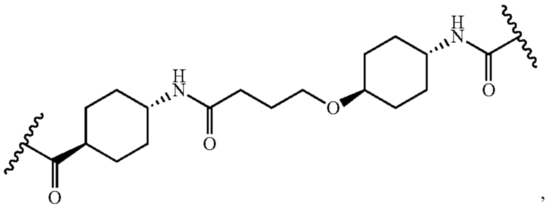
,
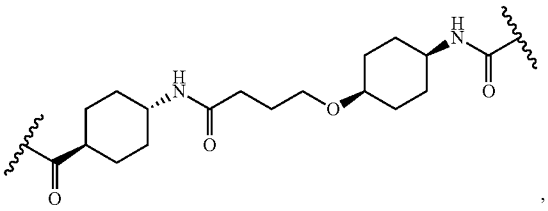
,
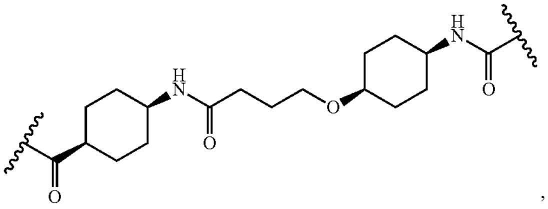
,
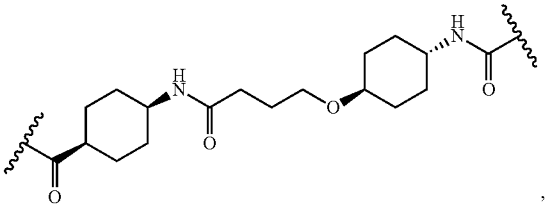
,
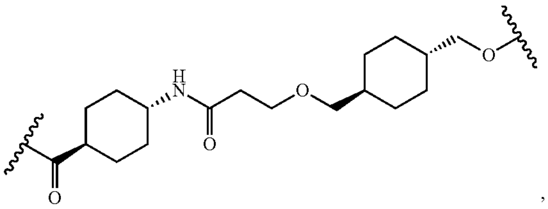
,
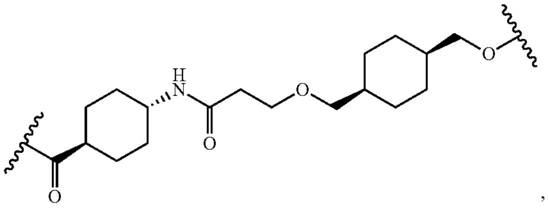
,
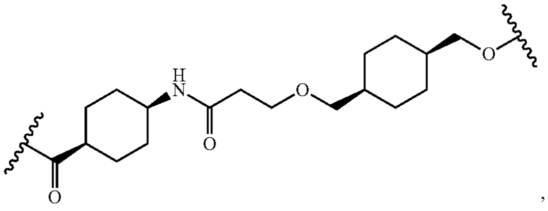
,
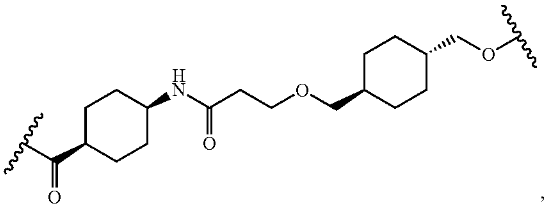
,
-continued
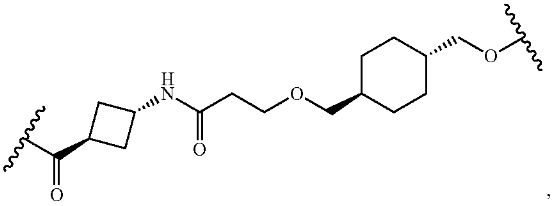
,
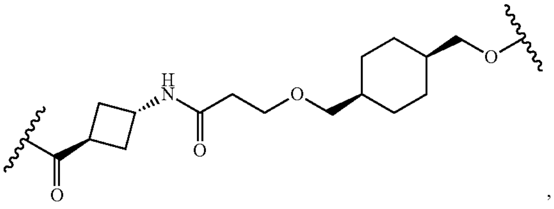
,
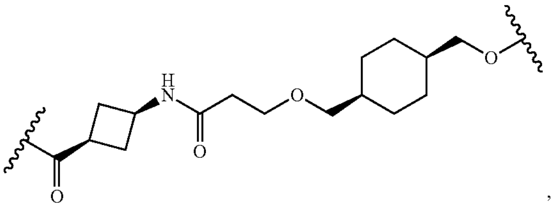
,
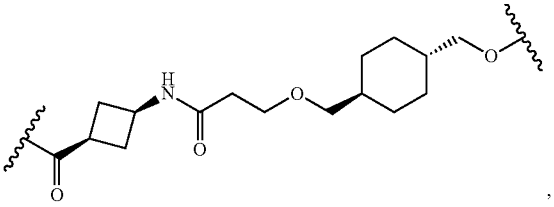
,
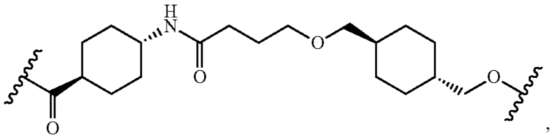
,
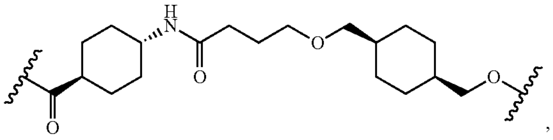
,
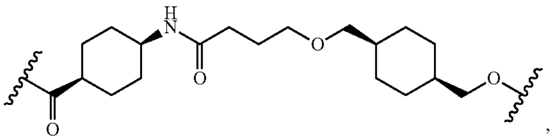
,
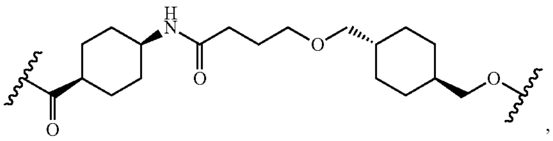
,
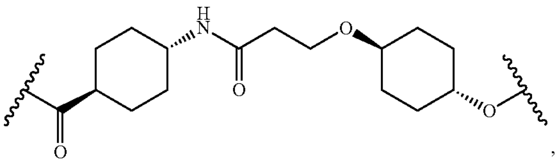
,
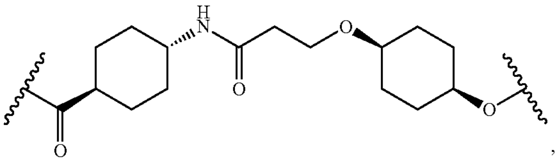
, -continued

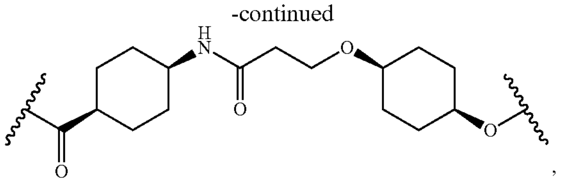

,

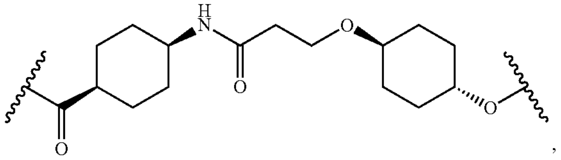

,

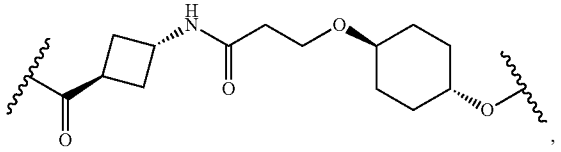

,

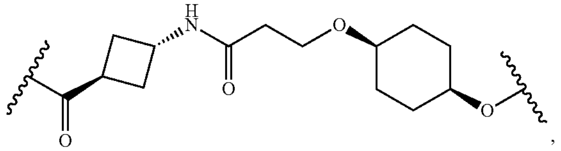

,

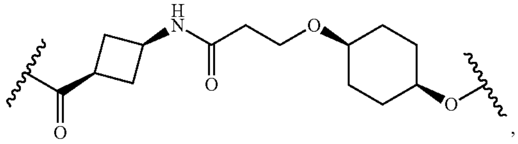

, and

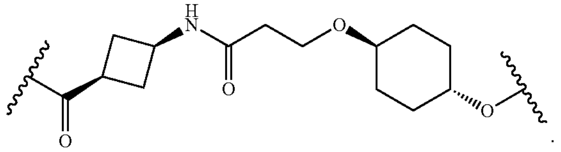

.

In another embodiment, L is a divalent linker of Formula (L-b):

(L-b)

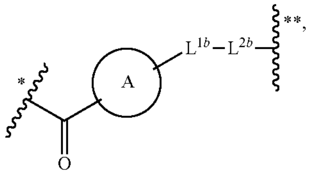

or a stereoisomer thereof, wherein:

Ring A is $C_{4-6}$ cycloalkylene or $C_{7-9}$ bridged bicyclic cycloalkylene;

$L^{1b}$ is —$CH_2$—NH—C(O)—, —NHC(O)—, or —C(O)NH—;

$L^{2b}$ is $C_{6-12}$ linear alkylene, wherein 1, 2, 3, or 4 methylene units are replaced with —O—, —$NR^{1b}$—, —C(O)$NR^{1b}$—, or —$NR^{1b}$C(O)—; or $L^{2b}$ is

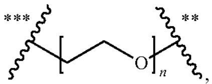

, wherein n is 1, 2, 3, or 4, and

represents a covalent bond to $L^{1b}$; and each $R^{1b}$ is independently hydrogen or $C_{1-3}$ alkyl;

wherein

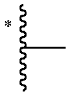

represents a covalent bond to the NH group of Formula (I), and

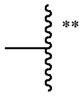

represents a covalent bond to the methylene group of Formula (I).

In another embodiment, Ring A of Formula (L-b) is

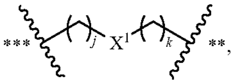

,

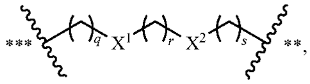

,

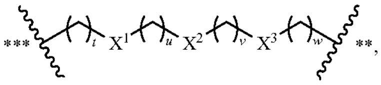

, or

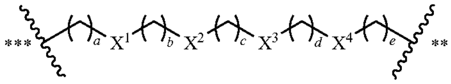

In another embodiment, L is a divalent linker of Formula (L-b-i):

(L-b-i)

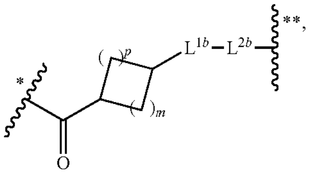

or a stereoisomer thereof, wherein:

$L^{1b}$ is —$CH_2$—NH—C(O)—, —NHC(O)—, or —C(O)NH—;

$L^2$b is $C_{6-12}$ linear alkylene, wherein 1, 2, 3, or 4 methylene units are replaced with —O—, —$NR^{1b}$—, —C(O)NR, or —NR C(O)—; or $L^{2b}$ is

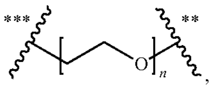

wherein n is 1, 2, 3, or 4, and

represents a covalent bond to $L^{1b}$;

each $R^{1b}$ is independently hydrogen or $C_{1-3}$ alkyl;

p is 1 or 2; and m is 1 or 2;

wherein

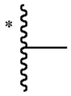

represents a covalent bond to the NH group of Formula (I), and

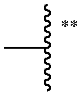

represents a covalent bond to the methylene group of Formula (I).

In another embodiment, $L^2$b of Formula (L-b) or (L-b-i) is selected from

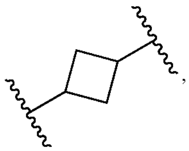,
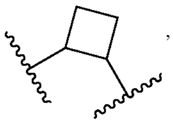,
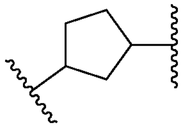,
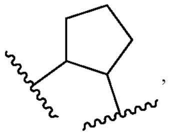,
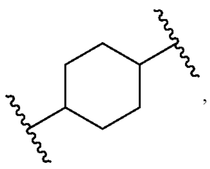,
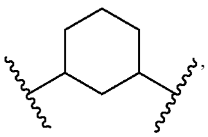,
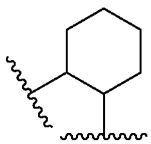, -continued

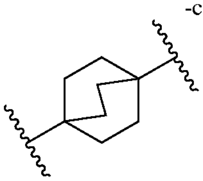, or 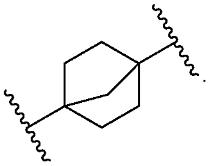.

wherein:

j is 1, 2, 3, 4, 5, 6, 7, 8, 9, or 10;

k is 1, 2, 3, 4, 5, 6, 7, 8, 9, or 10;

the sum of j and k is 5, 6, 7, 8, 9, 10, or 11;

q is 1, 2, 3, 4, 5, 6, 7, 8, or 9;

r is 1, 2, 3, 4, 5, 6, 7, 8, or 9;

s is 0, 1, 2, 3, 4, 5, 6, 7, or 8;

the sum of q, r, and s is 4, 5, 6, 7, 8, 9, or 10;

t is 1, 2, 3, 4, 5, 6, or 7;

u is 1, 2, 3, 4, 5, 6, or 7;

v is 1, 2, 3, 4, 5, 6, or 7;

w is 0, 1, 2, 3, 4, 5, or 6;

the sum oft, u, v, and w is 3, 4, 5, 6, 7, 8, or 9;

a is 1, 2, 3, 4, or 5;

b is 1, 2, 3, 4, or 5;

c is 1, 2, 3, 4, or 5;

d is 1, 2, 3, 4, or 5;

e is 0, 1, 2, 3, or 4;

the sum of a, b, c, d, and e is 4, 5, 6, 7, or 8;

$X^1$, $X^2$, $X^3$, and $X^4$ are independently —O—, —$NR^{1b}$—, —C(O)$NR^{1b}$—, or —$NR^{1b}$C(O)—; and each $R^{1b}$ is independently hydrogen or $C_{1-3}$ alkyl;

wherein

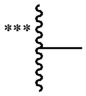

represents a covalent bond to $L^{1b}$ of Formula (L-b) or (L-b-i), and

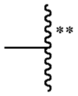

represents a covalent bond to the methylene group of Formula (I).

In another embodiment, L is a divalent linker of Formula (L-b) selected from the group consisting of:

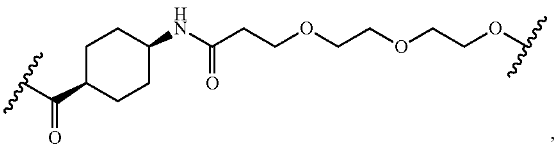,

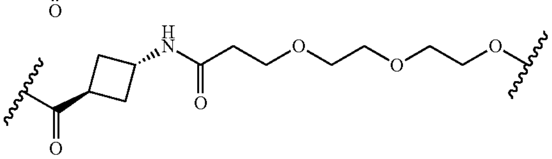,

-continued
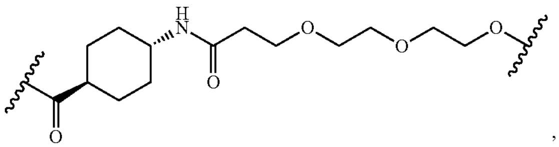
,
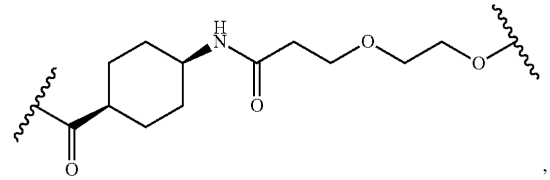
,
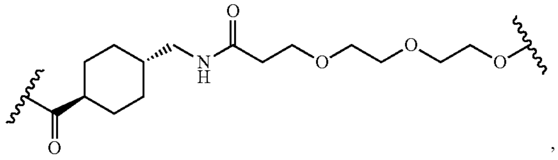
,
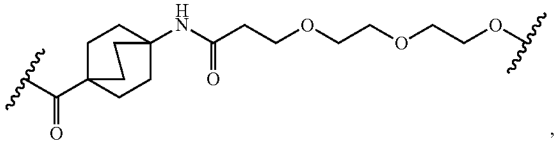
,
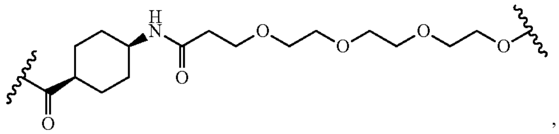
,
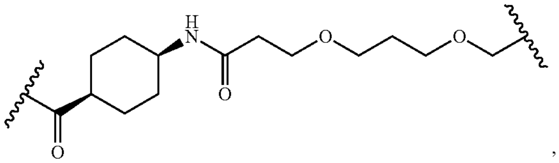
,
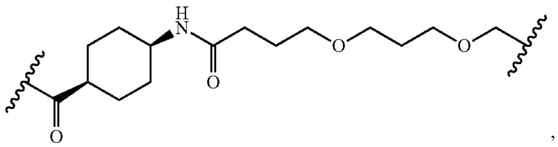
,
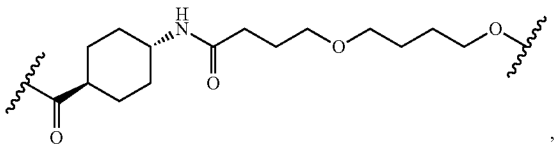
,
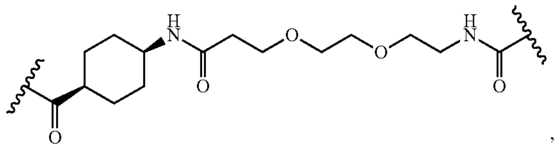
,
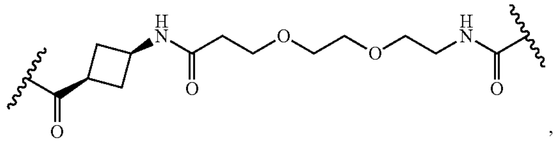
,
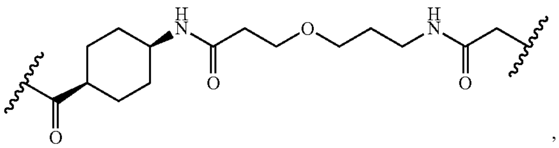
,
-continued
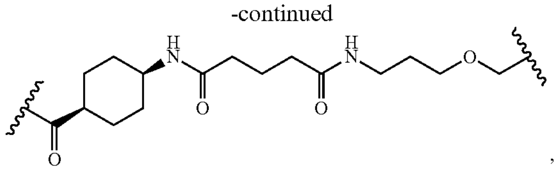
,
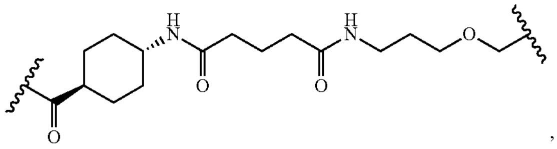
,
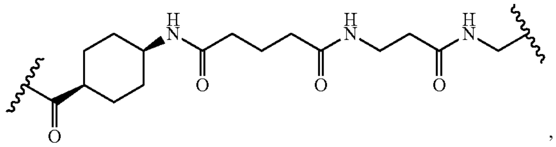
,
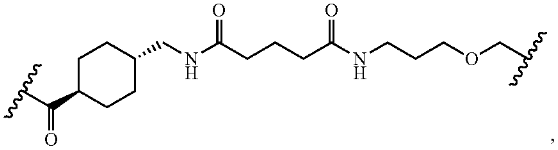
,
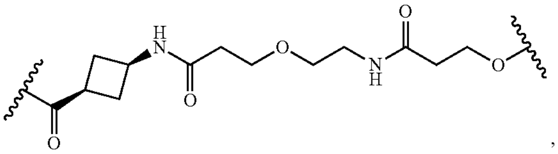
,
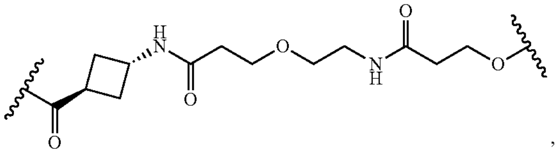
,
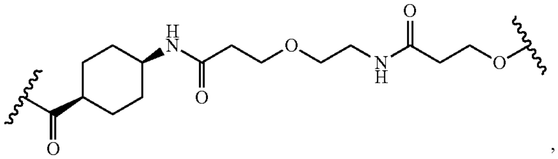
,
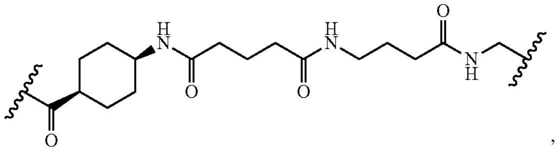
,
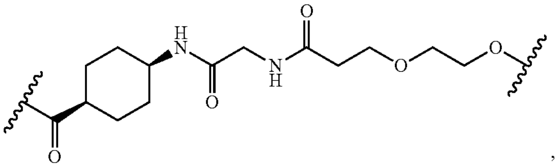
,
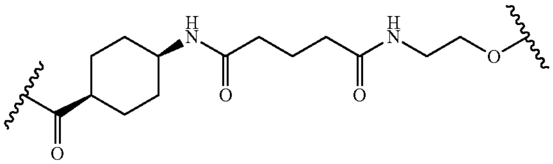
,
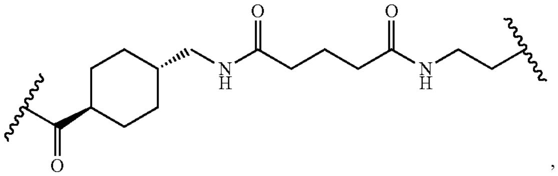
, -continued

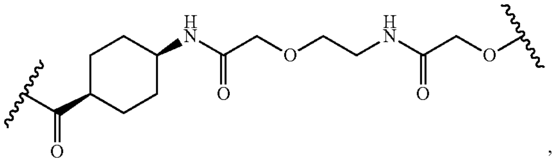

,

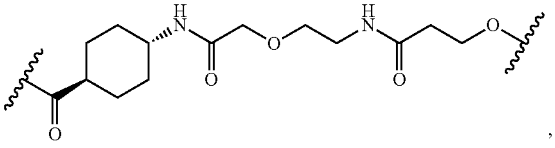

,

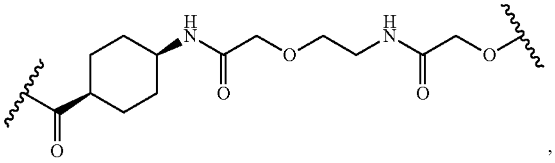

,

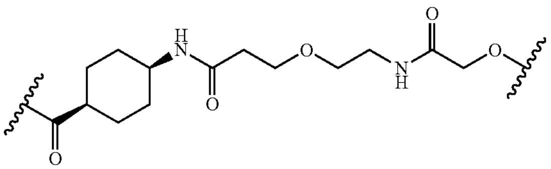

,

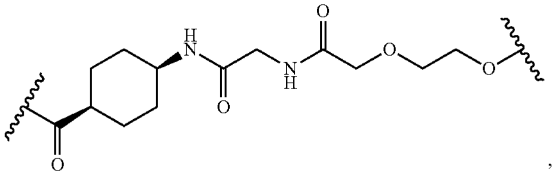

,

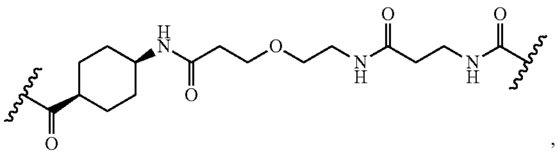

,

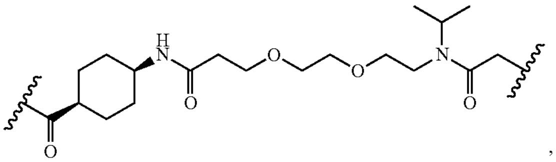

,

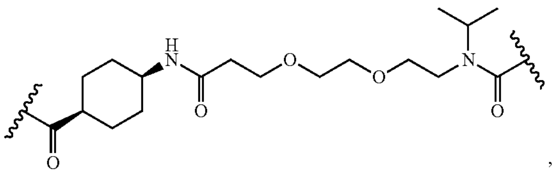

,

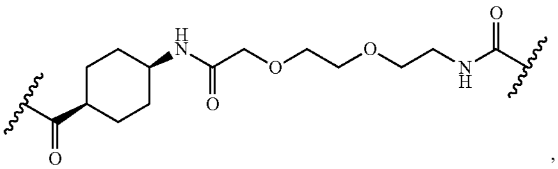

,

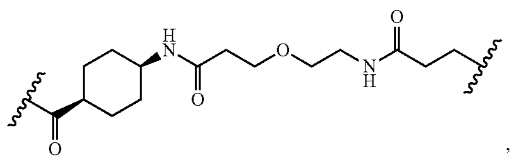

, and

-continued

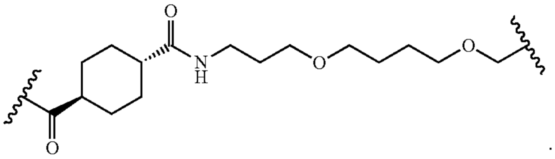

.

In another embodiment, L is a divalent linker of Formula (L-c):

(L-c)

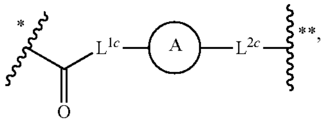

or a stereoisomer thereof, wherein:

$L^{1c}$ is $C_{2-10}$ linear alkylene, wherein 1, 2, or 3 methylene units are replaced with —O—, —NH—, —NHC(O)—, or —C(O)NH—;

Ring A is $C_{4-6}$ cycloalkylene or $C_{7-9}$ bridged bicyclic cycloalkylene; and $L^{2c}$ is —O— or a saturated $C_{2-10}$ linear alkylene, wherein 1, 2, or 3 methylene units are replaced with —O—, —NH—, —NHC(O)—, or —C(O)NH—;

wherein

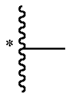

represents a covalent bond to the NH group of Formula (I), and

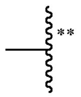

represents a covalent bond to the methylene group of Formula (I).

In another embodiment, Ring A of Formula (L-c) is

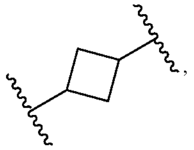

,

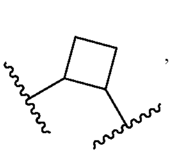

,

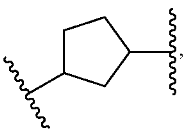

,

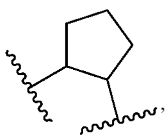

,

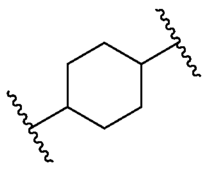

,

-continued

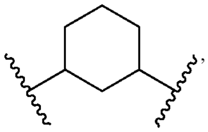, 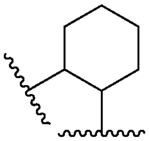,

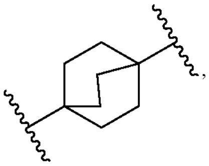, or 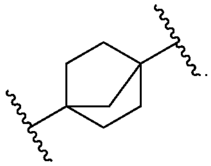.

In another embodiment, L is a divalent linker of Formula (L-c-i):

(L-c-i)

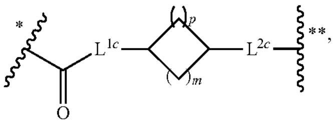

or a stereoisomer thereof, wherein:

$L^{1c}$ is $C_{2-10}$ linear alkylene, wherein 1, 2, or 3 methylene units are replaced with —O—, —NH—, —NHC(O)—, or —C(O)NH—;

$L^{2c}$ is —O— or a saturated $C_{2-10}$ linear alkylene, wherein 1, 2, or 3 methylene units are replaced with —O—, —NH—, —NHC(O)—, or —C(O)NH—;

p is 1 or 2; and m is 1 or 2;

wherein

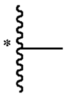

represents a covalent bond to the NH group of Formula (I), and

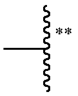

represents a covalent bond to the methylene group of Formula (I).

In another embodiment, $L^{1c}$ of Formula (L-c) or (L-c-i) is selected from

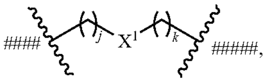,

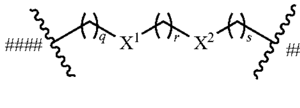, or

-continued

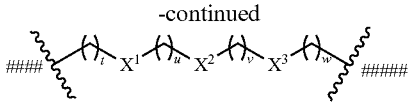

wherein:

j is 1, 2, 3, 4, 5, 6, 7, 8, or 9;

k is 0, 1, 2, 3, 4, 5, 6, 7, or 8;

the sum of j and k is 1, 2, 3, 4, 5, 6, 7, 8, or 9;

g is 1, 2, 3, 4, 5, 6, or 7;

r is 1, 2, 3, 4, 5, 6, or 7;

s is 0, 1, 2, 3, 4, 5, or 6;

the sum of q, r, and s is 2, 3, 4, 5, 6, 7, or 8;

t is 1, 2, 3, 4, or 5;

u is 1, 2, 3, 4, or 5;

v is 1, 2, 3, 4, or 5;

w is 0, 1, 2, 3, or 4;

the sum oft, u, v, and w is 3, 4, 5, 6, or 7; and $X^1$, $X^2$ and $X^3$ are independently —O—, —NH—, —NHC(O)—, or —C(O)NH—;

wherein

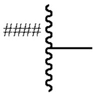

represents a covalent bond to the C(O) group of Formula (L-c) or (L-c-i), and

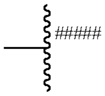

represents a covalent bond to the ring of Formula (L-c) or (L-c-i).

In another embodiment, $L^{2c}$ of Formula (L-c) or (L-c-i) is selected from

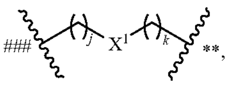, 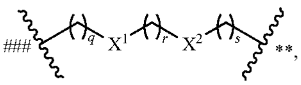, or

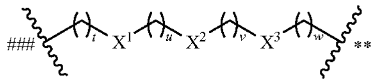

wherein:

j is 0, 1, 2, 3, 4, 5, 6, 7, 8, or 9;

k is 0, 1, 2, 3, 4, 5, 6, 7, 8, or 9;

the sum of j and k is 1, 2, 3, 4, 5, 6, 7, 8, or 9;

g is 0, 2, 3, 4, 5, 6, or 7;

r is 1, 2, 3, 4, 5, 6, 7, or 8;

s is 0, 1, 2, 3, 4, 5, 6, or 7;

the sum of q, r, and s is 1, 2, 3, 4, 5, 6, 7, or 8;

t is 0, 1, 2, 3, 4, or 5;

u is 1, 2, 3, 4, 5, or 6;

v is 1, 2, 3, 4, 5, or 6;

w is 0, 1, 2, 3, 4, or 5;

the sum oft, u, v, and w is 2, 3, 4, 5, 6, or 7; and $X^1$, $X^2$ and $X^3$ are independently —O—, —NH—, —NHC(O)—, or —C(O)NH—;

wherein

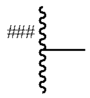

represents a covalent bond to the ring of Formula (L-c) or (L-c-i), and

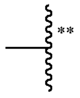

represents a covalent bond to the methylene group of Formula (I).

In another embodiment, L is a divalent linker of Formula (L-c) selected from the group consisting of:

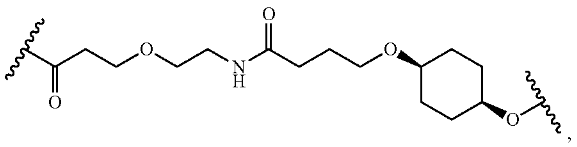

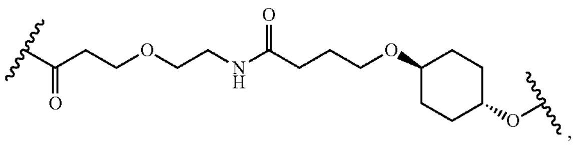

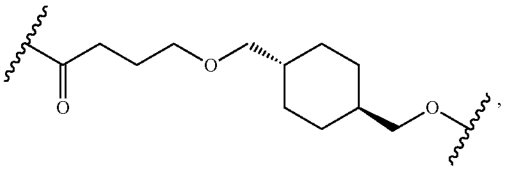

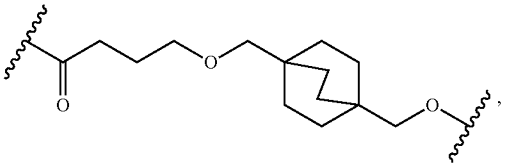

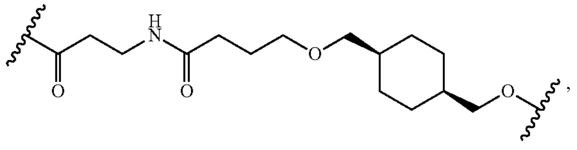

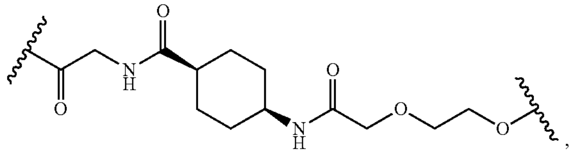

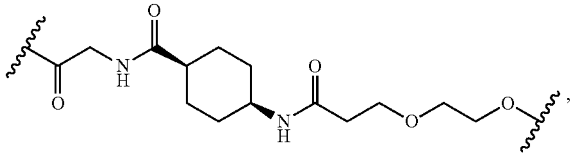

-continued

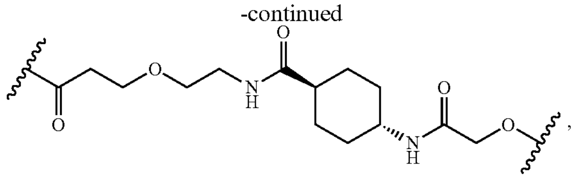

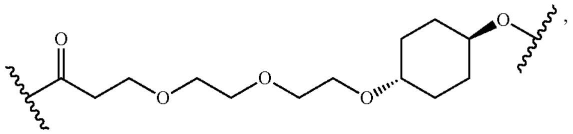

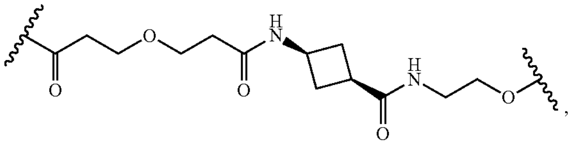

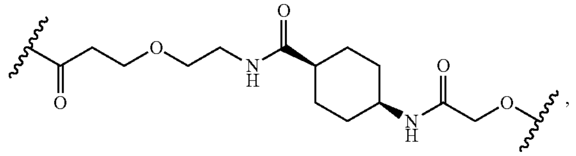

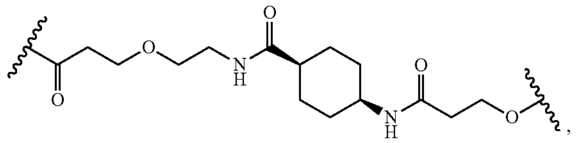

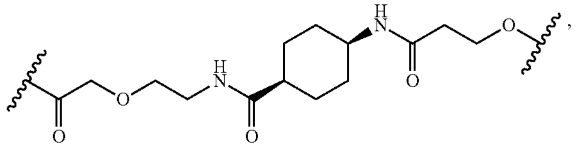

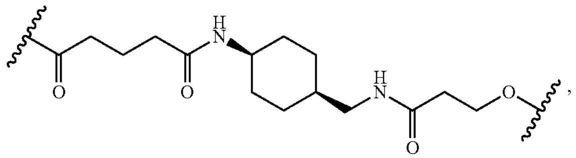

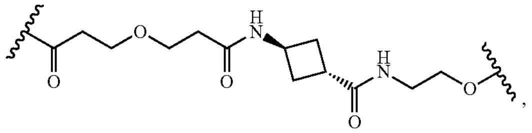

and

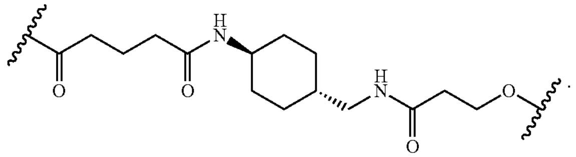

In another embodiment, L is a divalent linker of Formula (L-d):

(L-d)

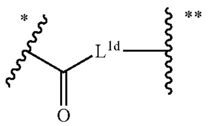

wherein:

$L^{1d}$ is $C_{12-22}$ linear alkylene, wherein 1, 2, 3, 4, or 5 methylene units are replaced with —NH—, —O—, —C(O)NH—, —NHC(O)—, or —NHC(O)—NH—;

wherein

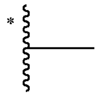

represents a covalent bond to the NH group of Formula (I), and

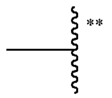

represents a covalent bond to the methylene group of Formula (I).

In another embodiment, $L^{1d}$ of Formula (L-d) is selected from

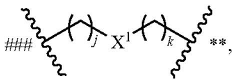,

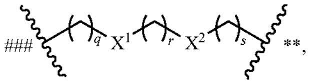,

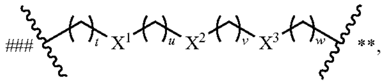,

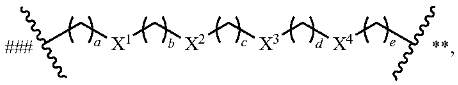, or

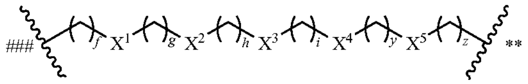

wherein:

j is 1, 2, 3, 4, 5, 6, 7, 8, 9, 10, 11, 12, 13, 14, 15, 16, 17, 18, 19, or 20;

k is 1, 2, 3, 4, 5, 6, 7, 8, 9, 10, 11, 12, 13, 14, 15, 16, 17, 18, 19, or 20;

the sum of j and k is 11, 12, 13, 14, 15, 16, 17, 18, 19, 20, or 21;

q is 1, 2, 3, 4, 5, 6, 7, 8, 9, 10, 11, 12, 13, 14, 15, 16, 17, 18, or 19;

r is 1, 2, 3, 4, 5, 6, 7, 8, 9, 10, 11, 12, 13, 14, 15, 16, 17, 18, or 19;

s is 0, 1, 2, 3, 4, 5, 6, 7, 8, 9, 10, 11, 12, 13, 14, 15, 16, 17, or 18;

the sum of q, r, and s is 10, 11, 12, 13, 14, 15, 16, 17, 18, 19, or 20;

t is 1, 2, 3, 4, 5, 6, 7, 8, 9, 10, 11, 12, 13, 14, 15, 16, or 17;

u is 1, 2, 3, 4, 5, 6, 7, 8, 9, 10, 11, 12, 13, 14, 15, 16, or 17;

v is 1, 2, 3, 4, 5, 6, 7, 8, 9, 10, 11, 12, 13, 14, 15, 16, or 17;

w is 0, 1, 2, 3, 4, 5, 6, 7, 8, 9, 10, 11, 12, 13, 14, 15, or 16;

the sum of t, u, v, and w is 9, 10, 11, 12, 13, 14, 15, 16, 17, 18, or 19;

a is 1, 2, 3, 4, 5, 6, 7, 8, 9, 10, 11, 12, 13, 14, or 15;

b is 1, 2, 3, 4, 5, 6, 7, 8, 9, 10, 11, 12, 13, 14, or 15;

c is 1, 2, 3, 4, 5, 6, 7, 8, 9, 10, 11, 12, 13, 14, or 15;

d is 1, 2, 3, 4, 5, 6, 7, 8, 9, 10, 11, 12, 13, 14, or 15;

e is 0, 1, 2, 3, 4, 5, 6, 7, 8, 9, 10, 11, 12, 13, or 14;

the sum of a, b, c, d, and e is 8, 9, 10, 11, 12, 13, 14, 15, 16, 17, or 18;

f is 1, 2, 3, 4, 5, 6, 7, 8, 9, 10, 11, 12, or 13;

g is 1, 2, 3, 4, 5, 6, 7, 8, 9, 10, 11, 12, or 13;

h is 1, 2, 3, 4, 5, 6, 7, 8, 9, 10, 11, 12, or 13;

i is 1, 2, 3, 4, 5, 6, 7, 8, 9, 10, 11, 12, or 13;

y is 1, 2, 3, 4, 5, 6, 7, 8, 9, 10, 11, 12, or 13;

z is 0, 1, 2, 3, 4, 5, 6, 7, 8, 9, 10, 11, or 12;

the sum of f, g, h, i, y, and z is 7, 8, 9, 10, 11, 12, 13, 14, 15, 16, or 17; and $X^1$, $X^2$, $X^3$, $X^4$, and $X^5$ are independently —NH—, —O—, —C(O)NH—, —NHC(O)—, or —NHC(O)—NH—;

wherein

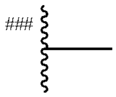

represents a covalent bond to the C(O) group of Formula (L-d), and

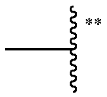

represents a covalent bond to the methylene group of Formula (I).

In another embodiment, L is a divalent linker of Formula (L-d) selected from the group consisting of:

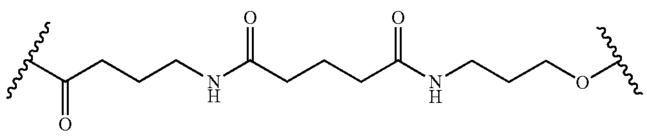,

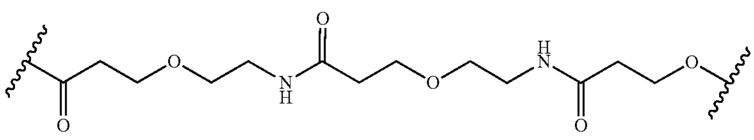,

-continued
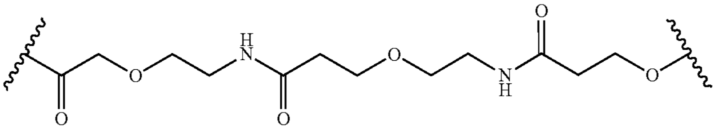
,
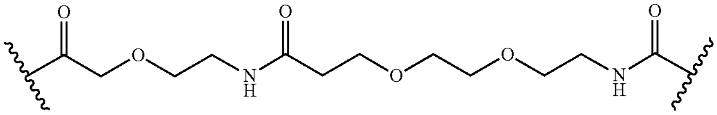
,
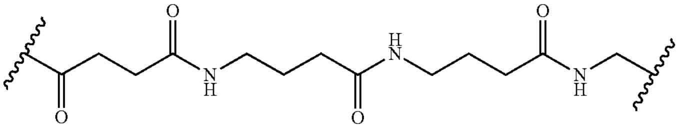
,
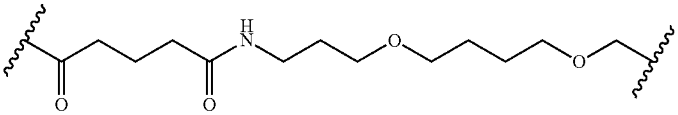
,
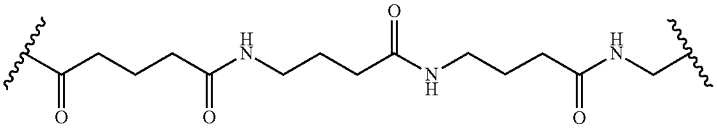
,
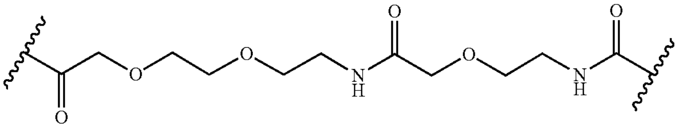
,
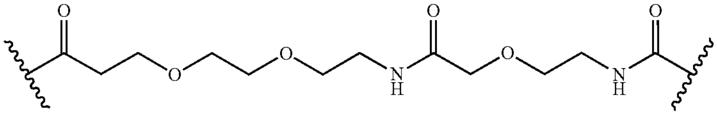
,
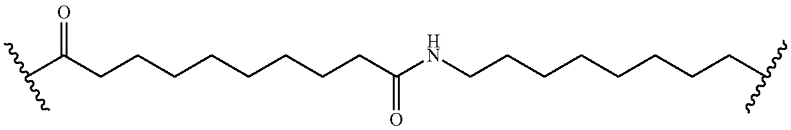
,
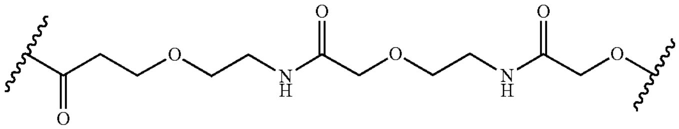
,
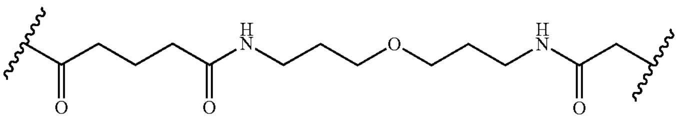
,
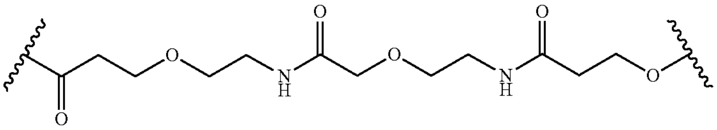
,
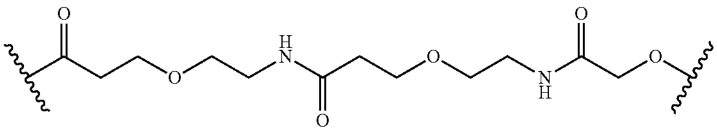
,
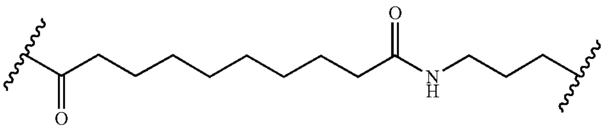
, -continued
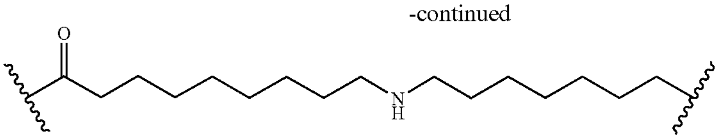
,
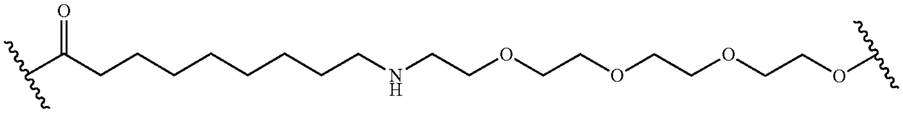
,
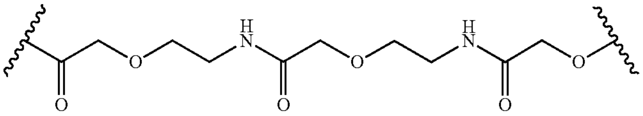
,
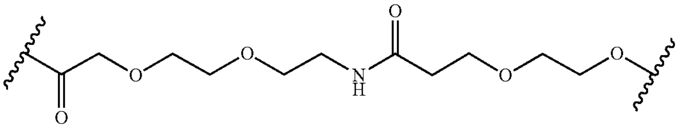
,
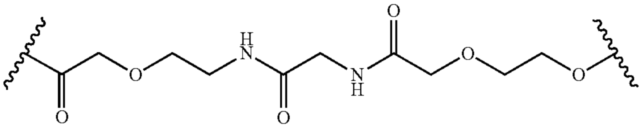
,
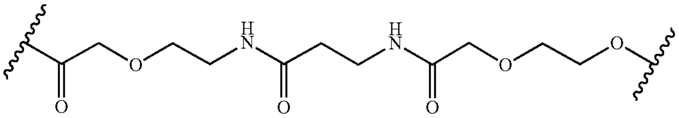
,
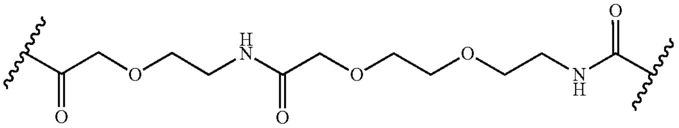
,
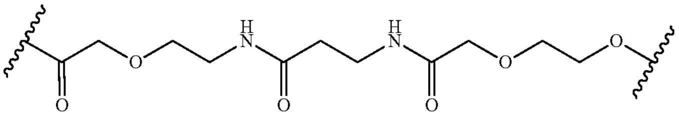
,
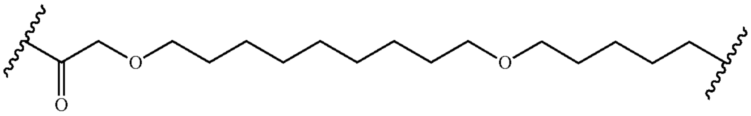
,
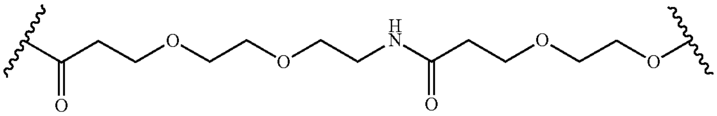
,
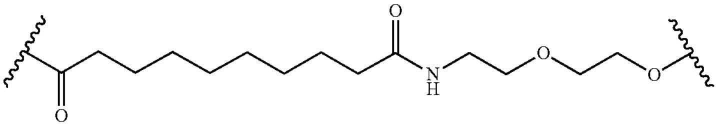
,
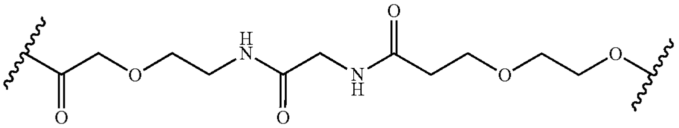
,
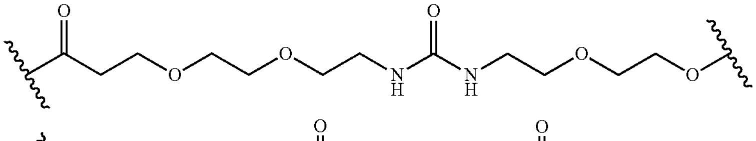
,
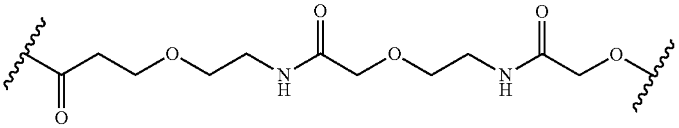
, -continued

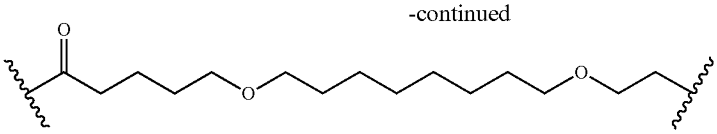
,

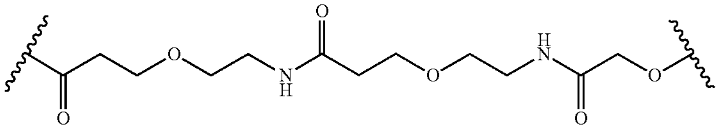
, and

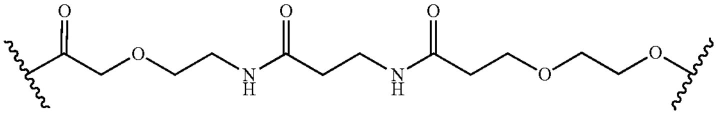
.

In another embodiment, L is a divalent linker of Formula (L-e):

(L-e)

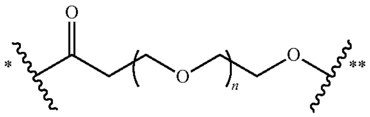

wherein:

n is an integer of 3 to 50;

wherein

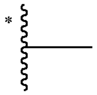

represents a covalent bond to the NH group of Formula (I), and

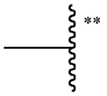

represents a covalent bond to the methylene group of Formula (I).

In another embodiment, n of Formula (L-e) is 3 to 25, 3 to 10, 3 to 8, 3 to 7, 3 to 5, or 3 to 4. In another embodiment, n of Formula (L-e) is 3, 4, 5, 7, 8, 22, or 50.

In another embodiment, L is a divalent linker of Formula (L-f):

(L-f)

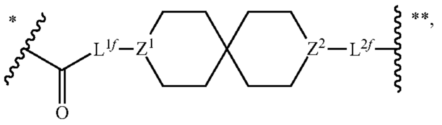

or a stereoisomer thereof, wherein:

$L^{1f}$ is a bond; $C_{1-6}$ linear alkylene, wherein 0, 1, or 2 methylene units are replaced with —O—, —NH—, or —C(O)—; or —($C_{3-6}$ cycloalkylene)-NHC(O)—;

$L^{2f}$ is a bond, —NHC(O)—, —C(O)NH—, or a $C_{1-6}$ linear alkylene, wherein 0, 1, or 2 methylene units are replaced with —O—; and each of $Z^1$ and $Z^2$ is independently N or CH;

wherein

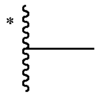

represents a covalent bond to the NH group of Formula (I), and,

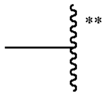

represents a covalent bond to the methylene group of Formula (I).

In another embodiment, $L^{1f}$ of Formula (L-f) is selected from

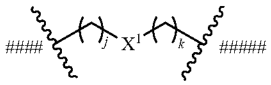
or

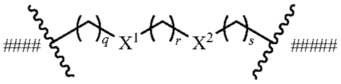

wherein:

j is 1, 2, 3, 4, or 5;

k is 0, 1, 2, 3, or 4;

the sum of j and k is 1, 2, 3, 4, or 5;

g is 1, 2, or 3;

r is 1, 2, or 3;

s is 0, 1, 2;

the sum of q, r, and s is 2, 3, or 4; and $X^1$ and $X^2$ are independently —O—, —NH—, or —C(O)—; or —($C_{3-6}$ cycloalkylene)-NHC(O)—;

wherein

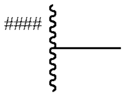

represents a covalent bond to the C(O) group of Formula (L-f), and

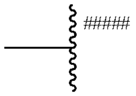

represents a covalent bond to the ring of Formula (L-f).

In another embodiment $L^{2f}$ of Formula (L-f) is selected from

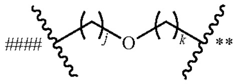 or 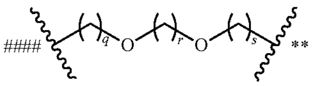

wherein:

j is 1, 2, 3, 4, or 5;

k is 0, 1, 2, 3, or 4;

the sum of j and k is 1, 2, 3, 4, or 5;

g is 1, 2, or 3;

r is 1, 2, or 3;

s is 0, 1, 2; and the sum of q, r, and s is 2, 3, or 4;

wherein

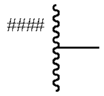

represents a covalent bond to the ring of Formula (L-f), and

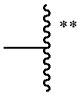

represents a covalent bond to the methylene group of Formula (I).

In another embodiment, L is a divalent linker of Formula (L-f) selected from the group consisting of:

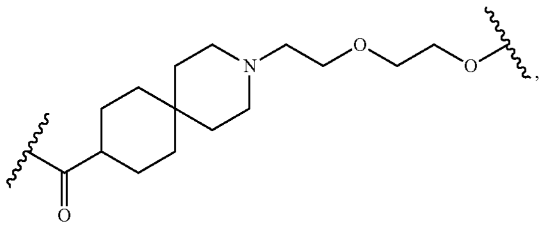,

-continued

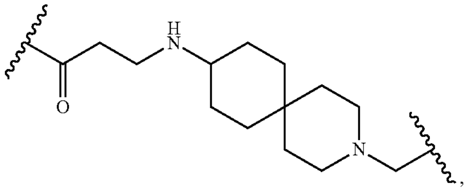,

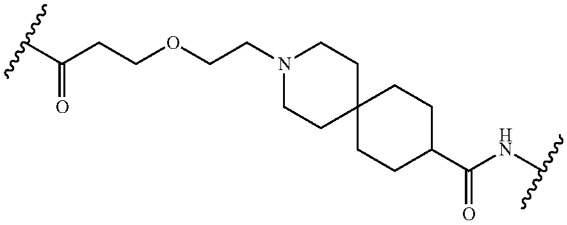,

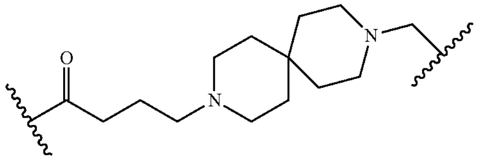,

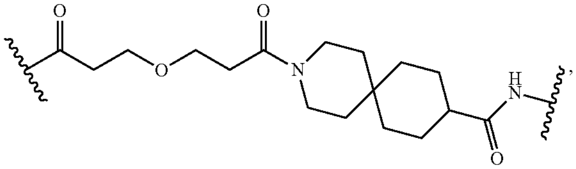,

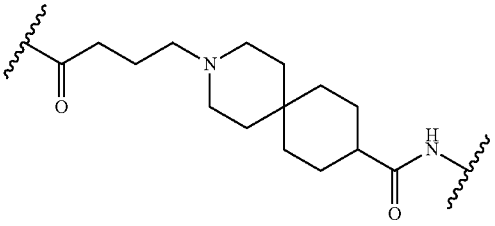, and

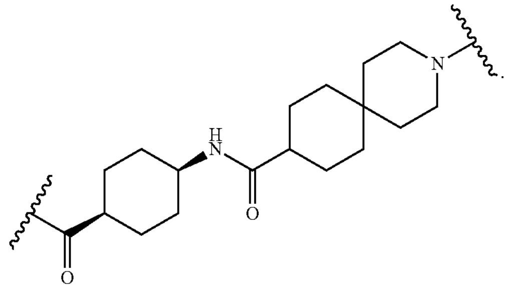.

In another embodiment, L is a divalent linker of Formula (L-g):

(L-g)

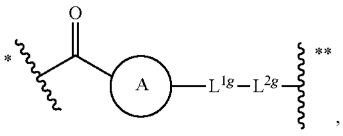, wherein:

Ring A is a 5 to 6 membered heteroarylene having 1 or 2 nitrogen ring atoms;

$L^{1g}$ is a bond, —$CH_2$—, —NH—, or —O—; and $L^{2g}$ is

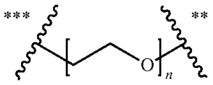

wherein n is 1, 2, 3, 4, or 5, and

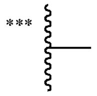

represents a covalent bond to $L^{1g}$;
wherein

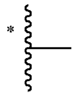

represents a covalent bond to the NH group of Formula (I), and

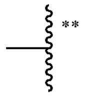

represents a covalent bond to the methylene group of Formula (I).

In another embodiment, L is a divalent linker of Formula (L-g-i):

(L-g-i)

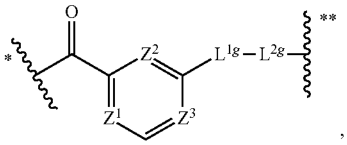

, wherein:

$L^{1g}$ is a bond, —$CH_2$—, —NH—, or —O—;

$L^{2g}$ is

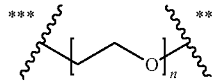

wherein n is 1, 2, 3, 4, or 5, and

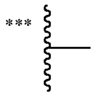

represents a covalent bond to $L^{1g}$;

$Z^1$, $Z^2$, and $Z^3$ are each independently selected from N or CH, provided that one or two of $Z^1$, $Z^2$, and $Z^3$ is N;

wherein

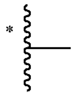

represents a covalent bond to the NH group of Formula (I), and

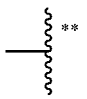

represents a covalent bond to the methylene group of Formula (I).

In another embodiment, L is a divalent linker of Formula (L-g) selected from the group consisting of:

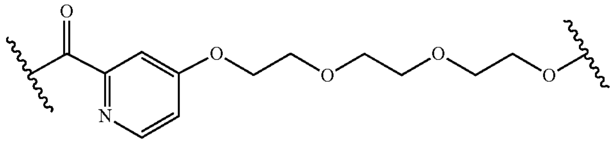

,

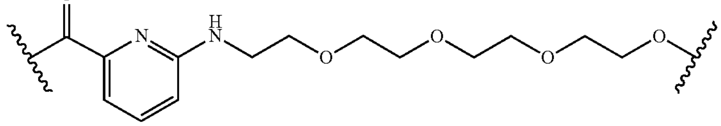

,

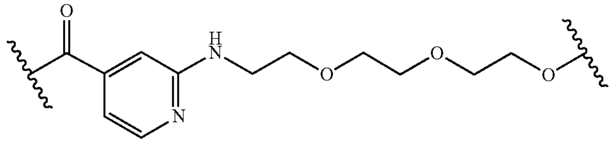

,

-continued

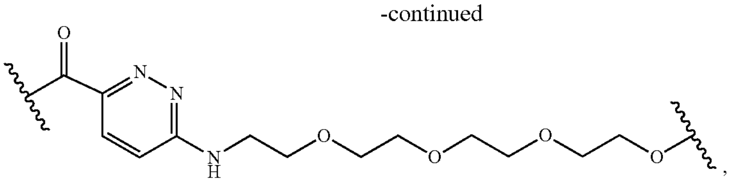

,

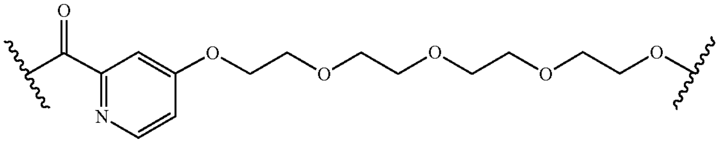

,

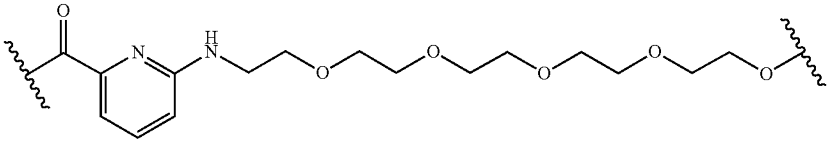

,

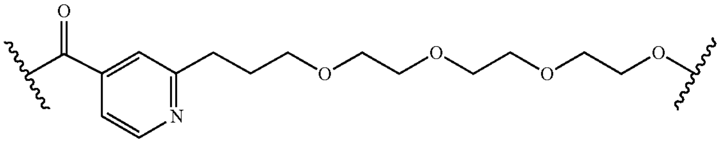

,

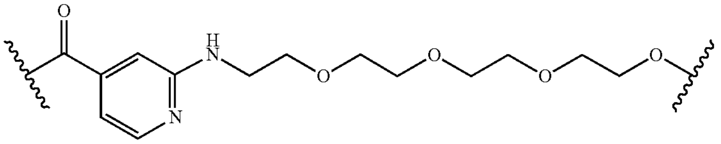

,

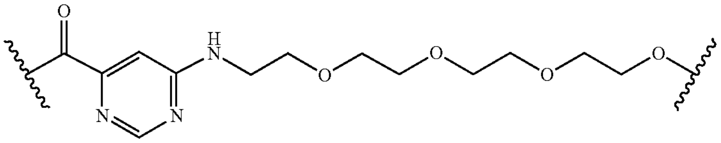

, and

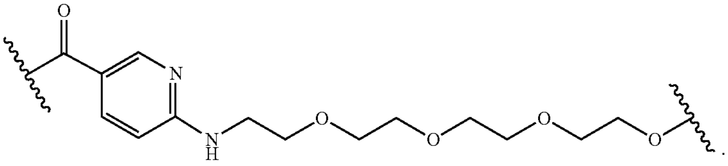 [SMILES: *OCCOCCOCCOCCNc1ccc(C(*)=O)cn1]

.

In another embodiment, L is a divalent linker of Formula (L-h):

(L-h)

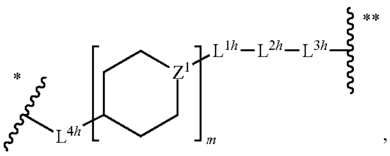

, or a stereoisomer thereof, wherein:

each $Z^1$ is independently N or CH;

$L^{1h}$ is a bond, —C(O)—, —C(O)—NH—, or —NHC(O)—;

$L^{2h}$ is $C_{2-10}$ linear alkylene or

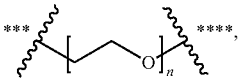

, wherein n is 1, 2, 3, or 4, and

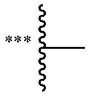

represents a covalent bond to $L^{1h}$ and

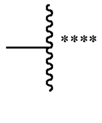

represents a covalent bond to $L^{3h}$;

$L^{3h}$ is a bond, —$C(O)CH_2$—, —O—($C_{3-6}$ cycloalkylene)-O—, or —$C(O)NH(CH_2)_3OCH_2$—;

$L^{4h}$ is a bond, —C(O)—, —$CH_2C(O)$—, or —C(O)$CH_2$—; and m is 1, 2, or 3,
wherein
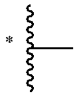
represents a covalent bond to the NH group of Formula (I), and
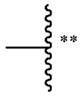
represents a covalent bond to the methylene group of Formula (I).
In another embodiment, L is a divalent linker of Formula (L-h) selected from the group consisting of:
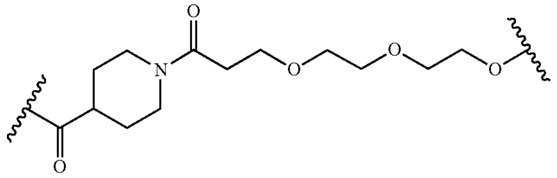
,
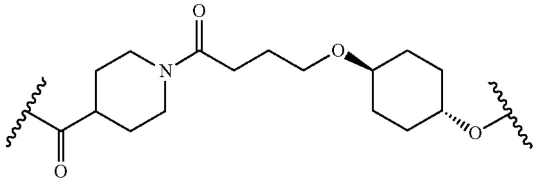
,
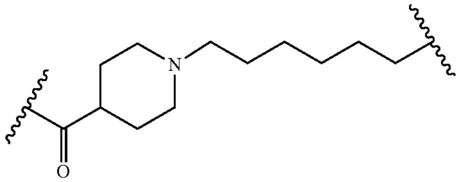
,
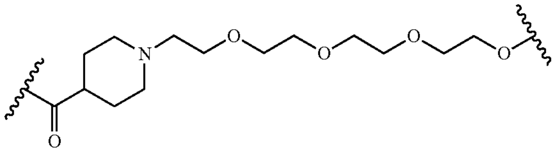
,
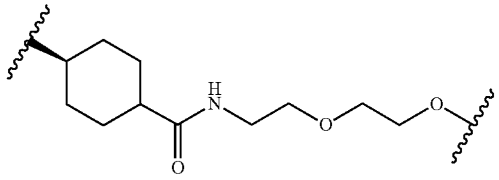
,
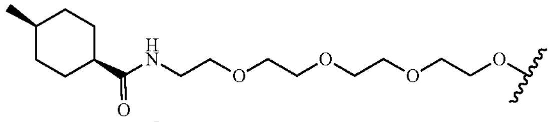
,
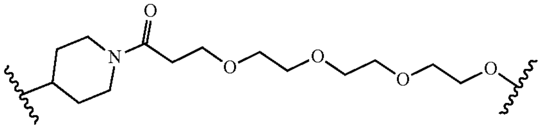
,
-continued
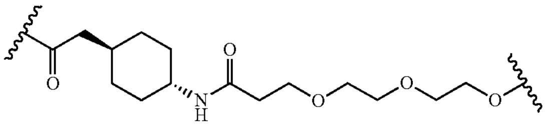
,
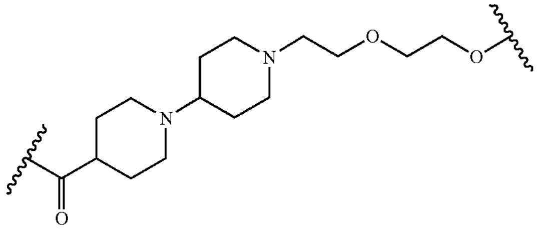
,
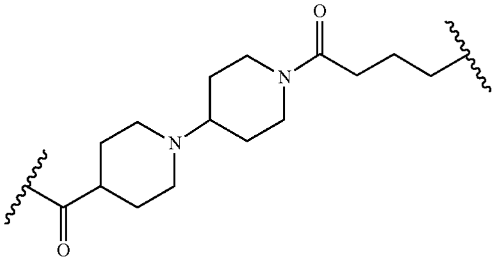
,
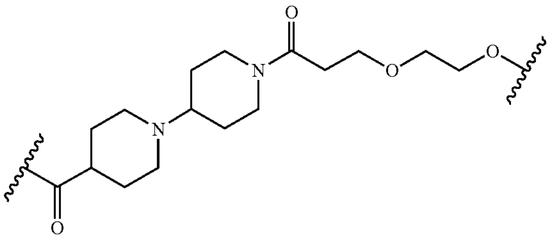
,
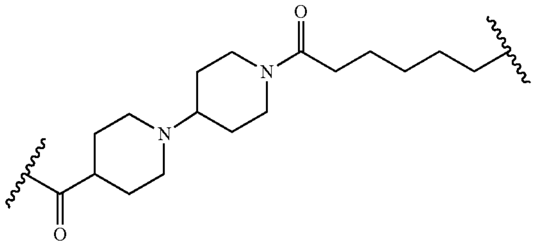
,
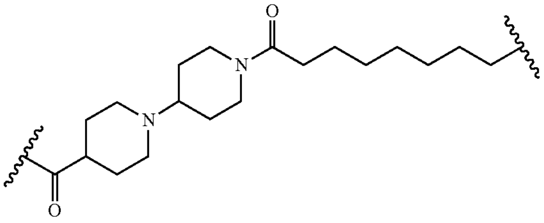
,
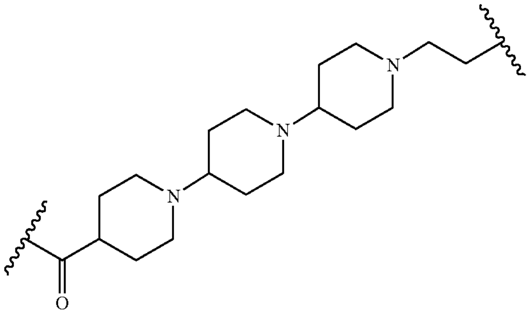
, -continued

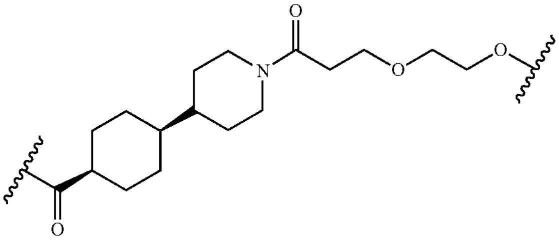

,

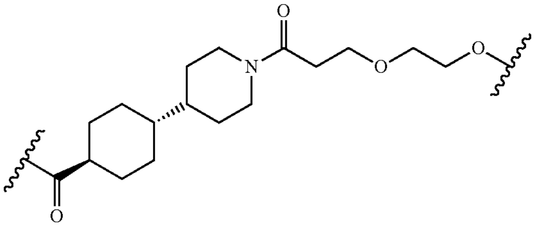

,

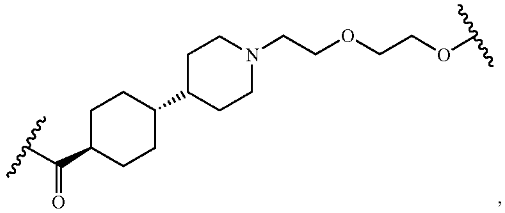

, and

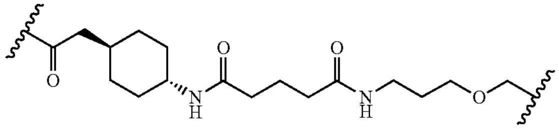

.

In another embodiment, L is a divalent linker of Formula (L-i):

(L-i)

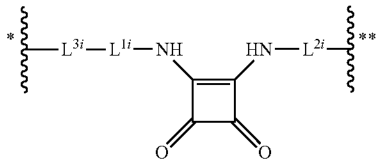

wherein:

$L^{1i}$ is a bond, $C_{1-12}$ linear alkylene, or

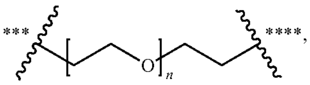

, wherein n is 1, 2, 3, 4, or 5, and

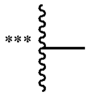

represents a covalent bond to $L^{3i}$ and

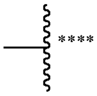

represents a covalent bond to NH;

$L^{2i}$ is a bond, $C_{1-12}$ linear alkylene, or

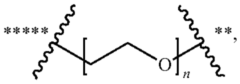

, wherein n is 1, 2, 3, 4, or 5, and

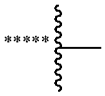

represents a covalent bond to HN; and $L^{3i}$ is a bond or —C(O)—;

wherein

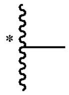

represents a covalent bond to the NH group of Formula (I), and

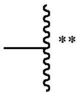

represents a covalent bond to the methylene group of Formula (I).

In another embodiment, L is a divalent linker of Formula (L-i) selected from the group consisting of:

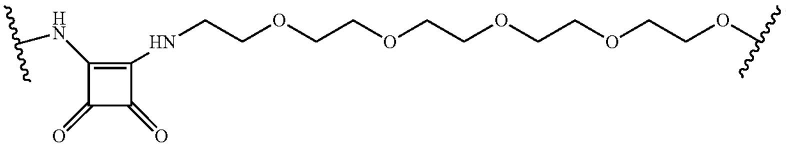

,

-continued

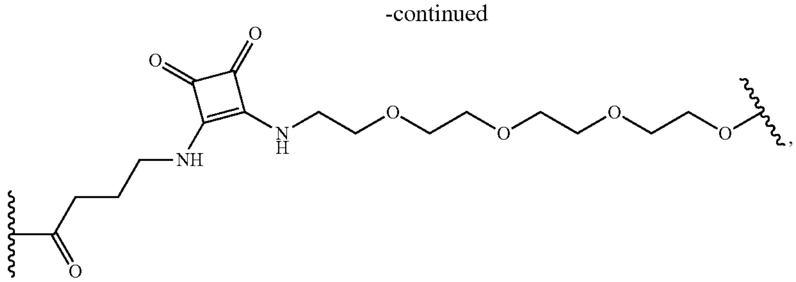

,

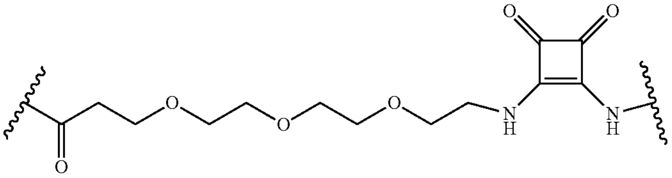

,

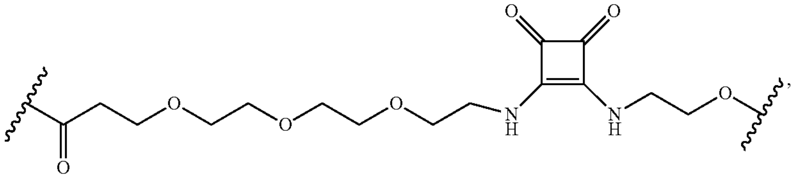

, and

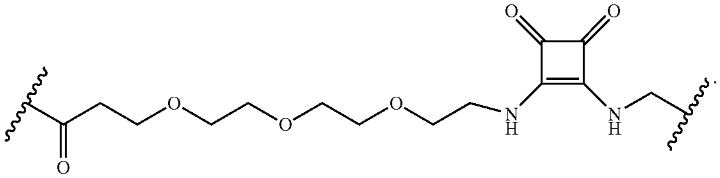

.

In another embodiment, L is a divalent linker of Formula (L-j):

(L-j)

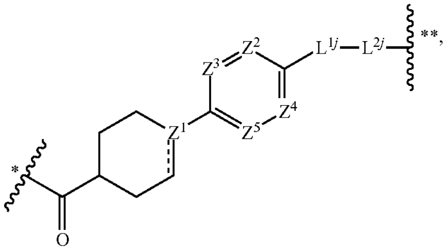

or a stereoisomer thereof, wherein:

$Z^1$ is C, CH, or N;

each of $Z^2$, $Z^3$, $Z^4$ and $Z^5$ is independently CH or N, provided that no more than two of $Z^2$, $Z^3$, $Z^4$ and $Z^5$ are N;

$L^{1j}$ is —NH—, —C(O)NH—, —NHC(O)—, or —O—;

$L^{2j}$ is $C_{1-6}$ linear alkylene or

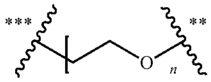

, wherein n is 1 or 2, and

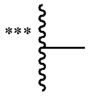

represents a covalent bond to $L^{1j}$; and  represents a single bond or a double bond;

wherein

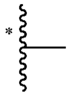

represents a covalent bond to the NH group of Formula (I), and

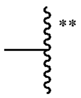

represents a covalent bond to the methylene group of Formula (I).

In another embodiment, L is a divalent linker of Formula (L-j) selected from the group consisting of:

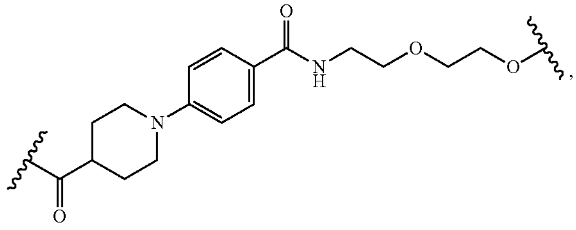

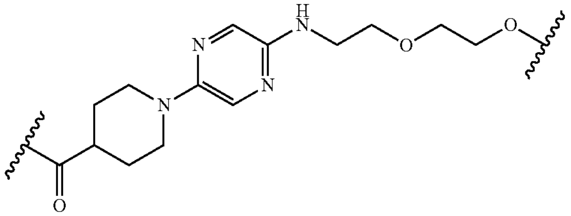

,

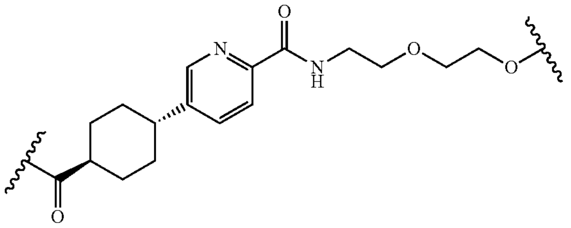

,

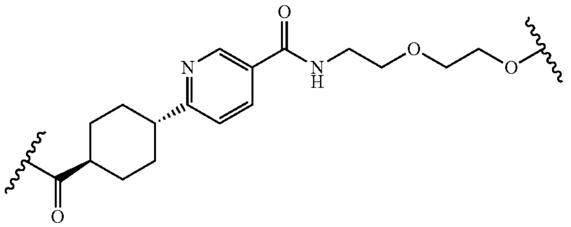

,

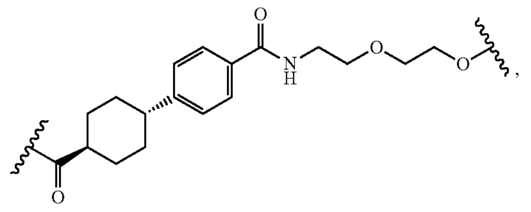

and

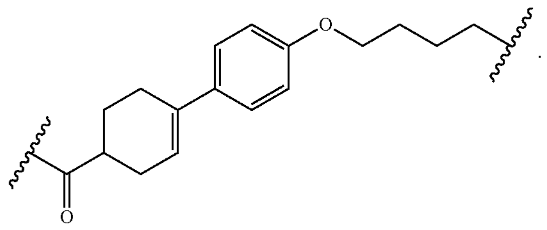

In another embodiment, L is a divalent linker of Formula (L-k):

(L-k)

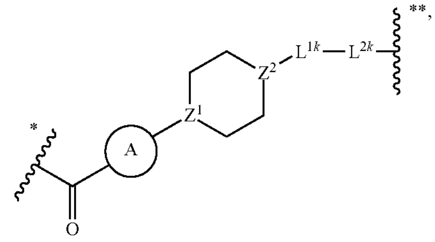

or a stereoisomer thereof, wherein:

Ring A is phenyl or a 5 or 6 membered heteroarylene having 1 or 2 nitrogen ring atoms;

each of $Z^1$ and $Z^2$ is independently CH or N;

$L^{1k}$ is a bond, —C(O)NH— or —NHC(O)—; and $L^{2k}$ is a $C_{3-8}$ straight chain alkylene or

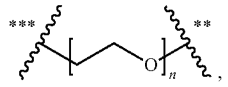

wherein n is 1, 2, or 3, and

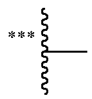

represents a covalent bond to $L^{1k}$;

wherein

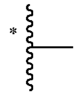

represents a covalent bond to the NH group of Formula (I), and

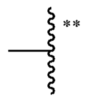

represents a covalent bond to the methylene group of Formula (I).

In another embodiment, L is a divalent linker of Formula (L-k) selected from the group consisting of:

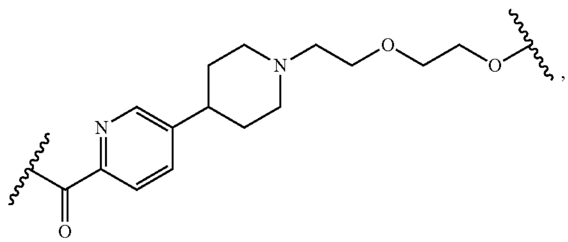

-continued

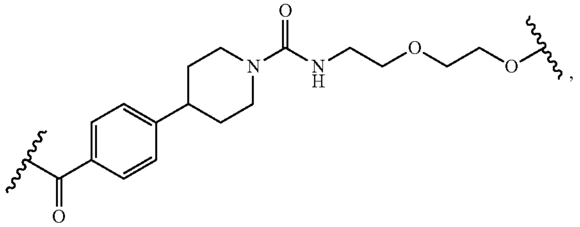

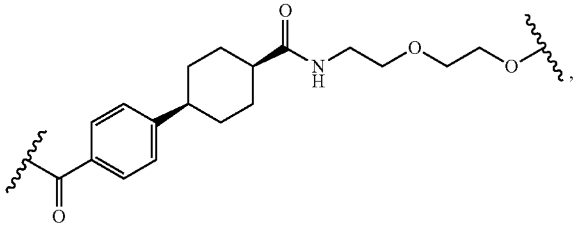

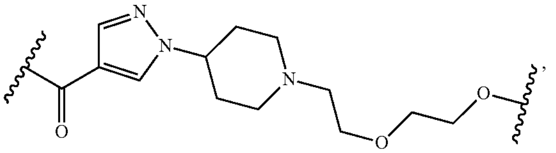

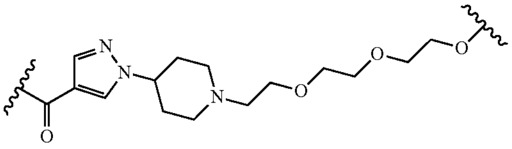
, and

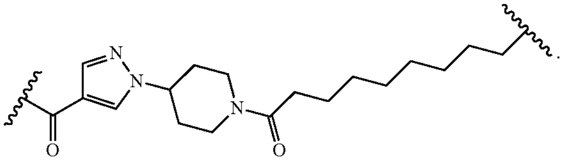

In another embodiment, L is a divalent linker of Formula (L-m):

(L-m)

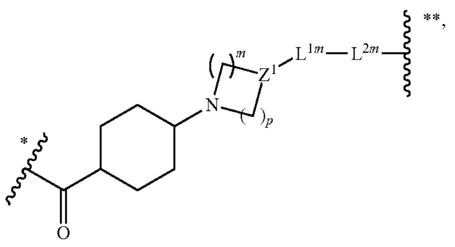

or a stereoisomer thereof, wherein:

$Z^1$ is CH or N;

m is 1 or 2;

p is 1 or 2;

0, 1, or 2 hydrogen atoms of

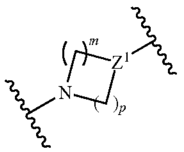

are replaced with F;

$L^{1m}$ is a bond, —C(O)—, —C(O)NH—, —NHC(O)—, —$S(O)_2$NH— or —$NHS(O)_2$—; and $L^{2m}$ is $C_{3-6}$ linear alkylene, $C_{3-6}$ cycloalkylene, or

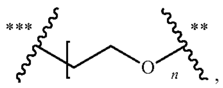

wherein n is 1 or 2, and

represents a covalent bond to $L^{1m}$;

wherein

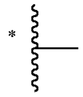

represents a covalent bond to the NH group of Formula (I), and

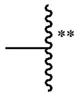

represents a covalent bond to the methylene group of Formula (I).

In another embodiment, L is a divalent linker of Formula (L-m) selected from the group consisting of:

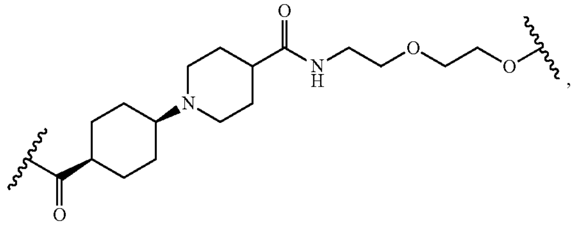

-continued
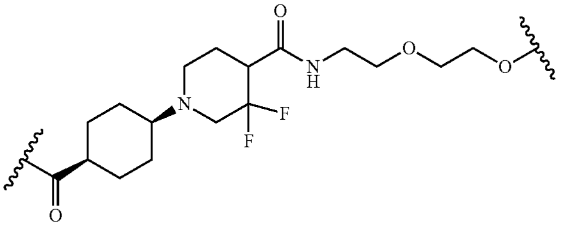
,
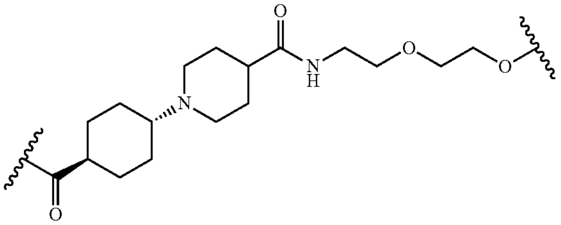
,
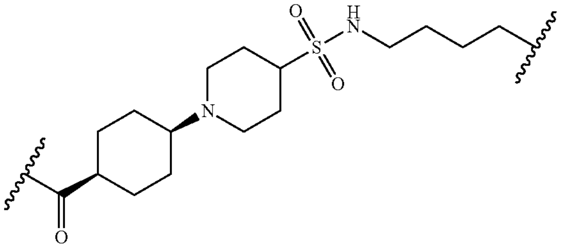
,
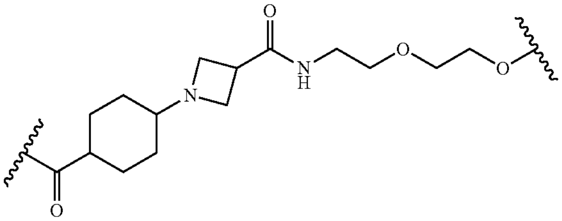
,
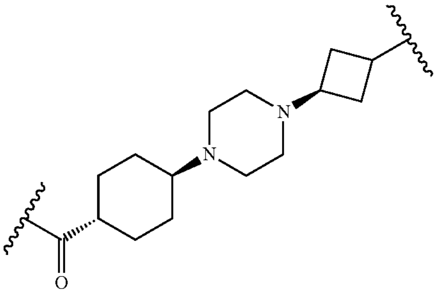
,
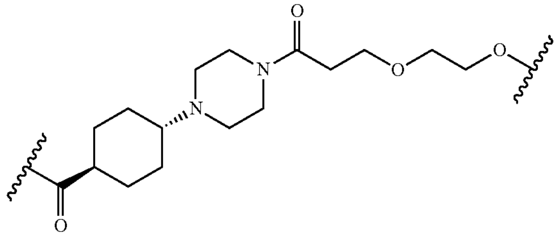
,
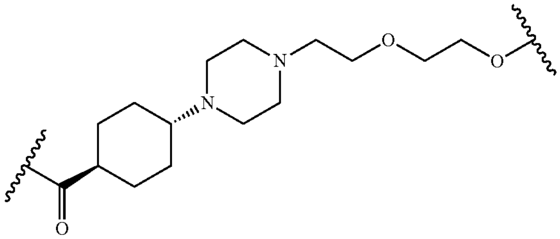
,
-continued
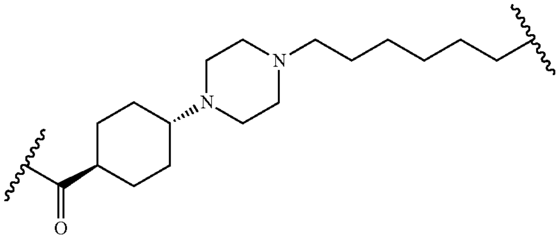
,
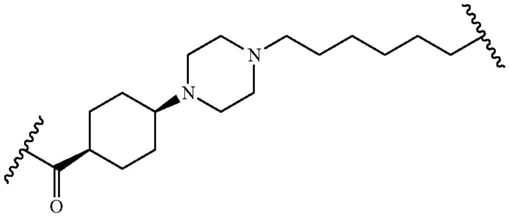
, and
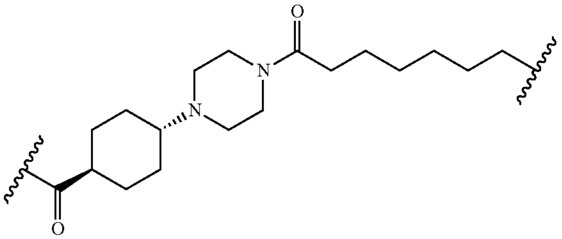
.
In another embodiment, L is a divalent linker of Formula (L-n-i):
(L-n-i)
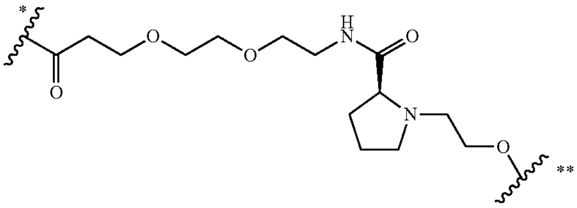
wherein
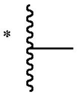
represents a covalent bond to the NH group of Formula (I), and
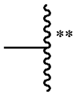
represents a covalent bond to the methylene group of Formula (I).

In another embodiment, L is a divalent linker of Formula (L-n-ii):

(L-n-ii)

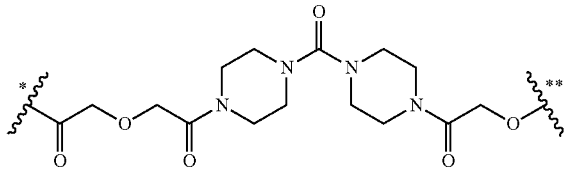

wherein

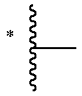

represents a covalent bond to the NH group of Formula (I), and

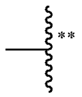

represents a covalent bond to the methylene group of Formula (I).

In another embodiment, L is a divalent linker of Formula (L-n-iii):

(L-n-iii)

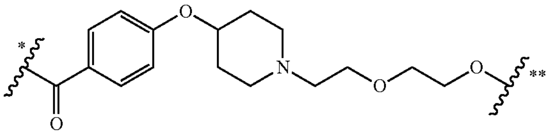

wherein

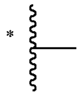

represents a covalent bond to the NH group of Formula (I), and

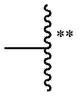

represents a covalent bond to the methylene group of Formula (I).

In another embodiment, L is a divalent linker of Formula (L-n-iv):

(L-n-iv)

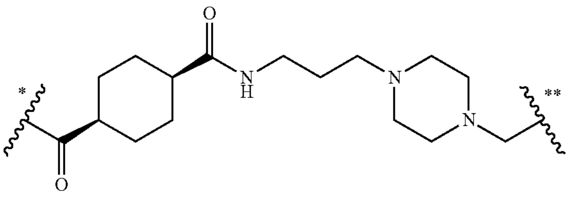

wherein

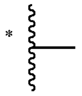

represents a covalent bond to the NH group of Formula (I), and

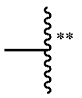

represents a covalent bond to the methylene group of Formula (I).

In another embodiment, $R^1$ is methyl, ethyl, 1-propyl, 2-propyl, 1-butyl, 2-butyl, or t-butyl. In another embodiment, $R^1$ is methyl. In another embodiment, $R^1$ is cyclopropyl, cyclobutyl, cyclopentyl, or cyclohexyl.

In another embodiment, the compound of Formula (I) is selected from a compound as listed in Table 1:

TABLE 1
| Example | Structure |
| --- | --- |
| 1 | 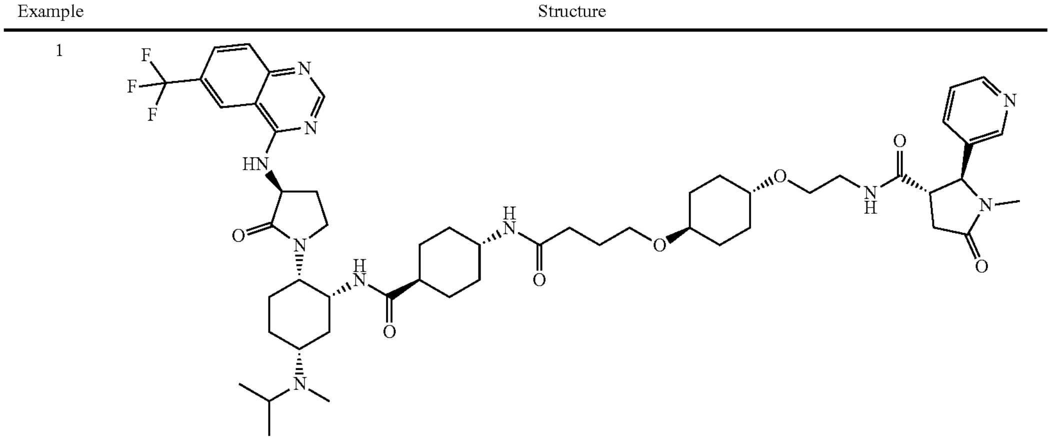 |
| 2 | 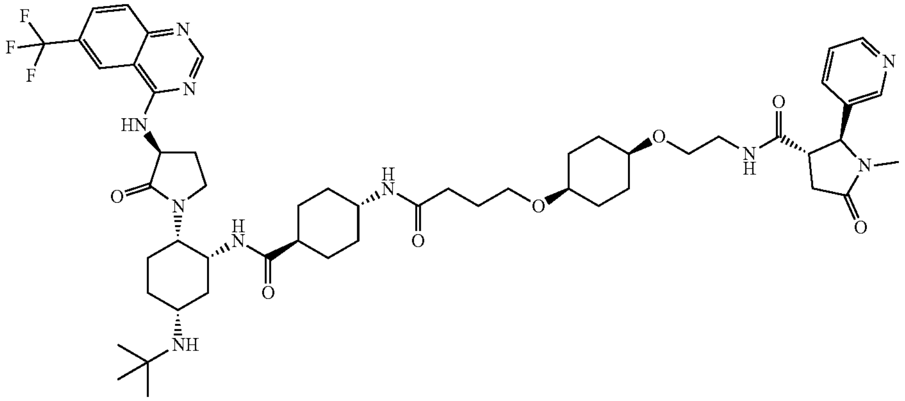 [SMILES: CN1C(=O)C[C@H](C(=O)NCCO[C@H]2CC[C@@H](OCCCC(=O)N[C@H]3CC[C@H](C(=O)N[C@@H]4C[C@H](NC(C)(C)C)CC[C@@H]4N4CC[C@H](Nc5ncnc6ccc(C(F)(F)F)cc56)C4=O)CC3)CC2)[C@H]1c1cccnc1] |
| 3 | 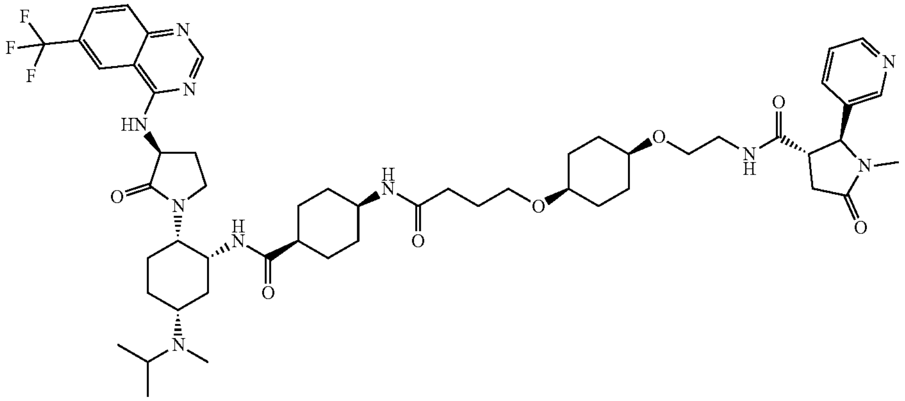 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCO[C@H]3CC[C@@H](OCCNC(=O)[C@H]4CC(=O)N(C)[C@@H]4c4cccnc4)CC3)CC2)C1] |
| 4 | 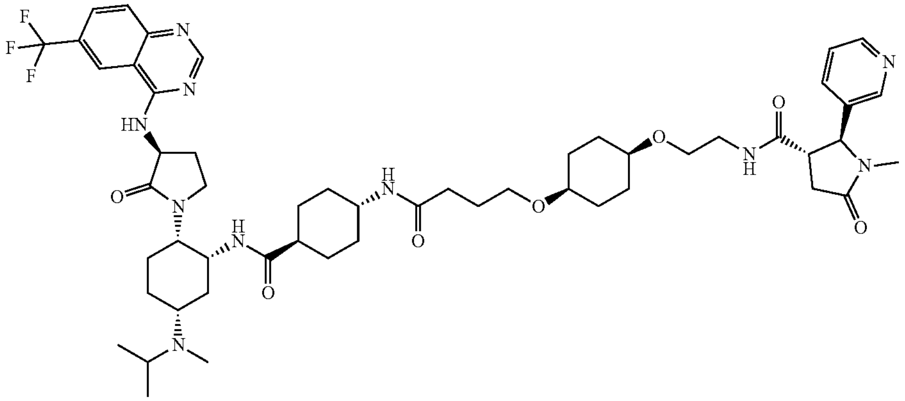 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCO[C@H]3CC[C@@H](OCCNC(=O)[C@H]4CC(=O)N(C)[C@@H]4c4cccnc4)CC3)CC2)C1] |

TABLE 1-continued
| Example | Structure |
| --- | --- |
| 5 | 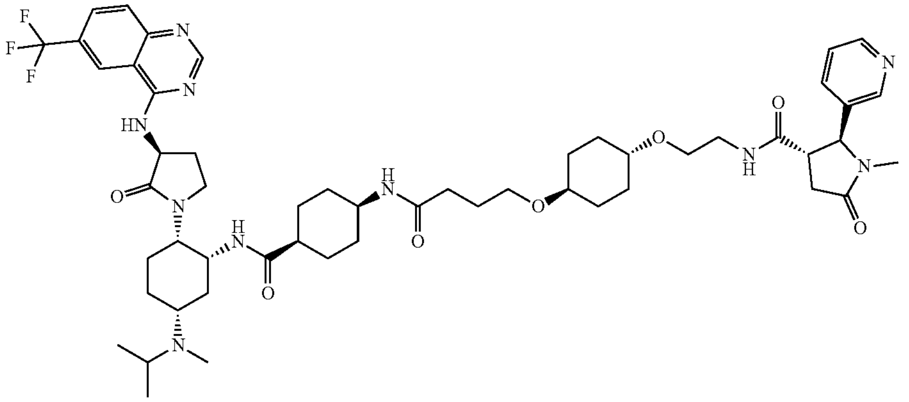 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCO[C@H]3CC[C@H](OCCNC(=O)[C@H]4CC(=O)N(C)[C@@H]4c4cccnc4)CC3)CC2)C1] |
| 6 | 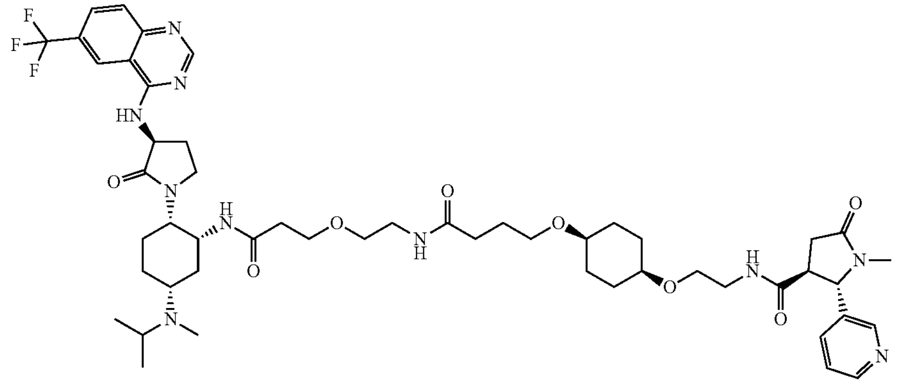 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)CCCO[C@H]2CC[C@@H](OCCNC(=O)[C@H]3CC(=O)N(C)[C@@H]3c3cccnc3)CC2)C1] |
| 7 | 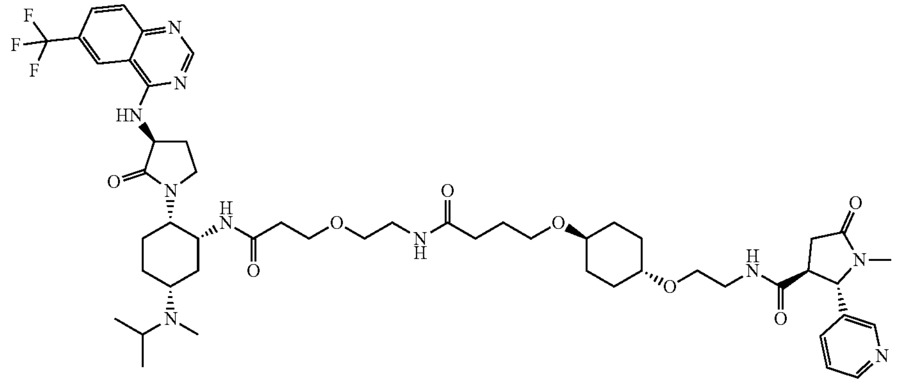 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)CCCO[C@H]2CC[C@H](OCCNC(=O)[C@H]3CC(=O)N(C)[C@@H]3c3cccnc3)CC2)C1] |
| 8 | 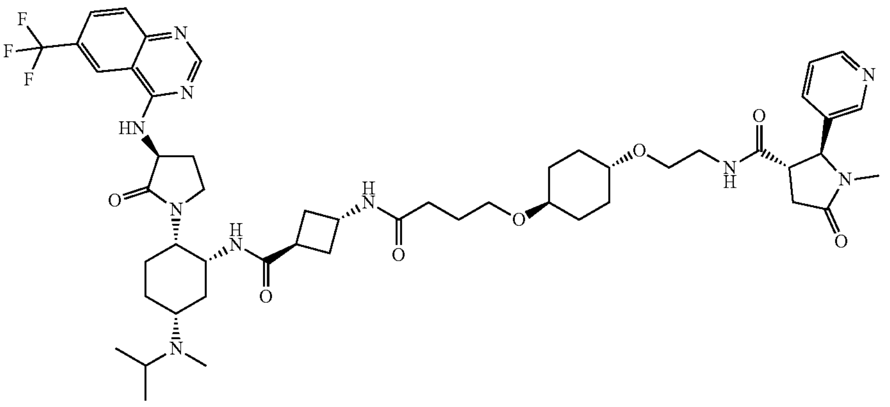 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCCO[C@H]3CC[C@H](OCCNC(=O)[C@H]4CC(=O)N(C)[C@@H]4c4cccnc4)CC3)C2)C1] |

TABLE 1-continued
| Example | Structure |
| --- | --- |
| 9 | 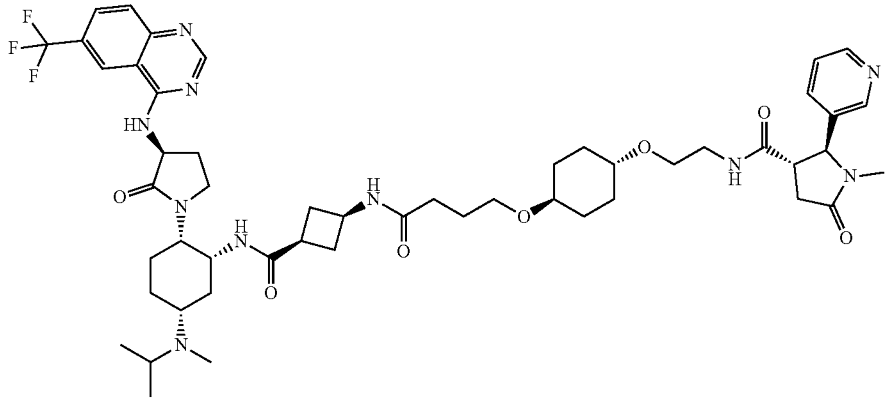 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCCO[C@H]3CC[C@H](OCCNC(=O)[C@H]4CC(=O)N(C)[C@@H]4c4cccnc4)CC3)C2)C1] |
| 10 | 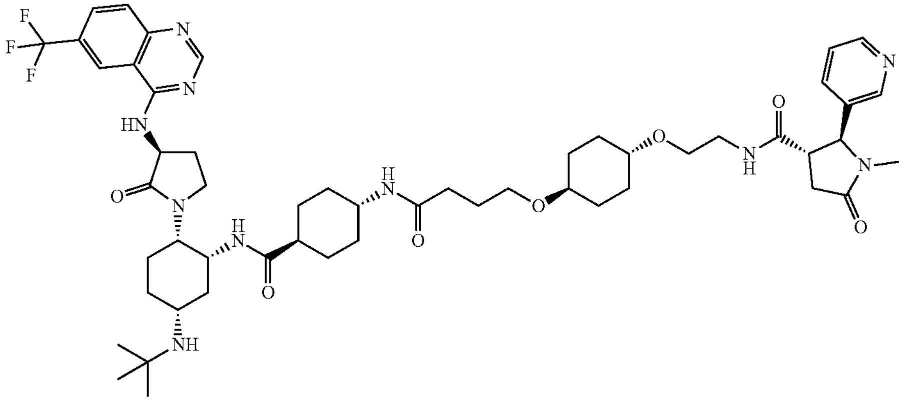 [SMILES: CN1C(=O)C[C@H](C(=O)NCCO[C@H]2CC[C@H](OCCCC(=O)N[C@H]3CC[C@H](C(=O)N[C@@H]4C[C@H](NC(C)(C)C)CC[C@@H]4N4CC[C@H](Nc5ncnc6ccc(C(F)(F)F)cc56)C4=O)CC3)CC2)[C@H]1c1cccnc1] |
| 11 | 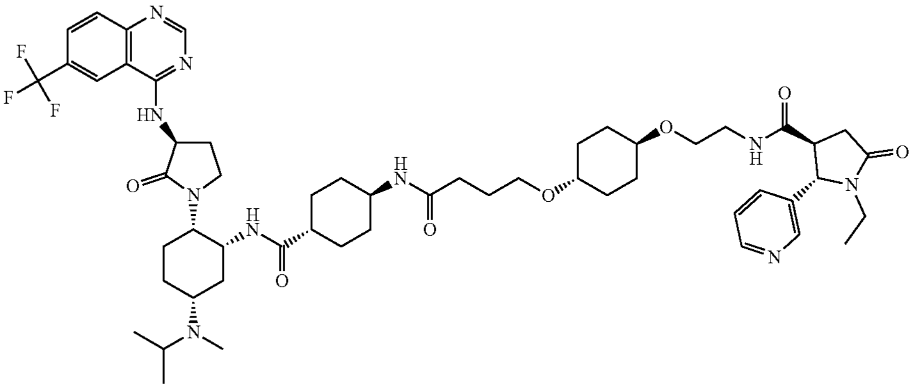 [SMILES: CCN1C(=O)C[C@H](C(=O)NCCO[C@H]2CC[C@H](OCCCC(=O)N[C@H]3CC[C@H](C(=O)N[C@@H]4C[C@H](N(C)C(C)C)CC[C@@H]4N4CC[C@H](Nc5ncnc6ccc(C(F)(F)F)cc56)C4=O)CC3)CC2)[C@H]1c1cccnc1] |

TABLE 1-continued
| Example | Structure |
|---|---|
| 12 | 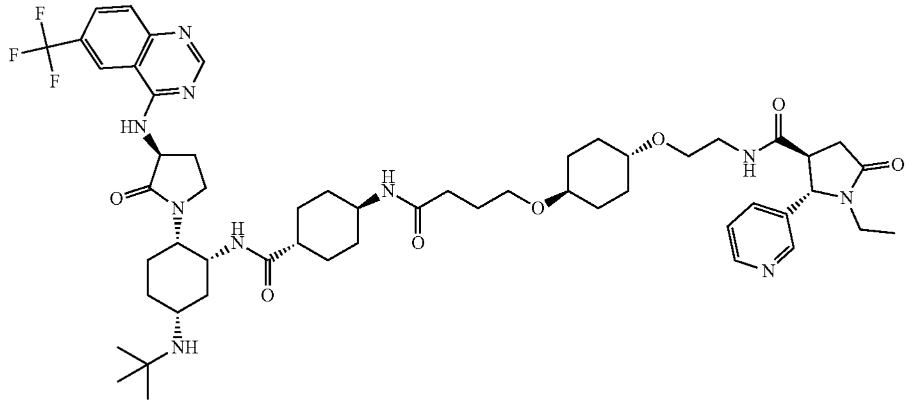 [SMILES: CCN1C(=O)C[C@H](C(=O)NCCO[C@H]2CC[C@H](OCCCC(=O)N[C@H]3CC[C@H](C(=O)N[C@@H]4C[C@H](NC(C)(C)C)CC[C@@H]4N4CC[C@H](Nc5ncnc6ccc(C(F)(F)F)cc56)C4=O)CC3)CC2)[C@H]1c1cccnc1] |
| 13 | 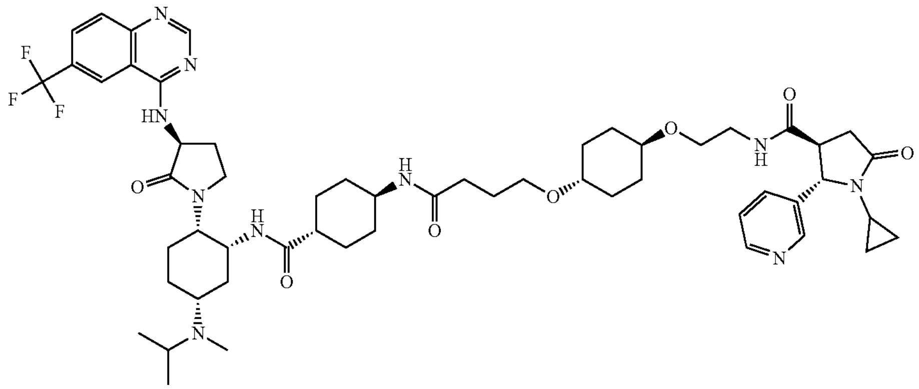 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCO[C@H]3CC[C@H](OCCNC(=O)[C@H]4CC(=O)N(C5CC5)[C@@H]4c4cccnc4)CC3)CC2)C1] |
| 14 | 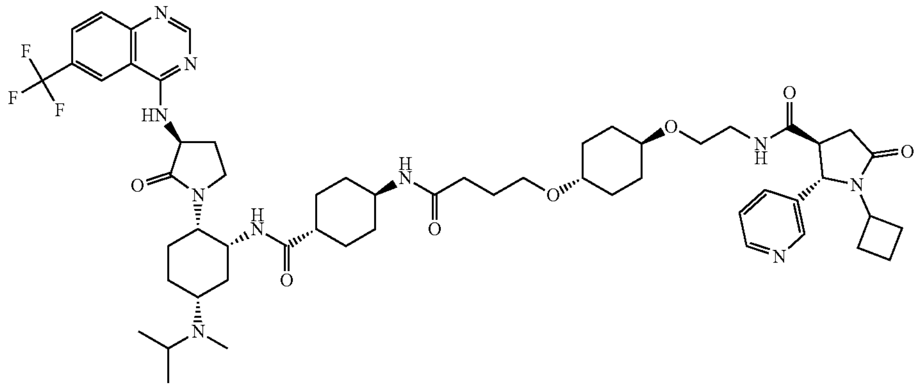 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCO[C@H]3CC[C@H](OCCNC(=O)[C@H]4CC(=O)N(C5CCC5)[C@@H]4c4cccnc4)CC3)CC2)C1] |
| 15 | 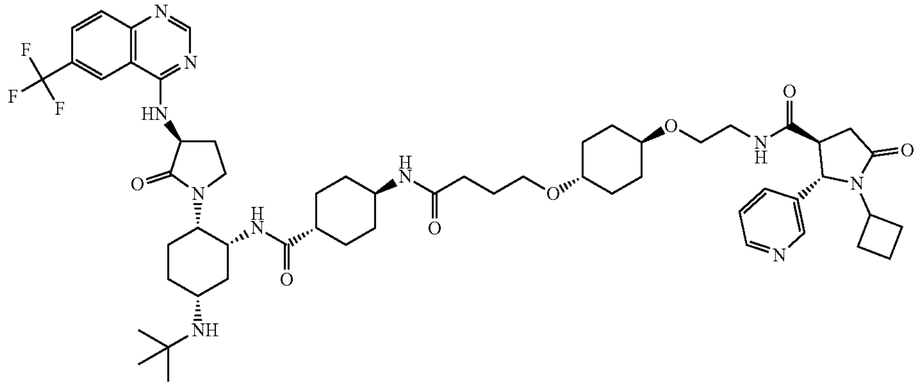 [SMILES: CC(C)(C)N[C@@H]1CC[C@H](N2CC[C@H](Nc3ncnc4ccc(C(F)(F)F)cc34)C2=O)[C@H](NC(=O)[C@H]2CC[C@H](NC(=O)CCCO[C@H]3CC[C@H](OCCNC(=O)[C@H]4CC(=O)N(C5CCC5)[C@@H]4c4cccnc4)CC3)CC2)C1] |

TABLE 1-continued
| Example | Structure |
| --- | --- |
| 15a | 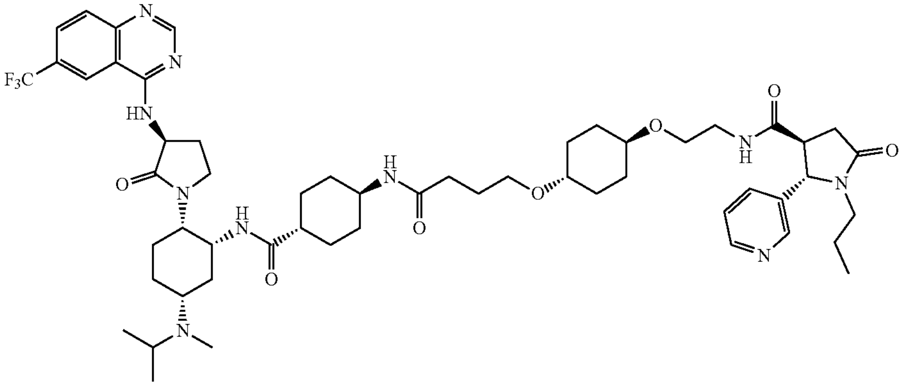 [SMILES: CCCN1C(=O)C[C@H](C(=O)NCCO[C@H]2CC[C@H](OCCCC(=O)N[C@H]3CC[C@H](C(=O)N[C@@H]4C[C@H](N(C)C(C)C)CC[C@@H]4N4CC[C@H](Nc5ncnc6ccc(C(F)(F)F)cc56)C4=O)CC3)CC2)[C@H]1c1cccnc1] |
| 16 | 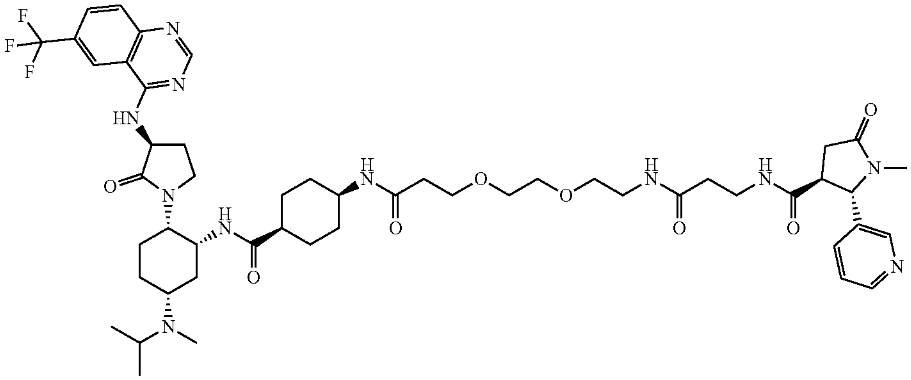 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCNC(=O)CCNC(=O)[C@H]3CC(=O)N(C)[C@@H]3c3cccnc3)CC2)C1] |
| 17 | 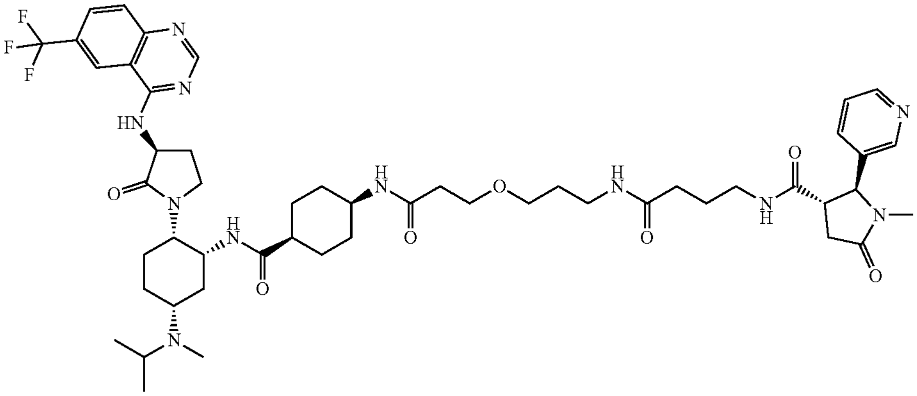 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCCNC(=O)CCCNC(=O)[C@H]3CC(=O)N(C)[C@@H]3c3cccnc3)CC2)C1] |
| 18 | 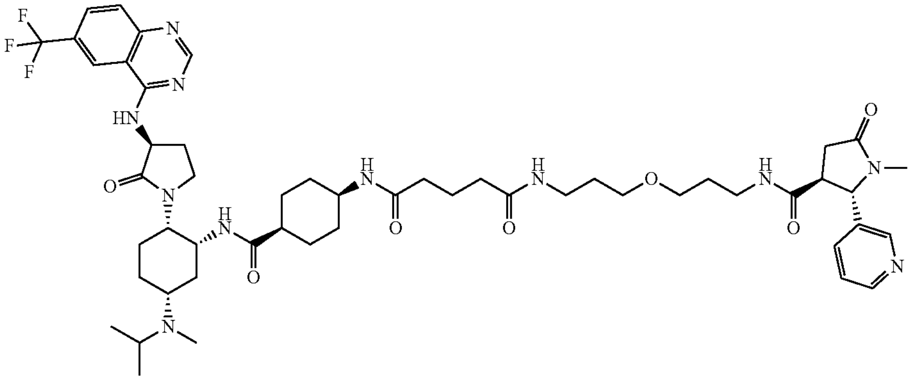 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCC(=O)NCCCOCCCNC(=O)[C@H]3CC(=O)N(C)[C@@H]3c3cccnc3)CC2)C1] |

TABLE 1-continued
| Example | Structure |
| --- | --- |
| 19 | 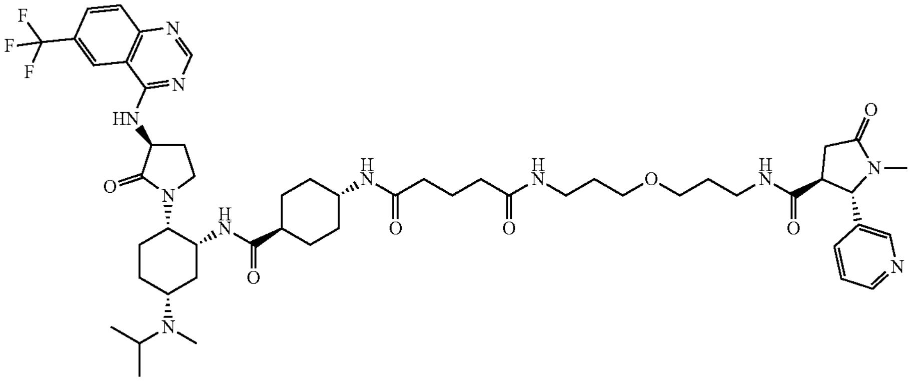 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCC(=O)NCCCOCCCNC(=O)[C@H]3CC(=O)N(C)[C@@H]3c3cccnc3)CC2)C1] |
| 20 | 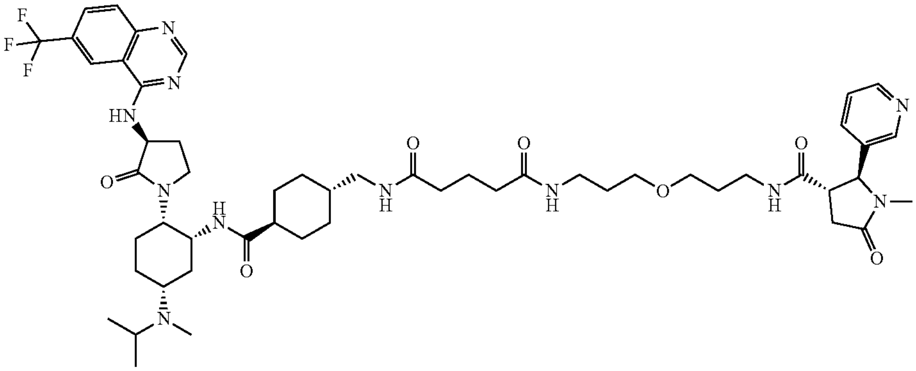 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](CNC(=O)CCCC(=O)NCCCOCCCNC(=O)[C@H]3CC(=O)N(C)[C@@H]3c3cccnc3)CC2)C1] |
| 21 | 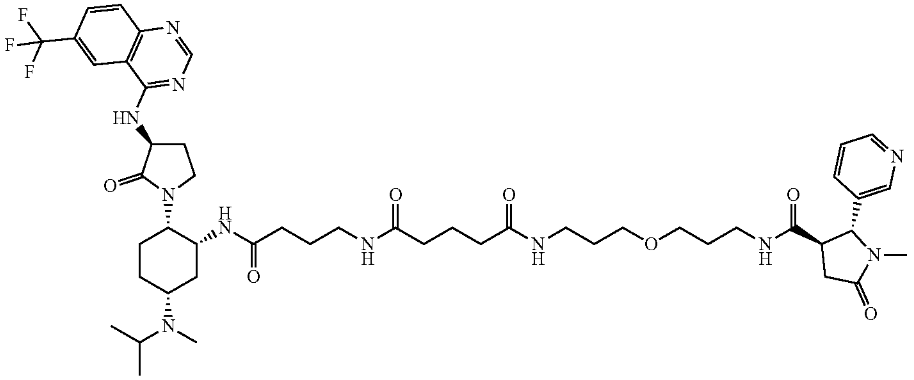 [SMILES: CC(C)N(C)[C@@H]1CC[C@H](N2CC[C@H](Nc3ncnc4ccc(C(F)(F)F)cc34)C2=O)[C@H](NC(=O)CCCNC(=O)CCCC(=O)NCCCOCCCNC(=O)[C@@H]2CC(=O)N(C)[C@H]2c2cccnc2)C1] |
| 22 | 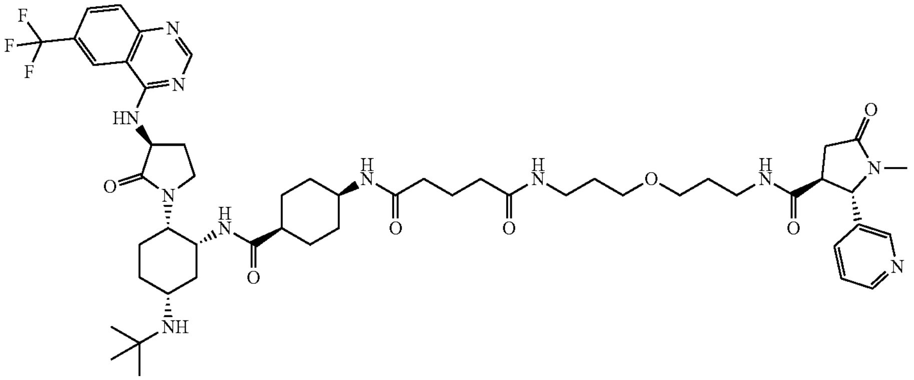 [SMILES: CN1C(=O)C[C@H](C(=O)NCCCOCCCNC(=O)CCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] |

TABLE 1-continued
| Example | Structure |
| --- | --- |
| 23 | 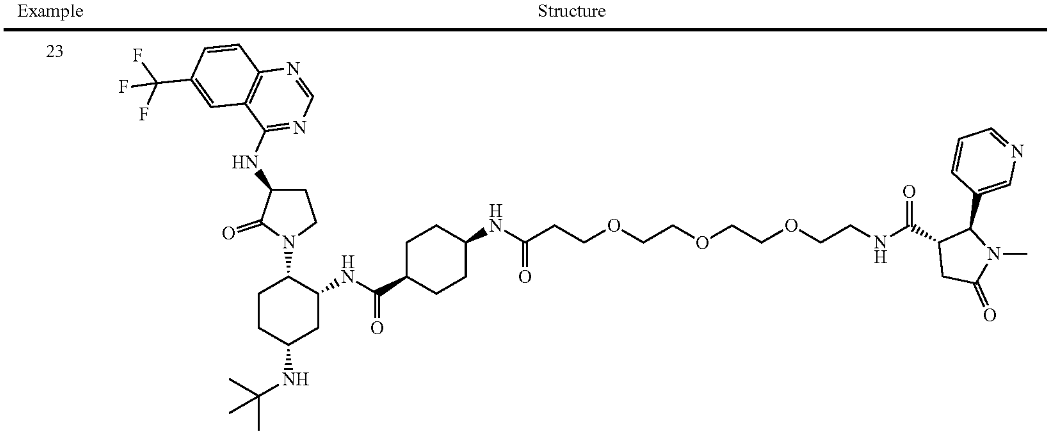 |
| 24 | 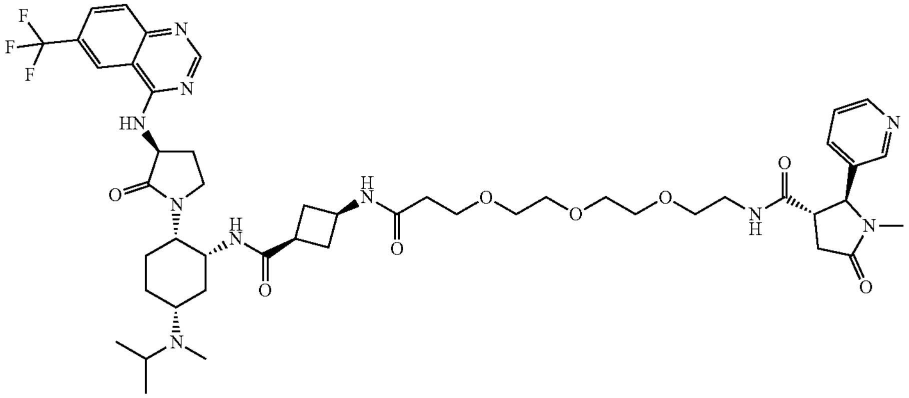 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCOCCOCCNC(=O)[C@H]3CC(=O)N(C)[C@@H]3c3cccnc3)C2)C1] |
| 25 | 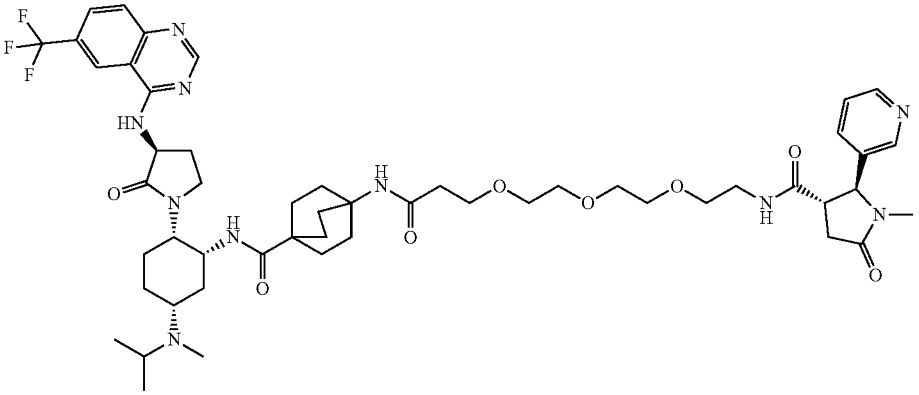 [SMILES: CC(C)N(C)[C@@H]1CC[C@H](N2CC[C@H](Nc3ncnc4ccc(C(F)(F)F)cc34)C2=O)[C@H](NC(=O)C23CCC(NC(=O)CCOCCOCCOCCNC(=O)[C@H]4CC(=O)N(C)[C@@H]4c4cccnc4)(CC2)CC3)C1] |
| 26 | 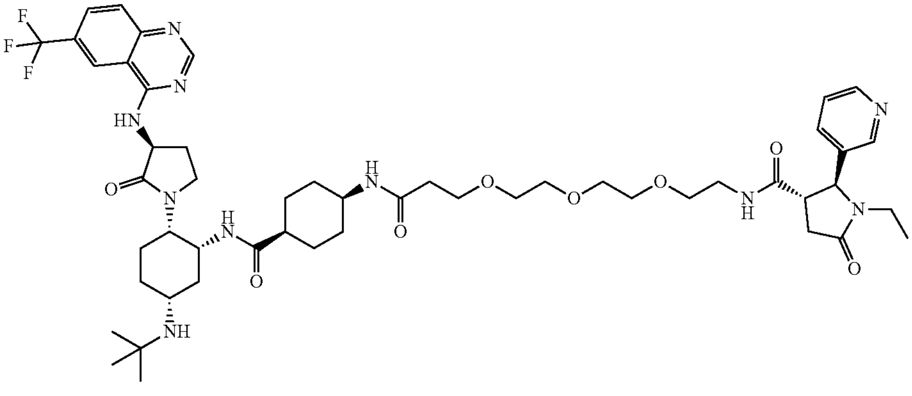 [SMILES: CCN1C(=O)C[C@H](C(=O)NCCOCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] |

TABLE 1-continued
| Example | Structure |
|---|---|
| 27 | 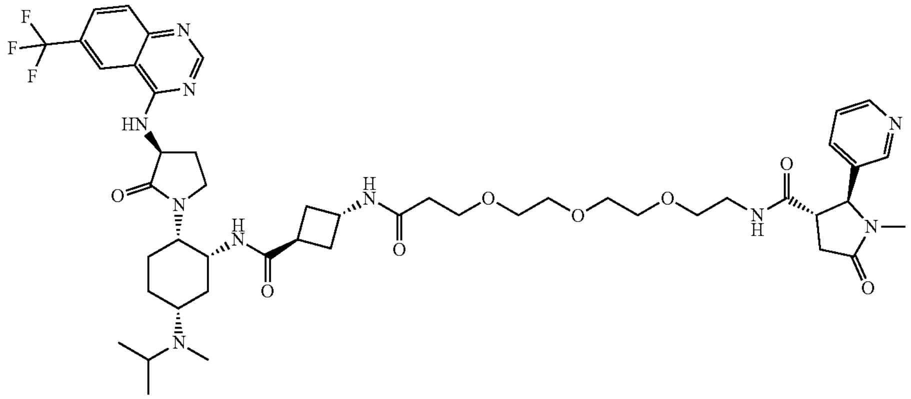 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCOCCOCCOCCNC(=O)[C@H]3CC(=O)N(C)[C@@H]3c3cccnc3)C2)C1] |
| 28 | 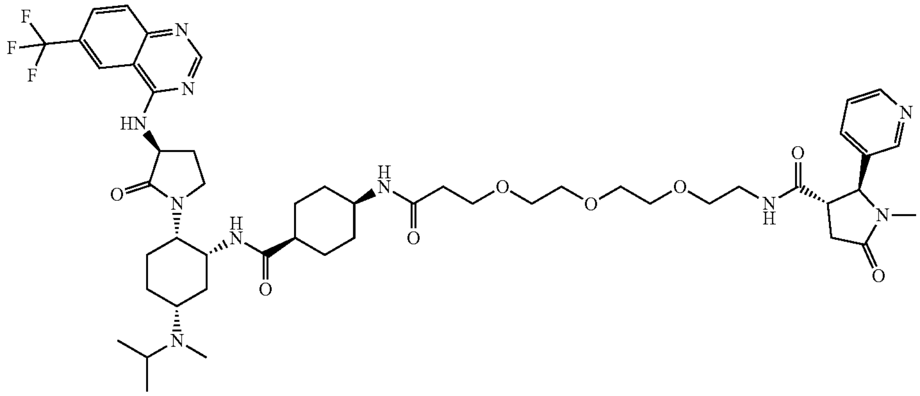 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCOCCNC(=O)[C@H]3CC(=O)N(C)[C@@H]3c3cccnc3)CC2)C1] |
| 29 | 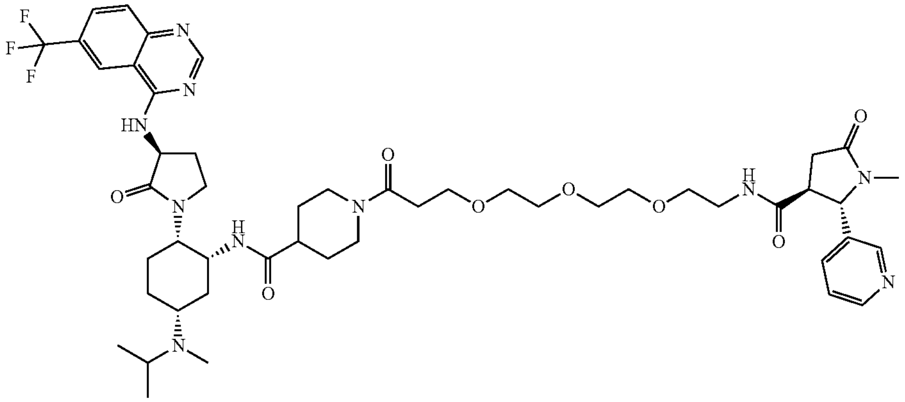 [SMILES: CC(C)N(C)[C@@H]1CC[C@H](N2CC[C@H](Nc3ncnc4ccc(C(F)(F)F)cc34)C2=O)[C@H](NC(=O)C2CCN(C(=O)CCOCCOCCOCCNC(=O)[C@H]3CC(=O)N(C)[C@@H]3c3cccnc3)CC2)C1] |
| 30 | 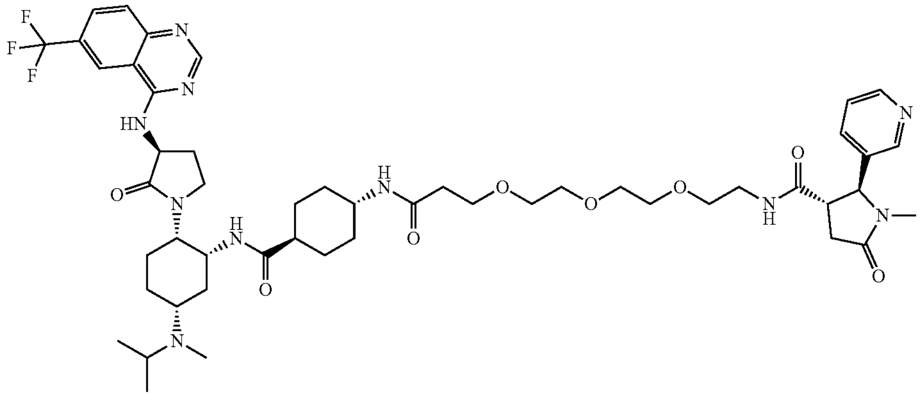 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCOCCOCCOCCNC(=O)[C@H]3CC(=O)N(C)[C@@H]3c3cccnc3)CC2)C1] |

TABLE 1-continued
| Example | Structure |
|---|---|
| 31 | 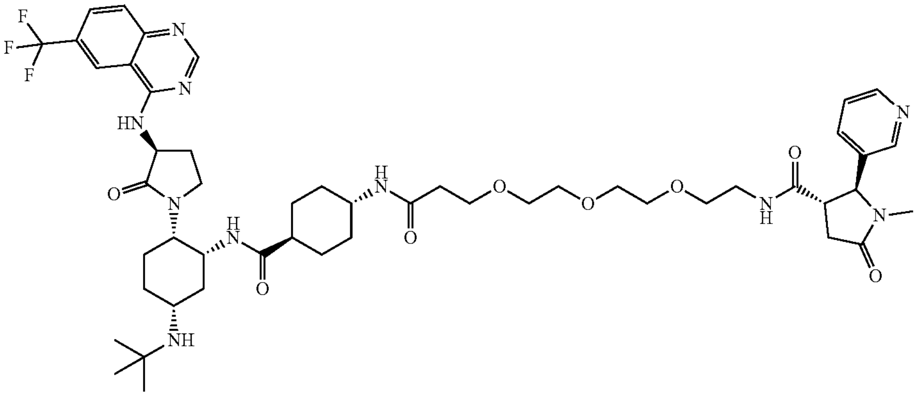 [SMILES: CN1C(=O)C[C@H](C(=O)NCCOCCOCCOCCC(=O)N[C@H]2CC[C@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] |
| 32 | 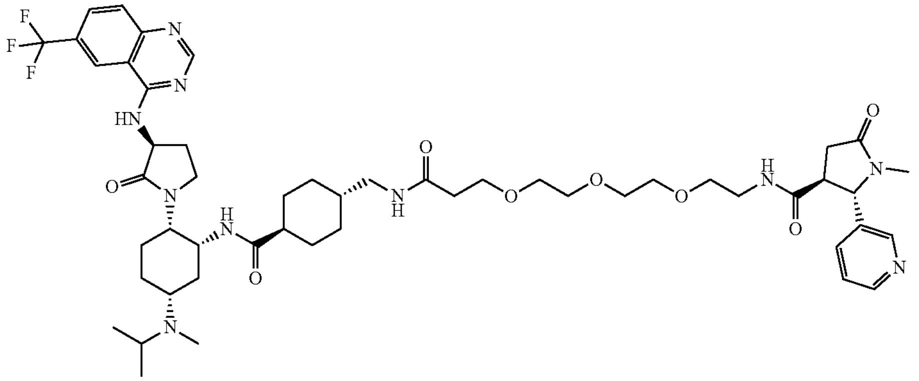 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](CNC(=O)CCOCCOCCOCCNC(=O)[C@H]3CC(=O)N(C)[C@@H]3c3cccnc3)CC2)C1] |
| 33 | 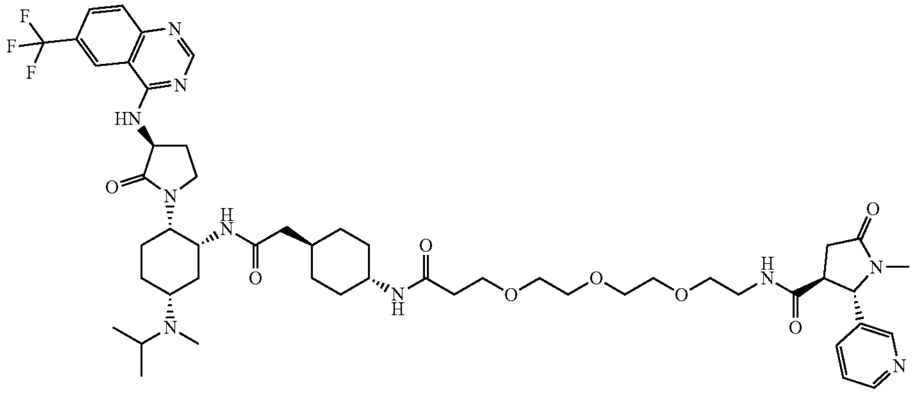 [SMILES: CC(C)N(C)[C@@H]1CC[C@H](N2CC[C@H](Nc3ncnc4ccc(C(F)(F)F)cc34)C2=O)[C@H](NC(=O)C[C@H]2CC[C@H](NC(=O)CCOCCOCCOCCNC(=O)[C@H]3CC(=O)N(C)[C@@H]3c3cccnc3)CC2)C1] |
| 34 | 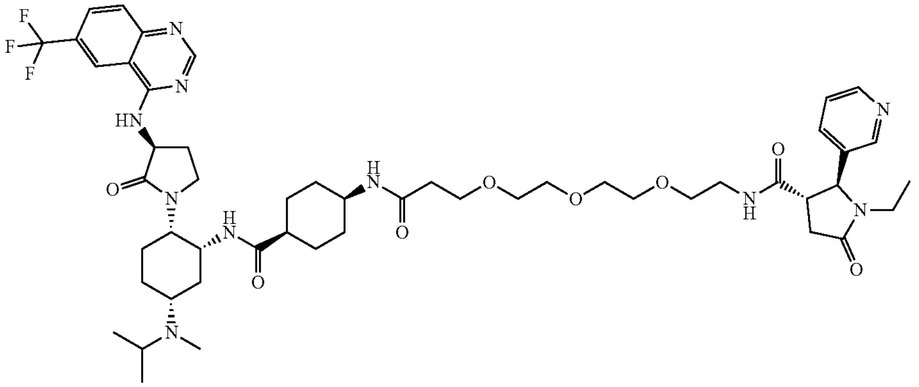 [SMILES: CCN1C(=O)C[C@H](C(=O)NCCOCCOCCOCCC(=O)N[C@H]2CC[C@@H](C(=O)N[C@@H]3C[C@H](N(C)C(C)C)CC[C@@H]3N3CC[C@H](Nc4ncnc5ccc(C(F)(F)F)cc45)C3=O)CC2)[C@H]1c1cccnc1] |

TABLE 1-continued
| Example | Structure |
|---|---|
| 35 | 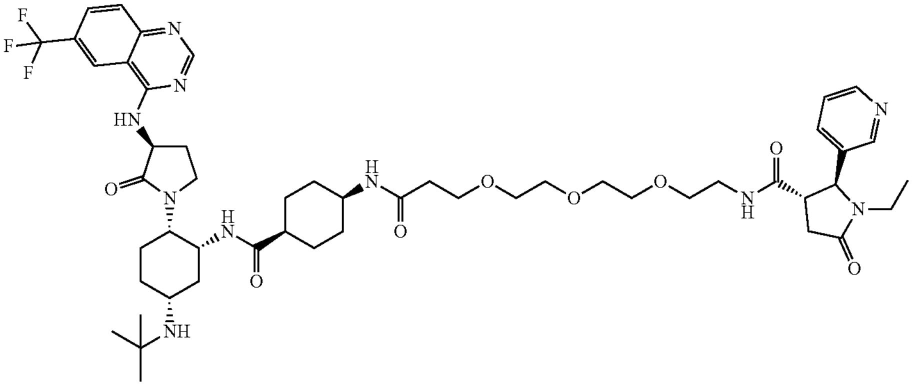 [SMILES: CCN1C(=O)C[C@H](C(=O)NCCOCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] |
| 36 | 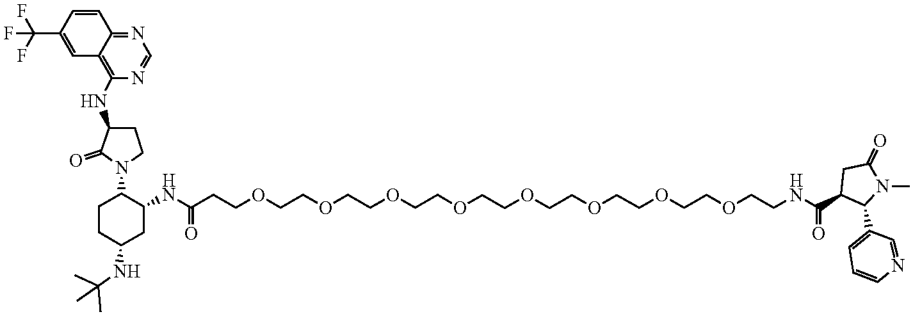 |
| 37 | 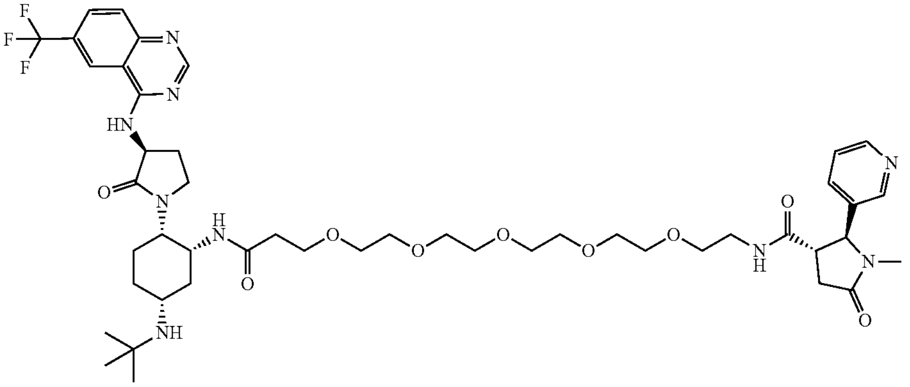 [SMILES: CN1C(=O)C[C@H](C(=O)NCCOCCOCCOCCOCCOCCC(=O)N[C@@H]2C[C@H](NC(C)(C)C)CC[C@@H]2N2CC[C@H](Nc3ncnc4ccc(C(F)(F)F)cc34)C2=O)[C@H]1c1cccnc1] |
| 38 | 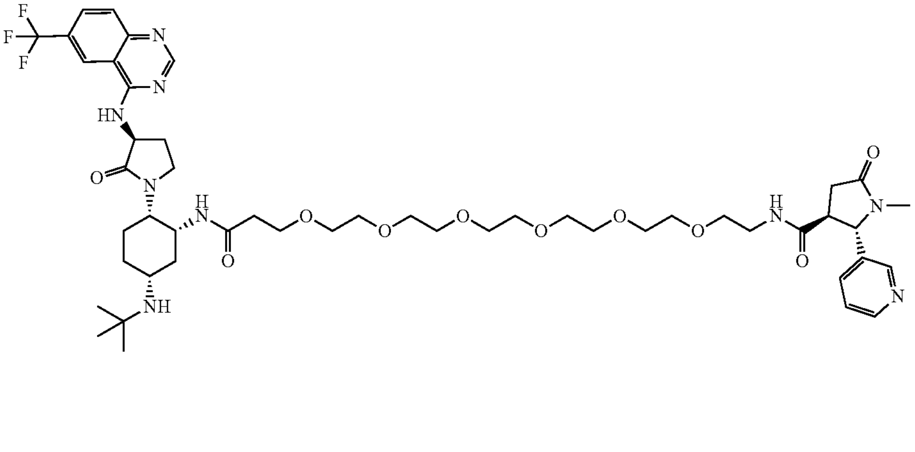 [SMILES: CN1C(=O)C[C@H](C(=O)NCCOCCOCCOCCOCCOCCOCCC(=O)N[C@@H]2C[C@H](NC(C)(C)C)CC[C@@H]2N2CC[C@H](Nc3ncnc4ccc(C(F)(F)F)cc34)C2=O)[C@H]1c1cccnc1] |

TABLE 1-continued
| Example | Structure |
|---|---|
| 39 | 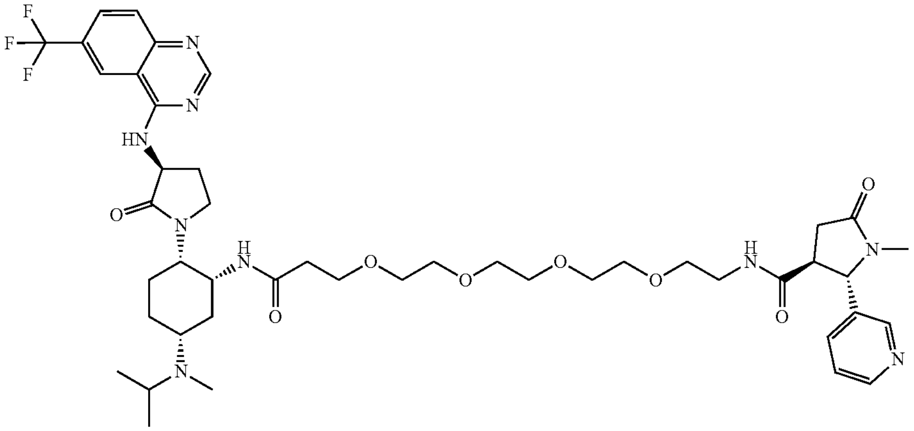 [SMILES: CC(C)N(C)[C@@H]1CC[C@H](N2CC[C@H](Nc3ncnc4ccc(C(F)(F)F)cc34)C2=O)[C@H](NC(=O)CCOCCOCCOCCOCCNC(=O)[C@H]2CC(=O)N(C)[C@@H]2c2cccnc2)C1] |
| 40 | 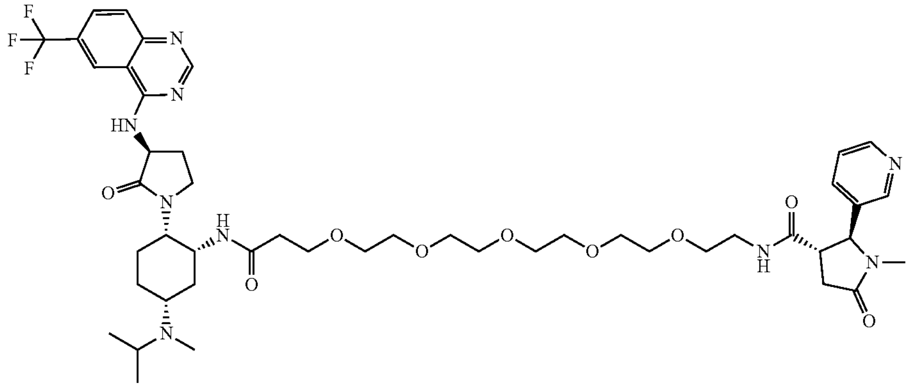 [SMILES: CC(C)N(C)[C@@H]1CC[C@H](N2CC[C@H](Nc3ncnc4ccc(C(F)(F)F)cc34)C2=O)[C@H](NC(=O)CCOCCOCCOCCOCCOCCNC(=O)[C@H]2CC(=O)N(C)[C@@H]2c2cccnc2)C1] |
| 41 | 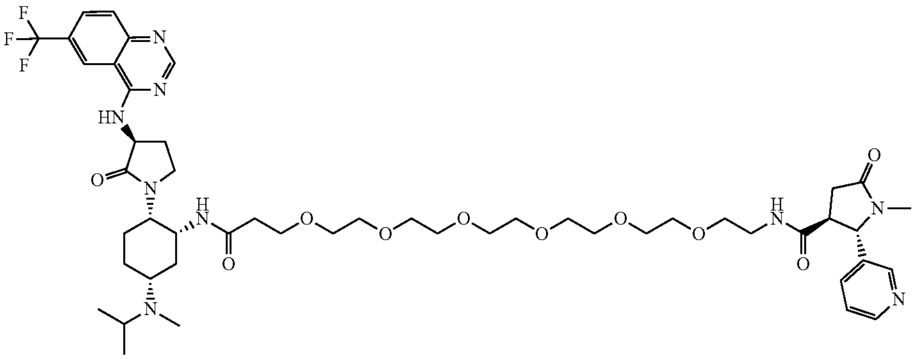 [SMILES: CC(C)N(C)[C@@H]1CC[C@H](N2CC[C@H](Nc3ncnc4ccc(C(F)(F)F)cc34)C2=O)[C@H](NC(=O)CCOCCOCCOCCOCCOCCOCCNC(=O)[C@H]2CC(=O)N(C)[C@@H]2c2cccnc2)C1] |
| 42 | 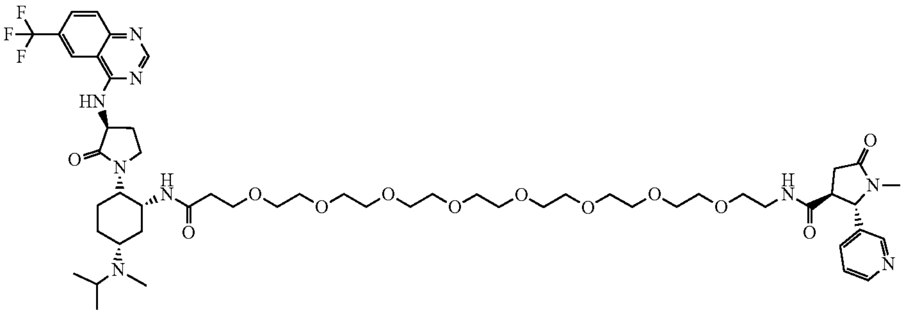 |

TABLE 1-continued
| Example | Structure |
|---|---|
| 43 | 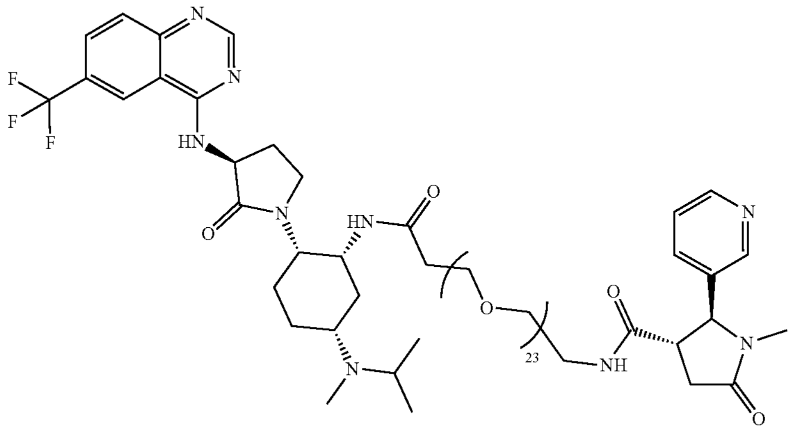 |
| 44 | 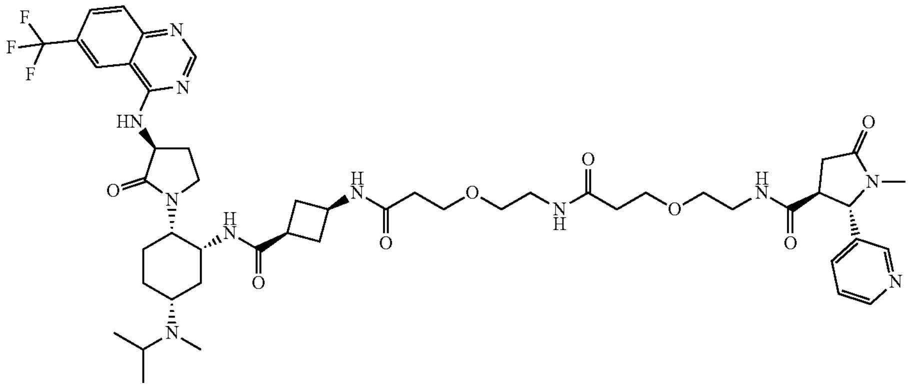 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCNC(=O)CCOCCNC(=O)[C@H]3CC(=O)N(C)[C@@H]3c3cccnc3)C2)C1] |
| 45 | 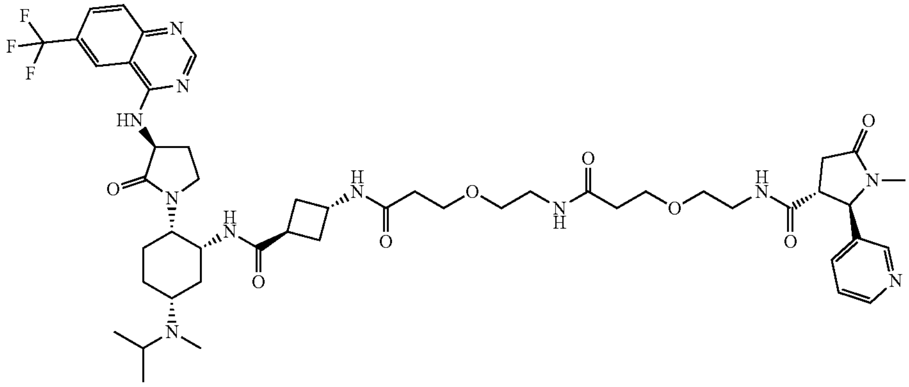 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCOCCNC(=O)CCOCCNC(=O)[C@@H]3CC(=O)N(C)[C@H]3c3cccnc3)C2)C1] |
| 46 | 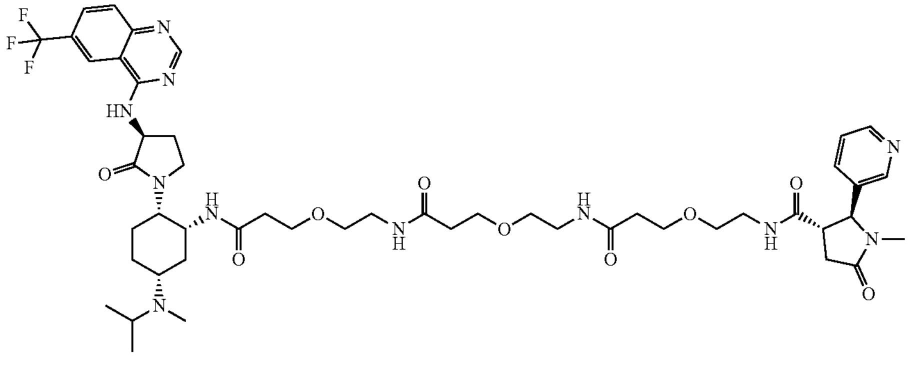 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)CCOCCNC(=O)CCOCCNC(=O)[C@H]2CC(=O)N(C)[C@@H]2c2cccnc2)C1] |

TABLE 1-continued
| Example | Structure |
| --- | --- |
| 47 | 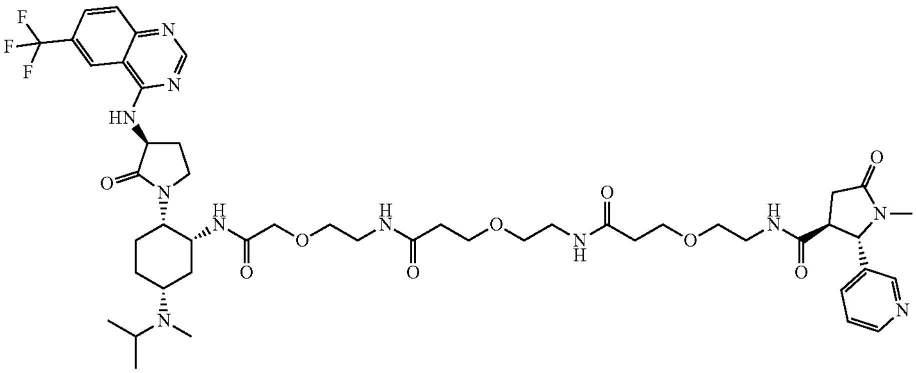 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCOCCNC(=O)CCOCCNC(=O)[C@H]2CC(=O)N(C)[C@@H]2c2cccnc2)C1] |
| 48 | 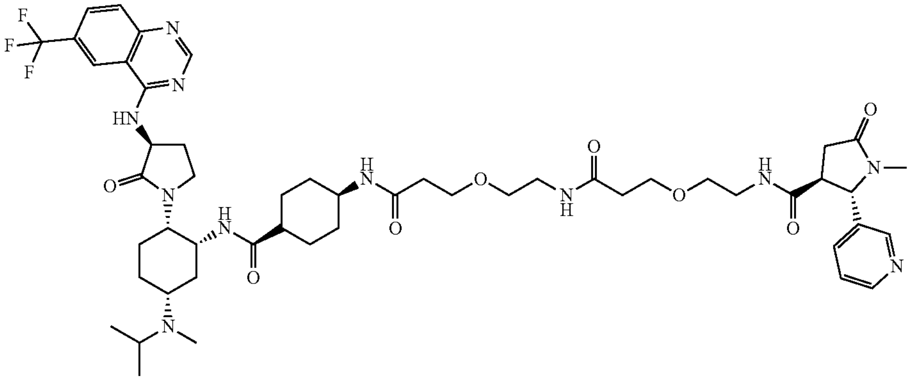 |
| 49 | 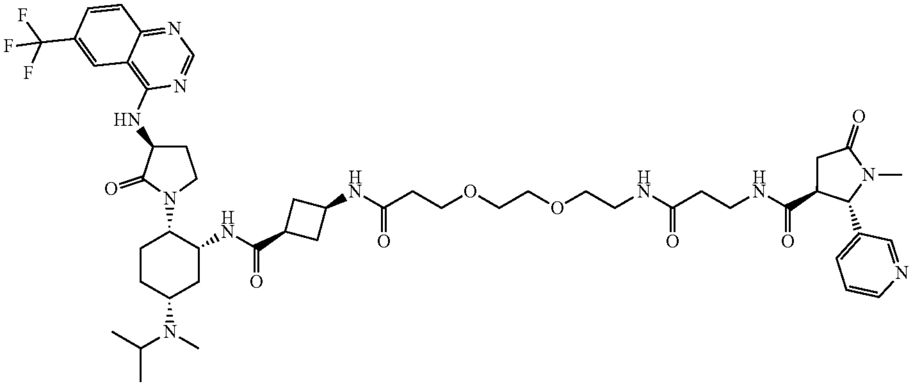 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCOCCNC(=O)CCNC(=O)[C@H]3CC(=O)N(C)[C@@H]3c3cccnc3)C2)C1] |
| 50 | 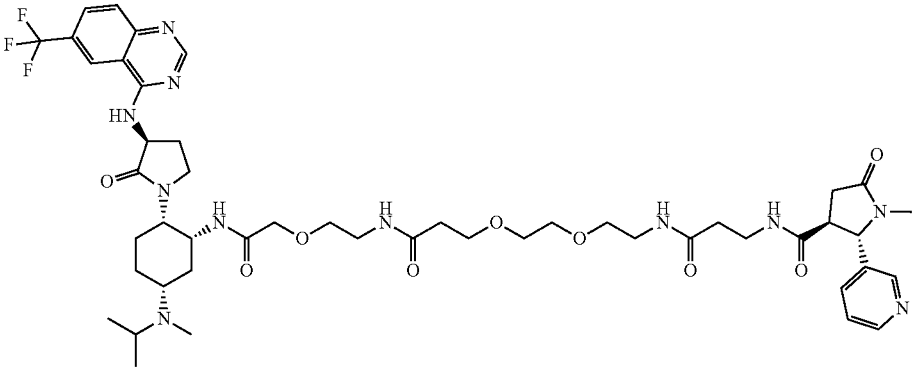 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCOCCOCCNC(=O)CCNC(=O)[C@H]2CC(=O)N(C)[C@@H]2c2cccnc2)C1] |

TABLE 1-continued
| Example | Structure |
| --- | --- |
| 51 | 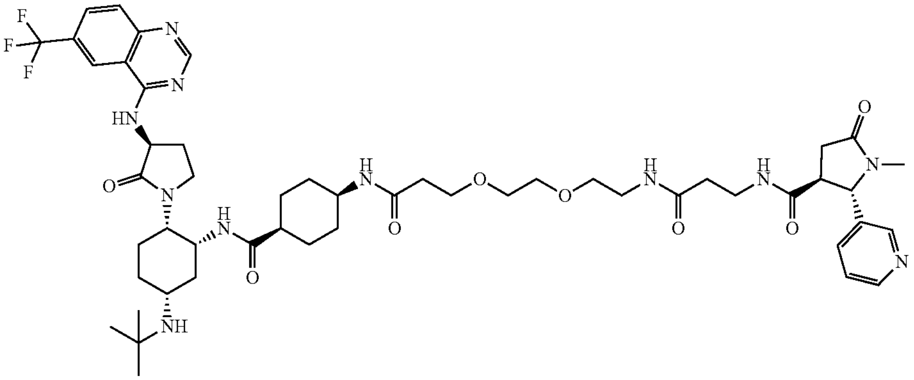 [SMILES: CN1C(=O)C[C@H](C(=O)NCCC(=O)NCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] |
| 52 | 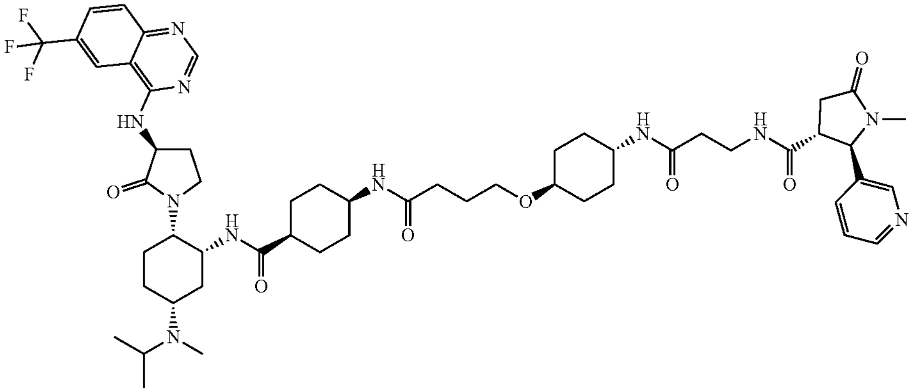 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCO[C@H]3CC[C@H](NC(=O)CCNC(=O)[C@@H]4CC(=O)N(C)[C@H]4c4cccnc4)CC3)CC2)C1] |
| 53 | 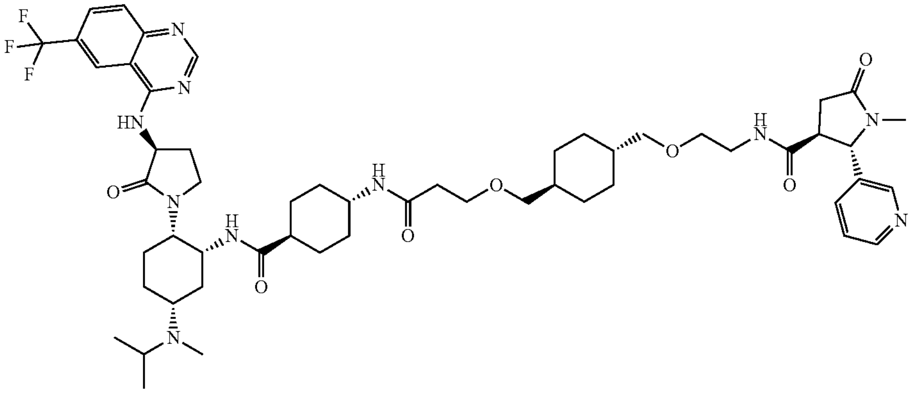 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCOC[C@H]3CC[C@H](COCCNC(=O)[C@H]4CC(=O)N(C)[C@@H]4c4cccnc4)CC3)CC2)C1] |
| 54 | 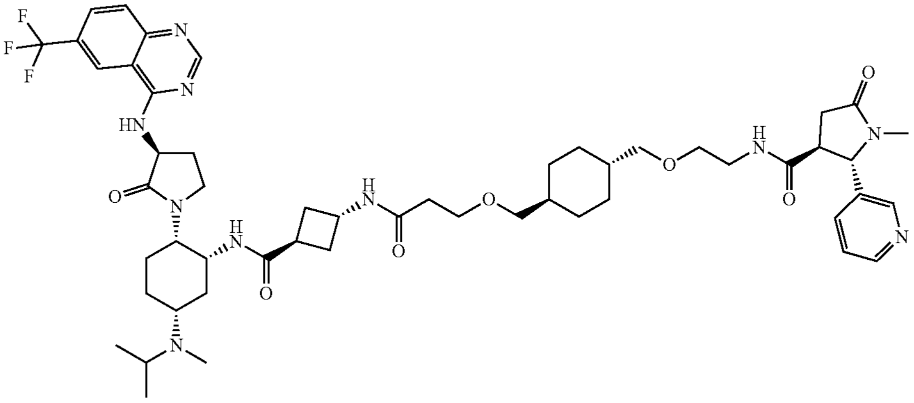 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCOC[C@H]3CC[C@H](COCCNC(=O)[C@H]4CC(=O)N(C)[C@@H]4c4cccnc4)CC3)C2)C1] |

TABLE 1-continued
| Example | Structure |
|---|---|
| 55 | 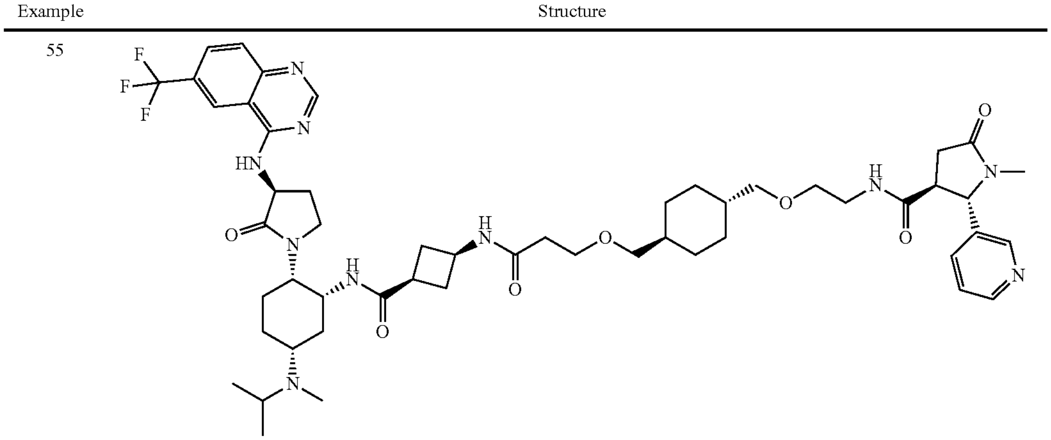 |
| 56 | 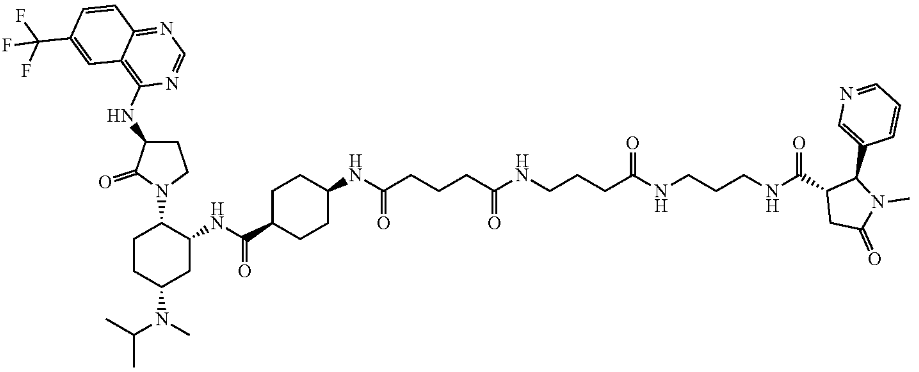 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCC(=O)NCCCC(=O)NCCCNC(=O)[C@H]3CC(=O)N(C)[C@@H]3c3cccnc3)CC2)C1] |
| 57 | 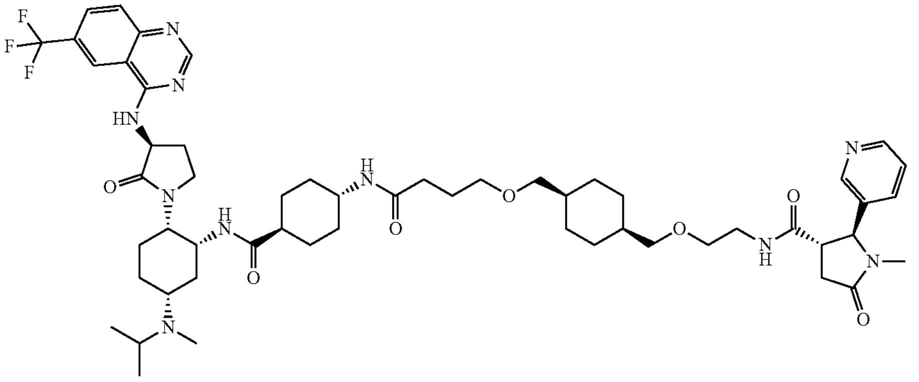 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCOC[C@H]3CC[C@@H](COCCNC(=O)[C@H]4CC(=O)N(C)[C@@H]4c4cccnc4)CC3)CC2)C1] |
| 58 | 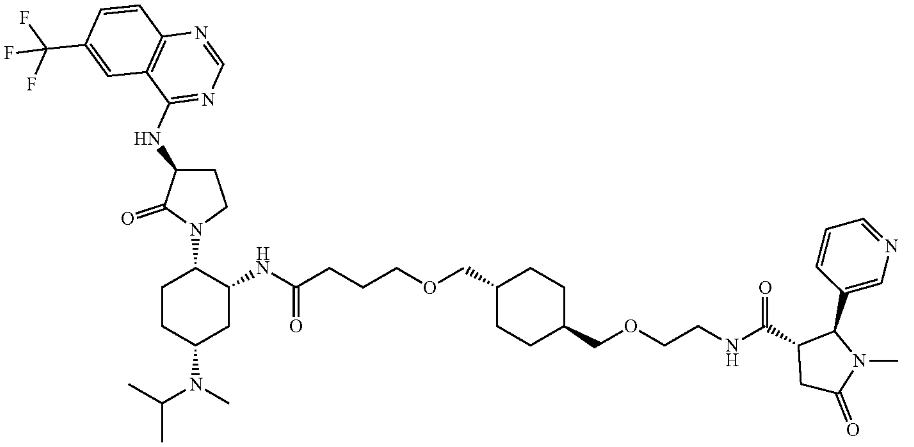 [SMILES: CC(C)N(C)[C@@H]1CC[C@H](N2CC[C@H](Nc3ncnc4ccc(C(F)(F)F)cc34)C2=O)[C@H](NC(=O)CCCOC[C@H]2CC[C@H](COCCNC(=O)[C@H]3CC(=O)N(C)[C@@H]3c3cccnc3)CC2)C1] |

TABLE 1-continued
| Example | Structure |
|---|---|
| 59 | 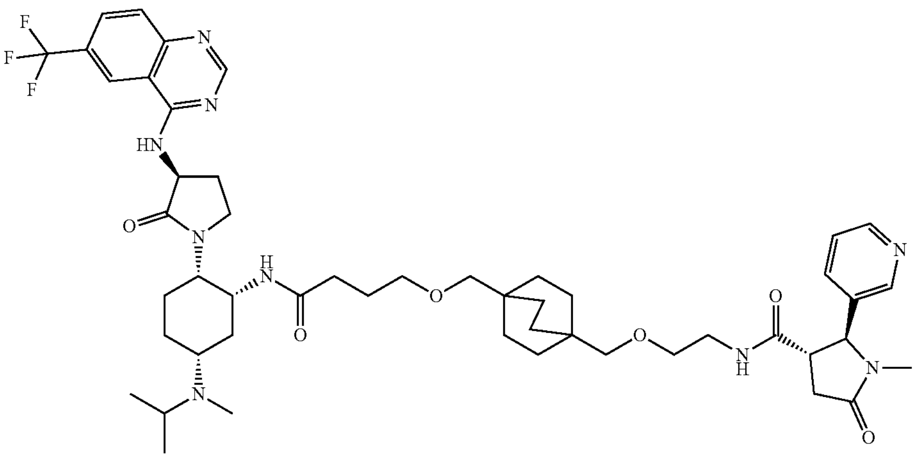 [SMILES: CC(C)N(C)[C@@H]1CC[C@H](N2CC[C@H](Nc3ncnc4ccc(C(F)(F)F)cc34)C2=O)[C@H](NC(=O)CCCOCC23CCC(COCCNC(=O)[C@H]4CC(=O)N(C)[C@@H]4c4cccnc4)(CC2)CC3)C1] |
| 60 | 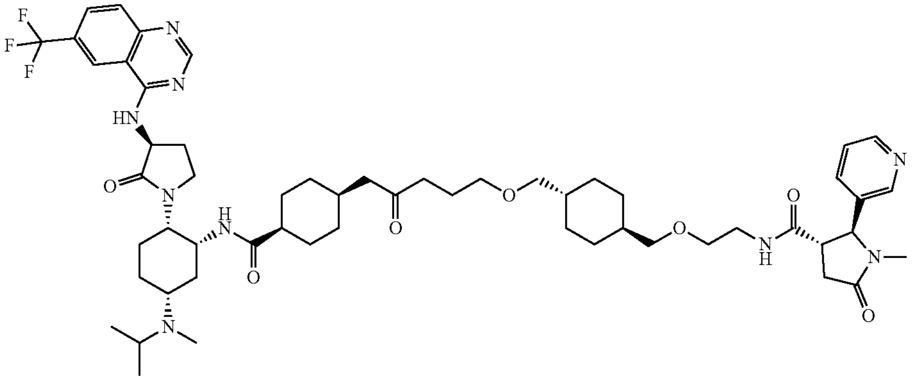 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](CC(=O)CCCOC[C@H]3CC[C@H](COCCNC(=O)[C@H]4CC(=O)N(C)[C@@H]4c4cccnc4)CC3)CC2)C1] |
| 61 | 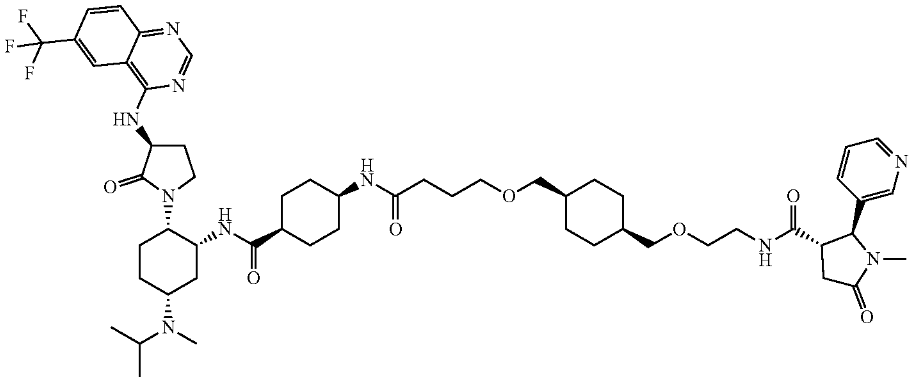 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCOC[C@H]3CC[C@@H](COCCNC(=O)[C@H]4CC(=O)N(C)[C@@H]4c4cccnc4)CC3)CC2)C1] |

TABLE 1-continued
| Example | Structure |
|---|---|
| 62 | 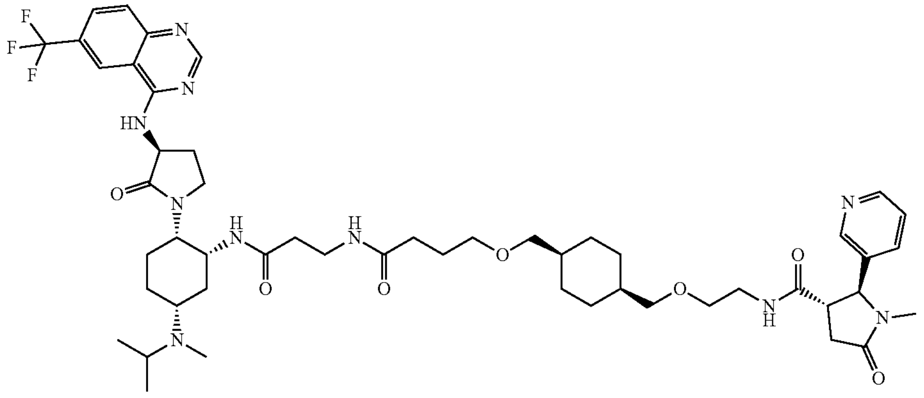 [SMILES: CC(C)N(C)[C@@H]1CC[C@H](N2CC[C@H](Nc3ncnc4ccc(C(F)(F)F)cc34)C2=O)[C@H](NC(=O)CCNC(=O)CCCOC[C@H]2CC[C@@H](COCCNC(=O)[C@H]3CC(=O)N(C)[C@@H]3c3cccnc3)CC2)C1] |
| 63 | 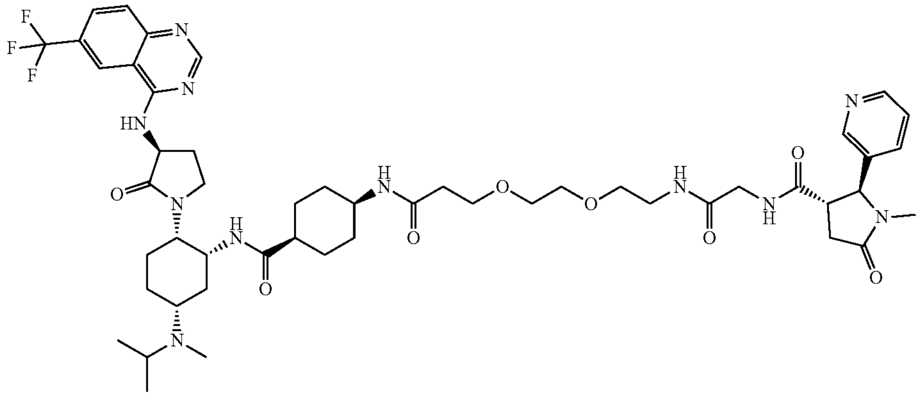 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCNC(=O)CNC(=O)[C@H]3CC(=O)N(C)[C@@H]3c3cccnc3)CC2)C1] |
| 64 | 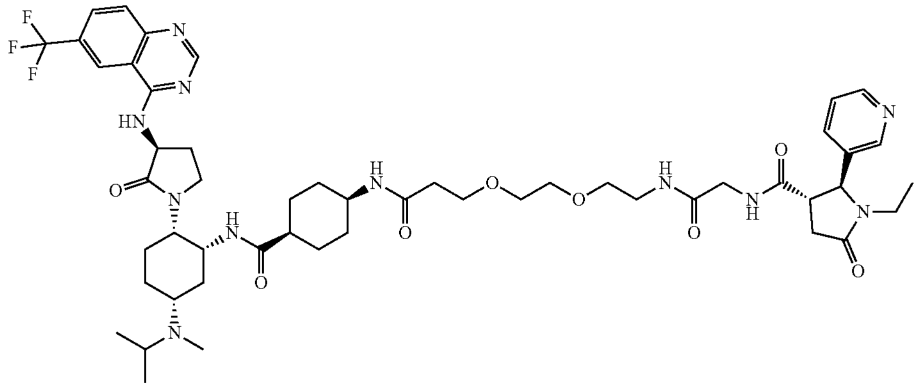 [SMILES: CCN1C(=O)C[C@H](C(=O)NCC(=O)NCCOCCOCCC(=O)N[C@H]2CC[C@@H](C(=O)N[C@@H]3C[C@H](N(C)C(C)C)CC[C@@H]3N3CC[C@H](Nc4ncnc5ccc(C(F)(F)F)cc45)C3=O)CC2)[C@H]1c1cccnc1] |
| 65 | 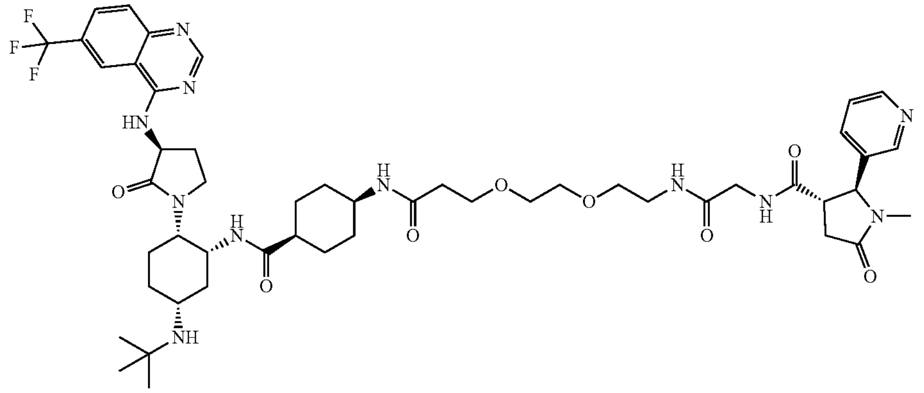 [SMILES: CN1C(=O)C[C@H](C(=O)NCC(=O)NCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] |

TABLE 1-continued
| Example | Structure |
|---|---|
| 66 | 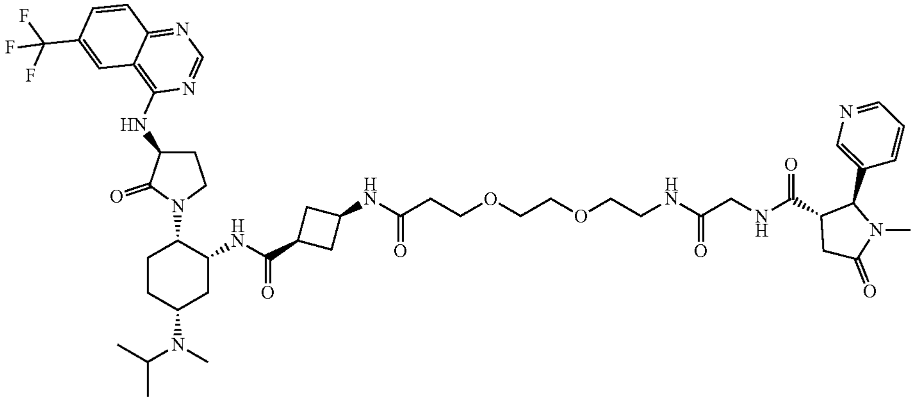 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCOCCNC(=O)CNC(=O)[C@H]3CC(=O)N(C)[C@@H]3c3cccnc3)C2)C1] |
| 67 | 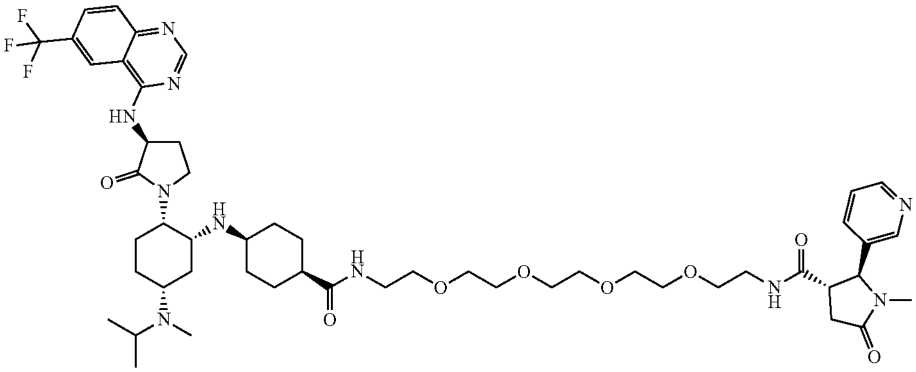 [SMILES: CC(C)N(C)[C@@H]1CC[C@H](N2CC[C@H](Nc3ncnc4ccc(C(F)(F)F)cc34)C2=O)[C@H](N[C@H]2CC[C@@H](C(=O)NCCOCCOCCOCCOCCNC(=O)[C@H]3CC(=O)N(C)[C@@H]3c3cccnc3)CC2)C1] |
| 68 | 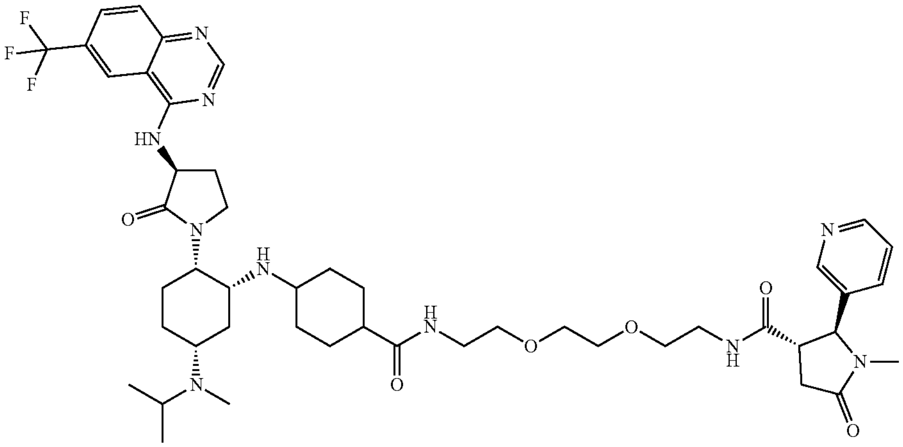 [SMILES: CC(C)N(C)[C@@H]1CC[C@H](N2CC[C@H](Nc3ncnc4ccc(C(F)(F)F)cc34)C2=O)[C@H](NC2CCC(C(=O)NCCOCCOCCNC(=O)[C@H]3CC(=O)N(C)[C@@H]3c3cccnc3)CC2)C1] |

TABLE 1-continued
| Example | Structure |
|---|---|
| 69 | 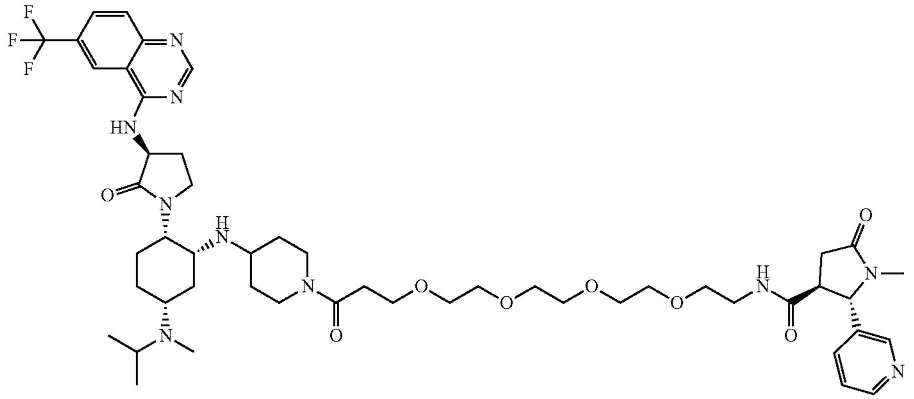 [SMILES: CC(C)N(C)[C@@H]1CC[C@H](N2CC[C@H](Nc3ncnc4ccc(C(F)(F)F)cc34)C2=O)[C@H](NC2CCN(C(=O)CCOCCOCCOCCOCCNC(=O)[C@H]3CC(=O)N(C)[C@@H]3c3cccnc3)CC2)C1] |
| 70 | 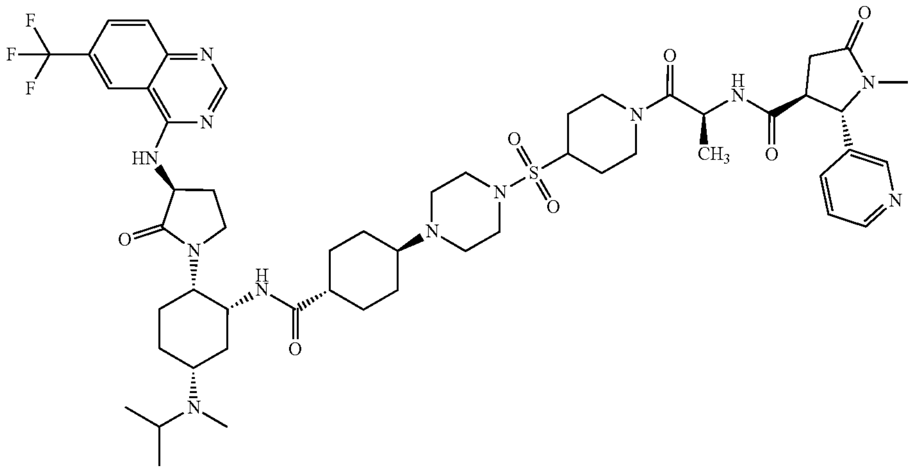 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(S(=O)(=O)C4CCN(C(=O)[C@H](C)NC(=O)[C@H]5CC(=O)N(C)[C@@H]5c5cccnc5)CC4)CC3)CC2)C1] |
| 71 | 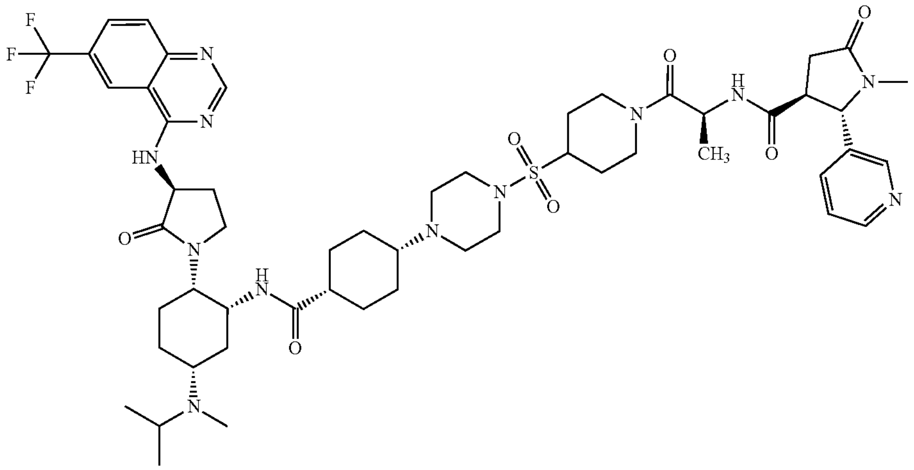 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](N3CCN(S(=O)(=O)C4CCN(C(=O)[C@H](C)NC(=O)[C@H]5CC(=O)N(C)[C@@H]5c5cccnc5)CC4)CC3)CC2)C1] |

TABLE 1-continued
| Example | Structure |
|---|---|
| 72 | 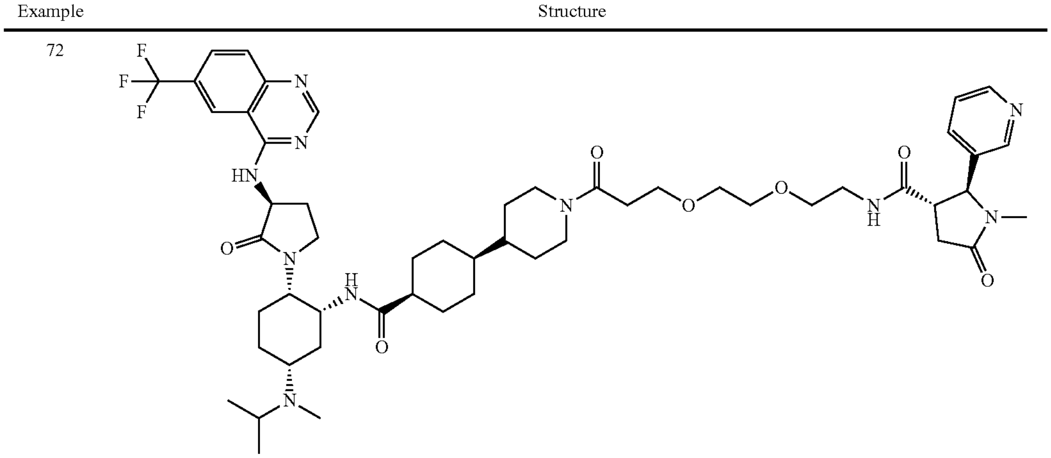 |
| 73 | 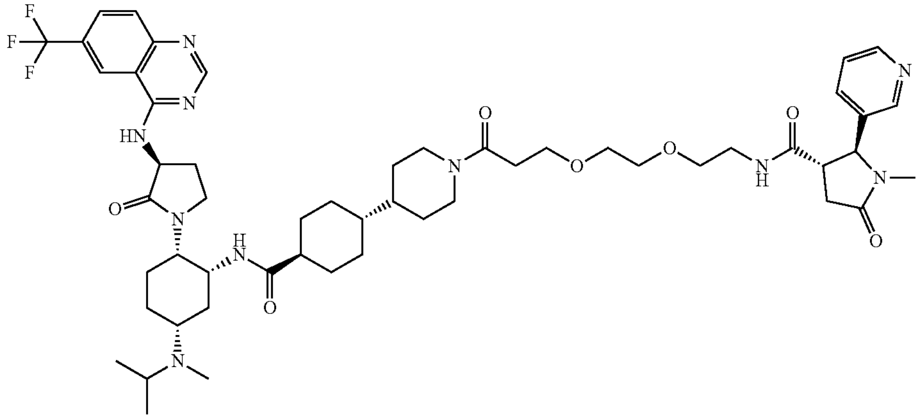 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](C3CCN(C(=O)CCOCCOCCNC(=O)[C@H]4CC(=O)N(C)[C@@H]4c4cccnc4)CC3)CC2)C1] |
| 74 | 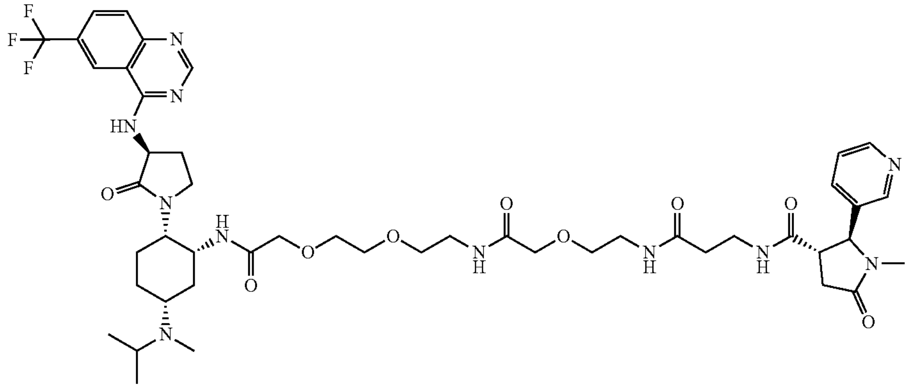 [SMILES: CC(C)N(C)[C@@H]1CC[C@H](N2CC[C@H](Nc3ncnc4ccc(C(F)(F)F)cc34)C2=O)[C@H](NC(=O)COCCOCCNC(=O)COCCNC(=O)CCNC(=O)[C@H]2CC(=O)N(C)[C@@H]2c2cccnc2)C1] |
| 75 | 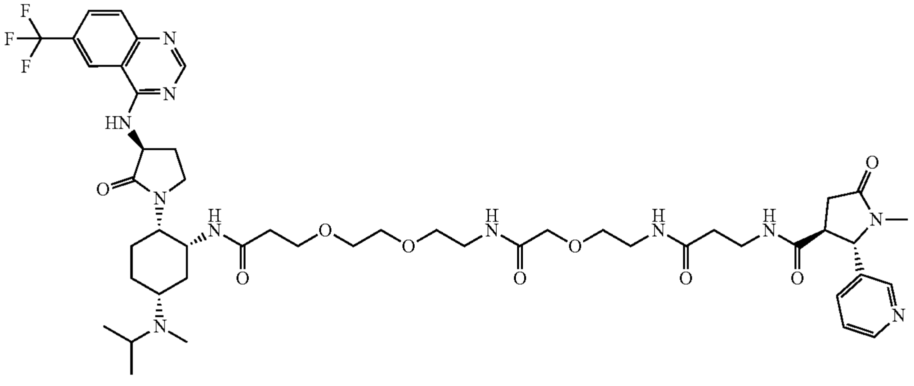 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)COCCNC(=O)CCNC(=O)[C@H]2CC(=O)N(C)[C@@H]2c2cccnc2)C1] |

TABLE 1-continued
| Example | Structure |
| --- | --- |
| 76 | 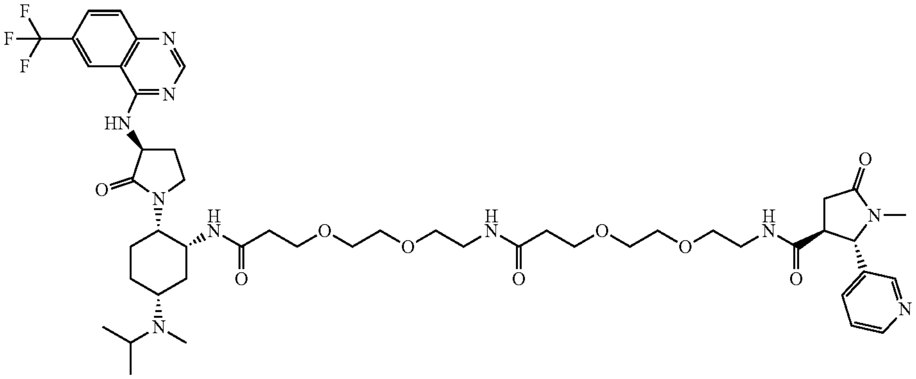 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)CCOCCOCCNC(=O)[C@H]2CC(=O)N(C)[C@@H]2c2cccnc2)C1] |
| 77 | 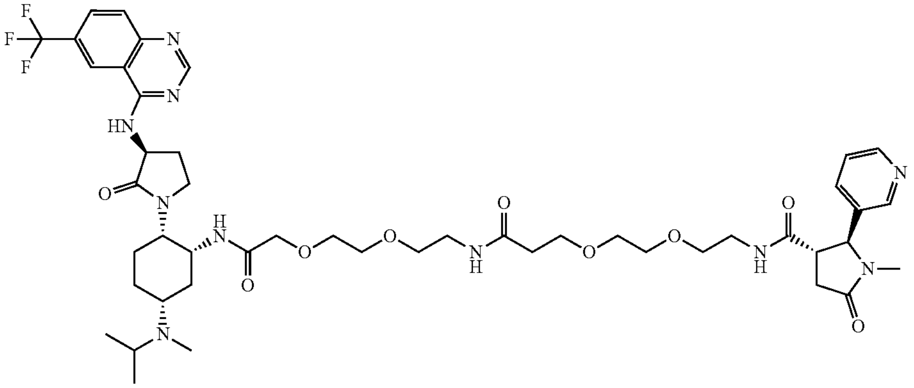 [SMILES: CC(C)N(C)[C@@H]1CC[C@H](N2CC[C@H](Nc3ncnc4ccc(C(F)(F)F)cc34)C2=O)[C@H](NC(=O)COCCOCCNC(=O)CCOCCOCCNC(=O)[C@H]2CC(=O)N(C)[C@@H]2c2cccnc2)C1] |
| 78 | 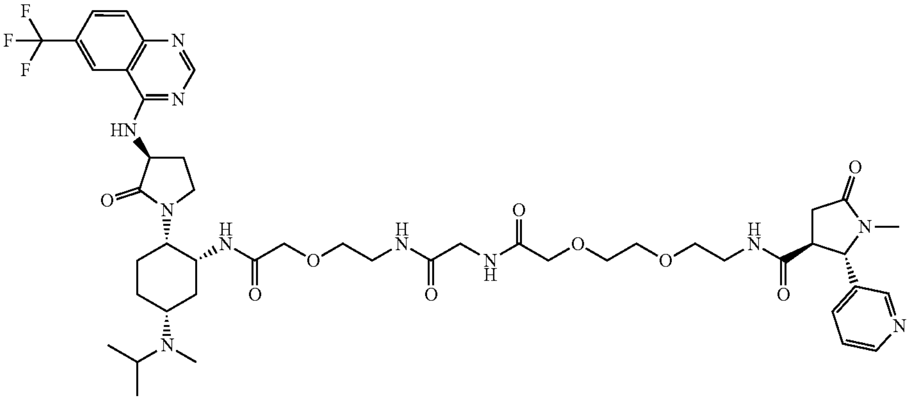 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CNC(=O)COCCOCCNC(=O)[C@H]2CC(=O)N(C)[C@@H]2c2cccnc2)C1] |
| 79 | 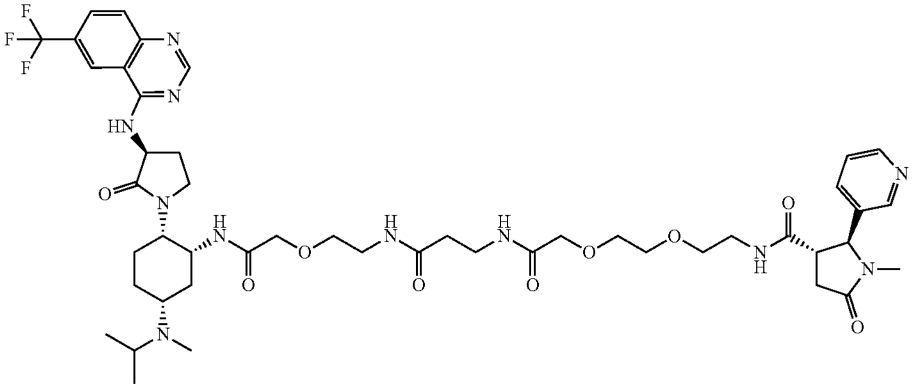 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCNC(=O)COCCOCCNC(=O)[C@H]2CC(=O)N(C)[C@@H]2c2cccnc2)C1] |

TABLE 1-continued
| Example | Structure |
|---|---|
| 80 | 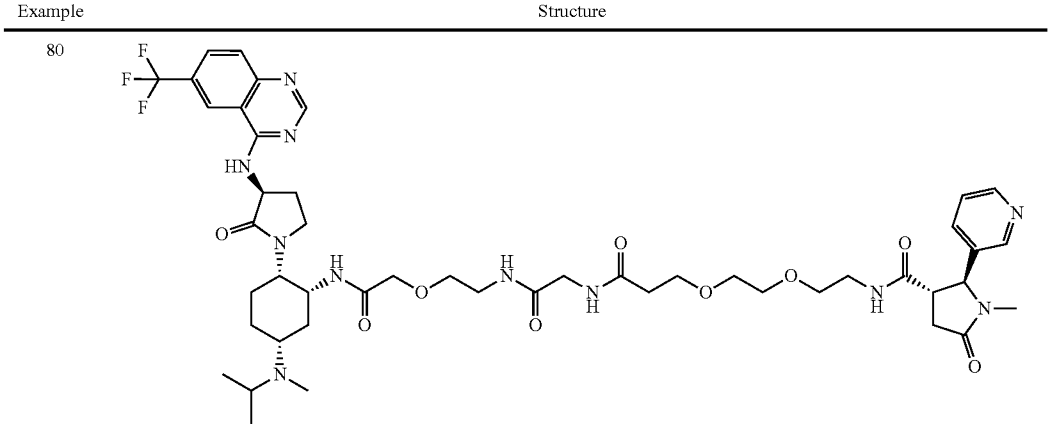 |
| 81 | 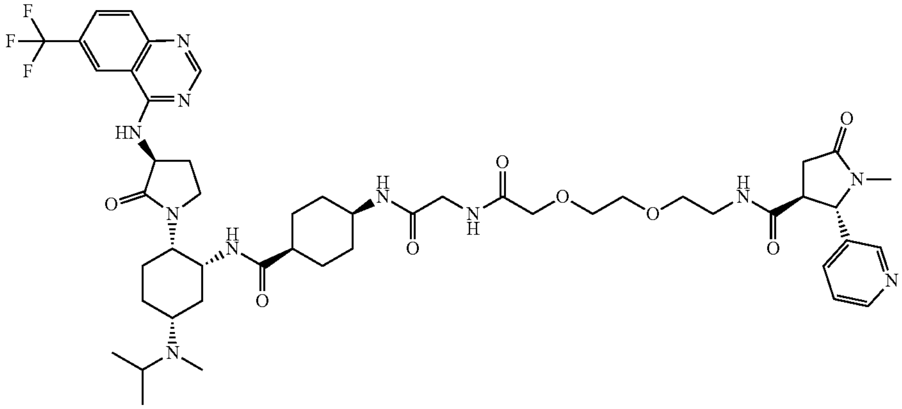 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CNC(=O)COCCOCCNC(=O)[C@H]3CC(=O)N(C)[C@@H]3c3cccnc3)CC2)C1] |
| 82 | 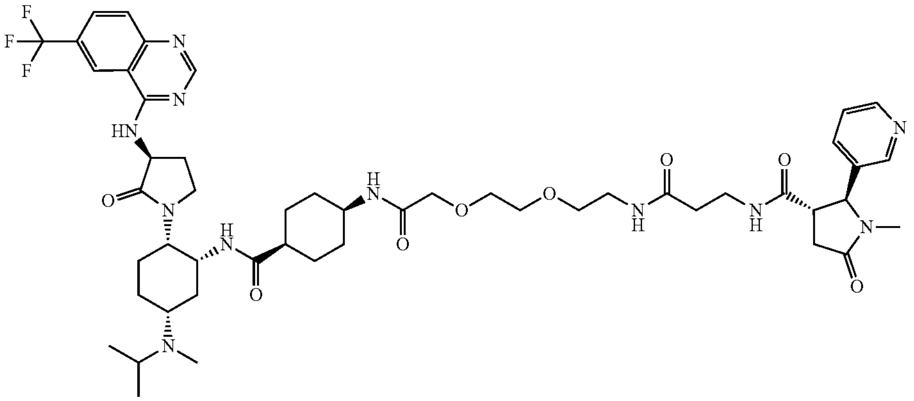 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCOCCNC(=O)CCNC(=O)[C@H]3CC(=O)N(C)[C@@H]3c3cccnc3)CC2)C1] |
| 83 | 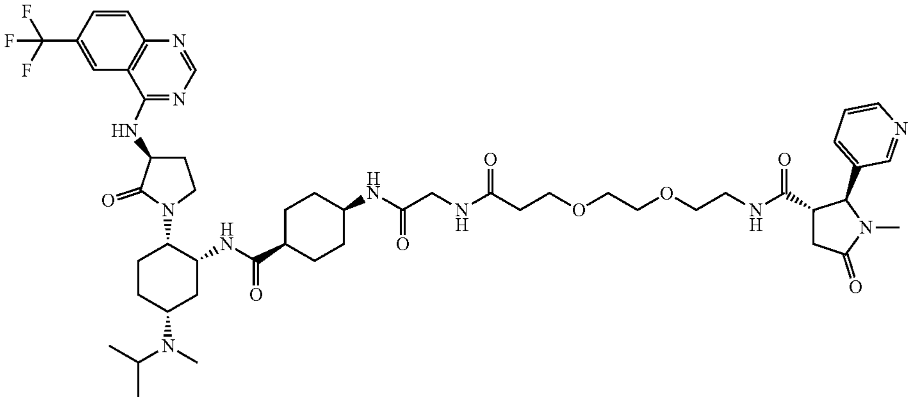 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CNC(=O)CCOCCOCCNC(=O)[C@H]3CC(=O)N(C)[C@@H]3c3cccnc3)CC2)C1] |

TABLE 1-continued
| Example | Structure |
| --- | --- |
| 84 | 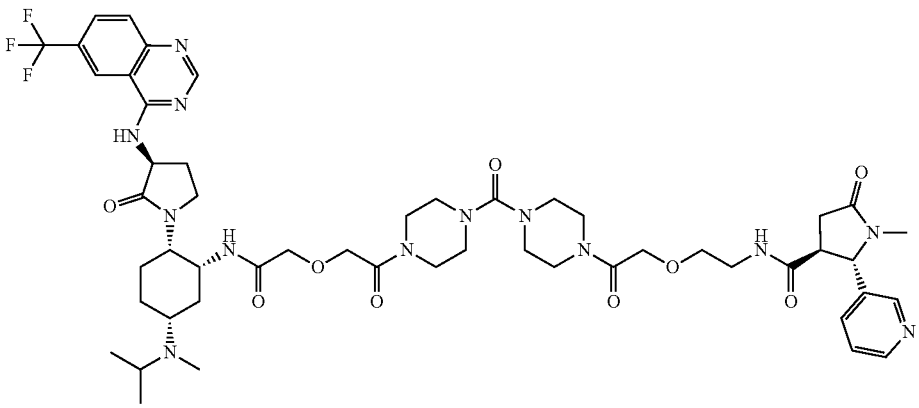 [SMILES: CC(C)N(C)[C@@H]1CC[C@H](N2CC[C@H](Nc3ncnc4ccc(C(F)(F)F)cc34)C2=O)[C@H](NC(=O)COCC(=O)N2CCN(C(=O)N3CCN(C(=O)COCCNC(=O)[C@H]4CC(=O)N(C)[C@@H]4c4cccnc4)CC3)CC2)C1] |
| 85 | 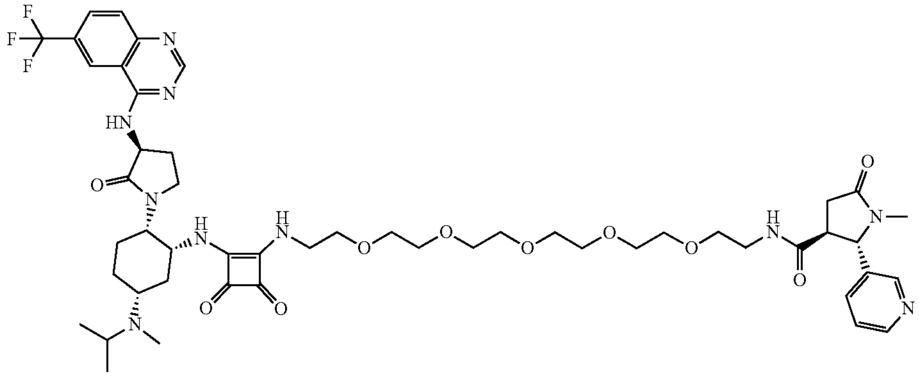 [SMILES: CC(C)N(C)[C@@H]1CC[C@H](N2CC[C@H](Nc3ncnc4ccc(C(F)(F)F)cc34)C2=O)[C@H](Nc2c(NCCOCCOCCOCCOCCOCCNC(=O)[C@H]3CC(=O)N(C)[C@@H]3c3cccnc3)c(=O)c2=O)C1] |
| 86 | 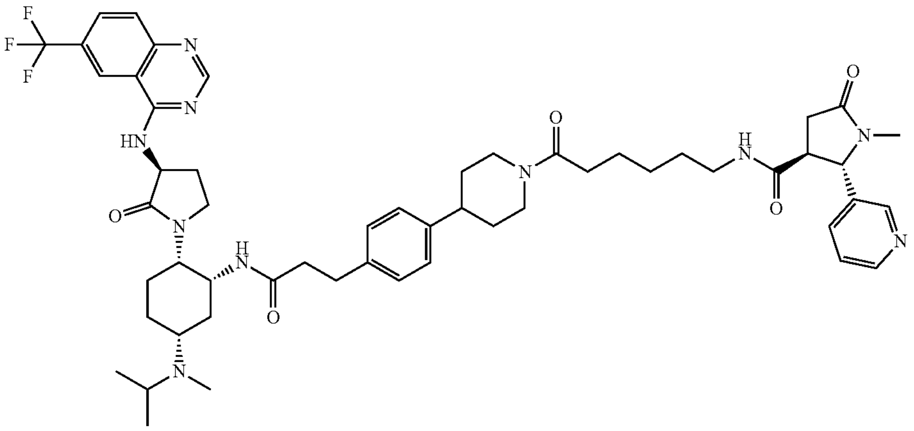 [SMILES: CC(C)N(C)[C@@H]1CC[C@H](N2CC[C@H](Nc3ncnc4ccc(C(F)(F)F)cc34)C2=O)[C@H](NC(=O)CCc2ccc(C3CCN(C(=O)CCCCCNC(=O)[C@H]4CC(=O)N(C)[C@@H]4c4cccnc4)CC3)cc2)C1] |

TABLE 1-continued
| Example | Structure |
| --- | --- |
| 87 | 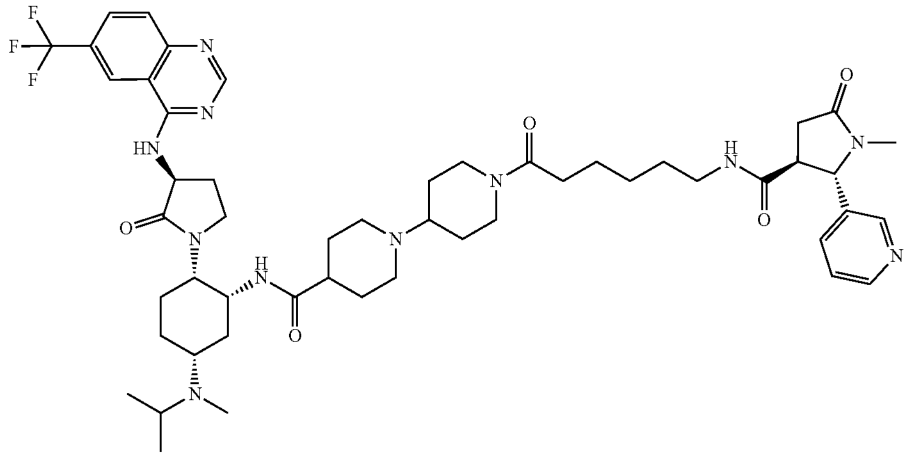 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C(=O)CCCCCNC(=O)[C@H]4CC(=O)N(C)[C@@H]4c4cccnc4)CC3)CC2)C1] |
| 88 | 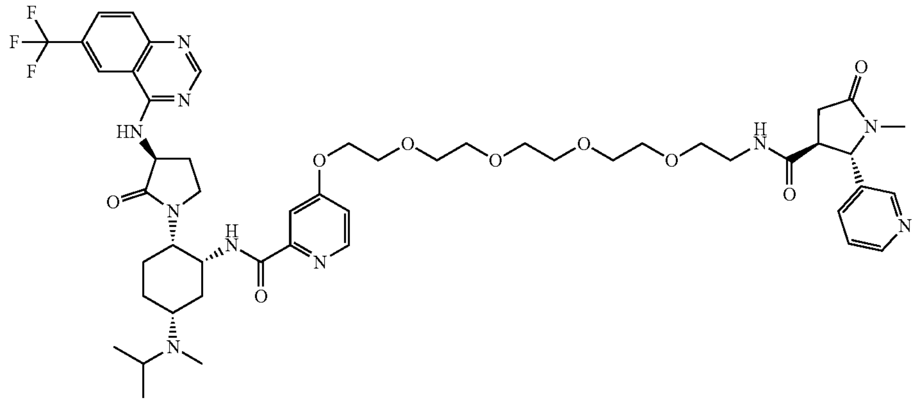 [SMILES: CC(C)N(C)[C@@H]1CC[C@H](N2CC[C@H](Nc3ncnc4ccc(C(F)(F)F)cc34)C2=O)[C@H](NC(=O)c2cc(OCCOCCOCCOCCOCCNC(=O)[C@H]3CC(=O)N(C)[C@@H]3c3cccnc3)ccn2)C1] |
| 89 | 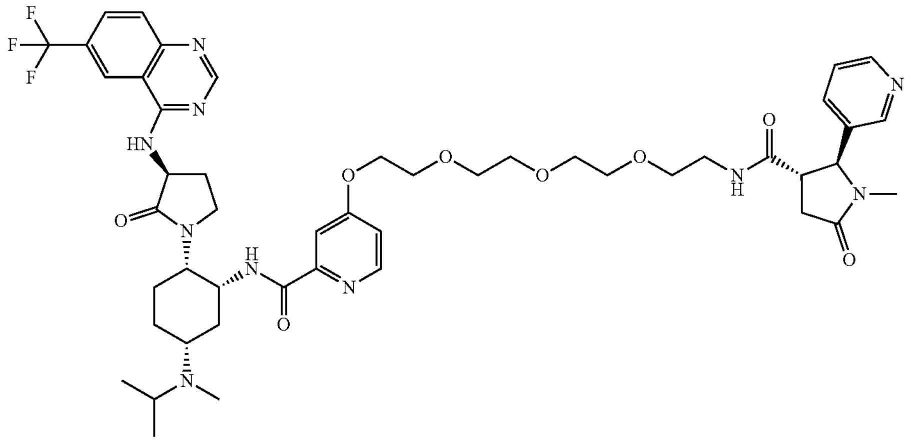 [SMILES: CC(C)N(C)[C@@H]1CC[C@H](N2CC[C@H](Nc3ncnc4ccc(C(F)(F)F)cc34)C2=O)[C@H](NC(=O)c2cc(OCCOCCOCCOCCNC(=O)[C@H]3CC(=O)N(C)[C@@H]3c3cccnc3)ccn2)C1] |

TABLE 1-continued
| Example | Structure |
| --- | --- |
| 90 | 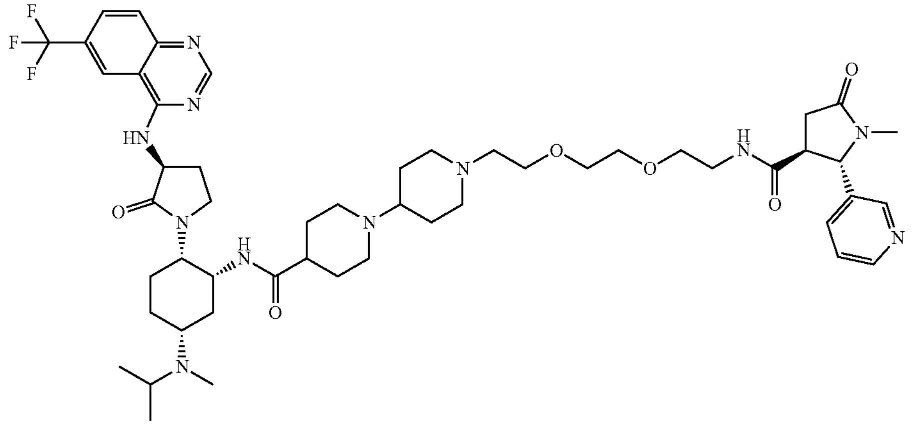 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(CCOCCOCCNC(=O)[C@H]4CC(=O)N(C)[C@@H]4c4cccnc4)CC3)CC2)C1] |
| 91 | 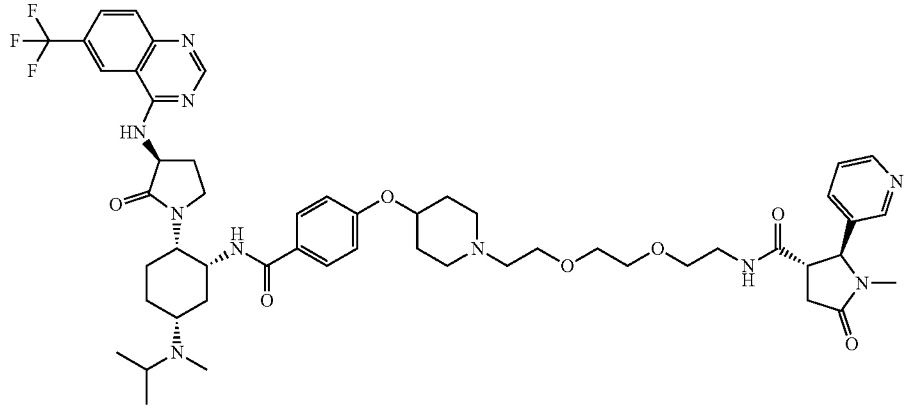 [SMILES: CC(C)N(C)[C@@H]1CC[C@H](N2CC[C@H](Nc3ncnc4ccc(C(F)(F)F)cc34)C2=O)[C@H](NC(=O)c2ccc(OC3CCN(CCOCCOCCNC(=O)[C@H]4CC(=O)N(C)[C@@H]4c4cccnc4)CC3)cc2)C1] |
| 92 | 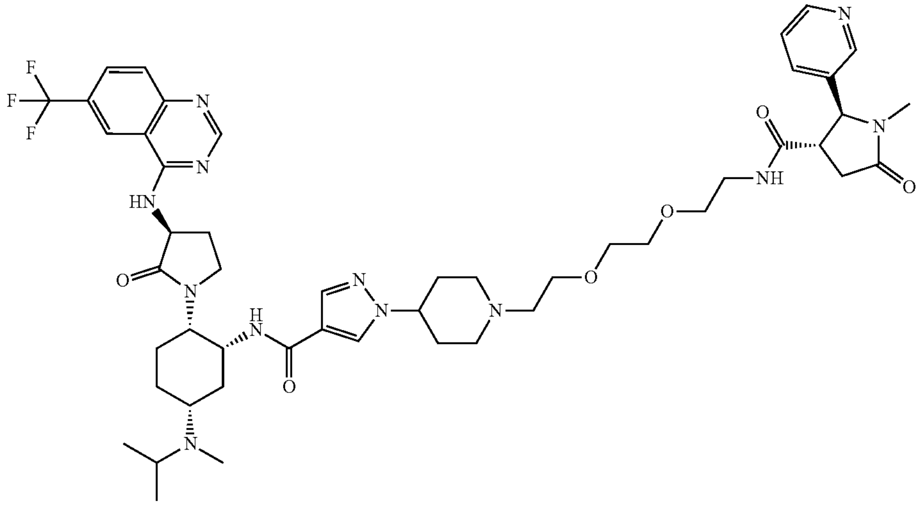 [SMILES: CC(C)N(C)[C@@H]1CC[C@H](N2CC[C@H](Nc3ncnc4ccc(C(F)(F)F)cc34)C2=O)[C@H](NC(=O)c2cnn(C3CCN(CCOCCOCCNC(=O)[C@H]4CC(=O)N(C)[C@@H]4c4cccnc4)CC3)c2)C1] |

TABLE 1-continued
| Example | Structure |
| --- | --- |
| 93 | 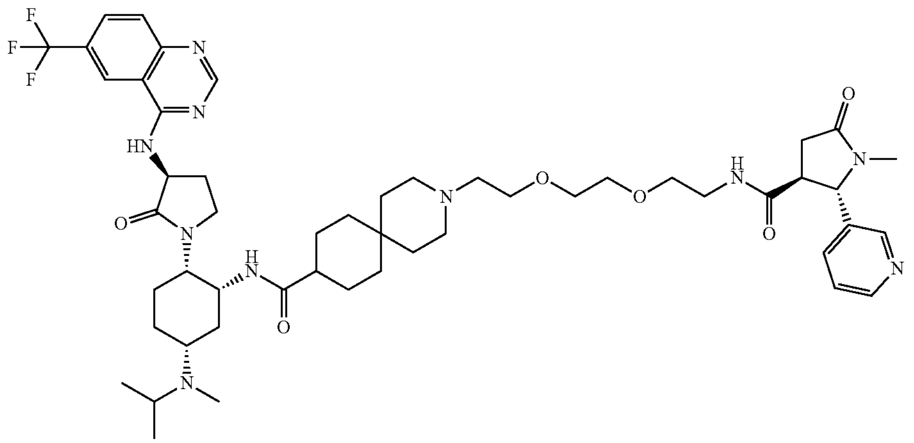 [SMILES: CC(C)N(C)[C@@H]1CC[C@H](N2CC[C@H](Nc3ncnc4ccc(C(F)(F)F)cc34)C2=O)[C@H](NC(=O)C2CCC3(CC2)CCN(CCOCCOCCNC(=O)[C@H]2CC(=O)N(C)[C@@H]2c2cccnc2)CC3)C1] |
| 94 | 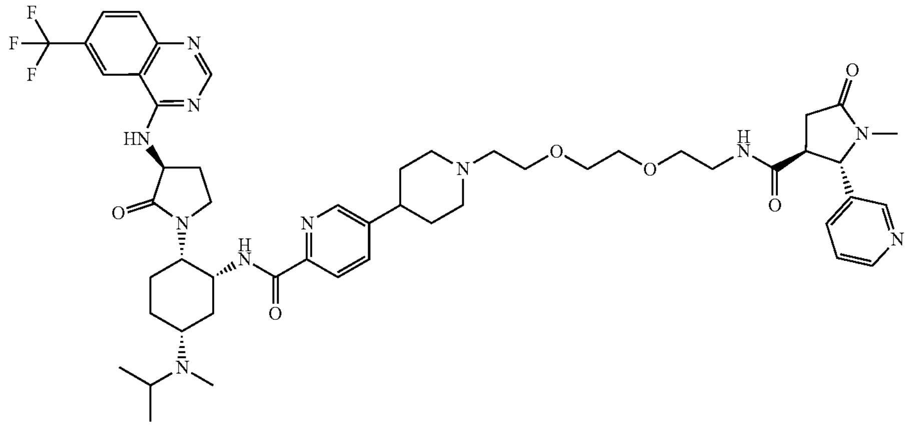 [SMILES: CC(C)N(C)[C@@H]1CC[C@H](N2CC[C@H](Nc3ncnc4ccc(C(F)(F)F)cc34)C2=O)[C@H](NC(=O)c2ccc(C3CCN(CCOCCOCCNC(=O)[C@H]4CC(=O)N(C)[C@@H]4c4cccnc4)CC3)cn2)C1] |
| 95 | 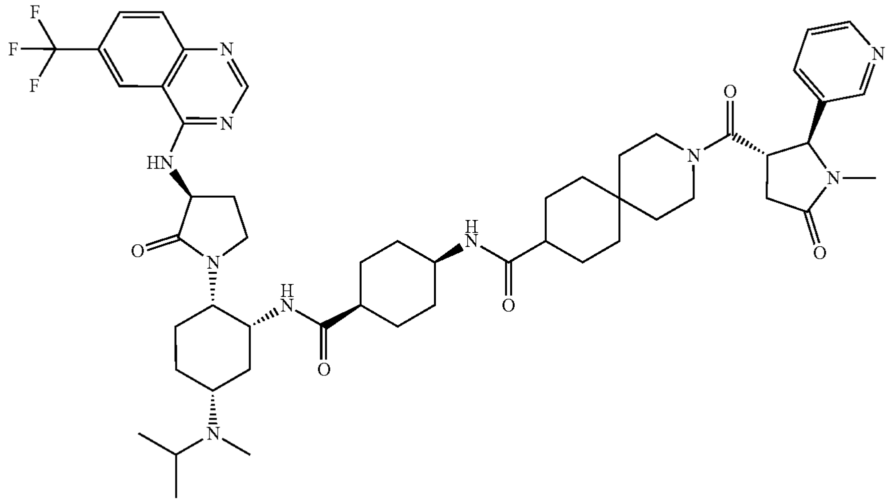 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CC3)CCN(C(=O)[C@H]3CC(=O)N(C)[C@@H]3c3cccnc3)CC4)CC2)C1] |

TABLE 1-continued
| Example | Structure |
|---|---|
| 96 | 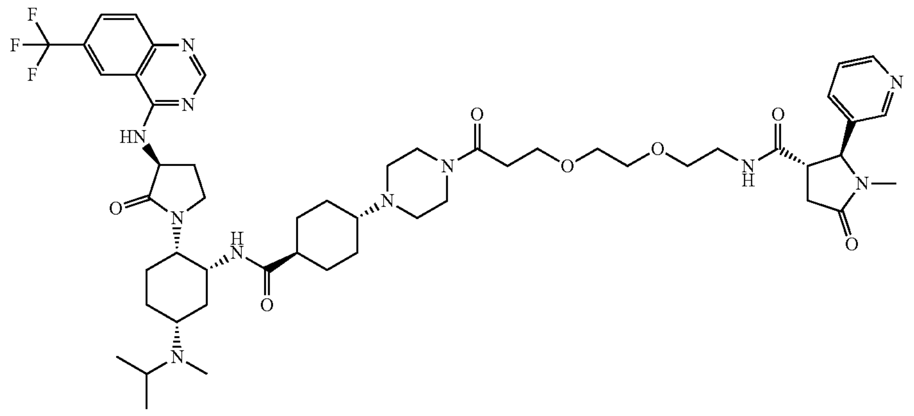 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(C(=O)CCOCCOCCNC(=O)[C@H]4CC(=O)N(C)[C@@H]4c4cccnc4)CC3)CC2)C1] |
| 97 | 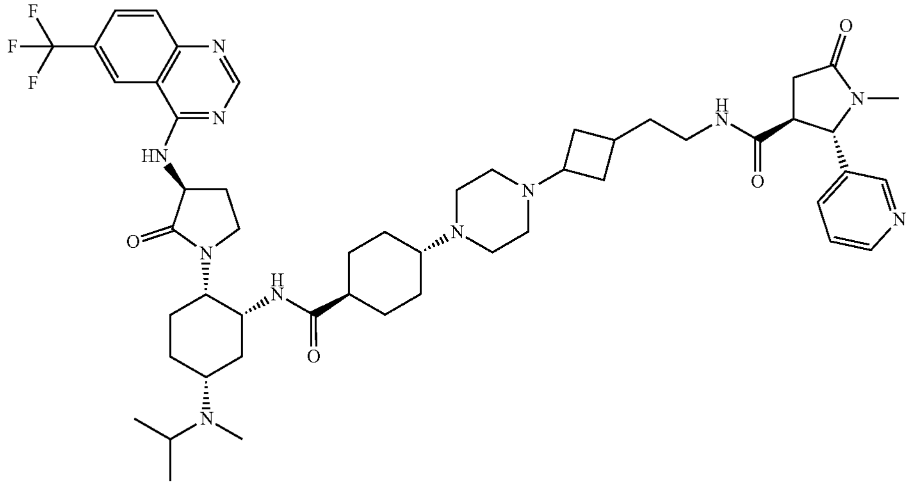 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(C4CC(CCNC(=O)[C@H]5CC(=O)N(C)[C@@H]5c5cccnc5)C4)CC3)CC2)C1] |
| 98 | 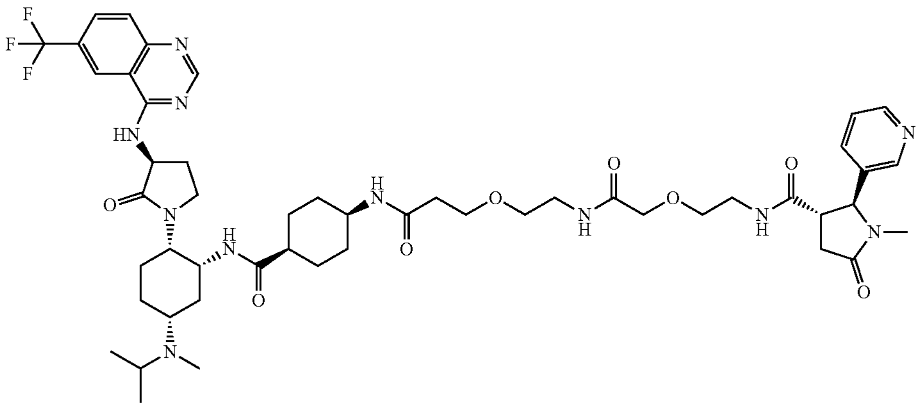 |

TABLE 1-continued
| Example | Structure |
| --- | --- |
| 99 | 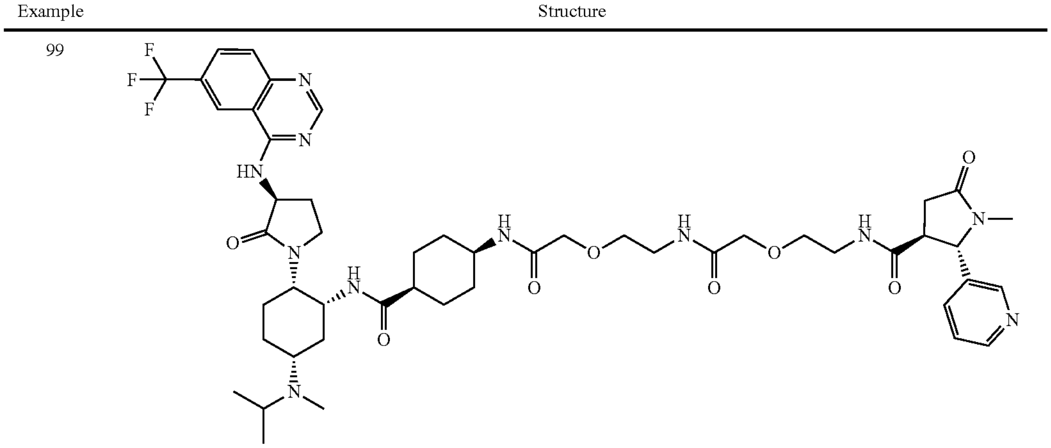 |
| 100 | 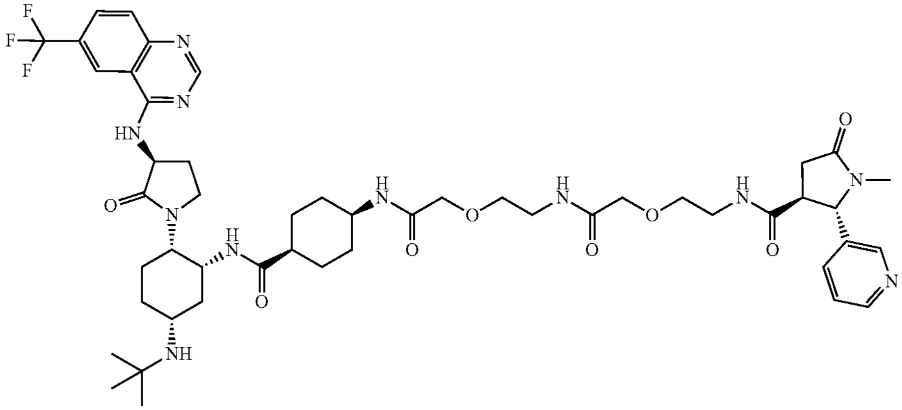 [SMILES: CN1C(=O)C[C@H](C(=O)NCCOCC(=O)NCCOCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] |
| 101 | 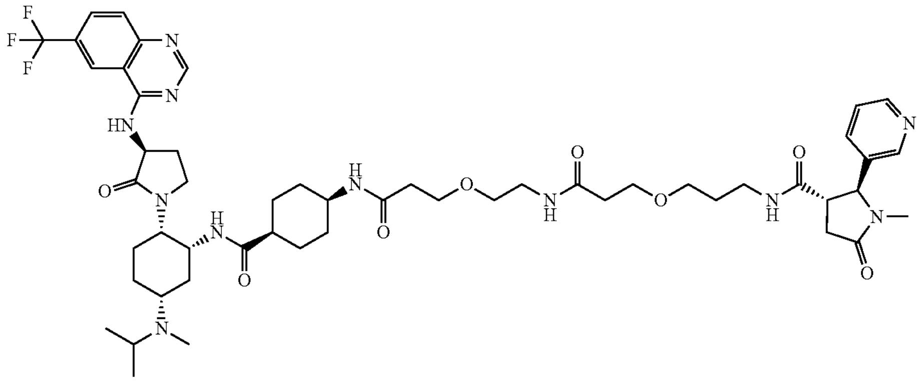 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCOCCCNC(=O)[C@H]3CC(=O)N(C)[C@@H]3c3cccnc3)CC2)C1] |
| 102 | 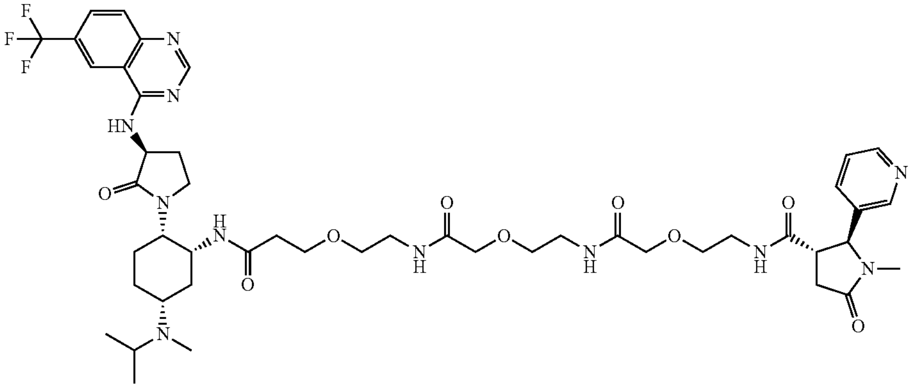 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)COCCNC(=O)COCCNC(=O)[C@H]2CC(=O)N(C)[C@@H]2c2cccnc2)C1] |

TABLE 1-continued
| Example | Structure |
| --- | --- |
| 103 | 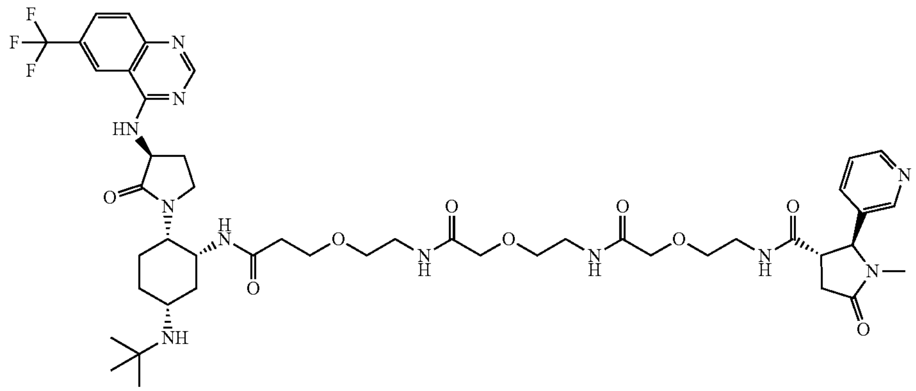 [SMILES: CN1C(=O)C[C@H](C(=O)NCCOCC(=O)NCCOCC(=O)NCCOCCC(=O)N[C@@H]2C[C@H](NC(C)(C)C)CC[C@@H]2N2CC[C@H](Nc3ncnc4ccc(C(F)(F)F)cc34)C2=O)[C@H]1c1cccnc1] |
| 104 | 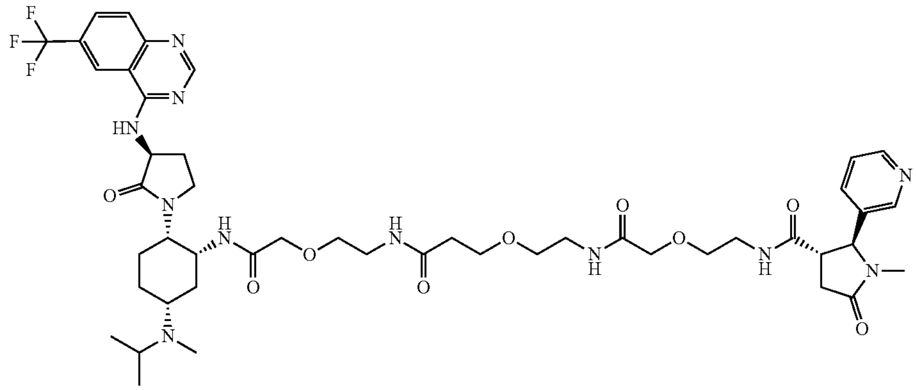 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCOCCNC(=O)COCCNC(=O)[C@H]2CC(=O)N(C)[C@@H]2c2cccnc2)C1] |
| 105 | 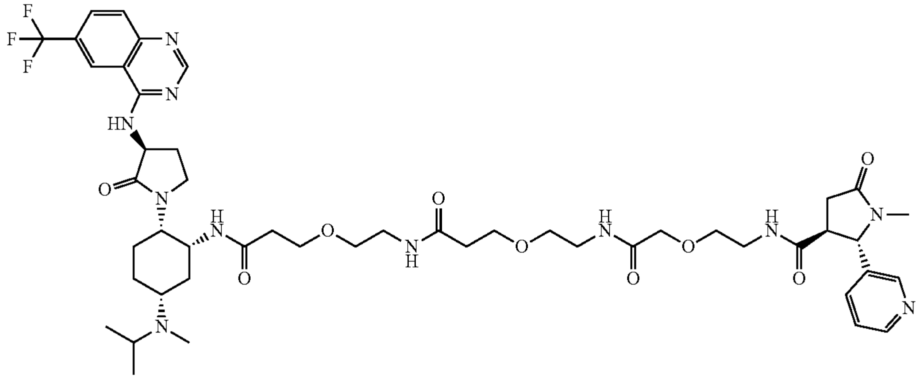 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)CCOCCNC(=O)COCCNC(=O)[C@H]2CC(=O)N(C)[C@@H]2c2cccnc2)C1] |
| 106 | 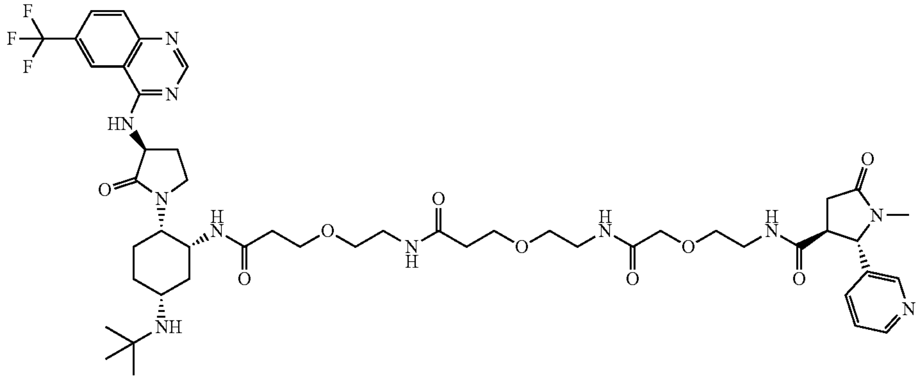 [SMILES: CN1C(=O)C[C@H](C(=O)NCCOCC(=O)NCCOCCC(=O)NCCOCCC(=O)N[C@@H]2C[C@H](NC(C)(C)C)CC[C@@H]2N2CC[C@H](Nc3ncnc4ccc(C(F)(F)F)cc34)C2=O)[C@H]1c1cccnc1] |

TABLE 1-continued
| Example | Structure |
|---|---|
| 107 | 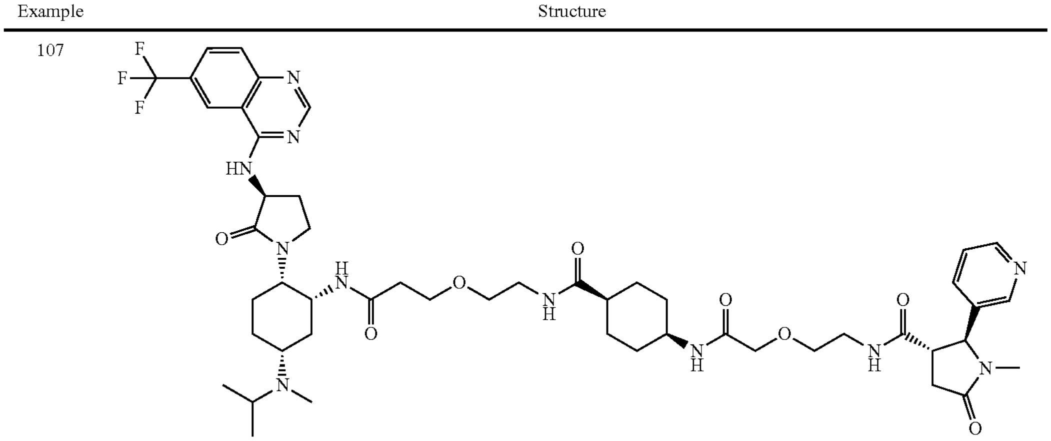 |
| 108 | 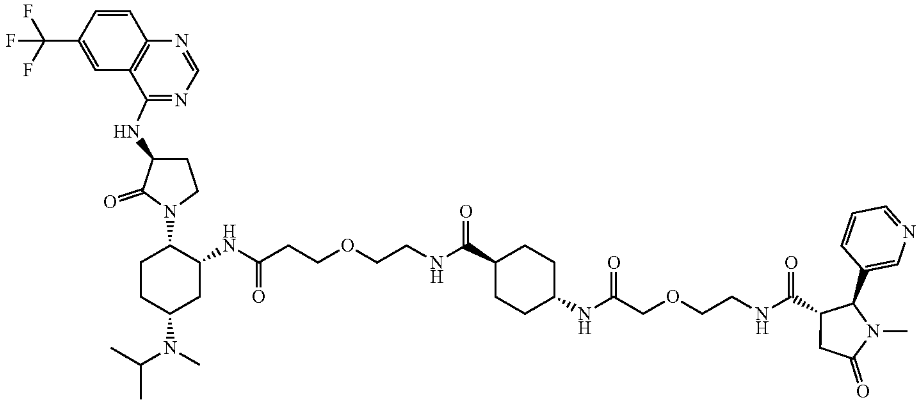 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)[C@H]2CC[C@H](NC(=O)COCCNC(=O)[C@H]3CC(=O)N(C)[C@@H]3c3cccnc3)CC2)C1] |
| 109 | 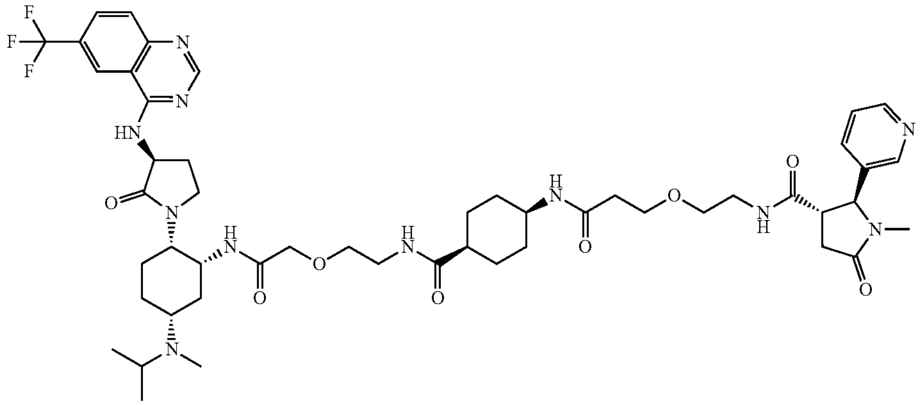 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)[C@H]2CC[C@@H](NC(=O)CCOCCNC(=O)[C@H]3CC(=O)N(C)[C@@H]3c3cccnc3)CC2)C1] |
| 110 | 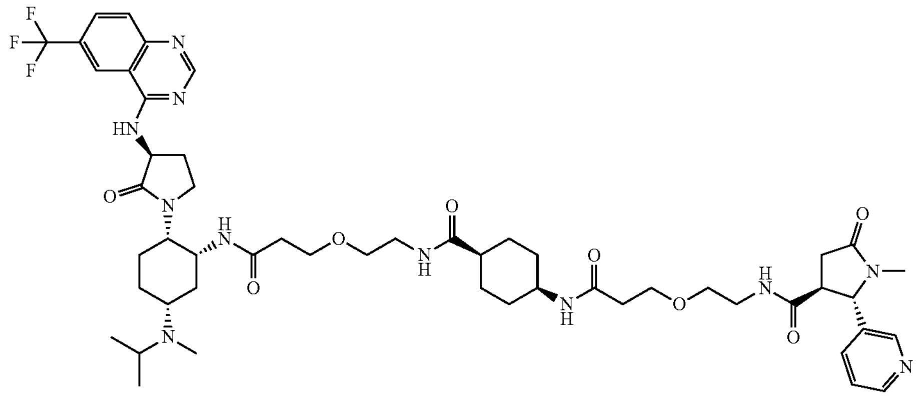 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)[C@H]2CC[C@@H](NC(=O)CCOCCNC(=O)[C@H]3CC(=O)N(C)[C@@H]3c3cccnc3)CC2)C1] |

TABLE 1-continued
| Example | Structure |
|---|---|
| 111 | 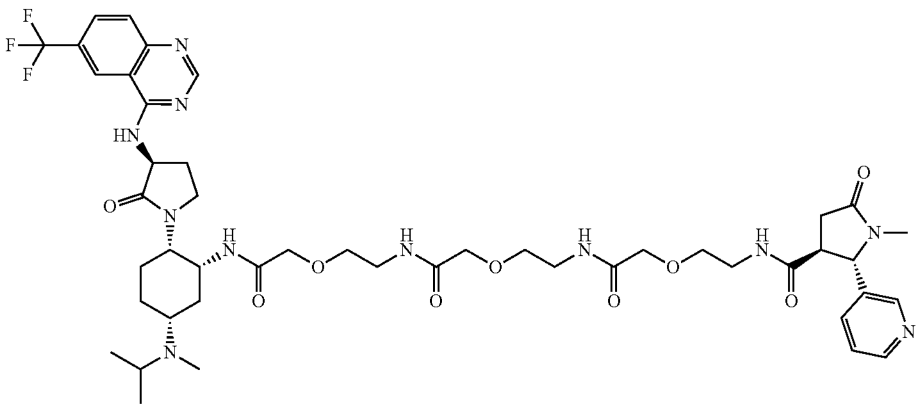 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)COCCNC(=O)COCCNC(=O)[C@H]2CC(=O)N(C)[C@@H]2c2cccnc2)C1] |
| 112 | 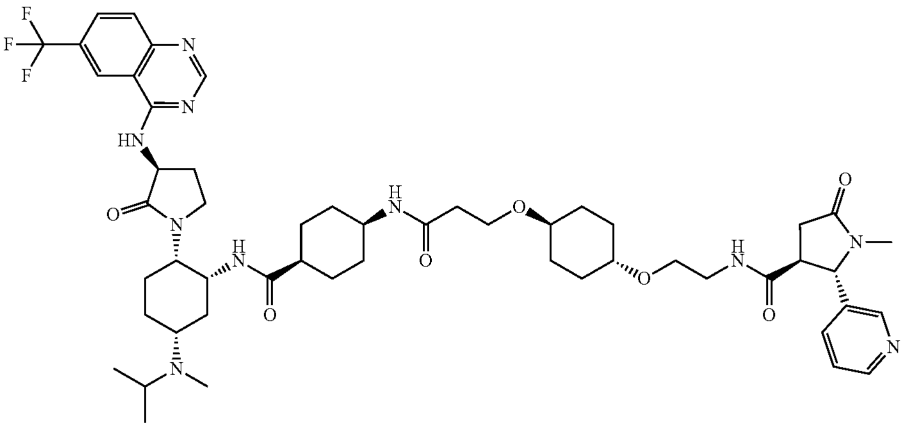 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCO[C@H]3CC[C@H](OCCNC(=O)[C@H]4CC(=O)N(C)[C@@H]4c4cccnc4)CC3)CC2)C1] |
| 113 | 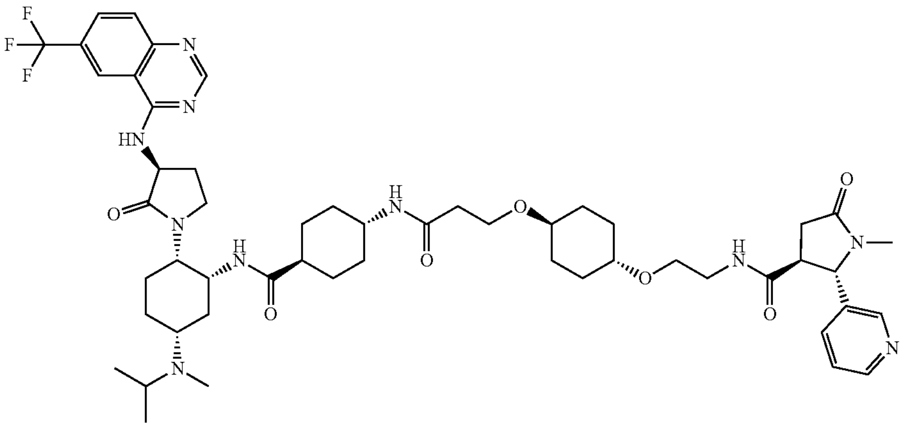 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCO[C@H]3CC[C@H](OCCNC(=O)[C@H]4CC(=O)N(C)[C@@H]4c4cccnc4)CC3)CC2)C1] |

TABLE 1-continued
| Example | Structure |
| --- | --- |
| 114 | 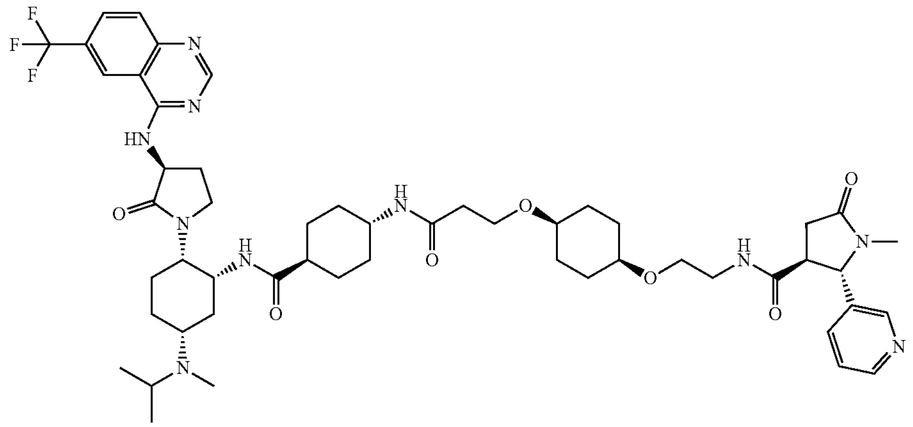 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCO[C@H]3CC[C@@H](OCCNC(=O)[C@H]4CC(=O)N(C)[C@@H]4c4cccnc4)CC3)CC2)C1] |
| 115 | 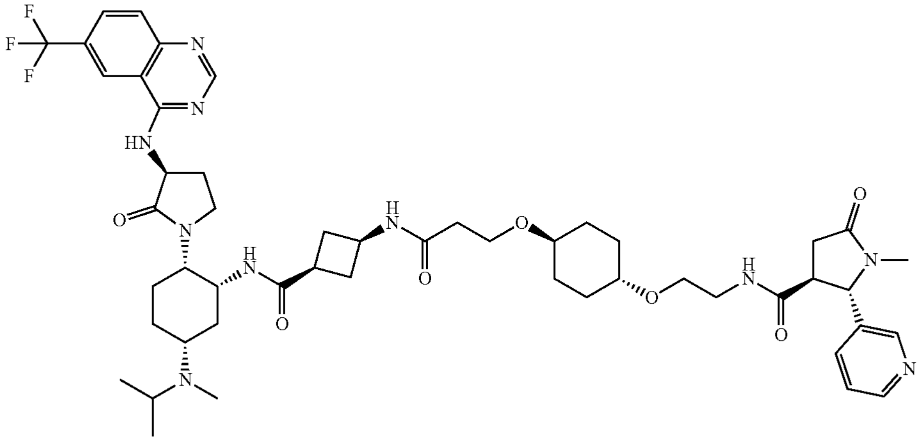 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCO[C@H]3CC[C@H](OCCNC(=O)[C@H]4CC(=O)N(C)[C@@H]4c4cccnc4)CC3)C2)C1] |
| 116 | 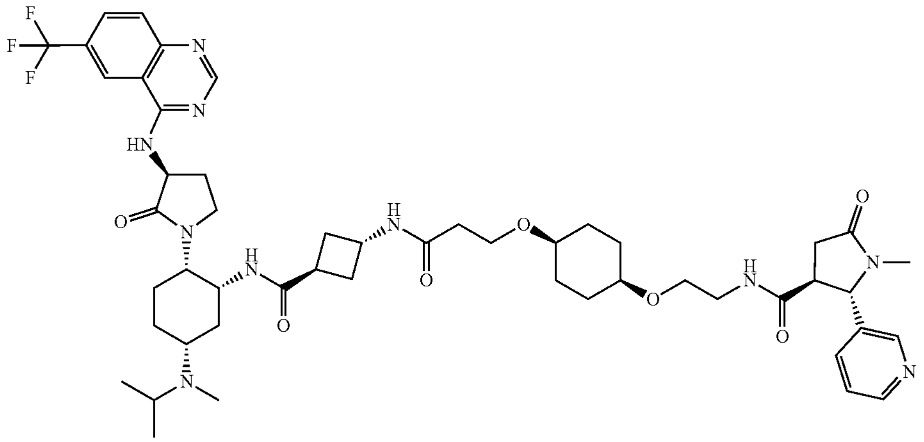 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCO[C@H]3CC[C@@H](OCCNC(=O)[C@H]4CC(=O)N(C)[C@@H]4c4cccnc4)CC3)C2)C1] |

TABLE 1-continued
| Example | Structure |
| --- | --- |
| 117 | 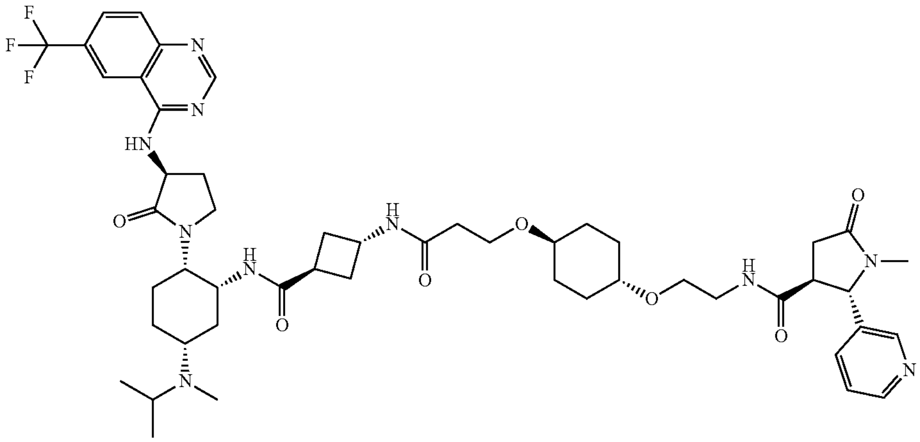 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCO[C@H]3CC[C@H](OCCNC(=O)[C@H]4CC(=O)N(C)[C@@H]4c4cccnc4)CC3)C2)C1] |
| 118 | 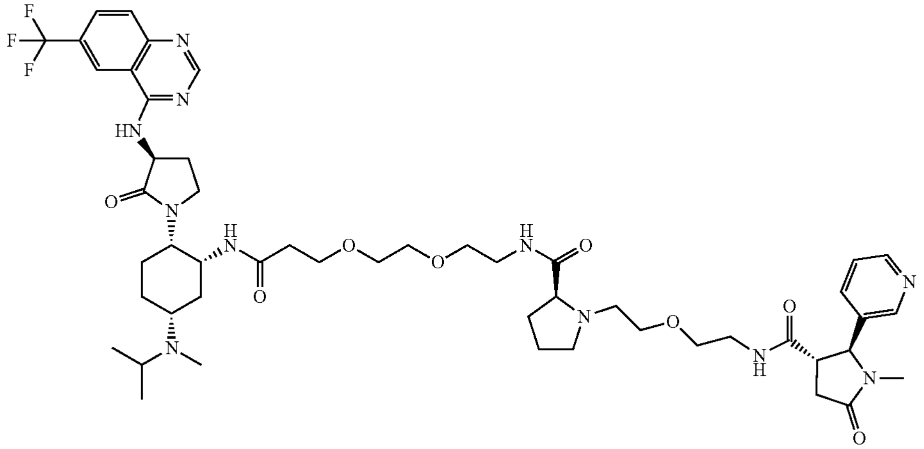 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)[C@@H]2CCCN2CCOCCNC(=O)[C@H]2CC(=O)N(C)[C@@H]2c2cccnc2)C1] |
| 119 | 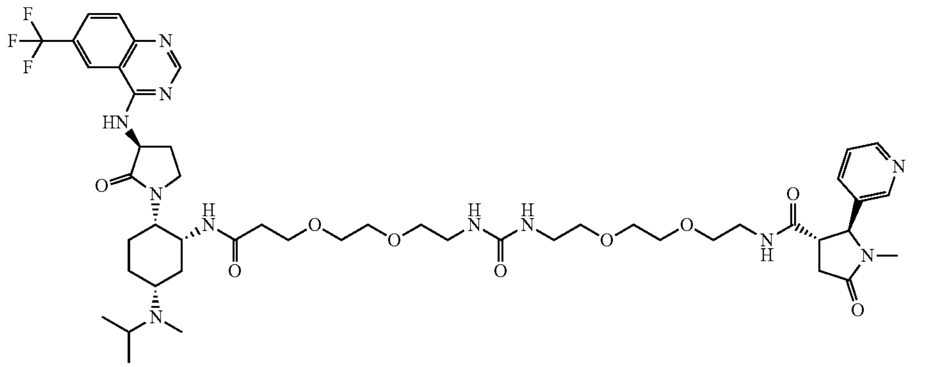 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)NCCOCCOCCNC(=O)[C@H]2CC(=O)N(C)[C@@H]2c2cccnc2)C1] |

TABLE 1-continued
| Example | Structure |
| --- | --- |
| 120 | 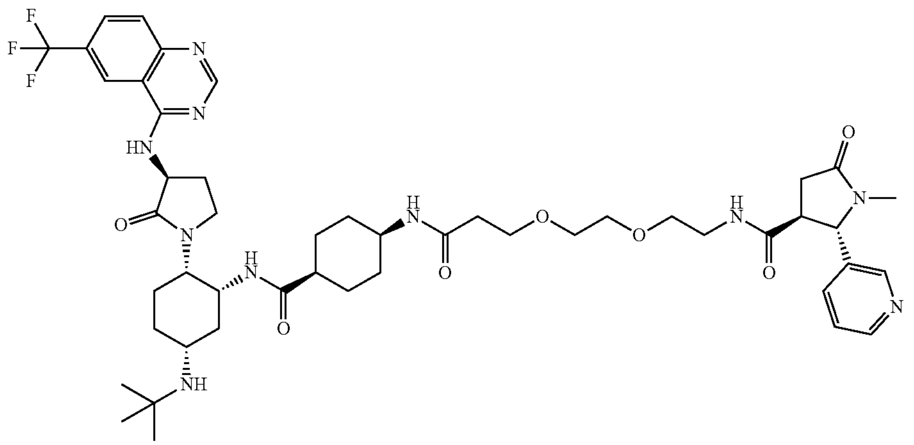 [SMILES: CN1C(=O)C[C@H](C(=O)NCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] |
| 121 | 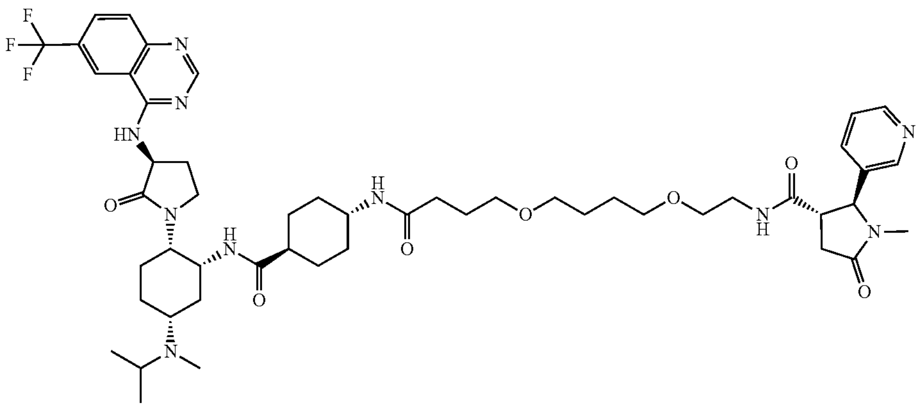 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCOCCCCOCCNC(=O)[C@H]3CC(=O)N(C)[C@@H]3c3cccnc3)CC2)C1] |
| 122 | 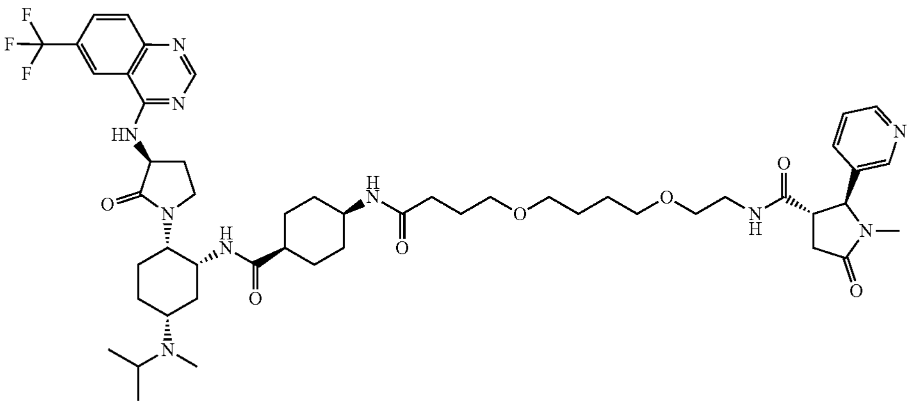 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCOCCCCOCCNC(=O)[C@H]3CC(=O)N(C)[C@@H]3c3cccnc3)CC2)C1] |

TABLE 1-continued
| Example | Structure |
| --- | --- |
| 123 | 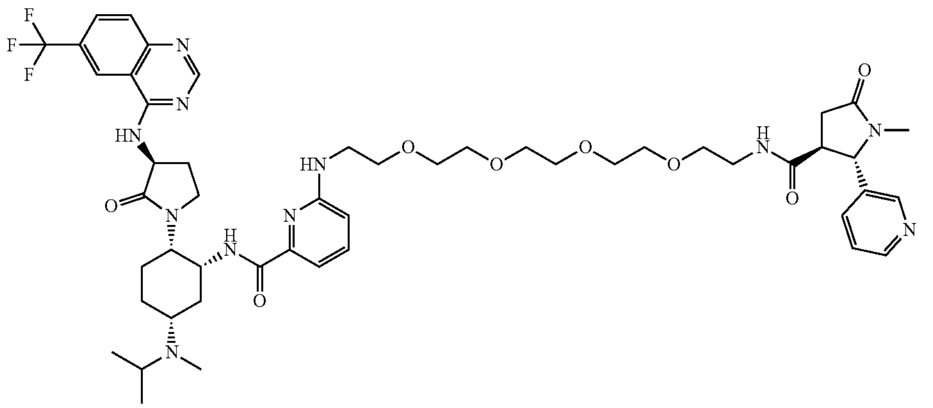 [SMILES: CC(C)N(C)[C@@H]1CC[C@H](N2CC[C@H](Nc3ncnc4ccc(C(F)(F)F)cc34)C2=O)[C@H](NC(=O)c2cccc(NCCOCCOCCOCCOCCNC(=O)[C@H]3CC(=O)N(C)[C@@H]3c3cccnc3)n2)C1] |
| 124 | 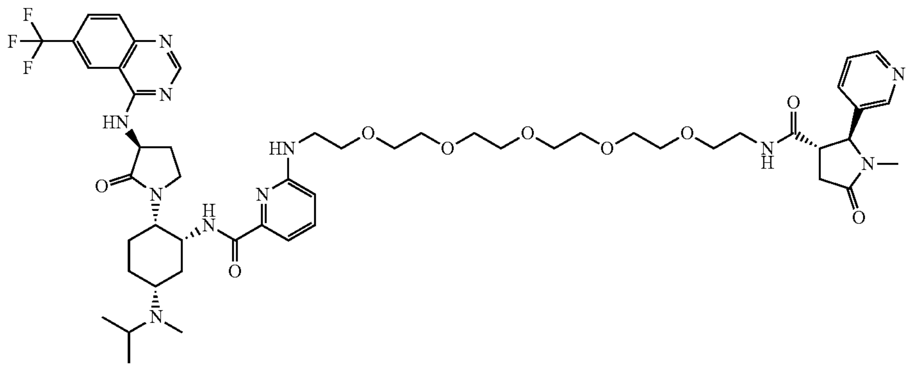 [SMILES: CC(C)N(C)[C@@H]1CC[C@H](N2CC[C@H](Nc3ncnc4ccc(C(F)(F)F)cc34)C2=O)[C@H](NC(=O)c2cccc(NCCOCCOCCOCCOCCOCCNC(=O)[C@H]3CC(=O)N(C)[C@@H]3c3cccnc3)n2)C1] |
| 125 | 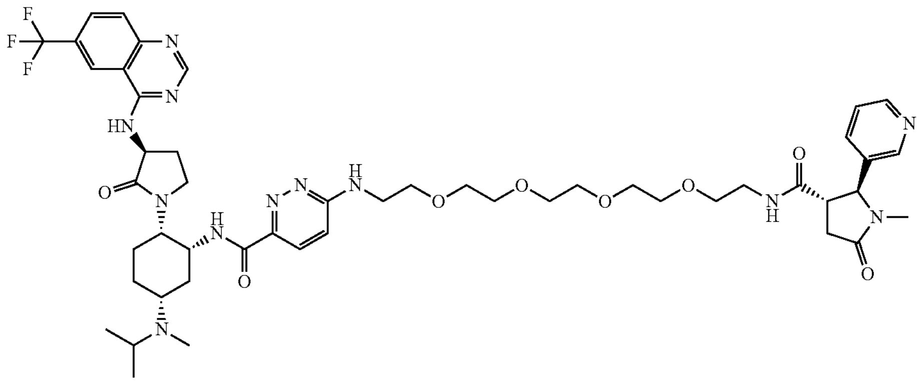 [SMILES: CC(C)N(C)[C@@H]1CC[C@H](N2CC[C@H](Nc3ncnc4ccc(C(F)(F)F)cc34)C2=O)[C@H](NC(=O)c2ccc(NCCOCCOCCOCCOCCNC(=O)[C@H]3CC(=O)N(C)[C@@H]3c3cccnc3)nn2)C1] |
| 126 | 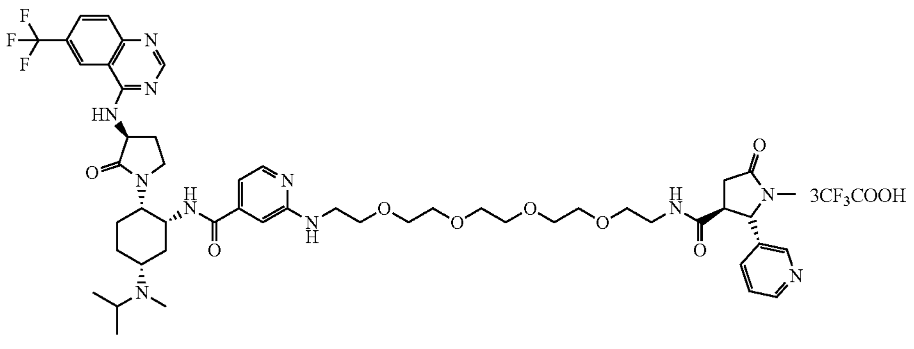 |

TABLE 1-continued
| Example | Structure |
| --- | --- |
| 127 | 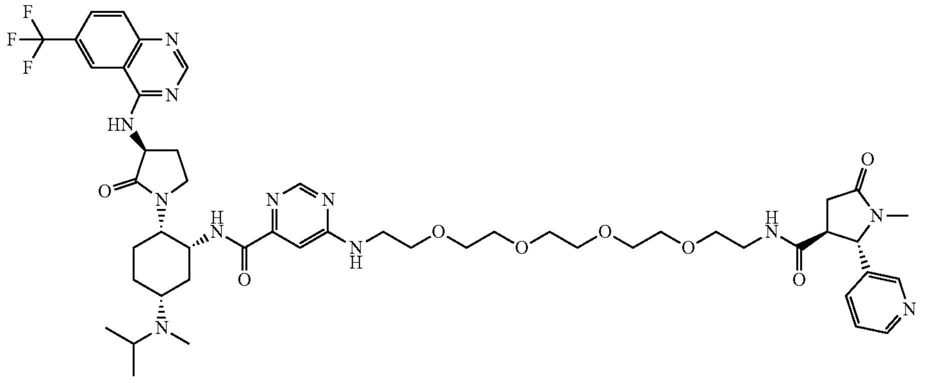 [SMILES: CC(C)N(C)[C@@H]1CC[C@H](N2CC[C@H](Nc3ncnc4ccc(C(F)(F)F)cc34)C2=O)[C@H](NC(=O)c2cc(NCCOCCOCCOCCOCCNC(=O)[C@H]3CC(=O)N(C)[C@@H]3c3cccnc3)ncn2)C1] |
| 128 | 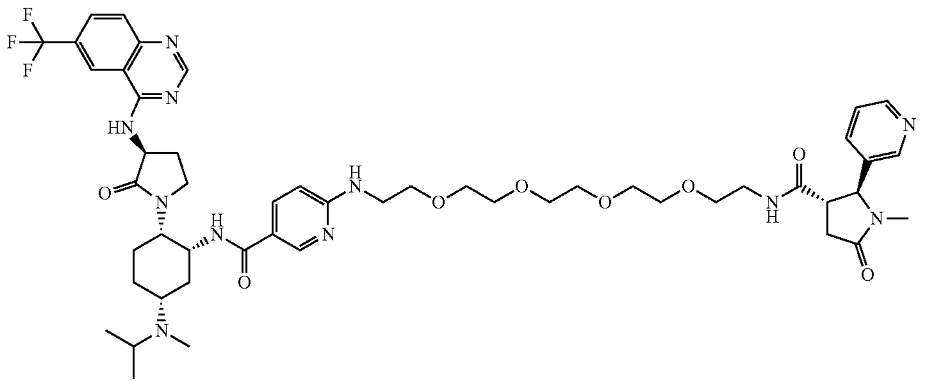 [SMILES: CC(C)N(C)[C@@H]1CC[C@H](N2CC[C@H](Nc3ncnc4ccc(C(F)(F)F)cc34)C2=O)[C@H](NC(=O)c2ccc(NCCOCCOCCOCCOCCNC(=O)[C@H]3CC(=O)N(C)[C@@H]3c3cccnc3)nc2)C1] |
| 129 | 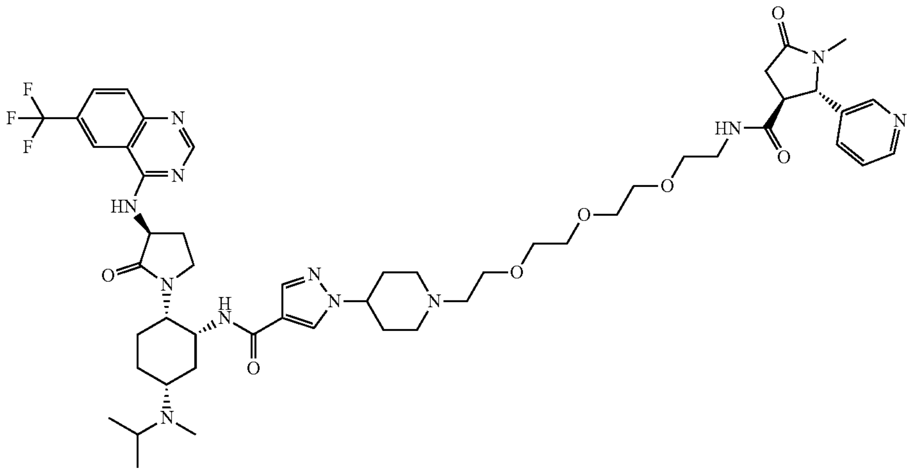 [SMILES: CC(C)N(C)[C@@H]1CC[C@H](N2CC[C@H](Nc3ncnc4ccc(C(F)(F)F)cc34)C2=O)[C@H](NC(=O)c2cnn(C3CCN(CCOCCOCCOCCNC(=O)[C@H]4CC(=O)N(C)[C@@H]4c4cccnc4)CC3)c2)C1] |

TABLE 1-continued
| Example | Structure |
| --- | --- |
| 130 | 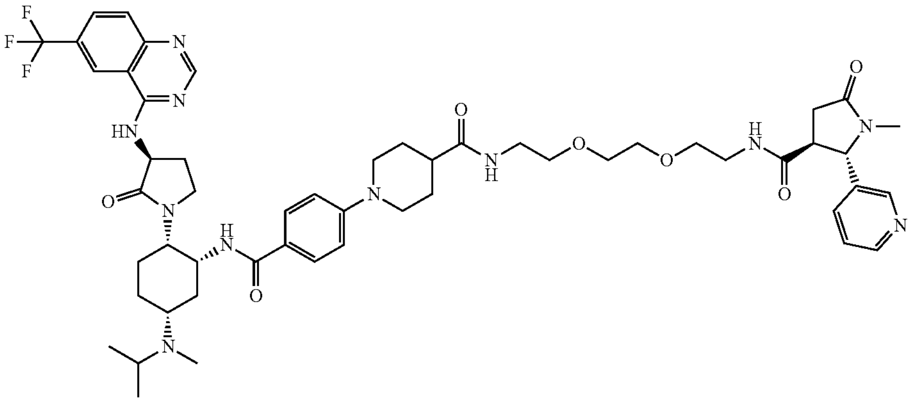 [SMILES: CC(C)N(C)[C@@H]1CC[C@H](N2CC[C@H](Nc3ncnc4ccc(C(F)(F)F)cc34)C2=O)[C@H](NC(=O)c2ccc(N3CCC(C(=O)NCCOCCOCCNC(=O)[C@H]4CC(=O)N(C)[C@@H]4c4cccnc4)CC3)cc2)C1] |
| 131 | 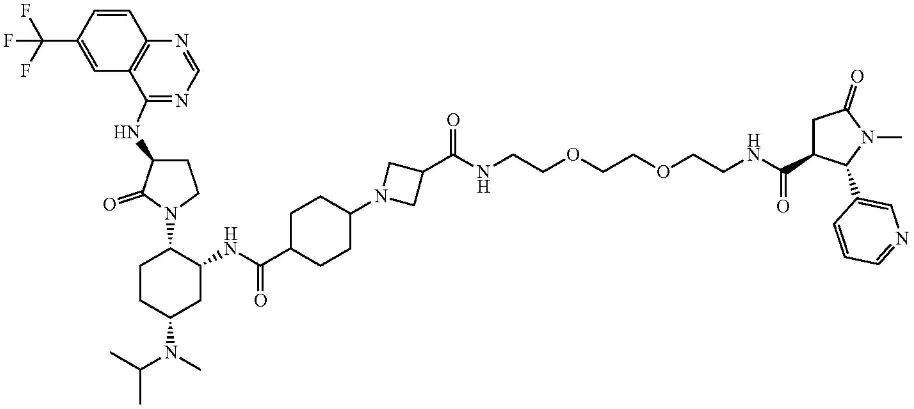 [SMILES: CC(C)N(C)[C@@H]1CC[C@H](N2CC[C@H](Nc3ncnc4ccc(C(F)(F)F)cc34)C2=O)[C@H](NC(=O)C2CCC(N3CC(C(=O)NCCOCCOCCNC(=O)[C@H]4CC(=O)N(C)[C@@H]4c4cccnc4)C3)CC2)C1] |
| 132 | 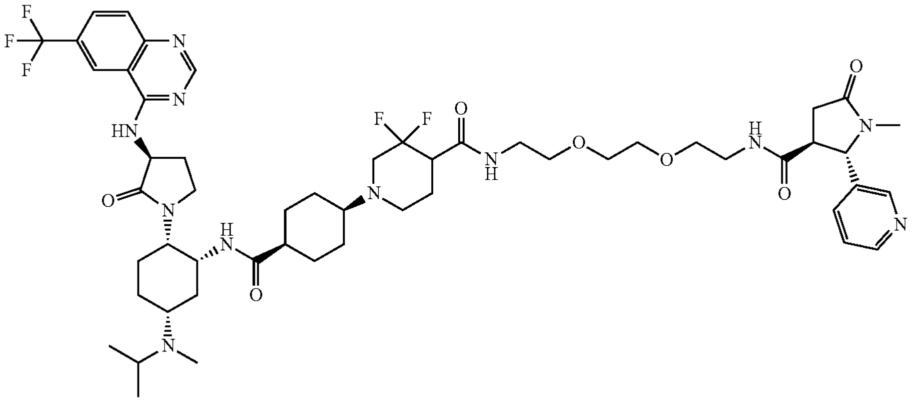 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](N3CCC(C(=O)NCCOCCOCCNC(=O)[C@H]4CC(=O)N(C)[C@@H]4c4cccnc4)C(F)(F)C3)CC2)C1] |

TABLE 1-continued
| Example | Structure |
|---|---|
| 133 | 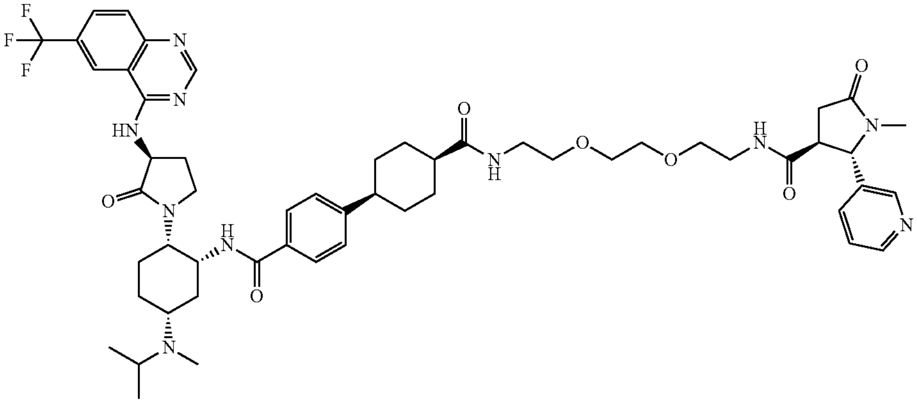 [SMILES: CC(C)N(C)[C@@H]1CC[C@H](N2CC[C@H](Nc3ncnc4ccc(C(F)(F)F)cc34)C2=O)[C@H](NC(=O)c2ccc([C@H]3CC[C@@H](C(=O)NCCOCCOCCNC(=O)[C@H]4CC(=O)N(C)[C@@H]4c4cccnc4)CC3)cc2)C1] |
| 134 | 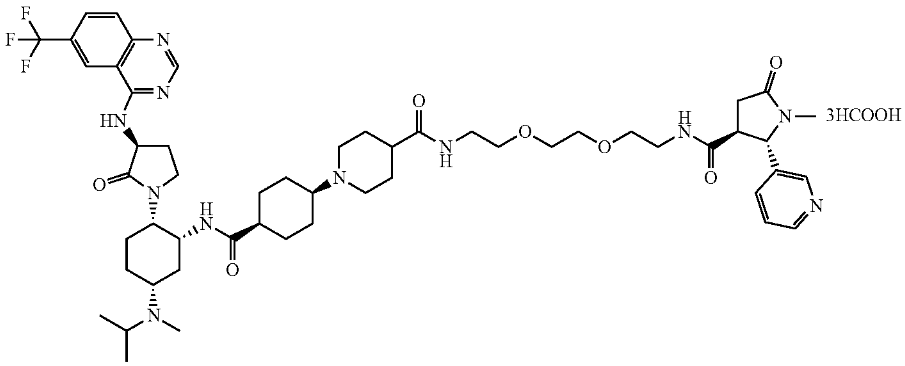 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](N3CCC(C(=O)NCCOCCOCCNC(=O)[C@H]4CC(=O)N(C)[C@@H]4c4cccnc4)CC3)CC2)C1] 3HCOOH |
| 135 | 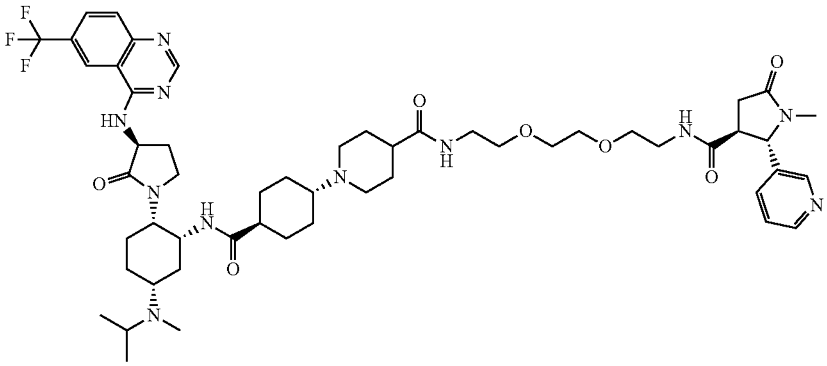 3HCOOH |
| 136 | 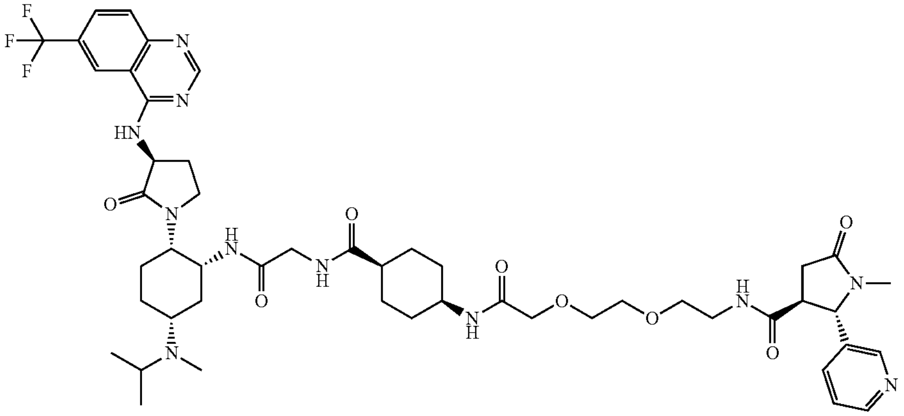 [SMILES: CC(C)N(C)[C@@H]1CC[C@H](N2CC[C@H](Nc3ncnc4ccc(C(F)(F)F)cc34)C2=O)[C@H](NC(=O)CNC(=O)[C@H]2CC[C@@H](NC(=O)COCCOCCNC(=O)[C@H]3CC(=O)N(C)[C@@H]3c3cccnc3)CC2)C1] |

TABLE 1-continued
| Example | Structure |
| --- | --- |
| 137 | 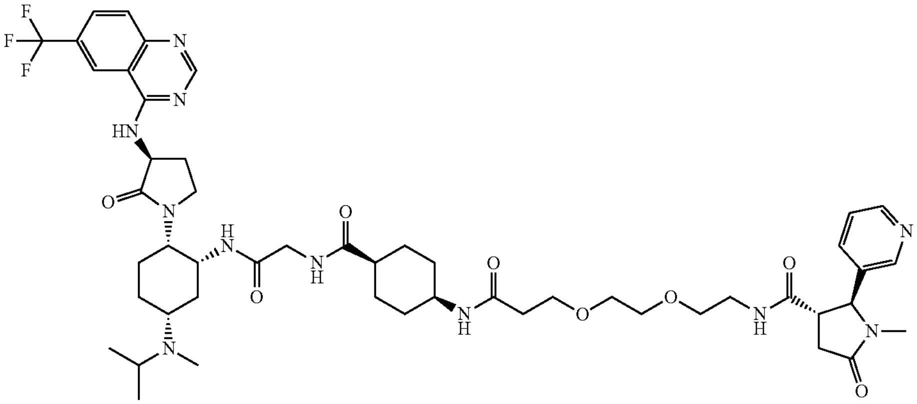 [SMILES: CC(C)N(C)[C@@H]1CC[C@H](N2CC[C@H](Nc3ncnc4ccc(C(F)(F)F)cc34)C2=O)[C@H](NC(=O)CNC(=O)[C@H]2CC[C@@H](NC(=O)CCOCCOCCNC(=O)[C@H]3CC(=O)N(C)[C@@H]3c3cccnc3)CC2)C1] |
| 138 | 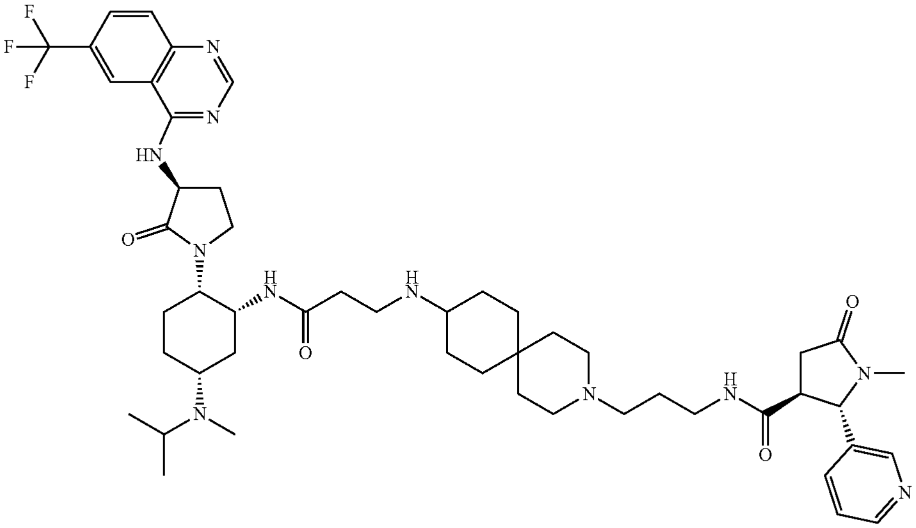 [SMILES: CC(C)N(C)[C@@H]1CC[C@H](N2CC[C@H](Nc3ncnc4ccc(C(F)(F)F)cc34)C2=O)[C@H](NC(=O)CCNC2CCC3(CC2)CCN(CCCNC(=O)[C@H]2CC(=O)N(C)[C@@H]2c2cccnc2)CC3)C1] |
| 139 | 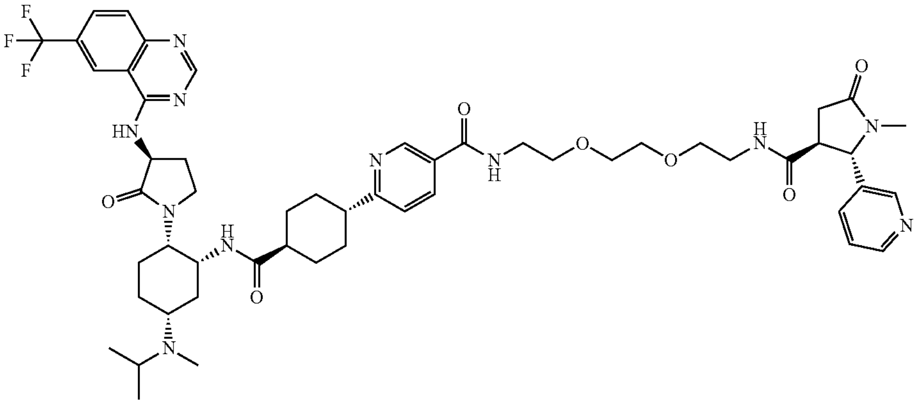 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](c3ccc(C(=O)NCCOCCOCCNC(=O)[C@H]4CC(=O)N(C)[C@@H]4c4cccnc4)cc3)CC2)C1] |

TABLE 1-continued
| Example | Structure |
| --- | --- |
| 140 | 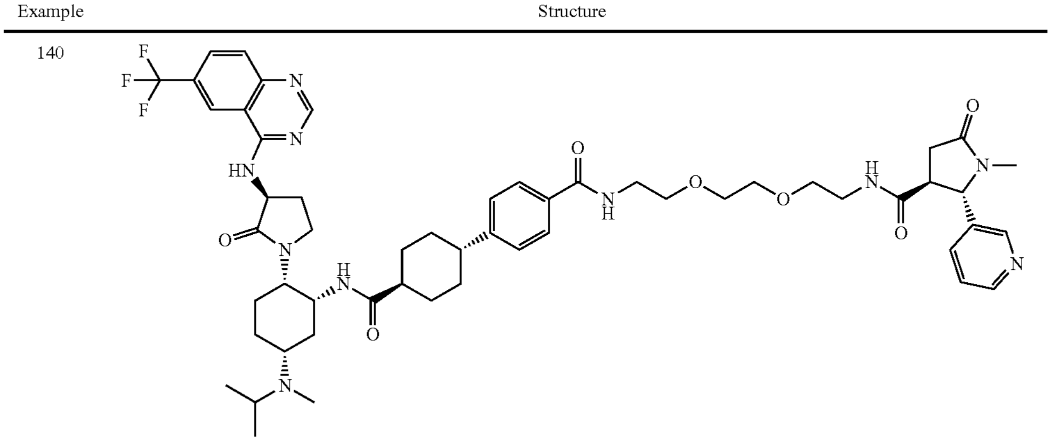 |
| 141 | 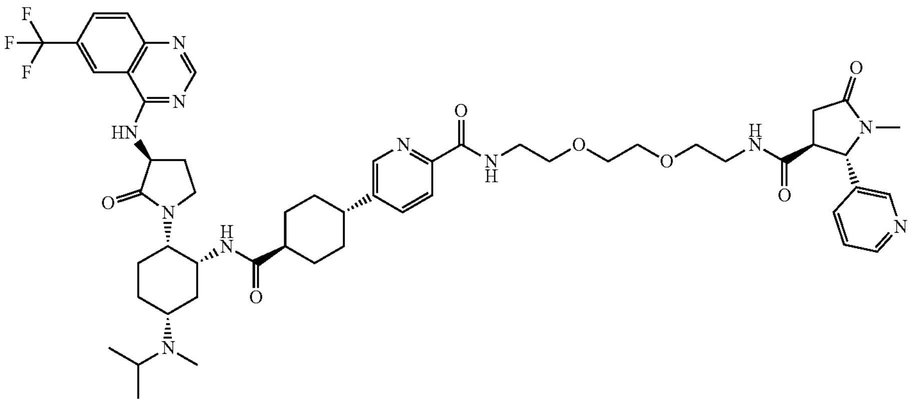 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](c3ccc(C(=O)NCCOCCOCCNC(=O)[C@H]4CC(=O)N(C)[C@@H]4c4cccnc4)nc3)CC2)C1] |
| 142 | 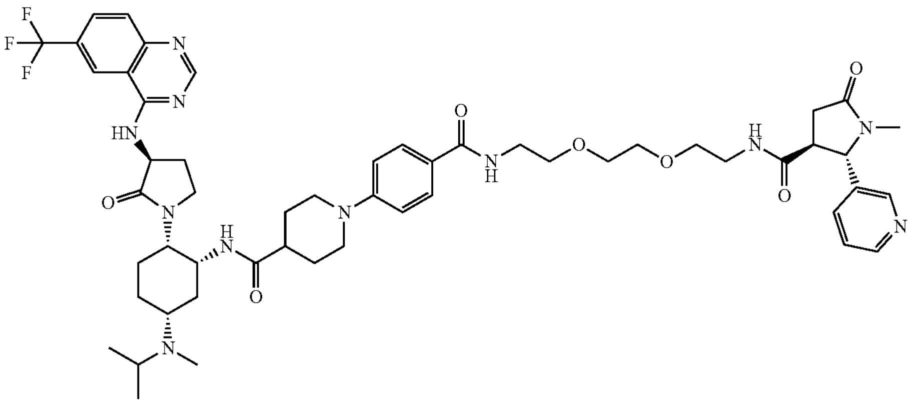 [SMILES: CC(C)N(C)[C@@H]1CC[C@H](N2CC[C@H](Nc3ncnc4ccc(C(F)(F)F)cc34)C2=O)[C@H](NC(=O)C2CCN(c3ccc(C(=O)NCCOCCOCCNC(=O)[C@H]4CC(=O)N(C)[C@@H]4c4cccnc4)cc3)CC2)C1] |
| 143 | 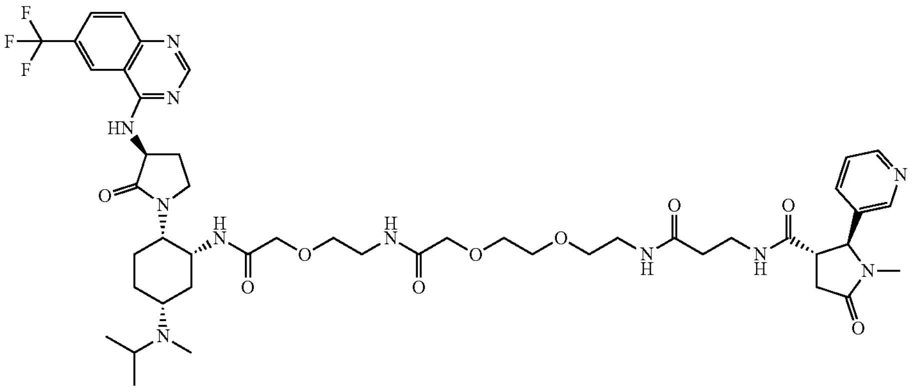 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)COCCOCCNC(=O)CCNC(=O)[C@H]2CC(=O)N(C)[C@@H]2c2cccnc2)C1] |

TABLE 1-continued
| Example | Structure |
| --- | --- |
| 144 | 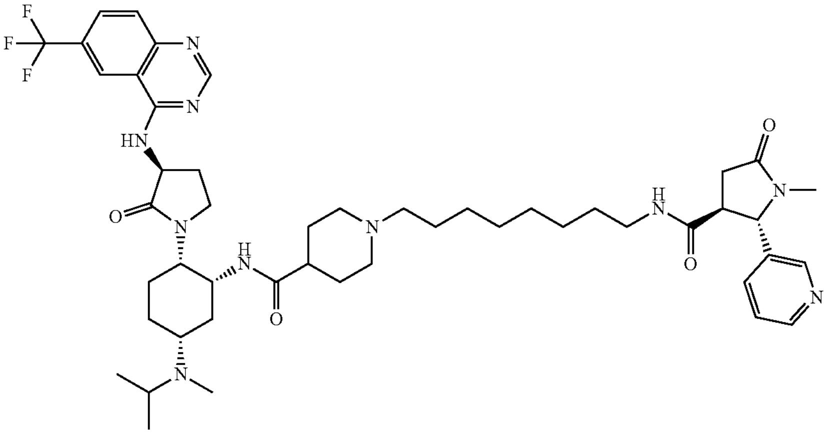 3HCOOH |
| 145 | 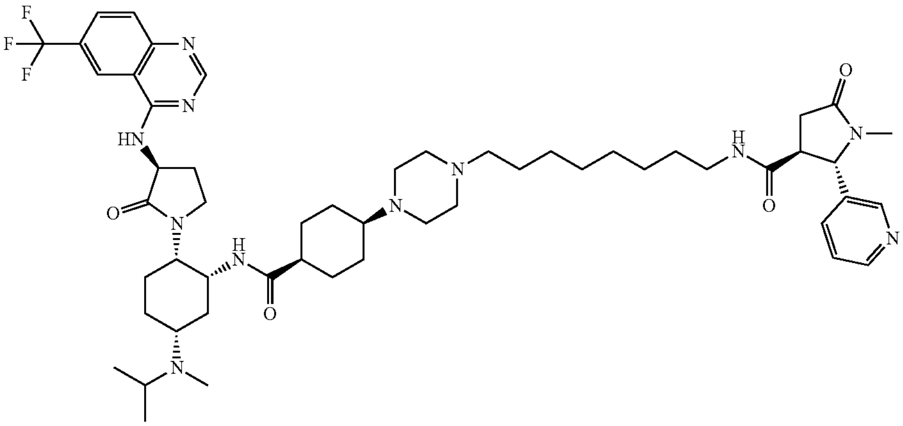 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](N3CCN(CCCCCCCCNC(=O)[C@H]4CC(=O)N(C)[C@@H]4c4cccnc4)CC3)CC2)C1] |
| 146 | 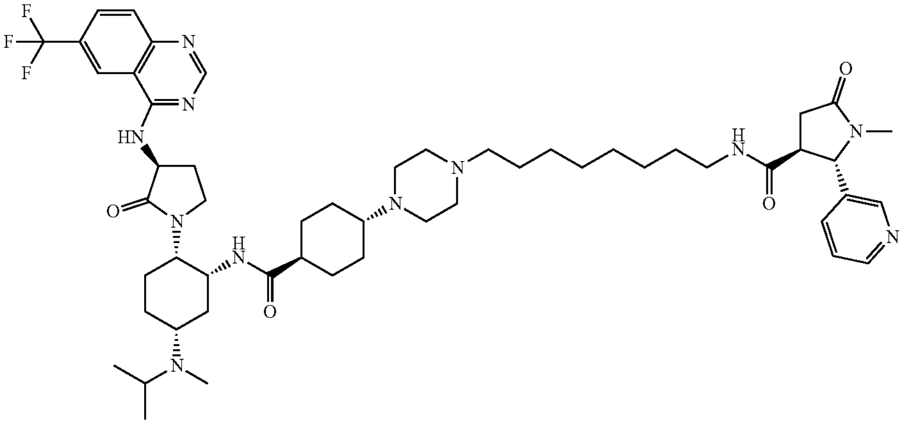 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(CCCCCCCCNC(=O)[C@H]4CC(=O)N(C)[C@@H]4c4cccnc4)CC3)CC2)C1] |

TABLE 1-continued
| Example | Structure |
| --- | --- |
| 147 | 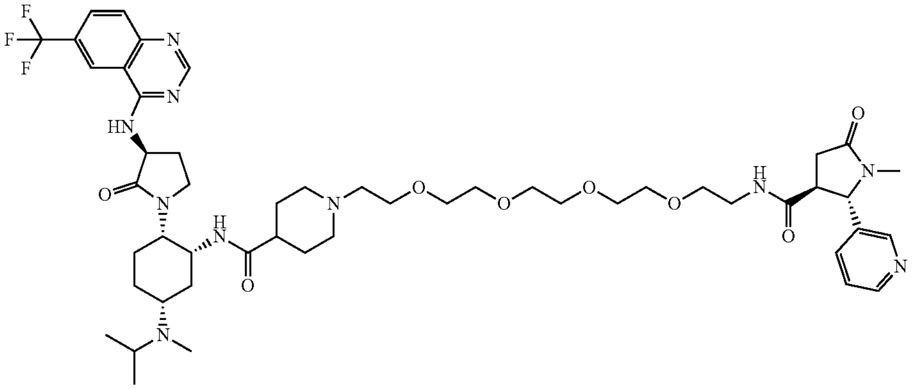 [SMILES: CC(C)N(C)[C@@H]1CC[C@H](N2CC[C@H](Nc3ncnc4ccc(C(F)(F)F)cc34)C2=O)[C@H](NC(=O)C2CCN(CCOCCOCCOCCOCCNC(=O)[C@H]3CC(=O)N(C)[C@@H]3c3cccnc3)CC2)C1] |
| 148 | 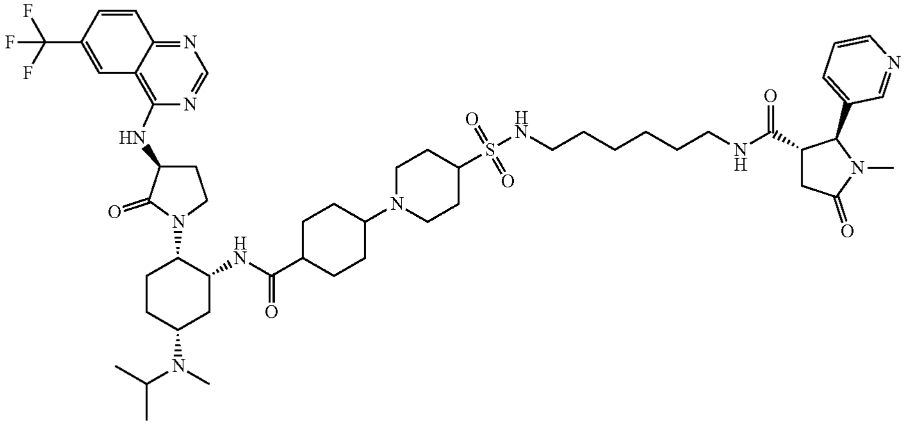 [SMILES: CC(C)N(C)[C@@H]1CC[C@H](N2CC[C@H](Nc3ncnc4ccc(C(F)(F)F)cc34)C2=O)[C@H](NC(=O)C2CCC(N3CCC(S(=O)(=O)NCCCCCCNC(=O)[C@H]4CC(=O)N(C)[C@@H]4c4cccnc4)CC3)CC2)C1] |
| 149 | 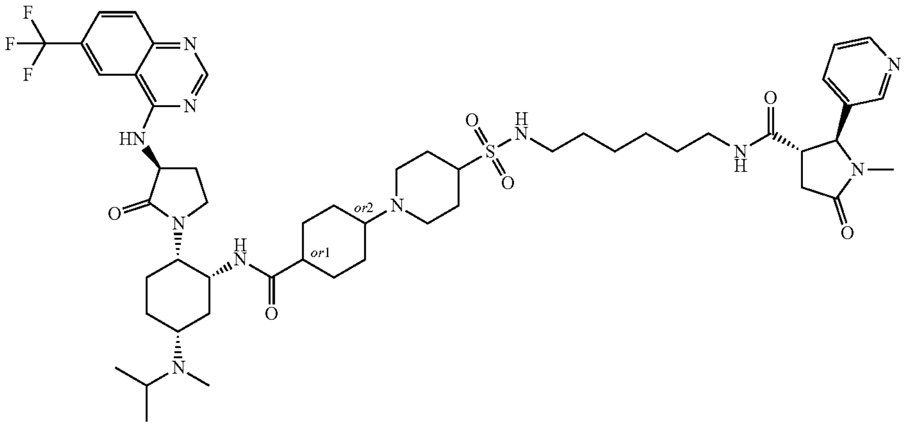 [SMILES: CC(C)N(C)[C@@H]1CC[C@H](N2CC[C@H](Nc3ncnc4ccc(C(F)(F)F)cc34)C2=O)[C@H](NC(=O)C2CCC(N3CCC(S(=O)(=O)NCCCCCCNC(=O)[C@H]4CC(=O)N(C)[C@@H]4c4cccnc4)CC3)CC2)C1] |

TABLE 1-continued
| Example | Structure |
| --- | --- |
| 150 | 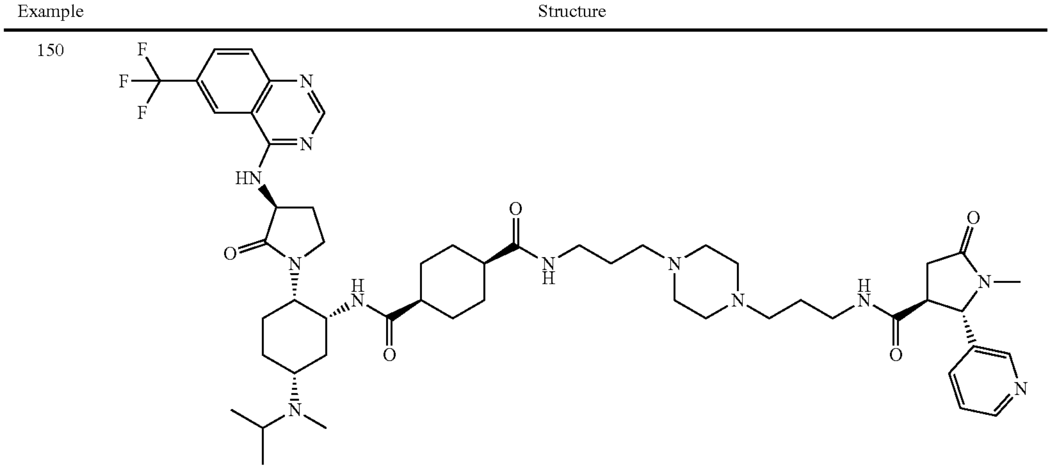 |
| 151 | 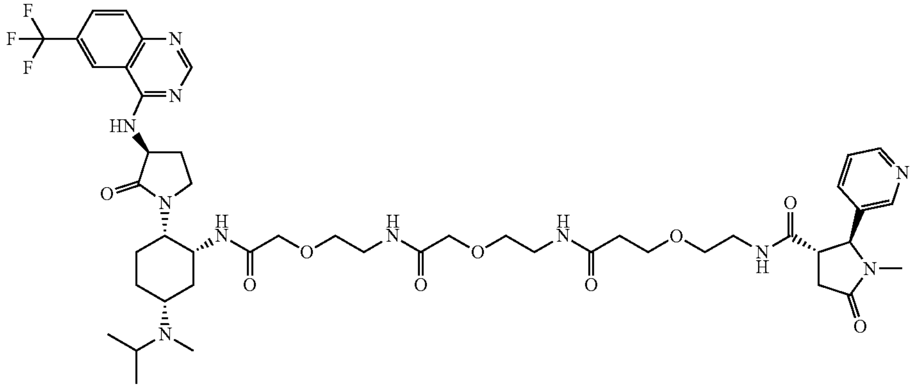 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)COCCNC(=O)CCOCCNC(=O)[C@H]2CC(=O)N(C)[C@@H]2c2cccnc2)C1] |
| 152 | 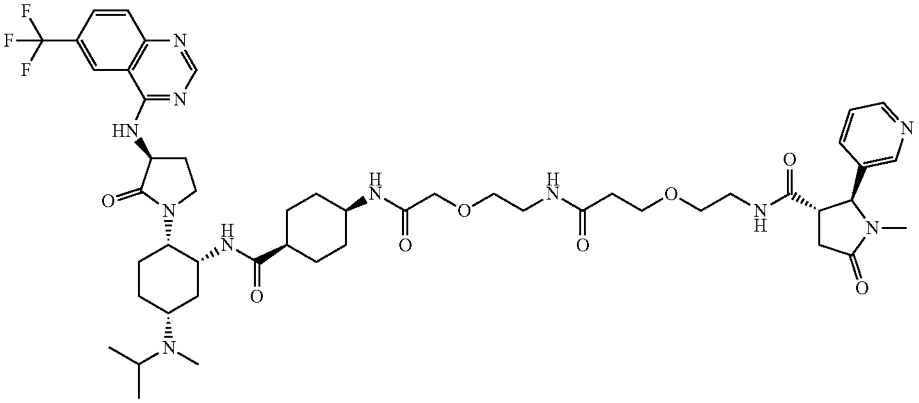 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCNC(=O)CCOCCNC(=O)[C@H]3CC(=O)N(C)[C@@H]3c3cccnc3)CC2)C1] |
| 153 | 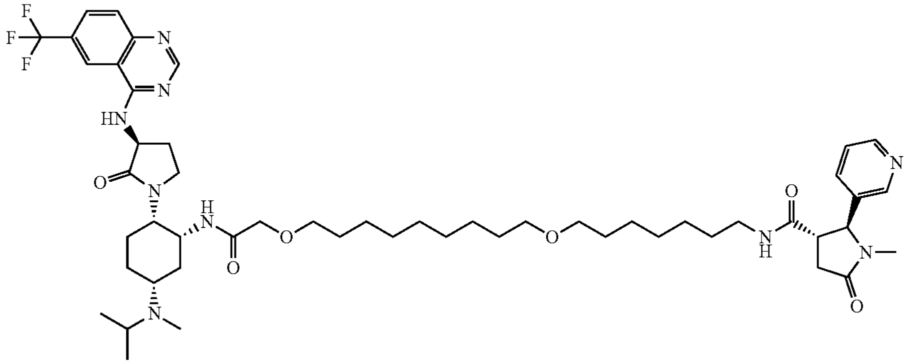 [SMILES: CC(C)N(C)[C@@H]1CC[C@H](N2CC[C@H](Nc3ncnc4ccc(C(F)(F)F)cc34)C2=O)[C@H](NC(=O)COCCCCCCCCCOCCCCCCCNC(=O)[C@H]2CC(=O)N(C)[C@@H]2c2cccnc2)C1] |

TABLE 1-continued
| Example | Structure |
| --- | --- |
| 154 | 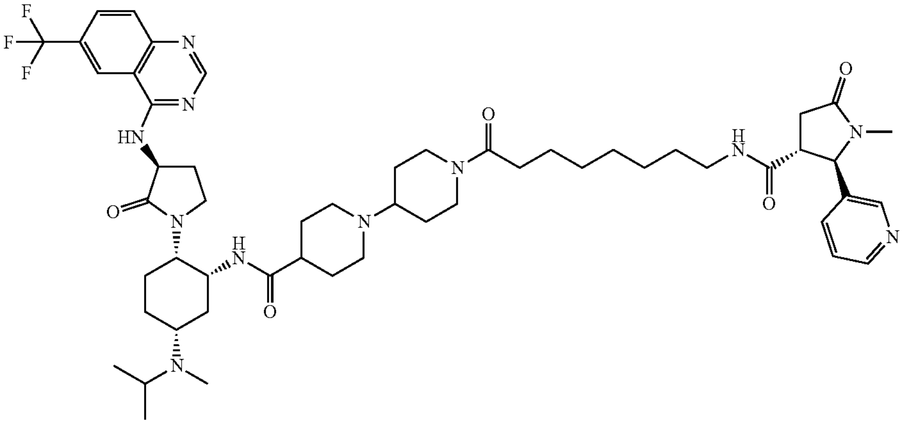 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C(=O)CCCCCCCNC(=O)[C@@H]4CC(=O)N(C)[C@H]4c4cccnc4)CC3)CC2)C1] |
| 155 | 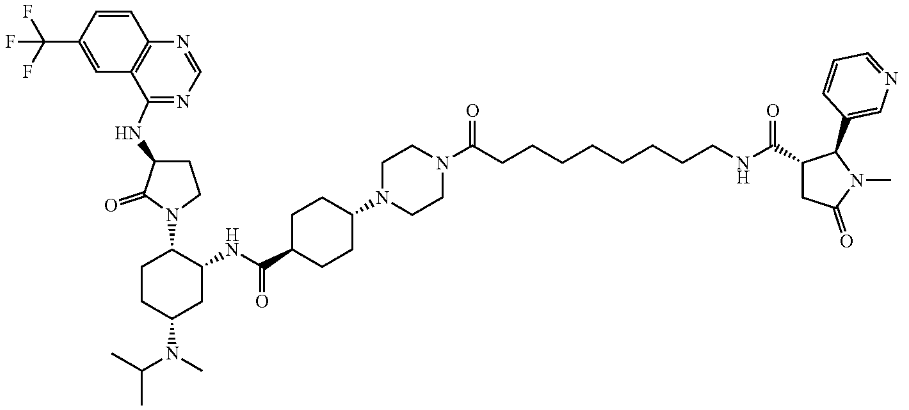 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(C(=O)CCCCCCCCNC(=O)[C@H]4CC(=O)N(C)[C@@H]4c4cccnc4)CC3)CC2)C1] |
| 156 | 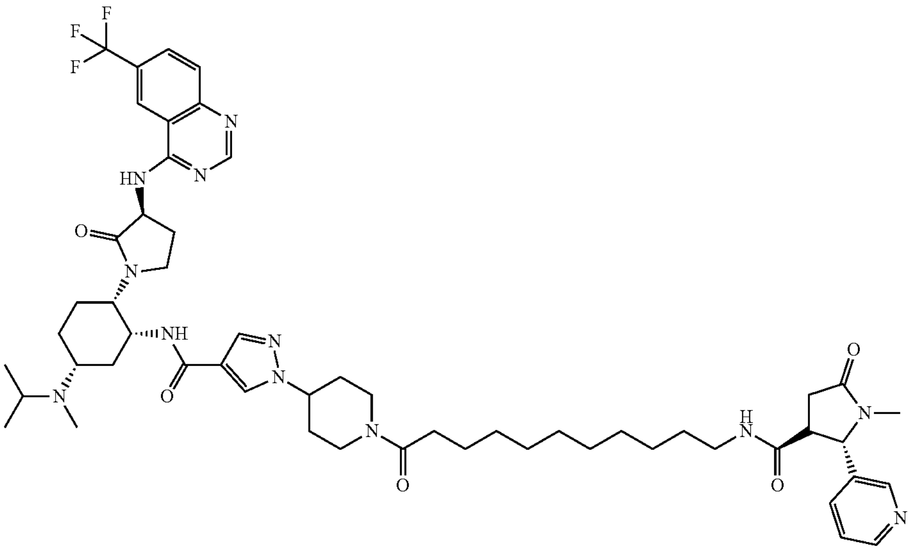 |

TABLE 1-continued
| Example | Structure |
|---|---|
| 157 | 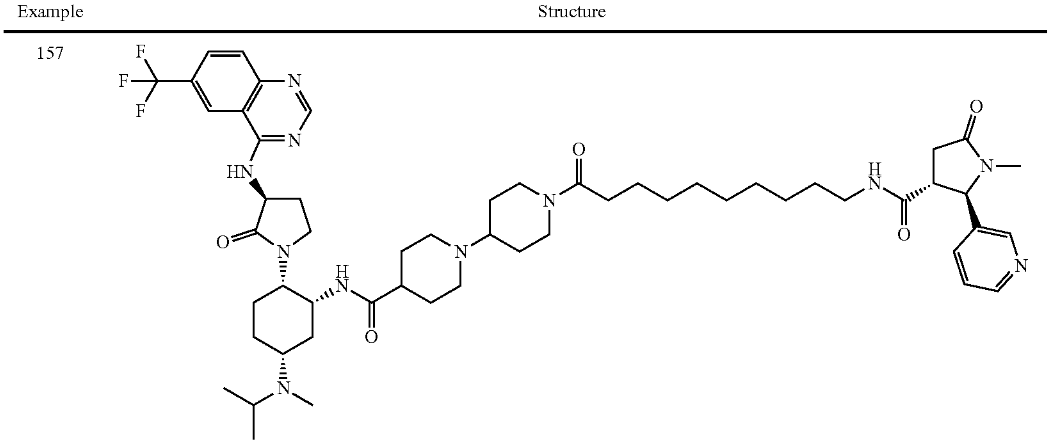 |
| 158 | 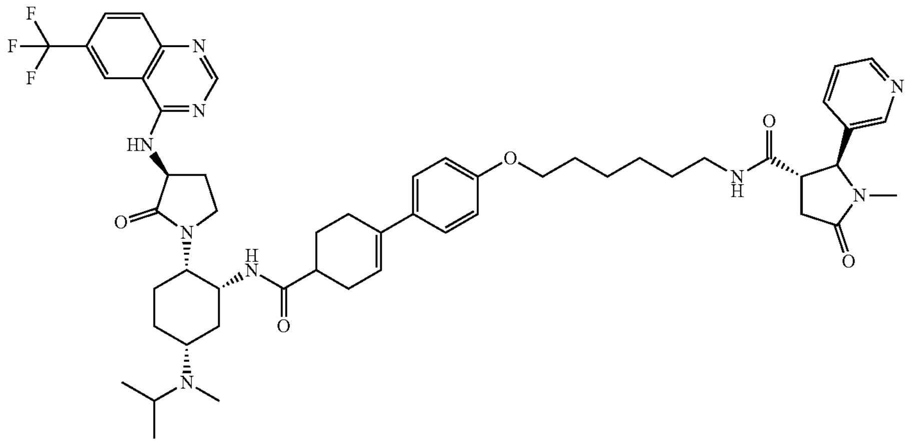 [SMILES: CC(C)N(C)[C@@H]1CC[C@H](N2CC[C@H](Nc3ncnc4ccc(C(F)(F)F)cc34)C2=O)[C@H](NC(=O)C2CC=C(c3ccc(OCCCCCCNC(=O)[C@H]4CC(=O)N(C)[C@@H]4c4cccnc4)cc3)CC2)C1] |
| 159 | 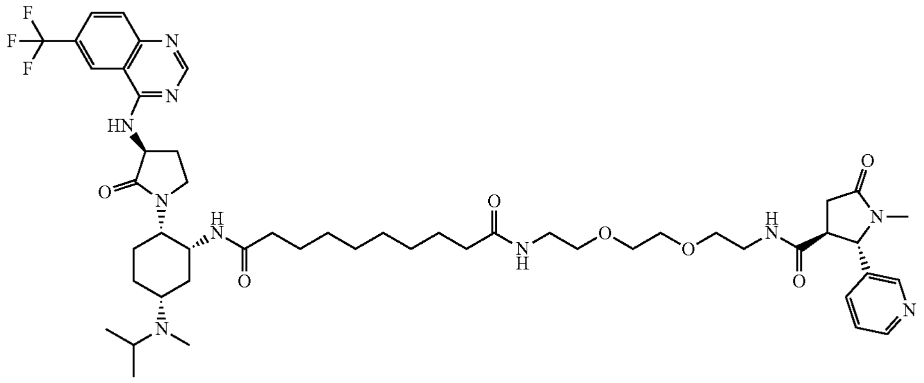 [SMILES: CC(C)N(C)[C@@H]1CC[C@H](N2CC[C@H](Nc3ncnc4ccc(C(F)(F)F)cc34)C2=O)[C@H](NC(=O)CCCCCCCCC(=O)NCCOCCOCCNC(=O)[C@H]2CC(=O)N(C)[C@@H]2c2cccnc2)C1] |
| 160 | 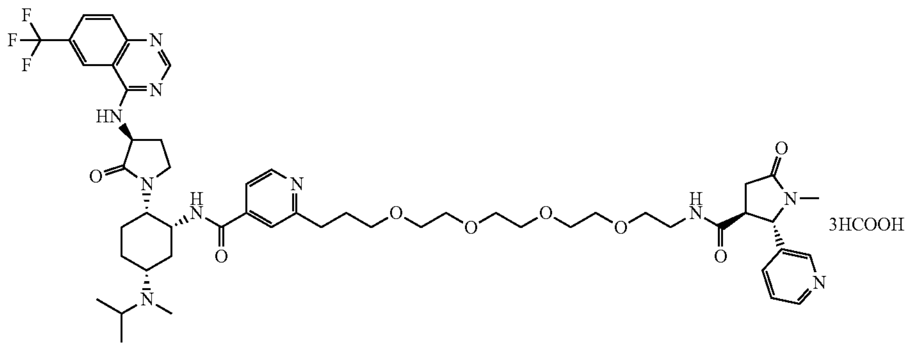 [SMILES: CC(C)N(C)[C@@H]1CC[C@H](N2CC[C@H](Nc3ncnc4ccc(C(F)(F)F)cc34)C2=O)[C@H](NC(=O)c2ccnc(CCCOCCOCCOCCOCCNC(=O)[C@H]3CC(=O)N(C)[C@@H]3c3cccnc3)c2)C1] |

TABLE 1-continued
| Example | Structure |
| --- | --- |
| 161 | 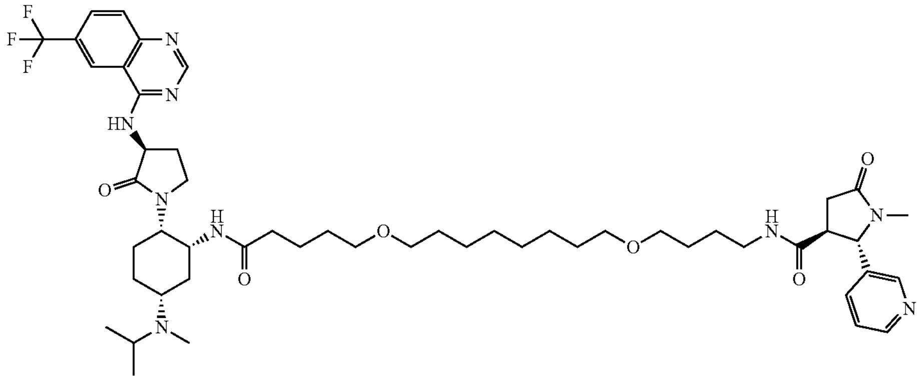 [SMILES: CC(C)N(C)[C@@H]1CC[C@H](N2CC[C@H](Nc3ncnc4ccc(C(F)(F)F)cc34)C2=O)[C@H](NC(=O)CCCCOCCCCCCCCOCCCCNC(=O)[C@H]2CC(=O)N(C)[C@@H]2c2cccnc2)C1] |
| 162 | 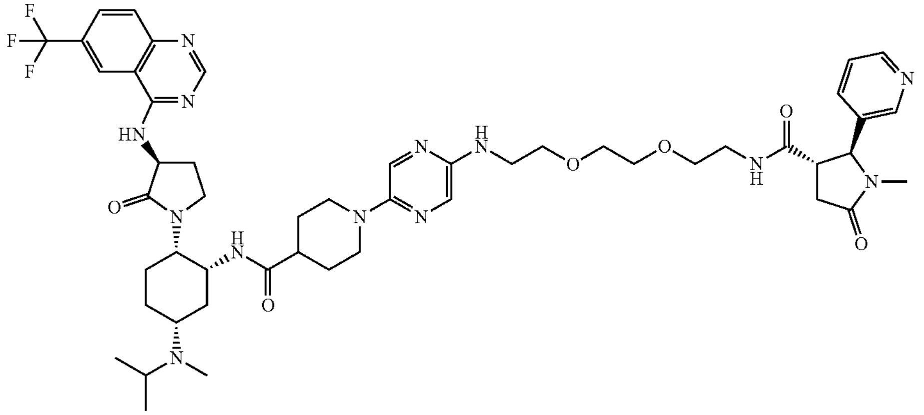 [SMILES: CC(C)N(C)[C@@H]1CC[C@H](N2CC[C@H](Nc3ncnc4ccc(C(F)(F)F)cc34)C2=O)[C@H](NC(=O)C2CCN(c3cnc(NCCOCCOCCNC(=O)[C@H]4CC(=O)N(C)[C@@H]4c4cccnc4)cn3)CC2)C1] |
| 163 | 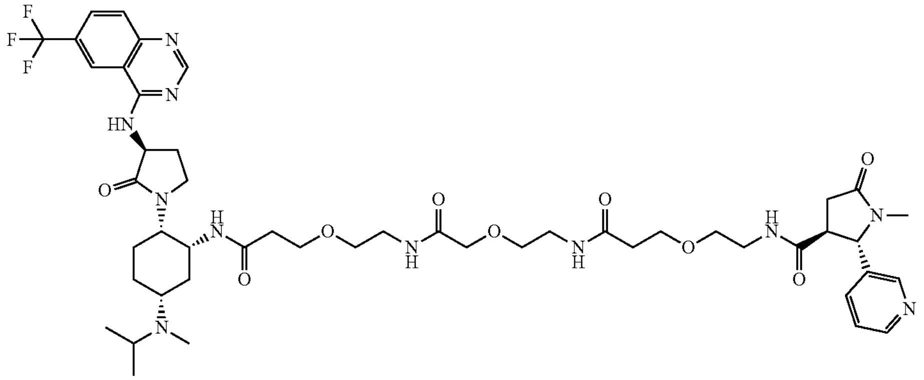 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)COCCNC(=O)CCOCCNC(=O)[C@H]2CC(=O)N(C)[C@@H]2c2cccnc2)C1] |
| 164 | 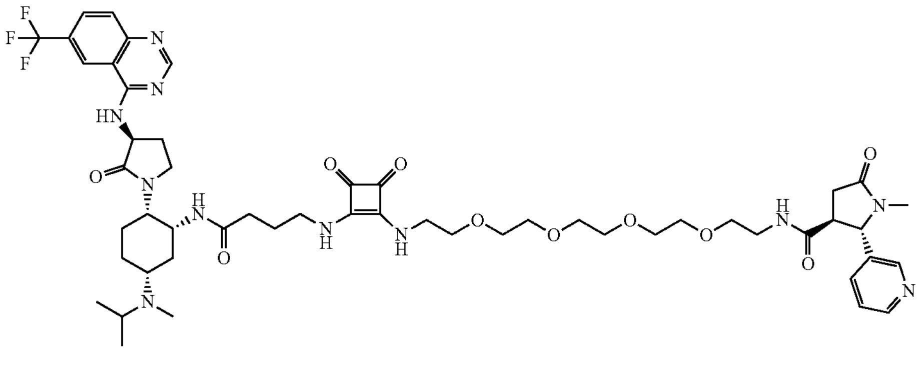 [SMILES: CC(C)N(C)[C@@H]1CC[C@H](N2CC[C@H](Nc3ncnc4ccc(C(F)(F)F)cc34)C2=O)[C@H](NC(=O)CCCNc2c(NCCOCCOCCOCCOCCNC(=O)[C@H]3CC(=O)N(C)[C@@H]3c3cccnc3)c(=O)c2=O)C1] |

TABLE 1-continued
| Example | Structure |
|---|---|
| 165 | 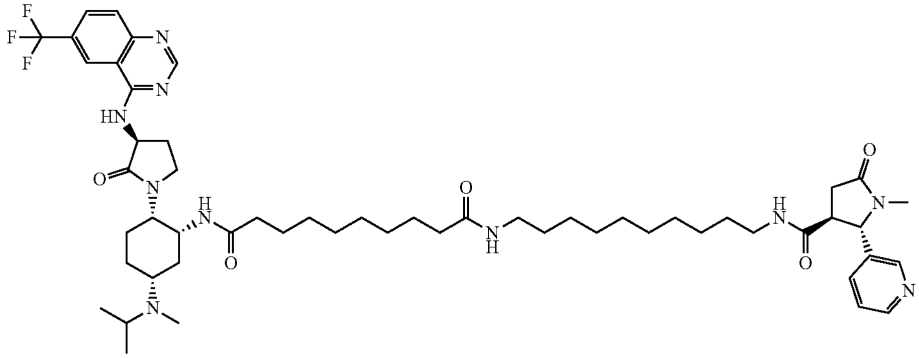 [SMILES: CC(C)N(C)[C@@H]1CC[C@H](N2CC[C@H](Nc3ncnc4ccc(C(F)(F)F)cc34)C2=O)[C@H](NC(=O)CCCCCCCCC(=O)NCCCCCCCCCCNC(=O)[C@H]2CC(=O)N(C)[C@@H]2c2cccnc2)C1] |
| 166 | 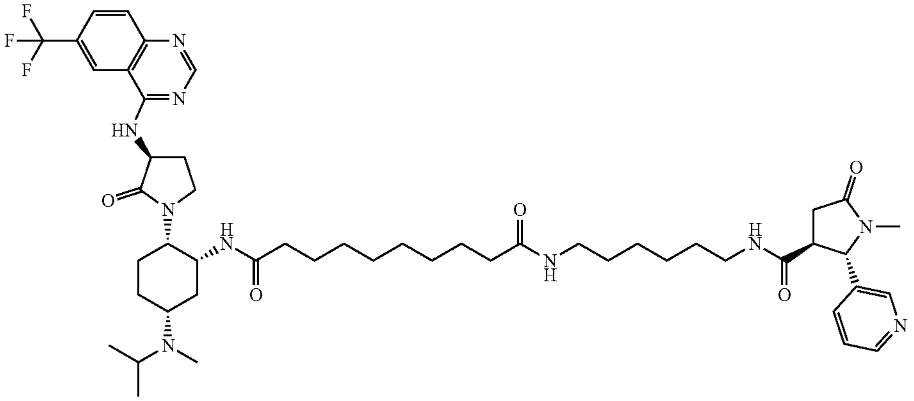 [SMILES: CC(C)N(C)[C@@H]1CC[C@H](N2CC[C@H](Nc3ncnc4ccc(C(F)(F)F)cc34)C2=O)[C@H](NC(=O)CCCCCCCCC(=O)NCCCCCCNC(=O)[C@H]2CC(=O)N(C)[C@@H]2c2cccnc2)C1] |
| 167 | 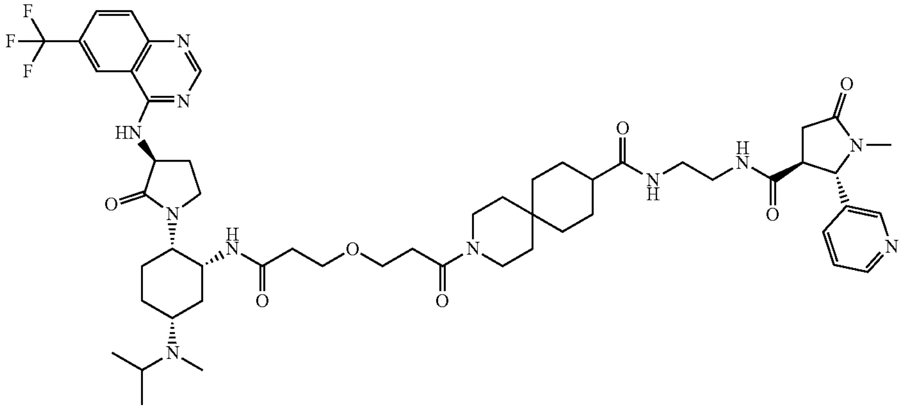 [SMILES: CC(C)N(C)[C@@H]1CC[C@H](N2CC[C@H](Nc3ncnc4ccc(C(F)(F)F)cc34)C2=O)[C@H](NC(=O)CCOCCC(=O)N2CCC3(CCC(C(=O)NCCNC(=O)[C@H]4CC(=O)N(C)[C@@H]4c4cccnc4)CC3)CC2)C1] |
| 168 | 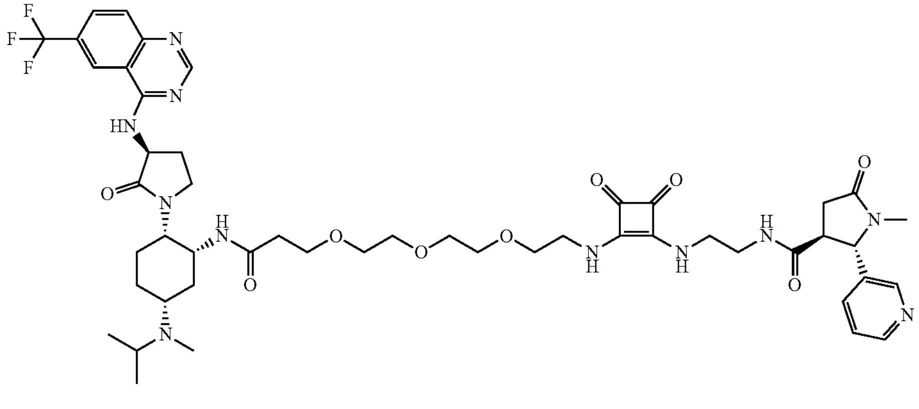 [SMILES: CC(C)N(C)[C@@H]1CC[C@H](N2CC[C@H](Nc3ncnc4ccc(C(F)(F)F)cc34)C2=O)[C@H](NC(=O)CCOCCOCCOCCNc2c(NCCNC(=O)[C@H]3CC(=O)N(C)[C@@H]3c3cccnc3)c(=O)c2=O)C1] |

TABLE 1-continued
| Example | Structure |
| --- | --- |
| 169 | 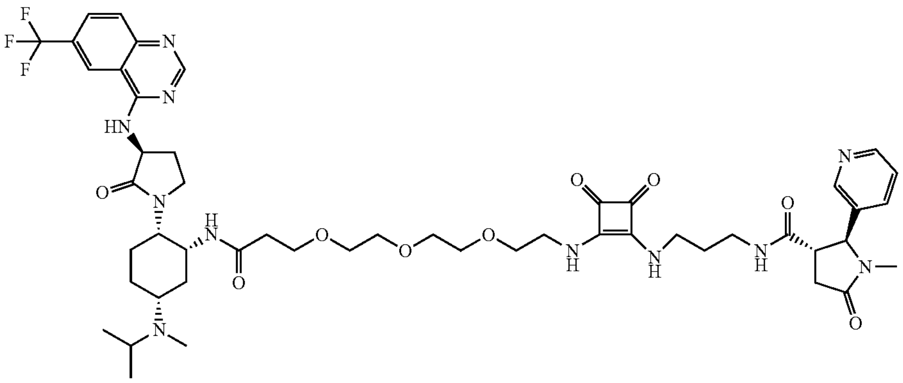 [SMILES: CC(C)N(C)[C@@H]1CC[C@H](N2CC[C@H](Nc3ncnc4ccc(C(F)(F)F)cc34)C2=O)[C@H](NC(=O)CCOCCOCCOCCNc2c(NCCCNC(=O)[C@H]3CC(=O)N(C)[C@@H]3c3cccnc3)c(=O)c2=O)C1] |
| 170 | 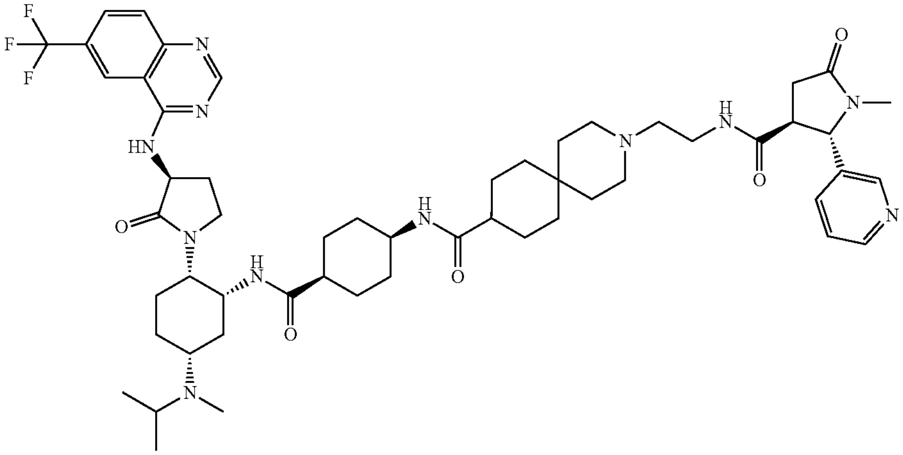 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CC3)CCN(CCNC(=O)[C@H]3CC(=O)N(C)[C@@H]3c3cccnc3)CC4)CC2)C1] |
| 171 | 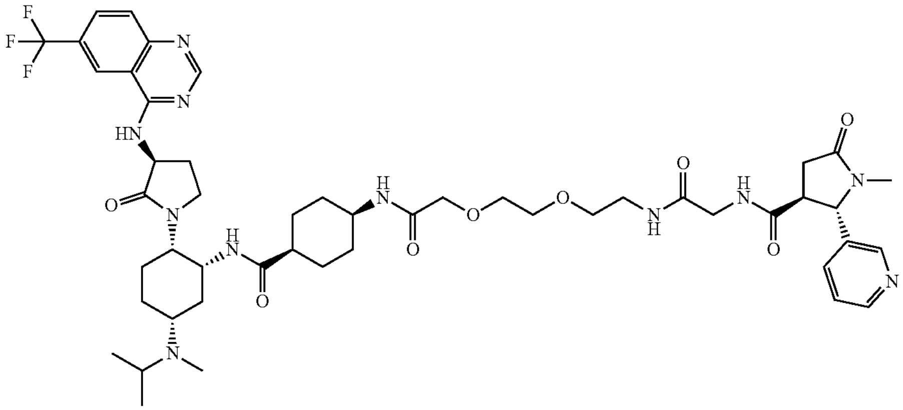 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCOCCNC(=O)CNC(=O)[C@H]3CC(=O)N(C)[C@@H]3c3cccnc3)CC2)C1] |

TABLE 1-continued
| Example | Structure |
|---|---|
| 172 | 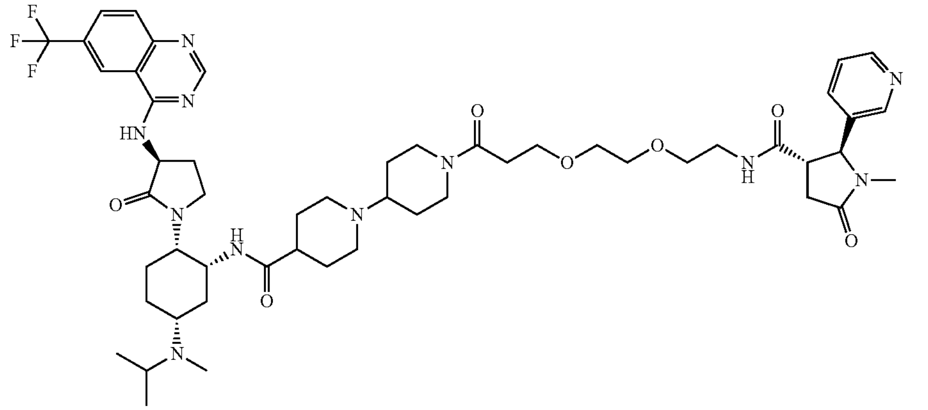 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C(=O)CCOCCOCCNC(=O)[C@H]4CC(=O)N(C)[C@@H]4c4cccnc4)CC3)CC2)C1] |
| 173 | 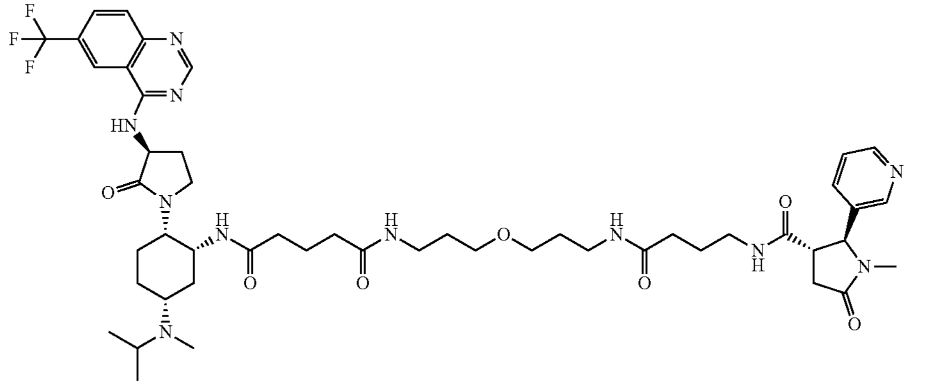 [SMILES: CC(C)N(C)[C@@H]1CC[C@H](N2CC[C@H](Nc3ncnc4ccc(C(F)(F)F)cc34)C2=O)[C@H](NC(=O)CCCC(=O)NCCCOCCCNC(=O)CCCNC(=O)[C@H]2CC(=O)N(C)[C@@H]2c2cccnc2)C1] |
| 175 | 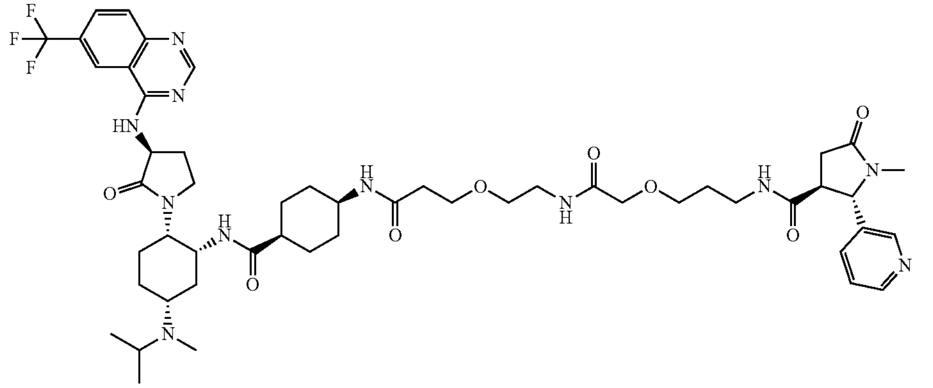 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)COCCCNC(=O)[C@H]3CC(=O)N(C)[C@@H]3c3cccnc3)CC2)C1] |
| 176 | 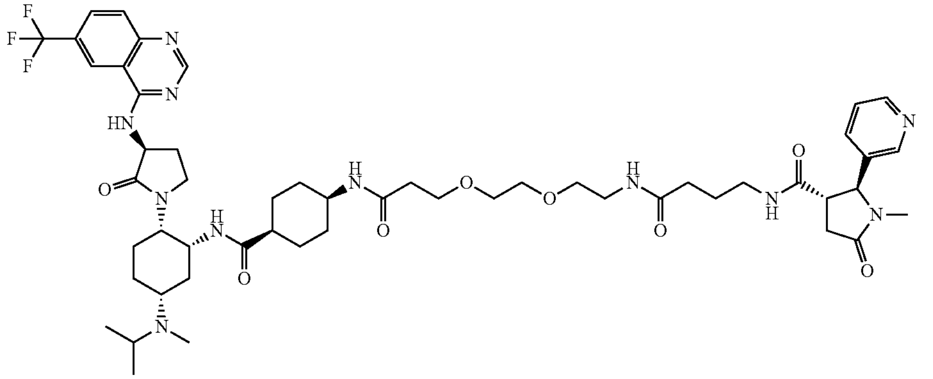 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCNC(=O)CCCNC(=O)[C@H]3CC(=O)N(C)[C@@H]3c3cccnc3)CC2)C1] |

TABLE 1-continued
| Example | Structure |
| --- | --- |
| 177 | 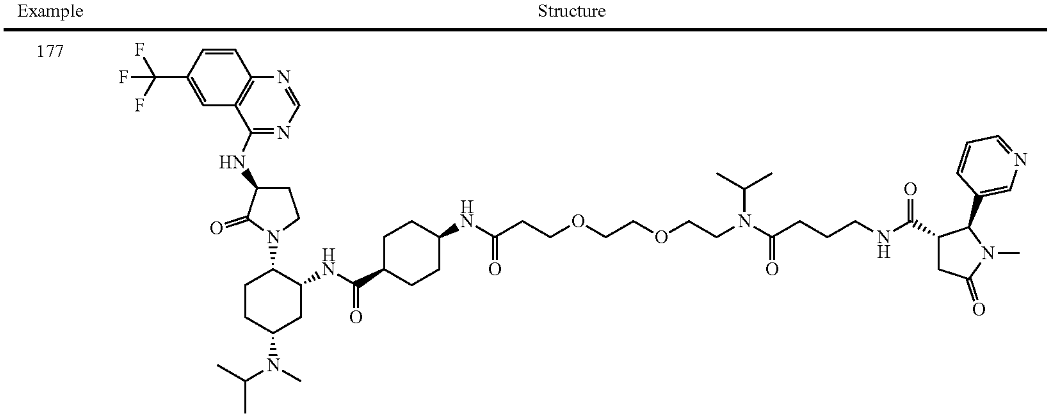 |
| 178 | 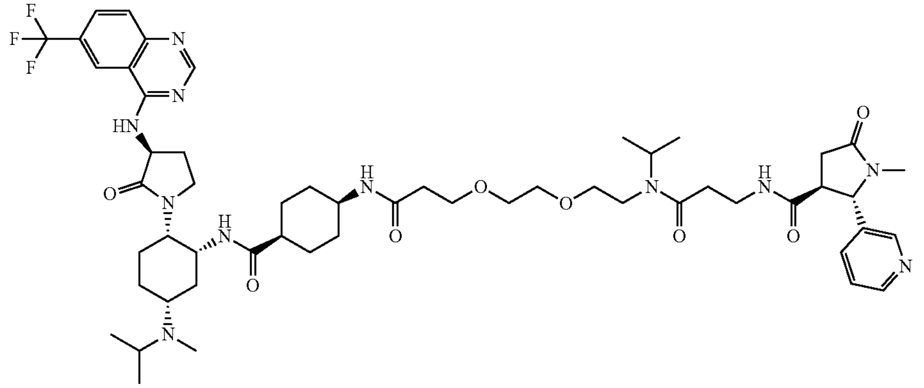 [SMILES: CC(C)N(CCOCCOCCC(=O)N[C@H]1CC[C@@H](C(=O)N[C@@H]2C[C@H](N(C)C(C)C)CC[C@@H]2N2CC[C@H](Nc3ncnc4ccc(C(F)(F)F)cc34)C2=O)CC1)C(=O)CCNC(=O)[C@H]1CC(=O)N(C)[C@@H]1c1cccnc1] |
| 179 | 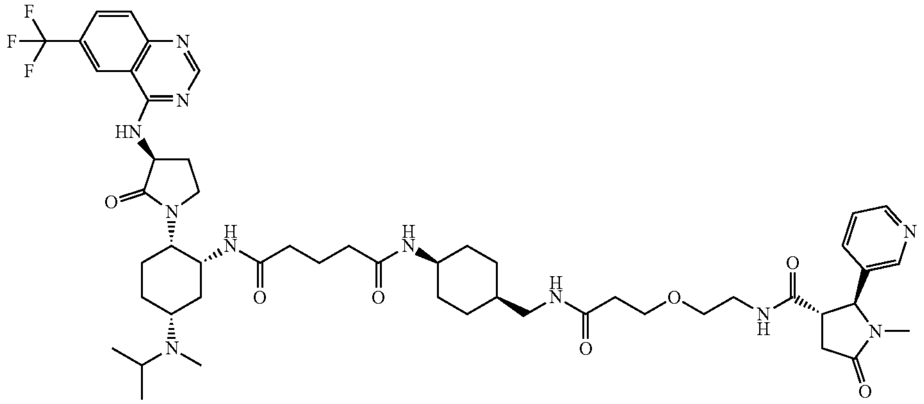 [SMILES: CC(C)N(C)[C@@H]1CC[C@H](N2CC[C@H](Nc3ncnc4ccc(C(F)(F)F)cc34)C2=O)[C@H](NC(=O)CCCC(=O)N[C@H]2CC[C@@H](CNC(=O)CCOCCNC(=O)[C@H]3CC(=O)N(C)[C@@H]3c3cccnc3)CC2)C1] |
| 180 | 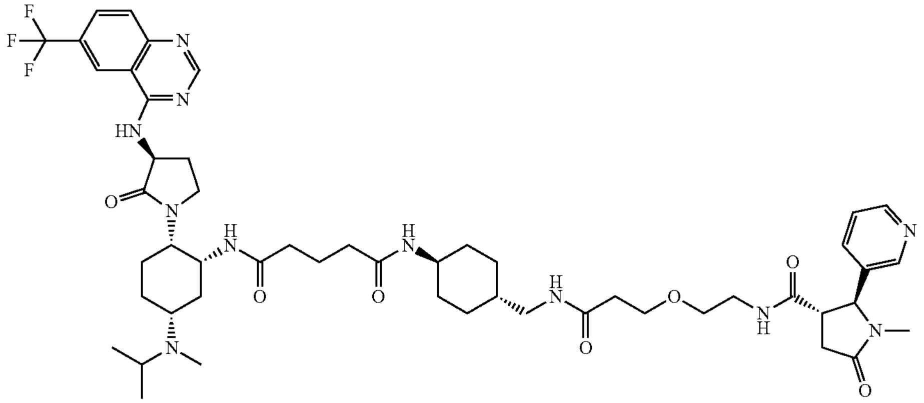 [SMILES: CC(C)N(C)[C@@H]1CC[C@H](N2CC[C@H](Nc3ncnc4ccc(C(F)(F)F)cc34)C2=O)[C@H](NC(=O)CCCC(=O)N[C@H]2CC[C@H](CNC(=O)CCOCCNC(=O)[C@H]3CC(=O)N(C)[C@@H]3c3cccnc3)CC2)C1] |

TABLE 1-continued
| Example | Structure |
| --- | --- |
| 181 | 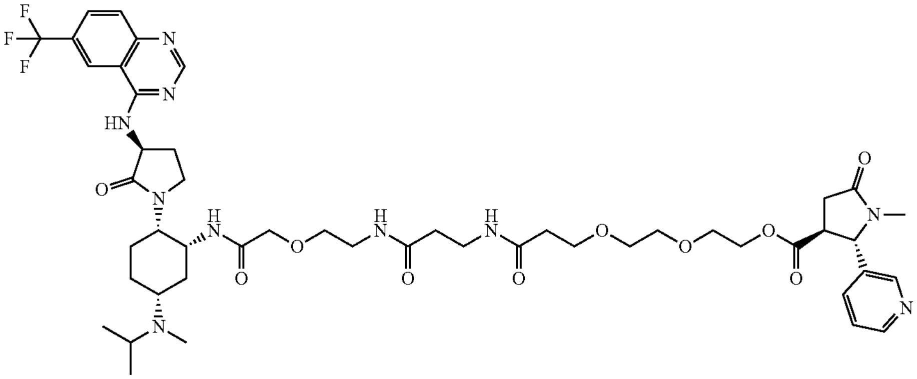 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCNC(=O)CCOCCOCCOC(=O)[C@H]2CC(=O)N(C)[C@@H]2c2cccnc2)C1] |
| 182 | 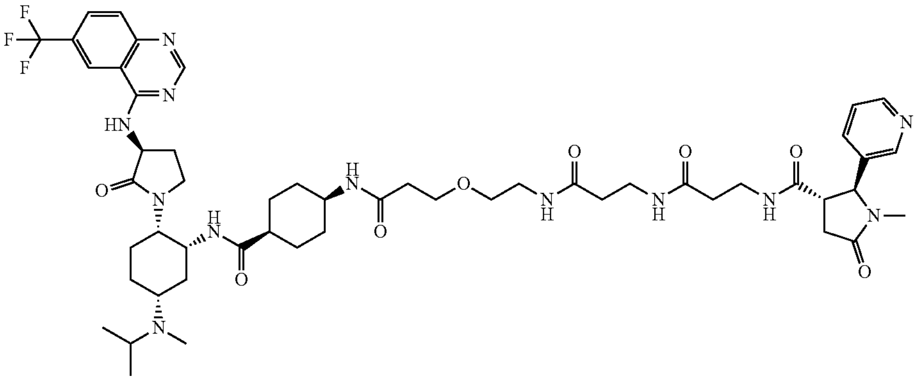 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCNC(=O)CCNC(=O)[C@H]3CC(=O)N(C)[C@@H]3c3cccnc3)CC2)C1] |
| 183 | 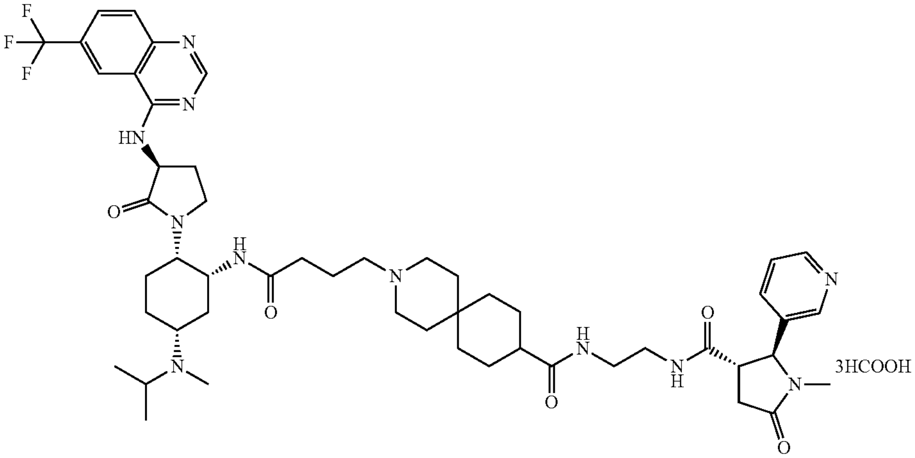 [SMILES: CC(C)N(C)[C@@H]1CC[C@H](N2CC[C@H](Nc3ncnc4ccc(C(F)(F)F)cc34)C2=O)[C@H](NC(=O)CCCN2CCC3(CCC(C(=O)NCCNC(=O)[C@H]4CC(=O)N(C)[C@@H]4c4cccnc4)CC3)CC2)C1] 3HCOOH |

TABLE 1-continued
| Example | Structure |
| --- | --- |
| 184 | 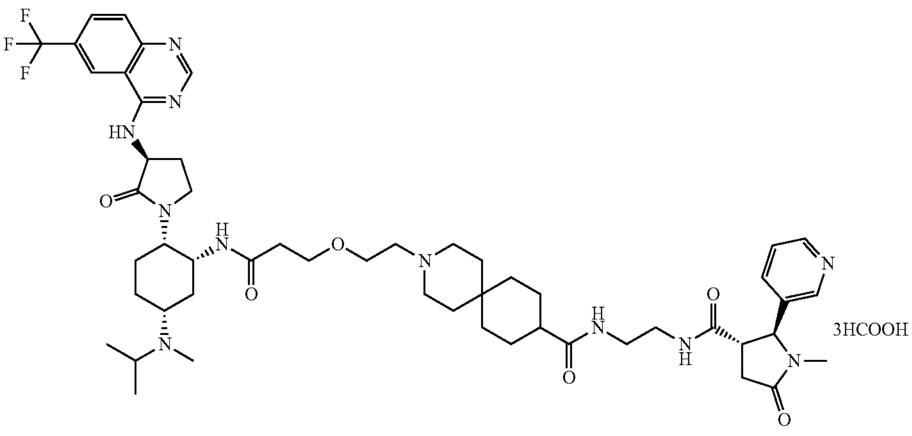 [SMILES: CC(C)N(C)[C@@H]1CC[C@H](N2CC[C@H](Nc3ncnc4ccc(C(F)(F)F)cc34)C2=O)[C@H](NC(=O)CCOCCN2CCC3(CCC(C(=O)NCCNC(=O)[C@H]4CC(=O)N(C)[C@@H]4c4cccnc4)CC3)CC2)C1] 3HCOOH |
| 185 | 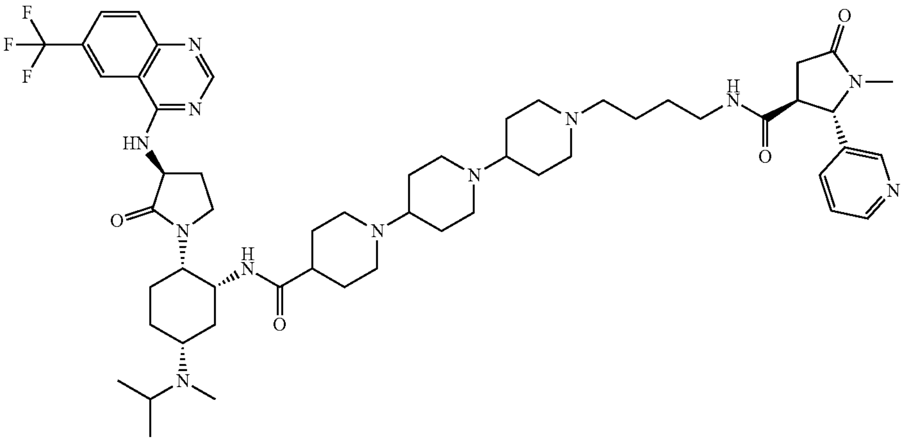 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C4CCN(CCCCNC(=O)[C@H]5CC(=O)N(C)[C@@H]5c5cccnc5)CC4)CC3)CC2)C1] |
| 186 | 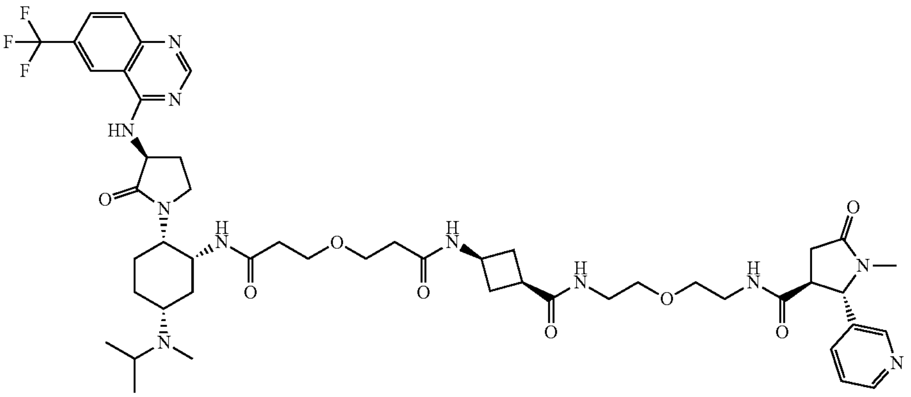 [SMILES: CC(C)N(C)[C@@H]1CC[C@H](N2CC[C@H](Nc3ncnc4ccc(C(F)(F)F)cc34)C2=O)[C@H](NC(=O)CCOCCC(=O)N[C@H]2C[C@@H](C(=O)NCCOCCNC(=O)[C@H]3CC(=O)N(C)[C@@H]3c3cccnc3)C2)C1] |

TABLE 1-continued
| Example | Structure |
| --- | --- |
| 187 | 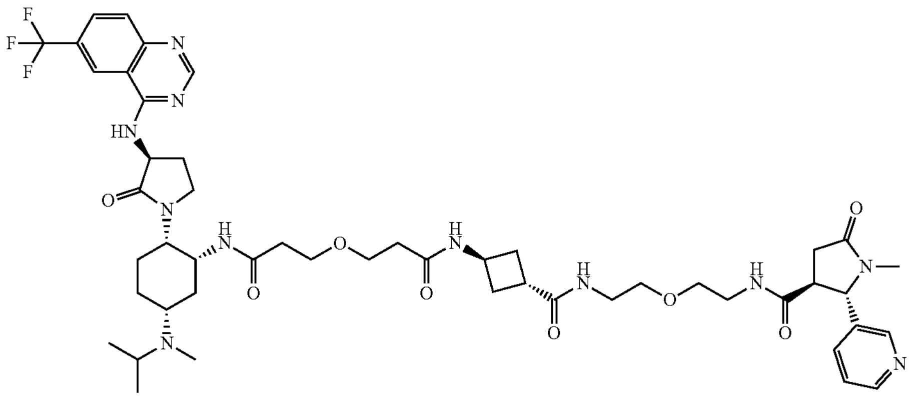 [SMILES: CC(C)N(C)[C@@H]1CC[C@H](N2CC[C@H](Nc3ncnc4ccc(C(F)(F)F)cc34)C2=O)[C@H](NC(=O)CCOCCC(=O)N[C@H]2C[C@H](C(=O)NCCOCCNC(=O)[C@H]3CC(=O)N(C)[C@@H]3c3cccnc3)C2)C1] |
| 188 | 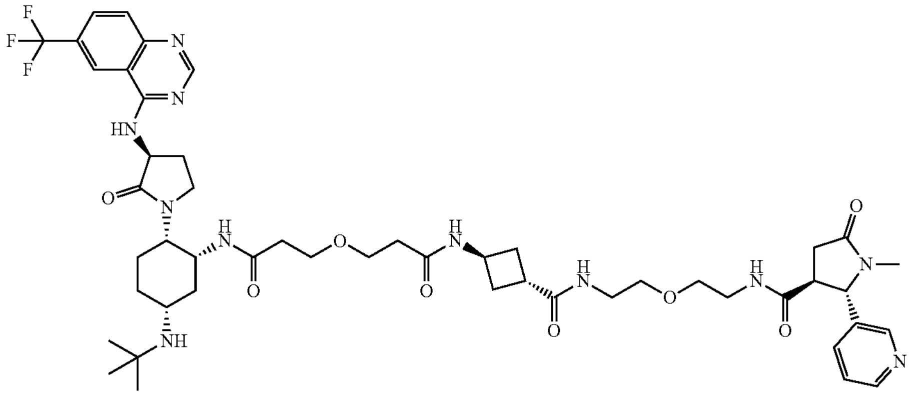 [SMILES: CN1C(=O)C[C@H](C(=O)NCCOCCNC(=O)[C@H]2C[C@H](NC(=O)CCOCCC(=O)N[C@@H]3C[C@H](NC(C)(C)C)CC[C@@H]3N3CC[C@H](Nc4ncnc5ccc(C(F)(F)F)cc45)C3=O)C2)[C@H]1c1cccnc1] |
| 189 | 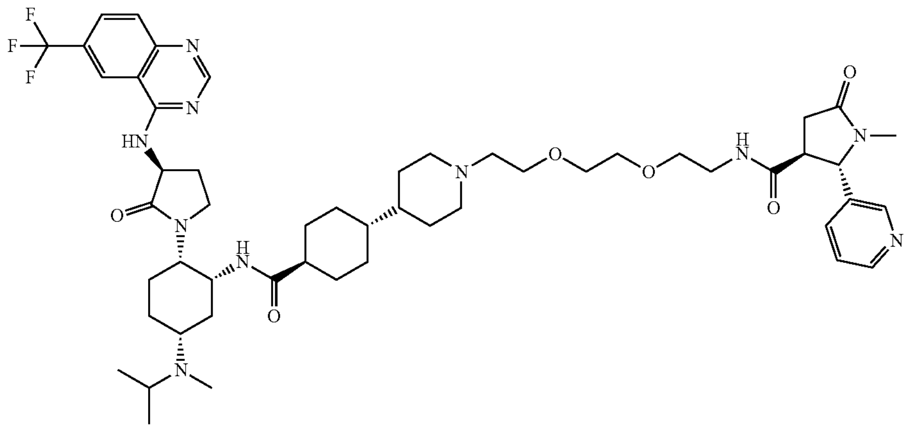 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](C3CCN(CCOCCOCCNC(=O)[C@H]4CC(=O)N(C)[C@@H]4c4cccnc4)CC3)CC2)C1] |

TABLE 1-continued
| Example | Structure |
| --- | --- |
| 190 | 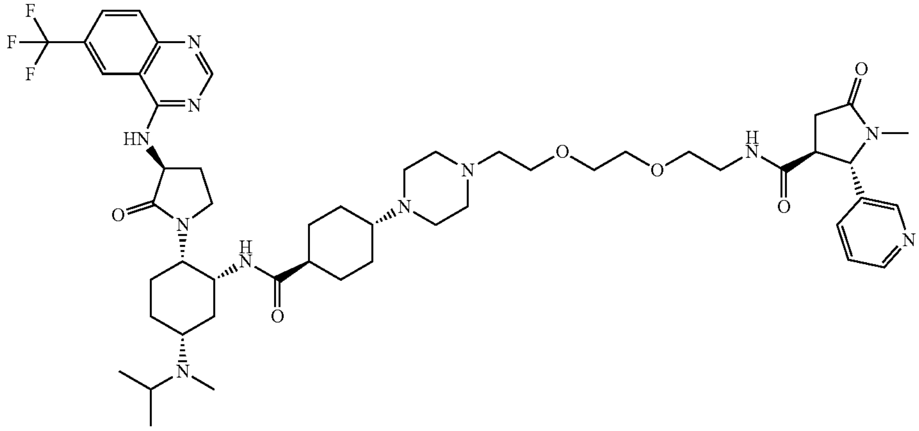 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(CCOCCOCCNC(=O)[C@H]4CC(=O)N(C)[C@@H]4c4cccnc4)CC3)CC2)C1] |
| 191 | 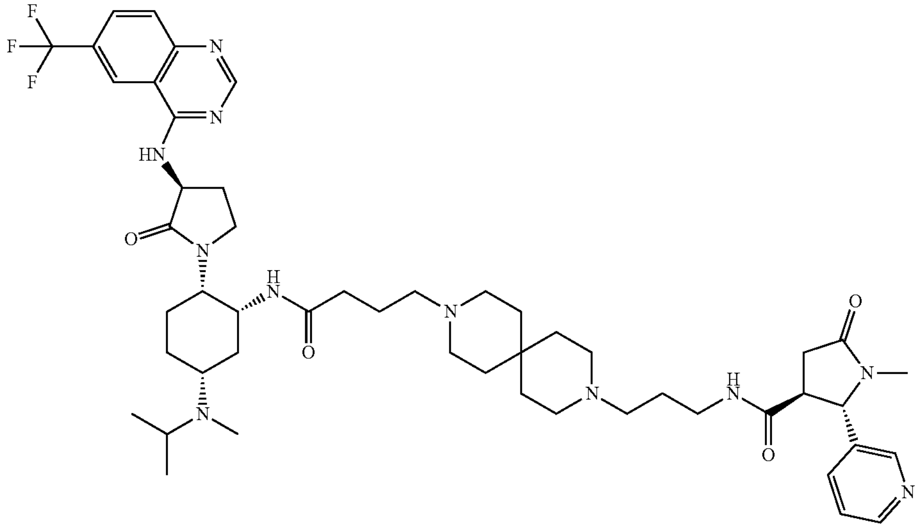 [SMILES: CC(C)N(C)[C@@H]1CC[C@H](N2CC[C@H](Nc3ncnc4ccc(C(F)(F)F)cc34)C2=O)[C@H](NC(=O)CCCN2CCC3(CCN(CCCNC(=O)[C@H]4CC(=O)N(C)[C@@H]4c4cccnc4)CC3)CC2)C1] |
| 192 | 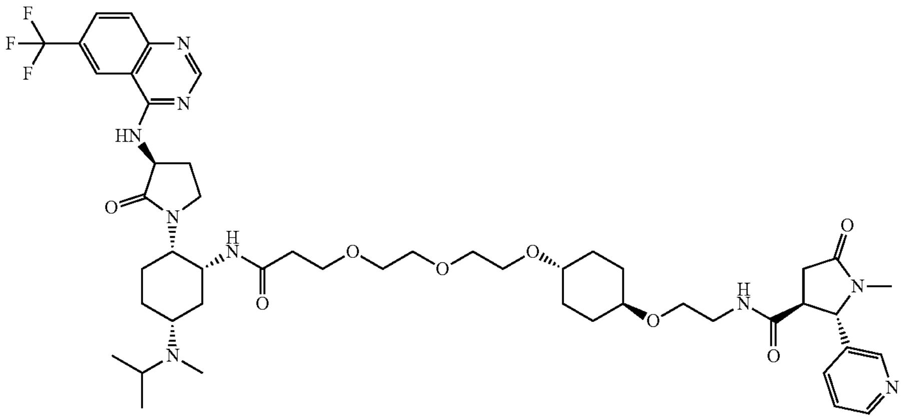 [SMILES: CC(C)N(C)[C@@H]1CC[C@H](N2CC[C@H](Nc3ncnc4ccc(C(F)(F)F)cc34)C2=O)[C@H](NC(=O)CCOCCOCCO[C@H]2CC[C@H](OCCNC(=O)[C@H]3CC(=O)N(C)[C@@H]3c3cccnc3)CC2)C1] |

TABLE 1-continued
| Example | Structure |
|---|---|
| 193 | 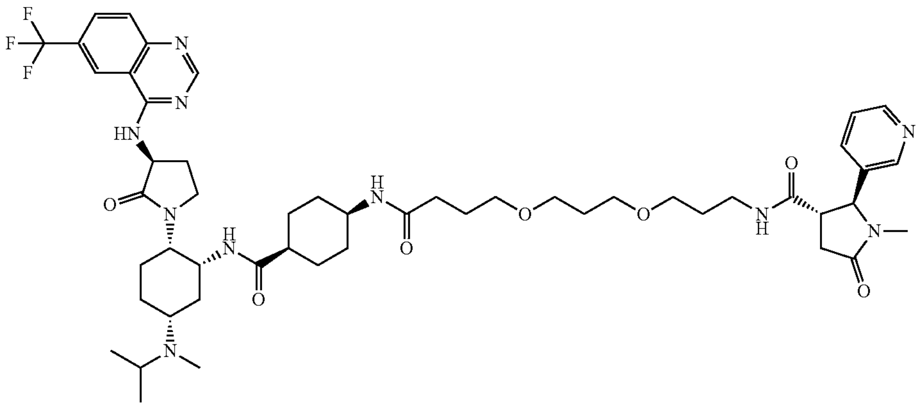 |
| 194 | 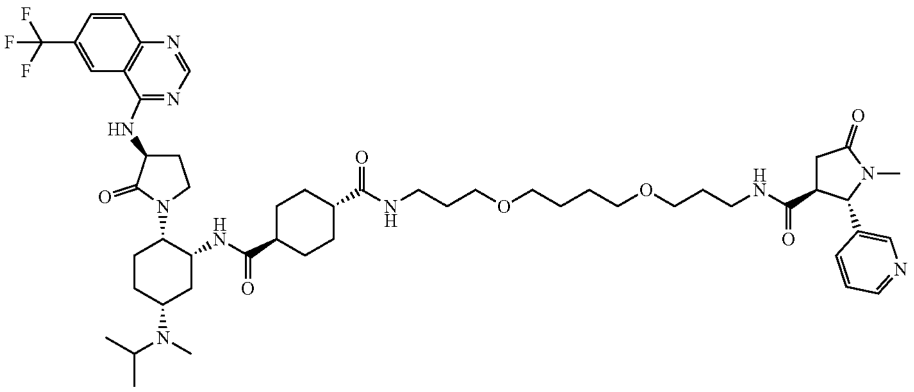 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](C(=O)NCCCOCCCCOCCCNC(=O)[C@H]3CC(=O)N(C)[C@@H]3c3cccnc3)CC2)C1] |
| 195 | 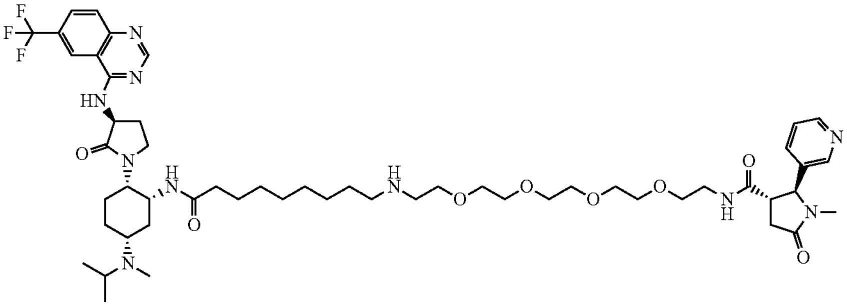 3TFA |
| 196 | 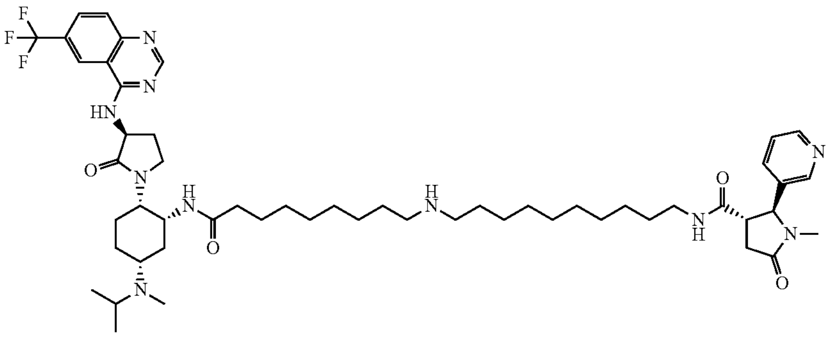 3HCOOH |

TABLE 1-continued

| Example | Structure |
| --- | --- |
| 197 | 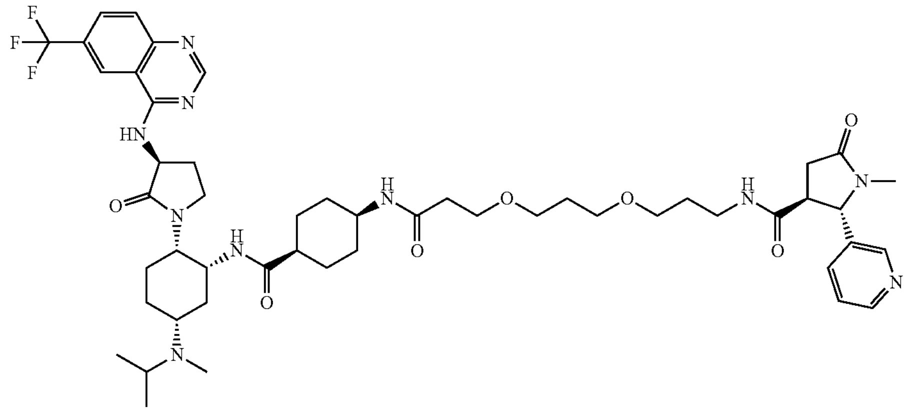 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCCOCCCNC(=O)[C@H]3CC(=O)N(C)[C@@H]3c3cccnc3)CC2)C1] |
| 198 | 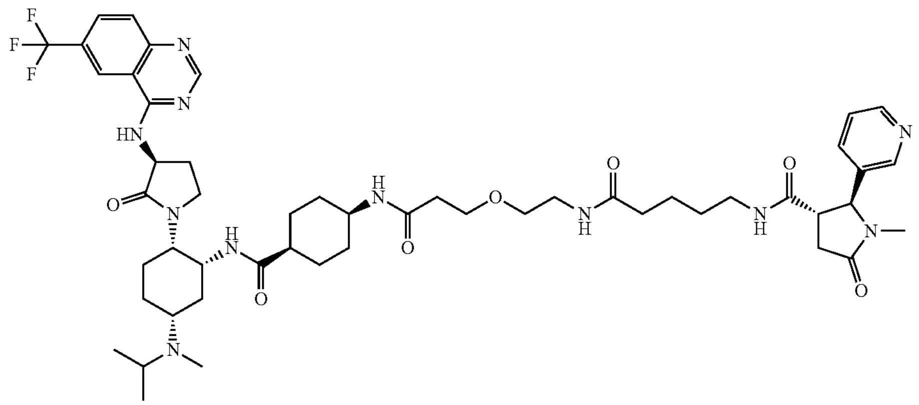 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCCCNC(=O)[C@H]3CC(=O)N(C)[C@@H]3c3cccnc3)CC2)C1] |

Definitions

As used herein and in the claims, the singular forms "a" and "the" include plural reference unless the context clearly dictates otherwise.

As used herein and in the claims, the term "comprising" encompasses "including" or "consisting" e.g. a composition "comprising" X may consist exclusively of X or may include something additional, e.g., X+Y.

The term "consisting essentially of" limits the scope of the feature to the specified materials or steps and those that do not materially affect the basic characteristic(s) of the claimed feature.

The term "consisting of" excludes the presence of any additional component(s).

The term "pathogenic cells" includes a cell subset that causes or is capable of causing disease. Examples of pathogenic cells include, but are not limited to, pathogenic immune cells, cancer or tumor cells, and stromal cells. A pathogenic cell can also be a pathogenic agent capable of causing an infection, such as a virus or a bacterial cell.

The term "pathogenic immune cells" includes a particular immune cell subset that causes or is capable of causing disease. These cellular subsets are resident cells or are recruited to particular locations and secrete cytokines, chemokines and other mediators and contribute to the persistence and progression of disease such as cancer in the case of a tumor microenvironment or chronic inflammation of the lung in the case of asthma. Examples of pathogenic immune cells include, but are not limited to myeloid-derived suppressor cells (MDSCs), T regulatory cells (Tregs), neutrophils, macrophages, B regulatory cells (Bregs), CD8 regulatory cells, (CD8regs), and exhausted T cells.

The term "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

The terms "effective amount" and "therapeutically effective amount" refer to an amount of a compound, or antibody, or antigen-binding portion thereof, according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a therapeutically effective amount can be determined routinely by one of ordinary skill in the art having regard to their own knowledge, the state of the art, and this disclosure.

The term "alkyl" represents a saturated, linear or branched hydrocarbon moiety having the specified number of carbon atoms. The term "$C_{1-3}$ alkyl" refers to an unsubstituted alkyl moiety containing 1, 2 or 3 carbon atoms; exemplary alkyls include methyl, ethyl and propyl.

The term "alkylene" represents a saturated, linear or branched hydrocarbon moiety having the specified number of carbon atoms, with two points of attachment. The two points of attachment can be from the same or different carbon atoms. The term "$C_{1-3}$ alkylene" refers to an unsubstituted alkyl moiety containing 1, 2 or 3 carbon atoms with two points of attachment; exemplary $C_{1-3}$ alkylene groups include methylene, ethylene and propylene.

The term "alkenyl" represents an unsaturated, linear or branched hydrocarbon moiety having the specified number of carbon atoms. The term "$C_{2-6}$ alkenyl" refers to an unsubstituted alkenyl moiety containing 2, 3, 4, 5, or 6 carbon atoms; exemplary alkenyls include propenyl, butenyl, pentenyl and hexenyl.

The term "alkenylene" represents an unsaturated, linear or branched hydrocarbon moiety having the specified number of carbon atoms, with two points of attachment. The two points of attachment can be from the same or different carbon atoms. The term "$C_{2-6}$ alkenylene" refers to an unsubstituted alkenyl moiety containing 2, 3, 4, 5, or 6 carbon atoms with two points of attachment; exemplary $C_{2-6}$ alkenylene groups include propenylene, butenylene, pentenylene and hexenylene.

The term "cycloalkyl" represents a saturated cyclic hydrocarbon moiety having the specified number of carbon atoms. The term "$C_{3-6}$ cycloalkyl" refers to an unsubstituted cycloalkyl moiety containing 3, 4, 5 or 6 carbon atoms; exemplary cycloalkyls include cyclopropyl, cyclobutyl, cyclopentyl, and cyclohexyl.

The term "cycloalkylene" represents a saturated cyclic hydrocarbon moiety having the specified number of carbon atoms, with two points of attachment. The two points of attachment can be from the same or different carbon atoms. The term "$C_{4-6}$ cycloalkylene" refers to an unsubstituted cycloalkylene moiety containing 4, 5, or 6 carbon atoms with two points of attachment. Exemplary cycloalkylene groups include cyclobutane-1,3-diyl, cyclopentane-1,3-diyl, cyclohexane-1,3-diyl, or cyclohexane-1,4-diyl.

The term "cycloalkenylene" represents an unsaturated cyclic hydrocarbon moiety having the specified number of carbon atoms, with two points of attachment. The two points of attachment can be from the same or different carbon atoms. The term "$C_{3-6}$ cycloalkenylene" refers to an unsubstituted cycloalkenylene moiety containing 3, 4, 5, or 6 carbon atoms with two points of attachment.

The term "heterocycloalkylene" refers to a saturated cyclic hydrocarbon moiety containing 1 or 2 heteroatoms independently selected from oxygen, sulphur or nitrogen atoms, with two points of attachment. The two points of attachment can be from the same or different carbon atoms. The term "3- to 6-membered heterocycloalkylene" refers to a 3- to 6-membered saturated cyclic moiety containing 2, 3, 4 or 5 carbon atoms in addition to 1 or 2 oxygen, sulphur or nitrogen atoms, with two points of attachment. Suitably, the 3- to 6-membered heterocycloalkylene group contains 1 oxygen or nitrogen atom. Suitably such group contains 3 carbon atoms and 1 oxygen or nitrogen atom, such as azetidindiyl or oxetandiyl. Suitably such group contains 4 or 5 carbon atoms and 1 oxygen or nitrogen atom, such as tetrahydrofurandiyl, tetrahydropyrandiyl, pyrrolidindiyl or piperidindiyl.

The term "bridged bicyclic cycloalkylene" refers to a saturated bicyclic hydrocarbon moiety having at least one bridge, with two points of attachment. A "bridge" is an unbranched chain of atoms or an atom or a valence bond connecting two bridgeheads, where a "bridgehead" is any skeletal atom of the ring system which is bonded to three or more skeletal atoms (excluding hydrogen). The two points of attachment can be from the same or different carbon atoms. The term "$C_{7-9}$ bridged bicyclic cycloalkylene" refers to an unsubstituted bridged bicyclic cycloalkylene moiety containing 7, 8, or 9 carbon atoms with two points of attachment.

The term "arylene" refers to a monocyclic or bicyclic ring system wherein at least one ring in the system is aromatic, with two points of attachment. Exemplary arylene groups include phenylene, biphenylene, naphthylene, and anthracylene.

The term "heteroarylene" refers to a monocyclic or bicyclic ring system wherein at least one ring in the system is aromatic, and having, in addition to carbon atoms, from one to five heteroatoms independently selected from oxygen, sulphur or nitrogen atoms, with two points of attachment. The term "5- to 6-membered heteroarylene" refers to a 5- to 6-membered cyclic aromatic moiety containing 2, 3, 4 or 5 carbon atoms in addition to 1, 2, or 3 heteroatoms independently selected from oxygen, sulphur or nitrogen atoms, with two points of attachment.

The skilled artisan will appreciate that salts, including pharmaceutically acceptable salts, of the compounds according to Formula (I) may be prepared. Indeed, in certain embodiments of the invention, salts including pharmaceutically-acceptable salts of the compounds according to Formula (I) may be preferred over the respective free or unsalted compound. Accordingly, the invention is further directed to salts, including pharmaceutically-acceptable salts, of the compounds according to Formula (I). The invention is further directed to free or unsalted compounds of Formula (I).

The salts, including pharmaceutically acceptable salts, of the compounds of the invention are readily prepared by those of skill in the art.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, trifluoroacetate, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), b/s-(2-hydroxyethyl) amine, bismuth, calcium, chloroprocaine, choline, clemizole (1-p chlorobenzyl-2-pyrrolidine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The compounds according to Formula (I) may contain one or more asymmetric centers (also referred to as a chiral center) and may, therefore, exist as individual enantiomers, diastereomers, or other stereoisomeric forms, or as mixtures thereof. Chiral centers, such as chiral carbon atoms, may be present in a substituent such as an alkyl group. Where the stereochemistry of a chiral center present in a compound of Formula (I), or in any chemical structure illustrated herein, if not specified the structure is intended to encompass all individual stereoisomers and all mixtures thereof. Thus, compounds according to Formula (I) containing one or more chiral centers may be used as racemic mixtures, enantiomerically enriched mixtures, or as enantiomerically pure individual stereoisomers.

Divalent groups are groups having two points of attachment. For all divalent groups, unless otherwise specified, the orientation of the group is implied by the direction in which the formula or structure of the group is written.

Unless defined otherwise, all technical and scientific terms used herein have the same meaning as commonly understood by one of ordinary skill in the art to which this invention belongs. Although any compositions and methods similar or equivalent to those described herein can be used in the practice or testing of the methods of the disclosure, exemplary compositions and methods are described herein. Any of the aspects and embodiments of the disclosure described herein may also be combined. For example, the subject matter of any dependent or independent claim disclosed herein may be multiply combined (e.g., one or more recitations from each dependent claim may be combined into a single claim based on the independent claim on which they depend).

Ranges provided herein include all values within a particular range described and values about an endpoint for a particular range.

Concentrations described herein are determined at ambient temperature and pressure. This may be, for example, the temperature and pressure at room temperature or in a particular portion of a process stream. Preferably, concentrations are determined at a standard state of 25° C. and 1 bar of pressure.

CCR2 Target and CCR2-Binding Moieties

The compounds of Formula (I) as disclosed herein are heterobifunctional synthetic agents designed such that one terminus interacts with a cell surface CCR2 target, while the other terminus binds a specific antibody. More specifically, the ARM simultaneously binds the cell surface CCR2 target as well as the specific antibody. This ternary complex directs immune surveillance to CCR2-expressing tissue/cells and unites the mechanisms of antibody function with the dose-control of small molecules. This mechanism may include antibody dependent cellular cytotoxicity (ADCC), antibody dependent cellular phagocytosis (ADCP), or complement dependant cytotocity (CDC), and preferably includes ADCC. The same Fc receptor expressing immune cells that initiate destruction of the ARM/antibody tagged cells also participate in presentation of endogenous antigens for the potential for long term cellular immunity.

The compounds of Formula (I) as disclosed herein include a CCR2-binding moiety that is capable of binding CCR2 present on the surface of a cell. In one embodiment, the CCR2 is expressed on a pathogenic cell.

In a further embodiment, the pathogenic cell is a pathogenic immune cell, a tumor cell or cancer cell, or a stromal cell (including stromal cells present in a tumor microenvironment).

In a further embodiment, the CCR2 target is present on the surface of a pathogenic agent selected from a virus or a bacterial cell. Examples of a virus expressing cell surface targets include, but are not limited to, influenza.

In a further embodiment, the pathogenic immune cells are monocytes, myeloid derived suppressor cells (MDSC), such as monocytic MDSCs (mMDSCs) and polymorphonuclear MDSCs (PMN_MDSCs), T regulatory cells (Tregs), neutrophils (e.g., N2 neutrophils), macrophages (e.g., M2 macrophages), B regulatory cells (Bregs, memory B cells), plasma cells, CD8 cells (e.g., CD8 regulatory cells (CD8regs), memory CD8 cells, effector CD8 cells, naïve CD8 Tcells, TEMRA), exhausted T cells, eosinophils, basophils, mast cells, dendritic cells, natural killer (NK cells), innate lymphoid cells, NK T cells (NKT), or γδT cells.

In a further embodiment, the pathogenic immune cells are myeloid derived suppressor cells (MDSC), such as monocytic MDSCs (mMDSCs) and polymorphonuclear MDSCs (PMN_MDSCs), T regulatory cells (Tregs), neutrophils (e.g., N2 neutrophils), macrophages (e.g., M2 macrophages), B regulatory cells (Bregs), CD8 regulatory cells (CD8regs), exhausted T cells.

In a further embodiment, the pathogenic immune cells expressing CCR2 are myeloid derived suppressor cells (MDSCs). In a further embodiment, the pathogenic immune cells expressing CCR2 are selected from monocytic MDSCs (mMDSCs) and polymorphonuclear MDSCs (PMN_MDSCs).

In a further embodiment, the tumor cells or cancer cells are solid tumor cells.

In a further embodiment, the tumor cells or cancer cells are non-small cell lung cancer (NSCLC) cells, hepatocellular carcinoma (HCC) cells, colorectal cancer (CRC) cells, cervical squamous cell carcinoma (CESC) cells, head and neck squamous cell carcinoma (HNSC) cells, pancreatic cancer cells, metastatic castration-resistant prostate cancer (mCRPC) cells, ovarian cancer cells, bladder cancer cells, or breast cancer cells, preferably NSCLC cells, HCC cells, or CRC cells.

In a further embodiment, the stromal cells are cancer associated fibroblasts (CAFs).

The present disclosure also provides a pharmaceutical composition comprising a compound of Formula (I) as disclosed herein, and a pharmaceutically acceptable excipient, carrier, or diluent.

Anti-Cotinine Antibodies

The present disclosure provides an antibody, or antigen-binding fragment thereof, that binds to a cotinine moiety. As used herein, the term "anti-cotinine antibody or antigen-binding fragment thereof" refers to an antibody, or antigen binding fragment thereof that binds to a cotinine moiety. Cotinine has the following structure:

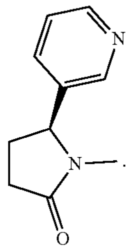

As used herein, the term "cotinine moiety" refers to cotinine or an analog of cotinine. Compounds of Formula (I) described herein comprise a cotinine moiety linked via a linker to a CCR2-binding moiety. In one embodiment, the cotinine moiety has the following structure:

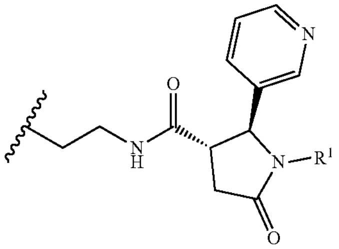

wherein $R^1$ is $C_{1-4}$ alkyl or $C_{3-6}$ cycloalkyl. In another embodiment, $R^1$ is methyl, ethyl, 1-propyl, 2-propyl, 1-butyl, 2-butyl, or t-butyl. In another embodiment, $R^1$ is methyl. In another embodiment, $R^1$ is cyclopropyl, cyclobutyl, cyclopentyl, or cyclohexyl.

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanised, multispecific antibodies, including bispecific antibodies, and heteroconjugate antibodies; a single variable domain (e.g., a domain antibody (DAB)), antigen binding antibody fragments, Fab, $F(ab')_2$, Fv, disulphide linked Fv, single chain Fv, disulphide-linked scFv, diabodies, TANDABS, etc. and modified versions of any of the foregoing (for a summary of alternative "antibody" formats see Holliger and Hudson, Nature Biotechnology, 2005, 23(9): 1126-1136).

The term, full, whole or intact antibody, used interchangeably herein, refers to a heterotetrameric glycoprotein with an approximate molecular weight of 150,000 daltons. An intact antibody is composed of two identical heavy chains (HCs) and two identical light chains (LCs) linked by covalent disulphide bonds. This H2L2 structure folds to form three functional domains comprising two antigen-binding fragments, known as 'Fab' fragments, and a 'Fc' crystallisable fragment. The Fab fragment is composed of the variable domain at the amino-terminus, variable heavy (VH) or variable light (VL), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE and IgD are defined by distinct heavy chain amino acid sequences, which are called p, a, y, E and b respectively, each heavy chain can pair with either a K or A light chain. The majority of antibodies in the serum belong to the IgG class, there are four isotypes of human IgG (IgG1, IgG2, IgG3 and IgG4), the sequences of which differ mainly in their hinge region.

"CDRs" are defined as the complementarity determining region amino acid sequences of an antibody or antigen binding fragment thereof. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and variable domain regions within full-length antigen binding sequences, e.g. within an antibody heavy chain sequence or antibody light chain sequence, are numbered according to the Kabat numbering convention. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full-length antibody sequences. There are also alternative numbering conventions for CDR sequences, for example those set out in Chothia et al., Nature, 1989, 342: 877-883. The structure and protein folding of the antigen binding protein may mean that other residues are considered part of the CDR sequence and would be understood to be so by a skilled person.

Other numbering conventions for CDR sequences available to a skilled person include "AbM" (University of Bath) and "contact" (University College London) methods.

Table 2 below represents one definition using each numbering convention for each CDR or binding unit. It should be noted that some of the CDR definitions may vary depending

TABLE 2

| | Kabat CDR | Chothia CDR | AbM CDR | Contact CDR |
|---|---|---|---|---|
| H1 | 31-35/35A/35B | 26-32/33/34 | 26-35/35A/35B | 30-35/35A/35B |
| H2 | 50-65 | 52-56 | 50-58 | 47-58 |
| H3 | 95-102 | 95-102 | 95-102 | 93-101 |
| L1 | 24-34 | 24-34 | 24-34 | 30-36 |
| L2 | 50-56 | 50-56 | 50-56 | 46-55 |
| L3 | 89-97 | 89-97 | 89-97 | 89-96 |

In a further embodiment, the anti-cotinine antibody is humanized. In a further embodiment, the Fc region of the anti-cotinine antibody is modified to increase ADCC activity, ADCP activity, and/or CDC activity, suitable modifications of which are provided below. In a further embodiment, the Fc region of the anti-cotinine antibody is modified to increase ADCC activity.

Fc engineering methods can be applied to modify the functional or pharmacokinetics properties of an antibody. Effector function may be altered by making mutations in the Fc region that increase or decrease binding to C1q or Fcγ receptors and modify CDC or ADCC activity respectively. Modifications to the glycosylation pattern of an antibody can also be made to change the effector function. The in vivo half-life of an antibody can be altered by making mutations that affect binding of the Fc to the FcRn (neonatal Fc receptor).

The term "effector function" as used herein refers to one or more of antibody-mediated effects including antibody-dependent cell-mediated cytotoxicity (ADCC), antibody-mediated complement activation including complement-dependent cytotoxicity (CDC), complement-dependent cell-mediated phagocytosis (CDCP), antibody dependent complement-mediated cell lysis (ADCML), and Fc-mediated phagocytosis or antibody-dependent cellular phagocytosis (ADCP).

The interaction between the Fc region of an antigen binding protein or antibody and various Fc receptors (FcR), including FcγRI (CD64), FcγRII (CD32), FcγRIII (CD16), FcRn, C1q, and type II Fc receptors is believed to mediate the effector functions of the antigen binding protein or antibody. Significant biological effects can be a consequence of effector functionality. Usually, the ability to mediate effector function requires binding of the antigen binding protein or antibody to an antigen and not all antigen binding proteins or antibodies will mediate every effector function.

Effector function can be assessed in a number of ways including, for example, evaluating ADCC effector function of antibody coated to target cells mediated by Natural Killer (NK) cells via FcγRIII, or monocytes/macrophages via FcγRI, or evaluating CDC effector function of antibody coated to target cells mediated by complement cascade via C1q. For example, an antibody, or antigen binding fragment thereof, of the present invention can be assessed for ADCC effector function in a Natural Killer cell assay. Examples of such assays can be found in Shields et al., The Journal of Biological Chemistry, 2001, 276: 6591-6604; Chappel et al., The Journal of Biological Chemistry, 1993, 268: 25124-25131; Lazar et al., PNAS, 2006, 103: 4005-4010.

Examples of assays to determine CDC function include those described in J Imm Meth, 1995, 184: 29-38.

The effects of mutations on effector functions (e.g., FcRn binding, FcγRs and C1q binding, CDC, ADCML, ADCC, ADCP) can be assessed, e.g., as described in Grevys et al., J Immunol., 2015,194(11): 5497-5508; Tam et al., Antibodies, 2017, 6(3): 12; or Monnet et al., mAbs, 2014, 6(2): 422-436.

Throughout this specification, amino acid residues in Fc regions, in antibody sequences or full-length antigen binding protein sequences, are numbered according to the EU index numbering convention.

Human IgG1 constant regions containing specific mutations have been shown to enhance binding to Fc receptors. In some cases these mutations have also been shown to enhance effector functions, such as ADCC and CDC, as described below. Antibodies, or antigen binding fragments thereof, of the present invention may include any of the following mutations.

Enhanced CDC: Fc engineering can be used to enhance complement-based effector function. For example (with reference to IgG1), K326W/E333S; S267E/H268F/S324T; and IgG1/IgG3 cross subclass can increase C1q binding; E345R (Diebolder et al., Science, 2014, 343: 1260-1293) and E345R/E430G/S440Y results in preformed IgG hexamers (Wang et al., Protein Cell, 2018, 9(1): 63-73).

Enhanced ADCC: Fc engineering can be used to enhance ADCC. For example (with reference to IgG1), F243L/R292P/Y300LN3051/P396L; S239D/1332E; and S298A/E333A/K334A increase FcγRIIIa binding; S239D/1332E/A330L increases FcγRIIIa binding and decreases FcγRIIb binding; G236A/S239D/1332E improves binding to FcγRIIa, improves the FcγRIIa/FcγRIIb binding ratio (activating/inhibitory ratio), and enhances phagocytosis of antibody-coated target cells by macrophages. An asymmetric Fc in which one heavy chain contains L234Y/L235Q/G236W/S239M/H268D/D270E/S298A mutations and D270E/K326D/A330M/K334E in the opposing heavy chain, increases affinity for FcγRIIIa F158 (a lower-affinity allele) and FcγRIIIa V158 (a higher-affinity allele) with no increased binding affinity to inhibitory FcγRIIb (Mimoto et al., mAbs, 2013, 5(2): 229-236).

Enhanced ADCP: Fc engineering can be used to enhance ADCP. For example (with reference to IgG1), G236A/S239D/1332E increases FcγRIIa binding and increases FcγRIIIa binding (Richards, J. et al., Mol. Cancer Ther., 2008, 7:2517-2527).

Increased co-engagement: Fc engineering can be used to increase co-engagement with FcRs. For example (with reference to IgG1), S267E/L328F increases FcγRIIb binding; N325S/L328F increases FcγRIIa binding and decreases FcγRIIIa binding Wang et al., Protein Cell, 2018, 9(1): 63-73).

In a further embodiment, an antibody, or antigen binding fragment thereof, of the present invention may comprise a heavy chain constant region with an altered glycosylation profile, such that the antibody, or antigen binding fragment thereof, has an enhanced effector function, e.g., enhanced ADCC, enhanced CDC, or both enhanced ADCC and CDC. Examples of suitable methodologies to produce an antibody, or antigen binding fragment thereof, with an altered glycosylation profile are described in WO 2003/011878, WO 2006/014679 and EP1229125.

The absence of the α1,6 innermost fucose residues on the Fc glycan moiety on N297 of IgG1 antibodies enhances affinity for FcγRIIIA. As such, afucosylated or low fucosylated monoclonal antibodies may have increased therapeutic efficacy (Shields et al., J Biol Chem., 2002, 277(30): 26733-40 and Monnet et al., mAbs, 2014, 6(2): 422-436).

In one embodiment there is provided an antibody, or antigen binding fragment thereof, comprising a chimeric heavy chain constant region. In an embodiment, the antibody, or antigen binding fragment thereof, comprises an IgG1/IgG3 chimeric heavy chain constant region, such that the antibody, or antigen binding fragment thereof, has an enhanced effector function, for example enhanced ADCC or enhanced CDC, or enhanced ADCC and CDC functions. For example, a chimeric antibody, or antigen binding fragment thereof, of the invention may comprise at least one CH2 domain from IgG3. In one such embodiment, the antibody, or antigen binding fragment thereof, comprises one CH2 domain from IgG3 or both CH2 domains may be from IgG3. In a further embodiment, the chimeric antibody, or antigen binding fragment thereof, comprises an IgG1 CH1 domain, an IgG3 CH2 domain, and an IgG3 CH3 domain. In a further embodiment, the chimeric antibody, or antigen binding fragment thereof, comprises an IgG1 CH1 domain, an IgG3 CH2 domain, and an IgG3 CH3 domain except for position 435 that is histidine.

In a further embodiment, the chimeric antibody, or antigen binding fragment thereof, comprises an IgG1 CH1 domain and at least one CH2 domain from IgG3. In an embodiment, the chimeric antibody, or antigen binding fragment thereof, comprises an IgG1 CH1 domain and the following residues, which correspond to IgG3 residues, in a CH2 domain: 274Q, 276K, 296F, 300F and 339T. In an embodiment, the chimeric antibody, or antigen binding fragment thereof, also comprises 356E, which corresponds to an IgG3 residue, within a CH3 domain.

In an embodiment, the antibody, or antigen binding fragment thereof, also comprises one or more of the following residues, which correspond to IgG3 residues within a CH3 domain: 358M, 384S, 392N, 397M, 4221, 435R, and 436F.

Also provided is a method of producing an antibody, or antigen binding fragment thereof, according to the invention comprising the steps of:

a) culturing a recombinant host cell comprising an expression vector comprising a nucleic acid sequence encoding a chimeric Fc region having both IgG1 and IgG3 Fc region amino acid residues (e.g. as described above); and b) recovering the antibody, or antigen binding fragment thereof.

Such methods for the production of antibody, or antigen binding fragment thereof, with chimeric heavy chain constant regions can be performed, for example, using the COMPLEGENT technology system available from BioWa, Inc. (Princeton, NJ) and Kyowa Hakko Kirin Co., Ltd. The COMPLEGENT system comprises a recombinant host cell comprising an expression vector in which a nucleic acid sequence encoding a chimeric Fc region having both IgG1 and IgG3 Fc region amino acid residues is expressed to produce an antibody, or antigen binding fragment thereof, having enhanced CDC activity, i.e. CDC activity is increased relative to an otherwise identical antibody, or antigen binding fragment thereof, lacking such a chimeric Fc region, as described in WO 2007/011041 and US 2007/0148165, each of which are incorporated herein by reference. In an alternative embodiment, CDC activity may be increased by introducing sequence specific mutations into the Fc region of an IgG chain. Those of ordinary skill in the art will also recognize other appropriate systems.

The present invention also provides a method of producing an antibody, or antigen binding fragment thereof, according to the invention comprising the steps of:

a) culturing a recombinant host cell comprising an expression vector comprising a nucleic acid encoding the antibody, or antigen binding fragment thereof, optionally wherein the FUT8 gene encoding alpha-1,6-fucosyltransferase has been inactivated in the recombinant host cell; and b) recovering the antibody, or antigen binding fragment thereof.

Such methods for the production of an antibody, or antigen binding fragment thereof, can be performed, for example, using the POTELLIGENT technology system available from BioWa, Inc. (Princeton, NJ) in which CHOK1SV cells lacking a functional copy of the FUT8 gene produce monoclonal antibodies having enhanced ADCC activity that is increased relative to an identical monoclonal antibody produced in a cell with a functional FUT8 gene as described in U.S. Pat. Nos. 7,214,775, 6,946,292, WO 00/61739 and WO 02/31240, all of which are incorporated herein by reference. Those of ordinary skill in the art will also recognize other appropriate systems.

In one embodiment, the antibody, or antigen binding fragment thereof, is produced in a host cell in which the FUT8 gene has been inactivated. In a further embodiment, the antibody, or antigen binding fragment thereof, is produced in a −/− FUT8 host cell. In a further embodiment, the antibody, or antigen binding fragment thereof, is afucosylated at Asn297 (IgG1).

It will be apparent to those skilled in the art that such modifications may not only be used alone but may be used in combination with each other in order to further enhance effector function.

In one such embodiment, there is provided an antibody, or antigen binding fragment thereof, comprising a heavy chain constant region that comprises a both a mutated and chimeric heavy chain constant region, individually described above. For example, an antibody, or antigen binding fragment thereof, comprising at least one CH2 domain from IgG3 and one CH2 domain from IgG1, and wherein the IgG1 CH2 domain has one or more mutations at positions selected from 239, 332 and 330 (for example the mutations may be selected from S239D, 1332E and A330L), such that the antibody, or antigen binding fragment thereof, has enhanced effector function, e.g. enhanced ADCC or enhanced CDC, or enhanced ADCC and enhanced CDC in comparison to an equivalent antibody, or antigen binding fragment thereof, with an IgG1 heavy chain constant region lacking said mutations. In one embodiment, the IgG1 CH2 domain has the mutations S239D and 1332E. In another embodiment, the IgG1 CH2 domain has the mutations S239D, A330L, and 1332E.

In an alternative embodiment, there is provided an antibody, or antigen binding fragment thereof, comprising both a chimeric heavy chain constant region and an altered glycosylation profile, as individually described above. In an embodiment, the antibody, or antigen binding fragment thereof, comprises an altered glycosylation profile such that the ratio of fucose to mannose is 0.8:3 or less. In one such embodiment, the heavy chain constant region comprises at least one CH2 domain from IgG3 and one CH2 domain from IgG1 and has an altered glycosylation profile such that the ratio of fucose to mannose is 0.8:3 or less, for example wherein the antibody, or antigen binding fragment thereof, is defucosylated. Said antibody, or antigen binding fragment thereof, has an enhanced effector function, e.g. enhanced ADCC or enhanced CDC, or enhanced ADCC and enhanced CDC, in comparison to an equivalent antibody, or antigen binding fragment thereof, with an IgG1 heavy chain constant region lacking said glycosylation profile.

In an alternative embodiment, the antibody, or antigen binding fragment thereof, has at least one IgG3 heavy chain CH2 domain and at least one heavy chain constant domain from IgG1 wherein both IgG CH2 domains are mutated in accordance with the limitations described herein.

In one aspect, there is provided a method of producing an antibody, or antigen binding fragment thereof, according to the invention described herein comprising the steps of:

a) culturing a recombinant host cell containing an expression vector comprising a nucleic acid sequence encoding a chimeric Fc domain having both IgG1 and IgG3 Fc domain amino acid residues (e.g. as described above); and wherein the FUT8 gene encoding alpha-1,6-fucosyltransferase has been inactivated in the recombinant host cell; and b) recovering the antibody, or antigen binding fragment thereof.

Such methods for the production of an antibody, or antigen binding fragment thereof, can be performed, for example, using the ACCRETAMAB technology system available from BioWa, Inc. (Princeton, NJ) that combines the POTELLIGENT and COMPLEGENT technology systems to produce an antibody, or antigen binding fragment thereof, having both enhanced ADCC and CDC activity relative to an otherwise identical monoclonal antibody that lacks a chimeric Fc domain and that is fucosylated.

In another embodiment, there is provided an antibody, or antigen binding fragment thereof, comprising a mutated and chimeric heavy chain constant region wherein said antibody, or antigen binding fragment thereof, has an altered glycosylation profile such that the antibody, or antigen binding fragment thereof, has enhanced effector function, e.g. enhanced ADCC or enhanced CDC, or both enhanced ADCC and CDC. In one embodiment the mutations are selected from positions 239, 332 and 330, e.g. S239D, 1332E and A330L. In a further embodiment the heavy chain constant region comprises at least one CH2 domain from IgG3 and one CH1 domain from IgG1. In one embodiment the heavy chain constant region has an altered glycosylation profile such that the ratio of fucose to mannose is 0.8:3 or less, e.g. the antibody, or antigen binding fragment thereof, is defucosylated, such that said antibody, or antigen binding fragment thereof, has an enhanced effector function in comparison with an equivalent non-chimeric antibody, or antigen binding fragment thereof, lacking said mutations and lacking said altered glycosylation profile.

In a further embodiment, the anti-cotinine antibody, or antigen binding fragment thereof, comprises a heavy chain CDR1 having SEQ ID NO: 1, a heavy chain CDR2 having SEQ ID NO: 2, a heavy chain CDR3 having SEQ ID NO: 3, a light chain CDR1 having SEQ ID NO: 4, a light chain CDR2 having SEQ ID NO: 5, and a light chain CDR3 having SEQ ID NO: 6. In a further embodiment, the anti-cotinine antibody has a heavy chain and a light chain, the heavy chain comprising a CDR1 having SEQ ID NO: 1, a CDR2 having SEQ ID NO: 2, and a CDR3 having SEQ ID NO: 3, and the light chain comprising a CDR1 having SEQ ID NO: 4, a CDR2 having SEQ ID NO: 5, and a CDR3 having SEQ ID NO: 6. In a further embodiment, the anti-cotinine antibody is of IgG1 isotype. In a further embodiment, the anti-cotinine antibody is of IgG1 isotype comprising a substitution in an Fc region to increase or enhance ADCC activity. In a further embodiment, the anti-cotinine antibody is of IgG1 isotype comprising a substitution in an Fc region to increase or enhance ADCC activity, wherein the substitution is S239D/1332E or S239D/1332E/A330L, wherein residue numbering is according to the EU Index. In a further embodiment, the anti-cotinine antibody is of IgG1 isotype comprising a substitution in an Fc region to increase or enhance ADCC activity, wherein the substitution is S239D/1332E, wherein residue numbering is according to the EU Index.

In a further embodiment, the anti-cotinine antibody, or antigen binding fragment thereof, comprises a heavy chain variable region (VH) having SEQ ID NO: 7, a light chain variable region (VL) having SEQ ID NO: 8. In a further embodiment, the anti-cotinine antibody has a heavy chain and a light chain, the heavy chain comprising a heavy chain variable region (VH) having SEQ ID NO: 7, and the light chain comprising a light chain variable region (VL) having SEQ ID NO: 8. In a further embodiment, the anti-cotinine antibody is of IgG1 isotype.

In a further embodiment, the anti-cotinine antibody is of IgG1 isotype comprising a substitution in an Fc region to increase or enhance ADCC activity. In a further embodiment, the anti-cotinine antibody is of IgG1 isotype comprising a substitution in an Fc region to increase or enhance ADCC activity, wherein the substitution is S239D/1332E or S239D/1332E/A330L, wherein residue numbering is according to the EU Index. In a further embodiment, the anti-cotinine antibody is of IgG1 isotype comprising a substitution in an Fc region to increase or enhance ADCC activity, wherein the substitution is S239D/1332E, wherein residue numbering is according to the EU Index.

In a further embodiment, the anti-cotinine antibody has a heavy chain comprising SEQ ID NO: 9 and a light chain comprising SEQ ID NO: 10.

The present disclosure also provides a pharmaceutical composition comprising an anti-cotinine antibody, or antigen binding fragment thereof as disclosed herein, and a pharmaceutically acceptable excipient, carrier, or diluent.

The present disclosure also provides a combination comprising the compound of Formula (I) as disclosed herein, and an anti-cotinine antibody, or antigen-binding fragment thereof as disclosed herein. The compound of Formula (I) and anti-cotinine antibody, or antigen binding fragment thereof can be present in the same composition or in separate compositions. In one embodiment, a combination comprises a pharmaceutical composition comprising the compound of Formula (I) as disclosed herein and an anti-cotinine antibody, or antigen binding fragment thereof as disclosed herein, and a pharmaceutically acceptable carrier, diluent, or excipient. In another embodiment, a combination comprises a first pharmaceutical composition comprising a compound of Formula (I) as disclosed herein and a pharmaceutically acceptable carrier, diluent, or excipient; and a second pharmaceutical composition comprising an anti-cotinine antibody or antigen binding fragment thereof as disclosed herein, and a pharmaceutically acceptable carrier, excipient, or diluent.

Statement of Use

The compounds of Formula (I) and pharmaceutically acceptable salts thereof are capable of simultaneously binding a cell surface-expressed CCR2 and an anti-cotinine antibody, or antigen binding fragment thereof to form a ternary complex for the treatment and/or prevention of diseases or disorders associated with CCR2-expressing cells.

In one embodiment, the present disclosure provides a method of treating and/or preventing a disease or disorder in a patient in need thereof comprising administering to the patient a therapeutically effective amount of the compound of Formula (I), or a pharmaceutically acceptable salt thereof, and an anti-cotinine antibody, or antigen-binding fragment thereof, wherein the disease or disorder is selected from a cancer, an inflammatory disease, an autoimmune disease, a viral infection, or a bacterial infection.

In a further embodiment, the compound and the antibody, or antigen-binding fragment thereof, are administered simultaneously. In a further embodiment, the compound and the antibody, or antigen-binding fragment thereof, are administered simultaneously from a single composition, including as a fixed-dose composition or by pre-mixing the compound and the antibody, or antigen-binding fragment thereof, prior to administration. For example, the compound and the antibody, or antigen-binding fragment thereof, can be premixed about 2 seconds to about 30 seconds, about 30 seconds to about 2 minutes, about 2 minutes to about 10 minutes, about 10 minutes to about 30 minutes, or about 30 minutes to about 2 hours prior to administration. In a further embodiment, the compound and the antibody, or antigen-binding fragment thereof, are administered simultaneously from two separate compositions.

In a further embodiment, the compound and the antibody, or antigen-binding fragment thereof, are administered sequentially.

In certain embodiments, the compound and the antibody, or antigen-binding fragment thereof, whether administered simultaneously or sequentially, may be administered by the same route or may be administered by different routes. In one embodiment, the compound and the antibody, or antigen-binding fragment thereof, are both administered intraveneously or subcutaneously, in the same composition or in separate compositions. In another embodiment, the compound is administered orally and the antibody or antigen-binding fragment thereof is administered intravenously or subcutaneously.

In a further embodiment, the compound and the antibody, or antigen-binding fragment thereof, are administered in a molar ratio of compound to antibody, or antigen-binding fragment thereof, of about 2:1, about 1.8:1, about 1.6:1, about 1.5:1, about 1.4:1, about 1.3:1, about 1.2:1, about 1:1, about 1:1.2, about 1:1.3, about 1:1.4, about 1:1.5, about 1:1.6, about 1:1.8, about 1:2, about 2:1 to about 1.5:1, about 1.5:1 to about 1.2:1, about 1.2:1 to about 1:1, about 1:1 to about 1:1.2, about 1:1.2 to about 1:1.5, or about 1:1.5 to about 1:2.

In a further embodiment, the compound and the antibody, or antigen-binding fragment thereof, are present as a combination in a molar ratio of compound to antibody, or antigen-binding fragment thereof, of about 2:1, about 1.8:1, about 1.6:1, about 1.5:1, about 1.4:1, about 1.3:1, about 1.2:1, about 1:1, about 1:1.2, about 1:1.3, about 1:1.4, about 1:1.5, about 1:1.6, about 1:1.8, about 1:2, about 2:1 to about 1.5:1, about 1.5:1 to about 1.2:1, about 1.2:1 to about 1:1, about 1:1 to about 1:1.2, about 1:1.2 to about 1:1.5, or about 1:1.5 to about 1:2.

In a further embodiment, the compound and the antibody, or antigen-binding fragment thereof, are administered at a dosage of compound of 0.0001 mg/kg to 1 mg/kg and antibody of 0.01 mg/kg to 100 mg/kg. For example, in a further embodiment, the compound is administered at a dosage of about 0.0001 mg/kg to about 0.0002 mg/kg, about 0.0002 mg/kg to about 0.0003 mg/kg, about 0.0003 mg/kg to about 0.0004 mg/kg, about 0.0004 mg/kg to about 0.0005 mg/kg, about 0.0005 mg/kg to about 0.001 mg/kg, about 0.001 mg/kg to about 0.002 mg/kg, about 0.002 mg/kg to about 0.003 mg/kg, about 0.003 mg/kg to about 0.004 mg/kg, about 0.004 mg/kg to about 0.005 mg/kg, about 0.005 mg/kg to about 0.01 mg/kg, about 0.01 mg/kg to about 0.02 mg/kg, about 0.02 mg/kg to about 0.03 mg/kg, about 0.03 mg/kg to about 0.04 mg/kg, about 0.04 mg/kg to about 0.05 mg/kg, about 0.05 mg/kg to about 0.1 mg/kg, about 0.1 mg/kg to about 0.2 mg/kg, about 0.2 mg/kg to about 0.3 mg/kg, about 0.3 mg/kg to about 0.4 mg/kg, about 0.4 mg/kg to about 0.5 mg/kg, and/or about 0.5 mg/kg to about 1 mg/kg, and the antibody, or antigen-binding fragment thereof, is administered at a dosage of about 0.01 mg/kg to about 0.02 mg/kg, about 0.02 mg/kg to about 0.03 mg/kg, about 0.03 mg/kg to about 0.04 mg/kg, about 0.04 mg/kg to about 0.05 mg/kg, about 0.05 mg/kg to about 0.1 mg/kg, about 0.1 mg/kg to about 0.2 mg/kg, about 0.2 mg/kg to about 0.3 mg/kg, about 0.3 mg/kg to about 0.4 mg/kg, about 0.4 mg/kg to about 0.5 mg/kg, about 0.5 mg/kg to about 1 mg/kg, about 1 mg/kg to about 2 mg/kg, about 2 mg/kg to about 3 mg/kg, about 3 mg/kg to about 4 mg/kg, about 4 mg/kg to about 5 mg/kg, about 5 mg/kg to about 10 mg/kg, about 10 mg/kg to about 15 mg/kg, about 15 mg/kg to about 20 mg/kg, about 20 mg/kg to about 25 mg/kg, about 25 mg/kg to about 30 mg/kg, about 30 mg/kg to about 35 mg/kg, about 35 mg/kg to about 40 mg/kg, about 40 mg/kg to about 45 mg/kg, about 45 mg/kg to about 50 mg/kg, about 50 mg/kg to about 60 mg/kg, about 60 mg/kg to about 70 mg/kg, about 70 mg/kg to about 80 mg/kg, about 80 mg/kg to about 90 mg/kg, and/or about 90 mg/kg to about 100 mg/kg.

In a further embodiment, the compound and the antibody, or antigen-binding fragment thereof, are administered at a dosage of compound of 0.007 mg to 70 mg and antibody of 0.7 mg to 7000 mg. For example, in a further embodiment, the compound is administered at a dosage of about 0.007 mg to about 0.01 mg, about 0.01 mg to about 0.02 mg, about 0.02 mg to about 0.03 mg, about 0.03 mg to about 0.04 mg, about 0.04 mg to about 0.05 mg, about 0.05 mg to about 0.1 mg, about 0.1 mg to about 0.2 mg, about 0.2 mg to about 0.3 mg, about 0.3 mg to about 0.4 mg, about 0.4 mg to about 0.5 mg, about 0.5 mg to about 1 mg, about 1 mg to about 2 mg, about 2 mg to about 3 mg, about 3 mg to about 4 mg, about 4 mg to about 5 mg, about 5 mg to about 10 mg, about 10 mg to about 20 mg, about 20 mg to about 30 mg, about 30 mg to about 40 mg, about 40 mg to about 50 mg, about 50 mg to about 60 mg, and/or about 60 mg to about 70 mg, and the antibody, or antigen-binding fragment thereof, is administered at a dosage of about 0.7 mg to about 1 mg, about 1 mg to about 2 mg, about 2 mg to about 3 mg, about 3 mg to about 4 mg, about 4 mg to about 5 mg, about 5 mg to about 10 mg, about 10 mg to about 20 mg, about 20 mg to about 30 mg, about 30 mg to about 40 mg, about 40 mg to about 50 mg, about 50 mg to about 100 mg, about 100 mg to about 500 mg, about 500 mg to about 1000 mg, about 1000 mg to about 1500 mg, about 1500 mg to about 2000 mg, about 2000 mg to about 2500 mg, about 2500 mg to about 3000 mg, about 3000 mg to about 3500 mg, about 3500 mg to about 4000 mg, about 4000 mg to about 4500 mg, about 4500 mg to about 5000 mg, about 5000 mg to about 5500 mg, about 5500 mg to about 6000 mg, about 6000 mg to about 6500 mg, and/or about 6500 mg to about 7000 mg.

In a further embodiment, the compound and the antibody, or antigen-binding fragment thereof, are administered in a molar ratio and/or dosage as described herein once every week, once every two weeks, once every three weeks, once every four weeks, once every five weeks, or once every six weeks for a period of one week to one year, such as a period of one week, one month, two months, three months, four months, five months, six months, seven months, eight months, nine months, ten months, eleven months, or twelve months.

In a further embodiment, the present disclosure provides a therapeutically effective amount of the compound of Formula (I), or a pharmaceutically acceptable salt thereof, and an anti-cotinine antibody, or antigen-binding fragment thereof for use in therapy. The compound of Formula (I), or a pharmaceutically acceptable salt thereof, and anti-cotinine antibody, or antigen-binding fragment thereof can be used in treating or preventing a disease or disorder selected from a cancer, an inflammatory disease, an autoimmune disease, a viral infection, or a bacterial infection.

In a further embodiment, the present disclosure provides a therapeutically effective amount of the compound of Formula (I), or a pharmaceutically acceptable salt thereof, and an anti-cotinine antibody, or antigen-binding fragment thereof for the manufacture of a medicament. The medicament can be used in treating or preventing a disease or disorder selected from a cancer, an inflammatory disease, an autoimmune disease, a viral infection, or a bacterial infection.

In a further embodiment, the disease or disorder is mediated by chemokine receptor 2 (CCR2) and/or is associated with CCR2-positive pathogenic cells. In a further embodiment, CCR-positive cell types are identified by testing for expression of CCR by immunohistochemistry or flow cytometry.

In a further embodiment, the disease or disorder is a cancer selected from non-small cell lung cancer (NSCLC), hepatocellular carcinoma (HCC), colorectal cancer (CRC), cervical squamous cell carcinoma (CESC), head and neck squamous cell carcinoma (HNSC), pancreatic cancer, metastatic castration-resistant prostate cancer (mCRPC), ovarian cancer, bladder cancer, or breast cancer, preferably a cancer selected from NSCLC, HCC, or CRC.

In a further embodiment, the disease or disorder is a solid tumor. In a further embodiment, the disease or disorder is a solid tumor selected from NSCLC, HCC, CRC, CESC, HNSC, pancreatic cancer, mCRPC, ovarian cancer, bladder cancer, or breast cancer, preferably a solid tumor selected from NSCLC, HCC, or CRC.

In a further embodiment, the disease or disorder is a PD-1 relapsed or refractory cancer, such as a PD-1 relapsed or refractory NSCLC, HCC, CRC, CESC, HNSC, pancreatic cancer, mCRPC, ovarian cancer, bladder cancer, or breast cancer, preferably a PD-1 relapsed or refractory NSCLC, HCC, or CRC.

In a further embodiment, the disease or disorder is a non-solid cancer. In a further embodiment, the disease or disorder is a leukemia, a lymphoma, or a myeloma.

In a further embodiment, the disease or disorder is a viral infection. In a further embodiment, the viral infection is caused by an influenza virus, a coronavirus (e.g., COVID-19), or a hepatitis B virus.

In a further embodiment, the disease or disorder is a bacterial infection. In a further embodiment, the bacterial infection is a chronic bacterial infection.

In one embodiment, the present disclosure provides a method of increasing antibody-dependent cell cytotoxicity (ADCC) of CCR2-expressing cells comprising contacting the cells with an effective amount of the compound of Formula (I), or pharmaceutically acceptable salt thereof, and an anti-cotinine antibody, or antigen-binding fragment thereof, wherein the CCR2-binding moiety of the compound binds the CCR2 expressed on the cells.

In one embodiment, the present disclosure provides a method of increasing antibody dependent cellular phagocytosis (ADCP) of CCR2-expressing cells comprising contacting the cells with an effective amount of the compound of Formula (I), or pharmaceutically acceptable salt thereof, and an anti-cotinine antibody, or antigen-binding fragment thereof, wherein the CCR2-binding moiety of the compound binds the CCR2 expressed on the cells.

In one embodiment, the present disclosure provides a method of increasing complement dependant cytotocity (CDC) of CCR2-expressing cells comprising contacting the cells with an effective amount of the compound of Formula (I), or pharmaceutically acceptable salt thereof, and an anti-cotinine antibody, or antigen-binding fragment thereof, wherein the CCR2-binding moiety of the compound binds the CCR2 expressed on the cells.

In one embodiment, the present disclosure provides a method of conditioning a patient for therapy with a chimeric antigen receptor (CAR) T cell therapy, comprising administering to a patient an effective amount of the compound of Formula (I), or pharmaceutically acceptable salt thereof, and an anti-cotinine antibody, or antigen-binding fragment thereof. In some embodiments, the compound of Formula (I), or pharmaceutically acceptable salt thereof, and an anti-cotinine antibody, or antigen-binding fragment thereof are administered in combination with the CAR-T cell therapy. A compound of Formula (I), or pharmaceutically acceptable salt thereof, and an anti-cotinine antibody, or antigen-binding fragment thereof may be administered as a conditioning therapy or combination therapy to improve efficacy in treatment of solid tumor cancers. In other embodiments, a compound of Formula (I), or pharmaceutically acceptable salt thereof, and an anti-cotinine antibody, or antigen-binding fragment thereof may be administered as a neoadjuvant treatment for other therapies, including but not limited to immunotherapy, surgical resection, radiation, and/or chemotherapy.

In one embodiment, the present disclosure provides a method of depleting CCR2-expressing cells comprising contacting the cells with the compound of Formula (I), or pharmaceutically acceptable salt thereof, and an anti-cotinine antibody, or antigen-binding fragment thereof, wherein the CCR2-binding moiety of the compound binds the CCR2 expressed on the cells.

In a further embodiment, the CCR2-expressing cells are pathogenic cells.

In a further embodiment, the pathogenic cell is a pathogenic immune cell, a tumor cell or cancer cell, or a stromal cell.

In a further embodiment, the pathogenic immune cells are monocytes, myeloid derived suppressor cells (MDSC), such as monocytic MDSCs (mMDSCs) and polymorphonuclear MDSCs (PMN_MDSCs), T regulatory cells (Tregs), neutrophils (e.g., N2 neutrophils), macrophages (e.g., M2 macrophages), B regulatory cells (Bregs, memory B cells), plasma cells, CD8 cells (e.g., CD8 regulatory cells (CD8regs), memory CD8 cells, effector CD8 cells, naïve CD8 Tcells, TEMRA), exhausted T cells, eosinophils, basophils, mast cells, dendritic cells, natural killer (NK cells), innate lymphoid cells, NK T cells (NKT), or γδT cells.

In a further embodiment, the pathogenic immune cells are myeloid derived suppressor cells (MDSC), such as monocytic MDSCs (mMDSCs) and polymorphonuclear MDSCs (PMN_MDSCs), T regulatory cells (Tregs), neutrophils (e.g., N2 neutrophils), macrophages (e.g., M2 macrophages), B regulatory cells (Bregs), CD8 regulatory cells (CD8regs), exhausted T cells.

In a further embodiment, the tumor cells or cancer cells are non-small cell lung cancer (NSCLC) cells, hepatocellular carcinoma (HCC) cells, colorectal cancer (CRC) cells, cervical squamous cell carcinoma (CESC) cells, head and neck squamous cell carcinoma (HNSC) cells, pancreatic cancer cells, metastatic castration-resistant prostate cancer (mCRPC) cells, ovarian cancer cells, bladder cancer cells, or breast cancer cells, preferably NSCLC cells, HCC cells, or CRC cells.

In a further embodiment, the stromal cells are cancer associated fibroblasts (CAFs).

Combination Therapies

The compounds of the invention may be employed alone or in combination with other therapeutic agents. Combination therapies according to the present invention thus comprise the administration of at least one compound of Formula (I) or a pharmaceutically acceptable salt thereof, and the use of at least one other pharmaceutically active agent. The compounds of the invention and the other pharmaceutically active agents may be administered together in a single pharmaceutical composition or separately and, when administered separately this may occur simultaneously or sequentially in any order. The amounts of the compounds of the invention and the other pharmaceutically active agents and the relative timings of administration will be selected in order to achieve the desired combined therapeutic effect.

It will be appreciated that when the compound of the present invention is administered in combination with one or more other therapeutically active agents normally administered by the inhaled, intravenous, oral, intranasal, ocular topical or other route, that the resultant pharmaceutical composition may be administered by the same route. Alternatively, the individual components of the composition may be administered by different routes.

In one embodiment, the compounds and pharmaceutical composition disclosed herein are used in combination with, or include, one or more additional therapeutic agents. In a further embodiment, the additional therapeutic agent is a checkpoint inhibitor or an immune modulator.

In a further embodiment, the checkpoint inhibitor is selected from a PD-1 inhibitor (e.g., an anti-PD-1 antibody including, but not limited to, pembrolizumab, nivolumab, cemiplimab, or dostarlimab), a PD-L1 inhibitor (e.g., an anti-PD-L1 antibody including, but not limited to, atezolizumab, avelumab, or durvalumab), or a CTLA-4 inhibitor (e.g., an anti-CTLA-4 antibody including, but not limited to, ipilimumab or tremilumumab).

In a further embodiment, the checkpoint inhibitor is selected from a CD226 axis inhibitor, including but not limited to a TIGIT inhibitor (e.g., an anti-TIGIT antibody), a CD96 inhibitor (e.g., an anti-CD96 antibody), and/or a PVRIG inhibitor (e.g., an anti-PVRIG antibody).

In a further embodiment, the immune modulator is an ICOS agonist (e.g., an anti-ICOS antibody including, but not limited to feladilimab), a PARP inhibitor (e.g., niraparib, olaparib), or a STING agonist.

Pharmaceutical Compositions, Dosages, and Dosage Forms

For the purposes of administration, in certain embodiments, the ARMs described herein are administered as a raw chemical or are formulated as pharmaceutical compositions. Pharmaceutical compositions disclosed herein include an ARM and one or more of: a pharmaceutically acceptable carrier, diluent or excipient. An ARM is present in the composition in an amount which is effective to treat a particular disease, disorder or condition of interest. The activity of the ARM can be determined by one skilled in the art, for example, as described in the biological assays described below. Appropriate concentrations and dosages can be readily determined by one skilled in the art. In certain embodiments, the ARM is present in the pharmaceutical composition in an amount from about 25 mg to about 500 mg. In certain embodiments, the ARM is present in the pharmaceutical composition in an amount of about 0.01 mg to about 300 mg. In certain embodiments, ARM is present in the pharmaceutical composition in an amount of about 0.01 mg, 0.1 mg, 1 mg, 5 mg, 10 mg, 25 mg, 50 mg, 100 mg, 200 mg, 300 mg, 400 mg or about 500 mg.

Administration of the compounds of the invention, or their pharmaceutically acceptable salts, in pure form or in an appropriate pharmaceutical composition, is carried out via any of the accepted modes of administration of agents for serving similar utilities. The pharmaceutical compositions of the invention are prepared by combining a compound of the invention with an appropriate pharmaceutically acceptable carrier, diluent or excipient, and in specific embodiments are formulated into preparations in solid, semi-solid, liquid or gaseous forms, such as tablets, capsules, powders, granules, ointments, solutions, suppositories, injections, inhalants, gels, microspheres, and aerosols. Exemplary routes of administering such pharmaceutical compositions include, without limitation, oral, topical, transdermal, inhalation, parenteral (e.g., intramuscular, subcutaneous, intravenous, or intradermal), sublingual, buccal, rectal, vaginal, and intranasal. Pharmaceutical compositions of the invention are formulated so as to allow the active ingredients contained therein to be bioavailable upon administration of the composition to a patient.

Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia. College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings described herein.

The pharmaceutical compositions disclosed herein are prepared by methodologies well known in the pharmaceutical art. For example, in certain embodiments, a pharmaceutical composition intended to be administered by injection is prepared by combining a compound of the invention with sterile, distilled water so as to form a solution. In some embodiments, a surfactant is added to facilitate the formation of a homogeneous solution or suspension. Surfactants are compounds that non-covalently interact with the compound of the invention so as to facilitate dissolution or homogeneous suspension of the compound in the aqueous delivery system.

Traditional antibody therapeutics have several disadvantages that are addressed by the ARMs approach described herein including difficulties in managing adverse events via adjusting dose and dose frequency of administration, challenges in generating antibodies to certain classes of drug targets (e.g., GPCRs, ion channels, and enzymes), and a new cell line for development is required for each new antibody which can be slow and costly. Moreover, different formats of biologics (e.g., bispecifics) can be challenging to manufacture. In contrast, the ARMs approach provides the following advantages: uniting the pharmacology of antibodies with the dose-control of small molecules, dose controlled PK/PD allowing temporal cell depletion, simpler multimerization, and rapid reversal of cell depletion through dosing of the antibody-binding component (e.g., cotinine hapten) which can uncouple therapeutic effects from potential adverse events.

Examples

The following examples illustrate the invention. These Examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made. References to preparations carried out in a similar manner to, or by the general method of, other preparations, may encompass variations in routine parameters such as time, temperature, workup conditions, minor changes in reagent amounts etc. Chemical names for all title compounds were generated using ChemDraw Plug-in version 16.0.1.13c (90) or ChemDraw desktop version 16.0.1.13 (90).

Compound Synthesis

The compounds according to Formula (I) are prepared using conventional organic synthetic methods. A suitable synthetic route is depicted below in the following general reaction schemes. All the starting materials are commercially available or are readily prepared from commercially available starting materials by those of skill in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Organic Synthesis* (4th ed.), John Wiley & Sons, NY (2006). In some instances, a substituent may be specifically selected to be reactive under the reaction conditions used. Under these circumstances, the reaction conditions convert the selected substituent into another substituent that is either useful as an intermediate compound or is a desired substituent in a target compound.

Scheme 1

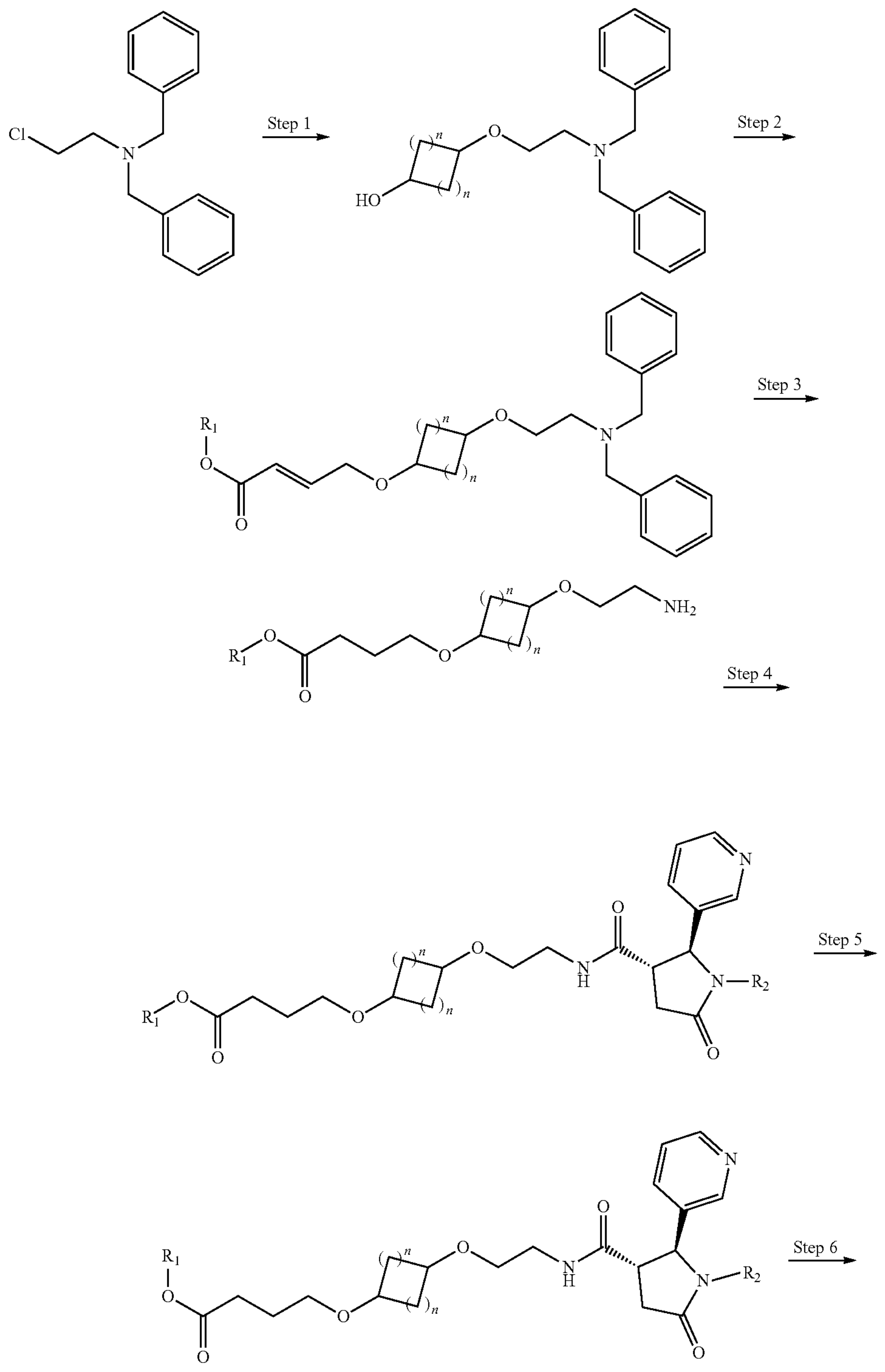

-continued
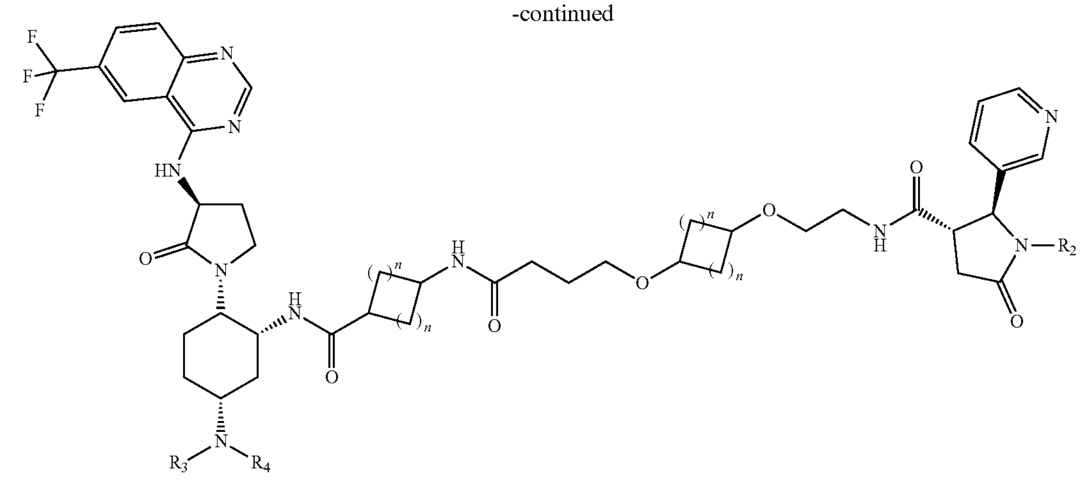
Intermediates
Intermediate 1
Ethyl (1R,2S)-2-((S)-3-(((benzyloxy)carbonyl) amino)-2-oxopyrrolidin-1-yl)-5-oxocyclohexane-1-carboxylate
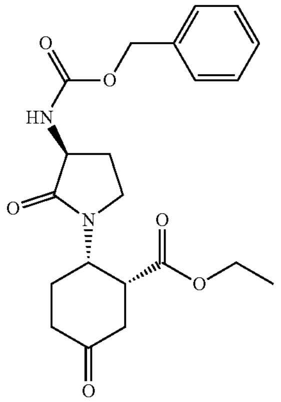
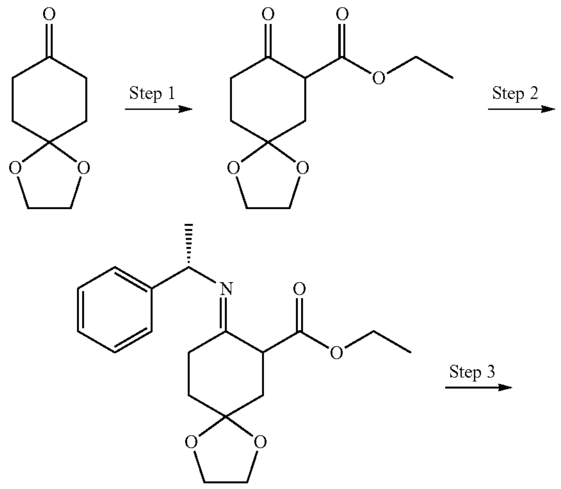
-continued
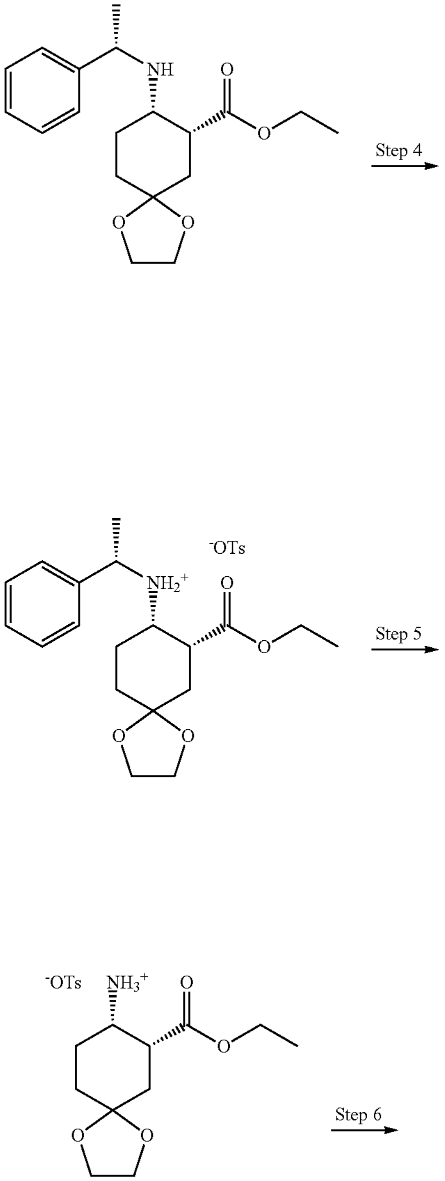

-continued

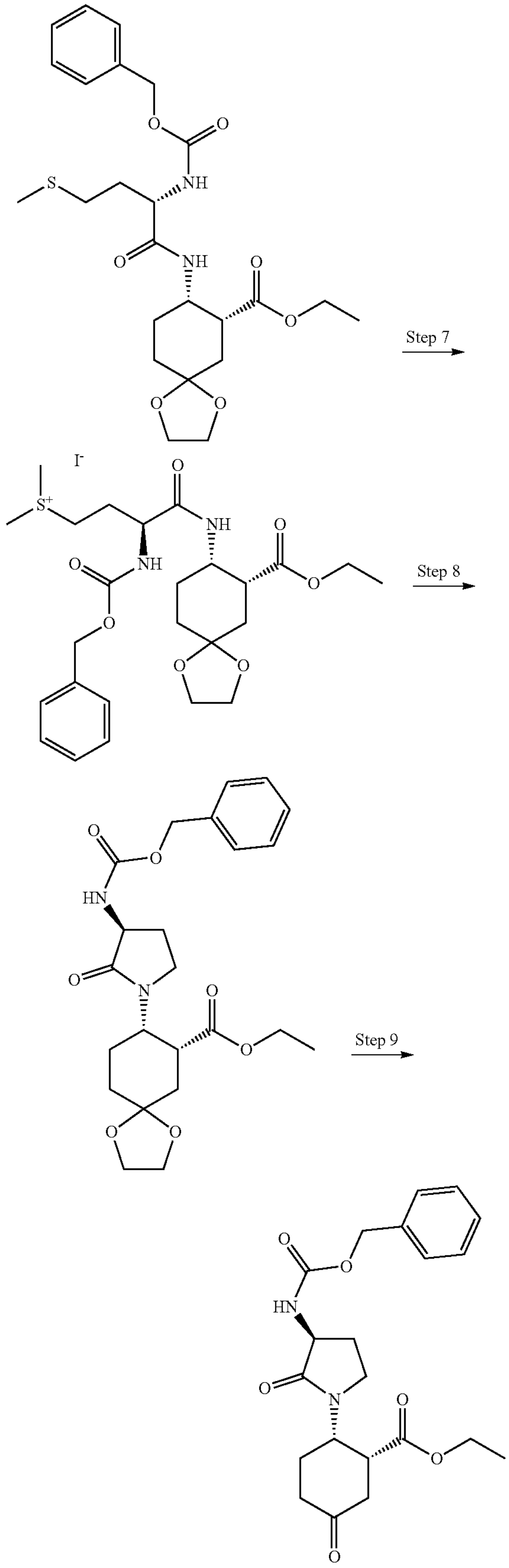

Step 1

Ethyl 8-oxo-1,4-dioxaspiro[4.5]decane-7-carboxylate

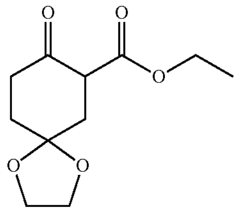 [SMILES: CCOC(=O)C1CC2(CCC1=O)OCCO2]

To a solution of 1,4-dioxaspiro[4.5]decan-8-one (125 g, 800 mmol) in tetrahydrofuran (THF) (1300 mL) was added lithium bis(trimethylsilyl)amide (800 mL, 800 mmol, 1 M in THF) at −78° C. for 2 h. Ethyl carbonocyanidate (79 g, 800 mmol) was added slowly and stirred at −78° C. for 6 h. Ice cold water was added (2 L) and the mixture was extracted with ethyl acetate (2×2000 mL). The combined organic extracts were washed with brine (500 mL), were dried over anhydrous $Na_2SO_4$, were filtered, and the filtrate was evaporated. Purification by normal phase chromatography (silica gel 60-120 mesh column) eluting with 10% ethyl acetate in hexane provided the title compound as pale-yellow liquid (95 g, 403 mmol, 50.3% yield). LC/MS: m/z 229.09 $(M+H)^+$.

Step 2

Ethyl (E)-8-(((S)-1-phenylethyl)imino)-1,4-dioxaspiro[4.5]decane-7-carboxylate

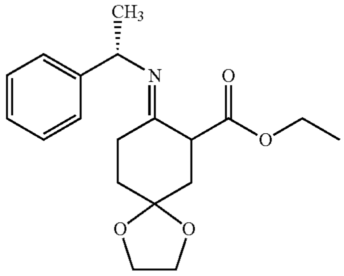 [SMILES: CCOC(=O)C1CC2(CC/C1=N\[C@@H](C)c1ccccc1)OCCO2]

To a solution of ethyl 8-oxo-1,4-dioxaspiro[4.5]decane-7-carboxylate (100 g, 438 mmol) in toluene (1000 mL) were added (S)-1-phenylethanamine (62.1 mL, 482 mmol) and ytterbium(III) trifluoromethanesulfonate (1.087 g, 1.753 mmol), and the mixture was stirred at reflux for 3 h using a Dean-Stark trap to remove water. The mixture was concentrated under reduced pressure. Trituration with hexane (500 mL) provided the title compound as a tan solid (110 g, 327 mmol, 74.6% yield). LC-MS m/z 332.28 $(M+H)^+$.

Step 3

Ethyl (7R,8S)-8-(((S)-1-phenylethyl)amino)-1,4-dioxaspiro[4.5]decane-7-carboxylate

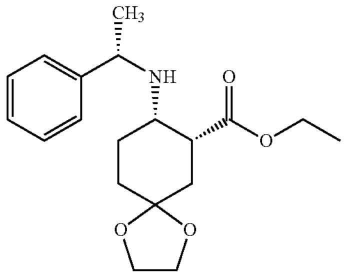 [SMILES: CCOC(=O)[C@@H]1CC2(CC[C@@H]1N[C@@H](C)c1ccccc1)OCCO2]

To a solution of (E)-ethyl 8-(((S)-1-phenylethyl)imino)-1,4-dioxaspiro[4.5]decane-7-carboxylate (110 g, 332 mmol) in acetonitrile (550 mL) and acetic acid (275 mL) was added portionwise sodium triacetoxyborohydride (125 g, 587 mmol) at 0° C., and the mixture was stirred at rt for 16 h. The mixture was evaporated and the residue was chased with dichloromethane (DCM) (2×150 mL). The residue was dissolved in dichloromethane (DCM) (1000 mL) and was neutralized with 30% sodium hydroxide solution (150 mL). The organic phase washed with brine (700 mL), was dried over anhydrous $Na_2SO_4$, was filtered, and the filtrate was evaporated. Purification by normal-phase chromatography (silica gel 100-200 mesh column) eluting with 10% ethyl acetate in petroleum ether provided the title compound as a yellow, gummy solid (90 g, 208 mmol, 62.8% yield). LC-MS m/z 334.29 $(M+H)^+$.

Step 4

(7R,8S)-7-(Ethoxycarbonyl)-N-((S)-1-phenylethyl)-1,4-dioxaspiro[4.5]decan-8-aminium, 4-Methyl benzenesulphonic acid salt

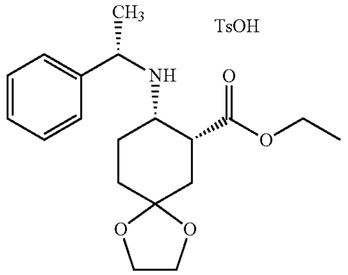 [SMILES: CCOC(=O)[C@@H]1CC2(CC[C@@H]1N[C@@H](C)c1ccccc1)OCCO2 ; "TsOH"]

To a solution of ethyl (7R,8S)-8-(((S)-1-phenylethyl)amino)-1,4-dioxaspiro[4.5]decane-7-carboxylate (90 g, 270 mmol) in dichloromethane (DCM) (900 mL) was added p-toluenesulfonic acid monohydrate (51.3 g, 270 mmol) at 0° C. and the mixture was stirred at 26° C. for 16 h. The mixture was concentrated under reduced pressure, diethyl ether (200 mL) was added, and the mixture was stirred for 30 min. The precipitate was collected by filtration and was dried to provide the title compound as a pale-yellow solid (100 g, 197 mmol, 73.1% yield). LC-MS m/z 334.35 $(M-172+H)^+$.

Step 5

(7R,8S)-7-(Ethoxycarbonyl)-1,4-dioxaspiro-[4.5]-decan-8-aminium, 4-Methylbenzenesulphonic acid salt

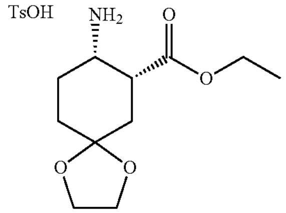 [SMILES: "TsOH" ; CCOC(=O)[C@@H]1CC2(CC[C@@H]1N)OCCO2]

To a solution of (7R,8S)-7-(ethoxycarbonyl)-N-((S)-1-phenylethyl)-1,4-dioxaspiro[4.5]decan-8-aminium, 4-methylbenzenesulphonic acid salt (100 g, 197 mmol) in ethanol (1 L) was added 10% Pd/C (30.5 g, 28.7 mmol) at rt, and the mixture was stirred under 40 psi of hydrogen in an autoclave at 40° C. for 16 h. The mixture was filtered through Celite® and the filtrate was evaporated to provide the title compound as a pale-yellow gummy solid (78 g, 194 mmol, 98% yield). LC-MS m/z 230.1 $(M+H)^+$.

Step 6

Ethyl (7R,8S)-8-((S)-2-(((benzyloxy)carbonyl)amino)-4-(methylthio)butanamido)-1,4-dioxaspiro[4.5]decane-7-carboxylate

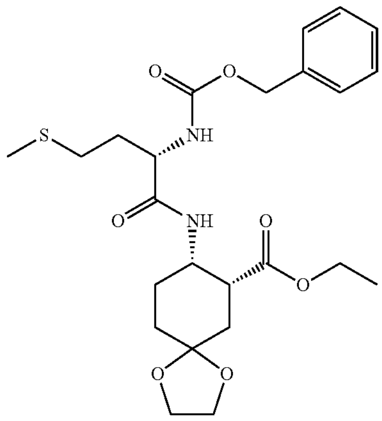 [SMILES: CCOC(=O)[C@@H]1CC2(CC[C@@H]1NC(=O)[C@H](CCSC)NC(=O)OCc1ccccc1)OCCO2]

To a solution of (7R,8S)-7-(ethoxycarbonyl)-1,4-dioxaspiro[4.5]decan-8-aminium, 4-methylbenzenesulphonic acid salt (78 g, 194 mmol) in acetonitrile (800 mL) were added EDC·HCl (37.2 g, 194 mmol), HOBt (29.7 g, 194 mmol) and triethylamine (81 mL, 581 mmol) at 26° C. Commercially-available (S)-2-(((benzyloxy)carbonyl)amino)-4-(methylthio)butanoic acid (54.9 g, 194 mmol) was added and the mixture was stirred at 26° C. for 16 h. Ice cold water (700 mL) was added and the mixture was extracted with ethyl acetate (2×800 mL). The combined organic extracts were dried over anhydrous $Na_2SO_4$, were filtered, and the filtrate was concentrated to provide the title compound as a brown liquid (95 g, 187 mmol, 96% yield). LC-MS m/z 495.34 $(M+H)^+$.

Step 7

((S)-3-(((benzyloxy)carbonyl)amino)-4-(((7R,8S)-7-(ethoxycarbonyl)-1,4-dioxaspiro[4.5]decan-8-yl amino)-4-oxobutyl)dimethylsulfonium iodide

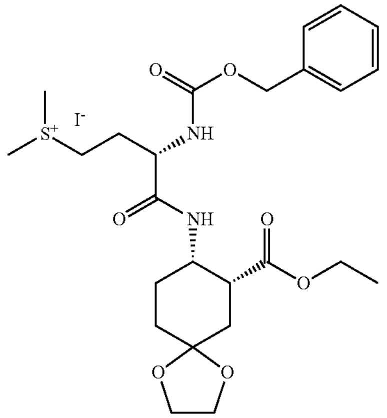 [SMILES: CCOC(=O)[C@@H]1CC2(CC[C@@H]1NC(=O)[C@H](CC[S+](C)C)NC(=O)OCc1ccccc1)OCCO2 ; [I-]]

To ethyl (7R,8S)-8-((S)-2-(((benzyloxy)carbonyl)amino)-4-(methylthio)butanamido)-1,4-dioxaspiro[4.5]decane-7-carboxylate (95 g, 192 mmol) was added iodomethane (120 mL, 1921 mmol) at 26° C., and the mixture was stirred at 26° C. for 24 h. The mixture was distilled to afford crude product. The crude product was washed with methyl t-butyl ether (MTBE) (300 mL) to provide the title compound as an off-white solid (115 g, 181 mmol, 94% yield). LC-MS m/z 509.2 $(M)^+$.

Step 8

Ethyl (7R,8S)-8-((S)-3-(((benzyloxy)carbonyl)amino)-2-oxopyrrolidin-1-yl)-1,4-dioxaspiro[4.5]decane-7-carboxylate

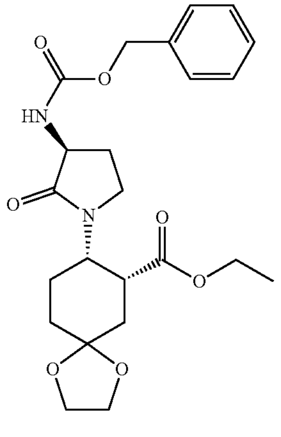 [SMILES: CCOC(=O)[C@@H]1CC2(CC[C@@H]1N1CC[C@H](NC(=O)OCc3ccccc3)C1=O)OCCO2]

To a solution of ((S)-3-(((benzyloxy)carbonyl)amino)-4-(((7R,8S)-7-(ethoxycarbonyl)-1,4-dioxaspiro[4.5]decan-8-yl)amino)-4-oxobutyl)dimethylsulfonium iodide (75 g, 118 mmol) in anhydrous DMSO (100 mL) under an atmosphere of nitrogen was added portionwise finely ground cesium carbonate (42.2 g, 130 mmol) every 2-3 minutes over 15 min and the mixture was stirred for 7 h. The mixture was filtered and was washed with ethyl acetate (300 mL). Ethyl acetate (1000 mL, cold) and brine (420 mL) were added to the filtrate, the organic phase was washed twice with brine (420 mL) and was concentrated under reduced pressure to provide the title compound as an orange oil (39.6 g, 88.8 mmol 75% yield). LC-MS m/z 447.1 $(M+H)^+$.

Step 9

Ethyl (1R,2S)-2-((S)-3-(((benzyloxy)carbonyl)amino)-2-oxopyrrolidin-1-yl)-5-oxocyclohexane-1-carboxylate

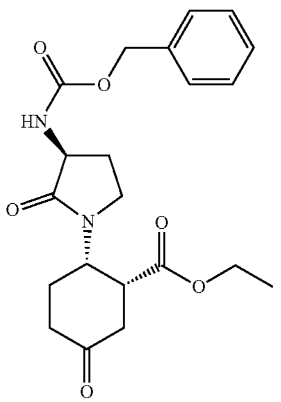 [SMILES: CCOC(=O)[C@@H]1CC(=O)CC[C@@H]1N1CC[C@H](NC(=O)OCc2ccccc2)C1=O]

A mixture of ethyl (7R,8S)-8-((S)-3-(((benzyloxy)carbonyl)amino)-2-oxopyrrolidin-1-yl)-1,4-dioxaspiro[4.5]decane-7-carboxylate (47.12 g, 106 mmol), ethyl acetate (156 mL), acetone (255 mL), water (287 mL), and concentrated HCl (13 mL) was stirred under an atmosphere of nitrogen at 60° C. for 3 h. The mixture was chilled in an ice bath and stored in a refrigerator overnight. The mixture was concentrated under reduced pressure to a suspension and was extracted with dichloromethane (DCM) (1×400 mL, 1×150 mL). The combined organic extracts were washed with brine (80 mL), were dried over $Na_2SO_4$, were filtered, and the filtrate was concentrated under reduced pressure. The residue was chased with dichloromethane (DCM) (3×100 mL), was dried under reduced pressure at 36° C. for 1 h, and was placed under vacuum at rt for 2 days to provide the title compound as a beige waxy solid (40.0 g, 94%). LC-MS m/z 403.3 $(M+H)^+$.

Intermediate 2
(S)-1-((1S,2R,4R)-2-Amino-4-(isopropyl(methyl)amino)cyclohexyl)-3-((6-(trifluoromethyl)quinazolin-4-yl)amino)pyrrolidin-2-one, 2Hydrochloric acid salt
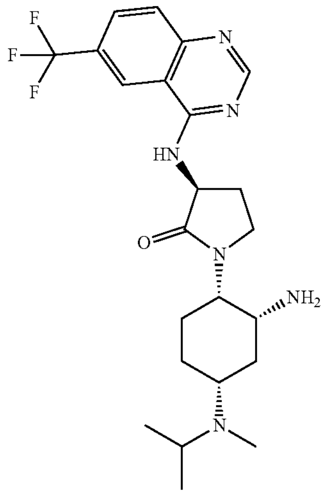
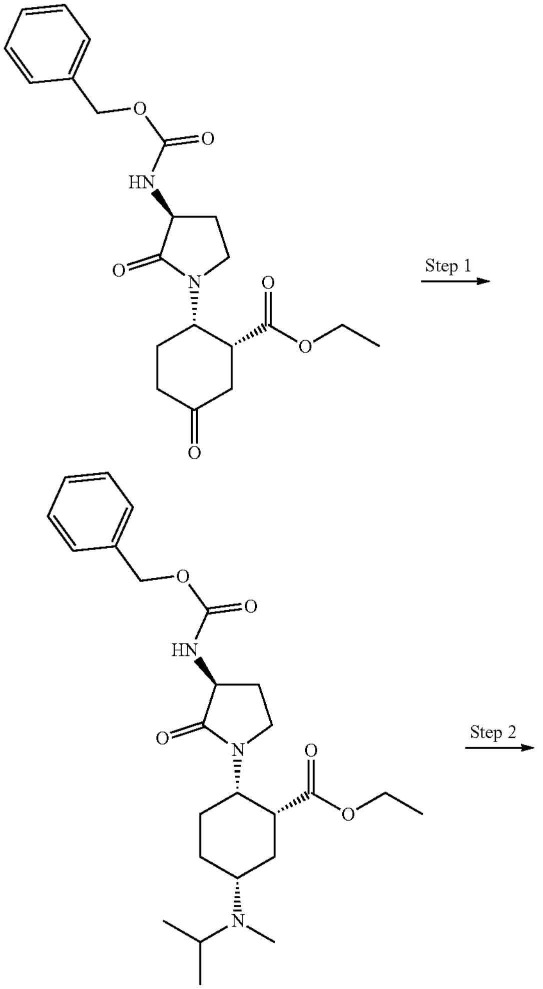
-continued
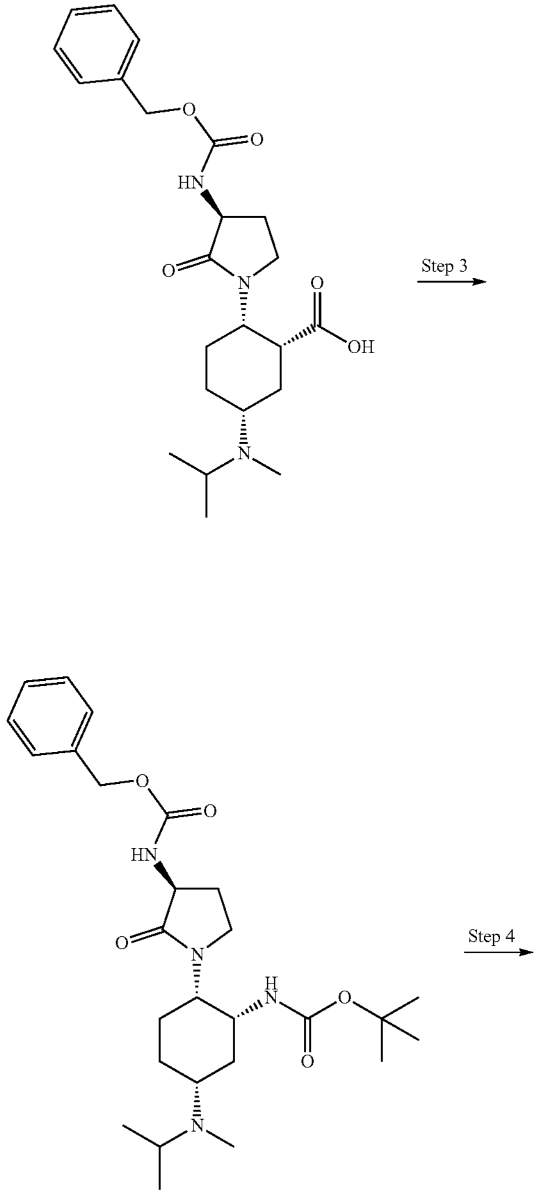
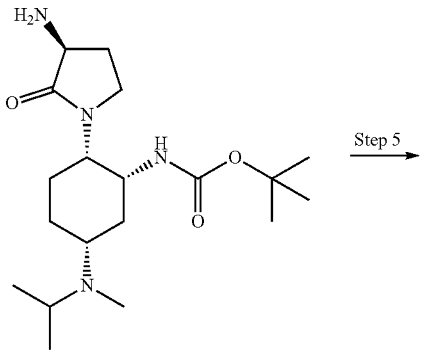

-continued

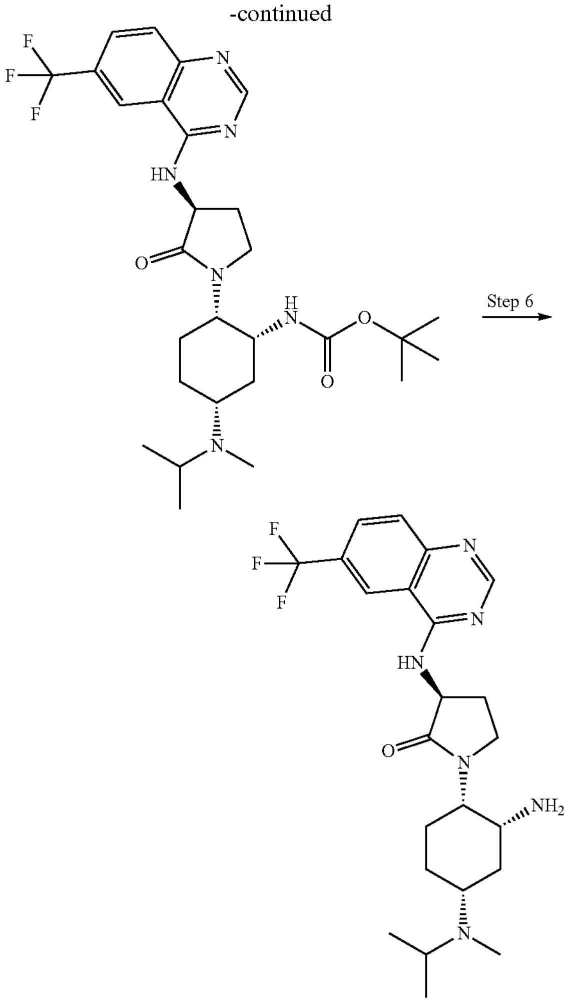

Step 1

Ethyl (1R,2S,5R)-2-((S)-3-(((benzyloxy)carbonyl)amino)-2-oxopyrrolidin-1-yl)-5-(isopropyl(methyl)amino)cyclohexane-1-carboxylate

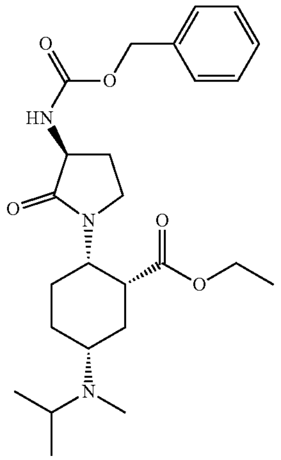 [SMILES: CCOC(=O)[C@@H]1C[C@H](N(C)C(C)C)CC[C@@H]1N1CC[C@H](NC(=O)OCc2ccccc2)C1=O]

To a mixture of ethyl (1R,2S)-2-((S)-3-(((benzyloxy)carbonyl)amino)-2-oxopyrrolidin-1-yl)-5-oxocyclohexane-1-carboxylate (Intermediate 1) (28.0 g, 69.6 mmol) and isopropyl methylamine (12.32 mL, 118 mmol) in dichloromethane (DCM) (270 mL) was added titanium(IV) isopropoxide (30.6 mL, 104 mmol) at rt. The mixture was stirred under an atmosphere of nitrogen at rt for 21 h. 5% Pt/C (4.07 g, 1.044 mmol) was added and the mixture was stirred under a balloon atmosphere of hydrogen at rt for 29 h. The hydrogen balloon was refilled after 7 h and 16 h. The mixture was filtered through Celite® and the catalyst was washed with dichloromethane (DCM). The combined filtrates were concentrated under reduced pressure. The residue was dissolved in dichloromethane (DCM) (80 mL), was placed in an ice bath, and ethyl acetate (250 mL) and Celite® (5 g) were added. The mixture was stirred at rt for 4 h and was sonicated at rt for 20 min. The mixture was filtered through Celite® with wet ethyl acetate (4×70 mL). The combined filtrates were concentrated under reduced pressure and were chased with dichloromethane (DCM) (3×100 mL) to provide the title compound as light-brown, oily foam (24.58 g, 77%). LC-MS m/z 460.5 $(M+H)^+$.

Step 2

(1R,2S,5R)-2-((S)-3-(((Benzyloxy)carbonyl)amino)-2-oxopyrrolidin-1-yl)-5-(isopropyl(methyl)amino)cyclohexanecarboxylic acid

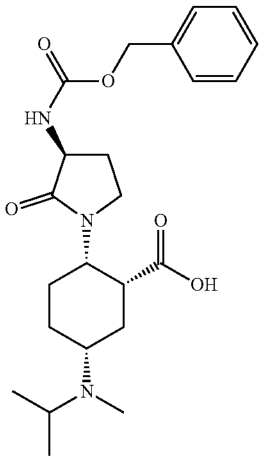 [SMILES: CC(C)N(C)[C@@H]1CC[C@H](N2CC[C@H](NC(=O)OCc3ccccc3)C2=O)[C@H](C(=O)O)C1]

Ethyl (1R,2S,5R)-2-((S)-3-(((benzyloxy)carbonyl)amino)-2-oxopyrrolidin-1-yl)-5-(isopropyl(methyl)amino)cyclohexane-1-carboxylate (24.58 g, 53.5 mmol) was dissolved in toluene (140 mL) and dichloromethane (DCM) (5 mL) and the solution was extracted with 2 N HCl (2×67 mL). The combined aqueous extracts were placed in a metal insert under an atmosphere of nitrogen and heated at 63° C. for 22 h. The mixture was placed in an ice bath and 10 N sodium hydroxide (32 mL) was added. The final temperature of the mixture was 16° C. The mixture was washed with toluene (150 mL) and the aqueous phase was filtered. An aqueous emulsion (20 mL) was separated and was filtered through Celite®. The combined aqueous phases were cooled in an ice bath, and the pH was adjusted to 6 to 7 with concentrated HCl. The mixture was saturated with NaCl and was extracted with dichloromethane (DCM) (200 mL). Concentrated HCl (0.5 mL) was added and the aqueous phase was extracted 10% methanol in dichloromethane (DCM) (2×100 mL). The combined organic extracts were dried over $Na_2SO_4$, were filtered, and the filtrate was concentrated under reduced pressure to provide the title compound as a beige, foamy solid (14.18 g, 2.74 mmol, 61%). LC-MS m/z 432.4 $(M+H)^+$.

Step 3 tert-Butyl ((1R,2S,5R)-2-((S)-3-(((benzyloxy)carbonyl)amino)-2-oxopyrrolidin-1-yl)-5-(isopropyl(methyl)amino)cyclohexyl)carbamate

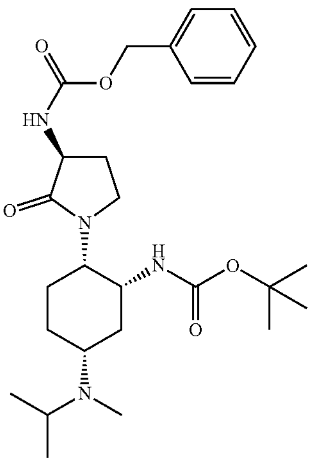 [SMILES: CC(C)N(C)[C@@H]1CC[C@H](N2CC[C@H](NC(=O)OCc3ccccc3)C2=O)[C@H](NC(=O)OC(C)(C)C)C1]

(1R,2S,5R)-2-((S)-3-(((benzyloxy)carbonyl)amino)-2-oxopyrrolidin-1-yl)-5-(isopropyl(methyl)amino)cyclohexane-1-carboxylic acid (14.18 g, 32.9 mmol) was chased with dichloromethane (DCM) (30 mL) and toluene (330 mL) (3×). To a solution of the residue in anhydrous toluene (121 mL) under an atmosphere of nitrogen was added anhydrous tert-butanol (31.0 mL, 329 mmol) and triethylamine (16.0 mL, 115 mmol), and the mixture was heated in a metal insert at 85° C. for 5 min. DPPA (7.79 mL, 36.1 mmol) was added dropwise over 14 min and the mixture was heated under an atmosphere of nitrogen at 85° C. for 2.75 h The mixture was cooled to rt, ethyl acetate (280 mL) was added, and the internal temp was adjusted to 2 to 3° C. using an ice bath. Saturated $NaHCO_3$ (280 mL) was added dropwise over a 20 min period and the mixture was stirred at rt for 2 h. The organic phase was washed with brine (40 mL), was dried over $Na_2SO_4$, was filtered, and the filtrate was concentrated under reduced pressure. The residue was placed under vacuum at rt for 2 days. tert-Butanol (100 mL) was added and the mixture was sonicated at rt for 20 min. 1 N sodium hydroxide (80 mL) was added, the mixture was stirred at rt for 30 min, and was concentrated under reduced pressure to 80 mL of volume. Dichloromethane (DCM) (200 mL) and water (40 mL) were added, the organic phase was dried over $Na_2SO_4$, was filtered, and the filtrate was concentrated under reduced pressure. The residue was chased with ethyl acetate (85 mL) (2×). The residue was stirred in ethyl acetate (30 mL) and heptane (40 mL), was collected by filtration, and was washed with 1:10 ethyl acetate/heptane solution to provide the title compound as a white solid (8.03 g, 15.02 mmol, 48.6%). LC-MS m/z 503.5 $(M+H)^+$.

Step 4 tert-Butyl ((1R,2S,5R)-2-((S)-3-amino-2-oxopyrrolidin-1-yl)-5-(isopropyl(methyl)amino) cyclohexyl) carbamate

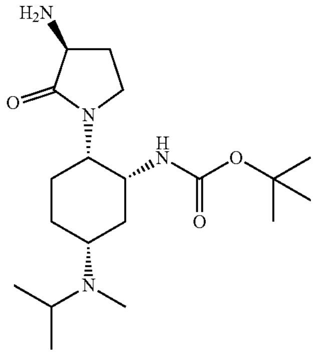 [SMILES: CC(C)N(C)[C@@H]1CC[C@H](N2CC[C@H](N)C2=O)[C@H](NC(=O)OC(C)(C)C)C1]

To a solution of tert-butyl ((1R,2S,5R)-2-((S)-3-(((benzyloxy)carbonyl)amino)-2-oxopyrrolidin-1-yl)-5-(isopropyl (methyl)amino)cyclohexyl)carbamate (4.99 g, 9.93 mmol) in ethanol (70 mL) was added 20 wt % $Pd(OH)_2/C$ (0.7 g, 0.993 mmol) and the mixture was stirred under a balloon atmosphere of hydrogen at rt for 23 h. The mixture was filtered through Celite® under an atmosphere of nitrogen, and the catalyst was washed with ethanol (3×10 mL). The combined filtrates were concentrated under reduced pressure and the residue was placed under vacuum at rt overnight to provide the title compound as a white solid (3.64 g, 9.38 mmol, 99% yield). LC-MS m/z 369.4 $(M+H)^+$.

Step 5 tert-Butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate

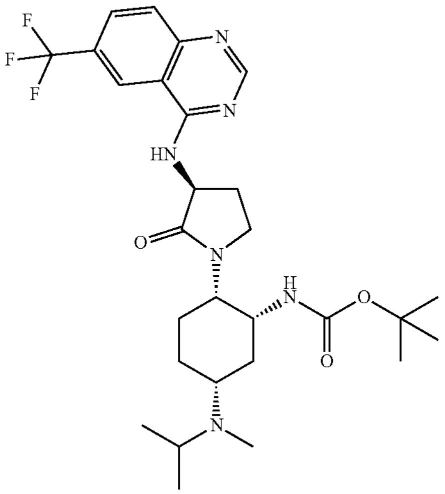 [SMILES: CC(C)N(C)[C@@H]1CC[C@H](N2CC[C@H](Nc3ncnc4ccc(C(F)(F)F)cc34)C2=O)[C@H](NC(=O)OC(C)(C)C)C1]

To a solution of tert-butyl ((1R,2S,5R)-2-((S)-3-amino-2-oxopyrrolidin-1-yl)-5-(isopropyl(methyl)amino)cyclohexyl)carbamate (3.64 g, 9.88 mmol) in ethanol (100 mL)

was added commercially-available 4-chloro-6-(trifluoromethyl)quinazoline (2.30 g, 9.88 mmol) and DIPEA (2.77 mL, 15.84 mmol), and the mixture was heated under an atmosphere of nitrogen in a metal insert at 50° C. for 3 h. The mixture was concentrated under reduced pressure, dichloromethane (DCM) (150 mL) was added, and the organic phase was washed with water (30 mL). The organic phase was dried over $Na_2SO_4$, was filtered, and the filtrate was concentrated under reduced pressure. The residue was purified by ISCO CombiFlash® Rf (220 g RediSep Rf Gold® column, 120 mL/min) eluting with a gradient of 0 to 75% DCM/DCM in MeOH with 1% $NH_4OH$ and then wash the column with MeOH. The desired fractions were combined and dried under reduced pressure to provide the title compound as a white solid (4.32 g, 7.57 mmol, 77% yield). LC-MS m/z 565.2 $(M+H)^+$.

Step 6

(S)-1-((1S,2R,4R)-2-Amino-4-(isopropyl(methyl)amino)cyclohexyl)-3-((6-(trifluoromethyl)quinazolin-4-yl)amino)pyrrolidin-2-one, 2Hydrochloric acid salt

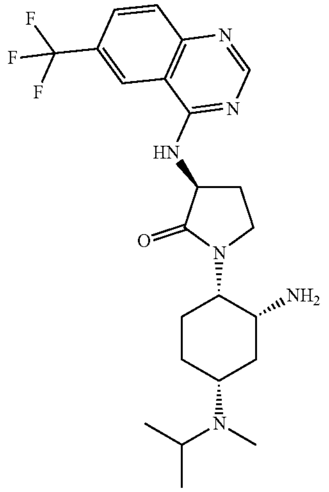 [SMILES: CC(C)N(C)[C@@H]1CC[C@H](N2CC[C@H](Nc3ncnc4ccc(C(F)(F)F)cc34)C2=O)[C@H](N)C1]

To a mixture of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (3.18 g, 5.63 mmol) in dichloromethane (DCM) (8 mL) was added HCl (7.04 mL, 28.2 mmol). The mixture was stirred at rt for 3 h and was concentrated to dryness to provide the title compound as a white solid (3.5 g, 6.51 mmol, 116% yield). LC-MS m/z 465.3 $(M+H)^+$.

Intermediate 3

(S)-1-((1S,2R,4R)-2-Amino-4-(tert-butylamino)cyclohexyl)-3-((6-(trifluoromethyl) quinazolin-4-yl) amino)pyrrolidin-2-one

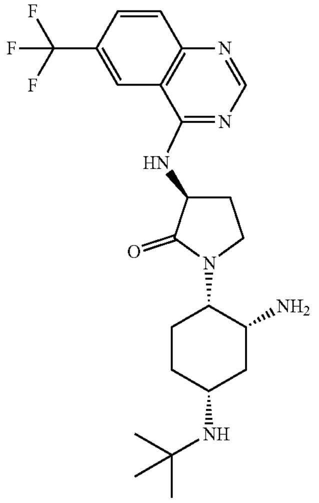

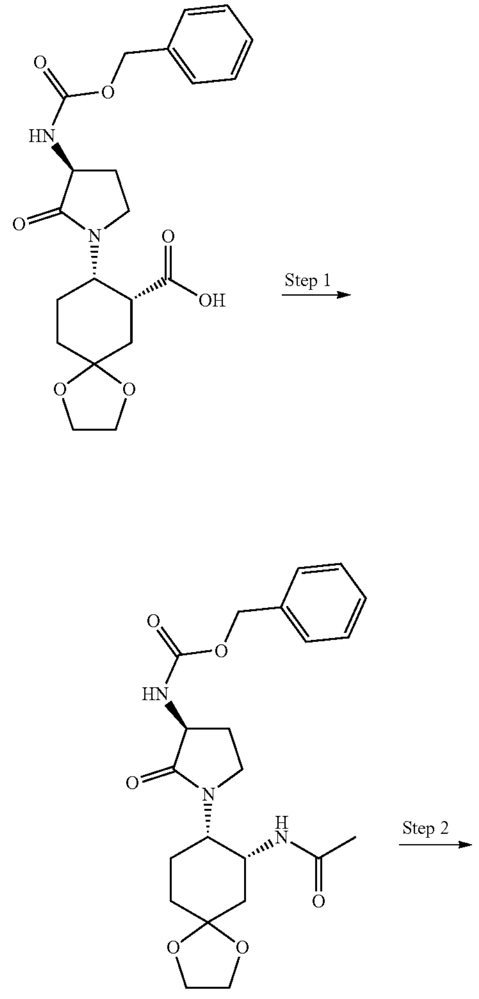

-continued
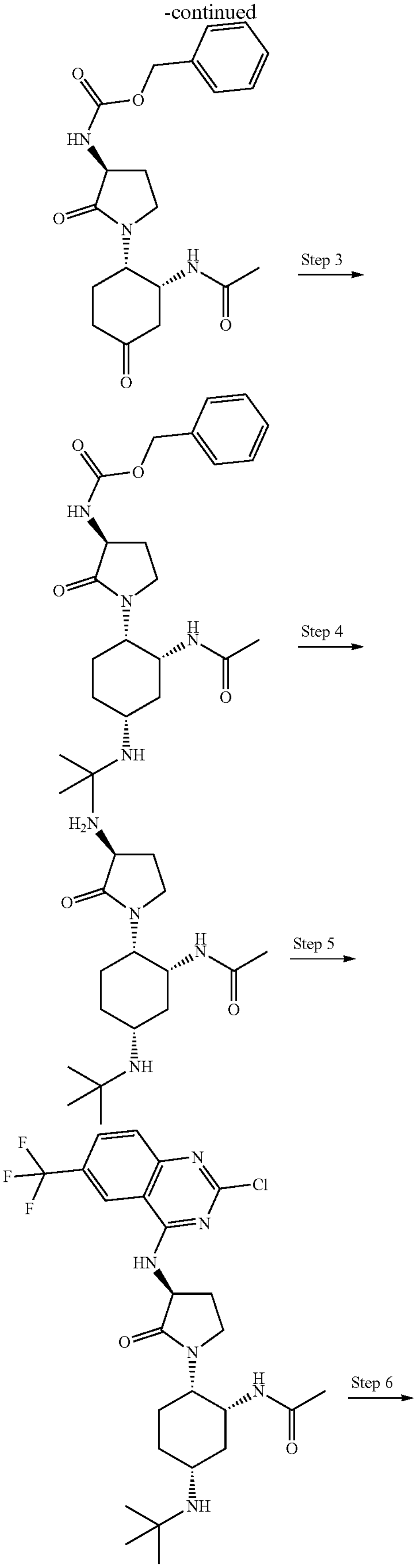
-continued
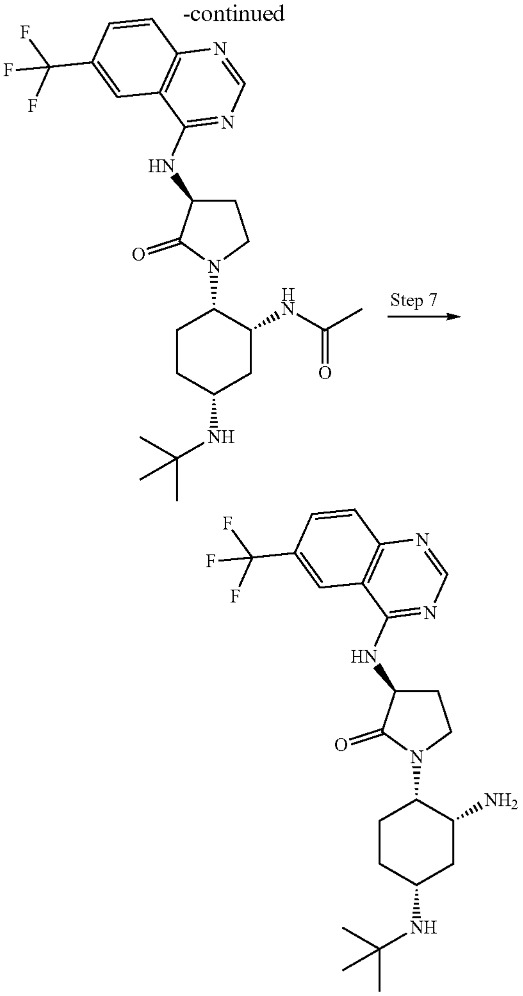
Step 1
Benzyl ((S)-1-((7R,8S)-7-acetamido-1,4-dioxaspiro[4.5]decan-8-yl)-2-oxopyrrolidin-3-yl)carbamate
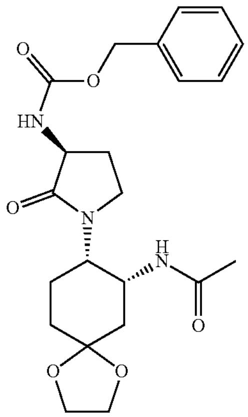 [SMILES: CC(=O)N[C@@H]1CC2(CC[C@@H]1N1CC[C@H](NC(=O)OCc3ccccc3)C1=O)OCCO2]
To a solution of (7R,8S)-8-((S)-3-(((benzyloxy)carbonyl)amino)-2-oxopyrrolidin-1-yl)-1,4-dioxaspiro[4.5]decane-7-carboxylic acid (1.5 g, 3.58 mmol) in toluene (15 mL) was added triethylamine (0.500 mL, 3.58 mmol) at rt. The mixture was cooled to −10° C., isobutyl chloroformate (0.471 mL, 3.58 mmol) was added, and the mixture was stirred at 0° C. to −10° C. for 30 min. A solution of sodium azide (0.419 g, 6.45 mmol) and tetrabutylammonium bromide (0.058 g, 0.179 mmol) in water (3.00 mL) was added, and the mixture was stirred at 0° C. to −10° C. for 2 h. Water (50 mL) and toluene (100 mL) were added and the mixture was stirred for 10 min. The organic phase was dried over molecular sieves (4A), acetic anhydride (0.744 mL, 7.89 mmol) and acetic acid (0.267 mL, 4.66 mmol) were added, and the mixture was stirred at 90° C. for 4 h. The mixture was cooled to rt and was concentrated under reduced pressure. The residue was triturated with pentane (20 mL) to provide the title compound as an off-white solid (0.8 g, 1.714 mmol, 47.8% yield). LC-MS m/z 432.2 $(M+H)^+$.

Step 2

Benzyl ((S)-1-((1S,2R)-2-acetamido-4-oxocyclohexyl)-2-oxopyrrolidin-3-yl)carbamate

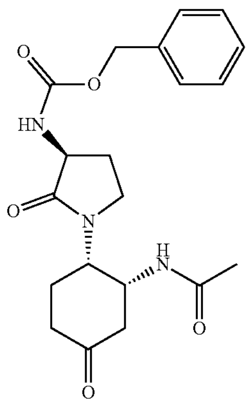 [SMILES: CC(=O)N[C@@H]1CC(=O)CC[C@@H]1N1CC[C@H](NC(=O)OCc2ccccc2)C1=O]

To a solution of benzyl ((S)-1-((7R,8S)-7-acetamido-1,4-dioxaspiro[4.5]decan-8-yl)-2-oxopyrrolidin-3-yl)carbamate (800 mg, 1.854 mmol) in acetone (10 mL) was added HCl (5 mL, 5.00 mmol) and the mixture was stirred at 50° C. for 2 h. The mixture was cooled to rt and was concentrated. Water (10 mL) was added and the mixture was extracted with dichloromethane (DCM) (2×50 mL). The combined organic extracts were dried over anhydrous $Na_2SO_4$, were filtered, and the filtrate was concentrated. The residue was triturated with diethyl ether (10 mL) to provide the title compound as an off-white solid (600 mg, 1.490 mmol, 80% yield). LC-MS m/z 388.2 $(M+H)^+$.

Step 3

Benzyl ((S)-1-((1S,2R,4R)-2-acetamido-4-(tert-butylamino)cyclohexyl)-2-oxopyrrolidin-3-yl)carbamate

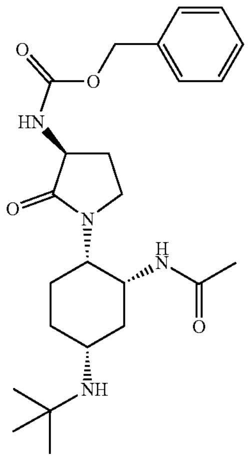 [SMILES: CC(=O)N[C@@H]1C[C@H](NC(C)(C)C)CC[C@@H]1N1CC[C@H](NC(=O)OCc2ccccc2)C1=O]

$TiCl_2(i\text{-}OPr)_2$ was pre-formed by adding titanium(IV) isopropoxide (0.282 mL, 0.964 mmol) to 1 M $TiCl_4$ in dichloromethane (DCM) (0.964 mL, 0.964 mmol) at 5-10° C. and the mixture was stirred for 15 min. The pre-formed $TiCl_2(i\text{-}OPr)_2$ was added to a solution of benzyl ((S)-1((1S,2R)-2-acetamido-4-oxocyclohexyl)pyrrolidin-3-yl)carbamate (600 mg, 1.607 mmol) and tert-butylamine (0.851 mL, 8.03 mmol) in dichloromethane (DCM) (10 mL) at −20° C. The mixture was warmed to rt and stirred for 2 h. Borane-dimethyl sulphide complex (0.153 mL, 1.607 mmol) was added and the mixture was stirred at rt for 16 h. Dichloromethane (DCM) (50 mL) and water (50 mL) were added and the mixture was stirred for 10 min. The emulsion was filtered through Celite® and the aqueous phase was extracted with dichloromethane (DCM) (50 mL). 1 N HCl (20 mL) was added to the combined organic extracts and the mixture was stirred for 10 min. Dichloromethane (DCM) (50 mL) was added and the pH was adjusted to 8 to 9 with ammonium hydroxide solution. The organic phase was washed with ammonium chloride solution (14%) (2×25 mL), was dried over anhydrous $Na_2SO_4$, was filtered, and the filtrate was evaporated. Purification by column chromatography (neutral alumina column) eluting with 2% methanol in dichloromethane (DCM) provided the title compound as an off-white solid (300 mg, 0.673 mmol, 41.9% yield). LC-MS m/z 445.48 $(M+H)^+$.

Step 4

N-((1R,2S,5R)-2-((S)-3-Amino-2-oxopyrrolidin-1-yl)-5-(tert-butylamino)cyclohexyl)acetamide

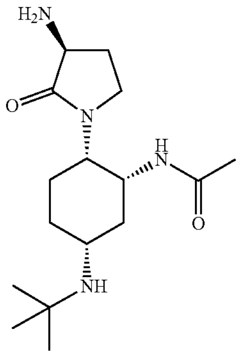 [SMILES: CC(=O)N[C@@H]1C[C@H](NC(C)(C)C)CC[C@@H]1N1CC[C@H](N)C1=O]

A mixture of benzyl ((S)-1-((1S,2R,4R)-2-acetamido-4-(tert-butylamino)cyclohexyl)-2-oxopyrrolidin-3-yl)carbamate (1.00 g, 2.249 mmol) and 10% Pd/C (100 mg, 0.094 mmol) in methanol (10 mL) was stirred under a balloon atmosphere of hydrogen at rt for 2 h. The mixture was filtered through Celite®, the catalyst was washed with methanol, and the combined filtrates were concentrated under reduced pressure to provide the title compound as an off-white solid (696.1 mg, 2.242 mmol, 100% yield). LC-MS m/z 311.5 $(M+H)^+$.

Step 5

N-((1R,2S,5R)-5-(tert-Butylamino)-2-((S)-3-((2-chloro-6-(trifluoromethyl)quinazolin-4-yl)amino)-2-oxopyrrolidin-1-yl)cyclohexyl)acetamide

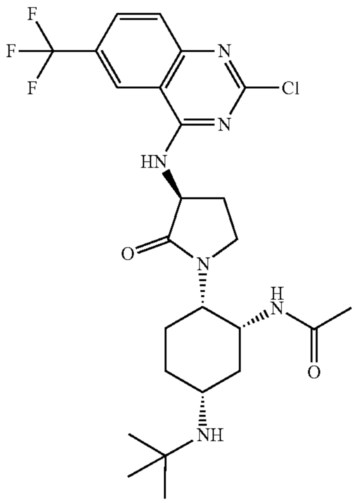 [SMILES: CC(=O)N[C@@H]1C[C@H](NC(C)(C)C)CC[C@@H]1N1CC[C@H](Nc2nc(Cl)nc3ccc(C(F)(F)F)cc23)C1=O]

A mixture of N-((1R,2S,5R)-2-((S)-3-amino-2-oxopyrrolidin-1-yl)-5-(tert-butylamino)cyclohexyl)acetamide (683 mg, 2.200 mmol), commercially-available 2,4-dichloro-6-(trifluoromethyl)quinazoline (587 mg, 2.200 mmol), and DIPEA (0.615 mL, 3.52 mmol) in ethanol (20 mL) was stirred at room temperature for 2 hours and the mixture was concentrated under reduced pressure. Saturated $NaHCO_3$ was added and mixture was extracted with ethyl acetate. The combined organic extracts were washed with saturated NaCl, were dried over $Na_2SO_4$, were filtered, and the filtrate was concentrated under reduced pressure to provide the title compound as a pale-yellow solid (1.128 g, 2.085 mmol, 95% yield). LC-MS m/z 541.5 $(M+H)^+$.

Step 6

N-((1R,2S,5R)-5-(tert-Butylamino)-2-((S)-2-oxo-3-((6-(trifluoromethyl)quinazolin-4-yl)amino)pyrrolidin-1-yl)cyclohexyl)acetamide

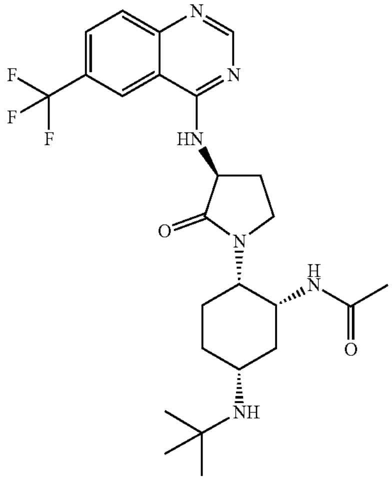 [SMILES: CC(=O)N[C@@H]1C[C@H](NC(C)(C)C)CC[C@@H]1N1CC[C@H](Nc2ncnc3ccc(C(F)(F)F)cc23)C1=O]

To a solution of N-((1R,2S,5R)-5-(tert-butylamino)-2-((S)-3-((2-chloro-6-(trifluoromethyl)quinazolin-4-yl)amino)-2-oxopyrrolidin-1-yl)cyclohexyl)acetamide (4.61 g, 8.52 mmol) in methanol (150 mL) was added 10% Pd/C (1.360 g, 1.278 mmol) and $Cs_2CO_3$ (4.16 g, 12.78 mmol). The mixture was stirred under a balloon atmosphere of hydrogen at rt for 3 h. The mixture was filtered and the catalyst was washed with methanol and with dichloromethane (DCM). The combined filtrates were concentrated to dryness, the residue was washed with dichloromethane (DCM), and the combined filtrates were concentrated to dryness to provide the title compound as a solid (4.97 g, 9.81 mmol, 115% yield). LC-MS m/z 507.1 $(M+H)^+$.

Step 7

(S)-1-((1S,2R,4R)-2-Amino-4-(tert-butylamino)cyclohexyl)-3-((6-(trifluoromethyl)quinazolin-4-yl)amino)pyrrolidin-2-one

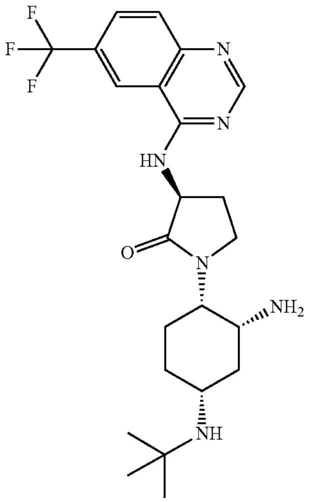 [SMILES: CC(C)(C)N[C@@H]1CC[C@H](N2CC[C@H](Nc3ncnc4ccc(C(F)(F)F)cc34)C2=O)[C@H](N)C1]

A mixture of N-((1R,2S,5R)-5-(tert-butylamino)-2-((S)-2-oxo-3-((6-(trifluoromethyl)quinazolin-4-yl)amino)pyrrolidin-1-yl)cyclohexyl)acetamide (814 mg, 1.607 mmol) and 2 M HCl (7231 μL, 14.46 mmol) was stirred at 50° C. for 6 days. The mixture was basified with saturated $NaHCO_3$ and was concentrated under reduced pressure to dryness. The residue was suspended in 10% methanol in dichloromethane (DCM), was stirred at rt for 1 h, and was filtered. The solid was washed with 10% methanol in dichloromethane (DCM) and the combined filtrates were concentrated. Purification by ISCO CombiFlash® chromatography (80 g RediSep Rf Gold® column, 60 mL/min) eluting with a gradient of 0 to 15% methanol containing ammonium hydroxide (10%) in dichloromethane (DCM) provided the title compound as a white solid (300 mg, 0.646 mmol, 40.2% yield). LC-MS m/z 465.4 $(M+H)^+$.

Intermediate 4

(1r,4R)-4-Amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2Hydrochloric acid salt

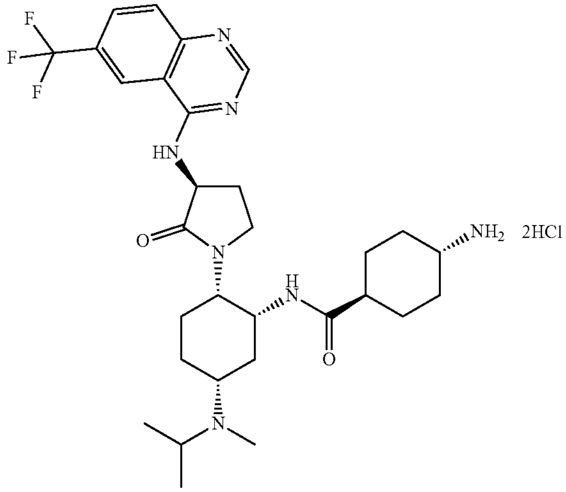

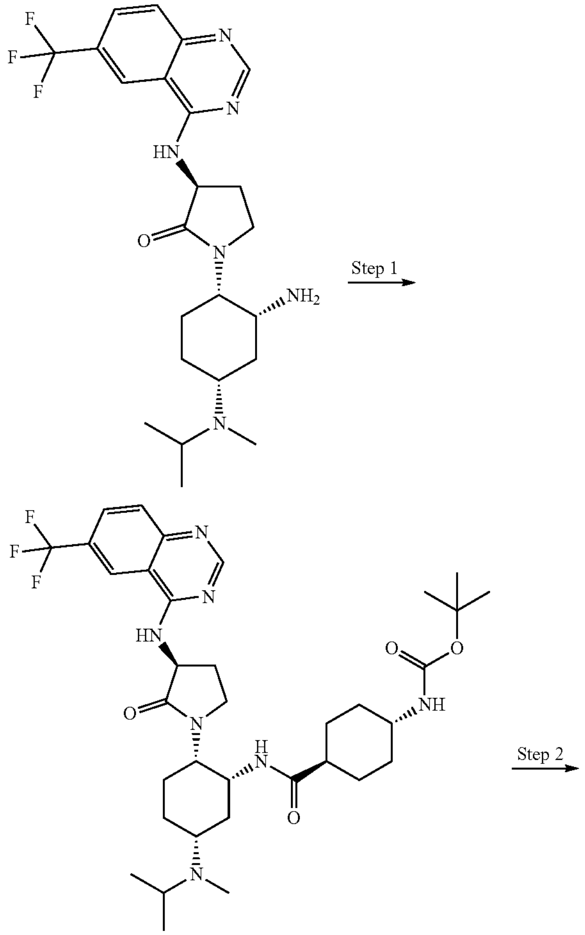

-continued

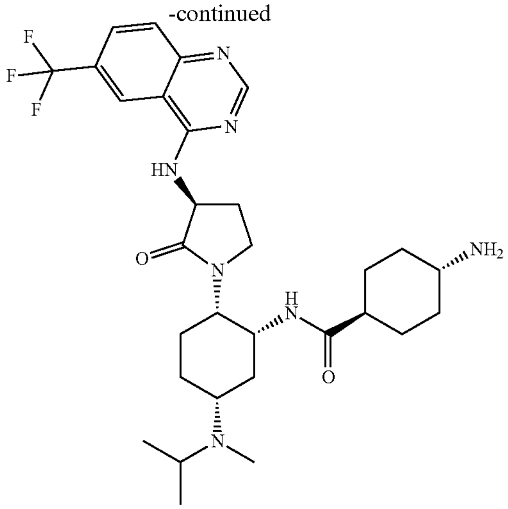

Step 1 tert-Butyl ((1R,4r)-4-(((1R,2S,5R)-5-(isopropyl (methyl)amino)-2-((S)-2-oxo-3-((6-(trifluoromethyl) quinazolin-4-yl)amino)pyrrolidin-1-yl)cyclohexyl) carbamoyl)cyclohexyl)carbamate

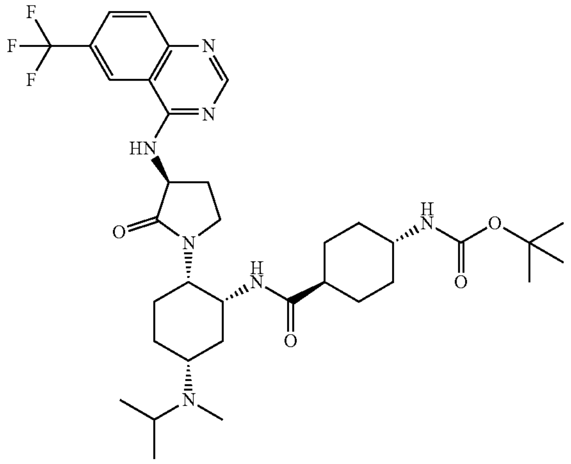 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)OC(C)(C)C)CC2)C1]

To a mixture of (S)-1-((1S,2R,4R)-2-amino-4-(isopropyl (methyl)amino)cyclohexyl)-3-((6-(trifluoromethyl)quinazolin-4-yl)amino)pyrrolidin-2-one, 2hydrochloric acid salt (Intermediate 2) (368 mg, 0.685 mmol) and commercially-available (1r,4r)-4-((tert-butoxycarbonyl)amino) cyclohexane-1-carboxylic acid (167 mg, 0.685 mmol) in dichloromethane (DCM) (1 mL) was added triethylamine (0.573 mL, 4.11 mmol) and HATU (312 mg, 0.822 mmol), and the mixture was stirred at rt for 2 h. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (356 mg, 0.511 mmol, 74.6% yield). LC-MS m/z 690.4 $(M+H)^+$.

Step 2

(1r,4R)-4-Amino-N-((1R,2S,5R)-5-(isopropyl (methyl)amino)-2-((S)-2-oxo-3-((6-(trifluoromethyl) quinazolin-4-yl)amino)pyrrolidin-1-yl)cyclohexyl) cyclohexanecarboxamide, 2Hydrochloric acid salt

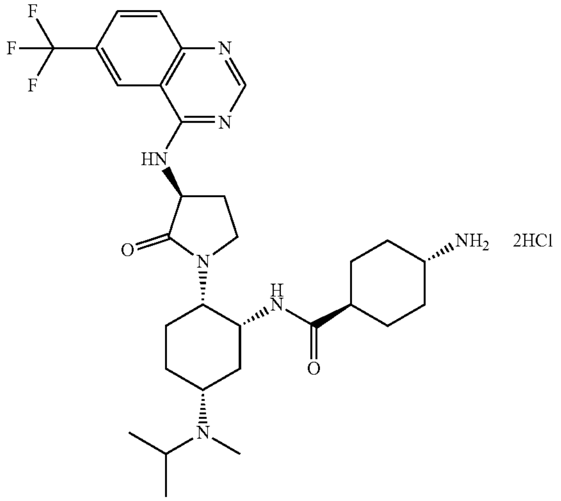 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N)CC2)C1]

To a mixture of tert-butyl ((1R,4r)-4-(((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl)carbamate (355 mg, 0.515 mmol) in dichloromethane (DCM) (0.5 mL) was added HCl (1.029 mL, 4.12 mmol) and the mixture was stirred at rt for 2 h. The mixture was concentrated to dryness to provide the title compound as a white solid (340 mg, 0.513 mmol, 100% yield). LC-MS m/z 590.3 $(M+H^+)$.

Intermediate 5

(1 s,4S)-4-Amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2Hydrochloric acid salt

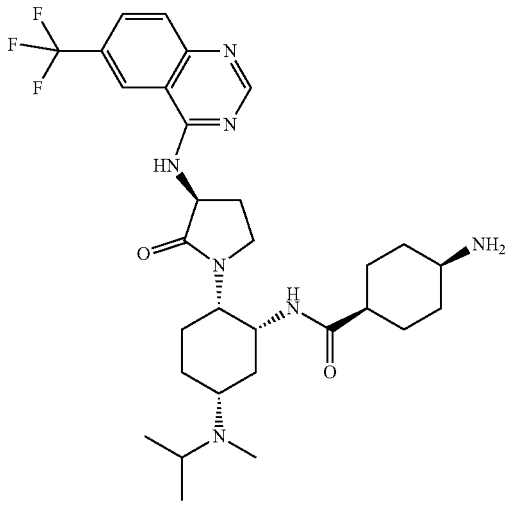

2HCl

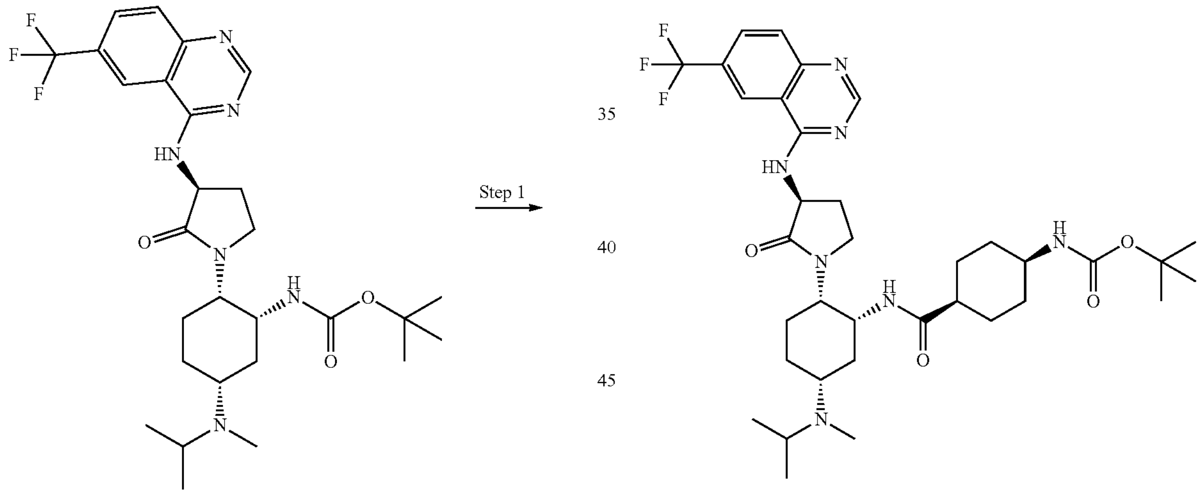

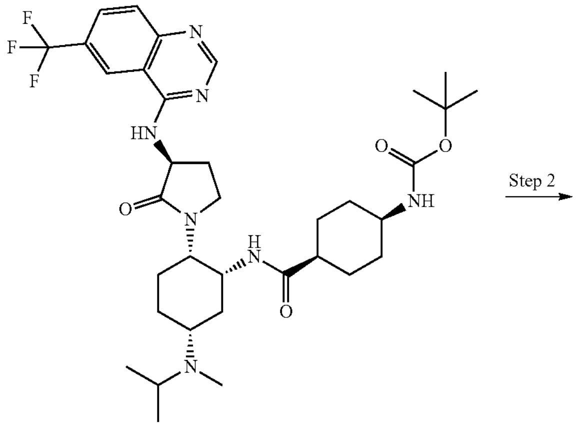

-continued

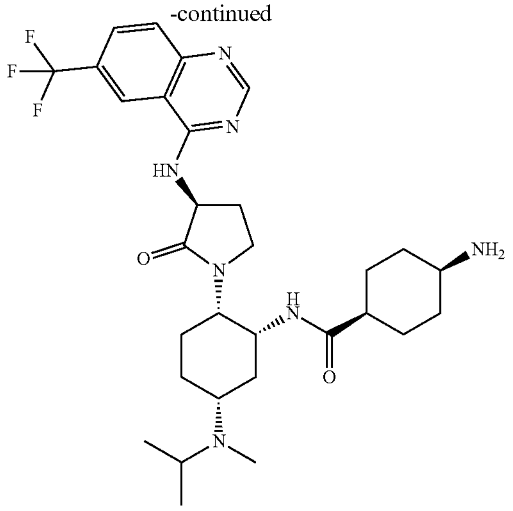

Step 1 tert-Butyl ((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)carbamate A mixture of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (Intermediate 2, Step 5) (3.022 g, 5.35 mmol), 4 N HCl in 1,4-dioxane (9.37 mL, 37.5 mmol), and dichloromethane (5 mL) was stirred at rt for 4 h and was concentrated to dryness. Commercially-available (1s,4s)-4-((tert-butoxycarbonyl)amino)cyclohexane-1-carboxylic acid (1.302 g, 5.35 mmol), dichloromethane (DCM) (30.00 mL), triethylamine (3.73 mL, 26.8 mmol), and HATU (2.442 g, 6.42 mmol) were added and the mixture was stirred at rt for 2 h. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (40 g Redisep Rf Gold® column, 40 mL/min) eluting with a gradient of 0 to 15% methanol containing ammonium hydroxide (10%) in dichloromethane (DCM) provided the title compound (3.35 g, 4.86 mmol, 91% yield). LC-MS m/z 690.4 $(M+H)^+$.

Step 2

(1 s,4S)-4-Amino-N-((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) cyclohexane-1-carboxamide, 2Hydrochloric acid salt

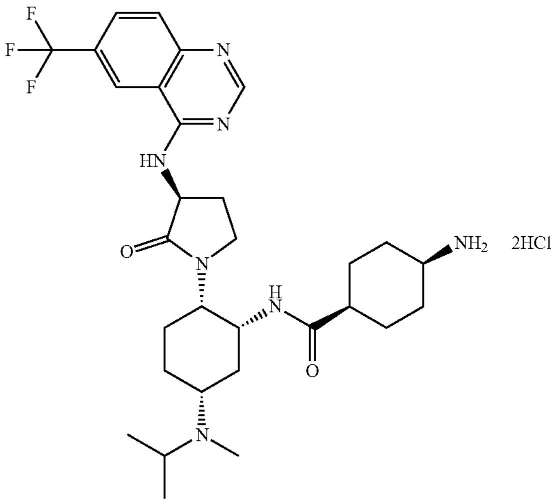 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](N)CC2)C1]

A mixture of tert-butyl ((1S,4s)-4-(((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl)carbamate (3.35 g, 4.86 mmol), 4 N HCl in 1,4-dioxane (7.28 mL, 29.1 mmol), and dichloromethane (DCM) (3 mL) was stirred at rt for 4 h. The mixture was concentrated to dryness to provide the title compound as a white solid (3.5 g, 5.28 mmol, 109% yield). LC-MS m/z 590.2 $(M+H)^+$.

The following intermediates were or could be prepared using procedures analogous to those described for Intermediates 4 and 5:

| Intermediate | Compound | Structure | LC-MS m/z $(M + H)^+$ |
|---|---|---|---|
| 6 | 3-(2-Aminoethoxy)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)propenamide, 2Hydrochloric acid salt | 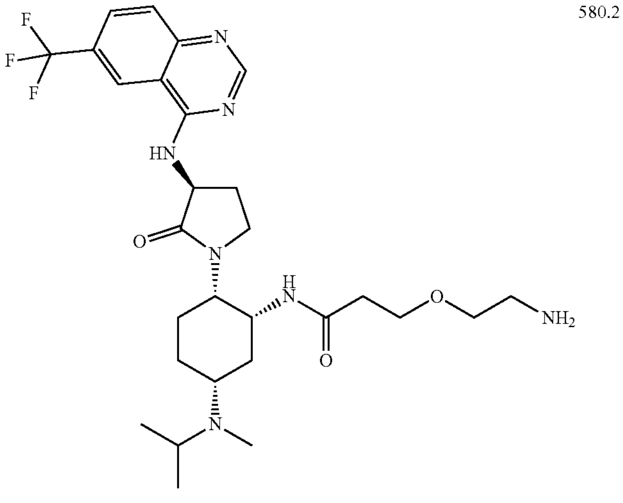 | 580.2 |

-continued

| Intermediate | Compound | Structure | LC-MS m/z (M + H)$^+$ |
| --- | --- | --- | --- |
| 7 | (1r,3R)-3-Amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl) cyclobutanecarboxamide, 2Hydrochloric acid salt | 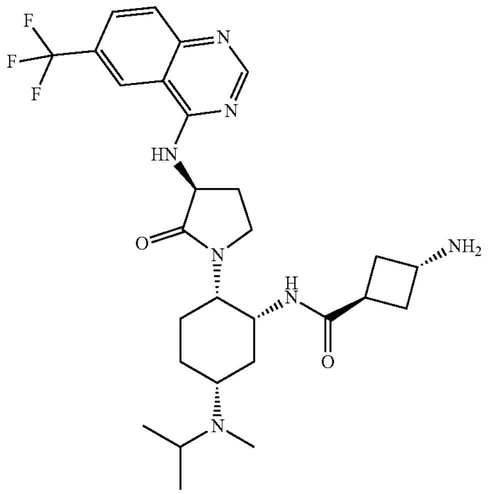 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](N)C2)C1] | 562.2 |
| 8 | (1s,3S)-3-Amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl) cyclobutanecarboxamide, 2Hydrochloric acid salt | 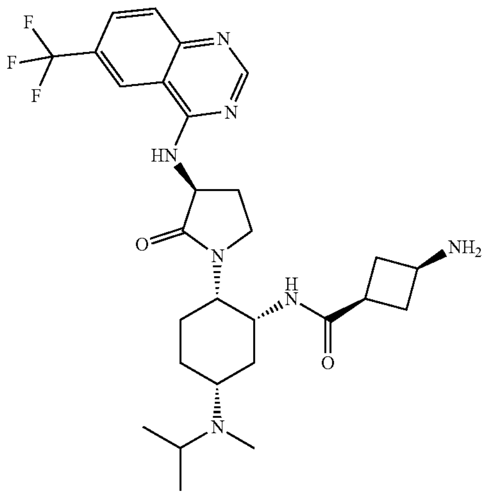 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](N)C2)C1] | 562.1 |

Intermediate 9

(1r,4R)-4-Amino-N-((1R,2S,5R)-5-(tert-butylamino)-2-((S)-2-oxo-3-((6-(trifluoromethyl)quinazolin-4-yl)amino)pyrrolidin-1-yl)cyclohexyl)cyclohexane-1-carboxamide, 2Hydrochloric acid salt

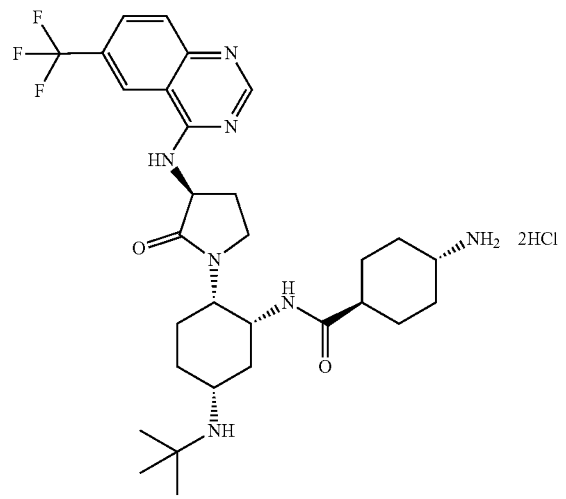

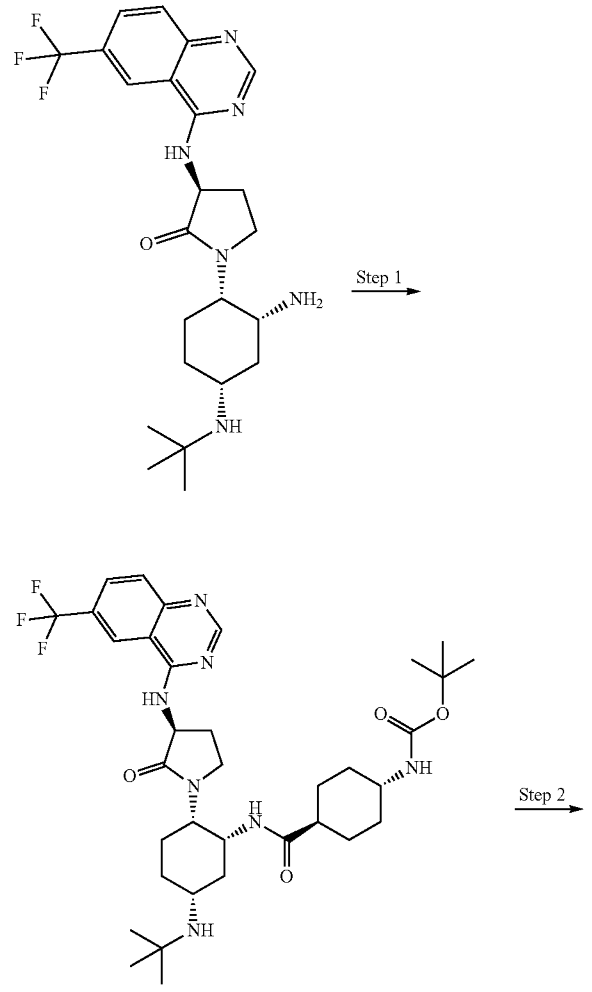

-continued

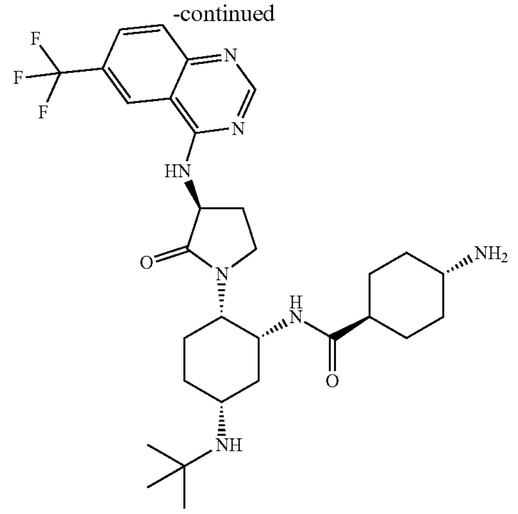

Step 1 tert-Butyl ((1R,4r)-4-(((1R,2S,5R)-5-(tert-butylamino)-2-((S)-2-oxo-3-((6-(trifluoromethyl)quinazolin-4-yl)amino)pyrrolidin-1-yl)cyclohexyl)carbamoyl)cyclohexyl)carbamate

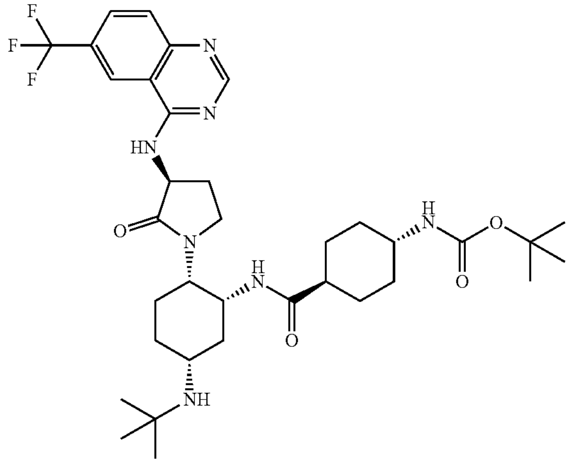 [SMILES: CC(C)(C)N[C@@H]1CC[C@H](N2CC[C@H](Nc3ncnc4ccc(C(F)(F)F)cc34)C2=O)[C@H](NC(=O)[C@H]2CC[C@H](NC(=O)OC(C)(C)C)CC2)C1]

To a mixture of (S)-1-((1S,2R,4R)-2-amino-4-(tert-butylamino)cyclohexyl)-3-((6-(trifluoromethyl)quinazolin-4-yl)amino)pyrrolidin-2-one (105 mg, 0.226 mmol) and commercially-available (1r,4r)-4-((tert-butoxycarbonyl)amino)cyclohexane-1-carboxylic acid (55.0 mg, 0.226 mmol (105 mg, 0.226 mmol) in dichloromethane (DCM) (2 mL) was added triethylamine (0.095 mL, 0.678 mmol) and HATU (103 mg, 0.271 mmol) and the mixture was stirred at rt for 2 h. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (24 g RediSep Rf Gold® column 40 mL/min) eluting with a gradient of 0 to 15% methanol containing ammonium hydroxide (10%) in dichloromethane (DCM) provided the title compound (120 mg, 0.174 mmol, 77% yield). LC-MS m/z 690.1 $(M+H)^+$.

Step 2

(1r,4R)-4-Amino-N-((1R,2S,5R)-5-(tert-butylamino)-2-((S)-2-oxo-3-((6-(trifluoromethyl)quinazolin-4-yl)amino)pyrrolidin-1-yl)cyclohexyl)cyclohexane-1-carboxamide, 2Hydrochloric acid salt

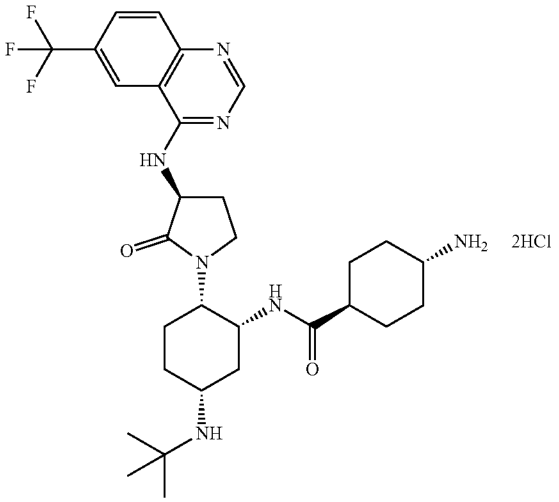 [SMILES: CC(C)(C)N[C@@H]1CC[C@H](N2CC[C@H](Nc3ncnc4ccc(C(F)(F)F)cc34)C2=O)[C@H](NC(=O)[C@H]2CC[C@H](N)CC2)C1]

A mixture of tert-butyl ((1R,4r)-4-(((1R,2S,5R)-5-(tert-butylamino)-2-((S)-2-oxo-3-((6-(trifluoromethyl)quinazolin-4-yl)amino)pyrrolidin-1-yl)cyclohexyl)carbamoyl)cyclohexyl)carbamate (70 mg, 0.101 mmol), 4 N HCl in 1,4-dioxane (0.2 mL, 0.800 mmol), and dichloromethane (DCM) (0.1 mL) was stirred at rt for 3 h. The mixture was concentrated to provide the title compound (70 mg, 0.106 mmol, 104% yield). LC-MS m/z 590.0 $(M+H)^+$.

The following intermediate was or could be prepared using procedures analogous to those described for Intermediate 9:

| Intermediate | Compound | Structure | LC-MS m/z $(M + H)^+$ |
|---|---|---|---|
| 10 | (1s,4S)-4-Amino-N-((1R,2S,5R)-5-(tert-butylamino)-2-((S)-2-oxo-3-((6-(trifluoromethyl)quinazolin-4-yl)amino)pyrrolidin-1-yl)cyclohexyl) cyclohexane-1-carboxamide, 2Hydrochloric acid salt. | 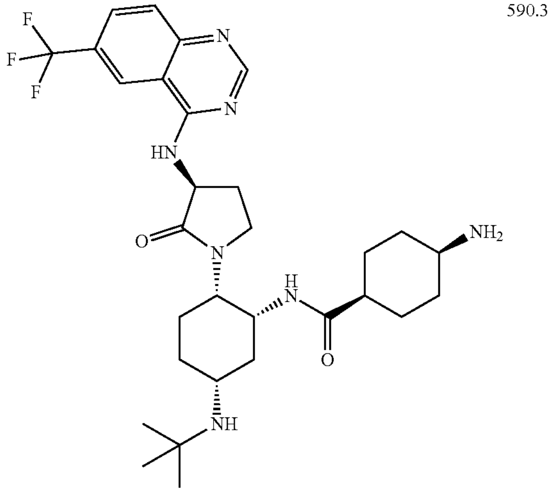 | 590.3 |

Intermediate 11
(1s,3S)-3-(3-(2-(2-Aminoethoxy)ethoxy)propanamido)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclobutanecarboxamide, 2Hydrochloric acid salt
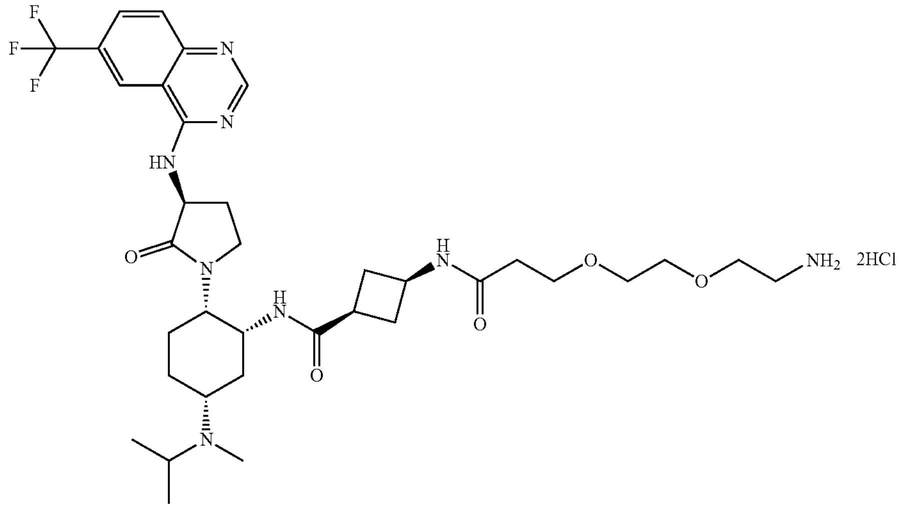
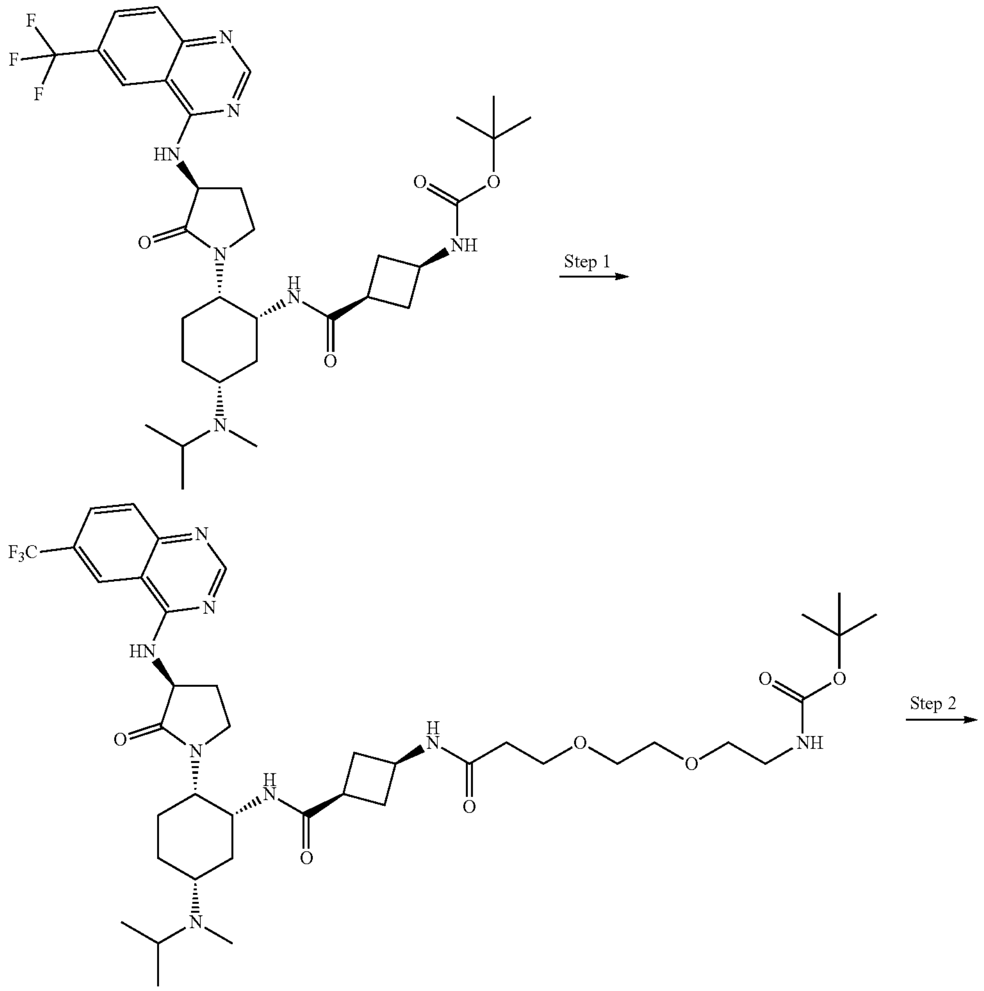

-continued

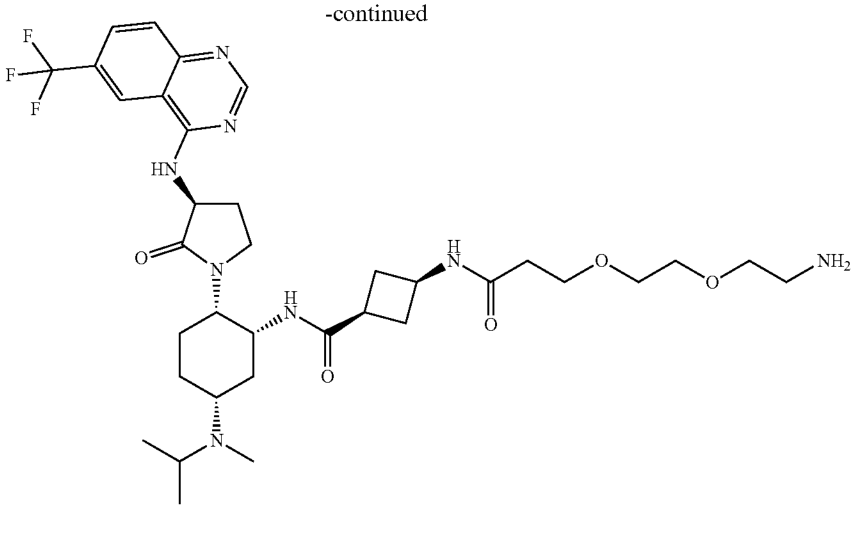

Step 1 tert-Butyl (2-(2-(3-(((1S,3s)-3-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)ethoxy)ethyl)carbamate

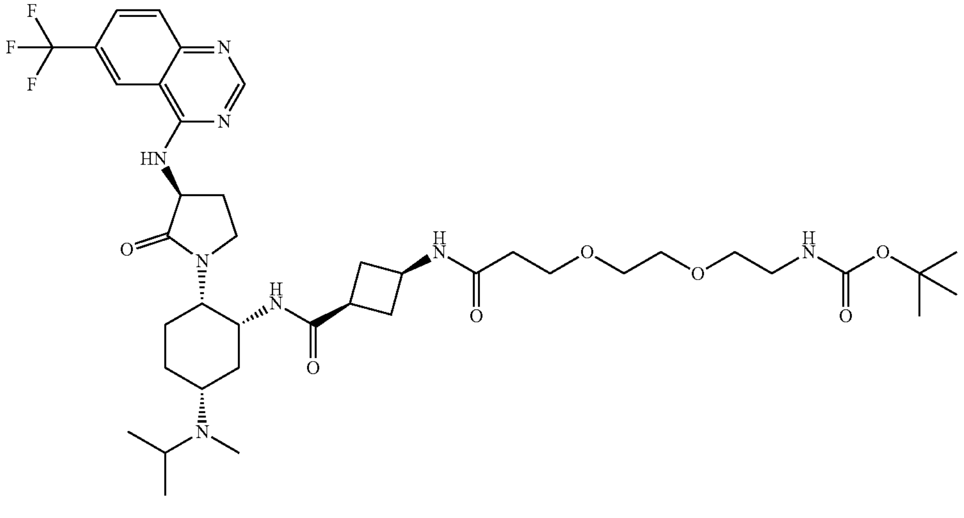 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCOCCNC(=O)OC(C)(C)C)C2)C1]

To a mixture of (1 s,3S)-3-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclobutanecarboxamide, 2hydrochloric acid salt (225 mg, 0.355 mmol) in dichloromethane (DCM) (2 mL) was added commercially available 2,2-dimethyl-4-oxo-3,8,11-trioxa-5-azatetradecan-14-oic acid (98 mg, 0.355 mmol), triethylamine (0.396 mL, 2.84 mmol), and HATU (162 mg, 0.426 mmol), and the mixture was stirred at rt for 1 h. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (24 g RediSep Rf Gold® column, 35 mL/min) eluting with a gradient of 0 to 15% methanol containing ammonium hydroxide (10%) in dichloromethane (DCM) provided the title compound (283 mg, 0.345 mmol, 97% yield). LC-MS m/z 821.1 $(M+H)^+$.

Step 2

(1s,3S)-3-(3-(2-(2-Aminoethoxy)ethoxy)propanamido)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclobutane-1-carboxamide, 2Hydrochloric acid salt

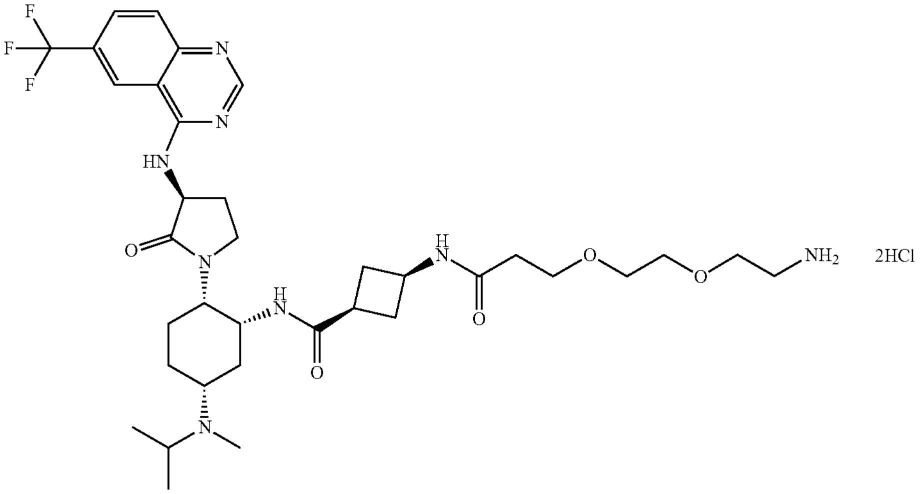 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCOCCN)C2)C1]

A mixture of tert-butyl (2-(2-(3-(((1S,3s)-3-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)ethoxy)ethyl)carbamate (283 mg, 0.345 mmol), 4 N HCl in 1,4-dioxane (0.862 mL, 3.45 mmol), and dichloromethane (DCM) (0.2 mL) was stirred at rt for 3 h. The mixture was concentrated to dryness to provide the title compound (280 mg, 0.353 mmol, 102% yield). LC-MS m/z 721.5 $(M+H)^+$.

Intermediate 12

(2S,3S)-1-Methyl-5-oxo-2-(pyridin-3-yl)pyrrolidine-3-carboxylic acid

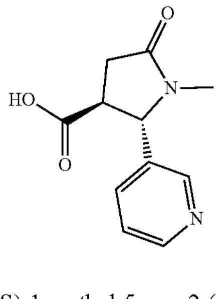

Racemic (2S,3S)-1-methyl-5-oxo-2-(pyridin-3-yl)pyrrolidine-3-carboxylic acid (200 g) was dissolved in boiling methanol (4000 mL) and acetonitrile (4000 mL) and was purified by chiral prep HPLC (27 injections) (Chiralpak 1A 101×210 mm 20 μm column, 500 mL/min) eluting with acetonitrile/methanol/formic acid (50:50:0.1). The desired fractions were collected and concentrated under reduced pressure. Enantioner-E1 was washed with acetonitrile and was dried under hi vacuum for 18 h to provide (2S,3S)-1-methyl-5-oxo-2-(pyridin-3-yl)pyrrolidine-3-carboxylic acid as a white solid (93.1 g). The other enantiomer was also isolated and characterized (76 g). Analytical chiral HPLC for Enantiomer-E1: 96% ee at retention time 2.3 min (Chiralpak 1A 5 μm 4.6×150 mm, 1.0 ml/min) eluting with acetonitrile/methanol/formic acid (50:50:1). Enantiomer-E2 had a 99% ee at retention time 7.2 min. VCD analysis was used to assign absolute stereochemistry.

(2S,3S)-1-methyl-5-oxo-2-(pyridin-3-yl) pyrrolidine-3-carboxylic acid (Enantiomer-E1), LC-MS m/z 221.0 $(M+H)^+$.

(2R,3R)-1-methyl-5-oxo-2-(pyridin-3-yl)pyrrolidine-3-carboxylic acid (Enantiomer-E2) LC-MS m/z 221.0 $(M+H)^+$.

Intermediate 13

(2S,3S)-1-Ethyl-5-oxo-2-(pyridin-3-yl)pyrrolidine-3-carboxylic acid

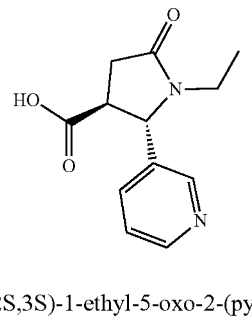

Racemic 1-((2S,3S)-1-ethyl-5-oxo-2-(pyridin-3-yl)pyrrolidine-3-carboxylic acid (630 mg) was dissolved in methanol (20 mL) and was purified by chiral SFC 80 (Chiralpak IG 20 mm×250 mm 5 μm, 50 g/min, 3 mL injection volume) eluting with 40% ethanol provided Enantiomer-E1 (2.8-3.4 min) and Enantiomer-E2 (5.1-7.4 min). These desired fractions were collected and were dried under reduced pressure. The samples were transferred to 20 mL vials and were dried under a stream of nitrogen at 40° C. The chiral purity of each enantiomer was determined using the analytical chiral SFC using method described below:

Chiral SFC Analytical QC Method

Instrument: Thar Investigator (1)

Column: Chiralpak IG 4.6×150 mm, 5 μm

Co-solvent: 30% EtOH

Flow rate: 3 g/min

Back pressure: 100 Bar

UV wavelength: 220 nm

Temperature: 35° C.

Injection vol: 5 μL

Based on the SFC-UV data, the chiral purity of sample Enantiomer-E1 (rt. 2.17 min, 0.21 g) was 100%; and Enantiomer-E2 (rt. 4.47 min, 0.22 g) was 100%.

(2S,3S)-1-ethyl-5-oxo-2-(pyridin-3-yl)pyrrolidine-3-carboxylic acid (Enantiomer-E1) LC-MS m/z 235.2 $(M+H)^+$. RT=0.26 min. $^1H$ NMR (400 MHz, METHANOL-$d_4$) δ ppm 1.02 (t, J=7.2 Hz, 3H) 2.64-2.84 (m, 2H) 2.86-2.96 (m, 1H) 3.15-3.25 (m, 1H) 3.63 (dd, J=14, 7.3 Hz, 1H) 5.08 (d, J=6.1 Hz, 1H) 7.54 (dd, J=7.6, 4.9 Hz, 1H) 7.88 (dt, J=8.0, 1.9 Hz, 1H) 8.58 (td, J=4.1, 1.8 Hz, 2H).

(2R,3R)-1-ethyl-5-oxo-2-(pyridin-3-yl) pyrrolidine-3-carboxylic acid (Enantiomer E-2) LC-MS m/z 235.2 $(M+H)^+$ RT=0.30 min. $^1H$ NMR (400 MHz, METHANOL-$d_4$) δ ppm 1.02 (t, J=7.2 Hz, 3H) 2.6-2.83 (m, 2H) 2.86-2.96 (m, 1H) 3.15-3.25 (m, 1H) 3.63 (dd, J=14, 7.2 Hz, 1H) 5.08 (d, J=6.1 Hz, 1H) 7.54 (dd, J=7.8, 4.9 Hz, 1H) 7.88 (dt, J=8.1, 2.0 Hz, 1H) 8.54-8.62 (m, 2H).

The following intermediate was or could be prepared using procedures analogous to those described for Intermediate 13:

| Inter. | Compound | LC-MS m/z | NMR |
|---|---|---|---|
| 14 | 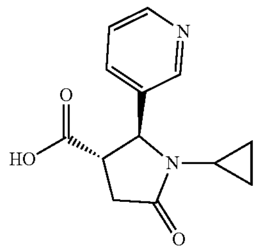 [SMILES: O=C(O)[C@H]1CC(=O)N(C2CC2)[C@@H]1c1cccnc1] (2S,3S)-1-Cyclopropyl-5-oxo-2-(pyridin-3-yl)pyrrolidine-3-carboxylic acid. | 247.2 $(M + H)^+$ | $^1H$ NMR (400 MHz, METHANOL-$d_4$) δ ppm 0.43 – 0.55 (m, 1H) 0.60 – 0.72 (m, 1H) 0.74 – 0.92 (m, 2H) 2.24 – 2.35 (m, 1H) 2.72 – 2.96 (m, 2H) 3.09 – 3.21 (m, 1H) 4.99 (d, J = 5.4 Hz, 1H) 7.54 (dd, J = 7.8, 4.9 Hz, 1H) 7.89 (dt, J = 7.8, 2.0 Hz, 1H) 8.56 (dd, J = 4.9, 1.5 Hz, 1H) 8.60 (d, J = 2.0 Hz, 1H). |
| 15 | 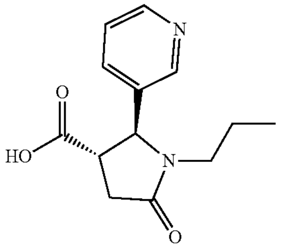 [SMILES: CCCN1C(=O)C[C@H](C(=O)O)[C@H]1c1cccnc1] (2S,3S)-5-oxo-1-propyl-2-(pyridin-3-yl)pyrrolidine-3-carboxylic acid | 249.2 $(M + H)^+$ | $^1H$ NMR (DMSO-$d_6$, 400 MHz): δ (ppm) 12.83 (br s, 1H), 8.54-8.59 (m, 2H), 7.76 (dt, J = 7.9, 2.0 Hz, 1H), 7.44 (dd, J = 7.8, 4.9 Hz, 1H), 4.84 (d, J = 5.4 Hz, 1H), 3.34-3.43 (m, 1H), 3.06-3.14 (m, 1H), 2.77 (dd, J = 17.1, 9.8 Hz, 1H), 2.57 (dd, J = 17.1, 6.8 Hz, 1H), 2.41 (ddd, J = 13.6, 7.9, 5.4 Hz, 1H), 1.16-1.41 (m, 2H), 0.71 (t, J = 7.3 Hz, 3H) |

Intermediate 16 tert-Butyl 4-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperidine-1-carboxylate

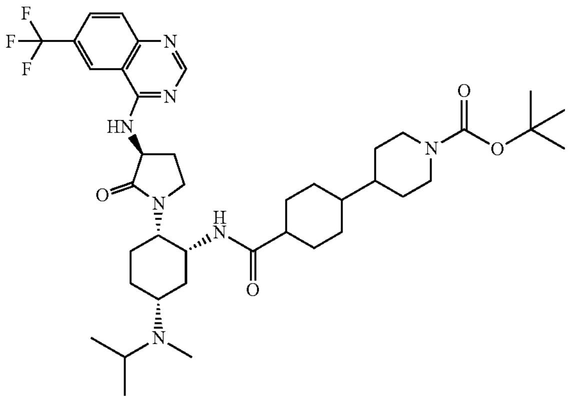 [SMILES: CC(C)N(C)[C@@H]1CC[C@H](N2CC[C@H](Nc3ncnc4ccc(C(F)(F)F)cc34)C2=O)[C@H](NC(=O)C2CCC(C3CCN(C(=O)OC(C)(C)C)CC3)CC2)C1]

Step 1 tert-Butyl 4-(4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohex-1-en-1-yl)-3,6-dihydropyridine-1(2H)-carboxylate

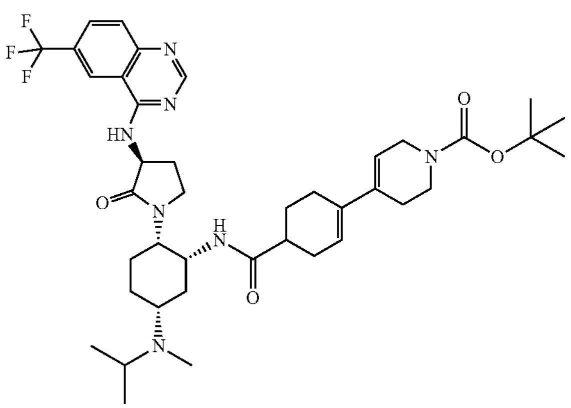 [SMILES: CC(C)N(C)[C@@H]1CC[C@H](N2CC[C@H](Nc3ncnc4ccc(C(F)(F)F)cc34)C2=O)[C@H](NC(=O)C2CC=C(C3=CCN(C(=O)OC(C)(C)C)CC3)CC2)C1]

Into a solution of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (70 mg, 0.124 mmol) in dichloromethane (DCM) (1 mL) was added 3 M HCl in cyclopentyl methyl ether (0.6 mL). The mixture was stirred at rt for 1 h and was concentrated under reduced pressure. The residue was suspended in dichloromethane (DCM) (5 mL) and triethylamine (0.060 mL, 0.434 mmol) was added. 4-(1-(tert-butoxycarbonyl)-1,2,3,6-tetrahydropyridin-4-yl)cyclohex-3-ene-1-carboxylic acid (45 mg, 0.146 mmol) and HATU (70.7 mg, 0.186 mmol) were added. The mixture was stirred at rt for 1 h and was concentrated under reduced pressure. The residue was dissolved in dimethyl sulfoxide (DMSO) (2 mL) and was purified by MDAP chromatography (XSelect™ CSH Prep C18 OBD column, 40 mL/min) eluting with a gradient of 15 to 55% acetonitrile in water both containing formic acid (0.1%) to provide the title compound as an off-white solid (50 mg, 0.065 mmol, 52.4% yield). LC-MS m/z 754.1 $(M+H)^+$.

Step 2 tert-Butyl 4-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperidine-1-carboxylate

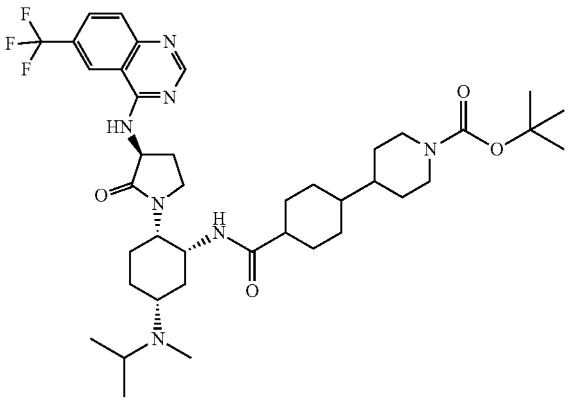

To a solution of tert-butyl 4-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohex-1-en-1-yl)-3,6-dihydropyridine-1(2H)-carboxylate (50 mg, 0.066 mmol) in methanol (5 mL) was added 10% Pd/C (7.06 mg, 6.63 µmol). The flask was backfilled with hydrogen several times and the mixture was stirred at rt overnight and was stirred at 50° C. over a weekend. The mixture filtered through Celite® and the filtrate was concentrated under reduced pressure to provide a mixture of trans- and cis-isomers as a white gummy solid (50 mg, 0.063 mmol, 95% yield). LC-MS m/z 758.5 $(M+H)^+$.

Intermediate 17

3-Ethoxy-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)cyclobut-3-ene-1,2-dione

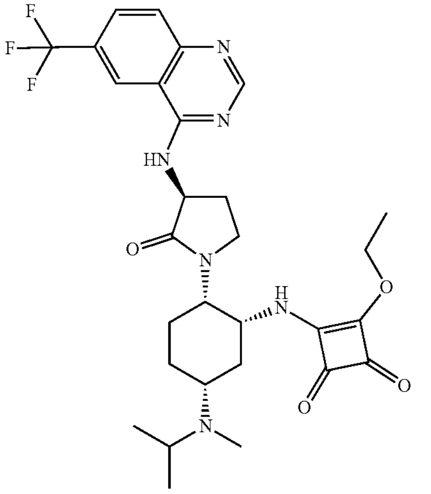 [SMILES: CCOc1c(N[C@@H]2C[C@H](N(C)C(C)C)CC[C@@H]2N2CC[C@H](Nc3ncnc4ccc(C(F)(F)F)cc34)C2=O)c(=O)c1=O]

Commercially-available 3,4-diethoxycyclobut-3-ene-1,2-dione (73.3 mg, 0.431 mmol) in THF (1 mL) was stirred at −5° C., (S)-1-((1S,2R,4R)-2-amino-4-(isopropyl(methyl)amino)cyclohexyl)-3-((6-(trifluoromethyl)quinazolin-4-yl)amino)pyrrolidin-2-one (200 mg, 0.431 mmol) in THF (2 mL) was added, followed by DIPEA (0.225 mL, 1.292 mmol) dropwise. The mixture was warmed to rt and was warmed to rt. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as white solid (220 mg, 0.336 mmol, 78% yield). LC-MS m/z 589.1 $(M+H)^+$.

Intermediate 18

(2S,3S)-1-cyclobutyl-5-oxo-2-(pyridin-3-yl)pyrrolidine-3-carboxylic acid

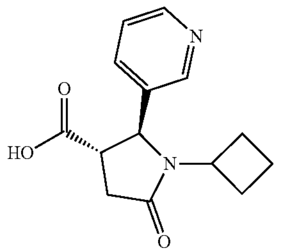 [SMILES: O=C(O)[C@H]1CC(=O)N(C2CCC2)[C@@H]1c1cccnc1]

Step 1

(Z)-N-Cyclobutyl-1-(pyridin-3-yl)methanimine

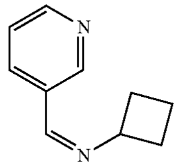 [SMILES: C(=N/C1CCC1)/c1cccnc1]

A mixture of nicotinaldehyde (0.709 mL, 9.34 mmol) and cyclobutanamine (0.833 mL, 9.34 mmol) was stirred at 100° C. for 25 min under a nitrogen atmosphere. The suspension was filtered through a pad of $MgSO_4$ and washed with deuterated dichloromethane ($CD2Cl_2$). The product was dried over nitrogen to provide the title compound (0.4517 g, 2.82 mmol, 30.2% yield). $^1H$ NMR (400 MHz, DICHLOROMETHANE-$d_2$) δ ppm 1.84-1.92 (m, 2H) 2.13-2.25 (m, 2H) 2.31-2.40 (m, 2H) 4.17-4.26 (m, 1H) 7.37 (dd, J=7.8, 4.9 Hz, 1H) 8.12 (dt, J=7.8, 2.0 Hz, 1H) 8.22 (d, J=1.5 Hz, 1H) 8.63 (dd, J=4.9, 1.5 Hz, 1H) 8.86 (d, J=2.0 Hz, 1H).

Step 2

(2S,3S)-1-cyclobutyl-5-oxo-2-(pyridin-3-yl)pyrrolidine-3-carboxylic acid

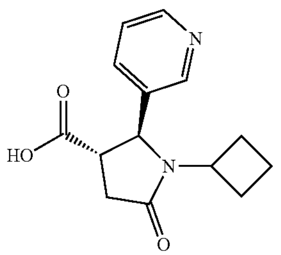 [SMILES: O=C(O)[C@H]1CC(=O)N(C2CCC2)[C@@H]1c1cccnc1]

(Z)-N-cyclobutyl-1-(pyridin-3-yl)methanimine (0.3372 g, 2.105 mmol) and dihydrofuran-2,5-dione (0.2150 g, 2.148 mmol) was stirred at 150° C. for 1 hr. Ethanol was added and the precipitate was collected by filtration to provide a mixture of diastereomers (0.1649 g, 0.634 mmol, 30.1% yield). The mixture was combined with additional preparations and separated according to the following method.

Racemic (2S,3S)-1-cyclobutyl-5-oxo-2-(pyridin-3-yl)pyrrolidine-3-carboxylic acid and (2R,3R)-1-cyclobutyl-5-oxo-2-(pyridin-3-yl)pyrrolidine-3-carboxylic acid (1.3 g) was dissolved in acetonitrile/methanol/formic acid (70:30:0.1) (120 mL) and was purified by chiral prep HPLC (Chiralpak 1A 30×250 mm 5 μm column, 45 mL/min, 25 mL injection volume) eluting with acetonitrile/methanol/formic acid (70:30:0.1). The desired fractions were collected and concentrated under reduced pressure. These fractions were collected and dried under reduced pressure. The chiral purity of each isomer was determined using analytical chiral UPLC using the method described below:

Chiral UPLC Analytical QC Method

Instrument: Acquity UPLC

Column: CHS C18 30×2.1 mm, 1.7 μm

Elution solvent: gradient from 1-99% of acetonitrile (containing 0.1% formic acid) in water (containing 0.1% formic acid)

Flow rate: 1.3 mL/min

Back pressure: 100 Bar

UV wavelength: 210 to 350 nm

Temperature: 55° C.

Injection vol: 0.55 μL

Based on the Chiral UPLC-UV data, the chiral purity of Enantiome-E1 (3.5 min) (rt. 3.5 min, 500 mg) was 100%; and Enantiomer-E2 (rt. 6.5 min, 450 mg) was 100%.

Enantiomer E1—$a_D$=+22 deg (c=0.2, CH3OH); LC-MS m/z 261.2 $(M+H)^+$. $^1H$ NMR (400 MHz, DMSO-$d_6$) δ=12.87 (br s, 1H), 8.63-8.47 (m, 2H), 7.71 (td, J=2.0, 7.8 Hz, 1H), 7.43 (dd, J=4.6, 8.1 Hz, 1H), 5.09 (d, J=4.4 Hz, 1H), 4.20-3.98 (m, 1H), 2.95 (td, J=4.8, 9.0 Hz, 1H), 2.84-2.72 (m, 1H), 2.52-2.44 (m, 1H), 2.29 (quin, J=10.0 Hz, 1H), 2.02-1.78 (m, 2H), 1.74-1.58 (m, 1H), 1.56-1.38 (m, 2H)

Intermediate 19 tert-Butyl 4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)-[1,4'-bipiperidine]-1'-carboxylate

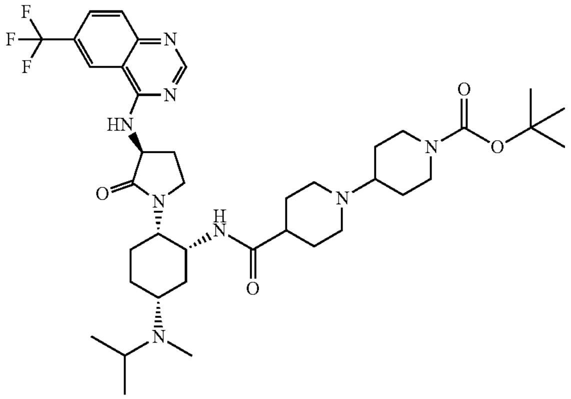 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C(=O)OC(C)(C)C)CC3)CC2)C1]

A solution of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (237 mg, 0.420 mmol) and 3 M HCl in cyclopentyl methyl ether (1 mL, 3.00 mmol) in dichloromethane (DCM) (1 mL) was stirred at rt for 1 h and was concentrated under reduced pressure. The residue was suspended in dichloromethane (DCM) (7 mL) with triethylamine (0.205 mL, 1.469 mmol). 1'-(tert-Butoxycarbonyl)-[1,4'-bipiperidine]-4-carboxylic acid (144 mg, 0.462 mmol) and HATU (239 mg, 0.630 mmol) were added, the mixture was stirred at rt for 1 h, and was concentrated under reduced pressure. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to pH 10 with ammonia provided the title compound as an off-white solid (267 mg, 0.345 mmol, 82% yield). LC-MS m/z 759.4 $(M+H)^+$.

Intermediate 20 tert-Butyl 2-(2-(((benzyloxy)carbonyl)amino)ethoxy)acetate

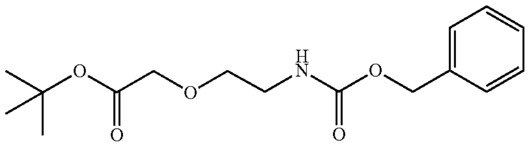 [SMILES: CC(C)(C)OC(=O)COCCNC(=O)OCc1ccccc1]

To a solution of benzyl (2-hydroxyethyl)carbamate (12.0 g, 61.5 mmol) and tert-butyl 2-bromoacetate (23.98 g, 123 mmol) in toluene (200 mL) was added tetrabutylammonium hydrogen sulfate (10.44 g, 30.7 mmol). The reaction mixture was vigorously stirred, a solution of 30% sodium hydroxide (27.2 mL, 61.5 mmol) was added slowly and the mixture was stirred overnight. Water was added and the mixture was extracted with ethyl acetate (3×). The combined organic extracts were washed brine (2×), were dried over $Na_2SO_4$, was filtered, and the filtrate was concentrated. Purification by CombiFlash® Rf chromatography (220 g silica column, 150 mL/min) eluting with a gradient of 0 to 40% ethyl acetate in heptane provided the title compound as a colorless oil (16.48 g, 53.3 mmol, 87% yield). LC-MS m/z 332.0 $(M+Na)^+$.

Intermediate 21

2-(2-((2S,3S)-1-Methyl-5-oxo-2-(pyridin-3-yl)pyrrolidine-3-carboxamido)ethoxy)acetic acid, Hydrochloric acid salt

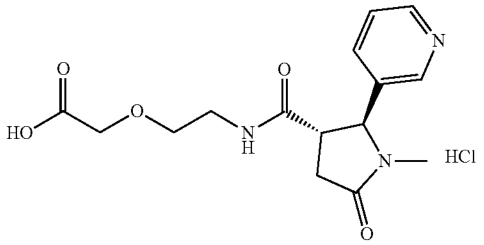 [SMILES: CN1C(=O)C[C@H](C(=O)NCCOCC(=O)O)[C@H]1c1cccnc1 ; Cl]

Step 1 tert-Butyl 2-(2-aminoethoxy)acetate

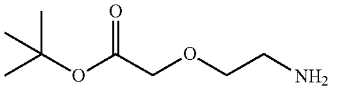

To a solution of tert-butyl 2-(2-(((benzyloxy)carbonyl)amino)ethoxy)acetate (7.08 g, 22.89 mmol) in ethanol under an atmosphere of nitrogen was added 10% Pd—C, Degussa type (0.244 g, 2.289 mmol). The mixture was vacuumed and was backfilled with hydrogen (3×). The mixture was stirred under a balloon atmosphere of hydrogen over the weekend and was filtered through Celite®. The filtrate was concentrated to afford provide the title compound as a wax (4.8 g, 22.74 mmol, 99% yield). LC-MS m/z 176.2 $(M+H)^+$.

Step 2 tert-Butyl 2-(2-((2S,3S)-1-methyl-5-oxo-2-(pyridin-3-yl)pyrrolidine-3-carboxamido) ethoxy)acetate

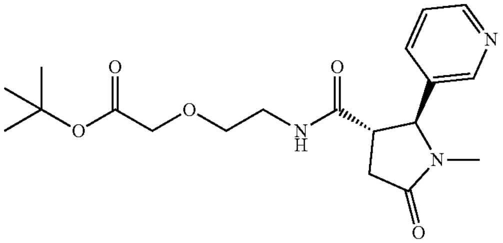 [SMILES: CN1C(=O)C[C@H](C(=O)NCCOCC(=O)OC(C)(C)C)[C@H]1c1cccnc1]

To a solution of (2S,3S)-1-methyl-5-oxo-2-(pyridin-3-yl) pyrrolidine-3-carboxylic acid (400 mg, 1.816 mmol) in N,N-dimethylformamide (DMF) (4.0 mL) were added sequentially DIPEA (1.586 mL, 9.08 mmol), HOBt (278 mg, 1.816 mmol), HATU (1036 mg, 2.72 mmol, and tert-butyl 2-(2-aminoethoxy)acetate (460 mg, 2.180 mmol) and the mixture was stirred overnight. Water was added and the mixture was extracted with ethyl acetate (3×). The combined organic extracts were washed with brine (2×), were dried over $Na_2SO_4$, were filtered, and the combined filtrates were concentrated. Purification by CombiFlash® Rf chromatography (40 g silica column, 40 mL/min) eluting with a gradient of 0 to 20% methanol in dichloromethane (DCM) provided the title compound as a light-colored wax (675 mg, 1.788 mmol, 98% yield) LC-MS m/z 378.3 $(M+H)^+$.

Step 3

2-(2-((2S,3S)-1-Methyl-5-oxo-2-(pyridin-3-yl)pyrrolidine-3-carboxamido)ethoxy)acetic acid, Hydrochloric acid salt

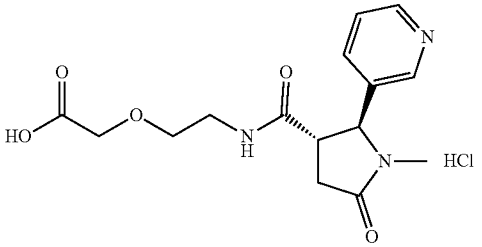 [SMILES: CN1C(=O)C[C@H](C(=O)NCCOCC(=O)O)[C@H]1c1cccnc1 ; Cl]

To a solution of tert-butyl 2-(2-((2S,3S)-1-methyl-5-oxo-2-(pyridin-3-yl) pyrrolidine-3-carboxamido)ethoxy)acetate (675 mg, 1.788 mmol) in dichloromethane (DCM) (2.0 mL) was added 4 M HCl in dioxane (5.0 mL, 20.00 mmol), the mixture was stirred for 1 h, and was concentrated to dryness to the title compound as an off-white solid (640 mg, 1.789 mmol, 100% yield). LC-MS m/z 322.1 $(M+H)^+$.

Intermediate 22 tert-Butyl 2-(2-(2-aminoethoxy)ethoxy)acetate

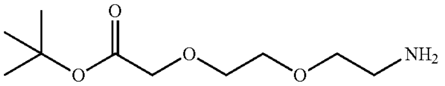

Step 1

Benzyl (2-(2-hydroxyethoxy)ethyl)carbamate

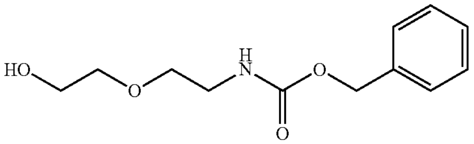 [SMILES: O=C(NCCOCCO)OCc1ccccc1]

To a solution of 2-(2-aminoethoxy)ethan-1-ol (3.0 g, 28.5 mmol) and triethylamine (3.98 mL, 28.5 mmol) in dichloromethane (DCM) (50 mL) at 0° C. was added benzyl carbonochloridate (4.87 g, 28.5 mmol) dropwise. The mixture was stirred at 0° C. for 2 h then at rt overnight. Saturated $NaHCO_3$ was added and the mixture was extracted with dichloromethane (DCM) (2×). The combined organic extracts were washed brine (3×), were dried over $Na_2SO_4$, were filtered, and the filtrate was concentrated. Purification by CombiFlash® Rf chromatography (120 g silica column, 80 mL/min) eluting with a gradient of 50 to 90% ethyl acetate in heptane provided the title compound as a colorless oil (6.48 g, 27.1 mmol, 95% yield). LC-MS m/z 240.3 $(M+H)^+$.

Step 2 tert-Butyl 3-oxo-1-phenyl-2,7,10-trioxa-4-azadodecan-12-oate

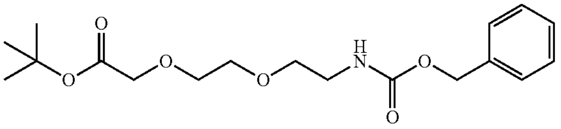 [SMILES: CC(C)(C)OC(=O)COCCOCCNC(=O)OCc1ccccc1]

To a solution of benzyl (2-(2-hydroxyethoxy)ethyl)carba mate (6.48 g, 27.1 mmol) and tert-butyl 2-bromoacetate (10.57 g, 54.2 mmol) in toluene (100 mL) was added tetrabutylammonium hydrogen sulfate (4.60 g, 13.54 mmol). The reaction mixture was vigorously stirred, a solution of 30% sodium hydroxide (12.0 mL, 27.1 mmol) was added slowly and the mixture was stirred overnight. Water was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (120 g silica column, 80 mL/min) eluting with a gradient of 0 to 40% ethyl acetate in heptane provided the title compound as a colorless oil (7.25 g, 20.51 mmol, 76% yield). LC-MS m/z 354.2 $(M+H)^+$.

Step 3 tert-Butyl 2-(2-(2-aminoethoxy)ethoxy)acetate

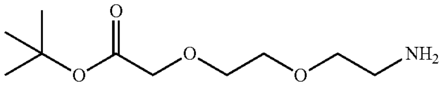

To a solution of tert-butyl 3-oxo-1-phenyl-2,7,10-trioxa-4-azadodecan-12-oate (4.20 g, 11.88 mmol) in ethyl acetate (40 mL) under a nitrogen atmosphere was added 10% Pd—C, Degussa type (0.126 g, 1.188 mmol). The reaction mixture was evacuated, backfilled with hydrogen (3×), and stirred under a balloon atmosphere of hydrogen over the weekend. The mixture was filtered through the Celite® and the filtrate was concentrated to provide the title compound as a colorless oil (2.65 g, 12.08 mmol, 102% yield). LC-MS m/z 220.3 $(M+H)^+$.

Intermediate 23 tert-Butyl (2-(2-(3-(((1R,2S,5R)-5-(isopropyl (methyl)amino)-2-((S)-2-oxo-3-((6-(trifluoromethyl) quinazolin-4-yl)amino)pyrrolidin-1-yl)cyclohexyl) amino)-3-oxopropoxy)ethoxy)ethyl)carbamate

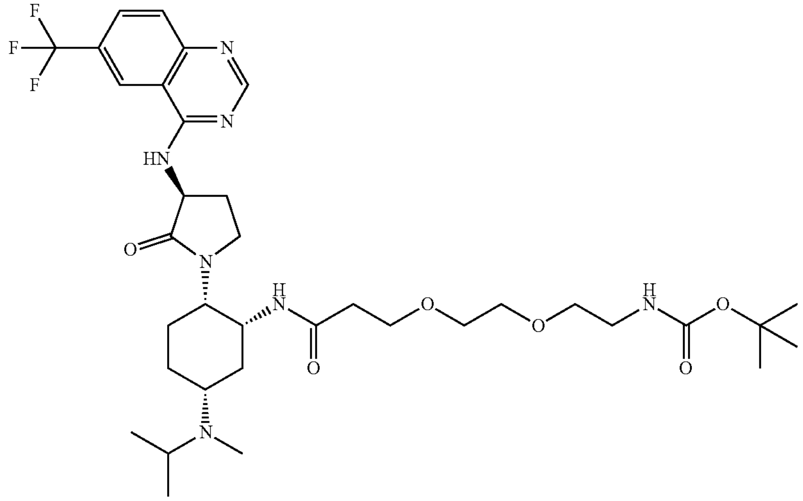 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)OC(C)(C)C)C1]

To a mixture of (S)-1-((1S,2R,4R)-2-amino-4-(isopropyl (methyl)amino)cyclohexyl)-3-((6-(trifluoromethyl)quinazolin-4-yl)amino)pyrrolidin-2-one, 2trifluoroacetic acid salt (124 mg, 0.179 mmol) and 2,2-dimethyl-4-oxo-3,8,11-trioxa-5-azatetradecan-14-oic acid (49.7 mg, 0.179 mmol) in dichloromethane (DCM) (1 mL) was added triethylamine (0.200 mL, 1.432 mmol) and the mixture was stirred at rt for 30 min. HATU (82 mg, 0.215 mmol) was added and the mixture was stirred at rt for 2 h. Purification by ISCO CombiFlash® chromatography (12 g RediSep Rf Gold® column, 30 mL/min) eluting with a gradient of 0 to 20% methanol containing ammonium hydroxide (10%) in dichloromethane (DCM) provided the title compound as a colorless oil (90 mg, 0.124 mmol, 69.4% yield) as a colorless oil. LC-MS m/z 724.4 $(M+H)^+$.

Intermediate 24

(1S,4s)-4-(4-(((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)carbamoyl)phenyl)cyclohexane-1-carboxylic acid, Hydrochloric acid salt

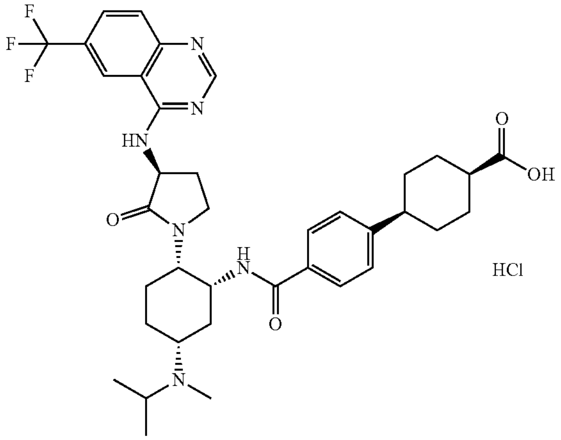 [SMILES: CC(C)N(C)[C@@H]1CC[C@H](N2CC[C@H](Nc3ncnc4ccc(C(F)(F)F)cc34)C2=O)[C@H](NC(=O)c2ccc([C@H]3CC[C@@H](C(=O)O)CC3)cc2)C1 ; Cl]

Step 1

4'-(tert-Butyl) 4-ethyl (S)-2,3,4,5-tetrahydro-[1,1'-biphenyl]-4,4'-dicarboxylate

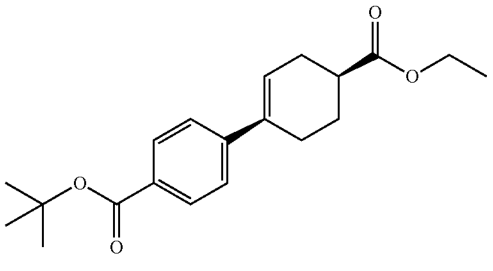

A mixture of tert-butyl 4-bromobenzoate (0.5 g, 1.945 mmol), ethyl 4-(4,4,5,5-tetramethyl-1,3,2-dioxaborolan-2-yl)cyclohex-3-ene-1-carboxylate (0.57 g, 2.034 mmol), sodium carbonate (0.824 g, 7.78 mmol) and tetrakis(triphenylphosphine)palladium(O) (0.225 g, 0.194 mmol) in 1,4-dioxane (10 mL) and water (5.0 mL) was degassed by vacuum/nitrogen backfilling cycles and stirred at 80 to 90° C. for 5 h. The mixture was cooled, poured into water (30 mL), and extracted with ethyl acetate. The combined organic extracts were washed with brine, were dried over $MgSO_4$, and were concentrated. Purification by ISCO CombiFlash® chromatography (80 g Redisep Rf Gold® column, 60 mL/min) eluting with a stepwise gradient of 0 to 50% ethyl acetate in heptane (25 min) and 50% ethyl acetate in heptane (4 min) provided the title compound as a white solid. LC-MS m/z 275.5 $(M+-tBu)^+$.

Step 2 tert-Butyl 4-(4-(ethoxycarbonyl)cyclohexyl)benzoate

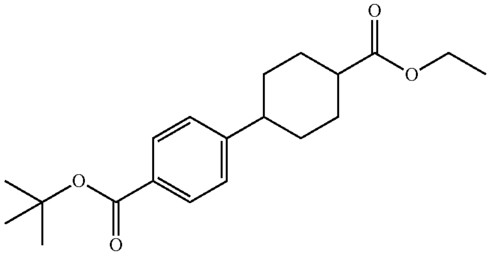 [SMILES: CCOC(=O)C1CCC(c2ccc(C(=O)OC(C)(C)C)cc2)CC1]

A mixture of 4'-(tert-butyl) 4-ethyl 2,3,4,5-tetrahydro-[1,1'-biphenyl]-4,4'-dicarboxylate (451 mg, 1.365 mmol) and 10% Pd/C (145 mg, 0.136 mmol) in ethanol (10 mL) was evacuated and backfilled with hydrogen several times. The mixture was stirred under a balloon atmosphere of hydrogen at rt for 24 h, was filtered through Celite®, and the filtrate was concentrated to provide the title compound as a colorless viscous liquid (461 mg, 1.317 mmol, 97% yield). $^1H$ NMR (400 MHz, CHLOROFORM-d) δ ppm 1.25-1.36 (m, 3H) 1.42-1.85 (m, 14H) 2.00 (br dd, J=13.8, 3.0 Hz, 1H) 2.11-2.21 (m, 1H) 2.22-2.31 (m, 1H) 2.52-2.68 (m, 1H) 2.73 (br d, J=3.0 Hz, 1H) 4.14-4.25 (m, 2H) 7.24-7.28 (m, 2H) 7.90-7.96 (m, 2H). The NMR is consistent for a mixture of cis and trans isomers (1:2).

Step 3

Ethyl (1S,4s)-4-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)phenyl)cyclohexane-1-carboxylate, Formic acid salt

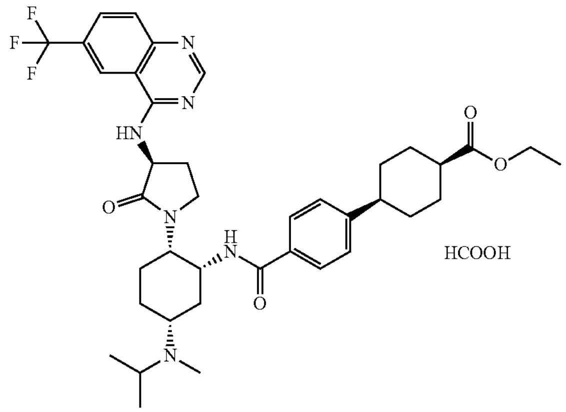 [SMILES: CCOC(=O)[C@H]1CC[C@@H](c2ccc(C(=O)N[C@@H]3C[C@H](N(C)C(C)C)CC[C@@H]3N3CC[C@H](Nc4ncnc5ccc(C(F)(F)F)cc45)C3=O)cc2)CC1 ; "HCOOH"]

A mixture of tert-butyl 4-(4-(ethoxycarbonyl)cyclohexyl)benzoate (120 mg, 0.361 mmol) and 3 M HCl in cyclopentyl methyl ether (1 mL, 3 mmol) in dichloromethane (DCM) (3 mL) was stirred at rt overnight and was concentrated under reduced pressure to provide 4-(4-(ethoxycarbonyl)cyclohexyl)benzoic acid. A mixture of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (114.3 mg, 0.202 mmol) and 3M HCl in cyclopentyl methyl ether (0.5 mL, 1.500 mmol) in dichloromethane (DCM) (1 mL) was stirred at rt for 1 h and was concentrated under reduced pressure. The residue was dissolved in dichloromethane (DCM) (5 mL) with triethylamine (0.15 mL, 1.076 mmol), 4-(4-(ethoxycarbonyl)cyclohexyl)benzoic acid was added, followed by HATU (148 mg, 0.389 mmol). The mixture was stirred at rt overnight and was concentrated under reduced pressure. Purification by MDAP chromatography (XSelect™ CSH Prep C18 5 μm OBD column, 40 mL/min) eluting with a gradient of 15 to 55% acetonitrile in water both containing formic acid (0.1%) provided the title compound as a white solid. LC-MS m/z 723.1 $(M+H)^+$. (36.9 mg, 0.047 mmol, 23.23% yield). $^1H$ NMR (400 MHz, METHANOL-$d_4$) δ ppm 1.28 (t, J=7.0 Hz, 3H) 1.33-1.58 (m, 7H) 1.76 (br t, J=16.1 Hz, 2H) 1.99-2.24 (m, 6H) 2.26-2.46 (m, 4H) 2.53 (br s, 3H) 2.80 (br s, 3H) 3.56-3.69 (m, 1H) 3.78-3.96 (m, 2H) 3.99-4.10 (m, 1H) 4.15 (q, J=7.1 Hz, 2H) 4.38 (br s, 1H) 4.52 (br s, 1H) 4.74-4.82 (m, 1H) 5.50 (s, 1H) 6.91 (br d, J=6.3 Hz, 2H) 7.50 (br d, J=7.8 Hz, 2H) 7.79 (br d, J=8.5 Hz, 1H) 8.07 (br d, J=8.5 Hz, 1H) 8.16 (br s, 1H) 8.36 (br s, 2H) 8.69 (s, 1H).

Step 4

(1S,4s)-4-(4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) phenyl)cyclohexane-1-carboxylic acid, Hydrochloric acid salt

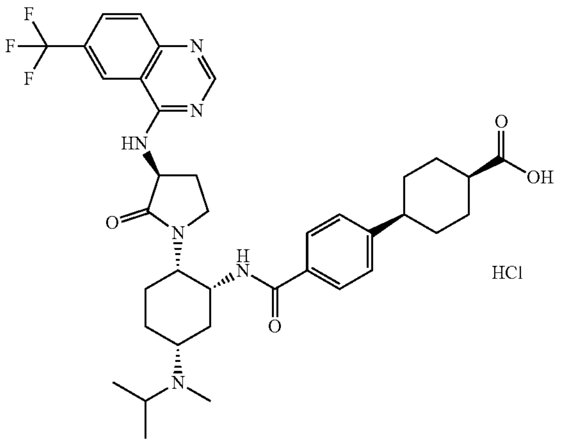 [SMILES: CC(C)N(C)[C@@H]1CC[C@H](N2CC[C@H](Nc3ncnc4ccc(C(F)(F)F)cc34)C2=O)[C@H](NC(=O)c2ccc([C@H]3CC[C@@H](C(=O)O)CC3)cc2)C1 ; Cl]

A mixture of ethyl (1S,4s)-4-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl) phenyl) cyclohexane-1-carboxylate (36.9 mg, 0.051 mmol) and 2 M HCl (1 mL, 2.000 mmol) was stirred at 50 to 55° C. for 4 h and was concentrated under reduced pressure to provide the title compound as a white solid (39 mg, 0.050 mmol, 98% yield). LC-MS m/z 695.5 $(M+H)^+$.

Intermediate 25

1-(4-(Ethoxycarbonyl)cyclohexyl)piperidine-4-carboxylic acid, Trifluoroacetic acid salt

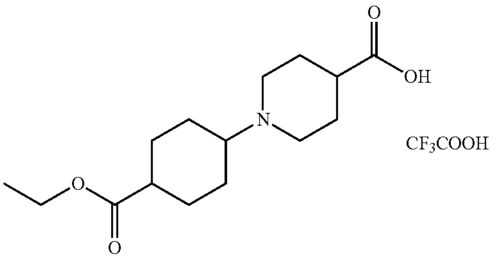 [SMILES: CCOC(=O)C1CCC(N2CCC(C(=O)O)CC2)CC1 ; "CF3COOH"]

Triethylamine (1.610 ml, 11.55 mmol) was added to a solution of piperidine-4-carboxylic acid, Trifluoroacetic acid salt (2.96 g, 12.17 mmol) and ethyl 4-oxocyclohexane-1-carboxylate (1.498 ml, 9.40 mmol) in methanol (72.3 ml) and the mixture was stirred at rt for 2 min. Picoline borane (1.106 g, 10.34 mmol) was added and the mixture was placed in a preheated aluminum block at 50° C. under a nitrogen atmosphere. The reaction was maintained at 50° C. for 1.5 h and was stirred at rt overnight. The mixture was heated to sequentially at 60° C. for 2 h, at 70° C. for 2 h, and at 75° C. for 1 h. The mixture was concentrated and dissolved in dichloromethane (DCM). The organic phase was washed with $NaHCO_3$ and the aqueous phase was acidified with 1 N HCl. The aqueous and organic extracts were concentrated under reduced pressure. Purification by reverse-phase HPLC (100 g TFA C18 column, 75 mL/min) eluting with a gradient of 0 to 50% acetonitrile in water containing 0.01% TFA provided the title compound as a clear oil (2.26 g, 2.218 mmol, 23.59% yield). LC-MS m/z 284.2 $(M+H)^+$.

The following intermediates were or could be prepared using procedures analogous to those described for Intermediate 25:

| Inter. | Compound | LC-MS m/z | NMR |
|---|---|---|---|
| 26 | 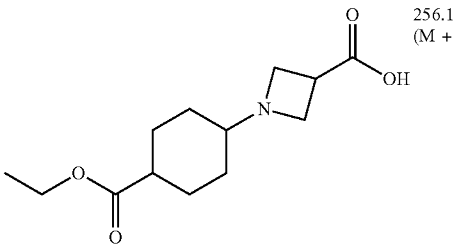 1-(4-(Ethoxycarbonyl)cyclohexyl) azetidine-3-carboxylic acid. | 256.1 $(M + H)^+$ | $^1H$ NMR (400 MHz, METHANOL-$d_4$) δ ppm 1.24 - 1.31 (m, 2H) 1.31 - 1.57 (m, 2H) 1.59 - 1.71 (m, 1H) 1.97 (s, 6H) 2.05 - 2.24 (m, 2H) 2.33 (tt, J = 12.0, 3.3 Hz, 1H) 2.67 (quin, J = 4.3 Hz, 1H) 3.06 - 3.20 (m, 1H) 3.36 - 3.47 (m, 1H) 4.06 - 4.32 (m, 3 H) |
| 27 | 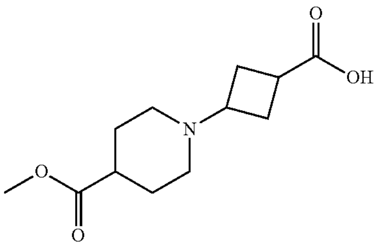 [SMILES: COC(=O)C1CCN(C2CC(C(=O)O)C2)CC1] 3-(4-(Methoxycarbonyl)piperidin-1-yl)cyclobutane-1-carboxylic acid. | 242.2 $(M + H)^+$ | $^1H$ NMR (400 MHz, METHANOL-$d_4$) δ ppm 1.32 (t, J = 7.4 Hz, 6H) 1.95 (s, 3H) 1.97 - 2.01 (m, 1H) 2.45 - 2.58 (m, 1H) 3.20 (q, J = 7.4 Hz, 4H) 3.37 (s, 3H) |

Intermediate 28 tert-Butyl ((1 s,4s)-4-aminocyclohexane-1-carbonyl)glycinate

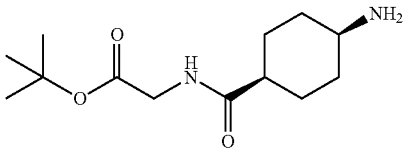 [SMILES: CC(C)(C)OC(=O)CNC(=O)[C@H]1CC[C@@H](N)CC1]

Step 1 tert-Butyl ((1s,4s)-4-(((benzyloxy)carbonyl)amino) cyclohexane-1-carbonyl)glycinate

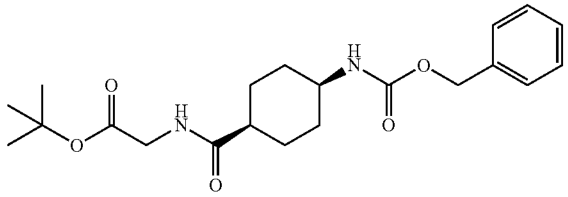 [SMILES: CC(C)(C)OC(=O)CNC(=O)[C@H]1CC[C@@H](NC(=O)OCc2ccccc2)CC1]

To a solution of (1 s,4s)-4-(((benzyloxy)carbonyl)amino) cyclohexane-1-carboxylic acid (827 mg, 2.98 mmol), HOBt (548 mg, 3.58 mmol), EDC (858 mg, 4.47 mmol) and tert-butyl glycinate, Hydrochloric acid salt (500 mg, 2.98 mmol) in dichloromethane (DCM) (10.0 mL) was added DIPEA (2.60 mL, 14.91 mmol) and the mixture was stirred overnight. Saturated $NaHCO_3$ was added and the mixture was extracted with dichloromethane (DCM((3×). The combined organic extracts were washed with brine (2×), were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 20% methanol in dichloromethane (DCM) provided the title compound as a colorless oil (1.16 g, 2.97 mmol, 100% yield). LC-MS m/z 391.3 $(M+H)^+$.

Step 2 tert-Butyl ((1s,4s)-4-aminocyclohexane-1-carbonyl)glycinate

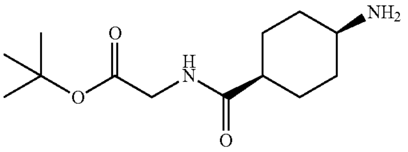 [SMILES: CC(C)(C)OC(=O)CNC(=O)[C@H]1CC[C@@H](N)CC1]

To a solution of tert-butyl ((1s,4s)-4-(((benzyloxy)carbonyl)amino)cyclohexane-1-carbonyl)glycinate (1.16 g, 2.97 mmol) in ethyl acetate (20 mL) under a nitrogen atmosphere was added 10% Pd—C, Degussa type (0.032 g, 0.297 mmol). The mixture was evacuated, was backfilled with hydrogen (3×), and was stirred under a balloon atmosphere of hydrogen over the weekend. The mixture was filtered through Celite® and the filtrate was concentrated to provide the title compound as a colorless oil (590 mg, 2.302 mmol, 77% yield). LC-MS m/z 257.3 $(M+H)^+$.

Intermediate 29

3-Azaspiro[5.5]undecan-9-one, Trifluoroacetic acid salt

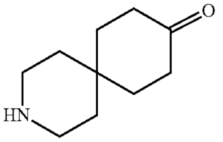

$CF_3COOH$

To a mixture of tert-butyl 9-oxo-3-azaspiro[5.5]undecane-3-carboxylate (336 mg, 1.257 mmol) in dichloromethane (DCM) (1.1 mL) was added TFA (1.1 mL, 14.28 mmol). The mixture was stirred at rt for 1 h and was concentrated to provide the title compound. LC-MS m/z 168.2 $(M+H)^+$.

Intermediate 30

3-(2-(2-(2-((2-Ethoxy-3,4-dioxocyclobut-1-en-1-yl) amino)ethoxy)ethoxy)ethoxy)-N-((1R,2S,5R)-5-(isopropyl(methyl)amino)-2-((S)-2-oxo-3-((6-(trifluoromethyl)quinazolin-4-yl)amino)pyrrolidin-1-yl) cyclohexyl)propenamide

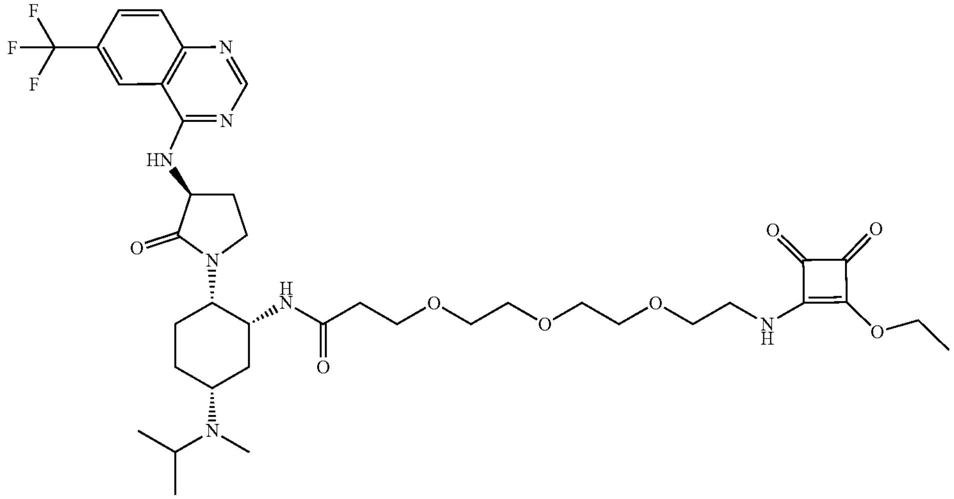 [SMILES: CCOc1c(NCCOCCOCCOCCC(=O)N[C@@H]2C[C@H](N(C)C(C)C)CC[C@@H]2N2CC[C@H](Nc3ncnc4ccc(C(F)(F)F)cc34)C2=O)c(=O)c1=O]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (861 mg, 1.5 mmol), 3-(2-(2-(2-((2-ethoxy-3,4-dioxocyclobut-1-en-1-yl)amino)ethoxy)ethoxy)ethoxy) propanoic acid (518 mg, 1.500 mmol), and DIPEA (2.62 mL, 15.00 mmol) in dichloromethane (DCM) (5 mL) was added T3P (1.161 mL, 1.950 mmol), and the mixture was stirred at rt for 2 h. Dichloromethane (DCM) (10 mL) and water (10 mL) were added. The organic layer was dried over $Na_2SO_4$, was filtered, and the filtrate was concentrated. Purification by MDAP chromatography (XSelect™ CSH C18 5 μm column, 40 mL/min) eluting with a gradient of 30 to 85% acetonitrile in water containing ammonium bicarbonate (10 mM) and ammonium hydroxide (0.075%) provided the title compound as a white solid (354 mg, 0.443 mmol, 29.5% yield). LC-MS m/z 792.4 $(M+H)^+$.

Intermediate 31 tert-Butyl ((1R,4r)-4-(2-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-2-oxoethyl)cyclohexyl)carbamate

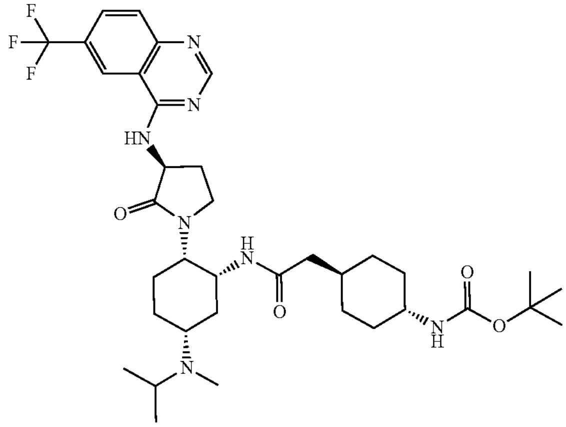 [SMILES: CC(C)N(C)[C@@H]1CC[C@H](N2CC[C@H](Nc3ncnc4ccc(C(F)(F)F)cc34)C2=O)[C@H](NC(=O)C[C@H]2CC[C@H](NC(=O)OC(C)(C)C)CC2)C1]

To a suspension of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (85 mg, 0.158 mmol) in dichloromethane (DCM) (3 mL) was added triethylamine (0.110 mL, 0.791 mmol), followed by 2-((trans)-4-((tert-butoxycarbonyl)amino)cyclohexyl) acetic acid (48.8 mg, 0.190 mmol) and HATU (90 mg, 0.237 mmol). The mixture was stirred at rt for 2 h and was concentrated under reduced pressure. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a white solid (86 mg, 0.120 mmol, 76% yield) as a white solid. LC-MS m/z 704.3 $(M+H)^+$.

Intermediate 32

1-Azido-4-iodobutane

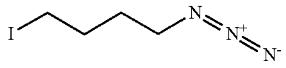

Step 1

4-Azidobutan-1-ol

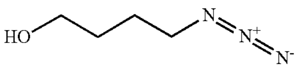

A mixture of 4-chlorobutan-1-ol (9.19 mL, 92 mmol) and sodium azide (11.98 g, 184 mmol) in dimethyl sulfoxide (DMSO) (65 mL) was heated at 85° C. overnight, was cooled, was poured into water (75 mL), and was extracted with ethyl acetate (3×100 mL). The combined organic extracts were washed with brine, were dried over $MgSO_4$, and were concentrated under reduced pressure. Purification by normal phase column chromatography (40 g RediSep Rf Gold® column, 60 mL/min) eluting with a stepwise gradient of 10 to 50% ethyl acetate in hexanes (10 column volumes) and 50% ethyl acetate in hexanes (5 column volumes) provided the title compound as a colorless liquid (9.56 g, 74.7 mmol, 81% yield). $^1$H NMR (400 MHz, CHLOROFORM-d) δ ppm 1.64-1.77 (m, 5H) 3.36 (t, J=6.2 Hz, 2H) 3.72 (t, J=6.1 Hz, 2H).

Step 2

4-Azidobutyl methanesulfonate

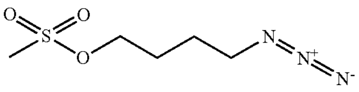

To a mixture of 4-azidobutan-1-ol (5.9 g, 51.2 mmol), triethylamine (7.14 mL, 51.2 mmol) and 4-dimethylaminopyridine (DMAP) (6.26 g, 51.2 mmol) in dichloromethane (DCM) (40 mL) was added methanesulfonyl chloride (3.99 mL, 51.2 mmol) dropwise at 0° C. The reaction mixture was stirred at 0° C. for 1 h, was poured into ice water (75 mL), and was extracted with dichloromethane (DCM) (3×100 mL). The combined organic extracts were washed with brine, were dried over $MgSO_4$, and were concentrated under reduced pressure. Purification by normal phase column chromatography (40 g RediSep Rf Gold® column, 40 mL/min) provided the title product as a pale-yellow liquid. $^1$H NMR (400 MHz, CHLOROFORM-d) δ ppm 1.69-1.80 (m, 2H) 1.85-1.93 (m, 2H) 3.05 (s, 3H) 3.39 (t, J=6.6 Hz, 2H) 4.30 (t, J=6.2 Hz, 2H).

Step 3

1-Azido-4-iodobutane

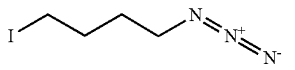

To a solution of 4-azidobutyl methanesulfonate (6.545 g, 33.9 mmol) in acetone (40 mL) was added anhydrous sodium iodide (10.15 g, 67.7 mmol). The reaction mixture was stirred at rt overnight and was diluted with diethyl ether (150 mL). The precipitate was removed by filtration and the filtrate was concentrated under reduced pressure. The residue was dissolved in diethyl ether (150 mL). The organic phase was washed with saturated $Na_2S_2O_3$ (100 mL), with brine, were dried over $MgSO_4$, and were concentrated under reduce pressure to provide the title compound as a pale brown oil (7.6 g, 30.4 mmol, 90% yield). $^1H$ NMR (400 MHz, CHLOROFORM-d) δ ppm 1.68-1.81 (m, 2H) 1.85-2.02 (m, 2H) 3.24 (t, J=6.8 Hz, 2H) 3.35 (t, J=6.7 Hz, 2H).

Intermediate 33

4-(4-(Methoxycarbonyl)piperidin-1-yl)benzoic acid

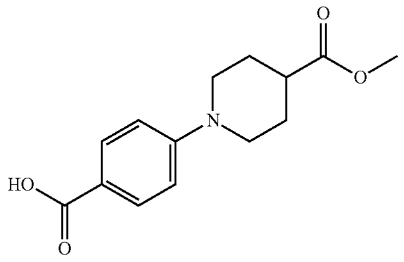 [SMILES: COC(=O)C1CCN(c2ccc(C(=O)O)cc2)CC1]

Step 1

Methyl 1-(4-(tert-butoxycarbonyl)phenyl)piperidine-4-carboxylate

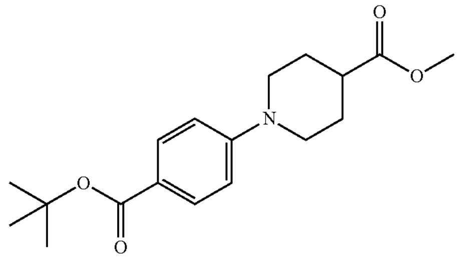 [SMILES: COC(=O)C1CCN(c2ccc(C(=O)OC(C)(C)C)cc2)CC1]

DIPEA (10.68 mL, 61.2 mmol) was added to a solution of tert-butyl 4-fluorobenzoate (4 g, 20.39 mmol) and methyl piperidine-4-carboxylate (3.30 mL, 24.46 mmol) in dimethyl sulfoxide (DMSO) (20 mL) at rt under a nitrogen atmosphere. The mixture was stirred at 145° C. for 16 h and was cooled to rt. Water (100 mL) was added and the mixture was extracted with ethyl acetate (3×50 mL). The combined organic extracts were washed with water (2×50 mL), with brine (1×50 mL), were dried over $Na_2SO_4$, were filtered, and the filtrate was concentrated under reduced pressure. Purification by Biotage® Isolera™ column chromatography (100 g SNAPS column) eluting with a gradient of 5 to 20% ethyl acetate in hexane provided the title compound as a white solid (1.4 g, 4.24 mmol, 20.80% yield). LC-MS m/z 320.2 $(M+H)^+$.

Step 2

4-(4-(Methoxycarbonyl)piperidin-1-yl)benzoic acid

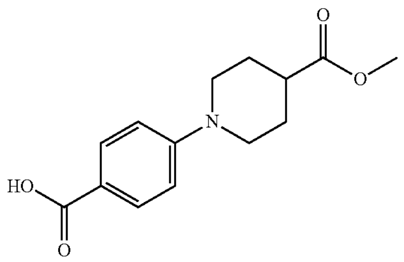 [SMILES: COC(=O)C1CCN(c2ccc(C(=O)O)cc2)CC1]

To a solution of methyl 1-(4-(tert-butoxycarbonyl)phenyl)piperidine-4-carboxylate (500 mg, 1.565 mmol)) in dichloromethane (DCM) (10 mL) was added HCl (1.957 mL, 7.83 mmol) in 1,4 dioxane at 0° C. The mixture was stirred at rt for 16 h and was concentrated under reduced pressure. The residue was triturated with diethyl ether (20 mL) to provide the title compound as a white solid (0.28 g, 0.957 mmol, 61.1% yield). LC-MS m/z 264.0 $(M+H)^+$.

Intermediate 34 tert-Butyl 4-((1r,4r)-4-(ethoxycarbonyl)cyclohexyl)piperazine-1-carboxylate

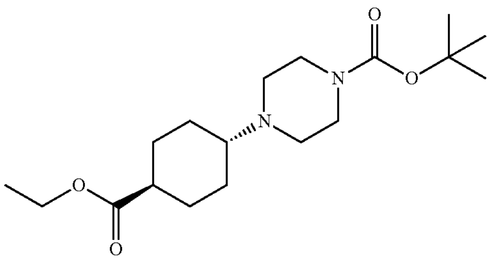 [SMILES: CCOC(=O)[C@H]1CC[C@H](N2CCN(C(=O)OC(C)(C)C)CC2)CC1]

Acetic acid (3.37 ml) was added to a solution of ethyl 4-oxocyclohexane-1-carboxylate (4.68 ml, 29.4 mmol) and tert-butyl piperazine-1-carboxylate (6.57 g, 35.3 mmol) in dichloromethane (DCM) (49.9 ml) under a nitrogen atmosphere and the mixture was stirred for 5 min. Sodium triacetoxyborohydride (9.60 g, 45.3 mmol) was added. The mixture was stirred in at 50° C. for 1 h. Water was added and the mixture basified to pH of 8 with 1 M sodium hydroxide and was extracted with dichloromethane (DCM) (3×). The combined organic extracts were dried over $Na_2SO_4$, were filtered, and the filtrate was concentrated under reduced pressure. It was purified by EZ-Prep using the 275 g Hp C18

Aq column in ACN/Water to provided the title compound as yellow oil (1.609 g, 4.58 mmol, 15.61% yield). LC-MS m/z 341.4 $(M+H)^+$.

Intermediate 35

4-(1-(tert-Butoxycarbonyl)-1,2,3,6-tetrahydropyridin-4-yl)cyclohex-3-ene-1-carboxylic acid

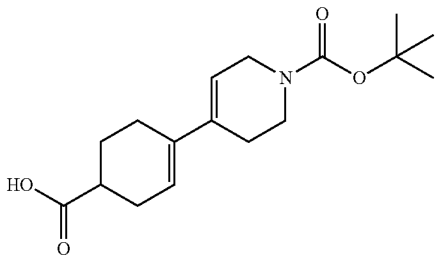 [SMILES: CC(C)(C)OC(=O)N1CC=C(C2=CCC(C(=O)O)CC2)CC1]

Step 1 tert-Butyl 4-(4-(ethoxycarbonyl)cyclohex-1-en-1-yl)-3,6-dihydropyridine-1(2H)-carboxylate

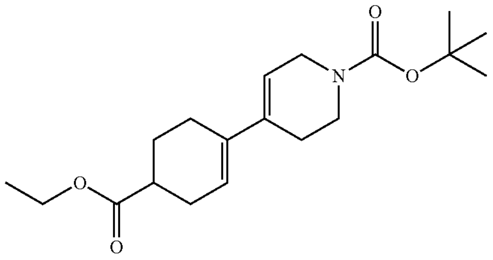 [SMILES: CCOC(=O)C1CC=C(C2=CCN(C(=O)OC(C)(C)C)CC2)CC1]

A mixture of tert-butyl 4-(((trifluoromethyl)sulfonyl)oxy)-3,6-dihydropyridine-1(2H)-carboxylate (1.11 g, 3.35 mmol), ethyl 4-(4,4,5,5-tetramethyl-1,3,2-dioxaborolan-2-yl)cyclohex-3-ene-1-carboxylate (1.0 g, 3.57 mmol), sodium carbonate (1.065 g, 10.05 mmol) and tetrakis(triphenylphosphine)palladium(O) (0.387 g, 0.335 mmol) in 1,4-dioxane (12 mL) and water (4.0 mL) was degassed by vacuum/nitrogen backfilling cycles and was stirred in a microwave reactor at 80° C. for 3 h. The mixture was cooled, water (30 mL) was added, and the mixture was extracted with ethyl acetate. The combined organic extracts were washed with brine, were dried over $MgSO_4$, and the filtrate was concentrated. The residue was purified by normal phase chromatography (40 g ISCO Gold® column, 45 mL/min) eluting with a stepwise gradient of 0 to 30% ethyl acetate in heptane (9 CV) and 30% ethyl acetate in heptane (5 CV) provided the title as a wax-like solid (527.2 mg, 1.493 mmol, 44.6% yield).

Step 2

4-(1-(tert-Butoxycarbonyl)-1,2,3,6-tetrahydropyridin-4-yl)cyclohex-3-ene-1-carboxylic acid

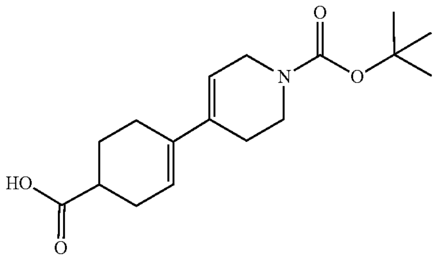 [SMILES: CC(C)(C)OC(=O)N1CC=C(C2=CCC(C(=O)O)CC2)CC1]

A mixture of tert-butyl 4-(4-(ethoxycarbonyl)cyclohex-1-en-1-yl)-3,6-dihydropyridine-1(2H)-carboxylate (349 mg, 1.040 mmol) and aqueous 2 N sodium hydroxide (1.5 mL, 3.00 mmol) in tetrahydrofuran (THF) (2 mL) and ethanol (2 mL) was stirred at rt overnight and was concentrated under reduced pressure to remove the organic solvents. The pH was adjusted to 4 to 5 with 1 N HCl and was stirred for 1 h. The precipitate was collected by filtration, was washed with water, and was dried in an air flow to provide the title compound as a beige solid (305 mg, 0.992 mmol, 95% yield). $^1H$ NMR (400 MHz, DMSO-$d_6$) δ ppm 1.41 (s, 9H) 1.52-1.63 (m, 1H) 1.92-2.07 (m, 1H) 2.10-2.46 (m, 7H) 3.36-3.48 (m, 2H) 3.91 (br s, 2H) 5.70 (br s, 1H) 5.78 (br s, 1H) 12.19 (br s, 1H).

The following intermediates were or could be prepared using procedures analogous to those described for Intermediate 35:

| Inter. | Compound | LC-MS m/z | NMR |
|---|---|---|---|
| 36 | 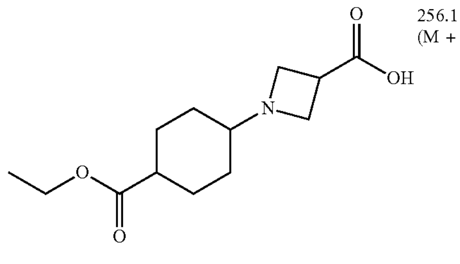 N 1-(4-(Ethoxycarbonyl)cyclohexyl) azetidine-3-carboxylic acid. | 256.1 $(M + H)^+$ | $^1H$ NMR (400 MHz, METHANOL-$d_4$) δ ppm 1.24 - 1.31 (m, 2H) 1.31 - 1.57 (m, 2H) 1.59 - 1.71 (m, 1H) 1.97 (s, 6H) 2.05 - 2.24 (m, 2H) 2.33 (tt, J = 12.0, 3.3 Hz, 1H) 2.67 (quin, J = 4.3 Hz, 1H) 3.06 - 3.20 (m, 1H) 3.36 - 3.47 (m, 1H) 4.06 - 4.32 (m, 3 H) |

-continued

| Inter. | Compound | LC-MS m/z | NMR |
|---|---|---|---|
| 37 | 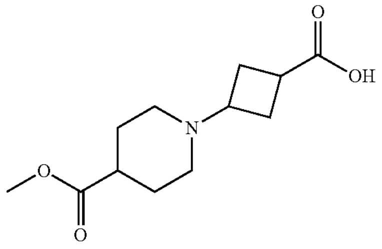 [SMILES: COC(=O)C1CCN(C2CC(C(=O)O)C2)CC1] C 3-(4-(Methoxycarbonyl)piperidin-1-yl)cyclobutane-1-carboxylic acid. | 242.2 $(M + H)^+$ | $^1H$ NMR (400 MHz, METHANOL-$d_4$) δ ppm 1.32 (t, J = 7.4 Hz, 6H) 1.95 (s, 3H) 1.97 - 2.01 (m, 1H) 2.45 - 2.58 (m, 1H) 3.20 (q, J = 7.4 Hz, 4H) 3.37 (s, 3H) |

Intermediate 38 tert-Butyl 3-(2-(2-(isopropylamino)ethoxy)ethoxy)propanoate

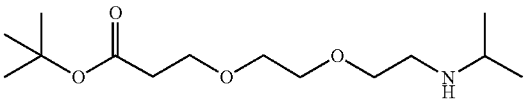 [SMILES: CC(C)NCCOCCOCCC(=O)OC(C)(C)C]

To a solution of tert-butyl 3-(2-(2-aminoethoxy)ethoxy) propanoate (1.00 g, 4.29 mmol) in acetone (0.373 g, 6.43 mmol) and dichloromethane (DCM) (20 mL) was added 2 drops of acetic acid followed by sodium triacetoxyborohydride (2.271 g, 10.72 mmol) and the mixture was stirred overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated to provide the title compound as a colorless oil (1.20 g, 4.36 mmol, 102% yield). LC-MS m/z 276.3 $(M+H)^+$. $^1H$ NMR (400 MHz, DMSO-$d_6$) δ ppm 0.99 (d, J=6.4 Hz, 6H) 1.40 (s, 9H) 2.42 (t, J=6.4 Hz, 2H) 2.68 (t, J=5.9 Hz, 2H) 2.72-2.81 (m, 1H) 3.46 (t, J=5.6 Hz, 2H) 3.49 (s, 4H) 3.59 (t, J=6.4 Hz, 2H) 5.77 (s, 1H).

Intermediate 39

2-(2-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-2-oxoethoxy)acetic acid

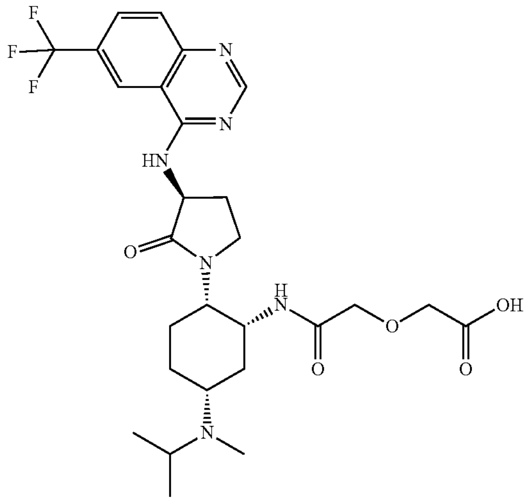 [SMILES: CC(C)N(C)[C@@H]1CC[C@H](N2CC[C@H](Nc3ncnc4ccc(C(F)(F)F)cc34)C2=O)[C@H](NC(=O)COCC(=O)O)C1]

To a solution of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (50 mg, 0.079 mmol) in dichloromethane (DCM) (0.25 mL) were added dropwise 1,4-dioxane-2,6-dione (10.20 mg, 0.079 mmol) and DIPEA (0.028 mL, 0.158 mmol) dissolved in dichloromethane The mixture was stirred at rt for 1 h and was concentrated to provide the title compound (0.0458 mg 0.079 mmol, 100% yield). LC-MS m/z 581.0 $(M+H)^+$.

Intermediate 40 tert-Butyl 4-(piperazine-1-carbonyl)piperazine-1-carboxylate

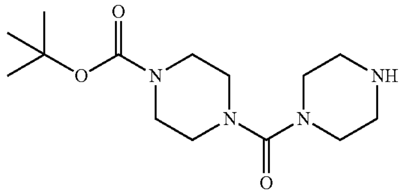 [SMILES: CC(C)(C)OC(=O)N1CCN(C(=O)N2CCNCC2)CC1]

To a solution of 1-tert-butyl 4-(4-nitrophenyl) piperazine-1,4-dicarboxylate (5.2 g, 14.80 mmol) in tetrahydrofuran (THF) (148 ml) was added piperazine (2.55 g, 29.6 mmol). The mixture was stirred at 70° C. for 16 h and was concentrated under reduced pressure. Purification by normal phase column chromatography eluting with 10% methanol in dichloromethane provided the title compound as a light-yellow solid (3.3 g, 11.06 mmol, 74.7% yield). LC-MS m/z 299.1 $(M+H)^+$.

Intermediate 41

9-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-9-oxononyl 4-methylbenzenesulfonate

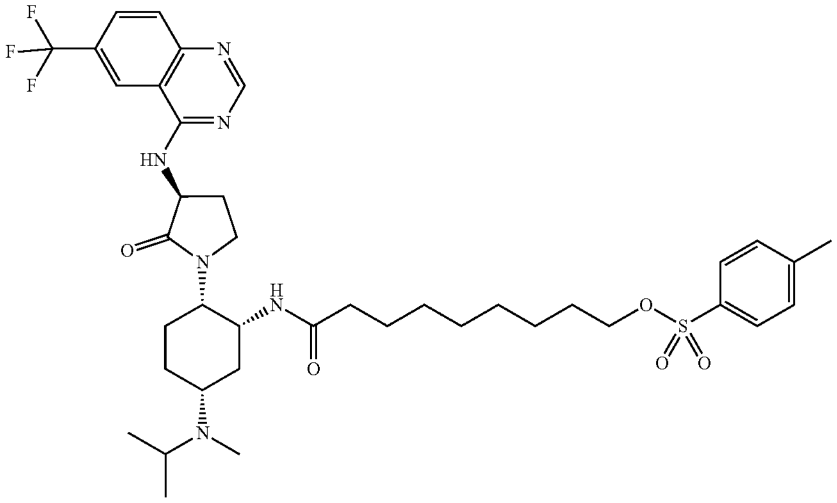 [SMILES: Cc1ccc(S(=O)(=O)OCCCCCCCCC(=O)N[C@@H]2C[C@H](N(C)C(C)C)CC[C@@H]2N2CC[C@H](Nc3ncnc4ccc(C(F)(F)F)cc34)C2=O)cc1]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2trifluoroacetic acid salt (154 mg, 0.222 mmol) in dichloromethane (DCM) (1 ml) was added triethylamine (0.248 mL, 1.779 mmol) and the mixture was stirred at rt for 30 min. 9-(Tosyloxy)nonanoic acid (73.0 mg, 0.222 mmol) and HATU (101 mg, 0.267 mmol) in DCM (1 ml) were added and the mixture was stirred at rt for 15 min. The mixture was partitioned between dichloromethane (DCM) and saturated $NaHCO_3$ and the aqueous layer was extracted with dichloromethane (DCM). The combined organic extracts were dried over $Na_2SO_4$, were filtered, and the filtrate was concentrated. Purification by ISCO CombiFlash® chromatography (12 g RediSep Rf Gold® column, 30 mL/min) eluting with a gradient of 0 to 50% methanol/dichloromethane (80:20) in dichloromethane (DCM) provided the title compound as a light-yellow oil (120 mg, 0.155 mmol, 69.6% yield). LC-MS m/z 775.2 $(M+H)^+$.

Example 1

(2S,3S)-N-(2-(((1R,4S)-4-(4-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-4-oxobutoxy)cyclohexyl)oxy)ethyl)-1-methyl-5-oxo-2-(pyridin-3-yl)pyrrolidine-3-carboxamide

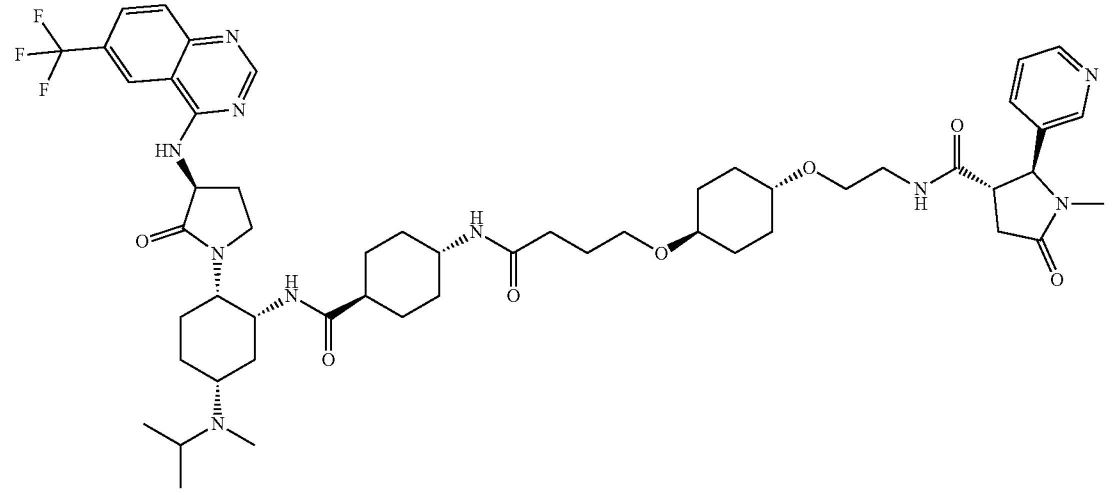 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCO[C@H]3CC[C@H](OCCNC(=O)[C@H]4CC(=O)N(C)[C@@H]4c4cccnc4)CC3)CC2)C1]

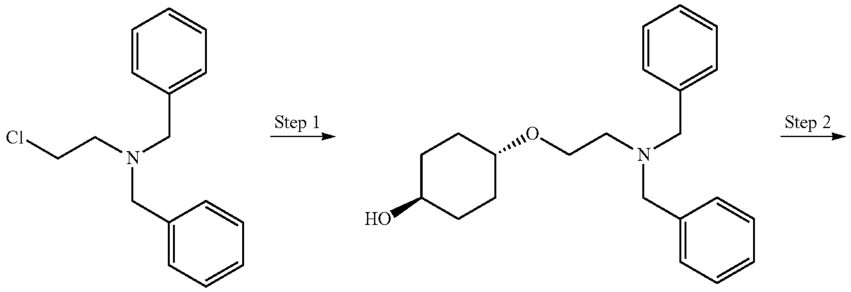

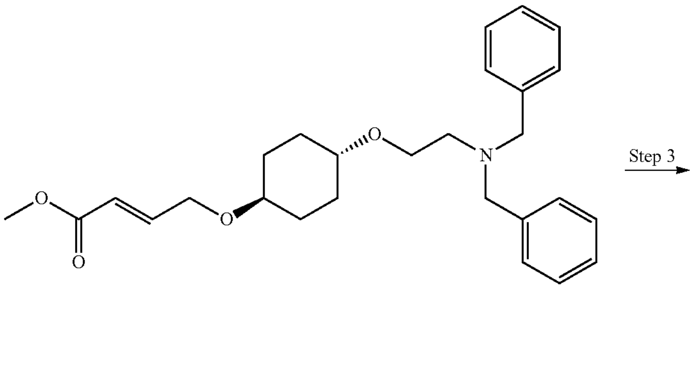

-continued

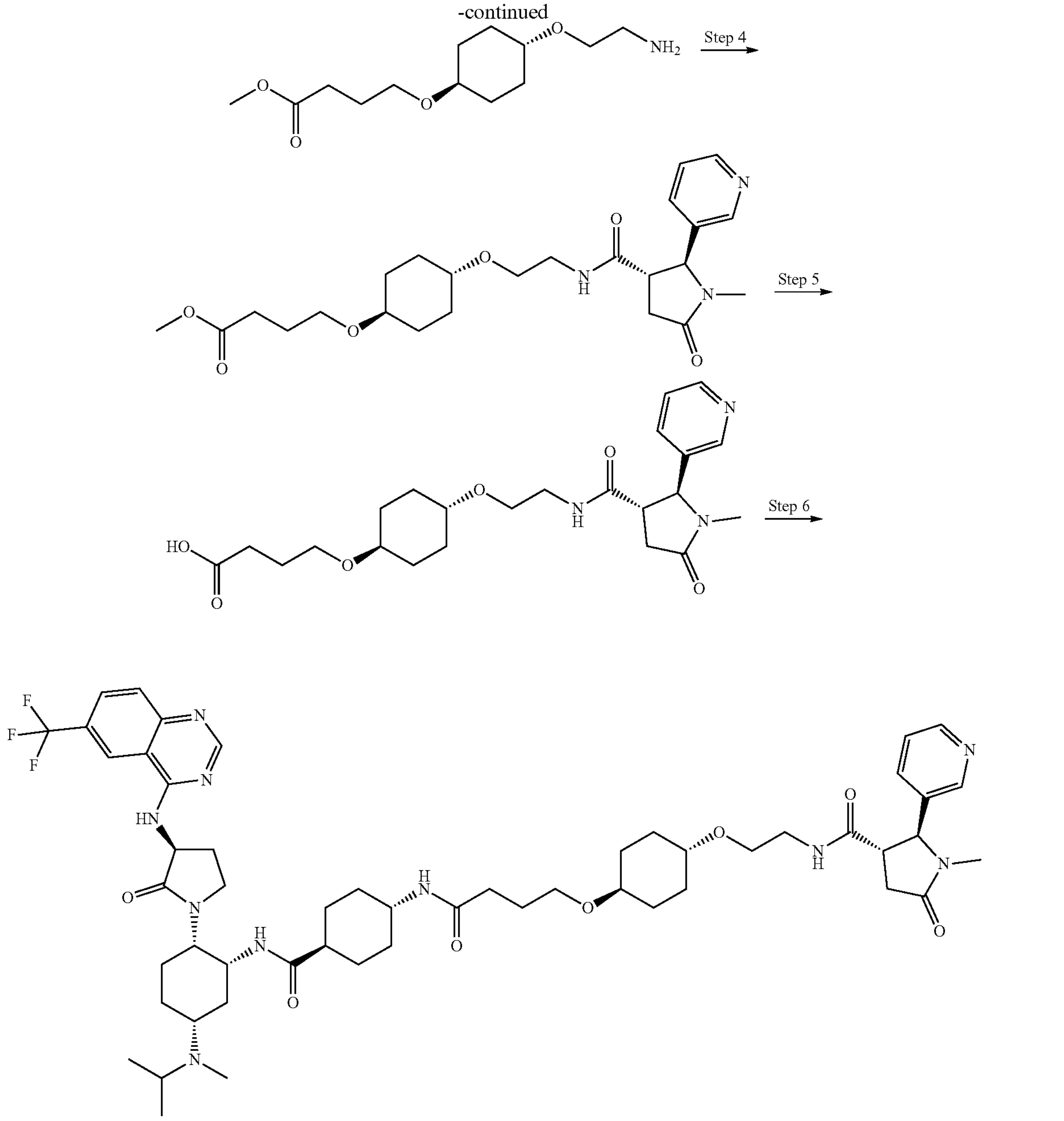

Step 1

(1r,4r)-4-(2-(Dibenzylamino)ethoxy)cyclohexanol

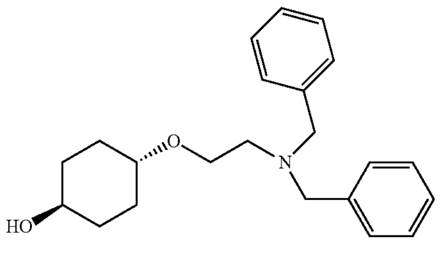 [SMILES: O[C@H]1CC[C@H](OCCN(Cc2ccccc2)Cc2ccccc2)CC1]

To a solution of commercially-available (1r,4r)-cyclohexane-1,4-diol (2.4 g, 20.66 mmol), in N,N-dimethylformamide (DMF) (20 mL) under an atmosphere of nitrogen was added sodium hydride (60% in mineral oil) (0.826 g, 20.66 mmol) at 0° C., and the mixture was stirred at rt for 30 min. N,N-dibenzyl-2-chloroethan-1-amine (4.29 g, 16.53 mmol) was added at 0° C. and the mixture was stirred at 80° C. for 6 h. Ice water (50 mL) and was added and the mixture was extracted with ethyl acetate (3x60 mL). The combined organic extracts were dried over $Na_2SO_4$ and were concentrated under reduced pressure. Purification by Biotage® Isolera™ column chromatography (50 g SNAPS column) eluting with a gradient of 0 to 20% ethyl acetate in hexane provided the title compound as a pale-yellow oil. (2.5 g, 7.29 mmol, 35.3% yield). LC-MS m/z 340.0 $(M+H)^+$.

Step 2

Methyl (E)-4-(((1r,4r)-4-(2-(dibenzylamino)ethoxy) cyclohexyl)oxy)but-2-enoate

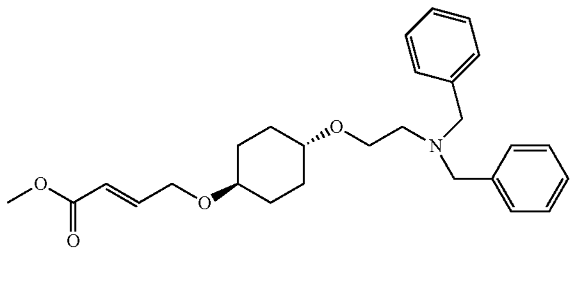 [SMILES: COC(=O)/C=C/CO[C@H]1CC[C@H](OCCN(Cc2ccccc2)Cc2ccccc2)CC1]

To a solution of the (1r,4r)-4-(2-(dibenzylamino)ethoxy) cyclohexanol (2.5 g, 7.36 mmol) in toluene (30 mL) under an atmosphere of nitrogen were added acetic acid (0.084 mL, 1.473 mmol), triphenylphosphine (0.097 g, 0.368 mmol) and methyl but-2-ynoate (1.084 g, 11.05 mmol) at rt. The mixture was stirred at 115° C. for 16 h, was cooled to rt, and ethyl acetate (100 mL) was added. The organic phase was washed with water (2×50 mL), was dried over $Na_2SO_4$, was filtered, and the filtrate was concentrated under reduced pressure. Purification by Biotage® Isolera™ column chromatography (25 g SNAPS column) eluting with a gradient of 0 to 30% ethyl acetate in hexane provided the title compound as a yellow oil (1.77 g, 3.56 mmol, 48.3% yield). LC-MS m/z 438.0 $(M+H)^+$.

Step 3

Methyl 4-(((1r,4r)-4-(2-aminoethoxy)cyclohexyl) oxy)butanoate

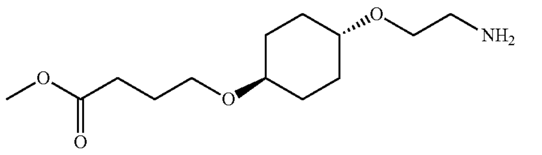 [SMILES: COC(=O)CCCO[C@H]1CC[C@H](OCCN)CC1]

To a stirred solution of methyl (E)-4-(((1r,4r)-4-(2-(dibenzylamino)ethoxy)cyclohexyl)oxy) but-2-enoate (1.7 g, 3.89 mmol) in Methanol (20 ML) at RT was added acetic acid (0.445 mL, 7.77 mmol) and 10% Pd/C (600 mg, 0.564 mmol). The resulting reaction mixture was stirred under an atmosphere of hydrogen at rt for 16 h. Methanol (50 mL) was added, the mixture was filtered through Celite®, the catalyst was washed with methanol (3×20 mL), and the combined filtrates were concentrated under reduced pressure to provide the title compound as a colorless oil (0.9 g, 3.44 mmol, 88% yield). LC-MS m/z 260.0 $(M+H)^+$.

Step 4

Methyl 4-(((1S,4r)-4-(2-((2S,3S)-1-methyl-5-oxo-2-(pyridin-3-yl)pyrrolidine-3-carboxamido)ethoxy) cyclohexyl)oxy)butanoate

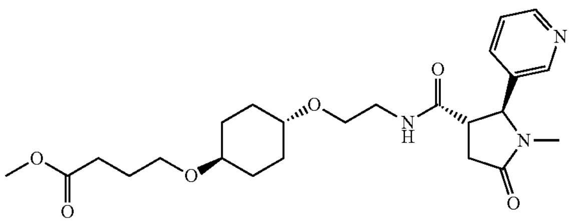

To a solution of (2S,3S)-1-methyl-5-oxo-2-(pyridin-3-yl) pyrrolidine-3-carboxylic acid (0.75 g, 3.41 mmol), in N,N-dimethylformamide (DMF) (10 mL) under an atmosphere of nitrogen were added DIPEA (1.190 mL, 6.81 mmol), HATU (1.942 g, 5.11 mmol) and methyl 4-(((1r,4r)-4-(2-aminoethoxy)cyclohexyl)oxy)butanoate (0.883 g, 3.41 mmol) and the mixture was stirred at rt for 16 h. Water (50 mL) was added the mixture was extracted with ethyl acetate (3×50 mL). The combined organic extracts were dried over $Na_2SO_4$, were filtered, and the filtrate was concentrated. Purification by Biotage® Isolera™ column chromatography (25 g SNAPS column) eluting with 5% methanol in dichloromethane (DCM) provided the title compound as a yellow oil (750 mg, 1.397 mmol, 41.0% yield). LC-MS m/z 462.0 $(M+H)^+$.

Step 5

4-(((1S,4r)-4-(2-((2S,3S)-1-methyl-5-oxo-2-(pyridin-3-yl)pyrrolidine-3-carboxamido) ethoxy)cyclohexyl) oxy)butanoic acid

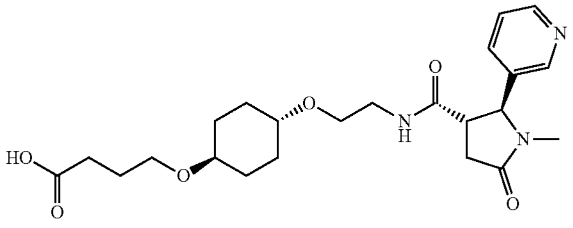

To a solution of the methyl 4-(((1S,4r)-4-(2-((2S,3S)-1-methyl-5-oxo-2-(pyridin-3-yl)pyrrolidine-3-carboxamido) ethoxy)cyclohexyl)oxy)butanoate (700 mg, 1.517 mmol) in methanol (5.0 mL) and water (5.00 mL) was added lithium hydroxide (54.5 mg, 2.275 mmol), and the mixture was stirred at rt for 2 h. Methanol was removed under reduced pressure, the pH was adjusted to 6 with 1.5 N HCl solution, and the mixture was concentrated under reduced pressure. Purification by preparative reverse phase HPLC (YMC-Triart C18 ExRS 5 μm column; 15 mL/min) eluting with a stepwise gradient of 10 to 50%, and 100% acetonitrile in water containing formic acid (0.1%) provided the title compound as a colorless oil (256 mg, 0.566 mmol, 37.3% yield). LC-MS m/z 448.1 $(M+H)^+$.

Step 6

(2S,3S)-N-(2-(((1R,4S)-4-(4-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-4-oxobutoxy)cyclohexyl)oxy)ethyl)-1-methyl-5-oxo-2-(pyridin-3-yl)pyrrolidine-3-carboxamide

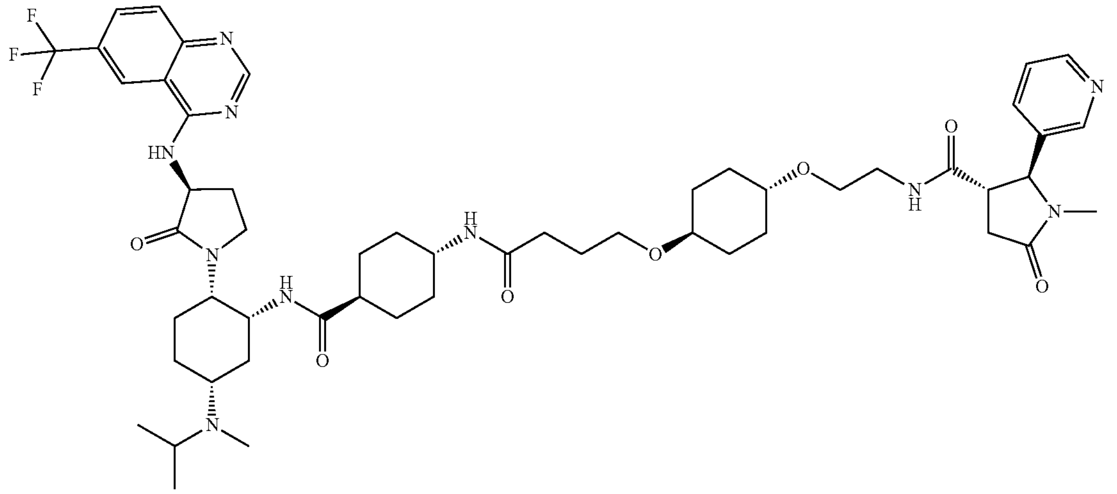 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCO[C@H]3CC[C@H](OCCNC(=O)[C@H]4CC(=O)N(C)[C@@H]4c4cccnc4)CC3)CC2)C1]

To a mixture of (1r,4R)-4-amino-N-((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)cyclohexane-1-carboxamide, 2hydrochloric acid salt (59.2 mg, 0.089 mmol) and 4-(((1S,4r)-4-(2-((2S,3S)-1-methyl-5-oxo-2-(pyridin-3-yl)pyrrolidine-3-carboxamido)ethoxy)cyclohexyl)oxy)butanoic acid (40 mg, 0.089 mmol) in dichloromethane (DCM) (1 mL) was added triethylamine (0.075 mL, 0.536 mmol) and HATU (40.8 mg, 0.107 mmol). The mixture was stirred at rt for 2 h and was concentrated. Purification by reverse-phase HPLC (XSelect™ CSH Prep C18 5 μm OBD column, 40 mL/min) eluting with a gradient of 30 to 85% acetonitrile containing ammonium hydroxide (1%) in water containing ammonium bicarbonate (10 mM) and ammonium hydroxide (0.075%) provided the title compound as a white solid (56.1 mg, 0.055 mmol, 61.6% yield). LC-MS m/z 1019.1 $(M)^+$. $^1$H NMR (400 MHz, METHANOL-$d_4$) δ ppm 1.03 (br d, J=6.4 Hz, 3H) 1.16 (br d, J=6.4 Hz, 3H) 1.20-1.34 (m, 7H) 1.58 (q, J=12.2 Hz, 2H) 1.67-1.89 (m, 6H) 1.88-2.04 (m, 10H) 2.05-2.18 (m, 2H) 2.18-2.26 (m, 3H) 2.28 (s, 3H) 2.31-2.39 (m, 1H) 2.49-2.59 (m, 1H) 2.66 (s, 3H) 2.68-2.76 (m, 2H) 2.77-2.93 (m, 1H) 3.02-3.10 (m, 1H) 3.22-3.31 (m, 2H) 3.34-3.55 (m, 9H) 3.56-3.69 (m, 2H) 4.03 (dt, J=12.7, 3.7 Hz, 1H) 4.66 (br d, J=2.4 Hz, 1H) 4.87-5.06 (m, 1H) 5.27 (t, J=8.1 Hz, 1H) 7.53 (dd, J=8.8, 4.9 Hz, 1H) 7.80 (dt, J=7.8, 2.0 Hz, 1H) 7.91 (d, J=8.8 Hz, 1H) 8.06 (dd, J=8.8, 2.0 Hz, 1H) 8.51 (d, J=2.0 Hz, 1H) 8.58 (dd, J=4.6, 1.7 Hz, 1H) 8.59 (s, 1H) 8.81 (s, 1H)

The following compounds were or could be prepared with procedures analogous to that described in Example 1:

| Ex. | Compound | LC-MS m/z | NMR |
|---|---|---|---|
| 2 | 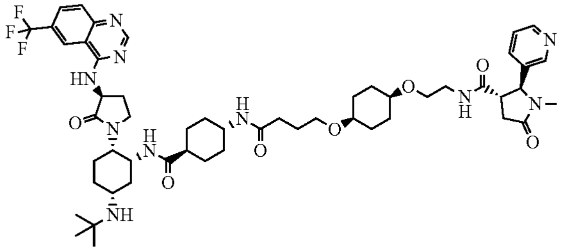 [SMILES: CN1C(=O)C[C@H](C(=O)NCCO[C@H]2CC[C@@H](OCCCC(=O)N[C@H]3CC[C@H](C(=O)N[C@@H]4C[C@H](NC(C)(C)C)CC[C@@H]4N4CC[C@H](Nc5ncnc6ccc(C(F)(F)F)cc56)C4=O)CC3)CC2)[C@H]1c1cccnc1] (2S,3S)-N-(2-(((1S,4R)-4-(4-(((1R,4R)-4-(((1R,2S,5R)-5-(tert-Butylamino)-2-((S)-2-oxo-3-((6-(trifluoromethyl) quinazolin-4-yl)amino) pyrrolidin-1-yl) cyclohexyl) carbamoyl)cyclohexyl) amino)-4-oxobutoxy) cyclohexyl)oxy)ethyl)-1-methyl-5-oxo-2-(pyridin-3-yl) pyrrolidine-3-carboxamide. | 510.6 (M/2 + H)+ | $^{1}$H NMR (400 MHz, METHANOL-$d_4$) δ ppm 1.19 (s, 9H) 1.21 - 1.36 (m, 3H) 1.44 - 2.09 (m, 24H) 2.16 (tt, J = 12, 3.1 Hz, 1H) 2.24 (t, J = 7.58 Hz, 3H) 2.27 - 2.34 (m, 1 H) 2.53 (dtd, J = 12, 8.1, 8.1, 4.2 Hz, 1H) 2.66 (s, 3H) 2.67 - 2.74 (m, 1H) 2.77 - 2.91 (m, 1H) 3.00 - 3.13 (m, 1H) 3.22 - 3.31 (m, 2H) 3.35 - 3.54 (m, 7 H) 3.57 - 3.71 (m, 2H) 3.99 (dt, J = 12., 3.8 Hz, 1 H) 4.64 (br d, J = 3.4 Hz, 1 H) 4.84 - 4.91 (m, 1H) 5.28 (t, J = 7.8 Hz, 1H) 7.50 - 7.55 (m, 1H) 7.80 (dt, J = 7.8, 2.0 Hz, 1H) 7.91 (d, J = 8.8 Hz, 1H) 8.06 (dd, J = 8.8, 2.0 Hz, 1 H) 8.51 (d, J = 1.5 Hz, 1H) 8.57 (dd, J = 4.9, 1.47 Hz, 1H) 8.59 (s, 1H) 8.83 (s, 1H). |
| 3 | 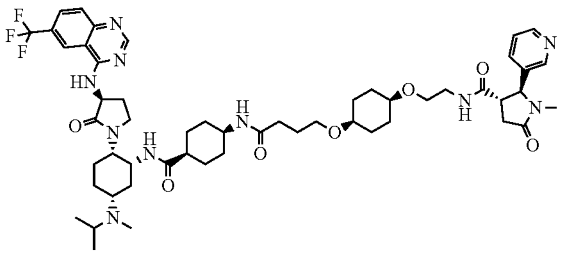 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCO[C@H]3CC[C@@H](OCCNC(=O)[C@H]4CC(=O)N(C)[C@@H]4c4cccnc4)CC3)CC2)C1] (2S,3S)-N-(2-(((1S,4R)-4-(4-(((1S,4S)-4-(((1R,2S,5R)-5-(Isopropyl (methyl)amino)-2-((S)-2-oxo-3-((6-(trifluoromethyl) quinazolin-4-yl)amino) pyrrolidin-1-yl)cyclohexyl) carbamoyl) cyclohexyl) amino)-4-oxobutoxy) cyclohexyl)oxy)ethyl)-1-methyl-5-oxo-2-(pyridin-3-yl)pyrrolidine-3-carboxamide. | 1019.6 (M + H)+ | $^{1}$H NMR (400 MHz, METHANOL-$d_4$) δ ppm 1.01 (d, J = 6.4 Hz, 3H) 1.16 (d, J = 6.4 Hz, 3H) 1.40 - 2.02 (m, 24H) 2.10 - 2.40 (m, 9H) 2.53 - 2.63 (m, 1H) 2.66 (s, 3 H) 2.68 - 2.75 (m, 2H) 2.80 - 2.89 (m, 1H) 3.00 - 3.12 (m, 1H) 3.23 - 3.31 (m, 2H) 3.36 - 3.58 (m, 8H) 3.60 - 3.70 (m, 2H) 3.85 - 3.93 (m, 1H) 4.03 (dt, J = 12, 3.85 Hz, 1H) 4.61 (br d, J = 2.9 Hz, 1H) 5.30 (t, J = 8.8 Hz, 1H) 7.52 (dd, J = 8.8, 4.9 Hz, 1H) 7.79 (dt, J = 7.8, 2.0 Hz, 1H) 7.91 (d, J = 8.8 Hz, 1H) 8.06 (dd, J = 8.8, 2.0 Hz, 1H) 8.51 (d, J = 2.0 Hz, 1H) 8.57 (dd, J = 4.9, 1.5 Hz, 1H) 8.59 (s, 1H) 8.73 (s, 1H). |
| 4 | 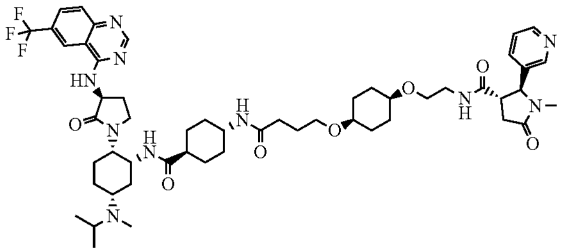 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCO[C@H]3CC[C@@H](OCCNC(=O)[C@H]4CC(=O)N(C)[C@@H]4c4cccnc4)CC3)CC2)C1] (2S,3S)-N-(2-(((1S,4R)-4-(4-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-4-oxobutoxy)cyclohexyl) oxy)ethyl)-1-methyl-5-oxo-2-(pyridin-3-yl) pyrrolidine-3-carboxamide | 1019.6 (M + H)+ | $^{1}$H NMR (400 MHz, METHANOL-$d_4$) δ ppm 1.02 (br d, J = 6.4 Hz, 3H) 1.16 (br d, J = 6.4 Hz, 3H) 1.19 - 1.33 (m, 2H) 1.45 - 1.87 (m, 16H) 1.88 - 2.05 (m, 5H) 2.07 - 2.17 (m, 2H) 2.18 - 2.26 (m, 3 H) 2.28 (s, 3H) 2.34 (br d, J = 14 Hz, 1H) 2.48 - 2.59 (m, 1H) 2.66 (s, 3H) 2.67 - 2.76 (m, 2H) 2.78 - 2.89 (m, 1H) 3.07 (ddd, J = 9.4, 8.2, 6.9 Hz, 1H) 3.26 - 3.31 (m, 1H) 3.35 - 3.54 (m, 8H) 3.57 - 3.67 (m, 2H) 4.02 (dt, J = 12, 3.6 Hz, 1H) 4.65 (br d, J = 3.0 Hz, 1H) 4.80 - 4.88 (m, 1H) 5.28 (t, J = 8.1 Hz, 1H) 7.53 (dd, J = 7.8, 4.9 Hz, 1H) 7.80 (dt, J = 8.3, 2.0 Hz, 1H) 7.91 (d, |

-continued

| Ex. | Compound | LC-MS m/z | NMR |
|---|---|---|---|
| | | | J = 8.8 Hz, 1H) 8.07 (dd, J = 9.3, 2.0 Hz, 1H) 8.52 (d, J = 2.0 Hz, 1H) 8.58 (dd, J = 4.9, 2.0 Hz, 1H) 8.59 (s, 1H) 8.81 (s, 1H). |
| 5 | 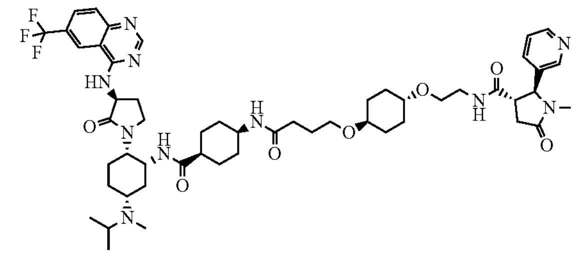 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCO[C@H]3CC[C@H](OCCNC(=O)[C@H]4CC(=O)N(C)[C@@H]4c4cccnc4)CC3)CC2)C1] (2S,3S)-N-(2-(((1R,4S)-4-(4-(((1S,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-4-oxobutoxy)cyclohexyl) oxy)ethyl)-1-methyl-5-oxo-2-(pyridin-3-yl) pyrrolidine-3-carboxamide. | 1019.1 $(M + H)^+$ | $^1H$ NMR (400 MHz, METHANOL-$d_4$) δ ppm 1.01 (d, J = 6.4 Hz, 3H) 1.16 (d, J = 6.4 Hz, 3H) 1.19 - 1.32 (m, 4H) 1.55 - 1.96 (m, 18H) 2.12 - 2.39 (m, 8H) 2.52 - 2.64 (m, 2H) 2.66 (s, 3H) 2.67 - 2.76 (m, 2H) 2.79 - 2.88 (m, 1H) 3.03 - 3.11 (m, 1H) 3.18 - 3.31 (m, 4H) 3.37 - 3.59 (m, 8H) 3.60 - 3.70 (m, 1H) 3.85 - 3.94 (m, 1H) 4.03 (dt, J = 12, 3.8 Hz, 1H) 4.61 (br d, J = 2.9 Hz, 1 H) 5.25 - 5.38 (m, 2H) 7.53 (dd, J = 7.6, 5.14 Hz, 1H) 7.80 (dt, J = 8.3, 2.0 Hz, 1H) 7.91 (d, J = 8.3 Hz, 1H) 8.06 (dd, J = 8.8, 2.0 Hz, 2H) 8.52 (d, J = 2.0 Hz, 1H) 8.56 - 8.60 (m, 2H) 8.73 (s, 1H). |
| 6 | 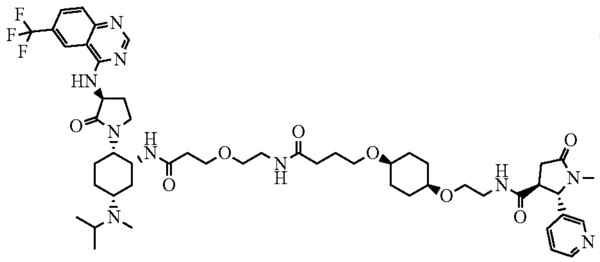 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)CCCO[C@H]2CC[C@@H](OCCNC(=O)[C@H]3CC(=O)N(C)[C@@H]3c3cccnc3)CC2)C1] (2S,3S)-N-(2-(((1s,4R)-4-(4-((2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethyl) amino)-4-oxobutoxy)cyclohexyl)oxy)ethyl)-1-methyl-5-oxo-2-(pyridin-3-yl)pyrrolidine-3-carboxamide. | 1010.5 $(M + H)^+$ | $^1H$ NMR (400 MHz, METHANOL-$d_4$) δ ppm 1.04 (br d, J = 6.4 Hz, 3 H) 1.14 (br d, J = 6.4 Hz, 3H) 1.42 - 1.86 (m, 13 H) 1.89 - 2.03 (m, 1H) 2.05 - 2.17 (m, 1H) 2.18 - 2.38 (m, 8H) 2.46 (t, J = 5.9 Hz, 2H) 2.54 (tt, J = 12, 3.7 Hz, 1H) 2.66 (s, 3H) 2.67 - 2.77 (m, 2 H) 2.78 - 2.89 (m, 1H) 2.98 - 3.16 (m, 1H) 3.26 - 3.31 (m, 4H) 3.36 - 3.53 (m, 10H) 3.54 - 3.63 (m, 1H) 3.64 - 3.74 (m, 2H) 3.75 - 3.85 (m, 1H) 4.06 (dt, J = 12, 3.9 Hz, 1H) 4.63 (br d, J = 3.4 Hz, 1H) 4.83 (d, J = 6.9 Hz, 1H) 5.31 (t, J = 8.1 Hz, 1H) 7.50 - 7.56 (m, 1H) 7.80 (dt, J = 7.8, 2.0 Hz, 1H) 7.91 (d, J = 8.8 Hz, 1H) 8.07 (dd, J = 8.8, 2.0 Hz, 1H) 8.52 (d, J = 1.5 Hz, 1H) 8.57 (dd, J = 4.9, 1.47 Hz, 1H) 8.59 (s, 1H) 8.81 (s, 1H). |

-continued

| Ex. | Compound | LC-MS m/z | NMR |
|---|---|---|---|
| 7 | 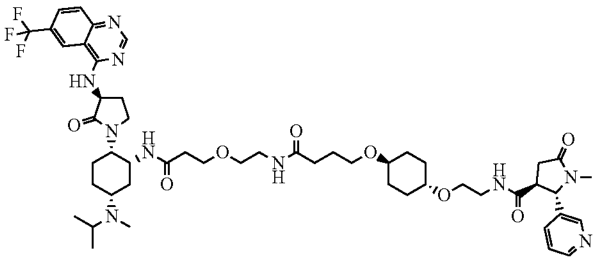 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)CCCO[C@H]2CC[C@H](OCCNC(=O)[C@H]3CC(=O)N(C)[C@@H]3c3cccnc3)CC2)C1] (2S,3S)-N-(2-(((1r,4S)-4-(4-((2-(3-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)amino)-3-oxopropoxy) ethyl)amino)-4-oxobutoxy)cyclohexyl)oxy)ethyl)-1-methyl-5-oxo-2-(pyridin-3-yl)pyrrolidine-3-carboxamide. | 1010.5 $(M + H)^+$ | $^1$H NMR (400 MHz, METHANOL-$d_4$) δ ppm 1.04 (br d, J = 6.4 Hz, 3H) 1.14 (br d, J = 6.4 Hz, 3H) 1.18 - 1.33 (m, 4H) 1.65 - 1.85 (m, 5H) 1.86 - 2.01 (m, 5H) 2.05 - 2.17 (m, 1 H) 2.18 - 2.28 (m, 6H) 2.28 - 2.38 (m, 1H) 2.47 (t, J = 5.6 Hz, 2H) 2.50 - 2.61 (m, 1H) 2.66 (s, 3H) 2.68 - 2.78 (m, 2H) 2.78 - 2.89 (m, 1H) 3.07 (ddd, J = 9.4, 8.0, 6.6 Hz, 1H) 3.20 - 3.31 (m, 6H) 3.34 - 3.52 (m, 10H) 3.55 - 3.63 (m, 1H) 3.64 - 3.74 (m, 2H) 3.79 (dt, J = 9.6, 6.2 Hz, 1H) 4.06 (dt, J = 12, 3.6 Hz, 1H) 4.63 (m, J = 3.4 Hz, 1H) 4.79 - 4.90 (m, 1H) 5.31 (t, J = 8.3 Hz, 1H) 7.54 (dd, J = 7.3, 4.9 Hz, 1H) 7.81 (dt, J = 8.3, 2.0 Hz, 1H) 7.91 (d, J = 8.8 Hz, 1H) 8.07 (dd, J = 8.8, 2.0 Hz, 1 H) 8.52 (d, J = 1.5 Hz, 1H) 8.57 - 8.61 (m, 2H) 8.81 (s, 1H). |
| 8 | 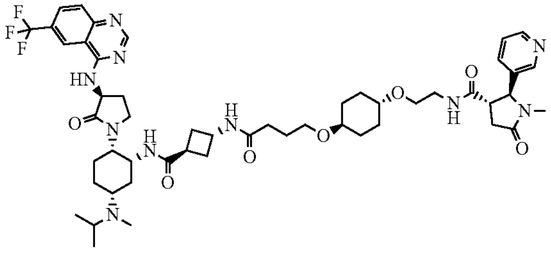 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCCO[C@H]3CC[C@H](OCCNC(=O)[C@H]4CC(=O)N(C)[C@@H]4c4cccnc4)CC3)C2)C1] (2S,3S)-N-(2-(((1R,4S)-4-(4-(((1R,3R)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclobutyl)amino)-4-oxobutoxy)cyclohexyl)oxy) ethyl)-1-methyl-5-oxo-2-(pyridin-3-yl)pyrrolidine-3-carboxamide. | 991.0 $(M + H)^+$ | $^1$H NMR (400 MHz, DMSO-d6) δ ppm 0.91 (d, J = 6.9 Hz, 3H) 1.00 (d, J = 6.4 Hz, 3H) 1.04 - 1.24 (m, 4H) 1.52 - 1.70 (m, 5H) 1.82 (br d, J = 7.8 Hz, 4H) 1.86 - 2.00 (m, 1H) 2.00 - 2.18 (m, 11 H) 2.28 - 2.47 (m, 5H) 2.53 - 2.61 (m, 1H) 2.65 - 2.74 (m, 1H) 2.86 (tt, J = 9.1, 4.6 Hz, 1H) 2.92 - 3.00 (m, 1H) 3.03 - 3.32 (m, 8H) 3.35 - 3.44 (m, 2H) 3.48 - 3.62 (m, 1H) 3.83 - 4.03 (m, 1H) 4.21 (sxt, J = 7.3 Hz, 1H) 4.43 (br d, J = 3.9 Hz, 1H) 4.66 (d, J = 6.4 Hz, 1H) 5.04 (q, J = 8.2 Hz, 1H) 7.44 (dd, J = 7.8, 4.9 Hz, 1H) 7.68 (dt, J = 8.3, 2.0 Hz, 1H) 7.89 (d, J = 8.8 Hz, 1H) 7.98 - 8.13 (m, 3H) 8.47 (d, J = 2.0 Hz, 1 H) 8.56 (dd, J = 4.7, 1.7 Hz, 1H) 8.58 (s, 1H) 8.72 (d, J = 8.3 Hz, 1H) 8.74 - 8.80 (m, 1H) 8.92 (s, 1H). |

-continued

| Ex. | Compound | LC-MS m/z | NMR |
|---|---|---|---|
| 9 | 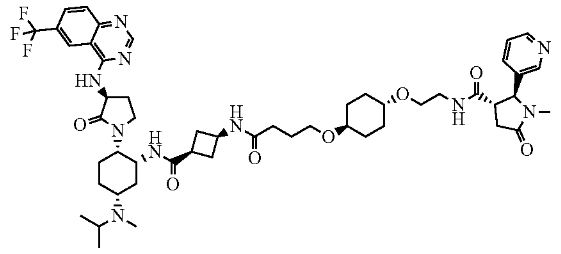 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCCO[C@H]3CC[C@H](OCCNC(=O)[C@H]4CC(=O)N(C)[C@@H]4c4cccnc4)CC3)C2)C1] (2S,3S)-N-(2-(((1S,4S)-4-(4-(((1S,3S)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclobutyl)amino)-4-oxobutoxy)cyclohexyl) oxy)ethyl)-1-methyl-5-oxo-2-(pyridin-3-yl)pyrrolidine-3-carboxamide. | 991.0 $(M + H)^+$ | $^1H$ NMR (400 MHz, DMSO-d6) δ ppm 0.91 (d, J = 6.4 Hz, 3H) 1.03 (d, J = 6.4 Hz, 3H) 1.07 - 1.20 (m, 4H) 1.55 - 1.67 (m, 4H) 1.73 - 1.85 (m, 4H) 1.87 - 2.10 (m, 7H) 2.13 (s, 3H) 2.25 - 2.46 (m, 4H) 2.49 (s, 3H) 2.51 (dt, J = 3.8, 1.8 Hz, 4 H) 2.60 - 2.74 (m, 2H) 2.84 - 3.00 (m, 1H) 2.93 - 2.93 (m, 1H) 3.04 - 3.23 (m, 4H) 3.27 (t, J = 6.4 Hz, 3H) 3.35 - 3.45 (m, 1H) 3.48 - 3.58 (m, 1H) 3.91 (dt, J = 11, 3.6 Hz, 1H) 4.04 (dq, J = 16, 8.3 Hz, 1H) 4.42 (br d, J = 3.9 Hz, 1H) 4.66 (d, J = 5.9 Hz, 1H) 5.04 (q, J = 8.2 Hz, 1H) 7.44 (dd, J = 7.8, 4.9 Hz, 1H) 7.68 (dt, J = 7.8, 2.0 Hz, 1H) 7.87 - 7.94 (m, 2H) 8.01 - 8.09 (m, 2H) 8.47 (d, J = 2.5 Hz, 1H) 8.56 (dd, J = 4.7, 1.7 Hz, 1H) 8.59 (s, 1H) 8.72 (br d, J = 7.8 Hz, 2H) 8.93 (s, 1H). |
| 10 | 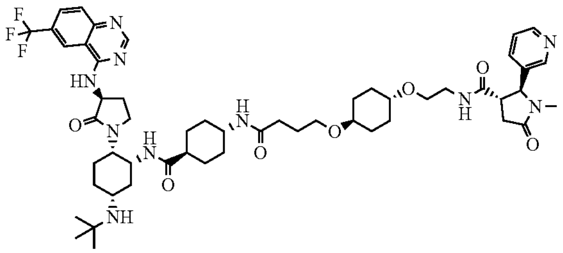 [SMILES: CN1C(=O)C[C@H](C(=O)NCCO[C@H]2CC[C@H](OCCCC(=O)N[C@H]3CC[C@H](C(=O)N[C@@H]4C[C@H](NC(C)(C)C)CC[C@@H]4N4CC[C@H](Nc5ncnc6ccc(C(F)(F)F)cc56)C4=O)CC3)CC2)[C@H]1c1cccnc1] (2S,3S)-N-(2-(((1R,4S)-4-(4-(((1R,4R)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl) carbamoyl) cyclohexyl)amino)-4-oxobutoxy)cyclohexyl)oxy)ethyl)-1-methyl-5-oxo-2-(pyridin-3-yl)pyrrolidine-3-carboxamide. | 1019.9 $(M + H)^+$ | $^1H$ NMR (400 MHz, METHANOL-$d_4$) δ ppm 1.19 (s, 9H), 1.22-1.35 (m, 6H), 1.54-1.69 (m, 2H), 1.70-2.07 (m, 17H), 2.10-2.33 (m, 4H), 2.47-2.59 (m, 1H), 2.63-2.74 (m, 4H), 2.78-2.89 (m, 1H), 3.06 (dd, J = 1.22, 8.07 Hz, 1H), 3.20-3.31 (m, 4H), 3.35-3.55 (m, 6H), 3.58-3.69 (m, 2H), 3.95-4.03 (m, 1H), 4.64 (d, J = 2.93 Hz, 1H), 4.84 (d, J = 6.85 Hz, 1H), 5.29 (t, J = 8.00 Hz, 1H), 7.53 (dd, J = 4.89, 7.82 Hz, 1H), 7.77-7.83 (m, 1H), 7.91 (d, J = 8.80 Hz, 1H), 8.06 (dd, J = 1.96, 8.80 Hz, 1H), 8.52 (d, J = 1.96 Hz, 1H), 8.56-8.61 (m, 2H), 8.83 (s, 1H). |
| 11 | 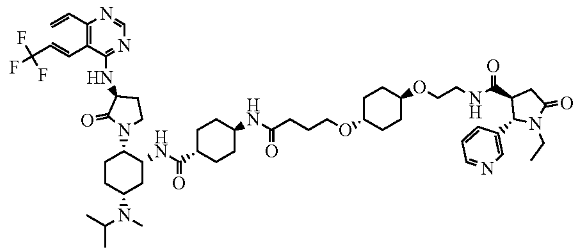 [SMILES: C=Cc1ncnc(N[C@H]2CCN([C@H]3CC[C@@H](N(C)C(C)C)C[C@H]3NC(=O)[C@H]3CC[C@H](NC(=O)CCCO[C@H]4CC[C@H](OCCNC(=O)[C@H]5CC(=O)N(CC)[C@@H]5c5cccnc5)CC4)CC3)C2=O)c1/C=C/C(F)(F)F] (2S,3S)-1-ethyl-N-(2-(((1,4-trans)-4-(4-(((1,4-trans)-4-(((1R,2S,5R)-5-(isopropyl(methyl) amino)-2-((S)-2-oxo-3-((6-(trifluoromethyl) quinazolin-4-yl)amino) pyrrolidin-1-yl)cyclohexyl)carbamoyl)cyclohexyl)amino)-4-oxobutoxy)cyclohexyl)oxy)ethyl)-5-oxo-2-(pyridin-3-yl)pyrrolidine-3-carboxamide | 1033.7 $(M + H)^+$ | $^1H$ NMR (400 MHz, DMSO-d6) δ ppm 0.85 (t, J = 7.09 Hz, 2H) 0.89 - 1.07 (m, 3H) 1.07 - 1.21 (m, 3H) 1.22 - 1.32 (m, 1H) 1.31 - 1.50 (m, 1H) 1.52 - 1.69 (m, 2H) 1.69 - 1.91 (m, 4H) 1.92 - 2.10 (m, 3H) 2.14 (s, 2 H) 2.27 - 2.36 (m, 1H) 2.36 - 2.48 (m, 1H) 2.59 (br s, 1H) 2.64 - 2.74 (m, 1H) 2.90 - 3.03 (m, 1H) 3.04 - 3.25 (m, 2H) 3.38 - 3.57 (m, 2H) 3.80 - 3.93 (m, 1H) 4.49 (br d, J = 2.45 Hz, 1H) 4.74 (d, J = 5.87 Hz, 1H) 4.92 - 5.02 (m, 1H) 7.43 (dd, J = 7.83, 4.40 Hz, 1H) 7.61 (br d, J = 7.82 Hz, 1 |

-continued

| Ex. | Compound | LC-MS m/z | NMR |
| --- | --- | --- | --- |
| | | | H) 7.72 (dt, J = 7.82, 1.96 Hz, 1H) 7.90 (d, J = 8.31 Hz, 1H) 8.01 (t, J = 5.38 Hz, 1H) 8.07 (dd, J = 8.80, 1.47 Hz, 1H) 8.51 (d, J = 1.96 Hz, 1H) 8.55 (dd, J = 4.65, 1.71 Hz, 1H) 8.59 (s, 1H) 8.61 (br d, J = 8.31 Hz, 1 H) 8.95 (br s, 1H) |
| 12 | 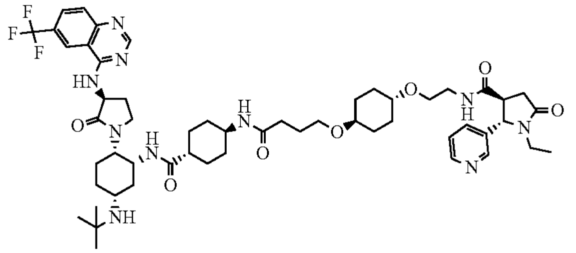 [SMILES: CCN1C(=O)C[C@H](C(=O)NCCO[C@H]2CC[C@H](OCCCC(=O)N[C@H]3CC[C@H](C(=O)N[C@@H]4C[C@H](NC(C)(C)C)CC[C@@H]4N4CC[C@H](Nc5ncnc6ccc(C(F)(F)F)cc56)C4=O)CC3)CC2)[C@H]1c1cccnc1] (2S,3S)-N-(2-(((trans)-4-(4-(((trans)-4-(((1R,2S,5R)-5-(tert-butylamino)-2-((S)-2-oxo-3-((6-(trifluoromethyl)quinazolin-4-yl)amino) pyrrolidin-1-yl)cyclohexyl)carbamoyl)cyclohexyl) amino)-4-oxobutoxy)cyclohexyl)oxy)ethyl)-1-ethyl-5-oxo-2-(pyridin-3-yl)pyrrolidine-3-carboxamide | 1033.7 (M + H)+ | $^1$H NMR (400 MHz, DMSO-d6) δ ppm 0.85 (t, J = 7.09 Hz, 4H) 1.03 - 1.27 (m, 18H) 1.34 - 1.51 (m, 2H) 1.63 (dt, J = 13.94, 6.72 Hz, 5H) 1.69 - 1.94 (m, 14H) 1.98 (br s, 1H) 2.00 - 2.09 (m, 3H) 2.10 - 2.36 (m, 2H) 2.40 (dd, J = 16.63, 7.83 Hz, 1H) 2.68 (dd, J = 16.63, 9.29 Hz, 1H) 2.93 - 3.01 (m, 1H) 3.04 - 3.14 (m, 2H) 3.14 - 3.26 (m, 4H) 3.27 - 3.32 (m, 3H) 3.38 - 3.57 (m, 4H) 3.75 - 3.91 (m, 1H) 4.10 (q, J = 5.22 Hz, 1H) 4.50 (br s, 1H) 4.74 (d, J = 5.87 Hz, 1H) 4.98 (br d, J = 4.89 Hz, 1 H) 7.43 (dd, J = 7.83, 4.89 Hz, 1H) 7.62 (br d, J = 7.34 Hz, 1H) 7.72 (dt, J = 7.82, 1.96 Hz, 1H) 7.89 (d, J = 8.80 Hz, 1H) 8.01 (t, J = 5.38 Hz, 1H) 8.07 (dd, J = 8.80, 1.96 Hz, 1H) 8.51 (d, J = 1.96 Hz, 1H) 8.55 (dd, J = 4.89, 1.47 Hz, 1H) 8.60 (s, 1H) 8.64 - 8.79 (m, 1H) 8.97 (br s, 1H) 9.98 (br s, 1H) |
| 13 | 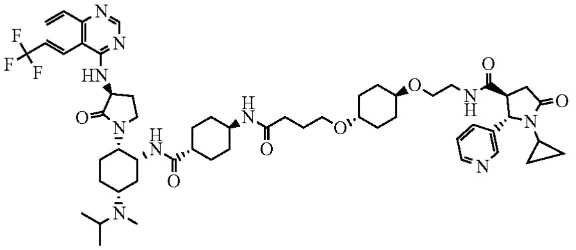 [SMILES: C=Cc1ncnc(N[C@H]2CCN([C@H]3CC[C@@H](N(C)C(C)C)C[C@H]3NC(=O)[C@H]3CC[C@H](NC(=O)CCCO[C@H]4CC[C@H](OCCNC(=O)[C@H]5CC(=O)N(C6CC6)[C@@H]5c5cccnc5)CC4)CC3)C2=O)c1/C=C/C(F)(F)F] (2S,3S)-1-cyclopropyl-N-(2-(((1R,4S)-4-(4-(((1R,4R)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-4-oxobutoxy)cyclohexyl)oxy)ethyl)-5-oxo-2-(pyridin-3-yl)pyrrolidine-3-carboxamide | 1045.9 (M + H)+ | $^1$H NMR (400 MHz, METHANOL-$d_4$) δ 8.81 (d, J = 1.0 Hz, 1H), 8.59 (s, 1H), 8.56 (dt, J = 4.9, 2.4 Hz, 2H), 8.07 (dd, J = 8.8, 2.0 Hz, 1H), 7.91 (d, J = 8.8 Hz, 1H), 7.86 (dt, J = 7.8, 2.0 Hz, 1H), 7.56 - 7.51 (m, 1H), 5.28 (t, J = 8.1 Hz, 1H), 4.86 - 4.83 (m, 1H), 4.68 - 4.63 (m, 1H), 4.06 - 3.99 (m, 1H), 3.67 - 3.58 (m, 2H), 3.55 - 3.42 (m, 7H), 3.31 - 3.23 (m, 4H), 3.10 - 3.02 (m, 1H), 2.86 - 2.77 (m, 1H), 2.76 - 2.71 (m, 1H), 2.69 - 2.61 (m, 1H), 2.58 - 2.50 (m, 1H), 2.28 (s, 3H), 2.39 - 2.18 (m, 4H), 2.18 - 2.06 (m, 2H), 2.03 - 1.88 (m, 10H), 1.86 - 1.51 (m, 8H), 1.3 - 1.19 (m, 4H), 1.16 (br d, J = 6.8 Hz, 3H), 1.05 - 1.00 (m, 3H), 0.87-0.77 (m, 2H), 0.68-0.60 (m, 1H), 0.51-0.42 (m, 1H) |

-continued

| Ex. | Compound | LC-MS m/z | NMR |
|---|---|---|---|
| 14 | 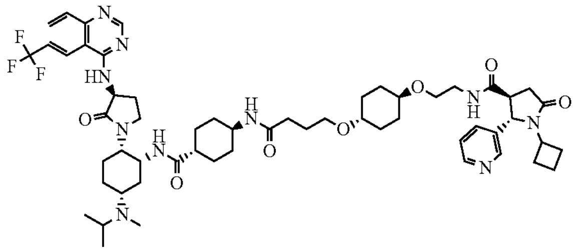 [SMILES: C=Cc1ncnc(N[C@H]2CCN([C@H]3CC[C@@H](N(C)C(C)C)C[C@H]3NC(=O)[C@H]3CC[C@H](NC(=O)CCCO[C@H]4CC[C@H](OCCNC(=O)[C@H]5CC(=O)N(C6CCC6)[C@@H]5c5cccnc5)CC4)CC3)C2=O)c1/C=C/C(F)(F)F] (2S,3S)-1-cyclobutyl-N-(2-(((trans)-4-(4-(((trans)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-4-oxobutoxy)cyclohexyl) oxy)ethyl)-5-oxo-2-(pyridin-3-yl)pyrrolidine-3-carboxamide | 1060.0 $(M + H)^+$ | $^1$H NMR (400 MHz, DMSO-d6) δ ppm 0.92 (br d, J = 5.87 Hz, 1H) 0.97 - 1.21 (m, 5H) 1.24 - 1.29 (m, 1H) 1.31 - 1.52 (m, 2H) 1.54 - 1.69 (m, 3H) 1.75 - 1.89 (m, 4H) 1.89 - 2.00 (m, 2H) 2.01 - 2.07 (m, 2H) 2.14 (s, 2H) 2.23 - 2.38 (m, 2 H) 2.55 - 2.63 (m, 1H) 2.65 - 2.75 (m, 1H) 2.84 (dt, J = 9.05, 4.77 Hz, 1H) 3.10 - 3.27 (m, 2H) 3.29 - 3.32 (m, 1H) 3.35 - 3.40 (m, 2H) 3.46 - 3.58 (m, 1H) 3.87 (br d, J = 10.76 Hz, 1H) 4.00 - 4.12 (m, 1H) 4.44 - 4.56 (m, 1H) 4.89 (d, J = 3.91 Hz, 1H) 4.94 - 5.04 (m, 1H) 7.41 (dd, J = 7.82, 4.89 Hz, 1H) 7.61 (br d, J = 7.82 Hz, 1H) 7.64 - 7.71 (m, 1H) 7.90 (d, J = 8.31 Hz, 1H) 7.99 - 8.12 (m, 1H) 8.48 - 8.56 (m, 1H) 8.57 - 8.68 (m, 1H) 8.95 (br s, 1H) |
| 15 | 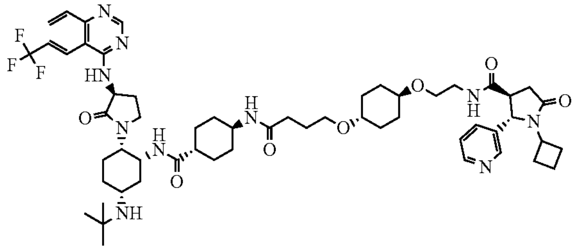 [SMILES: C=Cc1ncnc(N[C@H]2CCN([C@H]3CC[C@@H](NC(C)(C)C)C[C@H]3NC(=O)[C@H]3CC[C@H](NC(=O)CCCO[C@H]4CC[C@H](OCCNC(=O)[C@H]5CC(=O)N(C6CCC6)[C@@H]5c5cccnc5)CC4)CC3)C2=O)c1/C=C/C(F)(F)F] (2S,3S)-N-(2-(((1R,4S)-4-(4-(((1R,4R)-4-(((1R,2S,5R)-5-(tert-butylamino)-2-((S)-2-oxo-3-((6-(trifluoromethyl)quinazolin-4-yl)amino)pyrrolidin-1-yl)cyclohexyl)carbamoyl) cyclohexyl)amino)-4-oxobutoxy)cyclohexyl)oxy) ethyl)-1-cyclobutyl-5-oxo-2-(pyridin-3-yl)pyrrolidine-3-carboxamide | 1059.7 $(M + H)^+$ | $^1$H NMR (400 MHz, DMSO-d6) δ ppm 1.10 (s, 8H) 1.14 - 1.21 (m, 4 H) 1.24 (s, 1H) 1.36 - 1.53 (m, 4H) 1.59 - 1.70 (m, 5H) 1.72 - 2.00 (m, 12H) 2.00 - 2.11 (m, 3 H) 2.13 - 2.24 (m, 1H) 2.25 - 2.37 (m, 3H) 2.51 (dt, J = 3.79, 1.77 Hz, 11 H) 2.64 - 2.75 (m, 1H) 2.84 (dt, J = 9.05, 4.77 Hz, 1H) 3.05 - 3.27 (m, 5H) 3.29 - 3.32 (m, 2H) 3.35 - 3.40 (m, 2H) 3.44 (td, J = 7.70, 4.16 Hz, 1H) 3.48 - 3.60 (m, 1H) 3.83 (br d, J = 12.72 Hz, 1H) 3.97 - 4.16 (m, 1H) 4.50 (br d, J = 1.96 Hz, 1H) 4.90 (d, J = 3.91 Hz, 1H) 4.98 (td, J = 7.95, 5.14 Hz, 1H) 7.42 (dd, J = 7.82, 4.89 Hz, 1H) 7.58 - 7.71 (m, 2H) 7.91 (d, J = 8.31 Hz, 1H) 7.98 - 8.16 (m, 2H) 8.47 - 8.56 (m, 2H) 8.61 (s, 1 H) 8.69 (br d, J = 8.31 Hz, 1H) 8.98 (s, 1H) 9.82 - 10.10 (m, 1H) |

-continued

| Ex. | Compound | LC-MS m/z | NMR |
|---|---|---|---|
| 15a | 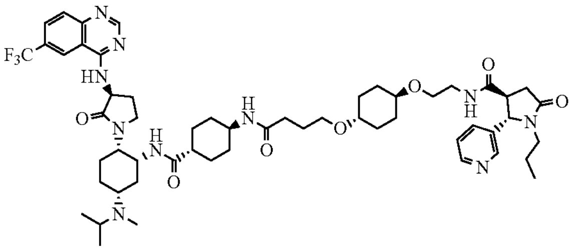 [SMILES: CCCN1C(=O)C[C@H](C(=O)NCCO[C@H]2CC[C@H](OCCCC(=O)N[C@H]3CC[C@H](C(=O)N[C@@H]4C[C@H](N(C)C(C)C)CC[C@@H]4N4CC[C@H](Nc5ncnc6ccc(C(F)(F)F)cc56)C4=O)CC3)CC2)[C@H]1c1cccnc1] (2S,3S)-N-(2-(((trans)-4-(4-(((trans)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-4-oxobutoxy)cyclohexyl)oxy)ethyl)-5-oxo-1-propyl-2-(pyridin-3-yl)pyrrolidine-3-carboxamide | 1047.7 $(M + H)^+$ | $^1H$ NMR (400 MHz, DMSO-$d_6$) δ ppm 8.96 (br s, 1H) 8.58 - 8.68 (m, 1H) 8.56 (dd, J = 4.65, 1.71 Hz, 1H) 8.51 (d, J = 1.96 Hz, 1H) 7.99 - 8.13 (m, 1H) 7.90 (d, J = 8.80 Hz, 1H) 7.71 (dt, J = 7.82, 1.96 Hz, 1H) 7.62 (br d, J = 7.34 Hz, 1H) 7.43 (dd, J = 7.82, 4.40 Hz, 1H) 4.98 (br d, J = 5.87 Hz, 1H) 4.72 (d, J = 5.38 Hz, 1H) 4.50 (br s, 1H) 3.87 (br d, J = 12.23 Hz, 1H) 3.53 (br d, J = 4.89 Hz, 1H) 3.27 - 3.48 (m, 15H) 3.04 - 3.26 (m, 2 H) 2.93 - 3.03 (m, 1H) 2.71 (dd, J = 16.63, 9.78 Hz, 1H) 2.60 (br s, 1H) 2.48 - 2.56 (m, 7H) 2.37 - 2.48 (m, 1 H) 2.15 (s, 2H) 2.04 (br t, J = 7.34 Hz, 3H) 1.83 (br d, J = 6.36 Hz, 4H) 1.56 - 1.71 (m, 3H) 0.86 - 1.48 (m, 11 H) 0.73 (t, J = 7.34 Hz, 2H) |

Example 16

(2S,3S)-N-(3-((2-(2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-3-oxopropoxy)ethoxy)ethyl)amino)-3-oxopropyl)-1-methyl-5-oxo-2-(pyridin-3-yl)pyrrolidine-3-carboxamide

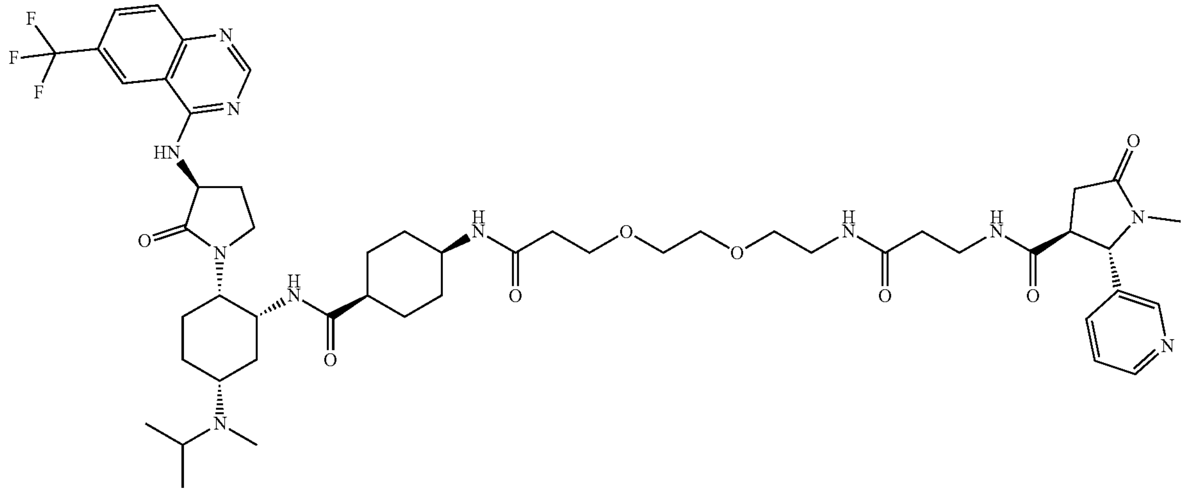

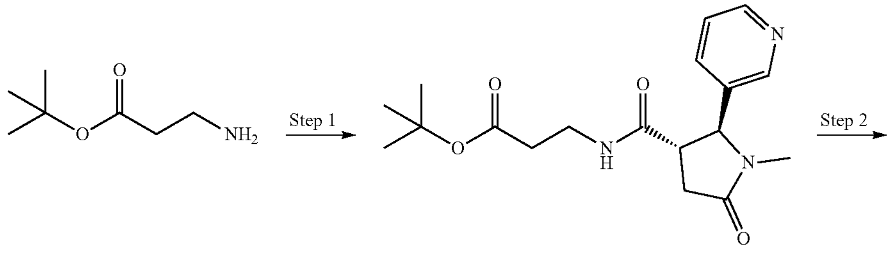

-continued

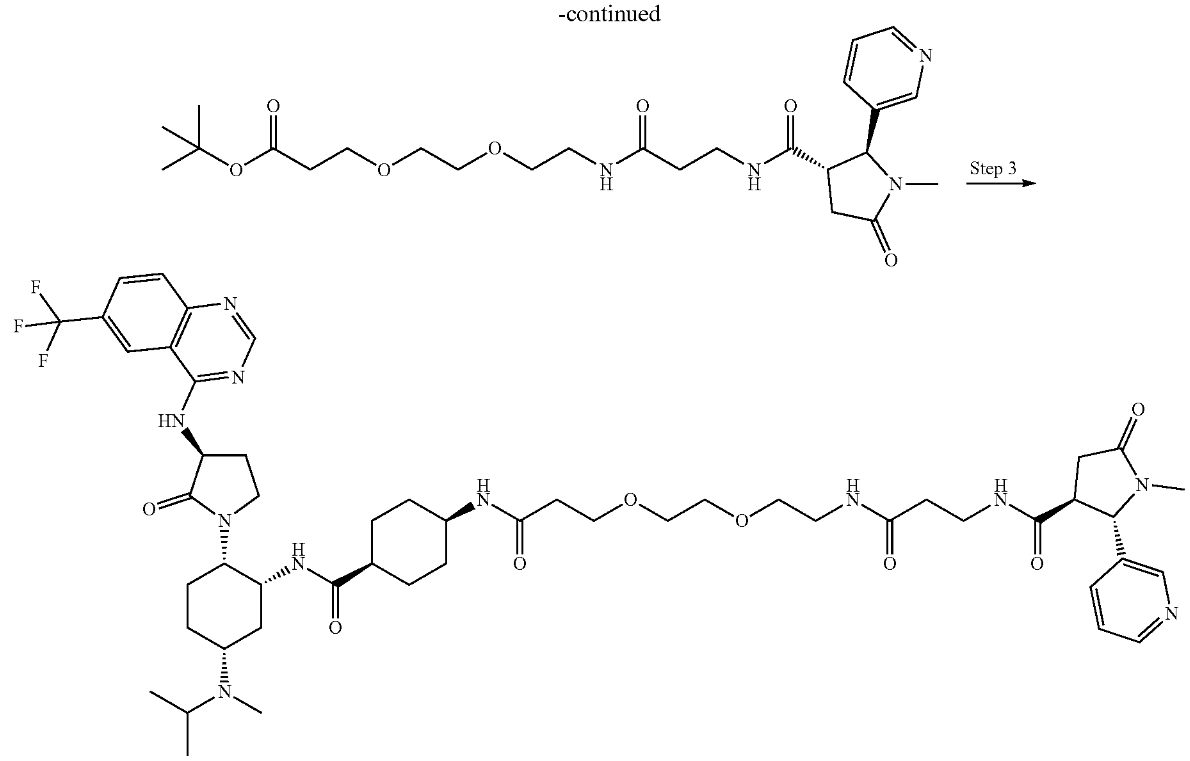

Step 1 tert-Butyl 3-((2S,3S)-1-methyl-5-oxo-2-(pyridin-3-yl)pyrrolidine-3-carboxamido) propanoate

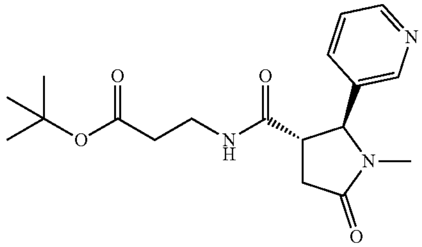 [SMILES: CN1C(=O)C[C@H](C(=O)NCCC(=O)OC(C)(C)C)[C@H]1c1cccnc1]

To a solution of (2S,3S)-1-methyl-5-oxo-2-(pyridin-3-yl) pyrrolidine-3-carboxylic acid (242 mg, 1.101 mmol) in dichloromethane (DCM) (10.0 mL) was added commercially-available tert-butyl 3-aminopropanoate, hydrochloric acid salt (200 mg, 1.101 mmol), HOBt (202 mg, 1.321 mmol), EDC (317 mg, 1.651 mmol), and DIPEA (0.961 mL, 5.50 mmol), and the mixture was stirred overnight. Water was added and the mixture was extracted dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a wax (370 mg, 1.065 mmol, 97% yield). LC-MS m/z 348.2 $(M+H)^+$.

Step 2 tert-Butyl 1-((2S,3S)-1-methyl-5-oxo-2-(pyridin-3-yl)pyrrolidin-3-yl)-1,5-dioxo-9,12-dioxa-2,6-diazapentadecan-15-oate

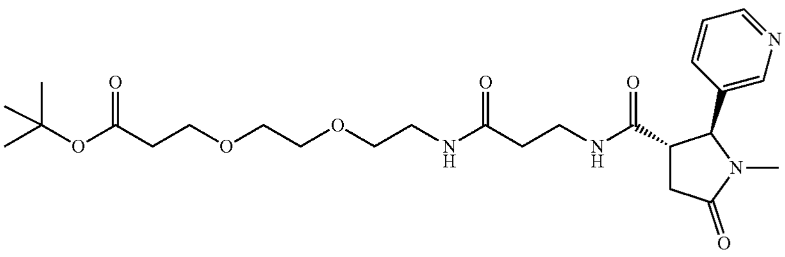 [SMILES: CN1C(=O)C[C@H](C(=O)NCCC(=O)NCCOCCOCCC(=O)OC(C)(C)C)[C@H]1c1cccnc1]

A mixture of tert-butyl 3-((2S,3S)-1-methyl-5-oxo-2-(pyridin-3-yl) pyrrolidine-3-carboxamido)propanoate (180 mg, 0.518 mmol), 4 M HCl in 1,4-dioxane (4 mL, 16.00 mmol), and dichloromethane (DCM) (2.0 mL) was stirred for 1 h and was concentrated. Dichloromethane (DCM) (2.0 mL), DIPEA (0.452 mL, 2.59 mmol) and HOBt (79 mg, 0.518 mmol), and commercially available tert-butyl 3-(2-(2-aminoethoxy)ethoxy)propanoate (121 mg, 0.518 mmol) were added. EDC (149 mg, 0.777 mmol) was added and the mixture was stirred at rt overnight. The mixture was diluted with saturated $NaHCO_3$ and was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as an off-white solid (240 mg, 0.474 mmol, 91% yield). LC-MS m/z 507.2 $(M+H)^+$.

Step 3

(2S,3S)-N-(3-((2-(2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl) carbamoyl)cyclohexyl)amino)-3-oxopropoxy)ethoxy)ethyl)amino)-3-oxopropyl)-1-methyl-5-oxo-2-(pyridin-3-yl)pyrrolidine-3-carboxamide A mixture of tert-butyl 1-((2S,3S)-1-methyl-5-oxo-2-(pyridin-3-yl)pyrrolidin-3-yl)-1,5-dioxo-9,12-dioxa-2,6-diazapentadecan-15-oate (49.5 mg, 0.098 mmol), 4 M HCl in 1,4-dioxane (4.0 mL, 16.00 mmol), and dichloromethane (DCM) (2.0 mL) was stirred for 1 hour and was concentrated. Dichloromethane (DCM) (2.0 mL), (1 s,4S)-4-amino-N-((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)cyclohexane-1-carboxamide, 2hydrochloric acid salt (60 mg, 0.081 mmol), HOBt (12.48 mg, 0.081 mmol), and DIPEA (0.071 mL, 0.407 mmol) were added. EDC (23.43 mg, 0.122 mmol) was added and the mixture was stirred at rt overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP chromatography (XSelect™ CSH Prep C18 5 μm OBD column, 40 mL/min), eluting with a gradient of 30 to 85% acetonitrile in water containing ammonium bicarbonate (10 mM) and ammonium hydroxide (0.075%) provided the title compound as an off-white solid (60.3 mg, 0.056 mmol, 68.8% yield). LC-MS m/z 1022.0 $(M)^+$. $^1H$ NMR (400 MHz, DMSO-$d_6$) δ ppm 0.89 (d, J=6.4 Hz, 3H) 1.04 (d, J=6.9 Hz, 3H) 1.44 (br d, J=13 Hz, 2H) 1.50-1.81 (m, 9H) 1.87-2.12 (m, 5H) 2.14 (s, 3H) 2.22 (t, J=6.9 Hz, 2H) 2.28 (t, J=6.6 Hz, 2H) 2.31-2.47 (m, 2H) 2.49 (s, 3H) 2.55-2.62 (m, 1H) 2.63-2.75 (m, 1H) 2.86-2.95 (m, 1H) 3.09-3.32 (m, 5H) 3.35-3.46 (m, 6H) 3.47-3.60 (m, 3H) 3.70 (br s, 1H) 3.89 (br d, J=11 Hz, 1H) 4.42 (br s, 1H) 4.63 (d, J=5.9 Hz, 1H) 5.03 (q, J=8.3 Hz, 1H) 7.43 (dd, J=7.8, 4.9 Hz, 1H) 7.56-7.75 (m, 2H) 7.89 (d, J=8.8 Hz, 1H) 7.93 (t, J=5.6 Hz, 1H) 8.00-8.15 (m, 2H) 8.47 (d, J=1.5 Hz, 1H) 8.55 (dd, J=4.7, 1.7 Hz, 1H) 8.58 (s, 1H) 8.62-8.77 (m, 2H) 8.89 (s, 1H).

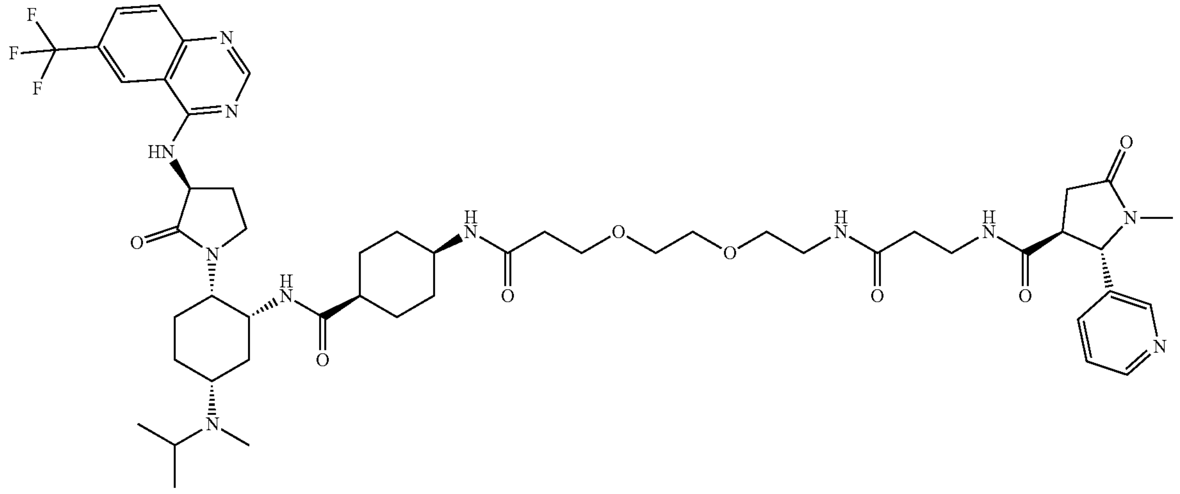 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCNC(=O)CCNC(=O)[C@H]3CC(=O)N(C)[C@@H]3c3cccnc3)CC2)C1]

Example 17
(2S,3S)-N-(4-((3-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)amino)-3-oxopropoxy)propyl)amino)-4-oxobutyl)-1-methyl-5-oxo-2-(pyridin-3-yl)pyrrolidine-3-carboxamide
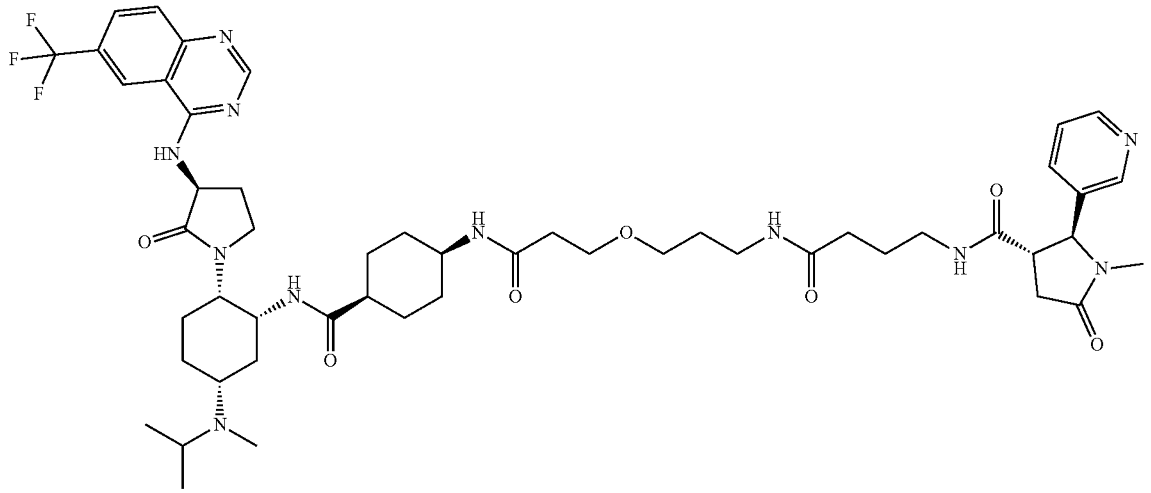
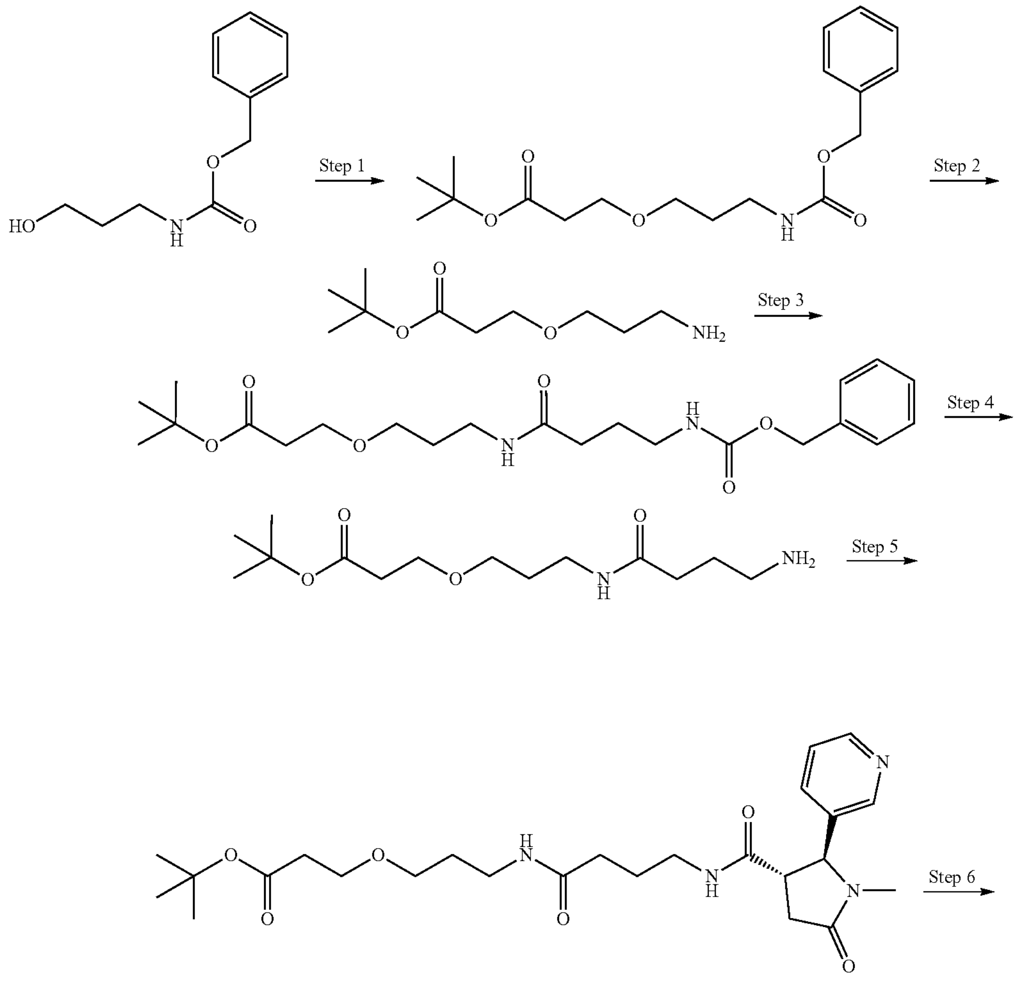

-continued

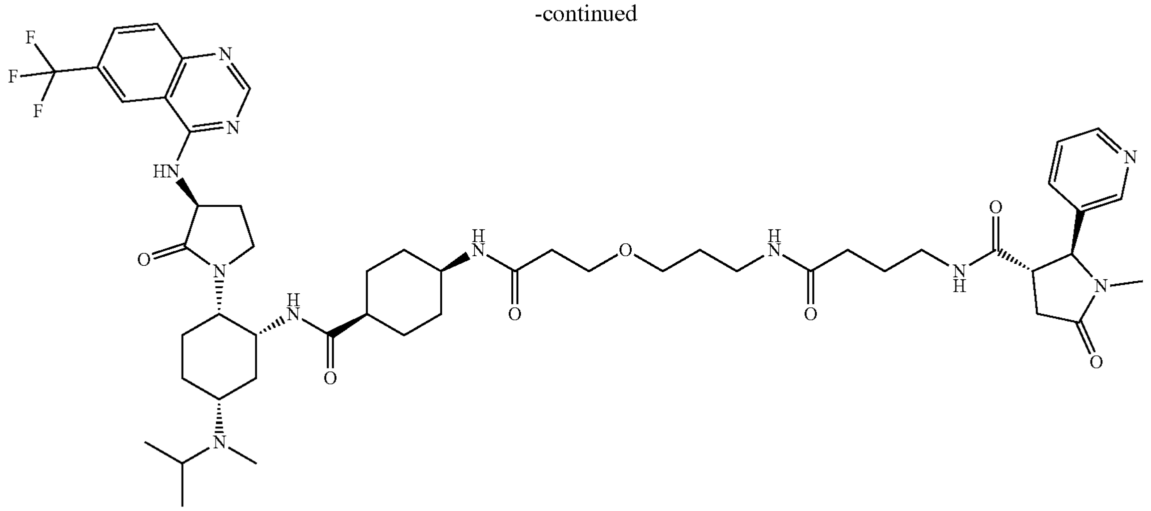

Step 1 tert-Butyl 3-(3-(((benzyloxy)carbonyl)amino)propoxy)propanoate

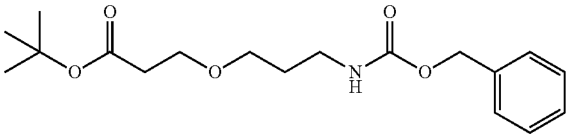 [SMILES: CC(C)(C)OC(=O)CCOCCCNC(=O)OCc1ccccc1]

To a solution of commercially-available benzyl (3-hydroxypropyl)carbamate (15.0 g, 71.7 mmol) and tert-butyl acrylate (13.78 g, 108 mmol) in tetrahydrofuran (THF) (200 mL) was added a solution of KOH (4.02 g, 71.7 mmol) in water (2.67 mL), and the mixture was stirred overnight. Water was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (300 g silica column, 200 mL/min) eluting with a gradient 0 to 40% ethyl acetate in heptane provided the title compound as a colorless oil (10.3 g, 30.5 mmol, 42.6% yield). LC-MS m/z 338.1 $(M+H)^+$.

Step 2 tert-Butyl 3-(3-aminopropoxy)propanoate

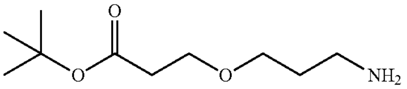

To a solution of tert-butyl 3-(3-(((benzyloxy)carbonyl)amino)propoxy)propanoate (500 mg, 1.482 mmol) in ethyl acetate (10 mL) under an atmosphere of nitrogen was added 10% Pd/C, Degussa type (15.77 mg, 0.148 mmol). The mixture was placed under reduced pressure, the reaction flask was backfilled with hydrogen (3×), and the mixture was stirred under a balloon atmosphere of hydrogen overnight. The mixture was filtered through Celite® and the filtrate was concentrated to provide the title compound as a colorless oil (301 mg, 1.481 mmol, 100% yield). LC-MS m/z 204.2 $(M+H)^+$. $^1H$ NMR (400 MHz, DMSO-$d_6$) δ ppm 1.41 (s, 8H) 1.50-1.61 (m, 2H) 2.37-2.43 (m, 2H) 2.56 (t, J=6.8 Hz, 2H) 3.41 (t, J=6.4 Hz, 2H) 3.54 (t, J=6.4 Hz, 2H).

Step 3 tert-Butyl 3,8-dioxo-1-phenyl-2,13-dioxa-4,9-diazahexadecan-16-oate

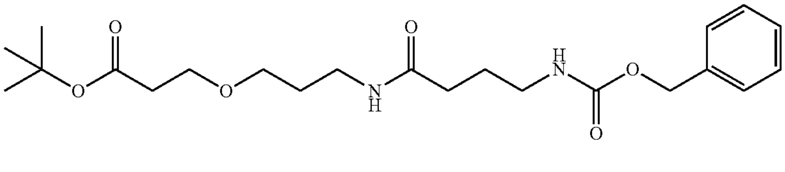 [SMILES: CC(C)(C)OC(=O)CCOCCCNC(=O)CCCNC(=O)OCc1ccccc1]

To a mixture of commercially-available 4-(((benzyloxy)carbonyl)amino)butanoic acid (420 mg, 1.771 mmol), tert-butyl 3-(3-aminopropoxy)propanoate (300 mg, 1.476 mmol), DIPEA (1.289 mL, 7.38 mmol), HOBt (271 mg, 1.771 mmol) in dichloromethane (DCM) (4.0 mL) was added EDC (424 mg, 2.214 mmol) and the mixture was stirred overnight. The mixture was diluted with water and was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a colorless oil (563 mg, 1.332 mmol, 90% yield). LC-MS m/z 423.2 $(M+H)^+$.

Step 4 tert-Butyl 3-(3-(4-aminobutanamido)propoxy)propanoate

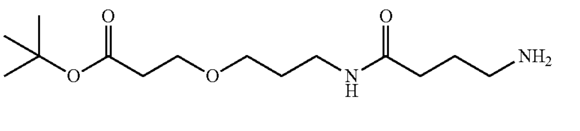 [SMILES: CC(C)(C)OC(=O)CCOCCCNC(=O)CCCN]

To a solution of tert-butyl 3,8-dioxo-1-phenyl-2,13-dioxa-4,9-diazahexadecan-16-oate (560 mg, 1.325 mmol) in ethyl acetate (5.0 mL) under an atmosphere of nitrogen was added 10% Pd/C, Degussa type (14.10 mg, 0.133 mmol). The mixture was placed under reduced pressure, the reaction flask was backfilled with hydrogen (3×), and the mixture was stirred under a balloon atmosphere of hydrogen overnight. The mixture was filtered through Celite® and the filtrate was concentrated to provide the title compound as a colorless oil (382 mg, 1.325 mmol, 100% yield). LC-MS m/z 289.2 $(M+H)^+$.

Step 5 tert-Butyl 3-(3-(4-((2S,3S)-1-methyl-5-oxo-2-(pyridin-3-yl)pyrrolidine-3-carboxamido) butanamido) propoxy)propanoate

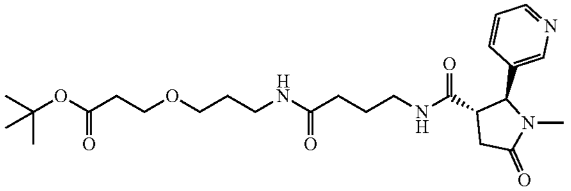 [SMILES: CN1C(=O)C[C@H](C(=O)NCCCC(=O)NCCCOCCC(=O)OC(C)(C)C)[C@H]1c1cccnc1]

To a solution of (2S,3S)-1-methyl-5-oxo-2-(pyridin-3-yl) pyrrolidine-3-carboxylic acid (240 mg, 1.090 mmol) in dichloromethane (10.0 mL) was added commercially-available tert-butyl 3-(3-(4-aminobutanamido)propoxy)propanoate (377 mg, 1.308 mmol), HOBt (200 mg, 1.308 mmol), and EDC (313 mg, 1.635 mmol). DIPEA (0.952 mL, 5.45 mmol) was added and the mixture was stirred overnight. Water was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound a wax (480 mg, 0.978 mmol, 90% yield). LC-MS m/z 491.1 $(M+H)^+$.

Step 6

(2S,3S)-N-(4-((3-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)amino)-3-oxopropoxy)propyl)amino)-4-oxobutyl)-1-methyl-5-oxo-2-(pyridin-3-yl)pyrrolidine-3-carboxamide

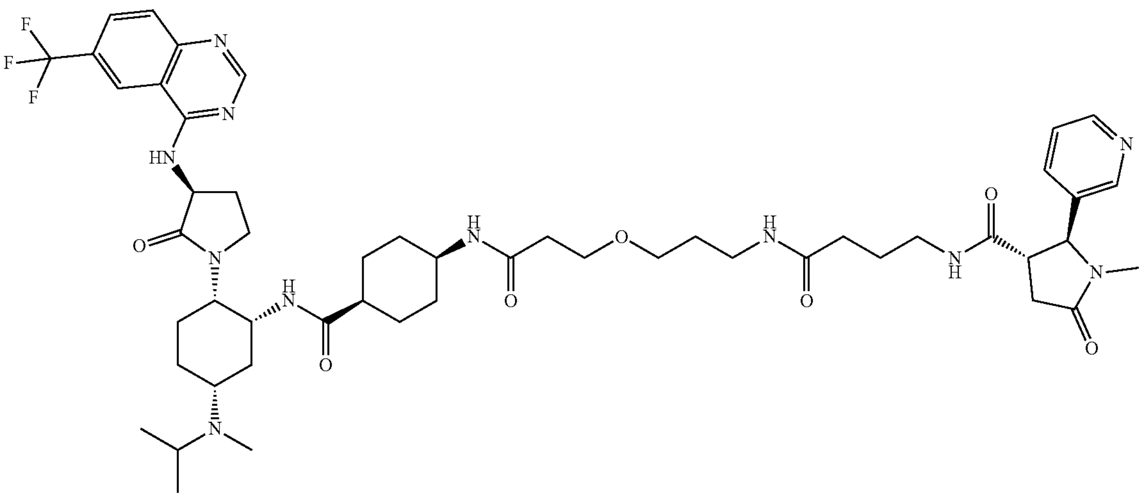 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCCNC(=O)CCCNC(=O)[C@H]3CC(=O)N(C)[C@@H]3c3cccnc3)CC2)C1]

A mixture of tert-butyl 3-(3-(4-((2S,3S)-1-methyl-5-oxo-2-(pyridin-3-yl)pyrrolidine-3-carboxamido)butanamido)propoxy)propanoate (62.2 mg, 0.127 mmol), 4 M HCl in 1,4-dioxane (4.0 mL, 16.00 mmol), and dichloromethane (2.0 mL) was stirred for 1 h and was concentrated. Dichloromethane (DCM) (2.0 mL), (1 s,4S)-4-amino-N-((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)cyclohexane-1-carboxamide, 2hydrochloric acid salt (60 mg, 0.091 mmol), HOBt (16.64 mg, 0.109 mmol), DIPEA (0.079 mL, 0.453 mmol), and EDC (26.0 mg, 0.136 mmol) were added, and the mixture was stirred at rt overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAC chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (52.8 mg, 0.050 mmol, 55.1% yield). LC-MS m/z 1006.0 (M)$^+$. $^1$H NMR (400 MHz, DMSO-$d_6$) δ ppm 0.89 (d, J=6.4 Hz, 3H) 1.04 (d, J=6.8 Hz, 3H) 1.36-1.49 (m, 2H) 1.51-1.76 (m, 13H) 1.88-2.12 (m, 7H) 2.14 (s, 3H) 2.27 (t, J=6.4 Hz, 2H) 2.31-2.39 (m, 1H) 2.40-2.49 (m, 2H) 2.56-2.62 (m, 1H) 2.67-2.74 (m, 1H) 2.89 (ddd, J=9.5, 7.3, 6.1 Hz, 1H) 3.02 (quin, J=6.8 Hz, 3H) 3.23-3.29 (m, 1H) 3.30 (s, 1H) 3.42 (br s, 1H) 3.47-3.58 (m, 3H) 3.71 (br s, 1H) 3.86-3.93 (m, 1H) 4.42 (br s, 1H) 4.65 (d, J=6.4 Hz, 1H) 5.03 (q, J=8.2 Hz, 1H) 7.44 (dd, J=7.6, 5.1 Hz, 1H) 7.63 (d, J=6.8 Hz, 1H) 7.68 (dt, J=8.1, 1.8 Hz, 1H) 7.72 (t, J=5.4 Hz, 1H) 7.89 (d, J=8.8 Hz, 1H) 7.99 (br t, J=5.6 Hz, 1H) 8.07 (dd, J=8.8, 2.0 Hz, 1H) 8.48 (d, J=1.5 Hz, 1H) 8.56 (dd, J=4.9, 1.5 Hz, 1H) 8.58 (s, 1H) 8.71 (br d, J=8.3 Hz, 2H) 8.89 (s, 1H).

Example 18

N$^1$-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-N$^5$-(3-(3-((2S,3S)-1-methyl-5-oxo-2-(pyridin-3-yl)pyrrolidine-3-carboxamido)propoxy)propyl)glutaramide

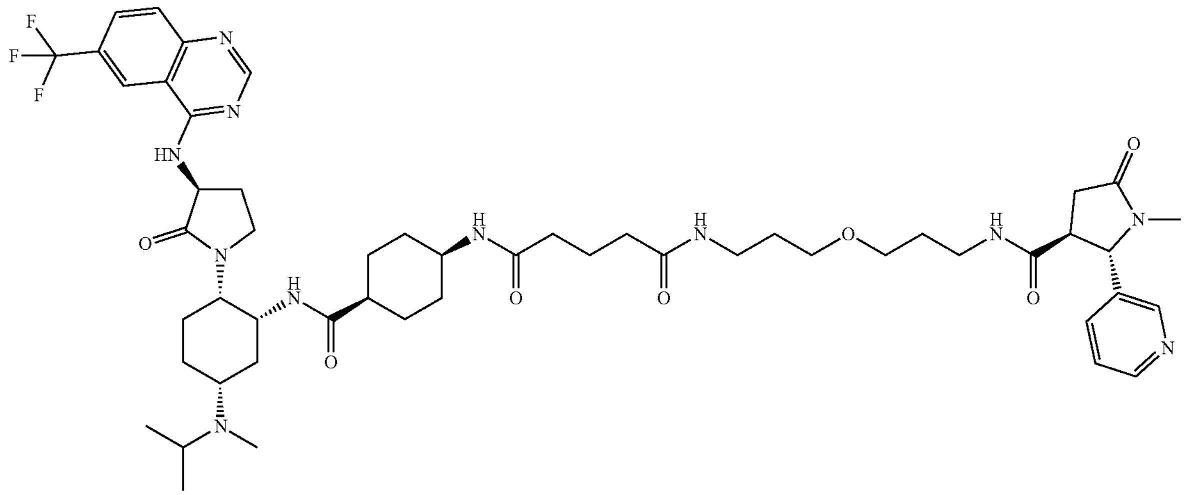

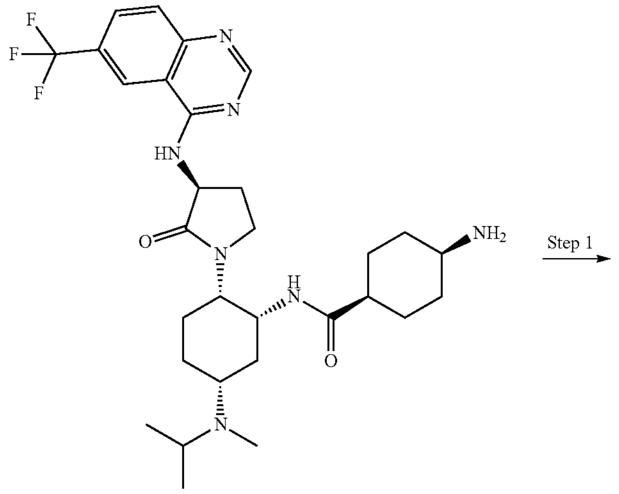

-continued
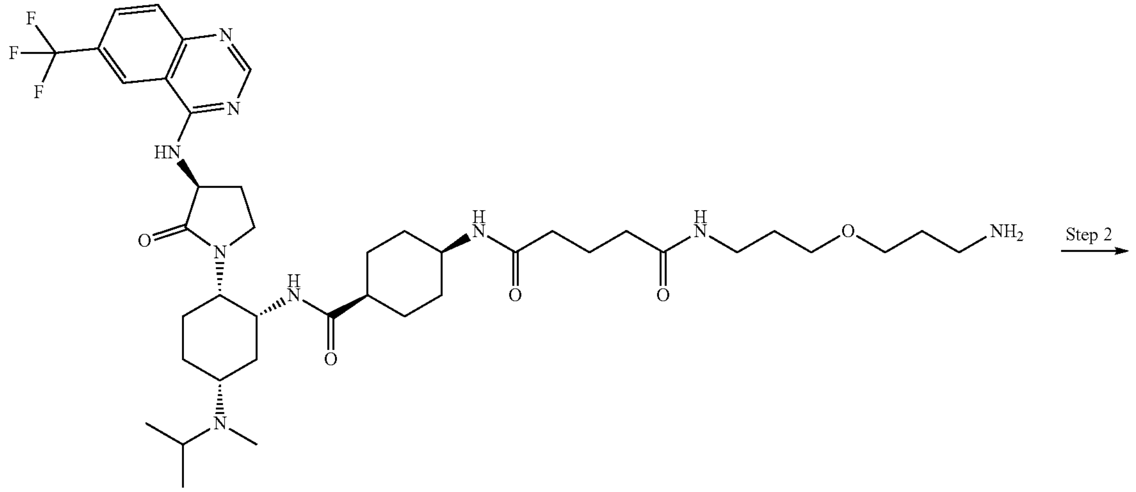
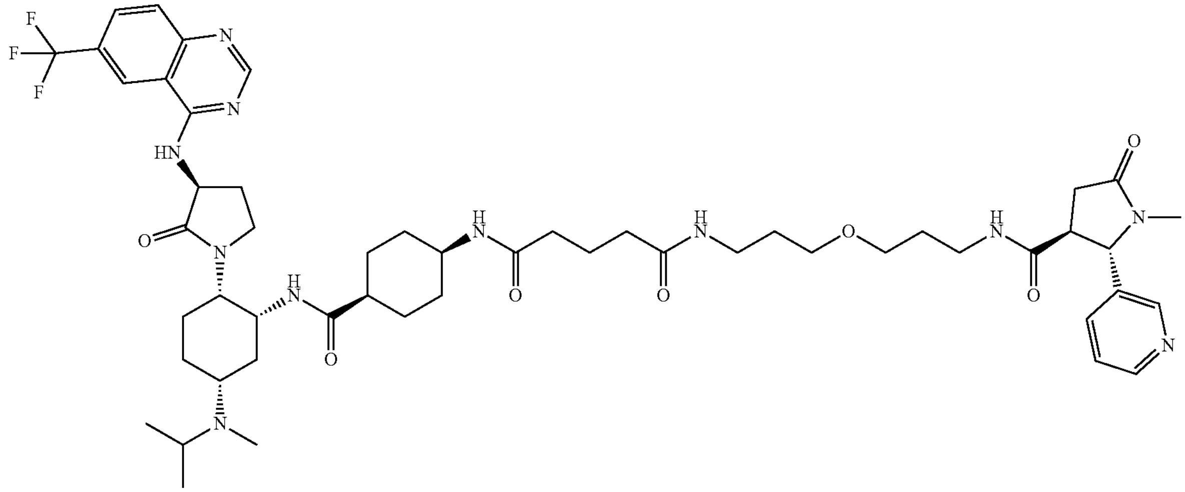

Step 1

N[1]-(3-(3-Aminopropoxy)propyl)-N[5]-((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)glutaramide

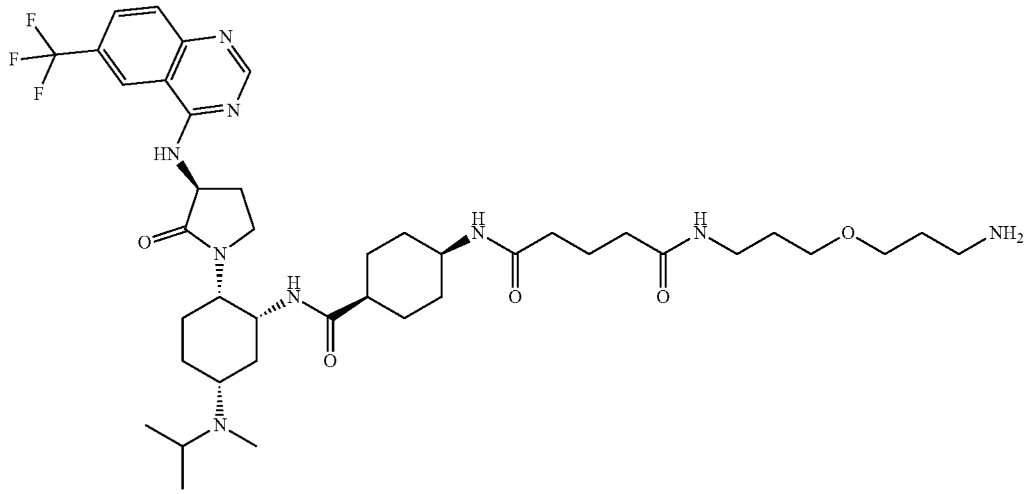 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCC(=O)NCCCOCCCN)CC2)C1]

To a suspension of (1 s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (62 mg, 0.089 mmol) in dichloromethane (DCM) (3 mL) was added triethylamine (0.1 mL, 0.717 mmol) and commercially available dihydro-2H-pyran-2,6(3H)-dione (10.12 mg, 0.089 mmol), and the mixture was stirred at rt for 2 h. The solvent was removed under reduced pressure and N,N-dimethylformamide (DMF) (1.0 mL), commercially-available 3,3'-oxybis(propan-1-amine), and HATU (43 mg, 0.113 mmol) were added and the mixture was stirred at rt for 2 h. The mixture was concentrated under reduced pressure. Purification by MDAP chromatography (XSelect™ CSH C18 5 μm column) eluting with a gradient of 30 to 85% acetonitrile in water containing ammonium bicarbonate (10 mM) and the pH adjusted to 10 with ammonia provided the title compound as a white foamy solid (24 mg, 0.028 mmol, 31.1% yield). LC-MS m/z 818.3 $(M+H)^+$.

Step 2

N[1]-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-N[5]-(3-(3-((2S,3S)-1-methyl-5-oxo-2-(pyridin-3-yl)pyrrolidine-3-carboxamido)propoxy)propyl)glutaramide

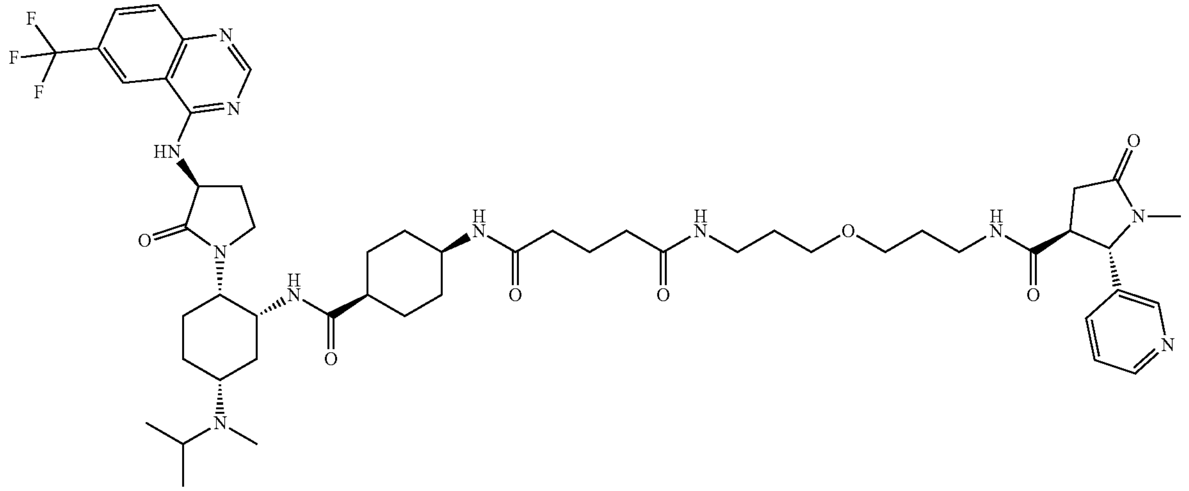 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCC(=O)NCCCOCCCNC(=O)[C@H]3CC(=O)N(C)[C@@H]3c3cccnc3)CC2)C1]

To a solution of $N^1$-(3-(3-aminopropoxy)propyl)-$N^5$-((1S, 4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)glutaramide (24 mg, 0.029 mmol) in dichloromethane (DCM) (2 mL) was added triethylamine (0.012 mL, 0.088 mmol), (2S,3S)-1-methyl-5-oxo-2-(pyridin-3-yl)pyrrolidine-3-carboxylic acid (9.69 mg, 0.044 mmol), and HATU (13.39 mg, 0.035 mmol), the mixture was stirred at rt for 1 h, and was concentrated. Purification by MDAP chromatography (XSelect™ CSH C18 5 μm column) eluting with a gradient of 30 to 85% acetonitrile in water containing ammonium bicarbonate (10 mM) and the pH adjusted to 10 with ammonia provided the title compound as a white solid (21 mg, 0.020 mmol, 68.8% yield). LC-MS m/z 1020.3 $(M)^+$. $^1H$ NMR (400 MHz, METHANOL-$d_4$) δ ppm 1.00 (d, J=6.4 Hz, 3H) 1.16 (d, J=6.4 Hz, 3H) 1.52-2.02 (m, 19H) 2.09-2.40 (m, 11H) 2.53-2.63 (m, 1H) 2.66 (s, 3H) 2.67-2.75 (m, 2H) 2.79-2.89 (m, 1H) 3.05 (ddd, J=9.3, 8.1, 6.6 Hz, 1H) 3.16-3.37 (m, 9H) 3.39-3.67 (m, 5H) 3.89 (br s, 1H) 4.03 (dt, J=12.2, 3.7 Hz, 1H) 4.61 (br d, J=3.4 Hz, 1H) 4.82 (d, J=6.4 Hz, 1H) 5.30 (t, J=8.6 Hz, 1H) 7.51-7.56 (m, 1H) 7.80 (dt, J=7.8, 2.0 Hz, 1H) 7.91 (d, J=8.8 Hz, 1H) 8.06 (dd, J=8.8, 2.0 Hz, 1H) 8.51 (d, J=1.5 Hz, 1H) 8.57 (dd, J=4.9, 1.5 Hz, 1H) 8.59 (s, 1H) 8.73 (s, 1H).

The following compounds were or could be prepared with procedures analogous to that described in Example 18:

| Ex. | Compound | LC-MS m/z | NMR |
|---|---|---|---|
| 19 | 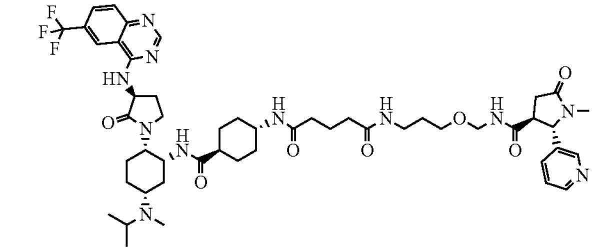<br>N1-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)-N5-(3-(3-((2S,3S)-1-methyl-5-oxo-2-(pyridin-3-yl)pyrrolidine-3-carboxamido)propoxy)propyl) glutaramide. | 1020.6 $(M + H)^+$ | $^1H$ NMR (400 MHz, METHANOL-$d_4$) δ ppm 1.02 (br d, J = 6.4 Hz, 3H) 1.16 (br d, J = 6.4 Hz, 3H) 1.18 - 1.33 (m, 3H) 1.50 - 1.79 (m, 10H) 1.80 - 2.04 (m, 8H) 2.04 - 2.39 (m, 13 H) 2.54 (dtd, J = 12.2, 8.1, 8.1, 3.9 Hz, 1H) 2.66 (s, 3 H) 2.67 - 2.76 (m, 2H) 2.79 - 2.88 (m, 1H) 3.06 (ddd, J = 9.3, 8.3, 6.8 Hz, 1 H) 3.21 - 3.38 (m, 6H) 3.41 - 3.55 (m, 3H) 3.57 - 3.67 (m, 2H) 4.02 (dt, J = 12.5, 3.5 Hz, 1H) 4.65 (br d, J = 2.9 Hz, 1H) 4.82 (d, J = 6.8 Hz, 1H) 5.27 (t, J = 8.1 Hz, 1H) 7.53 (dd, J = 7.8, 4.9 Hz, 1H) 7.80 (dt, J = 7.8, 2.0 Hz, 1H) 7.91 (d, J = 8.8 Hz, 1H) 8.06 (dd, J = 8.8, 2.0 Hz, 1 H) 8.51 (d, J = 2.0 Hz, 1H) 8.58 (dd, J = 4.9, 1.5 Hz, 1 H) 8.59 (s, 1H) 8.81 (s, 1 H). |
| 20 | 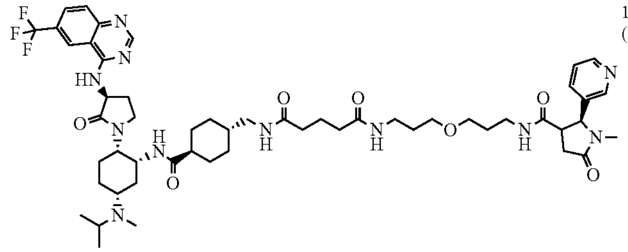<br>N1-(((1R,4r)-4-(((1R,2S,5R)-5-(Isopropyl (methyl)amino)-2-((S)-2-oxo-3-((6-(trifluoromethyl) quinazolin-4-yl)amino) pyrrolidin-1-yl)cyclohexyl) carbamoyl)cyclohexyl)methyl)-N5-(3-(3-((2S,3S)-1-methyl-5-oxo-2-(pyridin-3-yl)pyrrolidine-3-carboxamido) propoxy) propyl)glutaramide. | 1034.3 $(M)^+$ | $^1H$ NMR (400 MHz, METHANOL-$d_4$) δ ppm 1.02 (br d, J = 6.4 Hz, 3H) 1.14 (br d, J = 6.4 Hz, 3H) 1.39 - 1.56 (m, 3H) 1.61 - 1.78 (m, 7H) 1.79 - 1.99 (m, 7H) 2.04 - 2.16 (m, 2 H) 2.20 (td, J = 7.6, 2.9 Hz, 5H) 2.26 (s, 3H) 2.33 (br d, J = 14.7 Hz, 1H) 2.54 (dtd, J = 12.2, 8.1, 8.1, 3.9 Hz, 1H) 2.66 (s, 3H) 2.67 - 2.75 (m, 2H) 2.79 - 2.88 (m, 1H) 3.02 (d, J = 6.4 Hz, 2H) 3.04 - 3.10 (m, 1H) 3.18 - 3.37 (m, 7H) 3.41 - 3.56 (m, 3H) 3.58 - 3.69 (m, 1H) 4.03 (dt, J = 12.5, 3.8 Hz, 1H) 4.66 (br d, J = 2.9 Hz, 1H) 4.82 (d, J = 6.8 Hz, 1H) 5.27 (t, J = 7.8 Hz, 1H) 7.53 (dd, J = 7.8, 4.9 Hz, 1H) 7.80 (dt, J = 7.8, 2.0 Hz, 1H) 7.91 (d, J = 8.8 Hz, 1H) 8.06 (dd, J = 8.8, 1.5 Hz, 1 H) 8.51 (d, J = 1.5 Hz, 1H) 8.58 (dd, J = 4.9, 1.5 Hz, 1 H) 8.59 (s, 1H) 8.81 (s, 1 H). |

-continued

| Ex. | Compound | LC-MS m/z | NMR |
|---|---|---|---|
| 21 | 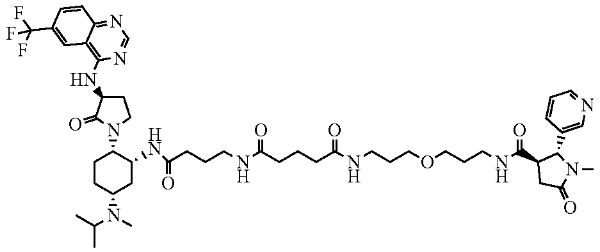 [SMILES: CC(C)N(C)[C@@H]1CC[C@H](N2CC[C@H](Nc3ncnc4ccc(C(F)(F)F)cc34)C2=O)[C@H](NC(=O)CCCNC(=O)CCCC(=O)NCCCOCCCNC(=O)[C@@H]2CC(=O)N(C)[C@H]2c2cccnc2)C1] N1-(4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-4-oxobutyl)-N5-(3-(3-((2S,3S)-1-methyl-5-oxo-2-(pyridin-3-yl)pyrrolidine-3-carboxamido) propoxy)propyl)glutaramide. | 980.7 $(M + H)^+$ | $^1H$ NMR (400 MHz, METHANOL-$d_4$) δ ppm 1.03 (br d, J = 6.4 Hz, 3H) 1.12 (br d, J = 6.4 Hz, 3H) 1.58 - 1.91 (m, 13H) 1.92 - 2.06 (m, 1H) 2.08 - 2.38 (m, 14H) 2.51 - 2.64 (m, 1 H) 2.66 (s, 3H) 2.67 - 2.75 (m, 2H) 2.79 - 2.88 (m, 1 H) 3.05 (ddd, J = 9.3, 8.2, 6.7 Hz, 1H) 3.16 - 3.36 (m, 9H) 3.39 - 3.46 (m, 2 H) 3.53 - 3.67 (m, 2H) 4.05 (dt, J = 11.9, 3.6 Hz, 1 H) 4.60 (br d, J = 2.9 Hz, 1 H) 4.82 (d, J = 6.6 Hz, 1H) 5.30 (t, J = 8.6 Hz, 1H) 7.51 - 7.56 (m, 1H) 7.80 (dt, J = 8.0, 1.9 Hz, 1H) 7.90 (d, J = 8.8 Hz, 1H) 8.05 (dd, J = 8.9, 1.8 Hz, 1H) 8.51 (d, J = 1.7 Hz, 1H) 8.58 (dd, J = 4.9, 1.5 Hz, 1H) 8.59 (s, 1H) 8.77 (s, 1H). |
| 22 | 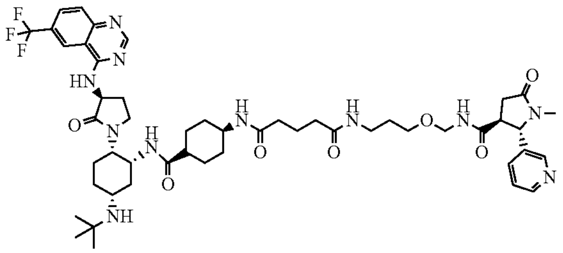 N1-((1R,4r)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl)carbamoyl) cyclohexyl)-N5-(3-(3-((2S,3S)-1-methyl-5-oxo-2-(pyridin-3-yl)pyrrolidine-3-carboxamido) propoxy)propyl)glutaramide. | 1020.7 $(M + H)^+$ | $^1H$ NMR (400 MHz, METHANOL-$d_4$) δ ppm 1.18 (s, 9H) 1.59 - 2.03 (m, 22H) 2.19 (td, J = 7.5, 2.7 Hz, 4H) 2.22 - 2.38 (m, 2H) 2.51 - 2.63 (m, 1 H) 2.66 (s, 3H) 2.67 - 2.74 (m, 1H) 2.79 - 2.88 (m, 1 H) 3.00 - 3.09 (m, 1H) 3.17 - 3.36 (m, 8H) 3.39 - 3.43 (m, 2H) 3.50 - 3.58 (m, 1H) 3.59 - 3.67 (m, 1 H) 3.87 - 3.92 (m, 1H) 4.00 (dt, J = 12.7, 3.4 Hz, 1 H) 4.59 (br d, J = 2.9 Hz, 1 H) 4.82 (d, J = 6.8 Hz, 1H) 5.33 (t, J = 8.6 Hz, 1H) 7.53 (dd, J = 7.8, 4.9 Hz, 1H) 7.80 (dt, J = 7.8, 2.0 Hz, 1 H) 7.91 (d, J = 8.3 Hz, 1H) 8.06 (dd, J = 8.8, 2.0 Hz, 1 H) 8.51 (d, J = 2.0 Hz, 1H) 8.57 (dd, J = 4.9, 1.5 Hz, 1 H) 8.59 (s, 1H) 8.74 (s, 1 H). |

Example 23
(2S,3S)-N-(2-(2-(2-(3-(((1S,4s)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl)carbamoyl) cyclohexyl)amino)-3-oxopropoxy)ethoxy)ethoxy)ethyl)-1-methyl-5-oxo-2-(pyridin-3-yl)pyrrolidine-3-carboxamide
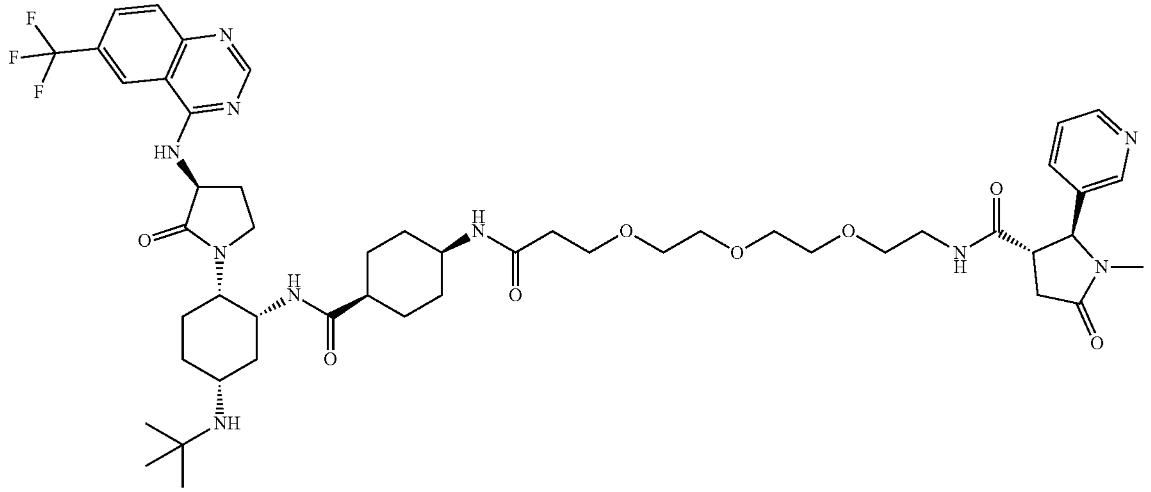
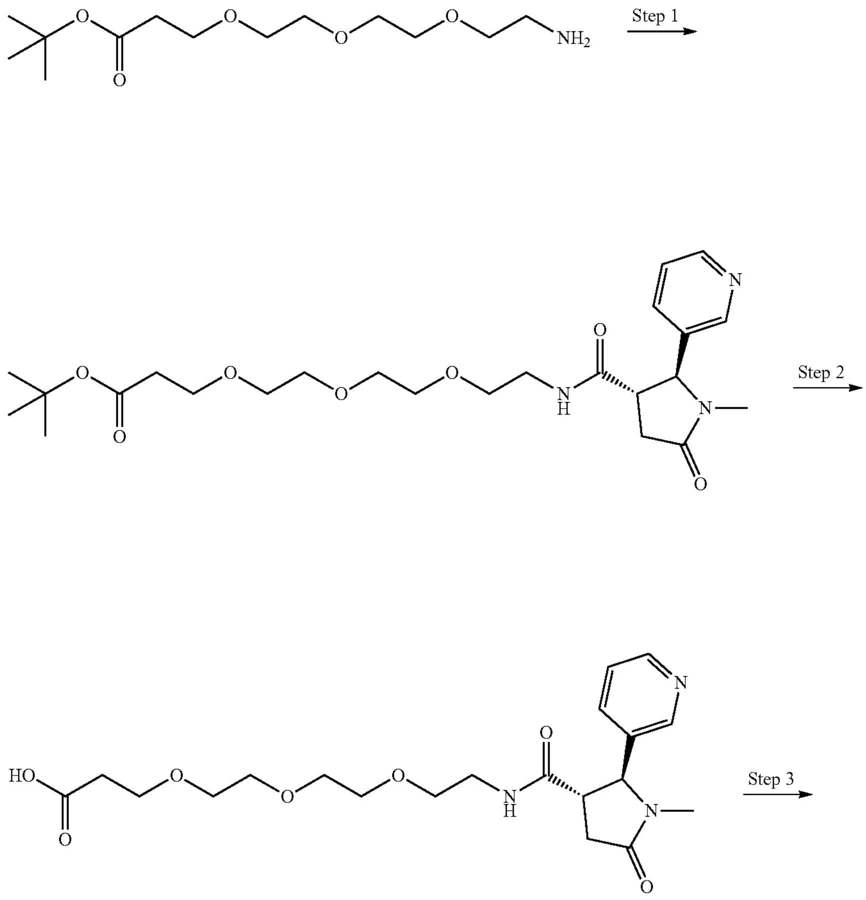

-continued

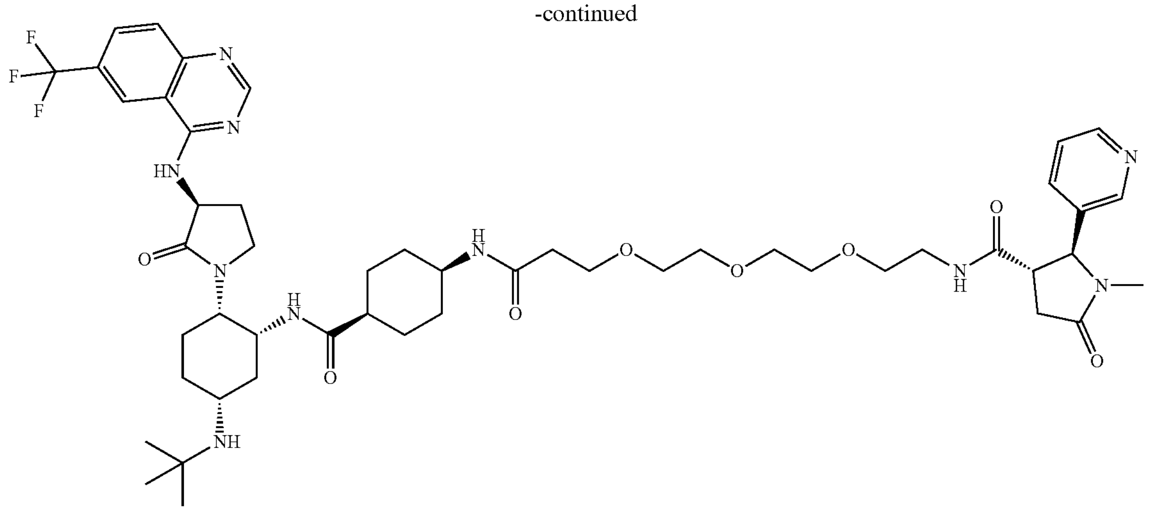

Step 1 tert-Butyl 1-((2S,3S)-1-methyl-5-oxo-2-(pyridin-3-yl)pyrrolidin-3-yl)-1-oxo-5,8,11-trioxa-2-azatetradecan-14-oate

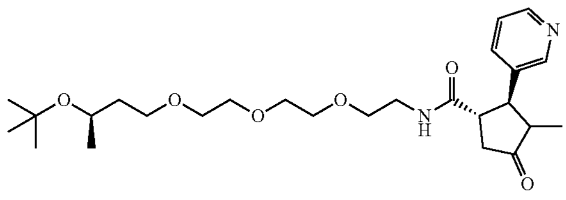 [SMILES: CC1C(=O)C[C@H](C(=O)NCCOCCOCCOCC[C@@H](C)OC(C)(C)C)[C@H]1c1cccnc1]

To a mixture of commercially-available tert-butyl 3-(2-(2-(2-aminoethoxy)ethoxy)ethoxy)propanoate (2 g, 7.21 mmol), (2S,3S)-1-methyl-5-oxo-2-(pyridin-3-yl)pyrrolidine-3-carboxylic acid (1.588 g, 7.21 mmol) and triethylamine (3.02 mL, 21.63 mmol) in dichloromethane (DCM) (20 mL) was added HATU (3.29 g, 8.65 mmol) and the mixture was stirred for 72 h. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (120 g RediSep Rf Gold® column, 80 mL/min) eluting with a gradient of 0 to 15% methanol containing ammonium hydroxide (10%) in dichloromethane (DCM) provided the title compound (1.91 g, 3.98 mmol, 55.2% yield). LC-MS m/z 480.2 $(M+H)^+$.

Step 2

1-((2S,3S)-1-Methyl-5-oxo-2-(pyridin-3-yl)pyrrolidin-3-yl)-1-oxo-5,8,11-trioxa-2-azatetradecan-14-oic acid, Hydrochloric acid salt

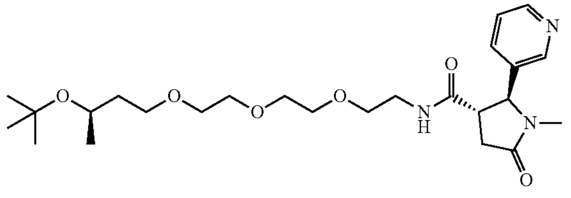 [SMILES: C[C@H](CCOCCOCCOCCNC(=O)[C@H]1CC(=O)N(C)[C@@H]1c1cccnc1)OC(C)(C)C]

To a mixture of tert-butyl 1-((2S,3S)-1-methyl-5-oxo-2-(pyridin-3-yl)pyrrolidin-3-yl)-1-oxo-5,8,11-trioxa-2-azatetradecan-14-oate (1.9 g, 3.96 mmol) in dichloromethane (DCM) (5 mL) at 0° C. was added 4 M HCl (4.95 mL, 19.81 mmol), The mixture was stirred at rt for 2 h and was concentrated to dryness to provide the title compound (1.8 g, 3.91 mmol, 99% yield). LC-MS (m/z) 424.2 $(M+H)^+$.

Step 3

(2S,3S)-N-(2-(2-(2-(3-(((1S,4s)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl)carbamoyl) cyclohexyl)amino)-3-oxopropoxy)ethoxy)ethoxy)ethyl)-1-methyl-5-oxo-2-(pyridin-3-yl)pyrrolidine-3-carboxamide

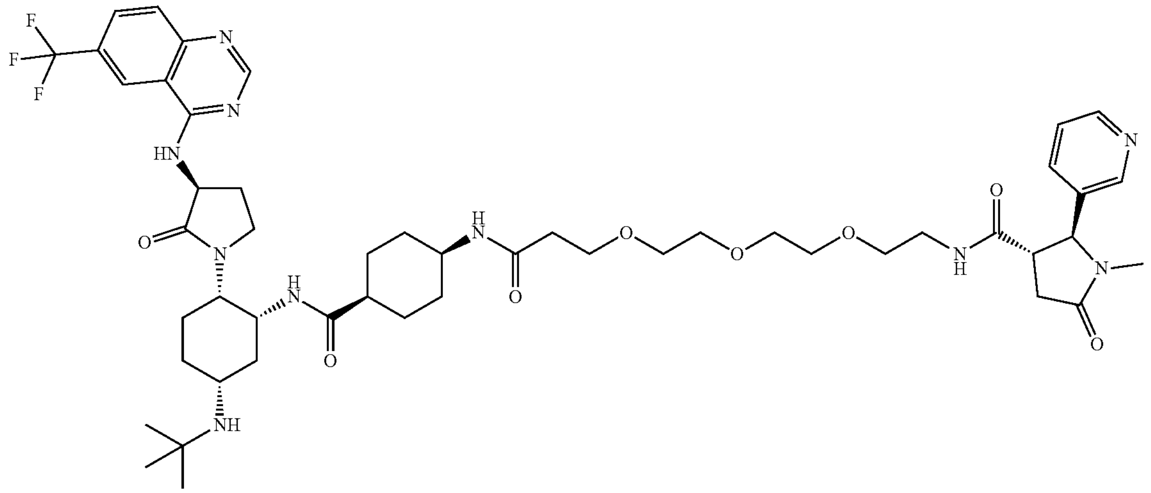 [SMILES: CN1C(=O)C[C@H](C(=O)NCCOCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1]

A mixture of tert-butyl ((1S,4S)-4-(((1R,2S,5R)-5-(tert-butylamino)-2-((S)-2-oxo-3-((6-(trifluoromethyl)quinazolin-4-yl)amino)pyrrolidin-1-yl)cyclohexyl)carbamoyl)cyclohexyl) carbamate (56 mg, 0.081 mmol) and 4 M HCl (0.142 mL, 0.568 mmol) in dichloromethane (DCM) (0.1 mL) was stirred at rt for 1 h, was stored in a freezer overnight, and was stirred at rt for 1 h. The mixture was concentrated to dryness and dichloromethane (DCM) (1 mL) was added. 1-((2S,3S)-1-methyl-5-oxo-2-(pyridin-3-yl) pyrrolidin-3-yl)-1-oxo-5,8,11-trioxa-2-azatetradecan-14-oic acid, hydrochloric acid salt (37.3 mg, 0.081 mmol), triethylamine (0.091 mL, 0.649 mmol), and HATU (37.0 mg, 0.097 mmol) were added and the mixture was stirred at rt for 1 h. Purification by MDAP chromatography (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a white solid (43.2 mg, 0.043 mmol, 53.5% yield). LC-MS m/z 997.0 $(M+H)^+$. $^1H$ NMR (400 MHz, METHANOL-$d_4$) δ ppm 1.18 (s, 9H) 1.52-2.09 (m, 15H) 2.21-2.37 (m, 2H) 2.41 (t, J=6.3 Hz, 2H) 2.53-2.63 (m, 1H) 2.66 (s, 3H) 2.67-2.75 (m, 1H) 2.77-2.90 (m, 1H) 3.05 (ddd, J=9.3, 8.0, 6.5 Hz, 1H) 3.23 (br s, 1H) 3.27-3.32 (m, 1H) 3.34-3.40 (m, 1H) 3.41-3.58 (m, 12H) 3.58-3.65 (m, 1H) 3.68 (t, J=6.4 Hz, 2H) 3.87-3.94 (m, 1H) 4.00 (dt, J=12.5, 3.6 Hz, 1H) 4.59 (br d, J=3.0 Hz, 1H) 5.32 (t, J=8.7 Hz, 1H) 7.49-7.54 (m, 1H) 7.79 (dt, J=8.0, 1.9 Hz, 1H) 7.91 (d, J=8.8 Hz, 1H) 8.06 (dd, J=8.8, 1.8 Hz, 1H) 8.51 (d, J=1.8 Hz, 1H) 8.56 (dd, J=4.8, 1.5 Hz, 1H) 8.59 (s, 1H) 8.73 (s, 1H).

The following compounds could be prepared with procedures analogous to that described in Example 23:

| Ex. | Compound | LC-MS m/z | NMR |
|---|---|---|---|
| 24 | 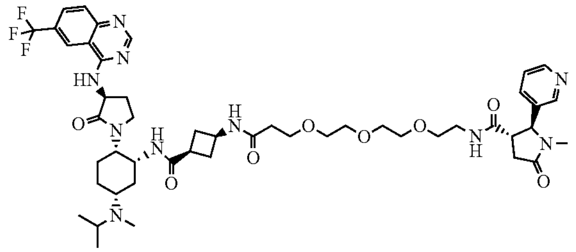 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCOCCOCCNC(=O)[C@H]3CC(=O)N(C)[C@@H]3c3cccnc3)C2)C1]<br>(2S,3S)-N-(2-(2-(2-(3-(((1S,3s)-3-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)carbamoyl)cyclobutyl)amino)-3-oxopropoxy)ethoxy)ethoxy)ethyl)-1-methyl-5-oxo-2-(pyridin-3-yl)pyrrolidine-3-carboxamide. | 968.5 $(M + H)^+$ | $^1H$ NMR (400 MHz, METHANOL-$d_4$) δ ppm 1.02 (d, J = 6.4 Hz, 3H) 1.15 (br d, J = 6.4 Hz, 3H) 1.60 – 1.81 (m, 3H) 1.83 – 2.00 (m, 1H) 2.09 – 2.24 (m, 4H) 2.26 (s, 3H) 2.34 (t, J = 6.4 Hz, 3H) 2.46 – 2.63 (m, 3H) 2.66 (s, 3H) 2.68 – 2.89 (m, 4H) 3.00 – 3.09 (m, 1H) 3.26 – 3.32 (m, 1H) 3.35 – 3.71 (m, 16H) 4.03 (dt, J = 12.3, 3.9 Hz, 1H) 4.15 – 4.27 (m, 1H) 4.60 (br d, J = 2.9 Hz, 1H) 4.82 (d, J = 6.8 Hz, 1H) 5.32 (t, J = 8.8 Hz, 1H) 7.52 (dd, J = 7.8, 4.9 Hz, 1H) 7.80 (dt, J = 7.8, |

-continued

| Ex. | Compound | LC-MS m/z | NMR |
|---|---|---|---|
| | | | 2.0 Hz, 1H) 7.91 (d, J = 8.8 Hz, 1H) 8.07 (dd, J = 8.8, 2.0 Hz, 1H) 8.50 - 8.53 (m, 1H) 8.57 (dd, J = 4.9, 2.0 Hz, 1H) 8.59 (s, 1H) 8.76 (s, 1H). |
| 25 | 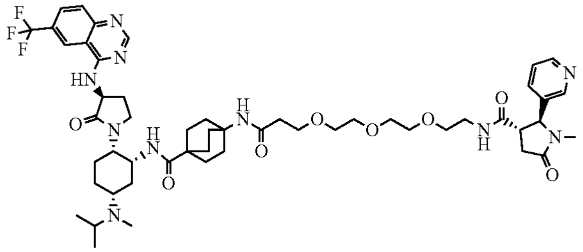 [SMILES: CC(C)N(C)[C@@H]1CC[C@H](N2CC[C@H](Nc3ncnc4ccc(C(F)(F)F)cc34)C2=O)[C@H](NC(=O)C23CCC(NC(=O)CCOCCOCCOCCNC(=O)[C@H]4CC(=O)N(C)[C@@H]4c4cccnc4)(CC2)CC3)C1] (2S,3S)-N-(2-(2-(2-(3-((4-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)carbamoyl)bicyclo[2.2.2]octan-1-yl)amino)-3-oxopropoxy)ethoxy)ethoxy)ethyl)-1-methyl-5-oxo-2-(pyridin-3-yl)pyrrolidine-3-carboxamide. | 1021.7 $(M + H)^+$ | $^1H$ NMR (400 MHz, METHANOL-$d_4$) δ ppm 1.27 - 1.37 (m, 3H) 1.70 - 2.00 (m, 13H) 2.09 - 2.27 (m, 3H) 2.29 - 2.38 (m, 3H) 2.50 - 2.61 (m, 2 H) 2.67 (s, 3H) 2.68 - 2.77 (m, 1H) 2.81 - 2.90 (m, 1H) 3.01 - 3.10 (m, 1 H) 3.29 (dt, J = 3.2, 1.6 Hz, 1H) 3.36 - 3.42 (m, 2H) 3.46 - 3.52 (m, 3H) 3.53 - 3.61 (m, 8H) 3.65 (t, J = 6.3 Hz, 3H) 3.67 - 3.75 (m, 2H) 4.04 - 4.19 (m, 1 H) 4.80 - 4.87 (m, 1H) 4.92 - 4.98 (m, 1H) 7.39 - 7.46 (m, 1H) 7.54 (dd, J = 7.7, 5.4 Hz, 1H) 7.81 (dt, J = 8.0, 1.7 Hz, 1H) 7.91 - 7.97 (m, 1H) 8.09 (dd, J = 8.9, 2.0 Hz, 1H) 8.37 (br s, 1H) 8.53 (d, J = 1.5 Hz, 1H) 8.56 - 8.62 (m, 2H) 8.75 (br s, 1H). |
| 26 | 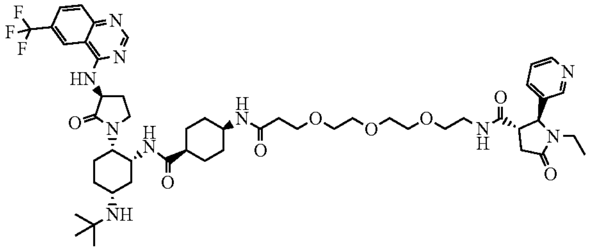 [SMILES: CCN1C(=O)C[C@H](C(=O)NCCOCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] (2S,3S)-N-(2-(2-(2-(3-(((1S,4s)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethoxy)ethyl)-1-ethyl-5-oxo-2-(pyridin-3-yl)pyrrolidine-3-carboxamide. | 1009.0 (M + H)* | $^1H$ NMR (400 MHz, METHANOL-$d_4$) δ ppm 1.01 (t, J = 7.3 Hz, 3H) 1.19 (s, 9H) 1.57 - 2.04 (m, 16H) 2.22 - 2.37 (m, 3H) 2.41 (t, J = 6.1 Hz, 2 H) 2.51 - 2.62 (m, 1H) 2.62 - 2.75 (m, 3H) 2.79 - 2.89 (m, 1H) 3.02 - 3.10 (m, 1H) 3.21 - 3.26 (m, 1 H) 3.44 - 3.53 (m, 5H) 3.54 (s, 5H) 3.59 - 3.66 (m, 2H) 3.68 (t, J = 6.1 Hz, 2H) 3.90 (br s, 2H) 3.97 - 4.05 (m, 1H) 4.59 (br d, J = 2.4 Hz, 1H) 4.95 (d, J = 6.4 Hz, 1H) 5.32 (t, J = 8.6 Hz, 1H) 7.52 (dd, J = 8.3, 4.9 Hz, 1H) 7.82 (dt, J = 7.8, 1.7 Hz, 1H) 7.91 (d, J = 8.8 Hz, 1H) 8.06 (dd, J = 8.6, 1.7 Hz, 1 H) 8.54 (d, J = 2.0 Hz, 1H) 8.57 (dd, J = 4.6, 1.2 Hz, 1 H) 8.59 (s, 1H) 8.73 (s, 2 H). |

-continued

| Ex. | Compound | LC-MS m/z | NMR |
|---|---|---|---|
| 27 | 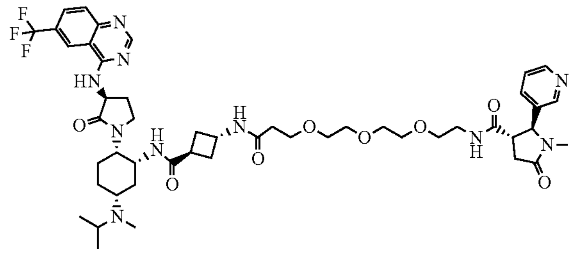 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCOCCOCCOCCNC(=O)[C@H]3CC(=O)N(C)[C@@H]3c3cccnc3)C2)C1] (2S,3S)-N-(2-(2-(2-(3-(((1R,3r)-3-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)carbamoyl)cyclobutyl)amino)-3-oxopropoxy)ethoxy)ethoxy)ethyl)-1-methyl-5-oxo-2-(pyridin-3-yl)pyrrolidine-3-carboxamide. | 968.5 $(M + H)^+$ | $^1H$ NMR (400 MHz, METHANOL-$d_4$) δ ppm 1.01 (d, J = 6.4 Hz, 3H) 1.12 (br d, J = 6.4 Hz, 3 H) 1.61 - 1.84 (m, 3H) 1.94 - 2.06 (m, 1H) 2.06 - 2.36 (m, 8H) 2.39 (t, J = 6.1 Hz, 2H) 2.52 - 2.62 (m, 3H) 2.66 (s, 3 H) 2.67 - 2.75 (m, 2H) 2.77 - 2.90 (m, 1H) 2.95 - 3.15 (m, 2H) 3.27 - 3.32 (m, 1H) 3.34 - 3.65 (m, 14H) 3.68 (t, J = 6.1 Hz, 2H) 4.05 (dt, J = 12.3, 3.6 Hz, 1H) 4.41 (quin, J = 7.5 Hz, 1H) 4.63 (br d, J = 2.9 Hz, 1H) 4.82 (d, J = 6.8 Hz, 1H) 5.32 (t, J = 8.6 Hz, 1H) 7.53 (dd, J = 7.3, 4.9 Hz, 1H) 7.80 (dt, J = 8.1, 1.8 Hz, 1H) 7.91 (d, J = 8.3 Hz, 1H) 8.06 (dd, J = 8.8, 2.0 Hz, 1H) 8.52 (d, J = 2.0 Hz, 1 H) 8.57 (dd, J = 4.9, 1.5 Hz, 1H) 8.59 (s, 1H) 8.77 (s, 1H). |
| 28 | 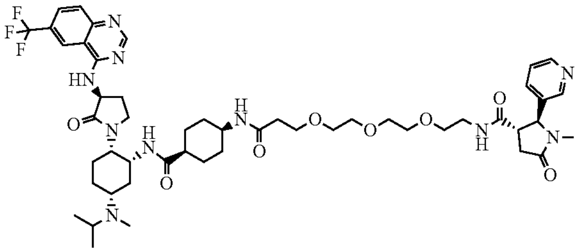 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCOCCNC(=O)[C@H]3CC(=O)N(C)[C@@H]3c3cccnc3)CC2)C1] (2S,3S)-N-(2-(2-(2-(3-(((1S,4s)-4-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl)amino)-3-oxopropoxy)ethoxy)ethoxy)ethyl)-1-methyl-5-oxo-2-(pyridin-3-yl)pyrrolidine-3-carboxamide. | 995.3 $(M + H)^+$ | $^1H$ NMR (400 MHz, METHANOL-$d_4$) δ ppm 1.01 (d, J = 6.5 Hz, 3H) 1.16 (d, J = 6.5 Hz, 3H) 1.49 - 2.07 (m, 14H) 2.08 - 2.38 (m, 8H) 2.41 (t, J = 6.3 Hz, 2H) 2.53 - 2.64 (m, 1H) 2.66 (s, 3H) 2.67 - 2.76 (m, 2H) 2.77 - 2.89 (m, 1H) 2.99 - 3.10 (m, 1 H) 3.34 - 3.65 (m, 14H) 3.68 (t, J = 6.3 Hz, 2H) 3.90 (br t, J = 4.0 Hz, 1H) 4.04 (dt, J = 12.2, 3.8 Hz, 1H) 4.60 (br d, J = 3.0 Hz, 1H) 4.78 - 4.82 (m, 1H) 4.85 - 4.89 (m, 1H) 5.30 (t, J = 8.8 Hz, 1H) 7.43 - 7.62 (m, 1H) 7.79 (dt, J = 7.9, 1.8 Hz, 1H) 7.91 (d, J = 8.8 Hz, 1H) 8.06 (dd, J = 8.8, 1.8 Hz, 1H) 8.51 (d, J = 1.8 Hz, 1H) 8.56 (dd, J = 4.9, 1.6 Hz, 1 H) 8.59 (s, 1H) 8.72 (s, 1 H). |
| 29 | 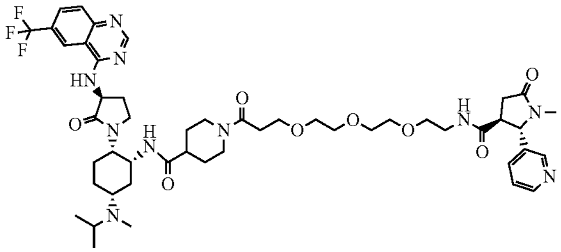 [SMILES: CC(C)N(C)[C@@H]1CC[C@H](N2CC[C@H](Nc3ncnc4ccc(C(F)(F)F)cc34)C2=O)[C@H](NC(=O)C2CCN(C(=O)CCOCCOCCOCCNC(=O)[C@H]3CC(=O)N(C)[C@@H]3c3cccnc3)CC2)C1] N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-1-(1-((2S,3S)-1-methyl-5-oxo-2-(pyridin-3-yl)pyrrolidin-3-yl)-1-oxo-5,8, 11-trioxa-2-azatetradecan-14-oyl)piperidine-4-carboxamide. | 491.7 $(M/2+H)^+$ | $^1H$ NMR (400 MHz, METHANOL-$d_4$) δ ppm 1.04 (br d, J = 6.3 Hz, 2H) 1.16 (br d, J = 6.3 Hz, 3H) 1.47 - 1.81 (m, 5H) 1.82 - 2.03 (m, 3H) 2.05 - 2.94 (m, 15H) 2.94 - 3.20 (m, 2H) 3.24 - 3.32 (m, 1H) 3.34 - 3.78 (m, 15H) 3.98 - 4.13 (m, 2H) 4.46 - 4.69 (m, 2H) 4.82 (dd, J = 6.4, 1.4 Hz, 1H) 5.22 - 5.31 (m, 1H) 7.52 (dd, J = 7.9, 4.9 Hz, 1H) 7.78 - 7.82 (m, 1H) 7.91 (d, J = 8.8 Hz, 1H) 8.06 (d, J = 8.8 Hz, 1H) 8.51 (s, 1H) 8.55 - 8.58 (m, 1H) 8.60 (s, 1 H) 8.78 (s, 1H). |

-continued

| Ex. | Compound | LC-MS m/z | NMR |
|---|---|---|---|
| 30 | 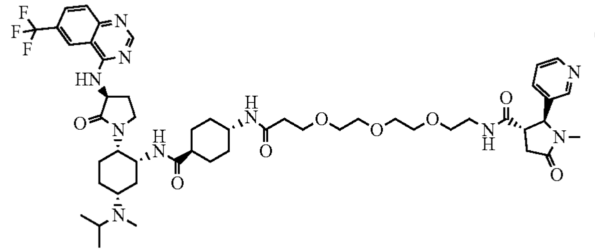 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCOCCOCCOCCNC(=O)[C@H]3CC(=O)N(C)[C@@H]3c3cccnc3)CC2)C1] (2S,3S)-N-(2-(2-(2-(3-(((1R,4r)-4-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl)amino)-3-oxopropoxy)ethoxy)ethoxy)ethyl)-1-methyl-5-oxo-2-(pyridin-3-yl)pyrrolidine-3-carboxamide. | 996.4 (M + H)+ | $^1$H NMR (400 MHz, METHANOL-$d_4$) δ ppm 1.03 (br d, J = 6.0 Hz, 3H) 1.17 (br d, J = 6.3 Hz, 3H) 1.21 − 1.34 (m, 2H) 1.46 − 1.86 (m, 6H) 1.87 − 2.45 (m, 15H) 2.48 − 2.60 (m, 1H) 2.66 (s, 3H) 2.68 − 2.77 (m, 2H) 2.79 − 2.90 (m, 1H) 3.00 − 3.10 (m, 1 H) 3.26 − 3.32 (m, 1H) 3.34 − 3.74 (m, 16H) 4.03 (dt, J = 12.2, 3.4 Hz, 1H) 4.53 − 4.71 (m, 1H) 4.82 (d, J = 6.5 Hz, 1H) 5.24 − 5.31 (m, 1H) 7.51 − 7.56 (m, 1H) 7.80 (dt, J = 8.0, 1.9 Hz, 1H) 7.91 (d, J = 8.8 Hz, 1H) 8.07 (dd, J = 8.9, 1.9 Hz, 1H) 8.52 (d, J = 1.8 Hz, 1H) 8.57 (dd, J = 4.9, 1.6 Hz, 1H) 8.60 (s, 1H) 8.81 (s, 1H). |
| 31 | 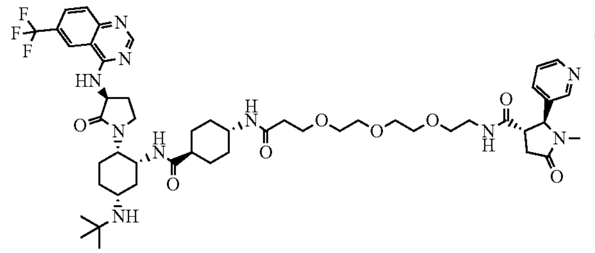 [SMILES: CN1C(=O)C[C@H](C(=O)NCCOCCOCCOCCC(=O)N[C@H]2CC[C@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] (2S,3S)-N-(2-(2-(2-(3-(((1S,4s)-4-(((1R,2S,5R)-5-(tert-Butylamino)-2-((S)-2-oxo-3-((6-(trifluoromethyl) quinazolin-4-yl)amino)pyrrolidin-1-yl)cyclohexyl)carbamoyl)cyclohexyl)amino)-3-oxopropoxy)ethoxy)ethoxy)ethyl)-1-methyl-5-oxo-2-(pyridin-3-yl)pyrrolidine-3-carboxamide. | 996.5 (M + H)+ | $^1$H NMR (400 MHz, METHANOL-$d_4$) δ ppm 1.11 − 1.39 (m, 12H) 1.50 − 1.80 (m, 5H) 1.80 − 2.09 (m, 10H) 2.10 − 2.32 (m, 2H) 2.39 (t, J = 6.4 Hz, 2 H) 2.48 − 2.62 (m, 1H) 2.66 (s, 3H) 2.67 − 2.75 (m, 1H) 2.79 − 2.89 (m, 1 H) 3.05 (ddd, J = 9.3, 8.1, 6.6 Hz, 1H) 3.23 (br s, 1 H) 3.27 − 3.32 (m, 1H) 3.36 − 3.75 (m, 16H) 3.99 (dt, J = 12.6, 3.5 Hz, 1H) 4.64 (br d, J = 2.9 Hz, 1H) 4.82 (d, J = 6.4 Hz, 1H) 5.29 (t, J = 8.1 Hz, 1H) 7.51 − 7.56 (m, 1H) 7.80 (dt, J = 8.3, 2.0 Hz, 1H) 7.91 (d, J = 8.8 Hz, 1H) 8.07 (dd, J = 9.0, 1.7 Hz, 1 H) 8.52 (d, J = 2.0 Hz, 1H) 8.57 (dd, J = 4.9, 2.0 Hz, 1 H) 8.59 (s, 1H) 8.83 (s, 1 H). |
| 32 | 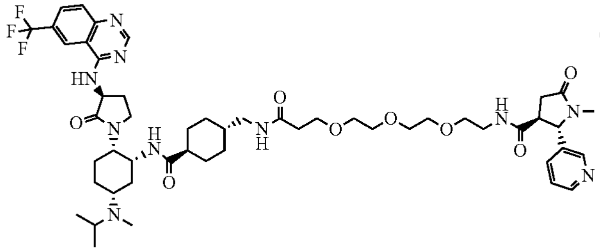 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](CNC(=O)CCOCCOCCOCCNC(=O)[C@H]3CC(=O)N(C)[C@@H]3c3cccnc3)CC2)C1] (2S,3S)-N-(1-((1S,4s)-4-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl)-3-oxo-6,9, 12-trioxa-2-azatetradecan-14-yl)-1-methyl-5-oxo-2-(pyridin-3-yl)pyrrolidine-3-carboxamide. | 1009.3 (M + H)+ | $^1$H NMR (400 MHz, METHANOL-$d_4$) δ ppm 1.02 (br d, J = 6.4 Hz, 3H) 1.15 (br d, J = 6.4 Hz, 3H) 1.41 − 1.54 (m, 3H) 1.63 − 1.77 (m, 3H) 1.78 − 2.04 (m, 5H) 2.04 − 2.16 (m, 2 H) 2.16 − 2.25 (m, 1H) 2.26 (s, 3H) 2.33 (br d, J = 15.2 Hz, 1H) 2.42 (t, J = 6.1 Hz, 2H) 2.48 − 2.60 (m, 1H) 2.66 (s, 3H) 2.67 − 2.75 (m, 2H) 2.79 − 2.90 (m, 1H) 3.00 − 3.08 (m, 3 H) 3.27 − 3.32 (m, 1H) 3.33 − 3.66 (m, 16H) 3.69 (t, J = 6.1 Hz, 2H) 4.03 (dt, J = 12.5, 3.8 Hz, 1H) 4.66 (br d, J = 2.9 Hz, 1H) 4.83 (d, J = 6.8 Hz, 1H) 5.27 (t, J = 7.8 Hz, 1H) 7.52 (dd, J = 7.8, 4.9 Hz, 1H) 7.80 (dt, J = 7.8, 2.0 Hz, 1H) 7.91 (d, J = 8.8 Hz, 1H) |

-continued

| Ex. | Compound | LC-MS m/z | NMR |
|---|---|---|---|
| | | | 8.06 (dd, J = 8.8, 2.0 Hz, 1 H) 8.52 (d, J = 2.0 Hz, 1H) 8.57 (dd, J = 4.9, 1.5 Hz, 1 H) 8.59 (s, 1H) 8.82 (s, 1 H). |
| 33 | 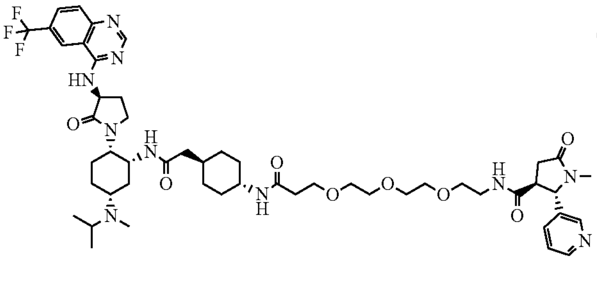 [SMILES: CC(C)N(C)[C@@H]1CC[C@H](N2CC[C@H](Nc3ncnc4ccc(C(F)(F)F)cc34)C2=O)[C@H](NC(=O)C[C@H]2CC[C@H](NC(=O)CCOCCOCCOCCNC(=O)[C@H]3CC(=O)N(C)[C@@H]3c3cccnc3)CC2)C1] (2S,3S)-N-(2-(2-(2-(3-(((1R,4r)-4-(2-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)amino)-2-oxoethyl)cyclohexyl) amino)-3-oxopropoxy)ethoxy)ethoxy)ethyl)-1-methyl-5-oxo-2-(pyridin-3-yl)pyrrolidine-3-carboxamide. | 1009.3 (M + H)+ | $^1$H NMR (400 MHz, METHANOL-$d_4$) δ ppm 1.03 (d, J = 6.4 Hz, 3H) 1.15 (br d, J = 6.4 Hz, 3H) 1.61 - 2.03 (m, 10H) 2.03 - 2.25 (m, 5H) 2.27 (s, 3 H) 2.31 (br d, J = 14.2 Hz, 1H) 2.38 (t, J = 6.4 Hz, 2 H) 2.49 - 2.59 (m, 1H) 2.66 (s, 3H) 2.67 - 2.76 (m, 2H) 2.81 - 2.88 (m, 1 H) 3.06 (ddd, J = 9.3, 8.1, 6.6 Hz, 1H) 3.21 - 3.21 (m, 1H) 3.28 - 3.66 (m, 20 H) 3.69 (t, J = 6.1 Hz, 2 H) 4.05 (dt, J = 12.2, 3.7 Hz, 1H) 4.64 (br d, J = 2.9 Hz, 1H) 4.83 (d, J = 6.8 Hz, 1H) 5.26 (t, J = 8.1 Hz, 1H) 7.53 (dd, J = 7.8, 4.9 Hz, 1H) 7.80 (dt, J = 7.8, 2.0 Hz, 1H) 7.91 (d, J = 8.8 Hz, 1H) 8.06 (dd, J = 8.8, 2.0 Hz, 1H) 8.52 (d, J = 2.0 Hz, 1H) 8.57 (dd, J = 4.6, 1.7 Hz, 1H) 8.60 (s, 1H) 8.80 (s, 1H). |
| 34 | 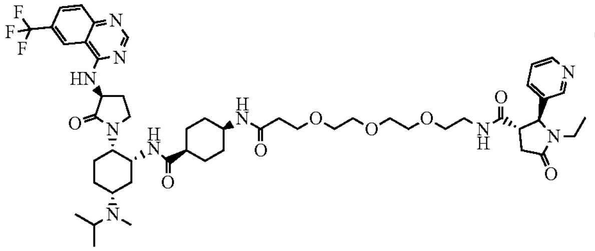 [SMILES: CCN1C(=O)C[C@H](C(=O)NCCOCCOCCOCCC(=O)N[C@H]2CC[C@@H](C(=O)N[C@@H]3C[C@H](N(C)C(C)C)CC[C@@H]3N3CC[C@H](Nc4ncnc5ccc(C(F)(F)F)cc45)C3=O)CC2)[C@H]1c1cccnc1] (2S,3S)-1-ethyl-N-(2-(2-(2-(3-((cis-4-(((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)carbamoyl)cyclohexyl)amino)-3-oxopropoxy)ethoxy)ethoxy)ethyl)-5-oxo-2-(pyridin-3-yl)pyrrolidine-3-carboxamide | 1009.5 (M + H)+ | $^1$H NMR (400 MHz, METHANOL-$d_4$) δ ppm 8.71 (s, 1H), 8.50 - 8.60 (m, 3H), 8.05 (dd, J = 8.87, 1.77 Hz, 1H), 7.89 (d, J = 8.87 Hz, 1H), 7.81 (dt, J = 8.05, 1.93 Hz, 1H), 7.50 (dd, J = 7.98, 4.94 Hz, 1H), 5.29 (t, J = 8.74 Hz, 1H), 4.58 (br. s., 1H), 4.02 (d, J = 12.42 Hz, 1H), 3.88 (br. s., 1H), 3.39 - 3.70 (m, 19H), 3.04 (td, J = 8.05, 6.97 Hz, 1H), 2.49 - 2.87 (m, 5H), 2.07 - 2.43 (m, 9H), 1.52 - 1.98 (m, 12H), 1.14 (d, J = 6.59 Hz, 3H), 0.93 - 1.04 (m, 6H) |
| 35 | 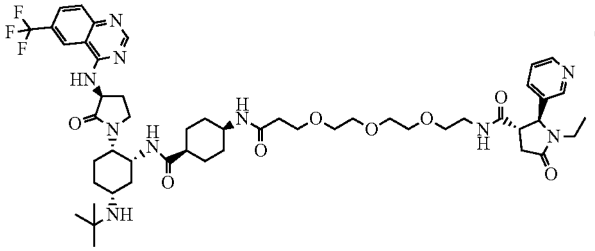 [SMILES: CCN1C(=O)C[C@H](C(=O)NCCOCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] (2S,3S)-N-(2-(2-(2-(3-(((1S,4s)-4-(((1R,2S,5R)-5-(tert-butylamino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethoxy)ethyl)-1-ethyl-5-oxo-2-(pyridin-3-yl)pyrrolidine-3-carboxamide | 1009.0 (M + H)+ | $^1$H NMR (400 MHz, METHANOL-$d_4$) δ ppm 1.01 (t, J = 7.34 Hz, 3H) 1.19 (s, 7H) 1.52 - 1.99 (m, 13H) 2.22 - 2.45 (m, 4H) 2.54 - 2.77 (m, 3H) 2.78 - 2.90 (m, 1H) 3.02 - 3.11 (m, 1H) 3.23 (br d, J = 2.93 Hz, 1H) 3.34 - 3.40 (m, 7H) 3.44 - 3.72 (m, 13H) 3.87 - 4.07 (m, 2H) 4.59 (br d, J = 2.45 Hz, 1H) 4.95 (d, J = 6.36 Hz, 1H) 5.32 (br t, J = 8.56 Hz, 1H) 7.46 - 7.56 (m, 1H) 7.82 (br d, J = 8.80 Hz, 1H) 8.02 - J = 7.83 Hz, 1H) 7.91 (d, 8.11 (m, 1H) 8.47 - 8.66 (m, 3H) 8.73 (s, 1H) |

Example 36

(2S,3S)-N-(27-(((1R,2S,5R)-5-(tert-Butylamino)-2-((S)-2-oxo-3-((6-(trifluoromethyl) quinazolin-4-yl) amino)pyrrolidin-1-yl)cyclohexyl)amino)-27-oxo-3,6,9,12,15,18,21,24-octaoxaheptacosyl)-1-methyl-5-oxo-2-(pyridin-3-yl)pyrrolidine-3-carboxamide

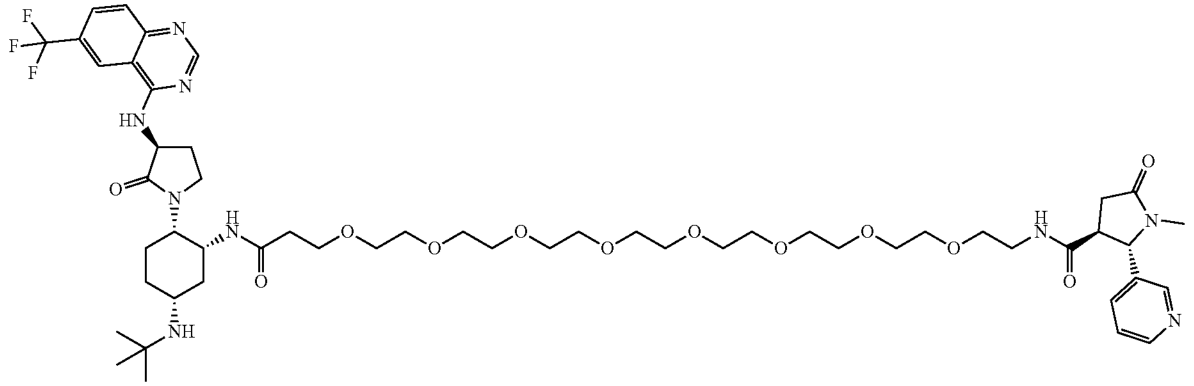 [SMILES: CN1C(=O)C[C@H](C(=O)NCCOCCOCCOCCOCCOCCOCCOCCOCCC(=O)N[C@@H]2C[C@H](NC(C)(C)C)CC[C@@H]2N2CC[C@H](Nc3ncnc4ccc(C(F)(F)F)cc34)C2=O)[C@H]1c1cccnc1]

Step 1

1-((2S,3S)-1-Methyl-5-oxo-2-(pyridin-3-yl)pyrrolidin-3-yl)-1-oxo-5,8,11,14,17,20,23,26-octaoxa-2-azanonacosan-29-oic acid, Trifluoroacetic acid salt

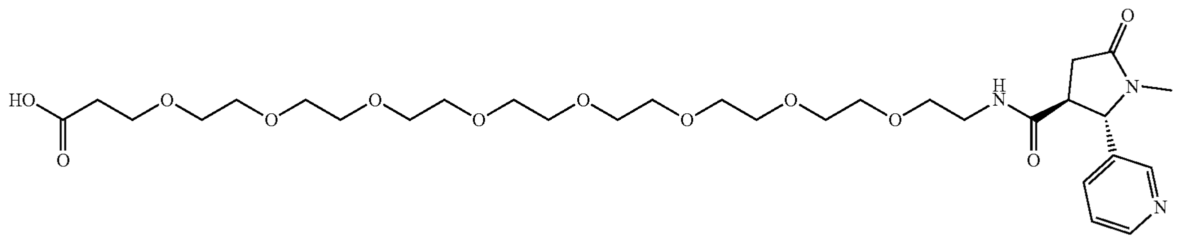 [SMILES: CN1C(=O)C[C@H](C(=O)NCCOCCOCCOCCOCCOCCOCCOCCOCCC(=O)O)[C@H]1c1cccnc1]

To a mixture of (2S,3S)-1-methyl-5-oxo-2-(pyridin-3-yl) pyrrolidine-3-carboxylic acid (252 mg, 1.144 mmol) and N,N-dimethylformamide (DMF) (1 mL) was added DIPEA (0.600 mL, 3.43 mmol) and 2-(2,5-dioxopyrrolidin-1-yl)-1,1,3,3-tetramethylisouronium tetrafluoroborate (344 mg, 1.144 mmol), and the mixture was stirred at rt for 2 h. A slurry of commercially-available 1-amino-3,6,9,12,15,18,21,24-octaoxaheptacosan-27-oic acid (505 mg, 1.144 mmol) in N,N-dimethylformamide (DMF) (1 mL) was added and the mixture was stirred at rt for 2 h. Purification by Gilson® reverse-phase chromatography (acidic Luna® column, 47 mL/min) eluting with a gradient of 5 to 25% acetonitrile in water containing TFA (0.1%) provided the title compound as a colorless oil (865 mg, 1.142 mmol, 100% yield). LC-MS m/z 644.2 $(M+H)^+$.

Step 2

(2S,3S)-N-(27-(((1R,2S,5R)-5-(tert-Butylamino)-2-((S)-2-oxo-3-((6-(trifluoromethyl) quinazolin-4-yl) amino)pyrrolidin-1-yl)cyclohexyl)amino)-27-oxo-3,6,9,12,15,18,21,24-octaoxaheptacosyl)-1-methyl-5-oxo-2-(pyridin-3-yl)pyrrolidine-3-carboxamide

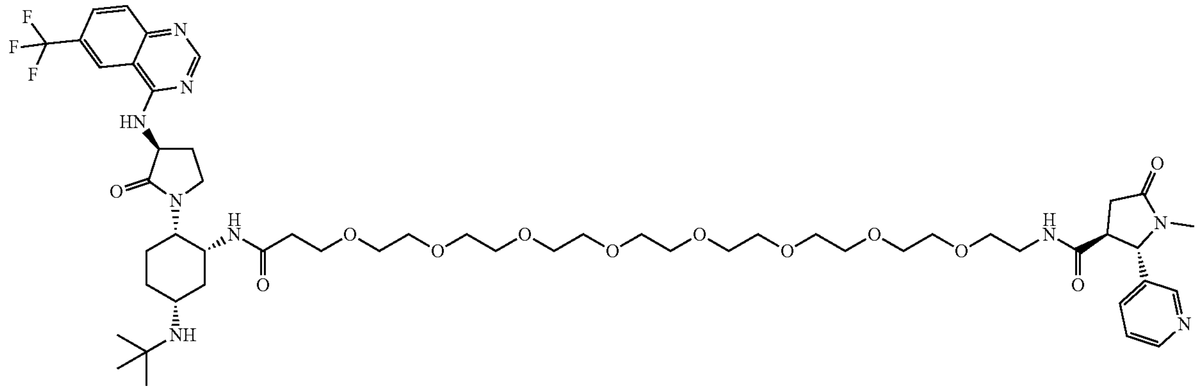 [SMILES: CN1C(=O)C[C@H](C(=O)NCCOCCOCCOCCOCCOCCOCCOCCOCCC(=O)N[C@@H]2C[C@H](NC(C)(C)C)CC[C@@H]2N2CC[C@H](Nc3ncnc4ccc(C(F)(F)F)cc34)C2=O)[C@H]1c1cccnc1]

To a mixture of 1-((2S,3S)-1-methyl-5-oxo-2-(pyridin-3-yl)pyrrolidin-3-yl)-1-oxo-5,8,11,14,17,20,23,26-octaoxa-2-azanonacosan-29-oic acid, trifluoroacetic acid salt (860 mg, 1.135 mmol) and dichloromethane (DCM) (2 mL) was added (S)-1-((1S,2R,4R)-2-amino-4-(tert-butylamino)cyclohexyl)-3-((6-(trifluoromethyl)quinazolin-4-yl)amino) pyrrolidin-2-one (527 mg, 1.135 mmol), DIPEA (0.793 mL, 4.54 mmol) and HATU (518 mg, 1.362 mmol), and the mixture was stirred at rt for 1 h. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (80 g RediSep Rf Gold® column) eluting with a gradient of 0 to 15% methanol containing ammonia hydroxide (10%) in dichloromethane (DCM) provided the title compound (800 mg, 0.734 mmol, 64.7% yield). LC-MS m/z 545.9 $(M/2)^+$. $^1H$ NMR (400 MHz, METHANOL-$d_4$) b ppm 1.20 (s, 9H) 1.30 (br d, J=6.4 Hz, 4H) 1.69-1.80 (m, 2H) 1.82-1.93 (m, 4H) 2.26 (qd, J=12.3, 5.5 Hz, 1H) 2.47-2.53 (m, 3H) 2.67 (s, 3H) 2.68-2.76 (m, 1H) 2.78-2.95 (m, 1H) 3.02-3.09 (m, 1H) 3.22-3.27 (m, 1H) 3.37 (s, 12H) 3.48-3.59 (m, 18H) 3.68-3.77 (m, 2H) 3.85 (ddd, J=9.5, 7.5, 5.0 Hz, 1H) 4.02 (dt, J=12.4, 3.7 Hz, 1H) 4.64 (br d, J=2.9 Hz, 1H) 4.83 (d, J=6.6 Hz, 2H) 5.31 (t, J=8.1 Hz, 1H) 7.51-7.56 (m, 1H) 7.81 (dt, J=8.0, 1.9 Hz, 1H) 7.91 (d, J=8.8 Hz, 1H) 8.06 (dd, J=8.8, 2.0 Hz, 1H) 8.52 (d, J=1.7 Hz, 1H) 8.58 (dd, J=4.9, 1.7 Hz, 1H) 8.60 (s, 1H) 8.86 (d, J=0.7 Hz, 1H).

The following compounds were or could be prepared with procedures analogous to that described in Example 36:

| Ex. | Compound | LC-MC m/z | NMR |
|---|---|---|---|
| 37 | 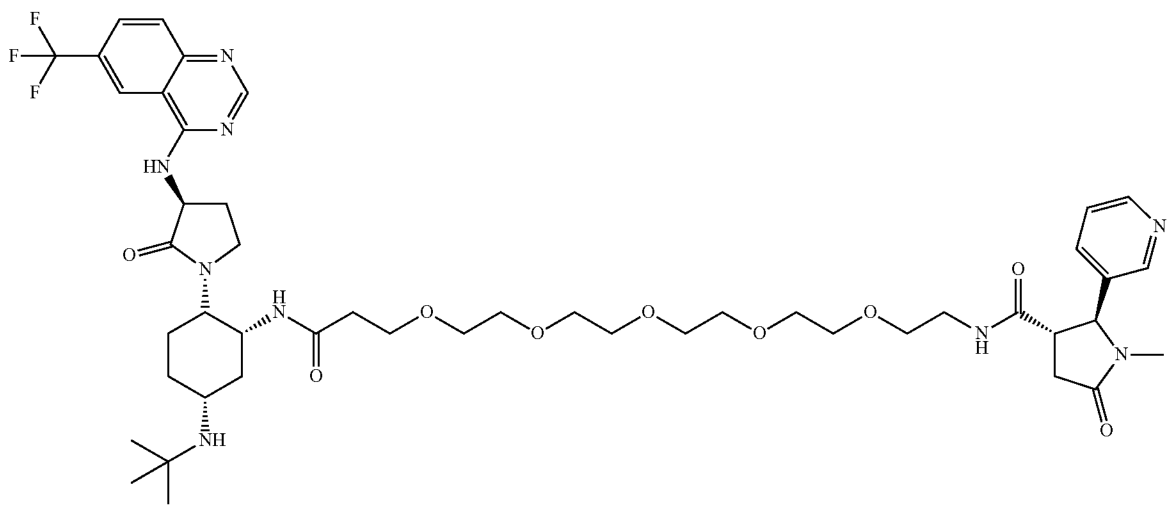 (2S,3S)-N-(18-(((1R,2S,5R)-5-(tert-Butylamino)-2-((S)-2-oxo-3-((6-(trifluoromethyl)quinazolin-4-yl)amino)pyrrolidin-1-yl)cyclohexyl)amino)-18-oxo-3,6,9,12,15-pentaoxaoctadecyl)-1-methyl-5-oxo-2-(pyridin-3-yl)pyrrolidine-3-carboxamide. | 958.5 $(M + H)^+$ | $^1$H NMR (400 MHz, METHANOL-$d_4$) δ ppm 1.19 (s, 9H) 1.69-1.82 (m, 2H) 1.84-2.01 (m, 4 H) 2.19-2.33 (m, 1H) 2.41-2.59 (m, 3H) 2.66 (s, 3H) 2.67-2.75 (m, 1 H) 2.78-2.90 (m, 1H) 3.00-3.09 (m, 1H) 3.21-3.31 (m, 1H) 3.36-3.64 (m, 23H) 3.68-3.79 (m, 2H) 3.84 (dq, J = 7.4, 4.8 Hz, 1H) 4.02 (dt, J = 12.7, 3.7 Hz, 1H) 4.64 (br d, J = 3.0 Hz, 1H) 4.84 (d, J = 4.3 Hz, 1H) 5.31 (t, J = 8.0 Hz, 1H) 7.50-7.55 (m, 1H) 7.80 (dt, J = 7.9, 2.0 Hz, 1H) 7.91 (d, J = 8.6 Hz, 1H) 8.06 (dd, J = 8.9, 2.0 Hz, 1H) 8.52 (d, J = 1.8 Hz, 1H) 8.57 (dd, J = 4.8, 1.5 Hz, 1H) 8.59 (s, 1H) 8.85 (s, 1H). |

-continued
| Ex. | Compound | LC-MC m/z | NMR |
| --- | --- | --- | --- |
| 38 | 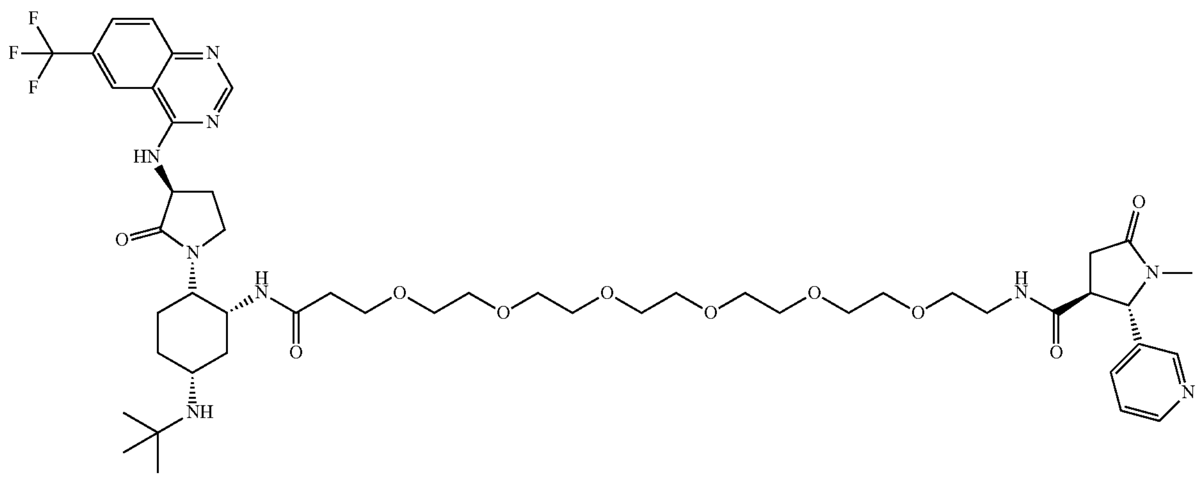 (2S,3S)-N-(21-(((1R,2S,5R)-5-(tert-Butylamino)-2-((S)-2-oxo-3-((6-(trifluoromethyl)quinazolin-4-yl)amino)pyrrolidin-1-yl)cyclohexyl)amino)-21-oxo-3,6,9,12,15,18-hexaoxahenicosyl)-1-methyl-5-oxo-2-(pyridin-3-yl)pyrrolidine-3-carboxamide. | 1002.5 $(M + H)^+$ | $^1H$ NMR (400 MHz, METHANOL-$d_4$) δ ppm 1.02-1.36 (m, 9H), 1.66-2.07 (m, 6H), 2.14-2.30 (m, 1H), 2.41-2.74 (m, 7H), 2.82 (d, J = 9.4 Hz, 1H), 2.99-3.10 (m, 1H), 3.26 (d, J = 15.5 Hz, 1H), 3.36-3.89 (m, 29H), 4.02 (d, J = 12.4 Hz, 1H), 4.64 (d, J = 2.5 Hz, 1H), 4.78-4.85 (m, 2H), 5.31-5.41 (m, 1H), 7.53 (dd, J = 7.9, 4.8 Hz, 1H), 7.80 (dt, J = 8.0, 2.0 Hz, 1H), 7.91 (d, J = 8.6 Hz, 1H), 8.06 (dd, J = 8.9, 1.8 Hz, 1H), 8.48-8.68 (m, 3H), 8.65 (s, 1H) |

-continued

| Ex. | Compound | LC-MC m/z | NMR |
|---|---|---|---|
| 39 | 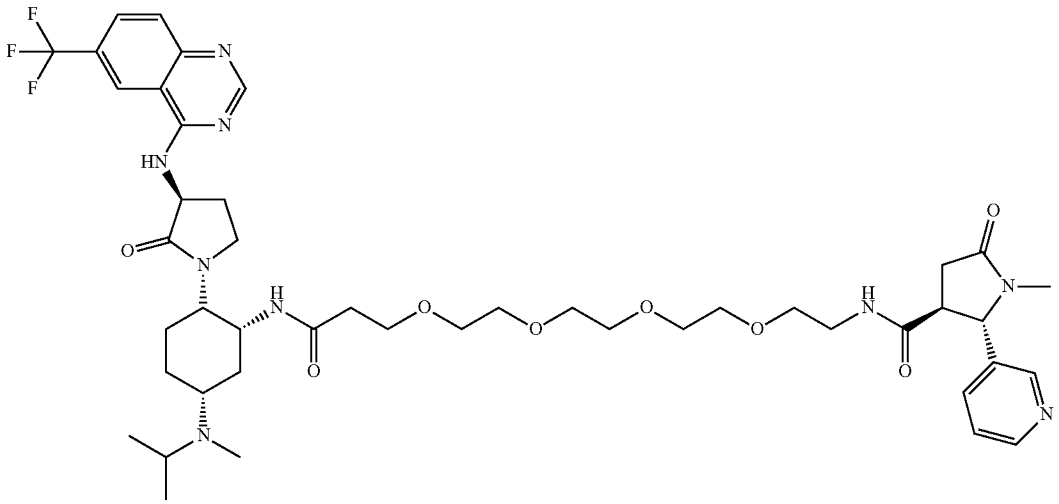 (2S,3S)-N-(15-(((1R,2S,5R)-5-(Isopropyl (methyl)amino)-2-((S)-2-oxo-3-((6-(trifluoromethyl)quinazolin-4-yl)amino)pyrrolidin-1-yl)cyclohexyl)amino)-15-oxo-3,6,9,12-tetraoxapentadecyl)-1-methyl-5-oxo-2-(pyridin-3-yl)pyrrolidine-3-carboxamide. | 914.4 $(M + H)^+$ | $^1$H NMR (400 MHz, METHANOL-$d_4$) δ ppm 1.04 (d, J = 6.3 Hz, 3H) 1.13 (d, J = 6.5 Hz, 3H) 1.61-1.82 (m, 3H) 1.96 (dq, J = 12.5, 7.8 Hz, 1H) 2.05-2.17 (m, 1H) 2.19-2.24 (m, 1H) 2.27 (s, 3 H) 2.29-2.37 (m, 1H) 2.46 (t, J = 5.8 Hz, 2H) 2.49-2.59 (m, 1H) 2.66 (s, 3H) 2.68-2.76 (m, 2 H) 2.77-2.89 (m, 1H) 3.04 (ddd, J = 9.3, 8.0, 6.5 Hz, 1H) 3.19-3.31 (m, 1 H) 3.35-3.60 (m, 17H) 3.64-3.76 (m, 2H) 3.81 (dt, J = 9.7, 6.1 Hz, 1H) 4.05 (dt, J = 12.4, 3.6 Hz, 1H) 4.66 (br d, J = 3.3 Hz, 1H) 4.81 (s, 1H) 5.29 (t, J = 8.0 Hz, 1H) 5.51 (s, 1 H) 7.51 (t, J = 6.3 Hz, 1H) 7.79 (dt, J = 7.8, 2.0 Hz, 1 H) 7.90 (d, J = 8.8 Hz, 1H) 8.05 (dd, J = 8.9, 1.9 Hz, 1 H) 8.51 (d, J = 1.8 Hz, 1H) 8.56 (dd, J = 4.9, 1.6 Hz, 1 H) 8.59 (s, 1H) 8.84 (s, 1 H). |

-continued

| Ex. | Compound | LC-MC m/z | NMR |
|---|---|---|---|
| 40 | 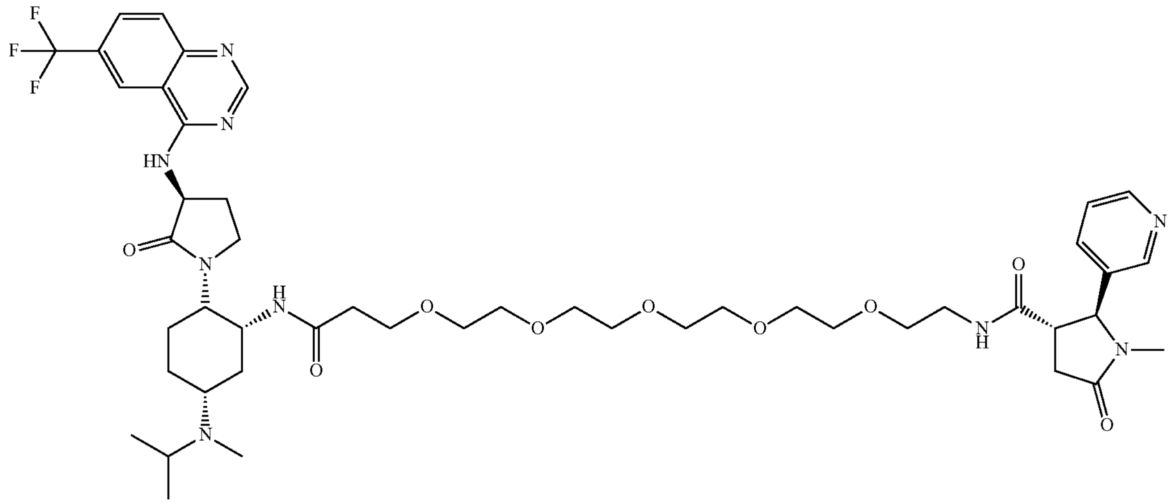 (2S,3S)-N-(18-(((1R,2S,5R)-5-(Isopropyl (methyl)amino)-2-((S)-2-oxo-3-((6-(trifluoromethyl) quinazolin-4-yl)amino)pyrrolidin-1-yl) cyclohexyl)amino)-18-oxo-3,6,9,12,15-pentaoxaoctadecyl)-1-methyl-5-oxo-2-(pyridin-3-yl)pyrrolidine-3-carboxamide. | 958.7 $(M + H)^+$ | $^1H$ NMR (400 MHz, METHANOL-$d_4$) δ ppm 1.04 (d, J = 6.5 Hz, 3H) 1.13 (d, J = 6.5 Hz, 3H) 1.63-1.78 (m, 3H) 1.91-2.01 (m, 1H) 2.05-2.17 (m, 1H) 2.19-2.25 (m, 1 H) 2.27 (s, 3H) 2.29-2.37 (m, 1H) 2.44-2.48 (m, 2H) 2.49-2.58 (m, 1 H) 2.66 (s, 3H) 2.67-2.77 (m, 2H) 2.79-2.90 (m, 1H) 3.05 (ddd, J = 9.3, 8.0, 6.5 Hz, 1H) 3.34-3.64 (m, 23H) 3.65-3.75 (m, 2H) 3.79-3.85 (m, 1 H) 4.05 (dt, J = 12.5, 3.6 Hz, 1H) 4.66 (br d, J = 3.3 Hz, 1H) 4.80-4.85 (m, 2 H), 5.30 (t, J = 8.0 Hz, 1H) 7.50-7.54 (m, 1H) 7.79 (dt, J = 8.0, 1.9 Hz, 1H) 7.90 (d, J = 8.8 Hz, 1H) 8.05 (dd, J = 8.9, 1.9 Hz, 1 H) 8.52 (d, J = 1.8 Hz, 1H) 8.57 (dd, J = 4.9, 1.6 Hz, 1 H), 8.59 (s, 1H) 8.84 (s, 1 H). |

-continued

| Ex. | Compound | LC-MC m/z | NMR |
|---|---|---|---|
| 41 | 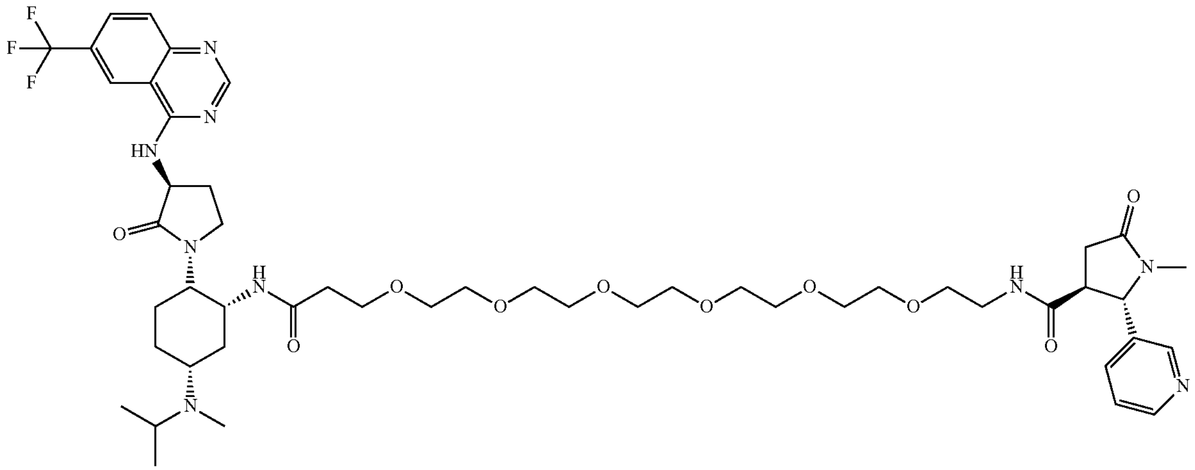 (2S,3S)-N-(21-(((1R,2S,5R)-5-(isopropyl(methyl) amino)-2-((S)-2-oxo-3-((6-(trifluoromethyl) quinazolin-4-yl)amino)pyrrolidin-1-yl)cyclohexyl) amino)-21-oxo-3,6,9,12,15,18-hexaoxahenicosyl)-1-methyl-5-oxo-2-(pyridin-3-yl)pyrrolidine-3-carboxamide | 1002.6 $(M + H)^+$ | $^1$H NMR (400 MHz, METHANOL-$d_4$) δ ppm 1.04 (d, J = 6.5 Hz, 3H) 1.14 (d, J = 6.5 Hz, 3H) 1.63-1.78 (m, 3H) 1.91-2.01 (m, 1H) 2.03-2.17 (m, 2H) 2.18-2.25 (m, 1 H) 2.27 (s, 3H) 2.29-2.38 (m, 1H) 2.44-2.48 (m, 2H) 2.49-2.58 (m, 1 H) 2.66 (s, 3H) 2.67-2.76 (m, 2H) 2.78-2.88 (m, 1H) 3.02-3.09 (m, 1 H) 3.26-3.32 (m, 1H) 3.40-3.63 (m, 26H) 3.65-3.75 (m, 2H) 3.79-3.85 (m, 1H) 4.05 (dt, J = 12.5, 3.6 Hz, 1H) 4.66 (br d, J = 3.3 Hz, 1H) 5.30 (t, J = 7.9 Hz, 1H) 7.50-7.55 (m, 1H) 7.79 (dt, J = 8.0, 1.9 Hz, 1H) 7.91 (d, J = 8.5 Hz, 1H) 8.06 (dd, J = 8.9, 1.9 Hz, 1H) 8.52 (d, J = 1.8 Hz, 1H) 8.57 (dd, J = 4.9, 1.6 Hz, 1H) 8.59 (s, 1H) 8.83-8.85 (m, 1H). |
| 42 | 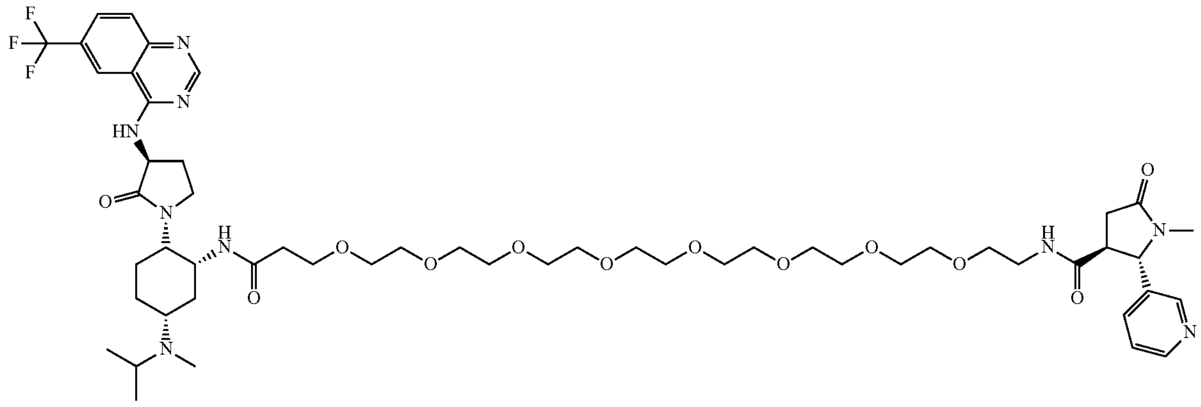 (2S,3S)-N-(27-(((1R,2S,5R)-5-(isopropyl(methyl) | 1091.5 $(M + H)^+$ | $^1$H NMR (400 MHz, METHANOL-$d_4$) δ ppm 1.05 (br d, J = 6.6 Hz, 3H) 1.15 (br d, J = 6.3 Hz, 3H) 1.65-1.78 (m, 3H) 1.92-2.01 (m, 1H) 2.06-2.17 (m, 1H) 2.20-2.27 (m, 1 H) 2.28 (s, 3H) 2.30-2.39 (m, 1H) 2.44-2.49 (m, 2H) 2.49-2.59 (m, 1 H) 2.67 (s, 3H) 2.68-2.77 (m, 2H) 2.80-2.89 (m, 1H) 3.06 (ddd, J = 9.4, 8.1, 6.6 Hz, 1H) 3.26-3.32 (m, 1H) 3.34-3.79 (m, 36H) 3.80-3.86 (m, 1H) 4.06 (dt, J = 12.5, 3.6 Hz, 1H) 4.66 (br d, J = 3.0 Hz, 1H) 4.83 (d, J = 6.6 Hz, 1H) 5.32 (t, J = 8.0 Hz, |

-continued

| Ex. | Compound | LC-MC m/z | NMR |
|---|---|---|---|
| | amino)-2-((S)-2-oxo-3-((6-(trifluoromethyl) quinazolin-4-yl)amino)pyrrolidin-1-yl)cyclohexyl)amino)-27-oxo-3,6,9,12,15,18,21,24-octaoxaheptacosyl)-1-methyl-5-oxo-2-(pyriidn-3-yl)pyrrolidine-3-carboxamide | | 1H) 7.47-7.64 (m, 1H) 7.82 (dt, J = 8.0, 1.9 Hz, 1 H) 7.92 (d, J = 8.6 Hz, 1H) 8.07 (dd, J = 9.0, 1.9 Hz, 1 H) 8.53 (d, J = 1.8 Hz, 1H) 8.58 (dd, J = 4.9, 1.6 Hz, 1 H) 8.60 (s, 1H) 8.85 (s, 1 H). |
| 43 | 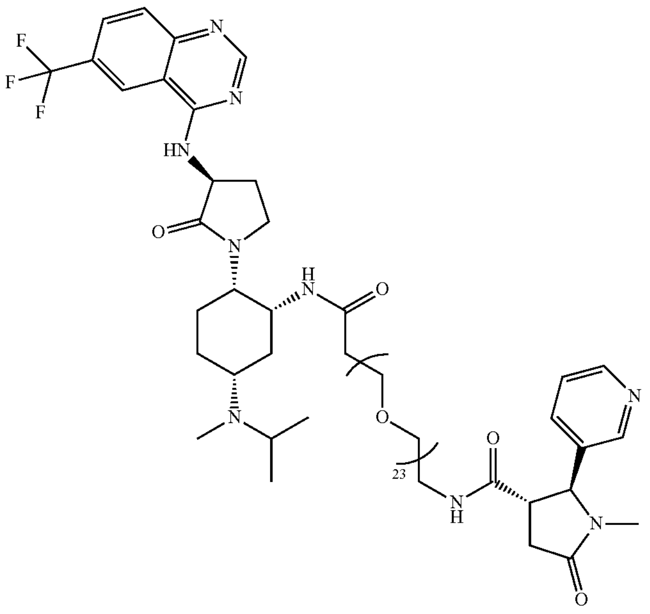 (2R,3R)-N-(72-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-72-oxo-3,6,9,12,15,18,21,24,27,30,33,36,39,42,45,48,51,54,57,60,63,66,69-tricosaoxadoheptacontyl)-1-methyl-5-oxo-2-(pyridin-3-yl)pyrrolidine-3-carboxamide | 876.0 (M/2 + H)$^+$ | $^1$H NMR (400 MHz, METHANOL-$d_4$) δ ppm 1.05 (d, J = 6.4 Hz, 3H) 1.14 (d, J = 6.4 Hz, 3H) 1.64-1.77 (m, 3H) 1.91-2.01 (m, 1H) 2.06-2.17 (m, 1H) 2.20-2.24 (m, 1 H) 2.28 (s, 3H) 2.30-2.39 (m, 1H) 2.44-2.49 (m, 2H) 2.49-2.60 (m, 1 H) 2.67 (s, 3H) 2.69-2.77 (m, 2H) 2.81-2.91 (m, 1H) 3.03-3.12 (m,1 H) 3.25-3.32 (m, 1H) 3.34-3.77 (m, 97H) 3.79-3.86 (m, 1H) 4.06 (dt, J = 12.6, 3.5 Hz, 1H) 4.66 (br d, J = 2.9 Hz, 1H) 5.31 (t, J = 7.8 Hz, 1H) 7.55 (dd, J = 7.8, 4.9 Hz, 1H) 7.82 (dt, J = 8.2, 1.8 Hz, 1 H) 7.91 (d, J = 8.8 Hz, 1H) 8.07 (dd, J = 8.8, 2.0 Hz, 1 H) 8.52-8.56 (m, 1H) 8.59 (dd, J = 4.9, 2.0 Hz, 1 H) 8.60 (s, 1H) 8.85 (s, 1 H) |

Example 44

(2S,3S)-N-(2-(3-((2-(3-(((1S,3s)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclobutyl)amino)-3-oxopropoxy)ethyl)amino)-3-oxopropoxy)ethyl)-1-methyl-5-oxo-2-(pyridin-3-yl)pyrrolidine-3-carboxamide

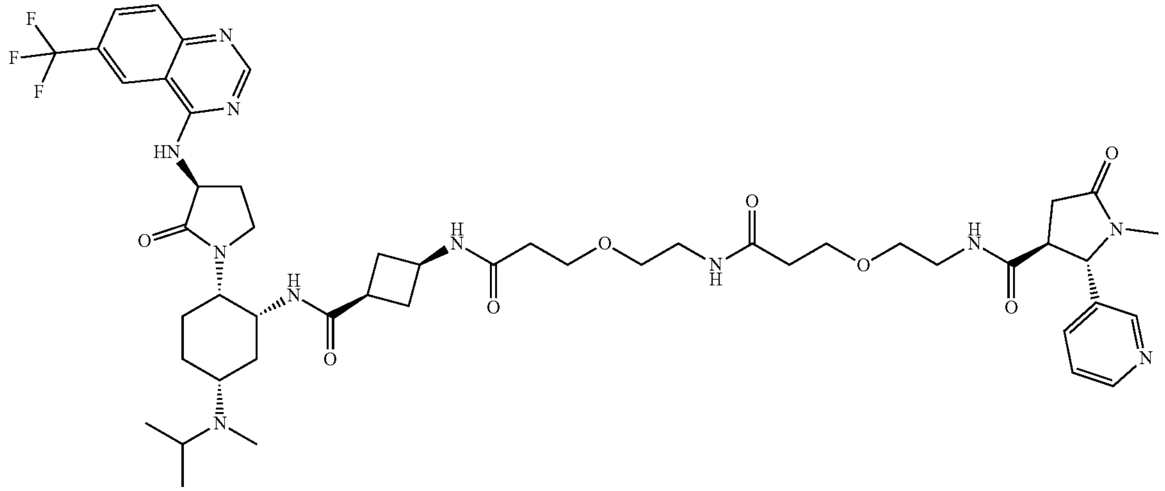 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCNC(=O)CCOCCNC(=O)[C@H]3CC(=O)N(C)[C@@H]3c3cccnc3)C2)C1]

Step 1 tert-Butyl 3-(2-((2S,3S)-1-methyl-5-oxo-2-(pyridin-3-yl)pyrrolidine-3-carboxamido) ethoxy)propanoate

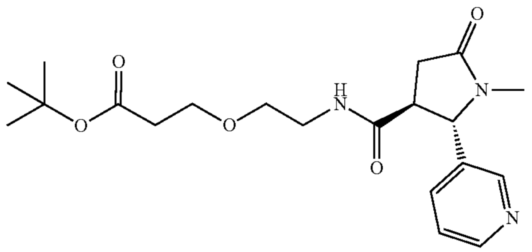 [SMILES: CN1C(=O)C[C@H](C(=O)NCCOCCC(=O)OC(C)(C)C)[C@H]1c1cccnc1]

To a mixture of (2S,3S)-1-methyl-5-oxo-2-(pyridin-3-yl) pyrrolidine-3-carboxylic acid (235 mg, 1.067 mmol) and commercially-available tert-butyl 3-(2-aminoethoxy)propanoate (202 mg, 1.067 mmol) in dichloromethane (DCM) (4 mL) was added HATU (487 mg, 1.281 mmol) and triethylamine (0.446 mL, 3.20 mmol) and the mixture was stirred at rt for 3 h. Purification by ISCO CombiFlash® chromatography (40 g RediSep Rf Gold® column, 40 mL/min) eluting with a gradient of 0 to 15% methanol containing ammonium chloride (10%) in dichloromethane (DCM) provided the title compound (465 mg, 1.188 mmol, 111% yield). LC-MS m/z 392.3 $(M+H)^+$.

Step 2

3-(2-((2S,3S)-1-Methyl-5-oxo-2-(pyridin-3-yl)pyrrolidine-3-carboxamido)ethoxy) propanoic acid, Hydrochloric acid salt

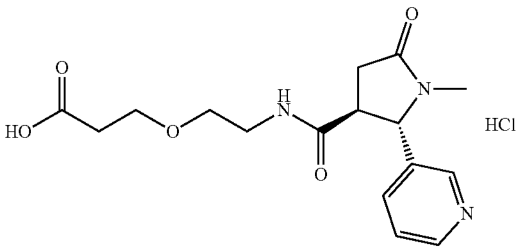 [SMILES: CN1C(=O)C[C@H](C(=O)NCCOCCC(=O)O)[C@H]1c1cccnc1 ; Cl]

A mixture of tert-butyl 3-(2-((2S,3S)-1-methyl-5-oxo-2-(pyridin-3-yl)pyrrolidine-3-carboxamido)ethoxy)propanoate (465 mg, 1.188 mmol). 4 N HCl 1,4-dioxane (1.782 mL, 7.13 mmol), and dichloromethane (0.5 mL) was stirred at rt for 4 h. The mixture was concentrated to dryness to provide the title compound (450 mg, 1.210 mmol, 102% yield). LC-MS m/z 336.1 $(M+H)^+$.

Step 3 tert-Butyl 1-((2S,3S)-1-methyl-5-oxo-2-(pyridin-3-yl)pyrrolidin-3-yl)-1,8-dioxo-5,12-dioxa-2,9-diazapentadecan-15-oate

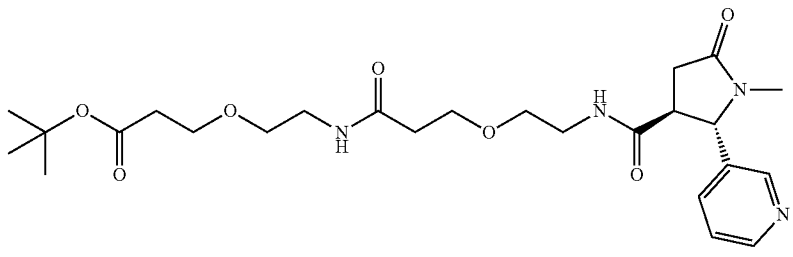 [SMILES: CN1C(=O)C[C@H](C(=O)NCCOCCC(=O)NCCOCCC(=O)OC(C)(C)C)[C@H]1c1cccnc1]

To a mixture of commercially-available tert-butyl 3-(2-aminoethoxy)propanoate (148 mg, 0.780 mmol) and 3-(2-((2S,3S)-1-methyl-5-oxo-2-(pyridin-3-yl)pyrrolidine-3-carboxamido)ethoxy)propanoic acid, hydrochloric acid salt (290 mg, 0.780 mmol) in dichloromethane (DCM) (2 mL) was added EDC (224 mg, 1.170 mmol), HOBt (179 mg, 1.170 mmol) and DIPEA (0.817 mL, 4.68 mmol), and the mixture was stirred at rt overnight. Saturated $NaHCO_3$ was added and the mixture was extracted with dichloromethane (DCM). The combined organic extracts were dried over $Na_2SO_4$, were filtered, and the filtrate was concentrated. Purification by reverse-phase chromatography (50 g C18 Aq Gold column, 40 mL/min) eluting with a gradient of 20 to 55% acetonitrile in water containing ammonium bicarbonate (10 mM) and ammonium hydroxide (0.075%) provided the title compound (225 mg, 56.9%). LC-MS m/z 507.1 $(M+H)^+$.

Step 4

1-((2S,3S)-1-Methyl-5-oxo-2-(pyridin-3-yl)pyrrolidin-3-yl)-1,8-dioxo-5,12-dioxa-2,9-diazapentadecan-15-oic acid, Hydrochloric acid salt

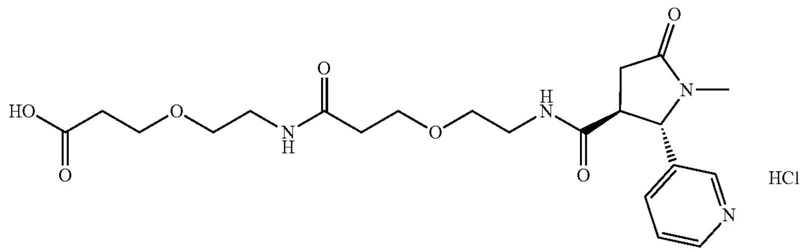 [SMILES: CN1C(=O)C[C@H](C(=O)NCCOCCC(=O)NCCOCCC(=O)O)[C@H]1c1cccnc1 ; Cl]

A mixture of tert-butyl 1-((2S,3S)-1-methyl-5-oxo-2-(pyridin-3-yl)pyrrolidin-3-yl)-1,8-dioxo-5,12-dioxa-2,9-diazapentadecan-15-oate (225 mg, 0.444 mmol), 4 N HCl in 1,4-dioxane (0.666 mL, 2.66 mmol), and dichloromethane (DCM) (0.02 mL) was stirred at rt for 3 h. The mixture was concentrated to provide the title compound (225 mg, 0.462 mmol, 104% yield). LC-MS m/z 451.4 $(M+H)^+$.

Step 5

(2S,3S)-N-(2-(3-((2-(3-(((1S,3s)-3-(((1R,2S,5R)-5-(isopropyl(methyl)amino)-2-((S)-2-oxo-3-((6-(trifluoromethyl)quinazolin-4-yl)amino)pyrrolidin-1-yl) cyclohexyl)carbamoyl) cyclobutyl)amino)-3-oxopropoxy)ethyl)amino)-3-oxopropoxy)ethyl)-1-methyl-5-oxo-2-(pyridin-3-yl)pyrrolidine-3-carboxamide

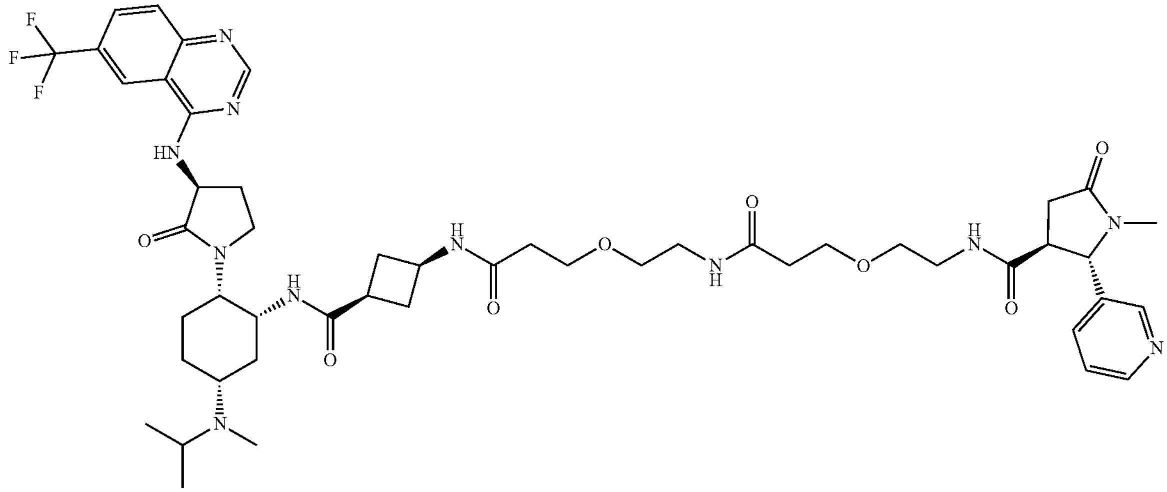 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCNC(=O)CCOCCNC(=O)[C@H]3CC(=O)N(C)[C@@H]3c3cccnc3)C2)C1]

To a mixture of (1 s,3S)-3-amino-N-((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)cyclobutane-1-carboxamide, 2hydrochloric acid salt (52.1 mg, 0.082 mmol) and 1-((2S,3S)-1-methyl-5-oxo-2-(pyridin-3-yl)pyrrolidin-3-yl)-1,8-dioxo-5,12-dioxa-2,9-diazapentadecan-15-oic acid hydrochloric acid salt (40 mg, 0.082 mmol) in dichloromethane was added DIPEA (115 μL, 0.657 mmol), EDC (23.62 mg, 0.123 mmol) and HOBt (18.87 mg, 0.123 mmol). The mixture was stirred at rt overnight and was concentrated. Purification by MDAP (XSelect™ CSH Prep C18 5 μm OBD column, 40 mL/min) eluting with a gradient of 30 to 85% acetonitrile containing ammonium hydroxide (1%) in water containing ammonium bicarbonate (10 mM) and ammonium hydroxide (0.075%) provided the title compound as a white solid (47.8 mg, 0.048 mmol, 58.5% yield). LC-MS m/z 994.6 $(M+H)^+$. $^1H$ NMR (400 MHz, METHANOL-$d_4$) δ ppm 1.02 (d, J=6.4 Hz, 3H) 1.14 (br d, J=6.4 Hz, 3H) 1.59-1.81 (m, 3H) 1.88-2.02 (m, 1H) 2.10-2.24 (m, 5H) 2.26 (s, 3H) 2.27-2.45 (m, 6H) 2.45-2.63 (m, 4H) 2.66 (s, 3H) 2.68-2.89 (m, 5H) 3.05 (ddd, J=9.3, 8.1, 6.6 Hz, 1H) 3.26-3.31 (m, 2H) 3.34-3.57 (m, 7H) 3.60-3.70 (m, 5H) 4.02 (dt, J=12.2, 3.7 Hz, 1H) 4.11-4.32 (m, 1H) 4.59 (br d, J=2.9 Hz, 1H) 4.82 (d, J=6.8 Hz, 1H) 5.32 (t, J=8.8 Hz, 1H) 7.53 (dd, J=7.3, 4.9 Hz, 1H) 7.79 (dt, J=7.8, 2.0 Hz, 1H) 7.91 (d, J=8.8 Hz, 1H) 8.07 (dd, J=8.8, 2.0 Hz, 1H) 8.51 (d, J=2.0 Hz, 1H) 8.57 (dd, J=4.9, 1.5 Hz, 1H) 8.59 (s, 1H) 8.75 (s, 1H)

The following compounds were or could be prepared with procedures analogous to that described in Example 44:

| Ex. | Compound | LC-MS m/z | NMR |
|---|---|---|---|
| 45 | 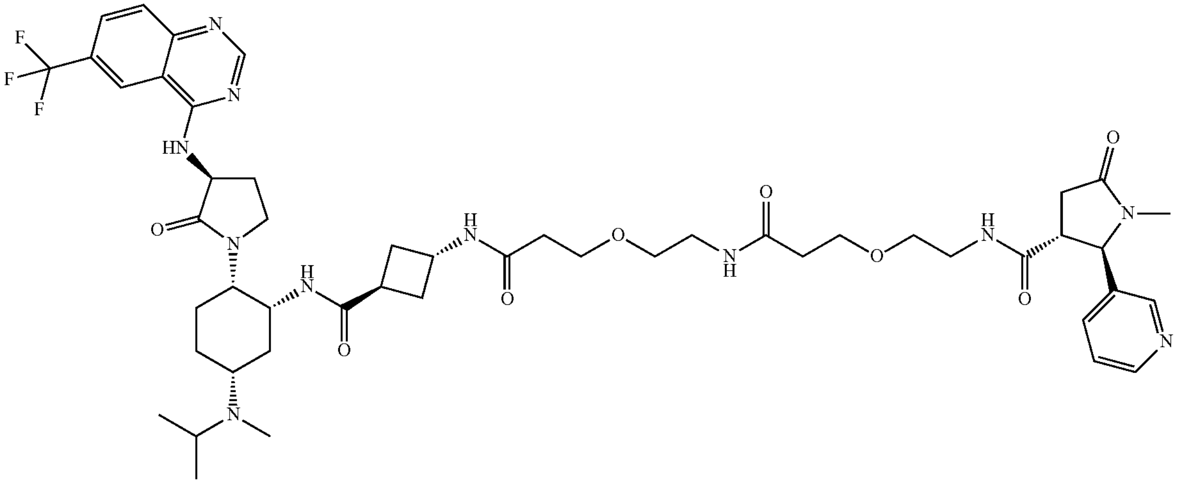 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCOCCNC(=O)CCOCCNC(=O)[C@@H]3CC(=O)N(C)[C@H]3c3cccnc3)C2)C1]<br>(2S,3S)-N-(2-(3-((2-(3-(((1R,3r)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)ethyl)amino)-3-ixopropoxy)ethyl)-1-methyl-5-oxo-2-(pyridin-3-yl)pyrrolidine-3-carboxamide. | 994.6 $(M + H)^+$ | $^1H$ NMR (40 0MHz, METHANOL-$d_4$) δ ppm 1.01 (d, J = 6.4 Hz, 3H) 1.12 (br d, J = 6.4 Hz, 3H) 1.62-1.82 (m, 3H) 1.99 (dq, J =12.7, 8.5 Hz, 1H) 2.05-2.35 (m, 9H) 2.36-2.50 (m, 4H) 2.51-2.65 (m, 3H) 2.66 (s, 3H) 2.67-2.77 (m, 2H) 2.77-2.88 (m, 1H) 2.96-3.09 (m, 2 H) 3.27-3.31 (m, 2H) 3.34-3.56 (m, 7H) 3.59-3.76 (m, 5H) 4.04 (dt, J = 12.5, 3.5 Hz, 1H) 4.43 (quin, J = 7.6 Hz, 1H) 4.63 (br d, J = 2.9 Hz, 1H) 4.82 (d, J = 6.4 Hz, 1H) 5.32 (t, J = 8.6 Hz, 1H) 7.53 (dd, J = 8.8, 4.9 Hz, 1H) 7.80 (dt, J = 8.1, 1.8 Hz, 1H) 7.91 (d, J = 8.8 Hz, 1H) 8.06 (dd, J = 8.8, 2.0 Hz, 1 H) 8.51 (d, J = 2.0 Hz, 1H) 8.57 (dd, J = 4.9, 1.5 Hz, 1 H) 8.59 (s, 1H) 8.77 (s, 1 H). |

-continued

| Ex. | Compound | LC-MS m/z | NMR |
|---|---|---|---|
| 46 | 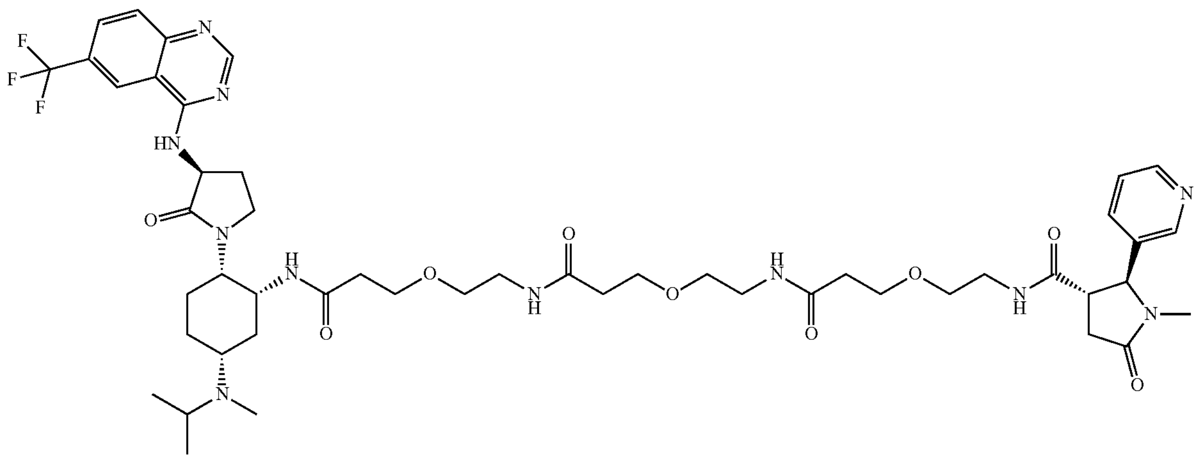 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)CCOCCNC(=O)CCOCCNC(=O)[C@H]2CC(=O)N(C)[C@@H]2c2cccnc2)C1] (2S,3S)-N-(20-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-6,13,20-trioxo-3,10,17-trioxa-7,14-diazaicosyl)-1-methyl-5-oxo-2-(pyridin-3-yl)pyrrolidine-3-carboxamide. | 507.1 $(M/2 + H)^+$ | $^1H$ NMR (400 MHz, DMSO-$d_6$) δ ppm 0.94 (d, J = 6.4 Hz, 3H) 1.01 (d, J = 6.4 Hz, 3H) 1.48-1.73 (m, 3H) 1.85-1.95 (m, 1 H) 1.95-2.13 (m, 3H) 2.14 (s, 3H) 2.23-2.38 (m, 7H) 2.39-2.47 (m, 1 H) 2.52-2.57 (m, 1H) 2.60 (br s, 1H) 2.65-2.75 (m, 1H) 2.90-2.97 (m, 1H) 3.04-3.33 (m, 12H) 3.42-3.66 (m, 8H) 3.88-3.97 (m, 1H) 4.40-4.48 (m, 1H) 4.65 (d, J = 6.4 Hz, 1H) 4.99-5.08 (m, 1H) 7.44 (dd, J = 7.8, 4.9 Hz, 1H) 7.67 (dt, J = 7.8, 2.0 Hz, 1H) 7.77-7.96 (m, 3H) 7.98-8.16 (m, 2H) 8.47 (d, J = 1.5 Hz, 1H) 8.56 (dd, J = 4.9, 1.5 Hz, 1H) 8.59 (s, 1H) 8.66 (d, J = 8.3 Hz, 1H) 8.96 (s, 2H). |

-continued

| Ex. | Compound | LC-MS m/z | NMR |
|---|---|---|---|
| 47 | 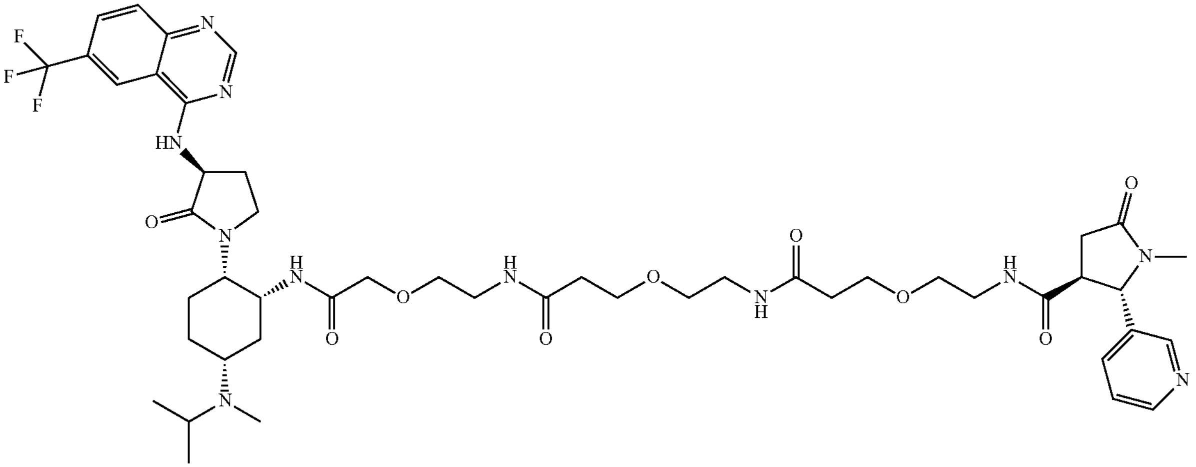 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCOCCNC(=O)CCOCCNC(=O)[C@H]2CC(=O)N(C)[C@@H]2c2cccnc2)C1] (2S,3S)-N-(1-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-1,7,14-trioxo-3,10,17-trioxa-6,13-diazanonadecan-19-yl)-1-methyl-5-oxo-2-(pyridin-3-yl)pyrrolidine-3-carboxamide | 998.5 $(M + H)^+$ | $^1H$ NMR (400 MHz, DMSO-$d_6$) δ ppm 0.89 (d, J = 6.4 Hz, 3H) 1.03 (d, J = 6.4 Hz, 3H) 1.48-1.73 (m, 4H) 1.86-1.96 (m, 1 H) 1.96-2.09 (m, 2H) 2.11 (s, 3H) 2.12-2.19 (m, 1H) 2.23-2.36 (m, 5 H) 2.43 (dd, J = 16.9, 7.6 Hz, 1H) 2.54-2.60 (m, 2 H) 2.65-2.75 (m, 1H) 2.89-2.98 (m, 1H) 3.08-3.33 (m, 10H) 3.43-3.60 (m, 7H) 3.87-4.02 (m, 3H) 4.48-4.55 (m, 1 H) 4.65 (d, J = 5.9 Hz, 1H) 5.01 (q, J = 7.8 Hz, 1H) 7.41-7.47 (m, 1H) 7.67 (dt, J = 7.9, 2.1 Hz, 1H) 7.85-7.93 (m, 3H) 8.06 (dd, J = 8.8, 2.0 Hz, 2H) 8.47 (d, J = 1.5 Hz, 1H) 8.54-8.57 (m, 1H) 8.59 (s, 1H) 8.64 (d, J = 8.3 Hz, 1H) 8.95 (s, 1H) 9.21 (br d, J = 8.8 Hz, 1H). |

-continued

| Ex. | Compound | LC-MS m/z | NMR |
|---|---|---|---|
| 48 | 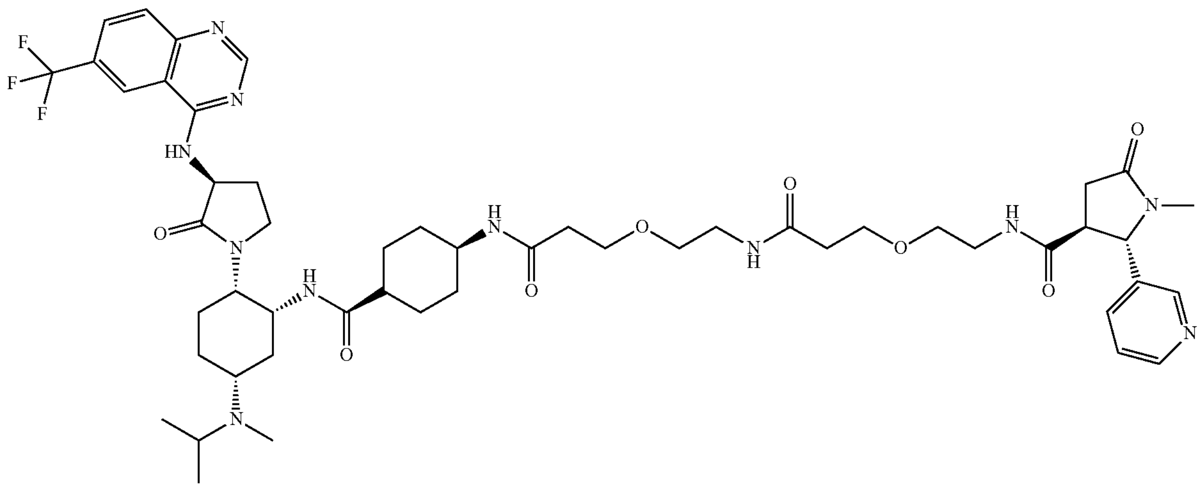 (2S,3S)-N-(2-(3-((2-(3-(((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethyl)amino)-3-oxopropoxy)ethyl)-1-methyl-5-oxo-2-(pyridin-3-yl)pyrrolidine-3-carboxamide. | 1022.3 $(M + H)^+$ | $^1H$ NMR (400 MHz, DMSO-$d_6$) δ ppm 0.89 (d, J = 6.4 Hz, 3H) 1.04 (d, J = 6.8 Hz, 3H) 1.44 (br d, J = 13.7 Hz, 2H) 1.52-1.81 (m, 9H) 1.87-2.05 (m, 3H) 2.06-2.12 (m, 3 H) 2.14 (s, 3H) 2.25-2.32 (m, 3H) 2.32-2.39 (m, 1H) 2.44 (dd, J = 16.9, 7.6 Hz, 1H) 2.56-2.63 (m, 1H) 2.64-2.75 (m, 1 H) 2.89-2.98 (m, 1H) 3.08-3.32 (m, 6H) 3.37-3.47 (m, 1H) 3.54 (t, J = 6.4 Hz, 4H) 3.70 (br s, 1H) 3.89 (br d, J = 11.2 Hz, 1H) 4.42 (br s, 1H) 4.65 (d, J = 6.4 Hz, 2H) 5.03 (q, J = 8.2 Hz, 1H) 7.31-7.55 (m, 1H) 7.57 7.77 (m, 2H) 7.81-7.97 (m, 2H) 8.00-8.17 (m, 2 H) 8.47 (d, J = 2.0 Hz, 1H) 8.56 (dd, J = 4.6, 1.7 Hz, 1 H) 8.58 (s, 1H) 8.63-8.69 (m, 1H) 8.72 (br d, J = 7.8 Hz, 1H) 8.90 (s, 1 H). |

Example 49
(2S,3S)-N-(3-((2-(2-(3-(((1S,3s)-3-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclobutyl)amino)-3-oxopropoxy)ethoxy)ethyl)amino)-3-oxopropyl)-1-methyl-5-oxo-2-(pyridin-3-yl)pyrrolidine-3-carboxamide
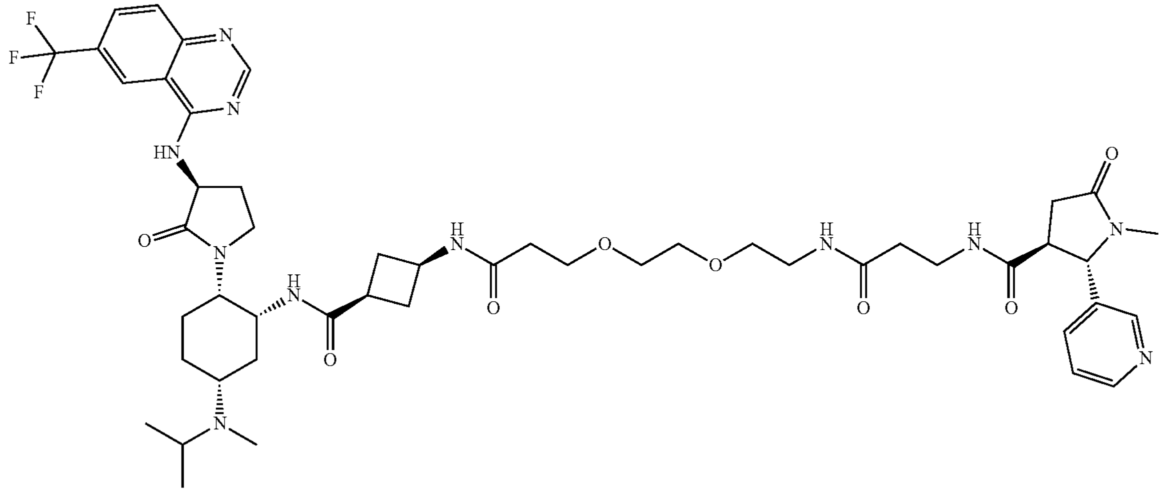
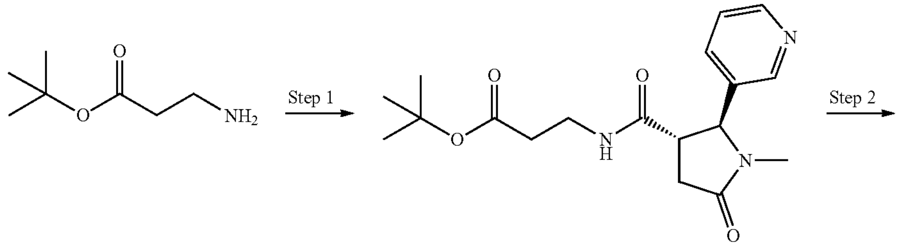
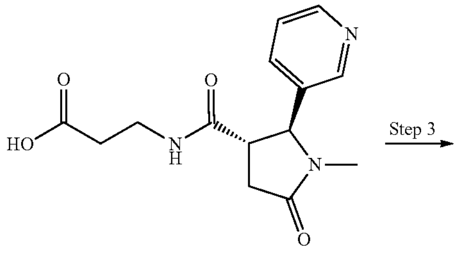

-continued

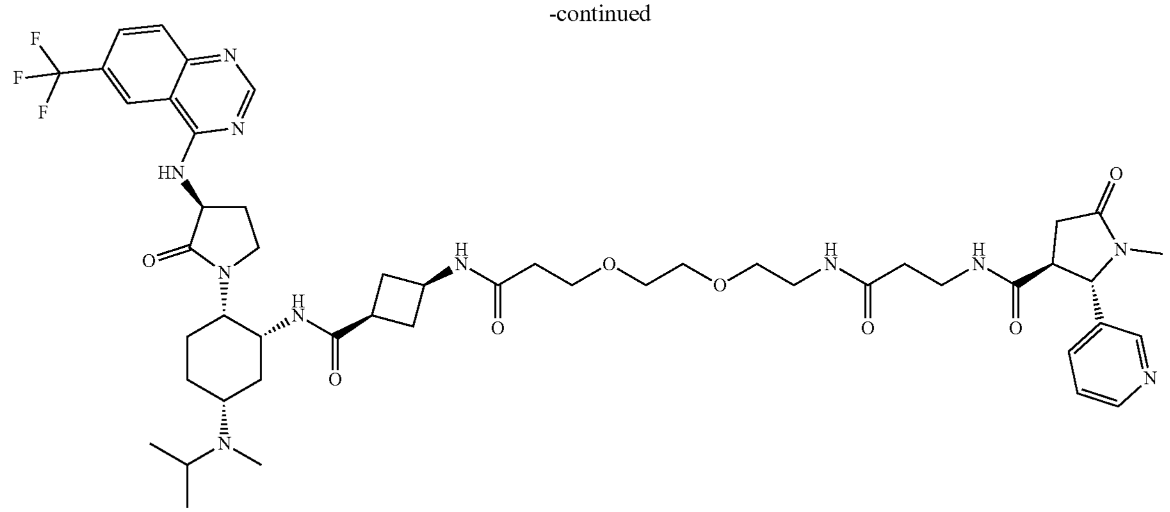

Step 1 tert-Butyl 3-((2S,3S)-1-methyl-5-oxo-2-(pyridin-3-yl)pyrrolidine-3-carboxamido) propanoate

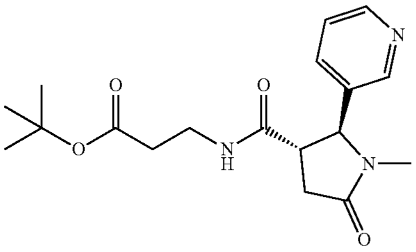 [SMILES: CN1C(=O)C[C@H](C(=O)NCCC(=O)OC(C)(C)C)[C@H]1c1cccnc1]

To a mixture of commercially-available tert-butyl 3-aminopropanoate hydrochloride (267 mg, 1.471 mmol) and (2S,3S)-1-methyl-5-oxo-2-(pyridin-3-yl)pyrrolidine-3-carboxylic acid (324 mg, 1.471 mmol) in dichloromethane (DCM) (3 mL) was added triethylamine (1.025 mL, 7.36 mmol) and HATU (671 mg, 1.765 mmol), and the mixture was stirred at rt for 2 h. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (525 mg, 1.511 mmol, 103% yield). LC-MS m/z 348.1 $(M+H)^+$.

Step 2

3-((2S,3S)-1-Methyl-5-oxo-2-(pyridin-3-yl)pyrrolidine-3-carboxamido)propanoic acid, Hydrochloric acid salt

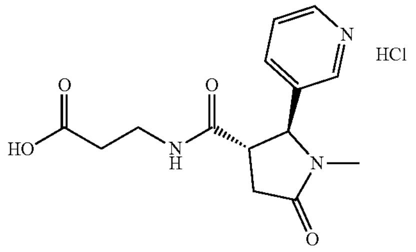 [SMILES: CN1C(=O)C[C@H](C(=O)NCCC(=O)O)[C@H]1c1cccnc1 ; Cl]

A mixture of tert-butyl 3-((2S,3S)-1-methyl-5-oxo-2-(pyridin-3-yl)pyrrolidine-3-carboxamido)propanoate (525 mg, 1.511 mmol), 4 N HCl in 1,4-dioxane (3.02 mL, 12.09 mmol), and dichloromethane (0.5 mL) was stirred at rt for 3 h. The mixture was concentrated to provide the title compound (560 mg, 1.537 mmol, 102% yield). LC-MS m/z 292.1 $(M+H)^+$.

Step 3

(2S,3S)-N-(3-((2-(2-(3-(((1S,3S)-3-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl) carbamoyl)cyclobutyl)amino)-3-oxopropoxy)ethoxy)ethyl)amino)-3-oxopropyl)-1-methyl-5-oxo-2-(pyridin-3-yl)pyrrolidine-3-carboxamide

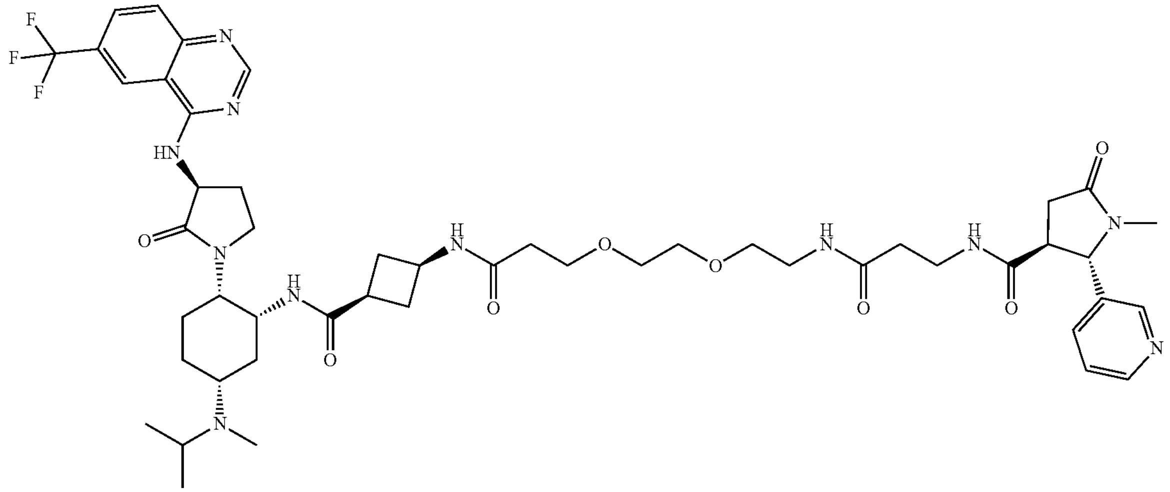 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCOCCNC(=O)CCNC(=O)[C@H]3CC(=O)N(C)[C@@H]3c3cccnc3)C2)C1]

To a mixture of (1 s,3S)-3-(3-(2-(2-aminoethoxy)ethoxy) propanamido)-N-((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)cyclobutane-1-carboxamide, 2hydrochloric acid salt (67 mg, 0.084 mmol) and 3-((2S, 3S)-1-methyl-5-oxo-2-(pyridin-3-yl) pyrrolidine-3-carboxamido) propanoic acid, hydrochloric acid salt (27.7 mg, 0.084 mmol) in dichloromethane (DCM) (1 mL) was added triethylamine (0.094 mL, 0.675 mmol) and HATU (38.5 mg, 0.101 mmol). The mixture was stirred at rt for 3 h and was concentrated. Purification by MDAP (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a white solid (45.7 mg, 0.046 mmol, 54.5% yield). LC-MS m/z 498.5 $(M/2+H)^+$. $^1$H NMR (400 MHz, METHANOL-$d_4$) δ ppm 1.03 (br d, J=5.9 Hz, 3H) 1.15 (br d, J=6.4 Hz, 3H) 1.61-1.81 (m, 3H) 1.89-2.04 (m, 1H) 2.08-2.25 (m, 4H) 2.27 (s, 3H) 2.30-2.46 (m, 5H) 2.46-2.65 (m, 3H) 2.64-2.91 (m, 7H) 2.96-3.07 (m, 1H) 3.26-3.31 (m, 1H) 3.35-3.64 (m, 11H) 3.68 (br t, J=6.1 Hz, 3H) 4.03 (br d, J=12.2 Hz, 1H) 4.12-4.35 (m, 1H) 4.60 (br s, 1H) 5.30 (t, J=8.8 Hz, 1H) 7.52 (dd, J=7.8, 4.9 Hz, 1H) 7.78 (br d, J=7.8 Hz, 1H) 7.91 (d, J=8.8 Hz, 1H) 8.06 (br d, J=9.3 Hz, 1H) 8.51 (s, 1H) 8.57 (d, J=4.9 Hz, 1H) 8.59 (s, 1H) 8.75 (s, 1H).

The following compounds were or could be prepared with procedures analogous to that described in Example 49:

| Ex. | Compound | LC-MS m/z | NMR |
|---|---|---|---|
| 50 | 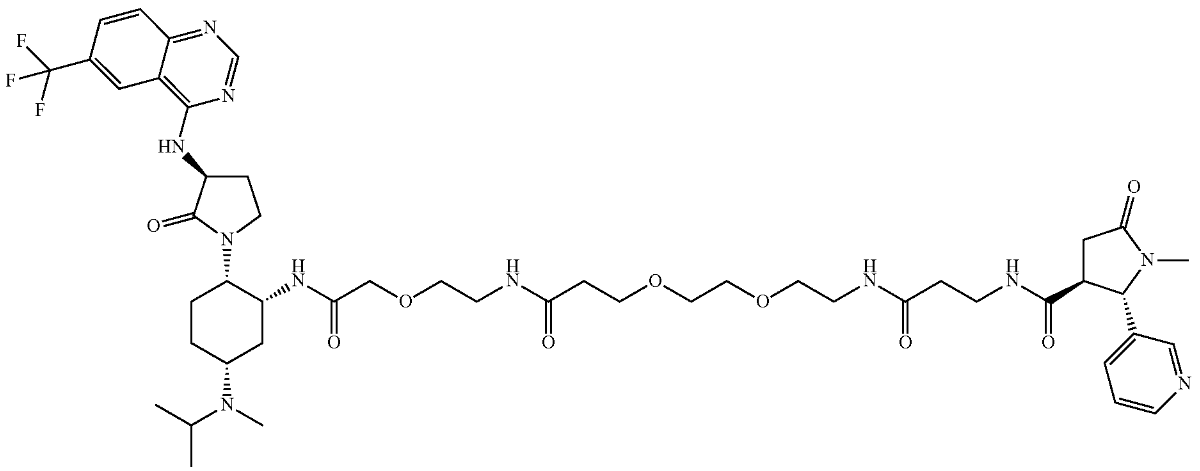 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCOCCOCCNC(=O)CCNC(=O)[C@H]2CC(=O)N(C)[C@@H]2c2cccnc2)C1] (2S,3S)-N-(1-(((1R,2S,5R)-5-(Isopropyl(methyl)amino)-2-((S)-2-oxo-3-((6-(trifluromethyl)quinazolin-4-yl)amino)pyrrolidin-1-yl)cyclohexyl)amino)-1,7,17-trioxo-3,10,13-trioxa-6,16-diazanonadecan-19-yl)-1-methyl-5-oxo-2-(pyridin-3-yl)pyrrolidine-3-carboxamide. | 998.8 $(M + H)^+$ | $^1H$ NMR (400 MHz, METHANOL-$d_4$) δ ppm 1.00 (d, J = 6.4 Hz, 3H) 1.16 (d, J = 6.4 Hz, 3H) 1.60-1.86 (m, 3H) 1.93-2.07 (m, 1H) 2.08-2.23 (m, 2H) 2.24 (s, 3 H) 2.27-2.35 (m, 1H) 2.38 (td, J = 6.7, 1.7 Hz, 2 H) 2.43 (td, J = 6.1, 1.5 Hz, 2H) 2.49-2.60 (m, 1H) 2.66 (m, 3H) 2.67-2.74 (m, 2H) 2.79-2.87 (m, 1H) 2.97-3.04 (m, 1H) 3.27-3.31 (m, 1H) 3.34-3.55 (m, 9H) 3.57 (s, 3H) 3.60-3.67 (m, 3 H) 3.68-3.73 (m, 2H) 4.01-4.11 (m, 3H) 4.67 (br s, 1H) 4.83 (d, J = 6.4 Hz, 1H) 5.29 (t, J = 8.6 Hz, 1H) 7.53 (dd, J = 7.8, 4.9 Hz, 1H) 7.79 (dt, J = 7.8, 2.0 Hz, 1H) 7.90 (d, J = 8.8 Hz, 1H) 8.06 (dd, J = 8.8, 2.0 Hz, 1H) 8.51 (d, J = 2.0 Hz, 1H) 8.57 (dd, J = 4.9, 1.5 Hz, 1H) 8.59 (s, 1H) 8.78 (s, 1H). |

-continued

| Ex. | Compound | LC-MS m/z | NMR |
|---|---|---|---|
| 51 | 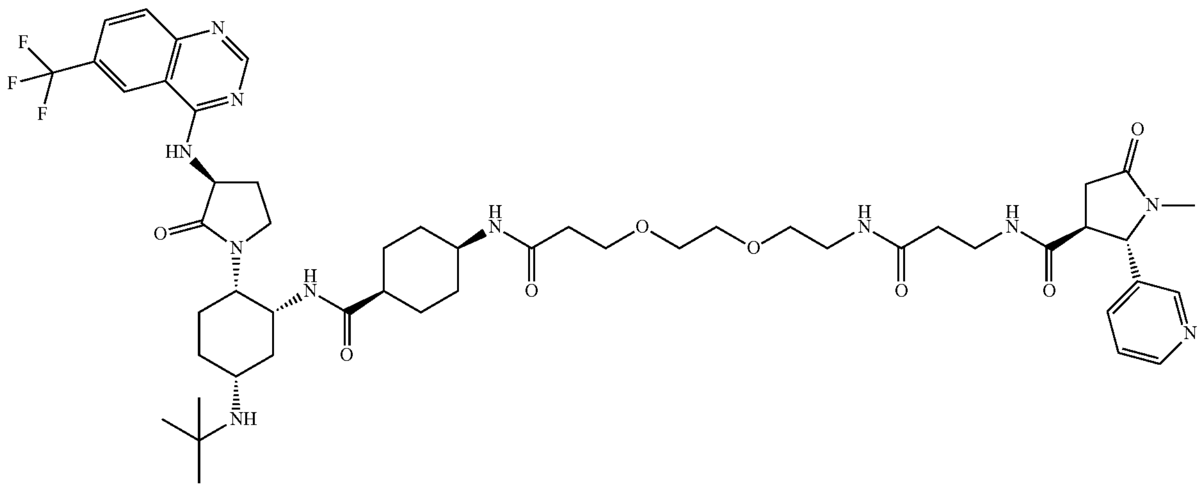 [SMILES: CN1C(=O)C[C@H](C(=O)NCCC(=O)NCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] (2S,3S)-N-(3-((2-(2-(3-(((1S,4s)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethyl)amino)-3-oxopropyl)-1-methyl-5-oxo-2-(pyridin-3-yl)pyrrolidine-3-carboxamide. | 1022.7 $(M + H)^+$ | $^1H$ NMR (400 MHz, METHANOL-$d_4$) δ ppm 8.71 (s, 1H) 8.53-8.60 (m, 2H) 8.49 (d, J = 1.96 Hz, 1H) 8.05 (dd, J = 8.93, 1.83 Hz, 1H) 7.90 (d, J = 8.80 Hz, 1H) 7.77 (dt, J = 8.01, 1.86 Hz, 1H) 7.50 (dd, J = 7.82, 4.89 Hz, 1H) 5.30 (t, J = 8.68 Hz, 1H) 4.81 (d, J = 6.36 Hz, 1H) 4.56 (d, J = 2.20 Hz, 1H) 3.99 (d, J = 12.47 Hz, 1 H) 3.89 (br. s., 1H) 3.37-3.73 (m, 13H) 3.18-3.29 (m, 3H) 2.94-3.03 (m, 1H) 2.75-2.87 (m, 1H) 2.51-2.72 (m ,5H) 2.19-2.45 (m, 6H) 1.54 2.00 (m, 14H) 1.17 (s, 9H). |

Example 52
(2S,3S)-N-(3-(((1R,4S)-4-(4-(((1S,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-4-oxobutoxy)cyclohexyl)amino)-3-oxopropyl)-1-methyl-5-oxo-2-(pyridin-3-yl)pyrrolidine-3-carboxamide
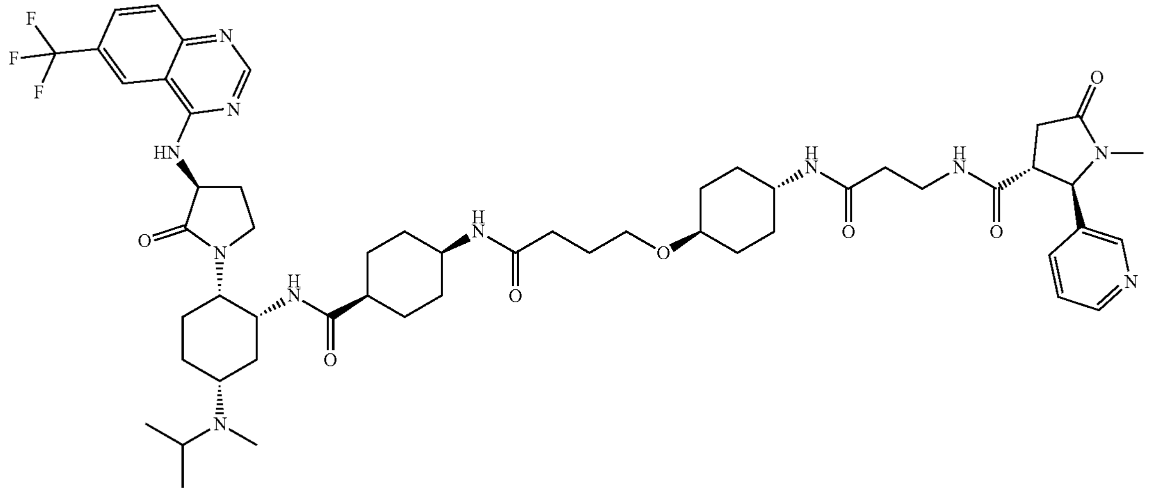
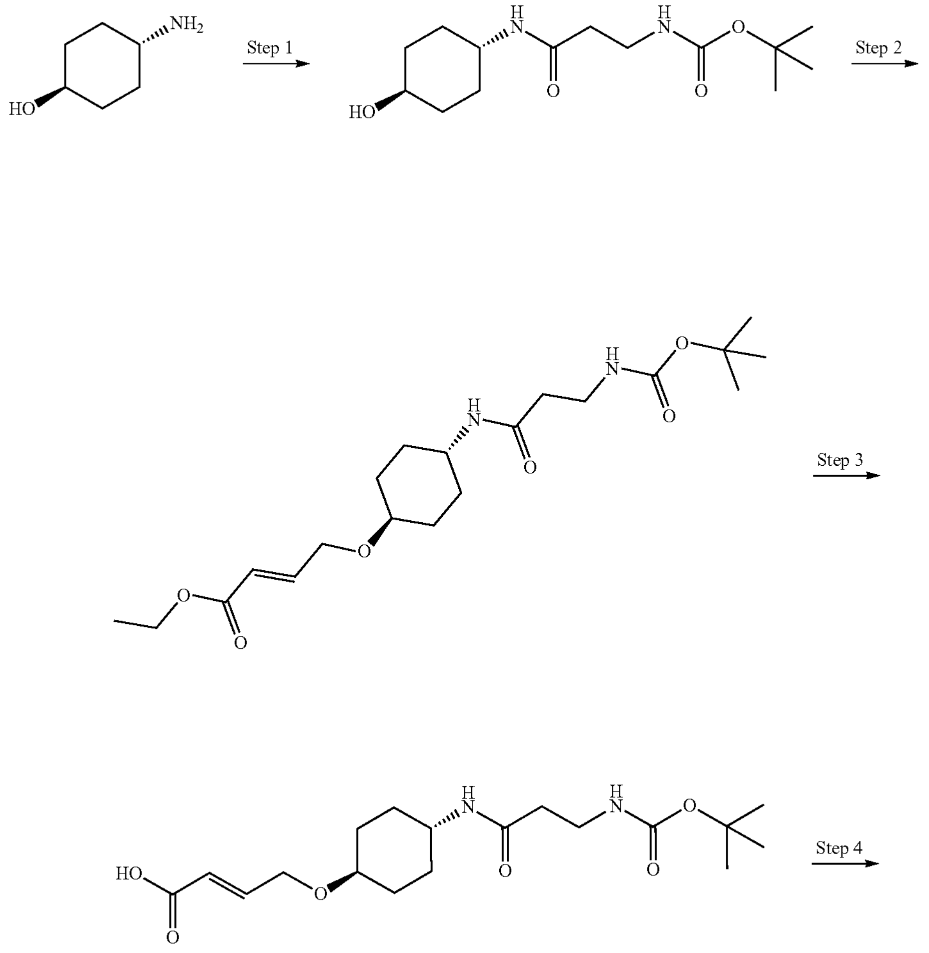

-continued
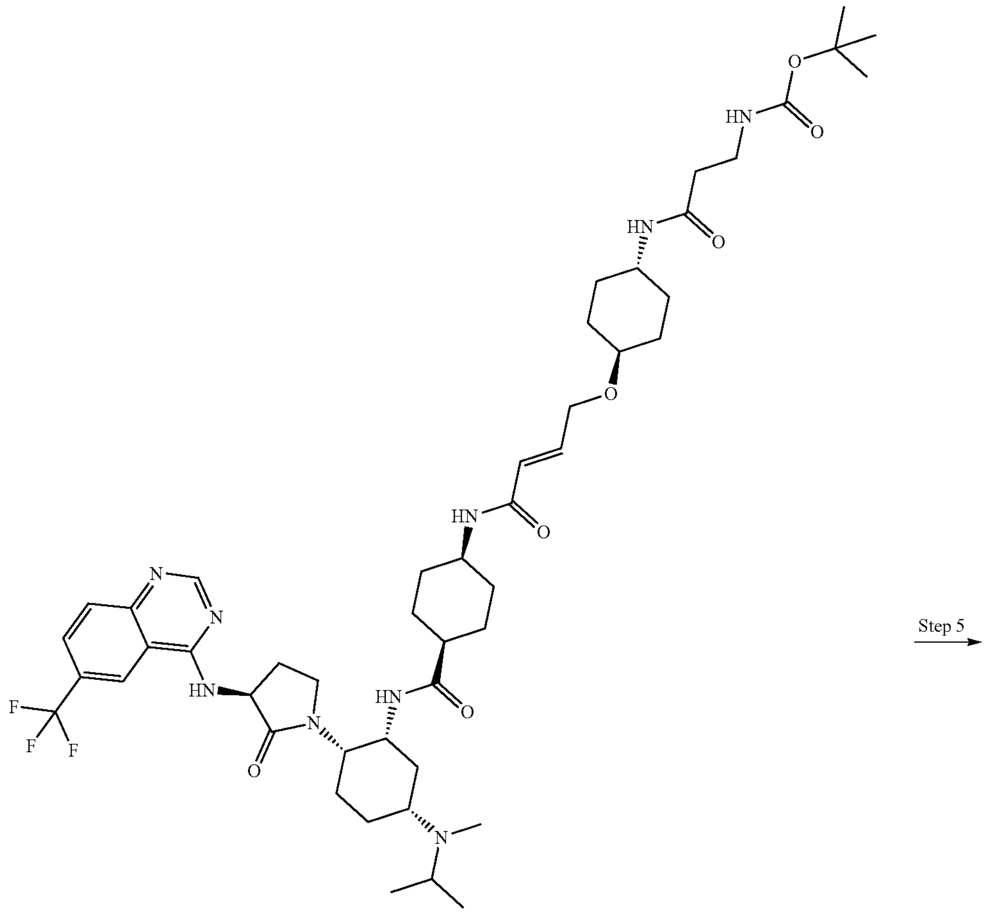

-continued

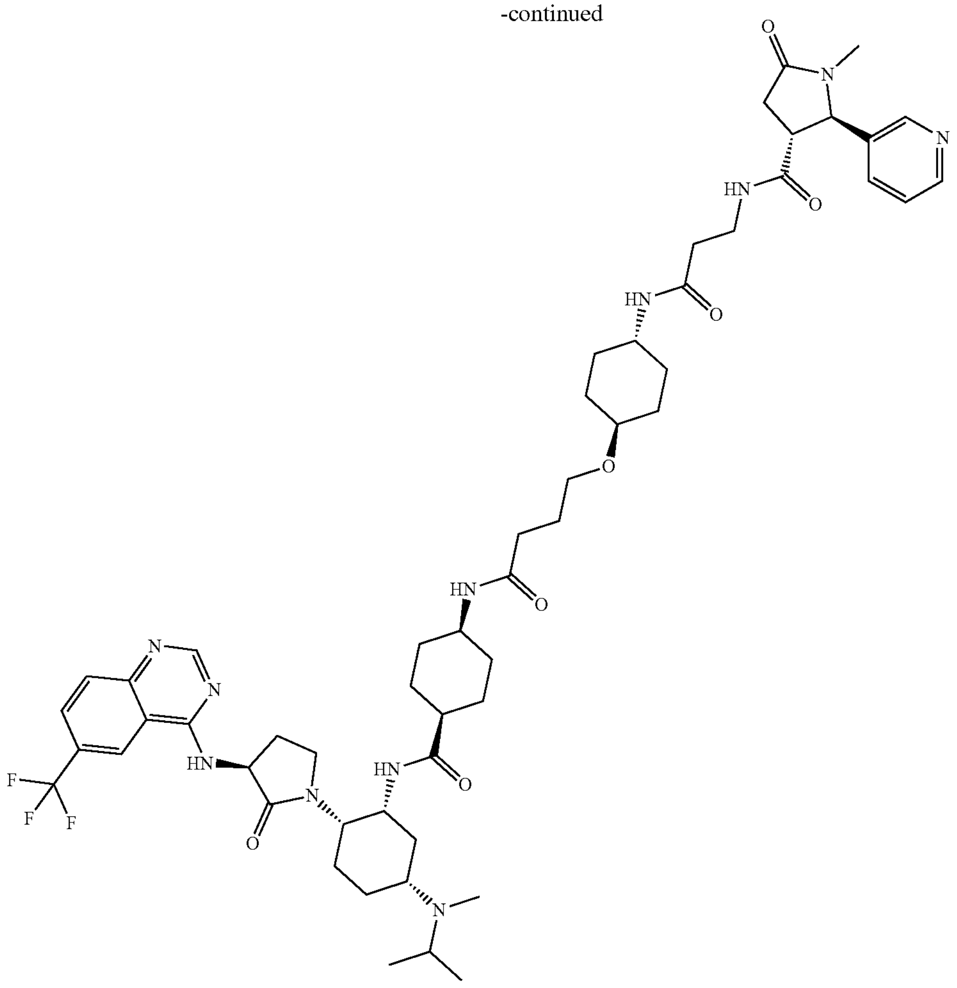

Step 1 tert-Butyl (3-(((1r,4r)-4-hydroxycyclohexyl)amino)-3-oxopropyl)carbamate

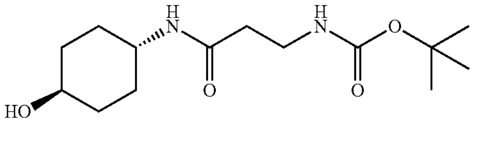 [SMILES: CC(C)(C)OC(=O)NCCC(=O)N[C@H]1CC[C@H](O)CC1]

To a mixture of commercially available (1r,4r)-4-aminocyclohexan-1-ol (1.2 g, 10.42 mmol) and 3-((tert-butoxycarbonyl)amino)propanoic acid (1.26 g, 6.66 mmol) in dichloromethane (DCM) (50 mL) was added triethylamine (3.71 mL, 26.6 mmol), EDC (1.532 g, 7.99 mmol), and HOBt (1.530 g, 9.99 mmol), and the mixture was stirred at rt overnight. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol in dichloromethane (DCM) provided the title compound (900 mg, 3.14 mmol, 47.2% yield). LC-MS m/z 287.2 $(M+H)^+$.

Step 2

Ethyl (E)-4-(((1r,4r)-4-(3-((tert-butoxycarbonyl)amino)propanamido)cyclohexyl)oxy)but-2-enoate

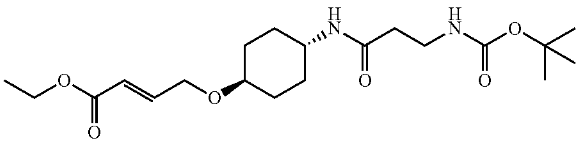 [SMILES: CCOC(=O)/C=C/CO[C@H]1CC[C@H](NC(=O)CCNC(=O)OC(C)(C)C)CC1]

To a mixture of tert-butyl (3-(((1r,4r)-4-hydroxycyclohexyl)amino)-3-oxopropyl)carbamate (317 mg, 1.107 mmol), triphenylphosphine (29.0 mg, 0.111 mmol) and acetic acid (0.056 mL, 0.978 mmol) in toluene (5 ml) was added commercially-available ethyl but-2-ynoate (0.334 mL, 2.87 mmol), and the mixture was stirred at 110° C. overnight. Water was added and the mixture was extracted with ethyl acetate. The combined organic extracts were washed with brine, were dried over $Na_2SO_4$, were filtered, and the filtrate was concentrated. The product was purified via ISCO CombiFlash® chromatography (40 g RediSep Rf Gold® column, 40 mL/min) eluting with a gradient of 0 to 15% methanol in dichloromethane (DCM) to provide the title compound (163 mg, 0.409 mmol, 37.0% yield). LC-MS m/z 399.2 $(M+H)^+$. $^1H$ NMR (400 MHz, METHANOL-$d_4$) δ ppm 1.22-1.41 (m, 7H) 1.45 (s, 9H) 1.95 (br dd, J=13.4, 2.2 Hz, 2H) 2.04-2.15 (m, 2H) 2.34 (t, J=6.8 Hz, 2H) 3.27-3.31 (m, 2H) 3.35-3.39 (m, 1H) 3.66 (tt, J=10.8, 3.9 Hz, 1H) 4.15-4.24 (m, 4H) 6.06 (dt, J=15.6, 2.2 Hz, 1H) 6.98 (dt, J=15.6, 4.2 Hz, 1H) Hz, 1H). (The cis isomer was seen in the NMR.)

Step 3

(E)-4-(((1r,4r)-4-(3-((tert-Butoxycarbonyl)amino) propanamido)cyclohexyl)oxy)but-2-enoic acid

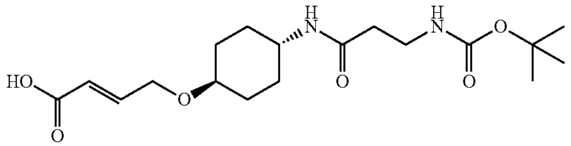 [SMILES: CC(C)(C)OC(=O)NCCC(=O)N[C@H]1CC[C@H](OC/C=C/C(=O)O)CC1]

A mixture of ethyl (E)-4-(((1r,4r)-4-(3-((tert-butoxycarbonyl) amino)propanamido)cyclohexyl)oxy)but-2-enoate (163 mg, 0.409 mmol) and sodium hydroxide (0.409 mL, 2.045 mmol) in methanol (0.4 mL) was stirred at rt for 2 h. The mixture was concentrated, was acidified with HCl (0.409 mL, 2.454 mmol), and was extracted with methanol in dichloromethane (DCM) (5%). The combined organic extracts were dried over $Na_2SO_4$, were filtered, and the filtrate was concentrated to provide the title compound as a white solid (130 mg, 0.351 mmol, 86% yield). LC-MS m/z 371.1 $(M+H)^+$.

Step 4 tert-Butyl (3-(((1R,4r)-4-(((E)-4-(((1S,4S)-4-(((1R, 2S,5R)-5-(isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-4-oxobut-2-en-1-yl)oxy)cyclohexyl)amino)-3-oxopropyl)carbamate

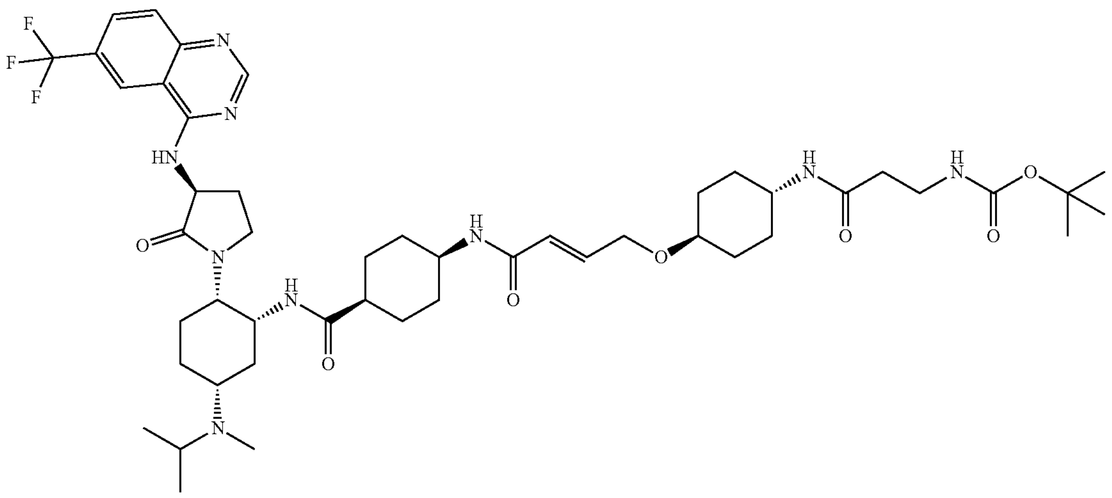 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)/C=C/CO[C@H]3CC[C@H](NC(=O)CCNC(=O)OC(C)(C)C)CC3)CC2)C1]

To a mixture of (1 s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (125 mg, 0.189 mmol) and (E)-4-(((1r,4r)-4-(3-((tert-butoxycarbonyl)amino)propanamido)cyclohexyl)oxy)but-2-enoic acid (84 mg, 0.226 mmol) in dichloromethane (DCM) (1 mL) was added triethylamine (0.158 mL, 1.132 mmol) and HATU (86 mg, 0.226 mmol), and the mixture was stirred at rt for 2 h. Saturated $NaHCO_3$ was added and the mixture and was extracted with dichloromethane (DCM). The combined organic extracts were dried over $Na_2SO_4$, were filtered, and the filtrate was concentrated. Purification by ISCO Combi-Flash® chromatography (12 g RediSep Rf Gold® column, 30 mL/min) eluting with a gradient of 0 to 15% methanol containing ammonium hydroxide (10%) in dichloromethane (DCM) provided the title compound (125 mg, 0.133 mmol, 70.3% yield). LC-MS m/z 942.1 $(M)^+$.

Step 5

(2S,3S)-N-(3-(((1R,4S)-4-(4-(((1S,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-4-oxobutoxy)cyclohexyl)amino)-3-oxopropyl)-1-methyl-5-oxo-2-(pyridin-3-yl)pyrrolidine-3-carboxamide

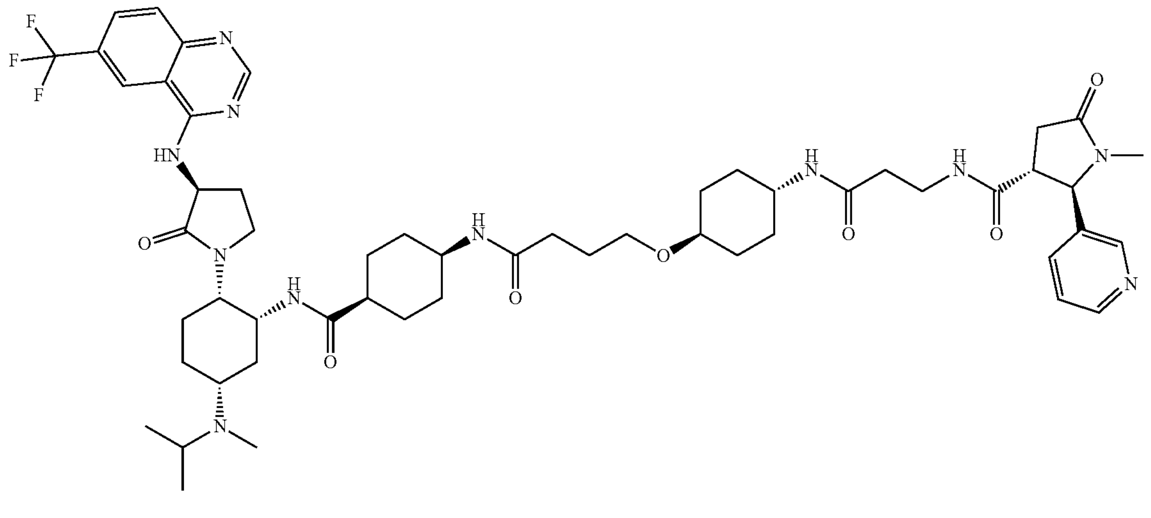 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCO[C@H]3CC[C@H](NC(=O)CCNC(=O)[C@@H]4CC(=O)N(C)[C@H]4c4cccnc4)CC3)CC2)C1]

To a mixture of tert-butyl (3-(((1R,4r)-4-(((E)-4-(((1S,4S)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-4-oxobut-2-en-1-yl)oxy)cyclohexyl)amino)-3-oxopropyl) carbamate (125 mg, 0.133 mmol) in methanol (1 mL) was added Pd/C (14.12 mg, 0.013 mmol), and the mixture was stirred at rt under a balloon atmosphere of hydrogen overnight. The mixture was filtered and the catalyst washed with methanol. The combined filtrates were concentrated to dryness. Dichloromethane (DCM) (0.1 mL) and 4 N HCl in 1,4-dioxane (0.332 mL, 1.327 mmol) were added, the mixture was stirred at rt for 2 h, and was concentrated to dryness. Dichloromethane (DCM) (1.000 mL), (2S,3S)-1-methyl-5-oxo-2-(pyridin-3-yl)pyrrolidine-3-carboxylic acid (29.2 mg, 0.133 mmol), triethylamine (0.111 mL, 0.796 mmol) and HATU (60.5 mg, 0.159 mmol) were added. The mixture was stirred at rt for 2 h and was concentrated. Purification by MDAP (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a white solid (64 mg, 0.061 mmol, 46.1% yield). LC-MS m/z 524.3 $(M/2+H)^+$. $^1H$ NMR (400 MHz, METHANOL-$d_4$) δ ppm 1.01 (d, J=6.4 Hz, 3H) 1.16 (d, J=6.4 Hz, 4H) 1.19-1.33 (m, 4H) 1.59-1.71 (m, 3H) 1.71-1.88 (m, 12H) 1.93-2.03 (m, 3H) 2.14-2.26 (m, 4H) 2.27 (s, 3H) 2.29-2.39 (m, 4H) 2.54-2.62 (m, 1H) 2.66 (s, 3H) 2.68-2.76 (m, 2H) 2.80-2.89 (m, 1H) 2.98-3.06 (m, 1H) 3.17-3.25 (m, 1H) 3.35-3.37 (m, 1H) 3.40-3.68 (m, 9H) 3.86-3.94 (m, 1H) 4.03 (dt, J=12.3, 3.6 Hz, 1H) 4.62 (br d, J=2.4 Hz, 1H) 4.84-4.87 (m, 2H) 5.30 (t, J=8.8 Hz, 1H) 7.52 (dd, J=8.3, 4.9 Hz, 1H) 7.79 (dt, J=8.2, 1.8 Hz, 1H) 7.91 (d, J=8.8 Hz, 1H) 8.06 (dd, J=8.8, 2.0 Hz, 1H) 8.51 (d, J=2.0 Hz, 1H) 8.57 (dd, J=4.9, 1.5 Hz, 1H) 8.59 (s, 1H) 8.73 (s, 1H).

Example 53
(2S,3S)-N-(2-(((1R,4S)-4-((3-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-3-oxopropoxy)methyl)cyclohexyl)methoxy)ethyl)-1-methyl-5-oxo-2-(pyridin-3-yl)pyrrolidine-3-carboxamide
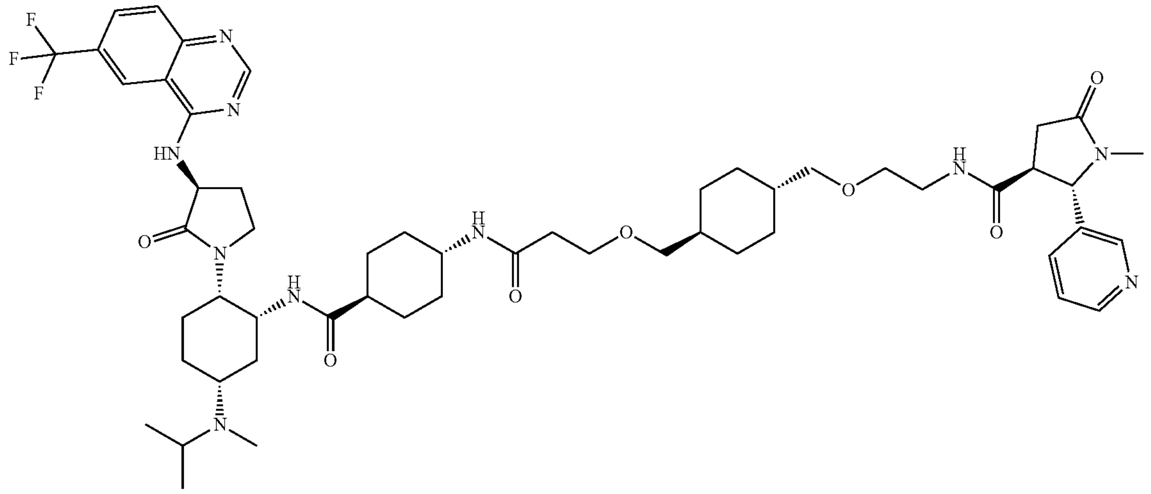
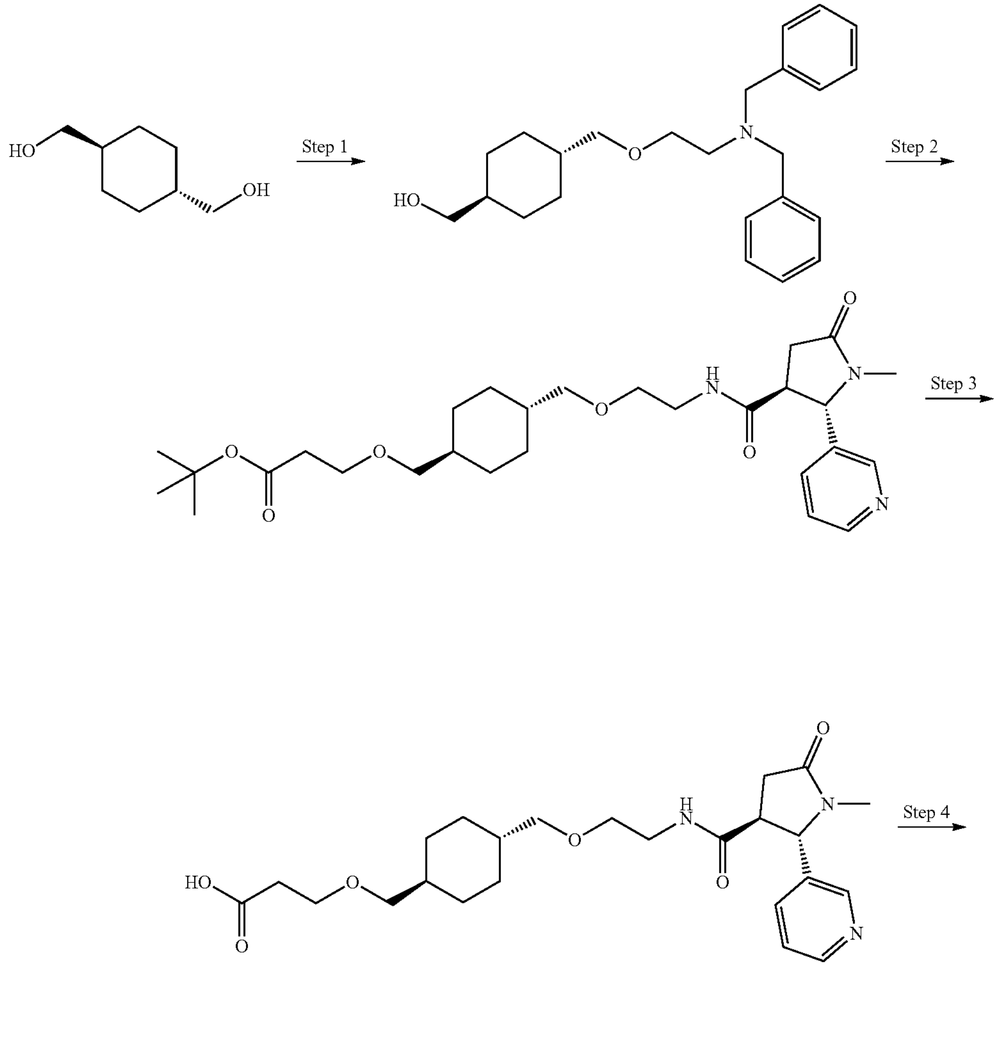

-continued

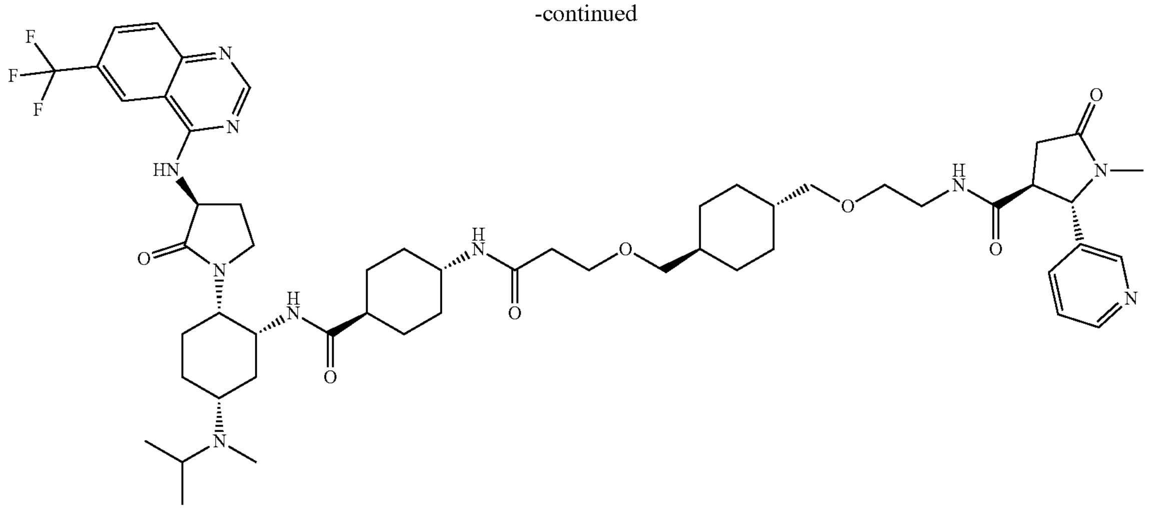

Step 1

((1r,4r)-4-((2-(Dibenzylamino)ethoxy)methyl)cyclohexyl)methanol

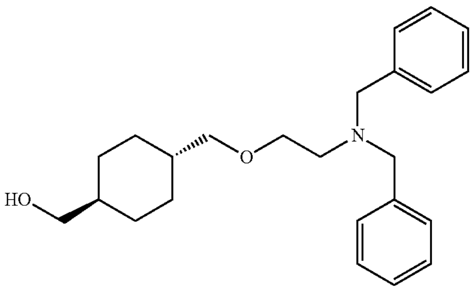 [SMILES: OC[C@H]1CC[C@H](COCCN(Cc2ccccc2)Cc2ccccc2)CC1]

To a mixture of commercially-available ((1r,4r)-cyclohexane-1,4-diyl)dimethanol (308 mg, 2.136 mmol) in N,N-dimethylformamide (DMF) (5.0 mL) at 0° C. was added sodium hydride (85 mg, 2.136 mmol) and the mixture was stirred at rt for 30 min. N,N-Dibenzyl-2-chloroethan-1-amine (555 mg, 2.136 mmol) was added and the mixture was stirred at rt over the weekend. The mixture was cooled to 0° C., saturated $NH_4Cl$ was added, and the mixture was extracted with ethyl acetate. The combined organic extracts were washed with water, with brine, were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 50% ethyl acetate in heptane provided the title compound (197 mg, 0.536 mmol, 25.09% yield). LC-MS m/z 368.5 $(M+H)^+$.

Step 2 tert-Butyl 3-(((1S,4r)-4-((2-((2S,3S)-1-methyl-5-oxo-2-(pyridin-3-yl)pyrrolidine-3-carboxamido)ethoxy)methyl)cyclohexyl)methoxy)propanoate

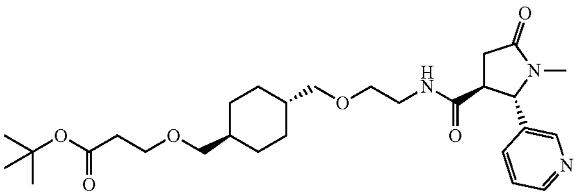 [SMILES: CN1C(=O)C[C@H](C(=O)NCCOC[C@H]2CC[C@H](COCCC(=O)OC(C)(C)C)CC2)[C@H]1c1cccnc1]

To a mixture of ((1r,4r)-4-((2-(dibenzylamino)ethoxy)methyl)cyclohexyl)methanol (197 mg, 0.536 mmol), tetrabutylammonium hydrogen sulfate (35 mg, 0.103 mmol) and sodium hydroxide (515 mg, 6.43 mmol) in dichloromethane (DCM) (3 mL) was added tert-butyl acrylate (0.157 mL, 1.072 mmol), and the mixture was stirred at rt for 2 h. Water was added and the mixture was extracted with dichloromethane (DCM). The combined organic extracts were dried over $Na_2SO_4$, were filtered, and the filtrate was concentrated to dryness. To the residue was added ethyl acetate (3.00 mL) and Pd/C (114 mg, 0.107 mmol) and the mixture was stirred under a balloon atmosphere of hydrogen for 16 h. Additional Pd/C (114 mg, 0.107 mmol) was added and the mixture was stirred under a balloon atmosphere of hydrogen for 24 h. The mixture was filtered, the catalyst was washed with methanol, and the combined filtrates were concentrated to dryness. To the residue in dichloromethane (DCM) (3.00 mL) was added (2S,3S)-1-methyl-5-oxo-2-(pyridin-3-yl)pyrrolidine-3-carboxylic acid (118 mg, 0.536 mmol), HATU (245 mg, 0.643 mmol) and triethylamine (0.224 mL, 1.608 mmol), and the mixture was stirred at rt for 2 h. Saturated $NaHCO_3$ was added and the mixture was extracted with dichloromethane (DCM). The combined organic extracts were dried over $Na_2SO_4$, were filtered, and the filtrate was concentrated. Purification by ISCO CombiFlash® chromatography (12 g RediSep Rf Gold® column, 30 mL/min) eluting with a gradient of 0 to 15% methanol containing ammonium hydroxide (10%) in dichloromethane (DCM) provided the title compound (212 mg, 0.410 mmol, 76% yield). LC-MS m/z 518.1 $(M+H)^+$.

Step 3

3-(((1S,4r)-4-((2-((2S,3S)-1-Methyl-5-oxo-2-(pyridin-3-yl)pyrrolidine-3-carboxamido) ethoxy)methyl) cyclohexyl)methoxy)propanoic acid, Hydrochloric acid salt

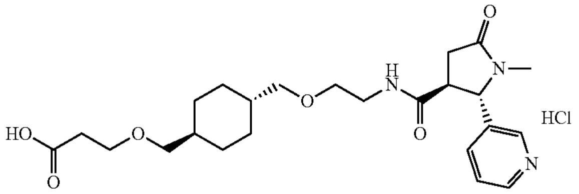 [SMILES: CN1C(=O)C[C@H](C(=O)NCCOC[C@H]2CC[C@H](COCCC(=O)O)CC2)[C@H]1c1cccnc1 ; Cl]

A mixture of tert-butyl 3-(((1S,4r)-4-((2-((2S,3S)-1-methyl-5-oxo-2-(pyridin-3-yl)pyrrolidine-3-carboxamido) ethoxy)methyl)cyclohexyl)methoxy)propanoate (212 mg, 0.410 mmol), 4 N HCl in 1,4-dioxane (1.024 mL, 4.10 mmol), and dichloromethane (DCM) (0.1 mL) was stirred at rt for 3 h. The mixture was concentrated to dryness to provide the title compound (210 mg, 0.422 mmol, 103% yield). LC-MS m/z 462.1 $(M+H)^+$.

Step 4

(2S,3S)-N-(2-(((1R,4S)-4-((3-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-3-oxopropoxy)methyl)cyclohexyl)methoxy)ethyl)-1-methyl-5-oxo-2-(pyridin-3-yl)pyrrolidine-3-carboxamide To a mixture of (1r,4R)-4-amino-N-((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)cyclohexane-1-carboxamide, 2hydrochloric acid salt (47.9 mg, 0.072 mmol) and 3-(((1S,4r)-4-((2-((2S,3S)-1-methyl-5-oxo-2-(pyridin-3-yl)pyrrolidine-3-carboxamido)ethoxy) methyl)cyclohexyl) methoxy)propanoic acid hydrochloric acid salt (36 mg, 0.072 mmol) in dichloromethane (DCM) (1 mL) was added DIPEA (0.101 mL, 0.578 mmol), EDC (20.79 mg, 0.108 mmol) and HOBt (16.60 mg, 0.108 mmol). The mixture was stirred at rt overnight and was concentrated. Purification by MDAP (XSelect™. CSH C18 5 μm column, 40 mL/min) eluting with a gradient of 30 to 85% gradient acetonitrile in water containing ammonium bicarbonate (10 mM) and the pH adjusted to 10 with ammonia provided the title compound as a white solid (38.1 mg, 0.037 mmol, 51.0% yield). LC-MS m/z 517.8 $(M/2+H)^+$. $^1H$ NMR (400 MHz, METHANOL-$d_4$) δ ppm 0.82-0.98 (m, 4H) 1.02 (br d, J=6.4 Hz, 3H) 1.16 (br d, J=6.4 Hz, 3H) 1.19-1.35 (m, 2H) 1.44-1.65 (m, 4H) 1.67-1.81 (m, 7H) 1.90-2.05 (m, 5H) 2.06-2.26 (m, 3H) 2.28 (s, 3H) 2.33 (br s, 1H) 2.38 (t, J=6.1 Hz, 2H) 2.44-2.60 (m, 1H) 2.66 (s, 3H) 2.68-2.77 (m, 2H) 2.78-2.88 (m, 1H) 3.05 (ddd, J=9.3, 8.1, 6.6 Hz, 1H) 3.23 (dd, J=16.6, 6.4 Hz, 4H) 3.34-3.56 (m, 6H) 3.62-3.69 (m, 4H) 4.02 (dt, J=12.5, 3.8 Hz, 1H) 4.66 (br d, J=2.9 Hz, 1H) 4.84-4.88 (m, 1H) 5.27 (t, J=8.1 Hz, 1H) 7.52 (dd, J=7.8, 4.9 Hz, 1H) 7.79 (dt, J=7.8, 2.0 Hz, 1H) 7.91 (d, J=8.8 Hz, 1H) 8.06 (dd, J=8.8, 2.0 Hz, 1H) 8.51 (d, J=2.0 Hz, 1H) 8.57 (dd, J=4.9, 1.5 Hz, 1H) 8.59 (s, 1H) 8.81 (s, 1H)

The following compounds were or could be prepared with procedures analogous to that described in Example 53:

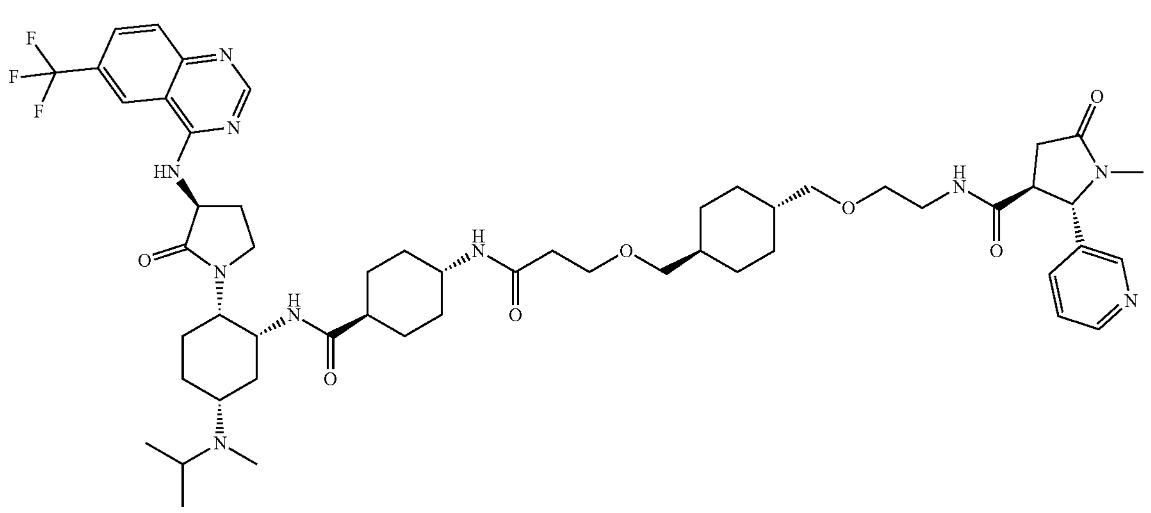 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCOC[C@H]3CC[C@H](COCCNC(=O)[C@H]4CC(=O)N(C)[C@@H]4c4cccnc4)CC3)CC2)C1]

| Ex. | Compound | LC-MS m/z | NMR |
|---|---|---|---|
| 54 | 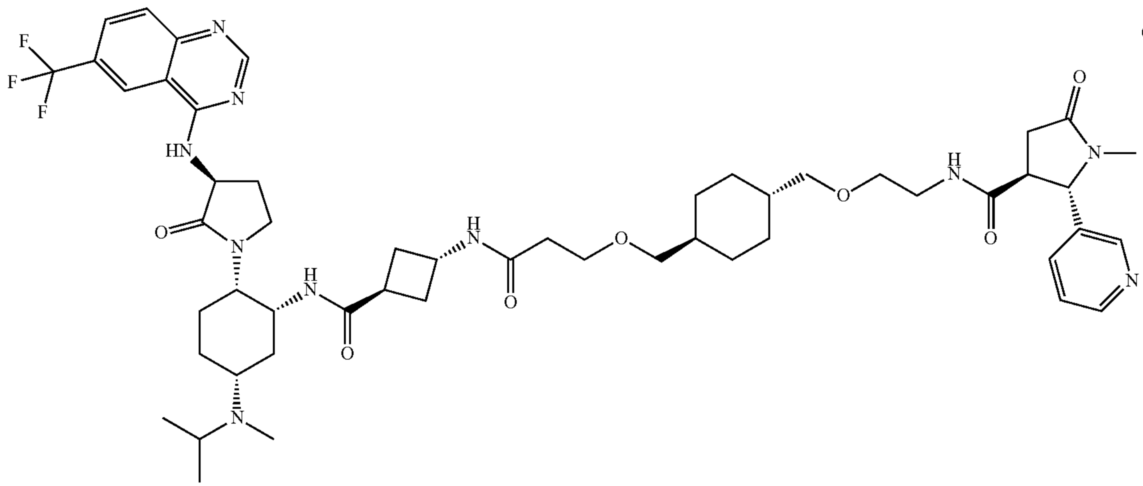 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCOC[C@H]3CC[C@H](COCCNC(=O)[C@H]4CC(=O)N(C)[C@@H]4c4cccnc4)CC3)C2)C1] (2S,3S)-N-(2-(((1R,4S)-4-((3-(((1R,3R)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)methyl)cyclohexyl)methoxy)ethyl)-1-methyl-5-oxo-2-(pyridin-3-yl)pyrrolidine-3-carboxamide | 504.0 (M/2 + H)$^+$ | H NMR (400 MHz, METHANOL-$d_4$) δ ppm 0.83-0.98 (m, 4H) 1.02 (br d, J = 6.4 Hz, 3H) 1.13 (br d, J = 6.4 Hz, 3H) 1.29-1.54 (m, 2H) 1.61-1.86 (m, 7H) 2.00 (br dd, J = 12, 8.6 Hz, 1 H) 2.07-2.35 (m, 8H) 2.38 (t, J = 6.1 Hz, 2H) 2.52-2.64 (m, 3H) 2.66 (s, 3H) 2.67-2.79 (m, 2 H) 2.79-2.89 (m, 1H) 2.94-3.11 (m, 2H) 3.17-3.26 (m, 4H) 3.26-3.32 (m, 1H) 3.35-3.55 (m, 5H) 3.58-3.71 (m, 3H) 4.05 (dt, J = 12, 3.4 Hz, 1H) 4.41 (quin, J = 7.5 Hz, 1H) 4.64 (br s, 1H) 4.84-4.89 (m, 1H) 5.31 (br t, J = 8.6 Hz, 1H) 7.52 (dd, J = 7.8, 4.9 Hz, 1H)7.79 (dt, J = 8.3, 2.0 Hz, 1H) 7.91 (d, J = 8.8 Hz, 1H) 8.05 (d, J = 8.8 Hz, 1H) 8.51 (d, J = 2.0 Hz, 1H) 8.57 (dd, J = 4.9, 1.5 Hz, 1H) 8.59 (s, 1H) 8.77 (s, 1H). |

-continued

| Ex. | Compound | LC-MS m/z | NMR |
|---|---|---|---|
| 55 | 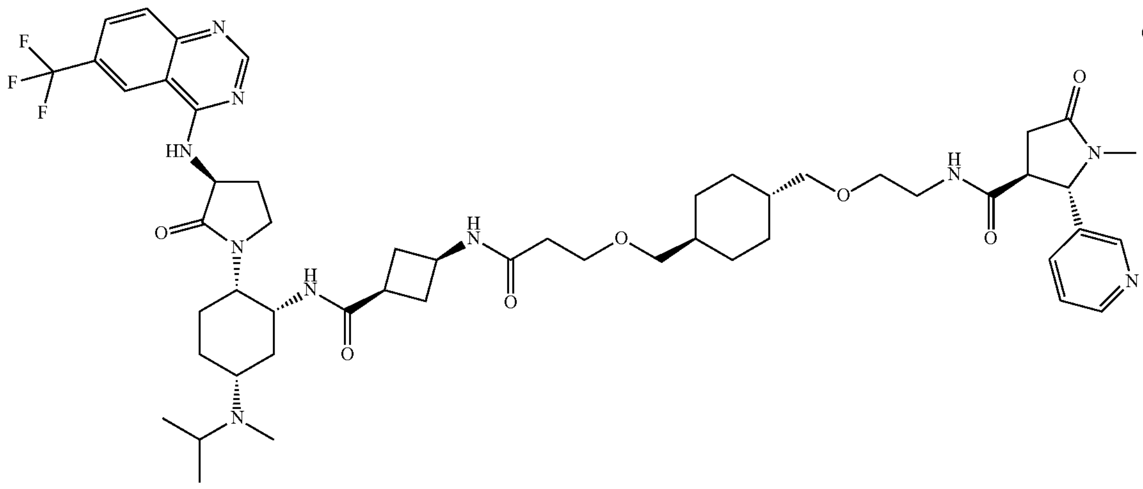 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOC[C@H]3CC[C@H](COCCNC(=O)[C@H]4CC(=O)N(C)[C@@H]4c4cccnc4)CC3)C2)C1] (2S,3S)-N-(2-(((1S,4S)-4-((3-(((1S,3S)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)methyl)cyclohexyl)methoxy)ethyl)-1-methyl-5-oxo-2-(pyridin-3-yl)pyrrolidine-3-carboxamide. | 503.8 $(M/2 + H)^+$ | $^1H$ NMR (400 MHz, METHANOL-$d_4$) δ ppm 0.77-0.95 (m, 4H) 1.02 (d, J = 6.4 Hz, 3H) 1.15 (d, J = 6.4 Hz, 3H) 1.29-1.52 (m, 2H) 1.61-1.81 (m, 7H) 1.84-2.00 (m, 1H) 2.10-2.24 (m, 4H) 2.26 (s, 3H) 2.33 (t, J = 6.1 Hz, 3H) 2.44-2.62 (m, 3H) 2.66 (s, 3H) 2.68-2.88 (m, 4H) 3.02-3.10 (m, 1H) 3.13 (dd, J = 6.3, 1.0 Hz, 2H) 3.19 (d, J = 6.4 Hz, 2H) 3.26-3.31 (m, 1H) 3.34-3.55 (m, 6H) 3.56-3.67 (m, 3H) 4.02 (dt, J = 12, 3.7 Hz, 1H) 4.17-4.28 (m, 1H) 4.61 (br d, J = 2.9 Hz, 1H) 4.84 (br s, 1H) 5.33 (t, J = 8.8 Hz, 1H) 7.52 (dd, J = 8.3, 4.9 Hz, 1H) 7.79 (dt, J = 8.2, 1.8 Hz, 1H) 7.91 (d, J = 8.8 Hz, 1H) 8.06 (dd, J = 8.8, 2.0 Hz, 1H) 8.51 (d, J = 2.0 Hz, 1H) 8.56-8.58 (m, 1H) 8.58 (s, 1H) 8.76 (s, 1H). |

Example 56
N[1]-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-N[5]-(4-((3-((2S,3S)-1-methyl-5-oxo-2-(pyridin-3-yl)pyrrolidine-3-carboxamido) propyl)amino)-4-oxobutyl)glutaramide
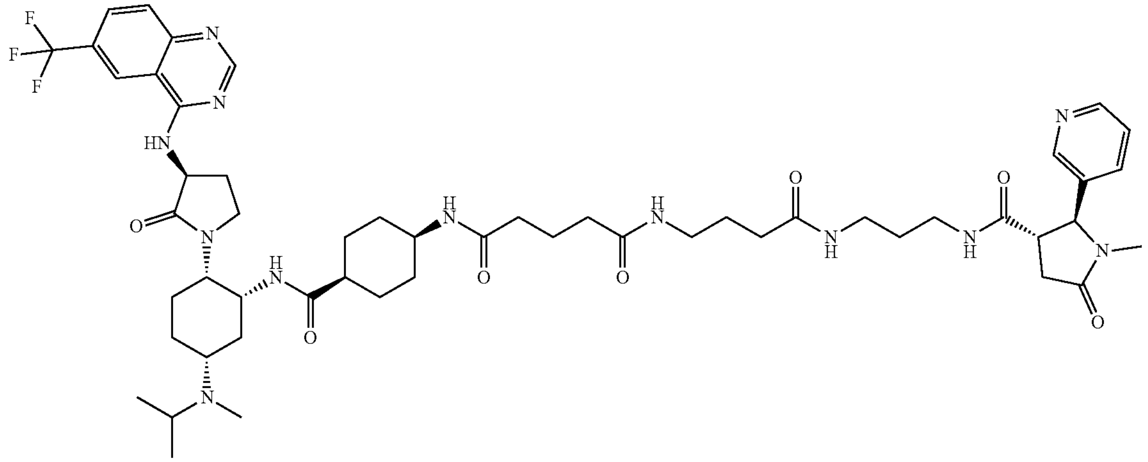
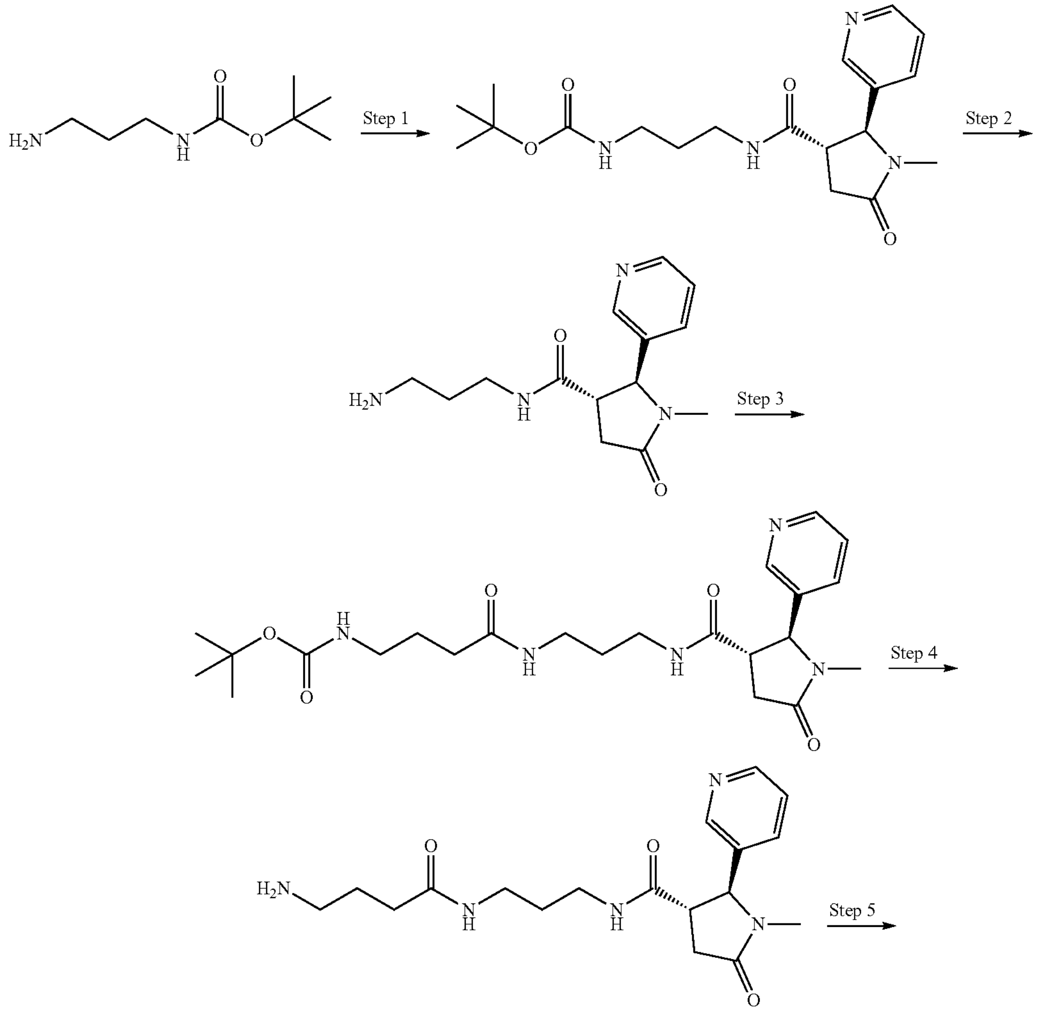

-continued

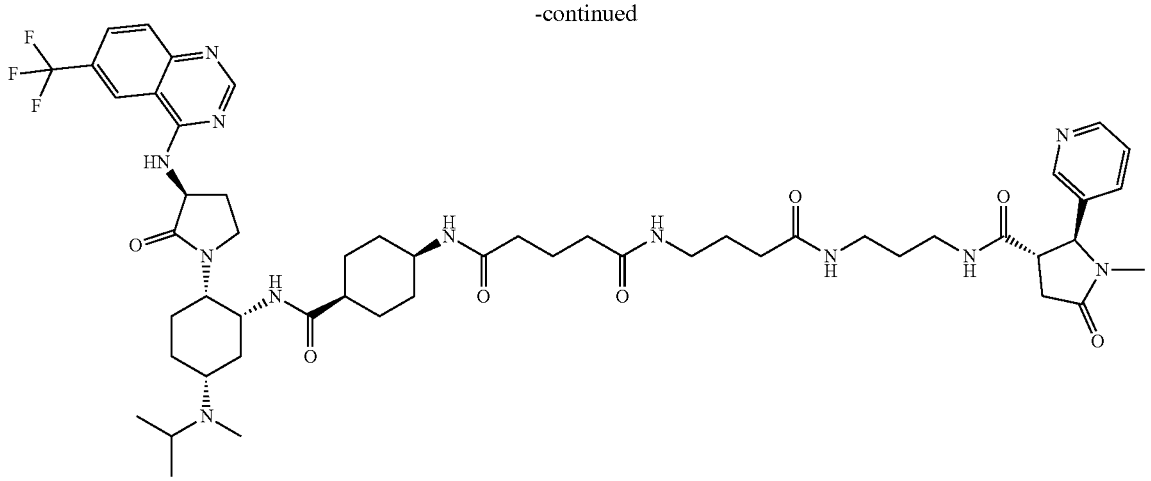

Step 1 tert-Butyl (3-((2S,3S)-1-methyl-5-oxo-2-(pyridin-3-yl)pyrrolidine-3-carboxamido)propyl) carbamate

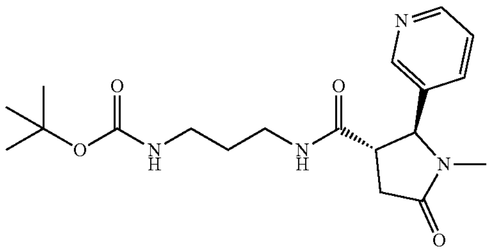 [SMILES: CN1C(=O)C[C@H](C(=O)NCCCNC(=O)OC(C)(C)C)[C@H]1c1cccnc1]

To a mixture of commercially-available tert-butyl (3-aminopropyl)carbamate (346 mg, 1.986 mmol) and (2S,3S)-1-methyl-5-oxo-2-(pyridin-3-yl) pyrrolidine-3-carboxylic acid (437 mg, 1.986 mmol) in dichloromethane (DCM) (5 mL) was added HATU (906 mg, 2.383 mmol) and triethylamine (0.830 mL, 5.96 mmol), and the mixture was stirred at rt for 2 h. Saturated $NaHCO_3$ was added and the mixture was extracted with dichloromethane (DCM). The combined organic extracts were washed with brine, were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (690 mg, 1.833 mmol, 92% yield). LC-MS m/z 377.2 $(M+H)^+$.

Step 2

(2S,3S)-N-(3-Aminopropyl)-1-methyl-5-oxo-2-(pyridin-3-yl)pyrrolidine-3-carboxamide, 2Hydrochloric acid salt

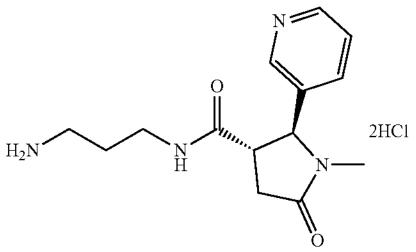 [SMILES: CN1C(=O)C[C@H](C(=O)NCCCN)[C@H]1c1cccnc1]

A mixture of tert-butyl (3-((2S,3S)-1-methyl-5-oxo-2-(pyridin-3-yl)pyrrolidine-3-carboxamido)propyl)carbamate (690 mg, 1.833 mmol), 4 M HCl in 1,4-dioxane (2.291 mL, 9.16 mmol), and dichloromethane (DCM) (0.5 mL) was stirred at rt for 3 h and concentrated to dryness to provide the title compound (810 mg, 2.319 mmol, 127% yield). LC-MS m/z 277.2 $(M+H)^+$ Step 3 tert-Butyl (4-((3-((2S,3S)-1-methyl-5-oxo-2-(pyridin-3-yl)pyrrolidine-3-carboxamido) propyl)amino)-4-oxobutyl)carbamate

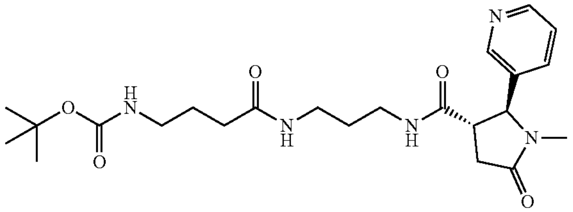 [SMILES: CN1C(=O)C[C@H](C(=O)NCCCNC(=O)CCCNC(=O)OC(C)(C)C)[C@H]1c1cccnc1]

To a mixture of commercially-available 4-((tert-butoxycarbonyl)amino)butanoic acid (152 mg, 0.750 mmol) and (2S,3S)-N-(3-aminopropyl)-1-methyl-5-oxo-2-(pyridin-3-yl)pyrrolidine-3-carboxamide 2ihydrochloric acid salt (262 mg, 0.750 mmol) in dichloromethane (DCM) (2 mL) was added triethylamine (0.627 mL, 4.50 mmol) and HATU (342 mg, 0.900 mmol) and the mixture was stirred at rt for 2 h. Water was added and the mixture was extracted with dichloromethane (DCM). The combined organic extracts were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (200 mg, 0.433 mmol, 57.8% yield). LC-MS m/z 462.2 $(M+H)^+$.

Step 4

(2S,3S)-N-(3-(4-Aminobutanamido)propyl)-1-methyl-5-oxo-2-(pyridin-3-yl)pyrrolidine-3-carboxamide, 2Hydrochloric acid salt

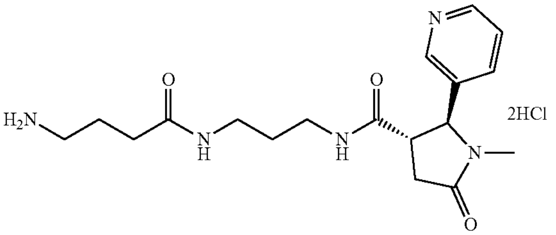 [SMILES: CN1C(=O)C[C@H](C(=O)NCCCNC(=O)CCCN)[C@H]1c1cccnc1]

A mixture of tert-butyl (4-((3-((2S,3S)-1-methyl-5-oxo-2-(pyridin-3-yl) pyrrolidine-3-carboxamido)propyl)amino)-4-oxobutyl)carbamate (200 mg, 0.433 mmol), 4 M HCl in 1,4-dioxane (0.542 mL, 2.167 mmol), and dichloromethane (DCM) (0.3 mL) was stirred at rt for 5 h and was concentrated to dryness to provide the title compound (200 mg, 0.460 mmol, 106% yield). LC-MS m/z 362.2 $(M+H)^+$.

Step 5

$N^1$-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-$N^5$-(4-((3-((2S,3S)-1-methyl-5-oxo-2-(pyridin-3-yl)pyrrolidine-3-carboxamido)propyl)amino)-4-oxobutyl)glutaramide

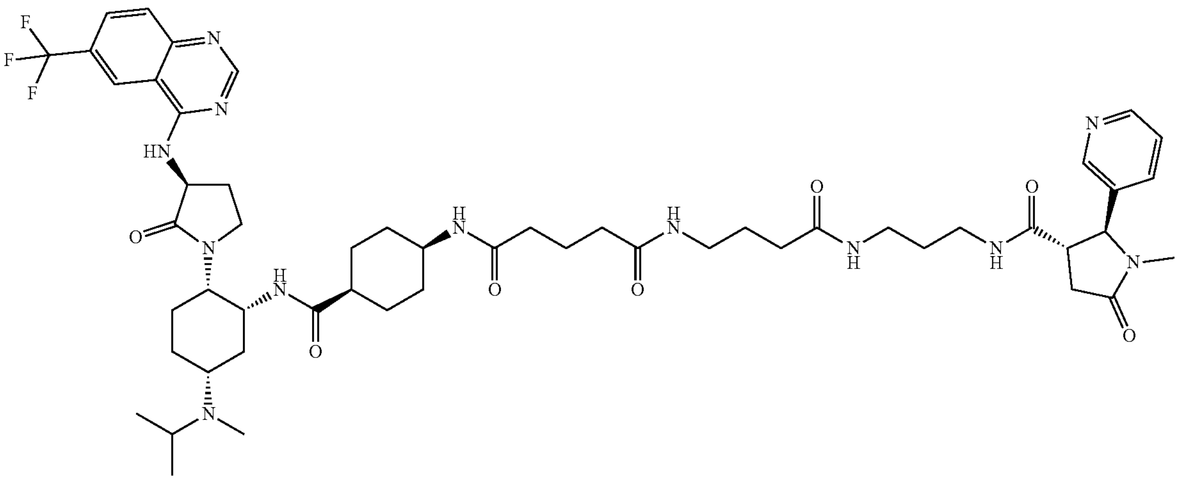 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCC(=O)NCCCC(=O)NCCCNC(=O)[C@H]3CC(=O)N(C)[C@@H]3c3cccnc3)CC2)C1]

To a mixture of (1 s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (53.4 mg, 0.081 mmol) in dichloromethane (DCM) (0.5 mL) was added commercially-available dihydro-2H-pyran-2,6(3H)-dione (9.19 mg, 0.081 mmol) and triethylamine (0.079 mL, 0.564 mmol) and the mixture was stirred at rt for 1.5 h. (2S,3S)-N-(3-(4-aminobutanamido) propyl)-1-methyl-5-oxo-2-(pyridin-3-yl) pyrrolidine-3-carboxamide, 2hydrochloric acid salt (35 mg, 0.081 mmol) and HATU (36.8 mg, 0.097 mmol) were added and the mixture was stirred at rt for 1.5 h. Triethylamine (50 μL, 0.357 mmol) and HATU (20 mg, 0.053 mmol) were added and the mixture was stirred for 1 h. Additional (2S,3S)-N-(3-(4-aminobutanamido) propyl)-1-methyl-5-oxo-2-(pyridin-3-yl) pyrrolidine-3-carboxamide, 2hydrochloric acid salt (20 mg, 0.046 mmol) was added, the mixture was stirred at rt overnight, and was concentrated. Purification by MDAP (XSelect™ CSH C18 5 μm column 40 mL/min) eluting with a gradient of 30 to 85% gradient acetonitrile in water containing ammonium bicarbonate (10 mM) and the pH adjusted to 10 with ammonia provided the title compound as a white solid (37.7 mg, 0.036 mmol, 44.7% yield). LC-MS m/z 1047.6 (M+H)$^1$H NMR (400 MHz, METHANOL-$d_4$) δ ppm 1.01 (d, J=6.4 Hz, 3H) 1.16 (d, J=6.4 Hz, 3H) 1.58-1.70 (m, 6H) 1.71-1.90 (m, 11H) 1.90-2.02 (m, 1H) 2.14-2.25 (m, 8H) 2.27 (s, 3H) 2.33 (br d, J=13.7 Hz, 1H) 2.53-2.63 (m, 1H) 2.67 (s, 3H) 2.68-2.75 (m, 2H) 2.80-2.88 (m, 1H) 2.97-3.06 (m, 1H) 3.10-3.27 (m, 7H) 3.40-3.48 (m, 1H) 3.50-3.59 (m, 1H) 3.60-3.70 (m, 1H) 3.89 (br s, 1H) 4.03 (dt, J=12.2, 3.7 Hz, 1H) 4.61 (br d, J=2.9 Hz, 1H) 4.83 (d, J=6.8 Hz, 1H) 5.31 (t, J=8.6 Hz, 1H) 7.54 (dd, J=7.8, 4.9 Hz, 1H) 7.82 (dt, J=7.8, 2.0 Hz, 1H) 7.91 (d, J=8.8 Hz, 1H) 8.07 (dd, J=8.8, 2.0 Hz, 1H) 8.53 (d, J=1.5 Hz, 1H) 8.57 (dd, J=4.9, 1.5 Hz, 1H) 8.59 (s, 1H) 8.73 (s, 1H).

Example 57

(2S,3S)-N-(2-(((1S,4R)-4-((4-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-4-oxobutoxy)methyl)cyclohexyl)methoxy)ethyl)-1-methyl-5-oxo-2-(pyridin-3-yl)pyrrolidine-3-carboxamide

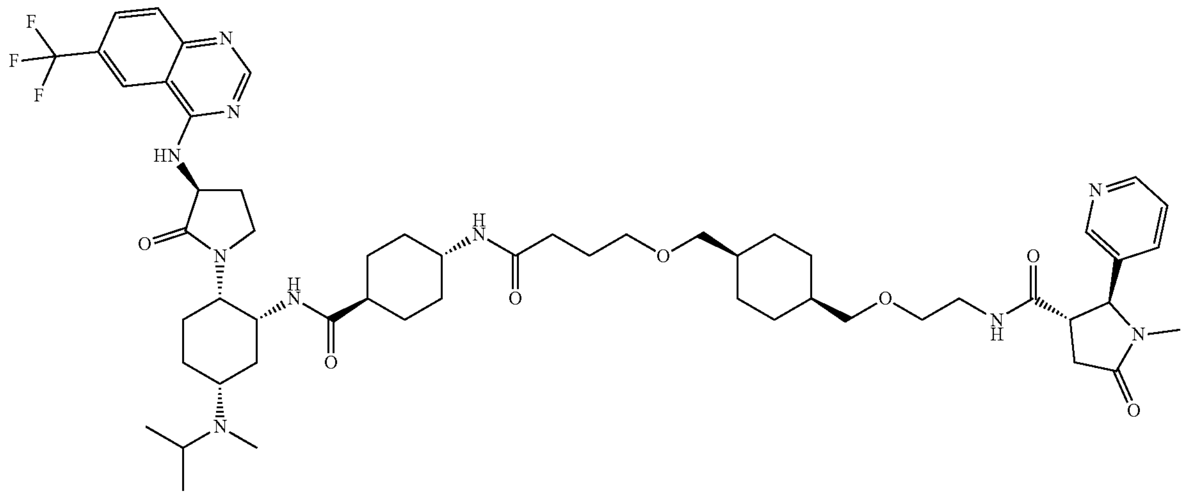

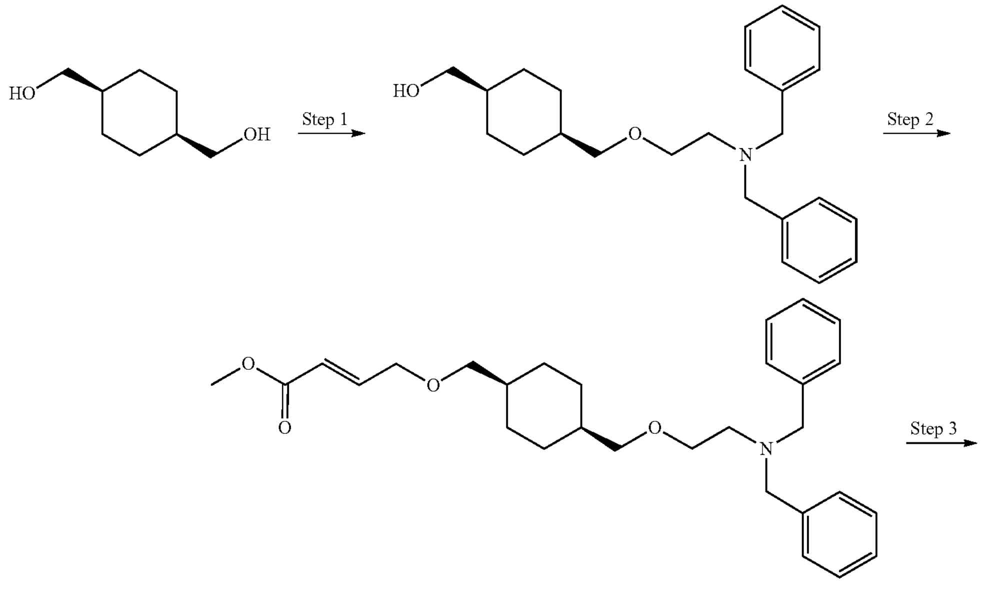

-continued
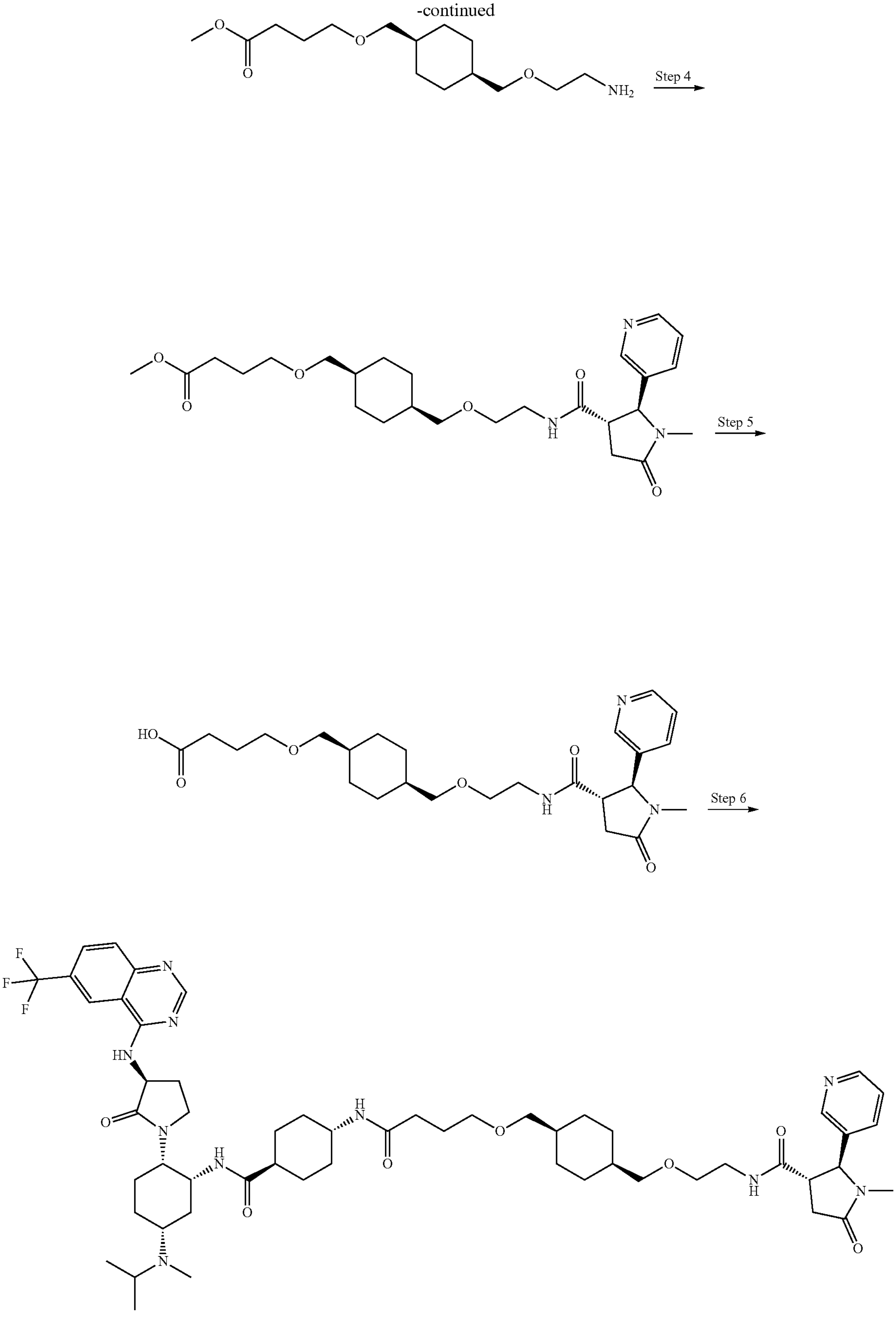

Step 1

((1s,4s)-4-((2-(dibenzylamino)ethoxy)methyl)cyclohexyl)methanol

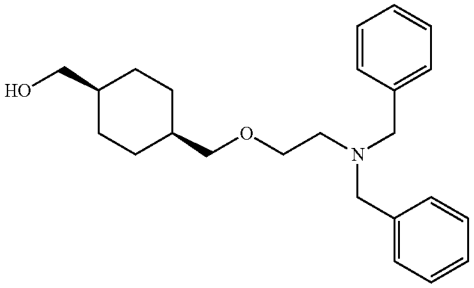 [SMILES: OC[C@H]1CC[C@@H](COCCN(Cc2ccccc2)Cc2ccccc2)CC1]

To a solution of ((1 s,4s)-cyclohexane-1,4-diyl)dimethanol (4.0 g, 27.7 mmol) in N,N-dimethylformamide (DMF) (20 mL) under an atmosphere of nitrogen was added sodium hydride (60%) (1.109 g, 27.7 mmol) at 0° C. and the mixture was stirred at rt for 30 min. N,N-dibenzyl-2-chloroethan-1-amine (5.76 g, 22.19 mmol) was added at 0° C., the mixture was warmed to rt, and was stirred for 16 h. Water (100 mL) was added and the mixture was extracted with ethyl acetate (3×60 mL). The combined organic extracts were dried over $Na_2SO_4$, were filtered, and the filtrate was concentrated under reduced pressure. Purification by Biotage® Isolera™ chromatography (50 g SNAPS column) eluting with a gradient of 0 to 20% hexane in ethyl acetate provided the title compound as a pale-yellow oil (1.7 g, 4.47 mmol, 16.11% yield). LC-MS m/z 368 $(M+H)^+$.

Step 2

Methyl (E)-4-(((1s,4s)-4-((2-(dibenzylamino)ethoxy)methyl)cyclohexyl)methoxy)but-2-enoate

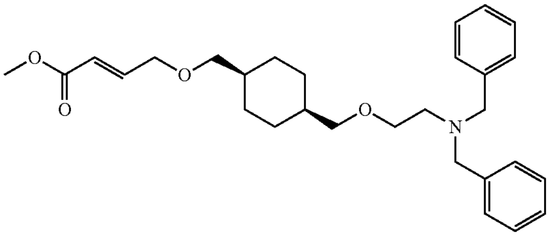 [SMILES: COC(=O)/C=C/COC[C@H]1CC[C@@H](COCCN(Cc2ccccc2)Cc2ccccc2)CC1]

To a solution of ((1 s,45)-4-((2-(dibenzylamino)ethoxy)methyl)cyclohexyl)methanol (1.7 g, 4.63 mmol) in toluene (20 mL) under an atmosphere of nitrogen was added acetic acid (0.053 mL, 0.925 mmol), triphenylphosphine (0.061 g, 0.231 mmol) and commercially available methyl but-2-ynoate (0.681 g, 6.94 mmol) at rt, and the mixture was stirred at 115° C. for 16 h. The mixture was cooled to rt, ethyl acetate (50 mL) was added and the organic phase was washed with water (2×50 mL). The organic phase was dried over $Na_2SO_4$ and was concentrated under reduced pressure. Purification by Biotage® Isolera™ chromatography (25 g SNAPS column) eluting with a gradient of 0 to 30% ethyl acetate in hexane provided the title compound as a pale-yellow oil (1.2 g, 2.397 mmol, 51.8% yield). LC-MS m/z 466 $(M+H)^+$.

Step 3

Methyl 4-(((1 s,4s)-4-((2-aminoethoxy)methyl)cyclohexyl)methoxy)butanoate

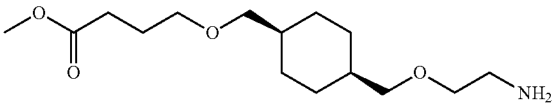 [SMILES: COC(=O)CCCOC[C@H]1CC[C@@H](COCCN)CC1]

To a stirred solution of methyl (E)-4-(((1 s,4s)-4-((2-(dibenzylamino)ethoxy)methyl)cyclohexyl)methoxy)but-2-enoate (1.2 g, 2.58 mmol) in methanol (20 mL) was added acetic acid (0.295 mL, 5.15 mmol) and 10% Pd/C (0.30 g, 0.282 mmol) at and the mixture was stirred under a balloon atmosphere of hydrogen at rt for 16 h. Methanol (50 mL) was added, the mixture was filtered through Celite®, and the combined filtrates were concentrated under reduced pressure to provide the title compound as a colorless liquid (700 mg, 2.433 mmol, 94% yield). LC-MS m/z 288 $(M+H)^+$.

Step 4

Methyl 4-(((1R,4s)-4-((2-((2S,3S)-1-methyl-5-oxo-2-(pyridin-3-yl)pyrrolidine-3-carboxamido)ethoxy)methyl)cyclohexyl)methoxy)butanoate

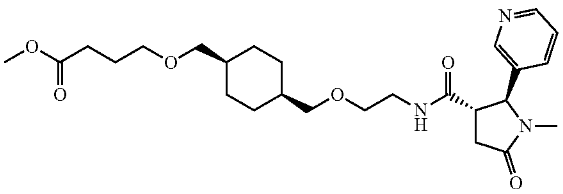 [SMILES: COC(=O)CCCOC[C@H]1CC[C@@H](COCCNC(=O)[C@H]2CC(=O)N(C)[C@@H]2c2cccnc2)CC1]

To a solution of (2S,3S)-1-methyl-5-oxo-2-(pyridin-3-yl)pyrrolidine-3-carboxylic acid (0.650 g, 2.95 mmol) in N,N-dimethylformamide (DMF) (10 mL) under an atmosphere of nitrogen was added DIPEA (1.031 mL, 5.90 mmol), HATU (1.683 g, 4.43 mmol), and methyl 4-(((1s,4s)-4-((2-aminoethoxy)methyl)cyclohexyl)methoxy)butanoate (0.763 g, 2.66 mmol), and the mixture was stirred at rt for 16 h. Water (50 mL) was added and the mixture was extracted with ethyl acetate (3×30 mL). The combined organic extracts were dried over $Na_2SO_4$ and were concentrated under reduced pressure. Purification by Biotage® Isolera™ chromatography (25 g SNAPS column) eluting with 5% methanol in dichloromethane (DCM) provided the title compound as a pale-yellow liquid (800 mg, 1.225 mmol, 41.5% yield). LC-MS m/z 490.1 $(M+H)^+$.

Step 5

4-(((1R,4s)-4-((2-((2S,3S)-1-Methyl-5-oxo-2-(pyridin-3-yl)pyrrolidine-3-carboxamido)ethoxy)methyl)cyclohexyl)methoxy)butanoic acid

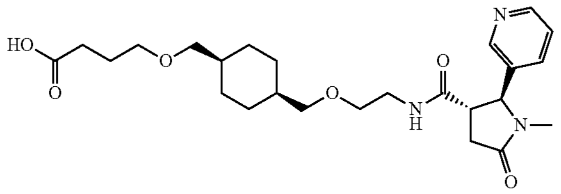 [SMILES: CN1C(=O)C[C@H](C(=O)NCCOC[C@H]2CC[C@@H](COCCCC(=O)O)CC2)[C@H]1c1cccnc1]

A mixture of methyl 4-(((1R,4s)-4-((2-((2S,3S)-1-methyl-5-oxo-2-(pyridin-3-yl) pyrrolidine-3-carboxamido)ethoxy)methyl)cyclohexyl)methoxy)butanoate (800 mg, 1.634 mmol) and lithium hydroxide (47.0 mg, 1.961 mmol) in tetrahydrofuran (THF) (5.0 mL) and water (5.00 mL) was stirred at room temperature for 2 h, and the mixture was concentrated under reduced pressure. The pH was adjusted to 6 using 1.5 N HCl and the mixture concentrated under reduced pressure. The residue was purified by reverse phase HPLC (YMC-Triart C18 ExRS 5 μm column, 15 mL/min) eluting with a stepwise gradient solvent of 10 to 50% (12 min) and 100% (4 min) acetonitrile in water containing formic acid (0.1%). A second purification by Chiral SFC (YMC Cellulose-C column, 3 mL/min, injection volume 15 μL, 100 bar, 35° C.) eluting with a co-solvent of 40% isopropyl alcohol provided the title compound as a colorless oil (195 mg, 0.408 mmol, 24.99% yield). LC-MS m/z 476.1 $(M+H)^+$.

Step 6

(2S,3S)-N-(2-(((1S,4R)-4-((4-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-4-oxobutoxy)methyl)cyclohexyl)methoxy)ethyl)-1-methyl-5-oxo-2-(pyridin-3-yl)pyrrolidine-3-carboxamide

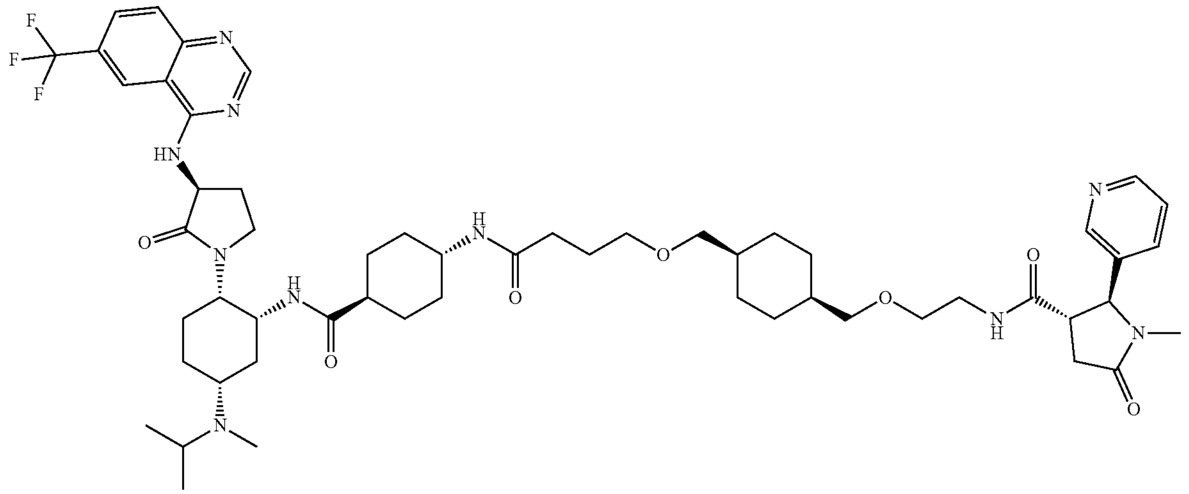 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCOC[C@H]3CC[C@@H](COCCNC(=O)[C@H]4CC(=O)N(C)[C@@H]4c4cccnc4)CC3)CC2)C1]

To a mixture of (1r,4R)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (48.8 mg, 0.074 mmol) and 4-(((1R,4s)-4-((2-((2S,3S)-1-methyl-5-oxo-2-(pyridin-3-yl)pyrrolidine-3-carboxamido)ethoxy)methyl)cyclohexyl) methoxy) butanoic acid (35 mg, 0.074 mmol) in dichloromethane (DCM) (1 mL) was added triethylamine (0.062 mL, 0.442 mmol) and HATU (33.6 mg, 0.088 mmol), and the mixture was stirred at rt for 2 h. Purification by MDAP (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a white solid (49.5 mg, 0.047 mmol, 64.2% yield). LC-MS m/z 1047.5 $(M+H)^+$. $^1H$ NMR (400 MHz, METHANOL-$d_4$) b ppm 1.02 (br d, J=6.4 Hz, 3H) 1.16 (br d, J=6.4 Hz, 3H) 1.18-1.31 (m, 3H) 1.33-1.79 (m, 16H) 1.79-1.89 (m, 2H) 1.90-2.02 (m, 5H) 2.06-2.18 (m, 2H) 2.19-2.26 (m, 3H) 2.28 (s, 3H) 2.34 (br d, J=14.2 Hz, 1H) 2.44-2.62 (m, 1H) 2.66 (s, 3H) 2.68-2.76 (m, 2H) 2.77-2.89 (m, 1H) 3.02-3.10 (m, 1H) 3.28-3.32 (m, 2H) 3.35-3.54 (m, 8H) 3.57-3.67 (m, 2H) 4.02 (dt, J=12.5, 3.8 Hz, 1H) 4.65 (br d, J=2.9 Hz, 1H) 4.83 (d, J=6.4 Hz, 1H) 5.28 (t, J=8.1 Hz, 1H) 7.51-7.56 (m, 1H) 7.80 (dt, J=7.8, 2.0 Hz, 1H) 7.91 (d, J=8.8 Hz, 1H) 8.07 (dd, J=8.8, 2.0 Hz, 1H) 8.51 (d, J=1.5 Hz, 1H) 8.58 (dd, J=4.9, 1.5 Hz, 1H) 8.59 (s, 1H) 8.81 (s, 1H).

The following compounds were or could be prepared with procedures analogous to that described in Example 57:

| Ex. | Compound | LC-MS m/z | NMR |
|---|---|---|---|
| 58 | 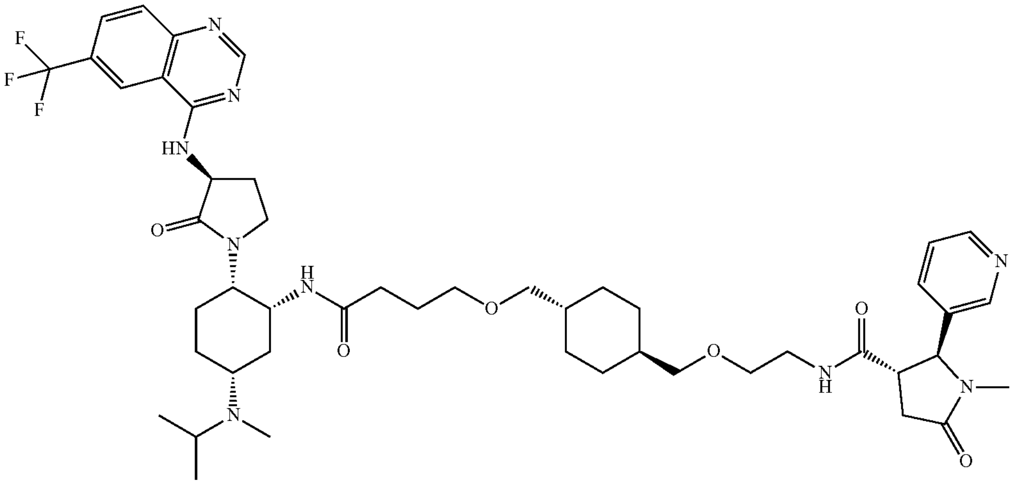 [SMILES: CC(C)N(C)[C@@H]1CC[C@H](N2CC[C@H](Nc3ncnc4ccc(C(F)(F)F)cc34)C2=O)[C@H](NC(=O)CCCOC[C@H]2CC[C@H](COCCNC(=O)[C@H]3CC(=O)N(C)[C@@H]3c3cccnc3)CC2)C1] (2S,3S)-N-(2-(((1R,4S)-4-((4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-4-oxobutoxy)methyl)cyclohexyl)methoxy)ethyl)-1-methyl-5-oxo-2-(pyridin-3-yl)pyrrolidine-3-carboxamide. | 922.3 $(M + H)^+$ | $^1H$ NMR (400 MHz, METHANOL-$d_4$) δ ppm 0.81-0.90 (m, 4H) 1.02 (br d, J = 6.3 Hz, 3H) 1.12 (br d, J = 6.5 Hz, 3H) 1.41 (br s, 2H) 1.62-1.79 (m, 7H) 1.83-2.01 (m, 3H) 2.05-2.38 (m, 8H) 2.50-2.61 (m, 1H) 2.66 (s, 3 H) 2.67-2.75 (m, 2H) 2.80-2.90 (m, 1H) 3.01-3.13 (m, 1H) 3.13-3.19 (m, 4H) 3.26-3.39 (m, 4 H) 3.43-3.46 (m, 2H) 3.54 (td, J = 9.2, 3.8 Hz, 1 H) 3.59-3.68 (m, 1H) 4.04 (dt, J = 12.4, 3.7 Hz, 1H) 4.64 (br d, J = 3.3 Hz, 1H) 4.84 (d, J = 6.5 Hz, 1 H) 5.27 (t, J = 8.0 Hz, 1H) 7.50-7.54 (m, 1H) 7.79 (dt, J = 8.0, 1.9 Hz, 1H) 7.90 (d, J = 8.8 Hz, 1H) 8.05 (dd, J = 8.8, 1.8 Hz, 1 H) 8.52 (d, J = 2.0 Hz, 1H) 8.57 (dd, J = 4.8, 1.5 Hz, 1 H) 8.58 (s, 1H) 8.81 (s, 1 H) |

-continued

| Ex. | Compound | LC-MS m/z | NMR |
|---|---|---|---|
| 59 | 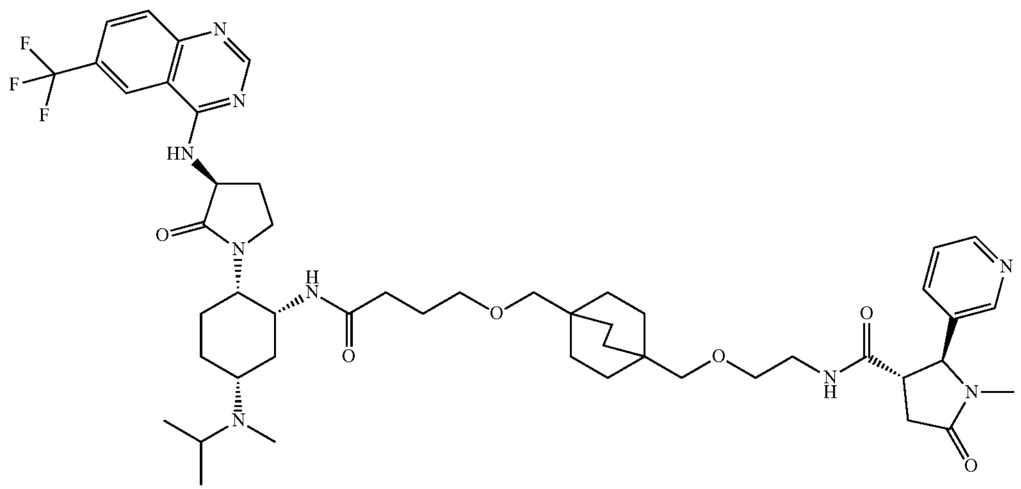 [SMILES: CC(C)N(C)[C@@H]1CC[C@H](N2CC[C@H](Nc3ncnc4ccc(C(F)(F)F)cc34)C2=O)[C@H](NC(=O)CCCOCC23CCC(COCCNC(=O)[C@H]4CC(=O)N(C)[C@@H]4c4cccnc4)(CC2)CC3)C1] (2S,3S)-N-(2-((4-((4-(((1R,2S,5R)-5-(Isopropoyl)methyl)amino)-2-((S)-2-oxo-3-((6-(trifluoromethyl)quinazolin-4-yl)amino)pyrrolidin-1-yl)cyclohexyl)amino)-4-oxobutoxy)methyl)bicyclo[2.2.2]octan-1-yl)methoxy)ethyl)-1-methyl-5-oxo-2-(pyridin-3-yl)pyrrolidine-3-carboxamide. | 948.4 $(M + H)^+$ | $^1H$ NMR (400 MHz, METHANOL-$d_4$) δ ppm 1.04 (br d, J = 6.3 Hz, 3H) 1.14 (br d, J = 6.6 Hz, 3H) 1.33 (s, 12H) 1.62-1.81 (m, 3H) 1.81-2.02 (m, 3 H) 2.07-2.26 (m, 2H) 2.27 (s, 3H) 2.29-2.37 (m, 3H) 2.51-2.63 (m, 1 H) 2.67 (s, 3H) 2.68-2.78 (m, 2H) 2.80-2.88 (m, 1H) 2.90-3.02 (m, 4 H) 3.03-3.11 (m, 1H) 3.23-3.38 (m, 5H) 3.44-3.48 (m, 1H) 3.50-3.58 (m, 1H) 3.60-3.70 (m, 1 H) 4.05 (dt, J = 12.3, 3.7 Hz, 1H) 4.66 (br d, J = 3.3 Hz, 1H) 4.82-4.86 (m, 1 H) 5.27 (t, J = 8.0 Hz, 1H) 7.47-7.58 (m, 1H) 7.80 (dt, J = 8.0, 1.9 Hz, 1H) 7.91 (d, J = 8.9 Hz, 1H) 8.06 (dd, J = 8.9, 1.8 Hz, 1 H) 8.52 (d, J = 1.8 Hz, 1H) 8.58 (dd, J = 4.8, 1.5 Hz, 1 H) 8.59 (s, 1H) 8.83 (s, 1 H). |

-continued

| Ex. | Compound | LC-MS m/z | NMR |
|---|---|---|---|
| 60 | 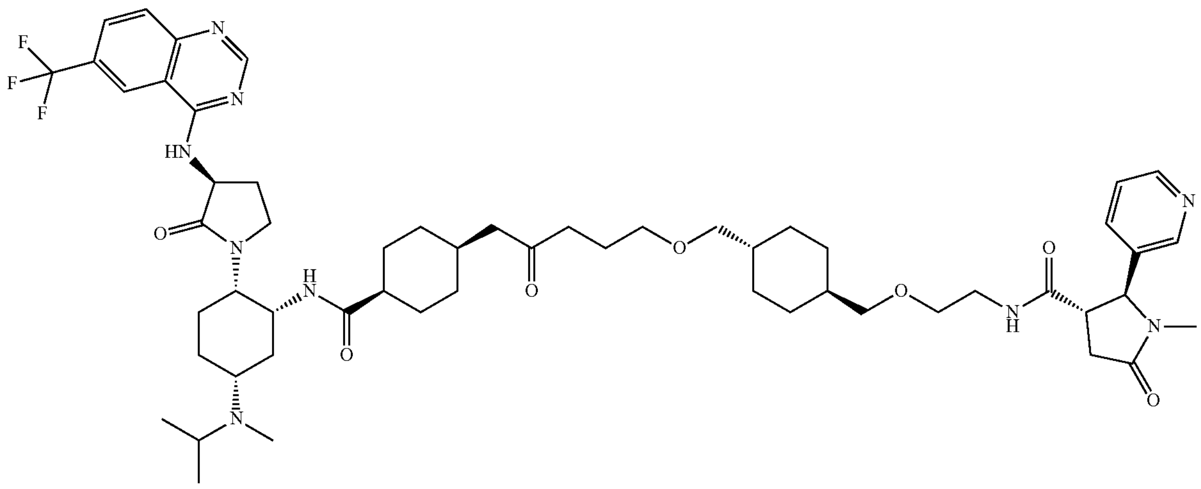 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](CC(=O)CCCOC[C@H]3CC[C@H](COCCNC(=O)[C@H]4CC(=O)N(C)[C@@H]4c4cccnc4)CC3)CC2)C1] (2S,3S)-N-(2-(((1R,4S)-4-(((5-((1S,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)-4-oxopentyl)oxy)methyl)cyclohexyl)methoxy)ethyl)-1-methyl-5-oxo-2-(pyridin-3-yl)pyrrolidine-3-carboxamide. | 1047.4 $(M + H)^+$ | $^1H$ NMR (400 MHz, METHANOL-$d_4$) δ ppm 0.85-0.94 (m, 4H) 0.97-1.07 (m, 3H) 1.17 (br d, J = 5.8 Hz, 3H) 1.37-1.52 (m, 3H) 1.54-1.88 (m, 18H) 1.89-2.02 (m, 2H) 2.10-2.35 (m, 10H) 2.51-2.63 (m, 2H) 2.66 (s, 3 H) 2.68-2.76 (m, 1H) 2.79-2.89 (m, 1H) 3.02-3.11 (m, 1H) 3.14-3.31 (m, 6H) 3.35-3.73 (m, 4 H) 3.85-3.94 (m, 1H) 3.98-4.11 (m, 1H) 4.61 (s, 2H) 4.83 (d, J = 6.6 Hz, 1H) 5.26-5.39 (m, 1H) 7.50-7.58 (m, 1H) 7.80 (dt, J = 7.9, 1.9 Hz, 1H) 7.91 (d, J = 8.9 Hz, 1H) 8.07 (dd, J = 9.0, 1.9 Hz, 1 H) 8.51 (d, J = 1.8 Hz, 1H) 8.56-8.59 (m, 2H) 8.73 (s, 1H). |

-continued

| Ex. | Compound | LC-MS m/z | NMR |
|---|---|---|---|
| 61 | 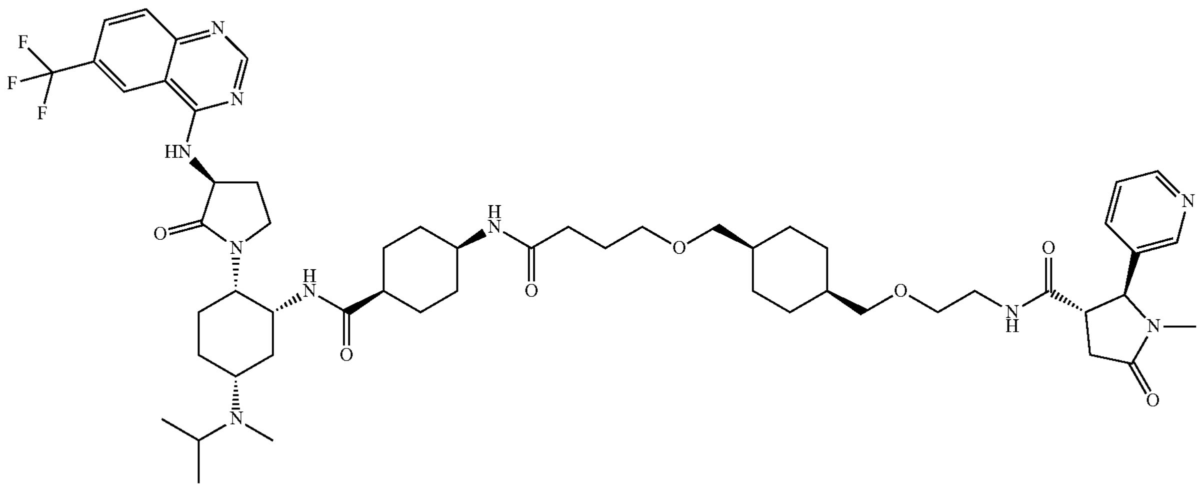 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCOC[C@H]3CC[C@@H](COCCNC(=O)[C@H]4CC(=O)N(C)[C@@H]4c4cccnc4)CC3)CC2)C1] (2S,3S)-N-(2-(((1S,4R)-4-((4-(((1S,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-4-oxobutoxy)methyl)cyclohexyl)methoxy)ethyl)-1-methyl-5-oxo-2-(pyridin-3-yl)pyrrolidine-3-carboxamide. | 1047.6 $(M + H)^+$ | $^1H$ NMR (400 MHz, METHANOL-$d_4$) δ ppm 1.00 (br d, J = 6.4 Hz, 3H) 1.16 (br d, J = 6.4 Hz, 3H) 1.30-1.48 (m, 8H) 1.59-1.87 (m, 15H) 1.91-1.99 (m, 1H) 2.10-2.35 (m, 9H) 2.54-2.62 (m, 1 H) 2.65-2.74 (m, 5H) 2.80-2.87 (m, 1H) 3.06 (ddd, J = 9.4, 8.2, 6.8 Hz, 1H) 3.25-3.41 (m, 11H) 3.43-3.48 (m, 2H) 3.51-3.57 (m, 1H) 3.60-3.67 (m, 1H) 3.89 (br t, J = 3.9 Hz, 1H) 4.03 (dt, J = 12.5, 3.5 Hz, 1H) 4.61 (br d, J = 2.9 Hz, 1H) 4.83 (d, J = 6.4 Hz, 1H) 5.32 (t, J = 8.8 Hz, 1H) 7.53 (dd, J = 7.8, 4.9 Hz, 1H) 7.80 (dt, J = 8.2, 1.8 Hz, 1H) 7.91 (d, J = 8.8 Hz, 1H) 8.07 (dd, J = 9.0, 1.7 Hz, 1 H) 8.51 (d, J = 2.0 Hz, 1H) 8.56-8.60 (m, 2H) 8.73 (s, 1H). |

-continued

| Ex. | Compound | LC-MS m/z | NMR |
|---|---|---|---|
| 62 | 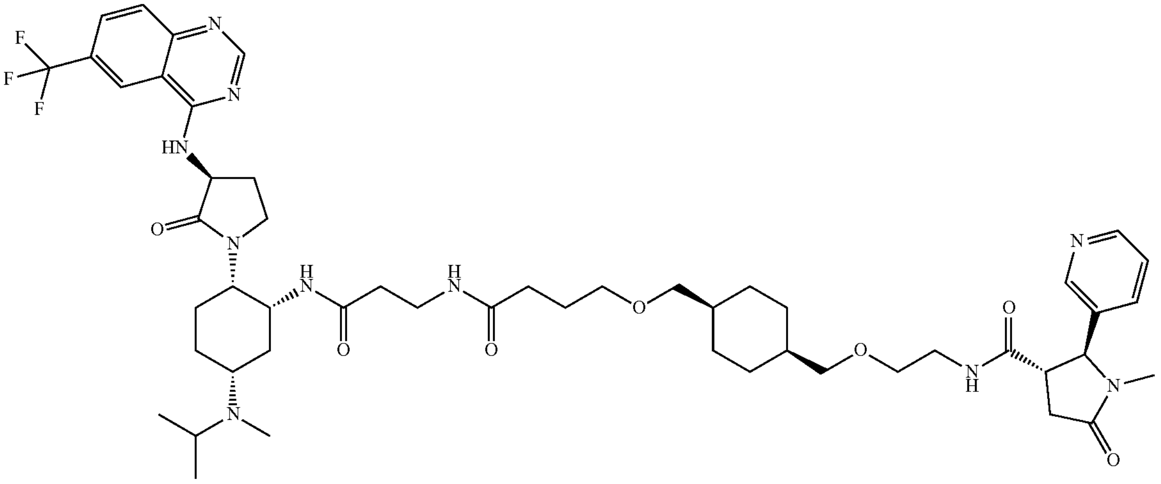 [SMILES: CC(C)N(C)[C@@H]1CC[C@H](N2CC[C@H](Nc3ncnc4ccc(C(F)(F)F)cc34)C2=O)[C@H](NC(=O)CCNC(=O)CCCOC[C@H]2CC[C@@H](COCCNC(=O)[C@H]3CC(=O)N(C)[C@@H]3c3cccnc3)CC2)C1] (2S,3S)-N-(2-(((1S,4R)-4-((4-((3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropyl)amino)-4-oxobutoxy)methyl)cyclohexyl)methoxy)ethyl)-1-methyl-5-oxo-2-(pyridin-3-yl)pyrrolidine-3-carboxamide. | 993.5 $(M + H)^+$ | $^1H$ NMR (400 MHz, METHANOL-$d_4$) δ ppm 1.03 (d, J = 6.4 Hz, 3H) 1.12 (d, J = 6.4 Hz, 3H) 1.29-1.54 (m, 8H) 1.61-1.86 (m, 7H) 2.00 (dq, J = 12.7, 8.7 Hz, 1H) 2.11-2.34 (m, 8H) 2.44 (t, J = 6.8 Hz, 2H) 2.53-2.63 (m, 1H) 2.66 (s, 3H) 2.67-2.78 (m, 2H) 2.79-2.89 (m, 1H) 3.00-3.11 (m, 1 H) 3.29 (dd, J = 10.3, 6.8 Hz, 4H) 3.34-3.60 (m, 9 H) 3.61-3.69 (m, 1H) 4.03 (dt, J = 11.7, 3.7 Hz, 1H) 4.57 (br d, J = 3.4 Hz, 1H) 4.83 (d, J = 6.8 Hz, 1 H) 5.31 (t, J = 8.8 Hz, 1H) 7.52 (dd, J = 7.8, 4.9 Hz, 1 H) 7.79 (dt, J = 8.2, 1.8 Hz, 1H) 7.91 (d, J = 8.8 Hz, 1 H) 8.06 (dd, J = 8.8, 2.0 Hz, 1H) 8.51 (d, J = 1.5 Hz, 1H) 8.57 (dd, J = 4.9, 1.5 Hz, 1H) 8.59 (s, 1H) 8.74 (s, 1H). |

Example 63
(2S,3S)-N-(2-((2-(2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)amino)-3-oxopropoxy)ethoxy)ethyl)amino)-2-oxoethyl)-1-methyl-5-oxo-2-(pyridin-3-yl)pyrrolidine-3-carboxamide
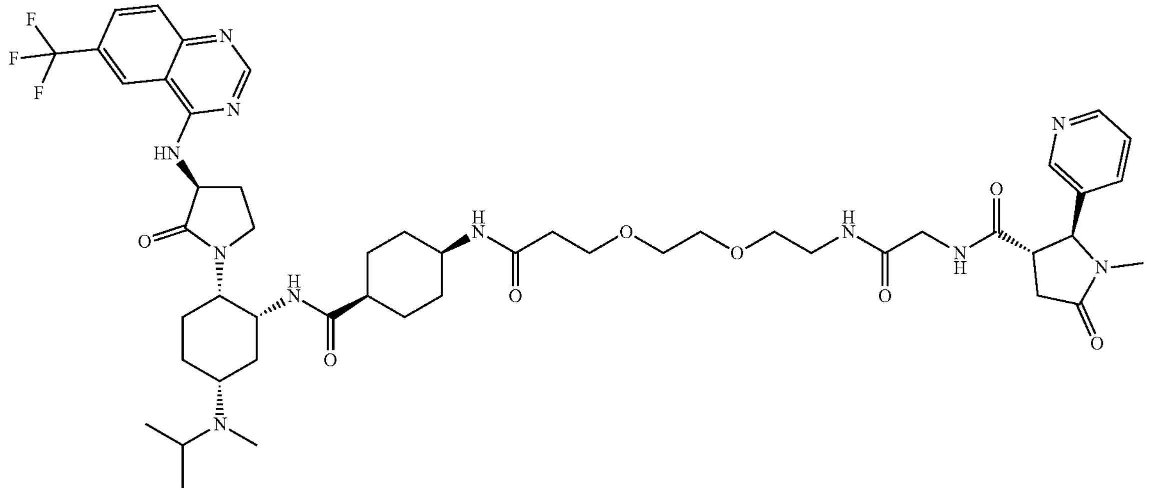
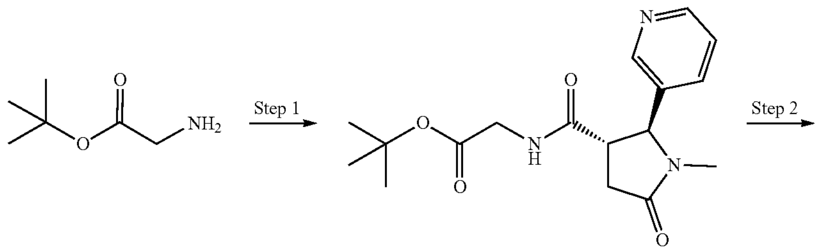
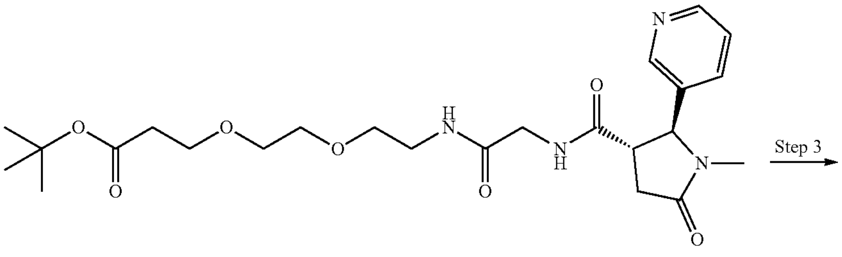

-continued

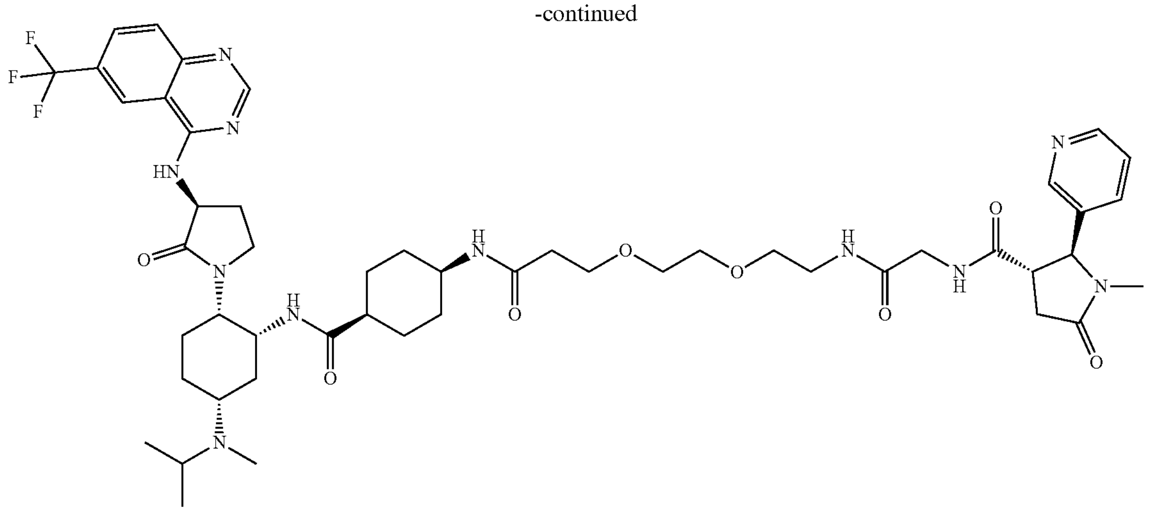

Step 1 tert-Butyl ((2S,3S)-1-methyl-5-oxo-2-(pyridin-3-yl) pyrrolidine-3-carbonyl)glycinate

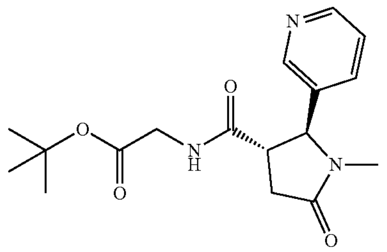 [SMILES: CN1C(=O)C[C@H](C(=O)NCC(=O)OC(C)(C)C)[C@H]1c1cccnc1]

To a solution of (2S,3S)-1-methyl-5-oxo-2-(pyridin-3-yl) pyrrolidine-3-carboxylic acid (150 mg, 0.681 mmol) in N,N-dimethylformamide (4.0 mL) was added DIPEA (440 mg, 3.41 mmol), HOBt (104 mg, 0.681 mmol), HATU (388 mg, 1.022 mmol) followed by tert-butyl glycinate, hydrochloric acid salt (114 mg, 0.681 mmol), and the mixture was stirred overnight. Water was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a wax (230 mg, 0.690 mmol, 101% yield). LC-MS m/z 334.0 $(M+H)^+$.

Step 2 tert-Butyl 1-((2S,3S)-1-methyl-5-oxo-2-(pyridin-3-yl)pyrrolidin-3-yl)-1,4-dioxo-8,11-dioxa-2,5-diazatetradecan-14-oate

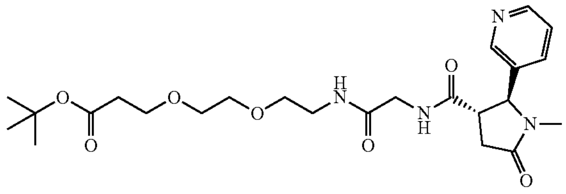 [SMILES: CN1C(=O)C[C@H](C(=O)NCC(=O)NCCOCCOCCC(=O)OC(C)(C)C)[C@H]1c1cccnc1]

A mixture of tert-butyl ((2S,3S)-1-methyl-5-oxo-2-(pyridin-3-yl) pyrrolidine-3-carbonyl)glycinate (230 mg, 0.690 mmol) and 4 M HCl in 1,4-Dioxane (4 mL, 16.00 mmol) was stirred for 1 h and was concentrated under reduced pressure to dryness. The residue was dissolved in N,N-dimethylformamide (4.0 mL), DIPEA (446 mg, 3.45 mmol), HOBt (106 mg, 0.690 mmol), and HATU (393 mg, 1.035 mmol) were added followed by commercially-available tert-butyl 3-(2-(2-aminoethoxy)ethoxy)propanoate (161 mg, 0.690 mmol), and the mixture was stirred overnight Water was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as an off-white solid (260 mg, 0.528 mmol, 77% yield). LC-MS (m/z) 493.1 $(M+H)^+$.

Step 3

(2S,3S)-N-(2-((2-(2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-3-oxopropoxy)ethoxy)ethyl)amino)-2-oxoethyl)-1-methyl-5-oxo-2-(pyridin-3-yl)pyrrolidine-3-carboxamide

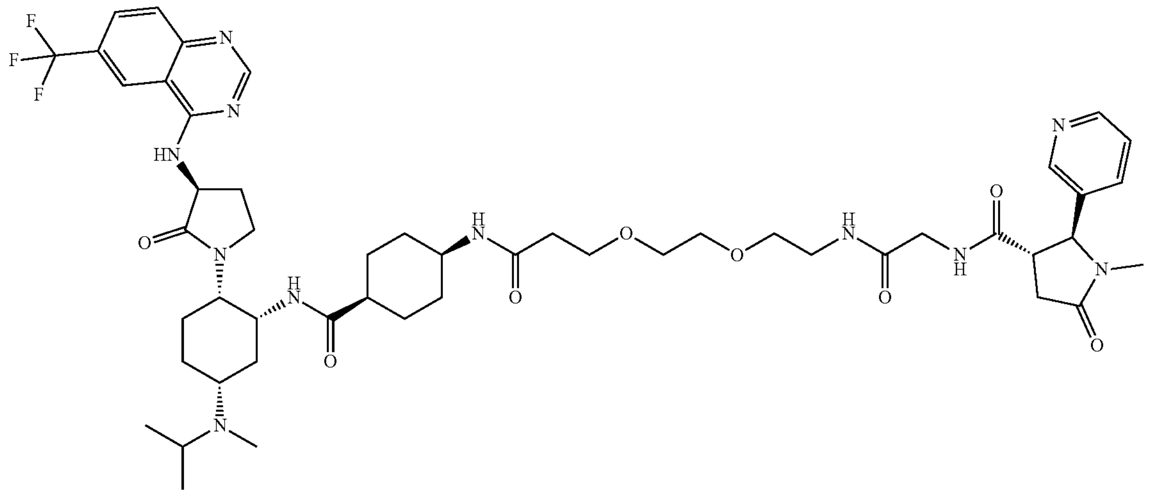 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCNC(=O)CNC(=O)[C@H]3CC(=O)N(C)[C@@H]3c3cccnc3)CC2)C1]

A mixture of tert-butyl 1-((2S,3S)-1-methyl-5-oxo-2-(pyridin-3-yl)pyrrolidin-3-yl)-1,4-dioxo-8,11-dioxa-2,5-diazatetradecan-14-oate (32.1 mg, 0.065 mmol), 4 M HCl in 1,4-dioxane (4 mL, 16.00 mmol), and dichloromethane (DCM) (2.0 mL) was stirred for 1 h and was concentrated under reduced pressure to dryness. Dichloromethane (DCM) (2.0 mL), (1s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (40 mg, 0.054 mmol), HOBt (8.32 mg, 0.054 mmol) and DIPEA (0.047 mL, 0.272 mmol) were added. HATU (31.0 mg, 0.081 mmol) were added and the mixture was stirred at rt for 3 h. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP (XSelect™ CSH C18 5 μm column, 40 mL/min) eluting with a gradient of 30 to 85% acetonitrile in water containing ammonium bicarbonate (10 mM) and ammonium hydroxide (0.075%) provided the title compound as an off white solid (25.6 mg, 0.024 mmol, 44.4% yield). LC-MS m/z 1008.5 $(M)^+$. $^1$H NMR (400 MHz, DMSO-$d_6$) δ ppm 0.90 (d, J=6.4 Hz, 3H) 0.98 (br s, 10H) 1.04 (d, J=6.4 Hz, 3H) 1.35-1.82 (m, 11H) 1.90-2.19 (m, 6H) 2.28 (t, J=6.6 Hz, 1H) 2.32-2.39 (m, 1H) 2.40-2.49 (m, 2H) 2.56-2.63 (m, 1H) 2.75 (dd, J=16.4, 10.0 Hz, 1H) 3.04 (ddd, J=9.5, 7.1, 5.9 Hz, 2H) 3.19 (q, J=5.7 Hz, 2H) 3.44 (s, 3H) 3.48-3.60 (m, 3H) 3.68 (d, J=5.9 Hz, 2H) 3.85-3.93 (m, 1H) 4.43 (br s, 1H) 4.69 (d, J=5.9 Hz, 1H) 5.03 (q, J=8.2 Hz, 1H) 7.44 (dd, J=7.8, 4.9 Hz, 1H) 7.65 (d, J=6.8 Hz, 1H) 7.69 (dt, J=7.8, 2.0 Hz, 1 H) 7.82-7.98 (m, 2H) 8.07 (dd, J=8.8, 2.0 Hz, 1H) 8.23 (t, J=5.6 Hz, 1H) 8.50 (d, J=2.0 Hz, 1H) 8.55 (dd, J=4.9, 1.5 Hz, 1H) 8.58 (s, 1H) 8.63-8.69 (m, 1H) 8.71 (d, J=8.3 Hz, 1H) 8.89 (s, 1H).

The following compounds were or could be prepared with procedures analogous to that described in Example 63:

| Ex. | Compound | LC-MS m/z | NMR |
|---|---|---|---|
| 64 | 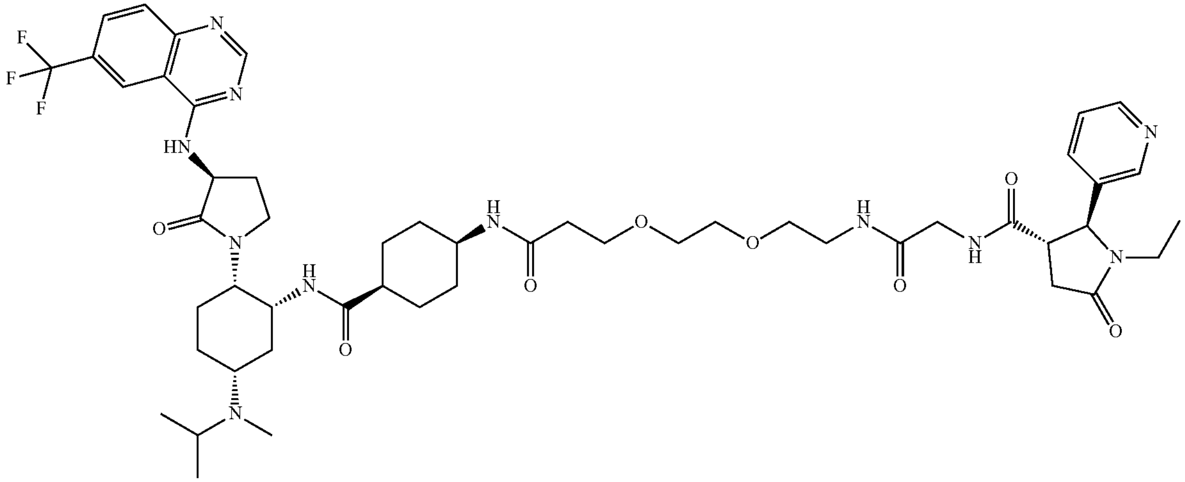 [SMILES: CCN1C(=O)C[C@H](C(=O)NCC(=O)NCCOCCOCCC(=O)N[C@H]2CC[C@@H](C(=O)N[C@@H]3C[C@H](N(C)C(C)C)CC[C@@H]3N3CC[C@H](Nc4ncnc5ccc(C(F)(F)F)cc45)C3=O)CC2)[C@H]1c1cccnc1] (2S,3S)-1-Ethyl-N-(2-((2-(2-(3-(((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethyl)amino)-2-oxoethyl)-5-oxo-2-(pyridin-3-yl)pyrrolidine-3-carboxamide | 1022.4 $(M + H)^+$ | $^1H$ NMR (400 MHz, METHANOL-$d_4$) δ ppm 0.96-1.07 (m, 6H) 1.16 (br d, J = 6.4, Hz, 3H) 1.34 (br d, J = 6.4 Hz, 3 H) 1.56-1.88 (m, 10H) 1.89-2.04 (m, 1H) 2.10-2.39 (m, 8H) 2.42 (t, J = 6.1 Hz, 2H) 2.53-2.64 (m, 1H) 2.66-2.79 (m, 3H) 2.86-2.96 (m, 1H) 3.14 (ddd, J = 9.5, 7.1, 5.9 Hz, 1H) 3.36 (d, J = 4.4 Hz, 1H) 3.40-3.46 (m, 1H) 3.47-3.51 (m, 2H) 3.52-3.59 (m, 5H) 3.60-3.75 (m, 5H) 3.85 (d, J = 2.4 Hz, 2H) 3.88-3.94 (m, 1H) 4.00-4.08 (m, 1H) 4.60 (br d, J = 2.4 Hz, 1H) 5.01 (d, J = 5.9 Hz, 1H) 5.30 (br t, J = 8.8 Hz, 1H) 7.52 (dd, J = 7.8, 4.9 Hz, 1H) 7.85 (dt, J = 7.9, 1.9 Hz, 1H) 7.91 (d, J = 8.8 Hz, 1H) 8.07 (dd, J = 8.8, 2.0 Hz, 2H) 8.56 (dd, J = 4.9, 1.5 Hz, 1H) 8.58 (d, J = 2.0 Hz, 1H) 8.59 (s, 1H) 8.73 (s, 1H). |

-continued

| Ex. | Compound | LC-MS m/z | NMR |
|---|---|---|---|
| 65 | 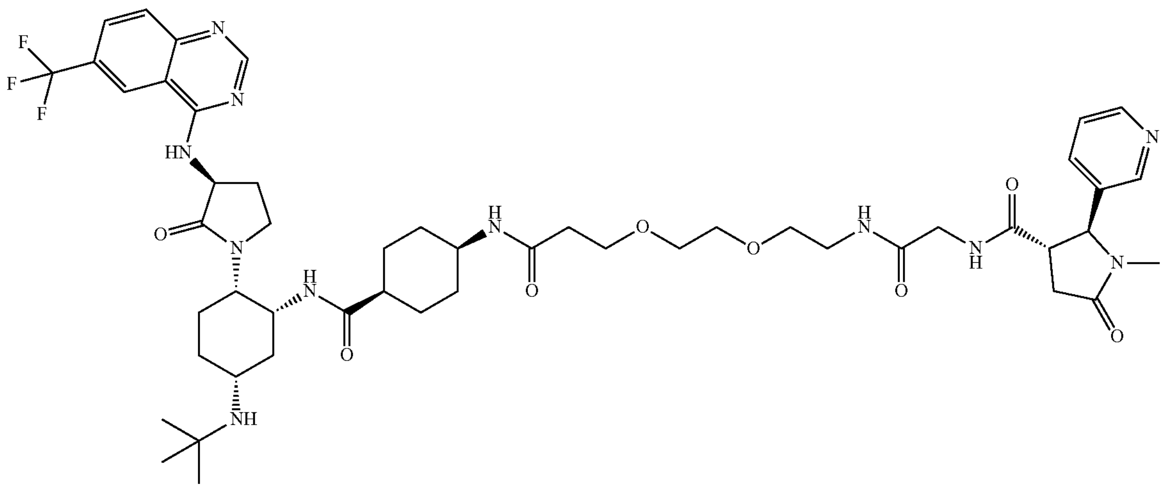 [SMILES: CN1C(=O)C[C@H](C(=O)NCC(=O)NCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1] (2S,3S)-N-(2-((2-(2-(3-(((1S,4s)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethyl)amino)-2-oxoethyl)-1-methyl-5-oxo-2-(pyridin-3-yl)pyrrolidine-3-carboxamide. | 1008.6 $(M + H)^+$ | $^1H$ NMR (400 MHz, DMSO-$d_6$) δ ppm 1.08 (s, 9H) 1.36-1.70 (m, 9 H) 1.71-1.84 (m, 4H) 1.84-1.95 (m, 1H) 2.11 (br d, J = 2.9 Hz, 2H) 2.28 (t, J = 6.6 Hz, 2H) 2.32-2.41 (m, 1H) 2.41-2.48 (m, 2H) 2.52-2.57 (m, 1H) 2.67-2.78 (m, 1H) 3.00-3.11 (m, 2H) 3.19 (q, J = 5.9 Hz, 2 H) 3,35-3.41 (m, 3H) 3.42-3.47 (m, 4H) 3.52-3.59 (m, 3H) 3.68 (d, J = 5.9 Hz, 2H) 3.70-3.75 (m, 1H) 3.84 (br d, J = 12.2 Hz, 1H) 4.45 (br s, 1H) 4.69 (d, J = 5.9 Hz, 1H) 5.00-5.09 (m, 1H) 7.44 (dd, J = 7.8, 5.4 Hz, 1H) 7.65 (d, J = 6.8 Hz, 1 H) 7.69 (dt, J = 7.8, 2.0 Hz, 1H) 7.86-7.93 (m, 2H) 8.07 (dd, J = 8.8, 1.5 Hz, 2H) 8.22 (t, J = 5.6 Hz, 1H) 8.50 (d, J = 1.5 Hz, 1H) 8.56 (dd, J = 4.6, 1.7 Hz, 1H) 8.59 (s, 1H) 8.73 (d, J = 8.3 Hz, 1H) 8.89 (s, 1H) 9.36-9.59 (m, 2H). |

-continued

| Ex. | Compound | LC-MS m/z | NMR |
|---|---|---|---|
| 66 | 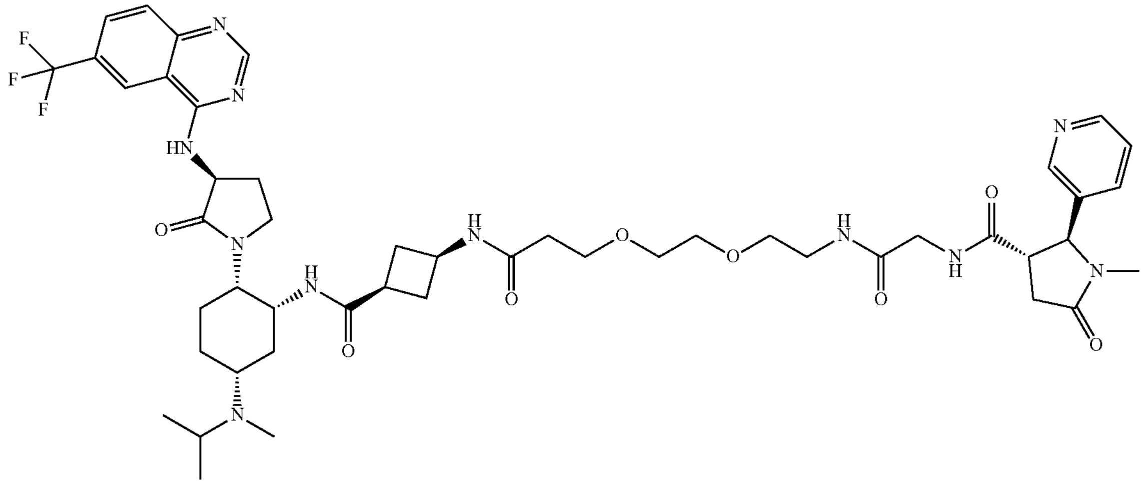 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCOCCOCCNC(=O)CNC(=O)[C@H]3CC(=O)N(C)[C@@H]3c3cccnc3)C2)C1]<br>(2S,3S)-N-(2-((2-(2-(3-(((1S,3s)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)ethoxy)ethyl)amino)-2-oxoethyl)-1-methyl-5-oxo-2-(pyridin-3-yl)pyrrolidine-3-carboxamide. | 980.0 $(M + H)^+$ | $^1H$ NMR (400 MHz, METHANOL-$d_4$) δ ppm 1.02 (d, J = 6.4 Hz, 3H) 1.15 (d, J = 6.8 Hz, 3H) 1.61-1.80 (m, 4H) 1.89-2.01 (m, 1H) 2.09-2.25 (m, 5H) 2.26 (s, 3 H) 2.28-2.39 (m, 3H) 2.45-2.64 (m, 3H) 2.67 (s, 3H) 2.69-2.84 (m, 4 H) 2.85-2.97 (m, 1H) 3.08-3.19 (m, 1H) 3.36-3.47 (m, 2H) 3.47-3.53 (m, 3H) 3.55 (s, 3 H) 3.58-3.75 (m, 3H) 3.85 (d, J = 1.5 Hz, 2H) 4.03 (dt, J = 12.3, 3.9 Hz, 1H) 4.15-4.30 (m, 1H) 4.60 (br d, J = 2.9 Hz, 1 H) 4.88 (d, J = 5.9 Hz, 1 H) 5.30 (t, J = 8.8 Hz, 1H) 7.51 (dd, J = 7.8, 4.9 Hz, 1H) 7.82 (dt, J = 7.8, 2.0 Hz, 1H) 7.91 (d, J = 8.3 Hz, 1H) 8.06 (dd, J = 8.8, 2.0 Hz, 1H) 8.54-8.58 (m, 2H) 8.59 (s, 1H) 8.75 (s, 1H). |

((2S,3S)-N-(1-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)cyclohexyl)-1-oxo-5,8,11,14-tetraoxa-2-azahexadecan-16-yl)-1-methyl-5-oxo-2-(pyridin-3-yl)pyrrolidine-3-carboxamide
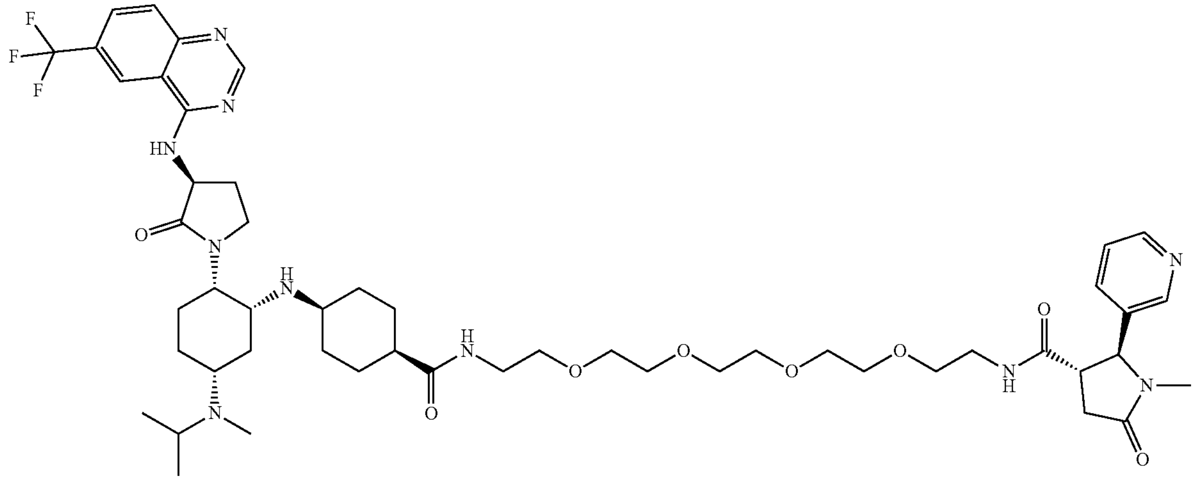
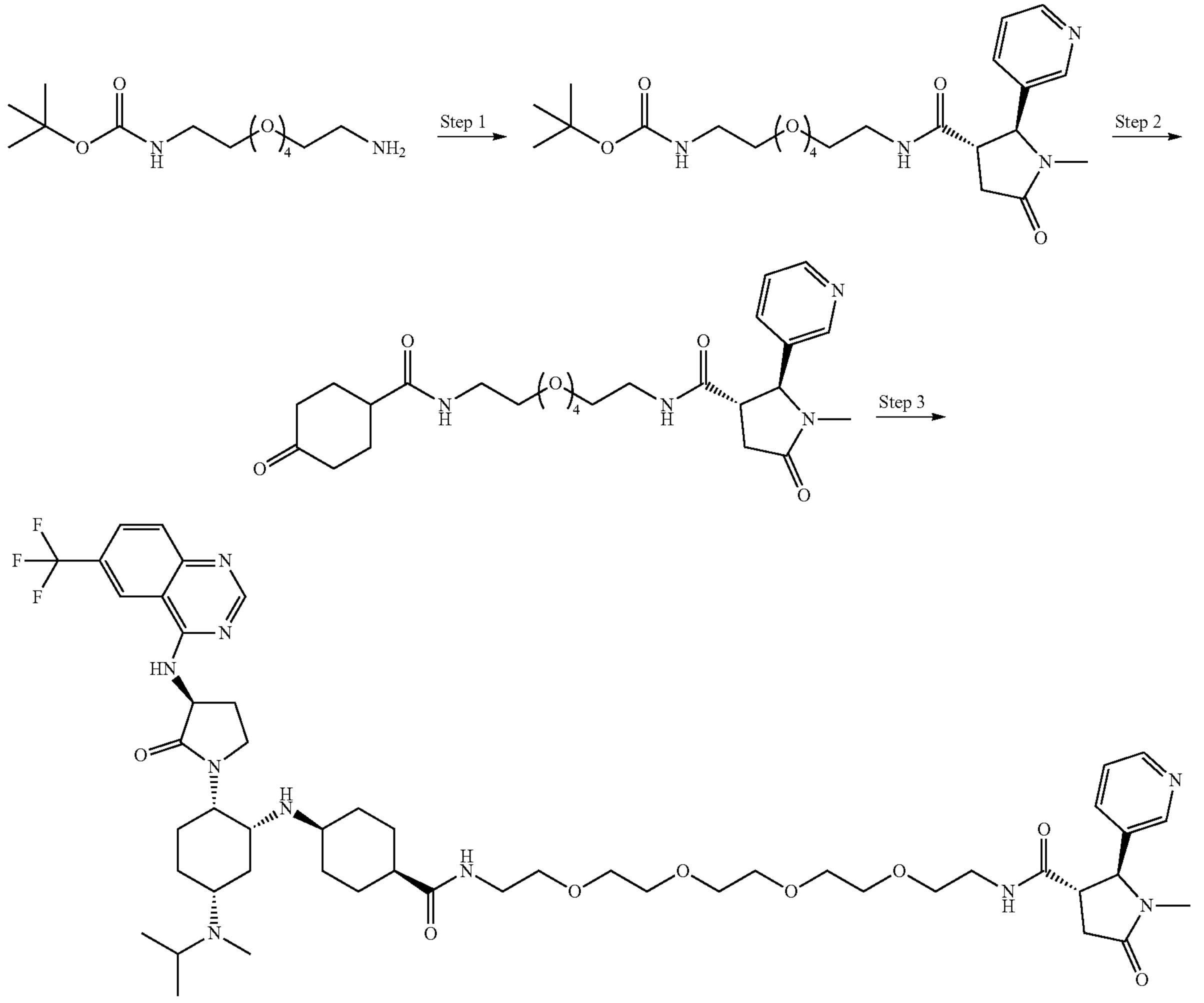

Step 1 tert-Butyl (1-((2S,3S)-1-methyl-5-oxo-2-(pyridin-3-yl)pyrrolidin-3-yl)-1-oxo-5,8,11,14-tetraoxa-2-aza-hexadecan-16-yl)carbamate

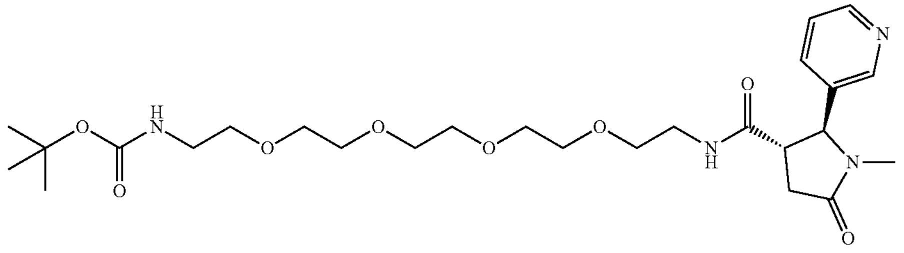 [SMILES: CN1C(=O)C[C@H](C(=O)NCCOCCOCCOCCOCCNC(=O)OC(C)(C)C)[C@H]1c1cccnc1]

A mixture of (2S,3S)-1-methyl-5-oxo-2-(pyridin-3-yl) pyrrolidine-3-carboxylic acid (122 mg, 0.554 mmol) and commercially available tert-butyl (14-amino-3,6,9,12-tetraoxatetradecyl)carbamate (205 mg, 0.609 mmol) was dried under reduced pressure. HATU (253 mg, 0.665 mmol) was added and mixture was dissolved in acetonitrile (4261 μL). DIPEA (387 μL, 2.216 mmol) was added slowly, the mixture was stirred for 30 min, and was concentrated under reduced pressure. Purification by ISCO CombiFlash® chromatography (24 g Redisep Rf Gold® column, 35 mL/min) eluting with a gradient of 0 to 20% methanol in dichloromethane (DCM) provided the title compound as an orange oil (323 mg, 0.582 mmol, 105% yield). LC-MS m/z 539.2 $(M+H)^+$.

Step 2

(2S,3S)-1-Methyl-5-oxo-N-(1-oxo-1-(4-oxocyclohexyl)-5,8,11,14-tetraoxa-2-azahexadecan-16-yl)-2-(pyridin-3-yl)pyrrolidine-3-carboxamide

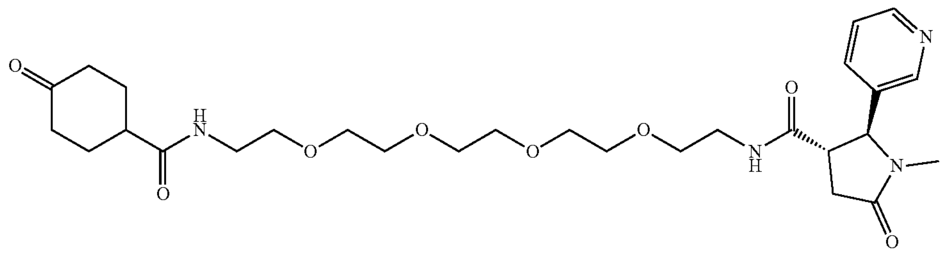 [SMILES: CN1C(=O)C[C@H](C(=O)NCCOCCOCCOCCOCCNC(=O)C2CCC(=O)CC2)[C@H]1c1cccnc1]

A mixture of tert-butyl (1-((2S,3S)-1-methyl-5-oxo-2-(pyridin-3-yl)pyrrolidin-3-yl)-1-oxo-5,8,11,14-tetraoxa-2-azahexadecan-16-yl)carbamate (323 mg, 0.600 mmol), HCl (0.40 mL) and dichloromethane (DCM) (2 mL) was stirred at rt for 15 min, was concentrated under reduced pressure, and was chased with dichloromethane (DCM) to provide (2S,3S)-N-(14-amino-3,6,9,12-tetraoxatetradecyl)-1-methyl-5-oxo-2-(pyridin-3-yl)pyrrolidine-3-carboxamide (324 mg, 0.739 mmol). Commercially available 4-oxocyclohexane-1-carboxylic acid (105 mg, 0.739 mmol) was dried under reduced pressure, TSTU (267 mg, 0.886 mmol) was added, and the mixture was dissolved in acetonitrile (5682 μL). Triethylamine (412 μL, 2.95 mmol) was added dropwise. (2S,3S)-N-(14-amino-3,6,9,12-tetraoxatetradecyl)-1-methyl-5-oxo-2-(pyridin-3-yl)pyrrolidine-3-carboxamide (324 mg, 0.739 mmol) was added, the mixture was stirred for 30 min, and was concentrated under reduced pressure. Purification by ISCO CombiFlash® chromatography (×2) (24 g Redisep Rf Gold® column, 35 mL/min) eluting with a gradient of 0 to 20% methanol in dichloromethane (DCM) provided the title compound (217.9 mg, 0.306 mmol, 41.4% yield). LC-MS m/z 563.1 $(M+H)^+$. $^1H$ NMR (400 MHz, METHANOL-$d_4$) δ ppm 1.63-2.04 (m, 2H) 2.08-2.21 (m, 1H) 2.37-2.54 (m, 1H) 2.68 (s, 3H) 2.70-2.80 (m, 1H) 2.84-2.94 (m, 1H) 3.01-3.21 (m, 1H) 3.31-3.45 (m, 13H) 3.50-3.69 (m, 11H) 7.58 (dd, J=7.9, 4.8 Hz, 1H) 7.85 (dt, J=7.9, 1.8 Hz, 1H) 8.08-8.27 (m, 1H) 8.54 (d, J=1.8 Hz, 1H) 8.61 (dd, J=4.8, 1.3 Hz, 1H).

Step 3

((2S,3S)-N-(1-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)cyclohexyl)-1-oxo-5,8,11,14-tetraoxa-2-azahexadecan-16-yl)-1-methyl-5-oxo-2-(pyridin-3-yl)pyrrolidine-3-carboxamide

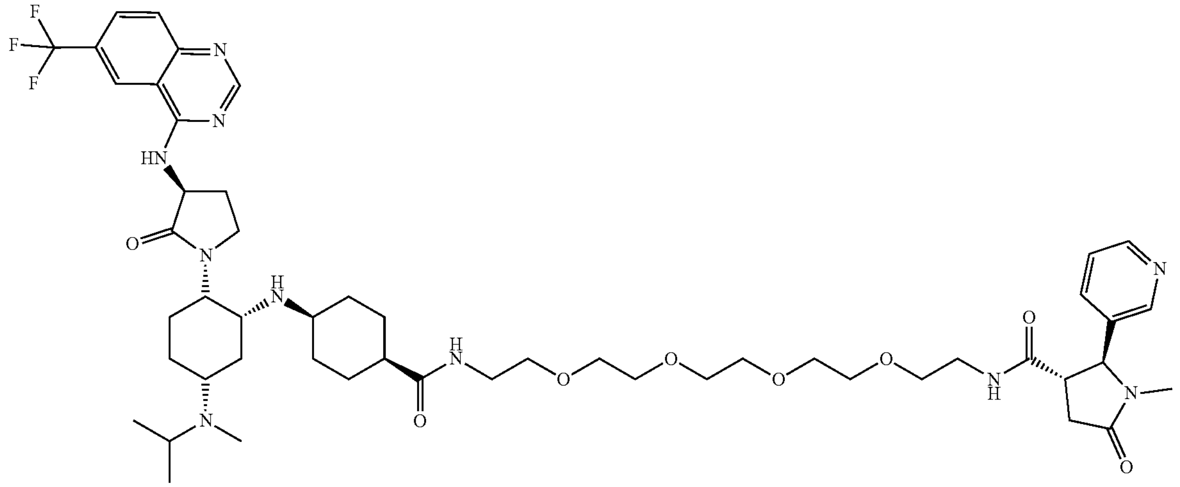

(S)-1-((1S,2R,4R)-2-Amino-4-(isopropyl(methyl)amino)cyclohexyl)-3-((6-(trifluoromethyl) quinazolin-4-yl)amino)pyrrolidin-2-one, 2hydrochloric acid salt (188 mg, 0.349 mmol) and (2S,3S)-1-methyl-5-oxo-N-(1-oxo-1-(4-oxocyclohexyl)-5,8,11,14-tetraoxa-2-azahexadecan-16-yl)-2-(pyridin-3-yl)pyrrolidine-3-carboxamide (217.9 mg, 0.387 mmol) were sonicated in N,N-dimethylformamide (DMF) (704 µL) (2 min). Additional N,N-dimethylformamide (DMF) added to ensure the solid starting material was dissolved. Sodium triacetoxyborohydride (243 mg, 1.147 mmol) was added and the mixture was stirred at 50° C. for 3 h. The mixture was concentrated under reduced pressure, was partitioned between dichloromethane (DCM) and water, and was basified by 1 M sodium hydroxide. The aqueous layer was extracted with dichloromethane (DCM) (3×). The aqueous layer contained the desired product, was concentrated under reduced pressure, and was dissolved in a mixture of methanol and water (1:1) (6 mL). The isomers were separated by purification by MDAP chromatography (XBridge™ column) eluting with acetonitrile in water containing ammonium carbonate modifier.

The desired isomer was purified by MDAP (Sunfire™ C18 column) eluting with acetonitrile in water containing TFA modifier. The desired fractions were concentrated under reduced pressure, were basified with 1 M sodium hydroxide, and were extracted with dichloromethane (DCM) to provide the title compound as a white solid (48.5 mg, 0.048 mmol, 12.38% yield). LC-MS m/z 1011.4 $(M+H)^+$. $^1H$ NMR (400 MHz, METHANOL-$d_4$) δ ppm 1.09-1.15 (m, 6H) 1.43-1.61 (m, 2H) 1.66-2.01 (m, 8H) 2.05-2.21 (m, 3H) 2.30 (s, 3H) 2.34-2.44 (m, 1H) 2.50-2.60 (m, 1H) 2.63-2.69 (m, 4H) 2.70-2.76 (m, 1H) 2.78-2.89 (m, 2H) 2.99-3.11 (m, 2H) 3.21 (dt, J=12.7, 6.3 Hz, 1H) 3.33-3.35 (m, 3H) 3.36-3.41 (m, 1H) 3.48-3.54 (m, 4H) 3.54-3.64 (m, 12H) 3.70-3.81 (m, 1H) 4.02-4.11 (m, 1H) 4.30-4.37 (m, 1H) 4.80-4.86 (m, 1H) 5.02-5.11 (m, 1H) 5.52 (s, 2H) 7.51-7.57 (m, 1H) 7.81 (dt, J=7.9, 2.0 Hz, 1H) 7.90 (d, J=8.6 Hz, 1H) 8.06 (dd, J=8.9, 1.8 Hz, 1H) 8.51-8.55 (m, 1H) 8.57-8.60 (m, 1H) 8.61-8.63 (m, 1H) 8.63-8.67 (m, 1H).

The following compounds were or could be prepared with procedures analogous to that described in Example 67:

| Ex. | Compound | LC-MS m/z | NMR |
|---|---|---|---|
| 68 | 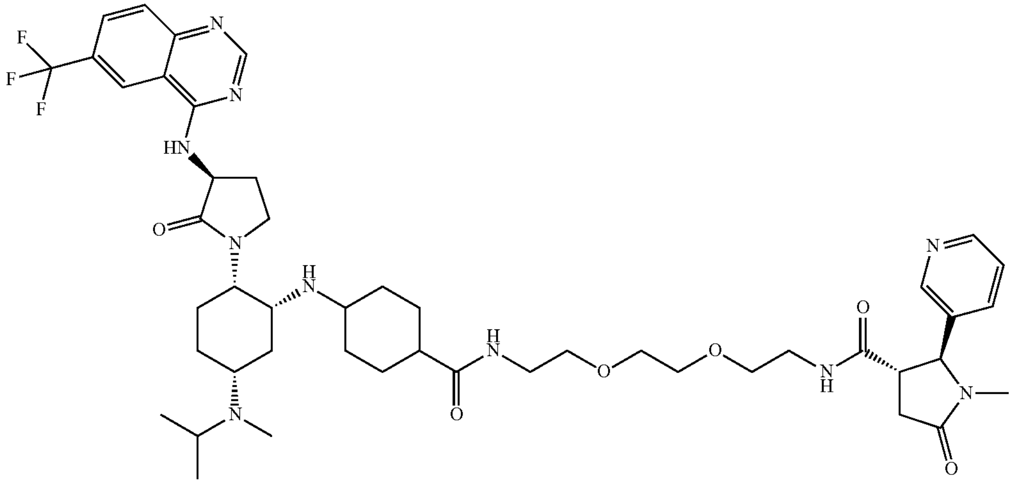 [SMILES: CC(C)N(C)[C@@H]1CC[C@H](N2CC[C@H](Nc3ncnc4ccc(C(F)(F)F)cc34)C2=O)[C@H](NC2CCC(C(=O)NCCOCCOCCNC(=O)[C@H]3CC(=O)N(C)[C@@H]3c3cccnc3)CC2)C1] (2S,3S)-N-(2-(2-(2-(4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)cyclohexane-1-carboxamido)ethoxy)ethoxy)ethyl)-1-methyl-5-oxo-2-(pyridin-3-yl)pyrrolidine-3-carboxamide. | 923.3 $(M + H)^+$ | $^1H$ NMR (400 MHz, METHANOL-$d_4$) δ ppm 1.09 (d, J = 6.3 Hz, 3H) 1.13 (d, J = 6.6 Hz, 3H) 1.45-1.63 (m, 3H) 1.66-1.96 (m, 10H) 2.12 (br dd, J = 5.6, 4.6 Hz, 1H) 2.26-2.45 (m, 5H) 2.53-2.62 (m, 1H) 2.67 (s, 3H) 2.69-2.76 (m, 1H) 2.78-2.90 (m, 2H) 2.98-3.11 (m ,3H) 3.23-3.32 (m, 3H) 3.36-3.44 (m, 2H) 3.45-3.57 (m, 8H) 3.70-3.79 (m, 1H) 4.13 (br t, J = 9.1 Hz, 1H) 4.23 (br d, J = 4.3 Hz, 1H) 4.83 (d, J = 6.6 Hz, 1H) 5.29 (t, J = 9.6 Hz, 1H) 7.52 (dd, J = 7.9, 4.8 Hz, 1H) 7.80 (dt, J = 8.0, 1.6 Hz, 1H) 7.90 (d, J = 8.9 Hz, 1H) 8.05 (dd, J = 8.9, 1.5 Hz, 1H) 8.52 (d, J = 2.0 Hz, 1H) 8.56-8.60 (m, 2H) 8.67 (s, 1H). |

-continued
| Ex. | Compound | LC-MS m/z | NMR |
|---|---|---|---|
| 69 | 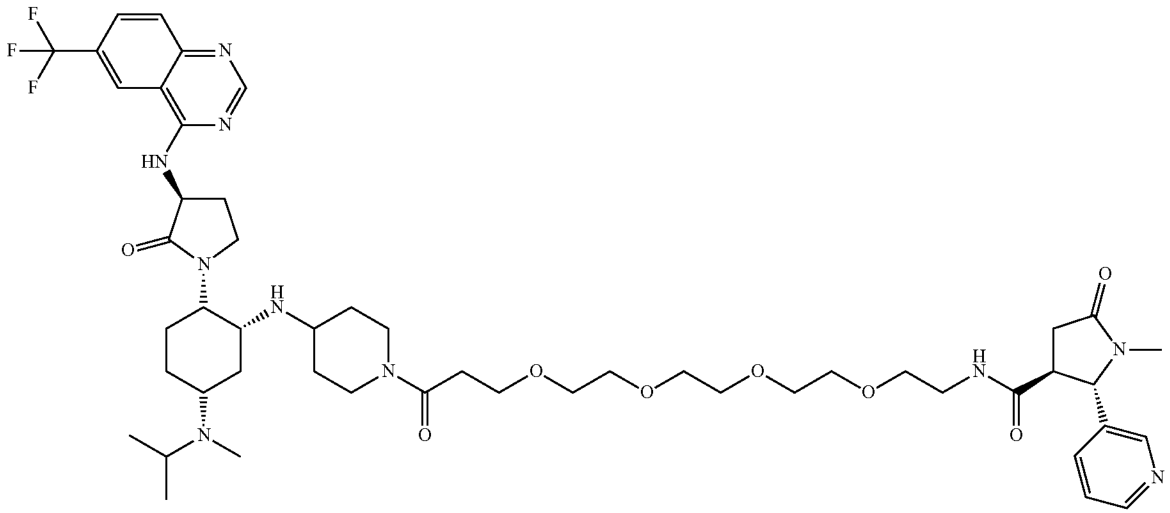 (2S,3S)-N-(15-(4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)piperidin-1-yl)-15-oxo-3,6,9,12-tetraoxapentadecyl)-1-methyl-5-oxo-2-(pyridin-3-yl)pyrrolidine-3-carboxamide. | 997.7 $(M + H)^+$ | $^1H$ NMR (400 MHz, METHANOl-$d_4$) δ ppm 1.06-1.17 (m, 6H) 1.19-1.37 (m, 3H) 1.74-2.06 (m, 7H) 2.08-2.15 (m, 1H) 2.29-2.42 (m, 4H) 2.49-2.57 (m, 1H) 2.59-2.68 (m, 5H) 2.69-2.78 (m, 2H) 2.79-2.90 (m, 2H) 3.05 (br dd, J = 7.7, 1.1 Hz, 5H) 3.35-3.43 (m, 2H) 3.48-3.52 (m, 2H) 3.54-3.61 (m, 11H) 3.67-3.77 (m, 3H) 3.86-4.04 (m, 1H) 4.06-4.15 (m, 1H) 4.26-4.47 (m, 2H) 4.79-4.85 (m, 1H) 5.00-5.14 (m, 1H) 7.51-7.56 (m, 1H) 7.78-7.83 (m, 1H) 7.89-7.94 (m, 1H) 8.04-8.10 (m, 1H) 8.51-8.53 (m, 1H) 8.56-8.59 (m, 1H) 8.59-8.61 (m, 1H) 8.64-8.67 (m, 1H). |

Example 70

(2S,3S)-N-((S)-1-(4-((4-((1R,4S)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperazin-1-yl)sulfonyl)piperidin-1-yl)-1-oxopropan-2-yl)-1-methyl-5-oxo-2-(pyridin-3-yl)pyrrolidine-3-carboxamide

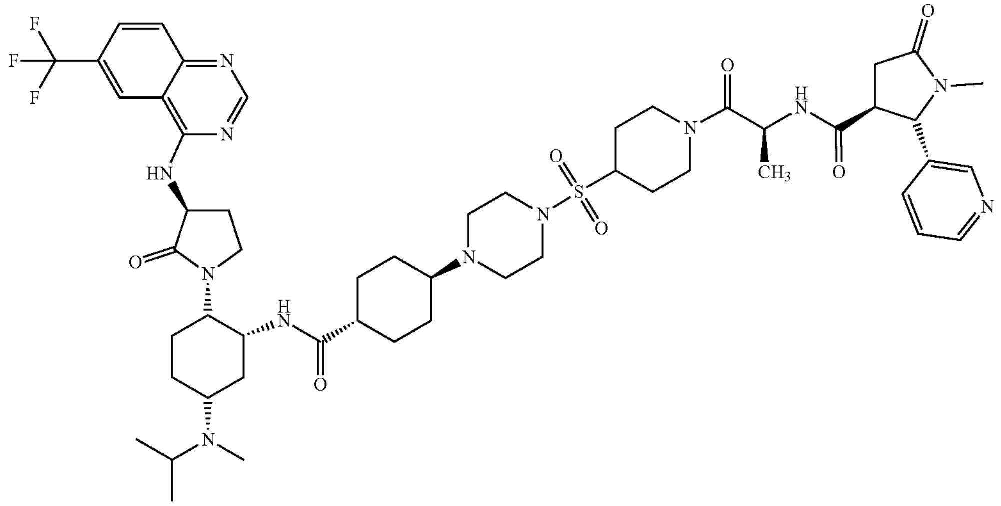

Step 1 tert-Butyl 4-((4-((1r,4r)-4-(ethoxycarbonyl)cyclohexyl)piperazin-1-yl)sulfonyl) piperidine-1-carboxylate

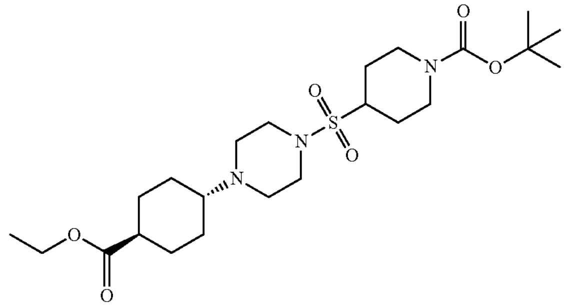 [SMILES: CCOC(=O)[C@H]1CC[C@H](N2CCN(S(=O)(=O)C3CCN(C(=O)OC(C)(C)C)CC3)CC2)CC1]

tert-Butyl 4-((1 s,4s)-4-(ethoxycarbonyl)cyclohexyl)piperazine-1-carboxylate (204 mg, 0.599 mmol) was dissolved in dichloromethane (DCM) (2 mL) and TFA (3 mL) and the mixture was stirred at rt for 5 min. The mixture was concentrated under reduced pressure and was chased with dichloromethane (DCM) (3×). The residue was dissolved in dichloromethane (DCM) (6072 μL) and triethylamine (250 μL, 1.792 mmol) was added. The mixture was cooled to 0° C. and a solution of tert-butyl 4-(chlorosulfonyl)piperidine-1-carboxylate (224 mg, 0.789 mmol) in dichloromethane (DCM) (1 mL) and added dropwise. The mixture was stirred at rt for 3 h and was concentrated under reduced pressure. Water was added and the mixture was extracted with ethyl acetate (4×). The combined organic extracts were concentrated under reduced pressure. Purification by normal phase column chromatography (24 g silica) eluting with a gradient of 0 to 100% ethyl acetate in heptane provided the title compound as a white crystalline solid (98.4 mg, 0.159 mmol, 20.19% yield). LC-MS m/z 488.2 $(M+H)^+$.

Step 2

Ethyl (1S,4r)-4-(4-((1-((tert-butoxycarbonyl)-L-alanyl)piperidin-4-yl)sulfonyl)piperazin-1-yl)cyclohexane-1-carboxylate

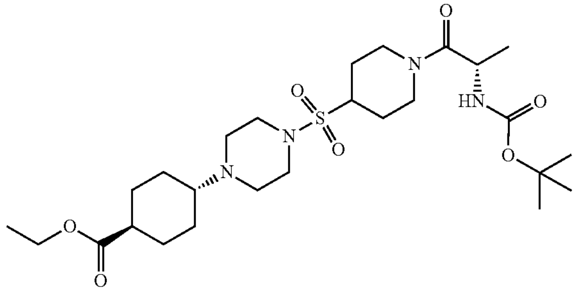 [SMILES: CCOC(=O)[C@H]1CC[C@H](N2CCN(S(=O)(=O)C3CCN(C(=O)[C@H](C)NC(=O)OC(C)(C)C)CC3)CC2)CC1]

tert-Butyl 4-((4-((1r,4r)-4-(ethoxycarbonyl)cyclohexyl)piperazin-1-yl)sulfonyl)piperidine-1-carboxylate (98.4 mg, 0.202 mmol) was dissolved in dichloromethane (DCM) (1 mL) and TFA (2 mL) and the mixture was stirred at rt for 10 min. The mixture was concentrated under reduced pressure and was chased with dichloromethane (DCM) (3×). A mixture of the residue, (tert-butoxycarbonyl)-L-alanine (40 mg, 0.211 mmol), and HATU (100 mg, 0.263 mmol) were dissolved in acetonitrile (1.626 mL). Triethylamine (0.105 mL, 0.753 mmol) was added dropwise. The mixture was stirred at rt for 30 min and was concentrated under reduced pressure. Purification by normal phase column chromatography (12 g silica) eluting with a gradient of 0 to 20% methanol in dichloromethane (DCM) provided the title compound (404.8 mg, 0.558 mmol, 264% yield). LC-MS m/z 559.2 $(M+H)^+$.

Step 3

(1S,4r)-4-(4-((1-(((2S,3S)-1-Methyl-5-oxo-2-(pyridin-3-yl)pyrrolidine-3-carbonyl)-L-alanyl)piperidin-4-yl)sulfonyl)piperazin-1-yl)cyclohexane-1-carboxylic acid

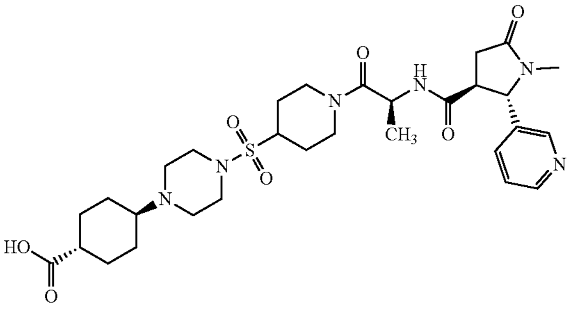 [SMILES: C[C@H](NC(=O)[C@H]1CC(=O)N(C)[C@@H]1c1cccnc1)C(=O)N1CCC(S(=O)(=O)N2CCN([C@H]3CC[C@H](C(=O)O)CC3)CC2)CC1]

TFA (2.0 mL) was added to a solution of (1S,4r)-4-(4-((1-((tert-butoxycarbonyl)-L-alanyl)piperidin-4-yl)sulfonyl)piperazin-1-yl)cyclohexane-1-carboxylic acid (404 mg, 0.761 mmol) in dichloromethane (DCM) (1.5 mL) and the mixture stirred at rt for 5 min. The mixture was concentrated by reduced pressure and was chased with dichloromethane (DCM) (3×) three times. to remove the excess TFA to provide (1S,4r)-4-(4-((1-(L-alanyl)piperidin-4-yl)sulfonyl)piperazin-1-yl)cyclohexane-1-carboxylic acid, 2trifluoroacetic acid salt (389 mg, 0.590 mmol).

To a mixture of 2-(2,5-dioxopyrrolidin-1-yl)-1,1,3,3-tetramethylisouronium tetrafluoroborate (213 mg, 0.708 mmol) and (2S,3S)-1-methyl-5-oxo-2-(pyridin-3-yl)pyrrolidine-3-carboxylic acid (130 mg, 0.590 mmol) in acetonitrile (4541 μL) was added triethylamine (329 μL, 2.361 mmol), and the mixture was stirred at rt for 30 min. (1S,4r)-4-(4-((1-(L-Alanyl)piperidin-4-yl)sulfonyl)piperazin-1-yl)cyclohexane-1-carboxylic acid, 2trifluoroacetic acid salt (389 mg, 0.590 mmol) was added. The mixture was concentrated under reduced pressure. Purification by normal-phase column chromatography (24 g column, 35 mL/min) eluting with a gradient of 0 to 80% methanol in dichloromethane (DCM) provided the title compound (101 mg, 0.067 mmol, 11.36% yield). LC-MS m/z 633.3 $(M+H)^+$.

Step 4

(2S,3S)-N-((S)-1-(4-((4-((1R,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)piperazin-1-yl)sulfonyl)piperidin-1-yl)-1-oxopropan-2-yl)-1-methyl-5-oxo-2-(pyridin-3-yl)pyrrolidine-3-carboxamide

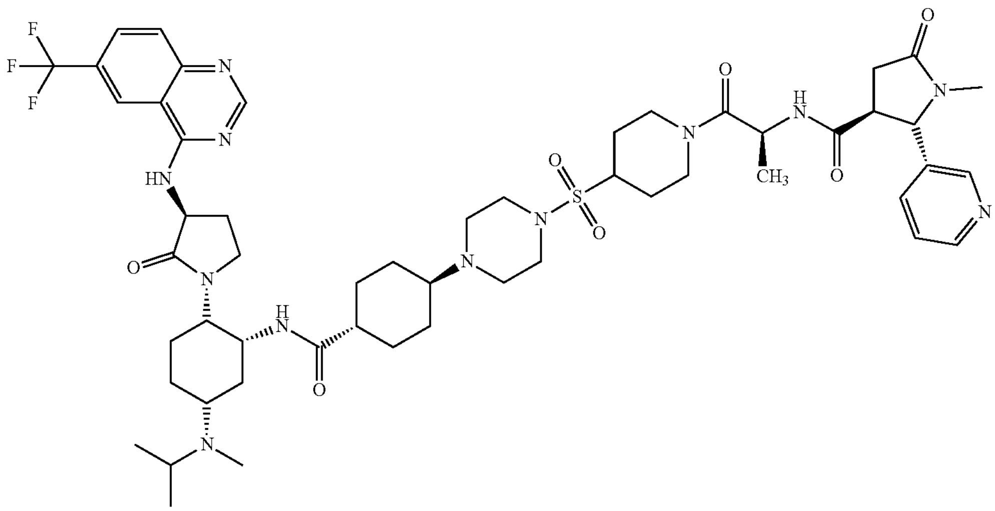

A mixture of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (108 mg, 0.192 mmol) and 4 M HCl in 1,4-dioxane (0.2 mL, 0.8 mmol) in dichloromethane (DCM) (1.0 mL) was stirred at rt for 30 min, the mixture was concentrated by reduced pressure, and was chased with dichloromethane (DCM). To a mixture of the residue and triethylamine (89 μL, 0.638 mmol) in dichloromethane (DCM) (4314 μL) was added (1S,4r)-4-(4-((1-(((2S,3S)-1-methyl-5-oxo-2-(pyridin-3-yl)pyrrolidine-3-carbonyl)-L-alanyl)piperidin-4-yl)sulfonyl)piperazin-1-yl)cyclohexane-1-carboxylic acid (101 mg, 0.160 mmol) and HATU (72.8 mg, 0.192 mmol) and the mixture was stirred at rt for 30 min. Purification by MDAP (XBridge™ column) eluting with acetonitrile in water containing ammonium carbonate modifier provided the title compound as a white solid (26.1 mg, 0.024 mmol, 14.93% yield). LC-MS m/z 1079.4 $(M+H)^+$. $^1H$ NMR (400 MHz, METHANOL-$d_4$) δ ppm 1.03 (br d, J=6.3 Hz, 3H) 1.15 (br d, J=6.3 Hz, 3H) 1.23-1.37 (m, 5H) 1.50-1.78 (m, 7H) 1.91-2.12 (m, 9H) 2.14-2.20 (m, 1H) 2.27(s, 3H) 2.30-2.38 (m, 2H) 2.50-2.75 (m, 11H) 2.83-2.91 (m, 1H) 3.07-3.23 (m, 2H) 3.33 (dt, J=3.3, 1.6 Hz, 3H) 3.37 (br s, 2H) 3.40-3.55 (m, 3H) 3.61-3.68 (m, 1H) 4.03 (dt, J=12.2, 3.7 Hz, 1H) 4.09-4.20 (m, 1H) 4.56 (br t, J=14.7 Hz, 1H) 4.66 (br d, J=3.0 Hz, 1H) 5.25 (t, J=7.8 Hz, 1H) 7.52 (dd, J=7.8, 5.0 Hz, 1H) 7.82 (dt, J=8.0, 1.9 Hz, 1H) 7.91 (d, J=8.8 Hz, 1H) 8.06 (dd, J=8.9, 1.9 Hz, 1H) 8.55-8.58 (m, 2H) 8.60 (s, 1H) 8.81 (s, 1H)

The following compound was or could be prepared with procedures analogous to that described in Example 70:

| Ex. | Compound | LC-MS m/z | NMR |
|---|---|---|---|
| 71 | 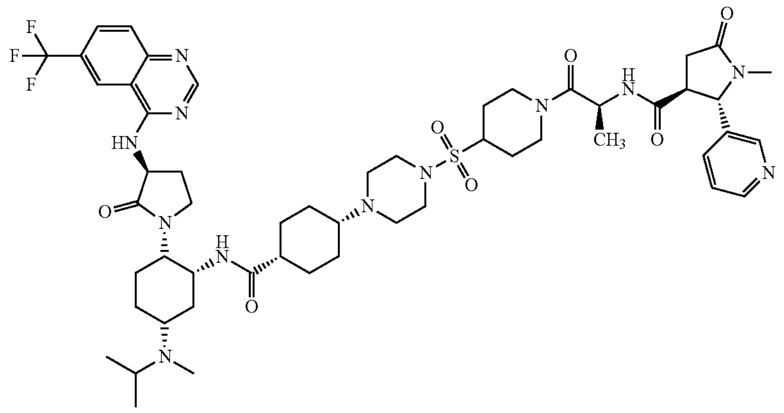<br>(2S,3S)-N-((S)-1-(4-((4-((1S,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperazin-1-yl)sulfonyl)piperidin-1-yl)-1-oxopropan-2-yl)-1-methyl-5-oxo-2-(pyridin-3-yl)pyrrolidine-3-carboxamide. | 1079.4 $(M+H)^+$ | $^1H$ NMR (400 MHz, METHANOL-$d_4$) δ ppm 0.99 (br d, J = 6.3 Hz, 3H) 1.15-1.20 (m, 3H) 1.24-1.32 (m, 3H) 1.56-1.83 (m, 10H) 1.90-2.05 (m, 4 H) 2.11-2.24 (m, 2H) 2.25-2.29 (m, 3H) 2.29-2.40 (m, 3H) 2.46-2.54 (m, 4H) 2.55-2.62 (m, 1H) 2.65-2.76 (m, 6H) 2.83-2.93 (m, 1H) 3.07-3.20 (m, 2H) 3.26 (br s, 4H) 3.37-3.48 (m, 2H) 3.50-3.57 (m, 1H) 3.60-3.69 (m, 1H) 4.00-4.07 (m, 1H) 4.07-4.21 (m, 1H) 4.50-4.68 (m, 3H) 4.80-4.87 (m, 3H) 5.25-5.32 (m, 1H) 7.49-7.57 (m, 1H) 7.79-7.85 (m, 1H) 7.92 (d, J = 8.8 Hz, 1H) 8.04-8.09 (m, 1H) 8.57 (br s, 2H) 8.60 (s, 1 H) 8.74-8.78 (m, 1H). |

Example 72
(2S,3S)-N-(2-(2-(3-(4-((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)piperidin-1-yl)-3-oxopropoxy)ethoxy)ethyl)-1-methyl-5-oxo-2-(pyridin-3-yl)pyrrolidine-3-carboxamide
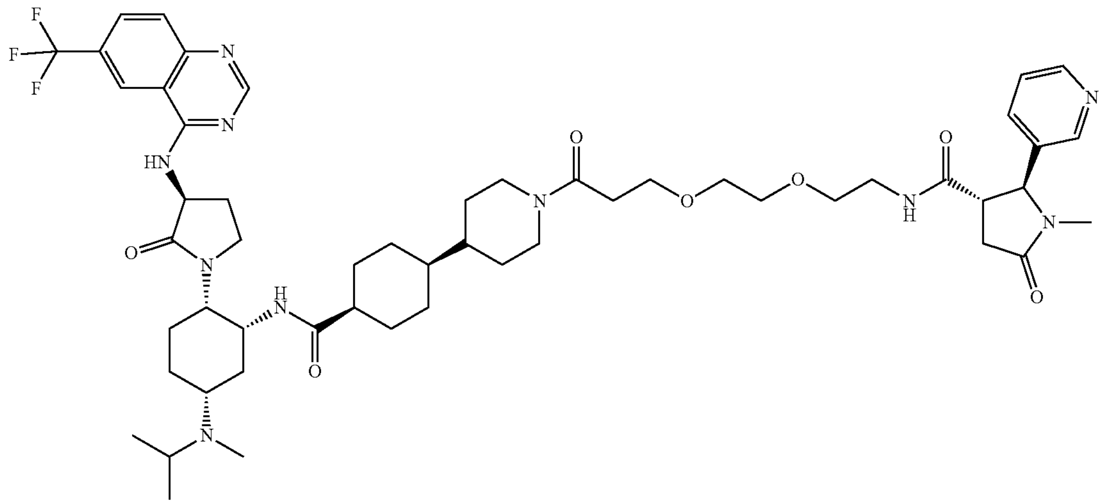
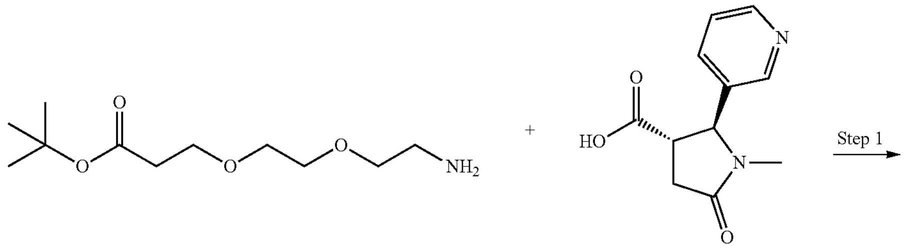
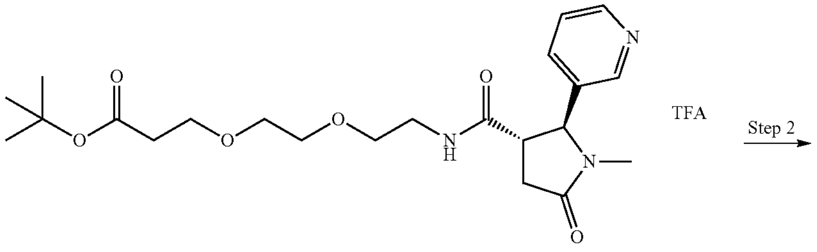

-continued

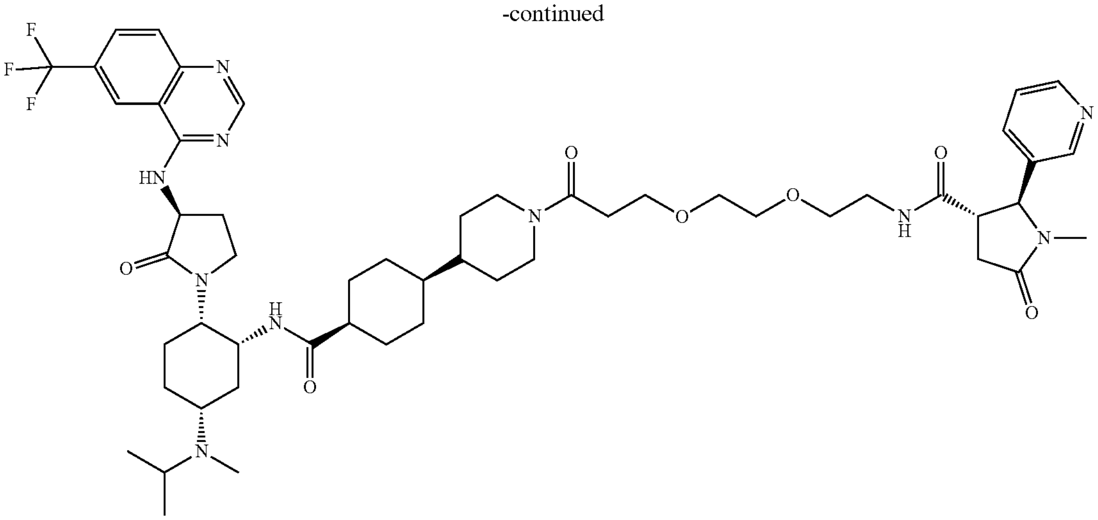

Step 1 tert-Butyl 3-(2-(2-((2S,3S)-1-methyl-5-oxo-2-(pyridin-3-yl)pyrrolidine-3-carboxamido) ethoxy)ethoxy) propanoate, Trifluoroacetic acid salt

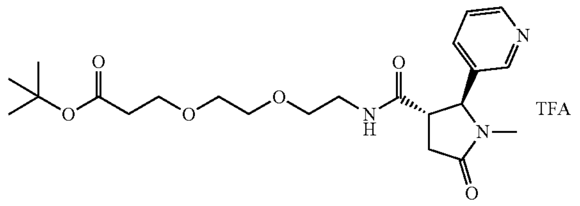 [SMILES: CN1C(=O)C[C@H](C(=O)NCCOCCOCCC(=O)OC(C)(C)C)[C@H]1c1cccnc1]

To a solution of tert-butyl 3-(2-(2-aminoethoxy)ethoxy) propanoate (1001 mg, 4.29 mmol) in dichloromethane (DCM) (35 mL) was added triethylamine (1.495 mL, 10.73 mmol), followed by (2S,3S)-1-methyl-5-oxo-2-(pyridin-3-yl) pyrrolidine-3-carboxylic acid (945 mg, 4.29 mmol) and HATU (1958 mg, 5.15 mmol). The mixture was stirred at rt overnight and was concentrated. Purification by MDAP (Method B) eluting with a gradient of 15 to 55% acetonitrile in water (both containing 0.1% TFA) provided the title compound as a pale-yellow liquid (2.22 g, 3.84 mmol, 89% yield). LC-MS m/z 436.3 $(M+H)^+$.

Step 2

(2S,3S)-N-(2-(2-(3-(4-((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)piperidin-1-yl)-3-oxopropoxy)ethoxy)ethyl)-1-methyl-5-oxo-2-(pyridin-3-yl)pyrrolidine-3-carboxamide

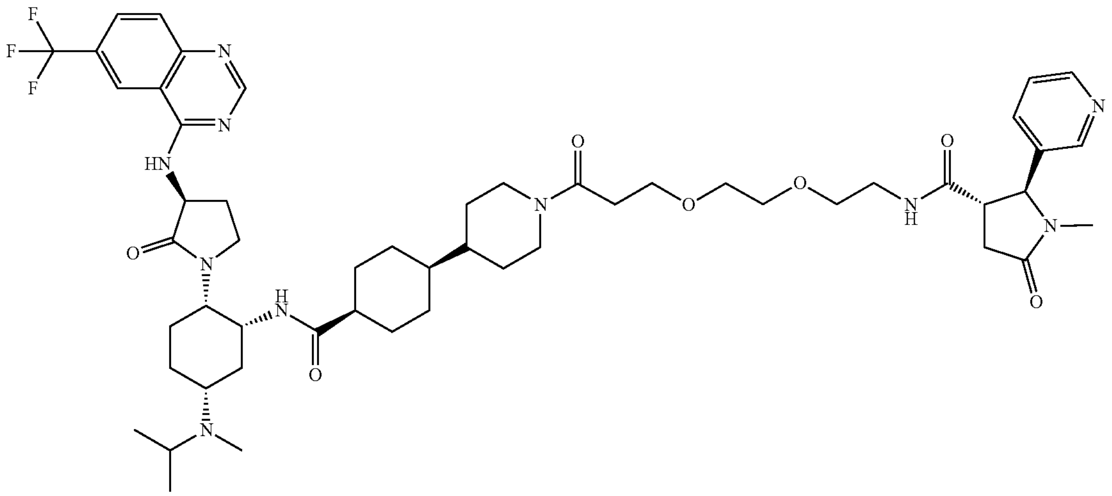 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](C3CCN(C(=O)CCOCCOCCNC(=O)[C@H]4CC(=O)N(C)[C@@H]4c4cccnc4)CC3)CC2)C1]

3 M HCl in cyclopentyl methyl ether (0.3 mL, 0.900 mmol) was added to a solution of tert-butyl 4-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperidine-1-carboxylate (38 mg, 0.050 mmol) in dichloromethane (DCM) (1 mL), the mixture was stirred at rt for 1 h, and was concentrated under reduced pressure. The residue was dissolved in dichloromethane (DCM) (2 mL) and triethylamine (0.035 mL, 0.251 mmol) was added.

3 M HCl in cyclopentyl methyl ether (0.3 mL, 0.900 mmol) was added to a solution of tert-butyl 3-(2-(2-((2S,3S)-1-methyl-5-oxo-2-(pyridin-3-yl) pyrrolidine-3-carboxamido)ethoxy) ethoxy)propanoate, trifluoroacetic acid salt (35 mg, 0.064 mmol) in dichloromethane (DCM) (0.5 mL), the mixture stirred at rt overnight, and was concentrated under reduced pressure. The amine solution obtained above was added, followed by HATU (28.6 mg, 0.075 mmol), the mixture was stirred at rt for 2 h, and was concentrated. Purification by MDAP chromatography (XSelect™ CSH C18 5 μm column, 40 mL/min) eluting with a gradient of 50 to 99% acetonitrile in water containing ammonium bicarbonate (10 mM) and ammonium hydroxide (0.075%) provided the title compound as a white solid (17.4 mg, 0.017 mmol, 33.4% yield). LC-MS m/z 1019.3 $(M+H)^+$. $^1H$ NMR (400 MHz, METHANOL-$d_4$) δ ppm 0.96-1.20 (m, 11H) 1.28-1.38 (m, 1H) 1.41-1.52 (m, 2H) 1.67-2.36 (m, 18H) 2.47-2.57 (m, 2H) 2.59-2.64 (m, 2H) 2.65-2.69 (m, 4H) 2.70-2.78 (m, 2H) 2.80-2.88 (m, 1H) 2.94-3.13 (m, 2H) 3.36-3.42 (m, 1H) 3.45-3.60 (m, 8H) 3.68-3.75 (m, 2H) 3.95-4.08 (m, 2H) 4.48-4.55 (m, 1H) 4.63-4.67 (m, 1H) 4.80-4.83 (m, 1H) 5.19-5.30 (m, 1H) 7.49-7.55 (m, 1H) 7.76-7.82 (m, 1H) 7.89-7.94 (m, 1H) 8.03-8.10 (m, 1H) 8.50-8.53 (m, 1H) 8.55-8.61 (m, 2H) 8.80-8.84 (m, 1H). (The trans isomer, Example 66, was also isolated and characterized.)

The following compound was or could be prepared with procedures analogous to that described in Example 72:

| Ex. | Compound | LC-MS m/z | NMR |
|---|---|---|---|
| 73 | 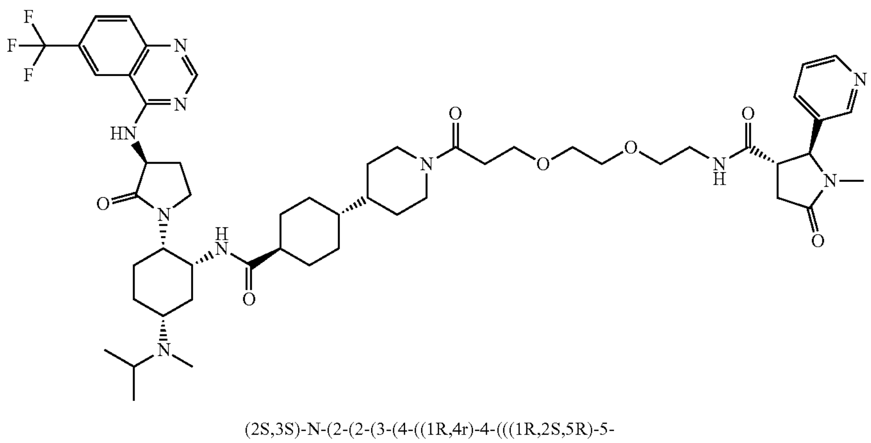<br>(2S,3S)-N-(2-(2-(3-(4-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperidin-1-yl)-3-oxopropoxy)ethoxy)ethyl)-1-methyl-5-oxo-2-(pyridin-3-yl)pyrrolidine-3-carboxamide. | 1019.3 $(M+H)^+$ | $^1H$ NMR (400 MHz, METHANOL-$d_4$) δ ppm 0.90-1.08 (m, 5H) 1.11-1.32 (m, 5 H) 1.43-1.68 (m, 8H) 1.70-1.79 (m, 4H) 1.80-1.99 (m, 3H) 2.07-2.30 (m, 5H) 2.31-2.48 (m, 3H) 2.51-2.63 (m, 3H) 2.65-2.68 (m, 3H) 2.71-2.75 (m, 2H) 2.79-2.93 (m, 2H) 3.03-3.12 (m, 1H) 3.36-3.47 (m, 2H) 3.48-3.52 (m, 2H) 3.53-3.58 (m, 5H) 3.61-3.73 (m, 3H) 3.88-3.98 (m, 1H) 3.99-4.09 (m, 1H) 4.41-4.51 (m, 1H) 4.62-4.70 (m, 1H) 4.81-4.83 (m, 1H) 5.20-5.32 (m, 1H) 7.49-7.55 (m, 1H) 7.76-7.82 (m, 1H) 7.89-7.94 (m, 1H) 8.04-8.10 (m, 1H) 8.49-8.53 (m, 1H) 8.55-8.58 (m, 1H) 8.59-8.62 (m, 1H) 8.74-8.82 (m, 1H). |

Example 74

(2S,3S)-N-(1-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-1,10,16-trioxo-3,6,12-trioxa-9,15-diazaoctadecan-18-yl)-1-methyl-5-oxo-2-(pyridin-3-yl)pyrrolidine-3-carboxamide

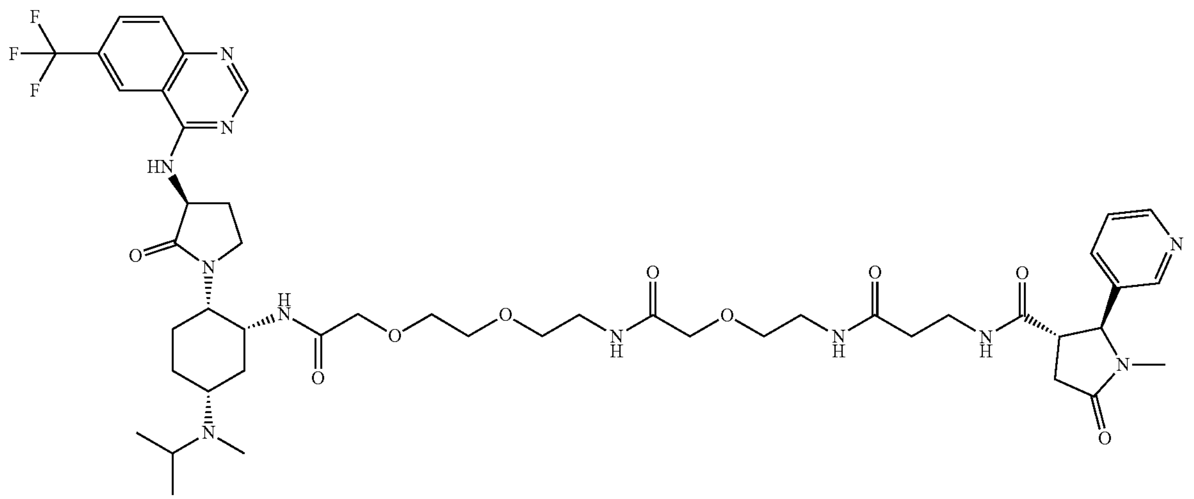 [SMILES: CC(C)N(C)[C@@H]1CC[C@H](N2CC[C@H](Nc3ncnc4ccc(C(F)(F)F)cc34)C2=O)[C@H](NC(=O)COCCOCCNC(=O)COCCNC(=O)CCNC(=O)[C@H]2CC(=O)N(C)[C@@H]2c2cccnc2)C1]

Step 1 tert-Butyl 3-((2S,3S)-1-methyl-5-oxo-2-(pyridin-3-yl)pyrrolidine-3-carboxamido) propanoate

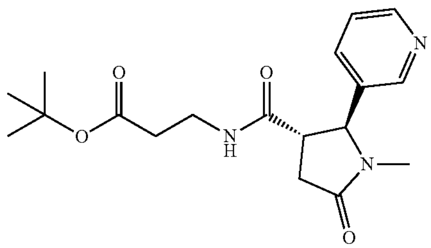 [SMILES: CN1C(=O)C[C@H](C(=O)NCCC(=O)OC(C)(C)C)[C@H]1c1cccnc1]

To a solution of (2S,3S)-1-methyl-5-oxo-2-(pyridin-3-yl) pyrrolidine-3-carboxylic acid (514 mg, 2.334 mmol) in dichloromethane (DCM) (6 mL) was added HOBt (429 mg, 2.80 mmol) and EDC (626 mg, 3.27 mmol) and the mixture was stirred for 30 minutes. tert-Butyl 3-aminopropanoate (428 mg, 2.80 mmol) and DIPEA (0.815 mL, 4.67 mmol) were added and the mixture was stirred overnight. The mixture was washed with saturated $NaHCO_3$ and the aqueous phase was extracted with dichloromethane (DCM) (3×20 mL). The combines organic extracts were washed with saturated NaCl, were dried over $Na_2SO_4$, and were concentrated onto silica. Purification by ISCO CombiFlash® chromatography (40 g RediSep Rf Gold® column, 60 mL/min) eluting with a stepwise gradient of 4% (10 min), 7% (20 min), and 10% (30 min) methanol in dichloromethane (DCM) provided the title compound as a clear tan oil (279 mg, 0.763 mmol, 32.7% yield). LC-MS m/z 348.1 $(M+H)^+$.

Step 2

3-((2S,3S)-1-Methyl-5-oxo-2-(pyridin-3-yl)pyrrolidine-3-carboxamido)propanoic acid Hydrochloric acid salt

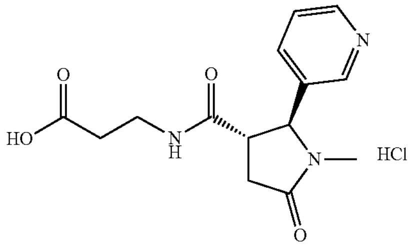 [SMILES: CN1C(=O)C[C@H](C(=O)NCCC(=O)O)[C@H]1c1cccnc1 ; Cl]

A mixture of 4 M HCl in 1,4-dioxane (4.53 mL, 18.11 mmol) and tert-butyl 3-((2S,3S)-1-methyl-5-oxo-2-(pyridin-3-yl)pyrrolidine-3-carboxamido)propanoate (276 mg, 0.755 mmol) stirred at rt for 4 h and was concentrated to provide the title compound as a white gum (547 mg, 0.751 mmol, 100% yield). LC-MS m/z 293.0 $(M+H)^+$.

Step 3 tert-Butyl 2-(2-(3-((2S,3S)-1-methyl-5-oxo-2-(pyridin-3-yl)pyrrolidine-3-carboxamido) propanamido) ethoxy)acetate

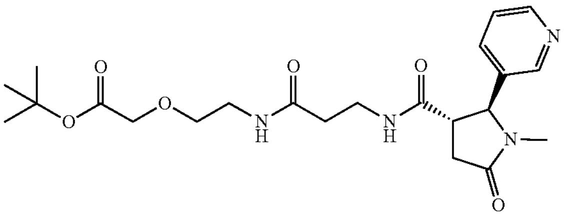 [SMILES: CN1C(=O)C[C@H](C(=O)NCCC(=O)NCCOCC(=O)OC(C)(C)C)[C@H]1c1cccnc1]

To a solution of 3-((2S,3S)-1-methyl-5-oxo-2-(pyridin-3-yl) pyrrolidine-3-carboxamido)propanoic acid, hydrochloric acid salt (540 mg, 0.741 mmol) in dichloromethane (DCM) (4 mL) was added HOBt (136 mg, 0.890 mmol) and EDC (199 mg, 1.038 mmol) and the mixture was stirred for 30 min. tert-Butyl 2-(2-aminoethoxy)acetate (188 mg, 0.890 mmol) and DIPEA (0.259 mL, 1.483 mmol) were added and the mixture was stirred overnight. HOBt (17 mg, 0.12 mmol), 25 mg of EDC (25 mg, 13 mmol) and DIPEA (0.05 mL, 0.29 mmol) were added and the mixture was stirred for 4 h. The mixture was washed with saturated $NaHCO_3$ and the aqueous phase was extracted with dichloromethane (DCM) (3×20 mL). The combined organic phases were washed with saturated brine, were dried over $Na_2SO_4$, and were concentrated onto silica. Purification by ISCO CombiFlash® chromatography (24 g RediSep Rf Gold® column, 35 mL/min) eluting with a stepwise gradient of 0% (5 mins), 5% (15 min), and 10% (35 min) methanol in dichloromethane (DCM) provided the title compound as a light-orange wax (268 mg, 0.514 mmol, 69.3% yield). LC-MS m/z 449.1 $(M+H)^+$.

Step 4

2-(2-(3-((2S,3S)-1-Methyl-5-oxo-2-(pyridin-3-yl) pyrrolidine-3-carboxamido) propanamido)ethoxy) acetic acid, Hydrochloric acid salt

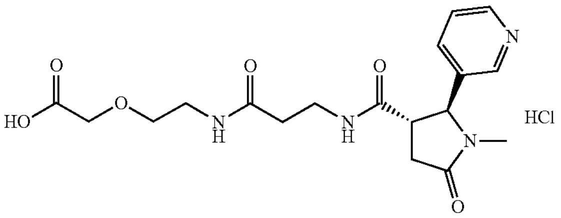 [SMILES: CN1C(=O)C[C@H](C(=O)NCCC(=O)NCCOCC(=O)O)[C@H]1c1cccnc1 ; Cl]

tert-Butyl 2-(2-(3-((2S,3S)-1-methyl-5-oxo-2-(pyridin-3-yl)pyrrolidine-3-carboxamido)propanamido)ethoxy)acetate (260 mg, 0.499 mmol) was suspended in 1,4-dioxane (1 mL) and 4 M HCl in 1,4-dioxane (2.99 mL, 11.96 mmol) was added. The mixture was stirred at rt for 4 h and was concentrated to provide the title compound as a white gum (769 mg, 0.484 mmol, 97% yield). LC-MS m/z 393.2 $(M+H)^+$.

Step 5 tert-Butyl 1-((2S,3S)-1-methyl-5-oxo-2-(pyridin-3-yl)pyrrolidin-3-yl)-1,5,11-trioxo-9,15,18-trioxa-2,6,12-triazaicosan-20-oate

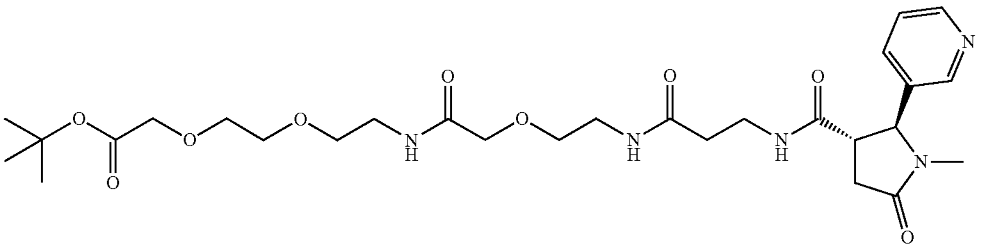 [SMILES: CN1C(=O)C[C@H](C(=O)NCCC(=O)NCCOCC(=O)NCCOCCOCC(=O)OC(C)(C)C)[C@H]1c1cccnc1]

To a solution of 2-(2-(3-((2S,3S)-1-methyl-5-oxo-2-(pyridin-3-yl)pyrrolidine-3-carboxamido)propanamido)ethoxy) acetic acid, hydrochloric acid salt (380 mg, 0.239 mmol) in dichloromethane (DCM) (2 mL) was added HOBt (44.0 mg, 0.287 mmol) and EDC (64.2 mg, 0.335 mmol) and the mixture was stirred for 30 min. tert-Butyl 2-(2-(2-aminoethoxy)ethoxy)acetate (61.7 mg, 0.239 mmol) and DIPEA (0.084 mL, 0.478 mmol) were added and the mixture was stirred overnight. The mixture was washed with saturated $NaHCO_3$ and the aqueous phase was extracted with dichloromethane (DCM) (3×20 mL). The combined organic extracts were washed with saturated NaCl, were dried over $Na_2SO_4$ and were concentrated onto silica. Purification by ISCO CombiFlash® chromatography (12 g RediSep Rf Gold® column, 30 mL/min) eluting with a stepwise gradient of 0 to 5% (5 min), 5% (10 min), 5-10% (25 min), and 10% (10 min) methanol in dichloromethane (DCM) provided the title compound as a clear tan oil (135 mg, 0.198 mmol, 83% yield). LC-MS m/z 594.3 $(M+H)^+$.

Step 6

1-((2S,3S)-1-Methyl-5-oxo-2-(pyridin-3-yl)pyrrolidin-3-yl)-1,5,11-trioxo-9,15,18-trioxa-2,6,12-triazaicosan-20-oic acid, Hydrochloric acid salt

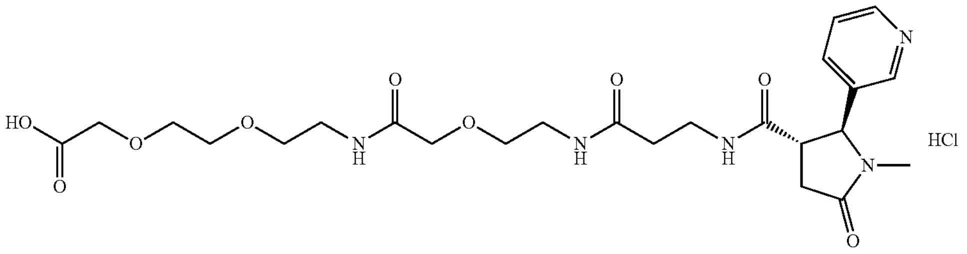 [SMILES: CN1C(=O)C[C@H](C(=O)NCCC(=O)NCCOCC(=O)NCCOCCOCC(=O)O)[C@H]1c1cccnc1 ; Cl]

tert-Butyl 1-((2S,3S)-1-methyl-5-oxo-2-(pyridin-3-yl)pyrrolidin-3-yl)-1,5,11-trioxo-9,15,18-trioxa-2,6,12-triazaicosan-20-oate (131 mg, 0.192 mmol) was suspended in 1,4-dioxane (1 mL) and 4 M HCl in 1,4-dioxane (1.152 mL, 4.61 mmol) was added. The mixture was stirred at rt for 4 h and was concentrated to provide the title compound as a white gum (267 mg, 0.163 mmol, 85% yield). LC-MS m/z 538.2 $(M+H)^+$.

Step 7

(2S,3S)-N-(1-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-1,10,16-trioxo-3,6,12-trioxa-9,15-diazaoctadecan-18-yl)-1-methyl-5-oxo-2-(pyridin-3-yl)pyrrolidine-3-carboxamide

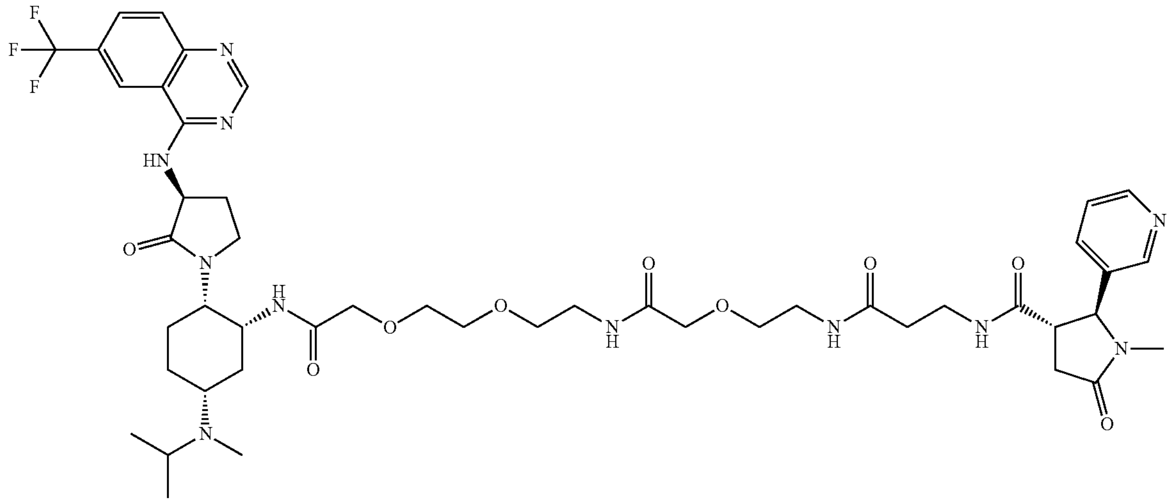 [SMILES: CC(C)N(C)[C@@H]1CC[C@H](N2CC[C@H](Nc3ncnc4ccc(C(F)(F)F)cc34)C2=O)[C@H](NC(=O)COCCOCCNC(=O)COCCNC(=O)CCNC(=O)[C@H]2CC(=O)N(C)[C@@H]2c2cccnc2)C1]

To a solution of 1-((2S,3S)-1-methyl-5-oxo-2-(pyridin-3-yl)pyrrolidin-3-yl)-1,5,11-trioxo-9,15,18-trioxa-2,6,12-tri-azaicosan-20-oic acid, hydrochloric acid salt (259 mg, 0.158 mmol) in dichloromethane (DCM) (1 mL) was added HOBt (29.1 mg, 0.190 mmol) and EDC (42.4 mg, 0.221 mmol) and the mixture was stirred for 30 min. (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2ihydrochloric acid salt (50 mg, 0.079 mmol) and DIPEA (0.055 mL, 0.316 mmol) were added and the mixture was stirred overnight. The mixture was washed with saturated $NaHCO_3$ and the aqueous phase was extracted with dichloromethane (DCM) (3×20 mL). The combined organic extracts were washed with saturated NaCl, were dried over $Na_2SO_4$, and were concentrated onto silica. Purification by MDAP (Xselect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as white solid (51 mg, 0.049 mmol, 62.3% yield). LC-MS m/z 984.8 $(M+H)^+$. $^1$H NMR (400 MHz, METHANOL-$d_4$) δ ppm 1.00 (d, J=6.4 Hz, 3H) 1.16 (br d, J=6.4 Hz, 3H) 1.62-1.80 (m, 2H) 1.89-2.02 (m, 1H) 2.05-2.16 (m, 1H) 2.24 (s, 4H) 2.31-2.43 (m, 3H) 2.51-2.62 (m, 1H) 2.65-2.74 (m, 5H) 2.79-2.88 (m, 1H) 2.97-3.05 (m, 1H) 3.35-3.46 (m, 8H) 3.50-3.64 (m, 6H) 3.65-3.71 (m, 2H) 3.72-3.77 (m, 2H) 3.95-3.98 (m, 2H) 4.04-4.12 (m, 3H) 4.71 (br d, J=2.9 Hz, 1H) 4.83 (d, J=6.4 Hz, 1H) 5.31 (t, J=8.6 Hz, 1H) 7.52 (dd, J=7.8, 4.9 Hz, 1H) 7.79 (dt, J=7.8, 2.0 Hz, 1H) 7.90 (d, J=8.8 Hz, 1H) 8.04-8.09 (m, 1H) 8.50-8.52 (m, 1H) 8.57 (dd, J=4.9, 2.0 Hz, 1H) 8.59 (s, 1H) 8.77-8.81 (m, 1H).

The following compounds were or could be prepared with procedures analogous to that described in Example 74:

| Ex. | Compound | LC-MS m/z | NMR |
|---|---|---|---|
| 75 | 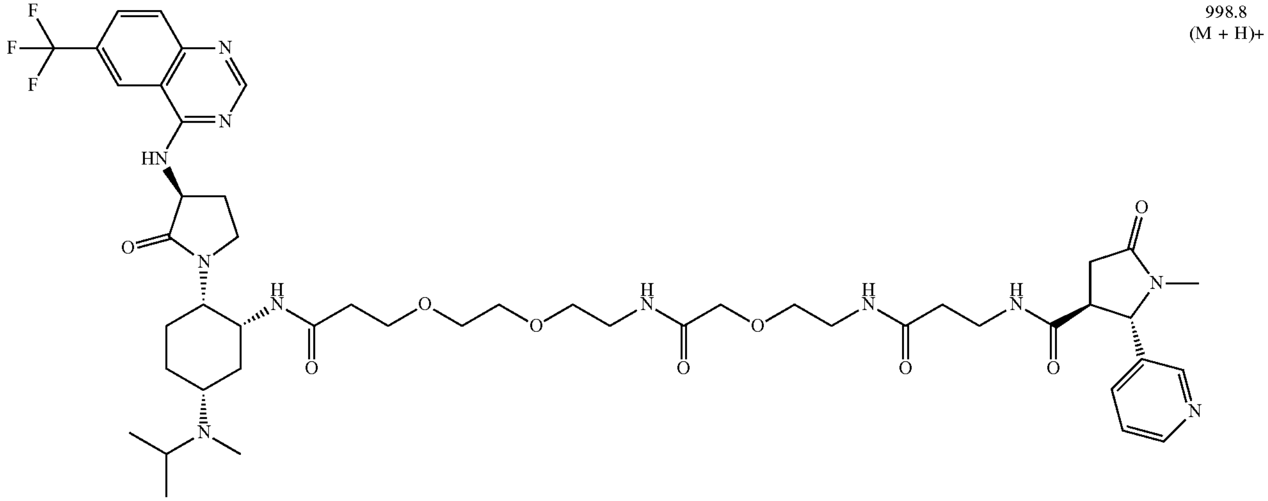 (2S,3S)-N-(19-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)amino)-3,9,19-trioxo-7,13, 16-trioxa-4, 10-diazanonadecyl)-1-methyl-5-oxo-2-(pyridin-3-yl)pyrrolidine-3-carboxamide. | 998.8 (M + H)+ | $^1$H NMR (400 MHz, METHANOL-$d_4$) δ ppm 0.98-1.10 (m, 4H) 1.14 (br d, J = 6.4 Hz, 3H) 1.64-1.77 (m, 3H) 1.91-2.01 (m, 1H) 2.06-2.19 (m, 1H) 2.20-2.24 (m, 1H) 2.27 (s, 4H) 2.31-2.57 (m, 7H) 2.64-2.75 (m, 5H) 2.79-2.84 (m, 1H) 3.01 (ddd, J = 9.5, 8.1, 6.4 Hz, 1H) 3.35-3.60 (m, 18H) 3.66-3.75 (m, 2H) 3.81 (dt, J = 9.5, 6.0 Hz, 1H) 3.96-3.98 (m, 2H) 4.03-4.09 (m, 1H) 4.64 (br d, J = 2.9 Hz, 1H) 4.82-4.88 (m, 1H) 5.31 (t, J = 8.1 Hz, 1 H) 7.52 (dd, J = 8.8, 4.9 Hz, 1 H) 7.79 (dt, J = 7.8, 2.0 Hz, 1 H) 7.91 (d, J = 8.8 Hz, 1H) 8.07 (dd, J = 8.8, 2.0 Hz, 1H) 8.51 (d, J = 1.5 Hz, 1H) 8.83 (s, 1H). |

-continued
| Ex. | Compound | LC-MS m/z | NMR |
| --- | --- | --- | --- |
| 76 | 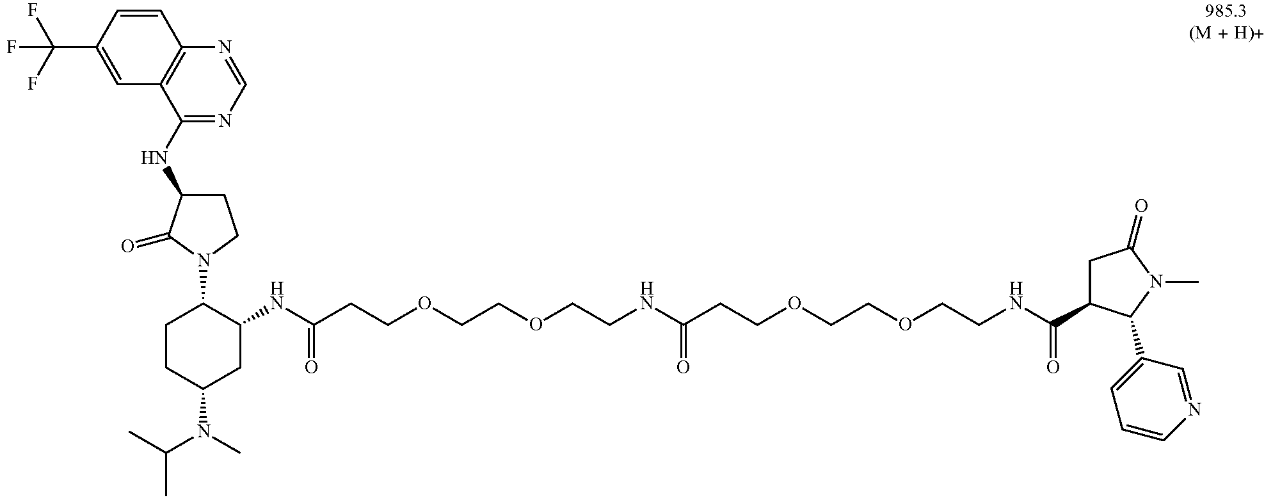 (2S,3S)-N-(19-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-9,19-dioxo-3,6,13,16-tetraoxa-10-azanonadecyl)-1-methyl-5-oxo-2-(pyridin-3-yl)pyrrolidine-3-carboxamide. | 985.3 (M + H)+ | $^1$H NMR (400 MHz, DMSO-$d_6$) δ ppm 1.54-1.65 (m, 3 H) 1.85-1.96 (m, 1H) 1.96-2.12 (m, 3H) 2.15 (s, 4H) 2.26-2.50 (m, 9H) 2.58-2.64 (m, 1H) 2.64-2.75 (m, 1H) 2.92-3.08 (m, 1H) 3.09-3.20 (m, 4H) 3.20-3.40 (m, 17H) 3.44-3.65 (m, 7H) 3.88-3.96 (m, 1H) 4.46 (br d, J = 3.9 Hz, 1H) 4.65 (d, J = 6.4 Hz, 1H) 4.98-5.04 (m, 1H) 7.41-7.46 (m, 1H) 7.67 (dt, J = 7.8, 2.0 Hz, 1H) 7.84-7.91 (m, 2H) 8.04-8.11 (m, 2H) 8.47 (d, J = 1.5 Hz, 1H) 8.52-8.58 (m, 1H) 8.60 (s, 1H) 8.64 (d, J = 8.3 Hz, 1H) 8.97 (s, 1 H). |

-continued

| Ex. | Compound | LC-MS m/z | NMR |
|---|---|---|---|
| 77 | 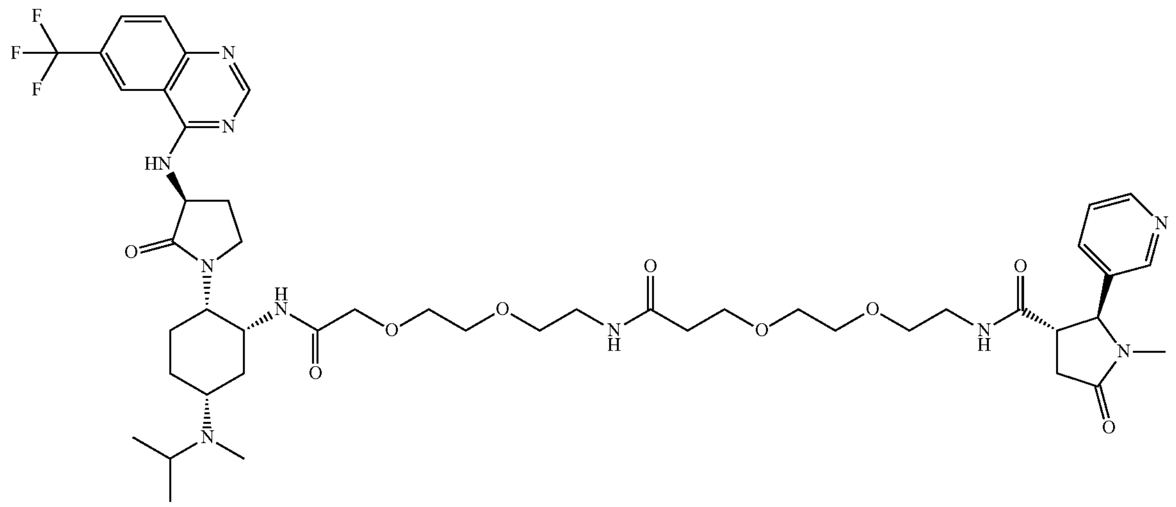 [SMILES: CC(C)N(C)[C@@H]1CC[C@H](N2CC[C@H](Nc3ncnc4ccc(C(F)(F)F)cc34)C2=O)[C@H](NC(=O)COCCOCCNC(=O)CCOCCOCCNC(=O)[C@H]2CC(=O)N(C)[C@@H]2c2cccnc2)C1] (2S,3S)-N-(1-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)amino)-1,10-dioxo-3,6,13,16-tetraoxa-9-azaoctadecan-18-yl)-1-methyl-5-oxo-2-(pyridin-3-yl)pyrrolidine-3-carboxamide. | 971.5 (M + H)+ | $^1$H NMR (400 MHz, DMSO-$d_6$) δ ppm 0.90 (d, J = 6.4 Hz, 3H) 1.04 (d, J = 6.4 Hz, 3H) 1.48-1.74 (m, 3H) 1.87-2.14 (m, 6H) 2.17 (br s, 1H) 2.23-2.36 (m, 3H) 2.40-2.49 (m, 3H) 2.52-2.61 (m, 3H) 2.62-2.80 (m, 2H) 2.84-3.04 (m, 1H) 3.09-3.33 (m, 6H) 3.35-3.62 (m, 14H) 3.86-4.03 (m, 3H) 4.49-4.59 (m, 1H) 4.64 (d, J = 6.4 Hz, 1H) 5.00 (q, J = 7.8 Hz, 1H) 7.43 (dd, J = 7.6, 5.1 Hz, 1H) 7.67 (dt, J = 8.1, 1.8 Hz, 1H) 7.83-7.95 (m, 2H) 7.98-8.16 (m, 2H) 8.47 (d, J = 2.0 Hz, 1H) 8.56 (dd, J = 4.6, 1.7 Hz, 1H) 8.59 (s, 1H) 8.63 (d, J = 7.8 Hz, 1H) 8.95 (s, 1H) 9.21 (br d, J = 8.8 Hz, 1H). |

-continued

| Ex. | Compound | LC-MS m/z | NMR |
|---|---|---|---|
| 78 | 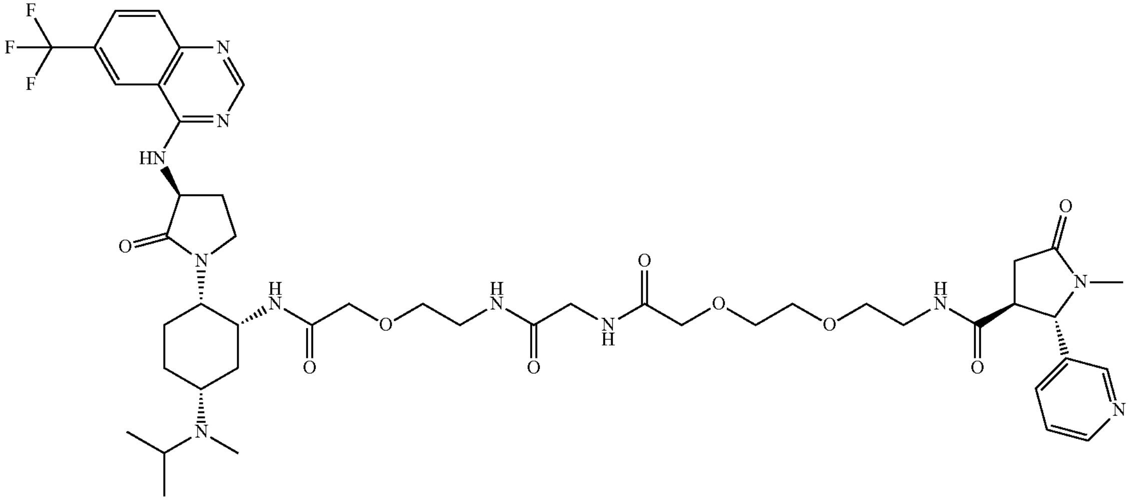 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CNC(=O)COCCOCCNC(=O)[C@H]2CC(=O)N(C)[C@@H]2c2cccnc2)C1] (2S,3S)-N-(1-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)amino)-1,7,10-trioxo-3,12,15-trioxa-6,9-diazaheptadecan-17-yl)-1-methyl-5-oxo-2-(pyridin-3-yl)pyrrolidine-3-carboxamide. | 970.3 (M + H)+ | $^1$H NMR (400 MHz, METHANOL-$d_4$) δ ppm 1.00 (br d, J = 6.4 Hz, 3H) 1.15 (br d, J = 6.4 Hz, 3H) 1.23-1.49 (m, 1H) 1.61-1.89 (m, 3H) 2.02 (br d, J = 8.3 Hz, 1H) 2.11-2.35 (m, 6H) 2.46-2.62 (m, 1H) 2.66 (s, 3H) 2.67-2.74 (m, 2H) 2.78-2.87 (m, 1H) 3.06 (ddd, J = 9.3, 8.1, 6.6 Hz, 1H) 3.22-3.31 (m, 1H) 3.35-3.47 (m, 4H) 3.49-3.72 (m, 10 H) 3.90 (d, J = 3.4 Hz, 2H) 4.02 (s, 2H) 4.05 (d, J = 1.5 Hz, 2H) 4.09 (br s, 1H) 4.65 (br s, 1H) 4.82 (d, J = 6.8 Hz, 1H) 5.24-5.32 (m, 1H) 7.52 (dd, J = 7.8, 4.9 Hz, 1H) 7.79 (dt, J = 8.3, 2.0 Hz, 1H) 7.90 (d, J = 8.8 Hz, 1H) 8.06 (dd, J = 8.8, 2.0 Hz, 1H) 8.52 (d, J = 2.0 Hz, 1H) 8.56 (dd, J = 4.9, 1.5 Hz, 1H) 8.58 (s, 1H) 8.77 (s, 1H). |

-continued

| Ex. | Compound | LC-MS m/z | NMR |
|---|---|---|---|
| 79 | 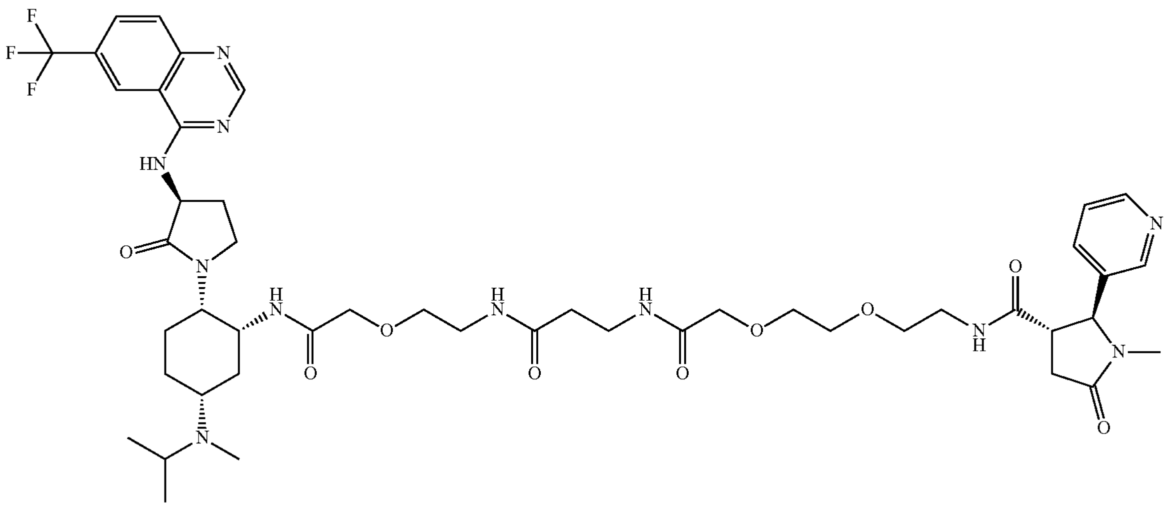 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCNC(=O)COCCOCCNC(=O)[C@H]2CC(=O)N(C)[C@@H]2c2cccnc2)C1] (2S,3S)-N-(18-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)amino)-8,12,18-trioxo-3,6,16-trioxa-9,13-diazaoctadecyl)-1-methyl-5-oxo-2-(pyridin-3-yl)pyrrolidine-3-carboxamide. | 984.3 (M + H)+ | $^1$H NMR (400 MHz, METHANOL-$d_4$) δ ppm 0.98-1.10 (m, 4H) 1.14 (br d, J = 6.4 Hz, 3H) 1.64-1.77 (m, 3H) 1.91-2.01 (m, 1H) 2.06-2.19 (m, 1H) 2.20-2.24 (m, 1H) 2.27 (s, 4H) 2.31-2.57 (m, 7H) 2.64-2.75 (m, 5H) 2.79-2.84 (m, 1H) 3.01 (ddd, J = 9.5, 8.1, 6.4 Hz, 1H) 3.35-3.60 (m, 18H) 3.66-3.75 (m, 2H) 3.81 (dt, J = 9.5, 6.0 Hz, 1H) 3.96-3.98 (m, 2H) 4.03-4.09 (m, 1H) 4.64 (br d, J = 2.9 Hz, 1H) 4.82-4.88 (m, 1H) 5.31 (t, J = 8.1 Hz, 1 H) 7.52 (dd, J = 8.8, 4.9 Hz, 1 H) 7.79 (dt, J = 7.8, 2.0 Hz, 1 H) 7.91 (d, J = 8.8 Hz, 1H) 8.07 (dd, J = 8.8, 2.0 Hz, 1H) 8.51 (d, J = 1.5 Hz, 1H) 8.83 (s, 1H). |

-continued

| Ex. | Compound | LC-MS m/z | NMR |
|---|---|---|---|
| 80 | 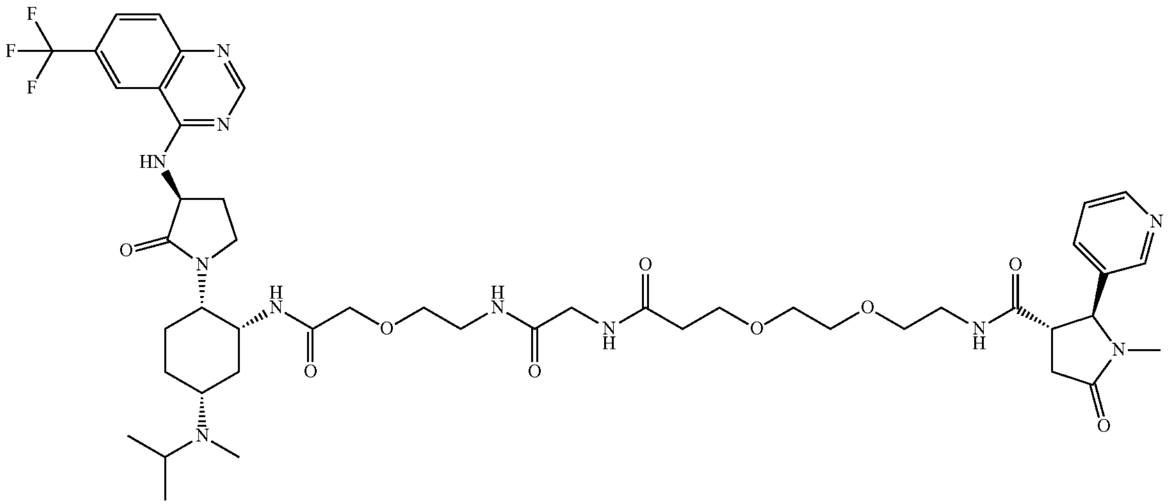 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CNC(=O)CCOCCOCCNC(=O)[C@H]2CC(=O)N(C)[C@@H]2c2cccnc2)C1] (2S,3S)-N-(1-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)amino)-1,7,10-trioxo-3,13,16-trioxa-6,9-diazaoctadecan-18-yl)-1-methyl-5-oxo-2-(pyridin-3-yl)pyrrolidine-3-carboxamide. | 984.5 (M + H)+ | $^1$H NMR (400 MHz, METHANOL-$d_4$) δ ppm 1.00 (d, J = 6.4 Hz, 3H) 1.15 (d, J = 6.4 Hz, 3H) 1.64-1.89 (m, 3H) 1.97-2.07 (m, 1H) 2.12-2.22 (m, 2H) 2.24 (s, 3H) 2.38 (br s, 2H) 2.49 (td, J = 6.1, 2.0 Hz, 2H) 2.53-2.62 (m, 1H) 2.66-2.68 (m, 3H) 2.73 (br d, J = 8.8 Hz, 1 H) 2.80-2.89 (m, 1H) 3.07 (ddd, J = 9.5, 8.1, 6.4 Hz, 1 H) 3.27-3.30 (m, 1H) 3.35-3.45 (m, 4H) 3.47-3.58 (m, 7H) 3.60-3.66 (m, 3H) 3.71 (t, J = 6.1 Hz, 2H) 3.83 (d, J = 1.0 Hz, 2H) 4.01-4.10 (m, 3H) 4.66 (br d, J = 3.4 Hz, 1H) 4.83 (d, J = 6.4 Hz, 1H) 5.27 (t, J = 8.6 Hz, 1H) 7.52 (dd, J = 8.3, 4.9 Hz, 1 H) 7.79 (dt, J = 7.8, 2.0 Hz, 1 H) 7.90 (d, J = 8.8 Hz, 1H) 8.05 (dd, J = 8.8, 2.0 Hz, 1H) 8.52 (d, J = 1.5 Hz, 1H) 8.56-8.59 (m, 2H) 8.78 (s, 1H). |

-continued

| Ex. | Compound | LC-MS m/z | NMR |
|---|---|---|---|
| 81 | 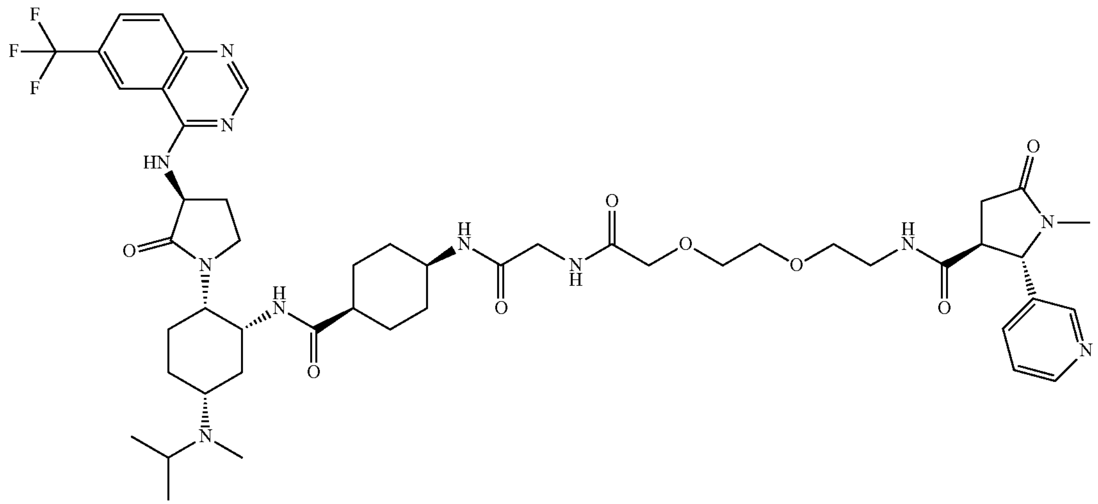 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CNC(=O)COCCOCCNC(=O)[C@H]3CC(=O)N(C)[C@@H]3c3cccnc3)CC2)C1] (2S,3S)-N-(2-(2-(2-((2-(((1S,4s)-4-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)carbamoyl)cyclohexyl)amino)-2-oxoethyl)amino)-2-oxoethoxy)ethoxy)ethyl)- 1-methyl-5-oxo-2-(pyridin-3-yl)pyrrolidine-3-carboxamide. | 994.6 (M + H)+ | $^1$H NMR (400 MHz, DMSO-$d_6$) δ ppm 0.90 (d, J = 6.4 Hz, 3H) 1.04 (d, J = 6.4 Hz, 3H) 1.52-1.73 (m, 9H) 1.89-2.16 (m, 8H) 2.33-2.49 (m, 5H) 2.62-2.75 (m, 2H) 2.91-3.00 (m, 1H) 3.36-3.46 (m, 4H) 3.49-3.60 (m, 5H) 3.71 (br d, J = 6.4 Hz, 3 H) 3.88 (s, 3H) 4.42 (br d, J = 3.9 Hz, 1H) 4.64 (d, J = 6.4 Hz, 1H) 5.04 (q, J = 8.2 Hz, 1 H) 7.43 (dd, J = 7.6, 5.1 Hz, 1 H) 7.62-7.72 (m, 2H) 7.89 (d, J = 8.8 Hz, 1H) 8.04-8.10 (m, 2H) 8.46 (d, J = 2.4 Hz, 1H) 8.52-8.57 (m, 1H) 8.58 (s, 1H) 8.60-8.68 (m, 1H) 8.72 (d, J = 8.3 Hz, 1H) 8.90 (s, 1H). |

-continued

| Ex. | Compound | LC-MS m/z | NMR |
|---|---|---|---|
| 82 | 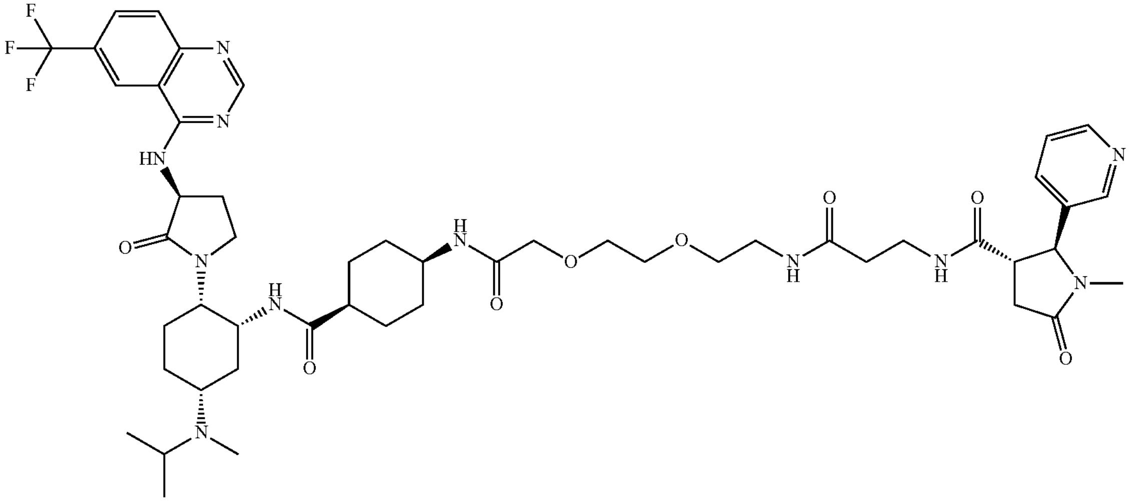 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCOCCNC(=O)CCNC(=O)[C@H]3CC(=O)N(C)[C@@H]3c3cccnc3)CC2)C1]<br>(2S,3S)-N-(3-((2-(2-(2-(((1S,4s)-4-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)carbamoyl)cyclohexyl)amino)-2-oxoethoxy)ethoxy)ethyl)amino)-3-oxopropyl)-1-methyl-5-oxo-2-(pyridin-3-yl)pyrrolidine-3-carboxamide. | 1008.1 (M + H)+ | $^1$H NMR (400 MHz, DMSO-$d_6$) δ ppm 0.89 (d, J = 6.4 Hz, 3H) 1.04 (d, J = 6.4 Hz, 3H) 1.42-1.52 (m, 2H) 1.54-1.71 (m, 9H) 1.89-1.97 (m, 1H) 2.09 (br s, 1H) 2.14 (s, 5H) 2.21 (t, J = 7.1 Hz, 2H) 2.30-2.37 (m, 1H) 2.39-2.46 (m, 1H) 2.48-2.49 (m, 3H) 2.56-2.61 (m, 1H) 2.65-2.73 (m, 1H) 2.86-2.93 (m, 1H) 3.32 (s, 5H) 3.36-3.41 (m, 3H) 3.43-3.58 (m, 6H) 3.77 (br s, 1H) 3.80 (s, 2H) 3.84-3.90 (m, 1H) 4.40-4.45 (m, 1H) 4.63 (d, J = 5.9 Hz, 1H) 5.03 (q, J = 8.2 Hz, 1H) 7.28 (d, J = 6.8 Hz, 1H) 7.43 (dd, J = 7.8, 4.9 Hz, 1H) 7.66 (dt, J = 7.8, 2.0 Hz, 1H) 7.87-7.95 (m, 2H) 8.03-8.10 (m, 2H) 8.46 (d, J = 2.0 Hz, 1H) 8.55 (dd, J = 4.6, 1.7 Hz, 1H) 8.58 (s, 1H) 8.69 (br d, J = 8.3 Hz, 2H) 8.88 (s, 1H). |

-continued
| Ex. | Compound | LC-MS m/z | NMR |
| --- | --- | --- | --- |
| 83 | 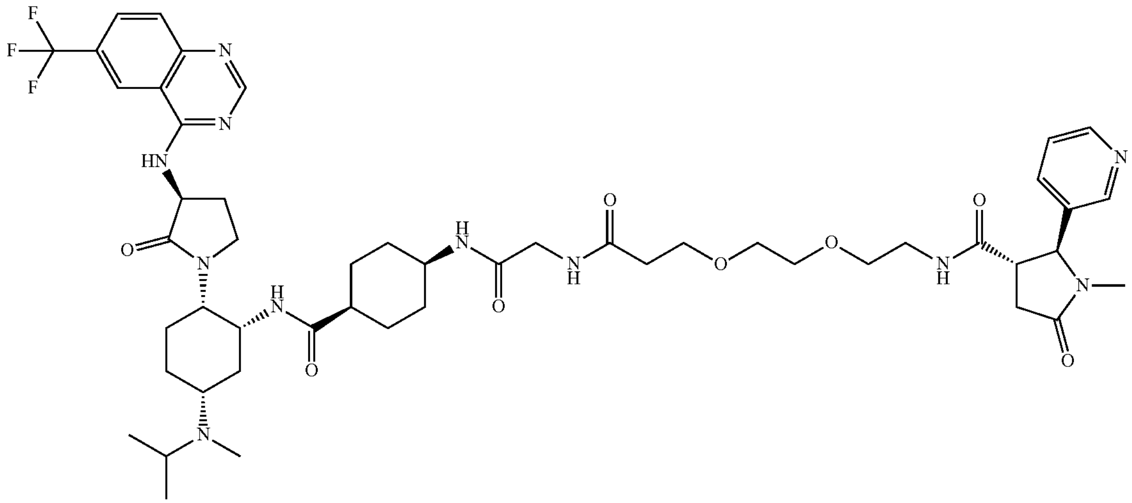 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CNC(=O)CCOCCOCCNC(=O)[C@H]3CC(=O)N(C)[C@@H]3c3cccnc3)CC2)C1] (2S,3S)-N-(2-(2-(3-((2-(((1S,4s)-4-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)carbamoyl)cyclohexyl)amino)-2-oxoethyl)amino)-3-oxopropoxy)ethoxy)ethyl)-1-methyl-5-oxo-2-(pyridin-3-yl)pyrrolidine-3-carboxamide. | 1008.6 (M + H)+ | H NMR (400 MHz, DMSO-$d_6$) δ ppm 0.85-0.93 (m, 3 H) 1.00-1.08 (m, 3H) 1.38-1.50 (m, 2H) 1.51-1.75 (m, 9H) 1.89-2.17 (m, 9H) 2.30-2.47 (m, 4H) 2.56-2.61 (m, 1H) 2.65-2.75 (m, 1H) 2.89-3.05 (m, 2H) 3.08-3.29 (m, 4H) 3.36-3.40 (m, 2H) 3.40-3.47 (m, 5H) 3.49-3.59 (m, 3H) 3.64-3.67 (m, 2H) 3.69-3.75 (m, 1H) 3.83-3.97 (m, 1H) 4.35-4.48 (m, 1H) 4.60-4.69 (m, 1H) 4.98-5.08 (m, 1H) 7.41-7.47 (m, 1H) 7.64-7.73 (m, 2H) 7.86-7.92 (m, 1H) 7.98-8.03 (m, 1H) 8.05-8.11 (m, 2H) 8.45-8.49 (m, 1H) 8.54-8.60 (m, 2H) 8.62-8.77 (m, 2H) 8.87-8.92 (m, 1H). |

-continued
| Ex. | Compound | LC-MS m/z | NMR |
|---|---|---|---|
| 84 | 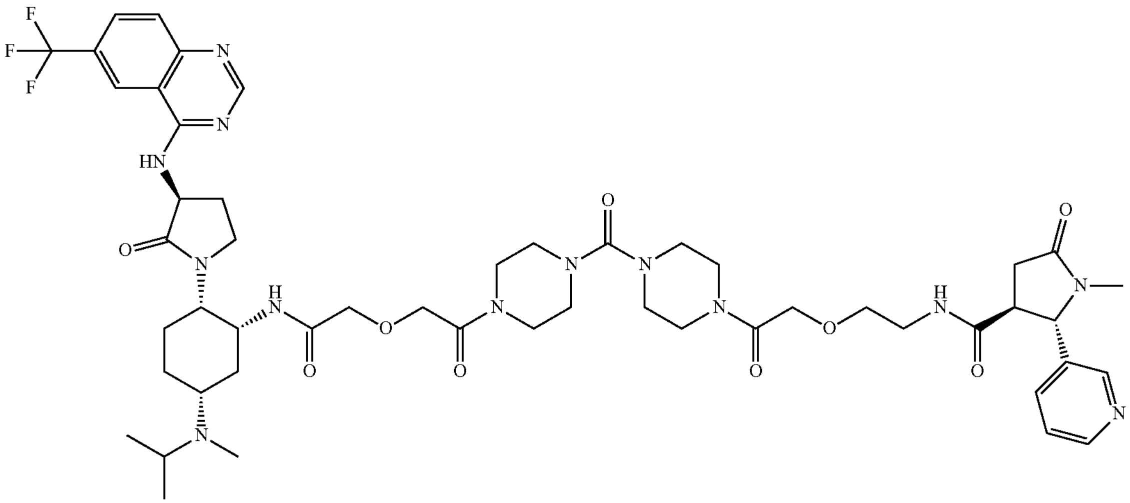 [SMILES: CC(C)N(C)[C@@H]1CC[C@H](N2CC[C@H](Nc3ncnc4ccc(C(F)(F)F)cc34)C2=O)[C@H](NC(=O)COCC(=O)N2CCN(C(=O)N3CCN(C(=O)COCCNC(=O)[C@H]4CC(=O)N(C)[C@@H]4c4cccnc4)CC3)CC2)C1] (2S,3S)-N-(2-(2-(4-(4-(2-(2-(((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)amino)-2-oxoethoxy)acetyl)piperazine-1-carbonyl)piperazin-1-yl)-2-oxoethoxy)ethyl)-1-methyl-5-oxo-2-(pyridin-3-yl)pyrrolidine-3-carboxamide. | 1064.8 (M + H)+ | $^1$H NMR (400 MHz, DMSO-$d_6$) δ ppm 0.85-0.93 (m, 3 H) 1.00-1.08 (m, 3H) 1.38-1.50 (m, 2H) 1.51-1.75 (m, 9H) 1.89-2.17 (m, 9H) 2.30-2.47 (m, 4H) 2.56-2.61 (m, 1H) 2.65-2.75 (m, 1H) 2.89-3.05 (m, 2H) 3.08-3.29 (m, 4H) 3.36-3.40 (m, 2H) 3.40-3.47 (m, 5H) 3.49-3.59 (m, 3H) 3.64-3.67 (m, 2H) 3.69-3.75 (m, 1H) 3.83-3.97 (m, 1H) 4.35-4.48 (m, 1H) 4.60-4.69 (m, 1H) 4.98-5.08 (m, 1H) 7.41-7.47 (m, 1H) 7.64-7.73 (m, 2H) 7.86-7.92 (m, 1H) 7.98-8.03 (m, 1H) 8.05-8.11 (m, 2H) 8.45-8.49 (m, 1H) 8.54-8.60 (m, 2H) 8.62-8.77 (m, 2H) 8.87-8.92 (m, 1H). |

Example 85

(2S,3S)-N-(17-((2-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3,4-dioxocyclobut-1-en-1-yl)amino)-3,6,9,12,15-pentaoxaheptadecyl)-1-methyl-5-oxo-2-(pyridin-3-yl)pyrrolidine-3-carboxamide

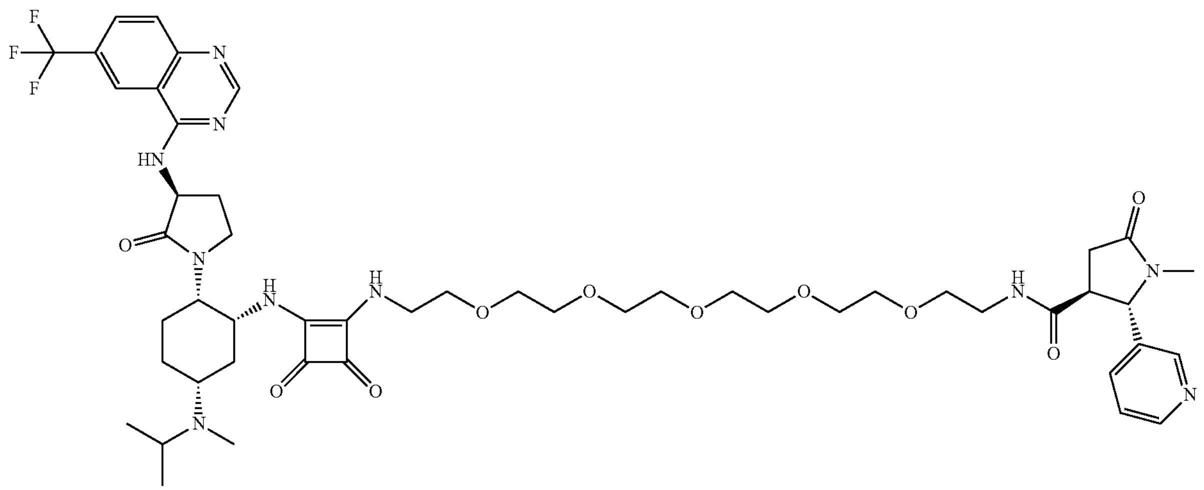 [SMILES: CC(C)N(C)[C@@H]1CC[C@H](N2CC[C@H](Nc3ncnc4ccc(C(F)(F)F)cc34)C2=O)[C@H](Nc2c(NCCOCCOCCOCCOCCOCCNC(=O)[C@H]3CC(=O)N(C)[C@@H]3c3cccnc3)c(=O)c2=O)C1]

Step 1

(2S,3S)-N-(17-Amino-3,6,9,12,15-pentaoxaheptadecyl)-1-methyl-5-oxo-2-(pyridin-3-yl)pyrrolidine-3-carboxamide. 2Hydrochloric acid salt

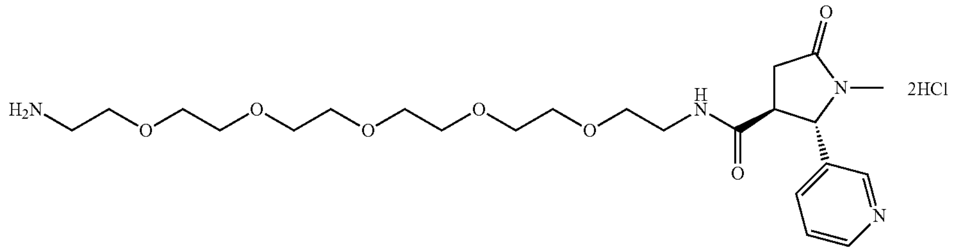 [SMILES: CN1C(=O)C[C@H](C(=O)NCCOCCOCCOCCOCCOCCN)[C@H]1c1cccnc1]

To a mixture of (2S,3S)-1-methyl-5-oxo-2-(pyridin-3-yl)pyrrolidine-3-carboxylic acid (370 mg, 1.680 mmol), tert-butyl (14-amino-3,6,9,12-tetraoxatetradecyl)carbamate (840 mg, 2.497 mmol) in dichloromethane (DCM) (10 mL) was added T3P (1.757 mL, 2.95 mmol). The mixture was stirred at rt for 2 h and was washed with water (10 mL). The organic phase was dried over $Na_2SO_4$ and was concentrated under reduced pressure to provide tert-butyl (1-((2S,3S)-1-methyl-5-oxo-2-(pyridin-3-yl)pyrrolidin-3-yl)-1-oxo-5,8,11,14-tetraoxa-2-azahexadecan-16-yl)carbamate as a white semi-solid (750 mg, 1.39 mmol, 82.7% yield). LC-MS m/z 539.1 $(M+H)^+$.

tert-Butyl (1-((2S,3S)-1-methyl-5-oxo-2-(pyridin-3-yl)pyrrolidin-3-yl)-1-oxo-5,8,11,14-tetraoxa-2-aza-hexadecan-16-yl)carbamate as a white semi-solid was treated with 4 N HCl in 1,4-dioxane was added to the product above. The mixture was stirred for 1 h and was concentrated under reduced pressure to provide the title compound (650 mg, 1.482 mmol, 75.6% yield). LC-MS m/z 439.2 $(M+H)^+$ Step 2

(2S,3S)-N-(17-((2-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-3,4-dioxocyclobut-1-en-1-yl)amino)-3,6,9,12,15-pentaoxaheptadecyl)-1-methyl-5-oxo-2-(pyridin-3-yl)pyrrolidine-3-carboxamide

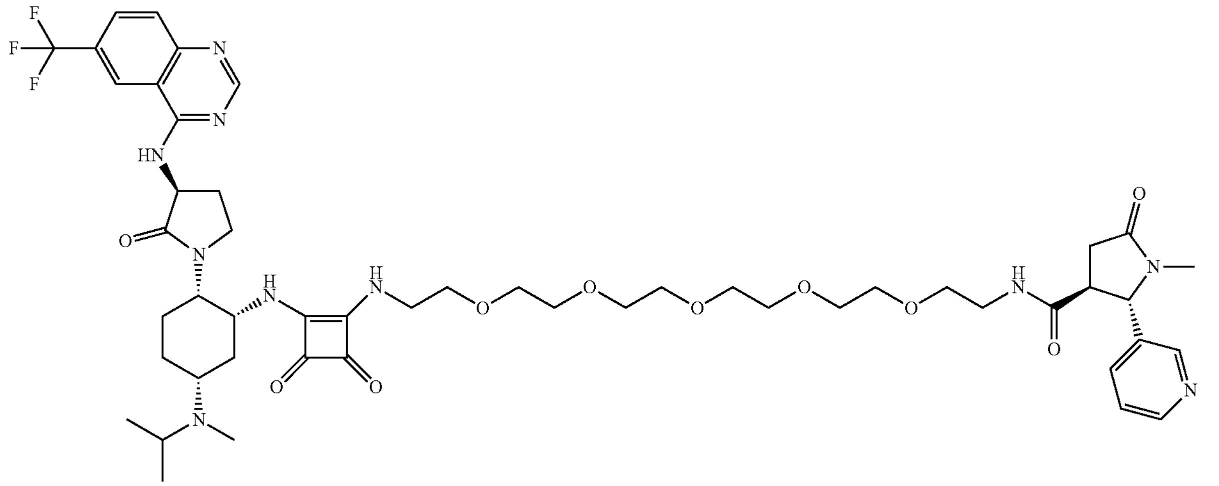 [SMILES: CC(C)N(C)[C@@H]1CC[C@H](N2CC[C@H](Nc3ncnc4ccc(C(F)(F)F)cc34)C2=O)[C@H](Nc2c(NCCOCCOCCOCCOCCOCCNC(=O)[C@H]3CC(=O)N(C)[C@@H]3c3cccnc3)c(=O)c2=O)C1]

A mixture of 3-ethoxy-4-(((1R,2S,5R)-5-(isopropyl (methyl)amino)-2-((S)-2-oxo-3-((6-(trifluoromethyl)quinazolin-4-yl)amino)pyrrolidin-1-yl)cyclohexyl)amino)cyclobut-3-ene-1,2-dione (60 mg, 0.102 mmol), (2S,3S)-N-(17-amino-3,6,9,12,15-pentaoxaheptadecyl)-1-methyl-5-oxo-2-(pyridin-3-yl)pyrrolidine-3-carboxamide (49.2 mg, 0.102 mmol), and DIPEA (0.036 mL, 0.204 mmol) in methanol (2 mL). was stirred in a sealed vial at 60° C. for 18 h and was concentrated. Purification by MDAP (XSelect™ CSH Prep C18 5 um OBD, 40 mL/min) eluting with a gradient of 15 to 65% acetonitrile in water containing ammonium bicarbonate (10 mM) and the ammonia hydroxide (0.075%) provided the title compound (95.3 mg, 0.088 mmol, 87% yield). LC-MS m/z 1025.4 $(M+H)^+$. $^1H$ NMR (400 MHz, METHANOL-$d_4$) δ ppm 1.00-1.20 (m, 6H) 1.29-1.39 (m, 1H) 1.68-1.92 (m, 4H) 2.29 (br s, 5H) 2.43-2.52 (m, 1H) 2.55-2.77 (m, 1H) 2.57-2.75 (m, 4H) 2.80-2.89 (m, 2H) 3.02-3.09 (m, 1H) 3.36-3.77 (m, 26H) 4.10-4.17 (m, 1H) 4.72 (br d, J=2.9 Hz, 1H) 4.83 (d, J=6.4 Hz, 1H) 5.23-5.34 (m, 1H) 7.53 (dd, J=7.8, 4.9 Hz, 1H) 7.80 (dt, J=7.8, 2.0 Hz, 1H) 7.91 (d, J=8.8 Hz, 1H) 8.06 (dd, J=8.8, 2.0 Hz, 1H) 8.50-8.53 (m, 1H) 8.56-8.59 (m, 2H) 8.71-8.81 (m, 1H).

Example 86

(2S,3S)-N-(6-(4-(4-(3-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-3-oxopropyl)phenyl)piperid in-1-yl)-6-oxohexyl)-1-methyl-5-oxo-2-(pyridin-3-yl) pyrrolidine-3-carboxamide

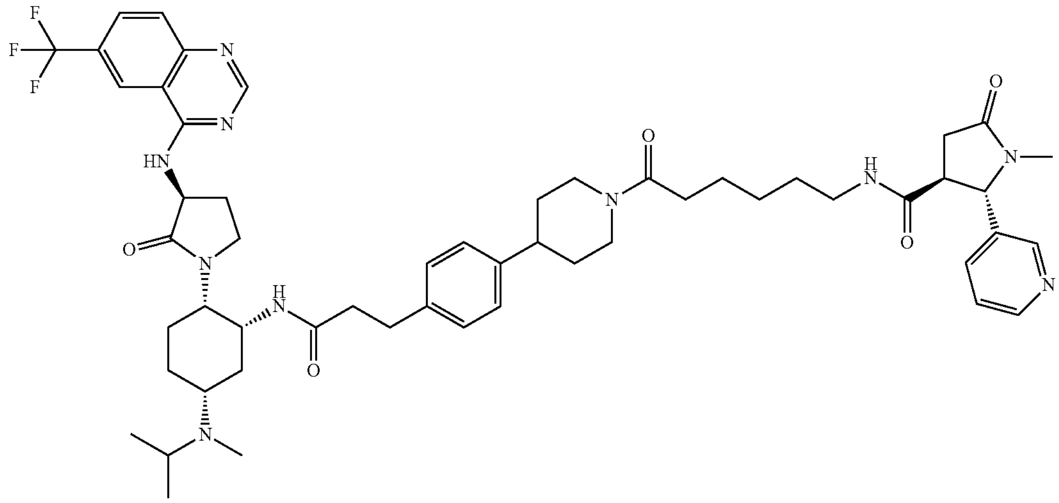 [SMILES: CC(C)N(C)[C@@H]1CC[C@H](N2CC[C@H](Nc3ncnc4ccc(C(F)(F)F)cc34)C2=O)[C@H](NC(=O)CCc2ccc(C3CCN(C(=O)CCCCCNC(=O)[C@H]4CC(=O)N(C)[C@@H]4c4cccnc4)CC3)cc2)C1]

Step 1 tert-Butyl (E)-4-hydroxy-4-(4-(3-methoxy-3-oxo-prop-1-en-1-yl)phenyl)piperidine-1-carboxylate

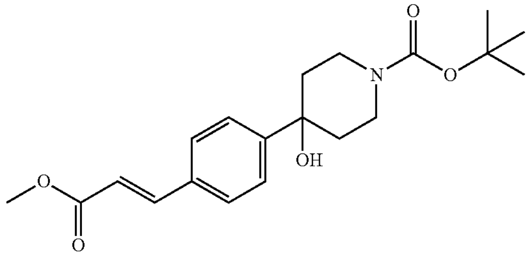 [SMILES: COC(=O)/C=C/c1ccc(C2(O)CCN(C(=O)OC(C)(C)C)CC2)cc1]

A mixture of tert-butyl 4-(4-bromophenyl)-4-hydroxypiperidine-1-carboxylate (528.3 mg, 1.483 mmol), methyl acrylate (1.344 mL, 14.83 mmol), triethylamine (0.827 mL, 5.93 mmol), palladium(II) acetate (71 mg, 0.316 mmol) and triphenylphosphine (160 mg, 0.610 mmol) in acetonitrile (15 mL) was degassed by vacuum and nitrogen backfilling cycles and was heated at 100° C. using a microwave reactor for 24 h, was cooled, was filtered through Celite®, and the filtrate was concentrated. Purification by normal-phase chromatography (24 g ISCO gold column, 35 mL/min) eluting with a stepwise gradient of 20 to 50% (15 column volumes) and 50% (5 column volumes) ethyl acetate in provided the title compound as a yellow semi-solid (324.3 mg, 0.897 mmol, 60.5% yield). $^1$H NMR (400 MHz, CHLOROFORM-d) δ ppm 1.44 (s, 9H) 1.69 (br d, J=12.3 Hz, 2H) 1.86-1.96 (m, 2H) 2.99 (br s, 1H) 3.22 (br s, 2H) 3.76 (s, 3H) 3.89-4.03 (m, 2H) 6.36 (d, J=16.1 Hz, 1H) 7.41-7.50 (m, 4H) 7.60 (d, J=16.1 Hz, 1H).

Step 2 tert-Butyl 4-(4-(3-methoxy-3-oxopropyl)phenyl) piperidine-1-carboxylate

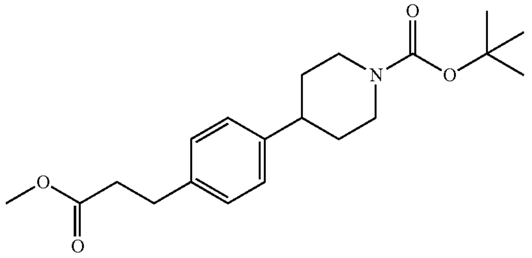 [SMILES: COC(=O)CCc1ccc(C2CCN(C(=O)OC(C)(C)C)CC2)cc1]

To a solution of tert-butyl (E)-4-hydroxy-4-(4-(3-methoxy-3-oxoprop-1-en-1-yl)phenyl)piperidine-1-carboxylate (337 mg, 0.932 mmol) in methanol (10 mL) was added 10% Pd/C (100 mg, 0.094 mmol). The reaction was purged by vacuum and hydrogen backfilling cycles. The mixture was stirred at rt for 2 h, was filtered, and the filtrate was concentrated. Purification by normal-phase chromatography (24 g ISCO gold column, 35 mL/min) eluting with a stepwise gradient of 20 to 50% (15 column volumes) and 50% (5 column volumes) ethyl acetate in provided the title compound as a colorless film (236.3 mg, 0.666 mmol, 71.5% yield). $^1$H NMR (400 MHz, CHLOROFORM-d) δ ppm 1.49 (s, 9H) 1.61 (td, J=12.8, 4.1 Hz, 2H) 1.80 (br d, J=13.7 Hz, 2H) 2.57-2.65 (m, 3H) 2.75-2.83 (m, 2H) 2.92 (t, J=7.9 Hz, 2H) 3.66 (s, 3H) 4.24 (br d, J=12.9 Hz, 2H) 7.13 (d, J=1.3 Hz, 4H)

Step 3

3-(4-(1-(tert-Butoxycarbonyl)piperidin-4-yl)phenyl) propanoic acid

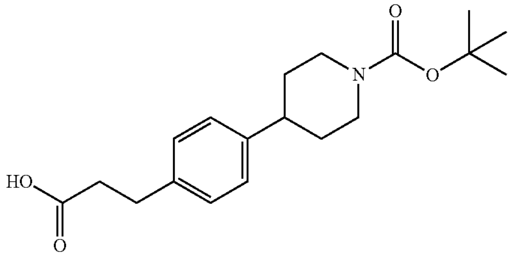 [SMILES: CC(C)(C)OC(=O)N1CCC(c2ccc(CCC(=O)O)cc2)CC1]

To a solution of tert-butyl 4-(4-(3-methoxy-3-oxopropyl) phenyl)piperidine-1-carboxylate (236 mg, 0.679 mmol) in tetrahydrofuran (THF) (1.5 mL) and ethanol (1.5 mL) was added 2 N sodium hydroxide (1.358 mL, 2.72 mmol). The mixture was stirred at rt for 1 and the pH was adjusted to 4 to 5 using 1 N HCl. The mixture was concentrated to remove the organic solvents. The residue was extracted with ethyl acetate (2×). The combined organic extracts were washed with brine, were dried over $MgSO_4$, and were concentrated to provide the title compound as a white solid (228.2 mg, 0.678 mmol, 100% yield). $^1$H NMR (400 MHz, CHLOROFORM-d) δ ppm 1.51 (s, 9H) 1.59-1.69 (m, 2H) 1.79-1.87 (m, 2H) 2.59-2.68 (m, 1H) 2.68-2.74 (m, 2H) 2.82 (td, J=13.1, 2.5 Hz, 2H) 2.97 (t, J=7.9 Hz, 2H) 4.26 (br d, J=13.0 Hz, 2H) 7.17 (d, J=4.3 Hz, 4H)

Step 4 tert-Butyl 4-(4-(3-(((1R,2S,5R)-5-(isopropyl(methyl) amino)-2-((S)-2-oxo-3-((6-(trifluoromethyl)quinazolin-4-yl)amino)pyrrolidin-1-yl)cyclohexyl)amino)-3-oxopropyl)phenyl)piperidine-1-carboxylate

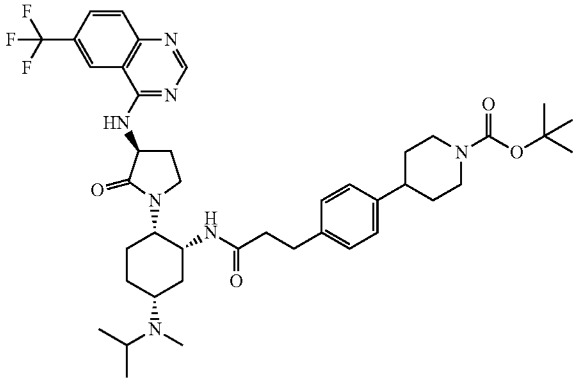 [SMILES: CC(C)N(C)[C@@H]1CC[C@H](N2CC[C@H](Nc3ncnc4ccc(C(F)(F)F)cc34)C2=O)[C@H](NC(=O)CCc2ccc(C3CCN(C(=O)OC(C)(C)C)CC3)cc2)C1]

To a solution of tert-butyl ((1R,2S,5R)-5-(isopropyl (methyl)amino)-2-((S)-2-oxo-3-((6-(trifluoromethyl)quinazolin-4-yl)amino)pyrrolidin-1-yl)cyclohexyl)carbamate (80 mg, 0.142 mmol) in dichloromethane (DCM) (1 mL) was added 3 M HCl in cyclopentyl methyl ether (0.5 mL, 1.500 mmol). The mixture was stirred at rt for 1 and was concentrated under reduced pressure. The residue was suspended in dichloromethane (DCM) (3 mL) with triethylamine (0.069 mL, 0.496 mmol). 3-(4-(1-(tert-butoxycarbonyl) piperidin-4-yl)phenyl)propanoic acid (55 mg, 0.165 mmol) and HATU (81 mg, 0.213 mmol) were added. The mixture was stirred at rt for 2 h and was concentrated. Purification by MDAP (XSelect™ CSH C18 5 μm column, 40 mL/min) eluting with a gradient of 80 to 99% acetonitrile in water containing ammonium bicarbonate (10 mM) and the pH adjusted to 10 with ammonia provided the title compound as a white solid (92.5 mg, 0.116 mmol, 82% yield). LC-MS m/z 780.2 $(M+H)^+$.

Step 5 tert-Butyl (6-(4-(4-(3-(((1R,2S,5R)-5-(isopropyl (methyl)amino)-2-((S)-2-oxo-3-((6-(trifluoromethyl) quinazolin-4-yl)amino)pyrrolidin-1-yl)cyclohexyl) amino)-3-oxopropyl)phenyl)piperidin-1-yl)-6-oxohexyl)carbamate

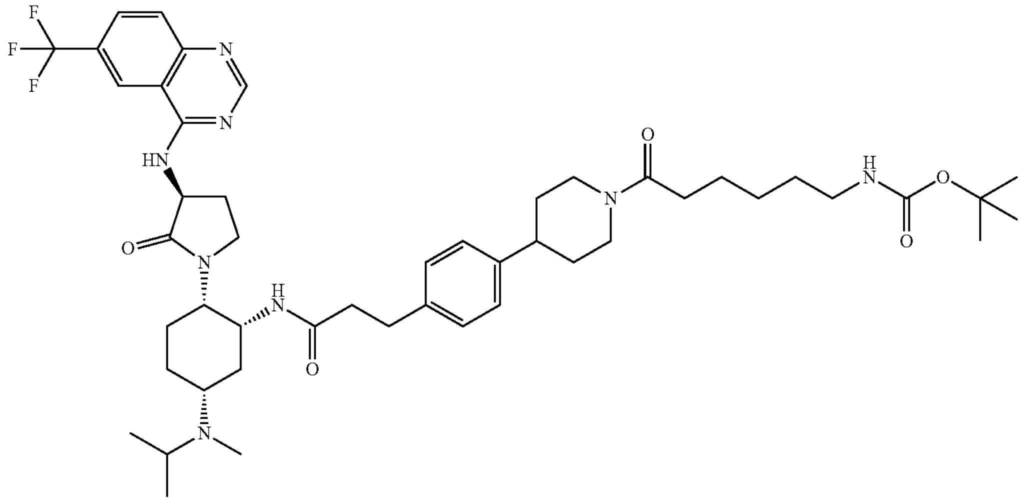 [SMILES: CC(C)N(C)[C@@H]1CC[C@H](N2CC[C@H](Nc3ncnc4ccc(C(F)(F)F)cc34)C2=O)[C@H](NC(=O)CCc2ccc(C3CCN(C(=O)CCCCCNC(=O)OC(C)(C)C)CC3)cc2)C1]

To a solution of tert-butyl 4-(4-(3-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-3-oxopropyl)phenyl)piperidine-1-carboxylate (36.5 mg, 0.047 mmol) in dichloromethane (DCM) (1 mL) was added 3M HCl in cyclopentyl methyl ether (0.5 mL, 1.500 mmol). The mixture was stirred at rt for 1 h and was concentrated to dryness. The white, solid residue was suspended in dichloromethane (DCM) (3 mL). DIPEA (0.041 mL, 0.234 mmol) was added, followed by 6-((tert-butoxycarbonyl)amino) hexanoic acid (12.99 mg, 0.056 mmol) and HATU (26.7 mg, 0.070 mmol). The resultant mixture was stirred at rt for 0.5 h and was concentrated. Purification by MDAP (XSelect™ CSH C18 5 μm column, 40 mL/min) eluting with a gradient of 50 to 99% acetonitrile in water containing ammonium bicarbonate (10 mM) and the pH adjusted to 10 with ammonia provided the title compound as a white solid (30.6 mg, 0.030 mmol, 79% yield). LC-MS m/z 893.3 $(M+H)^+$.

Step 6

(2S,3S)-N-(6-(4-(4-(3-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-3-oxopropyl)phenyl)piperid in-1-yl)-6-oxohexyl)-1-methyl-5-oxo-2-(pyridin-3-yl) pyrrolidine-3-carboxamide

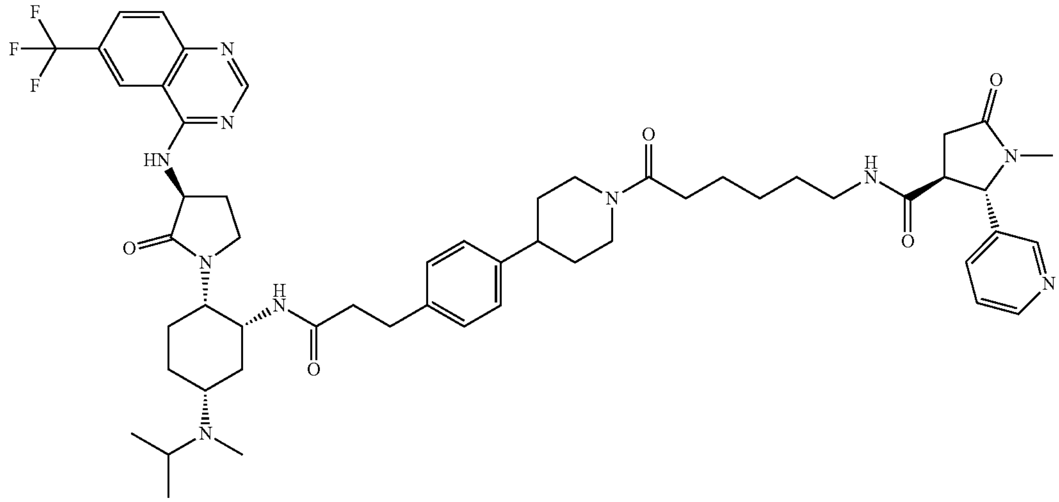 [SMILES: CC(C)N(C)[C@@H]1CC[C@H](N2CC[C@H](Nc3ncnc4ccc(C(F)(F)F)cc34)C2=O)[C@H](NC(=O)CCc2ccc(C3CCN(C(=O)CCCCCNC(=O)[C@H]4CC(=O)N(C)[C@@H]4c4cccnc4)CC3)cc2)C1]

A solution of tert-butyl (6-(4-(4-(3-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-3-oxopropyl)phenyl)piperidin-1-yl)-6-oxohexyl)carbamate (34 mg, 0.038 mmol) in dichloromethane (DCM) (1 mL) was treated with 3 M HCl in cyclopentyl methyl ether (0.25 mL, 0.750 mmol). The mixture was stirred at rt for 1 h and was concentrated under reduced pressure. The residue was suspended in dichloromethane (DCM) (3 mL) with triethylamine (0.027 mL, 0.190 mmol). (2S,3S)-1-methyl-5-oxo-2-(pyridin-3-yl)pyrrolidine-3-carboxylic acid (10.06 mg, 0.046 mmol) and HATU (21.71 mg, 0.057 mmol) were added. The mixture was stirred at rt for 1 h and was concentrated. Purification by MDAP (XSelect™ CSH C18 5 μm column, 40 mL/min) eluting with a gradient of 50 to 99% acetonitrile in water containing ammonium bicarbonate (10 mM) and the pH adjusted to 10 with ammonia provided the title compound as a white solid (30.6 mg, 0.030 mmol, 79% yield). LC-MS m/z 995.3 $(M+H)^+$. $^1$H NMR (400 MHz, METHANOL-$d_4$) δ ppm 1.00 (br d, J=6.1 Hz, 3H) 1.13 (br d, J=6.3 Hz, 3H) 1.28-1.39 (m, 2H) 1.45-1.72 (m, 10H) 1.73-1.86 (m, 2H) 1.95-2.17 (m, 5H) 2.24-2.55 (m, 5H) 2.58-2.76 (m, 8H) 2.79-2.88 (m, 1H) 2.93 (t, J=7.0 Hz, 2H) 3.02 (ddd, J=9.4, 8.4, 6.8 Hz, 1H) 3.13-3.28 (m, 4H) 3.36-3.46 (m, 2H) 3.96-4.10 (m, 2H) 4.57 (br d, J=3.0 Hz, 1H) 4.65 (br d, J=13.9 Hz, 1H) 4.81-4.87 (m, 1H) 5.18 (t, J=8.0 Hz, 1H) 7.02-7.13 (m, 4H) 7.54 (dd, J=7.9, 4.8 Hz, 1H) 7.77-7.85 (m, 1H) 7.92 (d, J=8.9 Hz, 1H) 8.08 (dd, J=8.9, 1.8 Hz, 1H) 8.52 (d, J=1.8 Hz, 1H) 8.57-8.62 (m, 2H) 8.84-8.88 (m, 1H).

The following compound was or could be prepared with procedures analogous to that described in Example 86:

| Ex. | Compound | LC-MS m/z | NMR |
|---|---|---|---|
| 87 | 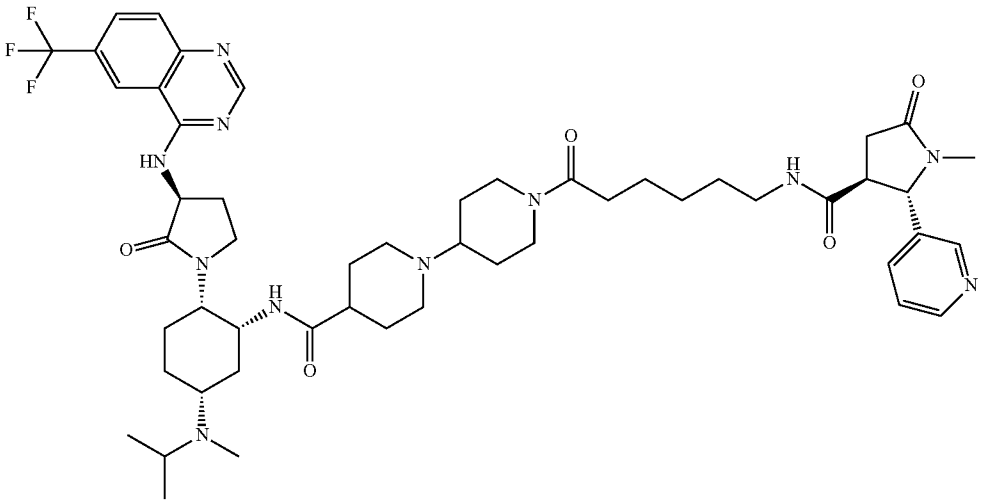 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C(=O)CCCCCNC(=O)[C@H]4CC(=O)N(C)[C@@H]4c4cccnc4)CC3)CC2)C1] N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-1'-(6-((2S,3S)-1-methyl-5-oxo-2-(pyridin-3-yl)pyrrolidine-3-carboxamido) hexanoyl)-[1,4'-bipiperidine]-4-carboxamide. | 974.8 (M + H)+ | $^1$H NMR (400 MHz, METHANOL-$d_4$) δ ppm 1.01 (br d, J = 6.3 Hz, 3H) 1.17 (br d, J = 6.6 Hz, 3H) 1.24-1.43 (m, 4H) 1.44-1.63 (m, 5H) 1.65-1.81 (m, 5H) 1.84-2.01 (m, 5 H) 2.10-2.29 (m, 8H) 2.30-2.43 (m, 3H) 2.50-2.64 (m, 3H) 2.67 (s, 3 H) 2.79-2.89 (m, 1H) 2.97-3.08 (m, 4H) 3.09-3.27 (m, 2H) 3.44 (dt, J = 13.0, 6.6 Hz, 1H) 3.53 (td, J = 9.2, 2.9 Hz, 1H) 3.59-3.71 (m, 1H) 3.95-4.12 (m, 2H) 4.57 (br d, J = 13.7 Hz, 1H) 4.66 (br d, J = 3.0 Hz, 1H) 4.82 (d, J = 6.8 Hz, 1H) 5.29 (t, J = 8.4 Hz, 1H) 7.54 (dd, J = 8.2, 5.2 Hz, 1H) 7.81 (dt, J = 8.0, 1.8 Hz, 1H) 7.91 (d, J = 8.9 Hz, 1H) 8.07 (dd, J = 8.9, 1.8 Hz, 1 H) 8.52 (d, J = 2.0 Hz, 1H) 8.58 (dd, J = 4.8, 1.5 Hz, 1 H) 8.60 (s, 1H) 8.77 (s, 1 H). |

Example 88

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-4-((1-((2S,3S)-1-methyl-5-oxo-2-(pyridin-3-yl)pyrrolidi n-3-yl)-1-oxo-5,8,11,14-tetraoxa-2-azahexadecan-16-yl)oxy) picolinamide

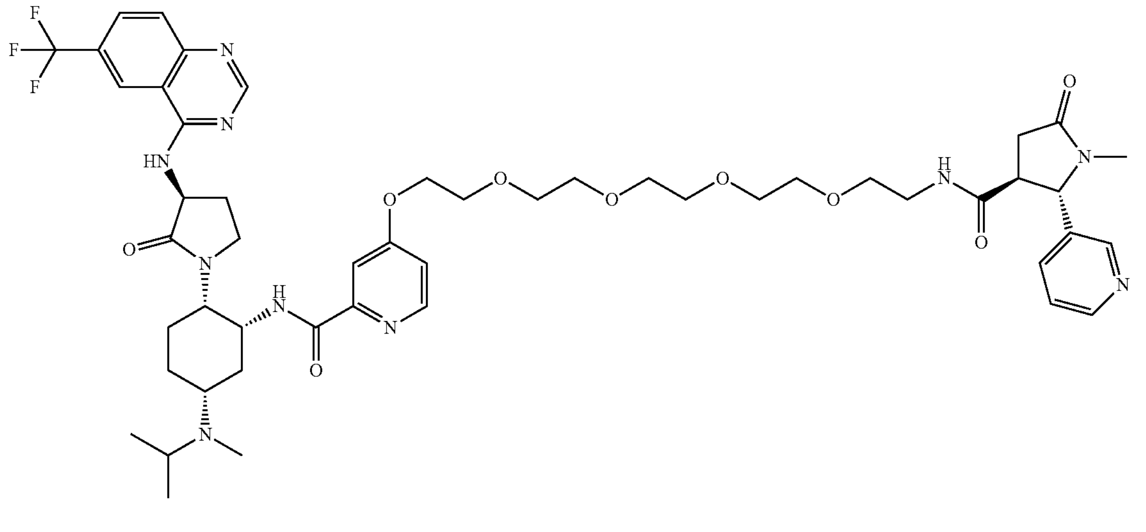 [SMILES: CC(C)N(C)[C@@H]1CC[C@H](N2CC[C@H](Nc3ncnc4ccc(C(F)(F)F)cc34)C2=O)[C@H](NC(=O)c2cc(OCCOCCOCCOCCOCCNC(=O)[C@H]3CC(=O)N(C)[C@@H]3c3cccnc3)ccn2)C1]

Step 1

Ethyl 4-((2,2-dimethyl-4-oxo-3,8,11,14,17-pentaoxa-5-azanonadecan-19-yl)oxy) picolinate

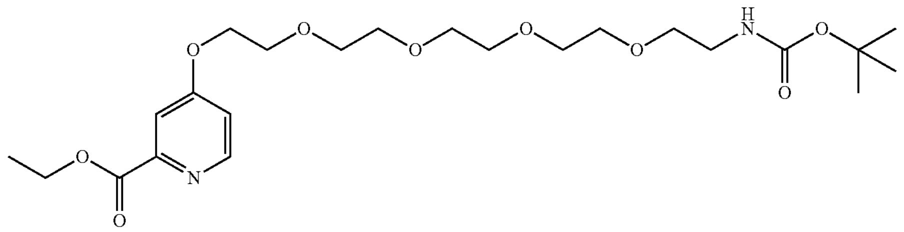 [SMILES: CCOC(=O)c1cc(OCCOCCOCCOCCOCCNC(=O)OC(C)(C)C)ccn1]

Triphenylphosphine, polymer bound (1.795 mmol) was added to a suspension of tert-butyl (14-hydroxy-3,6,9,12-tetraoxatetradecyl)carbamate (606 mg, 1.795 mmol) and ethyl 4-hydroxypicolinate (150 mg, 0.897 mmol) in tetrahydrofuran (THF) (8973 μL). A 40% solution of diethyl azodicarboxylate in toluene (710 μL, 1.795 mmol) was added dropwise and the mixture was stirred at reflux for 20 h. Ethyl acetate was added and the organic phase was washed with saturated $NH_4Cl$, with $Na_2CO_3$ solution, and with brine. The organic phase was dried over $Na_2SO_4$, was filtered, and the filtrate was concentrated. Purification by ISCO CombiFlash® chromatography (80 g RediSep Rf Gold® column, 60 mL/min) eluting with a stepwise gradient of 0% (10 column volumes), 0 to 7% (25 column volumes), and 7% (4 column volumes) methanol in dichloromethane (DCM) provided the title compound as a colorless oil (220 mg, 0.439 mmol, 48.9% yield). LC-MS m/z 487.2 $(M+H)^+$.

Step 2

4-((2,2-Dimethyl-4-oxo-3,8,11,14,17-pentaoxa-5-azanonadecan-19-yl)oxy)picolinic acid

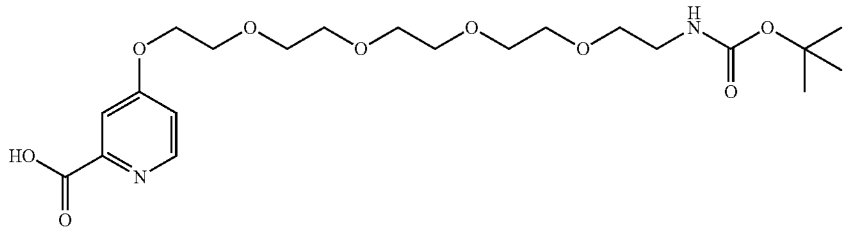 [SMILES: CC(C)(C)OC(=O)NCCOCCOCCOCCOCCOc1ccnc(C(=O)O)c1]

10 M sodium hydroxide (265 μL, 2.65 mmol) was added to a solution of ethyl 4-((2,2-dimethyl-4-oxo-3,8,11,14,17-pentaoxa-5-azanonadecan-19-yl)oxy)picolinate (215 mg, 0.442 mmol) in a mixture of methanol: tetrahydrofuran (THF):$H_2O$ (2:1:1) and was stirred 20° C. for 20 h. The pH was adjusted to 7 using 1 N HCl. The mixture was concentrated, dichloromethane (DCM) was added, the undissolved solids were removed by filtration, and the filtrate was concentrated under reduced pressure to provide the title compound as a clear, colorless oil (214 mg, 0.443 mmol, 100% yield). LC-MS m/z 459.1 $(M+H)^+$.

Step 3 tert-Butyl (14-((2-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)pyridin-4-yl)oxy)-3,6,9,12-tetraoxatetradecyl)carbamate

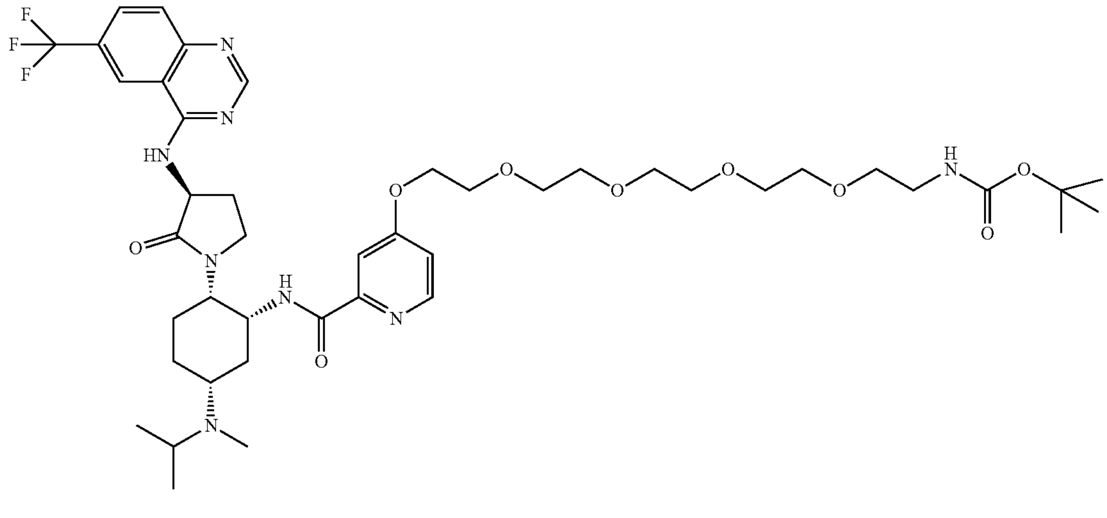

4 M HCl in 1,4-dioxane (815 µL, 3.26 mmol) was added to a solution of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (184 mg, 0.326 mmol) in 1,4-dioxane (1086 µL) and the mixture was stirred at heated to 45° C. for 30 min. The mixture was concentrated under reduced pressure. The residue and 4-((2,2-dimethyl-4-oxo-3,8,11,14,17-pentaoxa-5-azanonadecan-19-yl)oxy)picolinic acid (179 mg, 0.391 mmol) were dissolved in dichloromethane (DCM) (0.5 mL), HOAt (48.8 mg, 0.358 mmol), DIPEA (569 µL, 3.26 mmol), and EDC (63.5 µL, 0.358 mmol) were added sequentially and the mixture was stirred at 37° C. for 20 h. The mixture was diluted with dichloromethane (DCM) and was washed with water, with saturated $NH_4Cl$, with saturated $Na_2CO_3$, and with brine. The organic phase was passed through a phase separator and was concentrated under reduced pressure. Purification by reverse-phase HPLC (XSelect™ CSH C18 5 µm column, 40 mL/min) eluting with a gradient of 50 to 99% acetonitrile in water containing ammonium bicarbonate (10 mM) provided the title compound as an off-white solid (186 mg, 0.203 mmol, 62.4% yield). LC-MS m/z 905.2 $(M+H)^+$.

Step 4

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-4-((1-((2S,3S)-1-methyl-5-oxo-2-(pyridin-3-yl)pyrrolidi n-3-yl)-1-oxo-5,8,11,14-tetraoxa-2-azahexadecan-16-yl)oxy) picolinamide 4 M HCl in 1,4-dioxane (503 µL 2.011 mmol) was added to a solution of tert-butyl (14-((2-(((1R,2S,5R)-5-(isopropyl (methyl)amino)-2-((S)-2-oxo-3-((6-(trifluoromethyl)quinazolin-4-yl)amino)pyrrolidin-1-yl)cyclohexyl)carbamoyl) pyridin-4-yl)oxy)-3,6,9,12-tetraoxatetradecyl) carbamate (182 mg, 0.201 mmol) in 1,4-dioxane (670 µL). A few drops of methanol were added and the mixture was stirred 45° C. for 30 min. The mixture was concentrated under reduced pressure and dichloromethane (DCM) was added. The organic phase was washed with saturated $Na_2CO_3$ and with brine. The organic phase was passed through a phase separator and the filtrate was concentrated under reduced pressure. The residue was dissolved in 0.4 mL of N,N-dimethylformamide (DMF) (0.4 mL) and (2S,3S)-1-methyl-5-oxo-2-(pyridin-3-yl)pyrrolidine-3-carboxylic acid (53.1 mg, 0.241 mmol) and HOAt (30.1 mg, 0.221 mmol) were added. EDC (39.2 µL, 0.221 mmol) and DIPEA (211 µL, 1.207 mmol) were added and the mixture was stirred stir at rt for 4 h. Purification by reverse-phase HPLC (XSelect™ CSH Prep C18 5 µm OBD column, 40 mL/min) eluting with a gradient of 50 to 99% acetonitrile in water containing ammonium bicarbonate (10 mM) provided the title compound as an off-white solid (126 mg, 0.124 mmol, 61.6% yield). LC-MS m/z 1007.3 $(M+H)^+$. $^1H$ NMR (400 MHz, METHANOL-$d_4$) δ ppm 0.89-1.42 (m, 6H) 1.76 (br dd, J=8.1, 4.6 Hz, 4H) 2.26 (s, 8H) 2.65 (s, 6H) 2.98-3.12 (m, 1H) 3.35-3.66 (m, 18H) 3.80 (t, J=4.6 Hz, 2H) 4.18 (br d, J=7.4 Hz, 3H) 4.80 (s, 2H) 5.32 (s, 1H) 7.11 (dd, J=5.6, 2.5 Hz, 1H) 7.53 (br d, J=5.1 Hz, 1H) 7.65 (d, J=2.5 Hz, 1H) 7.79 (d, J=8.1 Hz, 1H) 7.93 (d, J=8.6 Hz, 1H) 8.03-8.21 (m, 1H) 8.36-8.68 (m, 4H) 8.84 (d, J=0.8 Hz, 1H).

The following compound was or could be prepared with procedures analogous to that described in Example 88:

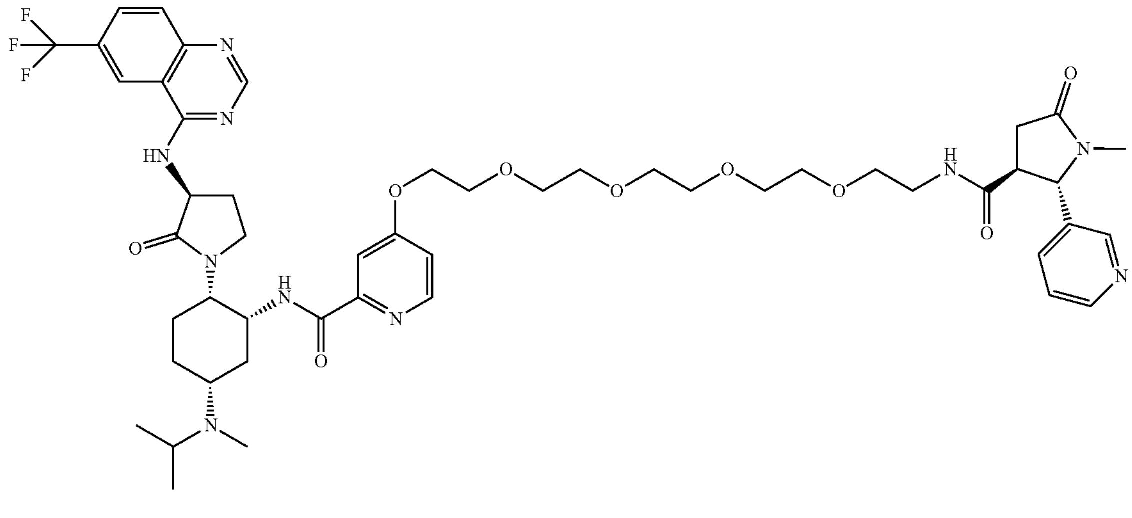

| Ex. | Compound | LC-MS m/z | NMR |
|---|---|---|---|
| 89 | 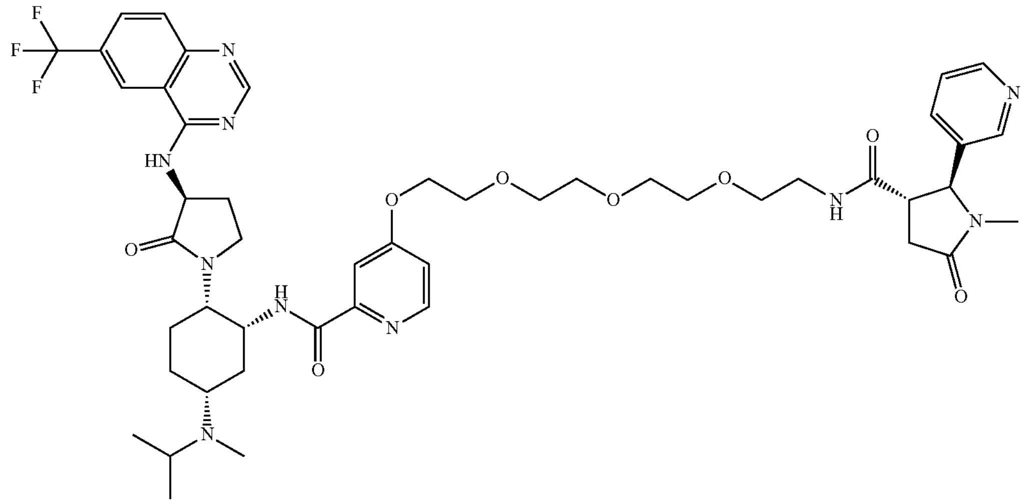 [SMILES: CC(C)N(C)[C@@H]1CC[C@H](N2CC[C@H](Nc3ncnc4ccc(C(F)(F)F)cc34)C2=O)[C@H](NC(=O)c2cc(OCCOCCOCCOCCNC(=O)[C@H]3CC(=O)N(C)[C@@H]3c3cccnc3)ccn2)C1]<br>N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-4-((1-((2S,3S)-1-methyl-5-oxo-2-(pyridin-3-yl)pyrrolidin-3-yl)-1-oxo-5,8,11-trioxa-2-azatridecan-13-yl)oxy)picolinamide. | 963.3 (M + H)+ | $^1$H NMR (400 MHz, METHANOL-$d_4$) δ ppm 0.90-1.08 (m, 3H) 1.28-1.43 (m, 3H) 1.66-1.90 (m, 4H) 2.13-2.54 (m, 7 H) 2.61-2.73 (m, 4H) 2.75-2.87 (m, 2H) 2.97-3.08 (m, 1H) 3.23-3.31 (m, 1H) 3.37-3.65 (m, 14 H) 3.76-3.83 (m, 2H) 4.10-4.25 (m, 3H) 4.77-4.82 (m, 1H) 4.84-4.87 (m, 1H) 5.26-5.36 (m, 1 H) 7.07-7.13 (m, 1H) 7.48-7.53 (m, 1H) 7.64 (d, J = 2.5 Hz, 1H) 7.74-7.81 (m, 1H) 7.90-7.96 (m, 1H) 8.07-8.13 (m, 1 H) 8.39-8.46 (m, 1H) 8.49-8.52 (m, 1H) 8.54-8.57 (m, 1H) 8.58-8.61 (m, 1H) 8.81-8.86 (m, 1 H). |

Example 90

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1'-(2-(2-(2-((2S, 3S)-1-methyl-5-oxo-2-(pyridin-3-yl)pyrrolidine-3-carboxamido)ethoxy)ethoxy)ethyl)-[1,4'-bipiperidine]-4-carboxamide

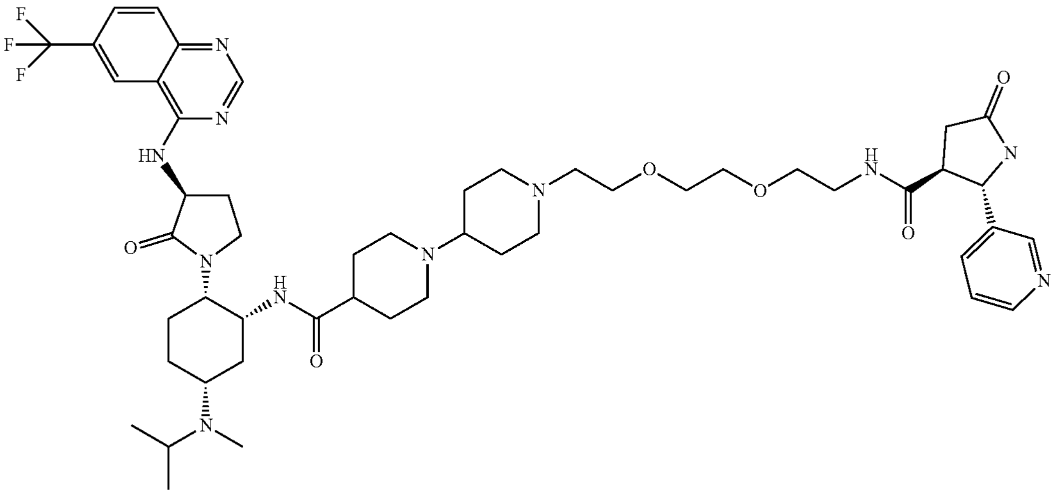

Step 1

2-(2-(2-Azidoethoxy)ethoxy)ethyl methanesulfonate

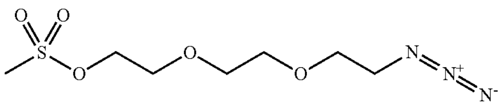 [SMILES: CS(=O)(=O)OCCOCCOCCN=[N+]=[N-]]

To a solution of 0.5 M2-(2-(2-azidoethoxy)ethoxy)ethan-1-ol in tert-butyl methyl ether (10 mL, 5.00 mmol) and triethylamine (2.091 mL, 15.00 mmol) in diethyl ether (10 mL) at 0° C. was added methanesulfonyl chloride (0.584 mL, 7.50 mmol) dropwise. The mixture was stirred at 0° C. for 1 h and was poured into water (30 mL). The mixture was extracted with diethyl ether (3×30 mL). The combined organic extracts were washed with dilute HCl, were dried over $MgSO_4$, and were concentrated under reduced pressure to provide the title compound as a colorless liquid. $^1H$ NMR (400 MHz, CHLOROFORM-d) δ ppm 3.03-3.17 (m, 3H) 3.42 (t, J=4.9 Hz, 2H) 3.65-3.75 (m, 6H) 3.79-3.85 (m, 2H) 4.35-4.47 (m, 2H).

Step 2

1'-(2-(2-(2-Azidoethoxy)ethoxy)ethyl)-N-((1R,2S, 5R)-5-(isopropyl(methyl)amino)-2-((S)-2-oxo-3-((6-(trifluoromethyl)quinazolin-4-yl)amino)pyrrolidin-1-yl)cyclohexyl)-[1,4'-bipiperidine]-4-carboxamide

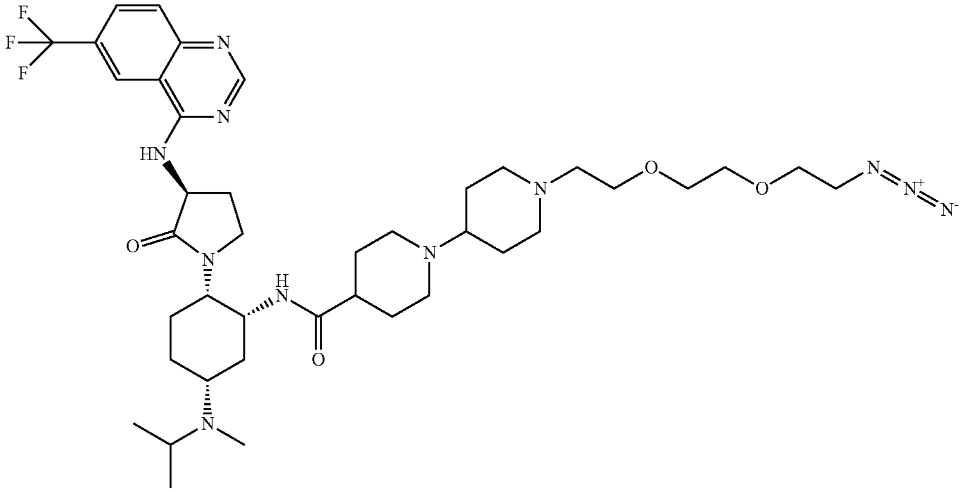

To a solution of tert-butyl 4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)-[1,4'-bipiperidine]-1'-carboxylate (105 mg, 0.138 mmol) in dichloromethane (DCM) (2 mL) was added 4 M HCl in 1,4-dioxane (1 mL, 4.00 mmol). The mixture was stirred at rt for 1 h and was concentrated to dryness. The resulting white solid was suspended in acetonitrile (7.5 mL). 2-(2-(2-azidoethoxy)ethoxy)ethyl methanesulfonate (44.0 mg, 0.174 mmol) was added, followed by potassium carbonate (97 mg, 0.702 mmol). The resultant mixture was stirred at 85° C. for 5 h, was filtered, and the filtrate was concentrated. Purification by MDAP (XSelect™ CSH C18 5 μm column, 40 mL/min) eluting with a gradient of 50 to 99% acetonitrile in water containing ammonium bicarbonate (10 mM) and the pH adjusted to 10 with ammonia provided the title compound as a pale-yellow film (83 mg, 0.100 mmol, 72.0% yield). LC-MS m/z 816.3 $(M+H)^+$.

Step 3

1'-(2-(2-(2-Aminoethoxy)ethoxy)ethyl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-[1,4'-bipiperidine]-4-carboxamide

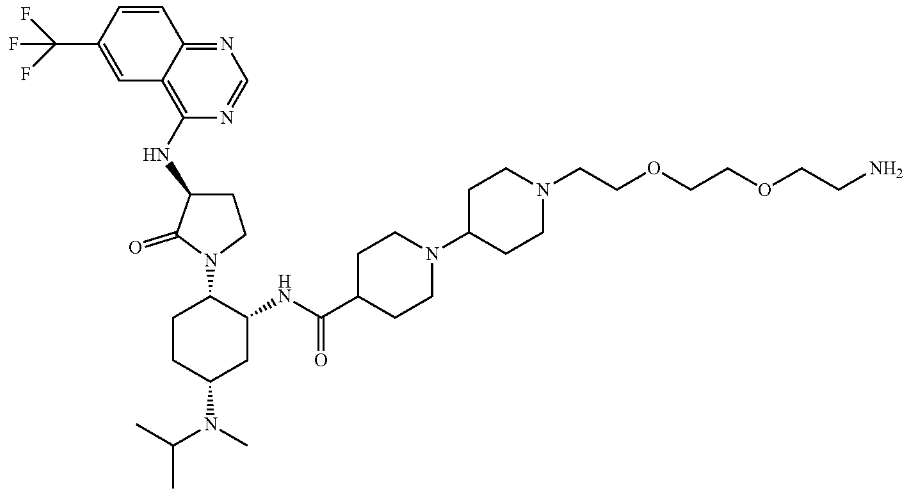

To a solution of 1'-(2-(2-(2-azidoethoxy)ethoxy)ethyl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-[1,4'-bipiperidine]-4-carboxamide (83 mg, 0.102 mmol) in methanol (7 mL) was added 10% Pd/C (10.82 mg, 10.17 μmol). The mixture was purged by vacuum and hydrogen backfilling. The mixture was stirred at rt for 2 h, was filtered, and the filtrate was concentrated to provide the title compound as a colorless film (66 mg, 0.082 mmol, 80% yield). LC-MS m/z 790.4 $(M+H)^+$.

Step 4

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1'-(2-(2-(2-((2S, 3S)-1-methyl-5-oxo-2-(pyridin-3-yl)pyrrolidine-3-carboxamido)ethoxy)ethoxy)ethyl)-[1,4'-bipiperidine]-4-carboxamide

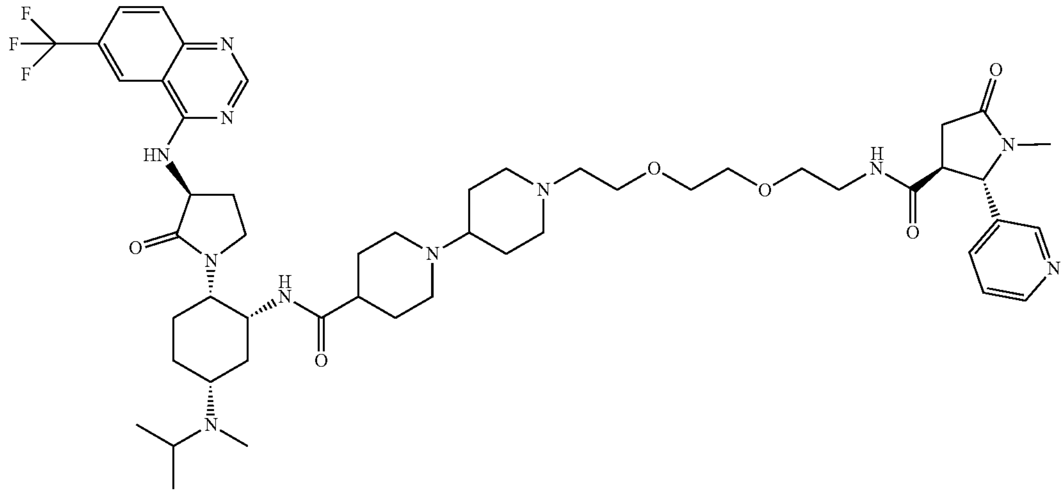

To a solution of 1'-(2-(2-(2-aminoethoxy)ethoxy)ethyl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-[1,4'-bipiperidine]-4-carboxamide (66 mg, 0.084 mmol) in dichloromethane (DCM) (5 mL) was added triethylamine (0.035 mL, 0.251 mmol), followed by (2S, 3S)-1-methyl-5-oxo-2-(pyridin-3-yl)pyrrolidine-3-carboxylic acid (22.08 mg, 0.100 mmol) and HATU (47.7 mg, 0.125 mmol). The mixture was stirred at rt for 1 h and was concentrated. Purification by MDAP (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a white solid (67.7 mg, 0.067 mmol, 80% yield). LC-MS m/z 992.4 $(M+H)^+$. $^1H$ NMR (400 MHz, METHANOL-$d_4$) δ ppm 0.91-1.10 (m, 3H) 1.17 (br d, J=6.3 Hz, 3H) 1.48-1.64 (m, 2H) 1.64-1.84 (m, 7H) 1.89-2.11 (m, 6H) 2.11 2.35 (m, 10H) 2.49-2.66 (m, 3H) 2.66-2.69 (m, 3H) 2.69-2.76 (m, 2H) 2.80-2.92 (m, 1H) 2.92-3.09 (m, 5H) 3.30-3.45 (m, 4H) 3.50-3.72 (m, 10H) 4.04 (dt, J=12.5, 3.6 Hz, 1H) 4.66 (br d, J=3.0 Hz, 1H) 4.79-4.89 (m, 1H) 5.30 (t, J=8.4 Hz, 1H) 7.54 (dd, J=8.0, 4.9 Hz, 1H) 7.81 (dt, J=8.0, 2.0 Hz, 1H) 7.91 (d, J=8.6 Hz, 1H) 8.07 (dd, J=8.9, 2.0 Hz, 1H) 8.53 (d, J=1.5 Hz, 1H) 8.58 (dd, J=4.9, 1.4 Hz, 1H) 8.60 (s, 1H) 8.77 (s, 1H).

The following compound was or could be prepared with procedures analogous to that described in Example 90:

| Ex. | Compound | LC-MS m/z | NMR |
| --- | --- | --- | --- |
| 91 | 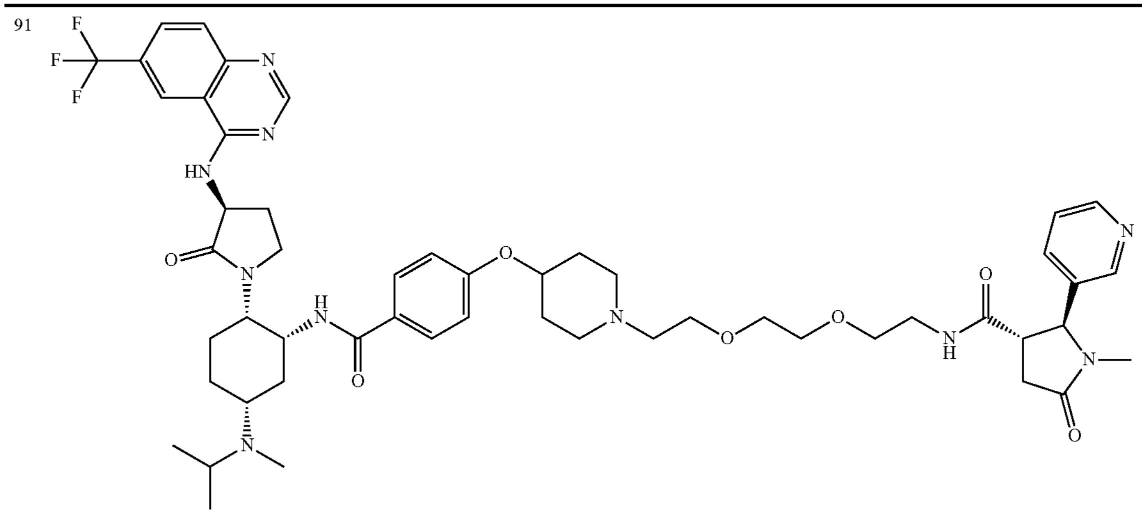 (2S,3S)-N-(2-(2-(2-(4-(4-(((1R,2S,5R)-5-((sopropyl(methyl)amino)-2-((S)-2-oxo-3-((6-(trifluoromethyl)quinazolin-4-yl)amino)pyrrolidin-1-yl)cyclohexyl)carbamoyl)phenoxy)piperidin-1-yl)ethoxy)ethoxy)ethyl)-1-methyl-5-oxo-2-(pyridin-3-yl)pyrrolidine-3-carboxamide. | 1001.0 (M + H)+ | $^1$H NMR (400 MHz, METHANOL-$d_4$) δ ppm 0.95 (br d, J = 6.3 Hz, 2H) 1.19 (br d, J = 6.3 Hz, 3H) 1.68-1.95 (m, 5H) 2.03 (td, J = 6.3, 2.9 Hz, 2H) 2.12-2.40 (m, 5H) 2.43-2.59 (m, 3H) 2.62-2.77 (m, 5H) 2.78-2.97 (m, 3 H) 3.05 (ddd, J = 9.5, 8.0, 6.5 Hz, 1H) 3.42-3.75 (m, 10H) 4.13-4.22 (m, 1 H) 4.41-4.59 (m, 1H) 4.79-4.88 (m, 11H) 5.19-5.33 (m, 1H) 6.97 (br d, J = 8.5 Hz, 2H) 7.49-7.54 (m, 1H) 7.74 (d, J = 8.8 Hz, 2H) 7.79 (dt, J = 8.0, 1.9 Hz, 1H) 7.89 (d, J = 8.8 Hz, 1H) 8.06 (dd, J = 8.9, 1.9 Hz, 1H) 8.50-8.53 (m, 2 H) 8.55-8.58 (m, 1H) 8.81 (s, 1H). |

Example 92

N-((1R,2S,5R)-5-(Isopropyl(methyl)amino)-2-((S)-2-oxo-3-((6-(trifluoro methyl) quinazolin-4-yl) amino)pyrrolidi n-1-yl)cyclohexyl)-1-(1-(2-(2-(2-((2S,3S)-1-methyl-5-oxo-2-(pyridin-3-yl) pyrrolidine-3-carboxamido)ethoxy)ethoxy)ethyl) piperidin-4-yl)-1H-pyrazole-4-carboxamide

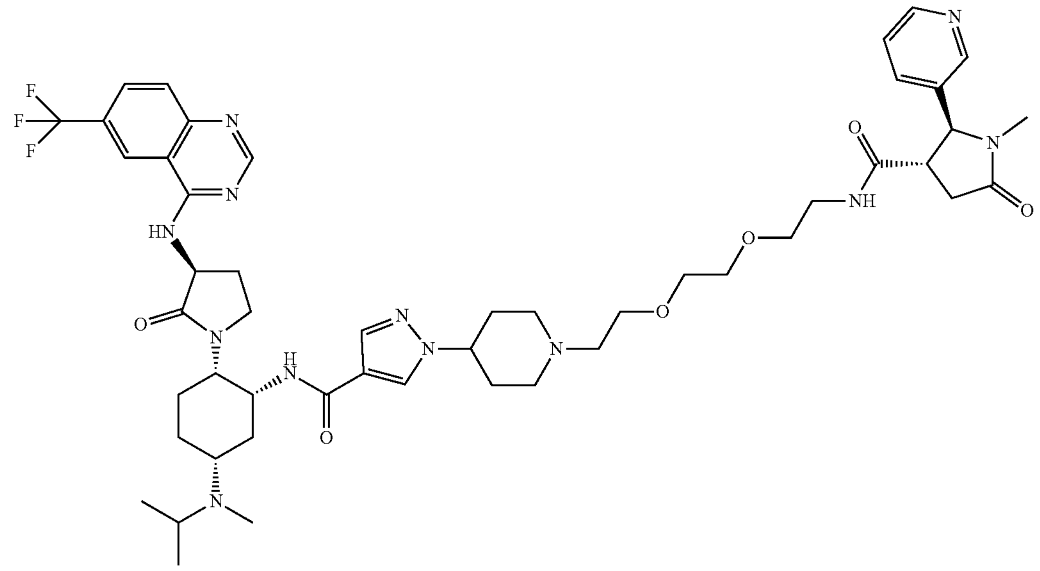

Step 1 tert-Butyl 4-(4-(ethoxycarbonyl)-1H-pyrazol-1-yl) piperidine-1-carboxylate

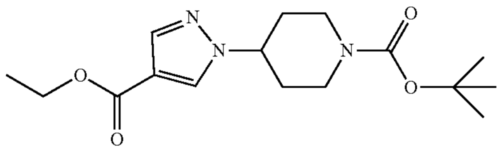 [SMILES: CCOC(=O)c1cnn(C2CCN(C(=O)OC(C)(C)C)CC2)c1]

To a stirred solution of ethyl 1H-pyrazole-4-carboxylate (1.0446 g, 7.45 mmol) in N,N-dimethylformamide (DMF) (30 mL) was added 60% sodium hydride mineral oil dispersion (0.328 g, 8.20 mmol) at 0° C. tert-Butyl 4-((methylsulfonyl)oxy)piperidine-1-carboxylate (2.290 g, 8.20 mmol) was added and the reaction mixture was stirred at 50° C. overnight, was poured into water (100 mL) and was stirred for 2 h. The precipitate was collected by filtration to provide the title compound as an off-white solid (2.35 g, 6.61 mmol, 89% yield). LC-MS m/z 324.1 $(M+H)^+$.

Step 2

Ethyl 1-(1-(2,2-dimethyl-4-oxo-3,8,11-trioxa-5-aza-tridecan-13-yl)piperidin-4-yl)-1H-pyrazole-4-carboxylate, Formic acid salt

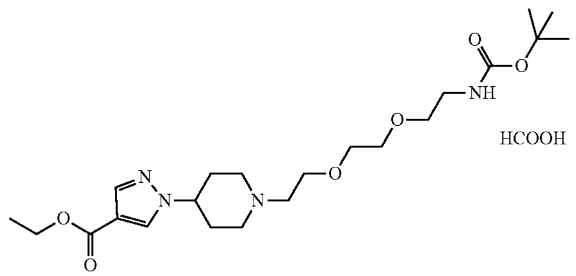 [SMILES: CCOC(=O)c1cnn(C2CCN(CCOCCOCCNC(=O)OC(C)(C)C)CC2)c1 ; "HCOOH"]

To a stirred solution of tert-butyl 4-(4-(ethoxycarbonyl)-1H-pyrazol-1-yl)piperidine-1-carboxylate (245 mg, 0.682 mmol) in dichloromethane (DCM) (2 mL) was added TFA (2 mL, 26.0 mmol). The mixture was stirred at rt 1 h and was concentrated under reduced pressure. N,N-Dimethylformamide (DMF) (3 mL) and potassium carbonate (321 mg, 2.321 mmol) were added, followed by tert-butyl (2-(2-(2-bromoethoxy)ethoxy)ethyl)carbamate (207 mg, 0.663 mmol) and the mixture was stirred at 60° C. for 2 h, was cooled, and was filtered. Purification by prep-HPLC (Agilent Eclipse Plus C18 5 µm column, 47 mL/min) eluting with a gradient of 5 to 40% acetonitrile in water with formic acid (0.1%) provided the title compound as a colorless film (260 mg, 0.493 mmol, 74.4% yield). LC-MS m/z 455.2 $(M+H)^+$.

Step 3

Ethyl 1-(1-(2-(2-(2-((2S,3S)-1-methyl-5-oxo-2-(pyridin-3-yl)pyrrolidine-3-carboxamido)ethoxy)ethoxy)ethyl)piperidin-4-yl)-1H-pyrazole-4-carboxylate

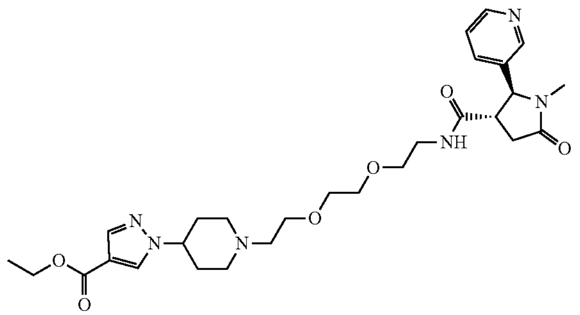 [SMILES: CCOC(=O)c1cnn(C2CCN(CCOCCOCCNC(=O)[C@H]3CC(=O)N(C)[C@@H]3c3cccnc3)CC2)c1]

A mixture of 4 M HCl in 1,4-dioxane (1 mL, 4.00 mmol) and ethyl 1-(1-(2,2-dimethyl-4-oxo-3,8,11-trioxa-5-azatridecan-13-yl)piperidin-4-yl)-1H-pyrazole-4-carboxylate, formic acid salt (260 mg, 0.519 mmol) in DCM (1.5 mL) was stirred at rt for 1 h and the was concentrated. The residue was dissolved in dichloromethane (DCM) (3 mL) and DIPEA (0.4 mL, 2.290 mmol), (2S,3S)-1-methyl-5-oxo-2-(pyridin-3-yl)pyrrolidine-3-carboxylic acid (137 mg, 0.623 mmol), and HATU (296 mg, 0.779 mmol) were added sequentially. The mixture was stirred at rt for 2 h and was concentrated. Purification by MDAP eluting with a gradient of 15 to 85% acetonitrile in water containing ammonium bicarbonate (10 mM) and the pH adjusted to 10 with ammonia provided the title compound as a pale-brown film (223 mg, 0.381 mmol, 73.3% yield). LC-MS m/z 557.1 $(M+H)^+$.

Step 4

1-(1-(2-(2-(2-((2S,3S)-1-Methyl-5-oxo-2-(pyridin-3-yl)pyrrolidine-3-carboxamido)ethoxy)ethoxy)ethyl)piperidin-4-yl)-1H-pyrazole-4-carboxylic acid

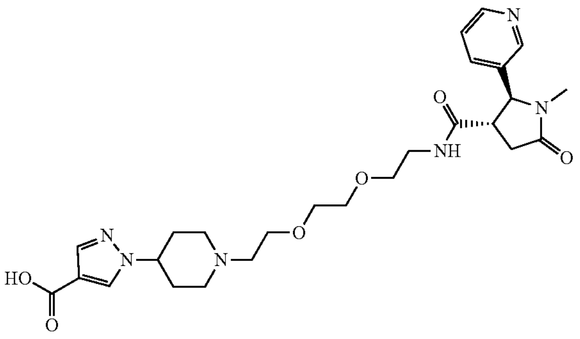 [SMILES: CN1C(=O)C[C@H](C(=O)NCCOCCOCCN2CCC(n3cc(C(=O)O)cn3)CC2)[C@H]1c1cccnc1]

A mixture of ethyl 1-(1-(2-(2-(2-((2S,3S)-1-methyl-5-oxo-2-(pyridin-3-yl) pyrrolidine-3-carboxamido)ethoxy)ethoxy)ethyl) piperidin-4-yl)-1H-pyrazole-4-carboxylate (223 mg, 0.401 mmol) and 2 N aqueous sodium hydroxide (0.401 mL, 0.801 mmol) in tetrahydrofuran (THF) (1.500 mL) and ethanol (1.5 mL) was stirred at rt for 2 h and was concentrated to remove the organic solvents. The mixture was cooled, the pH was adjusted to 4 to 5 using 2 N HCl, and the mixture was concentrated under reduced pressure. Methanol in dichloromethane (DCM) (2%) (30 mL) was added and the mixture was stirred, was sonicated, and was filtered. The filtrate was concentrated under reduced pressure to provide the title compound as a pale-yellow film (201 mg, 0.247 mmol, 61.7% yield). LC-MS m/z 529.1 $(M+H)^+$.

Step 5

N-((1R,2S,5R)-5-(Isopropyl(methyl)amino)-2-((S)-2-oxo-3-((6-(trifluoro methyl) quinazolin-4-yl) amino)pyrrolidi n-1-yl)cyclohexyl)-1-(1-(2-(2-(2-((2S,3S)-1-methyl-5-oxo-2-(pyridin-3-yl) pyrrolidine-3-carboxamido)ethoxy)ethoxy)ethyl) piperidin-4-yl)-1H-pyrazole-4-carboxamide

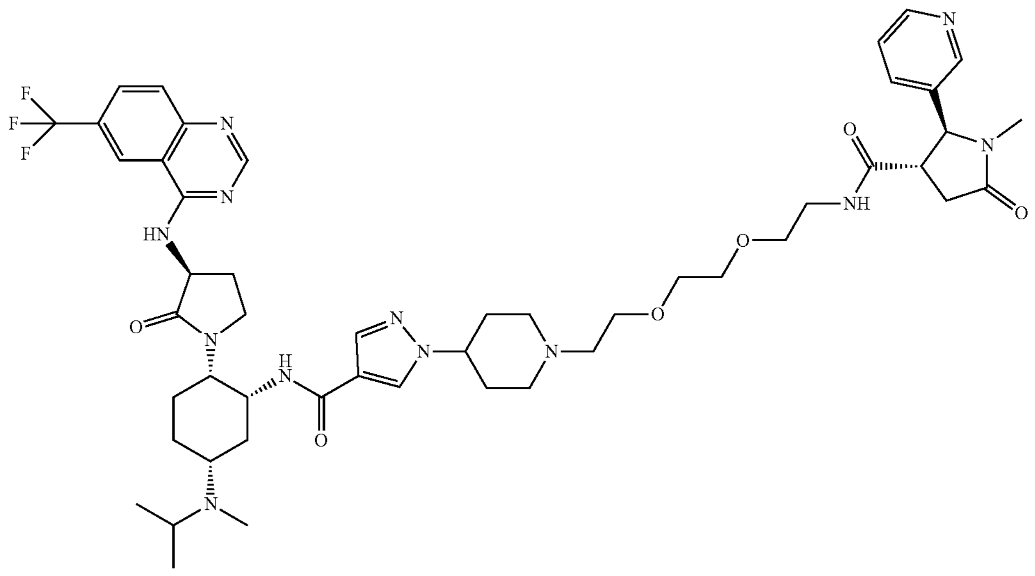

A mixture of 4 M HCl in 1,4-dioxane (1 mL, 4.00 mmol) and tert-butyl ((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)carbamate (100 mg, 0.177 mmol) in dichloromethane (DCM) (1 mL) was stirred at rt for 1 h and was concentrated under reduced pressure. The residue was suspended in dichloromethane (DCM) (5 mL). Triethylamine (0.086 mL, 0.620 mmol), 1-(1-(2-(2-(2-((2S,3S)-1-methyl-5-oxo-2-(pyridin-3-yl) pyrrolidine-3-carboxamido)ethoxy)ethoxy)ethyl) piperidin-4-yl)-1H-pyrazole-4-carboxylic acid (202 mg, 0.248 mmol), and HATU (101 mg, 0.266 mmol) were added. The mixture was stirred at rt for 1 h and was concentrated under reduced pressure. The residue was purified by prep-HPLC (Agilent Eclipse Plus C18 5 μm column, 47 mL/min) eluting with a gradient of 5 to 35% acetonitrile in water with TFA (0.1%). A second purification by MDAP eluting with a gradient of 30 to 85% acetonitrile in water containing ammonium bicarbonate (10 mM) and the pH adjusted to 10 using ammonia provided the title compound as white powder (59 mg, 0.059 mmol, 33.5% yield). LC-MS m/z 975.3 $(M+H)^+$. $^1H$ NMR (400 MHz, DMSO-$d_6$) δ ppm 0.81-0.90 (m, 3H) 1.04-1.13 (m, 3H) 1.55-1.75 (m, 3H) 1.77-1.97 (m, 5H) 2.04-2.22 (m, 8H) 2.26-2.36 (m, 1H) 2.42-2.47 (m, 2H) 2.48-2.49 (m, 3H) 2.60-2.76 (m, 3H) 2.86-3.00 (m, 3H) 3.11-3.30 (m, 3H) 3.36-3.41 (m, 2H) 3.43-3.55 (m, 8H) 3.95-4.16 (m, 2H) 4.45-4.56 (m, 1H) 4.62-4.72 (m, 1H) 4.99-5.14 (m, 1H) 7.40-7.47 (m, 1H) 7.63-7.71 (m, 2H) 7.86-7.92 (m, 1H) 8.01-8.11 (m, 3H) 8.44-8.49 (m, 1H) 8.52-8.58 (m, 2H) 8.74-8.83 (m, 1H) 8.92-9.03 (m, 2H).

The following compounds were or could be prepared with procedures analogous to that described in Example 92:

| Ex. | Compound | LC-MS m/z | NMR |
|---|---|---|---|
| 93 | 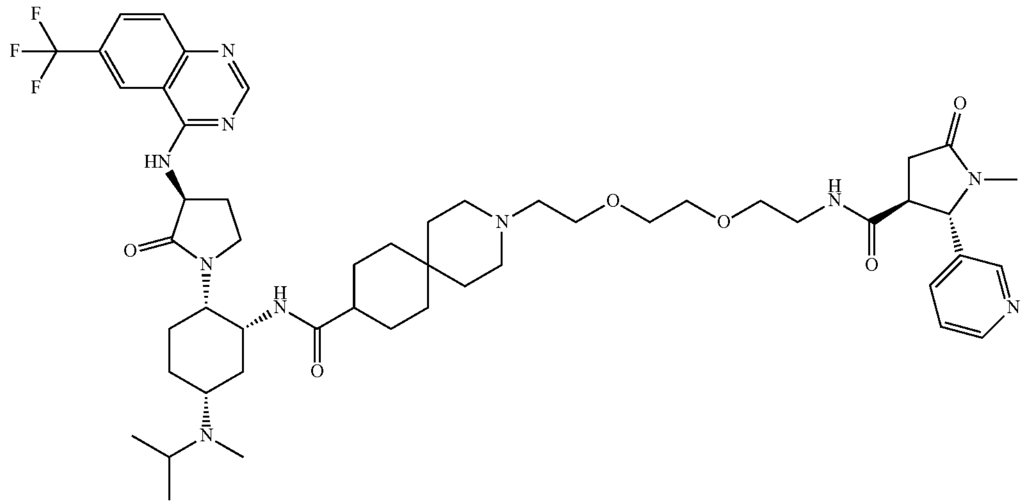 [SMILES: CC(C)N(C)[C@@H]1CC[C@H](N2CC[C@H](Nc3ncnc4ccc(C(F)(F)F)cc34)C2=O)[C@H](NC(=O)C2CCC3(CC2)CCN(CCOCCOCCNC(=O)[C@H]2CC(=O)N(C)[C@@H]2c2cccnc2)CC3)C1] N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-3-(2-(2-(2-((2S,3S)-1-methyl-5-oxo-2-(pyridin-3-yl)pyrrolidine-3-carboxamido)ethoxy)ethoxy)ethyl)-3-azaspiro [5.5]undecane-9-carboxamide. | 977.4 (M + H)+ | $^1$H NMR (400 MHz, METHANOL-$d_4$) δ ppm 1.03 (br d, J = 6.3 Hz, 3H) 1.07-1.22 (m, 5H) 1.36-1.48 (m, 2H) 1.51-1.84 (m, 10H) 1.90-2.02 (m, 1H) 2.04-2.19 (m, 2H) 2.19-2.29 (m, 4H) 2.31-2.39 (m, 1H) 2.42-2.65 (m, 6H) 2.67 (s, 3H) 2.69-2.77 (m, 2H) 2.79-2.90 (m, 1H) 3.01-3.09 (m, 1 H) 3.30 (br d, J = 9.4 Hz, 1 H) 3.35-3.40 (m, 1H) 3.41-3.48 (m, 1H) 3.49-3.72 (m, 9H) 4.04 (dt, J = 12.5, 3.6 Hz, 1H) 4.67 (br d, J = 3.0 Hz, 1H) 4.81-4.87 (m, 1H) 5.25 (t, J = 7.9 Hz, 1H) 7.50-7.57 (m, 1H) 7.80 (dt, J = 7.9, 2.0 Hz, 1H) 7.92 (d, J = 8.6 Hz, 1H) 8.07 (dd, J = 8.7, 1.9 Hz, 1H) 8.52 (d, J = 1.8 Hz, 1H) 8.58 (dd, J = 4.8, 1.5 Hz, 1H) 8.60 (s, 1H) 8.81 (s, 1H). |

-continued

| Ex. | Compound | LC-MS m/z | NMR |
|---|---|---|---|
| 94 | 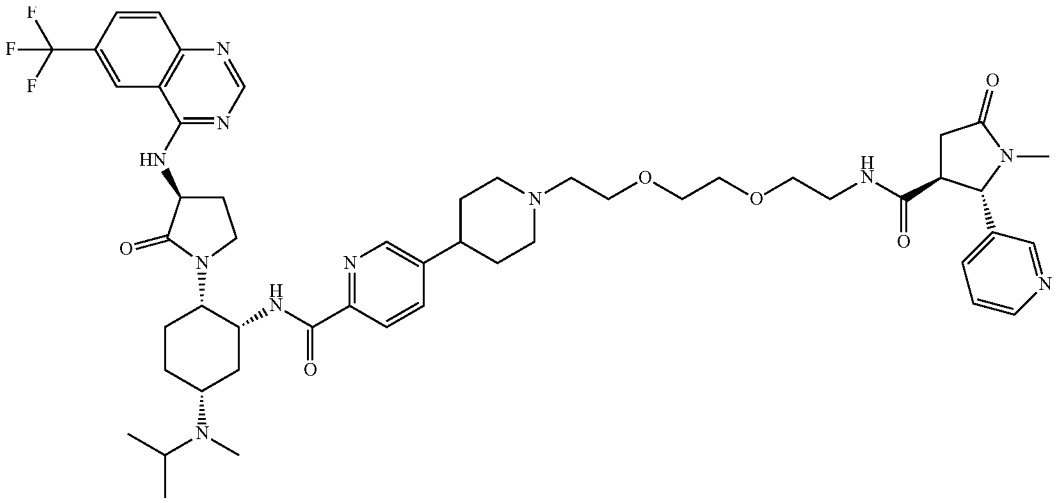 [SMILES: CC(C)N(C)[C@@H]1CC[C@H](N2CC[C@H](Nc3ncnc4ccc(C(F)(F)F)cc34)C2=O)[C@H](NC(=O)c2ccc(C3CCN(CCOCCOCCNC(=O)[C@H]4CC(=O)N(C)[C@@H]4c4cccnc4)CC3)cn2)C1]<br>N-((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)-5-(1-(2-(2-(2-((2S,3S)-1-methyl-5-oxo-2-(pyridin-3-yl)pyrrolidine-3-carboxamido)ethoxy)ethoxy)ethyl)piperidin-4-yl)picolinamide. | 986.7 | $^1$H NMR (400 MHz, METHANOL-$d_4$) δ ppm 1.00 (br d, J = 6.3 Hz, 3H) 1.36 (br d, J = 5.5 Hz, 3H) 1.68-1.93 (m, 8H) 2.18-2.23 (m, 1H) 2.24-2.50 (m, 8H) 2.66 (s, 3H) 2.67-2.89 (m, 6H) 3.04 (ddd, J = 9.3, 8.1, 6.7 Hz, 1H) 3.14-3.25 (m, 2H) 3.35-3.44 (m, 3H) 3.48-3.58 (m, 4H) 3.58-3.63 (m, 4 H) 3.65-3.71 (m, 2H) 4.20 (dt, J = 12.5, 3.8 Hz, 1H) 4.80-4.86 (m, 2H) 5.31 (br t, J = 8.4 Hz, 1H) 7.50-7.55 (m, 1H) 7.77-7.84 (m, 2H) 7.92 (d, J = 8.8 Hz, 1H) 8.06-8.12 (m, 2H) 8.51 (d, J = 1.8 Hz, 2H) 8.55-8.59 (m, 2 H) 8.84 (s, 1H). |

Example 95

N-((1S,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-3-((2S,3S)-1-methyl-5-oxo-2-(pyridin-3-yl)pyrrolidine-3-carbonyl)-3-azaspiro[5.5]undecane-9-carboxamide

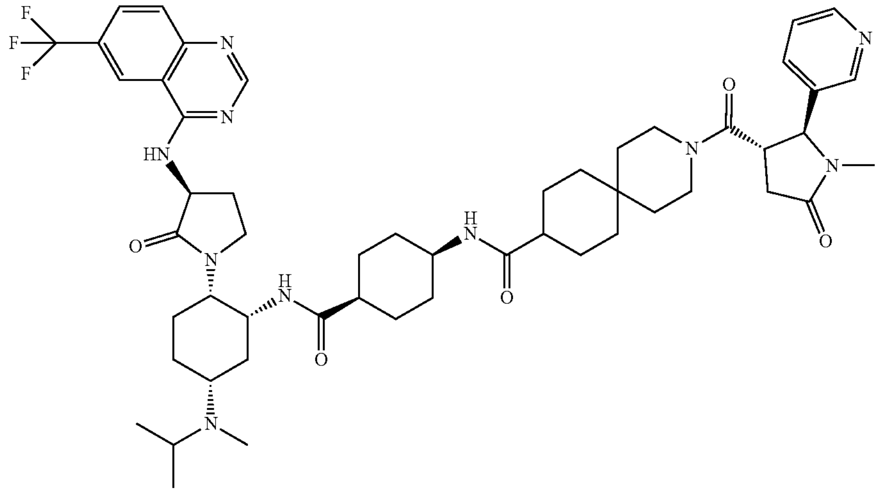

Step 1 tert-Butyl 9-(((1S,4s)-4-(((1R,2S,5R)-5-(isopropyl(methyl)am i no)-2-((S)-2-oxo-3-((6-(trifluoromethyl)quinazolin-4-yl)amino)pyrrolidin-1-yl)cyclohexyl)carbamoyl) cyclohexyl)carbamoyl)-3-azaspiro[5.5]undecane-3-carboxylate

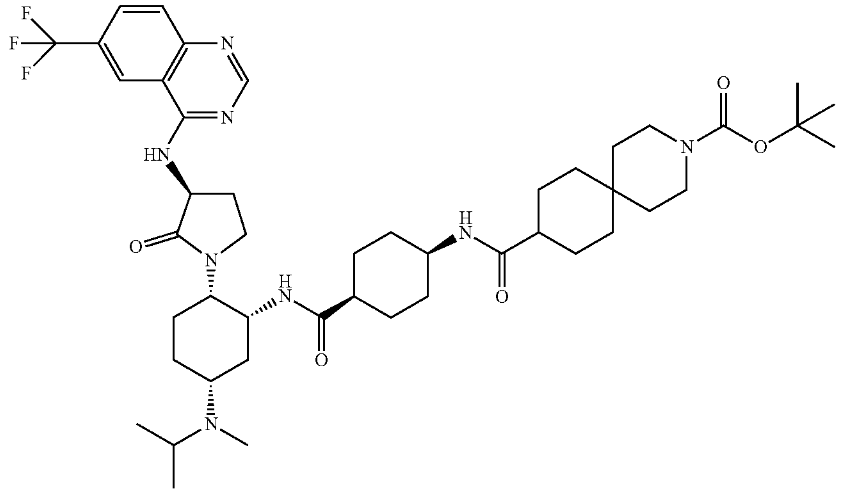

To a mixture of (1 s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (80 mg, 0.121 mmol) in dichloromethane (DCM) (0.5 mL) was added sequentially triethylamine (0.101 mL, 0.724 mmol), 3-(tert-butoxycarbonyl)-3-azaspiro[5.5]undecane-9-carboxylic acid (35.9 mg, 0.121 mmol), and HATU (55.1 mg, 0.145 mmol), and the mixture was stirred at rt for 2 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound as a solid (75 mg, 0.086 mmol, 71.5% yield). LC-MS m/z 869.3 $(M+H)^+$.

Step 2

N-((1S,4s)-4-(((1R,2S,5R)-5-(isopropyl(methyl) amino)-2-((S)-2-oxo-3-((6-(trifluoromethyl)quinazolin-4-yl)amino)pyrrolidin-1-yl)cyclohexyl) carbamoyl) cyclohexyl)-3-azaspiro[5.5]undecane-9-carboxamide, 2Hydrochloric acid salt

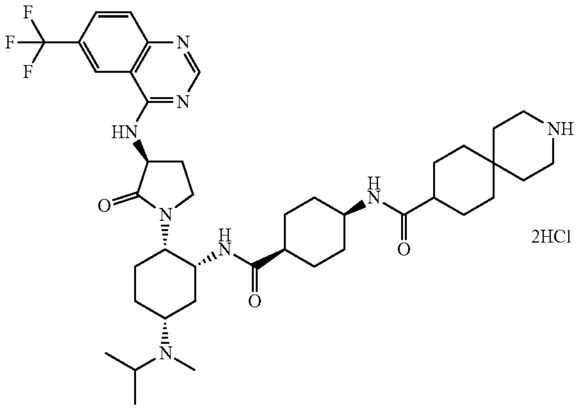 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CCNCC4)CC3)CC2)C1]

A mixture of 4 M HCl (0.170 mL, 0.681 mmol) and tert-butyl 9-(((1S,4s)-4-(((1R,2S,5R)-5-(isopropyl(methyl) amino)-2-((S)-2-oxo-3-((6-(trifluoromethyl)quinazolin-4-yl)amino) pyrrolidin-1-yl)cyclohexyl)carbamoyl)cyclohexyl)carbamoyl)-3-azaspiro[5.5]undecane-3-carboxylate (74 mg, 0.085 mmol) in dichloromethane (DCM) (0.1 mL) was stirred at rt for 3 h. The mixture was concentrated to provide the title compound as a solid (81 mg, 0.096 mmol, 113% yield). LC-MS m/z 769.4 $(M+H)^+$.

Step 3

N-((1S,4R)-4-(((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)carbamoyl) cyclohexyl)-3-((2S,3S)-1-methyl-5-oxo-2-(pyridin-3-yl)pyrrolidine-3-carbonyl)-3-azaspiro [5.5]undecane-9-carboxamide

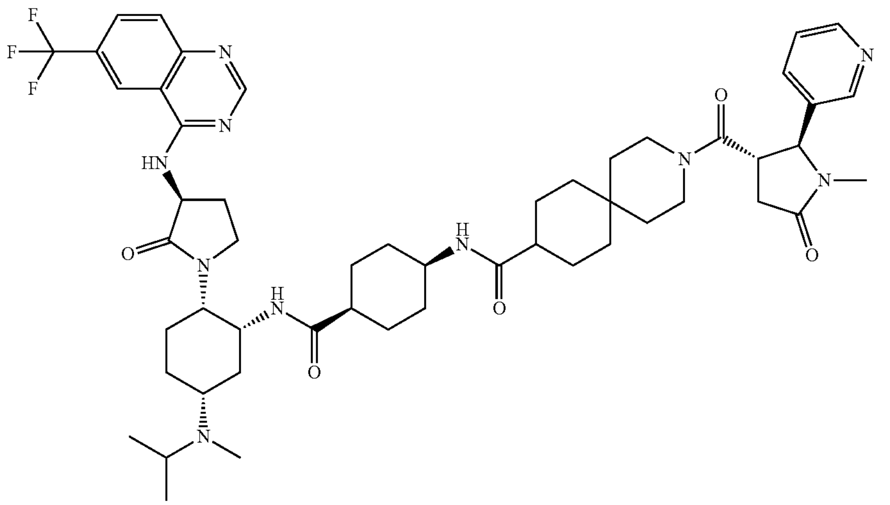 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CC3)CCN(C(=O)[C@H]3CC(=O)N(C)[C@@H]3c3cccnc3)CC4)CC2)C1]

To a mixture of N-((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)-3-azaspiro[5.5]undecane-9-carboxamide, 2Hydrochloride (29 mg, 0.034 mmol) in dichloromethane (DCM) (0.5 mL) was added triethylamine (0.029 mL, 0.207 mmol), (2S,3S)-1-methyl-5-oxo-2-(pyridin-3-yl)pyrrolidine-3-carboxylic acid (7.59 mg, 0.034 mmol), and HATU (15.72 mg, 0.041 mmol), and the mixture was stirred at rt for 5 h. Purification by ISCO CombiFlash® chromatography (24 g RediSep Rf Gold® column, 35 mL/min) eluting with a gradient of 0 to 15% methanol containing ammonium hydroxide (10%) in dichloromethane (DCM) provided the title as a solid (23.6 mg, 0.024 mmol, 70.5% yield). LC-MS m/z 971.3 $(M+H)^+$. $^1H$ NMR (400 MHz, METHANOL-$d_4$) δ ppm 0.95-1.09 (m, 5H) 1.12-1.33 (m, 6H) 1.42-1.88 (m, 19H) 1.91-2.02 (m, 1H) 2.05-2.14 (m, 1H) 2.16-2.37 (m, 7H) 2.53-2.60 (m, 1H) 2.62-2.77 (m, 5H) 2.86-2.97 (m, 1H) 3.23-3.29 (m, 1H) 3.40-3.73 (m, 6H) 3.81-3.87 (m, 1H) 3.95-4.05 (m, 1H) 4.56-4.65 (m, 1H) 4.97-5.02 (m, 1H) 5.25-5.34 (m, 1H) 7.52-7.58 (m, 1H) 7.83-7.88 (m, 1H) 7.89-7.94 (m, 1H) 8.04-8.09 (m, 1H) 8.54-8.56 (m, 1H) 8.57-8.61 (m, 2H) 8.71-8.74 (m, 1H).

Example 96

(2S,3S)-N-(2-(2-(3-(4-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)piperazin-1-yl)-3-oxopropoxy)ethoxy)ethyl)-1-methyl-5-oxo-2-(pyridin-3-yl)pyrrolidine-3-carboxamide

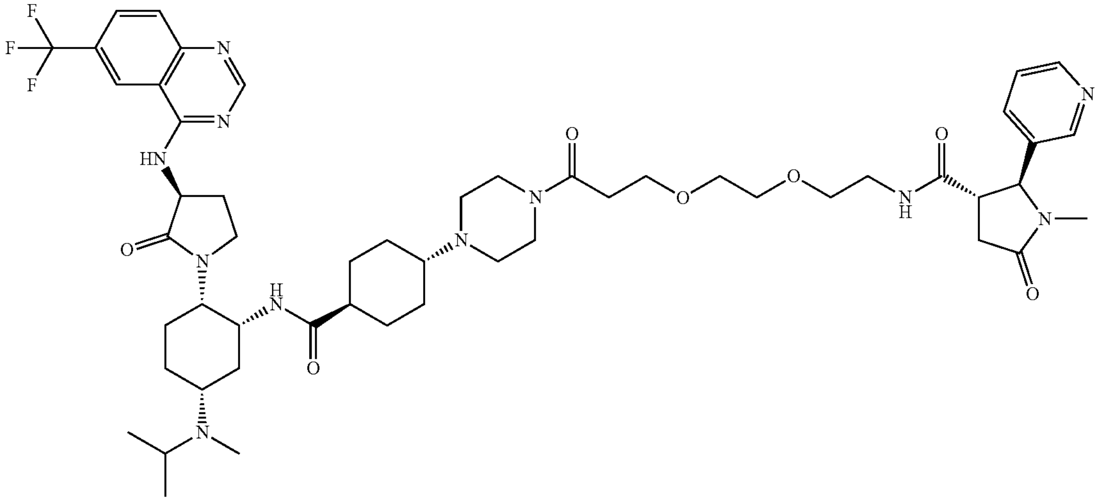 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(C(=O)CCOCCOCCNC(=O)[C@H]4CC(=O)N(C)[C@@H]4c4cccnc4)CC3)CC2)C1]

Step 1

Ethyl (1r,4r)-4-(4-(2,2-dimethyl-4-oxo-3,8,11-trioxa-5-azatetradecan-14-oyl)piperazin-1-yl)cyclohexane-1-carboxylate

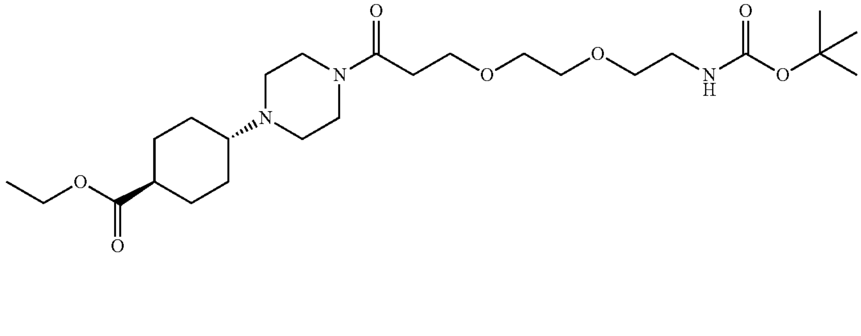 [SMILES: CCOC(=O)[C@H]1CC[C@H](N2CCN(C(=O)CCOCCOCCNC(=O)OC(C)(C)C)CC2)CC1]

tert-Butyl 4-((1r,4r)-4-(ethoxycarbonyl)cyclohexyl)piperazine-1-carboxylate (246 mg, 0.721 mmol) was dissolved in dichloromethane (DCM) (1.4 mL) and TFA (1.4 mL) and was stirred at rt for 10 min. The mixture was concentrated by reduced pressure and was chased with dichloromethane (DCM) (3×). The residue, 2,2-dimethyl-4-oxo-3,8,11-trioxa-5-azatetradecan-14-oic acid (200 mg, 0.721 mmol) and HATU (329 mg, 0.865 mmol) dissolved in acetonitrile (5548 μL). Triethylamine (402 μL, 2.88 mmol) was added dropwise and the mixture was stirred at rt for 30 min. Purification by normal-phase chromatography (24 g silica column, 35 mL/min) eluting with a gradient of 0 to 20% methanol in dichloromethane (DCM) provided the title compound (403 mg, 0.758 mmol, 105% yield). LC-MS m/z 500.5 $(M+H)^+$.

Step 2

Ethyl (1r,4r)-4-(4-(3-(2-(2-((2S,3S)-1-methyl-5-oxo-2-(pyridin-3-yl)pyrrolidine-3-carboxamido)ethoxy)ethoxy)propanoyl)piperazin-1-yl)cyclohexane-1-carboxylate

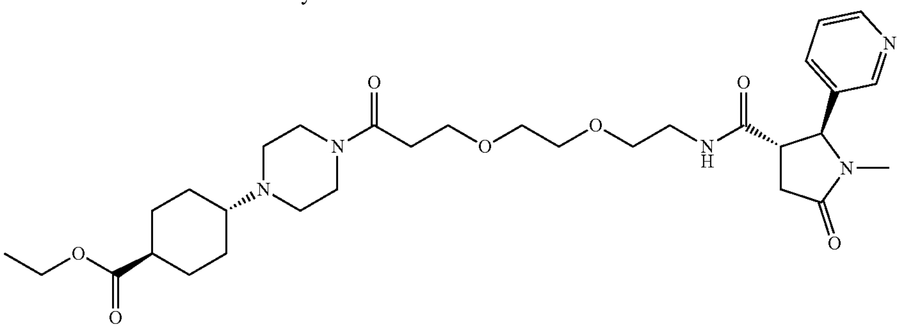

Ethyl (1r,4r)-4-(1-(2,2-dimethyl-4-oxo-3,8,11-trioxa-5-azatetradecan-14-oyl) piperidin-4-yl)cyclohexane-1-carboxylate (100 mg, 0.201 mmol) was dissolved in dichloromethane (DCM) and TFA (1 mL) and was stirred at rt for 10 min. The mixture was concentrated under reduced pressure and wad chased with dichloromethane (DCM) (3×). The residue, (2S,3S)-1-methyl-5-oxo-2-(pyridin-3-yl)pyrrolidine-3-carboxylic acid (40 mg, 0.182 mmol), and TSTU (65.6 mg, 0.218 mmol) dissolved in acetonitrile (1400 μL). Triethylamine (201 μL, 1.442 mmol) was added dropwise and the mixture was stirred at rt for 30 min. Purification by normal-phase chromatography (12 g silica column, 30 mL/min) eluting with a gradient of 0 to 20% methanol in dichloromethane (DCM) provided the title compound (25.5 mg, 0.024 mmol, 13.30% yield). LC-MS m/z 602.3 $(M+H)^+$.

Step 3

(1r,4r)-4-(4-(3-(2-(2-((2S,3S)-1-Methyl-5-oxo-2-(pyridin-3-yl)pyrrolidine-3-carboxamido)ethoxy)ethoxy)propanoyl)piperazin-1-yl)cyclohexane-1-carboxylic acid

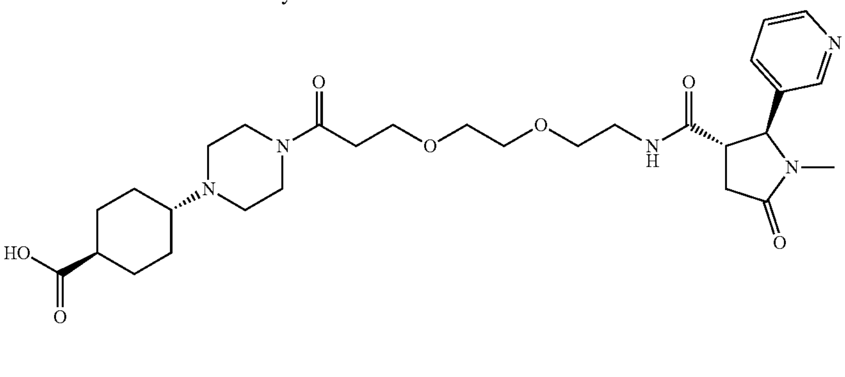

Ethyl (1r,4r)-4-(4-(3-(2-(2-((2S,3S)-1-methyl-5-oxo-2-(pyridin-3-yl) pyrrolidine-3-carboxamido)ethoxy)ethoxy) propanoyl)piperazin-1-yl)cyclohexane-1-carboxylate (25.5 mg, 0.042 mmol) was dissolved in methanol (170 μL), water (170 μL), and tetrahydrofuran (THF) (170 μL), and lithium hydroxide monohydrate (11.17 mg, 0.266 mmol) was added. The mixture was stirred at rt overnight and was concentrated under reduced pressure. The residue was dissolved in dichloromethane (DCM) using a minimal amount of methanol, ISOLUTE® was added, and the mixture was concentrated by reduced pressure. Purification by MDAP (XBridge™ column) eluting with acetonitrile in water containing ammonium carbonate modifier provided the title compound (13.2 mg, 0.018 mmol, 27.0% yield). LC-MS m/z 574.2 $(M+H)^+$.

Step 4

(2S,3S)-N-(2-(2-(3-(4-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)piperazin-1-yl)-3-oxopropoxy)ethoxy)ethyl)-1-methyl-5-oxo-2-(pyridin-3-yl)pyrrolidine-3-carboxamide

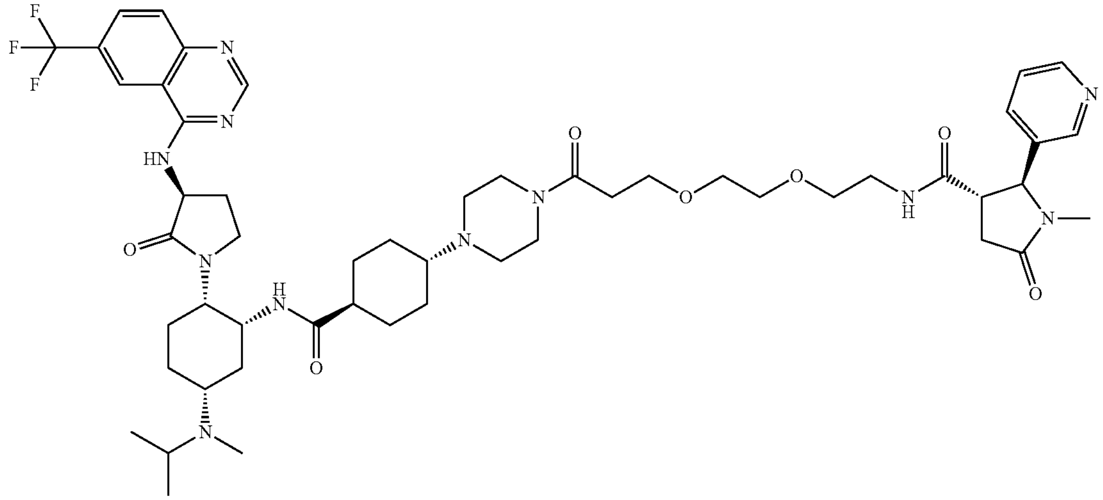 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(C(=O)CCOCCOCCNC(=O)[C@H]4CC(=O)N(C)[C@@H]4c4cccnc4)CC3)CC2)C1]

tert-Butyl ((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)carbamate (14 mg, 0.025 mmol) was dissolved in dichloromethane (DCM) (0.5 mL) and 4 M HCl in 1,4-dioxane (0.1 mL, 0.4 mmol) and the mixture was stirred at rt for 15 min. The reaction was concentrated by reduced pressure and was chased with dichloromethane (DCM). The residue was dissolved in dichloromethane (DCM) (670 μL) and triethylamine (13.82 μL, 0.099 mmol) and the mixture was added to (1r,4r)-4-(4-(3-(2-(2-((2S,3S)-1-methyl-5-oxo-2-(pyridin-3-yl) pyrrolidine-3-carboxamido)ethoxy)ethoxy)propanoyl)piperazin-1-yl)cyclohexanecarboxylic acid (14.22 mg, 0.025 mmol) and was stirred for several minutes. HATU (12.26 mg, 0.032 mmol) was added and the mixture was stirred at rt for 4 h. The mixture was concentrated under reduced pressure. Purification by MDAP (XBridge™ column) eluting with acetonitrile in water containing ammonium carbonate modifier provided the title compound as a white solid (9.8 mg, 9.61 μmol, 38.7% yield). LC-MS m/z 1020.4 $(M+H)^+$. $^1H$ NMR (400 MHz, METHANOL-$d_4$) δ ppm 0.99-1.08 (m, 3H) 1.12-1.20 (m, 3H) 1.26-1.39 (m, 2H) 1.48-1.60 (m, 2H) 1.64-1.80 (m, 3H) 1.92-2.36 (m, 14H) 2.50-2.76 (m, 13H) 2.79-2.90 (m, 1H) 3.03-3.14 (m, 1H) 3.42-3.58 (m, 12H) 3.62-3.67 (m, 1H) 3.69-3.77 (m, 2H) 3.99-4.08 (m, 1H) 4.64-4.68 (m, 1H) 4.81-4.85 (m, 1H) 5.21-5.31 (m, 1H) 7.51-7.57 (m, 1H) 7.77-7.85 (m, 1H) 7.88-7.95 (m, 1H) 8.04-8.11 (m, 1H) 8.50-8.54 (m, 1H) 8.56-8.63 (m, 2H) 8.79-8.87 (m, 1H).

Example 97

(2S,3S)-N-(2-(3-(4-((1R,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)piperazin-1-yl) cyclobutyl)ethyl)-1-methyl-5-oxo-2-(pyridin-3-yl) pyrrolidine-3-carboxamide

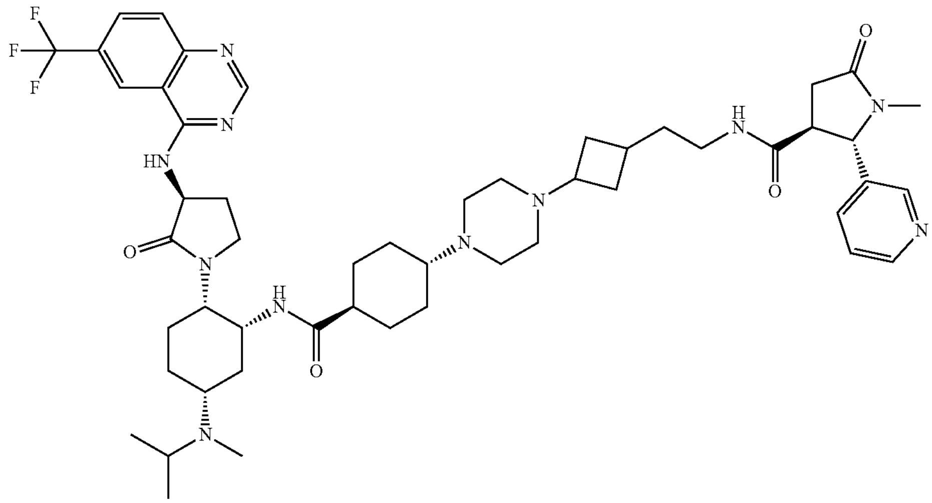 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(C4CC(CCNC(=O)[C@H]5CC(=O)N(C)[C@@H]5c5cccnc5)C4)CC3)CC2)C1]

Step 1

Ethyl (1r,4r)-4-(piperazin-1-yl)cyclohexane-1-carboxylate, 2Trifluoroacetic acid salt

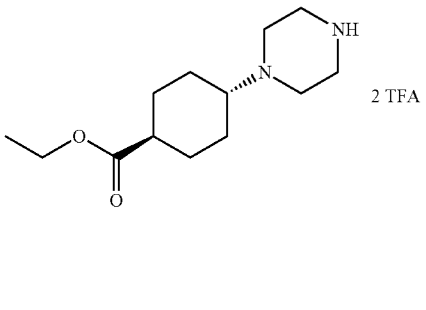 [SMILES: CCOC(=O)[C@H]1CC[C@H](N2CCNCC2)CC1]

tert-Butyl 4-((1r,4r)-4-(ethoxycarbonyl)cyclohexyl)piperazine-1-carboxylate (220 mg, 0.646 mmol) was dissolved in dichloromethane (DCM) (1.40 mL) and TFA (1.400 mL, 18.17 mmol) and was stirred for 2 min. The mixture was concentrated under a stream of nitrogen at 50° C. and was chased with dichloromethane (DCM) (3×) to provide the title compound as a deep-orange oil (364 mg, 0.606 mmol, 94% yield). LC-MS m/z 241.2 $(M+H)^+$.

Step 2

Ethyl (1r,4r)-4-(4-(3-(2-((tert-butoxycarbonyl) amino)ethyl)cyclobutyl)piperazin-1-yl)cyclohexane-1-carboxylate

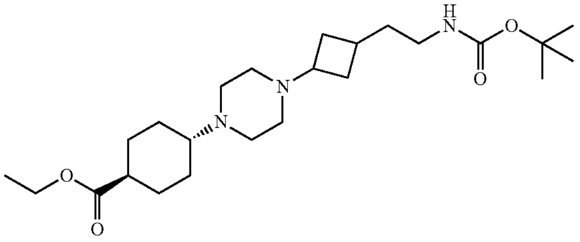 [SMILES: CCOC(=O)[C@H]1CC[C@H](N2CCN(C3CC(CCNC(=O)OC(C)(C)C)C3)CC2)CC1]

tert-Butyl (2-(3-oxocyclobutyl)ethyl)carba mate (181 mg, 0.849 mmol) was dissolved in dichloromethane (DCM) (6528 μL) and ethyl (1r,4r)-4-(piperazin-1-yl)cyclohexane-1-carboxylate, 2trifluoroacetic acid salt (143 mg, 0.594 mmol) and triethylamine (154 μL, 1.103 mmol) were added sequentially. The mixture was stirred at rt for 2 min. Sodium triacetoxyborohydride (180 mg, 0.849 mmol) was added and the reaction was stirred at 50° C. for 1 h. Purification by normal-phase chromatography (24 g silica column, 35 mL/min) eluting with a gradient of 0 to 20% methanol in dichloromethane (DCM) provided the title compound as an orange oil (193 mg, 0.362 mmol, 42.6% yield). LC-MS m/z 438.3 $(M+H)^+$. This material was combined with another run to provide the title compound (256 mg, 0.486 mmol).

Step 3

(1r,4r)-4-(4-(3-(2-((tert-Butoxycarbonyl)amino)ethyl)cyclobutyl)piperazin-1-yl)cyclohexane-1-carboxylic acid

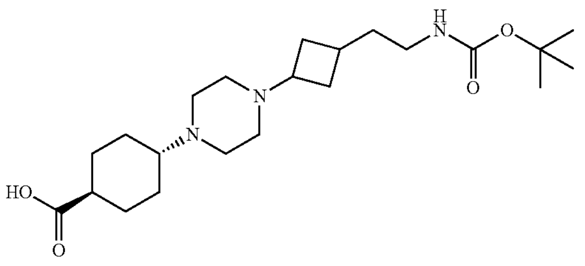 [SMILES: CC(C)(C)OC(=O)NCCC1CC(N2CCN([C@H]3CC[C@H](C(=O)O)CC3)CC2)C1]

Ethyl (1r,4r)-4-(4-(3-(2-((tert-butoxycarbonyl)amino)ethyl)cyclobutyl) piperazin-1-yl)cyclohexane-1-carboxylate (256 mg, 0.585 mmol) was dissolved in methanol (1500 μL), water (1500 μL), and tetrahydrofuran (THF) (1500 μL), lithium hydroxide monohydrate (98 mg, 2.340 mmol) was added. The mixture was stirred at rt overnight and was concentrated under reduced pressure. Purification by normal-phase chromatography (12 g silica column, 30 mL/min) eluting with a gradient of 0 to 80% of methanol containing ammonium hydroxide (10%) in dichloromethane (DCM) provided the title compound (183.5 mg, 0.421 mmol, 72.0% yield). LC-MS m/z 410.3 $(M+H)^+$.

Step 4

(1S,4r)-4-(4-(3-(2-((2S,3S)-1-Methyl-5-oxo-2-(pyridin-3-yl)pyrrolidine-3-carboxamido)ethyl)cyclobutyl)piperazin-1-yl)cyclohexane-1-carboxylic acid

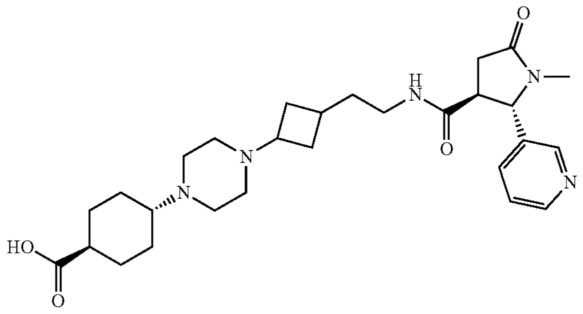 [SMILES: CN1C(=O)C[C@H](C(=O)NCCC2CC(N3CCN([C@H]4CC[C@H](C(=O)O)CC4)CC3)C2)[C@H]1c1cccnc1]

(1r,4r)-4-(4-(3-(2-((tert-Butoxycarbonyl)amino)ethyl)cyclobutyl)piperazin-1-yl)cyclohexane-1-carboxylic acid (183 mg, 0.447 mmol) was dissolved in dichloromethane (DCM) (1.5 mL) and TFA (2.0 mL) and was stirred at rt for 5 min. The mixture was concentrated under reduced pressure and was chased with dichloromethane (DCM) (3×) to provide (1r,4r)-4-(4-(3-(2-aminoethyl)cyclobutyl)piperazin-1-yl)cyclohexane-1-carboxylic acid, 2trifluoroacetic acid salt (183 mg, 0.340 mmol). To a mixture of (2S,3S)-1-methyl-5-oxo-2-(pyridin-3-yl)pyrrolidine-3-carboxylic acid (85 mg, 0.386 mmol) and TSTU (139 mg, 0.463 mmol) in acetonitrile (2969 μL) was added triethylamine (215 μL, 1.544 mmol) and the mixture was stirred at rt for 1.5 h. (1r,4r)-4-(4-(3-(2-Aminoethyl)cyclobutyl)piperazin-1-yl)cyclohexane-1-carboxylic acid, 2trifluoroacetic acid salt (183 mg, 0.340 mmol) was added and the reaction was stirred for 30 min. The reaction was concentrated under reduced pressure. Purification by MDAP (Xbridge™ column) using acetonitrile in water with an ammonium carbonate modifier provided the title compound (29 mg, 0.049 mmol, 12.63% yield). LC-MS m/z 512.12 $(M+H)^+$.

Step 5

(2S,3S)-N-(2-(3-(4-((1R,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)piperazin-1-yl) cyclobutyl)ethyl)-1-methyl-5-oxo-2-(pyridin-3-yl) pyrrolidine-3-carboxamide

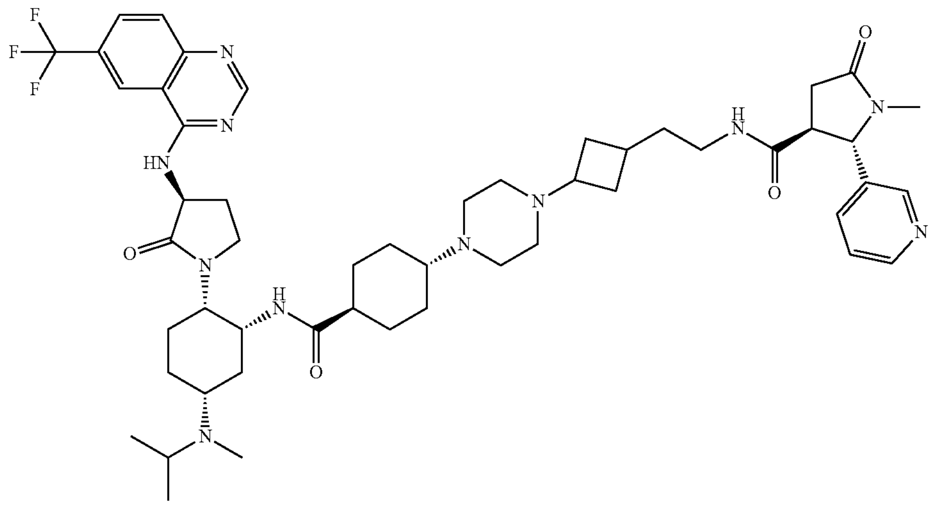 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(C4CC(CCNC(=O)[C@H]5CC(=O)N(C)[C@@H]5c5cccnc5)C4)CC3)CC2)C1]

tert-Butyl ((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)carbamate (50 mg, 0.089 mmol) was dissolved in dichloromethane (DCM) (0.5 mL) and HCl (0.1 mL) and the mixture was stirred at rt for 15 min. The reaction was concentrated under reduced pressure and was chased with dichloromethane (DCM). The residue was dissolved in dichloromethane (DCM) (1532 μL) and triethylamine (31.6 μl, 0.227 mmol) was added. 80% of the mixture was added to (1S,4r)-4-(4-(3-(2-((2S,3S)-1-methyl-5-oxo-2-(pyridin-3-yl) pyrrolidine-3-carboxamido)ethyl)cyclobutyl) piperazin-1-yl)cyclohexane-1-carboxylic acid (29 mg, 0.057 mmol) and stirred at rt for 30 min. Purification by MDAP (Xbridge™ column) using acetonitrile in water with an ammonium carbonate modifier provided the title compound as a white solid (18.8 mg, 0.019 mmol, 33.8% yield). LC-MS m/z 958.4 $(M+H)^+$. $^1$H NMR (400 MHz, METHANOL-$d_4$) δ ppm 0.97-1.08 (m, 3H) 1.10-1.18 (m, 3H) 1.22-1.36 (m, 2H) 1.38-1.60 (m, 6H) 1.66-1.78 (m, 3H) 1.91-2.12 (m, 7H) 2.17-2.38 (m, 10H) 2.48-2.89 (m, 13H) 2.94-3.21 (m, 4H) 3.41-3.58 (m, 2H) 3.61-3.70 (m, 1H) 3.98-4.08 (m, 1H) 4.65-4.69 (m, 1H) 4.81-4.86 (m, 2H) 5.21-5.31 (m, 1H) 7.52-7.58 (m, 1H) 7.78-7.84 (m, 1H) 7.89-7.95 (m, 1H) 8.03-8.11 (m, 1H) 8.50-8.53 (m, 1H) 8.57-8.63 (m, 2H) 8.80-8.86 (m, 1H).

Example 98

(2S,3S)-N-(2-(2-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-3-oxopropoxy)ethyl)amino)-2-oxoethoxy)ethyl)-1-methyl-5-oxo-2-(pyridin-3-yl)pyrrolidine-3-carboxamide

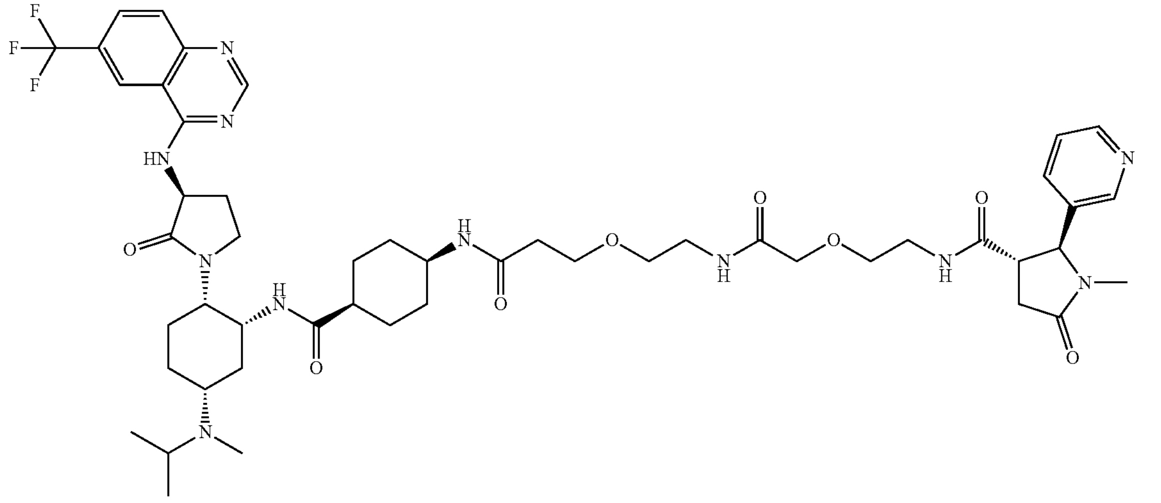

Step 1 tert-Butyl 1-((2S,3S)-1-methyl-5-oxo-2-(pyridin-3-yl)pyrrolidin-3-yl)-1,7-dioxo-5,11-dioxa-2,8-diazatetradecan-14-oate

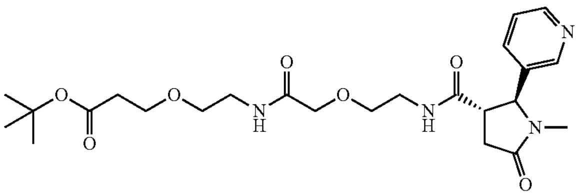 [SMILES: CN1C(=O)C[C@H](C(=O)NCCOCC(=O)NCCOCCC(=O)OC(C)(C)C)[C@H]1c1cccnc1]

To a solution of 2-(2-((2S,3S)-1-methyl-5-oxo-2-(pyridin-3-yl) pyrrolidine-3-carboxamido)ethoxy)acetic acid, hydrochloric acid salt (106 mg, 0.296 mmol) in N,N-dimethylformamide (DMF) (4.0 mL) was added sequentially DIPEA (0.259 mL, 1.481 mmol), HOBt (45.4 mg, 0.296 mmol), HATU (169 mg, 0.444 mmol), and tert-butyl 3-(2-aminoethoxy)propanoate (81 mg, 0.356 mmol) and the mixture was stirred overnight. Water was added and the mixture was extracted with ethyl acetate (3×). The combined organic extracts were washed brine (2×), were dried over $Na_2SO_4$. were filtered, and the filtrate was concentrated. Purification by ISCO CombiFlash® chromatography (40 g silica column, 40 mL/min) eluting with a gradient of 0 to 20% methanol in dichloromethane (DCM) provided the title compound a light-colored wax (28 mg, 0.057 mmol, 19.19% yield). LC-MS m/z 493.3

Step 2

(2S,3S)-N-(2-(2-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-3-oxopropoxy)ethyl)amino)-2-oxoethoxy)ethyl)-1-methyl-5-oxo-2-(pyridin-3-yl)pyrrolidine-3-carboxamide

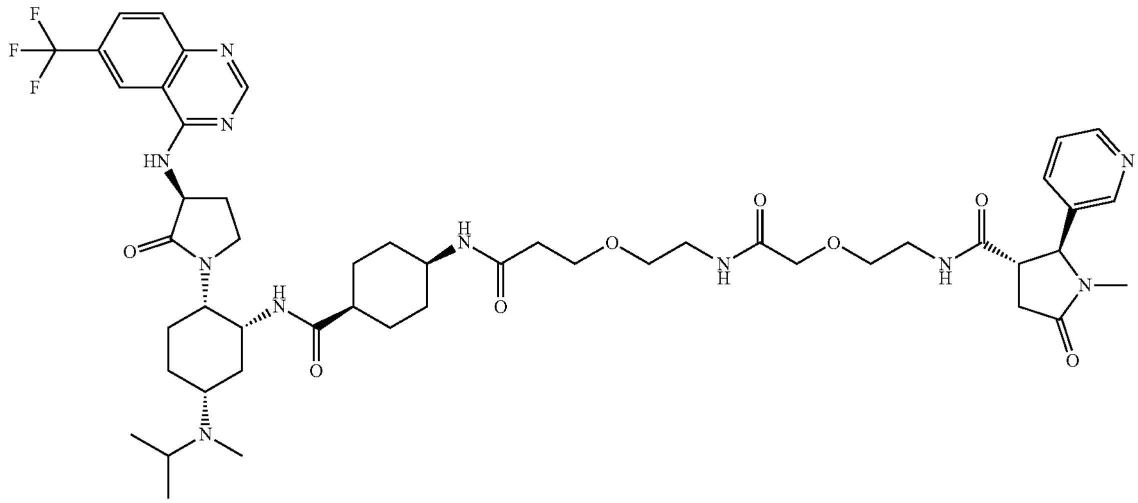 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)COCCNC(=O)[C@H]3CC(=O)N(C)[C@@H]3c3cccnc3)CC2)C1]

A mixture of 4 M HCl in 1,4-dioxane (4 mL, 16.00 mmol) and tert-butyl 1-((2S,3S)-1-methyl-5-oxo-2-(pyridin-3-yl)pyrrolidin-3-yl)-1,7-dioxo-5,11-dioxa-2,8-diazatetradecan-14-oate (26.8 mg, 0.054 mmol) in dichloromethane (DCM) (2.0 mL) was stirred for 1 hour and was concentrated. To the residue in dichloromethane (DCM) (2.0 mL) was added sequentially (1 s,4S)-4-amino-N-((1R,2S,5R)-5-(isopropyl (methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (40 mg, 0.054 mmol), HOBt (8.32 mg, 0.054 mmol), DIPEA (0.047 mL, 0.272 mmol) and HATU (31.0 mg, 0.081 mmol) and the mixture was stirred at rt for 3 h.

Saturated $NaHCO_3$ was added and the mixture was extracted with dichloromethane (DCM) (3×). The combined organic extracts were washed brine (2×), were dried over $Na_2SO_4$ were filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (18.6 mg, 0.018 mmol, 32.3% yield). LC-MS m/z 1008.6 $(M+H)^+$. $^1H$ NMR (400 MHz, DMSO-$d_6$) δ ppm 0.87-0.93 (m, 3H) 1.01-1.08 (m, 3H) 1.37-1.49 (m, 2H) 1.51-1.77 (m, 9H) 1.89-2.17 (m, 8H) 2.24-2.31 (m, 2H) 2.32-2.39 (m, 1H) 2.41-2.47 (m, 1H) 2.57-2.62 (m, 1H) 2.66-2.77 (m, 1H) 2.91-2.99 (m, 1H) 3.15-3.29 (m, 5H) 3.34-3.38 (m, 2H) 3.40-3.46 (m, 3H) 3.51-3.57 (m, 3H) 3.67-3.74 (m, 1H) 3.80-3.84 (m, 2H) 3.86-3.93 (m, 1H) 4.38-4.48 (m, 1H) 4.63-4.70 (m, 1H) 4.99-5.08 (m, 1H) 7.39-7.47 (m, 1H) 7.58-7.65 (m, 2H) 7.65-7.69 (m, 1H) 7.87-7.92 (m, 1H) 8.04-8.08 (m, 1H) 8.09-8.13 (m, 1H) 8.46-8.49 (m, 1H) 8.53-8.57 (m, 1H) 8.58-8.60 (m, 1H) 8.61-8.67 (m, 1H) 8.68-8.73 (m, 1H) 8.86-8.93 (m, 1H).

The following compounds were or could be prepared with procedures analogous to that described in Example 98:

| Ex. | Compound | LC-MS m/z | NMR |
|---|---|---|---|
| 99 | 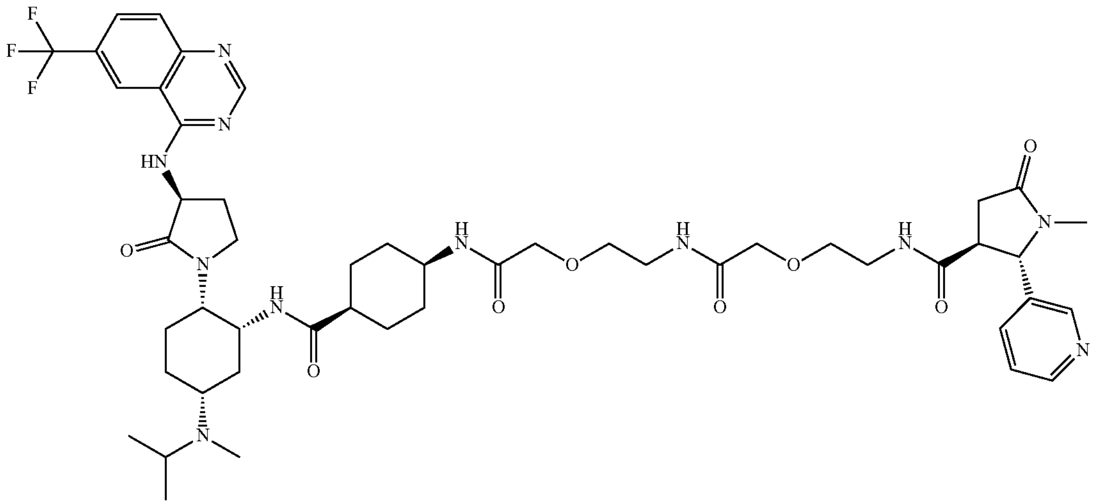 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCNC(=O)COCCNC(=O)[C@H]3CC(=O)N(C)[C@@H]3c3cccnc3)CC2)C1] (2S,3S)-N-(2-(2-((2-(2-(((1S,4s)-4-(((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)carbamoyl)cyclohexyl)amino)-2-oxoethoxy)ethyl)amino)-2-oxoethoxy)ethyl)-1-methyl-5-oxo-2-(pyridin-3-yl)pyrrolidine-3-carboxamide. | 994.3 (M + H)+ | $^1$H NMR (400 MHz, DMSO-$d_6$) δ ppm 0.89 (d, J = 6.4 Hz, 3H) 1.05 (d, J = 6.8 Hz, 3H) 1.54-1.73 (m, 9H) 1.89-2.01 (m, 2 H) 2.01-2.17 (m, 7H) 2.30-2.39 (m, 1H) 2.39-2.48 (m, 2H) 2.58 (br s, 1H) 2.67-2.75 (m, 1H) 2.90-2.97 (m, 1H) 3.18-3.30 (m, 6H) 3.38-3.45 (m, 5H) 3.50-3.57 (m, 1 H) 3.70-3.77 (m, 1H) 3.80 (s, 2H) 3.82 (s, 2H) 3.87 (dt, J = 7.5, 3.9 Hz, 1 H) 4.33-4.49 (m, 1H) 4.65 (d, J = 5.9 Hz, 1H) 5.02 (s, 1H) 5.80-6.45 (m, 1H) 7.36 (d, J = 7.3 Hz, 1H) 7.42 (dd, J = 7.8, 4.4 Hz, 1H) 7.67 (dt, J = 7.8, 2.0 Hz, 1H) 7.77 (t, J = 5.6 Hz, 1H) 7.89 (d, J = 8.8 Hz, 1H) 8.02 - 8.15 (m, 2H) 8.47 (d, J = 2.0 Hz, 1H) 8.54 (dd, J = 4.6, 1.7 Hz, 1H) 8.58 (s, 1H) 8.69 (br d, J = 8.3 Hz, 2H) 8.88 (s, 1H). |

-continued
| Ex. | Compound | LC-MS m/z | NMR |
| --- | --- | --- | --- |
| 100 | 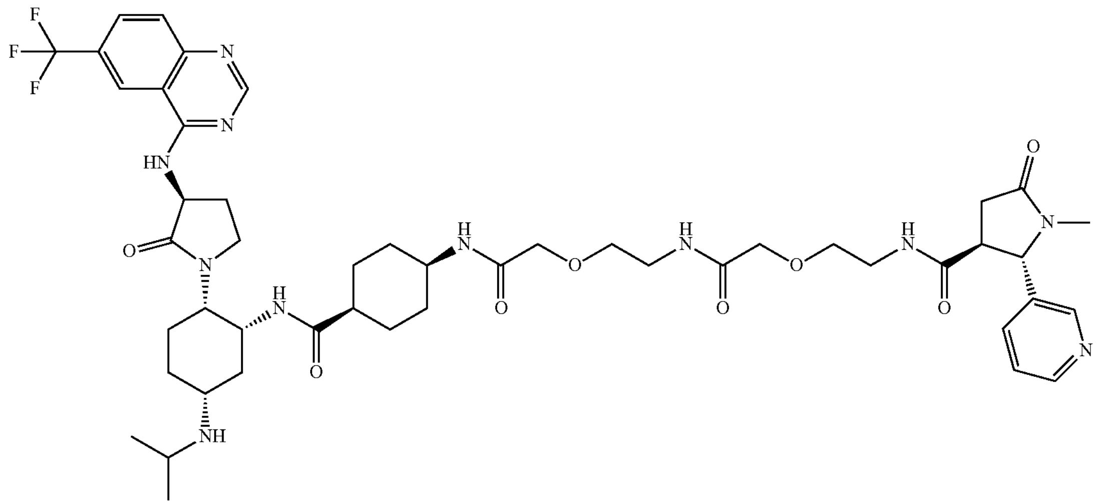 (2S,3S)-N-(2-(2-((2-(2-(((1S,4s)-4-(((1R,2S,5R)-5-(tert-Butylamino)-2-((S)-2-oxo-3-((6-(trifluoromethyl)quinazolin-4-yl)amino) pyrrolidin-1-yl)cyclohexyl)carbamoyl)cyclohexyl)amino)-2-oxoethoxy)ethyl)amino)-2-oxoethoxy)ethyl)-1-methyl-5-oxo-2-(pyridin-3-yl)pyrrolidine-3-carboxamide. | 994.7 (M + H)+ | $^1$H NMR (400 MHz, METHANOL-$d_4$) δ ppm 1.18 (s, 9H) 1.57-2.06 (m, 14H) 2.18-2.41 (m, 2H) 2.47-2.60 (m, 1H) 2.66 (s, 4H) 2.78-2.90 (m, 1H) 3.01-3.11 (m, 1 H) 3.18-3.26 (m, 1H) 3.35-3.48 (m, 4H) 3.48-3.58 (m, 5H) 3.59-3.68 (m, 1H) 3.92 (d, J = 5.9 Hz, 6H) 4.52-4.69 (m, 1 H) 4.81-4.84 (m, 1H) 5.25-5.42 (m, 1H) 7.34-7.60 (m, 1H) 7.72-7.87 (m, 1H) 7.87-7.99 (m, 1 H) 8.02-8.15 (m, 1H) 8.58 (s, 3H) 8.69-8.80 (m, 1H). |

-continued

| Ex. | Compound | LC-MS m/z | NMR |
| --- | --- | --- | --- |
| 101 | 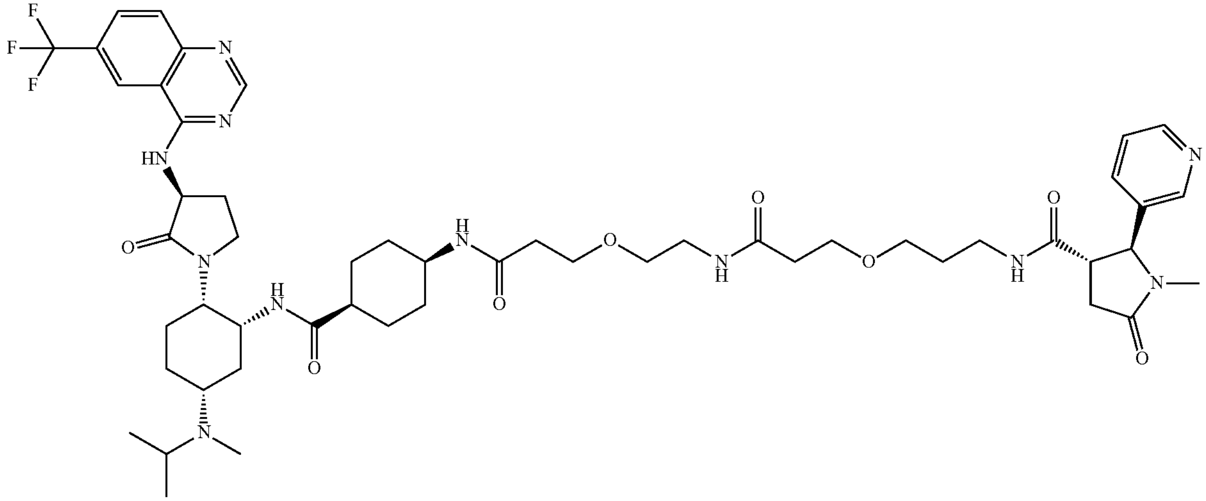 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCOCCCNC(=O)[C@H]3CC(=O)N(C)[C@@H]3c3cccnc3)CC2)C1] (2S,3S)-N-(3-(3-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethyl)amino)-3-oxopropoxy)propyl)-1-methyl-5-oxo-2-(pyridin-3-yl)pyrrolidine-3-carboxamide. | 1036.0 (M + H)+ | $^1$H NMR (400 MHz, DMSO-$d_6$) δ ppm 0.87-0.92 (m, 3H) 1.02-1.07 (m, 3H) 1.38-1.48 (m, 2H) 1.53-1.76 (m, 11 H) 1.89-2.05 (m, 2H) 2.07-2.16 (m, 6H) 2.26-2.31 (m, 4H) 2.32-2.39 (m, 1H) 2.41-2.47 (m, 1H) 2.57-2.62 (m, 1H) 2.65-2.74 (m, 1H) 2.85-2.95 (m, 1H) 2.98-3.11 (m, 2H) 3.12-3.18 (m, 2H) 3.24-3.30 (m, 4H) 3.39-3.46 (m, 1H) 3.50-3.57 (m, 5H) 3.67-3.74 (m, 1H) 3.85-3.92 (m, 1H) 4.38-4.47 (m, 1H) 4.61-4.69 (m, 1H) 4.97-5.08 (m, 1H) 7.40-7.50 (m, 1H) 7.62-7.70 (m, 2H) 7.83-7.92 (m, 2H) 7.93-7.98 (m, 1H) 8.04-8.09 (m, 1H) 8.46-8.48 (m, 1H) 8.54-8.57 (m, 1H) 8.58-8.59 (m, 1H) 8.63-8.69 (m, 1H) 8.70-8.73 (m, 1H) 8.88-8.91 (m, 1H). |

Example 102

(2S,3S)-N-(18-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-5,11,18-trioxo-3,9,15-trioxa-6,12-diazaoctadecyl)-1-methyl-5-oxo-2-(pyridin-3-yl)pyrrolidine-3-carboxamide

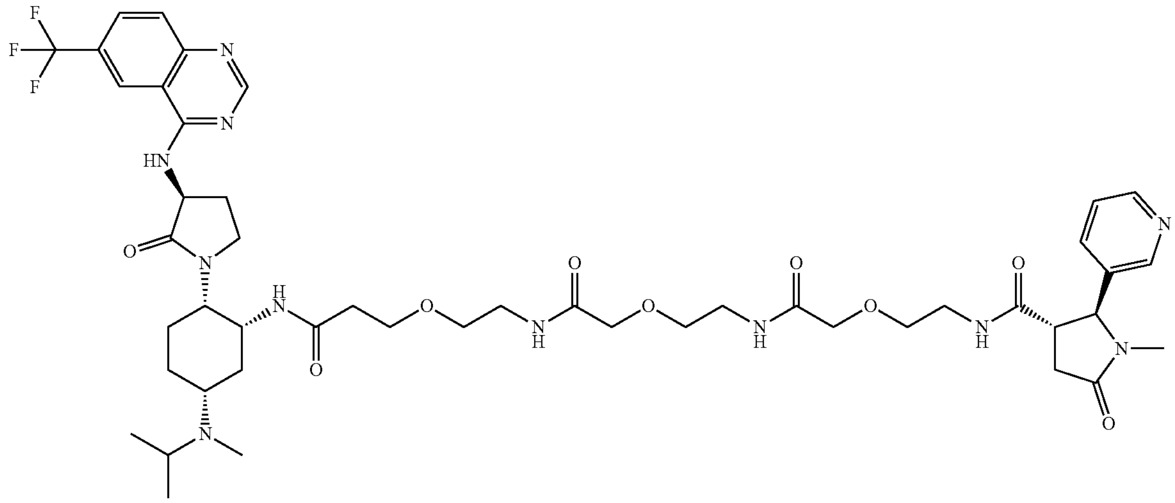 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)COCCNC(=O)COCCNC(=O)[C@H]2CC(=O)N(C)[C@@H]2c2cccnc2)C1]

Step 1 tert-Butyl 3-(2-(((benzyloxy)carbonyl)amino)ethoxy)propanoate

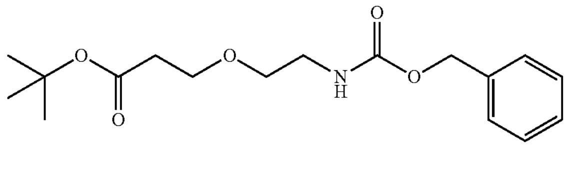 [SMILES: CC(C)(C)OC(=O)CCOCCNC(=O)OCc1ccccc1]

To a solution of benzyl (2-hydroxyethyl)carbamate (12.0 g, 61.5 mmol) and tert-butyl acrylate (11.82 g, 92 mmol) in tetrahydrofuran (THF) (100 mL) was added a solution of KOH (5.75 g, 61.5 mmol) in water (3.9 mL) and the mixture was stirred overnight. Water was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (220 g silica column, 150 mL/min) eluting with a gradient of 0 to 40% ethyl acetate in heptane provided the title compound as a colorless oil (9.75 g, 30.1 mmol, 49.0% yield). LC-MS m/z 346.2 $(M+H)^+$.

Step 2 tert-Butyl 3,9-dioxo-1-phenyl-2,7,13-trioxa-4,10-diazahexadecan-16-oate

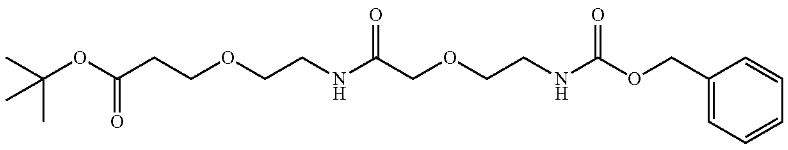

To a solution of tert-butyl 3-(2-(((benzyloxy)carbonyl) amino)ethoxy)propanoate (1.200 g, 3.71 mmol) in ethyl acetate (20 mL) under an atmosphere of nitrogen was added 10% Pd—C, Degussa type (0.034 g, 0.323 mmol). The mixture was vacuumed and was backfilled with hydrogen (3×). The mixture was stirred under a balloon atmosphere of hydrogen overnight and was filtered through Celite®. The filtrate was concentrated to about 5.0 mL in volume to provide tert-butyl 3-(2-aminoethoxy)propanoate.

4 M HCl in 1,4-dioxane (10.0 mL, 40.0 mmol) was added to tert-butyl 2-(2-(((benzyloxy)carbonyl)amino)ethoxy)acetate (1.00 g, 3.23 mmol). The mixture was stirred overnight and was concentrated to dryness to provide tert-butyl 2-(2-aminoethoxy)acetate, hydrochloric acid salt. LC-MS m/z 210.2 $(M+H)^+$. Some SM remained by LCMS. Removed solvent to dryness.

To tert-butyl 2-(2-aminoethoxy)acetate, hydrochloric acid salt in dichloromethane (DCM) (20.00 mL) was added DIPEA (2.82 mL, 16.16 mmol), HOBt (0.594 g, 3.88 mmol) and the solution of tert-butyl 3-(2-aminoethoxy)propanoate described above. EDC (0.930 g, 4.85 mmol) was added, the mixture was stirred overnight. Saturated. $NaHCO_3$ was added and the mixture was extracted with dichloromethane (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 10% methanol in dichloromethane (DCM) provided the title compound as a colorless oil (810 mg, 1.908 mmol, 59.0% yield). LC-MS m/z 425.3$(M+H)^+$.

Step 3 tert-Butyl 3-(2-(2-(2-aminoethoxy)acetamido) ethoxy)propanoate

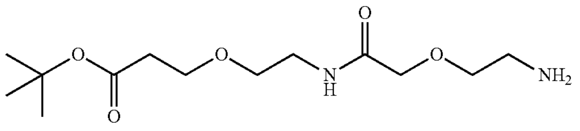 [SMILES: CC(C)(C)OC(=O)CCOCCNC(=O)COCCN]

To a solution of tert-butyl 3,9-dioxo-1-phenyl-2,7,13-trioxa-4,10-diazahexadecan-16-oate (250 mg, 0.589 mmol) in ethyl acetate (10 mL) under an atmosphere of nitrogen was added 10% Pd—C, Degussa type (6.27 mg, 0.059 mmol) and the mixture was vacuumed and was backfilled with hydrogen (3×). The mixture was stirred under a balloon atmosphere of hydrogen over the weekend and was filtered through Celite®. The filtrate was concentrated to provide the title compound as a colorless wax (148 mg, 0.510 mmol, 87% yield). LC-MS m/z 291.3 $(M+H)^+$.

Step 4 tert-Butyl 1-((2S,3S)-1-methyl-5-oxo-2-(pyridin-3-yl)pyrrolidi n-3-yl)-1,7,13-trioxo-5,11,17-trioxa-2,8,14-triazaicosan-20-oate

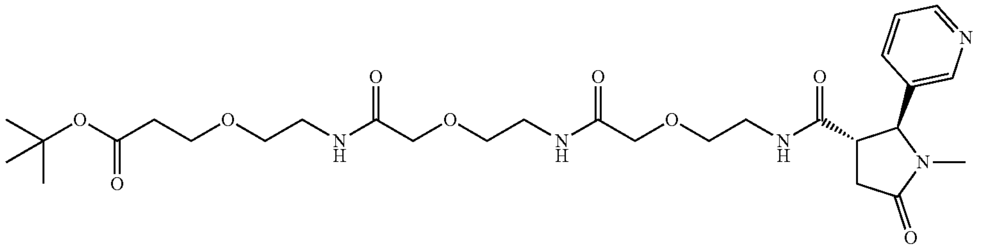 [SMILES: CN1C(=O)C[C@H](C(=O)NCCOCC(=O)NCCOCC(=O)NCCOCCC(=O)OC(C)(C)C)[C@H]1c1cccnc1]

To a solution of 2-(2-((2S,3S)-1-methyl-5-oxo-2-(pyridin-3-yl)pyrrolidine-3-carboxamido)ethoxy)acetic acid, hydrochloric acid salt (197 mg, 0.549 mmol) in dichloromethane (DCM) (5 mL) was added DIPEA (0.436 mL, 2.497 mmol), HOBt (92 mg, 0.599 mmol), EDC (144 mg, 0.749 mmol) followed by tert-butyl 3-(2-(2-(2-aminoethoxy)acetamido)ethoxy)propanoate (145 mg, 0.499 mmol) and the mixture was stirred overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a light-colored wax (147 mg, 0.248 mmol, 49.6% yield). LC-MS m/z 594.3 $(M+H)^+$.

Step 5

(2S,3S)-N-(18-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-5,11,18-trioxo-3,9,15-trioxa-6,12-diazaoctadecyl)-1-methyl-5-oxo-2-(pyridin-3-yl)pyrrolidine-3-carboxamide

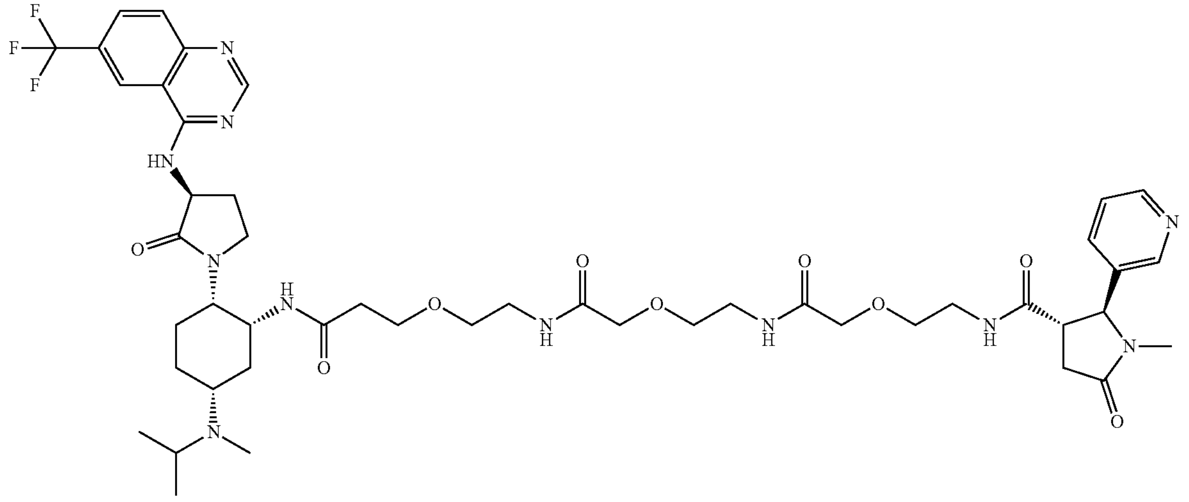 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)COCCNC(=O)COCCNC(=O)[C@H]2CC(=O)N(C)[C@@H]2c2cccnc2)C1]

To a solution of tert-butyl 1-((2S,3S)-1-methyl-5-oxo-2-(pyridin-3-yl)pyrrolidin-3-yl)-1,7,13-trioxo-5,11,17-trioxa-2,8,14-triazaicosan-20-oate (53.0 mg, 0.089 mmol) in dichloromethane (DCM) (2.0 mL) was added 4 M HCl in 1,4-dioxane (4 mL, 16.00 mmol). The mixture was stirred for 1 h and was concentrated to dryness. Dichloromethane (DCM) (2.0 mL) was added to the residue, followed by (S)-1-((1S,2R,4R)-2-amino-4-(isopropyl(methyl)amino)cyclohexyl)-3-((6-(trifluoromethyl)quinazolin-4-yl)amino) pyrrolidin-2-one, 2Hydrochloric acid salt (50 mg, 0.074 mmol) and HOBt (13.68 mg, 0.089 mmol) and DIPEA (0.065 mL, 0.372 mmol), and EDC (21.40 mg, 0.112 mmol). The mixture was stirred at rt for 3 h. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (54.5 mg, 0.053 mmol, 70.7% yield). LC-MS m/z 984.2 $(M+H)^+$. $^1H$ NMR (400 MHz, DMSO-$d_6$) δ ppm 0.81-1.10 (m, 6H) 1.54-1.72 (m, 3H) 2.14 (s, 7H) 2.28-2.42 (m, 3H) 2.59-2.78 (m, 3H) 2.88-2.99 (m, 1H) 3.10-3.31 (m, 9H) 3.39-3.69 (m, 8H) 3.82 (d, J=5.4 Hz, 5H) 4.37-4.51 (m, 1H) 4.60-4.75 (m, 1H) 4.93-5.17 (m, 1H) 7.37-7.54 (m, 1H) 7.63-7.73 (m, 2H) 7.75-7.97 (m, 2H) 8.02-8.22 (m, 2H) 8.59 (s, 4H) 8.96 (s, 2H).

The following compound was or could be prepared with procedures analogous to that described in Example 102:

| Ex. | Compound | LC-MS m/z | NMR |
|---|---|---|---|
| 103 | 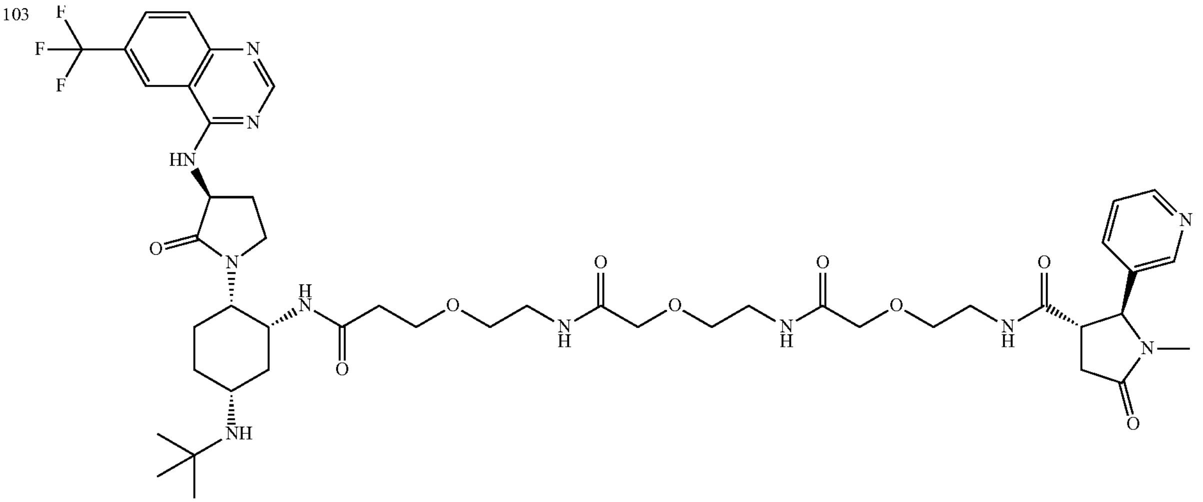 (2S,3S)-N-(18-(((1R,2S,5R)-5-(tert-Butylamino)-2-((S)-2-oxo-3-((6-(trifluoromethyl)quinazolin-4-yl)amino)pyrrolidin-1-yl)cyclohexyl)amino)-5,11,18-trioxo-3,9,15-trioxa-6, 12-diazaoctadecyl)-1-methyl-5-oxo-2-(pyridin-3-yl)pyrrolidine-3-carboxamide. | 984.6 (M + H)+ | $^1$H NMR (400 MHz, DMSO-$d_6$) δ ppm 1.09 (s, 9H) 1.53-1.94 (m, 7H) 2.16 (br dd, J = 12.7, 3.9 Hz, 1H) 2.28-2.48 (m, 4 H) 2.50 (br s, 3H) 2.68-2.76 (m, 1H) 2.90-2.96 (m, 1H) 3.08 (br s, 1H) 3.12-3.20 (m, 2H) 3.22-3.31 (m, 6H) 3.40-3.54 (m, 6H) 3.60-3.70 (m, 2 H) 3.82 (d, J = 4.9 Hz, 4H) 4.47 (br dd, J = 6.8, 3.4 Hz, 1H) 4.65 (d, J = 5.9 Hz, 1 H) 5.02 (td, J = 7.9, 6.1 Hz, 1H) 7.40-7.46 (m, 1H) 7.67 (dt, J = 7.9, 2.1 Hz, 2 H) 7.76 (t, J = 5.9 Hz, 1H) 7.90 (d, J = 8.8 Hz, 1H) 8.05-8.14 (m, 2H) 8.47 (d, J = 1.5 Hz, 1H) 8.53-8.56 (m, 1H) 8.60 (s, 1H) 8.69 (d, J = 8.3 Hz, 1H) 8.99 (s, 1H) 9.93-10.00 (m, 1H). |

Example 104

(2S,3S)-N-(18-(((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)amino)-5,12,18-trioxo-3,9,16-trioxa-6,13-diazaoctadecyl)-1-methyl-5-oxo-2-(pyridin-3-yl)pyrrolidine-3-carboxamide

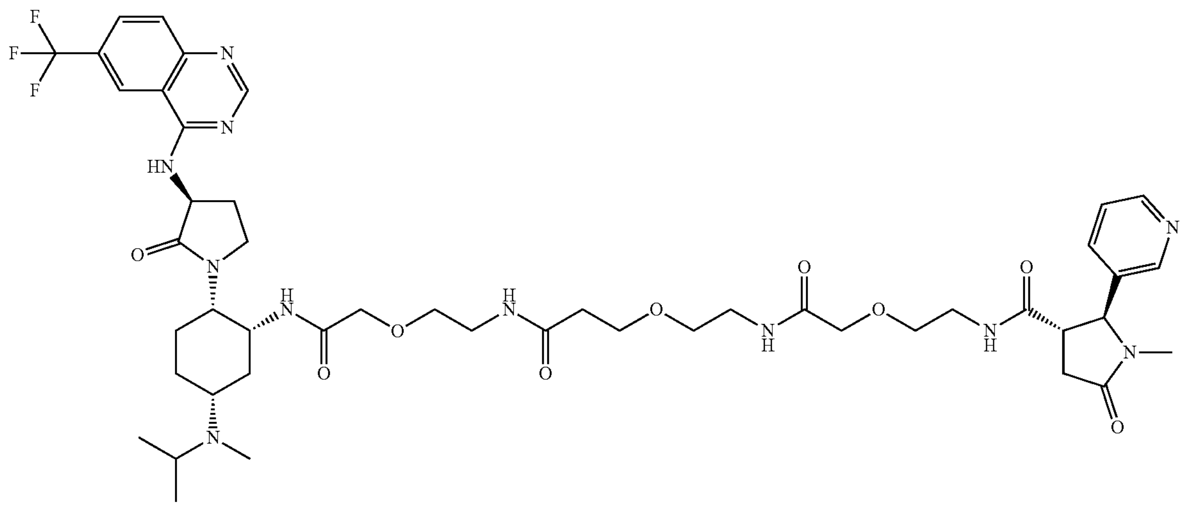 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCOCCNC(=O)COCCNC(=O)[C@H]2CC(=O)N(C)[C@@H]2c2cccnc2)C1]

Step 1 tert-Butyl 3,9-dioxo-1-phenyl-2,7,13-trioxa-4,10-diazahexadecan-16-oate

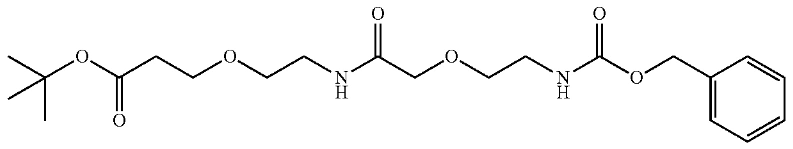 [SMILES: CC(C)(C)OC(=O)CCOCCNC(=O)COCCNC(=O)OCc1ccccc1]

A mixture of tert-butyl 2-(2-(((benzyloxy)carbonyl) amino)ethoxy)acetate (1.00 g, 3.23 mmol) and 4 M HCl in 1,4-dioxane (10.0 mL, 40.0 mmol) was stirred overnight and was evaporated. To the residue was added sequentially dichloromethane (DCM) (20.00 mL), DIPEA (2.82 mL, 16.16 mmol), HOBt (0.594 g, 3.88 mmol), a solution of tert-butyl 2-(2-aminoethoxy)acetate (0.650 g, 3.71 mmol) in ethyl acetate (5.0 mL), and EDC (0.930 g, 4.85 mmol), and the mixture was stirred overnight. Saturated $NaHCO_3$ was added and the mixture was extracted with dichloromethane (DCM) (3×). The combined organic extracts were washed brine (2×), were dried over $Na_2SO_4$, were filtered, and the filtrate was concentrated.

Purification by ISCO CombiFlash® chromatography (40 g silica column, 40 mL/min) eluting with a gradient of 0 to 10% methanol in dichloromethane (DCM) provided the title compound as a colorless oil (810 mg, 1.908 mmol, 59.0% yield). LC-MS m/z 425.3 $(M+H)^+$.

Step 2 tert-butyl 3,9,16-trioxo-1-phenyl-2,7,13,20-tetraoxa-4,10,17-triazadocosan-22-oate

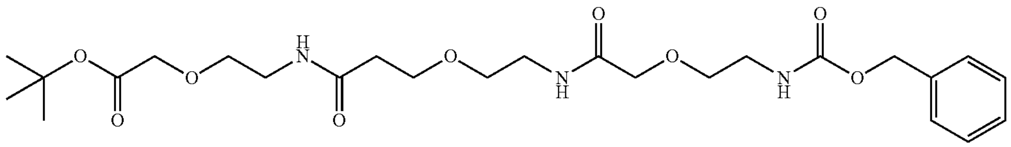 [SMILES: CC(C)(C)OC(=O)COCCNC(=O)CCOCCNC(=O)COCCNC(=O)OCc1ccccc1]

A mixture of tert-butyl 3,9-dioxo-1-phenyl-2,7,13-trioxa-4,10-diazahexadecan-16-oate (270 mg, 0.636 mmol) and 4 M HCl in 1,4-dioxane (5.0 mL, 20.00 mmol) was stirred overnight and was concentrated. To the residue was added sequentially dichloromethane (DCM) (2.0 mL), DIPEA (0.555 mL, 3.18 mmol), HOBt (117 mg, 0.763 mmol), EDC (183 mg, 0.954 mmol), and tert-butyl 2-(2-aminoethoxy) acetate (134 mg, 0.763 mmol), and the mixture was stirred overnight. Saturated $NaHCO_3$ was added and the mixture was extracted with dichloromethane (DCM) (3×). The combined organic extracts were washed brine (2×), were dried over $Na_2SO_4$, were filtered, and the filtrate was concentrated. Purification by ISCO CombiFlash® chromatography (40 g silica column, 40 mL/min) eluting with a gradient of 0 to 10% methanol in dichloromethane (DCM) provided the title compound as a colorless oil (220 mg, 0.419 mmol, 65.8% yield). LC-MS m/z 526.3 $(M+H)^+$.

Step 3 tert-Butyl 1-amino-5,12-dioxo-3,9,16-trioxa-6,13-diazaoctadecan-18-oate

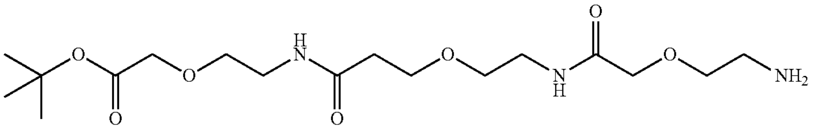 [SMILES: CC(C)(C)OC(=O)COCCNC(=O)CCOCCNC(=O)COCCN]

To a solution of tert-butyl 3,9,16-trioxo-1-phenyl-2,7,13,20-tetraoxa-4,10,17-triazadocosan-22-oate (220 mg, 0.419 mmol) in ethyl acetate (10 mL) under an atmosphere of nitrogen was added 10% Pd—C, Degussa type (4.45 mg, 0.042 mmol). The mixture was evacuated, was backfilled with hydrogen (3×), and was stirred under a balloon atmosphere of hydrogen for 4 h. The mixture was filtered through Celite® and the filtrate was concentrated to provide the title compound as a wax (146 mg, 0.373 mmol, 89% yield). LC-MS m/z 392.3 $(M+H)^+$.

Step 4 tert-Butyl 1-((2S,3S)-1-methyl-5-oxo-2-(pyridin-3-yl)pyrrolidin-3-yl)-1,7,14-trioxo-5,11,18-trioxa-2,8,15-triazaicosan-20-oate

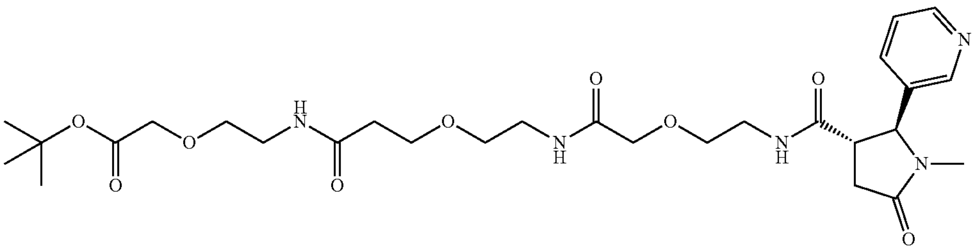 [SMILES: CN1C(=O)C[C@H](C(=O)NCCOCC(=O)NCCOCCC(=O)NCCOCC(=O)OC(C)(C)C)[C@H]1c1cccnc1]

To a solution of (2S,3S)-1-methyl-5-oxo-2-(pyridin-3-yl) pyrrolidine-3-carboxylic acid (99 mg, 0.448 mmol), HOBt (68.5 mg, 0.448 mmol), EDC (107 mg, 0.559 mmol) and tert-butyl 1-amino-5,12-dioxo-3,9,16-trioxa-6,13-diazaoctadecan-18-oate (146 mg, 0.373 mmol) in dichloromethane (DCM) (5.0 mL) was added DIPEA (0.326 mL, 1.865 mmol) and the mixture was stirred overnight. Saturated $NaHCO_3$ was added and the mixture was extracted with dichloromethane (DCM) (3×). The combined organic extracts were washed brine (2×), were dried over $Na_2SO_4$, were filtered, and the filtrate was concentrated. Purification by ISCO CombiFlash® chromatography (40 g silica column, 40 mL/min) eluting with a gradient of 0 to 20% methanol in dichloromethane (DCM) provided the title compound as a wax (220 mg, 0.371 mmol, 99% yield). LC-MS m/z 594.3 $(M+H)^+$.

Step 5

(2S,3S)-N-(18-(((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)amino)-5,12,18-trioxo-3,9,16-trioxa-6,13-diazaoctadecyl)-1-methyl-5-oxo-2-(pyridin-3-yl)pyrrolidine-3-carboxamide To a solution of tert-butyl 1-((2S,3S)-1-methyl-5-oxo-2-(pyridin-3-yl)pyrrolidin-3-yl)-1,7,14-trioxo-5,11,18-trioxa-2,8,15-triazaicosan-20-oate (48 mg, 0.081 mmol) in dichloromethane (DCM) (2.0 mL) was added 4 M HCl in 1,4-dioxane (4 mL, 16.00 mmol), the mixture was stirred for 1 h, and was concentrated. To the residue was added sequentially dichloromethane (DCM) (2.0 mL), (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (50 mg, 0.074 mmol), HOBt (13.68 mg, 0.089 mmol), DIPEA (0.065 mL, 0.372 mmol) and EDC (21.40 mg, 0.112 mmol), and the mixture was stirred at rt overnight. Saturated $NaHCO_3$ was added and the mixture was extracted with dichloromethane (DCM) (3×). The combined organic extracts were washed brine (2×), were dried over $Na_2SO_4$, were filtered, and the filtrate was concentrated. Purification by MDAP (XSelect™ CSH C18 5 μm column, 40 mL/min) eluting with a gradient of 30 to 85% gradient acetonitrile in water containing ammonium bicarbonate (10 mM) and ammonium hydroxide (0.075%) provided the title compound as an off-white solid (21.4 mg, 0.021 mmol, 27.8% yield). LC-MS m/z 984.3 $(M+H)^+$. $^1H$ NMR (400 MHz, DMSO-$d_6$) δ ppm 0.89 (d, J=6.4 Hz, 3H) 1.03 (d, J=6.4 Hz, 3H) 1.53-1.69 (m, 3H) 1.88-2.16 (m, 8H) 2.23-2.36 (m, 3H) 2.41-2.50 (m, 4H) 2.62-2.76 (m, 1H) 2.90-2.97 (m, 1H) 3.15-3.33 (m, 9H) 3.35-3.55 (m, 9H) 3.81 (s, 2H) 3.86-4.00 (m, 3H) 4.48-4.55 (m, 1H) 4.65 (d, J=5.9 Hz, 1H) 5.01 (q, J=7.8 Hz, 1H) 7.41-7.45 (m, 1H) 7.62-7.70 (m, 2H) 7.86-7.92 (m, 2H) 8.04-8.16 (m, 2H) 8.95 (s, 1H) 9.21 (br d, J=7.8 Hz, 1H).

The following compounds were or could be prepared with procedures analogous to that described in Example 104:

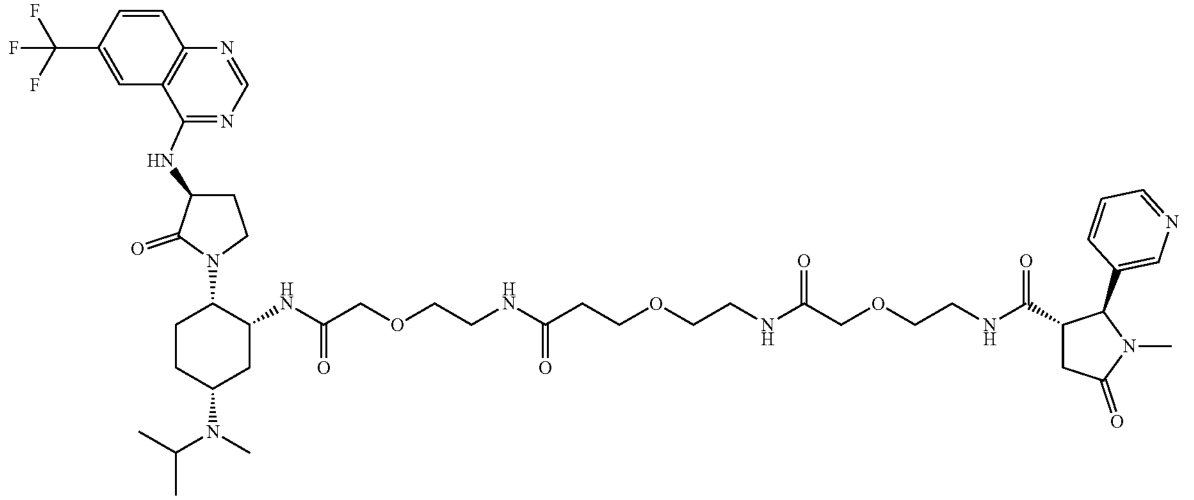 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCOCCNC(=O)COCCNC(=O)[C@H]2CC(=O)N(C)[C@@H]2c2cccnc2)C1]

| Ex. | Compound | LC-MS m/z | NMR |
|---|---|---|---|
| 105 | 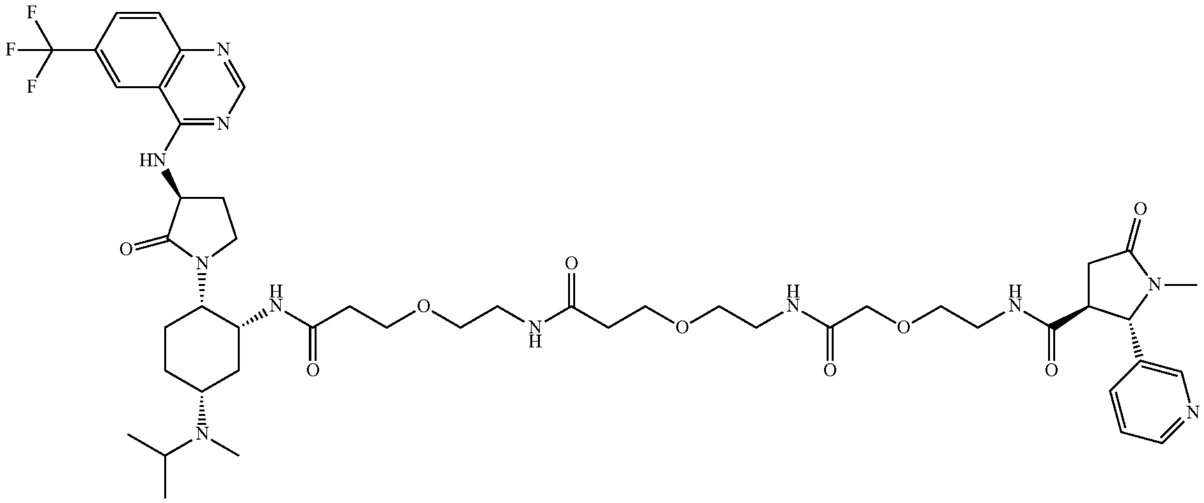 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)CCOCCNC(=O)COCCNC(=O)[C@H]2CC(=O)N(C)[C@@H]2c2cccnc2)C1] (2S,3S)-N-(19-(((1R,2S,5R)-5-(Isopropyl(methyl)amino)-2-((S)-2-oxo-3-((6-(trifluoromethyl)quinazolin-4-yl) amino) pyrrolidin-1-yl)cyclohexyl)amino)-5,12,19-trioxo-3,9,16-trioxa-6,13-diazanonadecyl)-1-methyl-5-oxo-2-(pyridin-3-yl)pyrrolidine-3-carboxamide. | 998.3 $(M + H)^+$ | $^1$H NMR (400 MHz, DMSO-$d_6$) δ ppm 0.94 (d, J = 6.4 Hz, 3H) 0.97-1.05 (m, 4 H) 1.60 (br d, J = 12.7 Hz, 3 H) 2.12-2.19 (m, 4H) 2.24-2.30 (m, 2H) 2.30-2.38 (m, 4H) 2.40-2.48 (m, 1 H) 2.61 (br s, 2H) 2.64-2.77 (m, 2H) 2.84-2.99 (m, 1H) 3.04-3.16 (m, 3 H) 3.16-3.32 (m, 8H) 3.37-3.67 (m, 10H) 3.81 (s, 2 H) 3.88-3.95 (m, 1H) 4.44 (br s, 1H) 4.65 (d, J = 6.4 Hz, 1H) 5.02 (q, J = 7.8 Hz, 1H) 7.43 (dd, J = 7.8, 4.9 Hz, 1H) 7.77-7.87 (m, 1 H) 7.89 (d, J = 8.8 Hz, 1H) 8.04-8.09 (m, 1H) 8.13 (t, J = 5.6 Hz, 1H) 8.47 (d, J = 1.5 Hz, 1H) 8.55 (dd, J = 4.6, 1.7 Hz, 1H) 8.59 (s, 1H) 8.65 (d, J = 8.3 Hz, 1H) 8.96 (s, 2H). |

-continued

| Ex. | Compound | LC-MS m/z | NMR |
| --- | --- | --- | --- |
| 106 | 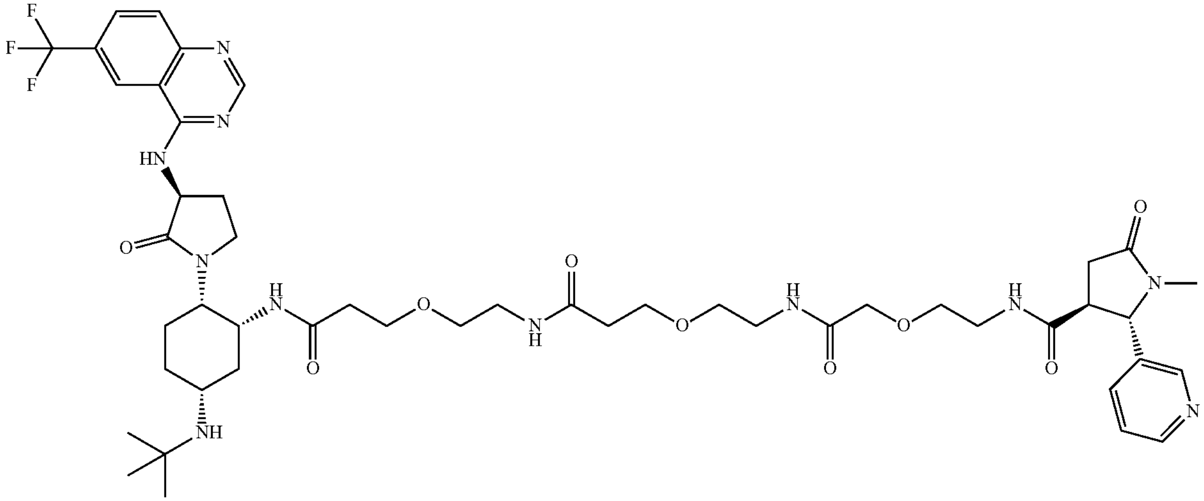 [SMILES: CN1C(=O)C[C@H](C(=O)NCCOCC(=O)NCCOCCC(=O)NCCOCCC(=O)N[C@@H]2C[C@H](NC(C)(C)C)CC[C@@H]2N2CC[C@H](Nc3ncnc4ccc(C(F)(F)F)cc34)C2=O)[C@H]1c1cccnc1] (2S,3S)-N-(19-(((1R,2S,5R)-5-(tert-Butylamino)-2-((S)-2-oxo-3-((6-(trifluoromethyl)quinazolin-4-yl)amino)pyrrolidin-1-yl)cyclohexyl)amino)-5,12,19-trioxo-3,9, 16-trioxa-6, 13-diazanonadecyl)-1-methyl-5-oxo-2-(pyridin-3-yl)pyrrolidine-3-carboxamide. | 998.6 $(M + H)^+$ | $^1H$ NMR (400 MHz, METHANOL-$d_4$) δ ppm 1.00 (br d, J = 6.4 Hz, 3H) 1.15 (br d, J = 6.4 Hz, 3H) 1.23-1.49 (m, 1H) 1.61-1.89 (m, 3H) 2.02 (br d, J = 8.3 Hz, 1H) 2.11-2.35 (m, 6H) 2.46-2.62 (m, 1 H) 2.66 (s, 3H) 2.67-2.74 (m, 2H) 2.78-2.87 (m, 1 H) 3.06 (ddd, J = 9.3, 8.1, 6.6 Hz, 1H) 3.22-3.31 (m, 1H) 3.35-3.47 (m, 4H) 3.49-3.72 (m, 10H) 3.90 (d, J = 3.4 Hz, 2H) 4.02 (s, 2 H) 4.05 (d, J = 1.5 Hz, 2H) 4.09 (br s, 1H) 4.65 (br s, 1 H) 4.82 (d, J = 6.8 Hz, 1H) 5.24-5.32 (m, 1H) 7.52 (dd, J = 7.8, 4.9 Hz, 1H) 7.79 (dt, J = 8.3, 2.0 Hz, 1H) 7.90 (d, J = 8.8 Hz, 1H) 8.06 (dd, J = 8.8, 2.0 Hz, 1H) 8.52 (d, J = 2.0 Hz, 1H) 8.56 (dd, J = 4.9, 1.5 Hz, 1H) 8.58 (s, 1H) 8.77 (s, 1H). |

Example 107

(2S,3S)-N-(2-(2-(((1S,4R)-4-((2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethyl)carbamoyl)cyclohexyl)amino)-2-oxoethoxy)ethyl)-1-methyl-5-oxo-2-(pyridin-3-yl)pyrrolidine-3-carboxamide

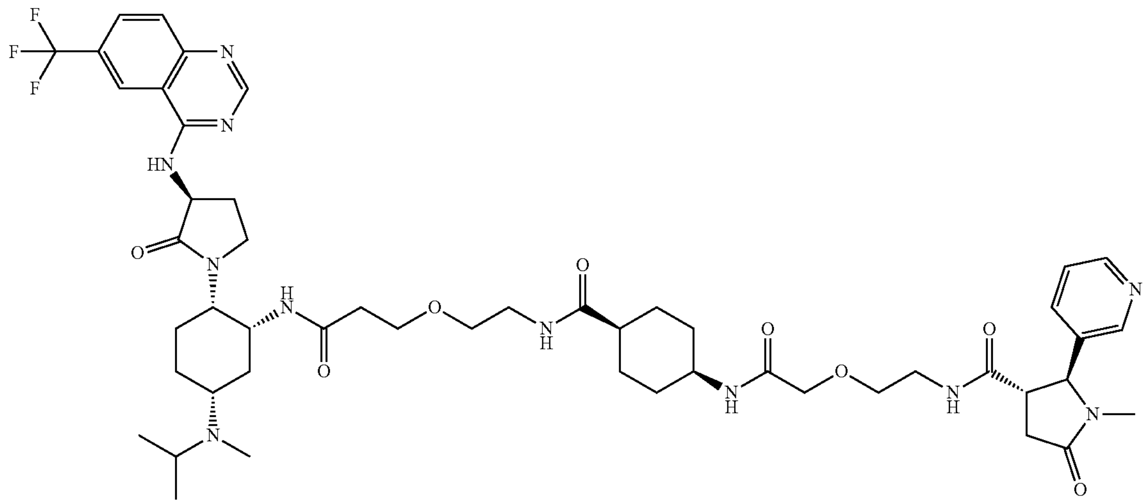 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)[C@H]2CC[C@@H](NC(=O)COCCNC(=O)[C@H]3CC(=O)N(C)[C@@H]3c3cccnc3)CC2)C1]

Step 1 tert-Butyl (2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethyl)carbamate

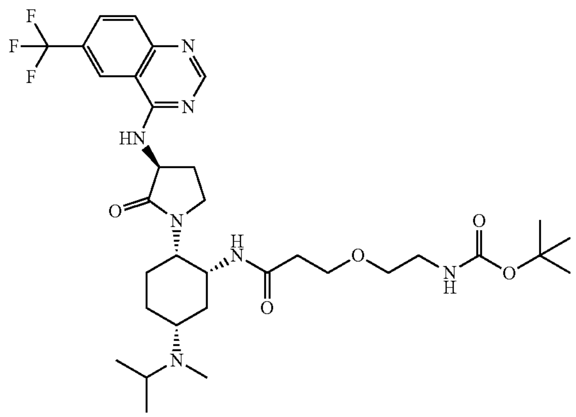 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)OC(C)(C)C)C1]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (220 mg, 0.409 mmol) and 3-(2-((tert-butoxycarbonyl)amino)ethoxy)propanoic acid (95 mg, 0.409 mmol) in dichloromethane (DCM) (0.5 mL) was added triethylamine (0.342 mL, 2.456 mmol) and HATU (187 mg, 0.491 mmol), and the mixture was stirred at rt for 2 h. Dichloromethane (DCM) and saturated $NaHCO_3$ were added and the aqueous phase was extracted with dichloromethane (DCM). The combined organic extracts were dried over $Na_2SO_4$, were filtered and the filtrate was concentrated. Purification by ISCO CombiFlash® chromatography (40 g silica column, 40 mL/min) eluting with a gradient of 0 to 20% methanol containing ammonium hydroxide (10%) in dichloromethane (DCM) provided the title compound (252 mg, 0.371 mmol, 91% yield). LC-MS m/z 680.4 $(M+H)^+$.

Step 2

3-(2-Aminoethoxy)-N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)propenamide, 2Hydrochloric acid salt

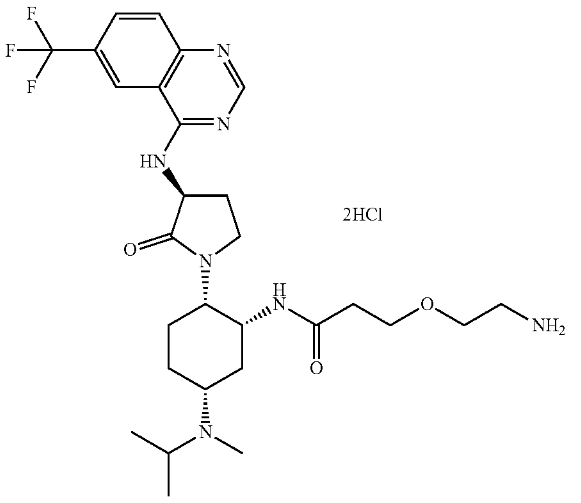 [SMILES: CC(C)N(C)[C@@H]1CC[C@H](N2CC[C@H](Nc3ncnc4ccc(C(F)(F)F)cc34)C2=O)[C@H](NC(=O)CCOCCN)C1]

To a mixture of tert-butyl (2-(3-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethyl)carbamate (250 mg, 0.368 mmol) in dichloromethane (DCM) (0.3 mL) was added HCl (0.552 mL, 2.207 mmol). The mixture was stirred at rt for 3 h and was concentrated provide the title compound (250 mg, 0.383 mmol, 104% yield). LC-MS m/z 580.2 $(M+H)^+$.

Step 3 tert-Butyl (1R,4s)-4-(2-(2-((2S,3S)-1-methyl-5-oxo-2-(pyridin-3-yl)pyrrolidine-3-carboxamido)ethoxy)acetamido)cyclohexane-1-carboxylate

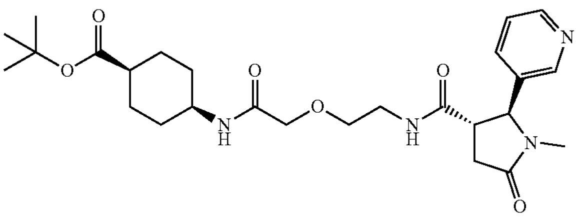 [SMILES: CN1C(=O)C[C@H](C(=O)NCCOCC(=O)N[C@H]2CC[C@@H](C(=O)OC(C)(C)C)CC2)[C@H]1c1cccnc1]

To a mixture of tert-butyl (1 s,45)-4-aminocyclohexane-1-carboxylate, hydrochloric acid salt (77 mg, 0.327 mmol) and 2-(2-((2S,3S)-1-methyl-5-oxo-2-(pyridin-3-yl)pyrrolidine-3-carboxamido)ethoxy)acetic acid (105 mg, 0.327 mmol) in dichloromethane (DCM) was added triethylamine (319 μL, 2.287 mmol) and HATU (149 mg, 0.392 mmol), the mixture was stirred at rt for 3 h, and was concentrated. Purification by ISCO CombiFlash® chromatography (40 g silica column, 40 mL/min) eluting with a gradient of 0 to 15% methanol containing ammonium hydroxide (10%) in dichloromethane (DCM) provided the title compound (87 mg, 0.173 mmol, 53.0% yield). LC-MS m/z 503.3 $(M+H)^+$.

Step 4

(1R,45)-4-(2-(2-((2S,3S)-1-Methyl-5-oxo-2-(pyridin-3-yl)pyrrolidine-3-carboxamido) ethoxy)acetamido)cyclohexane-1-carboxylic acid, Hydrochloric acid salt

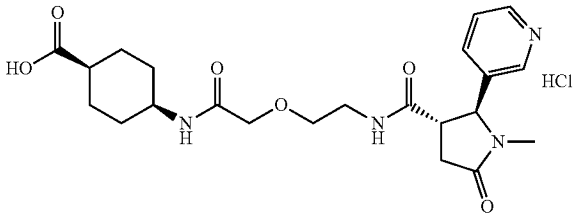 [SMILES: CN1C(=O)C[C@H](C(=O)NCCOCC(=O)N[C@H]2CC[C@@H](C(=O)O)CC2)[C@H]1c1cccnc1 ; Cl]

To a mixture of tert-butyl (1R,4s)-4-(2-(2-((2S,3S)-1-methyl-5-oxo-2-(pyridin-3-yl)pyrrolidine-3-carboxamido)ethoxy)acetamido)cyclohexane-1-carboxylate (85 mg, 0.169 mmol) in dichloromethane (DCM) (0.1 mL) was added HCl (0.211 mL, 0.846 mmol), the mixture was stirred at rt for 3 h, and was concentrated to dryness to provide the title compound (90 mg, 0.186 mmol, 110% yield). LC-MS m/z 447.2 $(M+H)^+$.

Step 5

(2S,3S)-N-(2-(2-(((1S,4R)-4-((2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethyl)carbamoyl)cyclohexyl)amino)-2-oxoethoxy)ethyl)-1-methyl-5-oxo-2-(pyridin-3-yl)pyrrolidine-3-carboxamide

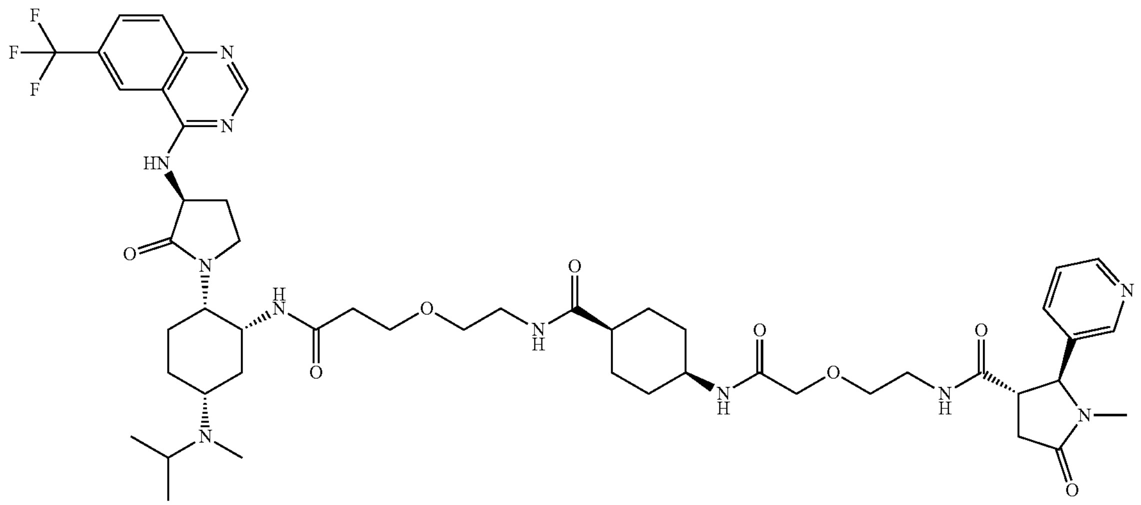 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)[C@H]2CC[C@@H](NC(=O)COCCNC(=O)[C@H]3CC(=O)N(C)[C@@H]3c3cccnc3)CC2)C1]

To a mixture of (1R,4s)-4-(2-(2-((2S,3S)-1-methyl-5-oxo-2-(pyridin-3-yl)pyrrolidine-3-carboxamido)ethoxy)acetamido)cyclohexane-1-carboxylic acid, hydrochloric acid salt (37 mg, 0.077 mmol) in dichloromethane (DCM) (0.5 mL) was added sequentially HATU (35.0 mg, 0.092 mmol), 3-(2-aminoethoxy)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)propanamide, 2hydrochloric acid salt (50.0 mg, 0.077 mmol), and triethylamine (0.075 mL, 0.536 mmol). The mixture was stirred at rt for 2 h and was concentrated. Purification by MDAP chromatography (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a white solid (42 mg, 0.042 mmol, 54.4% yield) as a white solid. LC-MS m/z 1009.5 $(M+H)^+$. $^1H$ NMR (400 MHz, METHANOL-$d_4$) δ ppm 1.04 (d, J=6.4 Hz, 3H) 1.13 (d, J=6.4 Hz, 3H) 1.53-1.81 (m, 12H) 2.05-2.33 (m, 8H) 2.42-2.62 (m, 4H) 2.64-2.66 (m, 1H) 2.69-2.78 (m, 2H) 2.79-2.88 (m, 1H) 3.01-3.10 (m, 1H) 3.22-3.31 (m, 3H) 3.37-3.48 (m, 6H) 3.51-3.73 (m, 5H) 3.76-3.82 (m, 1H) 3.95 (s, 3H) 4.06 (dt, J=12.3, 3.6 Hz, 1H) 4.63 (br d, J=3.4 Hz, 1H) 4.78-4.84 (m, 1H) 5.30 (t, J=8.3 Hz, 1H) 7.51 (dd, J=7.8, 4.9 Hz, 1H) 7.80 (dt, J=7.8, 2.0 Hz, 1H) 7.91 (d, J=8.8 Hz, 1H) 8.06 (dd, J=8.8, 2.0 Hz, 1H) 8.52 (d, J=2.0 Hz, 1H) 8.56 (dd, J=4.9, 2.0 Hz, 1H) 8.59 (s, 1H) 8.80 (s, 1H)

The following compounds were or could be prepared with procedures analogous to that described in Example 107:

| Ex. | Compound | LC-MS m/z | NMR |
|---|---|---|---|
| 108 | 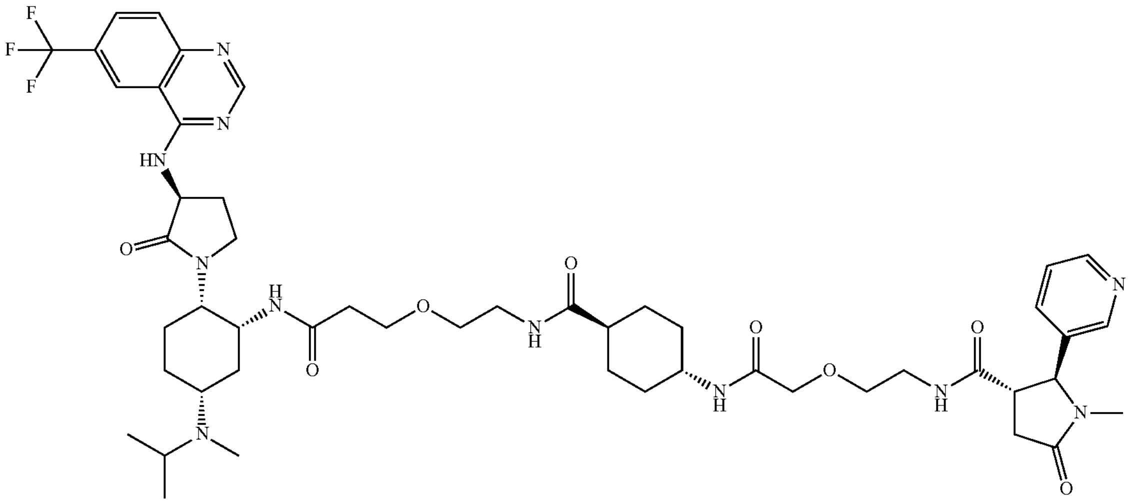 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)[C@H]2CC[C@H](NC(=O)COCCNC(=O)[C@H]3CC(=O)N(C)[C@@H]3c3cccnc3)CC2)C1] (2S,3S)-N-(2-(2-(((1R,4S)-4-((2-(3-(((1R,2S,5R)-5-(Isopropyl(methyl)amino)-2-((S)-2-oxo-3-((6-(trifluoromethyl)quinazolin-4-yl) amino) pyrrolidin-1-yl)cyclohexyl)amino)-3-oxopropoxy)ethyl)carbamoyl)cyclohexyl)amino)-2-oxoethoxy)ethyl)-1-methyl-5-oxo-2-(pyridin-3-yl)pyrrolidine-3-carboxamide. | 1008.5 (M + H)+ | $^1$H NMR (400 MHz, METHANOL-$d_4$) δ ppm 1.08 (br s, 3H) 1.17 (br d, J = 4.9 Hz, 3H) 1.23-1.36 (m, 2H) 1.47-1.62 (m, 2 H) 1.72-2.05 (m, 8H) 2.10-2.37 (m, 8H) 2.46 (t, J = 5.6 Hz, 2H) 2.51-2.60 (m, 1H) 2.67 (s, 3H) 2.69-2.76 (m, 1H) 2.79-2.93 (m, 2H) 3.04 (ddd, J = 9.3, 8.1, 6.6 Hz, 1H) 3.24-3.31 (m, 2H) 3.38-3.74 (m, 10H) 3.79 (dt, J = 9.4, 6.1 Hz, 1H) 3.91 (s, 2H) 4.07 (br d, J = 11.2 Hz, 1H) 4.44-4.72 (m, 1H) 4.83 (d, J = 6.4 Hz, 1H) 5.13-5.41 (m, 1H) 7.53 (dd, J = 7.8, 4.9 Hz, 1H) 7.80 (dt, J = 8.2, 1.8 Hz, 1 H) 7.91 (d, J = 8.8 Hz, 1H) 8.07 (dd, J = 8.8, 2.0 Hz, 1 H) 8.52 (s, 1H) 8.58 (br d, J = 3.4 Hz, 1H) 8.60 (s, 1 H) 8.79 (s, 1H). |

-continued

| Ex. | Compound | LC-MS m/z | NMR |
|---|---|---|---|
| 109 | 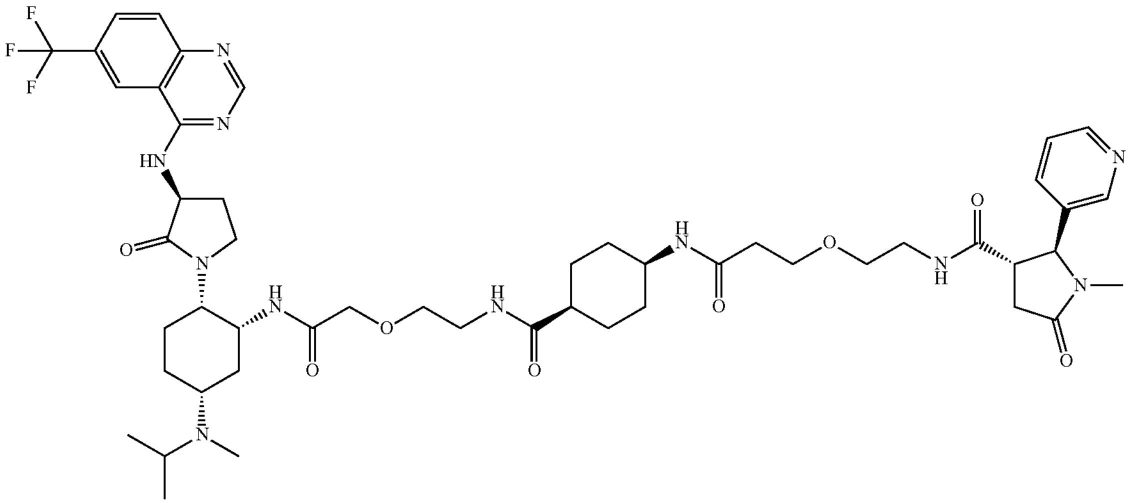 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)[C@H]2CC[C@@H](NC(=O)CCOCCNC(=O)[C@H]3CC(=O)N(C)[C@@H]3c3cccnc3)CC2)C1] (2S,3S)-N-(2-(3-(((1S,4R)-4-((2-(2-(((1R,2S,5R)-5-(Isopropyl(methyl)amino)-2-((S)-2-oxo-3-((6-(trifluoromethyl)quinazolin-4-yl) amino) pyrrolidin-1-yl)cyclohexyl)amino)-2-oxoethoxy)ethyl)carbamoyl)cyclohexyl)amino)-3-oxopropoxy)ethyl)-1-methyl-5-oxo-2-(pyridin-3-yl)pyrrolidine-3-carboxamide. | 1008.5 (M + H)+ | $^1$H NMR (400 MHz, METHANOL-$d_4$) δ ppm 0.99 (d, J = 6.8 Hz, 3H) 1.14 (d, J = 6.4 Hz, 3H) 1.43-1.84 (m, 12H) 1.93-2.07 (m, 1H) 2.16-2.35 (m, 8H) 2.37-2.47 (m, 2 H) 2.48-2.60 (m, 1H) 2.65-2.68 (m, 4H) 2.69-2.76 (m, 2H) 2.78-2.87 (m, 1H) 3.06 (ddd, J = 9.3, 8.1, 6.6 Hz, 1H) 3.35-3.55 (m, 7H) 3.59-3.69 (m, 5H) 3.81-3.98 (m, 1 H) 3.99-4.10 (m, 3H) 4.68 (br d, J = 2.9 Hz, 1H) 5.29 (t, J = 8.6 Hz, 1H) 7.49-7.55 (m, 1H) 7.79 (dt, J = 7.8, 2.0 Hz, 1H) 7.90 (d, J = 8.8 Hz, 1H) 8.05 (dd, J = 8.8, 2.0 Hz, 1H) 8.51-8.58 (m, 2H) 8.59 (s, 1H) 8.77 (s, 1H). |

-continued

| Ex. | Compound | LC-MS m/z | NMR |
| --- | --- | --- | --- |
| 110 | 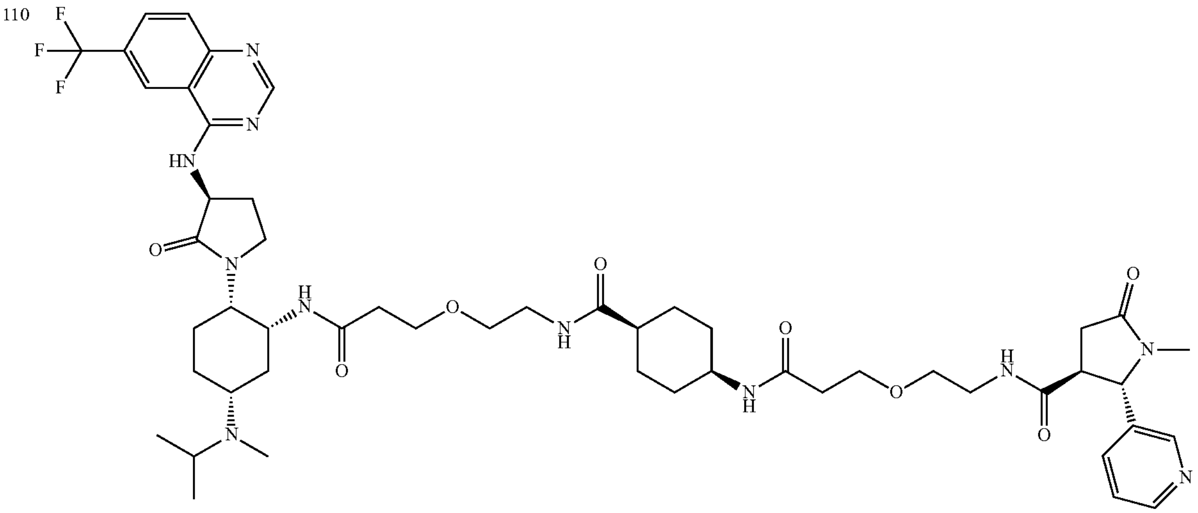 (2S,3S)-N-(2-(3-(((1S,4R)-4-((2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethyl)carbamoyl)cyclohexyl)amino)-3-oxopropoxy)ethyl)-1-methyl-5-oxo-2-(pyridin-3-yl)pyrrolidine-3-carboxamide. | 1022.5 (M + H)+ | $^1$H NMR (400 MHz, DMSO-$d_6$) δ ppm 0.23 (d, J = 6.4 Hz, 3H) 0.32 (d, J = 6.8 Hz, 3H) 0.75 (br dd, J = 8.6, 5.1 Hz, 5H) 0.83-0.98 (m, 8H) 1.09-1.42 (m, 4H) 1.42-1.49 (m, 5 H) 1.54-1.77 (m, 6H) 1.88-1.96 (m, 2H) 2.00 (d, J = 9.8 Hz, 1H) 2.25 (dd, J = 7.8, 1.5 Hz, 1H) 2.43-2.50 (m, 3H) 2.55-2.72 (m, 7H) 2.75-2.92 (m, 6H) 2.94-3.02 (m, 1 H) 3.04-3.12 (m, 1H) 3.25 (dt, J = 12.3, 3.6 Hz, 1 H) 3.83 (br d, J = 2.9 Hz, 1 H) 4.49 (t, J = 8.3 Hz, 1H) 6.71 (dd, J = 7.8, 4.9 Hz, 1 H) 6.96-7.00 (m, 1H) 7.10 (d, J = 8.8 Hz, 1H) 7.25 (dd, J = 8.8, 2.0 Hz, 1 H) 7.71 (d, J = 2.0 Hz, 1H) 7.77 (dd, J = 4.9, 1.5 Hz, 1 H) 7.79 (s, 1H) 7.99 (s, 1 H). |

Example 111

(2S,3S)-N-(17-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-5,11,17-trioxo-3,9,15-trioxa-6,12-diazaheptadecyl)-1-methyl-5-oxo-2-(pyridin-3-yl)pyrrolidine-3-carboxamide

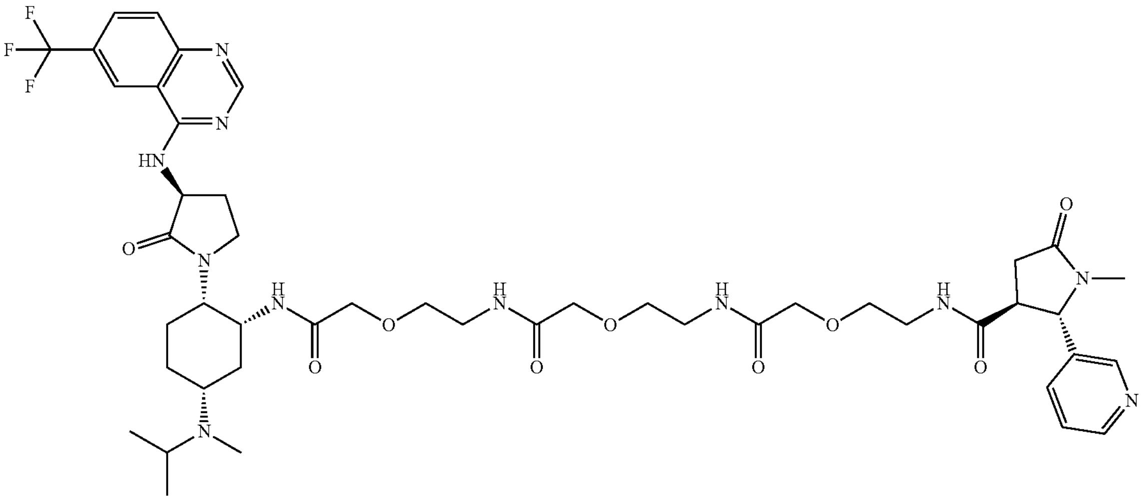 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)COCCNC(=O)COCCNC(=O)[C@H]2CC(=O)N(C)[C@@H]2c2cccnc2)C1]

Step 1 tert-Butyl 1-((2S,3S)-1-methyl-5-oxo-2-(pyridin-3-yl)pyrrolidin-3-yl)-1,7-dioxo-5,11-dioxa-2,8-diazatridecan-13-oate

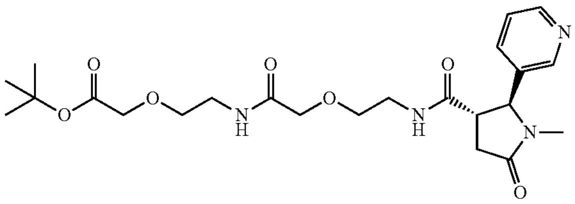 [SMILES: CN1C(=O)C[C@H](C(=O)NCCOCC(=O)NCCOCC(=O)OC(C)(C)C)[C@H]1c1cccnc1]

To a solution of 2-(2-((2S,3S)-1-methyl-5-oxo-2-(pyridin-3-yl) pyrrolidine-3-carboxamido)ethoxy)acetic acid, hydrochloric acid salt (320 mg, 0.894 mmol) in N,N-dimethylformamide (DMF) (4.0 mL) was added sequentially DIPEA (0.781 mL, 4.47 mmol), HOBt (137 mg, 0.894 mmol), HATU (510 mg, 1.342 mmol), and tert-butyl 2-(2-aminoethoxy)acetate (227 mg, 1.073 mmol) and the mixture was stirred for 4 h. Water was added and the mixture was extracted with ethyl acetate (3×). The combined organic extracts were washed with brine (2×), were dried over $Na_2SO_4$ were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a light-colored wax (295 mg, 0.616 mmol, 68.9% yield). LC-MS m/z 479.4 $(M+H)^+$.

Step 2 tert-Butyl 1-((2S,3S)-1-methyl-5-oxo-2-(pyridin-3-yl)pyrrolidin-3-yl)-1,7,13-trioxo-5,11,17-trioxa-2,8,14-triazanonadecan-19-oate

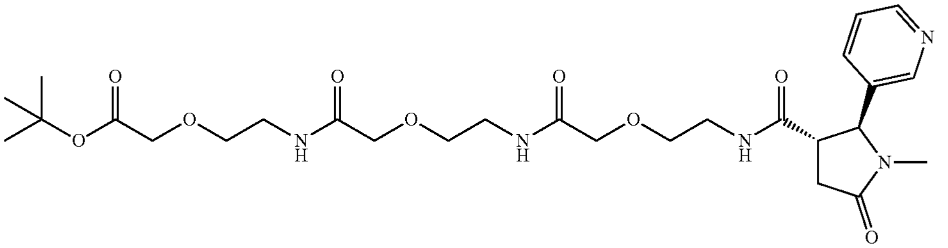 [SMILES: CN1C(=O)C[C@H](C(=O)NCCOCC(=O)NCCOCC(=O)NCCOCC(=O)OC(C)(C)C)[C@H]1c1cccnc1]

A mixture of tert-butyl 1-((2S,3S)-1-methyl-5-oxo-2-(pyridin-3-yl)pyrrolidin-3-yl)-1,7-dioxo-5,11-dioxa-2,8-diazatridecan-13-oate (130 mg, 0.272 mmol) and 4 M HCl in 1,4-dioxane (4 mL, 16.00 mmol) was stirred for 1 h and was concentrated. The residue was dissolved in N,N-dimethylformamide (DMF) (4.0 mL) and DIPEA (176 mg, 1.358 mmol), HOBt (41.6 mg, 0.272 mmol), HATU (155 mg, 0.407 mmol), and tert-butyl 2-(2-aminoethoxy)acetate (68.8 mg, 0.326 mmol) were added sequentially and the mixture was stirred overnight. Water was added and the mixture was extracted with ethyl acetate (3×). The combined organic extracts were washed with brine (2×), were dried over $Na_2SO_4$ were filtered, and the filtrate was concentrated. Purification by CombiFlash® Rf chromatography (40 g silica column, 40 mL/min) eluting with a gradient of 0 to 20% methanol in dichloromethane (DCM) provided the title compound as an off-white solid (95 mg, 0.164 mmol, 60.3% yield). LC-MS m/z 580.3 $(M+H)^+$.

Step 3

(2S,3S)-N-(17-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-5,11,17-trioxo-3,9,15-trioxa-6,12-diazaheptadecyl)-1-methyl-5-oxo-2-(pyridin-3-yl)pyrrolidine-3-carboxamide

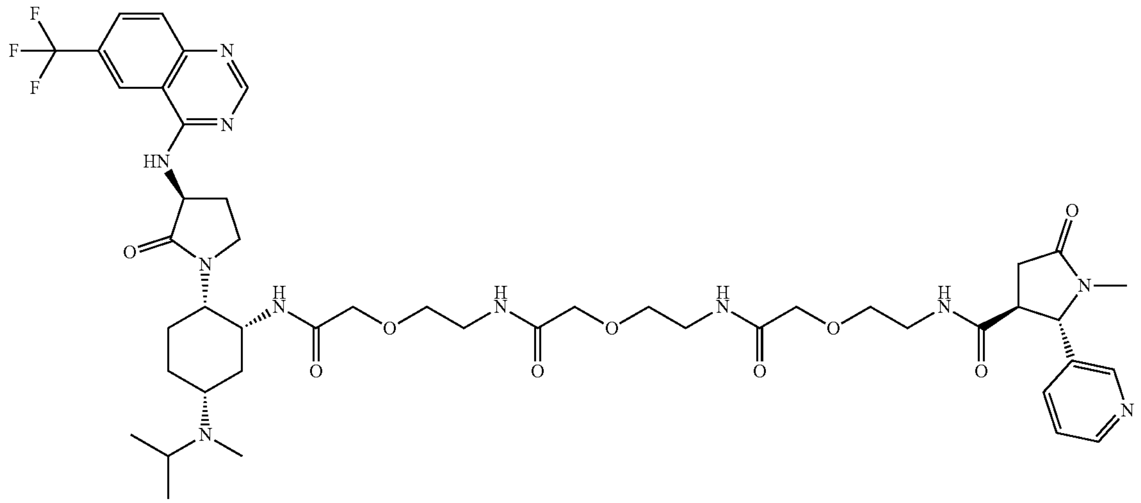 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)COCCNC(=O)COCCNC(=O)[C@H]2CC(=O)N(C)[C@@H]2c2cccnc2)C1]

To a solution of tert-butyl 1-((2S,3S)-1-methyl-5-oxo-2-(pyridin-3-yl)pyrrolidin-3-yl)-1,7,13-trioxo-5,11,17-trioxa-2,8,14-triazanonadecan-19-oate (43.1 mg, 0.074 mmol) in dichloromethane (DCM) (2.0 mL) was added 4 M HCl in 1,4-dioxane (4 mL, 16.00 mmol), the mixture was stirred for 1 h, and was concentrated. To the residue was added sequentially dichloromethane (DCM) (2.0 mL), (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (50 mg, 0.074 mmol), HOBt (11.40 mg, 0.074 mmol), DIPEA (0.065 mL, 0.372 mmol) and HATU (42.4 mg, 0.112 mmol), and the mixture was stirred at rt for 3 h. Saturated $NaHCO_3$ was added and the mixture was extracted with dichloromethane (DCM) (3×). The combined organic extracts were washed with brine (2×), were dried over $Na_2SO_4$ were filtered, and the filtrate was concentrated. Purification by MDAP chromatography (XSelect™ CSH C18 5 μm column, 40 mL/min) eluting with a gradient of 30 to 85% acetonitrile in water containing ammonium bicarbonate (10 mM) and ammonium hydroxide (0.075%) provided the title compound as an off-white solid (49.3 mg, 0.048 mmol, 64.9% yield). LC-MS m/z 970.2 $(M+H)^+$. $^1H$ NMR (400 MHz, DMSO-$d_6$) δ ppm 0.89 (d, J=6.4 Hz, 3H) 1.03 (d, J=6.4 Hz, 3H) 1.51-1.75 (m, 3H) 1.80-2.06 (m, 3H) 2.11 (s, 3H) 2.16 (br s, 1H) 2.22-2.36 (m, 1H) 2.41-2.50 (m, 3H) 2.52-2.62 (m, 3H) 2.64-2.81 (m, 2H) 2.83-2.97 (m, 1H) 3.20-3.32 (m, 6H) 3.36-3.57 (m, 8H) 3.83 (s, 4H) 3.86-4.03 (m, 4H) 4.52 (br d, J=4.4 Hz, 1H) 4.65 (d, J=6.4 Hz, 1H) 4.96-5.05 (m, 1H) 7.41-7.46 (m, 1H) 7.68 (dt, J=7.8, 2.0 Hz, 1H) 7.74-7.84 (m, 2H) 7.89 (d, J=8.8 Hz, 1H) 8.06 (dd, J=8.8, 2.0 Hz, 1H) 8.12 (br t, J=5.6 Hz, 1H) 8.47 (d, J=1.5 Hz, 1H) 8.55 (dd, J=4.9, 1.5 Hz, 1H) 8.59 (s, 1H) 8.63 (br d, J=8.3 Hz, 1H) 8.95 (s, 1H) 9.24 (br d, J=8.3 Hz, 1H).

Example 112

(2S,3S)-N-(2-(((1S,4S)-4-(3-(((1S,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)cyclohexyl)oxy)ethyl)-1-methyl-5-oxo-2-(pyridin-3-yl)pyrrolidine-3-carboxamide

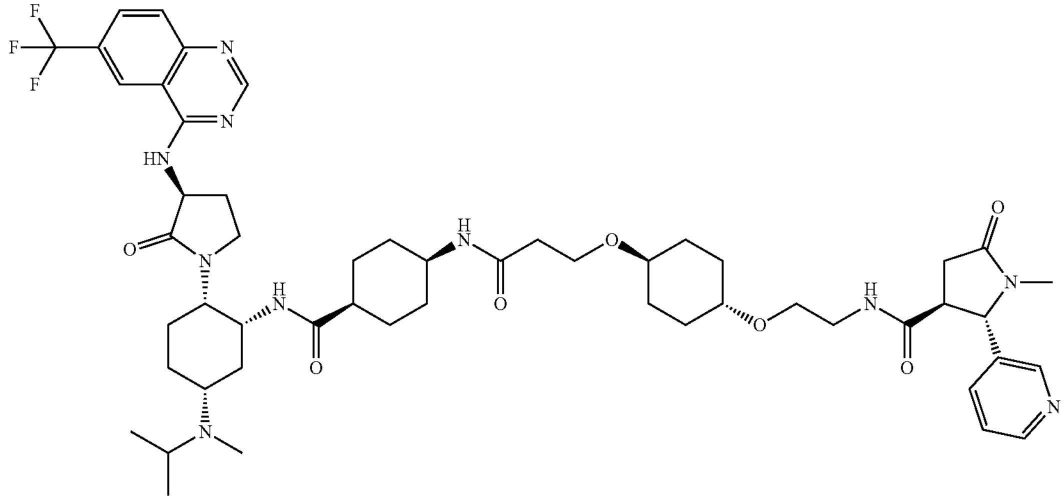 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCO[C@H]3CC[C@H](OCCNC(=O)[C@H]4CC(=O)N(C)[C@@H]4c4cccnc4)CC3)CC2)C1]

Step 1

N,N-Dibenzyl-2-chloroethan-1-amine

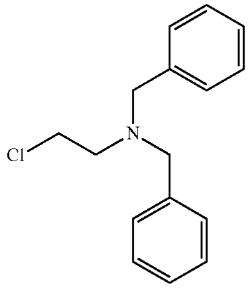 [SMILES: ClCCN(Cc1ccccc1)Cc1ccccc1]

Saturated $NaHCO_3$ was added to N,N-dibenzyl-2-chloroethan-1-amine, Hydrochloride (21 g, 70.9 mmol) (21 g, 70.9 mmol) at 0° C. and the mixture was extracted with dichloromethane (DCM). The combined organic extracts were dried over $Na_2SO_4$, were filtered, and the filtrate was concentrated to provide the title compound (18 g, 69.3 mmol, 98% yield). LC-MS m/z 260.3 $(M+H)^+$.

Step 2

(1r,4r)-4-(2-(Dibenzylamino)ethoxy)cyclohexan-1-ol

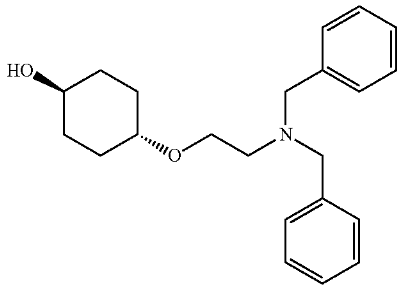 [SMILES: O[C@H]1CC[C@H](OCCN(Cc2ccccc2)Cc2ccccc2)CC1]

To a mixture of (1r,4r)-cyclohexane-1,4-diol (2 g, 17.22 mmol) in N,N-dimethylformamide (DMF) (20 mL) at 0° C. was added 60% sodium hydride (2.4 g, 60.0 mmol) and the mixture was stirred at rt for 30 min. The mixture was cooled to 0° C., N,N-dibenzyl-2-chloroethan-1-amine (5 g, 19.25 mmol) was added, and the mixture was stirred at 80° C. for 2 days. The mixture was cooled to rt, was poured into ice, and was extracted with ethyl acetate. The combined organic extracts were washed with water, with brine, were dried over $Na_2SO_4$, were filtered, and the filtrate was concentrated. Purification by reverse-phase HPLC (C18 Aq Gold 275 g column, 150 mL/min) eluting with a gradient of 40 to 63% acetonitrile containing ammonium hydroxide (1%) in water containing ammonium bicarbonate (10 mM) and ammonium hydroxide (0.075%) provided the title compound (961 mg, 2.83 mmol, 16.44% yield). LC-MS m/z 340.3 $(M+H)^+$.

Step 3 tert-Butyl 3-(((1S,4r)-4-(2-((2S,3S)-1-methyl-5-oxo-2-(pyridin-3-yl)pyrrolidine-3-carboxamido)ethoxy)cyclohexyl)oxy)propanoate

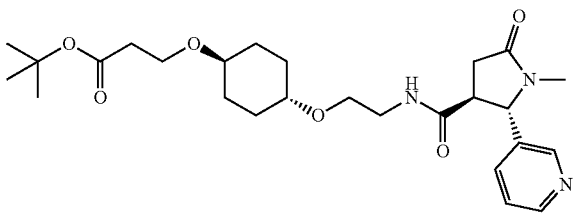 [SMILES: CN1C(=O)C[C@H](C(=O)NCCO[C@H]2CC[C@H](OCCC(=O)OC(C)(C)C)CC2)[C@H]1c1cccnc1]

To a mixture of (1r,4r)-4-(2-(dibenzylamino)ethoxy)cyclohexan-1-ol (144 mg, 0.424 mmol), tetrabutylammonium hydrogen sulfate (18.72 mg, 0.055 mmol), and sodium hydroxide (339 mg, 4.24 mmol) in dichloromethane (DCM) (3 mL) was added tert-butyl acrylate (0.249 ml, 1.697 mmol), and the mixture was stirred at rt for 4 h. Water and dichloromethane (DCM) were added and the aqueous phase was extracted with dichloromethane (DCM). The combined organic extracts were dried over $Na_2SO_4$, were filtered, and the filtrate was concentrated to provide intermediate tert-butyl 3-(((1r,4r)-4-(2-(dibenzylamino)ethoxy)cyclohexyl)oxy)propanoate. LC-MS m/z 468.2 $(M+H)^+$. 10% Pd—C(90 mg, 0.085 mmol) was added to tert-butyl 3-(((1r,4r)-4-(2-(dibenzylamino)ethoxy)cyclohexyl)oxy)propanoate in ethyl acetate (3 mL) and the mixture was stirred under a balloon atmosphere of hydrogen overnight. The mixture was filtered, the catalyst was washed with methanol, and the combined filtrates were concentrated. LC-MS m/z 288.2 $(M+H)^+$.

The residue was placed in dichloromethane (DCM) (2.00 mL), (2S,3S)-1-methyl-5-oxo-2-(pyridin-3-yl)pyrrolidine-3-carboxylic acid (93 mg, 0.424 mmol), HATU (194 mg, 0.509 mmol) and triethylamine (0.177 ml, 1.273 mmol) were added, and the mixture was stirred at rt for 2 h. Saturated $NaHCO_3$ and dichloromethane (DCM) were added and the aqueous phase was extracted with dichloromethane (DCM). The combined organic extracts were dried over $Na_2SO_4$, were filtered, and the filtrate was concentrated. Purification by ISCO CombiFlash® chromatography (24 g RediSep Rf Gold® column, 35 mL/min) eluting with a gradient of 0 to 15% methanol containing ammonium hydroxide (10%) in dichloromethane (DCM) provided the title compound (170 mg, 0.347 mmol, 82% yield). LC-MS m/z 490.1 $(M+H)^+$.

Step 4

3-(((1S,4r)-4-(2-((2S,3S)-1-Methyl-5-oxo-2-(pyridin-3-yl)pyrrolidine-3-carboxamido) ethoxy)cyclohexyl)oxy)propanoic acid, Hydrochloric acid salt

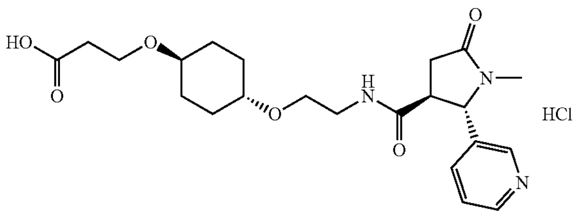 [SMILES: CN1C(=O)C[C@H](C(=O)NCCO[C@H]2CC[C@H](OCCC(=O)O)CC2)[C@H]1c1cccnc1 ; Cl]

To tert-butyl 3-(((1S,4r)-4-(2-((2S,3S)-1-methyl-5-oxo-2-(pyridin-3-yl)pyrrolidine-3-carboxamido)ethoxy)cyclohexyl)oxy)propanoate (170 mg, 0.347 mmol) in dichloromethane (DCM) (0.1 mL) was added 4 M HCl in dioxane (0.694 mL, 2.78 mmol), the mixture was stirred at rt for 3 h, and was concentrated to provide the title compound (175 mg, 0.372 mmol, 107% yield). LC-MS m/z 434.1 $(M+H)^+$.

Step 5

(2S,3S)-N-(2-(((1S,4S)-4-(3-(((1S,4S)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl) carbamoyl)cyclohexyl)amino)-3-oxopropoxy)cyclohexyl)oxy)ethyl)-1-methyl-5-oxo-2-(pyridin-3-yl)pyrrolidine-3-carboxamide

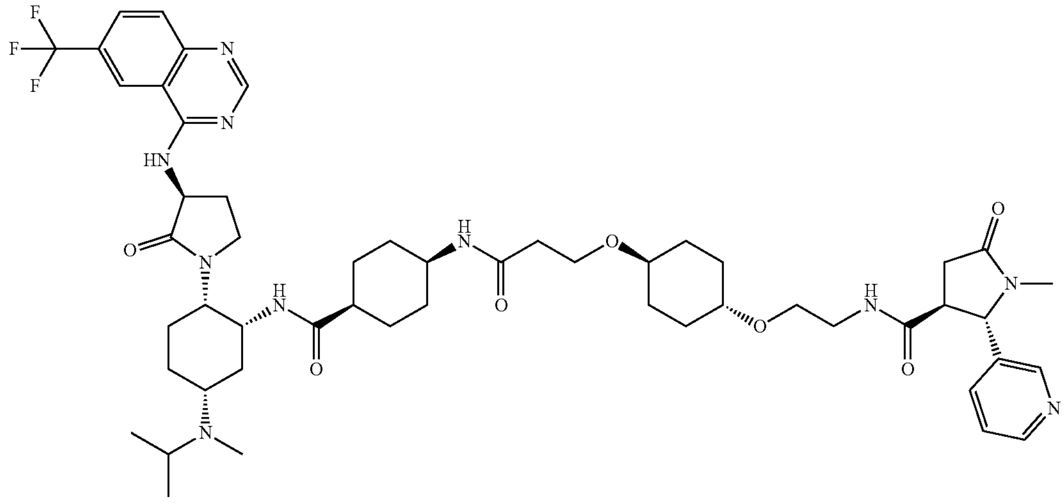 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCO[C@H]3CC[C@H](OCCNC(=O)[C@H]4CC(=O)N(C)[C@@H]4c4cccnc4)CC3)CC2)C1]

To (1 s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (56.4 mg, 0.085 mmol) and 3-(((1S,4r)-4-(2-((2S,3S)-1-methyl-5-oxo-2-(pyridin-3-yl)pyrrolidine-3-carboxamido)ethoxy)cyclohexyl)oxy)propanoic acid, hydrochloric acid salt (40 mg, 0.085 mmol) in dichloromethane (DCM) was added triethylamine (95 μL, 0.681 mmol) and HATU (38.8 mg, 0.681 mmol), the mixture was stirred at rt for 2 h, and was concentrated. Purification by reverse-phase chromatography (XSelect™ CSH Prep C18 5 μm OBD column, 40 mL/min) eluting with a gradient of 30 to 85% acetonitrile containing ammonium hydroxide (1%) in water containing ammonium bicarbonate (10 mM) and ammonium hydroxide (0.075%) provided the title compound as a solid (56 mg, 0.056 mmol, 65.5% yield). LC-MS m/z 503.4 $(M/2+H)^+$. $^1H$ NMR (400 MHz, METHANOL-$d_4$) δ ppm 1.01 (d, J=6.4 Hz, 3H) 1.12-1.28 (m, 7H) 1.66 (td, J=8.9, 4.2 Hz, 3H) 1.70-1.83 (m, 9H) 1.83-1.97 (m, 4H) 2.09-2.26 (m, 3H) 2.27 (s, 3H) 2.30-2.42 (m, 3H) 2.52-2.63 (m, 1H) 2.66 (s, 3H) 2.67-2.77 (m, 2H) 2.78-2.89 (m, 1H) 3.01-3.10 (m, 1H) 3.12-3.20 (m, 1H) 3.21-3.31 (m, 3H) 3.34-3.49 (m, 4H) 3.52-3.59 (m, 1H) 3.59-3.72 (m, 3H) 3.86-3.95 (m, 1H) 4.04 (dt, J=12.5, 3.8 Hz, 1H) 4.61 (br d, J=2.9 Hz, 1H) 5.32 (t, J=8.8 Hz, 1H) 7.52 (dd, J=7.8, 4.9 Hz, 1H) 7.79 (dt, J=7.8, 2.0 Hz, 1H) 7.91 (d, J=8.8 Hz, 1H) 8.07 (dd, J=8.8, 2.0 Hz, 1H) 8.51 (d, J=2.0 Hz, 1H) 8.56-8.61 (m, 2H) 8.73 (s, 1H)

The following compounds were or could be prepared with procedures analogous to that described in Example 112:

| Ex. | Compound | LC-MS m/z | NMR |
|---|---|---|---|
| 113 | 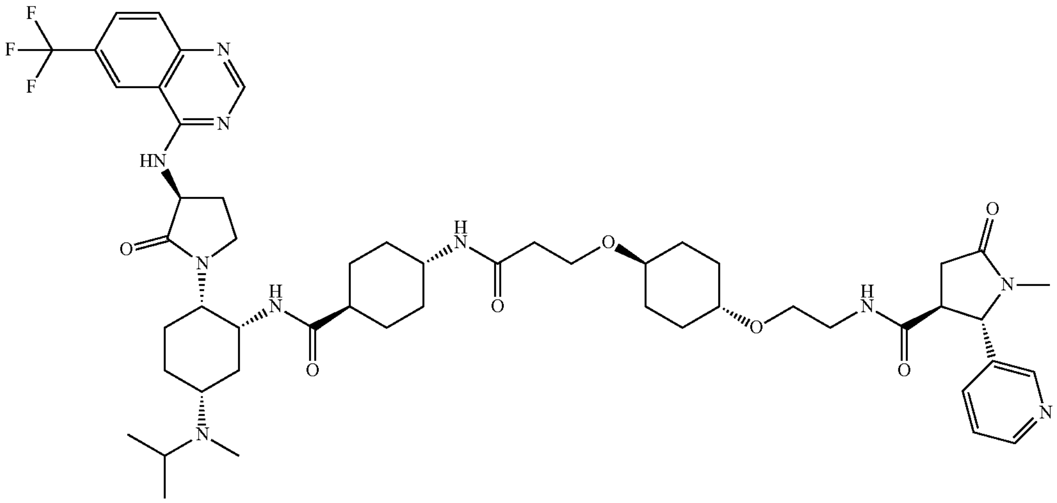 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCO[C@H]3CC[C@H](OCCNC(=O)[C@H]4CC(=O)N(C)[C@@H]4c4cccnc4)CC3)CC2)C1]<br>(2S,3S)-N-(2-(((1R,4S)-4-(3-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)cyclohexyl)oxy)ethyl)- 1-methyl-5-oxo-2-(pyridin-3-yl)pyrrolidine-3-carboxamide. | 503.5 (M/2 + H)+ | 1H NMR (400 MHz, METHANOL-d4) δ ppm 0.95-1.65 (m, 10H) 1.74-2.44 (m, 13H) 2.51-2.91 (m, 8H) 3.02-3.13 (m, 1 H) 3.21-4.04 (m, 23H) 4.13-4.38 (m, 2H) 4.85 (d, J = 6.85 Hz, 1H) 5.12-5.26 (m, 1H) 7.57 (dd, J = 8.07, 4.65 Hz, 1H) 7.85 (dt, J = 7.95, 1.90 Hz, 1H) 7.97 (d, J = 8.80 Hz, 1H) 8.20 (dd, J = 8.80, 1.47 Hz, 1H) 8.47-8.65 (m, 2H) 8.74 (s, 1H) 8.88 (s, 1H) |

-continued

| Ex. | Compound | LC-MS m/z | NMR |
|---|---|---|---|
| 114 | 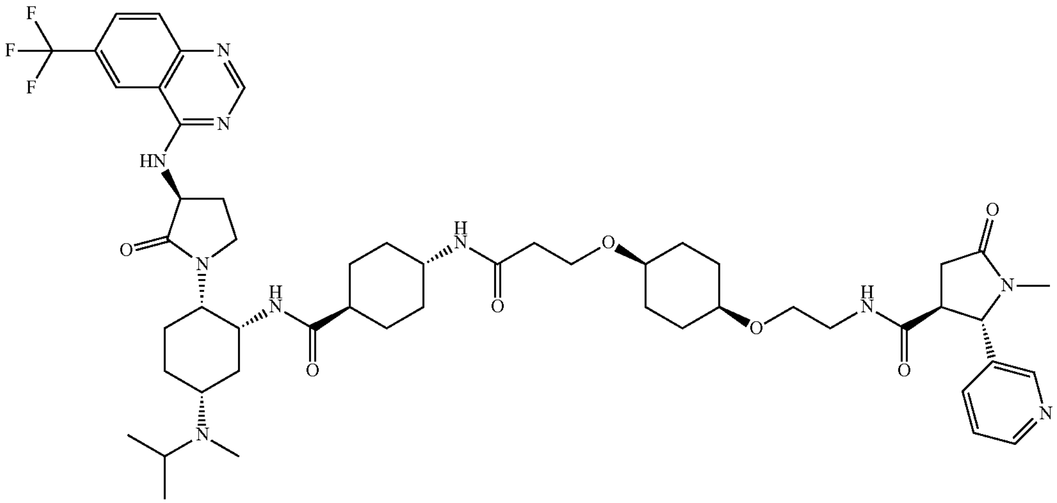 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCO[C@H]3CC[C@@H](OCCNC(=O)[C@H]4CC(=O)N(C)[C@@H]4c4cccnc4)CC3)CC2)C1] (2S,3S)-N-(2-(((1S,4R)-4-(3-(((1R,4R)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)cyclohexyl)oxy)ethyl)-1-methyl-5-oxo-2-(pyridin-3-yl)pyrrolidine-3-carboxamide. | 1005.2 (M + H)+ | $^1$H NMR (400 MHz, METHANOL-$d_4$) δ ppm 1.02 (d, J = 6.4 Hz, 3H) 1.16 (br d, J = 6.4 Hz, 3H) 1.19-1.31 (m, 2H) 1.49-1.77 (m, 14 H) 1.90-2.03 (m, 6H) 2.07-2.17 (m, 2H) 2.20-2.39 (m, 7H) 2.54 (dtd, J = 12.3, 8.2, 8.2, 3.7 Hz, 1H) 2.63-2.74 (m, 6H) 3.02-3.09 (m, 1H) 3.25-3.35 (m, 6H) 3.38-3.54 (m, 5H) 3.59-3.70 (m, 4H) 4.02 (dt, J = 12.6, 3.5 Hz, 1H) 4.66 (br d, J = 2.9 Hz, 1H) 5.27 (t, J = 8.1 Hz, 1H) 7.52 (dd, J = 7.8, 4.9 Hz, 1H) 7.79 (dt, J = 7.8, 2.0 Hz, 1H) 7.91 (d, J = 8.3 Hz, 1H) 8.06 (dd, J = 8.8, 2.0 Hz, 1H) 8.51 (d, J = 2.4 Hz, 1H) 8.57 (dd, J = 4.9, 1.5 Hz, 1H) 8.59 (s, 1H) 8.81 (s, 1H). |

-continued

| Ex. | Compound | LC-MS m/z | NMR |
|---|---|---|---|
| 115 | 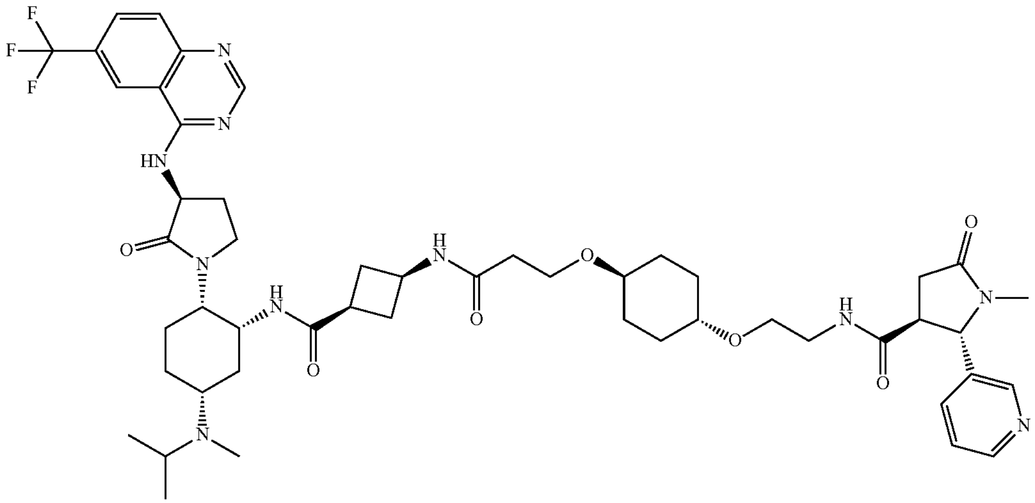 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@@H](NC(=O)CCO[C@H]3CC[C@H](OCCNC(=O)[C@H]4CC(=O)N(C)[C@@H]4c4cccnc4)CC3)C2)C1] (2S,3S)-N-(2-(((1S,4S)-4-(3-(((1S,3S)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)cyclohexyl)oxy)ethyl)-1-methyl-5-oxo-2-(pyridin-3-yl)pyrrolidine-3-carboxamide. | 978.0 (M + H)+ | $^1$H NMR (400 MHz, METHANOL-$d_4$) δ ppm 1.02 (br d, J = 6.4 Hz, 3H) 1.15 (br d, J = 6.4 Hz, 3H) 1.17-1.29 (m, 4H) 1.59-2.03 (m, 8H) 2.09-2.23 (m, 4H) 2.26 (s, 3H) 2.31 (t, J = 6.1 Hz, 3H) 2.48-2.63 (m, 3H) 2.66 (s, 3H) 2.69-2.79 (m, 3H) 2.79-2.91 (m, 1H) 3.02-3.11 (m, 1H) 3.13-3.21 (m, 1H) 3.21-3.30 (m, 2H) 3.35-3.39 (m, 1H) 3.39-3.46 (m, 3H) 3.50 (td, J = 9.3, 2.4 Hz, 1H) 3.59-3.74 (m, 3H) 4.02 (dt, J = 12.2, 3.7 Hz, 1H) 4.15-4.34 (m, 1H) 4.61 (br d, J = 2.9 Hz, 1H) 4.84 (s, 1H) 5.32 (t, J = 8.8 Hz, 1H) 7.52 (dd, J = 7.8, 4.9 Hz, 1H) 7.79 (dt, J = 7.8, 2.0 Hz, 1H) 7.91 (d, J = 8.8 Hz, 1 H) 8.06 (dd, J = 8.8, 2.0 Hz, 1 H) 8.51 (d, J = 2.0 Hz, 1H) 8.55-8.62 (m, 2H) 8.76 (s, 1H). |

-continued

| Ex. | Compound | LC-MS m/z | NMR |
|---|---|---|---|
| 116 | 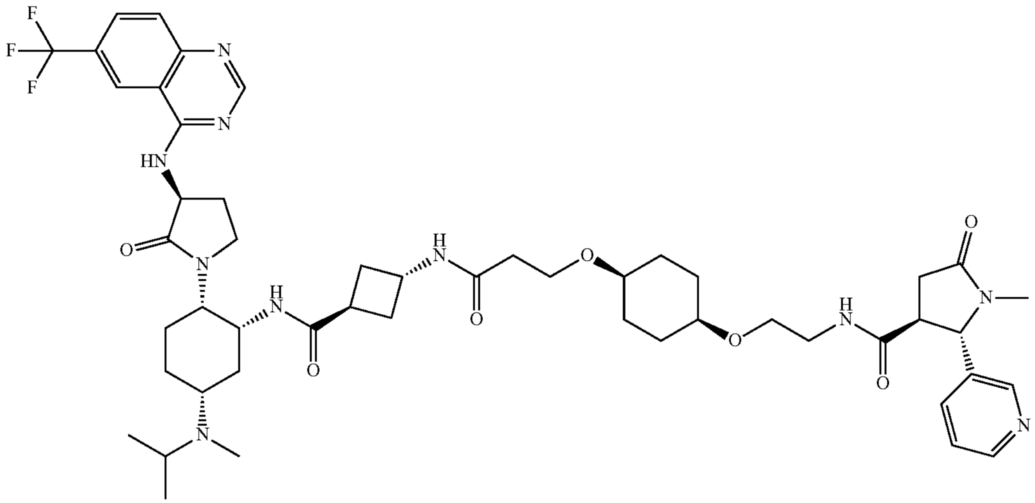 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCO[C@H]3CC[C@@H](OCCNC(=O)[C@H]4CC(=O)N(C)[C@@H]4c4cccnc4)CC3)C2)C1] (2S,3S)-N-(2-(((1S,4R)-4-(3-(((1R,3R)-3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)cyclohexyl)oxy)ethyl)-1-methyl-5-oxo-2-(pyridin-3-yl)pyrrolidine-3-carboxamide | 977.6 (M + H)+ | $^1$H NMR (400 MHz, METHANOL-$d_4$) δ ppm 0.90-1.29 (m, 6H) 1.42-1.57 (m, 4H) 1.58-1.72 (m, 4H) 1.74-1.90 (m, 2H) 1.95-2.45 (m, 11H) 2.47-2.62 (m, 4H) 2.63-2.67 (m, 3H) 2.67-3.13 (m, 6H) 3.37-3.52 (m, 3H) 3.61-3.69 (m, 3H) 3.96-4.73 (m, 5H) 4.83 (d, J = 6.8 Hz, 1H) 5.10-5.56 (m, 2H) 7.49-7.57 (m, 1H) 7.80 (dt, J = 7.8, 2.0 Hz, 1H) 7.91 (d, J = 8.8 Hz, 1 H) 8.07 (dd, J = 8.8, 2.0 Hz, 1 H) 8.51 (d, J = 2.0 Hz, 1H) 8.57 (dd, J = 4.9, 2.0 Hz, 1H) 8.58-8.61 (m, 1H) 8.75 (br s, 2H). |

-continued
| Ex. | Compound | LC-MS m/z | NMR |
|---|---|---|---|
| 117 | 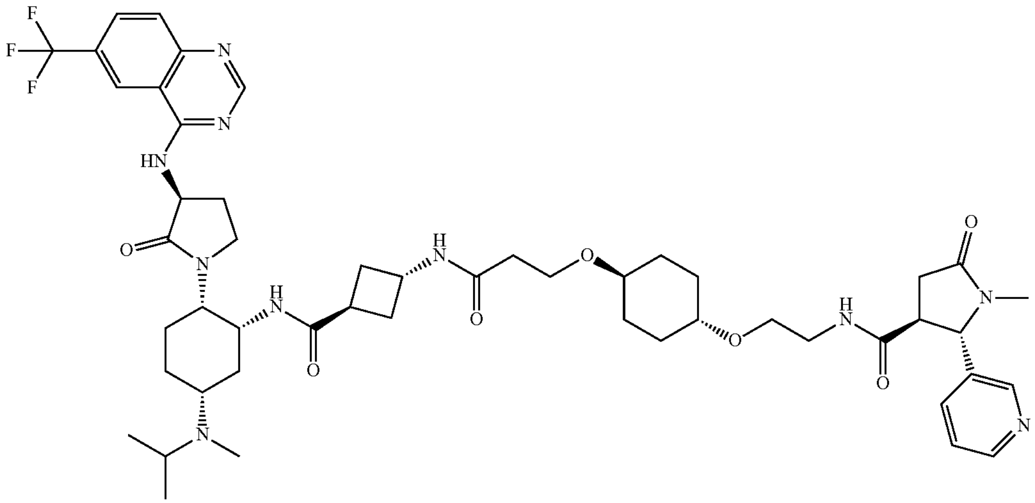 [SMILES: CC(C)N(C)[C@@H]1CC[C@H](N2CC[C@H](Nc3ncnc4ccc(C(F)(F)F)cc34)C2=O)[C@H](NC(=O)[C@H]2C[C@H](NC(=O)CCO[C@H]3CC[C@H](OCCNC(=O)[C@H]4CC(=O)N(C)[C@@H]4c4cccnc4)CC3)C2)C1] (2S,3S)-N-(2-(((1R,4S)-4-(3-(((1R,3R)-3-(((1R,2S,5R)-5-lisopropyl(methyl)amino)-2-((S)-2-oxo-3-((6-(trifluoromethyl)quinazolin-4-yl)amino)pyrrolidin-1-yl)cyclohexyl)carbamoyl)cyclobutyl)amino)-3-oxopropoxy)cyclohexyl)oxy)ethyl)-1-methyl-5-oxo-2-(pyridin-3-yl)pyrrolidine-3-carboxamide. | 977.1 (M + H)+ | $^{1}$H NMR (400 MHz, METHANOL-$d_4$) δ ppm 0.99 (br d, J = 5.9 Hz, 3H) 1.06-1.14 (m, 3H) 1.16-1.29 (m, 4H) 1.62-1.77 (m, 3H) 1.79-1.93 (m, 4H) 1.93-2.01 (m, 1H) 2.08-2.37 (m, 10H) 2.48-2.86 (m, 10H) 2.95-3.09 (m, 2H) 3.34-3.52 (m, 5H) 3.59-3.68 (m, 3H) 3.99-4.07 (m, 1H) 4.35-4.44 (m, 1H) 4.60-4.65 (m, 1H) 4.80-4.83 (m, 1H) 5.25-5.34 (m, 1H) 7.47-7.55 (m, 1H) 7.75-7.81 (m, 1H) 7.85-7.92 (m, 1H) 8.00-8.08 (m, 1H) 8.47-8.52 (m, 1H) 8.53-8.59 (m, 2H) 8.73-8.78 (m, 1H). |

Example 118

(S)-N-(2-(2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethoxy)ethyl)-1-(2-(2-((2S,3S)-1-methyl-5-oxo-2-(pyridin-3-yl)pyrrolidine-3-carboxamido)ethoxy)ethyl)pyrrolidine-2-carboxamide

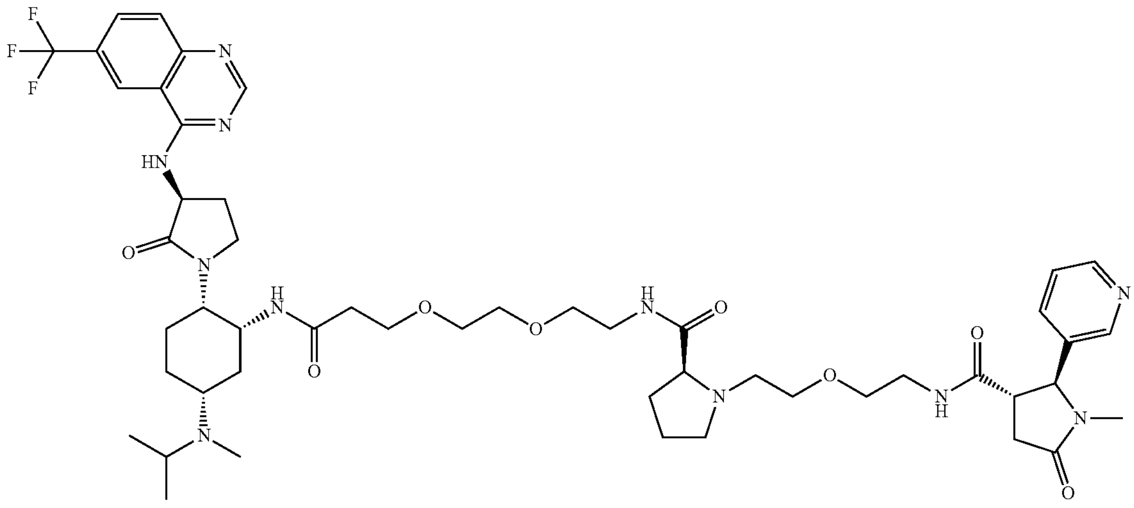 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)[C@@H]2CCCN2CCOCCNC(=O)[C@H]2CC(=O)N(C)[C@@H]2c2cccnc2)C1]

Step 1

3-(2-(2-Aminoethoxy)ethoxy)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)propenamide, 2Hydrochloric acid salt

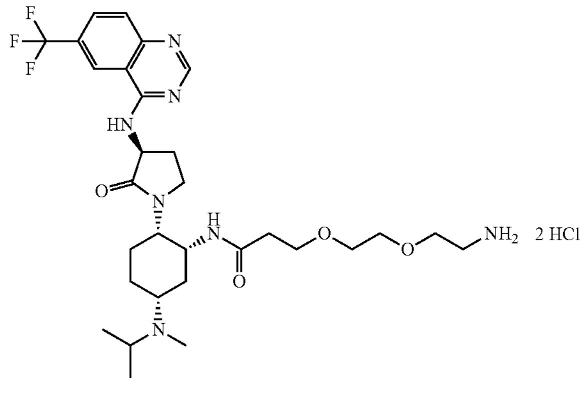 [SMILES: CC(C)N(C)[C@@H]1CC[C@H](N2CC[C@H](Nc3ncnc4ccc(C(F)(F)F)cc34)C2=O)[C@H](NC(=O)CCOCCOCCN)C1]

HCl (0.028 mL, 0.113 mmol) was added to tert-butyl (2-(2-(3-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethoxy)ethyl) carbamate (90 mg, 0.124 mmol) in dichloromethane (DCM) (0.5 mL) and the mixture was stirred at rt for 40 min. Dichloromethane (DCM) (0.5 ml) and HCl (0.028 mL, 0.113 mmol) were added and the mixture was stirred at rt for 1 h. The mixture was concentrated to provide the title compound as a solid (100 mg, 0.144 mmol, 127% yield). LC-MS m/z 624.2 $(M+H)^+$.

Step 2 tert-Butyl (2-(2-((tert-butoxycarbonyl)amino)ethoxy)ethyl)-L-prolinate

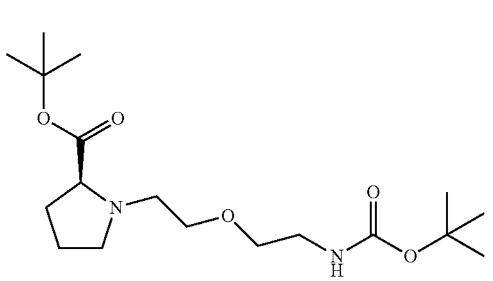 [SMILES: CC(C)(C)OC(=O)NCCOCCN1CCC[C@H]1C(=O)OC(C)(C)C]

To a mixture of tert-butyl (2-(2-bromoethoxy)ethyl)carbamate (310 mg, 1.156 mmol) and tert-butyl L-prolinate (H-Pro-OtBu) (198 mg, 1.156 mmol) in acetonitrile (8 mL) was added potassium carbonate (240 mg, 1.734 mmol). The mixture was stirred at 80° C. for 2 h, at rt over the weekend, and at 80° C. for 3 h. Water and dichloromethane (DCM) were added and the aqueous phase was extracted with dichloromethane (DCM). The combined organic phases were dried over $Na_2SO_4$, were filtered, and the filtrate was concentrated. Purification by ISCO CombiFlash® chromatography (24 g RediSep Rf Gold® column, 35 mL/min) eluting with a gradient of 0 to 12% methanol in dichloromethane (DCM) provided the title compound as a colorless oil (300 mg, 0.837 mmol, 72.4% yield). LC-MS m/z 359.3 $(M+H)^+$.

Step 3

(2-(2-Aminoethoxy)ethyl)-L-proline, 2Hydrochloric acid salt

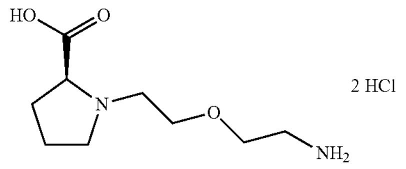 [SMILES: NCCOCCN1CCC[C@H]1C(=O)O]

To tert-butyl (2-(2-((tert-butoxycarbonyl)amino)ethoxy)ethyl)-L-prolinate (300 mg, 0.837 mmol) in dichloromethane (DCM) (1 mL) was added HCl (1.046 mL, 4.18 mmol). The mixture was stirred at rt for 2 h and was concentrated to provide the title compound as a foam (280 mg, 1.018 mmol, 122% yield). LC-MS m/z 203.2 $(M+H)^+$.

Step 4

(2-(2-((2S,3S)-1-Methyl-5-oxo-2-(pyridin-3-yl)pyrrolidine-3-carboxamido)ethoxy)ethyl)-L-proline

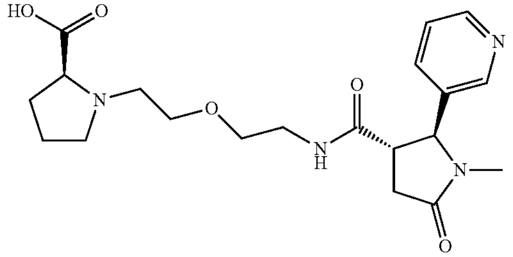 [SMILES: CN1C(=O)C[C@H](C(=O)NCCOCCN2CCC[C@H]2C(=O)O)[C@H]1c1cccnc1]

To a mixture of (2S,3S)-1-methyl-5-oxo-2-(pyridin-3-yl)pyrrolidine-3-carboxylic acid (106 mg, 0.481 mmol) in DMSO (0.5 ml) was added TSTU (145 mg, 0.481 mmol) and triethylamine (0.201 mL, 1.444 mmol) and the mixture was stirred at rt for 40 min. (2-(2-Aminoethoxy)ethyl)-L-proline, 2hydrochloric acid salt (159 mg, 0.578 mmol) and triethylamine (0.201 mL, 1.444 mmol) were added and the mixture was stirred at rt for 2 h. Purification by ISCO CombiFlash® EZ Prep chromatography (C18 Aq Gold column, 40 mL/min) eluting with a gradient of acetonitrile in water containing ammonium bicarbonate (10 mM) and ammonium hydroxide (0.075%) provided the title compound (100 mg, 0.227 mmol, 47.1% yield). LC-MS m/z 405.1 $(M+H)^+$.

Step 5

(S)-N-(2-(2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethoxy)ethyl)-1-(2-(2-((2S,3S)-1-methyl-5-oxo-2-(pyridin-3-yl)pyrrolidine-3-carboxamido)ethoxy)ethyl)pyrrolidine-2-carboxamide

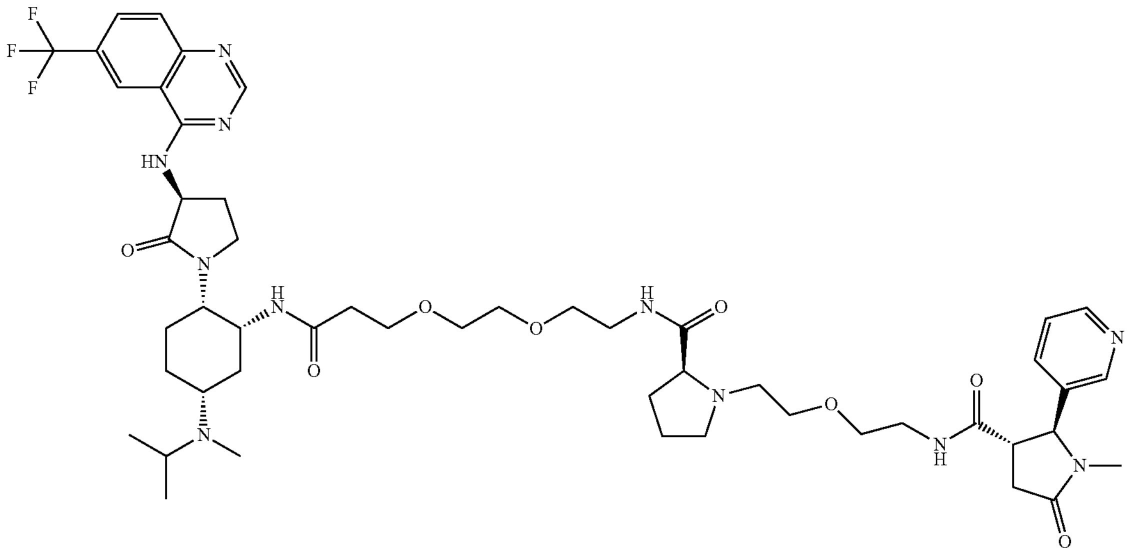 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)[C@@H]2CCCN2CCOCCNC(=O)[C@H]2CC(=O)N(C)[C@@H]2c2cccnc2)C1]

To a mixture of 3-(2-(2-aminoethoxy)ethoxy)-N-((1R,2S,5R)-5-(isopropyl(methyl)amino)-2-((S)-2-oxo-3-((6-(trifluoromethyl)quinazolin-4-yl)amino) pyrrolidin-1-yl)cyclohexyl) propanamide, 2hydrochloric acid salt (52 mg, 0.075 mmol) and (2-(2-((2S,3S)-1-methyl-5-oxo-2-(pyridin-3-yl) pyrrolidine-3-carboxamido)ethoxy)ethyl)-L-proline (30.2 mg, 0.075 mmol) in dichloromethane (DCM) (0.5 mL) was added triethylamine (0.052 mL, 0.373 mmol) and the mixture was stirred at rt for 1 h. HATU (34.1 mg, 0.090 mmol) was added and the mixture was stirred at rt for 1 h. The mixture was purified by ISCO CombiFlash® chromatography (24 g RediSep Rf Gold® column, 35 mL/min) eluting with a gradient of 0 to 15% methanol containing ammonium hydroxide (10%) in dichloromethane (DCM). A second purification by ISCO CombiFlash® chromatography (12 g RediSep Rf Gold® column, 30 mL/min) eluting with a gradient of 0 to 15% methanol containing ammonium hydroxide (10%) in dichloromethane (DCM) provided the title compound as a solid (36 mg, 0.036 mmol, 47.7% yield). LC-MS m/z 1010.3 $(M+H)^+$. $^1H$ NMR (400 MHz, METHANOL-$d_4$) δ ppm 0.94-1.08 (m, 3H) 1.15 (br d, J=6.3 Hz, 3H) 1.57-1.85 (m, 6H) 1.90-2.02 (m, 1H) 2.04-2.19 (m, 2H) 2.20-2.59 (m, 8H) 2.63-2.79 (m, 7H) 2.80-2.92 (m, 1H) 2.96-3.05 (m, 1H) 3.08-3.21 (m, 2H) 3.24-3.33 (m, 2H) 3.34-3.63 (m, 13H) 3.65-3.76 (m, 2H) 3.77-3.86 (m, 1H) 3.98-4.18 (m, 1H) 4.58-4.70 (m, 1H) 4.80-4.85 (m, 1H) 5.31 (t, J=8.1 Hz, 1H) 7.49-7.56 (m, 1H) 7.77-7.85 (m, 1H) 7.92 (d, J=8.9 Hz, 1H) 8.06 (d, J=1.8 Hz, 1H) 8.50-8.54 (m, 1H) 8.55-8.59 (m, 1H) 8.59-8.63 (m, 1H) 8.83 (s, 1H).

Example 119

(2S,3S)-N-(20-(((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)amino)-10,20-dioxo-3,6,14,17-tetraoxa-9,11-diazaicosyl)-1-methyl-5-oxo-2-(pyridin-3-yl)pyrrolidine-3-carboxamide

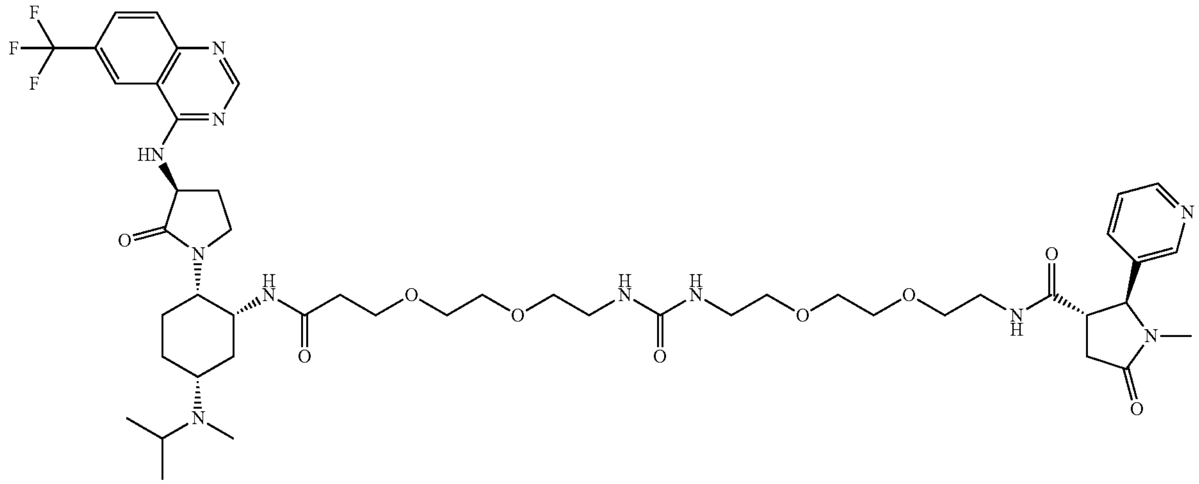 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)NCCOCCOCCNC(=O)[C@H]2CC(=O)N(C)[C@@H]2c2cccnc2)C1]

Step 1 tert-Butyl (2-(2-(2-((2S,3S)-1-methyl-5-oxo-2-(pyridin-3-yl)pyrrolidine-3-carboxamido)ethoxy)ethoxy) ethyl)carbamate

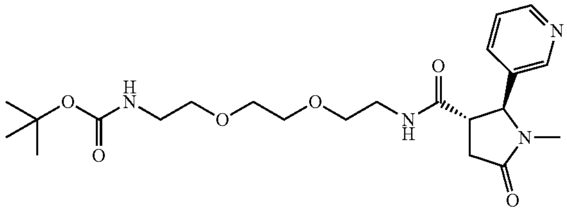 [SMILES: CN1C(=O)C[C@H](C(=O)NCCOCCOCCNC(=O)OC(C)(C)C)[C@H]1c1cccnc1]

To a mixture of tert-butyl (2-(2-(2-aminoethoxy)ethoxy) ethyl)carbamate (262 mg, 1.055 mmol) and (2S,3S)-1-methyl-5-oxo-2-(pyridin-3-yl)pyrrolidine-3-carboxylic acid (232 mg, 1.055 mmol) in dichloromethane (DCM) (3517 µL) was added DIPEA (737 µL, 4.22 mmol) and EDC (196 µL, 1.108 mmol), the mixture was stirred at rt for 20 h, and was concentrated under reduced pressure. Purification by ISCO CombiFlash® Rf chromatography (24 g silica column, 35 mL/min) eluting with a gradient of 0% (5 column volumes), 0 to 5% (30 column volumes), 5% (4 column volumes) methanol in dichloromethane containing triethylamine (0.1%) provided the title compound as a clear, sticky solid (323 mg, 0.645 mmol, 61.2% yield). LC-MS m/z 451.3 $(M+H)^+$.

Step 2

(2S,3S)-N-(2-(2-(2-Aminoethoxy)ethoxy)ethyl)-1-methyl-5-oxo-2-(pyridin-3-yl)pyrrolidine-3-carboxamide, 2Hydrochloric acid salt

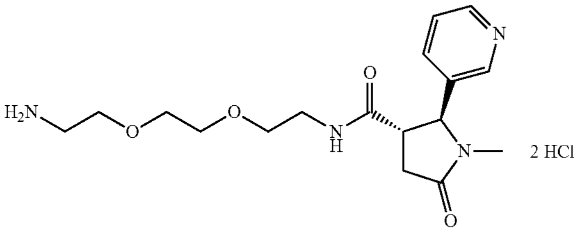 [SMILES: CN1C(=O)C[C@H](C(=O)NCCOCCOCCN)[C@H]1c1cccnc1]

4 M HCl in 1,4-dioxane (1770 μL, 7.08 mmol) was added to a solution of tert-butyl (2-(2-(2-((2S,3S)-1-methyl-5-oxo-2-(pyridin-3-yl) pyrrolidine-3-carboxamido)ethoxy)ethoxy) ethyl)carbamate (319 mg, 0.708 mmol) in 1,4-dioxane (2360 μL), the mixture was stirred at 40° C. for 1 h, and was concentrated under reduced pressure to provide the title compound as an off-white, sticky solid (306 mg, 0.651 mmol, 92% yield). LC-MS m/z 351.3 $(M+H)^+$.

Step 3 tert-Butyl 1-((2S,3S)-1-methyl-5-oxo-2-(pyridin-3-yl)pyrrolidin-3-yl)-1,12-dioxo-5,8,16,19-tetraoxa-2,11,13-triazadocosan-22-oate

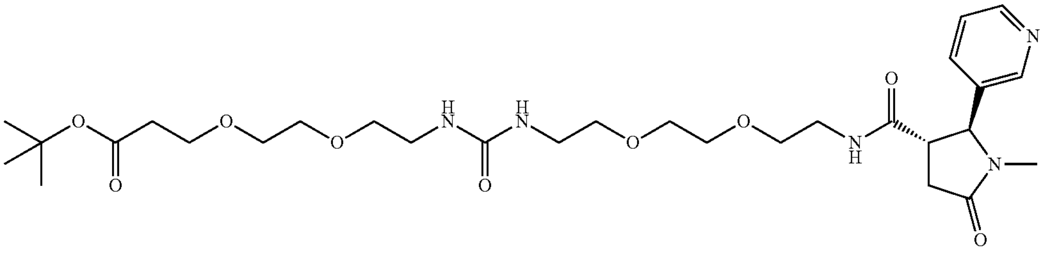 [SMILES: CN1C(=O)C[C@H](C(=O)NCCOCCOCCNC(=O)NCCOCCOCCC(=O)OC(C)(C)C)[C@H]1c1cccnc1]

Triethylamine (45.4 μL, 0.326 mmol) was added to a solution of commercially available tert-butyl 3-(2-(2-aminoethoxy)ethoxy)propanoate (38 mg, 0.163 mmol) in N,N-dimethylformamide (DMF) (543 μL) and the mixture was stirred for 10 min. CDI (26.4 mg, 0.163 mmol) was added and the mixture was stirred for 30 min. (2S,3S)-N-(2-(2-(2-Aminoethoxy)ethoxy)ethyl)-1-methyl-5-oxo-2-(pyridin-3-yl)pyrrolidine-3-carboxamide, 2hydrochloric acid salt (69 mg, 0.163 mmol) was added with triethylamine (23 μL, 0.18 mmol) and the mixture was stirred at rt for 20 h. Purification by reverse-phase HPLC (XSelect™ CSH Prep C18 5 μm OBD column, 40 mL/min) eluting with a gradient of 15 to 99% acetonitrile in water containing ammonium bicarbonate (10 mM) and the pH adjusted to 10 with ammonia provided the title compound as a clear, sticky solid (54 mg, 0.080 mmol, 48.9% yield). LC-MS m/z 610.3 $(M+H)^+$.

Step 4

1-((2S,3S)-1-Methyl-5-oxo-2-(pyridin-3-yl)pyrrolidin-3-yl)-1,12-dioxo-5,8,16,19-tetraoxa-2,11,13-triazadocosan-22-oic acid, Hydrochloric acid salt

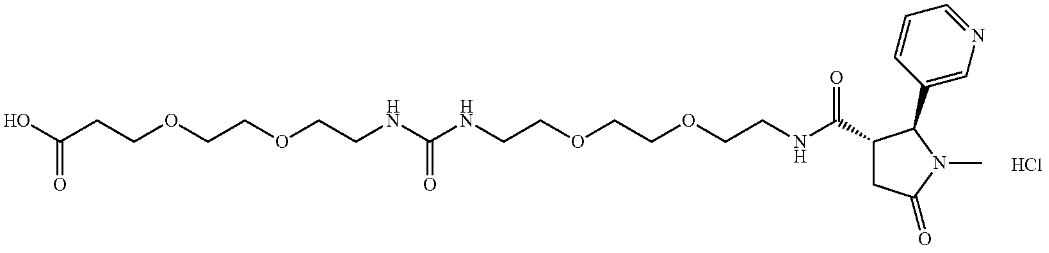 [SMILES: CN1C(=O)C[C@H](C(=O)NCCOCCOCCNC(=O)NCCOCCOCCC(=O)O)[C@H]1c1cccnc1 ; Cl]

4 M HCl in 1,4-dioxane (205 μL, 0.820 mmol) was added to a solution of tert-butyl 1-((2S,3S)-1-methyl-5-oxo-2-(pyridin-3-yl)pyrrolidin-3-yl)-1,12-dioxo-5,8,16,19-tetraoxa-2,11,13-triazadocosan-22-oate (50 mg, 0.082 mmol) in 1,4-dioxane (273 μL) and the mixture was stirred at 40° C. for 4 h. A small amount of acetonitrile was added to keep the solution homogeneous. The mixture was concentrated under reduced pressure to provide title compound as an off-white, sticky solid (46.6 mg, 0.071 mmol, 87% yield). LC-MS m/z 554.3 $(M+H)^+$.

Step 5

(2S,3S)-N-(20-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-10,20-dioxo-3,6,14,17-tetraoxa-9,11-diazaicosyl)-1-methyl-5-oxo-2-(pyridin-3-yl)pyrrolidine-3-carboxamide

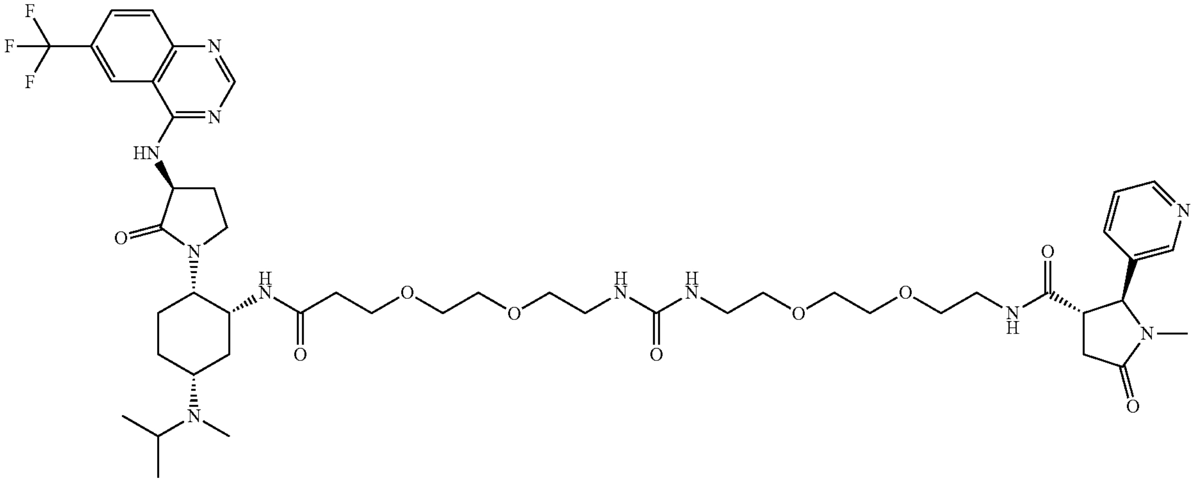 [SMILES: CC(C)N(C)[C@@H]1CC[C@H](N2CC[C@H](Nc3ncnc4ccc(C(F)(F)F)cc34)C2=O)[C@H](NC(=O)CCOCCOCCNC(=O)NCCOCCOCCNC(=O)[C@H]2CC(=O)N(C)[C@@H]2c2cccnc2)C1]

A mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (42 mg, 0.078 mmol), 1-((2S,3S)-1-methyl-5-oxo-2-(pyridin-3-yl)pyrrolidin-3-yl)-1,12-dioxo-5,8,16,19-tetraoxa-2,11,13-triazadocosan-22-oic acid, hydrochloric acid salt (47.5 mg, 0.080 mmol), and HOAt (10.46 mg, 0.077 mmol) was dissolved in N,N-dimethylformamide (DMF) (1 mL) at room temperature. DIPEA (0.128 mL, 0.732 mmol) and EDC (0.014 mL, 0.077 mmol) were added and the mixture was stirred a rt for 3 days. Purification by reverse-phase HPLC (Gemini C18 5 μm column, 40 mL/min) eluting with a gradient of 15 to 45% acetonitrile in water containing ammonium hydroxide (0.1%) provided the title compound as an off-white solid (26.1 mg, 0.025 mmol, 33.9% yield). LC-MS m/z 1000.4 $(M+H)^+$. $^1$H NMR (400 MHz, METHANOL-$d_4$) δ ppm 1.05 (br d, J=6.4 Hz, 3H) 1.14 (br d, J=6.4 Hz, 3H) 1.63-1.79 (m, 3H) 1.92-2.02 (m, 1H) 2.06-2.18 (m, 1H) 2.20-2.38 (m, 5H) 2.46 (t, J=5.6 Hz, 2H) 2.50-2.58 (m, 1H) 2.66 (s, 3H) 2.68-2.77 (m, 2H) 2.81-2.88 (m, 1H) 3.00-3.08 (m, 1H) 3.23-3.29 (m, 4H) 3.37-3.40 (m, 1H) 3.44 (t, J=5.6 Hz, 3H) 3.47-3.53 (m, 8H) 3.55-3.59 (m, 5H) 3.67-3.76 (m, 2H) 3.78-3.86 (m, 1H) 4.06 (dt, J=12.3, 3.6 Hz, 1H) 4.64 (br d, J=2.0 Hz, 1H) 4.79-4.85 (m, 1H) 4.79-4.84 (m, 1H) 5.29 (t, J=8.1 Hz, 1H) 7.52 (dd, J=8.1, 5.1 Hz, 1H) 7.79 (dt, J=7.8, 2.0 Hz, 1H) 7.91 (d, J=8.8 Hz, 1H) 8.06 (dd, J=8.8, 2.0 Hz, 1H) 8.52 (d, J=2.0 Hz, 1H) 8.57 (dd, J=4.9, 1.5 Hz, 1H) 8.60 (s, 1H) 8.83 (s, 1H).

Example 120

(2S,3S)-N-(2-(2-(3-(((1S,4s)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethyl)-1-methyl-5-oxo-2-(pyridin-3-yl)pyrrolidine-3-carboxamide

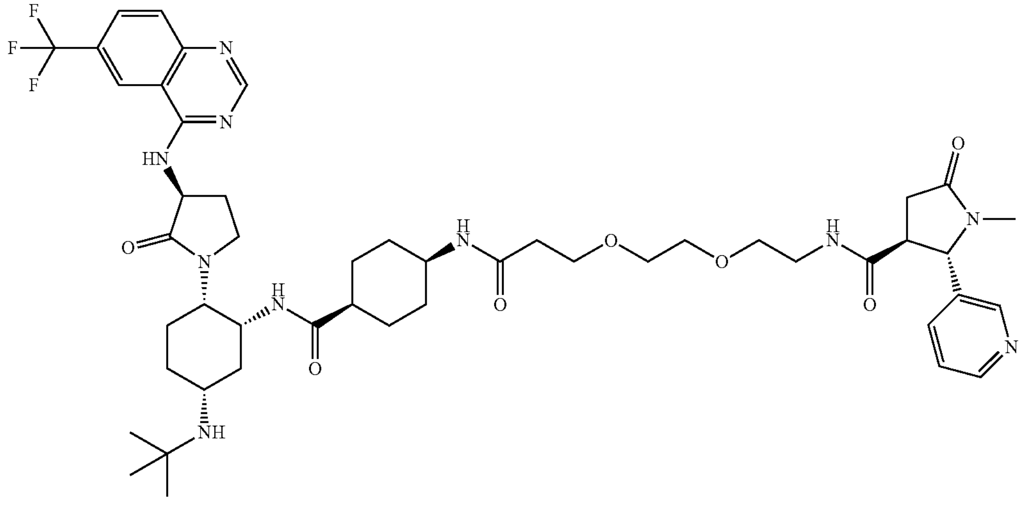 [SMILES: CN1C(=O)C[C@H](C(=O)NCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1]

Step 1 tert-Butyl 3-(2-(2-((2S,3S)-1-methyl-5-oxo-2-(pyridin-3-yl)pyrrolidine-3-carboxamido)ethoxy)ethoxy)propanoate

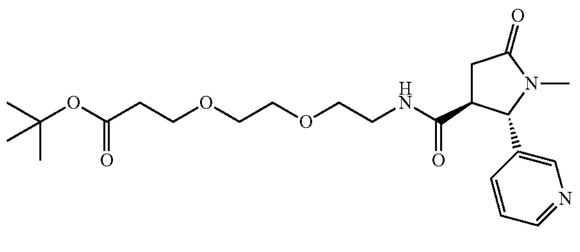 [SMILES: CN1C(=O)C[C@H](C(=O)NCCOCCOCCC(=O)OC(C)(C)C)[C@H]1c1cccnc1]

To a mixture of tert-butyl 3-(2-(2-aminoethoxy)ethoxy)propanoate (332 mg, 1.423 mmol) and (2S,3S)-1-methyl-5-oxo-2-(pyridin-3-yl) pyrrolidine-3-carboxylic acid (296 mg, 1.344 mmol) in dichloromethane (DCM) (5 mL) was added HATU (620 mg, 1.631 mmol) and triethylamine (0.595 mL, 4.27 mmol) and the mixture was stirred at rt for 2 h. Saturated $NaHCO_3$ and dichloromethane (DCM) were added and the aqueous phase was extracted with dichloromethane (DCM). The combined organic phases were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (600 mg, 1.378 mmol, 97% yield). LC-MS m/z 437.2 $(M+2H)^+$.

Step 2

3-(2-(2-((2S,3S)-1-Methyl-5-oxo-2-(pyridin-3-yl)pyrrolidine-3-carboxamido)ethoxy)ethoxy)propanoic acid, Hydrochloric acid salt

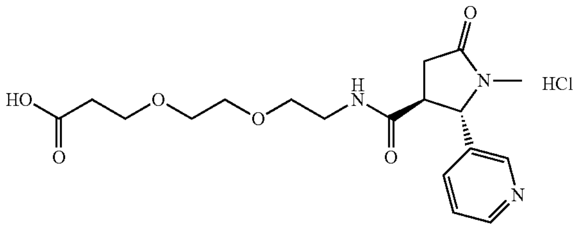 [SMILES: CN1C(=O)C[C@H](C(=O)NCCOCCOCCC(=O)O)[C@H]1c1cccnc1 ; Cl]

HCl (3 mL, 12.00 mmol) was added to tert-butyl 3-(2-(2-((2S,3S)-1-methyl-5-oxo-2-(pyridin-3-yl)pyrrolidine-3-carboxamido)ethoxy)ethoxy)propanoate (600 mg, 1.378 mmol) in dichloromethane (DCM) (0.5 mL), the mixture was stirred at rt for 4 h, and was concentrated to provide the title compound (580 mg, 1.395 mmol, 101% yield). LC-MS m/z 380.4 $(M+H)^+$.

Step 3 tert-Butyl (1s,4s)-4-(3-(2-(2-((2S,3S)-1-methyl-5-oxo-2-(pyridin-3-yl)pyrrolidine-3-carboxamido)ethoxy)ethoxy)propanamido)cyclohexane-1-carboxylate

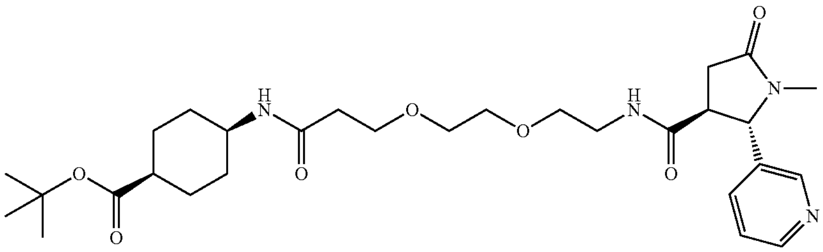 [SMILES: CN1C(=O)C[C@H](C(=O)NCCOCCOCCC(=O)N[C@H]2CC[C@@H](C(=O)OC(C)(C)C)CC2)[C@H]1c1cccnc1]

To a mixture of tert-butyl (1s,4s)-4-aminocyclohexane-1-carboxylate, hydrochloric acid salt (69.2 mg, 0.293 mmol) and 3-(2-(2-((2S,3S)-1-methyl-5-oxo-2-(pyridin-3-yl)pyrrolidine-3-carboxamido)ethoxy)ethoxy)propanoic acid, hydrochloric acid salt (122 mg, 0.293 mmol) in dichloromethane (DCM) (1 mL) was added triethylamine (0.245 mL, 1.760 mmol) and HATU (134 mg, 0.352 mmol) and the mixture was stirred at rt for 1 h. Saturated $NaHCO_3$ and dichloromethane (DCM) were added and the aqueous phase was extracted with dichloromethane (DCM). The combined organic phases were dried over $Na_2SO_4$, were filtered, and the filtrate was concentrated. Purification by ISCO Combi-Flash® chromatography (12 g RediSep Rf Gold® column, 40 mL/min) eluting with a gradient of 0 to 15% methanol containing ammonium hydroxide (10%) in dichloromethane (DCM) provided the title compound (160 mg, 0.285 mmol, 97% yield). LC-MS m/z 561.4 $(M+H)^+$.

Step 4

(1 s,4s)-4-(3-(2-(2-((2S,3S)-1-Methyl-5-oxo-2-(pyridin-3-yl)pyrrolidine-3-carboxamido)ethoxy)ethoxy)propanamido)cyclohexane-1-carboxylic acid

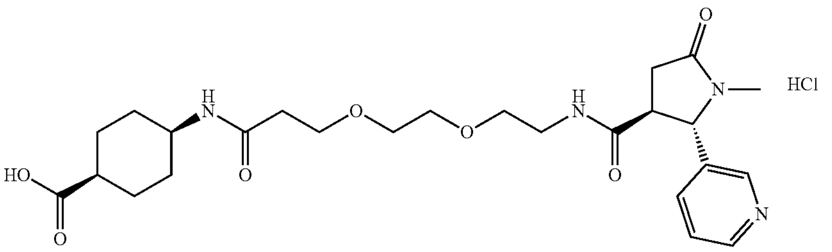 [SMILES: CN1C(=O)C[C@H](C(=O)NCCOCCOCCC(=O)N[C@H]2CC[C@@H](C(=O)O)CC2)[C@H]1c1cccnc1 ; Cl]

HCl (0.357 mL, 1.427 mmol) was added to tert-butyl (1s,4s)-4-(3-(2-(2-((2S,3S)-1-methyl-5-oxo-2-(pyridin-3-yl)pyrrolidine-3-carboxamido)ethoxy)ethoxy)propanamido)cyclohexane-1-carboxylate (160 mg, 0.285 mmol) in dichloromethane (DCM) (0.1 mL), the mixture was stirred at rt for 4 h, and was concentrated to provide the title compound (160 mg, 0.296 mmol, 104% yield). LC-MS m/z 505.4 $(M+H)^+$.

Step 5

(2S,3S)-N-(2-(2-(3-(((1S,4s)-4-(((1R,2S,5R)-5-(tert-Butylamino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethyl)-1-methyl-5-oxo-2-(pyridin-3-yl)pyrrolidine-3-carboxamide

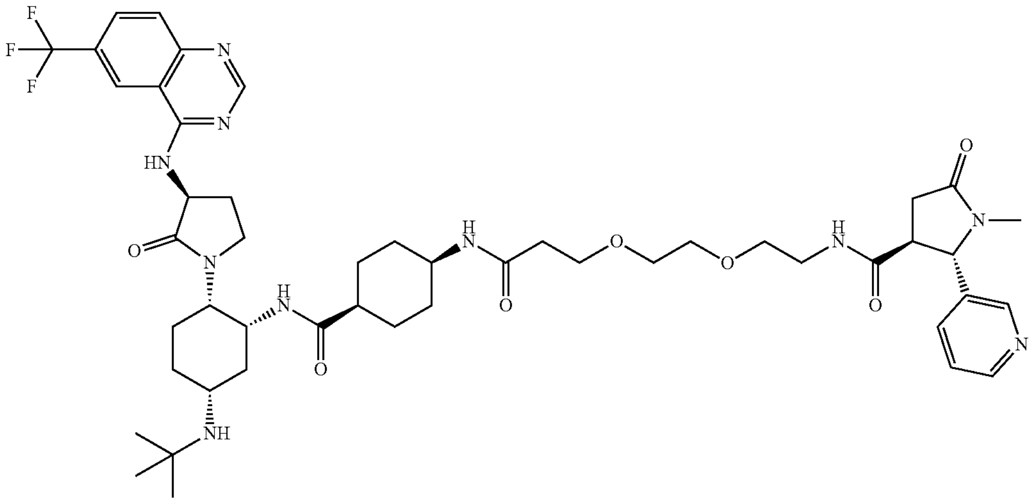 [SMILES: CN1C(=O)C[C@H](C(=O)NCCOCCOCCC(=O)N[C@H]2CC[C@@H](C(=O)N[C@@H]3C[C@H](NC(C)(C)C)CC[C@@H]3N3CC[C@H](Nc4ncnc5ccc(C(F)(F)F)cc45)C3=O)CC2)[C@H]1c1cccnc1]

To a mixture of (S)-1-((1S,2R,4R)-2-amino-4-(tert-butylamino)cyclohexyl)-3-((6-(trifluoromethyl)quinazolin-4-yl)amino)pyrrolidin-2-one (38.6 mg, 0.083 mmol) and (1 s,4s)-4-(3-(2-(2-((2S,3S)-1-methyl-5-oxo-2-(pyridin-3-yl)pyrrolidine-3-carboxamido)ethoxy)ethoxy)propanamido)cyclohexane-1-carboxylic acid, hydrochloric acid salt (45 mg, 0.083 mmol) in dichloromethane (DCM) (0.5 mL) was added triethylamine (0.070 mL, 0.499 mmol) and HATU (38.0 mg, 0.100 mmol). The mixture was stirred at rt for 1 h and was concentrated. Purification by MDAP chromatography (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a white solid (35.7 mg, 0.038 mmol, 45.1% yield) as a white solid. LC-MS m/z 951.5 $(M+H)^+$. $^1H$ NMR (400 MHz, METHANOL-$d_4$) δ ppm 1.18 (s, 8H) 1.58-1.69 (m, 2H) 1.71-1.98 (m, 11H) 2.22-2.47 (m, 4H) 2.52-2.63 (m, 1H) 2.66 (s, 3H) 2.67-2.73 (m, 1H) 2.77-2.91 (m, 1H) 3.03-3.11 (m, 1H) 3.15 (d, J=1.5 Hz, 1H) 3.21-3.31 (m, 2H) 3.35-3.39 (m, 1H) 3.41-3.71 (m, 10H) 3.88 (br t, J=4.2 Hz, 1H) 4.01 (dt, J=12.3, 3.6 Hz, 1H) 4.58 (br d, J=2.9 Hz, 1H) 4.82 (d, J=6.8 Hz, 1H) 5.32 (t, J=8.6 Hz, 1H) 7.49-7.55 (m, 1H) 7.79 (dt, J=8.2, 1.8 Hz, 1H) 7.76-7.81 (m, 1H) 7.91 (d, J=8.8 Hz, 1H) 8.07 (dd, J=8.8, 2.0 Hz, 1H) 8.51 (d, J=2.0 Hz, 1H) 8.56 (dd, J=4.9, 1.5 Hz, 1H) 8.59 (s, 1H) 8.73 (s, 1H).

Example 121

(2S,3S)-N-(2-(4-(4-(((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-4-oxobutoxy)butoxy)ethyl)-1-methyl-5-oxo-2-(pyridin-3-yl)pyrrolidine-3-carboxamide

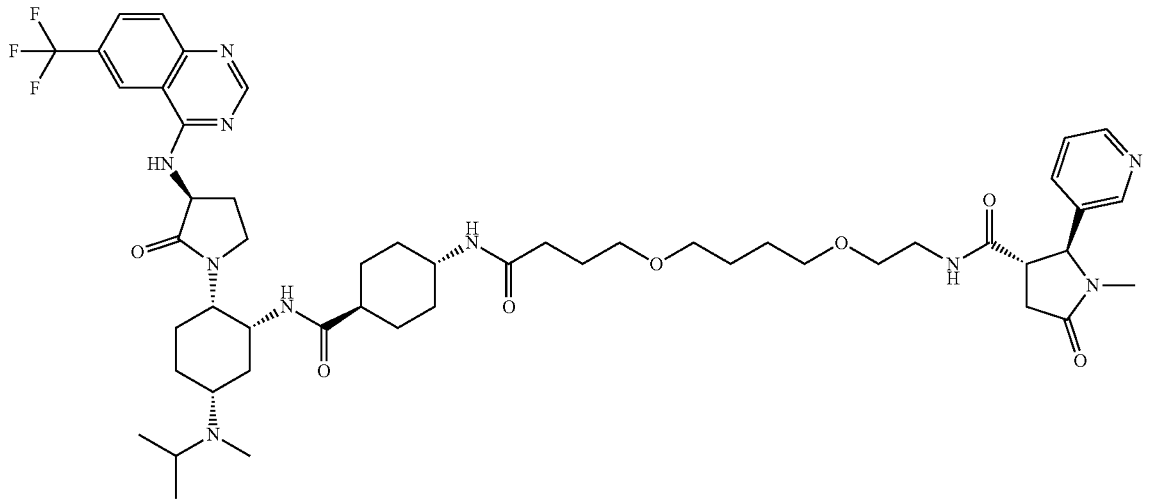 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCOCCCCOCCNC(=O)[C@H]3CC(=O)N(C)[C@@H]3c3cccnc3)CC2)C1]

Step 1

N,N-Dibenzyl-2-chloroethan-1-amine

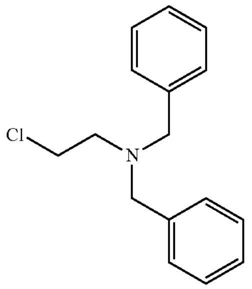 [SMILES: ClCCN(Cc1ccccc1)Cc1ccccc1]

To a solution of 2-(dibenzylamino)ethan-1-ol (20 g, 83 mmol) in dichloromethane (DCM) (180 mL) under an atmosphere of nitrogen was added triethylamine (23.10 mL, 166 mmol) and the mixture was stirred at rt for 20 min. 4-Methylbenzenesulfonyl chloride (18.96 g, 99 mmol) was added and the mixture was stirred for 16 h. Water (300 ml) was added and the aqueous phase was extracted with dichloromethane (DCM) (2×200 mL). The combined organic phases were washed with saturated NaCl (50 mL), with water (50 mL), were dried over $Na_2SO_4$, and were concentrated under reduced pressure. Purification by Biotage® Isolera™ column chromatography (100 g SNAPS column, 230 to 400 mesh silica) eluting with a gradient of 0 to 10% ethyl acetate in petroleum ether provided the title compound as a colorless liquid (14.42 g, 52.1 mmol, 62.9% yield). LC-MS m/z 260.0 $(M+H)^+$.

Step 2

4-(2-(Dibenzylamino)ethoxy)butan-1-ol

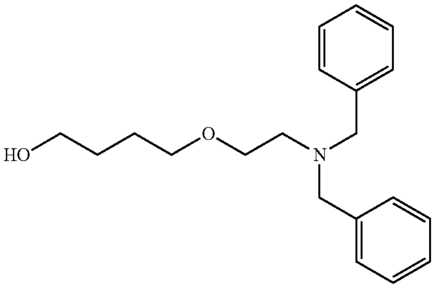 [SMILES: OCCCCOCCN(Cc1ccccc1)Cc1ccccc1]

To a solution of butane-1,4-diol (5.5 g, 61.0 mmol) in N,N-dimethylformamide (DMF) (30 mL) at 0° C. under an atmosphere of nitrogen was added in portions 60% sodium hydride in mineral oil (2.441 g, 61.0 mmol) over 15 min and the mixture was stirred for 30 min. A solution of N,N-dibenzyl-2-chloroethan-1-amine (14.27 g, 54.9 mmol) dissolved in N,N-dimethylformamide (DMF) (10 mL) was added dropwise and the mixture was stirred at rt for 16 h. Ice water (150 mL) was added and the mixture was extracted with ethyl acetate (3×80 mL). The combined organic phases were washed with saturated NaCl (100 mL), with ice water (2×50 mL), were dried over $Na_2SO_4$, and were concentrated under reduced pressure. Purification by Biotage® Isolera™ column chromatography (100 g SNAPS column, 230 to 400 mesh silica) eluting with a gradient of 20 to 35% ethyl acetate in petroleum ether provided the title compound as a pale-yellow liquid (4.021 g, 12.20 mmol, 19.99% yield). LC-MS m/z 314.1 $(M+H)^+$.

Step 3

Methyl (E)-4-(4-(2-(dibenzylamino)ethoxy)butoxy)but-2-enoate

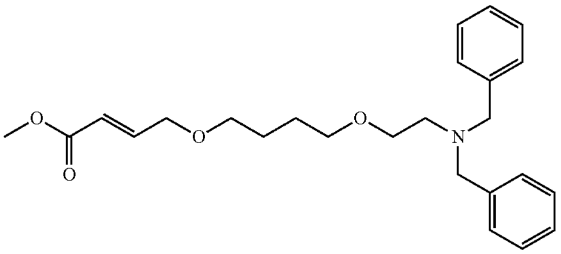 [SMILES: COC(=O)/C=C/COCCCCOCCN(Cc1ccccc1)Cc1ccccc1]

To a stirred solution of 4-(2-(dibenzylamino)ethoxy)butan-1-ol (4.0 g, 12.76 mmol) and methyl but-2-ynoate (2.504 g, 25.5 mmol) in toluene (40 mL) under an atmosphere of nitrogen at rt was added triphenylphosphine (0.335 g, 1.276 mmol) and acetic acid (0.292 mL, 5.10 mmol) The mixture was stirred at 115° C. for 20 h and was concentrated under reduced pressure. The residue was partitioned between water (100 mL) and ethyl acetate (50 mL). The aqueous phase was extracted with ethyl acetate (2×50 mL). The combined organic phases were washed with saturated NaCl (50 mL), with water (30 mL), were dried over $Na_2SO_4$, and were concentrated under reduced pressure. Purification by Biotage® Isolera™ column chromatography (100 g SNAPS column, 230 to 400 mesh silica) eluting with a gradient of 0 to 20% ethyl acetate in petroleum ether provided the title compound as a pale-yellow liquid (4.28 g, 7.92 mmol, 62.0% yield). LC-MS m/z 412.2 $(M+H)^+$.

Step 4

Methyl 4-(4-(2-aminoethoxy)butoxy)butanoate

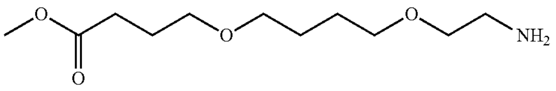 [SMILES: COC(=O)CCCOCCCCOCCN]

To a stirred solution of methyl (E)-4-(4-(2-(dibenzylamino)ethoxy)butoxy)but-2-enoate (4.25 g, 10.33 mmol) in methanol (30 mL) under an atmosphere of nitrogen was added Pd—C(1.5 g, 1.410 mmol). The mixture was flushed with hydrogen and was stirred under a balloon atmosphere of pressure for 16 h. The mixture was filtered through Celite® bed and the catalyst was washed with methanol (3×40 mL). The combined filtrates were concentrated under reduced pressure to provide the title compound as a colorless liquid (2.17 g, 9.27 mmol, 90% yield). LC-MS m/z 234.2 $(M+H)^+$.

Step 5

Methyl 4-(4-(2-((2S,3S)-1-methyl-5-oxo-2-(pyridin-3-yl)pyrrolidine-3-carboxamido) ethoxy)butoxy) butanoate

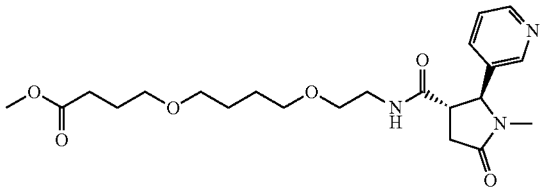 [SMILES: COC(=O)CCCOCCCCOCCNC(=O)[C@H]1CC(=O)N(C)[C@@H]1c1cccnc1]

To a stirred solution of (2S,3S)-1-methyl-5-oxo-2-(pyridin-3-yl) pyrrolidine-3-carboxylic acid (1.85 g, 8.40 mmol) and HATU (6.39 g, 16.80 mmol) in dichloromethane (DCM) (30 mL) under an atmosphere of nitrogen was added DIPEA (7.34 mL, 42.0 mmol). The mixture was stirred at rt for 20 min and a solution of ethyl 4-(4-(2-aminoethoxy)butoxy) butanoate (2.156 g, 9.24 mmol) in dichloromethane (DCM) (20 mL) was added at 0° C. The mixture was stirred at rt for 16 h. Water (50 mL) and dichloromethane (DCM) (50 mL) were added and the aqueous phase was extracted with methanol in dichloromethane (DCM) (10%) (3×60 mL). The combined organic phases were washed with saturated $NaHCO_3$(50 mL), with water (30 mL), were dried over $Na_2SO_4$, and were concentrated under reduced pressure. Purification by Biotage® Isolera™ column chromatography (100 g SNAPS column, 230 to 400 mesh silica) eluting with a gradient of 0 to 10% methanol in dichloromethane (DCM)

provided the title compound as a brown liquid (4.41 g, 5.54 mmol, 65.9% yield). LC-MS m/z 436.1 $(M+H)^+$.

Step 6

4-(4-(2-((2S,3S)-1-Methyl-5-oxo-2-(pyridin-3-yl)pyrrolidine-3-carboxamido)ethoxy)butoxy)butanoic acid

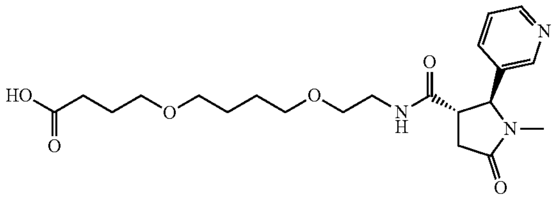 [SMILES: CN1C(=O)C[C@H](C(=O)NCCOCCCCOCCCC(=O)O)[C@H]1c1cccnc1]

To a solution of methyl 4-(4-(2-((2S,3S)-1-methyl-5-oxo-2-(pyridin-3-yl) pyrrolidine-3-carboxamido)ethoxy)butoxy) butanoate (4.4 g, 10.10 mmol) in tetrahydrofuran (THF) (20 mL) stirred under nitrogen at 0° C. was added dropwise a solution of lithium hydroxide monohydride (0.424 g, 10.10 mmol) in water (20.00 mL) over 5 min at 0° C. The mixture was stirred at rt for 16 h and was concentrated under reduced pressure. The residue was partitioned between water (20 mL) and ethyl acetate (30 mL). The aqueous phase was washed with ethyl acetate (2×40 mL) and pH was adjusted to 5 to 6 using 6 N HCl. Purification by Buchi Reveleris® chromatography (C18 330 g 40 μm 23.5 cm×6.5 cm column, 30 mL/min) eluting with a gradient of 15 to 35% acetonitrile in water both containing formic acid (0.1%) provide the title compound as a yellow liquid (1.604 g, 3.73 mmol, 36.9% yield). LC-MS m/z 422.2 $(M+H)^+$.

Step 7

(2S,3S)-N-(2-(4-(4-(((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)amino)-4-oxobutoxy)butoxy)ethyl)-1-methyl-5-oxo-2-(pyridin-3-yl)pyrrolidine-3-carboxamide

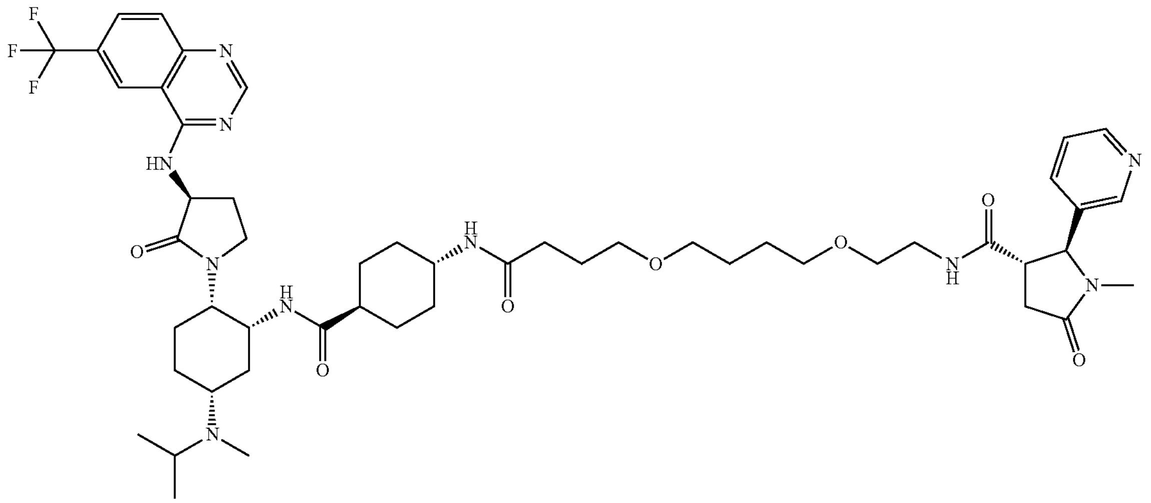 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](NC(=O)CCCOCCCCOCCNC(=O)[C@H]3CC(=O)N(C)[C@@H]3c3cccnc3)CC2)C1]

To a mixture of (1r,4R)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (53.5 mg, 0.081 mmol) and 4-(4-(2-((2S,3S)-1-methyl-5-oxo-2-(pyridin-3-yl)pyrrolidine-3-carboxamido)ethoxy)butoxy)butanoic acid (34 mg, 0.081 mmol) in dichloromethane (DCM) (1 mL) was added triethylamine (0.067 mL, 0.484 mmol) and HATU (36.8 mg, 0.097 mmol). The mixture was stirred at rt for 2 h and was concentrated. Purification by MDAP chromatography (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a white solid (37.8 mg, 0.038 mmol, 47.2% yield) as a white solid. LC-MS m/z 993.7 $(M+H)^+$. $^1H$ NMR (400 MHz, METHANOL-$d_4$) δ ppm 1.02 (br d, J=6.4 Hz, 3H) 1.16 (br d, J=6.4 Hz, 3H) 1.19-1.31 (m, 2H) 1.54-1.65 (m, 6H) 1.66-1.78 (m, 3H) 1.79-1.87 (m, 2H) 1.90-2.02 (m, 5H) 2.07-2.17 (m, 2H) 2.19-2.25 (m, 3H) 2.28 (s, 3H) 2.34 (br d, J=14.2 Hz, 1H) 2.48-2.61 (m, 1H) 2.66 (s, 3H) 2.68-2.75 (m, 3H) 2.77-2.89 (m, 1H) 3.05 (ddd, J=9.4, 7.9, 6.6 Hz, 1H) 3.33 (quin, J=1.7 Hz, 7H) 3.44-3.56 (m, 4H) 3.57-3.68 (m, 2H) 4.03 (dt, J=12.6, 3.7 Hz, 1H) 4.65 (br d, J=3.4 Hz, 1H) 4.83 (d, J=6.4 Hz, 1H) 5.28 (t, J=8.1 Hz, 1H) 7.53 (dd, J=7.3, 4.9 Hz, 1H) 7.80 (dt, J=7.8, 2.0 Hz, 1H) 7.91 (d, J=8.8 Hz, 1H) 8.07 (dd, J=8.8, 2.0 Hz, 1H) 8.51 (d, J=2.0 Hz, 1H) 8.58 (dd, J=4.9, 1.5 Hz, 1H) 8.59 (s, 1H) 8.81 (s, 1H).

The following compound was or could be prepared with procedures analogous to that described in Example 121:

| Ex. | Compound | LC-MS m/z | NMR |
|---|---|---|---|
| 122 | 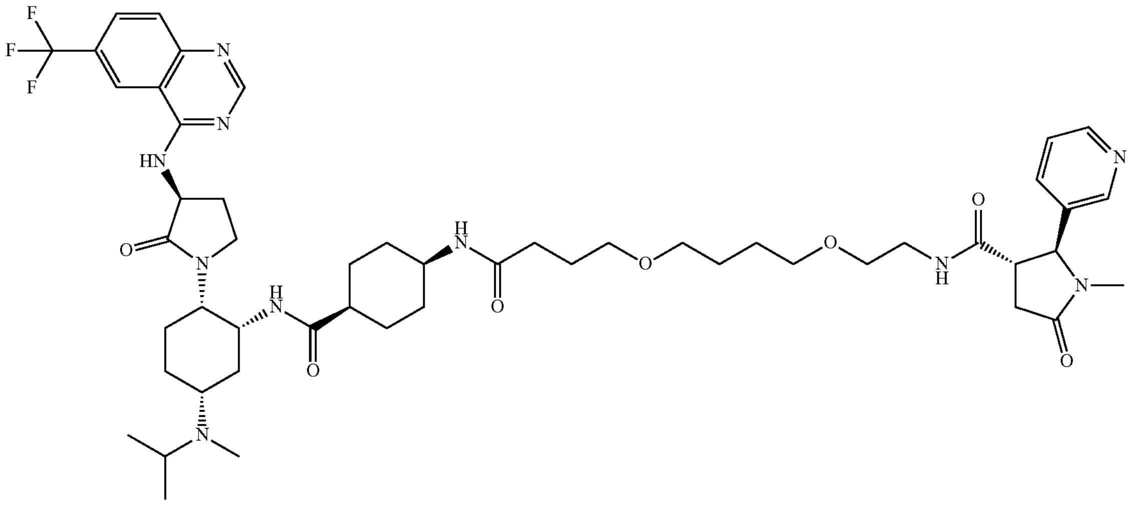 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCOCCCCOCCNC(=O)[C@H]3CC(=O)N(C)[C@@H]3c3cccnc3)CC2)C1] (2S,3S)-N-(2-(4-(4-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-4-oxobutoxy)butoxy)ethyl)-1-methyl-5-oxo-2-(pyridin-3-yl)pyrrolidine-3-carboxamide. | 993.6 (M + H)+ | $^1$H NMR (400 MHz, METHANOL-$d_4$) δ ppm 0.95-1.04 (m, 3H) 1.12-1.19 (m, 3H) 1.51-1.57 (m, 4H) 1.59-1.69 (m, 3H) 1.71-1.86 (m, 10H) 1.90-1.99 (m, 1H) 2.13 2.38 (m, 9H) 2.53-2.62 (m, 1H) 2.64-2.69 (m, 3H) 2.69-2.75 (m, 2H) 2.78-2.90 (m, 1H) 3.00-3.11 (m, 1H) 3.32-3.34 (m, 5H) 3.37-3.41 (m, 6H) 3.50-3.58 (m, 1H) 3.60-3.69 (m, 1H) 3.86-3.90 (m, 1H) 4.00-4.07 (m, 1H) 4.59-4.63 (m, 1H) 4.81-4.84 (m, 1H) 5.25-5.36 (m, 1H) 7.48-7.56 (m, 1H) 7.76-7.82 (m, 1H) 7.88-7.93 (m, 1H) 8.03-8.09 (m, 1H) 8.49-8.52 (m, 1H) 8.54-8.61 (m, 2H) 8.71-8.76 (m, 1H). |

Example 123

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-6-((1-((2S,3S)-1-methyl-5-oxo-2-(pyridin-3-yl)pyrrolidin-3-yl)-1-oxo-5,8,11,14-tetraoxa-2-azahexadecan-16-yl) amino)picolinamide

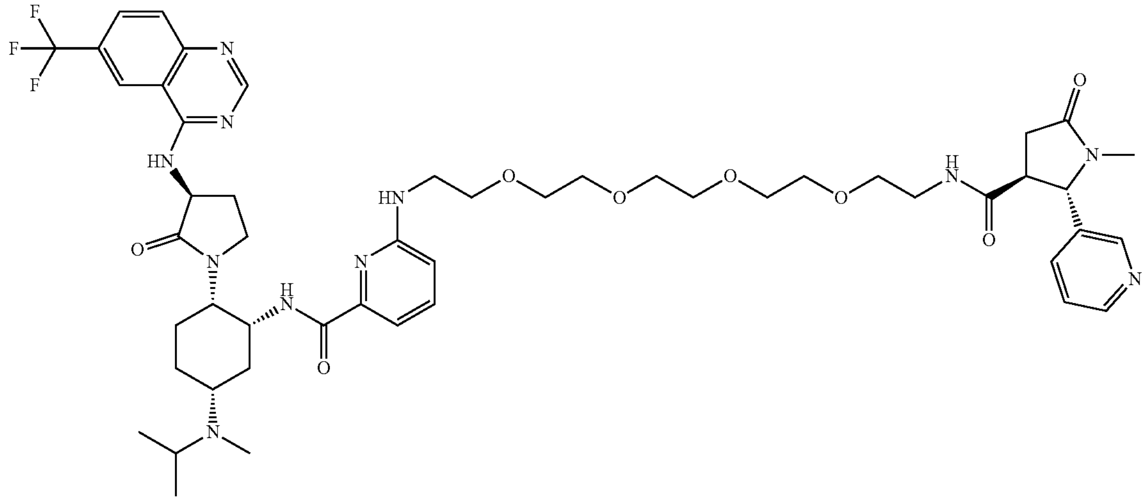 [SMILES: CC(C)N(C)[C@@H]1CC[C@H](N2CC[C@H](Nc3ncnc4ccc(C(F)(F)F)cc34)C2=O)[C@H](NC(=O)c2cccc(NCCOCCOCCOCCOCCNC(=O)[C@H]3CC(=O)N(C)[C@@H]3c3cccnc3)n2)C1]

Step 1

Methyl 6-((2,2-dimethyl-4-oxo-3,8,11,14,17-pentaoxa-5-azanonadecan-19-yl)amino)picolinate

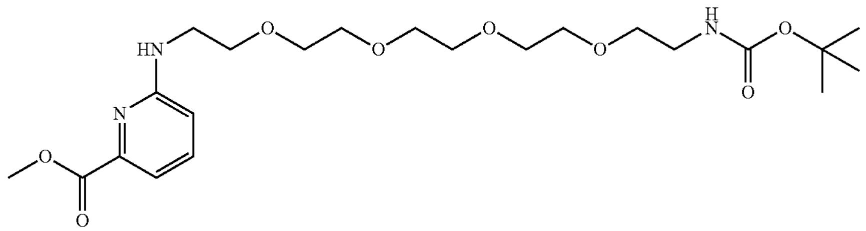 [SMILES: COC(=O)c1cccc(NCCOCCOCCOCCOCCNC(=O)OC(C)(C)C)n1]

To a solution of tert-butyl (14-amino-3,6,9,12-tetraoxatetradecyl)carbamate (1822 mg, 5.41 mmol) and methyl 6-fluoropicolinate (800 mg, 5.16 mmol) in N,N-dimethylformamide (DMF) (19 mL) was added potassium carbonate (1425 mg, 10.31 mmol) and the mixture was stirred at 100° C. for 5 days. Ethyl acetate was added and the organic phase was washed with water, with saturated $NH_4Cl$, with saturated $NaHCO_3$, with brine, was dried over $Na_2SO_4$, was filtered, and the filtrate was concentrated under reduced pressure. Purification by ISCO CombiFlash® Rf chromatography (40 g silica column, 40 mL/min) eluting with a gradient of 0% (5 column volumes), 0 to 5% (25 column volumes), 5% (4 column volumes) methanol in dichloromethane provided the title compound as a clear, colorless oil (407 mg, 0.690 mmol, 13.39% yield) as a clear colorless oil. LC-MS m/z 472.4 $(M+H)^+$.

Step 2

6-((2,2-Dimethyl-4-oxo-3,8,11,14,17-pentaoxa-5-azanonadecan-19-yl)amino)picolinic acid

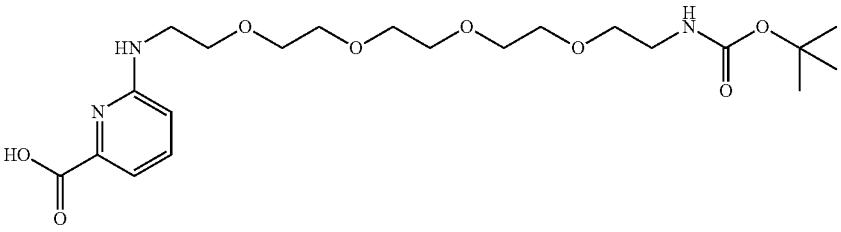 [SMILES: CC(C)(C)OC(=O)NCCOCCOCCOCCOCCNc1cccc(C(=O)O)n1]

10 M aqueous sodium hydroxide (512 μL, 5.12 mmol) was added to a solution of methyl 6-((2,2-dimethyl-4-oxo-3,8,11,14,17-pentaoxa-5-azanonadecan-19-yl)amino)picolinate (402 mg, 0.853 mmol) in methanol, tetrahydrofuran (THF), and water (2:1:1) and the mixture was stirred at rt for 20 h. The pH was adjusted to 7 with 1 N HCl, the mixture was concentrated, and dichloromethane (DCM) was added. The undissolved solids were removed by filtration and were washed with dichloromethane (DCM). The combined filtrates were concentrated under reduced pressure to provide the title compound as an orange, gummy solid (489 mg, 0.855 mmol, 100% yield). LC-MS m/z 458.2 $(M+H)^+$.

Step 3 tert-Butyl (14-((6-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)pyridin-2-yl)amino)-3,6,9,12-tetraoxatetradecyl)carbamate

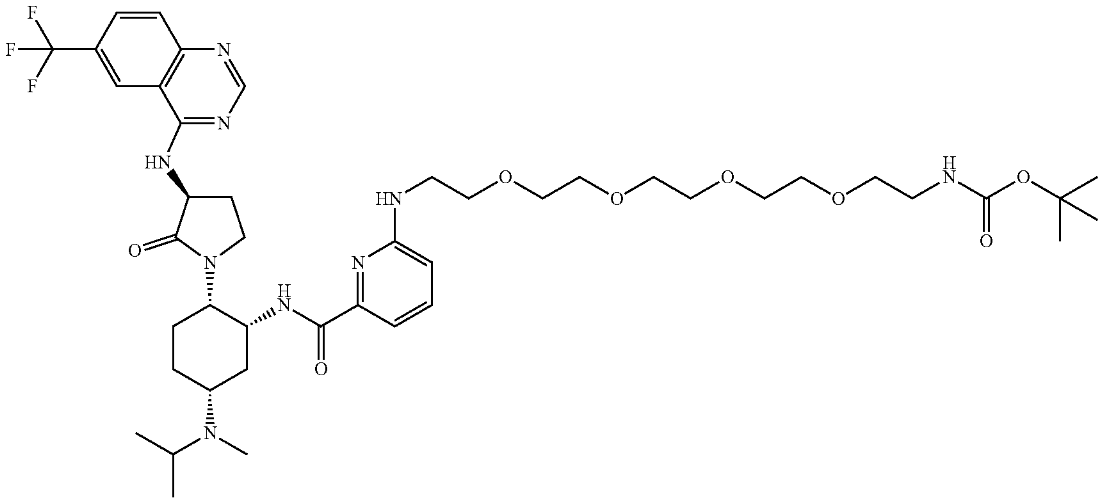 [SMILES: CC(C)N(C)[C@@H]1CC[C@H](N2CC[C@H](Nc3ncnc4ccc(C(F)(F)F)cc34)C2=O)[C@H](NC(=O)c2cccc(NCCOCCOCCOCCOCCNC(=O)OC(C)(C)C)n2)C1]

4 M HCl in 1,4-dioxane (1.768 ml, 7.07 mmol) was added to a solution of tert-butyl ((1R,2S,5R)-5-(isopropyl(methyl) amino)-2-((S)-2-oxo-3-((6-(trifluoromethyl)quinazolin-4-yl)amino)pyrrolidin-1-yl)cyclohexyl)carbamate (0.1997 g, 0.354 mmol) in 1,4-dioxane (1.179 ml) and the mixture was stirred at 45° C. for 30 min. The mixture was concentrated under reduced pressure and the residue was dissolved in dichloromethane (DCM) (0.5 mL). 6-((2,2-dimethyl-4-oxo-3,8,11,14,17-pentaoxa-5-azanonadecan-19-yl)amino)picolinic acid (0.194 g, 0.424 mmol), HOAt (0.053 g, 0.389 mmol), DIPEA (0.618 ml, 3.54 mmol), EDC (0.069 mL, 0.389 mmol) were added sequentially and the mixture was stirred at 37° C. for 20 h. Dichloromethane (DCM) was added and the organic phase was washed with water, with saturated $NH_4Cl$, with saturated $NaHCO_3$, and with brine. The organic phased was passed through a phase separator and was concentrated under reduced pressure. The residue was purified by reverse-phase HPLC (XSelect™ CSH Prep C18 5 μm OBD column, 40 mL/min) eluting with a gradient of 15 to 55% acetonitrile in water containing formic acid (0.1%). The fractions containing the desired product were combined and concentrated to remove the acetonitrile, the pH was adjusted to 8 using saturated $NaHCO_3$, and the aqueous phase was extracted with dichloromethane (DCM). The combined organic extracts were washed with brine, were passed through a phase separator, and were concentrated under reduced pressure to provide the title compound as an off-white solid (74 mg, 0.076 mmol, 21.52% yield). LC-MS m/z 904.3 $(M+H)^+$.

Step 4

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-6-((1-((2S,3S)-1-methyl-5-oxo-2-(pyridin-3-yl)pyrrolidi n-3-yl)-1-oxo-5,8,11,14-tetraoxa-2-azahexadecan-16-yl) amino)picolinamide

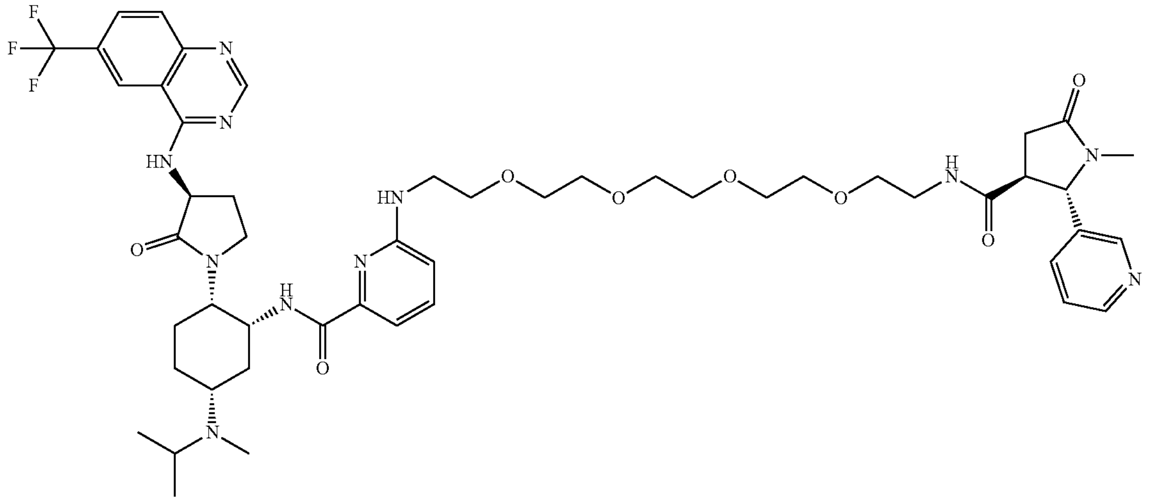 [SMILES: CC(C)N(C)[C@@H]1CC[C@H](N2CC[C@H](Nc3ncnc4ccc(C(F)(F)F)cc34)C2=O)[C@H](NC(=O)c2cccc(NCCOCCOCCOCCOCCNC(=O)[C@H]3CC(=O)N(C)[C@@H]3c3cccnc3)n2)C1]

4 M HCl in 1,4-dioxane (186 μL, 0.742 mmol) was added to a solution of tert-butyl (14-((6-(((1R,2S,5R)-5-(isopropyl (methyl)amino)-2-((S)-2-oxo-3-((6-(trifluoromethyl)quinazolin-4-yl)amino)pyrrolidin-1-yl)cyclohexyl)carbamoyl) pyridin-2-yl)amino)-3,6,9,12-tetraoxatetradecyl)carbamate (67.1 mg, 0.074 mmol) in 1,4-dioxane (247 μL). A few drops of methanol were added to keep the mixture homogenous. The reaction was stirred at 45° C. for 30 min and was concentrated under reduced pressure. Dichloromethane (DCM) was added and the organic phase was washed with saturated $NaHCO_3$, with brine, was passed through a phase separator, and was concentrated under reduced pressure. The residue was dissolved in N,N-dimethylformamide (DMF) (0.4 mL), (2S,3S)-1-methyl-5-oxo-2-(pyridin-3-yl)pyrrolidine-3-carboxylic acid (19.61 mg, 0.089 mmol), HOAt (11.11 mg, 0.082 mmol), EDC (14.45 μL, 0.082 mmol), and DIPEA (78 μL, 0.445 mmol) were added sequentially and the mixture was stirred at rt for 4 h. The mixture was purified by MDAP chromatography (XSelect™ CSH Prep C18 5 μm OBD column, 40 mL/min) eluting with a gradient of 5 to 35% acetonitrile in water containing TFA (0.1%). The fractions containing the desired product were combined and concentrated to remove the acetonitrile, the pH was adjusted to 8 using saturated $NaHCO_3$, and the aqueous phase was extracted with dichloromethane (DCM). The combined organic extracts were washed with brine, were passed through a phase separator, and were concentrated under reduced pressure to provide the title compound as an off-white solid (29 mg, 0.029 mmol, 38.4% yield). LC-MS m/z 1006.3 $(M+H)^+$. $^1$H NMR (400 MHz, METHANOL-$d_4$) δ ppm 0.86-1.05 (m, 6H) 1.12-1.35 (m, 3H) 1.41 (br d, J=11.0 Hz, 1H) 1.60-1.88 (m, 4H) 2.18 (s, 1H) 2.22-2.30 (m, 3H) 2.34 (br d, J=12.5 Hz, 2H) 2.39-2.55 (m, 1H) 2.66 (s, 3H) 2.67-2.74 (m, 1H) 2.77-2.90 (m, 2H) 2.95-3.11 (m, 1H) 3.22-3.31 (m, 1H) 3.35-3.43 (m, 2H) 3.46-3.69 (m, 15H) 3.72-3.97 (m, 1H) 4.18 (dt, J=12.5, 3.5 Hz, 1H) 4.79-4.89 (m, 2H) 4.92 (s, 1H) 5.34 (t, J=8.8 Hz, 1H) 6.69 (dd, J=8.5, 0.8 Hz, 1H) 7.29 (dd, J=7.0, 0.8 Hz, 1H) 7.47-7.56 (m, 2H) 7.80 (dt, J=8.0, 1.9 Hz, 1H) 7.90 (d, J=8.8 Hz, 1H) 8.07 (dd, J=8.9, 1.9 Hz, 1H) 8.52 (d, J=2.0 Hz, 1H) 8.54-8.61 (m, 2H) 8.78 (s, 1H).

The following compounds were or could be prepared with procedures analogous to that described in Example 116:

| Ex. | Compound | LC-MS m/z | NMR |
|---|---|---|---|
| 124 | 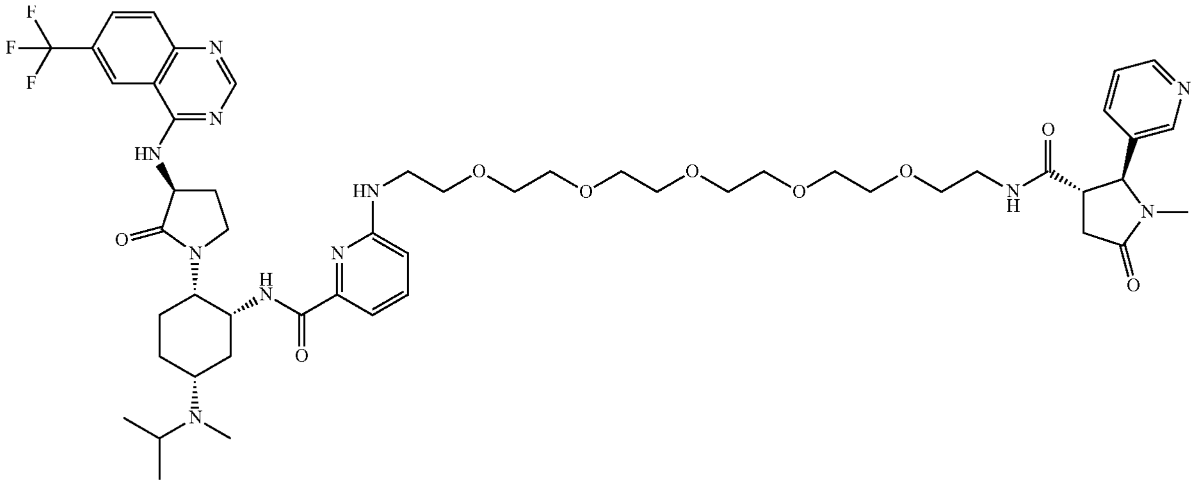 [SMILES: CC(C)N(C)[C@@H]1CC[C@H](N2CC[C@H](Nc3ncnc4ccc(C(F)(F)F)cc34)C2=O)[C@H](NC(=O)c2cccc(NCCOCCOCCOCCOCCOCCNC(=O)[C@H]3CC(=O)N(C)[C@@H]3c3cccnc3)n2)C1] N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-6-((1-((2S,3S)-1-methyl-5-oxo-2-(pyridin-3-yl)pyrrolidin-3-yl)-1-oxo-5,8, 11, 14, 17-pentaoxa-2-azanonadecan-19-yl)amino)picolinamide. | 1050.3 $(M + H)^+$ | $^1H$ NMR (400 MHz, METHANOL-$d_4$) δ ppm 0.92-1.02 (m, 6H) 1.65-1.90 (m, 4H) 2.27 (s, 4H) 2.35 (br d, J = 11.9 Hz, 2H) 2.46 (br s, 1H) 2.66 (s, 3 H) 2.68-2.75 (m, 1H) 2.80-2.88 (m, 1H) 3.05 (ddd, J = 9.4, 8.0, 6.8 Hz, 1 H) 3.35-3.45 (m, 2H) 3.48-3.70 (m, 24H) 3.80 (br d, J = 13.2 Hz, 2H) 4.19 (dt, J = 12.5, 3.5 Hz, 1H) 4.83 (d, J = 6.6 Hz, 1H) 5.35 (t, J = 8.7 Hz, 1H) 6.69 (dd, J = 8.4, 0.8 Hz, 1H) 7.29 (dd, J = 7.1, 0.8 Hz, 1 H) 7.49-7.56 (m, 2H) 7.81 (dt, J = 8.0, 1.8 Hz, 2 H) 7.91 (d, J = 8.9 Hz, 1H) 8.08 (dd, J = 9.0, 1.9 Hz, 1 H) 8.53 (d, J = 2.0 Hz, 1H) 8.56-8.59 (m, 2H) 8.79 (s, 1H). |

-continued

| Ex. | Compound | LC-MS m/z | NMR |
| --- | --- | --- | --- |
| 125 | 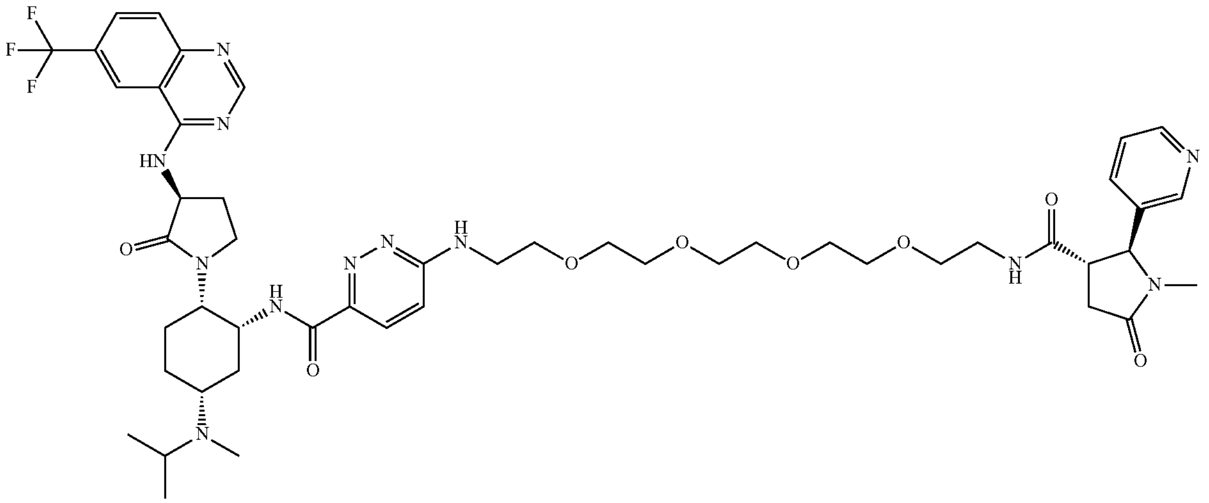 [SMILES: CC(C)N(C)[C@@H]1CC[C@H](N2CC[C@H](Nc3ncnc4ccc(C(F)(F)F)cc34)C2=O)[C@H](NC(=O)c2ccc(NCCOCCOCCOCCOCCNC(=O)[C@H]3CC(=O)N(C)[C@@H]3c3cccnc3)nn2)C1] N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-6-((1-((2S,3S)-1-methyl-5-oxo-2-(pyridin-3-yl)pyrrolidin-3-yl)-1-oxo-5,8,11,14-tetraoxa-2-azahexadecan-16-yl) amino) pyridazine-3-carboxamide. | 1007.3 (M + H)+ | $^1$H NMR (400 MHz, METHANOL-$d_4$) δ ppm 0.99 (d, J = 6.3 Hz, 3H) 1.22 (br d, J = 5.1 Hz, 3H) 1.66-1.92 (m, 4H) 2.16-2.30 (m, 4H) 2.31-2.44 (m, 2H) 2.45-2.59 (m, 1 H) 2.62-2.75 (m, 6H) 2.75-2.90 (m, 2H) 2.96-3.11 (m, 1H) 3.47-3.53 (m, 3H) 3.53-3.62 (m, 9 H) 3.62-3.70 (m, 7H) 3.71 (br d, J = 4.3 Hz, 2H) 4.15-4.26 (m, 1H) 4.82 (d, J = 6.6 Hz, 1H) 4.86 (br d, J = 3.3 Hz, 1H) 5.33 (t, J = 8.6 Hz, 1H) 6.94 (d, J = 9.4 Hz, 1H) 7.53 (dd, J = 7.9, 4.8 Hz, 1H) 7.80 (dt, J = 8.0, 1.8 Hz, 1H) 7.83 (d, J = 9.4 Hz, 1H) 7.92 (d, J = 8.9 Hz, 1H) 8.08 (dd, J = 8.7, 1.6 Hz, 1 H) 8.52 (s, 1H) 8.55-8.61 (m, 2H) 8.79 (s, 1H). |

-continued

| Ex. | Compound | LC-MS m/z | NMR |
|---|---|---|---|
| 126 | 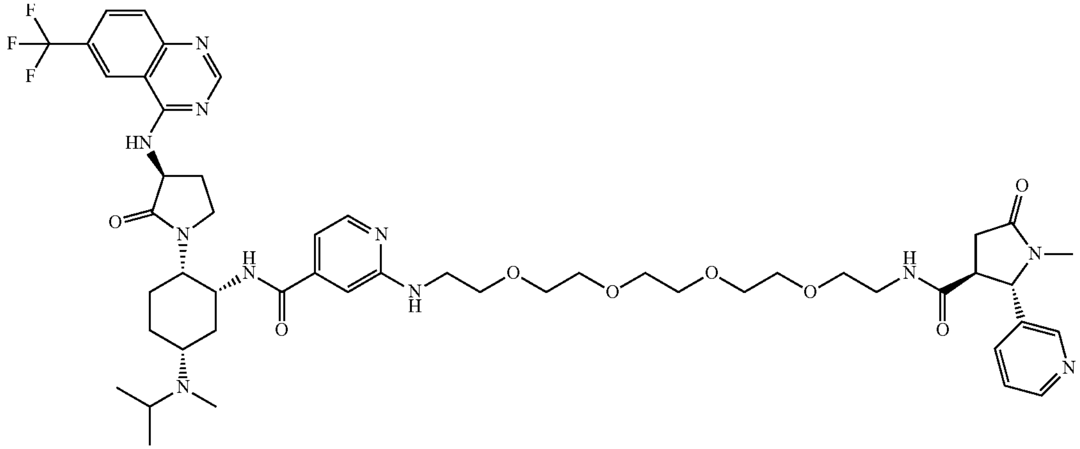 3 $CF_3COOH$ N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-2-((1-((2S,3S)-1-methyl-5-oxo-2-(pyridin-3-yl)pyrrolidin-3-yl)-1-oxo-5,8,11,14-tetraoxa-2-azahexadecan-16-yl) amino)isonicotinamide, 3Trifluoroacetic acid salt, | 1006.3 $(M + H)^+$ | $^1H$ NMR (400 MHz, METHANOL-$d_4$) δ ppm 1.38 (br dd, J = 6.4, 2.7 Hz, 3H) 1.47 (br d, J = 6.4 Hz, 3H) 1.92-2.19 (m, 3H) 2.19-2.40 (m, 3H) 2.41-2.60 (m, 1H) 2.61-2.80 (m, 5H) 2.81-2.91 (m, 4 H) 2.97-3.18 (m, 1H) 3.19-3.31 (m, 1H) 3.56-3.75 (m, 16H) 3.79-3.86 (m, 1H) 3.89-4.02 (m, 2 H) 4.35-4.44 (m, 1H) 4.58 (br s, 1H) 5.00-5.07 (m, 2H) 5.70 (t, J = 9.8 Hz, 1H) 7.08 (dd, J = 6.6, 1.5 Hz, 1H) 7.31-7.35 (m, 1 H) 7.74 (d, J = 6.8 Hz, 1H) 8.03 (d, J = 8.8 Hz, 1H) 8.10 (dd, J = 8.2, 5.7 Hz, 1 H) 8.34 (dd, J = 8.8, 1.7 Hz, 1H) 8.52 (dt, J = 8.2, 1.5 Hz, 1H) 8.83-8.93 (m, 3 H) 9.01 (s, 1H). |

-continued
| Ex. | Compound | LC-MS m/z | NMR |
|---|---|---|---|
| 127 | 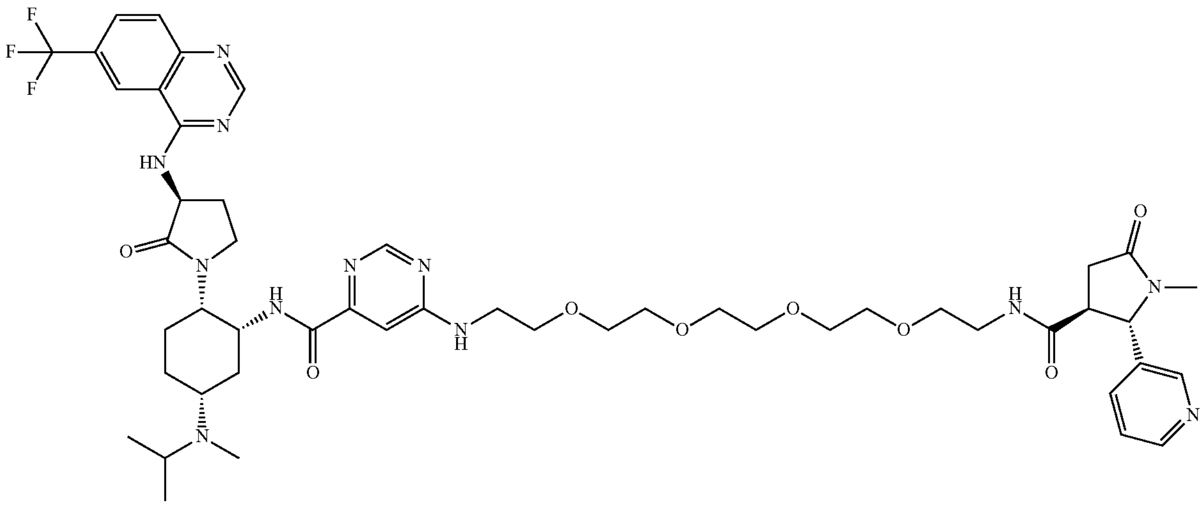 [SMILES: CC(C)N(C)[C@@H]1CC[C@H](N2CC[C@H](Nc3ncnc4ccc(C(F)(F)F)cc34)C2=O)[C@H](NC(=O)c2cc(NCCOCCOCCOCCOCCNC(=O)[C@H]3CC(=O)N(C)[C@@H]3c3cccnc3)ncn2)C1] N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-6-((1-((2S,3S)-1-methyl-5-oxo-2-(pyridin-3-yl)pyrrolidin-3-yl)-1-oxo-5,8,11, 14-tetraoxa-2-azahexadecan-16-yl) amino) pyrimidine-4-carboxamide. | 1007.3 $(M + H)^+$ | $^1H$ NMR (400 MHz, METHANOL-$d_4$) δ ppm 1.02-1.55 (m, 6H) 1.85-2.36 (m, 6H) 2.45-2.92 (m, 9H) 3.04 (ddd, J = 9.3, 8.1, 6.7 Hz, 1H) 3.36-3.84 (m, 24H) 4.25-4.71 (m, 2H) 4.82 (d, J = 6.8 Hz, 1H) 5.00-5.23 (m, 1H) 7.13 (s, 1H) 7.42-7.60 (m, 1H) 7.79 (dt, J = 8.0, 1.9 Hz, 1H) 7.91 (d, J = 8.8 Hz, 1H) 8.08 (dd, J = 8.9, 1.9 Hz, 2H) 8.38 (s, 1H) 8.46-8.62 (m, 3H) 8.64-8.79 (m, 1H). |

-continued
| Ex. | Compound | LC-MS m/z | NMR |
|---|---|---|---|
| 128 | 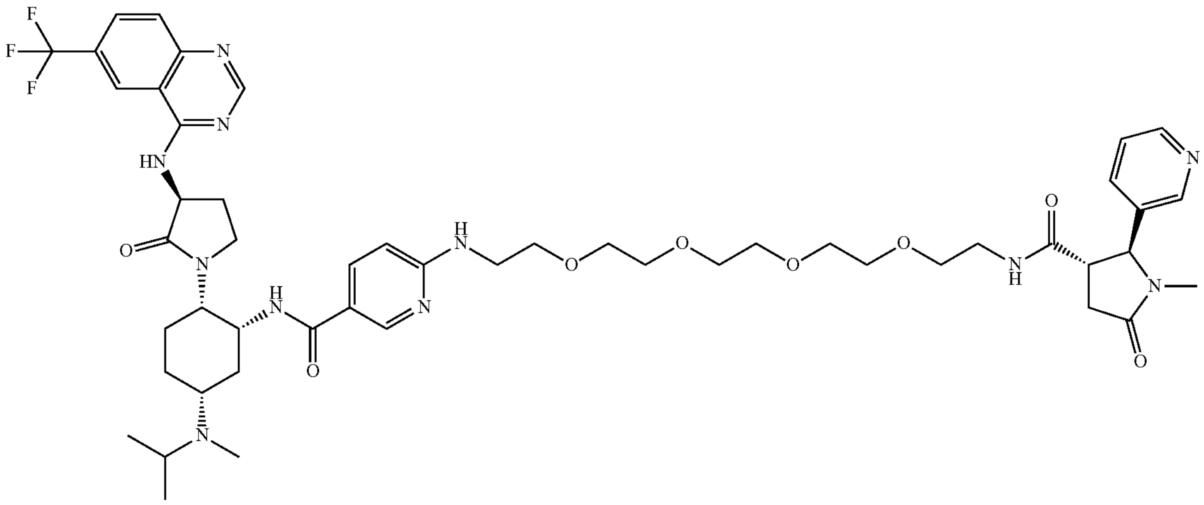 N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-6-((1-((2S,3S)-1-methyl-5-oxo-2-(pyridin-3-yl)pyrrolidin-3-yl)-1-oxo-5,8,11, 14-tetraoxa-2-azahexadecan-16-yl) amino) nicotinamide. | 1006.3 $(M + H)^+$ | $^1H$ NMR ( (400 MHz, METHANOL-$d_4$) δ ppm 0.87-1.07 (m, 3H) 1.14-1.29 (m, 3H) 1.72-1.94 (m, 4H) 2.18-2.43 (m, 6 H) 2.47-2.55 (m, 1H) 2.69-2.76 (m, 1H) 2.78-2.86 (m, 2H) 3.00-3.09 (m, 1H) 3.15-3.17 (m, 1 H) 3.27-3.30 (m, 1H) 3.36-3.41 (m, 2H) 3.47-3.69 (m, 22H) 4.12-4.22 (m, 1H) 4.80-4.87 (m, 2 H) 5.26-5.36 (m, 1H) 6.51-6.59 (m, 1H) 7.50-7.56 (m, 1H) 7.75-7.83 (m, 2H) 7.87-7.93 (m, 1 H) 8.05-8.10 (m, 1H) 8.40-8.44 (m, 1H) 8.50-8.59 (m, 3H) 8.79-8.83 (m, 1H). |

Example 129

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1-(1-(1-((2S,3S)-1-methyl-5-oxo-2-(pyridin-3-yl)pyrrolidin-3-yl)-1-oxo-5,8,11-trioxa-2-azatridecan-13-yl)piperidin-4-yl)-1H-pyrazole-4-carboxamide

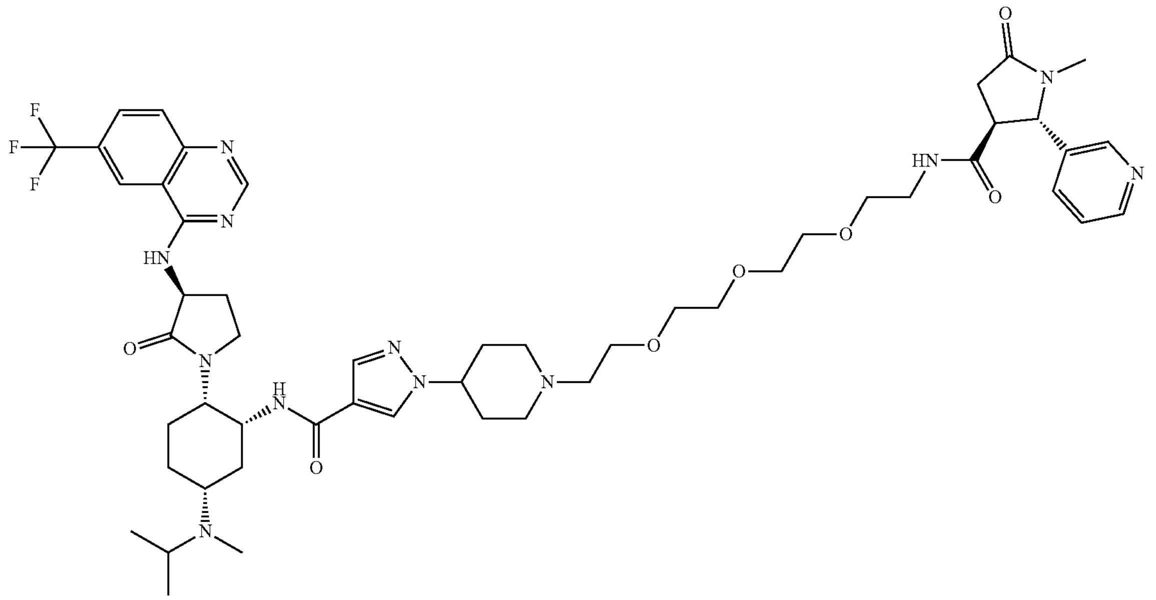 [SMILES: CC(C)N(C)[C@@H]1CC[C@H](N2CC[C@H](Nc3ncnc4ccc(C(F)(F)F)cc34)C2=O)[C@H](NC(=O)c2cnn(C3CCN(CCOCCOCCOCCNC(=O)[C@H]4CC(=O)N(C)[C@@H]4c4cccnc4)CC3)c2)C1]

Step 1 (Also Described in Step 1, Example 85)

tert-Butyl 4-(4-(ethoxycarbonyl)-1H-pyrazol-1-yl) piperidine-1-carboxylate

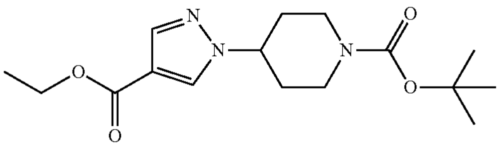 [SMILES: CCOC(=O)c1cnn(C2CCN(C(=O)OC(C)(C)C)CC2)c1]

To a stirred solution of ethyl 1H-pyrazole-4-carboxylate (1.0446 g, 7.45 mmol) in N,N-dimethylformamide (DMF) (30 mL) was added 60% sodium hydride mineral oil dispersion (0.328 g, 8.20 mmol) at 0° C. After hydrogen evolution had ceased, tert-butyl 4-((methylsulfonyl)oxy)piperidine-1-carboxylate (2.290 g, 8.20 mmol) was added and the reaction mixture was stirred at 50° C. overnight, was poured into water (100 mL) and was stirred for 2 h. The precipitate was collected by filtration to provide the title compound as an off-white solid (2.35 g, 6.61 mmol, 89% yield). LC-MS m/z 324.1 $(M+H)^+$.

Step 2

Ethyl 1-(1-(2,2-dimethyl-4-oxo-3,8,11,14-tetraoxa-5-azahexadecan-16-yl)piperidin-4-yl)-1H-pyrazole-4-carboxylate, Formic acid salt

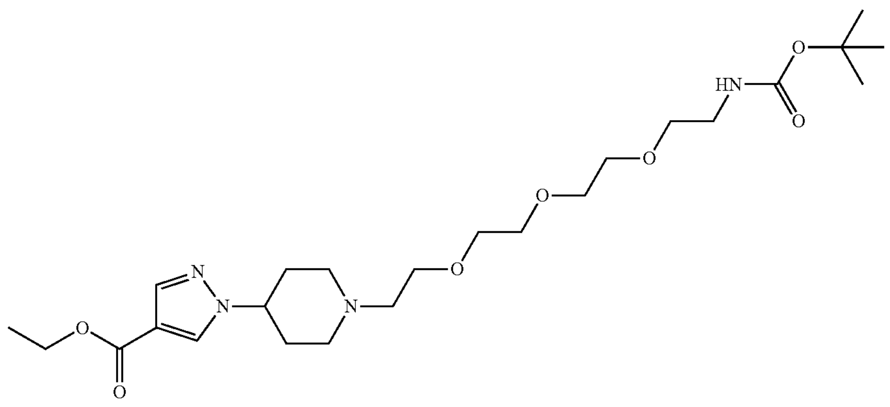 [SMILES: CCOC(=O)c1cnn(C2CCN(CCOCCOCCOCCNC(=O)OC(C)(C)C)CC2)c1]

TFA (1 mL, 12.98 mmol) was added slowly to a solution of tert-butyl 4-(4-(ethoxycarbonyl)-1H-pyrazol-1-yl)piperidine-1-carboxylate (255 mg, 0.710 mmol) in dichloromethane (DCM) (2 mL), the mixture was stirred at rt for 1 h, and was concentrated under reduced pressure. The residue was dissolved in DMF (3 mL), potassium carbonate (490 mg, 3.55 mmol) and tert-butyl (2-(2-(2-(2-bromoethoxy)ethoxy)ethoxy)ethyl)carbamate (250 mg, 0.702 mmol) were added sequentially. The mixture was stirred at 60° C. for 2 h, was cooled, and was filtered. Purification by MDAP chromatography (XSelect™ CSH Prep C18 5 μm OBD column, 40 mL/min) eluting with a gradient of 15 to 55% acetonitrile in water both containing formic acid (0.1%) provided the title compound as a colorless film (276 mg, 0.44 mmol, 62.6% yield.) LC-MS m/z 499.5$(M+H)^+$.

Step 3

Ethyl 1-(1-(1-((2S,3S)-1-methyl-5-oxo-2-(pyridin-3-yl)pyrrolidin-3-yl)-1-oxo-5,8,11-trioxa-2-azatridecan-13-yl)piperidin-4-yl)-1H-pyrazole-4-carboxylate, 2Trifluoroacetic acid salt

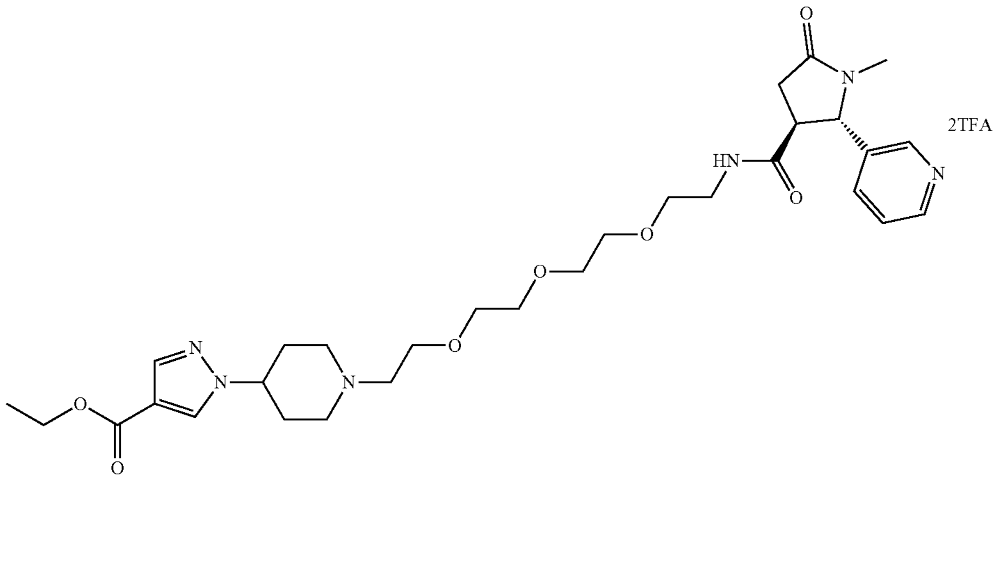 [SMILES: CCOC(=O)c1cnn(C2CCN(CCOCCOCCOCCNC(=O)[C@H]3CC(=O)N(C)[C@@H]3c3cccnc3)CC2)c1]

2TFA

4 M HCl in 1,4dioxane (1 mL, 4.00 mmol) was added to a solution of ethyl 1-(1-(2,2-dimethyl-4-oxo-3,8,11,14-tetraoxa-5-azahexadecan-16-yl)piperidin-4-yl)-1H-pyrazole-4-carboxylate, formic acid salt (270 mg, 0.496 mmol) in dichloromethane (DCM) (1.5 mL), the mixture was stirred at rt for 1 h, and was concentrated. The residue was dissolved in dichloromethane (DCM) (3 mL). Triethylamine (0.242 mL, 1.735 mmol), (2S,3S)-1-methyl-5-oxo-2-(pyridin-3-yl)pyrrolidine-3-carboxylic acid (120 mg, 0.545 mmol) and HATU (283 mg, 0.744 mmol) were added sequentially, the mixture was stirred at rt for 2 h, and was concentrated. Purification by MDAP chromatography (XSelect™ CSH C18 5 μm column, 40 mL/min) eluting with a gradient of 15 to 55% acetonitrile in water both containing TFA (0.1%) provided the title compound as a colorless (285 mg, 0.344 mmol, 69.4% yield). LC-MS m/z 499.5 $(M+H)^+$.

Step 4

1-(1-(1-((2S,3S)-1-Methyl-5-oxo-2-(pyridin-3-yl)pyrrolidin-3-yl)-1-oxo-5,8,11-trioxa-2-azatridecan-13-yl)piperidin-4-yl)-1H-pyrazole-4-carboxylic acid, 2Formic acid salt

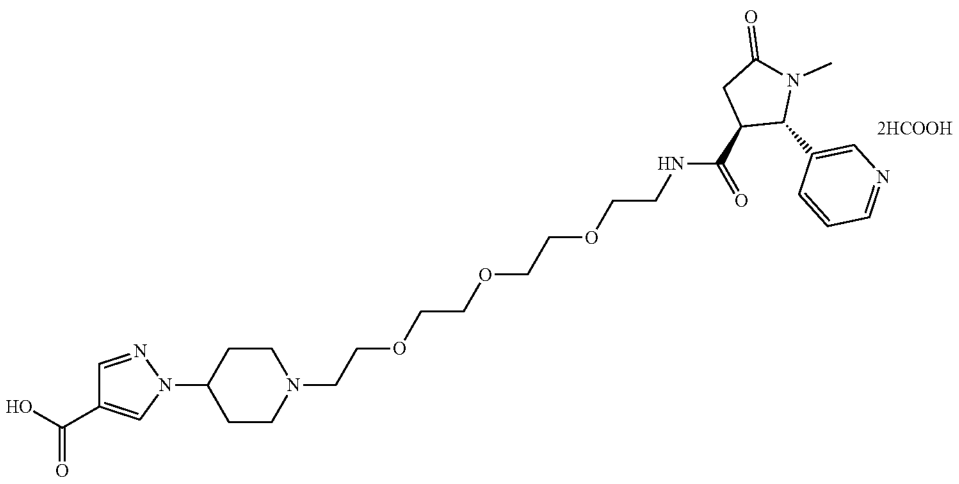 [SMILES: CN1C(=O)C[C@H](C(=O)NCCOCCOCCOCCN2CCC(n3cc(C(=O)O)cn3)CC2)[C@H]1c1cccnc1]

2 N lithium hydroxide (0.860 mL, 1.719 mmol) was added to a solution of ethyl 1-(1-(1-((2S,3S)-1-methyl-5-oxo-2-(pyridin-3-yl)pyrrolidin-3-yl)-1-oxo-5,8,11-trioxa-2-azatridecan-13-yl)piperidin-4-yl)-1H-pyrazole-4-carboxylate, ditrifluoroacetic acid salt (285 mg, 0.344 mmol) in ethanol (1.5 mL) and THE (1.5 mL) and was stirred at 0° C. for 1 h. The reaction was and stirred at rt overnight and was concentrated. The pH was adjusted to 3 to 4 with 1 N HCl. Purification by MDAP chromatography (XSelect™ CSH C18 5 μm column, 40 mL/min) eluting with a gradient of 0 to 25% acetonitrile in water both containing formic acid (0.1%) provided the title compound as a colorless film (131 mg, 0.197 mmol, 57.3% yield). LC-MS m/z 573.4 $(M+H)^+$. $^1$H NMR (400 MHz, METHANOL-$d_4$) δ ppm 0.69-0.80 (m, 4H) 0.99-1.07 (m, 4H) 1.17 (d, J=9.5 Hz, 1H) 1.40 (dt, J=8.0, 1.4 Hz, 1H) 1.61-1.79 (m, 6H) 1.83-1.88 (m, 2H) 1.90-2.05 (m, 8H) 2.12 (br d, J=12.8 Hz, 2H) 2.20-2.23 (m, 2H) 2.93-2.99 (m, 1H) 3.17 (d, J=6.5 Hz, 1H) 5.88 (dd, J=7.9, 4.9 Hz, 1H) 6.15 (dt, J=7.9, 1.8 Hz, 1H) 6.25 (s, 1H) 6.57 (s, 1H) 6.64 (s, 1H) 6.86 (s, 1H) 6.92 (br d, J=4.3 Hz, 1H).

Step 5

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1-(1-(1-((2S,3S)-1-methyl-5-oxo-2-(pyridin-3-yl)pyrrolidin-3-yl)-1-oxo-5,8,11-trioxa-2-azatridecan-13-yl)piperidin-4-yl)-1H-pyrazole-4-carboxamide

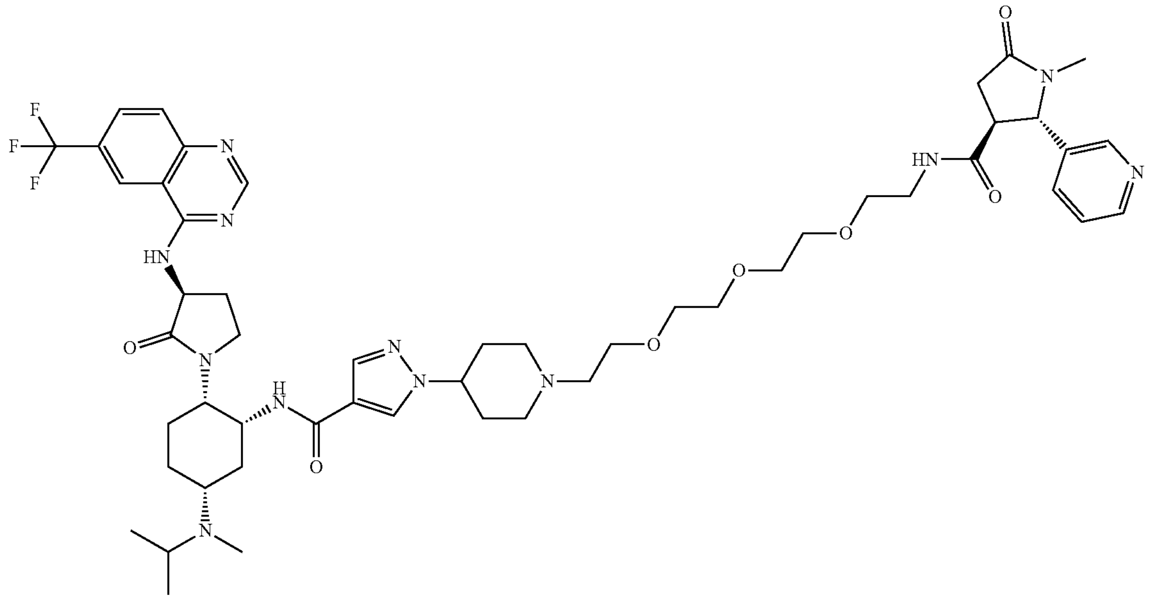 [SMILES: CC(C)N(C)[C@@H]1CC[C@H](N2CC[C@H](Nc3ncnc4ccc(C(F)(F)F)cc34)C2=O)[C@H](NC(=O)c2cnn(C3CCN(CCOCCOCCOCCNC(=O)[C@H]4CC(=O)N(C)[C@@H]4c4cccnc4)CC3)c2)C1]

4 M HCl in 1,4-dioxane (0.25 mL, 1.000 mmol) was added to a solution of tert-butyl ((1R,2S,5R)-5-(isopropyl (methyl)amino)-2-((S)-2-oxo-3-((6-(trifluoromethyl)quinazolin-4-yl)amino)pyrrolidin-1-yl)cyclohexyl)carbamate (57.9 mg, 0.103 mmol) in dichloromethane (DCM) (1.5 mL), the mixture was stirred at rt for 1 h, and was concentrated to dryness, The residue was suspended in dichloromethane (DCM) (3 mL) and triethylamine (0.06 mL, 0.430 mmol), and 1-(1-(1-((2S,3S)-1-methyl-5-oxo-2-(pyridin-3-yl)pyrrolidin-3-yl)-1-oxo-5,8,11-trioxa-2-azatridecan-13-yl)piperidin-4-yl)-1H-pyrazole-4-carboxylic acid, 2formic acid salt (65 mg, 0.098 mmol) and HATU (58.5 mg, 0.154 mmol) were added. The mixture was stirred at rt for 1 and was concentrated. Purification by MDAP chromatography (XSelect™ CSH C18 5 µm column, 40 mL/min) eluting with a gradient of 30 to 85% acetonitrile in water containing ammonium bicarbonate (10 mM) and the pH adjusted to 10 with ammonia provided the title compound as a white solid (72.4 mg, 0.070 mmol, 71.4% yield). LC-MS m/z 1019.8 $(M+H)^+$. $^1H$ NMR (400 MHz, METHANOL-$d_4$) δ ppm 0.95-1.02 (m, 3H) 1.16-1.31 (m, 3H) 1.69-1.94 (m, 4H) 1.99-2.11 (m, 4H) 2.33 (s, 8H) 2.46-2.56 (m, 1H) 2.60-2.75 (m, 6H) 2.76-2.88 (m, 2H) 3.00-3.13 (m, 3H) 3.35-3.72 (m, 17H) 4.10-4.24 (m, 2H) 4.72-4.80 (m, 1H) 4.81-4.85 (m, 1H) 5.25-5.35 (m, 1H) 7.53 (dd, J=7.9, 4.9 Hz, 1H) 7.77-7.82 (m, 2H) 7.88-7.94 (m, 1H) 8.03 (s, 1H) 8.06 (br d, J=1.8 Hz, 1H) 8.51-8.54 (m, 1H) 8.55-8.59 (m, 2H) 8.78-8.84 (m, 1H).

Example 130

1-(4-(((1R,2S,5R)-5-(Isopropyl(methyl)amino)-2-((S)-2-oxo-3-((6-(trifluoromethyl) quinazolin-4-yl) amino)pyrrolidin-1-yl)cyclohexyl)carbamoyl)phenyl)-N-(2-(2-(2-((2S,3S)-1-methyl-5-oxo-2-(pyridin-3-yl)pyrrolidine-3-carboxamido)ethoxy) ethoxy) ethyl)piperidine-4-carboxamide

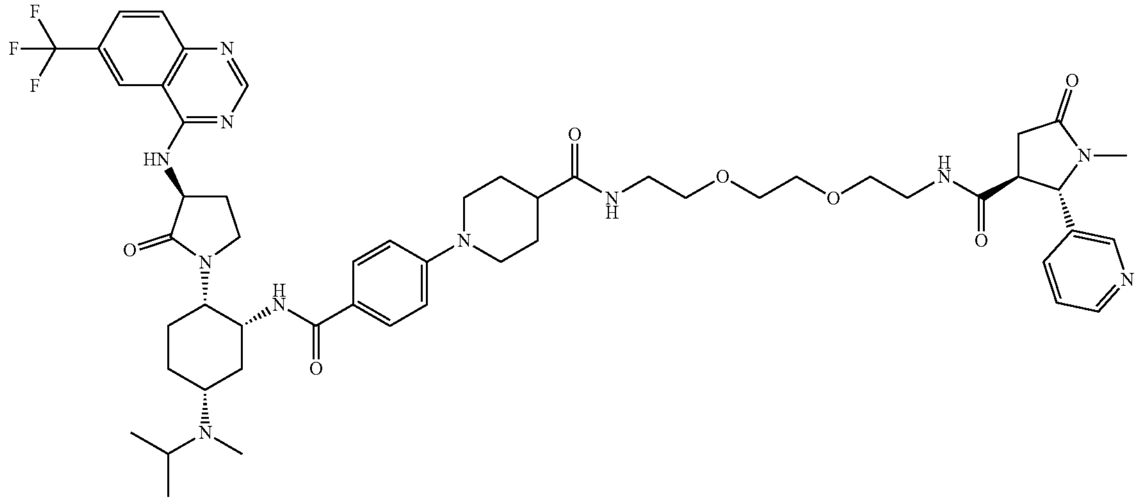 [SMILES: CC(C)N(C)[C@@H]1CC[C@H](N2CC[C@H](Nc3ncnc4ccc(C(F)(F)F)cc34)C2=O)[C@H](NC(=O)c2ccc(N3CCC(C(=O)NCCOCCOCCNC(=O)[C@H]4CC(=O)N(C)[C@@H]4c4cccnc4)CC3)cc2)C1]

Step 1 tert-Butyl (2-(2-(2-((2S,3S)-1-methyl-5-oxo-2-(pyridin-3-yl)pyrrolidine-3-carboxamido) ethoxy)ethoxy) ethyl)carbamate

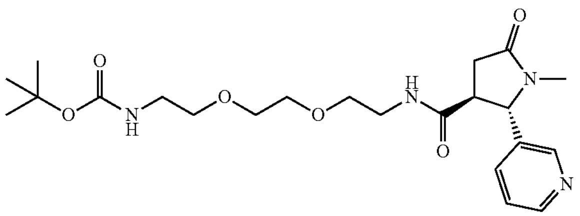 [SMILES: CN1C(=O)C[C@H](C(=O)NCCOCCOCCNC(=O)OC(C)(C)C)[C@H]1c1cccnc1]

To a solution of (2S,3S)-1-methyl-5-oxo-2-(pyridin-3-yl) pyrrolidine-3-carboxylic acid (2.0 g, 9.08 mmol) in N,N-dimethylformamide (DMF) (20 mL) was added DIPEA (4.76 mL, 27.2 mmol), EDC (2.61 g, 13.62 mmol) and HOBt (2.086 g, 13.62 mmol) and the mixture was stirred under an atmosphere of nitrogen at rt. tert-Butyl (2-(2-(2-aminoethoxy)ethoxy)ethyl)carbamate (2.59 mL, 10.90 mmol) was added and the mixture was stirred at rt for 52 h. Water (50 mL) was added and the aqueous phase was extracted with ethyl acetate (3×25 mL). The combined organic extracts were washed with water (2×25 mL), with brine (25 mL), were dried over $Na_2SO_4$, and were concentrated. Purification by Biotage® Isolera™ chromatography (100 g SNAPS column, 230 to 400 mesh) eluting with a gradient of 5 to 10% methanol in dichloromethane (DCM) provided the title compound as an off-white gummy solid (2.4 g, 5.06 mmol, 55.7% yield). LC-MS m/z 451.0 $(M+H)^+$.

Step 2

(2S,3S)-N-(2-(2-(2-Aminoethoxy)ethoxy)ethyl)-1-methyl-5-oxo-2-(pyridin-3-yl) pyrrolidine-3-carboxamide, 2Hydrochloric acid salt

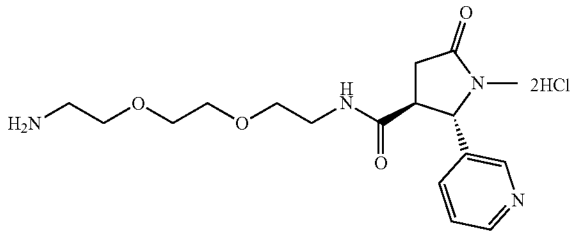 [SMILES: CN1C(=O)C[C@H](C(=O)NCCOCCOCCN)[C@H]1c1cccnc1]

HCl in 1,4-dioxane (5.92 mL, 26.6 mmol) was added to a solution of tert-butyl (2-(2-(2-((2S,3S)-1-methyl-5-oxo-2-(pyridin-3-yl) pyrrolidine-3-carboxamido)ethoxy)ethoxy) ethyl) carbamate (2.4 g, 5.33 mmol) in dichloromethane (DCM) (24 mL), the mixture was stirred at rt for 16 h, and was concentrated under reduced pressure to provide the title compound as a yellow, gummy solid (2 g, 4.72 mmol, 89% yield). LC-MS m/z 351.2 $(M+H)^+$.

Step 3

Methyl 4-(4-((2-(2-(2-((2S,3S)-1-methyl-5-oxo-2-(pyridin-3-yl)pyrrolidine-3-carboxamido) ethoxy) ethoxy)ethyl)carbamoyl)piperidin-1-yl)benzoate

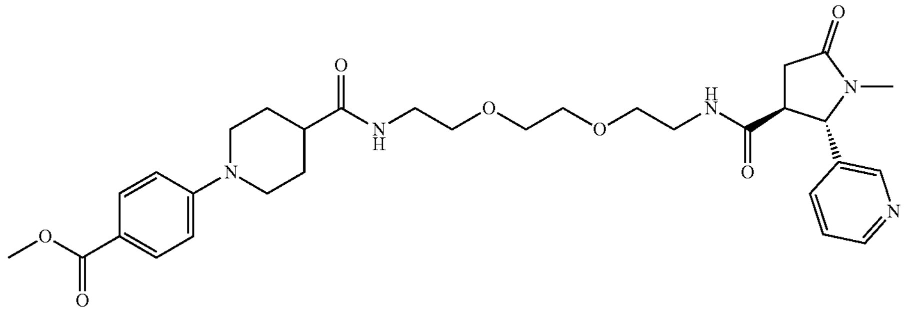 [SMILES: COC(=O)c1ccc(N2CCC(C(=O)NCCOCCOCCNC(=O)[C@H]3CC(=O)N(C)[C@@H]3c3cccnc3)CC2)cc1]

To a solution of 1-(4-(methoxycarbonyl)phenyl)piperidine-4-carboxylic acid (600 mg, 2.279 mmol) in dichloromethane (DCM) (12 mL) and N-N-dimethylformamide (DMF) (3 mL) were added sequentially EDC, hydrochloric acid salt (655 mg, 3.42 mmol), HOBt (462 mg, 3.42 mmol), triethylamine (0.953 ml, 6.84 mmol), and (2S,3S)-N-(2-(2-(2-aminoethoxy)ethoxy)ethyl)-1-methyl-5-oxo-2-(pyridin-3-yl) pyrrolidine-3-carboxamide, 2hydrochloric acid salt (882 mg, 2.095 mmol), and the mixture was stirred at rt for 16 h. Dichloromethane (DCM) was added, the organic phase was washed with water (10 mL), was dried over $Na_2SO_4$, and was concentrated. Purification by Biotage® Isolera™ chromatography (50 g SNAPS column) eluting with 5% methanol in dichloromethane (DCM) provided the title compound as a yellow, gummy solid (700 mg, 0.858 mmol, 41.0% yield). LC-MS m/z 596.2 $(M+H)^+$.

Step 4

4-(4-((2-(2-(2-((2S,3S)-1-Methyl-5-oxo-2-(pyridin-3-yl)pyrrolidine-3-carboxamido) ethoxy)ethoxy) ethyl)carbamoyl)piperidin-1-yl)benzoic acid

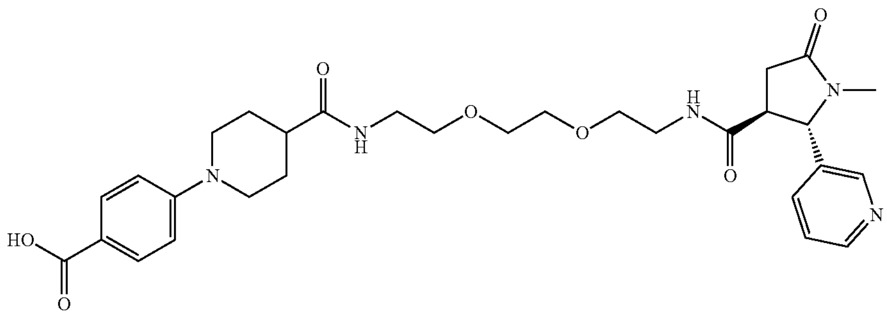 [SMILES: CN1C(=O)C[C@H](C(=O)NCCOCCOCCNC(=O)C2CCN(c3ccc(C(=O)O)cc3)CC2)[C@H]1c1cccnc1]

To a solution of methyl 4-(4-((2-(2-(2-((2S,3S)-1-methyl-5-oxo-2-(pyridin-3-yl) pyrrolidine-3-carboxamido)ethoxy) ethoxy)ethyl)carbamoyl)piperidin-1-yl)benzoate (700 mg, 1.175 mmol) in tetrahydrofuran (THF) (7 mL) and water (3.5 mL) was added lithium hydroxide monohydrate (148 mg, 3.53 mmol) at 0° C., the mixture was stirred at rt for 16 h, and was concentrated under reduced pressure. The residue was acidified with 1.5 N HCl (2 mL) and was concentrated. Purification by reverse-phase HPLC (XSelect™ CSH Prep C18 5 μm column, 15 mL/min) eluting with 15 to 100% acetonitrile in water containing ammonium acetate (10 mM) provided the title compound as a light-brown gum (435 mg, 0.740 mmol, 63.0% yield). LC-MS m/z 582.3 $(M+H)^+$.

Step 5

1-(4-(((1R,2S,5R)-5-(Isopropyl(methyl)amino)-2-((S)-2-oxo-3-((6-(trifluoromethyl) quinazolin-4-yl) amino)pyrrolidin-1-yl)cyclohexyl)carbamoyl)phenyl)-N-(2-(2-(2-((2S,3S)-1-methyl-5-oxo-2-(pyridin-3-yl)pyrrolidine-3-carboxamido)ethoxy) ethoxy) ethyl)piperidine-4-carboxamide

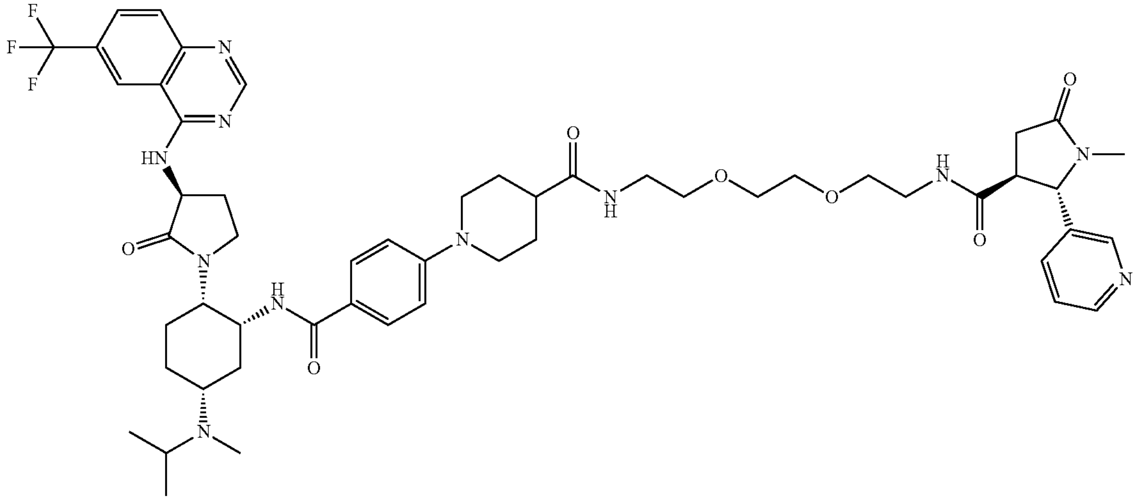 [SMILES: CC(C)N(C)[C@@H]1CC[C@H](N2CC[C@H](Nc3ncnc4ccc(C(F)(F)F)cc34)C2=O)[C@H](NC(=O)c2ccc(N3CCC(C(=O)NCCOCCOCCNC(=O)[C@H]4CC(=O)N(C)[C@@H]4c4cccnc4)CC3)cc2)C1]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (37.9 mg, 0.070 mmol) and 4-(4-((2-(2-(2-((2S,3S)-1-methyl-5-oxo-2-(pyridin-3-yl) pyrrolidine-3-carboxamido)ethoxy)ethoxy)ethyl)carbamoyl)piperidin-1-yl)benzoic acid (41 mg, 0.070 mmol) in dichloromethane (DCM) (0.5 mL) was added triethylamine (0.069 mL, 0.493 mmol) and HATU (32.2 mg, 0.085 mmol) and the mixture was stirred at rt overnight. Purification by MDAP chromatography (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a solid (34 mg, 0.033 mmol, 46.9% yield). LC-MS m/z 1028.3 $(M+H)^+$. $^1H$ NMR (400 MHz, METHANOL-$d_4$) δ ppm 0.95 (br d, J=6.3 Hz, 3H) 1.11-1.29 (m, 3H) 1.64-1.96 (m, 8H) 2.12-2.30 (m, 2H) 2.32 (s, 3H) 2.36-2.55 (m, 3H) 2.65 (s, 3H) 2.67-2.76 (m, 1H) 2.77-2.93 (m, 4H) 3.05 (ddd, J=9.4, 8.0, 6.7 Hz, 1H) 3.35 (s, 4H) 3.45-3.55 (m, 6H) 3.56-3.68 (m, 5H) 3.92 (br dd, J=8.8, 3.8 Hz, 2H) 4.16 (br d, J=12.8 Hz, 1H) 4.78-4.87 (m, 2H) 5.21-5.47 (m, 1H) 6.96 (br d, J=8.5 Hz, 2H) 7.48-7.56 (m, 1H) 7.69 (d, J=8.8 Hz, 2H) 7.79 (dt, J=7.9, 1.9 Hz, 1H) 7.90 (d, J=8.8 Hz, 1H) 8.07 (dd, J=8.9, 1.9 Hz, 1H) 8.52 (d, J=1.8 Hz, 1H) 8.54-8.61 (m, 2H) 8.84 (s, 1H).

The following compounds were or could be prepared with procedures analogous to that described in Example 130:

| Ex. | Compound | LC-MS m/z | NMR |
|---|---|---|---|
| 131 | 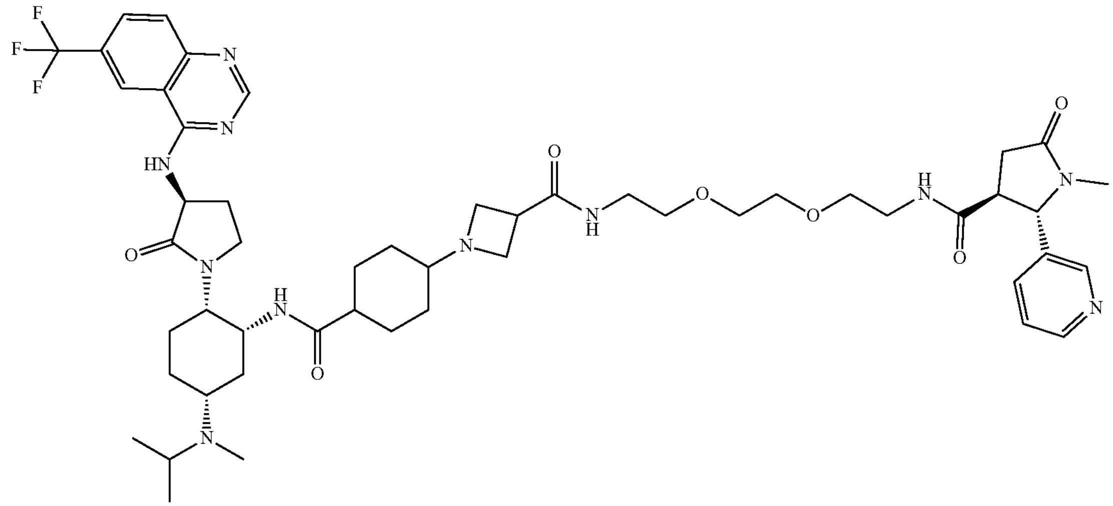 [SMILES: CC(C)N(C)[C@@H]1CC[C@H](N2CC[C@H](Nc3ncnc4ccc(C(F)(F)F)cc34)C2=O)[C@H](NC(=O)C2CCC(N3CC(C(=O)NCCOCCOCCNC(=O)[C@H]4CC(=O)N(C)[C@@H]4c4cccnc4)C3)CC2)C1] (2S,3S)-N-(2-(2-(2-(1-(4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)azetidine-3-carboxamido)ethoxy)ethoxy)ethyl)-1-methyl-5-oxo-2-(pyridin-3-yl)pyrrolidine-3-carboxamide. | 1006.4 (M + H)+ | $^1$H NMR (400 MHz, METHANOL-$d_4$) δ ppm 0.91-1.26 (m, 6H) 1.28-2.42 (m, 20 H) 2.48-2.61 (m, 1H) 2.62-2.91 (m, 6H) 3.14 (br d, J = 6.3 Hz, 4H) 3.37-3.70 (m, 15H) 3.96-4.11 (m, 1H) 4.65 (br d, J = 3.0 Hz, 1H) 4.83 (d, J = 6.8 Hz, 2H) 5.32 (s, 1H) 7.44-7.60 (m, 1H) 7.92 (s, 2H) 8.05 (s, 1H) 8.47-8.65 (m, 3H) 8.79 (s, 1H). |

-continued
| Ex. | Compound | LC-MS m/z | NMR |
| --- | --- | --- | --- |
| 132 | 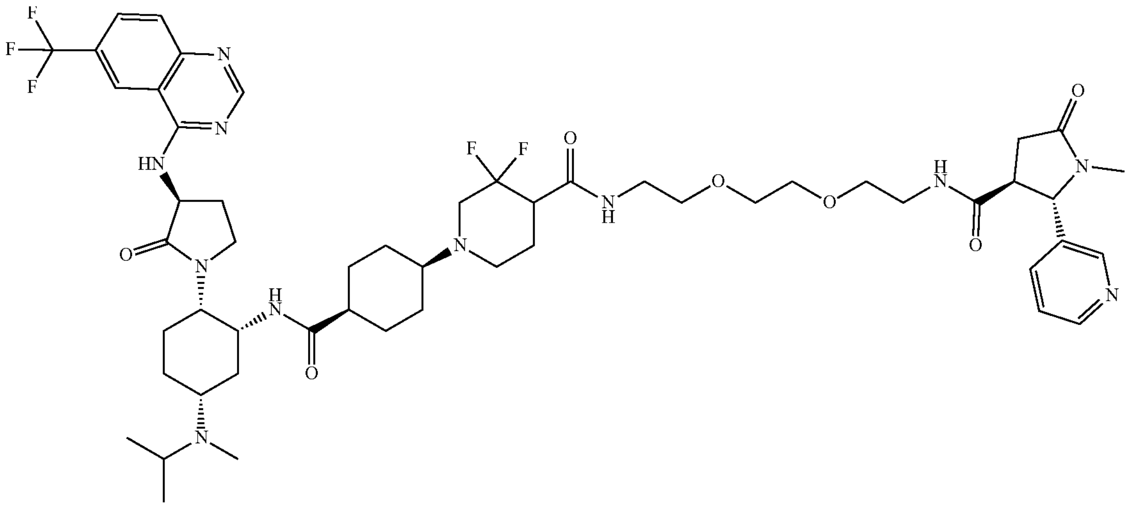 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](N3CCC(C(=O)NCCOCCOCCNC(=O)[C@H]4CC(=O)N(C)[C@@H]4c4cccnc4)C(F)(F)C3)CC2)C1] 3,3-Difluoro-1-((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)-N-(2-(2-(2-((2S,3S)-1-methyl-5-oxo-2-(pyridin-3-yl)pyrrolidine-3-carboxamido)ethoxy)ethoxy)ethyl)piperidine-4-carboxamide. | 1070.1 (M + H)+ | $^1$H NMR (400 MHz, METHANOL-$d_4$) δ ppm 0.95-0.97 (m, 1H) 1.21-1.60 (m, 15H) 1.61-2.47 (m, 23H) 2.48-2.63 (m, 2H) 2.64-2.65 (m, 1H) 2.89-2.97 (m, 1H) 2.98-3.00 (m, 1H) 3.33 (dt, J = 3.3, 1.7 Hz, 7H) 3.40-3.43 (m, 1H) 3.97-4.20 (m, 1H) 4.59-4.69 (m, 1H) 5.14-5.31 (m, 1H) 7.50-7.60 (m, 1H) 7.73-7.99 (m, 1H) 7.74-7.75 (m, 1H) 7.98-8.00 (m, 1H) 8.45-8.48 (m, 3H) 8.81 (s, 1H). |

-continued

| Ex. | Compound | LC-MS m/z | NMR |
|---|---|---|---|
| 133 | 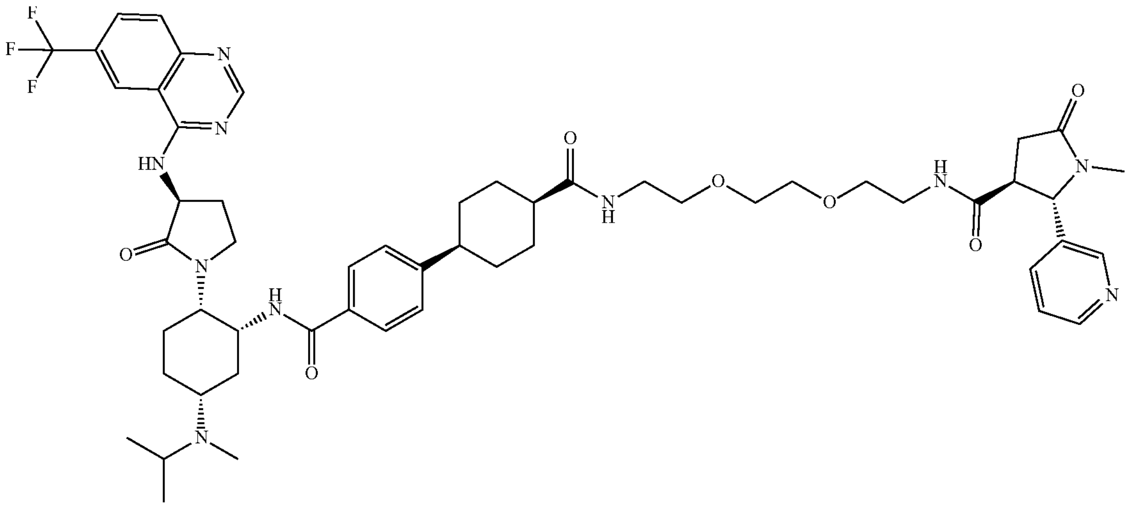 [SMILES: CC(C)N(C)[C@@H]1CC[C@H](N2CC[C@H](Nc3ncnc4ccc(C(F)(F)F)cc34)C2=O)[C@H](NC(=O)c2ccc([C@H]3CC[C@@H](C(=O)NCCOCCOCCNC(=O)[C@H]4CC(=O)N(C)[C@@H]4c4cccnc4)CC3)cc2)C1]<br>(2S,3S)-N-(2-(2-(2-((1S,4s)-4-(4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)phenyl)cyclohexane-1-carboxamido)ethoxy)ethoxy)ethyl)-1-methyl-5-oxo-2-(pyridin-3-yl)pyrrolidine-3-carboxamide. | 1027.6 (M + H)+ | $^{1}$H NMR (400 MHz, METHANOL-$d_4$) δ ppm 0.87-0.97 (m, 3H) 1.15-1.25 (m, 3H) 1.48-1.98 (m, 12H) 2.32 (s, 9H) 2.66 (s, 8H) 2.97-3.11 (m, 2H) 3.00-3.10 (m, 1H) 3.15 (s, 1H) 3.38-3.68 (m, 11H) 4.16 (br d, J = 11.8 Hz, 1H) 4.83 (d, J = 6.8 Hz, 1H) 5.31 (br t, J = 8.0 Hz, 1H) 7.33 (s, 1H) 7.34-7.37 (m, 1H) 7.50-7.55 (m, 1H) 7.74 (s, 1H) 7.76 (s, 1H) 7.80 (dt, J = 7.9, 1.9 Hz, 1H) 7.91 (d, J = 8.8 Hz, 1H) 8.08 (dd, J = 9.0, 1.8 Hz, 1H) 8.52 (d, J = 1.8 Hz, 1H) 8.55 (s, 1H) 8.57 (dd, J = 5.0, 1.5 Hz, 1H) 8.80-8.85 (m, 1H) |

-continued

| Ex. | Compound | LC-MS m/z | NMR |
|---|---|---|---|
| 134 | 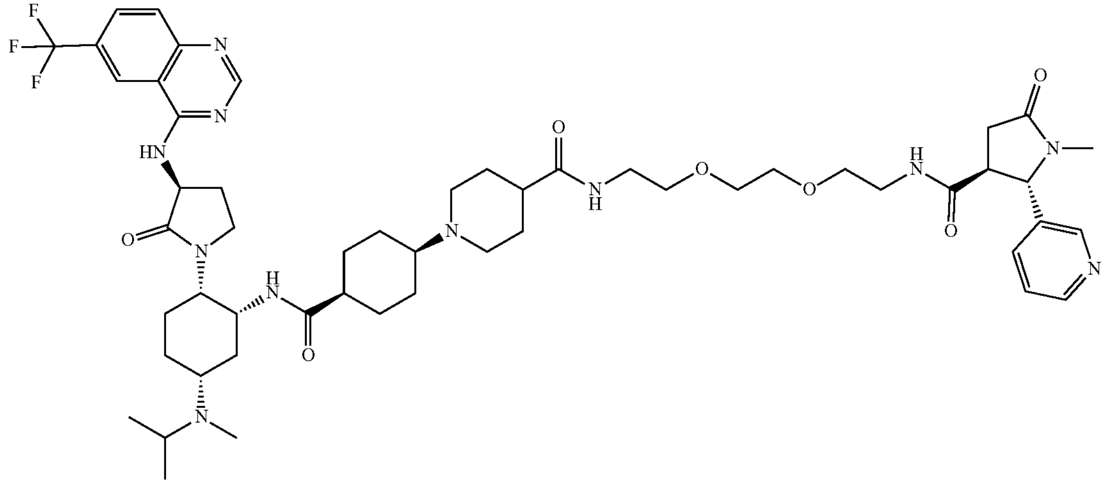 3HCOOH<br>1-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)-N-(2-(2-(2-((2S,3S)-1-methyl-5-oxo-2-(pyridin-3-yl)pyrrolidine-3-carboxamido)ethoxy)ethoxy)ethyl)piperidine-4-carboxamide, 3Formic acid salt | 1034.6 (M + H)+ | $^1$H NMR (400 MHz, METHANOL-$d_4$) δ ppm 1.15-1.34 (m, 1H) 1.34-1.43 (m, 5H) 1.43-1.63 (m, 3H) 1.86-2.19 (m, 14H) 2.25 (br d, J = 13.9 Hz, 2H) 2.45-2.66 (m, 3H) 2.66-2.69 (m, 3H) 2.69-2.91 (m, 4H) 2.97-3.16 (m, 3H) 3.35-3.45 (m, 11H) 3.50-3.58 (m, 4H) 3.58-3.63 (m, 4H) 3.69-3.80 (m, 1H) 3.81-4.03 (m, 2H) 4.22 (br d, J = 1.8 Hz, 1H) 4.35 (br s, 1H) 4.81-4.90 (m, 1H) 7.55 (dd, J = 7.9, 4.8 Hz, 1H) 7.82 (dt, J = 8.0, 1.8 Hz, 1H) 7.94 (d, J = 8.6 Hz, 1H) 8.10 (dd, J = 8.9, 1.5 Hz, 1H) 8.47 (s, 2H) 8.54 (d, J = 1.5 Hz, 1H) 8.57-8.62 (m, 1H) 8.66 (s, 1H) 8.76 (s, 1H). |

-continued

| Ex. | Compound | LC-MS m/z | NMR |
|---|---|---|---|
| 135 | 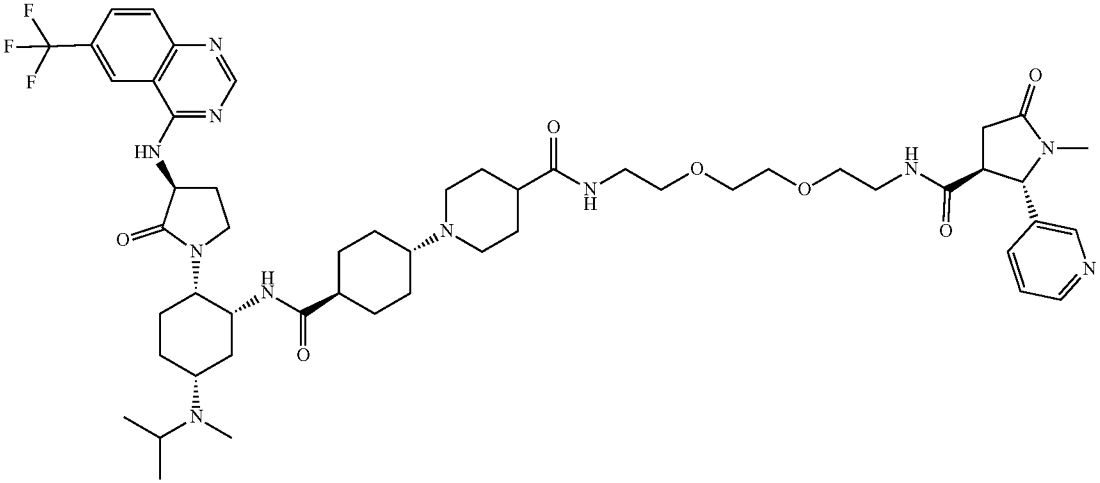 3HCOOH<br>1-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)-N-(2-(2-(2-((2S,3S)-1-methyl-5-oxo-2-(pyridin-3-yl)pyrrolidine-3-carboxamido)ethoxy)ethoxy)ethyl)piperidine-4-carboxamide 3Formic acid salt. | 1034.3 (M + H)+ | $^1$H NMR (400 MHz, METHANOL-$d_4$) δ ppm 1.24-1.50 (m, 8H) 1.50-2.35 (m, 18H) 2.38-2.62 (m, 4H) 2.63-2.76 (m, 4H) 2.77-2.90 (m, 4H) 2.91-3.18 (m, 4H) 3.38-3.43 (m, 1H) 3.44-3.67 (m, 11H) 3.74-3.82 (m, 1H) 3.84-4.06 (m, 2H) 4.15-4.27 (m, 1H) 4.34-4.43 (m, 1H) 4.81-4.87 (m, 1H) 4.98-5.05 (m, 1H) 7.50-7.59 (m, 1H) 7.79-7.85 (m, 1H) 7.90-7.97 (m, 1H) 8.06-8.13 (m, 1H) 8.51-8.56 (m, 1H) 8.57-8.62 (m, 1H) 8.62-8.66 (m, 1H) 8.70-8.76 (m, 1H). |

Example 136

(2S,3S)-N-(2-(2-(2-(((1S,4R)-4-((2-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-2-oxoethyl)carbamoyl)cyclohexyl)amino)-2-oxoethoxy)ethoxy)ethyl)-1-methyl-5-oxo-2-(pyridin-3-yl)pyrrolidine-3-carboxamide

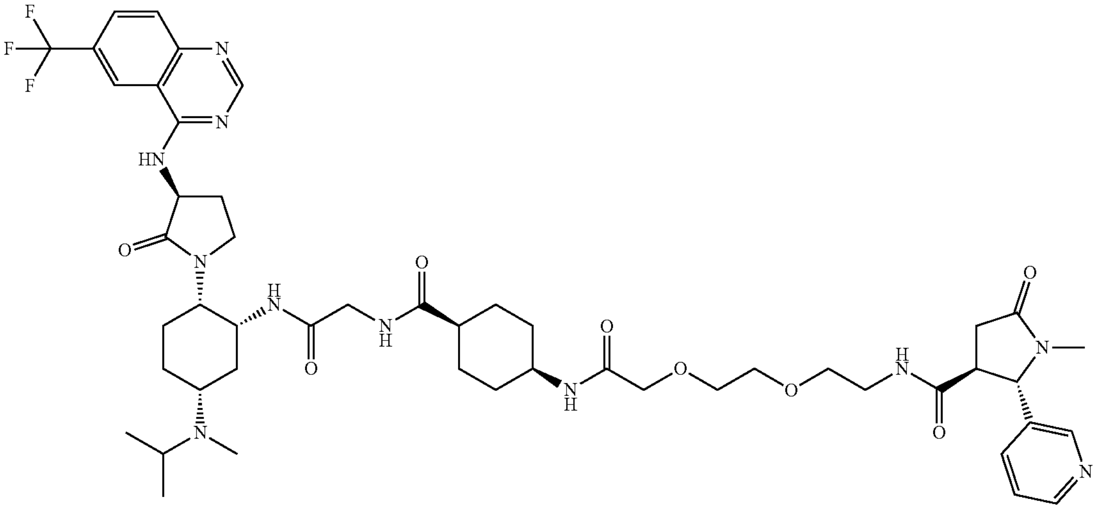 [SMILES: CC(C)N(C)[C@@H]1CC[C@H](N2CC[C@H](Nc3ncnc4ccc(C(F)(F)F)cc34)C2=O)[C@H](NC(=O)CNC(=O)[C@H]2CC[C@@H](NC(=O)COCCOCCNC(=O)[C@H]3CC(=O)N(C)[C@@H]3c3cccnc3)CC2)C1]

Step 1 tert-Butyl 2-(2-(2-((2 S, 3S)-1-methyl-5-oxo-2-(pyridin-3-yl)pyrrolidine-3-carboxamido)ethoxy)ethoxy)acetate

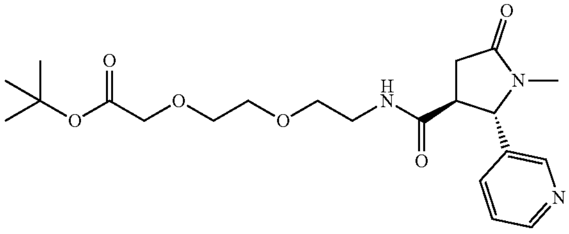 [SMILES: CN1C(=O)C[C@H](C(=O)NCCOCCOCC(=O)OC(C)(C)C)[C@H]1c1cccnc1]

To a solution of (2S,3S)-1-methyl-5-oxo-2-(pyridin-3-yl)pyrrolidine-3-carboxylic acid (500 mg, 2.270 mmol) in N,N-dimethylformamide (DMF) (4.0 mL) was added sequentially tert-butyl 2-(2-(2-aminoethoxy)ethoxy)acetate (498 mg, 2.270 mmol), HOBt (348 mg, 2.270 mmol), HATU (1295 mg, 3.41 mmol), and DIPEA (1.983 mL, 11.35 mmol) and the mixture was stirred overnight. Water was added and the aqueous phase was extracted with ethyl acetate (3×). The combined organic extracts were washed brine (2×), were dried over $Na_2SO_4$, were filtered, and the filtrate was concentrated. Purification by ISCO CombiFlash® Rf chromatography (40 g silica column, 40 mL/min) eluting with a gradient of 0 to 20% methanol in dichloromethane (DCM) provided the title compound as a light-colored solid (890 mg, 2.112 mmol, 93% yield). LC-MS m/z 422.3 $(M+H)^+$.

Step 2 tert-Butyl ((1R,4s)-4-(2-(2-(2-((2S,3S)-1-methyl-5-oxo-2-(pyridin-3-yl)pyrrolidine-3-carboxamido)ethoxy)ethoxy)acetamido)cyclohexane-1-carbonyl)glycinate

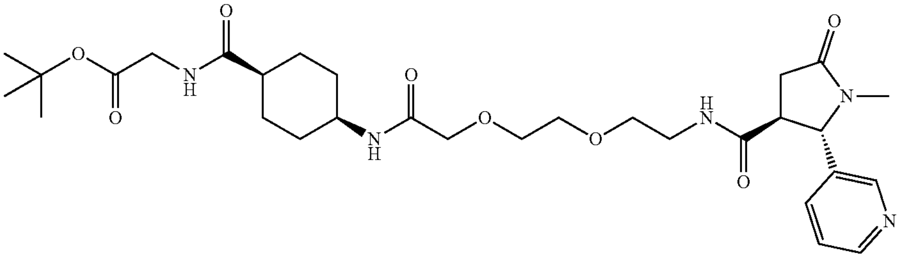 [SMILES: CN1C(=O)C[C@H](C(=O)NCCOCCOCC(=O)N[C@H]2CC[C@@H](C(=O)NCC(=O)OC(C)(C)C)CC2)[C@H]1c1cccnc1]

4 M HCl in 1,4-dioxane (5.0 mL, 20.00 mmol) was added to a solution of tert-butyl 2-(2-(2-((2S,3S)-1-methyl-5-oxo-2-(pyridin-3-yl) pyrrolidine-3-carboxamido)ethoxy)ethoxy) acetate (100 mg, 0.237 mmol) in acetone (0.50 mL), the mixture was stirred for 1 h, and was concentrated. The residue was dissolved in dichloromethane (DCM) (4.0 mL), and DIPEA (153 mg, 1.186 mmol), HOBt (43.6 mg, 0.285 mmol), EDC (68.2 mg, 0.356 mmol) and tert-butyl ((1s,4s)-4-aminocyclohexane-1-carbonyl)glycinate (66.9 mg, 0.261 mmol) were added sequentially, and the mixture was stirred overnight. Water was added and the mixture was extracted with ethyl acetate (3×). The combined organic extracts were washed brine (2×), were dried over $Na_2SO_4$, were filtered, and the filtrate was concentrated. Purification by ISCO CombiFlash® Rf chromatography (40 g silica column, 40 mL/min) eluting with a gradient of 0 to 20% methanol in dichloromethane (DCM) provided the title compound as a wax. LC-MS m/z 422.3 $(M+H)^+$.

Step 3

(2S,3S)-N-(2-(2-(2-(((1S,4R)-4-((2-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-2-oxoethyl)carbamoyl)cyclo hexyl)amino)-2-oxoethoxy)ethoxy)ethyl)-1-methyl-5-oxo-2-(pyridin-3-yl)pyrrolidine-3-carboxamide

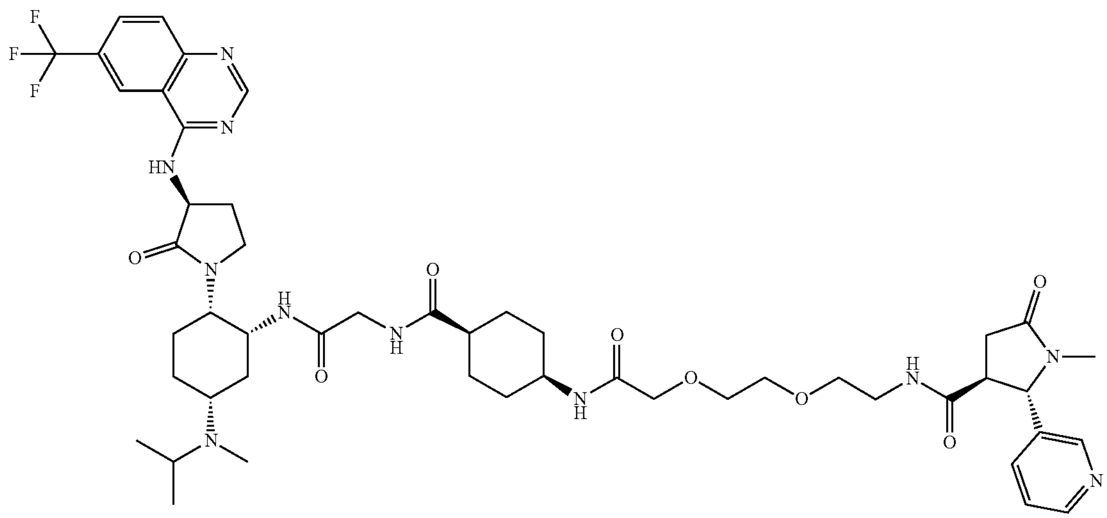 [SMILES: CC(C)N(C)[C@@H]1CC[C@H](N2CC[C@H](Nc3ncnc4ccc(C(F)(F)F)cc34)C2=O)[C@H](NC(=O)CNC(=O)[C@H]2CC[C@@H](NC(=O)COCCOCCNC(=O)[C@H]3CC(=O)N(C)[C@@H]3c3cccnc3)CC2)C1]

4 M HCl in 1,4-dioxane (4.0 mL, 16.00 mmol) was added to a solution of tert-butyl ((1R,4s)-4-(2-(2-(2-((2S,3S)-1-methyl-5-oxo-2-(pyridin-3-yl) pyrrolidine-3-carboxamido) ethoxy)ethoxy)acetamido)cyclohexane-1-carbonyl)glycinate (44 mg, 0.073 mmol) in dichloromethane (DCM) (2.0 mL), the mixture was stirred for 1 h, and was concentrated. To the residue was added sequentially dichloromethane (DCM) (2.0 mL), (S) 1-((1S,2R,4R)-2-amino-4-(isopropyl (methyl)amino)cyclohexyl)-3-((6-(trifluoromethyl)quinazolin-4-yl)amino)pyrrolidin-2-one, 2hydrochloric acid salt (49.0 mg, 0.073 mmol), HOBt (13.39 mg, 0.087 mmol), DIPEA (0.064 mL, 0.364 mmol), and EDC (20.96 mg, 0.109 mmol) and the mixture was stirred at rt overnight. Saturated $NaHCO_3$ was added and the mixture was extracted with dichloromethane (DCM) (3×). The combined organic extracts were washed brine (2×), were dried over $Na_2SO_4$, were filtered, and the filtrate was concentrated. Purification by MDAP chromatography (XSelect™ CSH C18 5 μm column, 40 mL/min) eluting with a gradient of 15 to 55% acetonitrile in water containing ammonium bicarbonate (10 mM) and ammonium hydroxide (0.075%) provided the title compound as an off-white solid (34.5 mg, 0.033 mmol, 45.2% yield). LC-MS m/z 994.8 $(M+H)^+$. $^1H$ NMR (400 MHz, DMSO-$d_6$) δ ppm 0.92 (d, J=6.4 Hz, 3H) 1.04 (d, J=6.4 Hz, 3H) 1.29-1.71 (m, 10H) 1.85-2.14 (m, 7H) 2.14-2.24 (m, 1H) 2.26-2.38 (m, 1H) 2.39-2.47 (m, 1H) 2.49 (s, 3H) 2.54-2.61 (m, 1H) 2.64-2.75 (m, 1H) 2.90-3.00 (m, 1H) 3.10-3.28 (m, 3H) 3.37-3.43 (m, 3H) 3.44-3.53 (m, 4H) 3.54-3.67 (m, 3H) 3.69-3.79 (m, 1H) 3.79-3.87 (m, 2H) 3.89-4.02 (m, 1H) 4.34-4.48 (m, 1H) 4.64 (d, J=6.4 Hz, 1H) 5.05 (d, J=8.3 Hz, 1H) 7.32-7.39 (m, 1H) 7.36 (d, J=7.3 Hz, 1H) 7.42 (dd, J=7.8, 4.9 Hz, 1H) 7.66 (dt, J=7.8, 2.0 Hz, 1H) 7.89 (d, J=8.8 Hz, 1H) 8.07 (s, 3H) 8.46 (d, J=2.0 Hz, 1H) 8.54 (dd, J=4.6, 1.7 Hz, 1H) 8.59 (s, 2H) 8.66 (d, J=8.3 Hz, 1H) 8.91-8.97 (m, 1H).

The following compound was or could be prepared with procedures analogous to that described in Example 136:

| Ex. | Compound | LC-MS m/z | NMR |
|---|---|---|---|
| 137 | 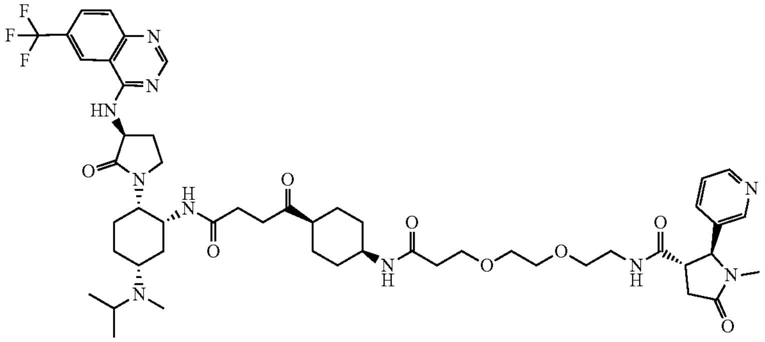 [SMILES: CC(C)N(C)[C@@H]1CC[C@H](N2CC[C@H](Nc3ncnc4ccc(C(F)(F)F)cc34)C2=O)[C@H](NC(=O)CCC(=O)[C@H]2CC[C@@H](NC(=O)CCOCCOCCNC(=O)[C@H]3CC(=O)N(C)[C@@H]3c3cccnc3)CC2)C1] (2S,3S)-N-(2-(2-(3-(((1S,4s)-4-((2-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-2-oxoethyl)carbamoyl)cyclohexyl)amino)-3-oxopropoxy)ethoxy)ethyl)-1-methyl-5-oxo-2-(pyridin-3-yl)pyrrolidine-3-carboxamide. | 1008.5 (M + H)+ | $^1$H NMR (400 MHz, DMSO-$d_6$) δ ppm 0.92 (d, J = 6.4 Hz, 3H) 1.04 (d, J = 6.8 Hz, 3H) 1.30-1.53 (m, 4H) 1.54-1.72 (m, 6H) 1.89-2.08 (m, 3H) 2.08-2.18 (m, 4H) 2.27-2.36 (m, 3H) 2.40-2.49 (m, 3H) 2.66-2.75 (m, 1H) 2.92-3.00 (m, 1H) 3.09-3.27 (m, 3H) 3.43 (s, 5H) 3.51-3.61 (m, 3H) 3.62-3.67 (m, 2H) 3.70 (br d, J = 4.9 Hz, 1H) 3.81-4.04 (m, 1H) 4.42 (br d, J = 3.9 Hz, 1H) 4.64 (d, J = 6.4 Hz, 1H) 5.05 (q, J = 8.3 Hz, 1H) 7.43 (dd, J = 7.6, 5.1 Hz, 1H) 7.67 (dt, J = 8.2, 2.0 Hz, 1H) 7.72 (d, J = 7.3 Hz, 1H) 7.89 (d, J = 8.8 Hz, 1H) 8.04-8.13 (m, 3H) 8.47 (d, J = 2.0 Hz, 1H) 8.55 (d, J = 2.0 Hz, 1H) 8.56 (d, J = 1.5 Hz, 1H) 8.59 (s, 1H) 8.60-8.67 (m, 2H) 8.95 (s, 1H). |

Example 138

(2S,3S)-N-(3-(9-((3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropyl)amino)-3-azaspiro[5.5]undecan-3-yl)propyl)-1-methyl-5-oxo-2-(pyridin-3-yl)pyrrolidine-3-carboxamide

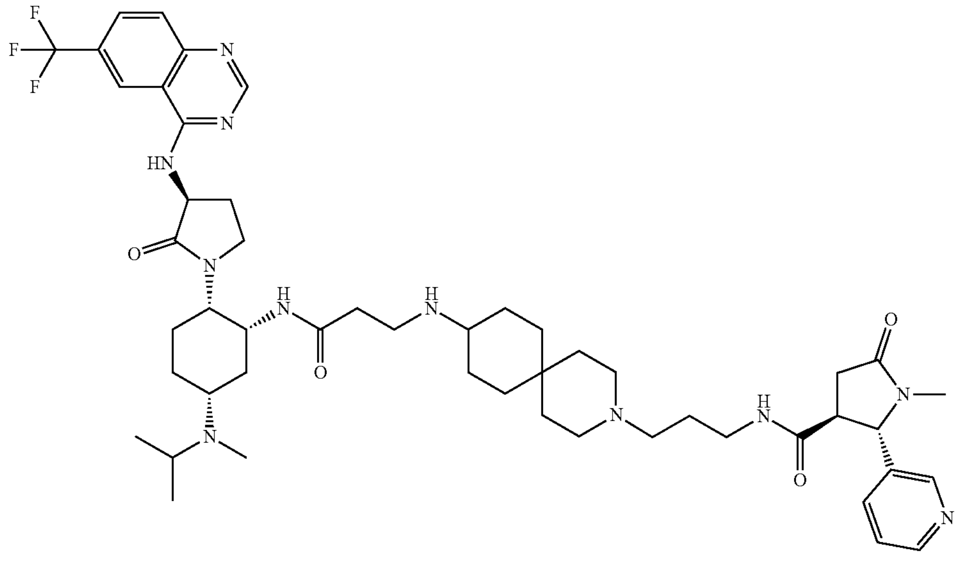 [SMILES: CC(C)N(C)[C@@H]1CC[C@H](N2CC[C@H](Nc3ncnc4ccc(C(F)(F)F)cc34)C2=O)[C@H](NC(=O)CCNC2CCC3(CC2)CCN(CCCNC(=O)[C@H]2CC(=O)N(C)[C@@H]2c2cccnc2)CC3)C1]

Step 1

(2S,3S)-N-(3-Hydroxypropyl)-1-methyl-5-oxo-2-(pyridin-3-yl)pyrrolidine-3-carboxamide

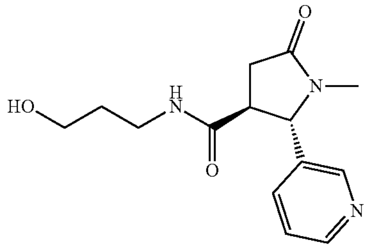 [SMILES: CN1C(=O)C[C@H](C(=O)NCCCO)[C@H]1c1cccnc1]

To a mixture of 3-aminopropan-1-ol (239 mg, 3.18 mmol) and (2S,3S)-1-methyl-5-oxo-2-(pyridin-3-yl)pyrrolidine-3-carboxylic acid (350 mg, 1.589 mmol) in dichloromethane (DCM) (5 mL) was added HATU (725 mg, 1.907 mmol) and triethylamine (0.665 mL, 4.77 mmol) and the mixture was stirred at rt overnight. The mixture was distributed between saturated $NaHCO_3$/solid $NaHCO_3$ and dichloromethane (DCM). The organic phase was extracted with saturated $NaHCO_3$. The combined aqueous extracts were filtered and the filtrate was concentrated. Methanol was added to the residue, the solids were filtered off and were washed with methanol. The combined filtrates were concentrated. Purification by ISCO CombiFlash® EZ Prep chromatography ($C_{1-8}$ Aq Gold column, 40 mL/min) eluting with a gradient of 0 to 10% acetonitrile in water containing ammonium bicarbonate (10 mM) and ammonium hydroxide (0.075%) provided the title compound (200 mg, 0.721 mmol, 45.4% yield). LC-MS m/z 278.1 $(M+H)^+$.

Step 2

3-((2S,3S)-1-Methyl-5-oxo-2-(pyridin-3-yl)pyrrolidine-3-carboxamido)propyl methanesulfonate

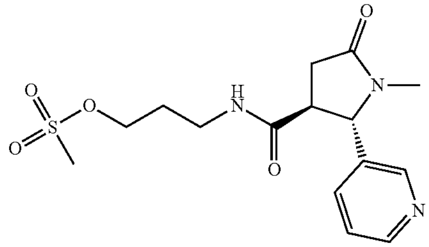 [SMILES: CN1C(=O)C[C@H](C(=O)NCCCOS(C)(=O)=O)[C@H]1c1cccnc1]

To a mixture of (2S,3S)-N-(3-hydroxypropyl)-1-methyl-5-oxo-2-(pyridin-3-yl) pyrrolidine-3-carboxamide (347 mg, 1.251 mmol) in dichloromethane (DCM) (5 mL) was added triethylamine (0.523 mL, 3.75 mmol) and methanesulfonyl chloride (0.194 mL, 2.502 mmol) and the mixture was stirred at rt for 2 h. Triethylamine (0.523 mL, 3.75 mmol) and methanesulfonyl chloride (0.194 mL, 2.502 mmol) were added and the mixture was stirred at rt for 1 h. Saturated $NaHCO_3$ was added and the aqueous phase was extracted with dichloromethane (DCM). The combined organic extracts were dried over $Na_2SO_4$, were filtered, and the filtrate was concentrated. Purification by normal-phase chromatography provided the title compound as a light-yellow oil (350 mg, 0.985 mmol, 79% yield). LC-MS m/z 356.2 $(M+H)^+$.

Step 3 (2S,3S)-1-Methyl-5-oxo-N-(3-(9-oxo-3-azaspiro[5.5]undecan-3-yl)propyl)-2-(pyridin-3-yl) pyrrolidine-3-carboxamide

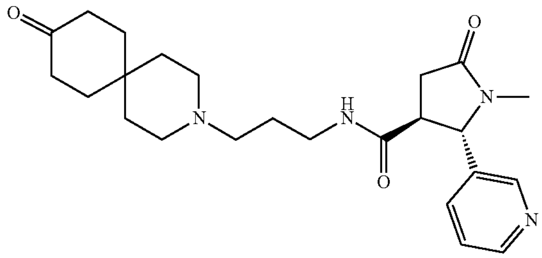 [SMILES: CN1C(=O)C[C@H](C(=O)NCCCN2CCC3(CCC(=O)CC3)CC2)[C@H]1c1cccnc1]

To a mixture of 3-azaspiro[5.5]undecan-9-one, trifluoroacetic acid salt (116 mg, 0.412 mmol) in acetonitrile (1 mL) was added potassium carbonate (228 mg, 1.650 mmol) and the mixture was stirred at rt for 20 min. 3-((2S,3S)-1-Methyl-5-oxo-2-(pyridin-3-yl)pyrrolidine-3-carboxamido) propyl methanesulfonate (147 mg, 0.412 mmol) was added and the mixture was stirred at 80° C. for 10 min. Additional 3-((2S,3S)-1-methyl-5-oxo-2-(pyridin-3-yl)pyrrolidine-3-carboxamido)propyl methanesulfonate (147 mg, 0.412 mmol) was added and the mixture was stirred at 50° C. for 4 h. Saturated $NaHCO_3$ and dichloromethane (DCM) were added and the aqueous phase was extracted with dichloromethane (DCM). The combined organic extracts were dried over $Na_2SO_4$, were filtered and the filtrate was concentrated. Purification by MDAP chromatography (XSelect™ CSH C18 5 μm column, 40 mL/min) eluting with a gradient of 15 to 85% acetonitrile in water containing ammonium bicarbonate (10 mM) and the pH adjusted to 10 with ammonia provided the title compound (42.3 mg, 0.099 mmol, 24.05% yield). LC-MS m/z 427.5 $(M+H)^+$.

Step 4 tert-Butyl (3-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-3-oxopropyl)carbamate

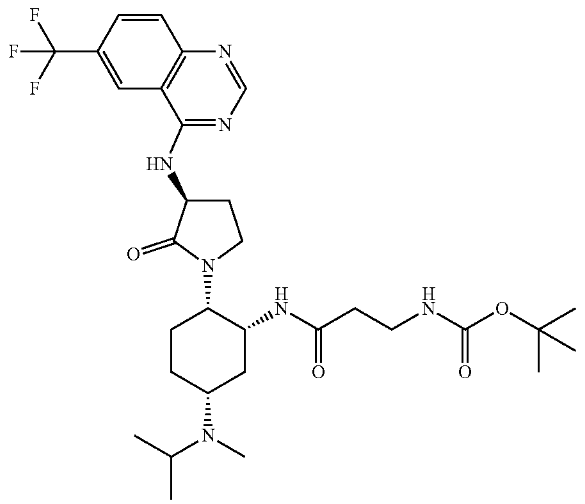 [SMILES: CC(C)N(C)[C@@H]1CC[C@H](N2CC[C@H](Nc3ncnc4ccc(C(F)(F)F)cc34)C2=O)[C@H](NC(=O)CCNC(=O)OC(C)(C)C)C1]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (65 mg, 0.121 mmol) and 3-((tert-butoxycarbonyl)amino)propanoic acid (22.88 mg, 0.121 mmol) in dichloromethane (DCM) (1 mL) was added triethylamine (0.084 mL, 0.605 mmol) and HATU (55.2 mg, 0.145 mmol) and the mixture was stirred at rt for 2 h. Purification by ISCO CombiFlash® chromatography (24 g RediSep Rf Gold® column, 35 mL/min) eluting with a gradient of 0 to 15% methanol containing ammonium hydroxide (10%) in dichloromethane (DCM) provided the title compound (54 mg, 0.085 mmol, 70.2% yield). LC-MS m/z 636.3 $(M+H)^+$.

Step 5

3-Amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)propenamide, 2Hydrochloric acid salt

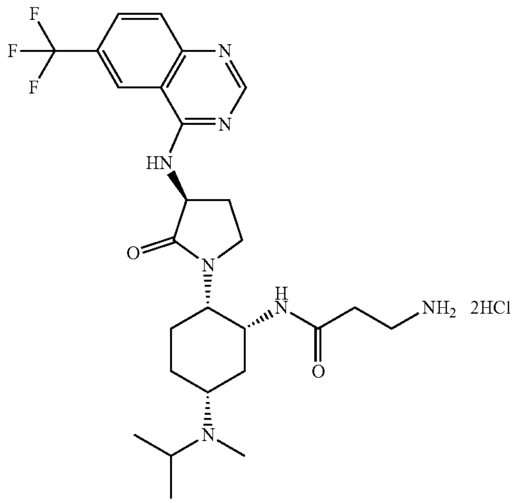 [SMILES: CC(C)N(C)[C@@H]1CC[C@H](N2CC[C@H](Nc3ncnc4ccc(C(F)(F)F)cc34)C2=O)[C@H](NC(=O)CCN)C1]

A mixture of HCl (0.106 mL, 0.425 mmol) tert-butyl (3-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-3-oxopropyl)carbamate (54 mg, 0.085 mmol) in dichloromethane (DCM) (0.1 mL) was stirred at rt for 1 h and was concentrated to provide the title compound (37.7 mg, 0.062 mmol, 73% yield). LC-MS m/z 536.4 $(M+H)^+$.

Step 6

(2S,3S)-N-(3-(9-((3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropyl)amino)-3-azaspiro[5.5]undecan-3-yl)propyl)-1-methyl-5-oxo-2-(pyridin-3-yl)pyrrolidine-3-carboxamide

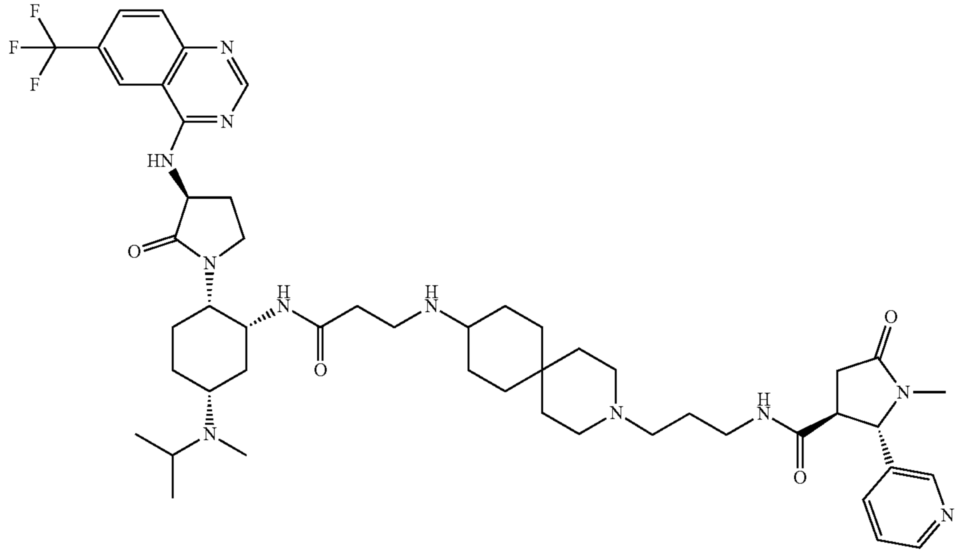 [SMILES: CC(C)N(C)[C@@H]1CC[C@H](N2CC[C@H](Nc3ncnc4ccc(C(F)(F)F)cc34)C2=O)[C@H](NC(=O)CCNC2CCC3(CC2)CCN(CCCNC(=O)[C@H]2CC(=O)N(C)[C@@H]2c2cccnc2)CC3)C1]

A mixture of 3-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)propenamide, 2hydrochloric acid salt (38 mg, 0.063 mmol) and (2S,3S)-1-methyl-5-oxo-N-(3-(9-oxo-3-azaspiro[5.5]undecan-3-yl)propyl)-2-(pyridin-3-yl)pyrrolidine-3-carboxamide (30.3 mg, 0.071 mmol) in dichloromethane (DCM) (1 mL) was stirred at rt for 20 min. Sodium triacetoxyborohydride (45.1 mg, 0.213 mmol) was added and the mixture was stirred at rt for 5 h and was concentrated under reduced pressure. Purification by MDAP chromatography (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as a solid (46.8 mg, 0.049 mmol, 77.7% yield). LC-MS m/z 947.4 $(M+H)^+$. $^1H$ NMR (400 MHz, METHANOL-$d_4$) δ ppm 0.83-1.02 (m, 2H) 1.07 (br d, J=6.3 Hz, 3H) 1.14 (br d, J=6.3 Hz, 4H) 1.19-1.25 (m, 1H) 1.26-1.34 (m, 2H) 1.40 (br s, 2H) 1.46-1.57 (m, 2H) 1.57-1.91 (m, 8H) 2.15-2.24 (m, 2H) 2.25-2.42 (m, 10H) 2.43-2.53 (m, 3H) 2.58 (br dd, J=6.3, 2.8 Hz, 1H) 2.65-2.76 (m, 5H) 2.77-2.90 (m, 2H) 2.91-3.11 (m, 3H) 3.12-3.29 (m, 2H) 3.36-3.48 (m, 1H) 3.57-3.78 (m, 2H) 4.09 (br s, 1H) 4.52 (br s, 1H) 5.19-5.42 (m, 1H) 7.54 (dd, J=7.9, 4.9 Hz, 1H) 7.82 (dt, J=8.0, 1.9 Hz, 1H) 7.92 (d, J=8.5 Hz, 1H) 8.08 (dd, J=8.8, 1.8 Hz, 1H) 8.52 (d, J=2.0 Hz, 1H) 8.58 (dd, J=4.9, 1.6 Hz, 1H) 8.62 (s, 1H) 8.77 (s, 1H).

Example 139

6-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-N-(2-(2-(2-((2S,3S)-1-methyl-5-oxo-2-(pyridin-3-yl)pyrrolidine-3-carboxamido) ethoxy)ethoxy)ethyl)nicotinamide

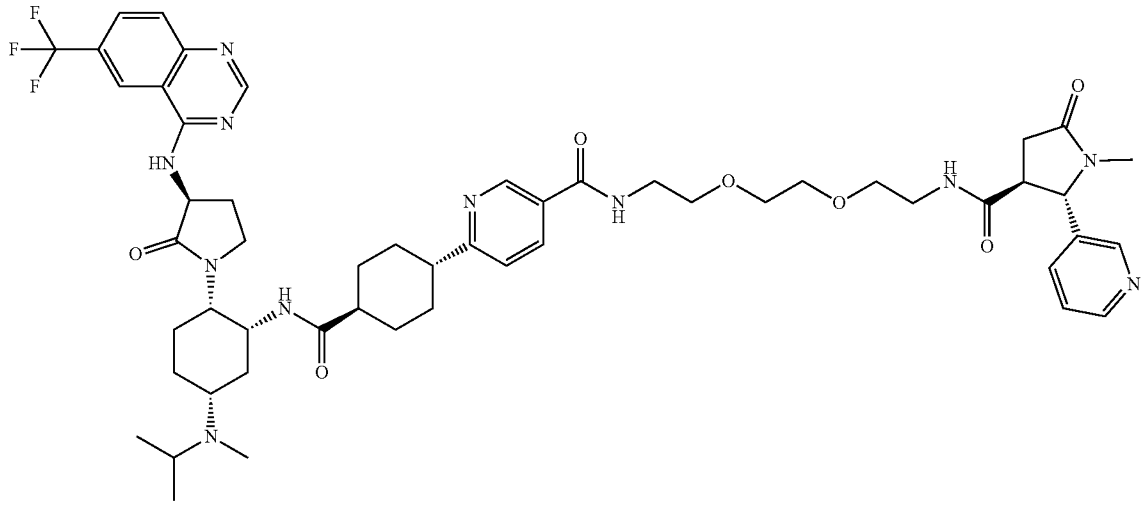 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](c3ccc(C(=O)NCCOCCOCCNC(=O)[C@H]4CC(=O)N(C)[C@@H]4c4cccnc4)cn3)CC2)C1]

Step 1 tert-Butyl (2-(2-(2-(6-bromonicotinamido)ethoxy) ethoxy)ethyl)carbamate

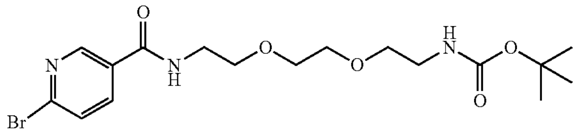 [SMILES: CC(C)(C)OC(=O)NCCOCCOCCNC(=O)c1ccc(Br)nc1]

To a stirred suspension of 6-bromonicotinic acid (2 g, 9.90 mmol) in dichloromethane (DCM) (20 mL) were added DIPEA (5.19 mL, 29.7 mmol) and HATU (5.65 g, 14.85 mmol). The solution was stirred at rt for 10 min and a solution of a solution of tert-butyl (2-(2-(2-aminoethoxy) ethoxy)ethyl)carbamate (2.70 g, 10.89 mmol) in dichloromethane (DCM) (4 mL). The mixture was stirred for 18 h, dichloromethane (DCM) (50 mL) and ice-cold water (50 mL) were added. The aqueous phase was extracted with dichloromethane (DCM) (50 mL). The combined organic phases were washed with brine (50 mL), were dried over $Na_2SO_4$, and were concentrated under reduced pressure. The residue was purified by Biotage® Isolera™ column chromatography (100 g SNAPS column) eluting with a gradient of 80 to 100% ethyl acetate in petroleum ether to provide a light-brown semi-solid. A second purification by Biotage® Isolera™ column chromatography (100 g SNAPS column) eluting with 60% ethyl acetate in petroleum ether provided the title compound as an off-white solid (3.5 g, 7.86 mmol, 79.4% yield). LC-MS m/z 432.1 $(M+H)^+$.

Step 2

Ethyl (S)-4-(5-((2,2-dimethyl-4-oxo-3,8,11-trioxa-5-azatridecan-13-yl)carbamoyl)pyridin-2-yl)cyclohex-3-ene-1-carboxylate

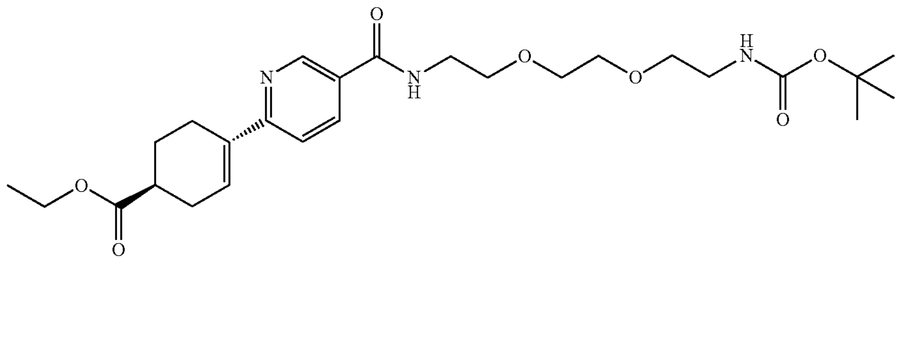

To a solution of tert-butyl (2-(2-(2-(6-bromonicotinamido)ethoxy)ethoxy)ethyl)carbamate (0.630 g, 1.457 mmol) in 1,4-dioxane (10 mL) and water (2 mL) was added sodium carbonate (0.463 g, 4.37 mmol) and ethyl 4-(4,4,5,5-tetramethyl-1,3,2-dioxaborolan-2-yl)cyclohex-3-ene-1-carboxylate (0.490 g, 1.749 mmol) and the mixture was de-gassed with nitrogen gas for 10 min. and was added tetrakis (triphenylphosphine)palladium(O) (0.084 g, 0.073 mmol) was added and the mixture was heated to 1200° C. in a microwave reactor for 15 min. The mixture was combined with an identical reaction mixture, dichloromethane (DCM) (100 mL) and ice-cold water (50 mL) were added. The aqueous phase was extracted with dichloromethane (DCM) (50 mL). The combined organic phases were washed with brine (50 mL), were dried over $Na_2SO_4$, and were concentrated under reduced pressure. Purification by Biotage® Isolera™ column chromatography (100 g SNAPS column) eluting with a gradient of 60 to 70% ethyl acetate in petroleum ether provided the title compound as a thick, colorless liquid (1.3 g, 1.851 mmol, 64% yield). LC-MS m/z 506.2 $(M+H)^+$.

Step 3

Ethyl (1r,4r)-4-(5-((2,2-dimethyl-4-oxo-3,8,11-trioxa-5-azatridecan-13-yl)carbamoyl) pyridin-2-yl) cyclohexane-1-carboxylate

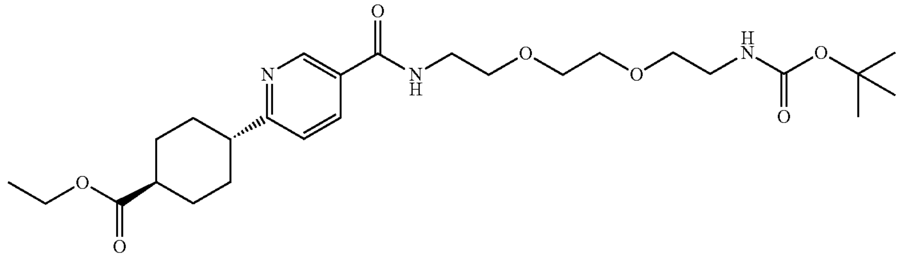 [SMILES: CCOC(=O)[C@H]1CC[C@H](c2ccc(C(=O)NCCOCCOCCNC(=O)OC(C)(C)C)cn2)CC1]

To a stirred solution of ethyl 4-(5-((2,2-dimethyl-4-oxo-3,8,11-trioxa-5-azatridecan-13-yl)carbamoyl)pyridin-2-yl) cyclohex-3-ene-1-carboxylate (1.3 g, 2.57 mmol) in ethanol (30 mL) and tetrahydrofuran (THF) (10 mL) at rt was added Pd—C(0.430 g, 0.404 mmol). The mixture was stirred under a balloon atmosphere of hydrogen for 16 h and was filtered through Celite®. The catalyst was washed with methanol in dichloromethane (10%) and the combined filtrate was concentrated under reduced pressure. Purification by SFC (CHIRALPAK® OX-H 250 mm×3 mm 5 μm column, 100 mL/min) eluting with 60% carbon dioxide in methanol provided the title compound as a colorless oil (730 mg, 1.237 mmol, 48.1% yield). LC-MS m/z 508.8 $(M+H)^+$.

Step 4

Ethyl (1r,4r)-4-(5-((2-(2-(2-aminoethoxy)ethoxy) ethyl)carbamoyl)pyridin-2-yl)cyclohexane-1-carboxylate, 2Hydrochloric acid salt

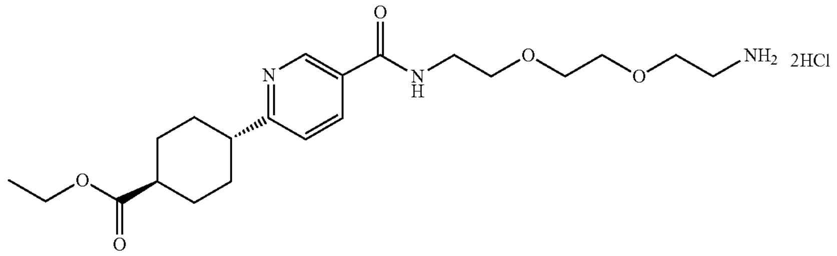 [SMILES: CCOC(=O)[C@H]1CC[C@H](c2ccc(C(=O)NCCOCCOCCN)cn2)CC1]

HCl (0.144 mL, 4.73 mmol) was added to a solution of ethyl (1r,4r)-4-(5-((2,2-dimethyl-4-oxo-3,8,11-trioxa-5-azatridecan-13-yl)carbamoyl)pyridin-2-yl)cyclohexane-1-carboxylate (200 mg, 0.394 mmol) in dichloromethane (DCM) (3 mL). The mixture was stirred for 1 h and was concentrated under reduced pressure. The residue was triturated with methyl t-butyl ether (2×5 mL) to provide the title compound as an off-white solid (180 mg, 0.377 mmol, 96% yield). LC-MS m/z 408.3 $(M+H)^+$.

Step 5

Ethyl (1r,4r)-4-(5-((2-(2-(2-((2S,3S)-1-methyl-5-oxo-2-(pyridin-3-yl)pyrrolidine-3-carboxamido)ethoxy)ethoxy)ethyl)carbamoyl)pyridin-2-yl)cyclohexane-1-carboxylate

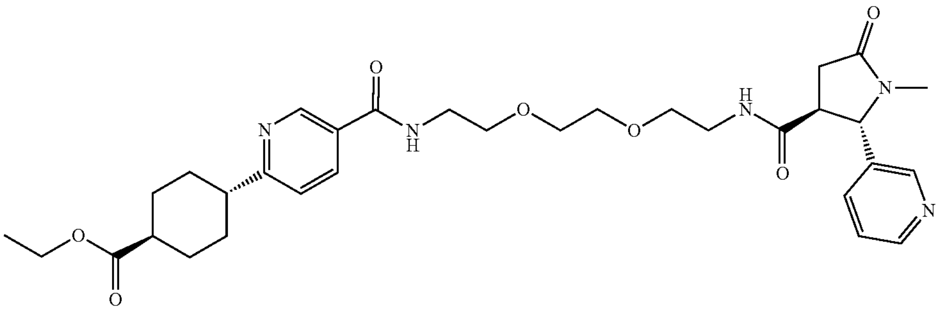 [SMILES: CCOC(=O)[C@H]1CC[C@H](c2ccc(C(=O)NCCOCCOCCNC(=O)[C@H]3CC(=O)N(C)[C@@H]3c3cccnc3)cn2)CC1]

To a stirred suspension of (2S,3S)-1-methyl-5-oxo-2-(pyridin-3-yl)pyrrolidine-3-carboxylic acid (85 mg, 0.386 mmol) in dichloromethane (DCM) (10 mL) were added triethylamine (0.215 mL, 1.544 mmol), EDC (111 mg, 0.579 mmol). and HOBt (89 mg, 0.579 mmol) and the mixture was stirred at rt for 10 min. A solution of ethyl (1r,4r)-4-(5-((2-(2-(2-aminoethoxy)ethoxy)ethyl)carbamoyl)pyridin-2-yl)cyclohexane-1-carboxylate, 2hydrochloric acid salt (171 mg, 0.358 mmol) in dichloromethane (DCM) (4 mL) was added dropwise. This mixture was stirred at rt for 16 h and dichloromethane (DCM) (50 mL) and ice water (15 mL) were added.

The aqueous phase was extracted with dichloromethane (DCM). The combined organic phases were washed with brine (15 ml), were dried over $Na_2SO_4$ and were concentrated under reduced pressure. Purification by Biotage® Isolera™ chromatography (10 g SNAPS column) eluting with a gradient of 0 to 8% methanol in dichloromethane (DCM) provided the title compound as a thick, white, gummy liquid (100 mg, 0.159 mmol, 44.4% yield). LC-MS m/z 610.40 $(M+H)^+$.

Step 6

(1r,4r)-4-(5-((2-(2-(2-((2S,3S)-1-Methyl-5-oxo-2-(pyridin-3-yl)pyrrolidine-3-carboxamido)ethoxy)ethoxy)ethyl)carbamoyl)pyridin-2-yl)cyclohexane-1-carboxylic acid

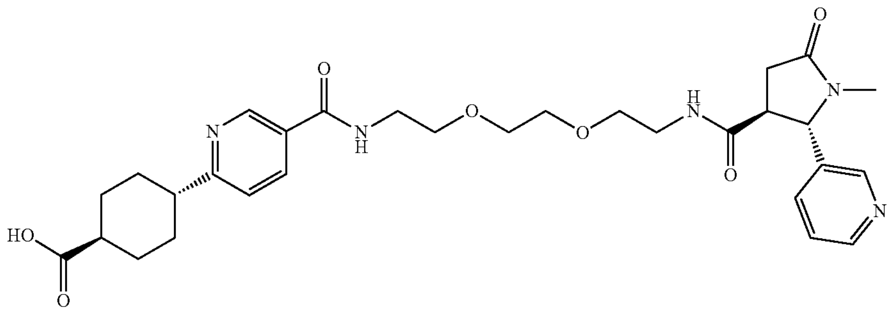 [SMILES: CN1C(=O)C[C@H](C(=O)NCCOCCOCCNC(=O)c2ccc([C@H]3CC[C@H](C(=O)O)CC3)nc2)[C@H]1c1cccnc1]

To a stirred solution of ethyl (1r,4r)-4-(5-((2-(2-(2-((2S,3S)-1-methyl-5-oxo-2-(pyridin-3-yl)pyrrolidine-3-carboxamido)ethoxy)ethoxy)ethyl)carbamoyl)pyridin-2-yl)cyclohexane-1-carboxylate (100 mg, 0.164 mmol) in tetrahydrofuran (THF) (5 mL), methanol (2 mL) and water (3 mL), was added lithium hydroxide hydrate (20.65 mg, 0.492 mmol) The mixture was stirred at rt for 24 h and was stored in a cold room over the weekend. The pH was adjusted to 7 using 1.5 M HCl at 0° C. and was concentrated under reduced pressure. Purification by MDAP chromatography (XSelect™ CSH C18 5 μm 19 mm×150 mm column, 5 mL/min) eluting with a gradient of 0 to 40% acetonitrile in water containing ammonium acetate (10 mM) provided the title compound as an off-white, thick, gummy solid (57 mg, 0.096 mmol, 58.4% yield). LC-MS m/z 582.2 $(M+H)^+$.

Step 7

6-((1R,4r)-4-(((1R,2S,5R)-5-(Isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl)-N-(2-(2-(2-((2S,3S)-1-methyl-5-oxo-2-(pyridin-3-yl)pyrrolidine-3-carboxamido)ethoxy)ethoxy) ethyl)nicotinamide

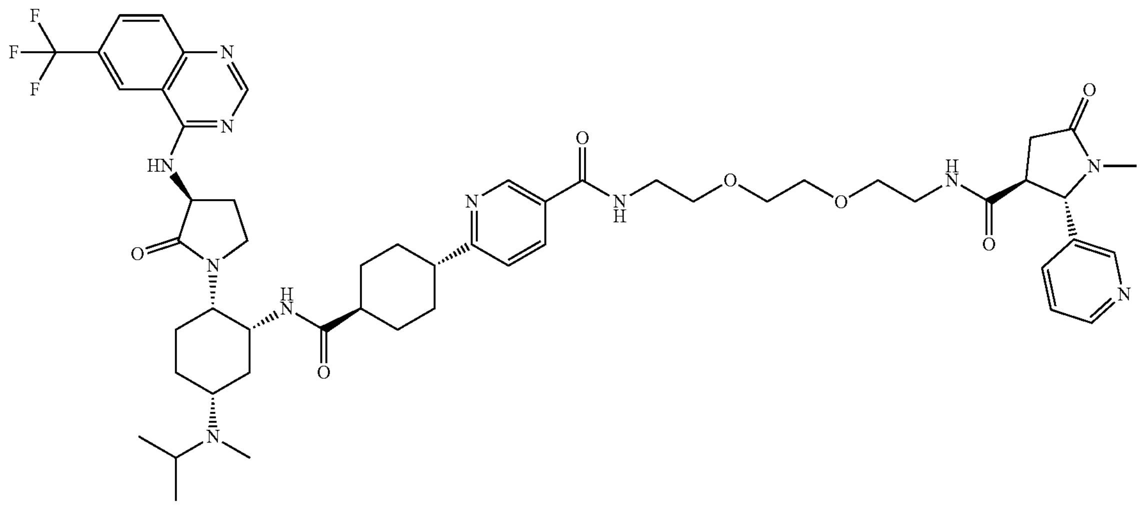 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](c3ccc(C(=O)NCCOCCOCCNC(=O)[C@H]4CC(=O)N(C)[C@@H]4c4cccnc4)cn3)CC2)C1]

3 M HCl in cyclopentyl methyl ether (0.5 mL, 1.500 mmol) was added to a solution of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl) carbamate (43.9 mg, 0.078 mmol) in dichloromethane (DCM) (1 mL). The mixture was stirred at rt for 1 h and was concentrated under reduced pressure. The residue was suspended in dichloromethane (DCM) (5 mL) and triethylamine (0.05 mL, 0.359 mmol) and (1r,4r)-4-(5-((2-(2-(2-((2S,3S)-1-methyl-5-oxo-2-(pyridin-3-yl)pyrrolidine-3-carboxamido)ethoxy)ethoxy)ethyl)carbamoyl)pyridin-2-yl) cyclohexane-1-carboxylic acid (49 mg, 0.084 mmol) and HATU (44.3 mg, 0.117 mmol) were added. The mixture was stirred at rt for 1 h and was concentrated under reduced pressure. Purification by MDAP chromatography (XSelect™ CSH C18 5 μm column, 40 mL/min) eluting with a gradient of 30 to 85% acetonitrile in water containing ammonium bicarbonate (10 mM) and the pH adjusted to 10 with ammonia provided the title compound as an off-white solid (33.9 mg, 0.033 mmol, 42.0% yield). LC-MS m/z 1028.8 $(M+H)^+$. $^1$H NMR (400 MHz, METHANOL-$d_4$) δ ppm 1.04 (br d, J=6.0 Hz, 3H) 1.17 (br d, J=6.3 Hz, 3H) 1.61-1.83 (m, 7H) 1.92-2.02 (m, 2H) 2.08-2.16 (m, 2H) 2.20-2.41 (m, 6H) 2.56 (dt d, J=12.3, 8.1, 8.1, 4.0 Hz, 1H) 2.65 (s, 3H) 2.66-2.89 (m, 4H) 2.99-3.13 (m, 1H) 3.37 (s, 4H) 3.44-3.53 (m, 3H) 3.53-3.60 (m, 5H) 3.61-3.72 (m, 5H) 4.05 (dt, J=12.5, 3.6 Hz, 1H) 4.69 (br d, J=3.0 Hz, 1H) 4.81 (d, J=6.5 Hz, 1H) 5.30 (t, J=8.0 Hz, 1H) 7.39 (d, J=8.3 Hz, 1H) 7.47-7.53 (m, 1H) 7.78 (dt, J=8.0, 1.9 Hz, 1H) 7.91 (d, J=8.8 Hz, 1H) 8.07 (dd, J=8.9, 1.9 Hz, 1H) 8.14 (dd, J=8.2, 2.4 Hz, 1H) 8.51 (d, J=2.3 Hz, 1H) 8.55 (dd, J=4.9, 1.6 Hz, 1H) 8.60 (s, 1H) 8.84 (s, 1H) 8.88 (dd, J=2.3, 0.8 Hz, 1H).

The following compounds were or could be prepared with procedures analogous to that described in Example 139:

| Ex. | Compound | LC-MS m/z | NMR |
|---|---|---|---|
| 140 | 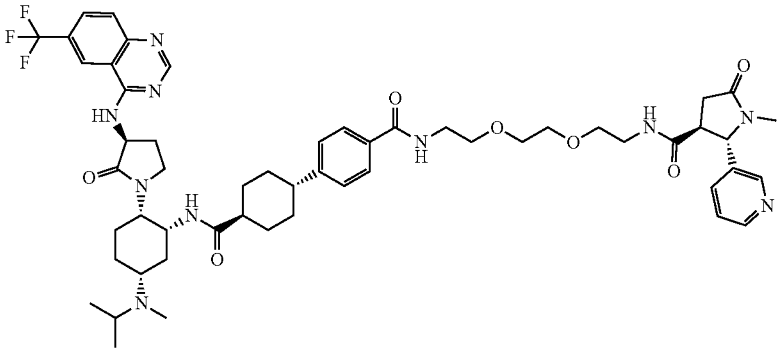 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](c3ccc(C(=O)NCCOCCOCCNC(=O)[C@H]4CC(=O)N(C)[C@@H]4c4cccnc4)cc3)CC2)C1] (2S,3S)-N-(2-(2-(2-(4-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)benzamido)ethoxy)ethoxy)ethyl)-1-methyl-5-oxo-2-(pyridin-3-yl)pyrrolidine-3-carboxamide. | 1027.6 (M + H)+ | $^1$H NMR (400 MHz, METHANOL-$d_4$) δ ppm 0.93-1.28 (m, 6H) 2.31 (s, 19H) 2.64 (s, 8H) 2.96-3.09 (m, 1H) 3.24-3.31 (m, 1H) 3.36-3.42 (m, 1 H) 3.42-3.77 (m, 13H) 3.96-4.18 (m, 1H) 4.50-4.84 (m, 3H) 5.19-5.41 (m, 1H) 7.17-7.37 (m, 2 H) 7.46-7.60 (m, 1H) 7.75 (d, J = 8.5 Hz, 3H) 7.89-8.02 (m, 1H) 8.06-8.20 (m, 1H) 8.61 (s, 3H) 8.75-8.91 (m, 1H). |
| 141 | 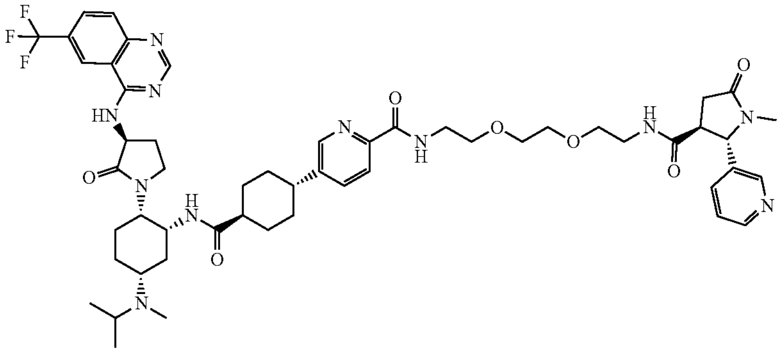 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](c3ccc(C(=O)NCCOCCOCCNC(=O)[C@H]4CC(=O)N(C)[C@@H]4c4cccnc4)nc3)CC2)C1] 5-((1R,4r)-4-(((1R,2S,5R)-5-(Isopropyl(methyl)amino)-2-((S)-2-oxo-3-((6-(trifluoromethyl)qinazolin-4-yl)amino)pyrrolidin-1-yl)cyclohexyl)carbamoyl)cyclohexyl)-N-(2-(2-(2-((2S,3S)-1-methyl-5-oxo-2-(pyridin-3-yl)pyrrolidine-3-carboxamido)ethoxy)ethoxy) ethyl)picolinamide. | 1028.6 (M + H)+ | $^1$H NMR (400 MHz, METHANOL-$d_4$) δ ppm 1.05 (br d, J = 6.3 Hz, 3H) 1.18 (br d, J = 6.1 Hz, 3H) 1.53-1.80 (m, 7H) 1.92-2.20 (m, 6H) 2.20-2.28 (m, 2H) 2.29 (s, 3H) 2.31-2.39 (m, 1H) 2.48-2.62 (m, 1H) 2.64 (s, 3H) 2.66-2.77 (m, 3H) 2.78-2.87 (m, 1H) 3.04 (ddd, J = 9.4, 8.1, 6.6 Hz, 1H) 3.23-3.32 (m, 1H) 3.36-3.54 (m, 4H) 3.54-3.69 (m, 10H) 4.05 (dt, J = 12.5, 3.6 Hz, 1H) 4.63-4.77 (m, 1H) 4.77-4.87 (m, 2H) 5.29 (t, J = 8.1 Hz, 1H) 7.46-7.55 (m, 1H) 7.74-7.84 (m, 2H) 7.91 (d, J = 8.9 Hz, 1H) 8.00 (d, J = 8.1 Hz, 1H) 8.07 (dd, J = 9.0, 1.9 Hz, 1H) 8.49 (dd, J = 10.4, 1.8 Hz, 2H) 8.56 (dd, J = 4.8, 1.5 Hz, 1H) 8.60 (s, 1H) 8.83 (s, 1H) |
| 142 | 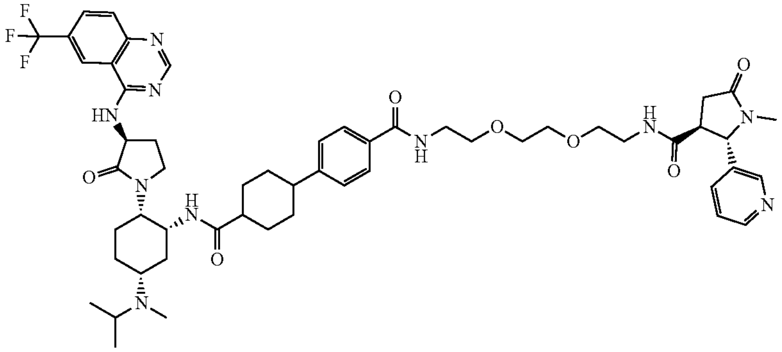 [SMILES: CC(C)N(C)[C@@H]1CC[C@H](N2CC[C@H](Nc3ncnc4ccc(C(F)(F)F)cc34)C2=O)[C@H](NC(=O)C2CCC(c3ccc(C(=O)NCCOCCOCCNC(=O)[C@H]4CC(=O)N(C)[C@@H]4c4cccnc4)cc3)CC2)C1] | 1028.3 (M + H)+ | $^1$H NMR (400 MHz, METHANOL-$d_4$) δ ppm 1.01 (br d, J = 6.3 Hz, 3H) 1.15 (br d, J = 6.5 Hz, 3H) 1.67-1.87 (m, 5H) 1.92-2.01 (m, 3H) 2.13-2.24 (m, 2H) 2.27 (s, 3H) 2.32-2.43 (m, 2H) 2.56 (td, J = 8.2, 4.6 Hz, 1H) 2.63 (s, 3H) 2.67-2.90 (m, 5H) 2.97-3.06 (m, 1H) 3.26-3.31 (m, 1H) 3.37-3.48 (m, 2H) 3.49-3.69 (m, 12H) 3.95 (br t, J = 13.2 Hz, 2H) 4.01-4.08 (m, 1H) 4.67 (br d, J = 2.8 Hz, 1H) |

-continued

| Ex. | Compound | LC-MS m/z | NMR |
|---|---|---|---|
| | N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-1-(4-((2-(2-(2-((2S,3S)-1-methyl-5-oxo-2-(pyridin-3-yl)pyrrolidine-3-carboxamido)ethoxy)ethoxy)ethyl)carbamoyl)phenyl)piperidine-4-carboxamide. | | 4.78 (d, J = 6.5 Hz, 1H) 5.28 (t, J = 8.3 Hz, 1H) 6.94 (d, J = 9.0 Hz, 2H) 7.47-7.54 (m, 1H) 7.68-7.72 (m, 2H) 7.74 (dt, J = 8.0, 1.9 Hz, 1H) 7.90 (d, J = 8.8 Hz, 1H) 8.04 (dd, J = 8.9, 1.9 Hz, 1H) 8.48 (d, J = 1.8 Hz, 1H) 8.55 (dd, J = 4.9, 1.6 Hz, 1H) 8.59 (s, 1H) 8.77 (d, J = 0.8 Hz, 1H) |

Example 143

(2S,3S)-N-(1-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-1,7,16-trioxo-3,9,12-trioxa-6,15-diazaoctadecan-18-yl)-1-methyl-5-oxo-2-(pyridin-3-yl)pyrrolidine-3-carboxamide

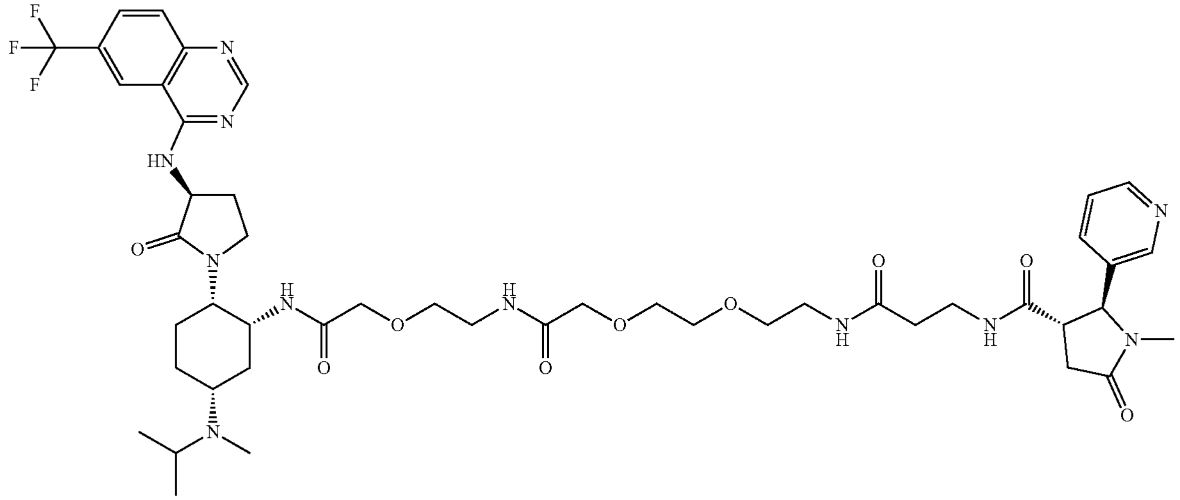 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)COCCOCCNC(=O)CCNC(=O)[C@H]2CC(=O)N(C)[C@@H]2c2cccnc2)C1]

Step 1 tert-Butyl 3-((2S,3S)-1-methyl-5-oxo-2-(pyridin-3-yl)pyrrolidine-3-carboxamido) propanoate

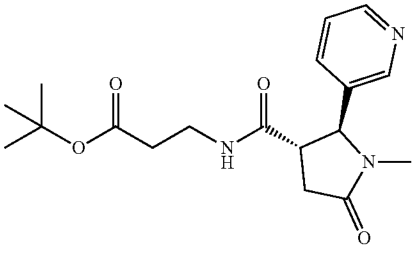 [SMILES: CN1C(=O)C[C@H](C(=O)NCCC(=O)OC(C)(C)C)[C@H]1c1cccnc1]

To a solution of (2S,3S)-1-methyl-5-oxo-2-(pyridin-3-yl)pyrrolidine-3-carboxylic acid (300 mg, 1.362 mmol) in dichloromethane (DCM) (6 mL) was added HATU (622 mg, 1.635 mmol), DIPEA (0.714 mL, 4.09 mmol), and tert-butyl 3-aminopropanoate (250 mg, 1.635 mmol). The mixture was stirred for 4 h and was washed with saturated $NaHCO_3$. The aqueous phase was extracted with dichloromethane (3×20 mL). The combined organic extracts were washed with saturated brine, were dried over $Na_2SO_4$, were filtered, and the filtrate was concentrated onto silica. Purification by ISCO CombiFlash® chromatography (24 g RediSep Rf Gold® column, 35 mL/min) eluting with a stepwise gradient of 0 to 5% (5 min), 5% (10 min), 5 to 7% (20 min), 7% (10 min), and 10% (35 min) methanol in dichloromethane (DCM) provided the title compound (424 mg, 1.013 mmol, 74.4% yield). LC-MS m/z 348.2 $(M+H)^+$.

Step 2

3-((2S,3S)-1-Methyl-5-oxo-2-(pyridin-3-yl)pyrrolidine-3-carboxamido)propanoic acid, Hydrochloric acid salt

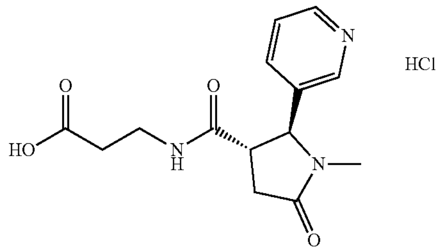 [SMILES: CN1C(=O)C[C@H](C(=O)NCCC(=O)O)[C@H]1c1cccnc1 ; Cl]

4 M HCl in 1,4-dioxane (6.08 mL, 24.31 mmol) was added to a suspension of tert-butyl 3-((2S,3S)-1-methyl-5-oxo-2-(pyridin-3-yl) pyrrolidine-3-carboxamido) propanoate (424 mg, 1.013 mmol) in 1,4-dioxane (3 mL). The mixture was stirred at rt for 4 h and was concentrated provide the title compound as a white gum (662 mg, 0.909 mmol, 90% yield). $^1H$ NMR (400 MHz, METHANOL-$d_4$) δ ppm 2.49-2.58 (m, 1H) 2.69-2.78 (m, 4H) 2.85-2.93 (m, 1H) 3.07 (s, 1H) 3.35-3.53 (m, 1H) 3.69-3.79 (m, 2H) 5.08 (d, J=6.4 Hz, 1H) 8.21 (dd, J=7.8, 5.9 Hz, 1H) 8.66 (dt, J=8.1, 1.8 Hz, 1H) 8.91-8.95 (m, 2H).

Step 3 tert-Butyl 1-((2S,3S)-1-methyl-5-oxo-2-(pyridin-3-yl)pyrrolidin-3-yl)-1,5-dioxo-9,12-dioxa-2,6-diazatetradecan-14-oate

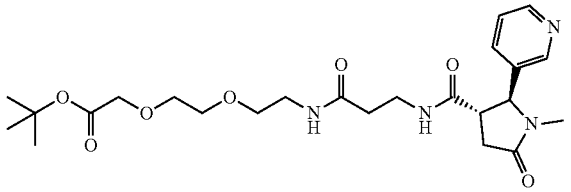 [SMILES: CN1C(=O)C[C@H](C(=O)NCCC(=O)NCCOCCOCC(=O)OC(C)(C)C)[C@H]1c1cccnc1]

To a solution of 3-((2S,3S)-1-methyl-5-oxo-2-(pyridin-3-yl)pyrrolidine-3-carboxamido)propanoic acid, hydrochloric acid (326 mg, 0.448 mmol) in dichloromethane (DCM) (2 mL) was added HOBt (82 mg, 0.537 mmol) and EDC (120 mg, 0.627 mmol) and the mixture was stirred for 30 min. tert-Butyl 2-(2-(2-aminoethoxy)ethoxy)acetate (115 mg, 0.448 mmol) and DIPEA (0.156 mL, 0.895 mmol) were added. The mixture was stirred overnight, was washed with saturated $NaHCO_3$, and was extracted with dichloromethane (DCM) (3×20 mL). The combined organic extracts were washed with saturated brine, were dried over $Na_2SO_4$, were filtered, and the filtrate was concentrated onto silica. Purification by ISCO CombiFlash® chromatography (40 g RediSep Rf Gold® column, 35 mL/min) eluting with a stepwise gradient of 0 to 20% (5 min), 20% (5 min), 20 to 35% (15 min), 35% (5 min), and 50% (30 min) dichloromethane (DCM)/methanol (4:1) in dichloromethane (DCM) provided the title compound as a clear, tan oil (180 mg, 0.296 mmol, 66.1% yield). LC-MS m/z 493.3 $(M+H)^+$.

Step 4

1-((2S,3S)-1-Methyl-5-oxo-2-(pyridin-3-yl)pyrrolidin-3-yl)-1,5-dioxo-9,12-dioxa-2,6-diazatetradecan-14-oic acid, Hydrochloric acid salt

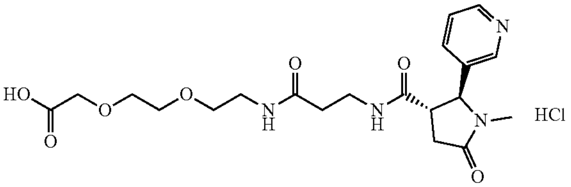 [SMILES: CN1C(=O)C[C@H](C(=O)NCCC(=O)NCCOCCOCC(=O)O)[C@H]1c1cccnc1 ; Cl]

4 M HCl in 1,4-dioxane (1.776 mL, 7.10 mmol) was added to a suspension of tert-butyl 1-((2S,3S)-1-methyl-5-oxo-2-(pyridin-3-yl)pyrrolidin-3-yl)-1,5-dioxo-9,12-dioxa-2,6-diazatetradecan-14-oate (180 mg, 0.296 mmol) in 1,4-Dioxane (2 mL). The mixture was stirred at rt for 4 h and was concentrated to provide the title compound as a white gum (231 mg, 0.259 mmol, 87% yield). LC-MS m/z 437.2 $(M+H)^+$.

Step 5 tert-Butyl 1-((2S,3S)-1-methyl-5-oxo-2-(pyridin-3-yl)pyrrolidi n-3-yl)-1,5,14-trioxo-9,12,18-trioxa-2,6,15-triazaicosan-20-oate

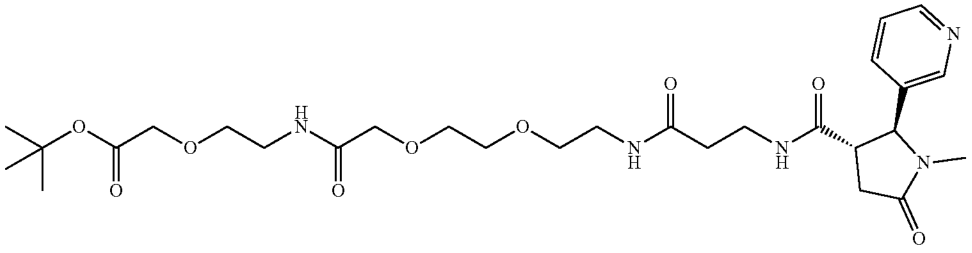 [SMILES: CN1C(=O)C[C@H](C(=O)NCCC(=O)NCCOCCOCC(=O)NCCOCC(=O)OC(C)(C)C)[C@H]1c1cccnc1]

To a solution of 1-((2S,3S)-1-methyl-5-oxo-2-(pyridin-3-yl)pyrrolidin-3-yl)-1,5-dioxo-9,12-dioxa-2,6-diazatetradecan-14-oic acid, hydrochloric acid salt (225 mg, 0.252 mmol) in dichloromethane (DCM) (2 mL) was added HOBt (46.3 mg, 0.303 mmol) and EDC (67.7 mg, 0.353 mmol) and the mixture was stirred for 30 min. tert-Butyl 2-(2-aminoethoxy)acetate (63.9 mg, 0.303 mmol) and DIPEA (0.088 mL, 0.504 mmol) were added and the mixture was stirred overnight. tert-Butyl 2-(2-aminoethoxy)acetate (35 mg, 0.0.20 mmol), HOBt (25 mg, 0.16 mmol), DIPEA (0.06 mL, 0.343 mmol), and EDC (37 mg, 0.193 mmol) was added and the mixture was stirred for 4 h. The mixture was washed with saturated $NaHCO_3$ and the aqueous phase was extracted with dichloromethane (DCM) (3×20 mL). The combined organic extracts were washed with saturated brine, were dried over $Na_2SO_4$, were filtered, and the filtrate was concentrated onto silica. Purification by ISCO Combi-Flash® chromatography (12 g RediSep Rf Gold® column, 30 mL/min) eluting with a stepwise gradient of 0 to 5% (5 min), 5% (10 min), 5 to 10% (25 min) and 10% (10 min) methanol in dichloromethane (DCM) provided the title compound as a light-orange wax (123 mg, 0.186 mmol, 73.9% yield). LC-MS m/z 594.0 $(M+H)^+$.

Step 6

1-((2S,3S)-1-Methyl-5-oxo-2-(pyridin-3-yl)pyrrolidin-3-yl)-1,5,14-trioxo-9,12,18-trioxa-2,6,15-triazaicosan-20-oic acid, Hydrochloric acid salt

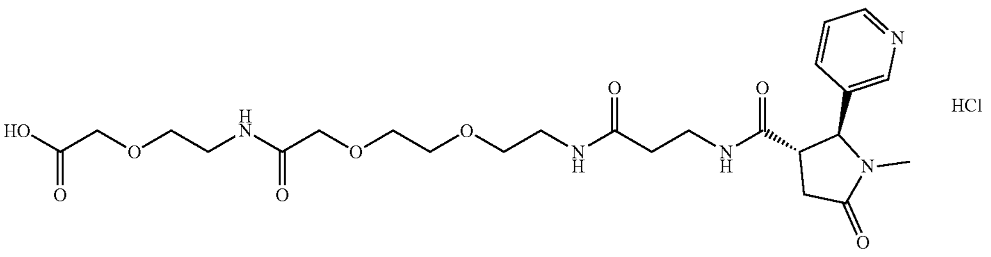 [SMILES: CN1C(=O)C[C@H](C(=O)NCCC(=O)NCCOCCOCC(=O)NCCOCC(=O)O)[C@H]1c1cccnc1 ; Cl]

4 M HCl in 1,4-dioxane (1.082 mL, 4.33 mmol) was added to a suspension of tert-butyl 1-((2S,3S)-1-methyl-5-oxo-2-(pyridin-3-yl)pyrrolidin-3-yl)-1,5,14-trioxo-9,12,18-trioxa-2,6,15-triazaicosan-20-oate (119 mg, 0.180 mmol) in 1,4-Dioxane (1 mL). The mixture was stirred at rt for 4 h and was concentrated to provide the title compound as a white gum (235 mg, 0.164 mmol, 91% yield). LC-MS m/z 538.0 $(M+H)^+$.

Step 7

(2S,3S)-N-(1-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-1,7,16-trioxo-3,9,12-trioxa-6,15-diazaoctadecan-18-yl)-1-methyl-5-oxo-2-(pyridin-3-yl)pyrrolidine-3-carboxamide

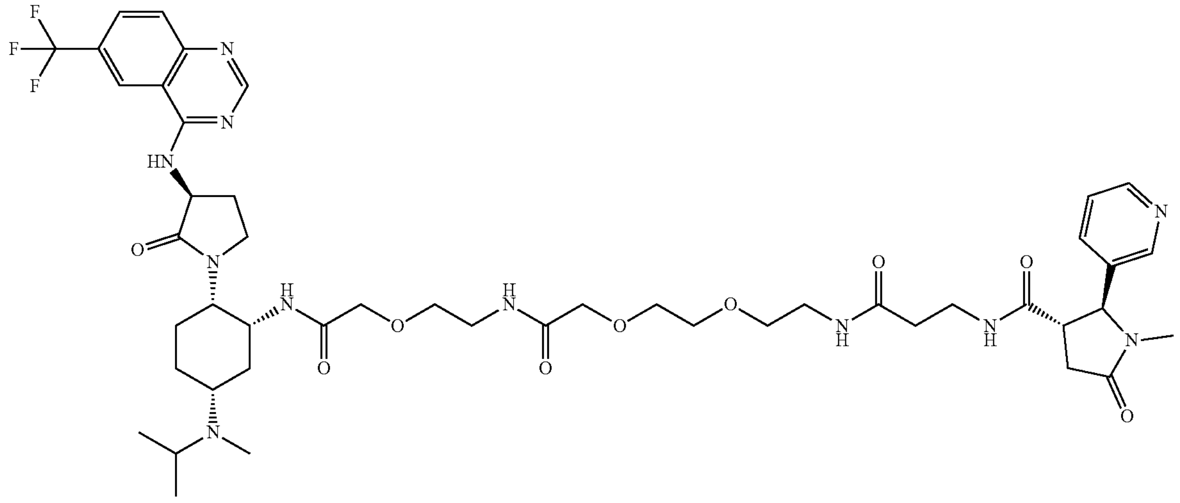 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)COCCOCCNC(=O)CCNC(=O)[C@H]2CC(=O)N(C)[C@@H]2c2cccnc2)C1]

To a solution of 1-((2S,3S)-1-methyl-5-oxo-2-(pyridin-3-yl)pyrrolidin-3-yl)-1,5,14-trioxo-9,12,18-trioxa-2,6,15-triazaicosan-20-oic acid, hydrochloric acid salt (236 mg, 0.164 mmol) in dichloromethane (DCM) (1 mL) was added HOBt (15.11 mg, 0.099 mmol) and EDC (22.07 mg, 0.115 mmol) and the mixture was stirred for 30 min. (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (52 mg, 0.082 mmol) and DIPEA (0.029 mL, 0.164 mmol) were added and the mixture was stirred overnight. The mixture was washed with saturated $NaHCO_3$ and the aqueous phase was extracted with dichloromethane (DCM) (3×20 mL). The combined organic extracts were washed with brine (2×), were dried over $Na_2SO_4$, were filtered, and the filtrate was concentrated onto silica. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as white solid (54 mg, 0.054 mmol, 65.4% yield). LC-MS m/z 984.8 $(M+H)^+$. $^1H$ NMR (400 MHz, METHANOL-$d_4$) δ ppm 1.00 (br d, J=6.4 Hz, 3H) 1.15 (br d, J=6.8 Hz, 3H) 1.60-1.84 (m, 3H) 1.90-2.04 (m, 1H) 2.05-2.15 (m, 1H) 2.15 2.27 (m, 4H) 2.28-2.45 (m, 3H) 2.50-2.61 (m, 1H) 2.66 (s, 3H) 2.67-2.76 (m, 2H) 2.78-2.89 (m, 1H) 2.95-3.06 (m, 1H) 3.34-3.38 (m, 2H) 3.39-3.46 (m, 3H) 3.47-3.57 (m, 4H) 3.58-3.77 (m, 6H) 3.99 (s, 2H) 4.02-4.13 (m, 3H) 4.69 (br d, J=2.9 Hz, 1H) 4.83 (d, J=6.4 Hz, 1H) 5.31 (t, J=8.6 Hz, 1H) 7.52 (dd, J=7.8, 4.9 Hz, 1H) 7.79 (dt, J=7.8, 2.0 Hz, 1H) 7.90 (d, J=8.8 Hz, 1H) 8.06 (dd, J=8.8, 2.0 Hz, 1H) 8.51 (d, J=2.0 Hz, 1H) 8.57 (dd, J=4.9, 2.0 Hz, 1H) 8.59 (s, 1H) 8.79 (s, 1H).

Example 144

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1-(8-((2S,3S)-1-methyl-5-oxo-2-(pyridin-3-yl)pyrrolidine-3-carboxamido)octyl)piperidine-4-carboxamide, 3Formic acid salt

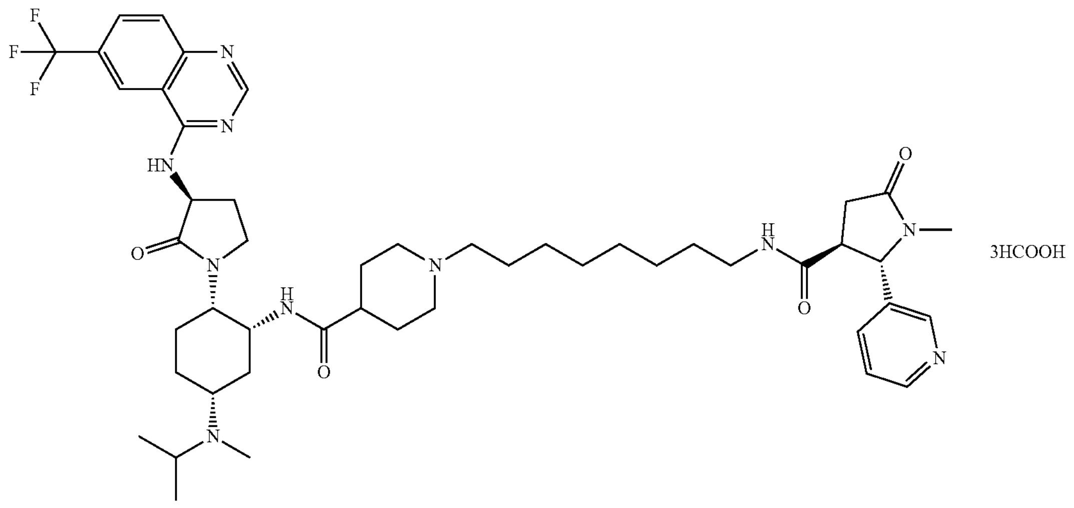 [SMILES: CC(C)N(C)[C@@H]1CC[C@H](N2CC[C@H](Nc3ncnc4ccc(C(F)(F)F)cc34)C2=O)[C@H](NC(=O)C2CCN(CCCCCCCCNC(=O)[C@H]3CC(=O)N(C)[C@@H]3c3cccnc3)CC2)C1]

Step 1

(2S,3S)-N-(8-Hydroxyoctyl)-1-methyl-5-oxo-2-(pyridin-3-yl)pyrrolidine-3-carboxamide

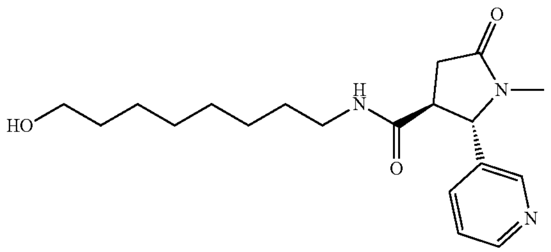 [SMILES: CN1C(=O)C[C@H](C(=O)NCCCCCCCCO)[C@H]1c1cccnc1]

To a mixture of (2S,3S)-1-methyl-5-oxo-2-(pyridin-3-yl) pyrrolidine-3-carboxylic acid (522 mg, 2.370 mmol), 8-aminooctan-1-ol (516 mg, 3.56 mmol) and HATU (1082 mg, 2.84 mmol) in dichloromethane (DCM) (0.5 mL) was added DIPEA (1.242 mL, 7.11 mmol). The mixture was stirred at rt over the weekend and was partitioned between saturated $NaHCO_3$ and dichloromethane (DCM). The aqueous phase was extracted with dichloromethane (DCM) and the combined organic extracts were washed with saturated $NaHCO_3$, were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 20% methanol containing ammonium hydroxide (10%) in dichloromethane (DCM) provided the title compound as a colorless oil (720 mg, 2.072 mmol, 87% yield). LC-MS m/z 348.2 $(M+H)^+$.

Step 2

8-((2S,3S)-1-Methyl-5-oxo-2-(pyridin-3-yl)pyrrolidine-3-carboxamido)octyl methanesulfonate

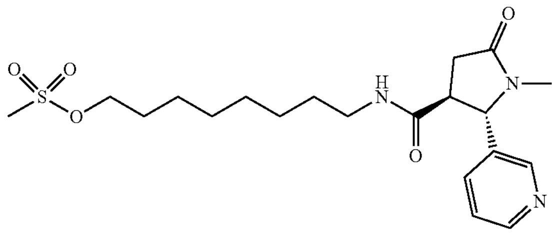

To a mixture of (2S,3S)-N-(8-hydroxyoctyl)-1-methyl-5-oxo-2-(pyridin-3-yl)pyrrolidine-3-carboxamide (170 mg, 0.489 mmol) in dichloromethane (DCM) (1 mL) was added triethylamine (0.102 mL, 0.734 mmol) and methanesulfonyl chloride (0.045 mL, 0.587 mmol). The mixture was stirred at rt for 2 h. Another portion of methanesulfonyl chloride and triethylamine were added. The mixture was stirred at rt for 1 h, saturated $NaHCO_3$ was added, and the mixture was extracted with dichloromethane (DCM). The combined organic extracts were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound as a light-yellow oil (185 mg, 0.435 mmol, 89% yield). LC-MS m/z 426.4 $(M+H)^+$.

Step 3 tert-Butyl 1-(8-((2S,3S)-1-methyl-5-oxo-2-(pyridin-3-yl)pyrrolidine-3-carboxamido)octyl) piperidine-4-carboxylate

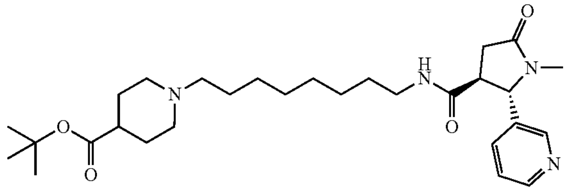 [SMILES: CN1C(=O)C[C@H](C(=O)NCCCCCCCCN2CCC(C(=O)OC(C)(C)C)CC2)[C@H]1c1cccnc1]

To a mixture of tert-butyl piperidine-4-carboxylate, hydrochloric acid salt (64.1 mg, 0.289 mmol) and 8-((2S,3S)-1-methyl-5-oxo-2-(pyridin-3-yl) pyrrolidine-3-carboxamido)octyl methanesulfonate (123 mg, 0.289 mmol) in acetonitrile (0.200 mL) was added potassium carbonate (120 mg, 0.867 mmol). The mixture was stirred at rt for 20 min, at 80° C. overnight, then at rt over the weekend. The mixture was partitioned between dichloromethane (DCM) and water and the aqueous phase was extracted with dichloromethane (DCM). The combined organic phases were washed with brine, were dried over $Na_2SO_4$, were filtered, and the filtrate was concentrated to provide the title compound (72 mg, 0.140 mmol, 48.4% yield). LC-MS m/z 515.5 $(M+H)^+$.

Step 4

1-(8-((2S,3S)-1-Methyl-5-oxo-2-(pyridin-3-yl)pyrrolidine-3-carboxamido)octyl) piperidine-4-carboxylic acid

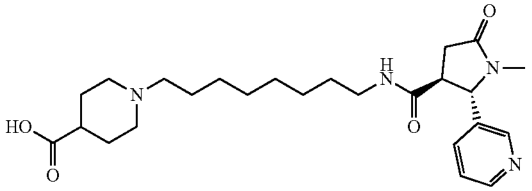 [SMILES: CN1C(=O)C[C@H](C(=O)NCCCCCCCCN2CCC(C(=O)O)CC2)[C@H]1c1cccnc1]

HCl (0.217 mL, 0.867 mmol) was added to a solution of tert-butyl 1-(8-((2S,3S)-1-methyl-5-oxo-2-(pyridin-3-yl) pyrrolidine-3-carboxamido)octyl)piperidine-4-carboxylate (72 mg, 0.140 mmol) in dichloromethane (DCM) (0.2 mL) and the mixture was stirred at rt for 3 h. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound (85 mg, 0.185 mmol, 64.1% yield). LC-MS m/z 459.3 $(M+H)^+$.

Step 5

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1-(8-((2S,3S)-1-methyl-5-oxo-2-(pyridin-3-yl)pyrrolidine-3-carboxamido)octyl)piperidine-4-carboxamide, 3Formic acid salt

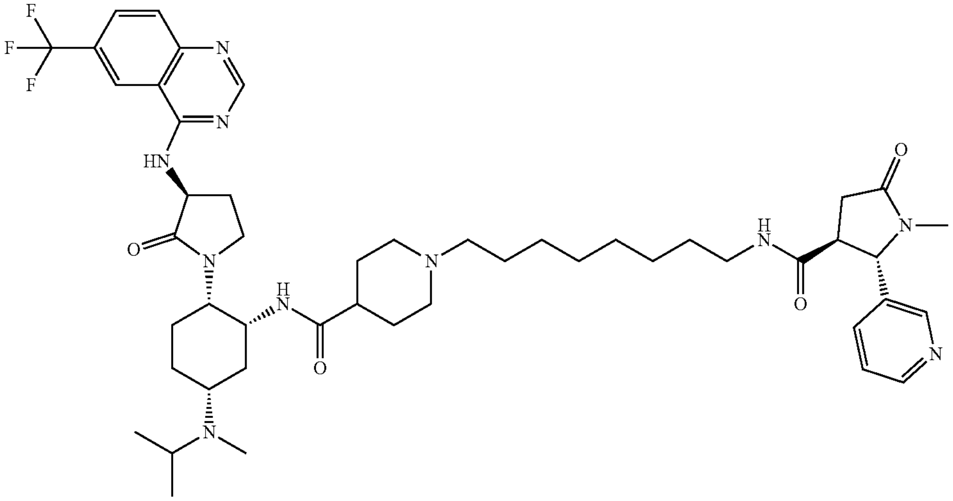

3HCOOH

To a mixture of (S)-1-((1S,2R,4R)-2-amino-4-(isopropyl (methyl)amino)cyclohexyl)-3-((6-(trifluoromethyl)quinazolin-4-yl)amino)pyrrolidin-2-one, 2Hydrochloric acid salt (35.4 mg, 0.066 mmol) and 1-(8-((2S,3S)-1-methyl-5-oxo-2-(pyridin-3-yl)pyrrolidine-3-carboxamido)octyl)piperidine-4-carboxylic acid, 2Hydrochloric acid salt (35 mg, 0.066 mmol) in dichloromethane (DCM) (0.5 mL) was added triethylamine (0.055 mL, 0.395 mmol) and HATU (30.0 mg, 0.079 mmol). The mixture was stirred at rt for 1 h and N,N-dimethylformamide (DMF) (0.20 mL) was added to effect dissolution. The mixture was stirred at rt for 30 min and was concentrated under reduced pressure. Purification by MDAP chromatography (XSelect™ CSH Prep C18 150 mm×30 mm 5 μm OBD column, 40 mL/min) eluting with a gradient of 5 to 85% acetonitrile in water both containing formic acid (0.1%) provided the title compound as a solid (26.3 mg, 0.02 mmol, 37.9% yield). LC-MS m/z 906.7 $(M+H)^+$. $^1H$ NMR (400 MHz, METHANOL-$d_4$) δ ppm 1.02-1.37 (m, 14H) 1.51-3.06 (m, 29H) 3.16 (br d, J=17.8 Hz, 3H) 3.41-3.78 (m, 3H) 3.95-4.17 (m, 1H) 4.47-4.72 (m, 2H) 5.12-5.36 (m, 1H) 7.45-7.66 (m, 1H) 7.75-8.20 (m, 3H) 8.44-8.65 (m, 4H) 8.72 (s, 1H).

The following compounds were or could be prepared with procedures analogous to that described in Example 144:

| Ex. | Compound | LC-MS m/z | NMR |
|---|---|---|---|
| 145 | 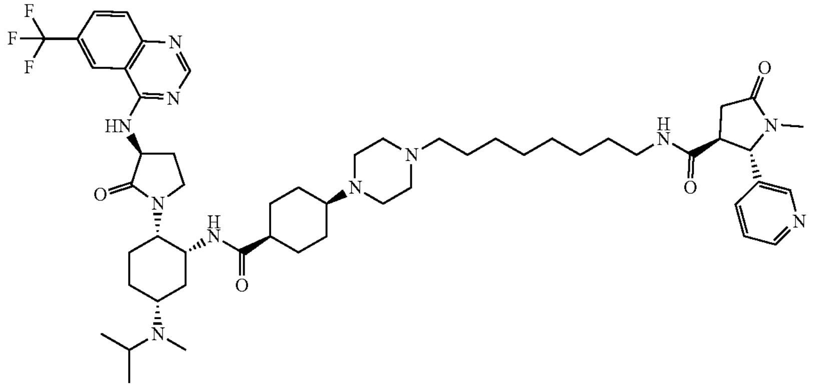 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](N3CCN(CCCCCCCCNC(=O)[C@H]4CC(=O)N(C)[C@@H]4c4cccnc4)CC3)CC2)C1] (2S,3S)-N-(8-(4-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperazin-1-yl)octyl)-1-methyl-5-oxo-2-(pyridin-3-yl)pyrrolidine-3-carboxamide. | 988.4 (M + H)+ | $^1H$ NMR (400 MHz, METHANOL-$d_4$) δ ppm 1.00 (d, J = 6.3 Hz, 3H) 1.18 (br d, J = 6.3 Hz, 3H) 1.24-1.35 (m, 8H) 1.46 (quin, J = 7.0 Hz, 4H) 1.55-1.85 (m, 9H) 1.89-2.19 (m, 5H) 2.20-2.30 (m, 8H) 2.34-2.63 (m, 8H) 2.67 (s, 3H) 2.73 (br d, J = 7.9 Hz, 2H) 2.79-2.88 (m, 1H) 2.99-3.07 (m, 1H) 3.09-3.27 (m, 2H) 3.45 (dt, J = 13.1, 6.5 Hz, 1H) 3.52-3.59 (m, 1H) 3.61-3.69 (m, 1H) 4.04 (dt, J = 12.5, 3.7 Hz, 1H) 4.68 (br d, J = 3.0 Hz, 1H) 4.80-4.87 (m, 2H) 5.29 (t, J = 8.4 Hz, 1H) 7.52-7.58 (m, 1H) 7.81 (dt, J = 7.9, 2.0 Hz, 1H) 7.92 (d, J = 8.9 Hz, 1H) 8.07 (dd, J = 8.9, 1.8 Hz, 1H) 8.52 (d, J = 1.8 Hz, 1H) 8.57-8.62 (m, 2H) 8.78 (s, 1H). |
| 146 | 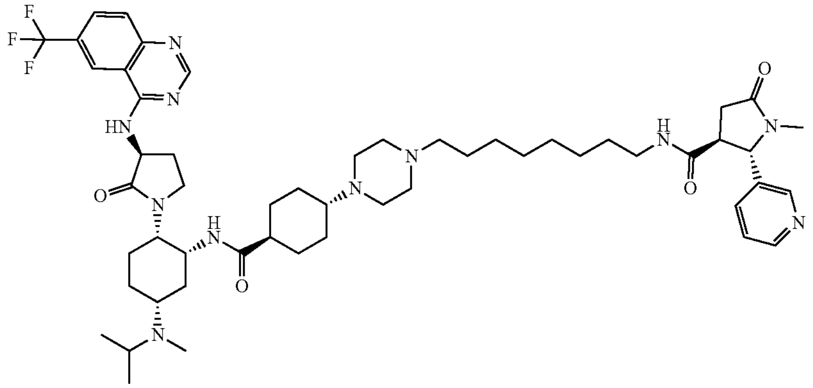 (2S,3S)-N-(8-(4-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperazin-1-yl)octyl)-1-methyl-5-oxo-2-(pyridin-3-yl)pyrrolidine-3-carboxamide. | 988.4 (M + H)+ | $^1H$ NMR (400 MHz, METHANOL-$d_4$) δ ppm 1.01-1.07 (m, 3H) 1.11-1.19 (m, 3H) 1.23-1.35 (m, 10H) 1.41-1.57 (m, 6H) 1.62-1.79 (m, 3H) 1.89-2.38 (m, 16H) 2.46-2.75 (m, 13H) 2.78-2.87 (m, 1H) 2.97-3.06 (m, 1H) 3.08-3.26 (m, 2 H) 3.37-3.57 (m, 2H) 3.61-3.70 (m, 1H) 3.99-4.08 (m, 1H) 4.64-4.69 (m, 1H) 4.80-4.84 (m, 1H) 5.21-5.31 (m, 1H) 7.51-7.58 (m, 1H) 7.78-7.84 (m, 1H) 7.89-7.95 (m, 1H) 8.05-8.10 (m, 1H) 8.49-8.53 (m, 1H) 8.57-8.61 (m, 2H) 8.81-8.86 (m, 1H). |

-continued

| Ex. | Compound | LC-MS m/z | NMR |
|---|---|---|---|
| 147 | 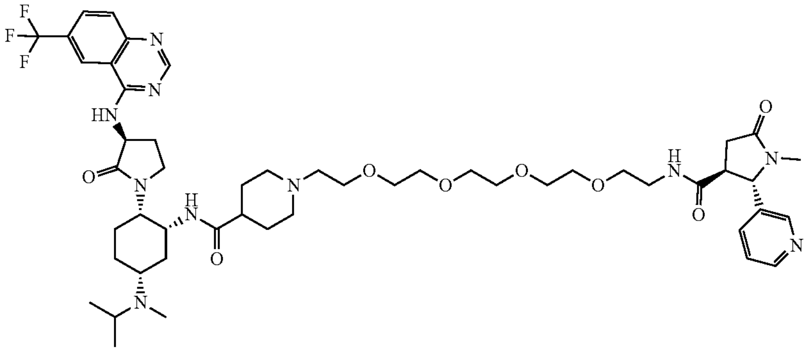 [SMILES: CC(C)N(C)[C@@H]1CC[C@H](N2CC[C@H](Nc3ncnc4ccc(C(F)(F)F)cc34)C2=O)[C@H](NC(=O)C2CCN(CCOCCOCCOCCOCCNC(=O)[C@H]3CC(=O)N(C)[C@@H]3c3cccnc3)CC2)C1] N-((1R,2S,5R)-5-Isopropyl(methyl)amino)-2-((S)-2-oxo-3-((6-(trifluoromethyl)quinazolin-4-yl)amino)pyrrolidin-1-yl)cyclohexyl)-1-(1-((2S,3S)-1-methyl-5-oxo-2-(pyridin-3-yl)pyrrolidin-3-yl)-1-oxo-5,8,11,14-tetraoxa-2-azahexadecan-16-yl)piperidine-4-carboxamide. | 997.5 (M + H)+ | $^{1}$H NMR (400 MHz, METHANOL-$d_4$) δ ppm 0.92-1.23 (m, 6H) 1.62-2.00 (m, 8H) 2.28 (s, 9H) 2.66 (s, 8H) 2.79-2.92 (m, 1H) 2.99-3.09 (m, 3H) 3.36-3.68 (m, 20 H) 3.95-4.11 (m, 1H) 4.61-4.70 (m, 1H) 4.79-4.86 (m, 1H) 5.15-5.39 (m, 1H) 7.40-7.59 (m, 1H) 7.74-7.98 (m, 2H) 8.01-8.15 (m, 1H) 8.60 (s, 3H) 8.68-8.80 (m, 1H). |

Example 148

(2S,3S)-N-(6-((1-(4-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) carbamoyl) cyclohexyl)piperidine)-4-sulfonamido) hexyl)-1-methyl-5-oxo-2-(pyridin-3-yl)pyrrolidine-3-carboxamide

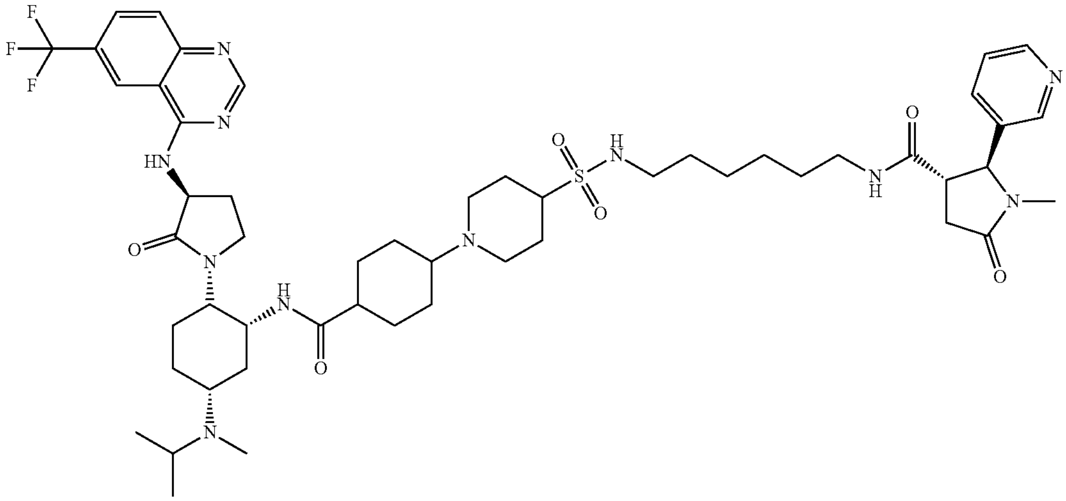

Step 1 tert-Butyl (6-((2S,3S)-1-methyl-5-oxo-2-(pyridin-3-yl)pyrrolidine-3-carboxamido)hexyl) carbamate

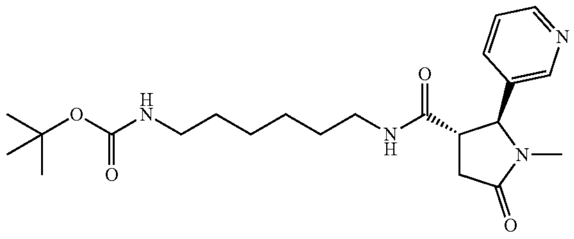 [SMILES: CN1C(=O)C[C@H](C(=O)NCCCCCCNC(=O)OC(C)(C)C)[C@H]1c1cccnc1]

To a solution of (2S,3S)-1-methyl-5-oxo-2-(pyridin-3-yl) pyrrolidine-3-carboxylic acid (100 mg, 0.454 mmol), tert-butyl (6-aminohexyl)carbamate hydrochloric acid salt (115 mg, 0.454 mmol), and TSTU (164 mg, 0.545 mmol) in acetonitrile (3493 μL) was added triethylamine (253 μL, 1.816 mmol). The mixture was stirred at rt for 30 min and was concentrated under reduced pressure. The residue was dissolved in a minimal amount of dichloromethane (DCM). ISOLUTE® was added and the mixture was concentrated under reduced pressure. Purification by normal-phase chromatography (40 g silica column, 40 mL/min) eluting with a gradient of 0 to 20% methanol in dichloromethane (DCM) provided the title compound as an orange oil (394.8 mg, 0.604 mmol, 133% yield) (solvents were seen in the NMR). LC-MS m/z 419.3 $(M+H)^+$.

Step 2 tert-Butyl 4-(N-(6-((2S,3S)-1-methyl-5-oxo-2-(pyridin-3-yl)pyrrolidine-3-carboxamido) hexyl)sulfamoyl)piperidine-1-carboxylate

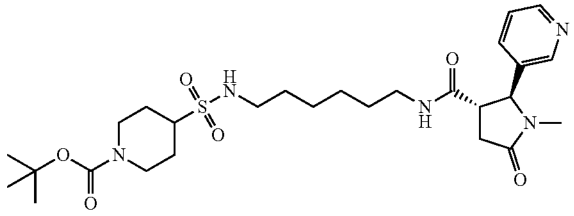 [SMILES: CN1C(=O)C[C@H](C(=O)NCCCCCCNS(=O)(=O)C2CCN(C(=O)OC(C)(C)C)CC2)[C@H]1c1cccnc1]

TFA (3 mL, 39.2 mmol) was added to a solution of tert-butyl (6-((2S,3S)-1-methyl-5-oxo-2-(pyridin-3-yl)pyrrolidine-3-carboxamido)hexyl)carbamate (394.8 mg, 0.943 mmol) in dichloromethane (DCM) (2 mL). The mixture was stirred at rt for 5 min, was concentrated under reduced pressure, and was azeotroped with dichloromethane (DCM) (3×) to provide (2S,3S)-N-(6-aminohexyl)-1-methyl-5-oxo-2-(pyridin-3-yl) pyrrolidine-3-carboxamide, 2trifluoroacetic acid salt (394.8 mg, 0.722 mmol). The residue was dissolved in was dissolved in dichloromethane (DCM) (7319 μL) and triethylamine (530 μL, 3.81 mmol) was added. The mixture was cooled to 0° C. and a solution of tert-butyl 4-(chlorosulfonyl)piperidine-1-carboxylate (270 mg, 0.951 mmol) in dichloromethane (DCM) (2 mL) added dropwise. The mixture was stirred at rt for 1.5 h and was concentrated under reduced pressure. Water was added and the mixture was extracted with ethyl acetate (5×). The combined organic extracts were concentrated. The residue was dissolved in a minimal amount of dichloromethane (DCM). ISOLUTE® was added and the mixture was concentrated under reduced pressure. Purification by normal-phase chromatography (12 g silica column, 30 mL/min) eluting with a gradient of 0 to 100% ethyl acetate in heptane provided the title compound as a yellow oil (342.7 mg, 0.545 mmol, 57.3% yield). LC-MS m/z 566.1 $(M+H)^+$.

Step 3

4-(4-(N-(6-((2S,3S)-1-Methyl-5-oxo-2-(pyridin-3-yl) pyrrolidine-3-carboxamido)hexyl)sulfamoyl)piperidin-1-yl)cyclohexane-1-carboxylic acid

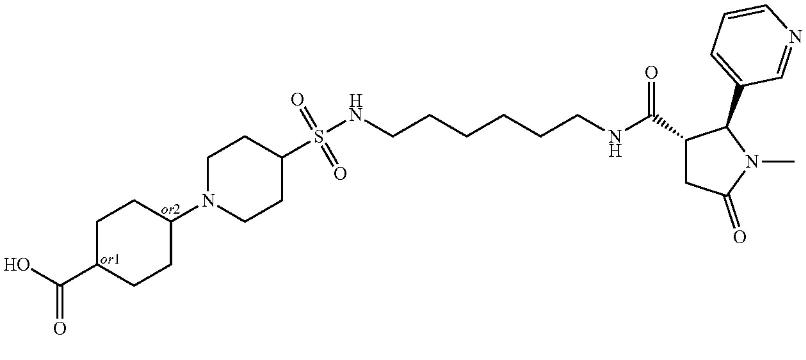 [SMILES: CN1C(=O)C[C@H](C(=O)NCCCCCCNS(=O)(=O)C2CCN(C3CCC(C(=O)O)CC3)CC2)[C@H]1c1cccnc1]

TFA (3 mL, 39.2 mmol) was added to a solution of tert-Butyl 4-(N-(6-((2S,3S)-1-methyl-5-oxo-2-(pyridin-3-yl) pyrrolidine-3-carboxamido)hexyl)sulfamoyl) piperidine-1-carboxylate (398 mg, 0.703 mmol) dichloromethane (DCM) (2 mL). The mixture was stirred at rt for 10 min and was azetroped with dichloromethane (DCM) (3×) to provide (2S,3S)-1-methyl-5-oxo-N-(6-(piperidine-4-sulfonamido) hexyl)-2-(pyridin-3-yl)pyrrolidine-3-carboxamide,trifluoroacetic acid salt. A solution of (2S,3S)-1-methyl-5-oxo-N-(6-(piperidine-4-sulfonamido)hexyl)-2-(pyridin-3-yl) pyrrolidine-3-carboxamide,trifluoroacetic acid salt (204 mg, 0.352 mmol) and 4-oxocyclohexane-1-carboxylic acid (100 mg, 0.703 mmol) in dichloromethane (DCM) (5411 μL) and triethylamine (147 μL, 1.055 mmol) was stirred at rt for 5 min and sodium triacetoxyhydroborohydride (447 mg, 2.110 mmol) was added. The mixture was heated to 50° C. for 2 h. Water was added and the mixture was concentrated under reduced pressure. Purification by MDAP (XBridge™ column) eluting with acetonitrile in water containing ammonium carbonate modifier provided two isomers. The stereochemistry of the cyclohexane ring was not assigned for the two isomers.

Isomer 1 (7.3 mg, 0.011 mmol, 1.578% yield). LC-MS m/z 592.3 $(M+H)^+$; 0.47 min retention time. $^1H$ NMR (400 MHz, METHANOL-$d_4$) δ ppm 1.23-1.57 (m, 12H) 1.73-1.88 (m, 2H) 1.89-2.14 (m, 7H) 2.21-2.44 (m, 4H) 2.67 (s, 3H) 2.68-2.75 (m, 1H) 2.77-2.90 (m, 1H) 2.93-3.16 (m, 7H) 3.19-3.31 (m, 1H) 4.81 (br s, 1H) 7.55 (dd, J=7.9, 4.9 Hz, 1H) 7.81 (dt, J=8.0, 1.9 Hz, 1H) 8.51 (d, J=1.8 Hz, 1H) 8.59 (dd, J=4.9, 1.6 Hz, 1H).

Isomer 2 (10.3 mg, 0.017 mmol, 2.474% yield). LC-MS m/z 592.3 $(M+H)^+$; 0.50 min retention time. $^1H$ NMR (400 MHz, METHANOL-$d_4$) δ ppm 1.18-1.61 (m, 12H) 1.66-1.83 (m, 2H) 1.88-2.11 (m, 4H) 2.17-2.39 (m, 4H) 2.46 (brs, 1H) 2.67 (s, 3H) 2.69-2.89 (m, 5H) 2.97-3.29 (m, 6H) 3.47-3.60 (m, 2H) 7.55 (dd, J=7.9, 4.9 Hz, 1H) 7.81 (dt, J=8.0, 1.9 Hz, 1H) 8.51 (d, J=2.0 Hz, 1H) 8.59 (dd, J=4.8, 1.5 Hz, 1H).

Step 4

(2S,3S)-N-(6-((1-(4-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) carbamoyl) cyclohexyl)piperidine)-4-sulfonamido) hexyl)-1-methyl-5-oxo-2-(pyridin-3-yl)pyrrolidine-3-carboxamide

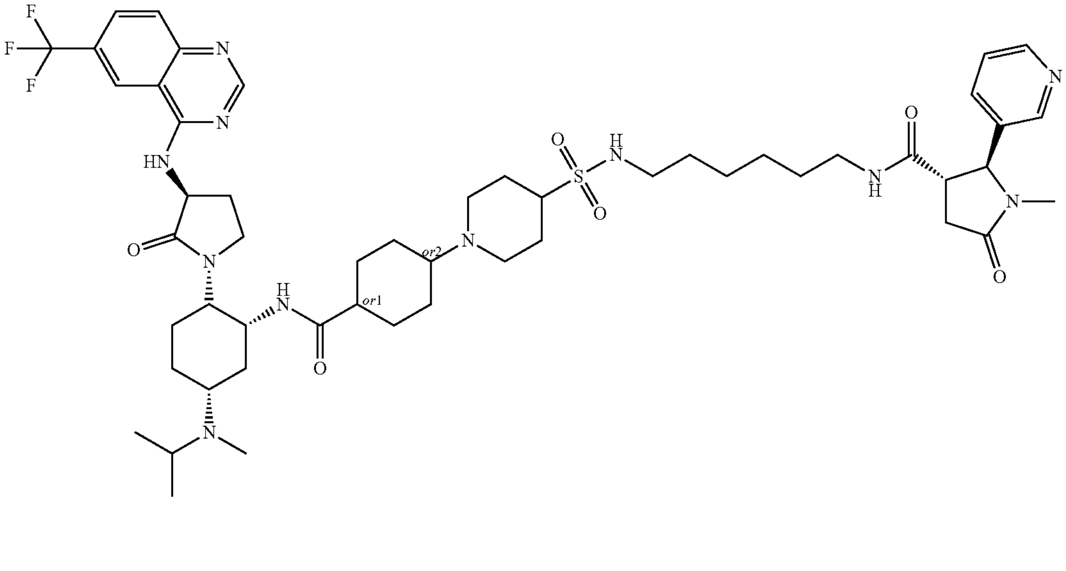

4 M HCl in 1,4-dioxane (0.2 mL, 0.8 mmol) was added to a solution of tert-butyl ((1R,2S,5R)-5-(isopropyl(methyl) amino)-2-((S)-2-oxo-3-((6-(trifluoromethyl)quinazolin-4-yl)amino)pyrrolidin-1-yl)cyclohexyl)carbamate (11.79 mg, 0.021 mmol) in dichloromethane (DCM). The mixture was stirred at rt for 30 and was concentrated under reduced pressure. The mixture was chased with dichloromethane (DCM) (1×). The residue was dissolved in dichloromethane (470 μL) with triethylamine (102 μL, 0.731 mmol). 60% of the mixture was added to 4-(4-(N-(6-((2S,3S)-1-methyl-5-oxo-2-(pyridin-3-yl) pyrrolidine-3-carboxamido) hexyl) sulfamoyl)piperidin-1-yl)cyclohexane-1-carboxylic acid (Isomer 2) (10.3 mg, 0.017 mmol) and HATU (10 mg, 0.026 mmol) and the mixture was stirred for 30 min at rt and was concentrated under reduced pressure. Purification by MDAP (XBridge™ column) eluting with acetonitrile in water containing ammonium carbonate modifier provided the title compound as a white solid (8.5 mg, 8.10 μmol, 46.6% yield). LC-MS m/z 1038.4 $(M+H)^+$. $^1H$ NMR (400 MHz, METHANOL-$d_4$) δ ppm 0.91-1.22 (m, 6H) 1.23-1.85 (m, 20H) 1.87-2.46 (m, 16H) 2.51-3.30 (m, 14H) 3.37 (s, 3H) 4.64-4.70 (m, 1H) 4.79-4.86 (m, 2H) 5.27-5.40 (m, 1H) 7.50-7.62 (m, 1H) 7.77-7.85 (m, 1H) 7.88-7.96 (m, 1H) 8.02-8.16 (m, 1H) 8.60 (s, 3H) 8.73-8.82 (m, 1H).

The following compound was or could be prepared with procedures analogous to that described in Example 148:

| Ex. | Compound | LC-MS m/z | NMR |
|---|---|---|---|
| 149 | 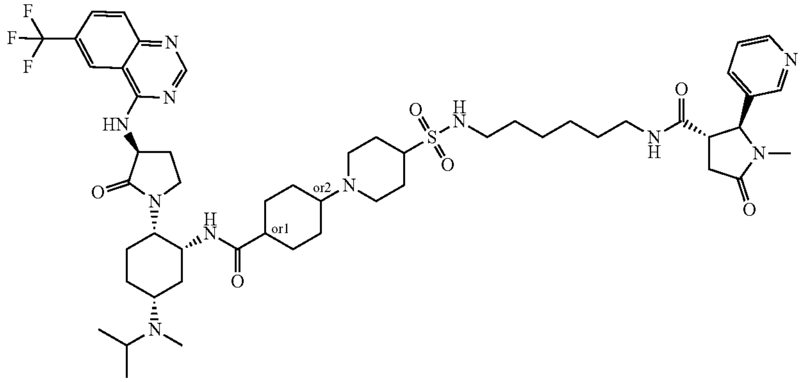 [SMILES: CC(C)N(C)[C@@H]1CC[C@H](N2CC[C@H](Nc3ncnc4ccc(C(F)(F)F)cc34)C2=O)[C@H](NC(=O)C2CCC(N3CCC(S(=O)(=O)NCCCCCCNC(=O)[C@H]4CC(=O)N(C)[C@@H]4c4cccnc4)CC3)CC2)C1]<br>(2S,3S)-N-(6-((1-(4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperidine)-4-sulfonamido)hexyl)-1-methyl-5-oxo-2-(pyridin-3-yl)pyrrolidine-3-carboxamide. | 1038.4 (M + H)+ | $^1H$ NMR (400 MHz, METHANOL-$d_4$) δ ppm 0.97-1.07 (m, 3H) 1.13-1.20 (m, 3H) 1.24-1.39 (m, 6H) 1.43-1.59 (m, 6H) 1.64-1.85 (m, 5H) 1.89-2.15 (m, 9H) 2.18-2.40 (m, 8H) 2.49-2.60 (m, 1H) 2.64-2.87 (m, 6H) 2.91-3.16 (m, 7H) 3.18-3.30 (m, 1H) 3.40-3.58 (m, 2H) 3.60-3.70 (m, 1H) 3.99-4.07 (m, 1H) 4.63-4.69 (m, 1H) 4.80-4.84 (m, 1H) 5.21-5.30 (m, 1H) 7.52-7.59 (m, 1H) 7.78-7.84 (m, 1H) 7.90-7.96 (m, 1H) 8.04-8.10 (m, 1H) 8.49-8.53 (m, 1H) 8.57-8.63 (m, 2H) 8.80-8.86 (m, 1H). The stereochemistry of the central 1,4-disubstituted cyclohexane ring was the opposite of Example 148. |

Example 150

(1 s,4S)-$N^1$-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-$N^4$-(3-(4-(3-((2S,3S)-1-methyl-5-oxo-2-(pyridin-3-yl)pyrrolidine-3-carboxamido)propyl)piperazin-1-yl)propyl)cyclohexane-1,4-dicarboxamide

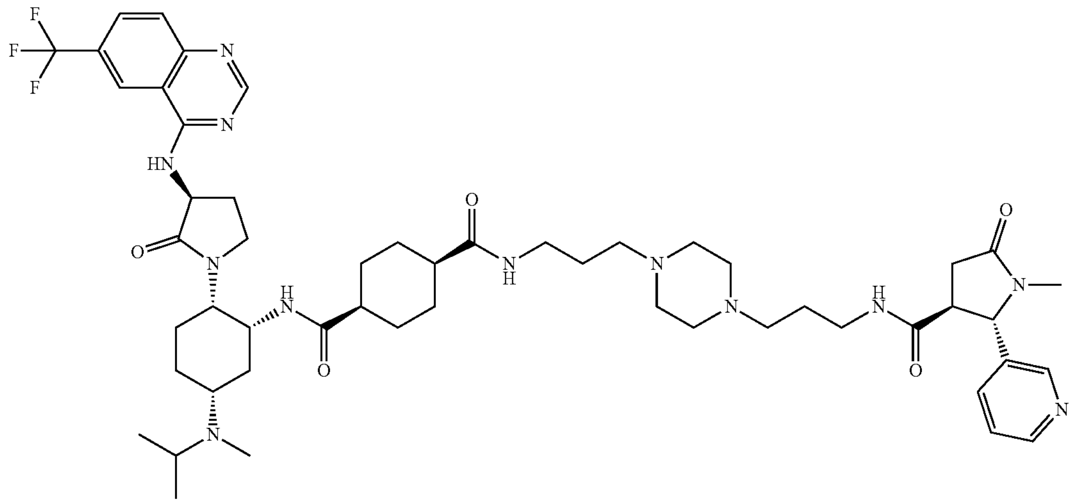 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](C(=O)NCCCN3CCN(CCCNC(=O)[C@H]4CC(=O)N(C)[C@@H]4c4cccnc4)CC3)CC2)C1]

Step 1

(1s,4s)-4-((Benzyloxy)carbonyl)cyclohexane-1-carboxylic acid

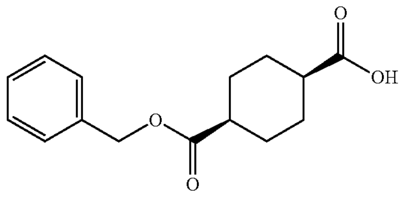 [SMILES: O=C(O)[C@H]1CC[C@@H](C(=O)OCc2ccccc2)CC1]

To (1 s,4s)-cyclohexane-1,4-dicarboxylic acid (888 mg, 5.16 mmol) in N,N-dimethylformamide (DMF) (3.5 ml) was added potassium carbonate (371 mg, 2.68 mmol), followed by (bromomethyl)benzene (0.553 ml, 4.64 mmol). The mixture was stirred at rt overnight and was partitioned between ethyl acetate and water. The aqueous phase was extracted with ethyl acetate. The combined organic extracts were washed with brine, were dried over $Na_2SO_4$, were filtered, and the filtrate was concentrated. Purification by ISCO CombiFlash® EZ Prep chromatography (C18 Aq Gold column, 40 mL/min) eluting with a gradient of acetonitrile in water containing ammonium bicarbonate (10 mM) and ammonium hydroxide (0.075%) provided the title compound (400 mg, 1.525 mmol, 29.6% yield). LC-MS m/z 263.1 $(M+H)^+$.

Step 2

Benzyl (1s,4s)-4-((3-(4-(3-aminopropyl)piperazin-1-yl)propyl)carbamoyl)cyclohexane-1-carboxylate

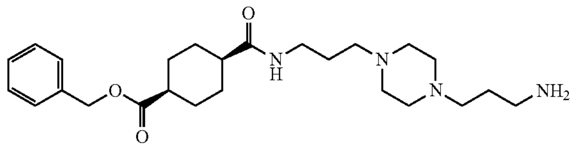 [SMILES: NCCCN1CCN(CCCNC(=O)[C@H]2CC[C@@H](C(=O)OCc3ccccc3)CC2)CC1]

To (1s,4s)-4-((benzyloxy)carbonyl)cyclohexane-1-carboxylic acid (162 mg, 0.618 mmol) in dichloromethane (DCM) (5 mL) was added HATU (282 mg, 0.741 mmol) and the mixture was stirred at rt for 5 min. 3,3'-(piperazine-1,4-diyl)bis(propan-1-amine) (192 mg, 0.958 mmol) and triethylamine (258 μL, 1.853 mmol) were added and the mixture was stirred at rt overnight. The mixture was partitioned between dichloromethane (DCM) and saturated $NaHCO_3$ and the aqueous phase was extracted with dichloromethane (DCM). The combined organic phases were dried over $Na_2SO_4$, were filtered, and the filtrate was concentrated. Purification by ISCO CombiFlash® chromatography (40 g RediSep Rf Gold® column, 35 mL/min) eluting with a gradient of 0 to 15% methanol containing ammonium hydroxide (10%) in dichloromethane (DCM) provided the title compound (110 mg, 0.247 mmol, 40.1% yield). LC-MS m/z 445.3 $(M+H)^+$.

Step 3

Benzyl (1 s,4s)-4-((3-(4-(3-((2S,3S)-1-methyl-5-oxo-2-(pyridin-3-yl)pyrrolidine-3-carboxamido)propyl)piperazin-1-yl)propyl)carbamoyl)cyclohexane-1-carboxylate

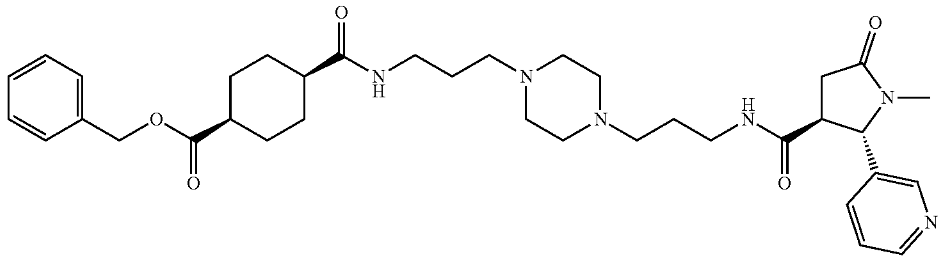 [SMILES: CN1C(=O)C[C@H](C(=O)NCCCN2CCN(CCCNC(=O)[C@H]3CC[C@@H](C(=O)OCc4ccccc4)CC3)CC2)[C@H]1c1cccnc1]

To a mixture of benzyl (1s,4s)-4-((3-(4-(3-aminopropyl) piperazin-1-yl)propyl)carbamoyl)cyclohexane-1-carboxylate (110 mg, 0.247 mmol) and (2S,3S)-1-methyl-5-oxo-2-(pyridin-3-yl)pyrrolidine-3-carboxylic acid (54.5 mg, 0.247 mmol) in dichloromethane (DCM) (0.8 mL) was added HATU (113 mg, 0.297 mmol) and triethylamine (0.103 mL, 0.742 mmol) and the mixture was stirred at rt for 1 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (100 mg, 0.155 mmol, 62.5% yield). LC-MS m/z 647.4 $(M+H)^+$.

Step 4

(1 s,4s)-4-((3-(4-(3-((2S,3S)-1-Methyl-5-oxo-2-(pyridin-3-yl)pyrrolidine-3-carboxamido)propyl) piperazin-1-yl)propyl)carbamoyl)cyclohexane-1-carboxylic acid

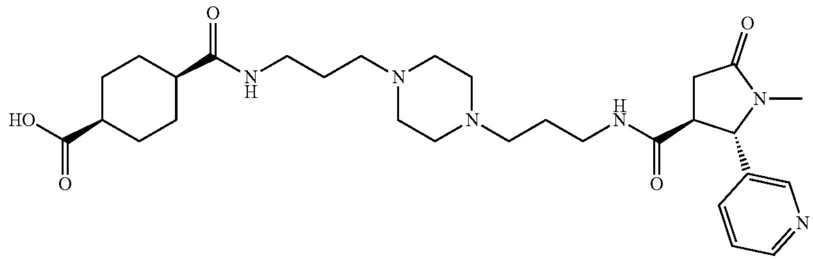 [SMILES: CN1C(=O)C[C@H](C(=O)NCCCN2CCN(CCCNC(=O)[C@H]3CC[C@@H](C(=O)O)CC3)CC2)[C@H]1c1cccnc1]

A mixture of benzyl (1s,4s)-4-((3-(4-(3-((2S,3S)-1-methyl-5-oxo-2-(pyridin-3-yl)pyrrolidine-3-carboxamido) propyl)piperazin-1-yl)propyl)carbamoyl)cyclohexane-1-carboxylate (100 mg, 0.155 mmol) and Pd—C(16.45 mg, 0.015 mmol) in methanol (2 mL) was stirred under a balloon atmosphere of hydrogen at rt for 1 h and was filtered through Celite®. The filtrate was concentrated to dryness to provide the title compound as a white solid (85 mg, 0.153 mmol, 99% yield). LC-MS m/z 557.3 $(M+H)^+$.

Step 5

(1 s,4S)-N1-((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)-N4-(3-(4-(3-((2S,3S)-1-methyl-5-oxo-2-(pyridin-3-yl) pyrrolidine-3-carboxamido)propyl)piperazin-1-yl) propyl)cyclohexane-1,4-dicarboxamide

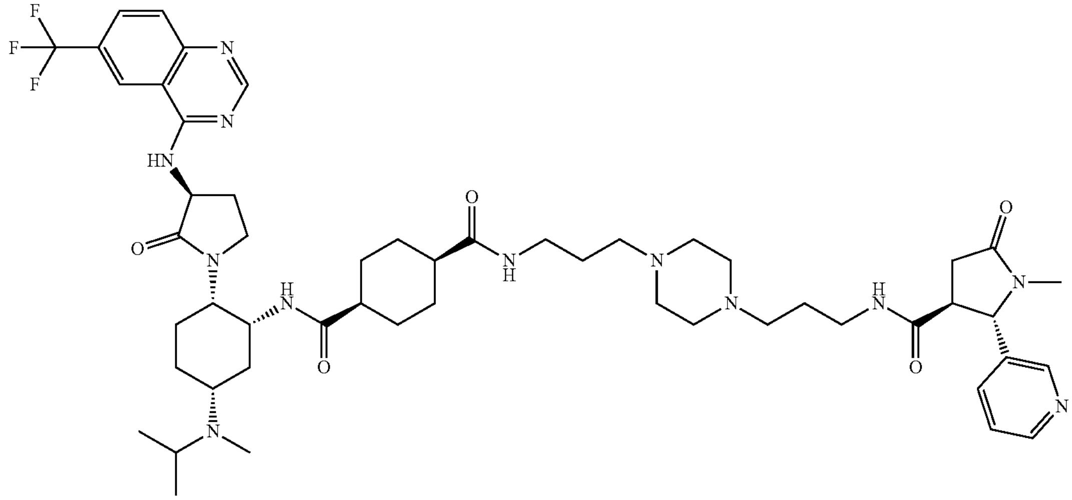 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](C(=O)NCCCN3CCN(CCCNC(=O)[C@H]4CC(=O)N(C)[C@@H]4c4cccnc4)CC3)CC2)C1]

To a mixture of (S)-1-((1S,2R,4R)-2-amino-4-(isopropyl (methyl)amino)cyclohexyl)-3-((6-(trifluoromethyl)quinazolin-4-yl)amino)pyrrolidin-2-one, dihydrochloride (33.8 mg, 0.063 mmol) and (1 s,4s)-4-((3-(4-(3-((2S,3S)-1-methyl-5-oxo-2-(pyridin-3-yl) pyrrolidine-3-carboxamido)propyl) piperazin-1-yl)propyl)carbamoyl)cyclohexane-1-carboxylic acid (35 mg, 0.063 mmol) in dichloromethane (DCM) (0.5 mL) was added triethylamine (0.053 mL, 0.377 mmol) followed by HATU (28.7 mg, 0.075 mmol). The mixture was stirred at room temperature for 3 h and was concentrated. Purification by MDAP chromatography (XSelect™ CSH Prep C18 150 mm×30 mm 5 μm OBD column, 40 mL/min) eluting with a gradient of 30 to 85% acetonitrile in water containing ammonium bicarbonate (10 mM) and the pH adjusted to 10 with ammonia provided the title compound as a white solid (44.2 mg, 0.044 mmol, 70.1% yield). LC-MS m/z 1003.4 $(M+H)^+$. $^1H$ NMR (400 MHz, METHANOL-$d_4$) δ ppm 0.90-1.30 (m, 5H) 1.46-2.07 (m, 16H) 2.08-2.93 (m, 27H) 2.93-3.08 (m, 1H) 3.09-3.28 (m, 4H) 3.40-3.78 (m, 4H) 4.00-4.26 (m, 1H) 4.50-4.73 (m, 1H) 5.15-5.38 (m, 1H) 7.46-7.65 (m, 1H) 7.74-7.86 (m, 1H) 7.87-7.97 (m, 1H) 8.01-8.15 (m, 1H) 8.59 (s, 3H) 8.69-8.79 (m, 1H).

Example 151

(2S,3S)-N-(1-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-1,7,13-trioxo-3,9,16-trioxa-6,12-diazaoctadecan-18-yl)-1-methyl-5-oxo-2-(pyridin-3-yl)pyrrolidine-3-carboxamide

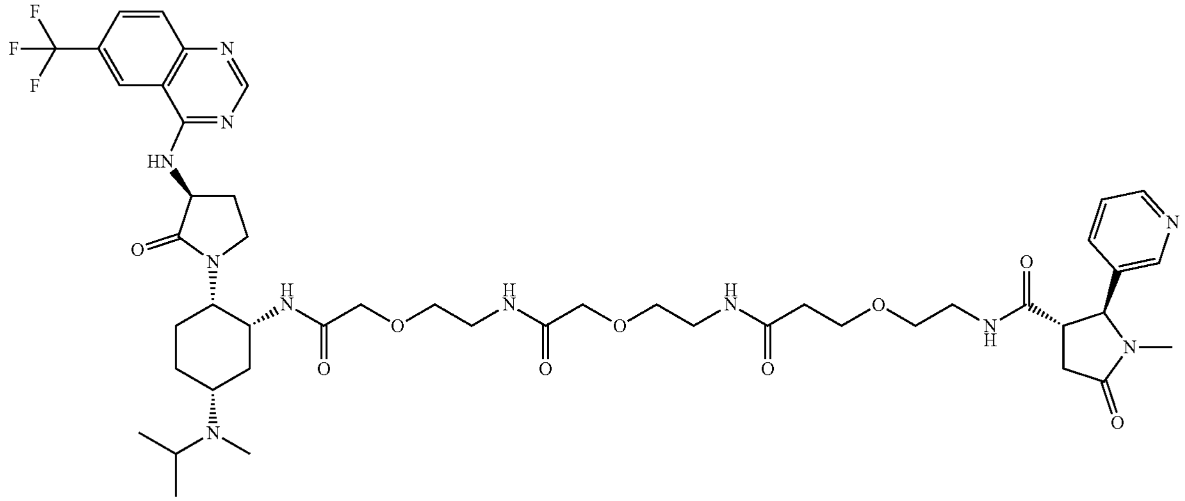 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)COCCNC(=O)CCOCCNC(=O)[C@H]2CC(=O)N(C)[C@@H]2c2cccnc2)C1]

Step 1 tert-Butyl 3,10-dioxo-1-phenyl-2,7,14-trioxa-4,11-diazahexadecan-16-oate

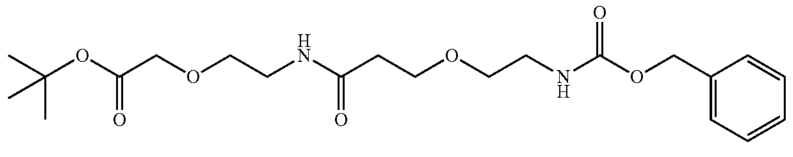 [SMILES: CC(C)(C)OC(=O)COCCNC(=O)CCOCCNC(=O)OCc1ccccc1]

To tert-butyl 3-(2-(((benzyloxy)carbonyl)amino)ethoxy)propanoate (Example 95, Step 1) (1.00 g, 3.09 mmol) was added 4 M HCl in 1,4-dioxane (10.0 mL, 40.0 mmol). The mixture was stirred for 2 h and was concentrated to dryness. The procedure was repeated (2×). To the residue in dichloromethane (DCM) (15 mL) was added DIPEA (2.70 mL, 15.46 mmol), HOBt (0.568 g, 3.71 mmol), EDC (0.889 g, 4.64 mmol) followed by tert-butyl 2-(2-aminoethoxy)acetate (0.542 g, 3.09 mmol) and the mixture was stirred overnight. Saturated $NaHCO_3$ was added and the mixture was extracted with extracted dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a colorless oil (520 mg, 1.225 mmol, 39.6% yield). LC-MS m/z 425.4 $(M+H)^+$.

Step 2 tert-Butyl 3,10,16-trioxo-1-phenyl-2,7,14,20-tetraoxa-4,11,17-triazadocosan-22-oate

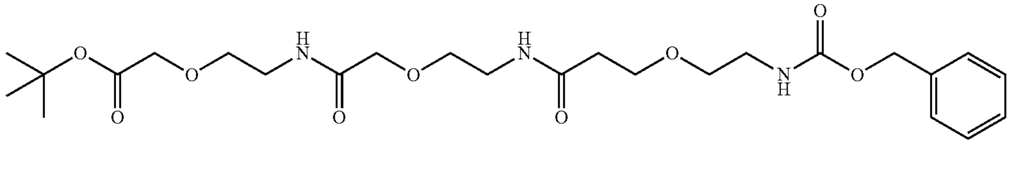 [SMILES: CC(C)(C)OC(=O)COCCNC(=O)COCCNC(=O)CCOCCNC(=O)OCc1ccccc1]

To tert-butyl 3,10-dioxo-1-phenyl-2,7,14-trioxa-4,11-diazahexadecan-16-oate (250 mg, 0.589 mmol) was added 4 M HCl in 1,4-dioxane (5.0 mL, 20.00 mmol). The mixture was stirred overnight and was concentrated to dryness. To the residue in dichloromethane (DCM) (2.0 mL) was added DIPEA (0.514 mL, 2.94 mmol), HOBt (108 mg, 0.707 mmol), EDC (169 mg, 0.883 mmol) followed by tert-butyl 2-(2-aminoethoxy)acetate (124 mg, 0.707 mmol), and the mixture was stirred overnight. Saturated $NaHCO_3$ was added and the mixture was extracted with extracted dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 10% methanol in dichloromethane (DCM) provided the title compound as a colorless oil (48 mg, 0.081 mmol, 63.3% yield). LC-MS m/z 526.3 $(M+H)^+$.

Step 3 tert-Butyl 18-amino-7,13-dioxo-3,9,16-trioxa-6,12-diazaoctadecanoate

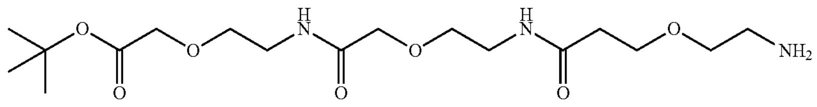 [SMILES: CC(C)(C)OC(=O)COCCNC(=O)COCCNC(=O)CCOCCN]

To a solution of tert-butyl 3,10,16-trioxo-1-phenyl-2,7,14,20-tetraoxa-4,11,17-triazadocosan-22-oate (180 mg, 0.342 mmol) in ethyl acetate (10 mL) under an atmosphere of nitrogen was added 10% Pd—C, Degussa type (3.64 mg, 0.034 mmol). The reaction mixture was vacuumed and backfilled with hydrogen (3×) and was stirred under a balloon atmosphere of hydrogen for 4 h. The mixture was filtered through Celite® and the filtrate was concentrated to provide the title compound as a wax (50 mg, 0.128 mmol, 37.3% yield). LC-MS m/z 392.3 $(M+H)^+$.

Step 4 tert-Butyl 1-((2S,3S)-1-methyl-5-oxo-2-(pyridin-3-yl)pyrrolidi n-3-yl)-1,8,14-trioxo-5,12,18-trioxa-2,9,15-triazaicosan-20-oate

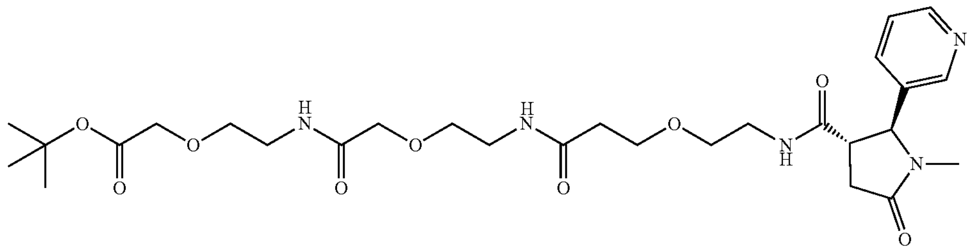

To a solution of (2S,3S)-1-methyl-5-oxo-2-(pyridin-3-yl) pyrrolidine-3-carboxylic acid (33.8 mg, 0.153 mmol), HOBt (23.47 mg, 0.153 mmol), EDC (36.7 mg, 0.192 mmol) and tert-butyl 18-amino-7,13-dioxo-3,9,16-trioxa-6,12-diazaoctadecanoate (50 mg, 0.128 mmol) in dichloromethane (DCM) (5.0 mL) was added DIPEA (0.112 mL, 0.639 mmol) and the mixture was stirred overnight. Saturated $NaHCO_3$ was added and the mixture was extracted with extracted dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a wax (48 mg, 0.081 mmol, 63.3% yield). LC-MS m/z 594.3 $(M+H)^+$.

Step 5

(2S,3S)-N-(1-(((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)amino)-1, 7,13-trioxo-3,9,16-trioxa-6,12-diazaoctadecan-18-yl)-1-methyl-5-oxo-2-(pyridin-3-yl)pyrrolidine-3-carboxamide To a solution of tert-butyl 1-((2S,3S)-1-methyl-5-oxo-2-(pyridin-3-yl)pyrrolidin-3-yl)-1,8,14-trioxo-5,12,18-trioxa-2,9,15-triazaicosan-20-oate (48 mg, 0.081 mmol) in dichloromethane (DCM) (2.0 mL) was added 4 M HCl in 1,4-dioxane (4 mL, 16.00 mmol). The mixture was stirred for 1 h and was concentrated to dryness. To the residue was added dichloromethane (DCM) (2.0 mL), (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2Hydrochloric acid salt (50 mg, 0.074 mmol), HOBt (13.68 mg, 0.089 mmol), and DIPEA (0.065 mL, 0.372 mmol) followed by EDC (21.40 mg, 0.112 mmol). The mixture was stirred at rt for 3 h. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonia hydroxide (0.075%) provided the title compound (16.3 mg, 0.016 mmol, 21.14% yield). LC-MS m/z 984.3 $(M+H)^+$. $^1H$ NMR (400 MHz, DMSO-$d_6$) δ ppm 0.81-1.10 (m, 6H) 1.49-1.72 (m, 3H) 2.11 (s, 7H) 2.25-2.37 (m, 3H) 2.38-2.48 (m, 1H) 2.63-2.77 (m, 2H) 2.87-3.00 (m, 1H) 3.23 (s, 7H)

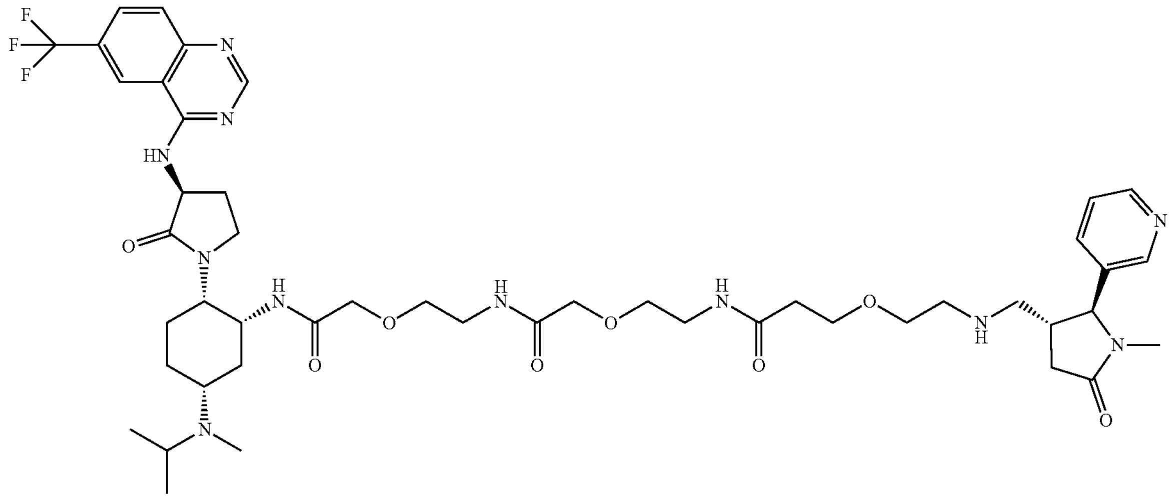

3.39-3.45 (m, 2H) 3.54 (br d, J=6.8 Hz, 5H) 3.72-4.16 (m, 6H) 4.65 (d, J=6.4 Hz, 2H) 4.89-5.14 (m, 1H) 7.34-7.54 (m, 1H) 7.60-8.14 (m, 6H) 8.43-8.72 (m, 4H) 8.95 (s, 1H) 9.16-9.33 (m, 1H).

The following compound was or could be prepared with procedures analogous to that described in Example 151:

| Ex. | Compound | LC-MS m/z | NMR |
|---|---|---|---|
| 152 | 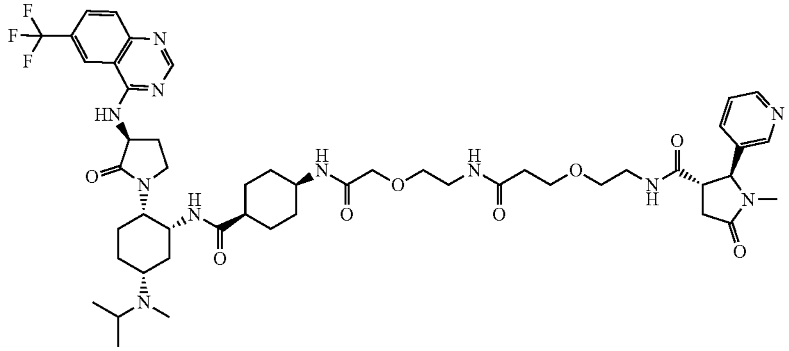 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCNC(=O)CCOCCNC(=O)[C@H]3CC(=O)N(C)[C@@H]3c3cccnc3)CC2)C1] (2S,3S)-N-(2-(3-((2-(2-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-2-oxoethoxy)ethyl)amino)-3-oxopropoxy)ethyl)-1-methyl-5-oxo-2-(pyridin-3-yl)pyrrolidine-3-carboxamide. | 1008.5 (M + H)+ | $^1$H NMR (400 MHz, DMSO-$d_6$) δ ppm 0.88 (d, J = 6.4 Hz, 3H) 1.04 (d, J = 6.4 Hz, 3H) 1.43-1.78 (m, 11H) 1.89-2.07 (m, 2H) 2.10-2.18 (m, 5H) 2.29 (t, J = 6.6 Hz, 2H) 2.32-2.37 (m, 1H) 2.43 (dd, J = 16.6, 7.3 Hz, 1H) 2.58 (br s, 1H) 2.66-2.74 (m, 1H) 2.90-2.97 (m, 1H) 3.11-3.30 (m, 5H) 3.32 (dd, J = 5.9, 2.0 Hz, 2H) 3.35-3.43 (m, 3H) 3.54 (t, J = 6.6 Hz, 3H) 3.74 (br s, 1H) 3.78 (s, 2H) 3.84-3.90 (m, 1H) 4.43 (br dd, J = 7.1, 3.7 Hz, 1H) 4.65 (d, J = 5.9 Hz, 1H) 5.04 (q, J = 8.3 Hz, 1H) 7.34 (d, J = 7.3 Hz, 1H) 7.41-7.47 (m, 1H) 7.67 (dt, J = 7.8, 2.0 Hz, 1H) 7.89 (d, J = 8.8 Hz, 1H) 7.97 (t, J = 5.6 Hz, 1H) 8.03-8.10 (m, 2H) 8.47 (d, J = 1.5 Hz, 1H) 8.52-8.59 (m, 2H) 8.70 (br d, J = 7.8 Hz, 2H) 8.88 (s, 1H). |

Example 153

(2S,3S)-N-(7-((9-(2-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-2-oxoethoxy)nonyl)oxy)heptyl)-1-methyl-5-oxo-2-(pyridin-3-yl)pyrrolidine-3-carboxamide

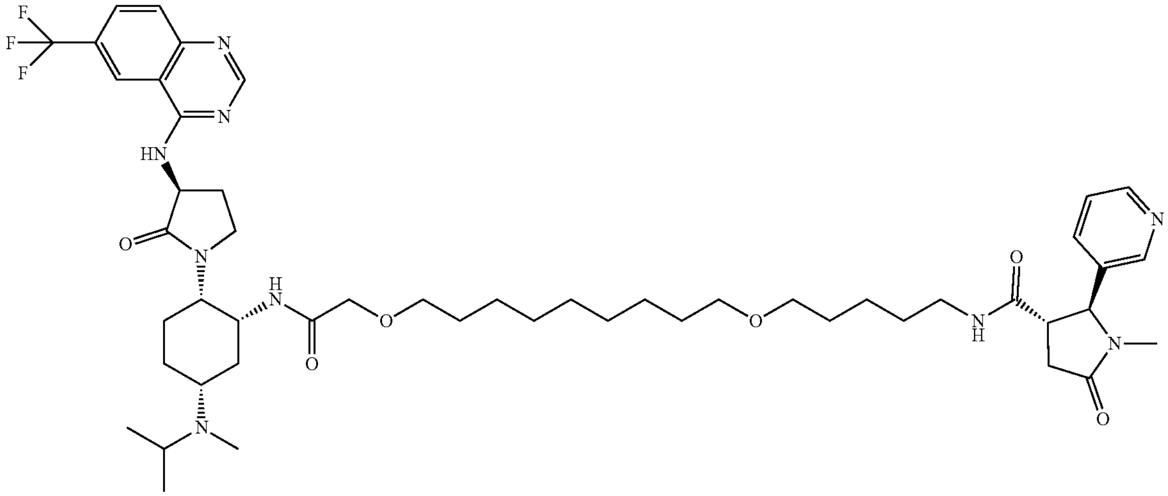

Step 1

7-((9-Hydroxynonyl)oxy)heptanenitrile

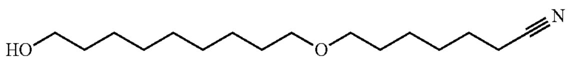 [SMILES: N#CCCCCCCOCCCCCCCCCO]

To a mixture of 60% sodium hydride in mineral oil (1.052 g, 26.3 mmol) in N,N-dimethylformamide (DMF) (0.2 ml) at 0° C. was added nonane-1,9-diol (3.37 g, 21.04 mmol). The mixture was stirred at 0° C. for 15 min and 7-bromoheptanenitrile (2 g, 10.52 mmol) in N,N-dimethylformamide (DMF) (0.3 ml) was added. The mixture was stirred at 0° C. for 10 min, then rt for 1 h. Saturated $NH_4Cl$ was added at 0° C. and the mixture was extracted with ethyl acetate. The combined organic extracts were washed with brine (2×), were dried over $Na_2SO_4$, were filtered, and the filtrate was concentrated. Water was added to the residue, the mixture was extracted with dichloromethane (DCM), and the combined organic extracts were washed with brine (2×), were dried over $Na_2SO_4$, were filtered, and the filtrate was concentrated. Purification by ISCO CombiFlash® chromatography (80 g RediSep Rf Gold® column, 60 mL/min) eluting with a gradient of 0 to 60% ethyl acetate in heptane provided the title compound (900 mg, 3.34 mmol, 31.7% yield). LC-MS m/z 270.2 $(M+H)^+$.

Step 2

9-((7-Aminoheptyl)oxy)nonan-1-ol

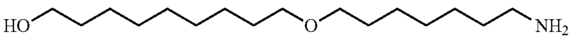

To a mixture of 7-((9-hydroxynonyl)oxy)heptanenitrile (507 mg, 1.882 mmol) in tetrahydrofuran (THF) (5 mL) at 0° C. was added borane tetrahydrofuran complex (3.76 mL, 3.76 mmol). The mixture was stirred at 0° C. for 15 min and at rt overnight, was cooled to 0° C., and methanol was added until bubbling evolution had ceased. The mixture was stirred at rt for 10 min and was concentrated under reduced pressure. The residue was partitioned between dichloromethane (DCM). The aqueous phase was extracted with dichloromethane (DCM). The combined organic phases were dried over $Na_2SO_4$, were filtered, and the filtrate was concentrated. Purification by ISCO CombiFlash® chromatography (24 g RediSep Rf Gold® column, 30 mL/min) eluting with a gradient of 0 to 25% methanol dichloromethane (DCM), provided the title compound as a colorless oil (400 mg, 1.463 mmol, 78% yield). LC-MS m/z 274.3 $(M+H)^+$.

Step 3

(2S,3S)-N-(7-((9-Hydroxynonyl)oxy)heptyl)-1-methyl-5-oxo-2-(pyridin-3-yl)pyrrolidine-3-carboxamide

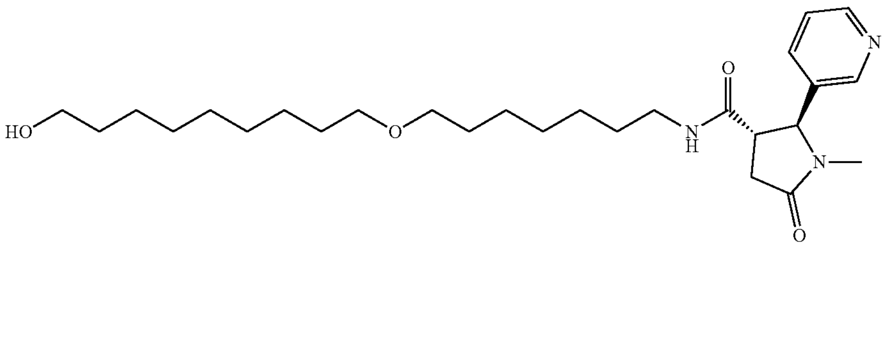 [SMILES: CN1C(=O)C[C@H](C(=O)NCCCCCCCOCCCCCCCCCO)[C@H]1c1cccnc1]

To a mixture of 9-((7-aminoheptyl)oxy)nonan-1-ol (200 mg, 0.732 mmol), (2S,3S)-1-methyl-5-oxo-2-(pyridin-3-yl) pyrrolidine-3-carboxylic acid (124 mg, 0.563 mmol) and HATU (257 mg, 0.676 mmol) in dichloromethane (DCM) (2 mL) was added DIPEA (0.295 mL, 1.689 mmol).

The mixture was stirred at rt overnight and was partitioned between saturated $NaHCO_3$ and dichloromethane (DCM). The aqueous phase was extracted with dichloromethane (DCM) and the combined organic phases were dried over $Na_2SO_4$, were filtered, and the filtrate was concentrated. Purification by ISCO CombiFlash® chromatography (24 g RediSep Rf Gold® column, 30 mL/min) eluting with a stepwise gradient of 0 to 60% methanol/ethyl acetate (20/80) in dichloromethane (DCM), followed by 30% methanol in dichloromethane (DCM) provided the title compound as a colorless oil (265 mg, 0.557 mmol, 99% yield). LC-MS m/z 476.3 $(M+H)^+$.

Step 4

2-((9-((7-((2S,3S)-1-Methyl-5-oxo-2-(pyridin-3-yl) pyrrolidine-3-carboxamido) heptyl)oxy)nonyl)oxy) acetic acid, Formic acid salt

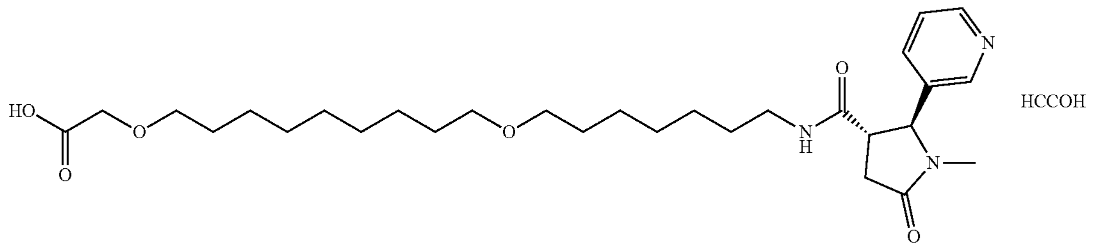

To a mixture of (2S,3S)-N-(7-((9-hydroxynonyl)oxy)heptyl)-1-methyl-5-oxo-2-(pyridin-3-yl)pyrrolidine-3-carboxamide (130 mg, 0.273 mmol) and 2-bromoacetic acid (38.0 mg, 0.273 mmol) in tert-Butanol (1 mL) was added potassium tert-butoxide (123 mg, 1.093 mmol). The mixture was stirred at 50° C. for 4 h. Potassium tert-butoxide (123 mg, 1.093 mmol) and 2-bromoacetic acid (38.0 mg, 0.273 mmol), were added and the mixture was stirred at 50° C. for 24 h. Water was added, the mixture was neutralized with 1 N HCl, and the mixture was extracted with a mixture of 2-propanol/dichloromethane (DCM). The combined organic extracts were dried over $Na_2SO_4$, were filtered, and the filtrate was concentrated. Purification by MDAP chromatography (XSelect™ CSH Prep C18 150 mm×30 mm 5 μm OBD column, 40 mL/min) eluting with a gradient of 15 to 55% acetonitrile in water both containing formic acid (0.1%) provided the title compound (11 mg, 0.019 mmol, 6.94% yield). LC-MS m/z 534.3 $(M+H)^+$.

Step 5

(2S,3S)-N-(7-((9-(2-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-2-oxoethoxy)nonyl)oxy)heptyl)-1-methyl-5-oxo-2-(pyridin-3-yl)pyrrolidine-3-carboxamide

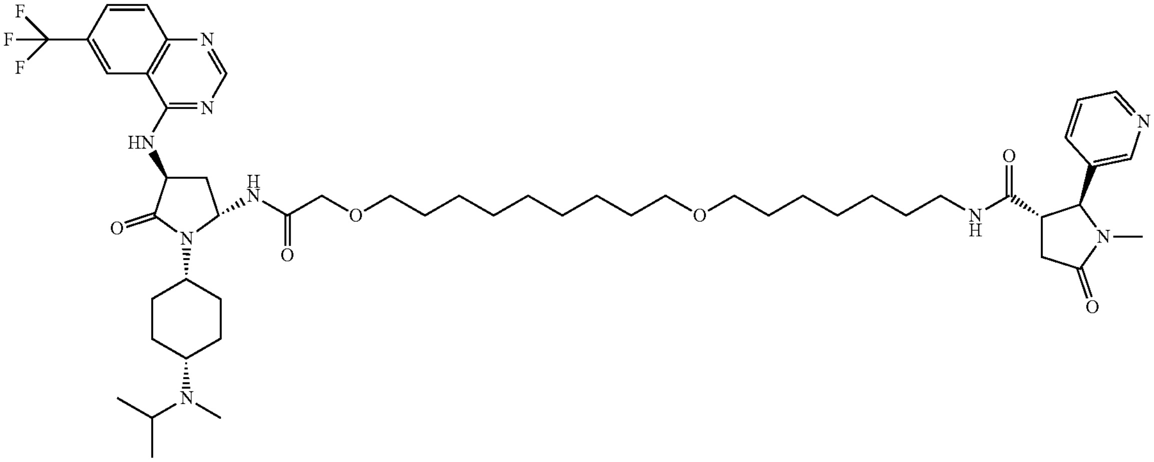

To (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2trifluoroacetic acid salt (13.14 mg, 0.019 mmol) in dichloromethane (DCM) (0.5 mL) was added triethylamine (0.021 mL, 0.152 mmol). The mixture was stirred at rt for 30 min and 2-((9-((7-((2S,3S)-1-methyl-5-oxo-2-(pyridin-3-yl)pyrrolidine-3-carboxamido)heptyl)oxy)nonyl)oxy)acetic acid, formic acid salt (11 mg, 0.019 mmol) and HATU (8.66 mg, 0.023 mmol) were added. The mixture was stirred at rt for 4 h and was partitioned between saturated $NaHCO_3$ and dichloromethane (DCM). The aqueous phase was extracted with dichloromethane (DCM). The combined organic phases were dried over $Na_2SO_4$, were filtered, and the filtrate was concentrated. Purification by MDAP chromatography (XSelect™ CSH Prep C18 150 mm×30 mm 5 μm OBD column, 40 mL/min) eluting with a gradient of 15 to 55% acetonitrile in water both containing formic acid (0.1%) provided the title compound as a solid (6.5 mg, 6.63 μmol, 34.9% yield). LC-MS m/z 980.6 $(M+H)^+$. $^1H$ NMR (400 MHz, METHANOL-$d_4$) δ ppm 1.01-1.40 (m, 25H) 1.40-1.62 (m, 8H) 1.71-1.87 (m, 2H) 2.02-2.63 (m, 8H) 2.65-2.68 (m, 3H) 2.68-2.74 (m, 1H) 2.75-2.90 (m, 1H) 2.92-3.08 (m, 1H) 3.08-3.24 (m, 2H) 3.37-3.45 (m, 4H) 3.50 (br s, 3H) 3.65 (br t, J=7.5 Hz, 2H) 3.89-4.03 (m, 2H) 4.06-4.18 (m, 1H) 4.46-4.70 (m, 1H) 4.99-5.33 (m, 1H) 7.53 (dd, J=7.9, 4.9 Hz, 1H) 7.79 (dt, J=7.9, 1.9 Hz, 1H) 7.91 (d, J=8.8 Hz, 1H) 8.06 (dd, J=8.9, 1.9 Hz, 1H) 8.51 (d, J=1.5 Hz, 1H) 8.58 (s, 2H) 8.77 (s, 1H).

Example 154

N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-1'-(8-((2R,3R)-1-methyl-5-oxo-2-(pyridin-3-yl)pyrrolidine-3-carboxamido)octanoyl)-[1,4'-bipiperidine]-4-carboxamide

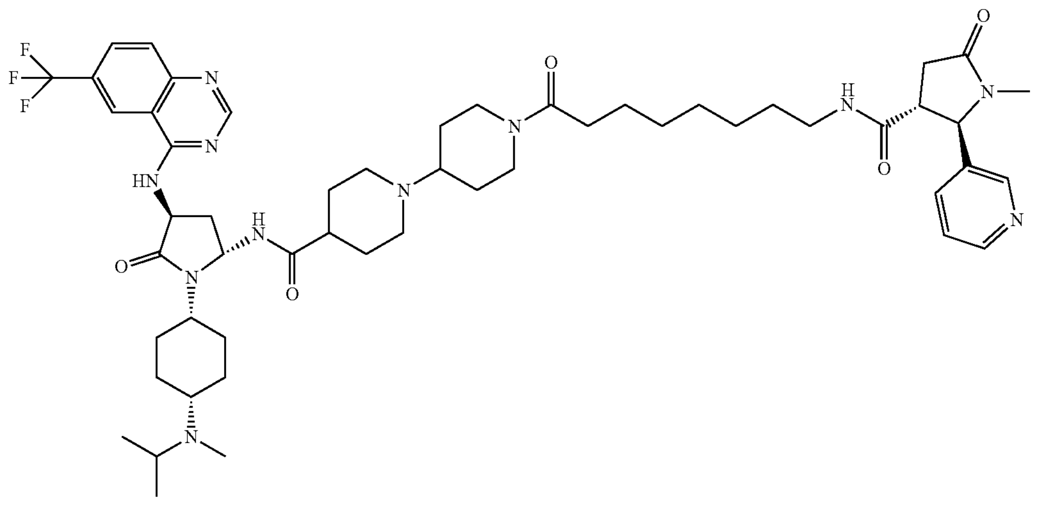

Step 1 tert-Butyl (8-(4-(((1R,2S,5R)-5-(isopropyl(methyl) amino)-2-((S)-2-oxo-3-((6-(trifluoromethyl)quinazolin-4-yl)amino)pyrrolidin-1-yl)cyclohexyl)carbamoyl)-[1,4'-bipiperidin]-1'-yl)-8-oxooctyl)carbamate

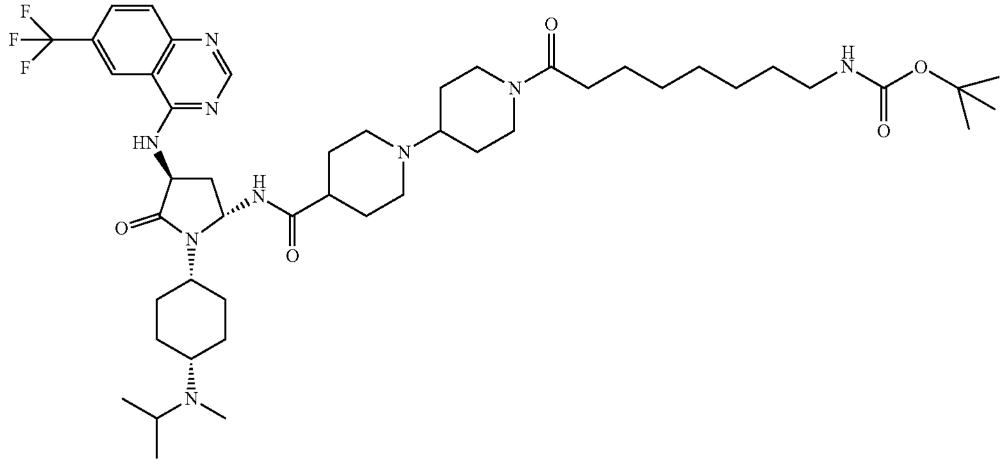

To a solution of tert-butyl 4-(((1R,2S,5R)-5-(isopropyl (methyl)amino)-2-((S)-2-oxo-3-((6-(trifluoromethyl)quinazolin-4-yl)amino)pyrrolidin-1-yl)cyclohexyl)carbamoyl)-[1,4'-bipiperidine]-1'-carboxylate (55 mg, 0.072 mmol) in dichloromethane (DCM) (2 mL) was added 3 M HCl in cyclopentyl methyl ether (0.5 mL, 1.500 mmol). The mixture was stirred at rt for 1 h and was concentrated. The resulting white solid was suspended in dichloromethane (DCM) (5 mL), DIPEA (0.044 mL, 0.254 mmol) was added, followed by 8-((tert-butoxycarbonyl) amino)octanoic acid (22.55 mg, 0.087 mmol) and HATU (41.3 mg, 0.109 mmol). The mixture was stirred at rt for 0.5 h and was concentrated. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a white solid (60.6 mg, 0.066 mmol, 91% yield). LC-MS m/z 900.8 $(M+H)^+$.

Step 2

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1'-(8-((2R,3R)-1-methyl-5-oxo-2-(pyridin-3-yl)pyrrolidine-3-carboxamido)octanoyl)-[1,4'-bipiperidine]-4-carboxamide

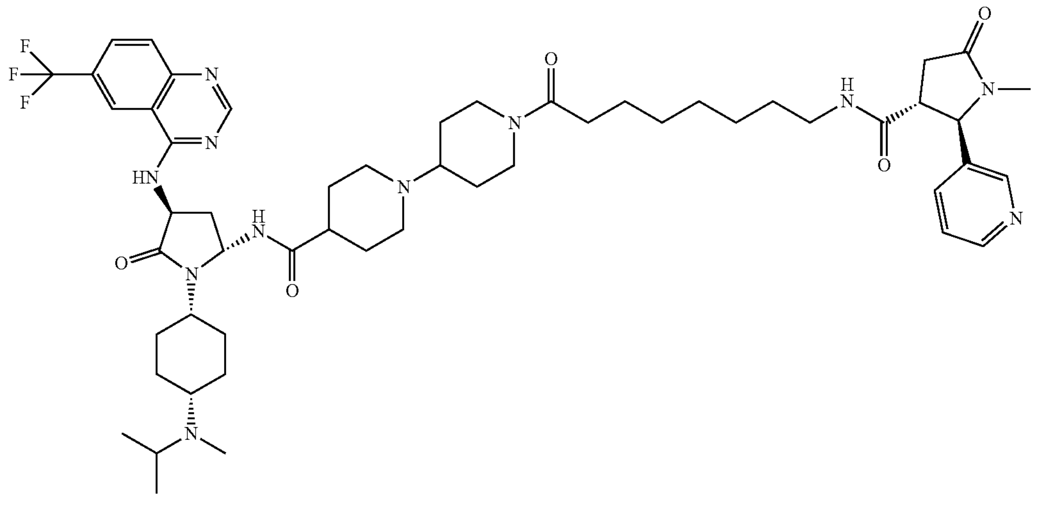

To a solution of tert-butyl (8-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)-[1,4'-bipiperidin]-1'-yl)-8-oxooctyl)carbamate (60 mg, 0.067 mmol) in dichloromethane (DCM) (1 mL) was added 3 M HCl in cyclopentyl methyl ether (0.5 mL, 1.500 mmol). The mixture was stirred at rt for 1 h and was concentrated to dryness. The residue was suspended in dichloromethane (DCM) (5 mL), triethylamine (0.05 mL, 0.359 mmol) was added, followed by (2S,3S)-1-methyl-5-oxo-2-(pyridin-3-yl)pyrrolidine-3-carboxylic acid (20 mg, 0.091 mmol) and HATU (44 mg, 0.116 mmol). The mixture was stirred at rt for 2 h and was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as a white solid (60 mg, 0.059 mmol, 89% yield). LC-MS m/z 1002.8 $(M+H)^+$. $^1H$ NMR (400 MHz, METHANOL-$d_4$) δ ppm 1.01 (d, J=6.3 Hz, 3H) 1.12-1.23 (m, 3H) 1.23-1.49 (m, 10H) 1.53-1.78 (m, 7H) 1.84-2.05 (m, 5H) 2.05-2.32 (m, 9H) 2.33-2.41 (m, 2H) 2.51-2.74 (m, 8H) 2.76-2.87 (m, 1H) 2.98-3.24 (m, 6H) 3.37-3.56 (m, 2H) 3.59-3.68 (m, 1H) 3.97-4.07 (m, 2H) 4.52-4.61 (m, 1H) 4.65 (br d, J=3.0 Hz, 1H) 4.79-4.83 (m, 1H) 5.28 (t, J=8.3 Hz, 1H) 7.51-7.55 (m, 1H) 7.79 (dt, J=8.0, 1.9 Hz, 1H) 7.91 (d, J=8.8 Hz, 1H) 8.06 (dd, J=8.8, 2.0 Hz, 1H) 8.51 (d, J=1.8 Hz, 1H) 8.58 (dd, J=4.9, 1.6 Hz, 1H) 8.59 (s, 1H) 8.77 (s, 1H).

The following compounds were or could be prepared with procedures analogous to that described in Example 154:

| Ex. | Compound | LC-MS m/z | NMR |
| --- | --- | --- | --- |
| 155 | 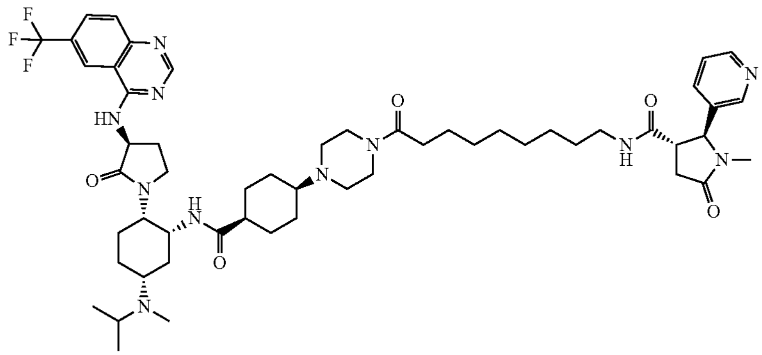 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](N3CCN(C(=O)CCCCCCCCNC(=O)[C@H]4CC(=O)N(C)[C@@H]4c4cccnc4)CC3)CC2)C1] (2S,3S)-N-(9-(4-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperazin-1-yl)-9-oxononyl)-1-methyl-5-oxo-2-(pyridin-3-yl)pyrrolidine-3-carboxamide. | 1016.6 (M + H)+ | $^1H$ NMR (400 MHz, METHANOL-$d_4$) δ ppm 1.04 (br d, J = 6.3 Hz, 3H) 1.15 (br d, J = 6.3 Hz, 3H) 1.25-1.36 (m, 9H) 1.42-1.63 (m, 6H) 1.65-1.80 (m, 3H) 1.93-2.25 (m, 8H) 2.26-2.42 (m, 7H) 2.51-2.63 (m, 5H) 2.67 (s, 3H) 2.69-2.76 (m, 2H) 2.79-2.87 (m, 1H) 2.97-3.06 (m, 1H) 3.07-3.25 (m, 2H) 3.45 (dt, J = 13.0, 6.3 Hz, 1H) 3.50-3.60 (m, 5H) 3.61-3.69 (m, 1H) 4.04 (dt, J = 12.5, 3.6 Hz, 1H) 4.66 (br d, J = 3.0 Hz, 1H) 4.80-4.86 (m, 2H) 5.26 (t, J = 8.0 Hz, 1H) 7.52-7.57 (m, 1H) 7.81 (dt, J = 7.9, 1.9 Hz, 1H) 7.92 (d, J = 8.9 Hz, 1H) 8.07 (dd, J = 8.9, 1.8 Hz, 1H) 8.51 (d, J = 1.8 Hz, 1H) 8.57-8.62 (m, 2H) 8.82 (s, 1H). |
| 156 | 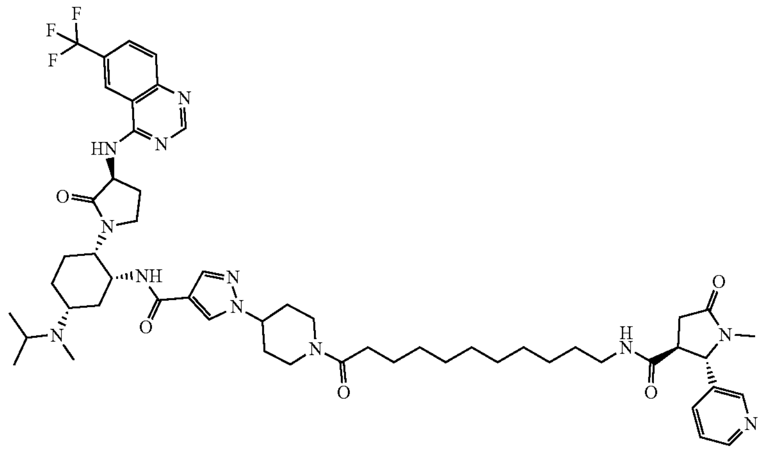 [SMILES: CC(C)N(C)[C@@H]1CC[C@H](N2CC[C@H](Nc3ncnc4ccc(C(F)(F)F)cc34)C2=O)[C@H](NC(=O)c2cnn(C3CCN(C(=O)CCCCCCCCCCNC(=O)[C@H]4CC(=O)N(C)[C@@H]4c4cccnc4)CC3)c2)C1] N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-1-(1-(11-((2S,3S)-1-methyl-5-oxo-2-(pyridin-3-yl)pyrrolidine-3-carboxamido)undecanoyl)piperidin-4-yl)-1H-pyrazole-4-carboxamide. | 1027.4 (M + H)+ | $^1H$ NMR (400 MHz, METHANOL-$d_4$) δ ppm 1.03-1.51 (m, 20 H) 1.56-1.65 (m, 2H) 1.71-2.32 (m, 11H) 2.37-2.44 (m, 2H) 2.47-2.59 (m, 3H) 2.62-2.88 (m, 7H) 2.94-3.27 (m, 6H) 3.56-3.86 (m, 3H) 3.94-4.11 (m, 1H) 4.21-4.37 (m, 2H) 4.53-4.63 (m, 2H) 4.78-4.84 (m, 1H) 7.51-7.57 (m, 1H) 7.69-7.74 (m, 1H) 7.77-7.83 (m, 1H) 7.86-7.95 (m, 2H) 8.06-8.13 (m, 1H) 8.39-8.47 (m, 1H) 8.48-8.53 (m, 1H) 8.56-8.61 (m, 1H) 8.73-8.78 (m, 1H). |

-continued

| Ex. | Compound | LC-MS m/z | NMR |
|---|---|---|---|
| 157 | 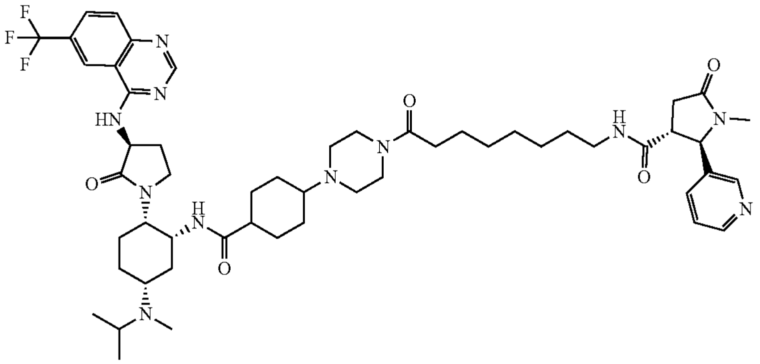 N-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-1'-(10-((2R,3R)-1-methyl-5-oxo-2-(pyridin-3-yl)pyrrolidine-3-carboxamido)decanoyl)-[1,4'-bipiperidine]-4-carboxamide. | 1030.4 (M + H)+ | $^1$H NMR (400 MHz, METHANOL-$d_4$) δ ppm 1.23-1.50 (m, 19H) 1.54-1.65 (m, 3H) 1.76-2.13 (m, 9H) 2.13-2.33 (m, 3H) 2.36-2.52 (m, 3H) 2.53-2.63 (m, 2H) 2.67 (s, 3H) 2.68-2.76 (m, 2H) 2.77-2.95 (m, 4H) 2.96-3.24 (m, 5H) 3.27-3.31 (m, 1H) 3.35-3.42 (m, 1H) 3.48-3.67 (m, 2H) 3.76 (br dd, J = 3.2, 2.4 Hz, 1H) 3.83-4.03 (m, 2H) 4.22 (br s, 1H) 4.40 (br s, 1H) 4.71 (br d, J = 13.2 Hz, 1H) 4.82 (d, J = 6.8 Hz, 1H) 5.11 (br t, J = 8.9 Hz, 1H) 7.55 (dd, J = 7.9, 4.8 Hz, 1H) 7.82 (dt, J = 8.1, 1.8 Hz, 1H) 7.94 (d, J = 8.9 Hz, 1H) 8.08-8.15 (m, 1H) 8.36-8.47 (m, 3H) 8.52 (br s, 1H) 8.56-8.63 (m, 1H) 8.65 (s, 1H) 8.79 (br s, 1H). |

Example 158

(2S,3S)-N-(6-((4'-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)-2',3',4',5'-tetrahydro-[1,1'-biphenyl]-4-yl)oxy)hexyl)-1-methyl-5-oxo-2-(pyridin-3-yl)pyrrolidine-3-carboxamide

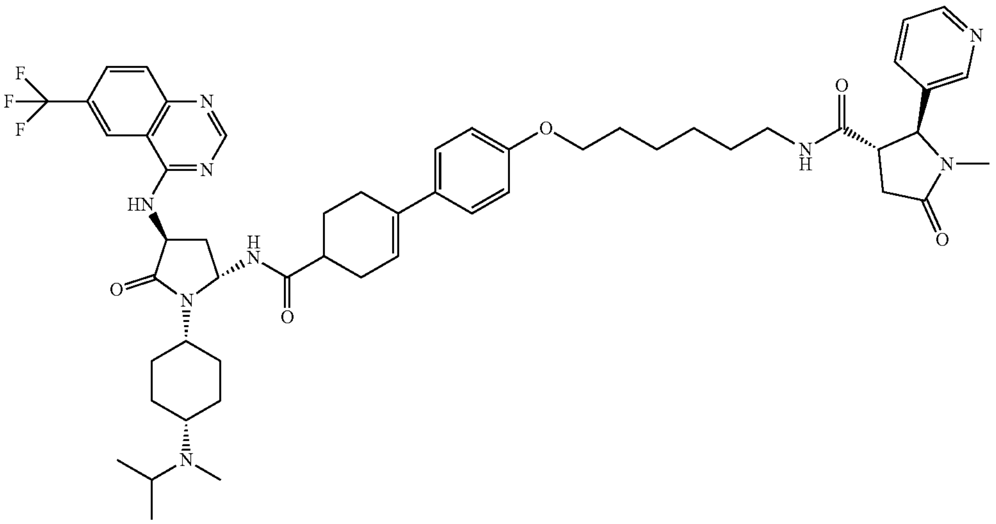

Step 1 tert-Butyl (6-(4-bromophenoxy)hexyl)carbamate

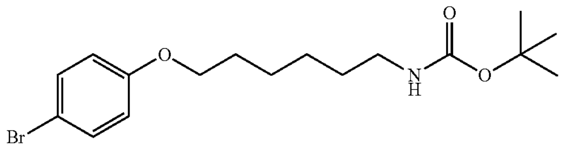 [SMILES: CC(C)(C)OC(=O)NCCCCCCOc1ccc(Br)cc1]

To a mixture of 4-bromophenol (0.648 g, 3.75 mmol) and tert-butyl (6-bromohexyl)carbamate (1.05 g, 3.75 mmol) in N,N-dimethylformamide (DMF) (4 mL) was added potassium carbonate (1.036 g, 7.49 mmol). The mixture was stirred at rt over the weekend and at 60° C. for 5 h. The mixture was partitioned between ethyl acetate and water. The aqueous phase extracted with ethyl acetate. The combined organics were washed with water and brine, were dried over $Na_2SO_4$, were filtered, and the filtrate was concentrated. Purification by CombiFlash® Rf chromatography (40 g RediSep Rf Gold® column, 40 mL/min) eluting with a gradient of 0 to 60% ethyl acetate in heptane provided the title compound (1.27 g, 3.41 mmol, 91% yield). LC-MS m/z 274.1 $(M+H)^+$.

Step 2

Methyl 4'-((6-((tert-butoxycarbonyl)amino)hexyl)oxy)-2,3,4,5-tetrahydro-[1,1'-biphenyl]-4-carboxylate

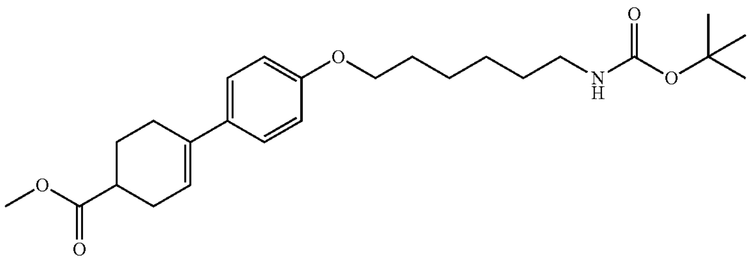 [SMILES: COC(=O)C1CC=C(c2ccc(OCCCCCCNC(=O)OC(C)(C)C)cc2)CC1]

To a mixture of tert-butyl (6-(4-bromophenoxy)hexyl)carbamate (519 mg, 1.394 mmol) and methyl 4-(4,4,5,5-tetramethyl-1,3,2-dioxaborolan-2-yl)cyclohex-3-ene-1-carboxylate (287 mg, 1.078 mmol) in N,N-dimethylformamide (DMF) (3 mL) was added tert-butyl (6-(4 bromophenoxy)hexyl)carbamate (519 mg, 1.394 mmol) and potassium phosphate (687 mg, 3.24 mmol). The mixture was purged with nitrogen for 10 min and PdCl2(dppf) (39.5 mg, 0.054 mmol) was added. The mixture was stirred at rt over the weekend and was filtered through Celite®. The catalyst was washed with ethyl acetate and the combined filtrates were concentrated. Purification by Biotage® Isolera™ column chromatography (24 g Gold column) eluting with a gradient of 0 to 30% ethyl acetate/ethanol (3:1) in heptane provided the title compound (54 mg, 0.125 mmol, 11.60% yield). LC-MS m/z 331.9 $(M+H)^+$.

Step 3

4'-((6-((tert-Butoxycarbonyl)amino)hexyl)oxy)-2,3,4,5-tetrahydro-[1,1'-biphenyl]-4-carboxylic acid

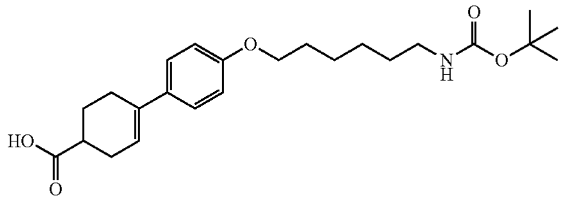 [SMILES: CC(C)(C)OC(=O)NCCCCCCOc1ccc(C2=CCC(C(=O)O)CC2)cc1]

To a slurry of methyl 4'-((6-((tert-butoxycarbonyl)amino)hexyl)oxy)-2,3,4,5-tetrahydro-[1,1'-biphenyl]-4-carboxylate (58 mg, 0.134 mmol) in methanol (1 mL) was added sodium hydroxide (0.806 mL, 0.806 mmol). The mixture was stirred at rt for 2 h, additional tetrahydrofuran (THF) (0.5 mL) was added, the mixture was stirred at rt overnight, and was concentrated. Water was added, the mixture was acidified with 1 N HCl (1.5 mL) and was extracted with dichloromethane (DCM). The combined organic extracts were dried over $Na_2SO_4$, were filtered, and the filtrate was concentrated to provide the title compound (55 mg, 0.132 mmol, 98% yield). LC-MS m/z 318.1 $(M+H)^+$.

Step 4 tert-Butyl (6-((4'-(((1R,2S,5R)-5-(isopropyl(methyl) amino)-2-((S)-2-oxo-3-((6-(trifluoromethyl)quinazolin-4-yl)amino)pyrrolidin-1-yl)cyclohexyl)carbamoyl)-2',3',4',5'-tetrahydro-[1,1'-biphenyl]-4-yl)oxy) hexyl)carbamate

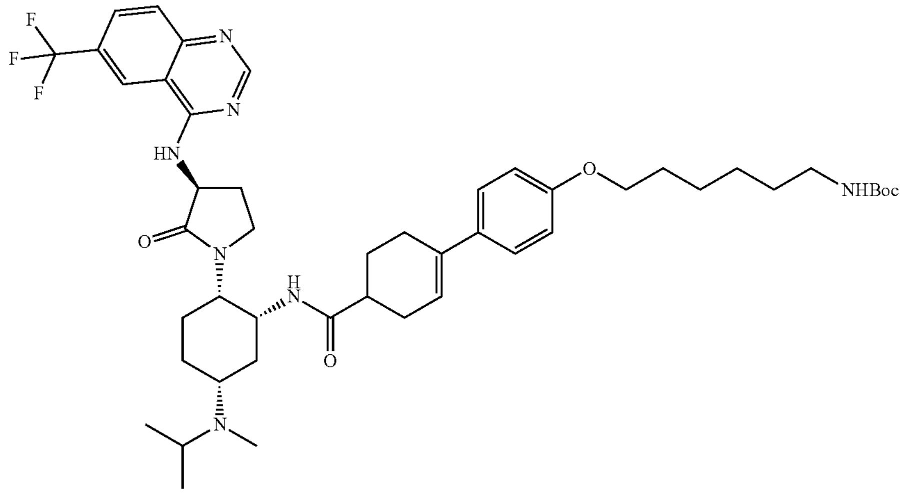 [SMILES: CC(C)N(C)[C@@H]1CC[C@H](N2CC[C@H](Nc3ncnc4ccc(C(F)(F)F)cc34)C2=O)[C@H](NC(=O)C2CC=C(c3ccc(OCCCCCCNC(=O)OC(C)(C)C)cc3)CC2)C1]

To (S)-1-((1S,2R,4R)-2-amino-4-(isopropyl(methyl) amino)cyclohexyl)-3-((6-(trifluoromethyl) quinazolin-4-yl) amino)pyrrolidin-2-one, 2hydrochloric acid salt (48.3 mg, 0.090 mmol) in dichloromethane (DCM) (1 mL) was added triethylamine (0.075 mL, 0.539 mmol), 4'-((6-((tert-butoxycarbonyl)amino)hexyl)oxy)-2,3,4,5-tetrahydro-[1,1'-biphenyl]-4-carboxylic acid (37.5 mg, 0.090 mmol) and HATU (41.0 mg, 0.108 mmol). The mixture was stirred at rt for 2 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (30 mg, 0.035 mmol, 38.7% yield). LC-MS m/z 864.5 $(M+H)^+$.

Step 5

(2S,3S)-N-(6-((4'-(((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)carbamoyl)-2',3',4',5'-tetrahydro-[1,1'-biphenyl]-4-yl)oxy) hexyl)-1-methyl-5-oxo-2-(pyridin-3-yl)pyrrolidine-3-carboxamide

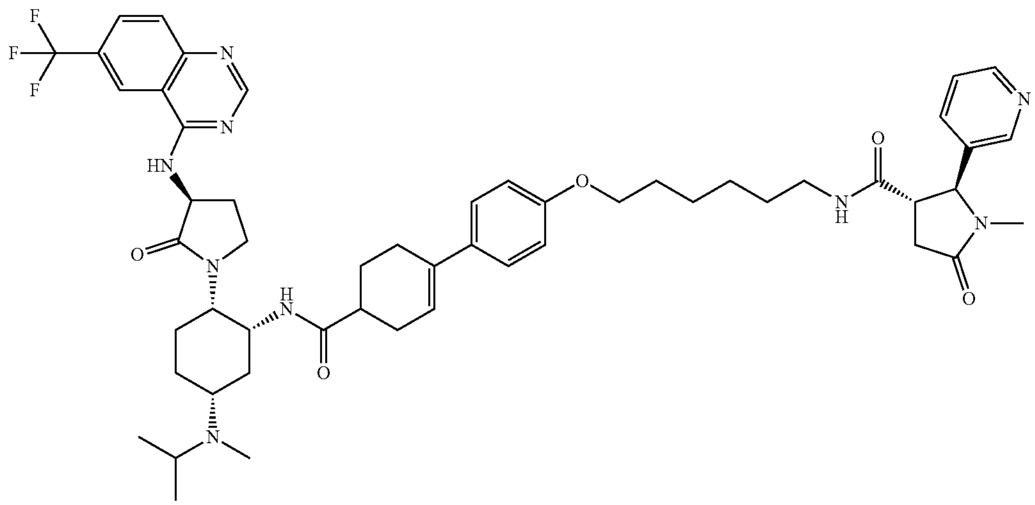 [SMILES: CC(C)N(C)[C@@H]1CC[C@H](N2CC[C@H](Nc3ncnc4ccc(C(F)(F)F)cc34)C2=O)[C@H](NC(=O)C2CC=C(c3ccc(OCCCCCCNC(=O)[C@H]4CC(=O)N(C)[C@@H]4c4cccnc4)cc3)CC2)C1]

4 M HCl in 1,4-dioxane (0.061 mL, 0.243 mmol) was added to tert-butyl (6-((4'-(((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)carbamoyl)-2',3',4',5'-tetrahydro-[1,1'-biphenyl]-4-yl)oxy) hexyl) carbamate (30 mg, 0.035 mmol) in dichloromethane (DCM) (0.05 mL). The mixture was stirred at rt for 2 h and was concentrated to dryness. To the residue in dichloromethane (DCM) (1 mL) was added (2S,3S)-1-methyl-5-oxo-2-(pyridin-3-yl)pyrrolidine-3-carboxylic acid (7.65 mg, 0.035 mmol), triethylamine (0.029 mL, 0.208 mmol) and HATU (15.84 mg, 0.042 mmol). The mixture was stirred at rt for 2 h. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a white solid (19.4 mg, 0.020 mmol, 57.8% yield). LC-MS m/z 966.4 $(M+H)^+$. $^1H$ NMR (400 MHz, METHANOL-$d_4$) δ ppm 0.98-1.11 (m, 3H) 1.17 (brt, J=5.1 Hz, 3H) 1.27-1.39 (m, 2H) 1.48 (sxt, J=7.3 Hz, 4H) 1.65-1.82 (m, 5H) 1.82-2.02 (m, 2H) 2.05-2.39 (m, 8H) 2.40-2.58 (m, 6H) 2.64-2.84 (m, 6H) 2.97-3.03 (m, 1H) 3.09-3.17 (m, 1H) 3.41-3.69 (m, 4H) 3.95 (td, J=6.4, 2.0 Hz, 2H) 4.06 (br d, J=1-1.8 Hz, 1H) 4.55 (s, 1H) 4.64-4.78 (m, 1H) 4.78-4.82 (m, 2H) 5.26 (br s, 1H) 6.00 (br s, 1H) 6.79-6.83 (m, 2H) 7.25 (d, J=8.5 Hz, 2H) 7.49-7.53 (m, 1H) 7.78 (dt, J=7.9, 1.8 Hz, 1H) 7.90 (dd, J=8.8, 5.8 Hz, 1H) 8.04 (ddd, J=8.8, 4.0, 2.0 Hz, 1H) 8.49 (d, J=2.3 Hz, 1H) 8.56 (dd, J=4.9, 1.6 Hz, 1H) 8.58-8.60 (m, 1H) 8.79 (s, 1H).

Example 159

N[1]-((1R,2S,5R)-5-(isopropyl(methyl)amino)-2-((S)-2-oxo-3-((6-(trifluoromethyl) quinazolin-4-yl) amino)pyrrolidin-1-yl)cyclohexyl)-N[10]-(2-(2-(2-((2S,3S)-1-methyl-5-oxo-2-(pyridin-3-yl) pyrrolidine-3-carboxamido)ethoxy)ethoxy)ethyl) decanediamide

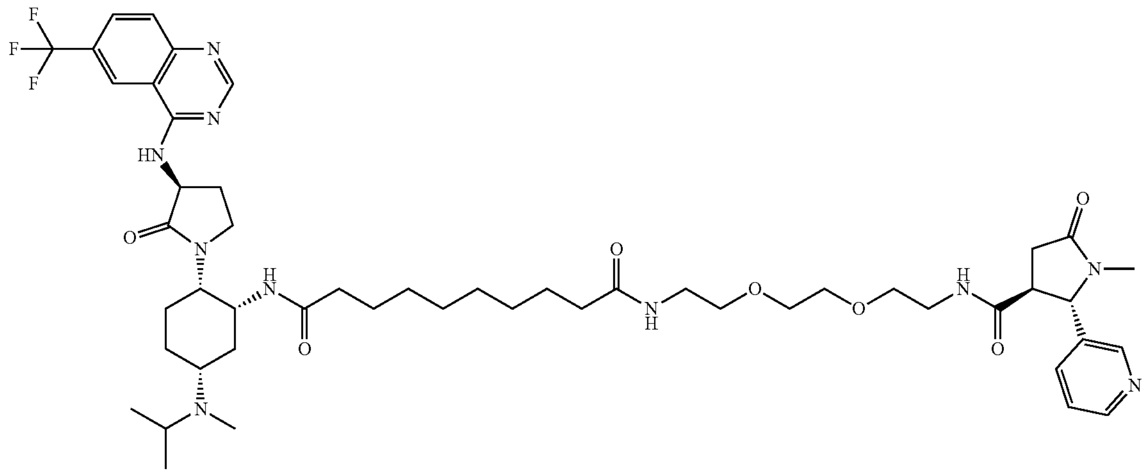 [SMILES: CC(C)N(C)[C@@H]1CC[C@H](N2CC[C@H](Nc3ncnc4ccc(C(F)(F)F)cc34)C2=O)[C@H](NC(=O)CCCCCCCCC(=O)NCCOCCOCCNC(=O)[C@H]2CC(=O)N(C)[C@@H]2c2cccnc2)C1]

Step 1 tert-Butyl (2-(2-(2-((2S,3S)-1-methyl-5-oxo-2-(pyridin-3-yl)pyrrolidine-3-carboxamido) oxy)ethoxy) ethyl)carbamate

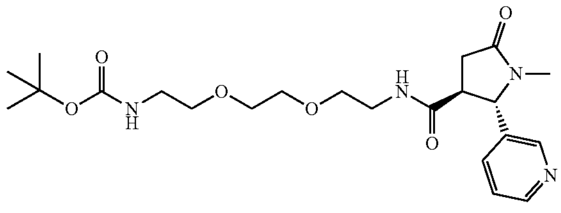 [SMILES: CN1C(=O)C[C@H](C(=O)NCCOCCOCCNC(=O)OC(C)(C)C)[C@H]1c1cccnc1]

To a mixture of (2S,3S)-1-methyl-5-oxo-2-(pyridin-3-yl) pyrrolidine-3-carboxylic acid (189 mg, 0.858 mmol) and tert-butyl (2-(2-(2-aminoethoxy)ethoxy)ethyl)carbamate (213 mg, 0.858 mmol) in dichloromethane (DCM) (2 mL) was added HATU (391 mg, 1.029 mmol) and DIPEA (0.375 mL, 2.144 mmol). The mixture was stirred at rt for 4 h. The mixture was partitioned between dichloromethane (DCM) and saturated $NaHCO_3$d the aqueous phase was extracted with dichloromethane (DCM). The combined organic extracts were dried over $Na_2SO_4$, were filtered, and the filtrate was concentrated. Purification by ISCO Combi-Flash® chromatography (40 g RediSep Rf Gold® column, 40 mL/min) eluting with a gradient of 0 to 60% methanol in dichloromethane (DCM) provided the title compound as a light-brown oil (178 mg, 0.395 mmol, 46.1% yield). LC-MS m/z 451.2 $(M+H)^+$.

Step 2

(2S,3S)-N-(2-(2-(2-Aminoethoxy)ethoxy)ethyl)-1-methyl-5-oxo-2-(pyridin-3-yl) pyrrolidine-3-carboxamide, 2Trifluoroacetic acid salt

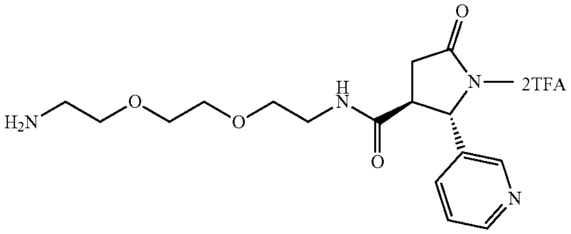 [SMILES: CN1C(=O)C[C@H](C(=O)NCCOCCOCCN)[C@H]1c1cccnc1]

TFA (0.48 mL, 6.23 mmol) was added to tert-butyl (2-(2-(2-((2S,3S)-1-methyl-5-oxo-2-(pyridin-3-yl)pyrrolidine-3-carboxamido)ethoxy)ethoxy)ethyl)carbamate (165 mg, 0.366 mmol) in dichloromethane (DCM) (0.2 mL). The mixture was stirred at rt for 2 h and was concentrated under reduced pressure. The residue was dried on high vacuum overnight to provide the tile compound as a light-yellow oil (225 mg, 0.389 mmol, 106% yield). LC-MS m/z 351.1 $(M+H)^+$.

Step 3

Oxacycloundecane-2,11-dione

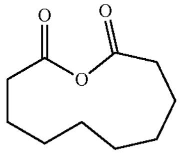 [SMILES: O=C1CCCCCCCCC(=O)O1]

Decanedioic acid (100 mg, 0.494 mmol) and acetic anhydride (0.233 mL, 2.469 mmol) were dissolved in N,N-dimethylformamide (DMF) (24.72 mL). The reaction was divided in two and was heated in the microwave reactor at 130° C. for 100 min. The mixtures were left at rt over the weekend, were combined and concentrated under reduced pressure. The residue was azeptroped with heptane (5×), and the remaining acetic anhydride was removed by distillation using a Dean-Stark apparatus and dichloromethane (DCM) as a solvent. The residue was concentrated under reduced pressure to provide the title compound (134.7 mg, 0.344 mmol, 69.5% yield). LC-MS m/z 256.1 $(M+H)^+$. (Pyrrolidine was used to determine the parent mass).

Step 4

10-(((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)amino)-10-oxodecanoic acid

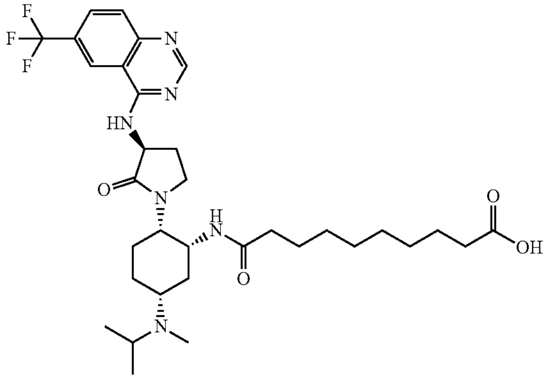 [SMILES: CC(C)N(C)[C@@H]1CC[C@H](N2CC[C@H](Nc3ncnc4ccc(C(F)(F)F)cc34)C2=O)[C@H](NC(=O)CCCCCCCCC(=O)O)C1]

To a solution of (S)-1-((1S,2R,4R)-2-amino-4-(isopropyl (methyl)amino)cyclohexyl)-3-((6-(trifluoromethyl)quinazolin-4-yl)amino)pyrrolidin-2-one, 2hydrochloric acid salt (39 mg, 0.084 mmol) in dichloromethane (DCM) (840 μL) was added triethylamine (58.5 μL, 0.420 mmol) Oxacycloundecane-2,11-dione (18.56 mg, 0.101 mmol) was added and the mixture was concentrated by reduced pressure. Purification by normal-phase chromatography (4 g silica column, 18 mL/min) eluting with 10% of methanol containing ammonium hydroxide (10%) in dichloromethane (DCM) provide the title compound as a pink oil (22.8 mg, 0.033 mmol, 39.3% yield). LC-MS m/z 649.2 $(M+H)^+$.

Step 5

N[1]-((1R,2S,5R)-5-(isopropyl(methyl)amino)-2-((S)-2-oxo-3-((6-(trifluoromethyl) quinazolin-4-yl) amino)pyrrolidin-1-yl)cyclohexyl)-N[10]-(2-(2-(2-((2S,3S)-1-methyl-5-oxo-2-(pyridin-3-yl) pyrrolidine-3-carboxamido)ethoxy)ethoxy)ethyl) decanediamide

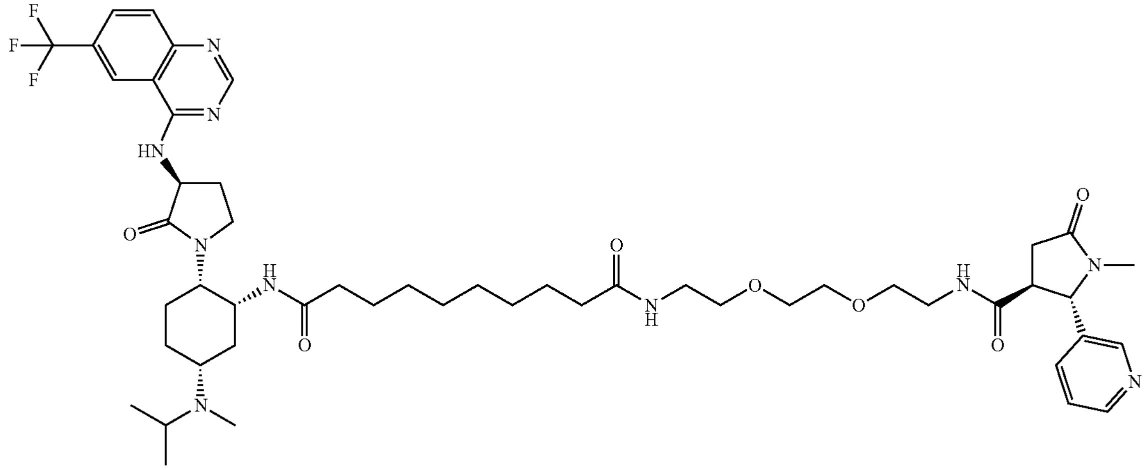 [SMILES: CC(C)N(C)[C@@H]1CC[C@H](N2CC[C@H](Nc3ncnc4ccc(C(F)(F)F)cc34)C2=O)[C@H](NC(=O)CCCCCCCCC(=O)NCCOCCOCCNC(=O)[C@H]2CC(=O)N(C)[C@@H]2c2cccnc2)C1]

To a mixture of 10-(((1R,2S,5R)-5-(isopropyl(methyl) amino)-2-((S)-2-oxo-3-((6-(trifluoromethyl)quinazolin-4-yl)amino)pyrrolidin-1-yl)cyclohexyl)amino)-10-oxodecanoic acid (22 mg, 0.034 mmol) and (2S,3S)-N-(2-(2-(2-aminoethoxy)ethoxy)ethyl)-1-methyl-5-oxo-2-(pyridin-3-yl)pyrrolidine-3-carboxamide, 2trifluoroacetic acid salt (19.2 mg, 0.032 mmol) in N,N-dimethylformamide (DMF) (0.3 mL) was added DIPEA (0.029 mL, 0.166 mmol), and HATU (15.15 mg, 0.040 mmol). The mixture was stirred at rt for 20 min. Purification by MDAP chromatography (XSelect™ CSH Prep C18 5 μm OBD column, 40 mL/min) eluting with a gradient of 50 to 99% acetonitrile in water containing ammonium bicarbonate (10 mM) and ammonium hydroxide (0.075%) provided the title compound as a solid (11.3 mg, 0.012 mmol, 34.0% yield). LC-MS m/z 981.6 $(M+H)^+$. $^1H$ NMR (400 MHz, METHANOL-$d_4$) δ ppm 0.99-1.10 (m, 3H) 1.10-1.19 (m, 4H) 1.19-1.35 (m, 8H) 1.47-1.60 (m, 2H) 1.60-1.79 (m, 5H) 1.92-2.02 (m, 1H) 2.06-2.35 (m, 11H) 2.50-2.59 (m, 1H) 2.65-2.76 (m, 5H) 2.81-2.88 (m, 1H) 3.06 (ddd, J=9.4, 8.1, 6.6 Hz, 1H) 3.39-3.68 (m, 13H) 4.05 (dt, J=12.2, 3.8 Hz, 1H) 4.66 (br d, J=3.3 Hz, 1H) 4.82-4.89 (m, 1H) 5.26 (t, J=7.9 Hz, 1H) 7.52-7.56 (m, 1H) 7.81 (dt, J=8.0, 1.8 Hz, 1H) 7.92 (d, J=8.9 Hz, 1H) 8.07 (dd, J=8.9, 1.8 Hz, 1H) 8.53 (d, J=2.3 Hz, 1H) 8.58 (dd, J=4.8, 1.5 Hz, 1H) 8.60 (s, 1H) 8.83-8.85 (m, 1H).

Example 160

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-2-(1-((2S,3S)-1-methyl-5-oxo-2-(pyridin-3-yl)pyrrolidin-3-yl)-1-oxo-5,8,11,14-tetraoxa-2-azaheptadecan-17-yl) isonicotinamide, 3Formic acid salt

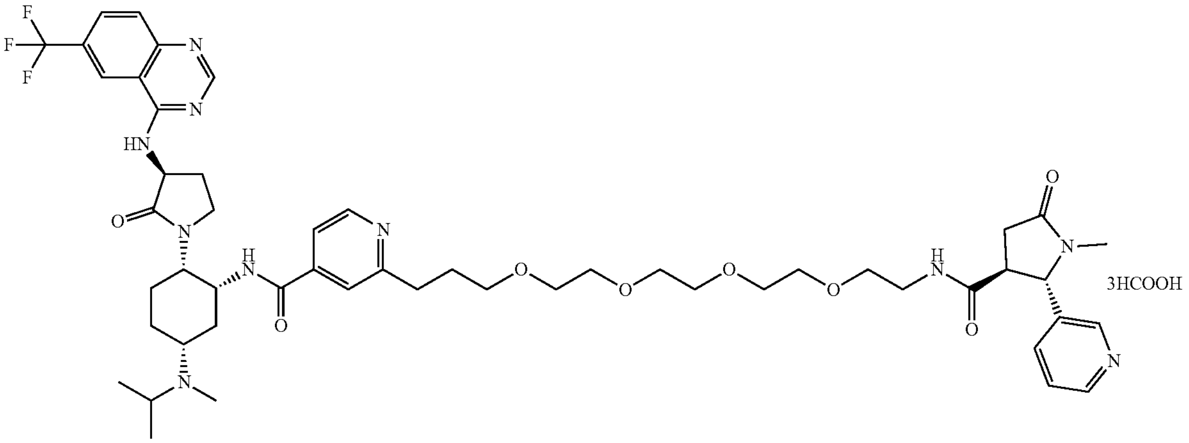 [SMILES: CC(C)N(C)[C@@H]1CC[C@H](N2CC[C@H](Nc3ncnc4ccc(C(F)(F)F)cc34)C2=O)[C@H](NC(=O)c2ccnc(CCCOCCOCCOCCOCCNC(=O)[C@H]3CC(=O)N(C)[C@@H]3c3cccnc3)c2)C1]

Step 1 tert-Butyl (2-(2-(2-(2-hydroxyethoxy)ethoxy) ethoxy)ethyl)carbamate

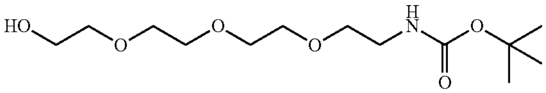 [SMILES: CC(C)(C)OC(=O)NCCOCCOCCOCCO]

To a stirred mixture of 2-(2-(2-(2-aminoethoxy)ethoxy) ethoxy)ethan-1-ol (2.35 g, 12.16 mmol) in 1,4-dioxane (15 mL) and 2 M $Na_2CO_3$ (15 mL) was added di-tert-butyl dicarbonate (3.25 mL, 13.98 mmol). The mixture was stirred at rt overnight. Brine was added and the mixture was extracted with dichloromethane (DCM) (3×60 mL). The combined organic extracts were washed with 0.5N HCl (50 mL), with saturated $NaHCO_3$, were dried over $MgSO_4$, and were concentrated under reduced pressure to provide the title compound as a colorless liquid (3.638 g, 11.16 mmol, 92% yield). LC-MS m/z 194.1 $(M+H)^+$.

Step 2 tert-Butyl (3,6,9,12-tetraoxapentadec-14-yn-1-yl)carbamate

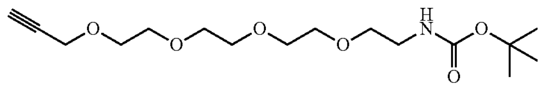 [SMILES: C#CCOCCOCCOCCOCCNC(=O)OC(C)(C)C]

To a stirred mixture of tert-butyl (2-(2-(2-(2-hydroxyethoxy)ethoxy)ethoxy)ethyl)carbamate (1.63 g, 5.56 mmol) in tetrahydrofuran (THF) (20 mL) was added slowly sodium tert-butoxide (0.587 g, 6.11 mmol). The mixture was stirred for 30 min. 80% 3-bromoprop-1-yne in toluene (0.599 mL, 5.56 mmol) was added and the mixture was stirred at rt overnight, Brine was added and the mixture was extracted with ethyl acetate (100 mL). The organic extract was washed with brine, was dried over $MgSO_4$, and was concentrated under reduced pressure. Purification by ISCO CombiFlash® chromatography (40 g RediSep Rf Gold® column, 40 mL/min) eluting with a stepwise gradient of 50 to 100% (10 column volumes), and 100% (5 column volumes) ethyl acetate in hexanes provided the title compound as a pale-yellow liquid (1.16 g, 3.33 mmol, 59.8% yield). LC-MS m/z 232.2 $(M+H)^+$.

Step 3

Methyl 2-(2,2-dimethyl-4-oxo-3,8,11,14,17-pentaoxa-5-azaicos-19-yn-20-yl) isonicotinate

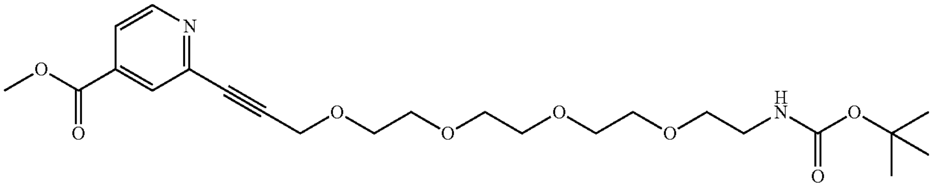 [SMILES: COC(=O)c1ccnc(C#CCOCCOCCOCCOCCNC(=O)OC(C)(C)C)c1]

To a mixture of methyl 2-bromoisonicotinate (0.477 g, 2.209 mmol) and tert-butyl (3,6,9,12-tetraoxapentadec-14-yn-1-yl)carbamate (0.61 g, 1.841 mmol) in tetrahydrofuran (THF) (0.5 mL) was added copper(I) iodide (0.035 g, 0.184 mmol) and triethylamine (1.5 mL, 10.76 mmol). The mixture was degassed by vacuuming and backfilling with nitrogen several times. Bis(triphenylphosphine)palladium(II) chloride (0.129 g, 0.184 mmol) was added. The mixture was heated at 75 to 77° C. for 2 h and was cooled. Purification by ISCO CombiFlash® chromatography (24 g RediSep Rf Gold® column, 35 mL/min) eluting with a stepwise gradient of 25 to 100% (15 column volumes), and 100% (5 column volumes) ethyl acetate in hexanes provided the title compound as a yellow, viscous liquid (0.5987 g, 1.258 mmol, 68.3% yield). LC-MS m/z 573.1 $(M+H)^+$.

Step 4 Methyl 2-(1-((2S,3S)-1-methyl-5-oxo-2-(pyridin-3-yl)pyrrolidin-3-yl)-1-oxo-5,8,11,14-tetraoxa-z-azaheptadecan-17-yl)isonicotinate

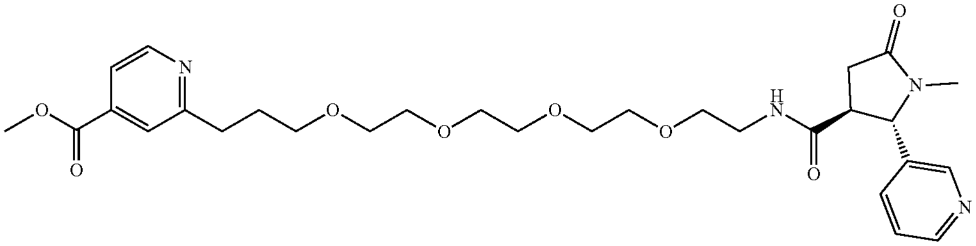 [SMILES: COC(=O)c1ccnc(CCCOCCOCCOCCOCCNC(=O)[C@H]2CC(=O)N(C)[C@@H]2c2cccnc2)c1]

4 M HCl in 1,4-dioxane (3 mL, 12.00 mmol) was added to a solution of methyl 2-(2,2-dimethyl-4-oxo-3,8,11,14,17-pentaoxa-5-azaicos-19-yn-20-yl)isonicotinate (590 mg, 1.265 mmol) in dichloromethane (DCM) (1.5 mL). The mixture was stirred at rt for 1 h was concentrated to dryness. The residue was dissolved in dichloromethane (DCM) (3 mL). Triethylamine (0.881 mL, 6.32 mmol) was added, followed by (2S,3S)-1-methyl-5-oxo-2-(pyridin-3-yl)pyrrolidine-3-carboxylic acid (306 mg, 1.391 mmol) and HATU (601 mg, 1.581 mmol). The mixture was stirred at rt overnight and was concentrated. The residue was purification by ISCO CombiFlash® chromatography (24 g RediSep Rf Gold® column, 35 mL/min) eluting with a stepwise gradient of 0 to 10% (15 column volumes), and 10% (10 column volumes) methanol in dichloromethane (DCM) to provide a yellow liquid that contained methyl 2-((Z)-16-chloro-1-((2S,3S)-1-methyl-5-oxo-2-(pyridin-3-yl)pyrrolidin-3-yl)-1-oxo-5,8,11,14-tetraoxa-2-azaheptadec-16-en-17-yl)isonicotinate (77%) [LC-MS m/z 605.1 $(M+H)^+$] and methyl 2-(1-((2S,3S)-1-methyl-5-oxo-2-(pyridin-3-yl)pyrrolidin-3-yl)-1-oxo-5,8,11,14-tetraoxa-2-azaheptadec-16-yn-17-yl)isonicotinate (15%) [LC-MS m/z 569.1 $(M+H)^+$]. 10% Pd/C (75 mg, 0.070 mmol) was added to a solution of the liquid in methanol (10 mL). The mixture was vacuumed and was backfilled with hydrogen and was stirred under a balloon atmosphere of hydrogen at rt for 2 h. The mixture was filtered and the filtrate was concentrated. Purification by ISCO CombiFlash® chromatography (24 g RediSep Rf Gold® column, 35 mL/min) eluting with a stepwise gradient of 0 to 10% (15 column volumes), and 10% (10 column volumes) methanol in dichloromethane (DCM) provided the title compound as a light-yellow, viscous liquid (0.6338 g, 1.018 mmol, 81% yield). LC-MS m/z 573.1 $(M+H)^+$.

Step 5

2-(1-((2S,3S)-1-Methyl-5-oxo-2-(pyridin-3-yl)pyrrolidin-3-yl)-1-oxo-5,8,11,14-tetraoxa-2-azaheptadecan-17-yl)isonicotinic acid

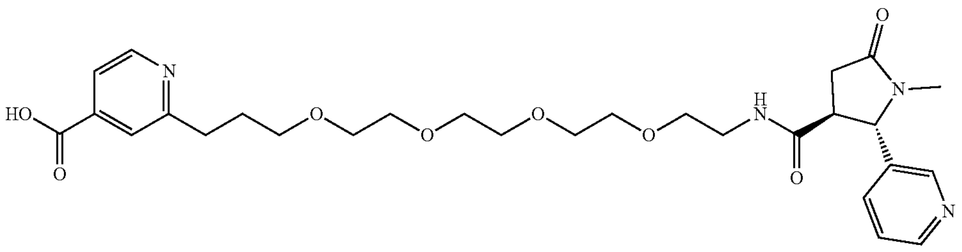 [SMILES: CN1C(=O)C[C@H](C(=O)NCCOCCOCCOCCOCCCc2cc(C(=O)O)ccn2)[C@H]1c1cccnc1]

To a solution of methyl 2-(1-((2S,3S)-1-methyl-5-oxo-2-(pyridin-3-yl)pyrrolidin-3-yl)-1-oxo-5,8,11,14-tetraoxa-2-azaheptadecan-17-yl)isonicotinate (0.63 g, 1.100 mmol) in tetrahydrofuran (THF) (1.500 mL) and ethanol (1.5 mL) was added 2 N sodium hydroxide (1.5 mL, 3.00 mmol). The mixture was stirred at rt for 2 h and was concentrated to remove the organic solvents. The residue was cooled and the pH was adjusted to 4 to 5 with 2 N HCl. The mixture was concentrated under reduced pressure. The residue was suspended in methanol/dichloromethane (DCM) (2%) (30 mL), was stirred and sonicated, and was filtered. The filtrate was concentrated under reduced pressure to provide the title compound as a pale-yellow foam (0.536 g, 0.812 mmol, 74% yield). LC-MS m/z 559.1 $(M+H)^+$.

Step 6

N-((1R,2S,5R)-5-(Isopropyl(methyl)amino)-2-((S)-2-oxo-3-((6-(trifluoromethyl)quinazolin-4-yl)amino) pyrrolidin-1-yl)cyclohexyl)-2-(1-((2S,3S)-1-methyl-5-oxo-2-(pyridin-3-yl)pyrrolidin-3-yl)-1-oxo-5,8,11,14-tetraoxa-2-azaheptadecan-17-yl)isonicotinamide, 3Formic acid salt

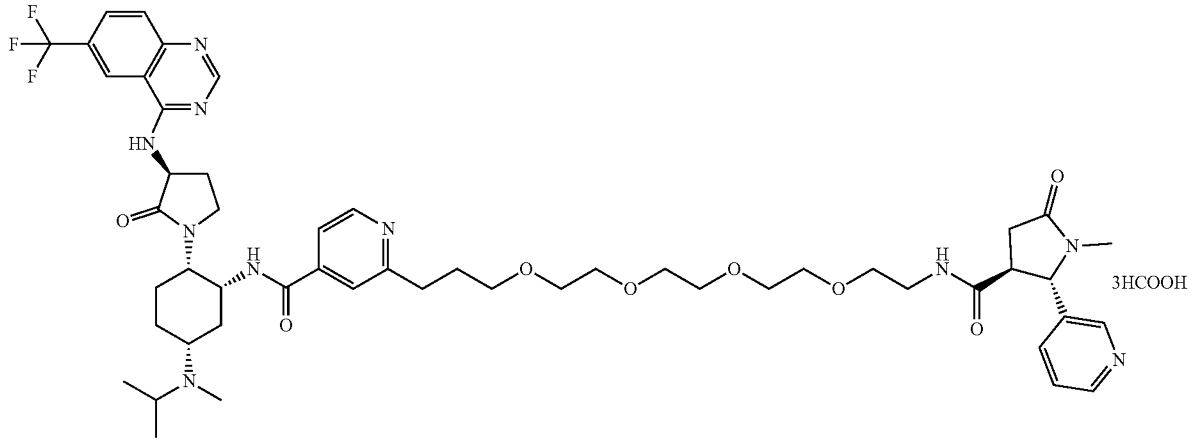 [SMILES: CC(C)N(C)[C@@H]1CC[C@H](N2CC[C@H](Nc3ncnc4ccc(C(F)(F)F)cc34)C2=O)[C@H](NC(=O)c2ccnc(CCCOCCOCCOCCOCCNC(=O)[C@H]3CC(=O)N(C)[C@@H]3c3cccnc3)c2)C1]

4 M HCl in 1,4-dioxane (1 mL, 4.00 mmol) was added to a solution of tert-butyl ((1R,2S,5R)-5-(isopropyl(methyl) amino)-2-((S)-2-oxo-3-((6-(trifluoromethyl)quinazolin-4-yl)amino) pyrrolidin-1-yl)cyclohexyl)carbamate (80 mg, 0.142 mmol) in dichloromethane (DCM) (1 mL). The mixture was stirred at rt for 1 h and was concentrated under reduced. The residue was suspended in dichloromethane (DCM) (5 mL) and triethylamine (0.069 mL, 0.496 mmol), 2-(1-((2S,3S)-1-methyl-5-oxo-2-(pyridin-3-yl)pyrrolidin-3-yl)-1-oxo-5,8,11,14-tetraoxa-2-azaheptadecan-17-yl)isonicotinic acid (130 mg, 0.197 mmol), and HATU (81 mg, 0.213 mmol) were added. The mixture was stirred at rt and was concentrated under reduced pressure. Purification by MDAP chromatography (XSelect™ CSH Prep C18 150 mm×30 mm 5 μm OBD column, 40 mL/min) eluting with a gradient of 0 to 25% acetonitrile in water both containing formic acid (0.1%) provided the title compound as a white, amorphous solid (105.7 mg, 0.104 mmol, 73.5% yield). LC-MS m/z 1005.2 $(M+H)^+$. $^1H$ NMR (400 MHz, METHANOL-$d_4$) δ ppm 1.44 (br t, J=6.5 Hz, 6H) 1.59-1.72 (m, 2H) 2.01-2.25 (m, 3H) 2.25-2.52 (m, 4H) 2.52-2.64 (m, 3H) 2.65-2.68 (m, 3H) 2.68-2.76 (m, 1H) 2.79-2.93 (m, 4H) 2.97-3.23 (m, 1H) 3.23-3.44 (m, 5H) 3.46-3.51 (m, 4H)

3.52-3.64 (m, 10H) 3.72 (br s, 1H) 3.80-3.92 (m, 1H) 3.92-4.04 (m, 1H) 4.12 (br s, 1H) 4.37 (br d, J=11.9 Hz, 1H) 4.58 (br s, 1H) 4.73-4.89 (m, 2H) 7.36 (s, 1H) 7.42 (dd, J=5.2, 1.1 Hz, 1H) 7.53 (dd, J=7.9, 4.8 Hz, 1H) 7.77-7.84 (m, 2H) 8.02-8.13 (m, 1H) 8.15 (s, 1H) 8.26 (br d, J=4.6 Hz, 3H) 8.53 (s, 1H) 8.58 (br d, J=4.1 Hz, 1H) 8.69 (s, 1H).

Example 161

(2S,3S)-N-(4-((8-((5-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-5-oxopentyl)oxy)octyl)oxy)butyl)-1-methyl-5-oxo-2-(pyridin-3-yl)pyrrolidine-3-carboxamide

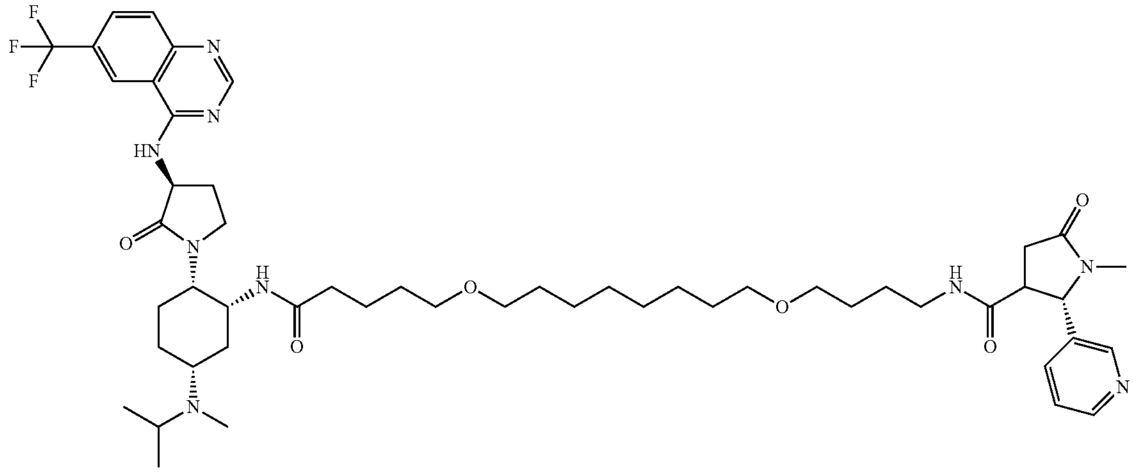 [SMILES: CC(C)N(C)[C@@H]1CC[C@H](N2CC[C@H](Nc3ncnc4ccc(C(F)(F)F)cc34)C2=O)[C@H](NC(=O)CCCCOCCCCCCCCOCCCCNC(=O)C2CC(=O)N(C)[C@@H]2c2cccnc2)C1]

Step 1

1,8-Bis(4-chlorobutoxy)octane

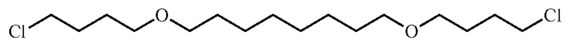 [SMILES: ClCCCCOCCCCCCCCOCCCCCl]

Sodium hydride (8.20 g, 205.14 mmol) was added at 0° C. under an atmosphere of nitrogen to a mixture of octane-1,8-diol (10.0 g, 68.38 mmol) in N,N-dimethylformamide (DMF) and the mixture was stirred for 30 min. 1-Bromo-4-chlorobutane (29.31 g, 10.96 mmol) was added dropwise over 10 min and the mixture was stirred at rt for 16 h. Ice (200 g) was added and the mixture was extracted with ethyl acetate (3×200 mL). The combined organic extracts were washed with ice-cold water (2×300 mL), were dried over $Na_2SO_4$, were filtered, and the filtrate was concentrated under reduced pressure. Purification by Biotage® Isolera™ column chromatography eluting with a gradient of 0 to 20% ethyl acetate in petroleum ether provided the title compound as a pale-yellow oil (3.8 g, 11.6 mmol, 17% yield). LC-MS m/z 328 $(M+H)^+$. 1-(4-bromobutoxy)-8-(4-chlorobutoxy) octane (7.9%) was observed.

Step 2

5-((8-(4-Chlorobutoxy)octyl)oxy)pentanenitrile

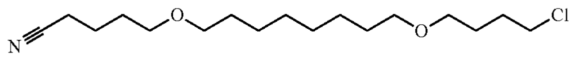 [SMILES: N#CCCCCOCCCCCCCCOCCCCCl]

Sodium cyanide (0.56 g, 11.60 mmol) was added to a mixture of 1,8-bis(4-chlorobutoxy)octane (3.8 g, 11.60 mmol) and the mixture was stirred at rt for 16 h. Ice-cold water (100 mL) was added and the mixture was extracted with ethyl acetate (3×100 mL). The combined organic extracts were dried over $Na_2SO_4$, were filtered, and the filtrate was concentrated under reduced pressure. Purification by Biotage® Isolera™ column chromatography eluting with a gradient of 0 to 15% ethyl acetate in petroleum ether provided the title compound as a colorless oil (1.3 g, 4.08 mmol, 35% yield). LC-MS m/z 318 $(M+H)^+$.

Step 3

5-((8-(4-(1,3-Dioxoisoindolin-2-yl)butoxy)octyl)oxy)pentanenitrile

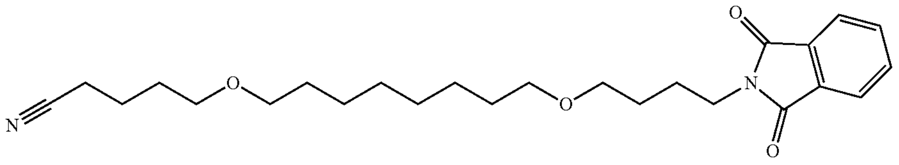 [SMILES: N#CCCCCOCCCCCCCCOCCCCN1C(=O)c2ccccc2C1=O]

To a mixture of 5-((8-(4-chlorobutoxy)octyl)oxy)pentanenitrile (1.3 g, 4.08 mmol) in N,N-dimethylformamide (DMF) (13 mL) was added potassium phthalimide (1.13 g, 6.13 mmol) and the mixture was stirred at 80° C. for 16 h. Ethyl acetate was added (100 mL) and the mixture was washed with ice-cold water (2×50 mL). The organic phase was dried over $Na_2SO_4$, was filtered, and the filtrate was concentrated under reduced pressure. Purification by Biotage® Isolera™ column chromatography eluting with a gradient of 0 to 20% ethyl acetate in petroleum ether provided the title compound as a pale-yellow oil (1.7 g, 2.83 mmol, 3.97 mmol, 97% yield). LC-MS m/z 429 $(M+H)^+$.

Step 4

5-((8-(4-Aminobutoxy)octyl)oxy)pentanenitrile

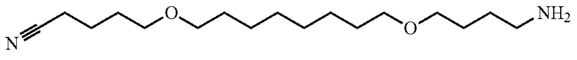 [SMILES: N#CCCCCOCCCCCCCCOCCCCN]

Hydrazine monohydrate (297 mg, 5.95 mmol) was added to a mixture of 5-((8-(4-(1,3-dioxoisoindolin-2-yl)butoxy)octyl)oxy)pentanenitrile (1.7 g, 3.96 mmol) in ethanol (20 mL) and the mixture was stirred at 90° C. for 16 h and was concentrated under reduced pressure. Dichloromethane (DCM) (100 mL) was added, the mixture was filtered, and the solid was washed with Dichloromethane (DCM) (50 mL). The combined filtrates were concentrated under reduced pressure to provide the title compound as a colorless oil (0.9 g, 3.02 mmol, 75.9% yield). LC-MS m/z 299 $(M+H)^+$.

Step 5 tert-Butyl (4-((8-(4-cyanobutoxy)octyl)oxy)butyl)carbamate

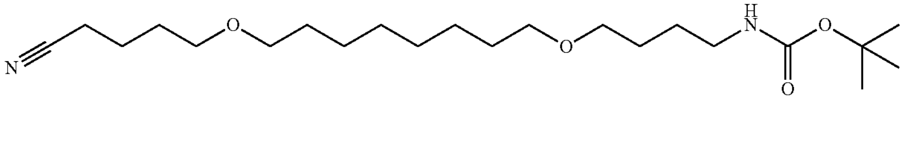 [SMILES: CC(C)(C)OC(=O)NCCCCOCCCCCCCCOCCCCC#N]

To a mixture 5-((8-(4-aminobutoxy)octyl)oxy)pentanenitrile (0.9 g, 3.01 mmol) in tetrahydrofuran (THF) (20 mL) was added triethylamine (0.6 g, 6.02 mmol) followed by di-t-butyl decarbonate (0.72 g, 3.31 mmol) and the mixture was stirred at rt for 4 h. Ice-cold water (20 mL) was added and the mixture was extracted with ethyl acetate (3×75 mL). The combined organic extracts were dried over $Na_2SO_4$ were filtered, and the filtrate was concentrated under reduced pressure. Purification by Biotage® Isolera™ column chromatography eluting with a gradient of 0 to 30% ethyl acetate in petroleum ether provided the title compound as a pale-yellow gum (1.13 g, 2.83 mmol, 94% yield). LC-MS m/z 399 $(M+H)^+$.

Step 6

2,2-Dimethyl-4-oxo-3,10,19-trioxa-5-azatetracosan-24-oic acid

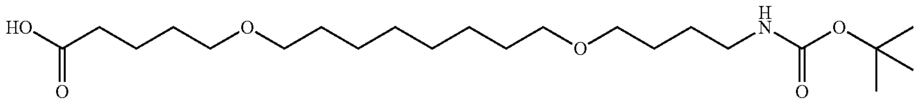 [SMILES: CC(C)(C)OC(=O)NCCCCOCCCCCCCCOCCCCC(=O)O]

Potassium hydroxide (0.635 g, 11.32 mmol) was added to a mixture of tert-butyl (4-((8-(4-cyanobutoxy)octyl)oxy)butyl)carbamate (1.13 g, 2.83 mmol) in ethanol (10 mL) and water (10 mL). The mixture was stirred at 100° C. for 16 h and was concentrated under reduced pressure. The residue was cooled to 10° C. and the pH was adjusted to 4 with 1.5 N HCl. The precipitate was collected by filtration to provide the title compound as a white solid (1.1 g, 2.63 mmol, 94.9% yield). LC-MS m/z 508 $(M+H)^+$.

Step 7

Benzyl 2,2-dimethyl-4-oxo-3,10,19-trioxa-5-azatetracosan-24-oate

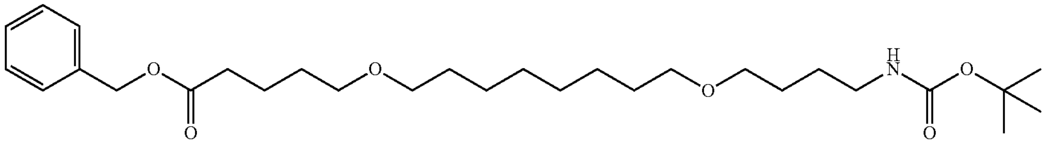 [SMILES: CC(C)(C)OC(=O)NCCCCOCCCCCCCCOCCCCC(=O)OCc1ccccc1]

To a mixture of 2,2-dimethyl-4-oxo-3,10,19-trioxa-5-azatetracosan-24-oic acid (1.1 g, 2.63 mmol) in dichloromethane (DCM) (20 mL) was added phenylmethanol (569 mg, 5.26 mmol), EDC·HCl (1.0 g, 5.26 mmol), 4-dimethylaminopyridine (DMAP), and triethylamine (531 mg, 5.26 mmol), and the mixture was stirred at rt for 18 h. Ice-cold water (50 mL) was added and the mixture was extracted with dichloromethane (DCM) (2×70 mL). The combined organic extracts were dried over $Na_2SO_4$ and were concentrated under reduced pressure. Purification by Biotage® Isolera™ column chromatography eluting with a gradient of 0 to 10% ethyl acetate in petroleum ether provided the title compound as a pale-yellow oil (1.3 g, 2.56 mmol, 97% yield). LC-MS m/z 418 $(M+H)^+$.

Step 8

Benzyl 5-((8-(4-aminobutoxy)octyl)oxy)pentanoate, Hydrochloric acid salt

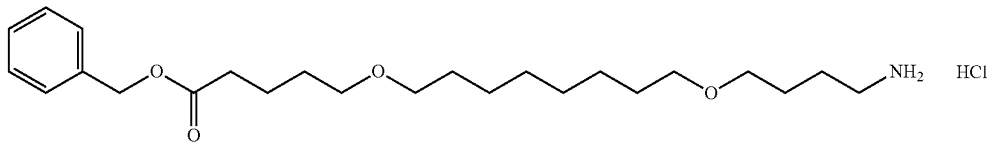 [SMILES: NCCCCOCCCCCCCCOCCCCC(=O)OCc1ccccc1 ; Cl]

4 M HCl in 1,4-dioxane (15 mL, 60 mmol) was added at 0° C. to a mixture of benzyl 2,2-dimethyl-4-oxo-3,10,19-trioxa-5-azatetracosan-24-oate (1.3 g, 2.56 mmol) in 1,4-dioxane (5 mL). The mixture was stirred at rt for 18 h and was concentrated under reduced pressure to provide the title compound as a pale-yellow oil (0.9 g, 2.03 mmol, 79% yield). LC-MS m/z 408 $(M+H)^+$.

Step 9

Benzyl 5-((8-(4-((2S,3S)-1-methyl-5-oxo-2-(pyridin-3-yl)pyrrolidine-3-carboxamido)butoxy)octyl)oxy)pentanoate

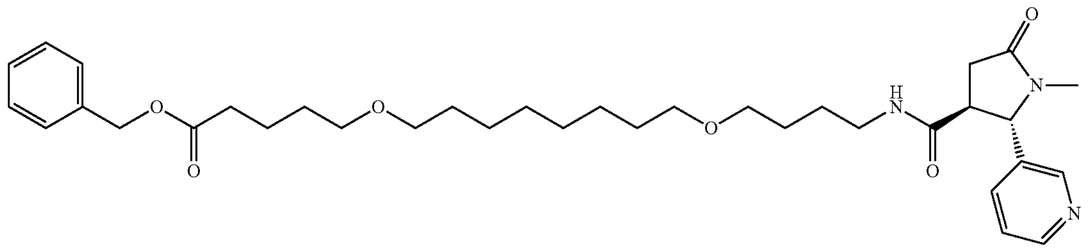 [SMILES: CN1C(=O)C[C@H](C(=O)NCCCCOCCCCCCCCOCCCCC(=O)OCc2ccccc2)[C@H]1c1cccnc1]

To a mixture of (2S,3S)-1-methyl-5-oxo-2-(pyridin-3-yl)pyrrolidine-3-carboxylic acid (350 mg, 1.58 mmol) and HATU (1.20 g, 3.16 mmol) in N,N-dimethylformamide (DMF) (8 mL) and DIPEA (611 mg, 4.74 mmol) was added a solution benzyl 5-((8-(4-aminobutoxy)octyl)oxy)pentanoate, hydrochloric acid salt. (701 mg, 1.58 mmol) in N,N-dimethylformamide (DMF) (2 mL). The mixture was stirred at rt for 16 h. Ethyl acetate (100 mL) was added and the mixture was washed with cold water (2×50 mL). The organic phase was dried over $Na_2SO_4$, was filtered, and the filtrate was concentrated under reduced pressure. The residue was purified by Biotage® Isolera™ column chromatography eluting with a gradient of 0 to 10% methanol in dichloromethane (DCM). A second purification by preparative reverse-phase HPLC (Sunfire™ C18 19 mm×150 mm 5 μm column) eluting with acetonitrile in water provided the title compound as a brown oil (245 mg, 0.402 mmol, 25% yield) LC-MS m/z 610 $(M+H)^+$.

Step 10

5-((8-(4-((2S,3S)-1-Methyl-5-oxo-2-(pyridin-3-yl) pyrrolidine-3-carboxamido)butoxy)octyl)oxy)pentanoic acid

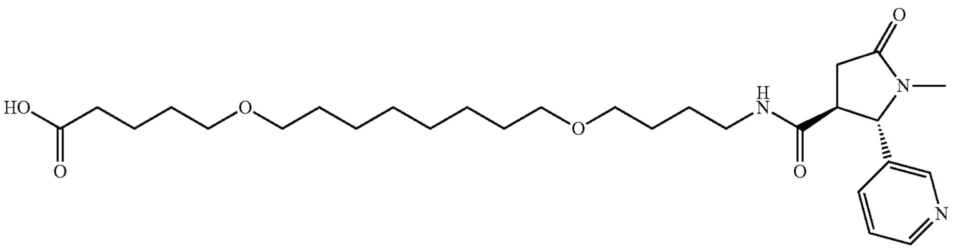 [SMILES: CN1C(=O)C[C@H](C(=O)NCCCCOCCCCCCCCOCCCCC(=O)O)[C@H]1c1cccnc1]

To a mixture of benzyl 5-((8-(4-((2S,3S)-1-methyl-5-oxo-2-(pyridin-3-yl) pyrrolidine-3-carboxamido)butoxy)octyl) oxy)pentanoate (245 mg, 0.402 mmol) in methanol (5 mL) was added Pd—C(42.8 mg, 0.040 mmol). The mixture was stirred at rt under a balloon atmosphere of hydrogen for 40 min. The mixture was filtered, the catalyst washed with methanol, and the combined filtrates were concentrated to dryness to provide the title compound as a solid (177 mg, 0.341 mmol, 85% yield). LC-MS m/z 520.3 $(M+H)^+$.

Step 11

(2S,3S)-N-(4-((8-((5-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-5-oxopentyl)oxy)octyl)oxy)butyl)-1-methyl-5-oxo-2-(pyridin-3-yl)pyrrolidine-3-carboxamide

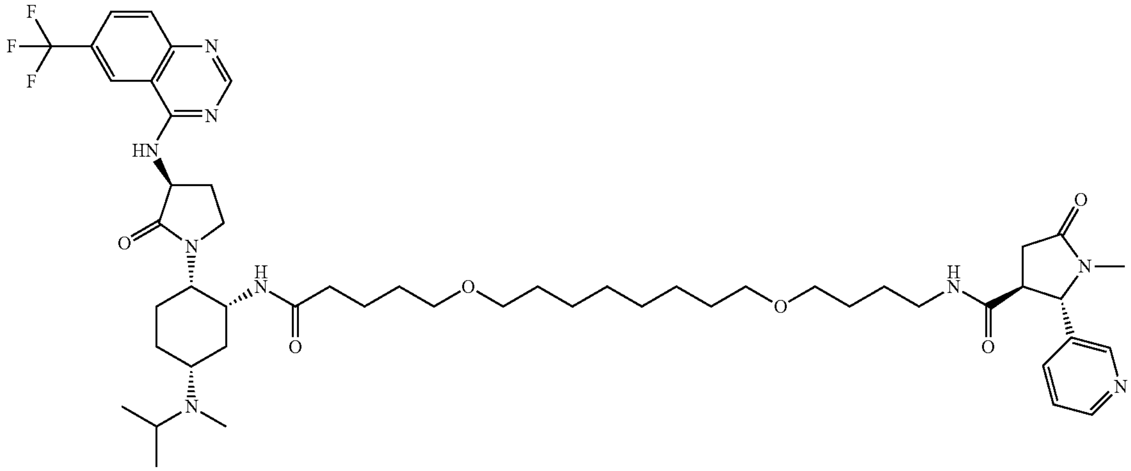 [SMILES: CC(C)N(C)[C@@H]1CC[C@H](N2CC[C@H](Nc3ncnc4ccc(C(F)(F)F)cc34)C2=O)[C@H](NC(=O)CCCCOCCCCCCCCOCCCCNC(=O)[C@H]2CC(=O)N(C)[C@@H]2c2cccnc2)C1]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2Hydrochloride (35 mg, 0.065 mmol) and 5-((8-(4-((2S,3S)-1-methyl-5-oxo-2-(pyridin-3-yl) pyrrolidine-3-carboxamido)butoxy)octyl)oxy)pentanoic acid (33.8 mg, 0.065 mmol) in dichloromethane (DCM) (0.5 mL) was added triethylamine (0.054 mL, 0.391 mmol), followed by HATU (29.7 mg, 0.078 mmol). The mixture was stirred at rt for 1.5 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (51.1 mg, 0.053 mmol, 81% yield). LC-MS m/z 967.7 $(M+H)^+$. $^1H$ NMR (400 MHz, METHANOL-$d_4$) δ ppm 1.04 (br d, J=5.8 Hz, 3H) 1.15 (br d, J=6.0 Hz, 3H) 1.24-1.38 (m, 9H) 1.46-1.62 (m, 10H) 1.67-1.82 (m, 5H) 1.94-2.05 (m, 1H) 2.11-2.36 (m, 8H) 2.51-2.60 (m, 1H) 2.66 (s, 3H) 2.69-2.77 (m, 2H) 2.79-2.88 (m, 1H) 2.97-3.06 (m, 1H) 3.14-3.26 (m, 2H) 3.35-3.48 (m, 8H) 3.54-3.69 (m, 2H) 4.05 (dt, J=12.2, 3.5 Hz, 1H) 4.65 (br s, 1H) 4.82 (d, J=6.5 Hz, 1H) 5.28 (br t, J=7.8 Hz, 1H) 7.51-7.56 (m, 1H) 7.80 (dt, J=8.0, 1.9 Hz, 1H) 7.91 (d, J=8.8 Hz, 1H) 8.06 (dd, J=8.9, 1.6 Hz, 1H) 8.51 (d, J=1.8 Hz, 1H) 8.56-8.61 (m, 2H) 8.82 (s, 1H).

Example 162

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1-(5-((2-(2-(2-((2S,3S)-1-methyl-5-oxo-2-(pyridin-3-yl) pyrrolidine-3-carboxamido)ethoxy)ethoxy)ethyl) amino)pyrazin-2-yl)piperidine-4-carboxamide Step 1 tert-Butyl (2-(2-(2-((5-chloropyrazine-2-yl)amino) ethoxy)ethoxy)ethyl)carbamate

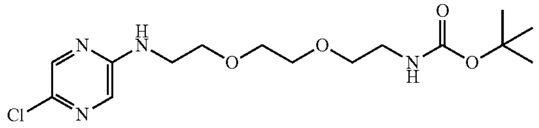

To a stirred solution of tert-butyl (2-(2-(2-aminoethoxy) ethoxy)ethyl)carbamate (5.5 g, 22.11 mmol) in N-methyl-2-pyrrolidinone (NMP) (5.5 mL) was added 2,5-dichloropyrazine (3.6 g, 24.36 mmol) and DIPEA (4.3 g, 33.2 mmol) and the mixture was stirred at 120° C. overnight. Ethyl acetate (250 mL) was added and the organic phase was washed with water (2×50 mL), was dried over $Na_2SO_4$, and was concentrated. Purification by normal-phase chromatography eluting with 40% ethyl acetate in hexanes provided the title compound as a pale-yellow liquid (3.2 g, 8.88 mmol, 40% yield). LC-MS m/z 361 $(M+H)^+$.

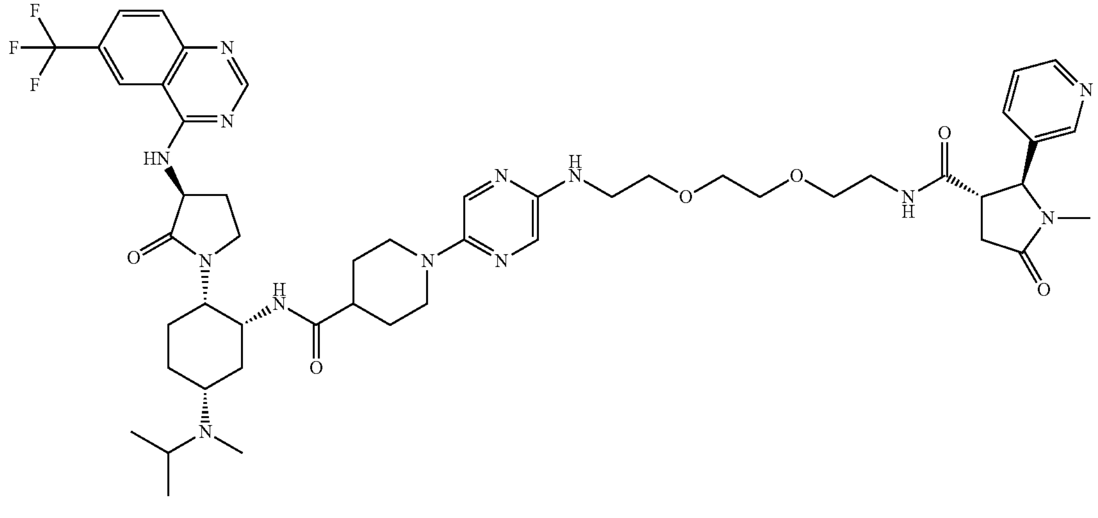 [SMILES: CC(C)N(C)[C@@H]1CC[C@H](N2CC[C@H](Nc3ncnc4ccc(C(F)(F)F)cc34)C2=O)[C@H](NC(=O)C2CCN(c3cnc(NCCOCCOCCNC(=O)[C@H]4CC(=O)N(C)[C@@H]4c4cccnc4)cn3)CC2)C1]

Step 2 tert-Butyl (tert-butoxycarbonyl)(5-(5-chloropyrazin-2-yl)-2,2-dimethyl-4-oxo-3,8,11-trioxa-5-azatridecan-13-yl)carbamate

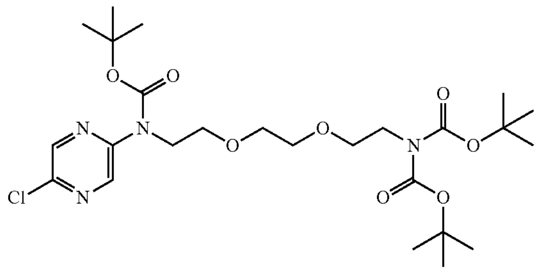 [SMILES: CC(C)(C)OC(=O)N(CCOCCOCCN(C(=O)OC(C)(C)C)c1cnc(Cl)cn1)C(=O)OC(C)(C)C]

To a stirred solution of tert-butyl (2-(2-(2-((5-chloropyrazin-2-yl)amino)ethoxy)ethoxy)ethyl)carbamate (1 g, 2.7716 mmol) in tetrahydrofuran (THF) (50 mL) was added 4-dimethylaminopyridine (DMAP) (67.6 mg, 0.5543 mmol) and di-tert-butyl dicarbonate (1.8 g, 8.3148 mmol) and the mixture was stirred overnight. Ethyl acetate (100 mL) was added. The organic phase was washed with water (20 mL) and was dried over $Na_2SO_4$. Purification by normal-phase chromatography eluting with a stepwise gradient of 12% and 25% ethyl acetate in petroleum ether provided the title compound as a brown liquid (370 mg, 0.659 mmol, 23/8% yield). LC-MS m/z 561 $(M+H)^+$.

Step 3

Methyl 1-(5-((tert-butoxycarbonyl)(5-(tert-butoxycarbonyl)-2,2-dimethyl-4-oxo-3,8,11-trioxa-5-azatridecan-13-yl)amino)pyrazin-2-yl)piperidine-4-carboxylate

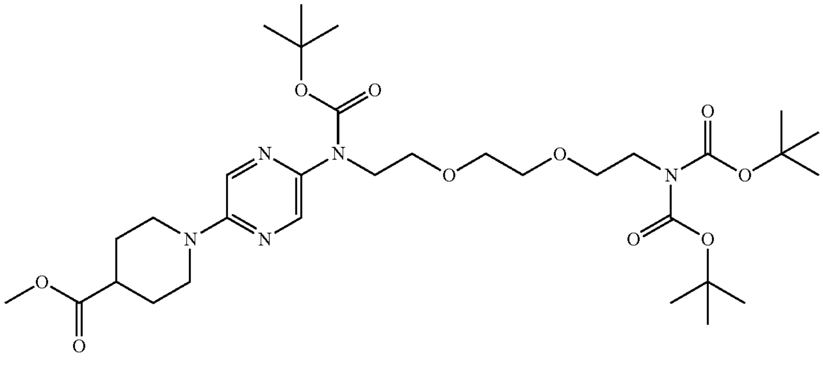 [SMILES: COC(=O)C1CCN(c2cnc(N(CCOCCOCCN(C(=O)OC(C)(C)C)C(=O)OC(C)(C)C)C(=O)OC(C)(C)C)cn2)CC1]

Methyl piperidine-4-carboxylate (573 mg, 4.0 mmol) was added to a stirred solution of tert-butyl (tert-butoxycarbonyl)(5-(5-chloropyrazin-2-yl)-2,2-dimethyl-4-oxo-3,8,11-trioxa-5-azatridecan-13-yl)carbamate (750 mg, 1.336 mmol) in N-methyl-2-pyrrolidone (NMP) (1.5 mL) and the mixture was stirred at 100° C.; for 1.5 days. Ethyl acetate (75 mL) was added and the organic phase was washed with water (25 mL), was dried over $Na_2SO_4$, and was concentrated. Purification by normal-phase chromatography eluting with 35% ethyl acetate in petroleum ether provided the title compound (440 mg, 0.659 mmol, 49.3% yield). LC-MS m/z 668 $(M+H)^+$.

Step 4 Methyl 1-(5-((2-(2-(2-aminoethoxy)ethoxy)ethyl)amino)pyrazin-2-yl)piperidine-4-carboxylate, Hydrochloric acid salt

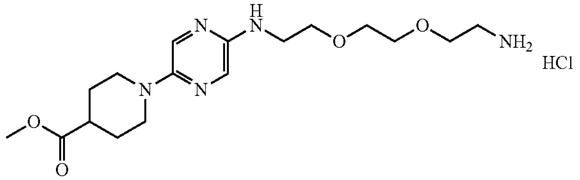 [SMILES: COC(=O)C1CCN(c2cnc(NCCOCCOCCN)cn2)CC1 ; Cl]

4 M HCl in 1,4-dioxane (4 mL, 16 mmol) was added to a stirred solution of methyl 1-(5-((tert-butoxycarbonyl)(5-(tert-butoxycarbonyl)-2,2-dimethyl-4-oxo-3,8,11-trioxa-5-azatridecan-13-yl)amino)pyrazin-2-yl)piperidine-4-carboxylate) (430 mg, 0.6439 mmol) in 1,4-dioxane (4 mL). The mixture was stirred at rt for 15 h and was concentrated under reduced pressure to provide the tittle compound as a yellow solid (336 mg, 0.832 mmol, 129% yield). LC-MS m/z 368 $(M+H)^+$.

Step 5

Methyl 1-(5-((2-(2-(2-((2S,3S)-1-methyl-5-oxo-2-(pyridin-3-yl)pyrrolidine-3-carboxamido) ethoxy)ethoxy)ethyl)amino)pyrazin-2-yl)piperidine-4-carboxylate

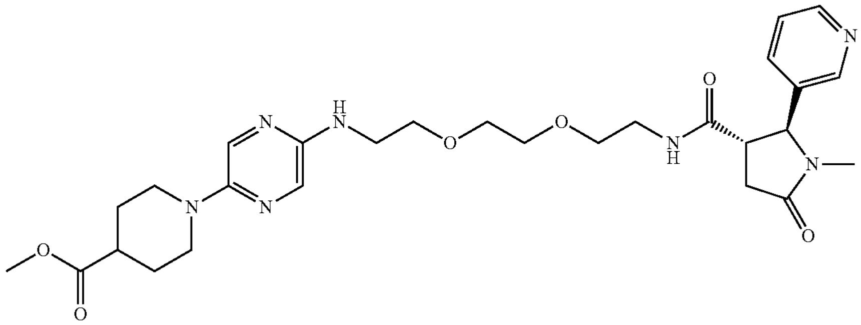

To a stirred solution of methyl 1-(5-((2-(2-(2-aminoethoxy)ethoxy)ethyl)amino)pyrazin-2-yl)piperidine-4-carboxylate (140 mg, 0.6356 mmol) in dichloromethane (DCM) (7 mL) was added triethylamine (192 mg, 1.902 mmol), EDC·HCL (183 mg, 0.9535 mmol), and HOBt (129 mg, 0.9535 mmol) and the mixture was stirred at rt for 15 min. (2S,3S)-1-methyl-5-oxo-2-(pyridin-3-yl)pyrrolidine-3-carboxylic acid (233 mg, 0.6356 mmol) was added and the mixture was stirred at rt for 16 h. Dichloromethane (DCM) (20 mL) was added and the organic phase was washed with water (4 mL), was dried over $Na_2SO_4$, and was concentrated under reduced pressure. Purification by normal-phase chromatography eluting with 50% ethyl acetate in petroleum ether provided the title compound as a brown, gummy solid (150 mg, 0.263 mmol, 41.4% yield). LC-MS m/z 570 $(M+H)^+$.

Step 6

1-(5-((2-(2-(2-((2S,3S)-1-Methyl-5-oxo-2-(pyridin-3-yl)pyrrolidine-3-carboxamido) ethoxy)ethoxy) ethyl)amino)pyrazin-2-yl)piperidine-4-carboxylic acid

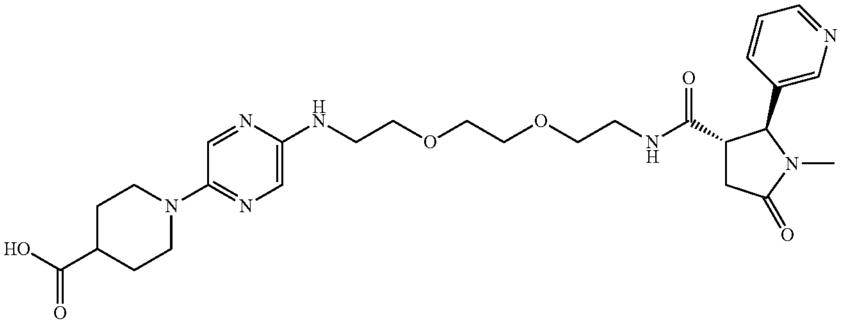 [SMILES: CN1C(=O)C[C@H](C(=O)NCCOCCOCCNc2cnc(N3CCC(C(=O)O)CC3)cn2)[C@H]1c1cccnc1]

To a mixture of methyl 1-(5-((2-(2-(2-((2S,3S)-1-methyl-5-oxo-2-(pyridin-3-yl)pyrrolidine-3-carboxamido)ethoxy) ethoxy)ethyl)amino) pyrazin-2-yl) piperidine-4-carboxylate (146 mg, 0.256 mmol) in tetrahydrofuran (THF) (0.5 mL) and methanol (0.500 mL) was added sodium hydroxide (1.281 mL, 1.281 mmol). The mixture was stirred at rt for 1 h. Purification by ISCO CombiFlash® EZ Prep chromatography (C18 Aq Gold column, 40 mL/min) eluting with a gradient of 0 to 25% acetonitrile in water containing ammonium bicarbonate (10 mM) and ammonium hydroxide (0.075%) provided the title compound (75 mg, 0.135 mmol, 52.7% yield). LC-MS m/z 556.4 $(M+H)^+$.

Step 7

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1-(5-((2-(2-(2-((2S,3S)-1-methyl-5-oxo-2-(pyridin-3-yl) pyrrolidine-3-carboxamido)ethoxy)ethoxy)ethyl) amino)pyrazin-2-yl)piperidine-4-carboxamide

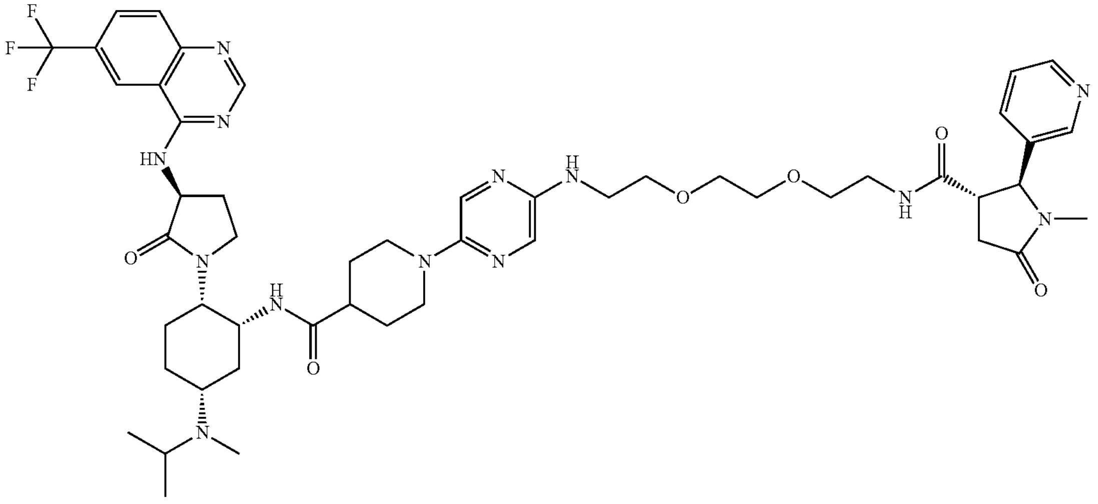 [SMILES: CC(C)N(C)[C@@H]1CC[C@H](N2CC[C@H](Nc3ncnc4ccc(C(F)(F)F)cc34)C2=O)[C@H](NC(=O)C2CCN(c3cnc(NCCOCCOCCNC(=O)[C@H]4CC(=O)N(C)[C@@H]4c4cccnc4)cn3)CC2)C1]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2Hydrochloride (38.7 mg, 0.072 mmol) and 1-(5-((2-(2-(2-((2S,3S)-1-methyl-5-oxo-2-(pyridin-3-yl) pyrrolidine-3-carboxamido)ethoxy)ethoxy)ethyl)amino) pyrazin-2-yl) piperidine-4-carboxylic acid (40 mg, 0.072 mmol) in dichloromethane (DCM) (0.5 mL) was added triethylamine(0.060 mL, 0.432 mmol) and the mixture was stirred at rt for 5 min. HATU (32.8 mg, 0.086 mmol) was added and the mixture was stirred at rt for 2 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound as a light-yellow solid (40 mg, 0.040 mmol, 55.4% yield). LC-MS m/z 1002.7 $(M+H)^+$. $^1H$ NMR (400 MHz, METHANOL-$d_4$) δ ppm 1.02 (br d, J=6.0 Hz, 3H) 1.16 (br d, J=6.3 Hz, 3H) 1.65-1.86 (m, 5H) 1.91-2.02 (m, 3H) 2.11-2.29 (m, 5H) 2.30-2.39 (m, 2H) 2.51-2.61 (m, 1H) 2.64 (s, 3H) 2.68-2.87 (m, 5H) 3.02 (ddd, J=9.3, 8.3, 6.5 Hz, 1H) 3.38-3.46 (m, 4H) 3.47-3.54 (m, 3H) 3.55-3.69 (m, 8H) 3.95-4.08 (m, 3H) 4.67 (br d, J=2.0 Hz, 1H) 4.81 (d, J=6.5 Hz, 1H) 5.29 (t, J=8.3 Hz, 1H) 7.48-7.53 (m, 1H) 7.61-7.65 (m, 2H) 7.77 (dt, J=7.9, 1.9 Hz, 1H) 7.90 (d, J=8.8 Hz, 1H) 8.05 (dd, J=8.9, 1.9 Hz, 1H) 8.51 (d, J=2.3 Hz, 1H) 8.55 (dd, J=4.9, 1.6 Hz, 1H) 8.60 (s, 1H) 8.78 (s, 1H).

Example 163

(2S,3S)-N-(19-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-6,12,19-trioxo-3,10,16-trioxa-7,13-diazanonadecyl)-1-methyl-5-oxo-2-(pyridin-3-yl)pyrrolidine-3-carboxamide

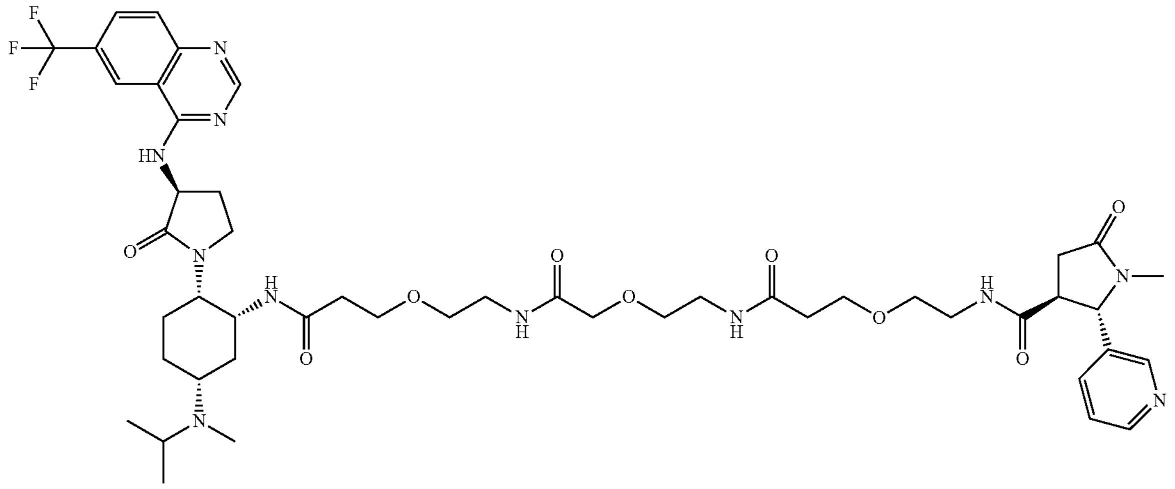 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)COCCNC(=O)CCOCCNC(=O)[C@H]2CC(=O)N(C)[C@@H]2c2cccnc2)C1]

Step 1

2-(2-(((Benzyloxy)carbonyl)amino)ethoxy)acetic acid

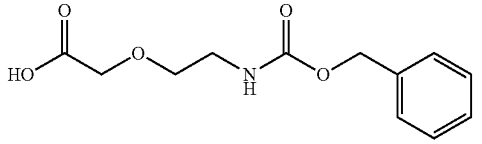 [SMILES: O=C(O)COCCNC(=O)OCc1ccccc1]

4 M HCl in 1,4-dioxane (2.3 mL, 9.28 mmol) was added to s solution of tert-butyl 2-(2-(((benzyloxy)carbonyl)amino)ethoxy)acetate (502 mg, 1.623 mmol) in acetonitrile (2.5 mL). The mixture was stirred at rt for 30 min and was concentrated under reduced pressure to give the title compound, which was carried onto the next step without purification. LC-MS m/z 254.1 $(M+H)^+$.

Step 2 tert-butyl 3,9-dioxo-1-phenyl-2,7,13-trioxa-4,10-diazahexadecan-16-oate

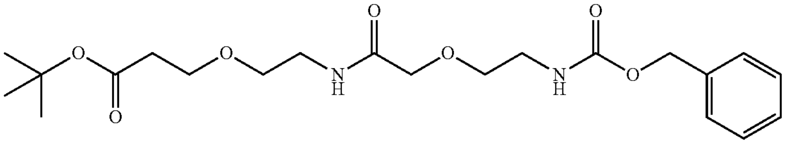 [SMILES: CC(C)(C)OC(=O)CCOCCNC(=O)COCCNC(=O)OCc1ccccc1]

A mixture of tert-butyl 3-(2-(((benzyloxy)carbonyl)amino)ethoxy)propanoate (500 mg, 1.546 mmol) and PD-C (181 mg, 1.701 mmol) was suspended in ethyl acetate (2577 μl) at room temperature in a RB flask. The flask was evacuated under vacuum and charged with hydrogen gas via a balloon. The reaction was stirred at room temperature for 2 hours. The mixture was filtered through a plug of celite and the filtrate was concentrated under vacuum. It was then dissolved in acetonitrile (2.5 mL). 2-(2-(((Benzyloxy)carbonyl)amino)ethoxy)acetic acid from step 1 was added, followed by addition of DIPEA (1.6 mL, 9.28 mmol) and HATU (617 mg, 1.623 mmol). The mixture was stirred at rt for 20 h. Dichloromethane (DCM) was added and the organic phase was washed with saturated $NH_4Cl$, with saturated $NaHCO_3$, with brine, was dried over $Na_2SO_4$, was filtered, and the filtrate was concentrated under reduced pressure. The crude material was purified by CombiFlash® Rf chromatography (24 g silica column, 35 mL/min) eluting with a gradient of 0 to 5% methanol containing triethylamine (0.1%) in dichloromethane (DCM) provided the title compound as clear colorless oil (320.8 mg, 0.756 mmol, 48.9% yield). LC-MS m/z 425.5 $(M+H)^+$.

Step 3

3-(2-(((Benzyloxy)carbonyl)amino)ethoxy)propanoic acid

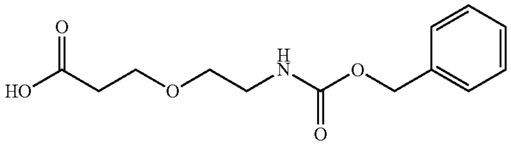 [SMILES: O=C(O)CCOCCNC(=O)OCc1ccccc1]

4 M HCl in 1,4-dioxane (1.12 mL, 4.48 mmol) was added to a solution of tert-butyl 3-(2-(((benzyloxy)carbonyl)amino)ethoxy)propanoate (254 mg, 0.784 mmol) in acetonitrile (0.58 mL). The mixture stirred at rt for 30 min and was concentrated under reduced pressure to give the title compound. It was carried onto next step without purification. LC-MS m/z 268.2 $(M+H)^+$.

Step 4 tert-Butyl 3,10,16-trioxo-1-phenyl-2,7,14,20-tetraoxa-4,11,17-triazatricosan-23-oate

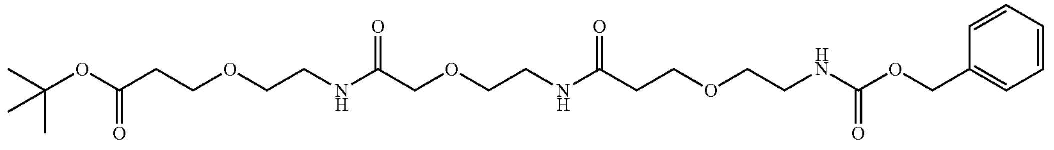 [SMILES: CC(C)(C)OC(=O)CCOCCNC(=O)COCCNC(=O)CCOCCNC(=O)OCc1ccccc1]

To a solution of tert-butyl 3-(2-(((benzyloxy)carbonyl)amino)ethoxy)propanoate (254 mg, 0.784 mmol) in Acetonitrile (582 μl) at room temperature was added 4M solution of hydrochloric acid in dioxane (1120 μl, 4.48 mmol). It was allowed to stir at room temperature for 30 minutes. The mixture was concentrated under vacuum to dryness, and the residue was carried onto the next step.

A mixture of tert-butyl 3,9-dioxo-1-phenyl-2,7,13-trioxa-4,10-diazahexadecan-16-oate (317 mg, 0.747 mmol) and PD-C(79 mg, 0.747 mmol) was suspended in Ethyl acetate (5816 μl) at room temperature in a RB flask. The flask was evacuated under vacuum and charged with hydrogen gas via a balloon. The reaction mixture was allowed to stir at room temperature for 72 hours. The mixture was filtered through a plug of celite and the filtrate was concentrated under vacuum to dryness.

To a solution of 3-(2-(((benzyloxy)carbonyl)amino)ethoxy)propanoic acid and tert-butyl 3-(2-(2-(2-aminoethoxy)acetamido)ethoxy)propanoate were suspended in Dichloromethane (DCM) (582 μl) was DIEA (783 μl, 4.48 mmol) and HATU (298 mg, 0.784 mmol). The reaction mixture was stirred at room temperature for 20 hours. The mixture was diluted with DCM and washed with sat. ammonium chloride, sat. sodium bicarb. and brine. The organic layer was dried over sodium sulfate, filtered and the filtrate was concentrated under vacuum. The residue was directly loaded onto a plug of silica and prified using flash chromatography on a Isco Combi Flash-RF using a 24 g silica column was used along with a gradient of 0%(5cv)-O—5%(30CV) 5%(4CV) MeOH/DCM (w/0.1% TEA) at a flow rate of 35 mL/min. All fractions containing the desired product were combined and concentrated to give the title compound as a clear oil (144.7 mg, 0.241 mmol, 32.3% yield). LC-MS m/z 540.5 $(M+H)^+$.

Step 5 tert-Butyl 1-amino-6,12-dioxo-3,10,16-trioxa-7,13-diazanonadecan-19-oate

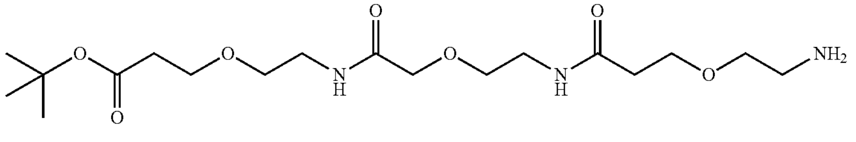 [SMILES: CC(C)(C)OC(=O)CCOCCNC(=O)COCCNC(=O)CCOCCN]

A mixture of tert-butyl 3,10,16-trioxo-1-phenyl-2,7,14,20-tetraoxa-4,11,17-triazatricosan-23-oate (137 mg, 0.254 mmol) and Pd—C(27.0 mg, 0.254 mmol) was suspended in ethyl acetate (1.5 mL) at room temperature. The mixture was evacuated under vacuum and was charged with hydrogen. The mixture was stirred under a balloon atmosphere of hydrogen at rt for 20 h. The mixture was filtered through Celite® and the filtrate was concentrated under reduced pressure. LC-MS m/z 406.2 $(M+H)^+$.

Step 6 tert-Butyl 1-((2S,3S)-1-methyl-5-oxo-2-(pyridin-3-yl)pyrrolidi n-3-yl)-1,8,14-trioxo-5,12,18-trioxa-2,9,15-triazahenicosan-21-oate

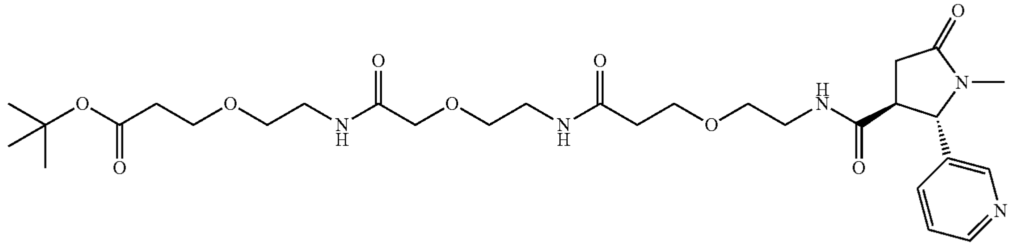 [SMILES: CN1C(=O)C[C@H](C(=O)NCCOCCC(=O)NCCOCC(=O)NCCOCCC(=O)OC(C)(C)C)[C@H]1c1cccnc1]

A mixture of tert-butyl 1-amino-6,12-dioxo-3,10,16-trioxa-7,13-diazanonadecan-19-oate (81.7 mg, 0.201 mmol) and (2S,3S)-1-methyl-5-oxo-2-(pyridin-3-yl)pyrrolidine-3-carboxylic acid (44.7 mg, 0.203 mmol) were suspended in dichloromethane (DCM) (0.15 mL), DIPEA (133 µL, 0.762 mmol) and HATU (97 mg, 0.254 mmol) were added, and the mixture was stirred at rt for 1 h. Dichloromethane (DCM) was added and the organic phase was washed with saturated $NH_4Cl$, with saturated $NaHCO_3$, was dried over $Na_2SO_4$, was filtered, and the filtrate was concentrated under reduced pressure. Purification by CombiFlash® Rf chromatography (40 g silica column, 40 mL/min) eluting with a gradient of 0 to 5% methanol containing triethylamine (0.1%) in dichloromethane (DCM) provided the title compound as an off-white, stick solid (93.7 mg, 0.139 mmol, 54.7% yield). LC-MS m/z 608.5 $(M+H)^+$.

Step 7

(2S,3S)-N-(19-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-6,12,19-trioxo-3,10,16-trioxa-7,13-diazanonadecyl)-1-methyl-5-oxo-2-(pyridin-3-yl)pyrrolidine-3-carboxamide

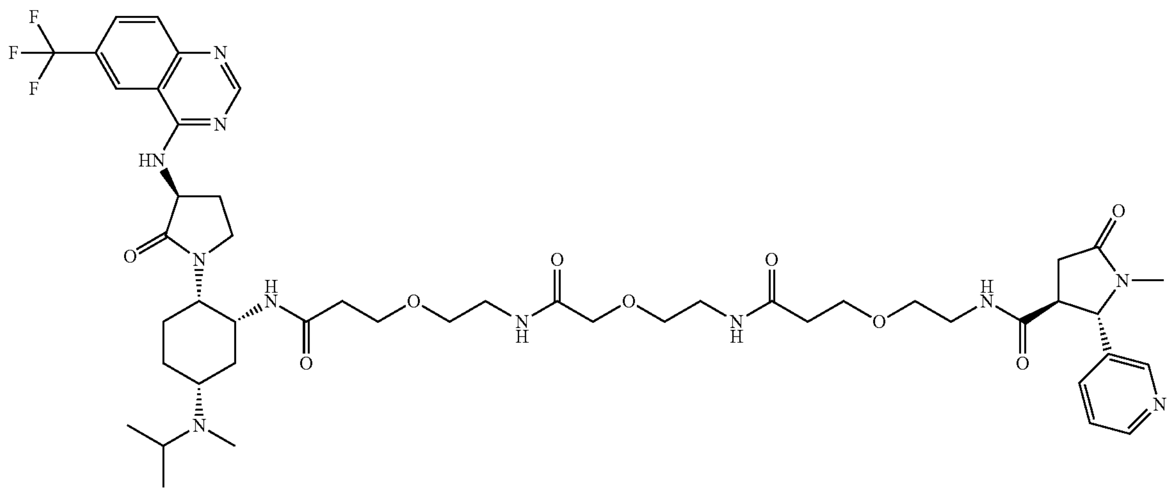 [SMILES: CC(C)N(C)[C@@H]1CC[C@H](N2CC[C@H](Nc3ncnc4ccc(C(F)(F)F)cc34)C2=O)[C@H](NC(=O)CCOCCNC(=O)COCCNC(=O)CCOCCNC(=O)[C@H]2CC(=O)N(C)[C@@H]2c2cccnc2)C1]

4 M HCl in 1,4-dioxane (212 μL, 0.848 mmol) was added to a suspension of tert-butyl 1-((2S,3S)-1-methyl-5-oxo-2-(pyridin-3-yl)pyrrolidin-3-yl)-1,8,14-trioxo-5,12,18-trioxa-2,9,15-triazahenicosan-21-oate (90 mg, 0.148 mmol) in acetonitrile (0.24 mL) The mixture was stirred at rt for 4 hours and was concentrated to dryness under reduced pressure. The residue and (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (76 mg, 0.141 mmol) were suspended in dichloromethane (DCM), DIPEA (148 μL, 0.848 mmol) and HATU (56.5 mg, 0.148 mmol) were added, and the mixture was stirred at rt for 20 h. Dichloromethane (DCM) was added and the organic phase was washed with saturated $NaHCO_3$, was dried over $Na_2SO_4$, was filtered, and the filtrate was concentrated under reduced pressure. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as an off-white solid (51.7 mg, 0.049 mmol, 34.8% yield). LC-MS m/z 998.0 $(M+H)^+$. $^1H$ NMR (400 MHz, METHANOL-$d_4$) δ ppm d ppm 8.78 (s, 1H) 8.53-8.59 (m, 2H) 8.50 (d, J=1.96 Hz, 1H) 8.04 (dd, J=8.80, 1.96 Hz, 1H) 7.89 (d, J=8.80 Hz, 1H) 7.77 (dt, J=8.01, 1.86 Hz, 1H) 7.51 (dd, J=7.83, 4.89 Hz, 1H) 5.27 (br. s., 1H) 4.80 (d, J=6.60 Hz, 1H) 4.58 (br. s., 1H) 4.05 (d, J=10.27 Hz, 1H) 3.92 (s, 2H) 3.34-3.85 (m, 18H) 2.98-3.07 (m, 1H) 2.61-2.87 (m, 6H) 1.60-2.58 (m, 17H) 0.97-1.19 (m, 6H).

Example 164

(2S,3S)-N-(14-((2-((4-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-4-oxobutyl)amino)-3,4-dioxocyclobut-1-en-1-yl)amino)-3,6,9,12-tetraoxatetradecyl)-1-methyl-5-oxo-2-(pyridin-3-yl)pyrrolidine-3-carboxamide

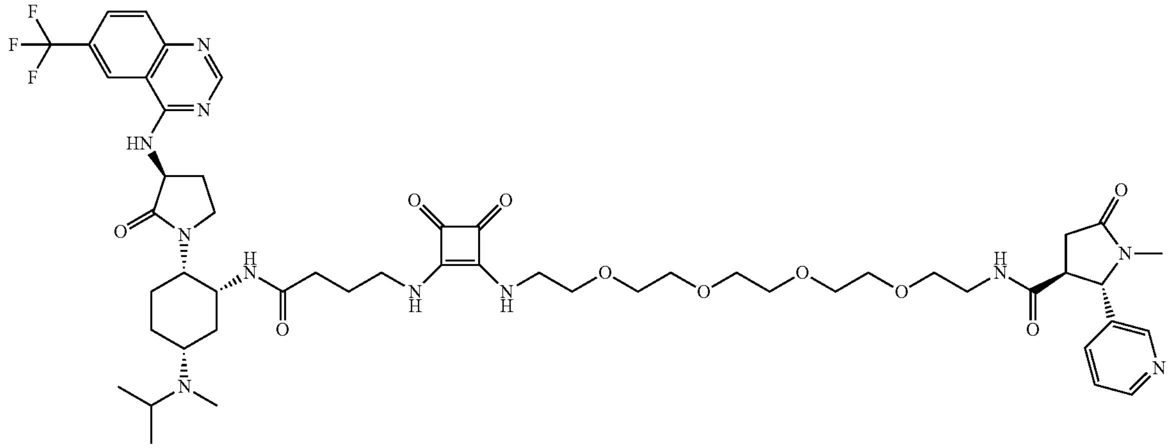 [SMILES: CC(C)N(C)[C@@H]1CC[C@H](N2CC[C@H](Nc3ncnc4ccc(C(F)(F)F)cc34)C2=O)[C@H](NC(=O)CCCNc2c(NCCOCCOCCOCCOCCNC(=O)[C@H]3CC(=O)N(C)[C@@H]3c3cccnc3)c(=O)c2=O)C1]

Step 1

(2S,3S)-N-(14-amino-3,6,9,12-tetraoxatetradecyl)-1-methyl-5-oxo-2-(pyridin-3-yl)pyrrolidine-3-carboxamide, 2Hydrochloric acid salt

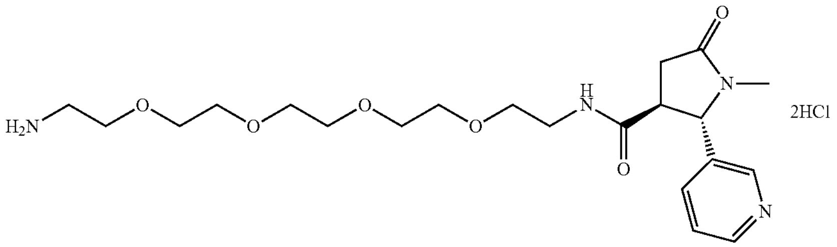 [SMILES: CN1C(=O)C[C@H](C(=O)NCCOCCOCCOCCOCCN)[C@H]1c1cccnc1]

To a mixture of (2S,3S)-1-methyl-5-oxo-2-(pyridin-3-yl) pyrrolidine-3-carboxylic acid (370 mg, 1.680 mmol), tert-butyl (29-amino-3,6,9,12,15,18,21,24,27-nonaoxanonacosyl)carbamate(1.0 g, 1.796 mmol), and DIPEA (0.587 mL, 3.36 mmol) in dichloromethane (DCM) (10 mL) was added HATU (767 mg, 2.016 mmol). The mixture was stirred at rt for 2 h and was washed with water (10 mL). The organic phase was dried over $Na_2SO_4$ and was concentrated under reduced pressure. to provide tert-butyl (1-((2S,3S)-1-methyl-5-oxo-2-(pyridin-3-yl)pyrrolidin-3-yl)-1-oxo-5,8,11,14-tetraoxa-2-azahexadecan-16-yl)carbamate as a white semi-solid (750 mg, 1.392 mmol, 61.3% yield). LC-MS m/z 539.1 $(M+H)^+$. The solid was stirred in 4 N HCl in 1,4-dioxane for 1 h and was concentrated under reduced pressure to provide the title compound (650 mg, 1.482 mmol, 65.3% yield). LC-MS m/z 439.2 $(M+H)^+$.

Step 2

4-((2-((1-((2S,3S)-1-Methyl-5-oxo-2-(pyridin-3-yl) pyrrolidin-3-yl)-1-oxo-5,8,11,14-tetraoxa-2-azahexadecan-16-yl)amino)-3,4-dioxocyclobut-1-en-1-yl) amino)butanoic acid

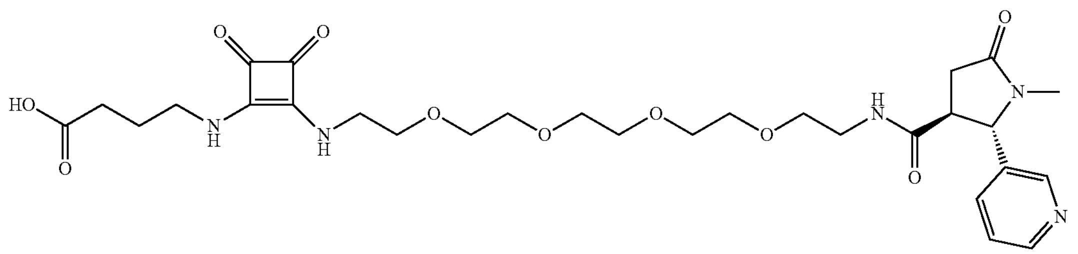 [SMILES: CN1C(=O)C[C@H](C(=O)NCCOCCOCCOCCOCCNc2c(NCCCC(=O)O)c(=O)c2=O)[C@H]1c1cccnc1]

A mixture of 3,4-diethoxycyclobut-3-ene-1,2-dione (80 mg, 0.470 mmol), (2S,3S)-N-(14-amino-3,6,9,12-tetraoxatetradecyl)-1-methyl-5-oxo-2-(pyridin-3-yl)pyrrolidine-3-carboxamide, 2hydrochloroic acid salt (206 mg, 0.398 mmol), and DIPEA (0.082 mL, 0.470 mmol) in methanol (2 mL) was stirred at rt for 1 h. 4-aminobutanoic acid (48.5 mg, 0.470 mmol) was added, the mixture was stirred at 60° C. overnight, and was concentrated. Purification by MDAP chromatography provide the title compound (120 mg, 0.174 mmol, 43.7%). LC-MS m/z 620.3 $(M+H)^+$.

Step 3

(2S,3S)-N-(14-((2-((4-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-4-oxobutyl)amino)-3,4-dioxocyclobut-1-en-1-yl)amino)-3,6,9,12-tetraoxatetradecyl)-1-methyl-5-oxo-2-(pyridin-3-yl)pyrrolidine-3-carboxamide

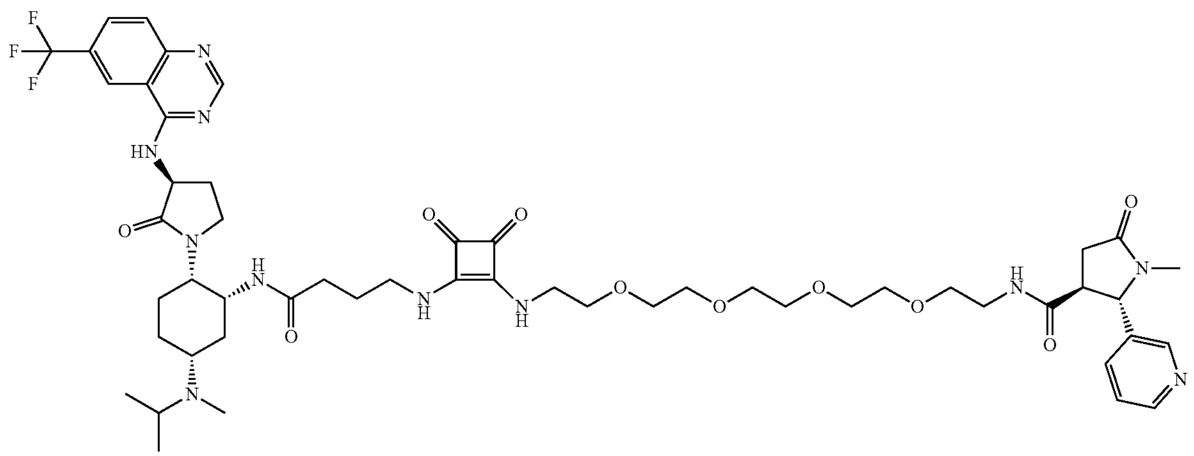 [SMILES: CC(C)N(C)[C@@H]1CC[C@H](N2CC[C@H](Nc3ncnc4ccc(C(F)(F)F)cc34)C2=O)[C@H](NC(=O)CCCNc2c(NCCOCCOCCOCCOCCNC(=O)[C@H]3CC(=O)N(C)[C@@H]3c3cccnc3)c(=O)c2=O)C1]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (37.5 mg, 0.069 mmol) and 4-((2-((1-((2S,3S)-1-methyl-5-oxo-2-(pyridin-3-yl)pyrrolidin-3-yl)-1-oxo-5,8,11,14-tetraoxa-2-azahexadecan-16-yl)amino)-3,4-dioxocyclobut-1-en-1-yl)amino)butanoic acid (50 mg, 0.081 mmol), in dichloromethane (DCM) (2 mL) was added DIPEA (0.014 mL, 0.081 mmol), followed by T3P (0.048 mL, 0.081 mmol). The mixture was stirred at rt for 2 h and was washed with water. The organic phase was dried over $Na_2SO_4$ and was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as a white solid (30 mg, 0.027 mmol, 39% yield). LC-MS m/z 1066.4 $(M+H)^+$. $^1H$ NMR (400 MHz, METHANOL-$d_4$) δ ppm 0.97-1.14 (m, 6H) 1.63-1.82 (m, 3H) 1.87-2.23 (m, 6H) 2.25 (s, 3H) 2.28-2.45 (m, 3H) 2.48-2.76 (m, 5H) 2.76-2.88 (m, 1H) 2.98-3.11 (m, 1H) 3.27-3.34 (m, 3H) 3.38-3.44 (m, 1H) 3.45-3.69 (m, 21H) 3.75 (br s, 1H) 4.04 (dt, J=11.9, 3.6 Hz, 1H) 4.59 (br d, J=2.9 Hz, 1H) 4.77-4.84 (m, 2H) 5.27 (t, J=8.6 Hz, 1H) 7.52 (dd, J=7.3, 4.9 Hz, 1H) 7.80 (d, J=7.6 Hz, 1H) 7.90 (d, J=8.3 Hz, 1H) 8.05 (dd, J=8.8, 2.0 Hz, 1H) 8.51-8.64 (m, 3H) 8.76 (s, 1H).

Example 165

N[1]-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-N[10]-(10-((2S,3S)-1-methyl-5-oxo-2-(pyridin-3-yl)pyrrolidine-3-carboxamido)decyl)decanediamide

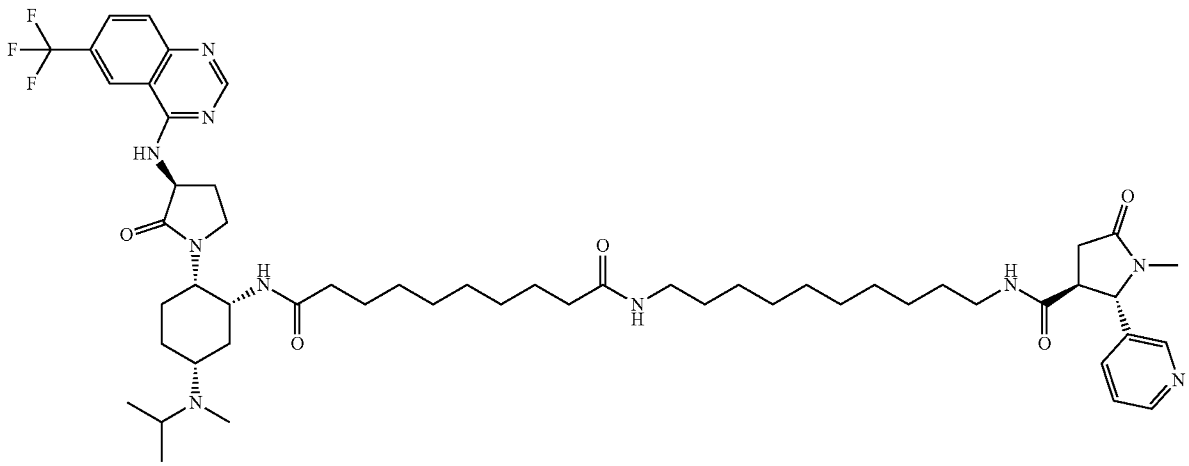 [SMILES: CC(C)N(C)[C@@H]1CC[C@H](N2CC[C@H](Nc3ncnc4ccc(C(F)(F)F)cc34)C2=O)[C@H](NC(=O)CCCCCCCCC(=O)NCCCCCCCCCCNC(=O)[C@H]2CC(=O)N(C)[C@@H]2c2cccnc2)C1]

Step 1 tert-Butyl (10-((2S,3S)-1-methyl-5-oxo-2-(pyridin-3-yl)pyrrolidine-3-carboxamido) decyl)carbamate

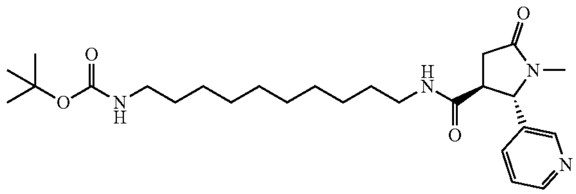 [SMILES: CN1C(=O)C[C@H](C(=O)NCCCCCCCCCCNC(=O)OC(C)(C)C)[C@H]1c1cccnc1]

To a mixture of (2S,3S)-1-methyl-5-oxo-2-(pyridin-3-yl) pyrrolidine-3-carboxylic acid (164 mg, 0.745 mmol) and tert-butyl (10-aminodecyl)carbamate (203 mg, 0.745 mmol) in dichloromethane (DCM) (2 mL) was added HATU (340 mg, 0.894 mmol) and triethylamine (0.208 mL, 1.489 mmol). The mixture was stirred at rt for 2 h and was partitioned between dichloromethane (DCM) and saturated $NaHCO_3$. The aqueous phase was extracted with dichloromethane (DCM). The combined organic phases were dried over $Na_2SO_4$, were filtered, and the filtrate was concentrated. Purification by ISCO CombiFlash® chromatography (24 g RediSep Rf Gold® column, 35 mL/min) eluting with a gradient of 0 to 70% methanol/dichloromethane (DCM) (20/80) in dichloromethane (DCM) provided the title compound as a brown oil (254 mg, 0.535 mmol, 71.9% yield). LC-MS m/z 475.3 $(M+H)^+$.

Step 2

10-((10-((2S,3S)-1-Methyl-5-oxo-2-(pyridin-3-yl) pyrrolidine-3-carboxamido)decyl) amino)-10-oxodecanoic acid

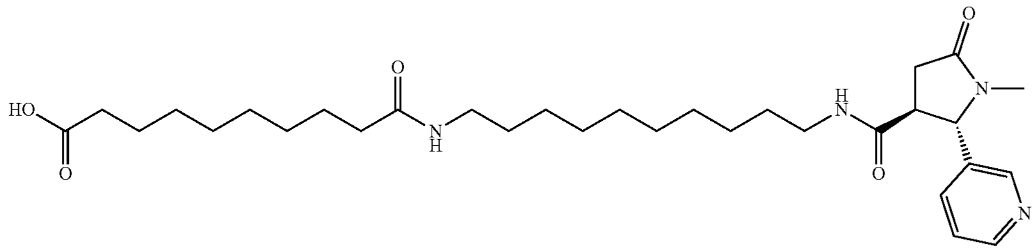 [SMILES: CN1C(=O)C[C@H](C(=O)NCCCCCCCCCCNC(=O)CCCCCCCCC(=O)O)[C@H]1c1cccnc1]

To a mixture of tert-butyl (10-((2S,3S)-1-methyl-5-oxo-2-(pyridin-3-yl) pyrrolidine-3-carboxamido)decyl)carbamate (76 mg, 0.160 mmol) in dichloromethane (DCM) (0.300 mL) was added TFA (0.247 mL, 3.20 mmol). The mixture was stirred at rt for 1 h and concentrated. To the residue was added N,N-dimethylformamide (DMF) (0.3 mL) and triethylamine (0.223 mL, 1.601 mmol). The mixture was stirred at rt for 5 min and decanedioic acid (97 mg, 0.480 mmol) and HATU (73.1 mg, 0.192 mmol) were added. The mixture was stirred at rt 1 h and was partitioned between dichloromethane (DCM) and saturated $NaHCO_3$. The aqueous phase was extracted with dichloromethane (DCM). The combined organic phases were dried over $Na_2SO_4$, were filtered, and the filtrate was concentrated. Purification by MDAP chromatography (XSelect™ CSH Prep C18 5 μm OBD column, 40 mL/min) eluting with a gradient of 15 to 55% acetonitrile in water both containing formic acid (0.1%) provided the title compound as a solid (26.3 mg, 0.02 mmol, 37.9% yield). LC-MS m/z 559.3 $(M+H)^+$.

Step 3

$N^1$-((1R,2S,5R)-5-(isopropyl(methyl)amino)-2-((S)-2-oxo-3-((6-(trifluoromethyl) quinazolin-4-yl) amino)pyrrolidin-1-yl)cyclohexyl)-$N^{10}$-(10-((2S,3S)-1-methyl-5-oxo-2-(pyridin-3-yl)pyrrolidine-3-carboxamido)decyl)decanediamide

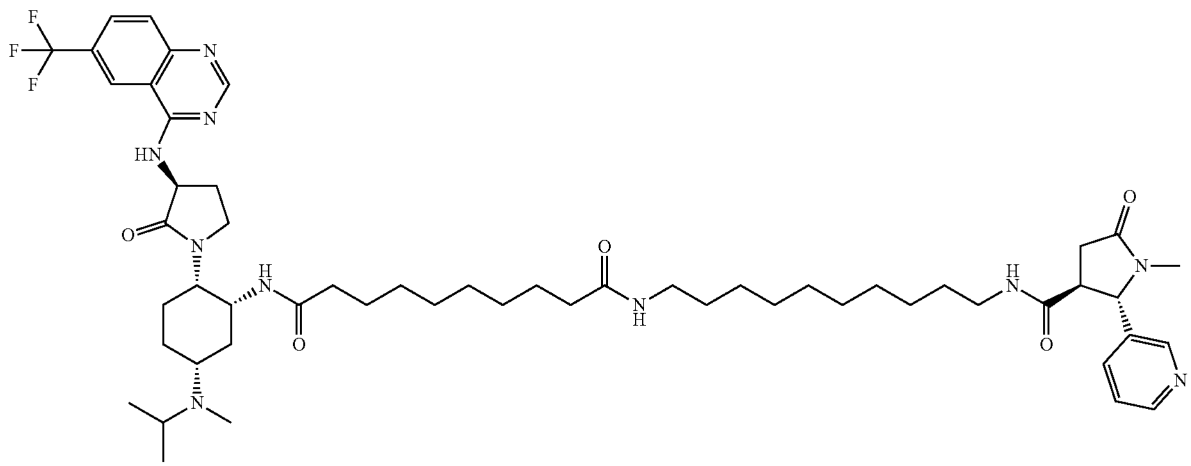 [SMILES: CC(C)N(C)[C@@H]1CC[C@H](N2CC[C@H](Nc3ncnc4ccc(C(F)(F)F)cc34)C2=O)[C@H](NC(=O)CCCCCCCCC(=O)NCCCCCCCCCCNC(=O)[C@H]2CC(=O)N(C)[C@@H]2c2cccnc2)C1]

To (S)-1-((1S,2R,4R)-2-amino-4-(isopropyl(methyl)amino)cyclohexyl)-3-((6-(trifluoromethyl) quinazolin-4-yl)amino)pyrrolidin-2-one, 2Trifluoroacetic acid salt (21.07 mg, 0.030 mmol) in dichloromethane (DCM) (0.3 mL) was added triethylamine (0.040 mL, 0.287 mmol). The mixture was stirred at rt for 40 min. A 10-((10-((2S,3S)-1-methyl-5-oxo-2-(pyridin-3-yl)pyrrolidine-3-carboxamido)decyl)amino)-10-oxodecanoic acid (17 mg, 0.030 mmol) and HATU (13.88 mg, 0.037 mmol) in DCM (0.5 mL) was added and the mixture was stirred at rt for 2 h. Purification by MDAP chromatography (XSelect™ CSH Prep C18 5 μm OBD column, 40 mL/min) eluting with a gradient of 15 to 55% acetonitrile in water both containing formic acid (0.1%) provided the title compound as a solid (16.1 mg, 0.015 mmol, 50.5% yield). LC-MS m/z 1005.4 $(M+H)^+$. $^1H$ NMR (400 MHz, METHANOL-$d_4$) δ ppm 0.92 (br d, J=7.4 Hz, 2H) 1.08-1.36 (m, 28H) 1.35-1.35 (m, 1H) 1.39-1.61 (m, 8H) 1.90 (br s, 1H) 2.00 (br s, 1H) 2.05-2.24 (m, 8H) 2.30 (s, 1H) 2.49 (br s, 1H) 2.56 (br d, J=6.8 Hz, 1H) 2.62 (br s, 1H) 2.65-2.86 (m, 6H) 2.99-3.24 (m, 6H) 3.28 (br s, 1H) 3.56-3.81 (m, 3H) 4.15 (br s, 1H) 4.82 (d, J=6.6 Hz, 1H) 7.54 (dd, J=7.9, 4.8 Hz, 1H) 7.81 (dt, J=8.0, 1.8 Hz, 1H) 7.93 (d, J=8.9 Hz, 1H) 8.08 (dd, J=8.9, 1.8 Hz, 1H) 8.51 (d, J=2.0 Hz, 1H) 8.58-8.63 (m, 2H) 8.76 (br s, 1H).

The following compound was or could be prepared with procedures analogous to that described in Example 165:

| Ex. | Compound | LC-MS m/z | NMR |
|---|---|---|---|
| 166 | 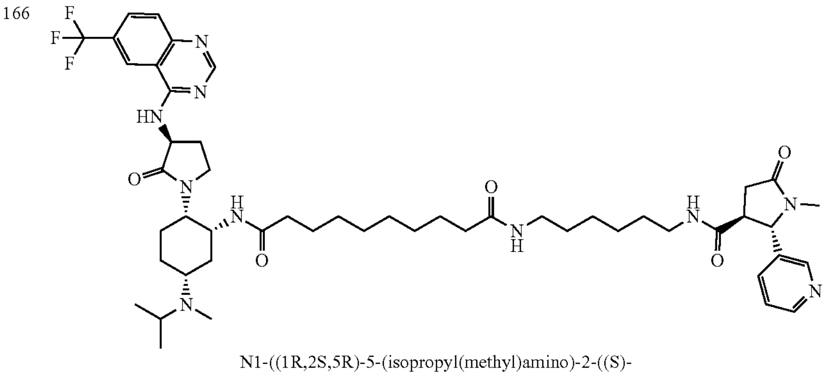 N1-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-N10-(6-((2S,3S)-1-methyl-5-oxo-2-(pyridin-3-yl)pyrrolidine-3-carboxamido)hexyl)decanediamide | 935.6 (M + H)+ | $^1H$ NMR (400 MHz, METHANOL-$d_4$) δ ppm 1.06-1.32 (m, 18H) 1.43-1.64 (m, 9H) 1.83-1.86 (m, 1H) 2.08-2.35 (m, 10H) 2.36-2.59 (m, 3H) 2.67 (s, 4H) 2.68-2.74 (m, 1H) 2.79-2.86 (m, 1H) 2.98-3.04 (m, 1H) 2.99-3.10 (m, 1H) 3.09-3.25 (m, 4H) 3.67 (br s, 2H) 4.11 (br s, 1H) 4.82 (d, J = 6.8 Hz, 1H) 7.55 (dd, J = 7.9, 4.8 Hz, 1H) 7.81 (dt, J = 7.9, 2.0 Hz, 1H) 7.91-7.97 (m, 2H) 8.08 (dd, J = 8.9, 1.8 Hz, 1H) 8.52 (d, J = 2.3 Hz, 1H) 8.59 (dd, J = 4.8, 1.5 Hz, 1H) 8.60-8.62 (m, 1H) 8.79 (br s, 1H). |

Example 167

3-(3-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)propanoyl)-N-(2-((2S,3S)-1-methyl-5-oxo-2-(pyridin-3-yl)pyrrolidine-3-carboxamido)ethyl)-3-azaspiro[5.5]undecane-9-carboxamide

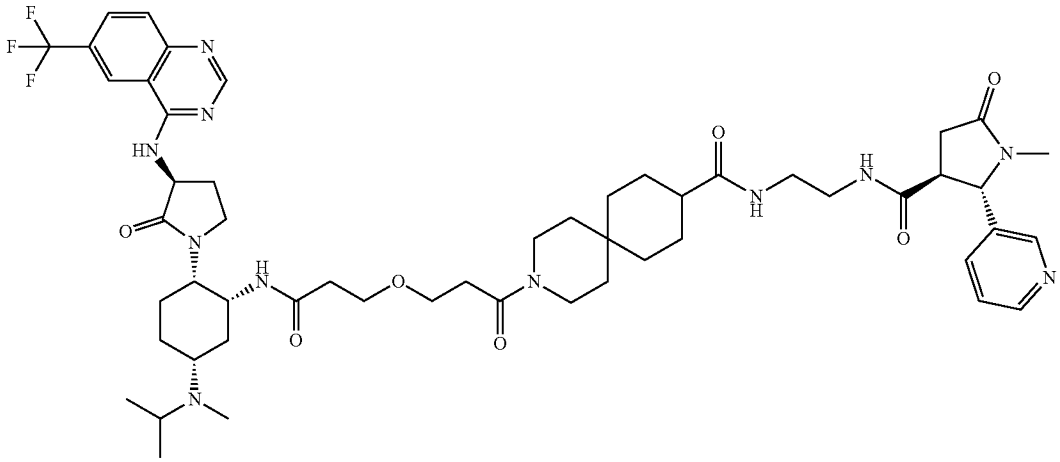 [SMILES: CC(C)N(C)[C@@H]1CC[C@H](N2CC[C@H](Nc3ncnc4ccc(C(F)(F)F)cc34)C2=O)[C@H](NC(=O)CCOCCC(=O)N2CCC3(CCC(C(=O)NCCNC(=O)[C@H]4CC(=O)N(C)[C@@H]4c4cccnc4)CC3)CC2)C1]

Step 1 tert-Butyl (2-((2S,3S)-1-methyl-5-oxo-2-(pyridin-3-yl)pyrrolidine-3-carboxamido)ethyl) carbamate

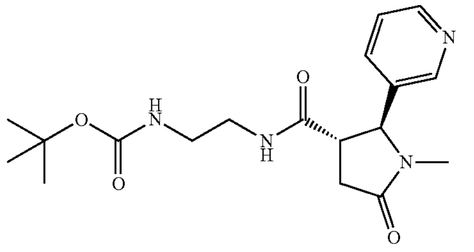 [SMILES: CN1C(=O)C[C@H](C(=O)NCCNC(=O)OC(C)(C)C)[C@H]1c1cccnc1]

To a mixture of tert-butyl (2-aminoethyl)carbamate (284 mg, 1.771 mmol) and (2S,3S)-1-methyl-5-oxo-2-(pyridin-3-yl)pyrrolidine-3-carboxylic acid (390 mg, 1.771 mmol) in dichloromethane (DCM) (5 mL) was added HATU (808 mg, 2.125 mmol) and triethylamine (0.741 mL, 5.31 mmol). The mixture was stirred at rt for 2 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (517 mg, 1.426 mmol, 81% yield). LC-MS m/z 363.2 $(M+H)^+$.

Step 2

(2S,3S)-N-(2-Aminoethyl)-1-methyl-5-oxo-2-(pyridin-3-yl)pyrrolidine-3-carboxamide

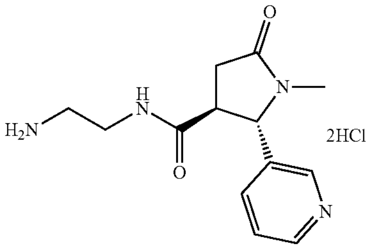 [SMILES: CN1C(=O)C[C@H](C(=O)NCCN)[C@H]1c1cccnc1]

4 M HCl in 1,4-dioxane (1.783 mL, 7.13 mmol) was added to a mixture of tert-butyl (2-((2S,3S)-1-methyl-5-oxo-2-(pyridin-3-yl)pyrrolidine-3-carboxamido)ethyl)carbamate (517 mg, 1.426 mmol) in dichloromethane (DCM) (2 mL). The mixture was stirred at rt for 3 h and was concentrated to dryness to provide the title compound as a solid (500 mg, 1.491 mmol, 105% yield). LC-MS m/z 263.2 $(M+H)^+$.

Step 3 tert-Butyl 9-((2-((2S,3S)-1-methyl-5-oxo-2-(pyridin-3-yl)pyrrolidine-3-carboxamido) ethyl)carbamoyl)-3-azaspiro[5.5]undecane-3-carboxylate

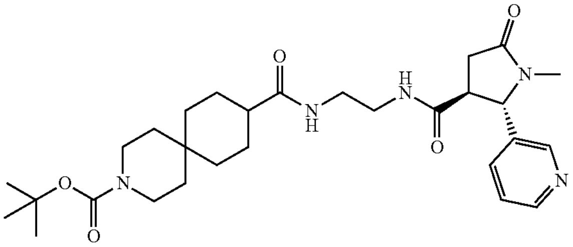 [SMILES: CN1C(=O)C[C@H](C(=O)NCCNC(=O)C2CCC3(CC2)CCN(C(=O)OC(C)(C)C)CC3)[C@H]1c1cccnc1]

To a mixture of (2S,3S)-N-(2-aminoethyl)-1-methyl-5-oxo-2-(pyridin-3-yl)pyrrolidine-3-carboxamide, 2hydrochloric acid salt (253 mg, 0.755 mmol) and 3-(tert-butoxycarbonyl)-3-azaspiro[5.5]undecane-9-carboxylic acid (224 mg, 0.755 mmol) in dichloromethane (DCM) (1.5 mL) was added triethylamine (0.526 mL, 3.77 mmol) and HATU (344 mg, 0.906 mmol). The mixture was stirred at rt overnight and was partitioned between dichloromethane (DCM) and saturated $NaHCO_3$. The aqueous phase was extracted with dichloromethane (DCM) and the combined organic phases were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (240 mg, 0.443 mmol, 58.7% yield). LC-MS m/z 542.3 $(M+H)^+$.

Step 4

N-(2-((2S,3S)-1-Methyl-5-oxo-2-(pyrid i n-3-yl) pyrrolidine-3-carboxamido)ethyl)-3-azaspiro[5.5] undecane-9-carboxamide, 2Hydrochloric acid salt

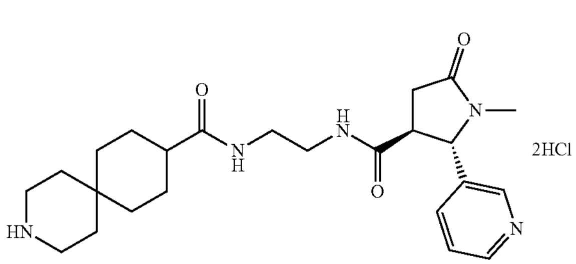 [SMILES: CN1C(=O)C[C@H](C(=O)NCCNC(=O)C2CCC3(CCNCC3)CC2)[C@H]1c1cccnc1]

4 M HCl in 1,4-dioxane (0.554 mL, 2.215 mmol) was added to a mixture of tert-butyl 9-((2-((2S,3S)-1-methyl-5-oxo-2-(pyridin-3-yl) pyrrolidine-3-carboxamido)ethyl)carbamoyl)-3-azaspiro[5.5]undecane-3-carboxylate (240 mg, 0.443 mmol) in dichloromethane (DCM) (0.5 mL). The mixture was stirred at rt for 2 and was concentrated to dryness to provide the title compound (291 mg, 0.566 mmol, 128% yield). LC-MS m/z 442.5 $(M+H)^+$.

Step 5 tert-Butyl 3-(3-(9-((2-((2S,3S)-1-methyl-5-oxo-2-(pyridin-3-yl)pyrrolidine-3-carboxamido) ethyl)carbamoyl)-3-azaspiro[5.5]undecan-3-yl)-3-oxo-propoxy)propanoate

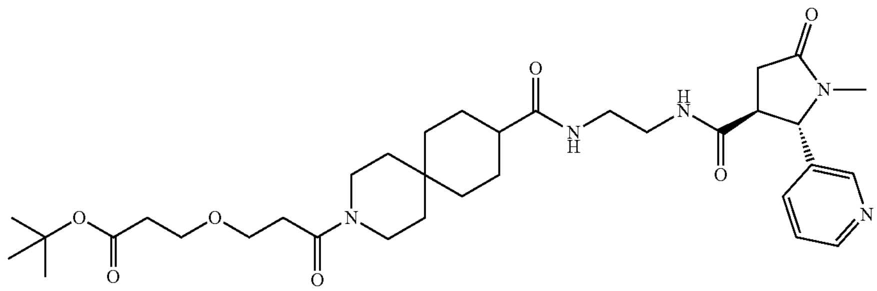 [SMILES: CN1C(=O)C[C@H](C(=O)NCCNC(=O)C2CCC3(CC2)CCN(C(=O)CCOCCC(=O)OC(C)(C)C)CC3)[C@H]1c1cccnc1]

To a mixture of N-(2-((2S,3S)-1-methyl-5-oxo-2-(pyridin-3-yl) pyrrolidine-3-carboxamido)ethyl)-3-azaspiro[5.5] undecane-9-carboxamide, 2Hydrochloric acid salt (100 mg, 0.194 mmol) and 3-(3-(tert-butoxy)-3-oxopropoxy)propanoic acid (46 mg, 0.211 mmol) in dichloromethane (DCM) (1 mL) was added triethylamine (0.147 mL, 1.054 mmol) and HATU (96 mg, 0.253 mmol). The mixture was stirred at rt for 2 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (91 mg, 0.142 mmol, 67.3% yield). LC-MS m/z 642.3 $(M+H)^+$.

Step 6

3-(3-(9-((2-((2S,3S)-1-Methyl-5-oxo-2-(pyridin-3-yl)pyrrolidine-3-carboxamido) ethyl)carbamoyl)-3-azaspiro[5.5]undecan-3-yl)-3-oxopropoxy)propanoic acid, Hydrochloric acid salt

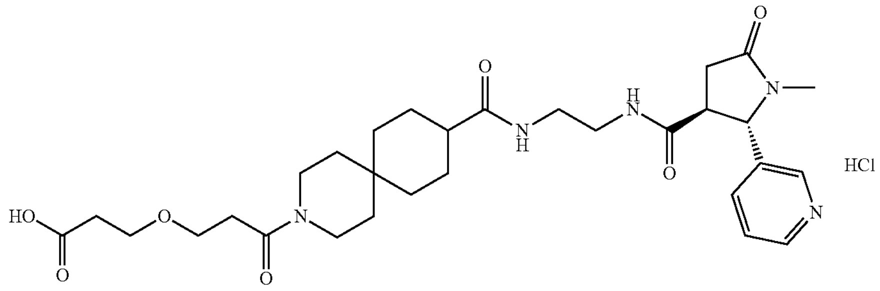 [SMILES: CN1C(=O)C[C@H](C(=O)NCCNC(=O)C2CCC3(CC2)CCN(C(=O)CCOCCC(=O)O)CC3)[C@H]1c1cccnc1 ; Cl]

4 M HCl in 1,4-dioxane (0.175 mL, 0.701 mmol) was added to a mixture of tert-butyl 3-(3-(9 ((2-((2S,3S)-1-methyl-5-oxo-2-(pyridin-3-yl)pyrrolidine-3-carboxamido) ethyl)carbamoyl)-3-azaspiro[5.5]undecan-3-yl)-3-oxo-propoxy)propanoate (90 mg, 0.140 mmol) in dichloromethane (DCM) (0.2 mL). The mixture was stirred at rt for 3 h and was concentrated to dryness to provide the title compound (90 mg, 0.145 mmol, 103% yield). LC-MS m/z 586.3 $(M+H)^+$.

Step 7

3-(3-(3-(((1R,2S,5R)-5-(Isopropyl(methyl)amino)-2-((S)-2-oxo-3-((6-(trifluoromethyl) quinazolin-4-yl) amino)pyrrolidin-1-yl)cyclohexyl)amino)-3-oxo-propoxy)propanoyl)-N-(2-((2S,3S)-1-methyl-5-oxo-2-(pyridin-3-yl)pyrrolidine-3-carboxamido)ethyl)-3-azaspiro[5.5]undecane-9-carboxamide

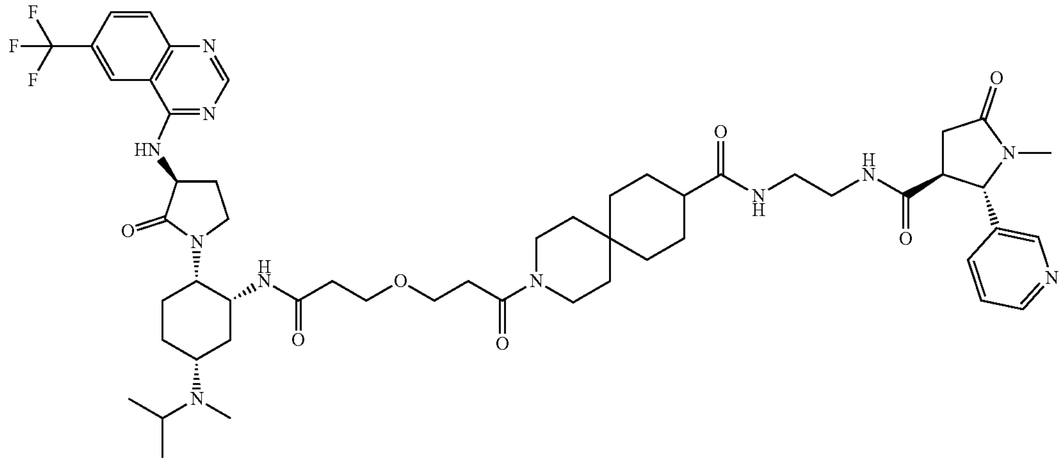 [SMILES: CC(C)N(C)[C@@H]1CC[C@H](N2CC[C@H](Nc3ncnc4ccc(C(F)(F)F)cc34)C2=O)[C@H](NC(=O)CCOCCC(=O)N2CCC3(CCC(C(=O)NCCNC(=O)[C@H]4CC(=O)N(C)[C@@H]4c4cccnc4)CC3)CC2)C1]

To a mixture of 3-(3-(9-((2-((2S,3S)-1-methyl-5-oxo-2-(pyridin-3-yl)pyrrolidine-3-carboxamido) ethyl)carbamoyl)-3-azaspiro[5.5]undecan-3-yl)-3-oxopropoxy)propanoic acid, hydrochloric acid salt (45 mg, 0.072 mmol) and (S)-1-((1S,2R,4R)-2-amino-4-(isopropyl(methyl)amino)cyclohexyl)-3-((6-(trifluoromethyl)quinazolin-4-yl)amino) pyrrolidin-2-one (38.9 mg, 0.072 mmol) in dichloromethane (DCM) (0.5 mL) was added triethylamine (0.060 mL, 0.434 mmol) and HATU (33.0 mg, 0.087 mmol). The mixture was stirred at rt for 2 h and was concentrated. Purification by MDAP chromatography (XSelect™ CSH Prep C18 5 µm OBD column, 40 mL/min) eluting with a gradient of 30 to 85% acetonitrile in water containing ammonium bicarbonate (10 mM) and the pH adjusted to 10 with ammonia provided the title compound (55 mg, 0.053 mmol, 73.7% yield). LC-MS m/z 1032.5 $(M+H)^+$. $^1H$ NMR (400 MHz, METHANOL-$d_4$) δ ppm 1.14 (br d, J=5.8 Hz, 10H) 1.57 (br s, 11H) 1.89-2.17 (m, 3H) 2.28 (br s, 5H) 2.43-2.59 (m, 5H) 2.67 (s, 5H) 2.81-2.92 (m, 1H) 2.95-3.09 (m, 1H) 3.22-3.30 (m, 3H) 3.36-3.72 (m, 10H) 3.76-3.86 (m, 1H) 4.00-4.12 (m, 1H) 4.55-4.73 (m, 2H) 4.86 (d, J=6.0 Hz, 1H) 5.24-5.37 (m, 1H) 7.46-7.59 (m, 1H) 7.77-7.96 (m, 2H) 8.01-8.13 (m, 1H) 8.60 (s, 3H) 8.77-8.94 (m, 1H).

Example 168

(2S,3S)-N-(2-((2-((2-(2-(2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethoxy)ethoxy)ethyl)amino)-3,4-dioxocyclobut-1-en-1-yl)amino)ethyl)-1-methyl-5-oxo-2-(pyridin-3-yl)pyrrolidine-3-carboxamide

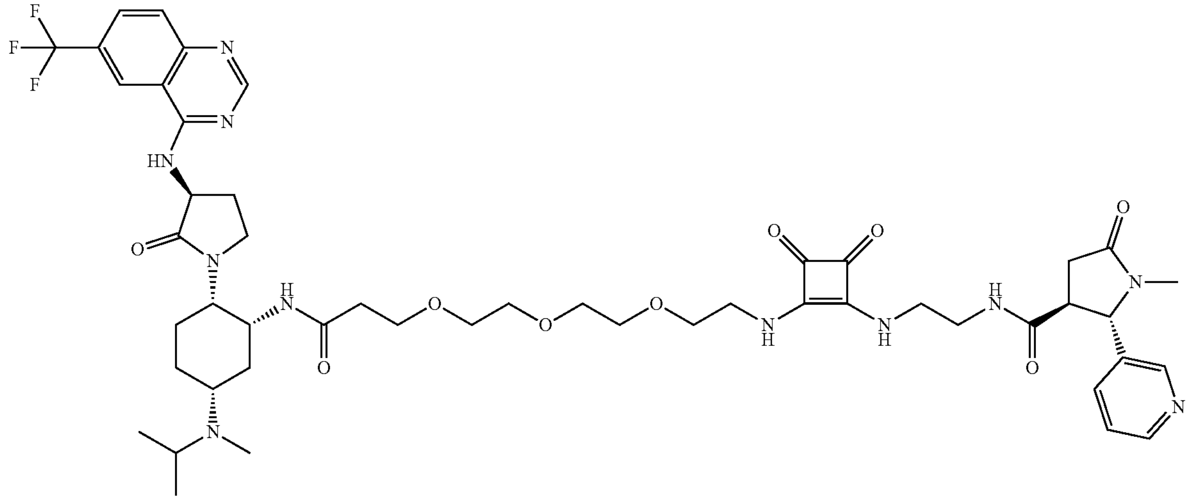 [SMILES: CC(C)N(C)[C@@H]1CC[C@H](N2CC[C@H](Nc3ncnc4ccc(C(F)(F)F)cc34)C2=O)[C@H](NC(=O)CCOCCOCCOCCNc2c(NCCNC(=O)[C@H]3CC(=O)N(C)[C@@H]3c3cccnc3)c(=O)c2=O)C1]

Step 1

3-(2-(2-(2-((2-Ethoxy-3,4-dioxocyclobut-1-en-1-yl)amino)ethoxy)ethoxy)ethoxy) propanoic acid

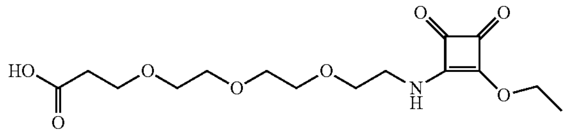 [SMILES: CCOc1c(NCCOCCOCCOCCC(=O)O)c(=O)c1=O]

To 3,4-diethoxycyclobut-3-ene-1,2-dione (300 mg, 1.763 mmol) in methanol at −5° C. was added 3-(2-(2-(2-aminoethoxy)ethoxy)ethoxy)propanoic acid (390 mg, 1.763 mmol) in methanol and DIPEA (924 μL, 5.29 mmol). The mixture was stirred at rt for 2 h and was concentrated under reduced pressure to provide the title compound (600 mg, 1.633 mmol, 93% yield). LC-MS m/z 346.1 $(M+H)^+$.

Step 2

3-(2-(2-(2-((2-Ethoxy-3,4-dioxocyclobut-1-en-1-yl)amino)ethoxy)ethoxy)ethoxy)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)propenamide

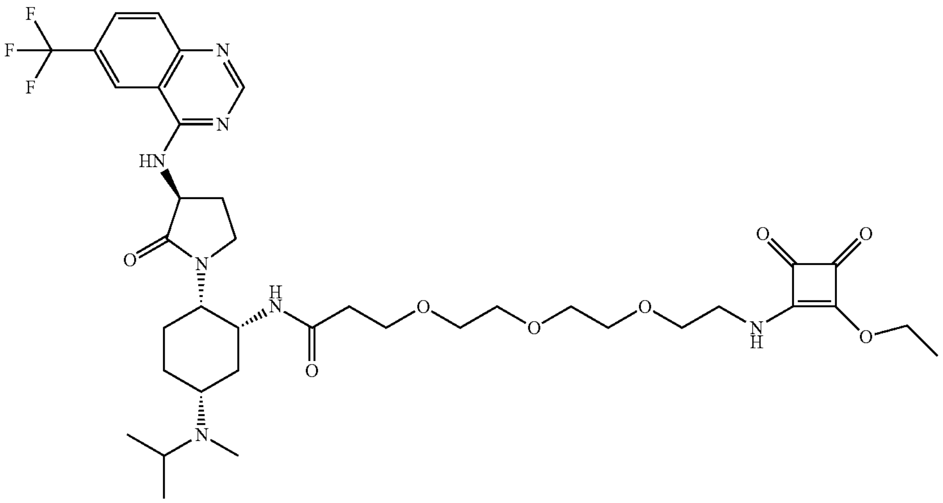 [SMILES: CCOc1c(NCCOCCOCCOCCC(=O)N[C@@H]2C[C@H](N(C)C(C)C)CC[C@@H]2N2CC[C@H](Nc3ncnc4ccc(C(F)(F)F)cc34)C2=O)c(=O)c1=O]

To a mixture of (S)-1-((1S,2R,4R)-2-amino-4-(isopropyl (methyl)amino)cyclohexyl)-3-((6-(trifluoromethyl)quinazolin-4-yl)amino)pyrrolidin-2-one, 2Hydrochloric acid salt (861 mg, 1.5 mmol), 3-(2-(2-(2-((2-ethoxy-3,4-dioxocyclobut-1-en-1-yl)amino)ethoxy)ethoxy)ethoxy) propanoic acid (518 mg, 1.500 mmol), and DIPEA (2.62 mL, 15.00 mmol) in dichloromethane (DCM) (5 mL) was added T3P (1.161 mL, 1.950 mmol). The mixture was stirred at rt for 2 h. Dichloromethane (DCM) (10 mL) and water (10 mL) were added. The organic phase was dried over $Na_2SO_4$, was filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as a white solid (354 mg, 0.443 mmol, 29.5% yield). LC-MS m/z 792.4 $(M+H)^+$.

Step 3

(2S,3S)-N-(2-((2-((2-(2-(2-(3-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)amino)-3-oxopropoxy)ethoxy)ethoxy) ethyl)amino)-3,4-dioxocyclobut-1-en-1-yl)amino) ethyl)-1-methyl-5-oxo-2-(pyridin-3-yl)pyrrolidine-3-carboxamide A mixture of 3-(2-(2-(2-((2-ethoxy-3,4-dioxocyclobut-1-en-1-yl)amino)ethoxy)ethoxy)ethoxy)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl) propanamide (50 mg, 0.063 mmol), (2S,3S)-N-(2-aminoethyl)-1-methyl-5-oxo-2-(pyridin-3-yl)pyrrolidine-3-carboxamide (16.56 mg, 0.063 mmol), and DIPEA (0.014 mL, 0.082 mmol) in methanol (3 mL) was stirred at 60° C. for 20 h. The mixture was cooled and was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as a light-brown solid (30 mg, 0.028 mmol, 44.8% yield). LC-MS m/z 1008.5 $(M+H)^+$. $^1H$ NMR (400 MHz, METHANOL-$d_4$) δ ppm 1.04 (d, J=6.4 Hz, 3H) 1.13 (br d, J=6.4 Hz, 3H) 1.59-1.78 (m, 3H) 1.88-2.05 (m, 2H) 2.05-2.25 (m, 3H) 2.27 (s, 3H) 2.28-2.37 (m, 1H) 2.41-2.64 (m, 4H) 2.64-2.71 (m, 3H) 2.74 (br s, 1H) 2.79-2.86 (m, 1H) 2.93-3.05 (m, 1H) 3.15-3.31 (m, 1H) 3.35-3.46 (m, 3H) 3.47-3.75 (m, 17H) 3.78-3.83 (m, 1H) 4.02-4.08 (m, 1H) 4.65 (br d, J=2.9 Hz, 1H) 4.79-4.83 (m, 1H) 5.30 (t, J=8.1 Hz, 1H) 7.50 (dd, J=8.3, 4.9 Hz, 1H) 7.78 (dt, J=8.3, 2.0 Hz, 1H) 7.90 (d, J=8.8 Hz, 1H) 8.06 (dd, J=8.8, 2.0 Hz, 1H) 8.49 (d, J=2.0 Hz, 1H) 8.56 (dd, J=4.9, 1.5 Hz, 1H) 8.58-8.64 (m, 1H) 8.83 (s, 1H).

The following compound was or could be prepared with procedures analogous to that described in Example 168:

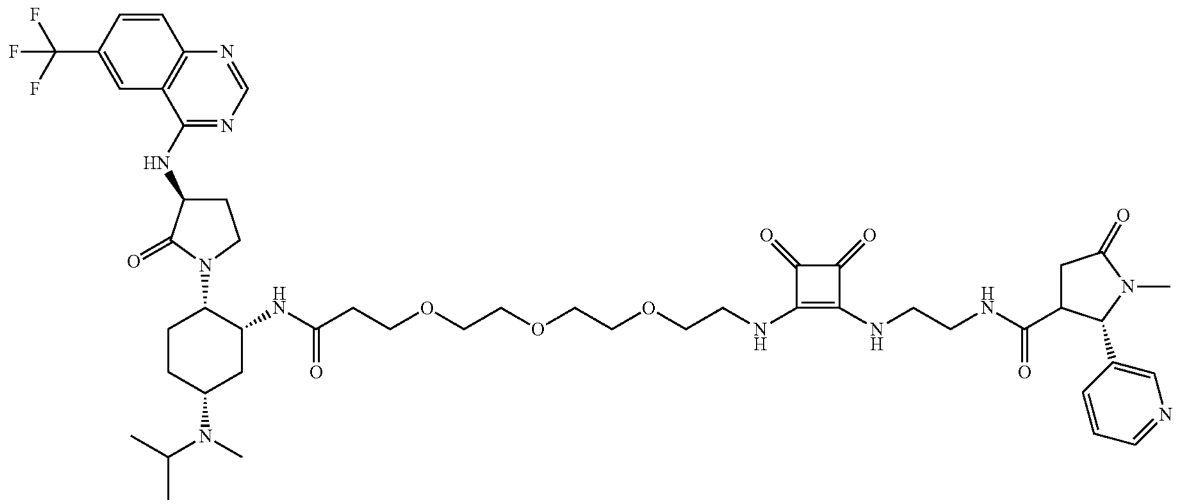 [SMILES: CC(C)N(C)[C@@H]1CC[C@H](N2CC[C@H](Nc3ncnc4ccc(C(F)(F)F)cc34)C2=O)[C@H](NC(=O)CCOCCOCCOCCNc2c(NCCNC(=O)C3CC(=O)N(C)[C@@H]3c3cccnc3)c(=O)c2=O)C1]

| Ex. | Compound | LC-MS m/z | NMR |
|---|---|---|---|
| 169 | 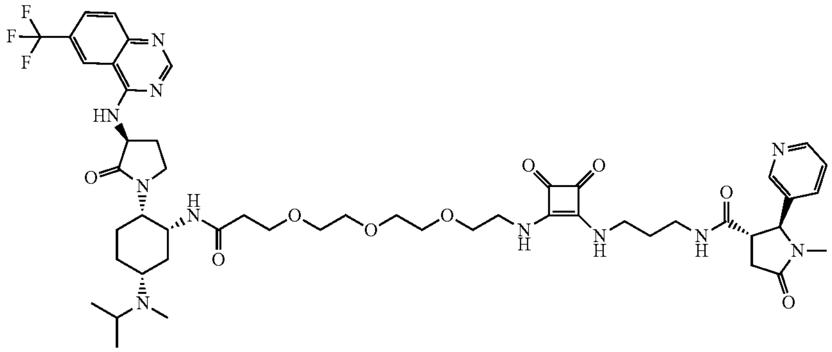 [SMILES: CC(C)N(C)[C@@H]1CC[C@H](N2CC[C@H](Nc3ncnc4ccc(C(F)(F)F)cc34)C2=O)[C@H](NC(=O)CCOCCOCCOCCNc2c(NCCCNC(=O)[C@H]3CC(=O)N(C)[C@@H]3c3cccnc3)c(=O)c2=O)C1] (2S,3S)-N-(3-((2-((2-(2-(2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethoxy)ethoxy)ethyl)amino)-3,4-dioxocyclobut-1-en-1-yl)amino)propyl)-1-methyl-5-oxo-2-(pyridin-3-yl)pyrrolidine-3-carboxamide. | 1022.6 (M + H)+ | $^1$H NMR (400 MHz, METHANOL-$d_4$) δ ppm 0.98-1.18 (m, 6H) 1.26-1.41 (m, 1H) 1.75 (s, 5H) 2.27 (s, 8H) 2.45-2.59 (m, 3H) 2.67 (s, 5H) 2.82-2.92 (m, 1H) 3.00-3.07 (m, 1H) 3.22-3.30 (m, 1H) 3.49-3.65 (m, 14H) 3.65-3.85 (m, 6H) 4.01-4.10 (m, 1H) 4.62-4.67 (m, 1H) 4.85 (d, J = 6.4 Hz, 1H) 5.31 (t, J = 8.3 Hz, 1H) 7.36-7.61 (m, 1H) 7.92 (s, 2H) 8.05 (d, J = 2.0 Hz, 1H) 8.48-8.64 (m, 3H) 8.83 (s, 1H). |

Example 170

N-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-3-(2-((2S,3S)-1-methyl-5-oxo-2-(pyridin-3-yl)pyrrolidine-3-carboxamido) ethyl)-3-azaspiro[5.5]undecane-9-carboxamide

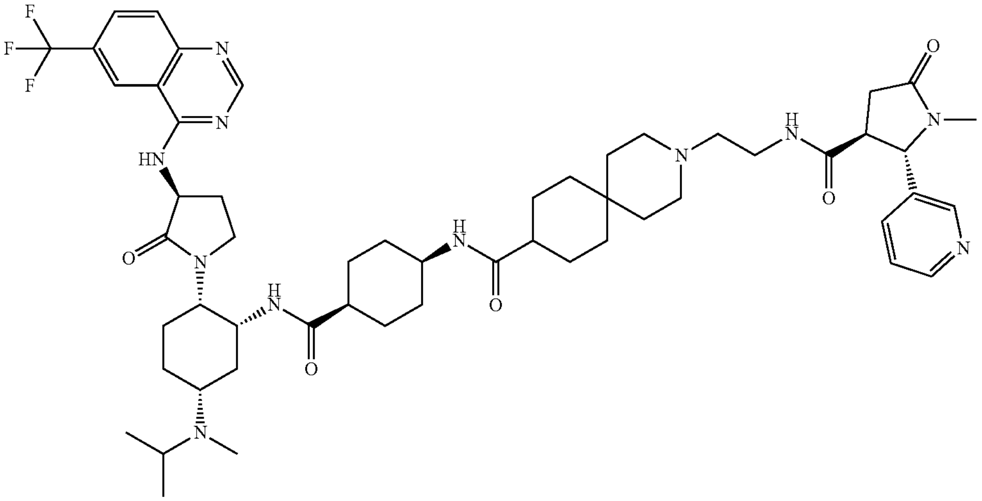 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CC3)CCN(CCNC(=O)[C@H]3CC(=O)N(C)[C@@H]3c3cccnc3)CC4)CC2)C1]

Step 1 tert-Butyl 9-(((1S,4s)-4-(((1R,2S,5R)-5-(isopropyl (methyl)am i no)-2-((S)-2-oxo-3-((6-(trifluoromethyl)quinazolin-4-yl)amino)pyrrolidin-1-yl)cyclohexyl)carbamoyl) cyclohexyl)carbamoyl)-3-azaspiro [5.5]undecane-3-carboxylate

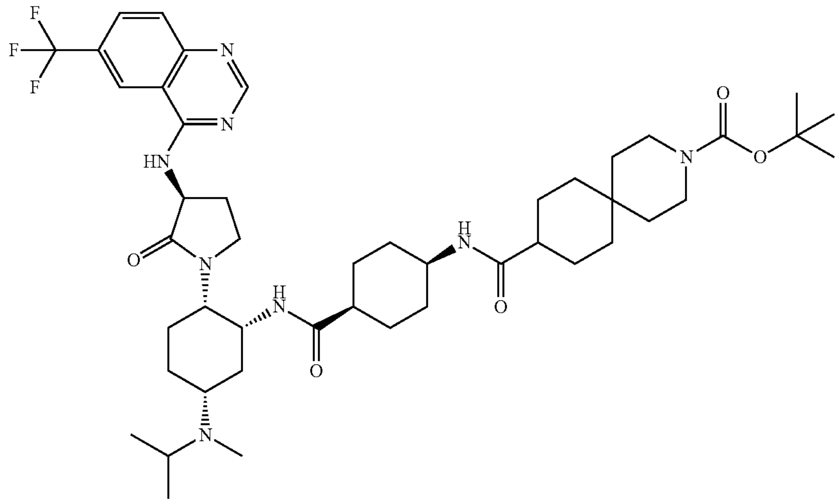 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CC3)CCN(C(=O)OC(C)(C)C)CC4)CC2)C1]

To a mixture of (1 s,4S)-4-amino-N-((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)cyclohexane-1-carboxamide, 2Hydrochloric acid salt (80 mg, 0.121 mmol) in dichloromethane (DCM) (0.5 mL) was added triethylamine (0.101 mL, 0.724 mmol), followed by 3-(tert-butoxycarbonyl)-3-azaspiro[5.5]undecane-9-carboxylic acid (35.9 mg, 0.121 mmol) and HATU (55.1 mg, 0.145 mmol). The mixture was stirred at rt for 2 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound as a solid (75 mg, 0.086 mmol, 71.5% yield). LC-MS m/z 869.3 $(M+H)^+$. LC-MS: N67608-77-A1: m/z 869.3 $(M+H)^+$, 0.80 min (ret. time).

Step 2

N-((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-3-azaspiro[5.5]undecane-9-carboxamide, 2Hydrochloric acid salt

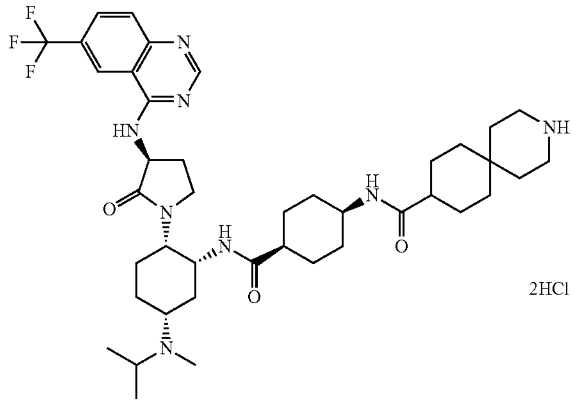 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CCNCC4)CC3)CC2)C1]

4 M HCl in 1,4-dioxane (0.170 mL, 0.681 mmol) was added to a mixture of tert-butyl 9-(((1 S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)carbamoyl)-3-azaspiro[5.5]undecane-3-carboxylate (74 mg, 0.085 mmol) in dichloromethane (DCM) (0.1 mL). the mixture was stirred at rt for 3 h and was concentrated to dryness to provide the title compound as a solid (81 mg, 0.096 mmol, 113% yield). LC-MS m/z 769.4 $(M+H)^+$.

Step 3 tert-Butyl (2-(9-(((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)carbamoyl)-3-azaspiro[5.5]undecan-3-yl)ethyl)carbamate

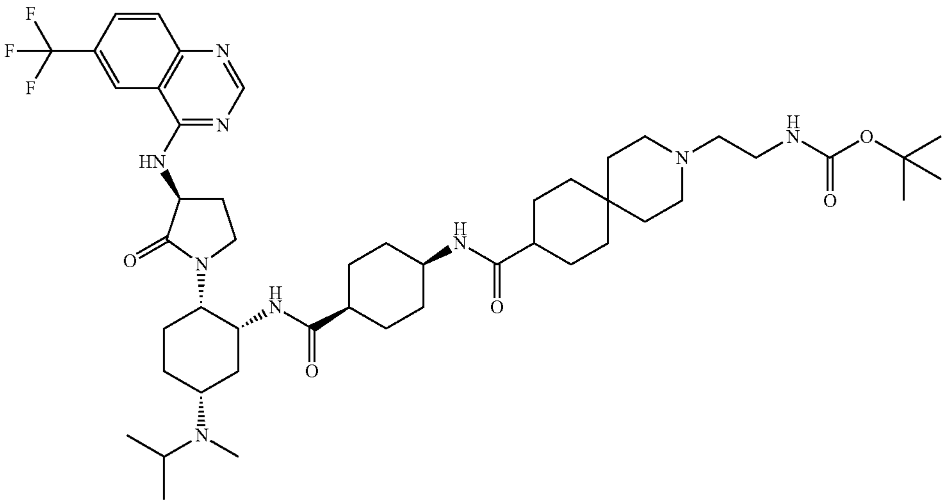 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CC3)CCN(CCNC(=O)OC(C)(C)C)CC4)CC2)C1]

A mixture of N-((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)-3-azaspiro[5.5]undecane-9-carboxamide, 2Hydrochloric acid salt (50 mg, 0.059 mmol), tert-butyl (2-bromoethyl)carbamate (13.31 mg, 0.059 mmol) and potassium carbonate (24.62 mg, 0.178 mmol) in acetonitrile (1 mL) was stirred at rt over the weekend and at 80° C. for 4 h. Water was added and the mixture was extracted with dichloromethane (DCM). The combined organic extracts were dried over $Na_2SO_4$, were filtered, and the filtrate was concentrated. Purification by ISCO CombiFlash® chromatography (4 g RediSep Rf Gold® column, 18 mL/min) eluting with a gradient of 0 to 15% methanol containing ammonium hydroxide (10%) in dichloromethane (DCM) provided the title compound (28 mg, 0.031 mmol, 51.7% yield). LC-MS m/z 912.4 $(M+H)^+$.

Step 4

N-((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)-3-(2-((2S,3S)-1-methyl-5-oxo-2-(pyridin-3-yl)pyrrolidine-3-carboxamido)ethyl)-3-azaspiro[5.5]undecane-9-carboxamide 4 M HCl in 1,4-dioxane (0.038 mL, 0.153 mmol) was added to a mixture of tert-butyl (2-(9-(((1 S,4s)-4-(((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl) carbamoyl)-3-azaspiro[5.5]undecan-3-yl)ethyl)carbamate (28 mg, 0.031 mmol) in dichloromethane (DCM) (0.1 mL). The mixture was stirred at rt for 2 h and was concentrated to dryness. To the residue was added dichloromethane (DCM) (0.1 mL), (2S,3S)-1-methyl-5-oxo-2-(pyridin-3-yl)pyrrolidine-3-carboxylic acid (6.76 mg, 0.031 mmol), triethylamine (0.021 mL, 0.153 mmol), and HATU (14.01 mg, 0.037 mmol). The mixture was stirred at rt for 3 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (19.9 mg, 0.020 mmol, 63.9% yield). LC-MS m/z 1014.8 $(M+H)^+$. $^1H$ NMR (400 MHz, METHANOL-$d_4$) δ ppm 0.97-1.08 (m, 4H) 1.12-1.20 (m, 3H) 1.29-1.38 (m, 2H) 1.44-1.87 (m, 18H) 1.90-2.03 (m, 1H) 2.07-2.15 (m, 1H) 2.17-2.33 (m, 6H) 2.41-2.59 (m, 6H) 2.64-2.77 (m, 5H) 2.80-2.89 (m, 1H) 2.98-3.07 (m, 1H) 3.35-3.37 (m, 1H) 3.42-3.58 (m, 2H) 3.60-3.72 (m, 1H) 3.82-3.89 (m, 1H) 3.97-4.05 (m, 1H) 4.56-4.66 (m, 1H) 4.81-4.86 (m, 1H) 5.26-5.34 (m, 1H) 7.51-7.58 (m, 1H) 7.78-7.85 (m, 1H) 7.89-7.95 (m, 1H) 8.03-8.11 (m, 1H) 8.51-8.54 (m, 1H) 8.57-8.62 (m, 2H) 8.71-8.75 (m, 1H).

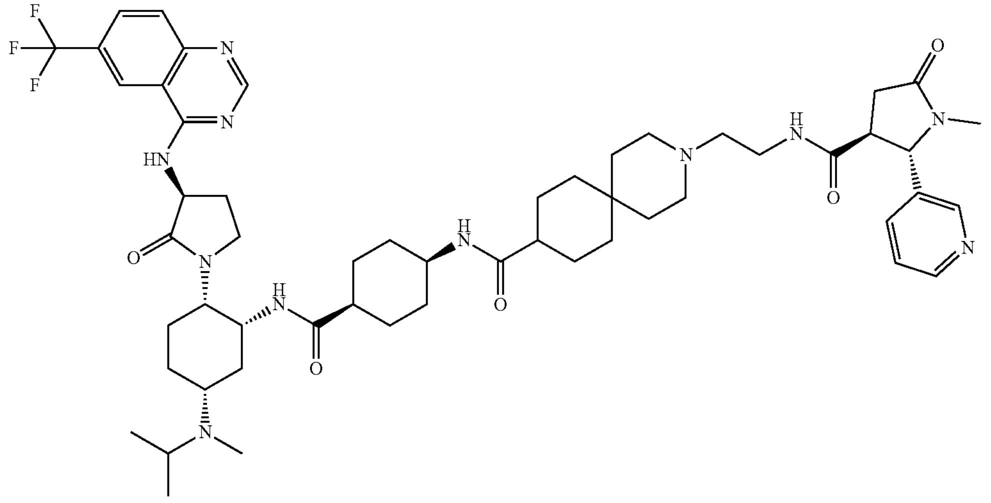 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)C3CCC4(CC3)CCN(CCNC(=O)[C@H]3CC(=O)N(C)[C@@H]3c3cccnc3)CC4)CC2)C1]

Example 171

(2S,3S)-N-(2-((2-(2-(2-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-2-oxoethoxy)ethoxy)ethyl)amino)-2-oxoethyl)-1-methyl-5-oxo-2-(pyridin-3-yl)pyrrolidine-3-carboxamide

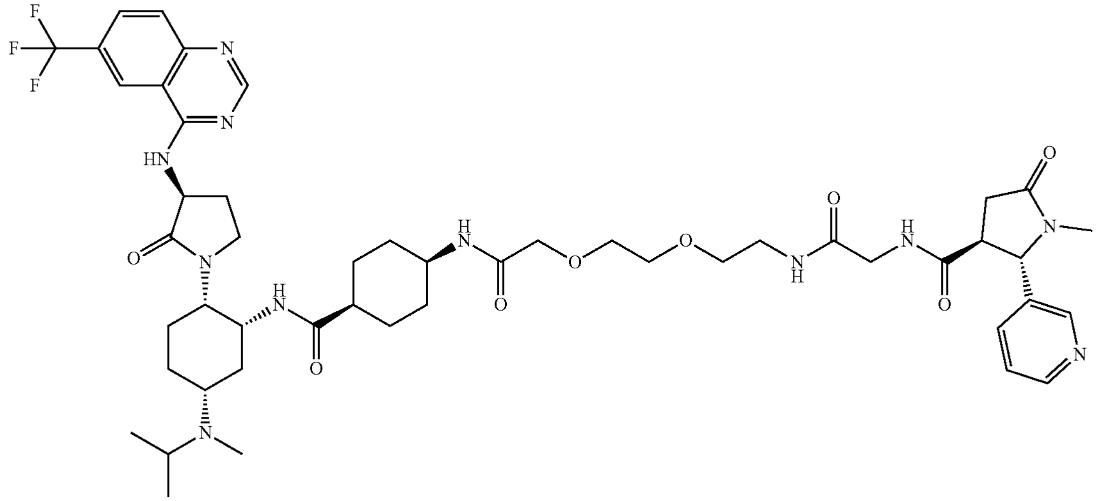 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCOCCNC(=O)CNC(=O)[C@H]3CC(=O)N(C)[C@@H]3c3cccnc3)CC2)C1]

Step 1 tert-Butyl 3,6-dioxo-1-phenyl-2,10,13-trioxa-4,7-diazapentadecan-15-oate

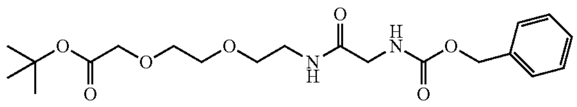 [SMILES: CC(C)(C)OC(=O)COCCOCCNC(=O)CNC(=O)OCc1ccccc1]

To a solution of tert-butyl 2-(2-(2-aminoethoxy)ethoxy) acetate (240 mg, 1.094 mmol), ((benzyloxy)carbonyl)glycine (252 mg, 1.204 mmol), HOBt (201 mg, 1.313 mmol) and EDC (315 mg, 1.642 mmol) was added DIPEA (0.956 mL, 5.47 mmol), and the mixture was stirred overnight and water was added. The mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a light-colored wax (360 mg, 0.877 mmol, 80% yield). LC-MS m/z 411.2 $(M+H)^+$.

Step 2 tert-Butyl 2-(2-(2-(2-aminoacetamido)ethoxy) ethoxy)acetate

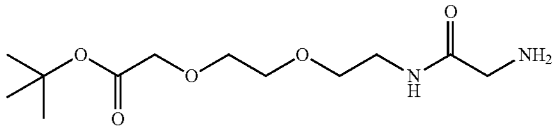 [SMILES: CC(C)(C)OC(=O)COCCOCCNC(=O)CN]

To a solution of tert-butyl 3,6-dioxo-1-phenyl-2,10,13-trioxa-4,7-diazapentadecan-15-oate (360 mg, 0.877 mmol) in ethyl acetate (10 mL) under an atmosphere of nitrogen was added 10% Pd—C, Degussa type (9.33 mg, 0.088 mmol). The mixture was vacuumed and was backfilled with hydrogen (3×) and was stirred under a balloon atmosphere of hydrogen for 4 h. The mixture was filtered through Celite® and the filtrate was concentrated to provide the title compound as a wax (242 mg, 0.876 mmol, 100% yield). LC-MS m/z 277.3 $(M+H)^+$.

Step 3 tert-Butyl 1-((2S,3S)-1-methyl-5-oxo-2-(421 yrrolid-3-yl) 421 yrrolidine-3-yl)-1,4-dioxo-8,11-dioxa-2,5-diazatridecan-13-oate

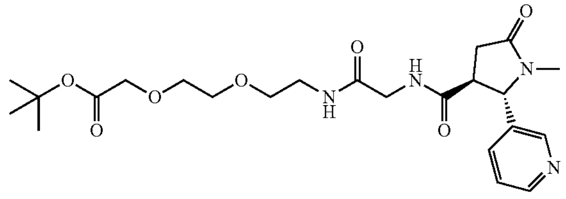 [SMILES: CN1C(=O)C[C@H](C(=O)NCC(=O)NCCOCCOCC(=O)OC(C)(C)C)[C@H]1c1cccnc1]

To a solution of (2S,3S)-1-methyl-5-oxo-2-(421 yrrolid-3-yl) pyrrolidine-3-carboxylic acid (123 mg, 0.557 mmol), HOBt (102 mg, 0.669 mmol), EDC (160 mg, 0.836 mmol) and tert-butyl 2-(2-(2-(2-aminoacetamido)ethoxy)ethoxy) acetate (154 mg, 0.557 mmol) in dichloromethane (DCM) (5.0 mL) was added DIPEA (0.487 mL, 2.79 mmol). The mixture was stirred overnight and saturated $NaHCO_3$ was added. The mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a wax (130 mg, 0.272 mmol, 48.7% yield). LC-MS m/z 479.4 $(M+H)^+$.

Step 4

(2S,3S)-N-(2-((2-(2-(2-(((1S,4s)-4-(((1R,2S,5R)-5-(Isopropyl(methyl)amino)-2-((S)-2-oxo-3-((6-(trifluoromethyl)quinazolin-4-yl)amino)$_{421}$yrrolidine-1-yl)cyclohexyl) carbamoyl)cyclohexyl)amino)-2-oxoethoxy)ethoxy)ethyl)amino)-2-oxoethyl)-1-methyl-5-oxo-2-(421 yrrolid-3-yl)pyrrolidine-3-carboxamide

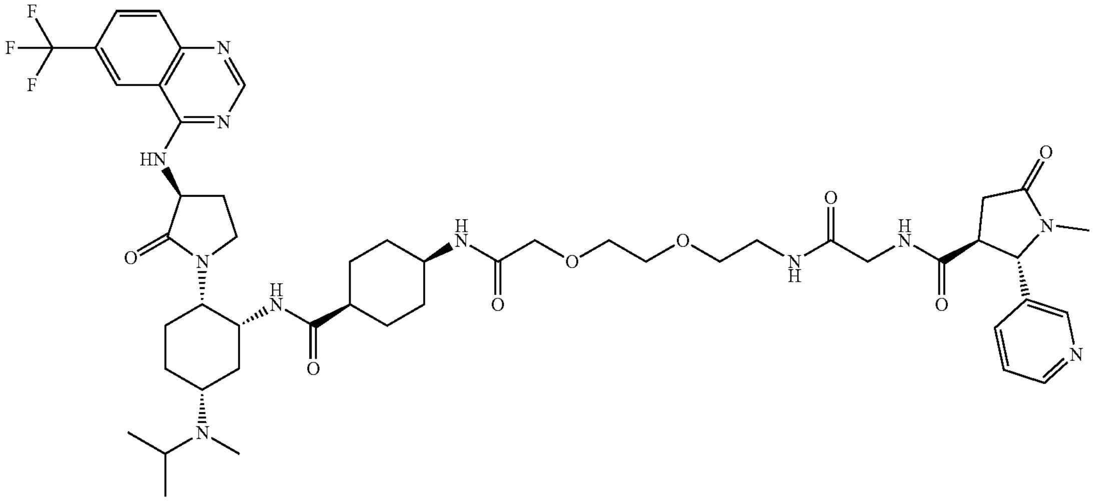 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCOCCNC(=O)CNC(=O)[C@H]3CC(=O)N(C)[C@@H]3c3cccnc3)CC2)C1]

4 M HCl in 1,4-dioxane (4 mL, 16.00 mmol) was added to a solution of tert-butyl 1-((2S,3S)-1-methyl-5-oxo-2-(421 yrrolid-3-yl)$_{421}$ yrrolidine-3-yl)-1,4-dioxo-8,11-dioxa-2,5-diazatridecan-13-oate (48 mg, 0.100 mmol) in dichloromethane (DCM) (2.0 mL). The mixture was stirred for 1 hour and was concentrated to dryness. To the residue in dichloromethane (DCM) (2.0 mL) was added (1 s,4S)-4-amino-N-((1R,2S,5R)-5-(isopropyl(methyl)amino)-2-((S)-2-oxo-3-((6-(trifluoromethyl)quinazolin-4-yl)amino)$_{422}$yrrolidine-1-yl)cyclohexyl)cyclohexane-1-carboxamide, 2Hydrochloric acid salt (66.5 mg, 0.100 mmol), HOBt (15.36 mg, 0.100 mmol) and DIPEA (0.088 mL, 0.502 mmol), followed by EDC (28.8 mg, 0.150 mmol). The mixture was stirred at rt overnight and saturated $NaHCO_3$ was added. The mixture was extracted with dichloromethane (DCM) (3×). The combined organic extracts were washed with brine (2×), were dried over $Na_2SO_4$, were filtered, and the filtrate was concentrated. Purification by MDAP chromatography (Xselect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (18.7 mg, 0.018 mmol, 17.82% yield). LC-MS m/z 994.7 $(M+H)^+$. $^1H$ NMR (400 MHz, DMSO-$d_6$) δ ppm 0.86-0.92 (m, 3H) 1.02-1.07 (m, 3H) 1.43-1.71 (m, 11H) 1.88-2.07 (m, 2H) 2.09-2.17 (m, 5H) 2.31-2.38 (m, 1H) 2.41-2.48 (m, 1H) 2.56-2.61 (m, 2H) 2.66-2.70 (m, 1H) 2.71-2.79 (m, 1H) 3.00-3.08 (m, 1H) 3.16-3.32 (m, 3H) 3.36-3.58 (m, 9H) 3.66-3.70 (m, 2H) 3.74-3.78 (m, 1H) 3.79-3.83 (m, 2H) 3.84-3.90 (m, 1H) 4.38-4.46 (m, 1H) 4.66-4.71 (m, 1H) 4.99-5.08 (m, 1H) 7.25-7.31 (m, 1H) 7.40-7.46 (m, 1H) 7.67-7.72 (m, 1H) 7.87-7.94 (m, 2H) 8.04-8.10 (m, 1H) 8.20-8.26 (m, 1H) 8.48-8.52 (m, 1H) 8.54-8.56 (m, 1H) 8.57-8.58 (m, 1H) 8.67-8.73 (m, 2H) 8.86-8.90 (m, 1H).

Example 172

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1'-(3-(2-(2-((2S,3S)-1-methyl-5-oxo-2-(pyridin-3-yl)pyrrolidine-3-carboxamido)ethoxy)ethoxy)propanoyl)-[1,4'-bipiperidine]-4-carboxamide

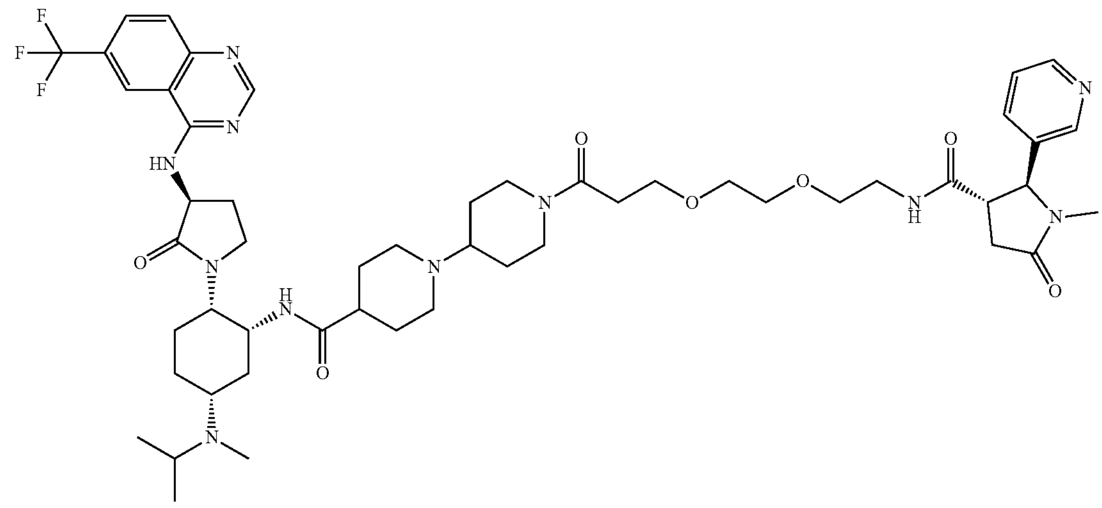 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C(=O)CCOCCOCCNC(=O)[C@H]4CC(=O)N(C)[C@@H]4c4cccnc4)CC3)CC2)C1]

Step 1 tert-butyl 3-(2-(2-((2S,3S)-1-methyl-5-oxo-2-(pyridin-3-yl)pyrrolidine-3-carboxamido)ethoxy)ethoxy) propanoate, Trifluoroacetic acid salt

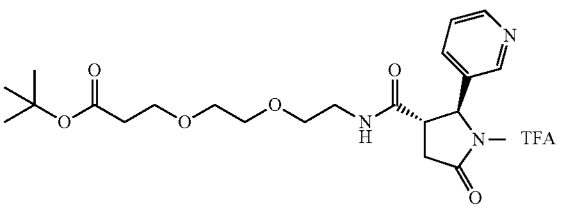 [SMILES: CN1C(=O)C[C@H](C(=O)NCCOCCOCCC(=O)OC(C)(C)C)[C@H]1c1cccnc1]

To a solution of tert-butyl 3-(2-(2-aminoethoxy)ethoxy) propanoate (1001 mg, 4.29 mmol) in dichloromethane (DCM) (35 mL) was added triethylamine (1.495 mL, 10.73 mmol), followed by (2S,3S)-1-methyl-5-oxo-2-(pyridin-3-yl) pyrrolidine-3-carboxylic acid (945 mg, 4.29 mmol) and HATU (1958 mg, 5.15 mmol). The mixture was stirred at rt overnight and was concentrated. Purification by MDAP chromatography (XSelect™ CSH Prep C18 150 mm×30 mm 5 μm OBD column, 40 mL/min) eluting with a gradient of 15 to 55% acetonitrile in water both containing trifluoroacetic acid (0.1%) provided the title compound as a pale-yellow liquid (2.22 g, 3.84 mmol, 89% yield). LC-MS m/z 436.3 $(M+H)^+$.

Step 2

N-((1R,2S,5R)-5-(Isopropyl(methyl)amino)-2-((S)-2-oxo-3-((6-(trifluoro methyl) quinazolin-4-yl) amino)pyrrolidin-1-yl)cyclohexyl)-1'-(3-(2-(2-((2S,3S)-1-methyl-5-oxo-2-(pyridin-3-yl)pyrrolidine-3-carboxamido)ethoxy)ethoxy)propanoyl)-[1,4'-bipiperidine]-4-carboxamide

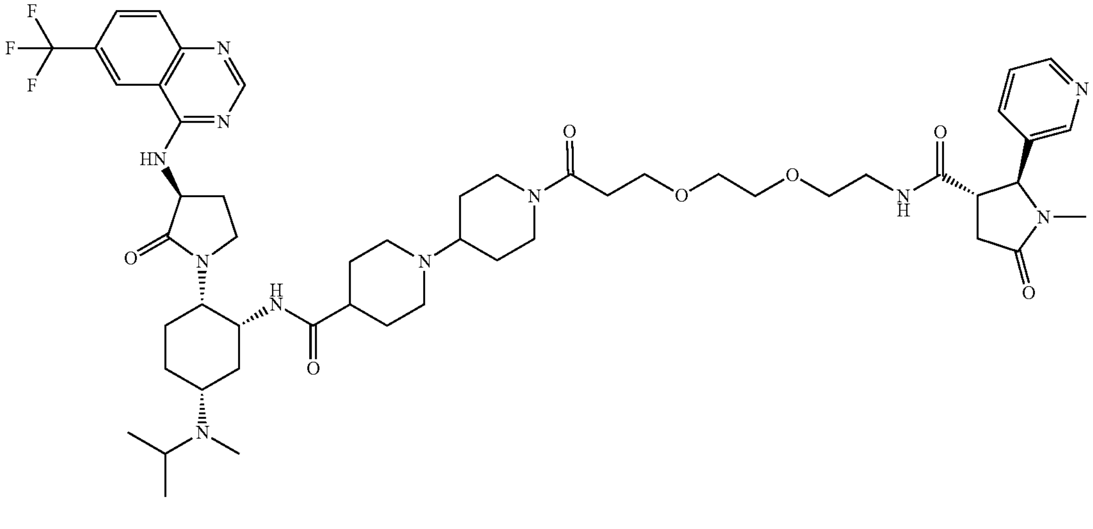 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C(=O)CCOCCOCCNC(=O)[C@H]4CC(=O)N(C)[C@@H]4c4cccnc4)CC3)CC2)C1]

4 M HCl in 1,4-dioxane (0.5 mL, 2.000 mmol) was added to a solution of tert-butyl 4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)-[1,4'-bipiperidine]-1'-carboxylate (82 mg, 0.108 mmol) in dichloromethane (DCM) (1.5 mL). The mixture was stirred at rt for 1 h and was concentrated to dryness. The solid residue was suspended in dichloromethane (DCM) (3 mL) and triethylamine (0.05 mL).

4 M HCl in 1,4-dioxane (0.5 mL, 2.000 mmol) was added to tert-butyl 3-(2-(2-((2S,3S)-1-methyl-5-oxo-2-(pyridin-3-yl)pyrrolidine-3-carboxamido)ethoxy)ethoxy)propanoate (56.5 mg, 0.130 mmol). The mixture was stirred at rt for 1 h and was concentrated. The residue was triturated with ether and was dissolved in dichloromethane (DCM) (2 mL) and triethylamine (0.05 mL). The solution was added to the above amine solution, HATU (61.6 mg, 0.162 mmol) was added, the mixture was stirred at rt for 1 h, and was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as a white solid (100.7 mg, 0.097 mmol, 90% yield). LC-MS m/z 1020.2 $(M+H)^+$. $^1H$ NMR (400 MHz, METHANOL-$d_4$) δ ppm 0.95-1.05 (m, 3H) 1.11-1.18 (m, 3H) 1.27-1.51 (m, 2H) 1.63-1.78 (m, 5H) 1.81-1.98 (m, 6H) 2.10-2.16 (m, 2H) 2.17-2.25 (m, 3H) 2.26-2.28 (m, 3H) 2.30-2.35 (m, 1H) 2.51-2.59 (m, 3H) 2.60-2.65 (m, 2H) 2.66-2.68 (m, 3H) 2.70-2.75 (m, 2H) 2.80-2.89 (m, 1H) 2.97-3.14 (m, 4H) 3.30-3.36 (m, 2H) 3.48-3.58 (m, 7H) 3.59-3.65 (m, 1H) 3.69-3.75 (m, 2H) 3.99-4.08 (m, 2H) 4.50-4.59 (m, 1H) 4.63-4.69 (m, 1H) 4.82-4.85 (m, 1H) 5.25-5.34 (m, 1H) 7.50-7.56 (m, 1H) 7.78-7.83 (m, 1H) 7.89-7.93 (m, 1H) 8.04-8.09 (m, 1H) 8.51-8.54 (m, 1H) 8.57-8.59 (m, 1H) 8.59-8.61 (m, 1H) 8.75-8.80 (m, 1H).

Example 173

$N^1$-((1R,2S,5R)-5-(Isopropyl(methyl)amino)-2-((S)-2-oxo-3-((6-(trifluoromethyl) quinazolin-4-yl) amino)pyrrolidin-1-yl)cyclohexyl)-N5-(3-(3-(4-((2S,3S)-1-methyl-5-oxo-2-(pyridin-3-yl)pyrrolidine-3-carboxamido)butanamido)propoxy)propyl) glutaramide

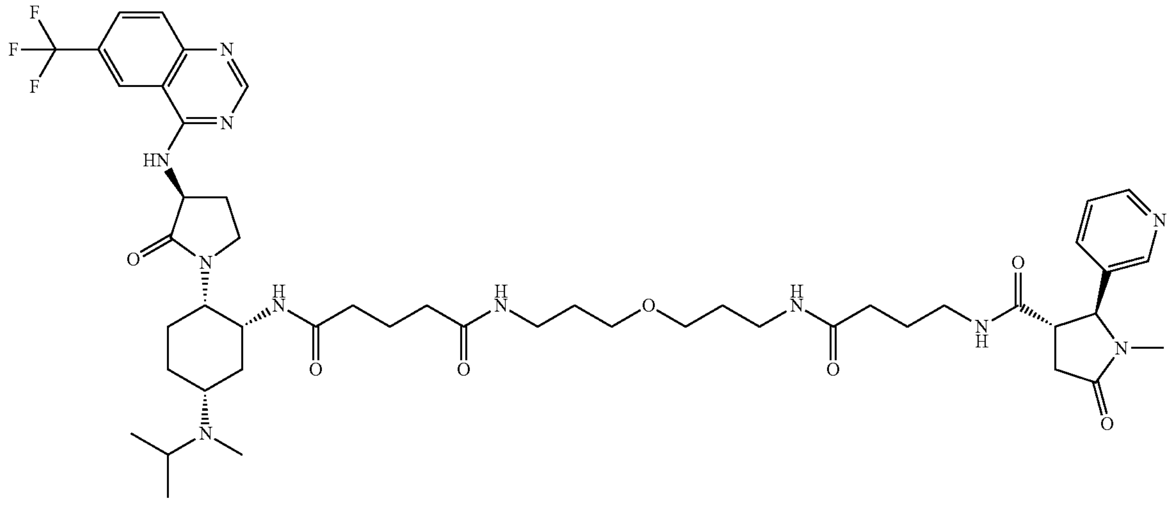 [SMILES: CC(C)N(C)[C@@H]1CC[C@H](N2CC[C@H](Nc3ncnc4ccc(C(F)(F)F)cc34)C2=O)[C@H](NC(=O)CCCC(=O)NCCCOCCCNC(=O)CCCNC(=O)[C@H]2CC(=O)N(C)[C@@H]2c2cccnc2)C1]

Step 1

N[1]-(3-(3-aminopropoxy)propyl)-N[5]-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)glutaramide

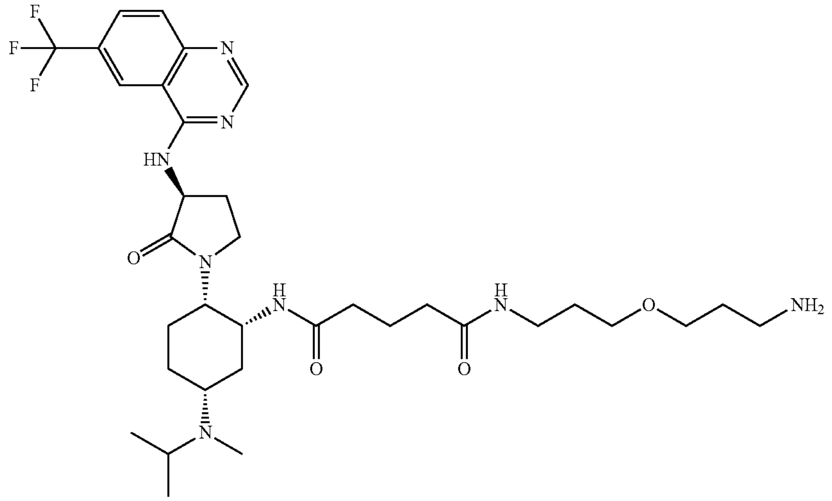 [SMILES: CC(C)N(C)[C@@H]1CC[C@H](N2CC[C@H](Nc3ncnc4ccc(C(F)(F)F)cc34)C2=O)[C@H](NC(=O)CCCC(=O)NCCCOCCCN)C1]

To a suspension of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2Hydrochloric acid salt (70 mg, 0.130 mmol) in dichloromethane (DCM) (3 mL) was added triethylamine (0.1 mL, 0.717 mmol), followed by dihydro-2H-pyran-2,6(3H)-dione (15 mg, 0.131 mmol). The solution was stirred at rt overnight. 3,3'-oxybis(propan-1-amine) (43 mg, 0.325 mmol) was added, followed by HATU (53 mg, 0.139 mmol). Dichloromethane (DCM) (1 mL) and N,N-dimethylformamide (DMF) (1.0 mL) were added to improve solubility. The mixture was stirred at rt for 2 h and was concentrated under reduced pressure. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as a white, foamy solid (44 mg, 0.060 mmol, 46.3% yield). LC-MS m/z 693.5 $(M+H)^+$.

Step 2 tert-Butyl (4-((3-(3-(5-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-5-oxopentanamido)propoxy)propyl)amino)-4-oxobutyl)carbamate

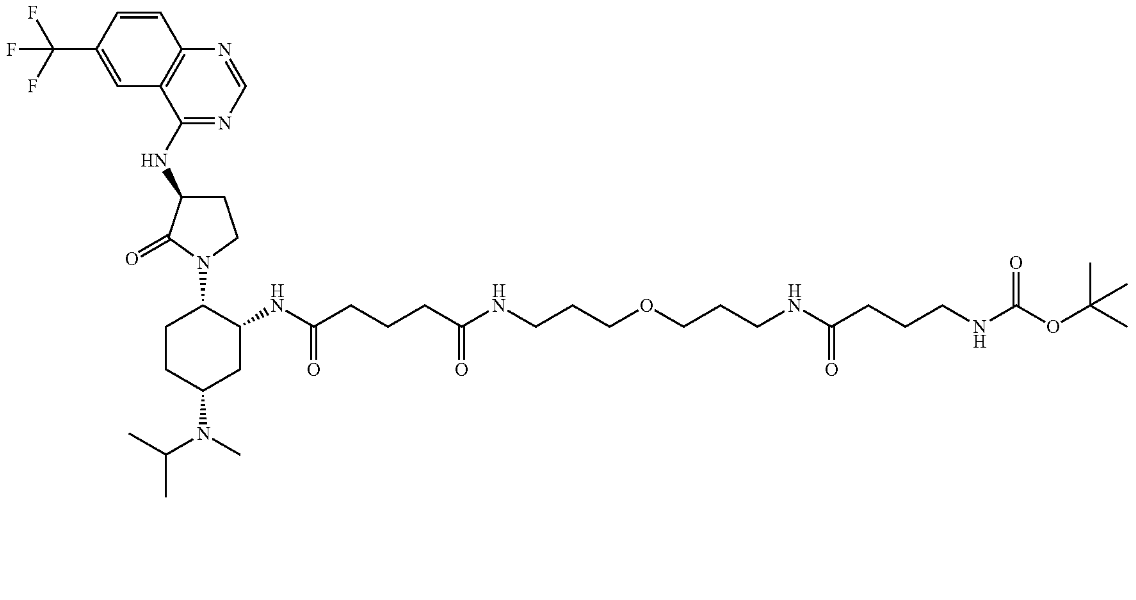 [SMILES: CC(C)N(C)[C@@H]1CC[C@H](N2CC[C@H](Nc3ncnc4ccc(C(F)(F)F)cc34)C2=O)[C@H](NC(=O)CCCC(=O)NCCCOCCCNC(=O)CCCNC(=O)OC(C)(C)C)C1]

To a suspension of $N^1$-(3-(3-aminopropoxy)propyl)-$N^5$-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)glutaramide (22 mg, 0.032 mmol) in dichloromethane (DCM) (3 mL) was added triethylamine (0.013 mL, 0.095 mmol), followed by 4-((tert-butoxycarbonyl)amino)butanoic acid (7.74 mg, 0.038 mmol) and HATU (18.11 mg, 0.048 mmol). N,N-Dimethylformamide (DMF) (1.0 mL) were added to improve solubility. The mixture was stirred at rt for 2 h and was concentrated under reduced pressure. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as a colorless film (23 mg, 0.026 mmol, 81% yield). LC-MS m/z 878.2 $(M+H)^+$.

Step 3

$N^1$-((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)-N5-(3-(3-(4-((2S,3S)-1-methyl-5-oxo-2-(pyridin-3-yl)pyrrolidine-3-carboxamido)butanamido)propoxy)propyl)glutaramide 3 M HCl in cyclopentyl methyl ether (0.2 mL, 0.600 mmol) was added to a solution of tert-butyl (4-((3-(3-(5-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-5-oxopentanamido) propoxy)propyl)amino)-4-oxobutyl)carbamate (23 mg, 0.026 mmol) in dichloromethane (DCM) (1 mL). The mixture was stirred at rt overnight and was concentrated. The residue was dissolved in dichloromethane (DCM) (2 mL) and triethylamine (0.018 mL, 0.131 mmol). (2S,3S)-1-methyl-5-oxo-2-(pyridin-3-yl)pyrrolidine-3-carboxylic acid (8.65 mg, 0.039 mmol) and HATU (14.94 mg, 0.039 mmol) were added. The resultant mixture was stirred at rt for 2 h and was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as a white solid (23.9 mg, 0.024 mmol, 91% yield). LC-MS m/z 980.3 $(M+H)^+$. $^1H$ NMR (400 MHz, METHANOL-$d_4$) δ ppm 1.03 (d, J=6.4 Hz, 3H) 1.13 (d, J=6.4 Hz, 3H) 1.64-1.81 (m, 9H) 1.86-2.06 (m, 3H) 2.09-2.32 (m, 12H) 2.49-2.65 (m, 1H) 2.66 (s, 3H) 2.68-2.78 (m, 2H) 2.77-2.89 (m, 1H) 2.95-3.06 (m, 1H) 3.11-3.30 (m, 6H) 3.36-3.48 (m, 5H) 3.51-3.69 (m, 2H) 4.04 (dt, J=12.0, 3.5 Hz, 1H) 4.60 (br d, J=2.9 Hz, 1H) 4.81-4.84 (m, 1H) 5.30 (t, J=8.6 Hz, 1H) 7.49-7.56 (m, 1H) 7.80 (dt, J=7.8, 2.0 Hz, 1H) 7.90 (d, J=8.8 Hz, 1H) 8.05 (dd, J=8.8, 2.0 Hz, 1H) 8.51 (d, J=1.5 Hz, 1H) 8.57 (dd, J=4.9, 1.5 Hz, 1H) 8.59 (s, 1H) 8.77 (s, 1H).

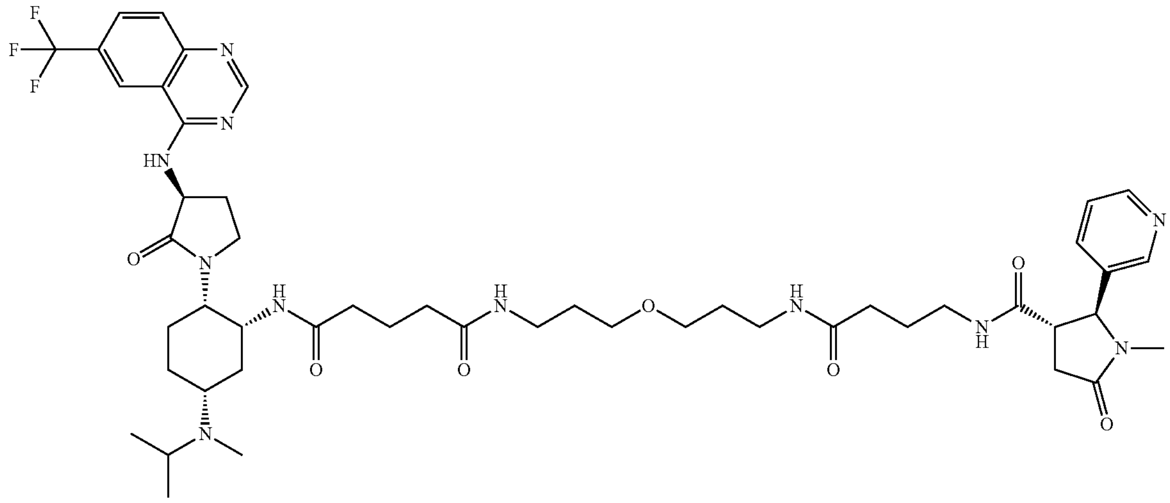 [SMILES: CC(C)N(C)[C@@H]1CC[C@H](N2CC[C@H](Nc3ncnc4ccc(C(F)(F)F)cc34)C2=O)[C@H](NC(=O)CCCC(=O)NCCCOCCCNC(=O)CCCNC(=O)[C@H]2CC(=O)N(C)[C@@H]2c2cccnc2)C1]

Example 175

(2S,3S)-N-(3-(2-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-3-oxopropoxy)ethyl)amino)-2-oxoethoxy)propyl)-1-methyl-5-oxo-2-(pyridin-3-yl)pyrrolidine-3-carboxamide

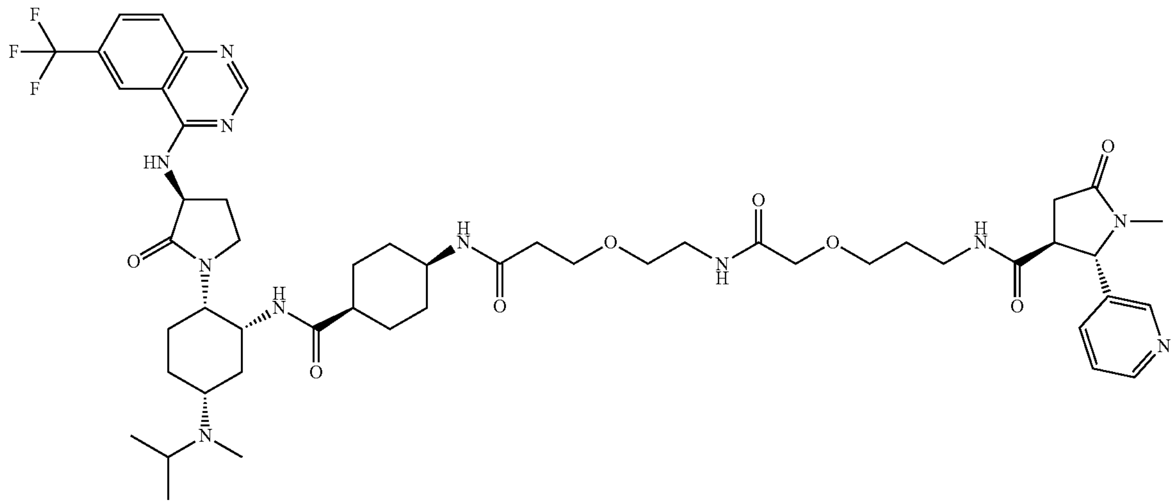 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)COCCCNC(=O)[C@H]3CC(=O)N(C)[C@@H]3c3cccnc3)CC2)C1]

Step 1 tert-Butyl 2-(3-(((benzyloxy)carbonyl)amino)propoxy)acetate

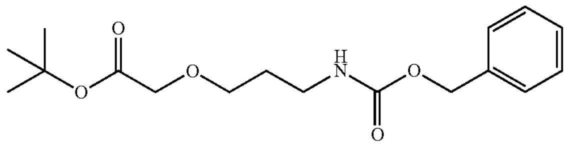 [SMILES: CC(C)(C)OC(=O)COCCCNC(=O)OCc1ccccc1]

To a solution of benzyl (3-hydroxypropyl)carbamate (11.5 g, 55.0 mmol) and tert-butyl 2-bromoacetate (21.44 g, 110 mmol) in toluene (200 mL) was added tetrabutylammonium hydrogen sulfate (9.33 g, 27.5 mmol). The reaction mixture was vigorously stirred, a solution of 30% sodium hydroxide (2.198 g, 55.0 mmol) in water (5.13 mL) was added slowly, and the mixture was stirred over the weekend. Water was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (220 g silica column, 150 mL/min) eluting with a gradient of 0 to 40% ethyl acetate in heptane provided the title compound as a colorless oil (3.53 g, 10.92 mmol, 19.86% yield). LC-MS m/z 346.1 $(M+H)^+$.

Step 2 tert-Butyl 3,10-dioxo-1-phenyl-2,8,14-trioxa-4,11-diazaheptadecan-17-oate

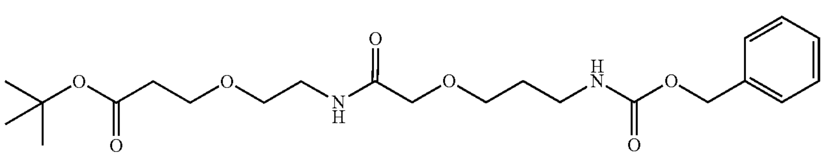 [SMILES: CC(C)(C)OC(=O)CCOCCNC(=O)COCCCNC(=O)OCc1ccccc1]

4 M HCl in 1,4-dioxane (10.0 mL, 40.0 mmol) was added to a solution of tert-butyl 2-(3-(((benzyloxy)carbonyl) amino)propoxy)acetate (636 mg, 1.966 mmol) in dichloromethane (DCM) (4.0 mL). The mixture was stirred overnight and was concentrated to dryness. The residue was dissolved in dichloromethane (DCM) (4.0 mL) and DIPEA (1.430 mL, 8.19 mmol), HOBt (301 mg, 1.966 mmol), tert-butyl 3-(2-aminoethoxy)propanoate (Example 167, Step 2) (310 mg, 1.638 mmol) were added, followed by EDC (471 mg, 2.457 mmol). The mixture was stirred overnight. Water was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a colorless oil (572 mg, 1.304 mmol, 80% yield). LC-MS m/z 439.2 $(M+H)^+$.

Step 3 tert-Butyl 3-(2-(2-(3-aminopropoxy)acetamido) ethoxy)propanoate

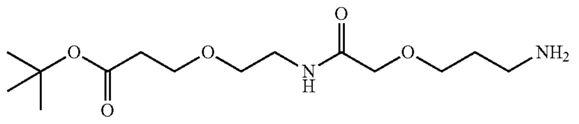 [SMILES: CC(C)(C)OC(=O)CCOCCNC(=O)COCCCN]

To a solution of tert-butyl 3,10-dioxo-1-phenyl-2,8,14-trioxa-4,11-diazaheptadecan-17-oate (570 mg, 1.300 mmol) in ethyl acetate (5.0 mL) under an atmosphere of nitrogen was added 10% Pd—C, Degussa type (13.83 mg, 0.130 mmol). The mixture was vacuumed and was backfilled with hydrogen (3×). The mixture was stirred under a balloon atmosphere of hydrogen overnight and was filtered through Celite®. The filtrate was concentrated to provide the title compound as a colorless oil (380 mg, 1.248 mmol, 96% yield). LC-MS m/z 305.1 $(M+H)^+$.

Step 4 tert-Butyl 1-((2S,3S)-1-methyl-5-oxo-2-(pyridin-3-yl)pyrrolidin-3-yl)-1,8-dioxo-6,12-dioxa-2,9-diazapentadecan-15-oate

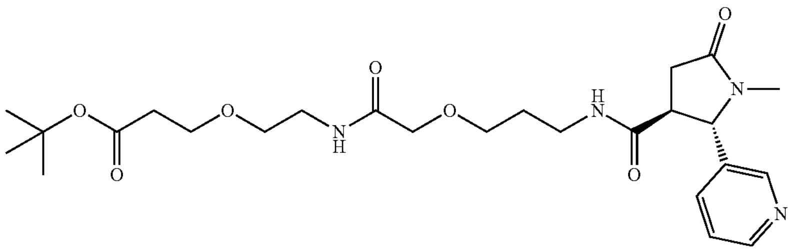 [SMILES: CN1C(=O)C[C@H](C(=O)NCCCOCC(=O)NCCOCCC(=O)OC(C)(C)C)[C@H]1c1cccnc1]

To a solution of (2S,3S)-1-methyl-5-oxo-2-(pyridin-3-yl) pyrrolidine-3-carboxylic acid (220 mg, 0.999 mmol) in dichloromethane (DCM) (10.0 mL) was added tert-butyl 3-(2-(2-(3-aminopropoxy)acetamido)ethoxy)propanoate (365 mg, 1.199 mmol), HOBt (184 mg, 1.199 mmol), EDC (287 mg, 1.498 mmol) followed by DIPEA (0.872 mL, 4.99 mmol) and the mixture was stirred overnight. Water was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a light-colored wax (320 mg, 0.632 mmol, 63.2% yield). LC-MS m/z 507.1 $(M+H)^+$.

Step 5

(2S,3S)-N-(3-(2-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl) carbamoyl)cyclohexyl)amino)-3-oxopropoxy)ethyl)amino)-2-oxoethoxy)propyl)-1-methyl-5-oxo-2-(pyridin-3-yl)pyrrolidine-3-carboxamide

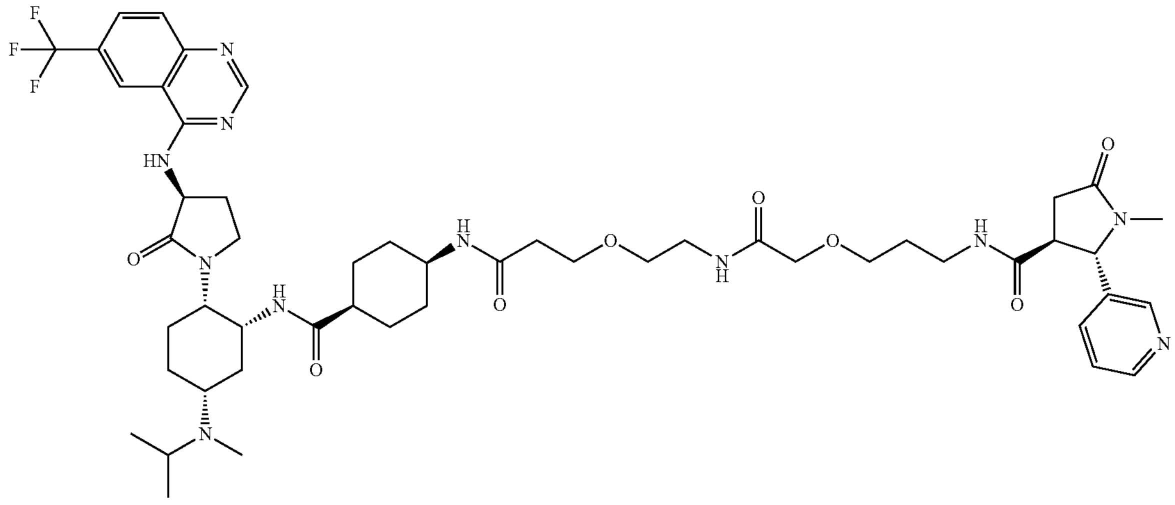 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)COCCCNC(=O)[C@H]3CC(=O)N(C)[C@@H]3c3cccnc3)CC2)C1]

4 M HCl in 1,4-dioxane (4.0 mL, 16.00 mmol) was added to a solution of tert-butyl 1-((2S,3S)-1-methyl-5-oxo-2-(pyridin-3-yl)pyrrolidin-3-yl)-1,8-dioxo-6,12-dioxa-2,9-diazapentadecan-15-oate (64.2 mg, 0.127 mmol) in solvent to dryness. To the residue in dichloromethane (DCM) (2.0 mL) was added (1 s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (60 mg, 0.091 mmol), HOBt (16.64 mg, 0.109 mmol) and DIPEA (0.079 mL, 0.453 mmol), followed by EDC (26.0 mg, 0.136 mmol). The mixture was stirred at rt overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (55.1 mg, 0.051 mmol, 56.6% yield). LC-MS m/z 1022.0 $(M+H)^+$. $^1H$ NMR (400 MHz, DMSO-$d_6$) δ ppm 0.90 (d, J=6.4 Hz, 3H) 1.05 (d, J=6.8 Hz, 3H) 1.39-1.52 (m, 2H) 1.52-1.75 (m, 10H) 1.91-2.17 (m, 7H) 2.63-2.75 (m, 1H) 2.87-2.94 (m, 1H) 3.07-3.30 (m, 5H) 3.33-3.45 (m, 5H) 3.49-3.60 (m, 3H) 3.71 (br s, 1H) 3.78 (s, 2H) 3.86-3.93 (m, 1H) 4.43 (br d, J=3.9 Hz, 1H) 4.65 (d, J=6.4 Hz, 1H) 5.03 (q, J=8.2 Hz, 1H) 7.33-7.51 (m, 1H) 7.56-7.64 (m, 2H) 7.68 (dt, J=8.2, 2.0 Hz, 1H) 7.89 (d, J=8.8 Hz, 1H) 8.01 (t, J=5.6 Hz, 1H) 8.03-8.08 (m, 1H) 8.47 (d, J=2.0 Hz, 1H) 8.56 (dd, J=4.9, 1.5 Hz, 1H) 8.58 (s, 1H) 8.60-8.72 (m, 2H) 8.89 (s, 1H).

Example 176

(2S,3S)-N-(4-((2-(2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)amino)-3-oxopropoxy)ethoxy)ethyl)amino)-4-oxobutyl)-1-methyl-5-oxo-2-(pyridin-3-yl)pyrrolidine-3-carboxamide

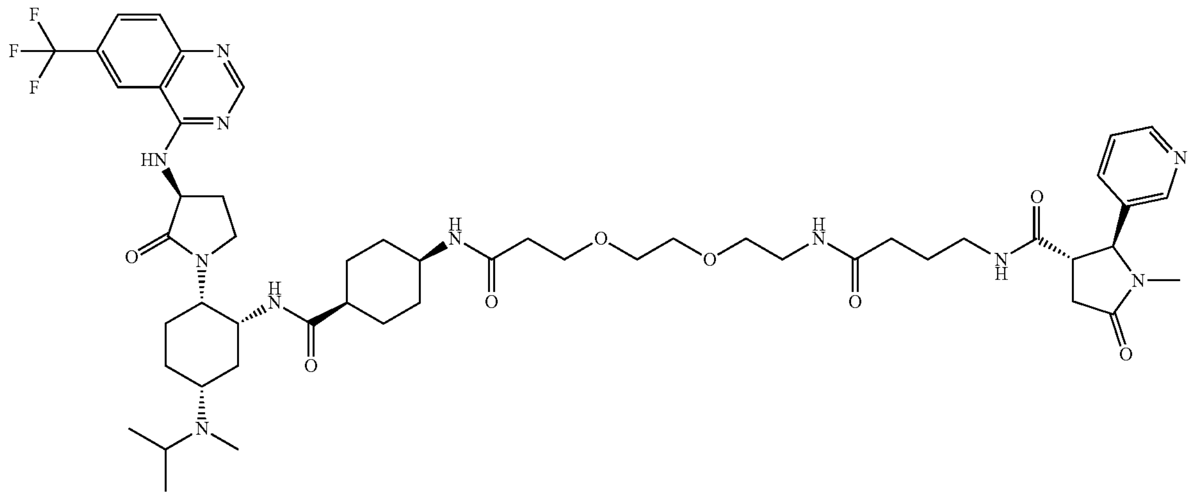 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCNC(=O)CCCNC(=O)[C@H]3CC(=O)N(C)[C@@H]3c3cccnc3)CC2)C1]

Step 1 tert-Butyl 3,8-dioxo-1-phenyl-2,12,15-trioxa-4,9-diazaoctadecan-18-oate

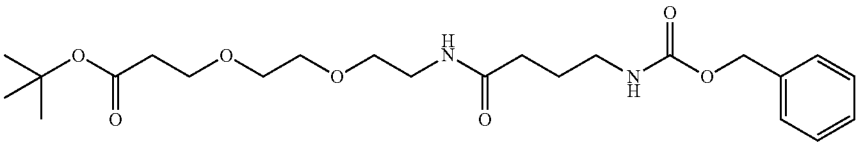 [SMILES: CC(C)(C)OC(=O)CCOCCOCCNC(=O)CCCNC(=O)OCc1ccccc1]

To a mixture of 4-(((benzyloxy)carbonyl)amino)butanoic acid (300 mg, 1.264 mmol), tert-butyl 3-(2-(2-aminoethoxy) ethoxy)propanoate (295 mg, 1.264 mmol), DIPEA (0.663 mL, 3.79 mmol), and HOBt (232 mg, 1.517 mmol) in dichloromethane (DCM) (4.0 mL) was added EDC (364 mg, 1.897 mmol) and the mixture was stirred overnight. Water was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 10% methanol in dichloromethane (DCM) provided the title compound as a colorless oil (575 mg, 1.271 mmol, 100% yield). LC-MS m/z 453.1 $(M+H)^+$.

Step 2 tert-Butyl 3-(2-(2-(4-aminobutanamido)ethoxy) ethoxy)propanoate

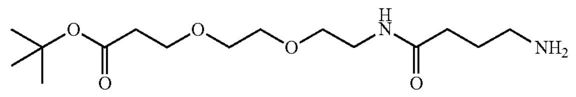 [SMILES: CC(C)(C)OC(=O)CCOCCOCCNC(=O)CCCN]

To a solution of tert-butyl 3,8-dioxo-1-phenyl-2,12,15-trioxa-4,9-diazaoctadecan-18-oate (575 mg, 1.271 mmol) in ethyl acetate (5.0 mL) under an atmosphere of nitrogen was added 10% Pd—C, Degussa type (54.1 mg, 0.508 mmol). The mixture was vacuumed and was backfilled with hydrogen (3×). The mixture was stirred under a balloon atmosphere of hydrogen overnight and was filtered through Celite®. The filtrate was concentrated to provide the title compound as a colorless (405 mg, 1.272 mmol, 100% yield). LC-MS m/z 319.0 $(M+H)^+$.

Step 3 tert-Butyl 1-((2S,3S)-1-methyl-5-oxo-2-(pyridin-3-yl)pyrrolidin-3-yl)-1,6-dioxo-10,13-dioxa-2,7-diaza-hexadecan-16-oate

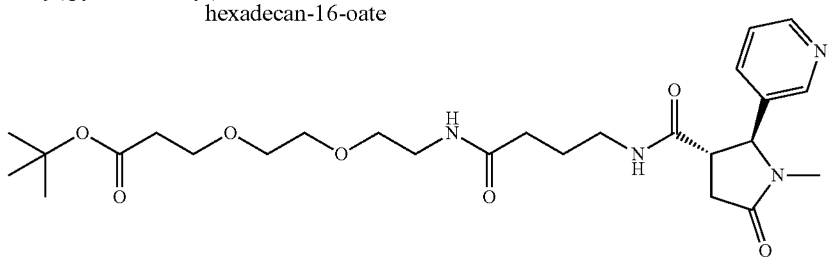

To a solution of (2S,3S)-1-methyl-5-oxo-2-(pyridin-3-yl) pyrrolidine-3-carboxylic acid (280 mg, 1.271 mmol) in dichloromethane (DCM) (10.0 mL) was added tert-butyl 3-(2-(2-(4-aminobutanamido)ethoxy)ethoxy)propanoate (405 mg, 1.271 mmol), HOBt (234 mg, 1.526 mmol), EDC (366 mg, 1.907 mmol). followed by DIPEA (1.110 mL, 6.36 mmol) and the mixture was stirred overnight. Water was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a light-colored wax (574 mg, 1.103 mmol, 87% yield). LC-MS m/z 521.1 $(M+H)^+$.

Step 4

(2S,3S)-N-(4-((2-(2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)amino)-3-oxopropoxy)ethoxy)ethyl)amino)-4-oxobutyl)-1-methyl-5-oxo-2-(pyridin-3-yl)pyrrolidine-3-carboxamide

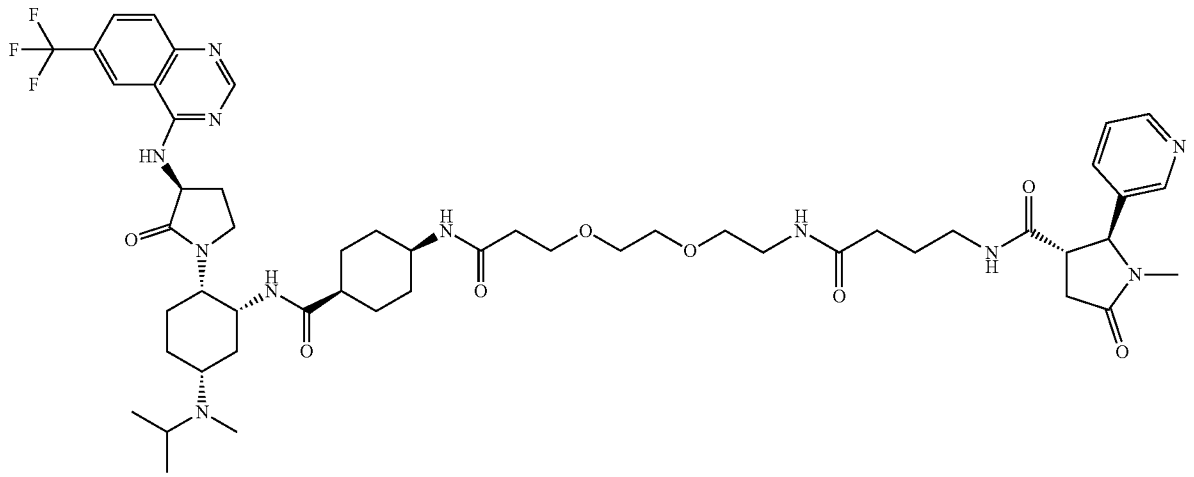 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCOCCNC(=O)CCCNC(=O)[C@H]3CC(=O)N(C)[C@@H]3c3cccnc3)CC2)C1]

4 M HCl in 1,4-dioxane (4.0 mL, 16.00 mmol) was added to a solution of tert-butyl 1-((2S,3S)-1-methyl-5-oxo-2-(pyridin-3-yl)pyrrolidin-3-yl)-1,6-dioxo-10,13-dioxa-2,7-diazahexadecan-16-oate (66.0 mg, 0.127 mmol) in dichloromethane (DCM). (2.0 mL). The mixture was stirred for 1 h and was concentrated to dryness. To the residue in dichloromethane (DCM) (2.0 mL) was added (1 s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide, 2hydrochloric acid salt (60 mg, 0.091 mmol), HOBt (16.64 mg, 0.109 mmol) and DIPEA (0.079 mL, 0.453 mmol), followed by EDC (26.0 mg, 0.136 mmol). The mixture was stirred at rt overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (60.9 mg, 0.056 mmol, 61.7% yield). LC-MS m/z 1036.7 $(M+H)^+$. $^1H$ NMR (400 MHz, DMSO-$d_6$) δ ppm 0.90 (d, J=6.4 Hz, 3H), 1.04 (d, J=6.4 Hz, 3H), 1.36-1.49 (m, 2H), 1.49-1.77 (m, 11H), 1.88-1.98 (m, 1H), 1.99-2.05 (m, 3H), 2.07-2.12 (m, 2H), 2.14 (s, 3H), 2.28 (t, J=6.6 Hz, 2H), 2.31-2.40 (m, 1H), 2.40-2.47 (m, 1H), 2.52-2.54 (m, 4H), 2.55-2.62 (m, 1H), 2.66-2.75 (m, 1H), 2.85-2.93 (m, 1H), 3.01 (q, J=6.5 Hz, 2H), 3.16 (q, J=5.9 Hz, 2H), 3.28-3.31 (m, 1H), 3.34-3.39 (m, 2H), 3.41-3.47 (m, 5H), 3.49-3.58 (m, 3H), 3.65-3.76 (m, 1H), 3.84-3.93 (m, 1H), 4.43 (br dd, J=6.8, 3.4 Hz, 1H), 4.65 (d, J=5.9 Hz, 1H), 5.03 (q, J=7.8 Hz, 1H), 7.44 (dd, J=8.3, 4.4 Hz, 1H), 7.64 (d, J=6.8 Hz, 1H), 7.68 (dt, J=7.9, 2.1 Hz, 1H), 7.83 (t, J=6.1 Hz, 1H), 7.89 (d, J=8.8 Hz, 1H), 7.96 (s, 1H), 8.07 (dd, J=8.8, 2.0 Hz, 1H), 8.48 (d, J=2.0 Hz, 1H), 8.56 (dd, J=4.9, 1.5 Hz, 1H), 8.59 (s, 1H), 8.62-8.68 (m, 1H), 8.69-8.75 (m, 1H), 8.89 (s, 1H).

The following compounds were or could be prepared with procedures analogous to that described in Example 176:

| Ex. | Compound | LC-MS m/z | NMR |
|---|---|---|---|
| 177 | 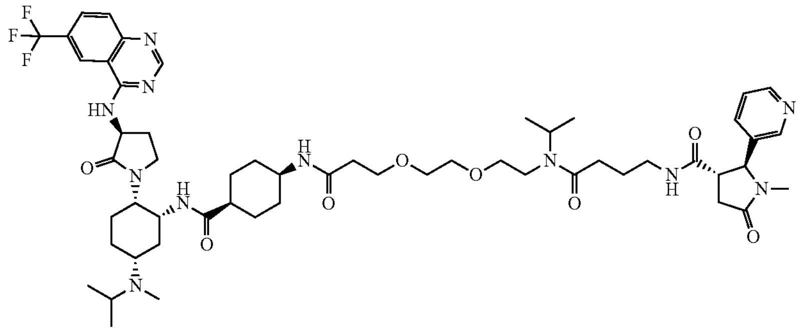 [SMILES: CC(C)N(CCOCCOCCC(=O)N[C@H]1CC[C@@H](C(=O)N[C@@H]2C[C@H](N(C)C(C)C)CC[C@@H]2N2CC[C@H](Nc3ncnc4ccc(C(F)(F)F)cc34)C2=O)CC1)C(=O)CCCNC(=O)[C@H]1CC(=O)N(C)[C@@H]1c1cccnc1] (2S,3S)-N-(4-(Isopropyl(2-(2-(3-(((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethyl)amino)-4-oxobutyl)-1-methyl-5-oxo-2-(pyridin-3-yl)pyrrolidine-3-carboxamide. | 1078.8 (M + H)+ | $^1H$ NMR (400 MHz, DMSO-$d_6$) δ ppm 0.90 (d, J = 6.4 Hz, 3H) 1.00-1.12 (m, 9H) 1.44 (br d, J = 11.7 Hz, 2H) 1.50-1.79 (m, 11H) 1.93 (br dd, J = 12.2, 7.8 Hz, 1H) 1.99-2.17 (m, 7H) 2.20-2.31 (m, 4H) 2.32-2.39 (m, 1H) 2.40-2.47 (m, 1H) 2.49 (br s, 3H) 2.53 (d, J = 2.0 Hz, 1H) 2.59 (br s, 1H) 2.66-2.75 (m, 1H) 2.85-2.94 (m, 1H) 2.97-3.12 (m, 2H) 3.19-3.31 (m, 3H) 3.35-3.39 (m, 1H) 3.40 3.50 (m, 6H) 3.50-3.58 (m, 3H) 3.71 (br s, 1H) 3.86-3.93 (m, 1H) 4.43 (br s, 1H) 4.65 (d, J = 5.9 Hz, 1H) 5.03 (q, J = 8.2 Hz, 1H) 7.41-7.47 (m, 1H) 7.60-7.72 (m, 2H) 7.89 (d, J = 8.8 Hz, 1H) 7.99 (t, J = 5.1 Hz, 1H) 8.07 (dd, J = 8.8, 2.0 Hz, 1H) 8.47 (d, J = 2.0 Hz, 1H) 8.56 (dt, J = 4.6, 1.8 Hz, 1H) 8.58 (s, 1H) 8.62-8.75 (m, 2H) 8.89 (s, 1H). |
| 178 | 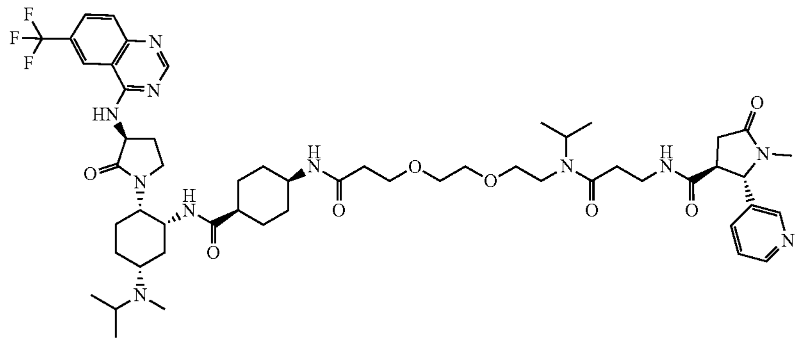 [SMILES: CC(C)N(CCOCCOCCC(=O)N[C@H]1CC[C@@H](C(=O)N[C@@H]2C[C@H](N(C)C(C)C)CC[C@@H]2N2CC[C@H](Nc3ncnc4ccc(C(F)(F)F)cc34)C2=O)CC1)C(=O)CCNC(=O)[C@H]1CC(=O)N(C)[C@@H]1c1cccnc1] | 1064.0 (M + H)+ | $^1H$ NMR (400 MHz, DMSO-$d_6$) δ ppm 0.90 (d, J = 6.4 Hz, 3H) 1.00-1.11 (m, 9H) 1.39-1.77 (m, 10H) 1.88-2.17 (m, 8H) 2.28 (t, J = 6.4 Hz, 2H) 2.32-2.50 (m, 8H) 2.53 (d, J = 2.0 Hz, 1H) 2.59 (br s, 1H) 2.63-2.73 (m, 1H) 2.89-2.97 (m, 1H) 3.26 (td, J = 13.1, 6.1 Hz, 6H) 3.37-3.49 (m, 6H) 3.51-3.57 (m, 3H) 3.71 (br s, 1H) 3.89 (dt, J = 7.6, 3.5 Hz, 1H) 4.42 (br d, J = 4.9 Hz, |

-continued

| Ex. | Compound | LC-MS m/z | NMR |
|---|---|---|---|
| | (2S,3S)-N-(3-(Isopropyl(2-(2-(3-(((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)amino)-3-oxopropoxy)ethoxy)ethyl)amino)-3-oxopropyl)-1-methyl-5-oxo-2-(pyridin-3-yl)pyrrolidine-3-carboxamide. | | 1H) 4.65 (d, J = 5.9 Hz, 1H) 5.03 (q, J = 7.8 Hz, 1H) 7.42 (ddd, J = 7.5, 4.8, 2.4 Hz, 1H) 7.61-7.70 (m, 2H) 7.89 (d, J = 8.8 Hz, 1H) 8.00 (br d, J = 2.4 Hz, 1H) 8.06 (dd, J = 8.8, 1.5 Hz, 1H) 8.46 (t, J = 2.7 Hz, 1H) 8.55 (td, J = 3.5, 2.2 Hz, 1H) 8.58 (s, 1H) 8.62-8.74 (m, 2H) 8.89 (s, 1H). |

Example 179

N[1]-((1R,2S,5R)-5-(isopropyl(methyl)amino)-2-((S)-2-oxo-3-((6-(trifluoromethyl) quinazolin-4-yl) amino)pyrrolidin-1-yl)cyclohexyl)-N[5]-((1R,4S)-4-((3-(2-((2S,3S)-1-methyl-5-oxo-2-(pyridin-3-yl) pyrrolidine-3-carboxamido)ethoxy)propanamido) methyl)cyclohexyl)glutaramide

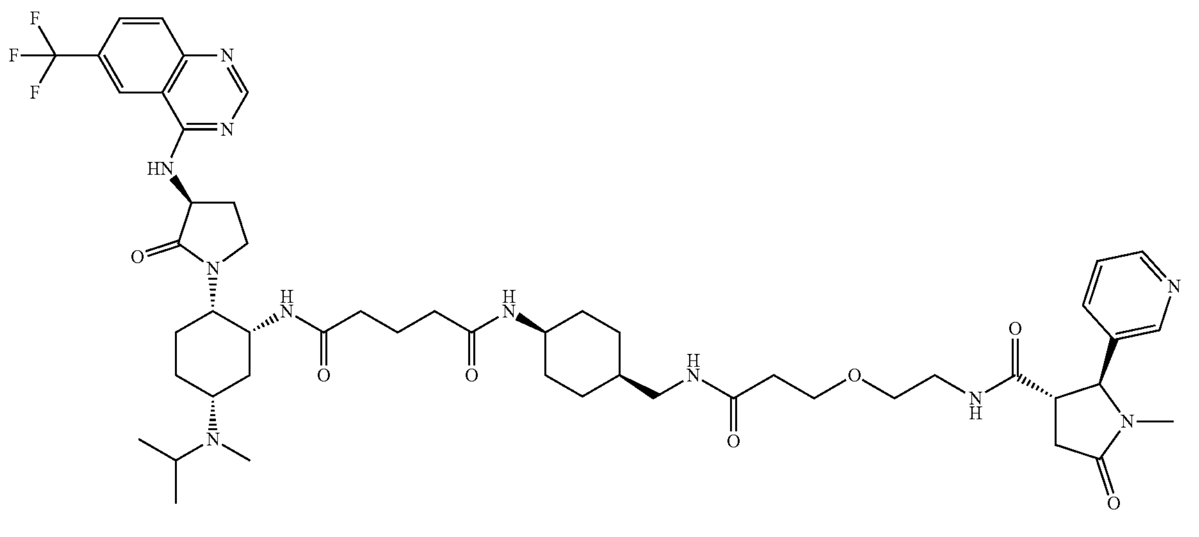 [SMILES: CC(C)N(C)[C@@H]1CC[C@H](N2CC[C@H](Nc3ncnc4ccc(C(F)(F)F)cc34)C2=O)[C@H](NC(=O)CCCC(=O)N[C@H]2CC[C@@H](CNC(=O)CCOCCNC(=O)[C@H]3CC(=O)N(C)[C@@H]3c3cccnc3)CC2)C1]

Step 1 tert-Butyl (((1S,4s)-4-(5-(((1R,2S,5R)-5-(isopropyl (methyl)amino)-2-((S)-2-oxo-3-((6-(trifluoromethyl) quinazolin-4-yl)amino)pyrrolidin-1-yl)cyclohexyl) amino)-5-oxopentanamido)cyclohexyl)methyl) carbamate

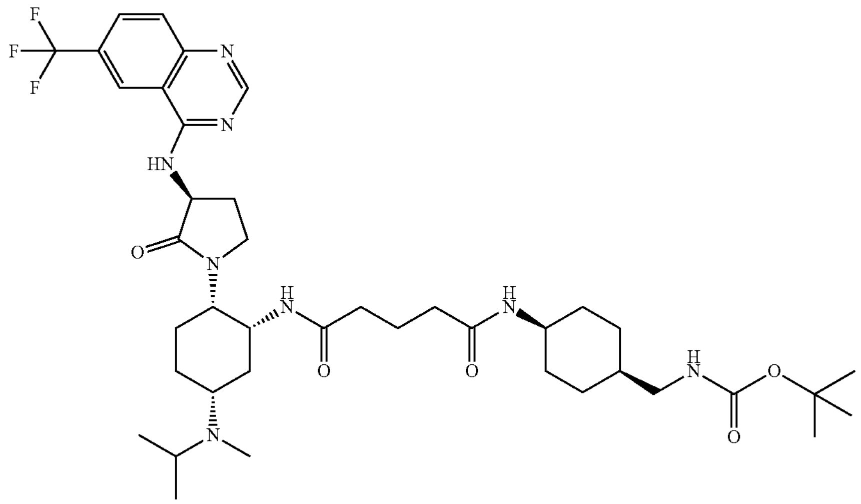 [SMILES: CC(C)N(C)[C@@H]1CC[C@H](N2CC[C@H](Nc3ncnc4ccc(C(F)(F)F)cc34)C2=O)[C@H](NC(=O)CCCC(=O)N[C@H]2CC[C@@H](CNC(=O)OC(C)(C)C)CC2)C1]

3 M HCl in cyclopentyl methyl ether (0.5 mL, 1.5 mmol) was added to a solution of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (53 mg, 0.094 mmol) in dichloromethane (DCM) (1 mL). The mixture was stirred at rt for 1 h and was concentrated under reduced pressure. The residue was dissolved in dichloromethane (DCM) (3 mL) and triethylamine (0.052 mL, 0.375 mmol). Dihydro-2H-pyran-2,6(3H)-dione (10.71 mg, 0.094 mmol) was added. The mixture was stirred at rt overnight. tert-Butyl (((cis)-4-aminocyclohexyl)methyl)carbamate (25.7 mg, 0.113 mmol) was added, followed by HATU (53.5 mg, 0.141 mmol). The resultant mixture was stirred at rt for 2 h and was concentrated under reduced pressure. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a brown, foamy solid (65 mg, 0.079 mmol, 84% yield). LC-MS m/z 789.3 $(M+H)^+$.

Step 2 tert-Butyl (2-(3-((((1S,4s)-4-(5-(((1R,2S,5R)-5-(isopropyl(methyl)amino)-2-((S)-2-oxo-3-((6-(trifluoromethyl)quinazolin-4-yl)amino)pyrrolidin-1-yl) cyclohexyl)amino)-5-oxopentanamido)cyclohexyl) methyl)amino)-3-oxopropoxy)ethyl)carbamate

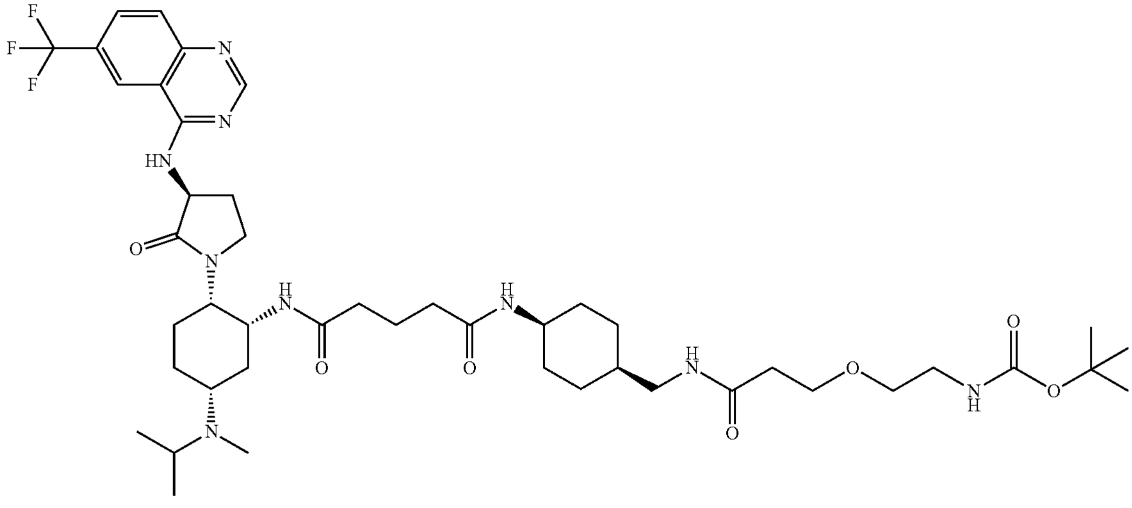 [SMILES: CC(C)N(C)[C@@H]1CC[C@H](N2CC[C@H](Nc3ncnc4ccc(C(F)(F)F)cc34)C2=O)[C@H](NC(=O)CCCC(=O)N[C@H]2CC[C@@H](CNC(=O)CCOCCNC(=O)OC(C)(C)C)CC2)C1]

3 M HCl in cyclopentyl methyl ether (0.5 mL, 1.500 mmol) was added to a solution of tert-butyl (((1S,4s)-4-(5-(((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)amino)-5-oxopentanamido)cyclohexyl) methyl)carbamate (64 mg, 0.081 mmol) in dichloromethane (DCM) (1 mL). The mixture was stirred at rt for 1 h and was concentrated under reduced pressure. The residue was suspended in dichloromethane (DCM) (3 mL). Triethylamine (0.05 mL, 0.359 mmol), 3-(2-((tert-butoxycarbonyl)amino) ethoxy)propanoic acid (21 mg, 0.090 mmol) and HATU (39.0 mg, 0.103 mmol) were added sequentially. The mixture was stirred at rt for 2 h and concentrated under reduced pressure. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as a pale-brown film (65 mg, 0.068 mmol, 84% yield). LC-MS m/z 904.3 $(M+H)^+$.

Step 3

$N^1$-((1R,2S,5R)-5-(isopropyl(methyl)amino)-2-((S)-2-oxo-3-((6-(trifluoromethyl) quinazolin-4-yl) amino)pyrrolidin-1-yl)cyclohexyl)-$N^5$-((1R,4S)-4-((3-(2-((2S,3S)-1-methyl-5-oxo-2-(pyridin-3-yl) pyrrolidine-3-carboxamido)ethoxy)propanamido) methyl) cyclohexyl)glutaramide 3 M HCl in cyclopentyl methyl ether (0.5 mL, 1.500 mmol) was added to a solution of tert-butyl (2-(3-((((1S, 4s)-4-(5-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)amino)-5-oxopentanamido) cyclohexyl)methyl)amino)-3-oxopropoxy)ethyl)carbamate (65 mg, 0.072 mmol) in dichloromethane (DCM) (1 mL). The mixture was stirred at rt for 2 h and was concentrated. The residue was dissolved in dichloromethane (DCM) (2 mL) and triethylamine (0.050 mL, 0.359 mmol), and (2S, 3S)-1-methyl-5-oxo-2-(pyridin-3-yl)pyrrolidine-3-carboxylic acid (19.00 mg, 0.086 mmol) and HATU (41.0 mg, 0.108 mmol) were added. The mixture was stirred at rt for 2 h and was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as a white solid (55.2 mg, 0.054 mmol, 74.8% yield). LC-MS m/z 1006.8 $(M+H)^+$. $^1H$ NMR (400 MHz, METHANOL-$d_4$) δ ppm 0.97-1.07 (m, 3H) 1.12 (br d, J=6.4 Hz, 3H) 1.26-1.47 (m, 3H) 1.47-1.66 (m, 8H) 1.66-1.78 (m, 3H) 1.89-2.16 (m, 4H) 2.16 2.32 (m, 11H) 2.35-2.48 (m, 2H) 2.50-2.65 (m, 1H) 2.67 (s, 3H) 2.68-2.76 (m, 2H) 3.02-3.11 (m, 3H) 3.25-3.31 (m, 1H) 3.35-3.50 (m, 4H) 3.56 (td, J=9.3, 2.4 Hz, 1H) 3.63-3.70 (m, 3H) 3.80-3.86 (m, 1H) 4.01 (dt, J=12.0, 3.8 Hz, 1H) 4.60 (br d, J=2.9 Hz, 1H) 4.83 (d, J=6.8 Hz, 1H) 5.31 (t, J=8.6 Hz, 1H) 7.54 (dd, J=7.3, 4.9 Hz, 1H) 7.80 (dt, J=8.3, 2.0 Hz, 1H) 7.90 (d, J=8.8 Hz, 1H) 8.05 (dd, J=9.0, 1.7 Hz, 1H) 8.52 (d, J=1.5 Hz, 1H) 8.56-8.59 (m, 2H) 8.77 (s, 1H).

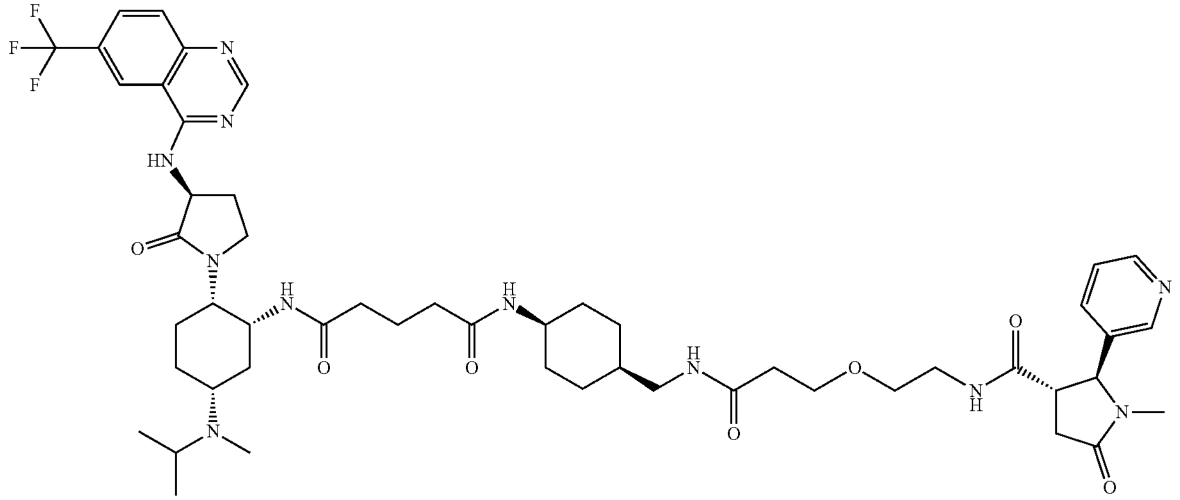 [SMILES: CC(C)N(C)[C@@H]1CC[C@H](N2CC[C@H](Nc3ncnc4ccc(C(F)(F)F)cc34)C2=O)[C@H](NC(=O)CCCC(=O)N[C@H]2CC[C@@H](CNC(=O)CCOCCNC(=O)[C@H]3CC(=O)N(C)[C@@H]3c3cccnc3)CC2)C1]

The following compound was or could be prepared with procedures analogous to that described in Example 179:

| Ex. | Compound | LC-MS m/z | NMR |
| --- | --- | --- | --- |
| 180 | 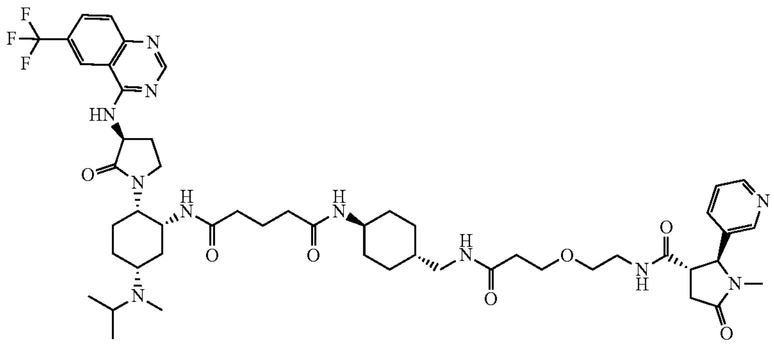 [SMILES: CC(C)N(C)[C@@H]1CC[C@H](N2CC[C@H](Nc3ncnc4ccc(C(F)(F)F)cc34)C2=O)[C@H](NC(=O)CCCC(=O)N[C@H]2CC[C@H](CNC(=O)CCOCCNC(=O)[C@H]3CC(=O)N(C)[C@@H]3c3cccnc3)CC2)C1] N1-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-N5-((1S,4R)-4-((3-(2-((2S,3S)-1-methyl-5-oxo-2-(pyridin-3-yl)pyrrolidine-3-carboxamido)ethoxy)propanamido)methyl)cyclohexyl) glutaramide. | 1006.4 (M + H)+ | $^1$H NMR (400 MHz, METHANOL-$d_4$) δ ppm 0.97-1.07 (m, 5H) 1.09-1.18 (m, 5H) 1.36-1.45 (m, 1H) 1.62-1.79 (m, 5H) 1.80-2.01 (m, 5H) 2.10-2.32 (m, 10H) 2.41 (td, J = 6.1, 2.4 Hz, 2H) 2.56 (dt, J = 7.7, 3.7 Hz, 1H) 2.67 (s, 3H) 2.70-2.76 (m, 2H) 2.79-2.89 (m, 1H) 2.99-3.09 (m, 3H) 3.26-3.32 (m, 1H) 3.35-3.45 (m, 2H) 3.46-3.59 (m, 4H) 3.62-3.69 (m, 3H) 4.03 (dt, J = 12.0, 3.5 Hz, 1H) 4.61 (br d, J = 2.9 Hz, 1H) 4.83 (d, J = 6.4 Hz, 1H) 5.30 (t, J = 8.6 Hz, 1H) 7.54 (dd, J = 7.8, 4.9 Hz, 1H) 7.81 (dt, J = 7.8, 2.0 Hz, 1H) 7.90 (d, J = 8.3 Hz, 1H) 8.06 (dd, J = 8.8, 2.0 Hz, 1H) 8.52 (d, J = 2.0 Hz, 1H) 8.56-8.60 (m, 2H) 8.78 (s, 1H). |

Example 181

(2S,3S)-N-(1-(((1R,2S,5R)-5-(Isopropyl(methyl) amino)-2-((S)-2-oxo-3-((6-(trifluoromethyl)quinazolin-4-yl)amino)pyrrolidin-1-yl)cyclohexyl)amino)-1,7,11-trioxo-3,14,17-trioxa-6,10-diazanonadecan-19-yl)-1-methyl-5-oxo-2-(pyridin-3-yl)pyrrolidine-3-carboxamide

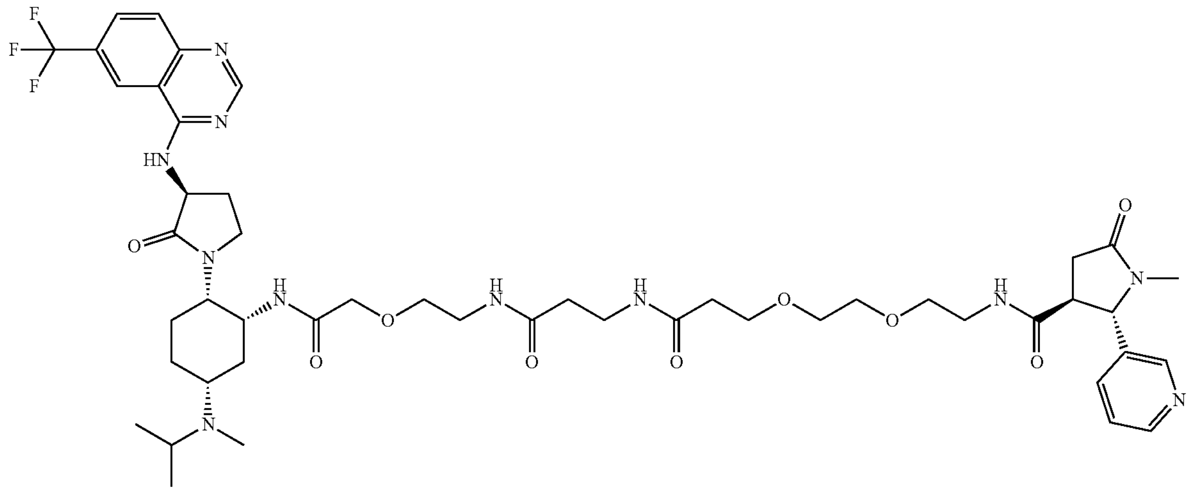 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCNC(=O)CCOCCOCCNC(=O)[C@H]2CC(=O)N(C)[C@@H]2c2cccnc2)C1]

Step 1 tert-Butyl 3-(2-(2-((2S,3S)-1-methyl-5-oxo-2-(pyridin-3-yl)pyrrolidine-3-carboxamido) ethoxy)ethoxy) propanoate

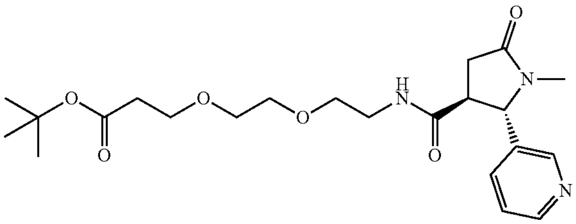 [SMILES: CN1C(=O)C[C@H](C(=O)NCCOCCOCCC(=O)OC(C)(C)C)[C@H]1c1cccnc1]

To a solution of (2S,3S)-1-methyl-5-oxo-2-(pyridin-3-yl) pyrrolidine-3-carboxylic acid (150 mg, 0.681 mmol) in dichloromethane (DCM) (2 mL) was added N,N'-carbonyldiimidazole (144 mg, 0.885 mmol). The mixture was stirred at rt for 30 min. tert-Butyl 3-(2-(2-aminoethoxy)ethoxy) propanoate (159 mg, 0.681 mmol) was added. The mixture was stirred for 2 h and was concentrated onto silica. Purification by MDAP chromatography (XSelect™ CSH Prep C18 5 μm OBD column, 40 mL/min) eluting with a gradient of 15 to 55% acetonitrile in water containing ammonium bicarbonate (10 mM) and ammonium hydroxide (0.075%) provided the title compound as clear oil (206 mg, 0.459 mmol, 67.4% yield). LC-MS m/z 436.2 $(M+H)^+$.

Step 2

3-(2-(2-((2S,3S)-1-Methyl-5-oxo-2-(pyridin-3-yl) pyrrolidine-3-carboxamido)ethoxy) ethoxy)propanoic acid

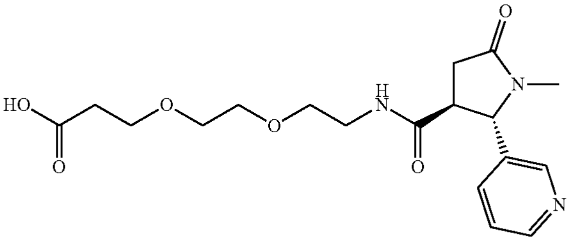 [SMILES: CN1C(=O)C[C@H](C(=O)NCCOCCOCCC(=O)O)[C@H]1c1cccnc1]

4 M HCl in 1,4-dioxane (2.73 mL, 10.90 mmol) was added to a suspension of 3-(2-(2-((2S,3S)-1-methyl-5-oxo-2-(pyridin-3-yl)pyrrolidine-3-carboxamido)ethoxy)ethoxy) propanoic acid (105 mg, 0.208 mmol) in 1,4-dioxane (1 mL). The mixture was stirred rt for 1 hour and was concentrated. Purification by MDAP chromatography (XSelect™ CSH Prep C18 5 μm OBD column, 40 mL/min) eluting with a gradient of 5 to 35% acetonitrile in water containing ammonium bicarbonate (10 mM) and ammonium hydroxide (0.075%) provided the title compound as white gum (105 mg, 0.208 mmol, 45.7% yield). LC-MS m/z 380.1 $(M+H)^+$.

Step 3 tert-Butyl 1-((2S,3S)-1-methyl-5-oxo-2-(pyridin-3-yl)pyrrolidin-3-yl)-1,11-dioxo-5,8-dioxa-2,12-diazapentadecan-15-oate

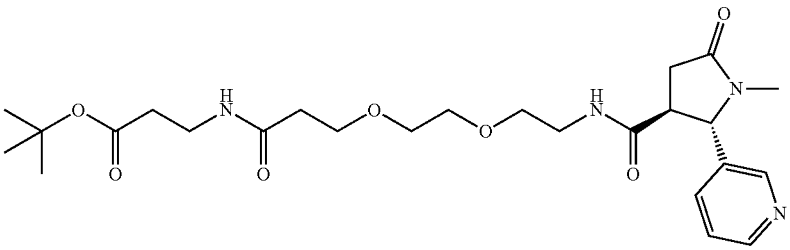 [SMILES: CN1C(=O)C[C@H](C(=O)NCCOCCOCCC(=O)NCCC(=O)OC(C)(C)C)[C@H]1c1cccnc1]

To a solution of 3-(2-(2-((2S,3S)-1-methyl-5-oxo-2-(pyridin-3-yl) pyrrolidine-3-carboxamido)ethoxy)ethoxy)propanoic acid (105 mg, 0.208 mmol) in dichloromethane (DCM) (1 mL) was added HOBt (38.1 mg, 0.249 mmol) and EDC (55.7 mg, 0.291 mmol), and the mixture was stirred for 30 min. tert-Butyl 3-aminopropanoate, hydrochloric acid salt (47.6 mg, 0.249 mmol) and DIPEA (0.073 mL, 0.415 mmol) were added, and the mixture was stirred over the weekend. The crude product was combined with a similar run beginning with 3-(2-(2-((2S,3S)-1-methyl-5-oxo-2-(pyridin-3-yl) pyrrolidine-3-carboxamido)ethoxy)ethoxy) propanoic acid (196 mg, 0.363 mmol) prior to extraction. The combined mixture was partitioned between saturated $NaHCO_3$ and dichloromethane (DCM). The aqueous layer was extracted with dichloromethane (DCM) (4×20 mL). The combined organic phases were washed with saturated NaCl, were dried over $Na_2SO_4$, and were concentrated onto silica. Purification by CombiFlash® Rf chromatography (24 g silica column, 30 mL/min) eluting with a gradient of 0 to 10% methanol in dichloromethane (DCM) provided the title compound as a light-orange oil (268 mg, 0.476 mmol, 83.4% yield). LC-MS m/z 507.4 $(M+H)^+$.

Step 4

1-((2S,3S)-1-Methyl-5-oxo-2-(pyridin-3-yl)pyrrolidin-3-yl)-1,11-dioxo-5,8-dioxa-2,12-diazapentadecan-15-oic acid, Hydrochloric acid salt

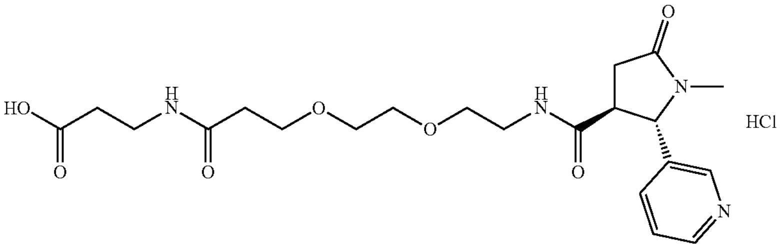 [SMILES: CN1C(=O)C[C@H](C(=O)NCCOCCOCCC(=O)NCCC(=O)O)[C@H]1c1cccnc1 ; Cl]

4 M HCl in 1,4-dioxane (2.79 mL, 11.17 mmol) was added to a suspension of tert-butyl 1-((2S,3S)-1-methyl-5-oxo-2-(pyridin-3-yl)pyrrolidin-3-yl)-1,11-dioxo-5,8-dioxa-2,12-diazapentadecan-15-oate (262 mg, 0.465 mmol) was suspended in 1,4-dioxane (1 mL). The reaction mixture was stirred at rt for 4 h and was concentrated to provide the title compound as a white gum (370 mg, 0.456 mmol, 98% yield). (N70851-11-1) as a white gum. LC-MS m/z 451.3 $(M+H)^+$.

Step 5 tert-Butyl 1-((2S,3S)-1-methyl-5-oxo-2-(pyridin-3-yl)pyrrolidin-3-yl)-1,11,15-trioxo-5,8,19-trioxa-2,12,16-triazahenicosan-21-oate

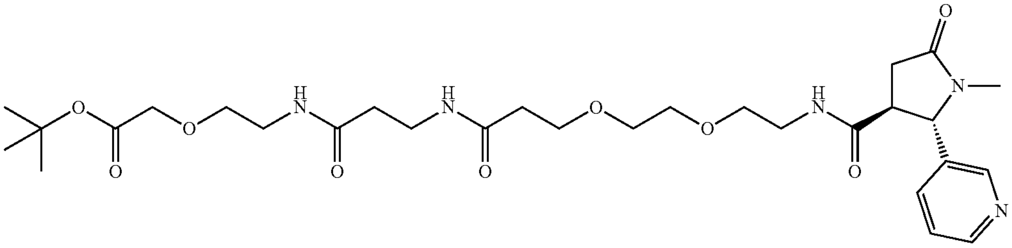 [SMILES: CN1C(=O)C[C@H](C(=O)NCCOCCOCCC(=O)NCCC(=O)NCCOCC(=O)OC(C)(C)C)[C@H]1c1cccnc1]

To a solution of 1-((2S,3S)-1-methyl-5-oxo-2-(pyridin-3-yl)pyrrolidin-3-yl)-1,11-dioxo-5,8-dioxa-2,12-diazapentadecan-15-oic acid (365 mg, 0.486 mmol) in dichloromethane (DCM) (2 mL) was added HOBt (89 mg, 0.583 mmol) and EDC (130 mg, 0.681 mmol), and the mixture was stirred for 30 min. tert-butyl 2-(2-aminoethoxy)acetate (123 mg, 0.583 mmol) and DIPEA (0.170 mL, 0.972 mmol) were added, and the mixture was stirred overnight. The mixture was partitioned between saturated $NaHCO_3$ and dichloromethane (DCM). The aqueous layer was extracted with dichloromethane (DCM) (4×20 mL). The combined organic phases were washed with saturated NaCl, were dried over $Na_2SO_4$, and were concentrated onto silica. Purification by CombiFlash® Rf chromatography (24 g silica column, 30 mL/min) eluting with a gradient of 0 to 10% methanol in dichloromethane (DCM) provided the title compound as a light-orange oil (210 mg, 0.318 mmol, 65.4% yield). LC-MS m/z 608.2 $(M+H)^+$.

Step 6

1-((2S,3S)-1-Methyl-5-oxo-2-(pyridin-3-yl)pyrrolidin-3-yl)-1,11,15-trioxo-5,8,19-trioxa-2,12,16-triazahenicosan-21-oic acid. Hydrochloric acid salt

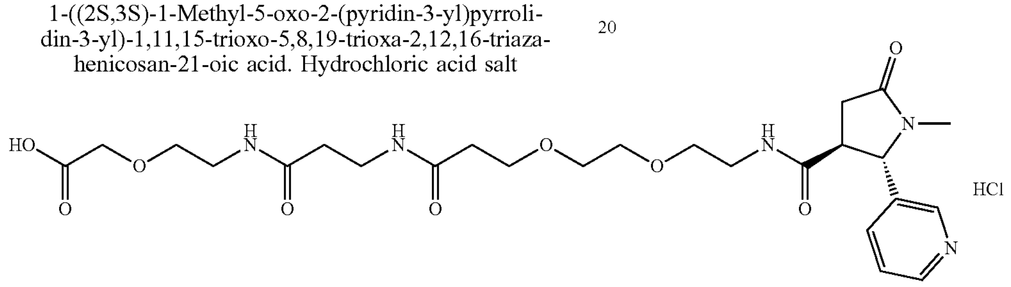

4 M HCl in 1,4-dioxane (1.908 mL, 7.63 mmol) was added to a suspension of tert-butyl 1-((2S,3S)-1-methyl-5-oxo-2-(pyridin-3-yl)pyrrolidin-3-yl)-1,11,15-trioxo-5,8,19-trioxa-2,12,16-triazahenicosan-21-oate (210 mg, 0.318 mmol) in 1,4-Dioxane (1 mL). The mixture was stirred at rt for 4 h and was concentrated. to provide the title compound as a white gum (399 mg, 0.305 mmol, 96% yield). LC-MS m/z 551.2 $(M+H)^+$.

Step 7

(2S,3S)-N-(1-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-1,7,11-trioxo-3,14,17-trioxa-6,10-diazanonadecan-19-yl)-1-methyl-5-oxo-2-(pyridin-3-yl)pyrrolidine-3-carboxamide

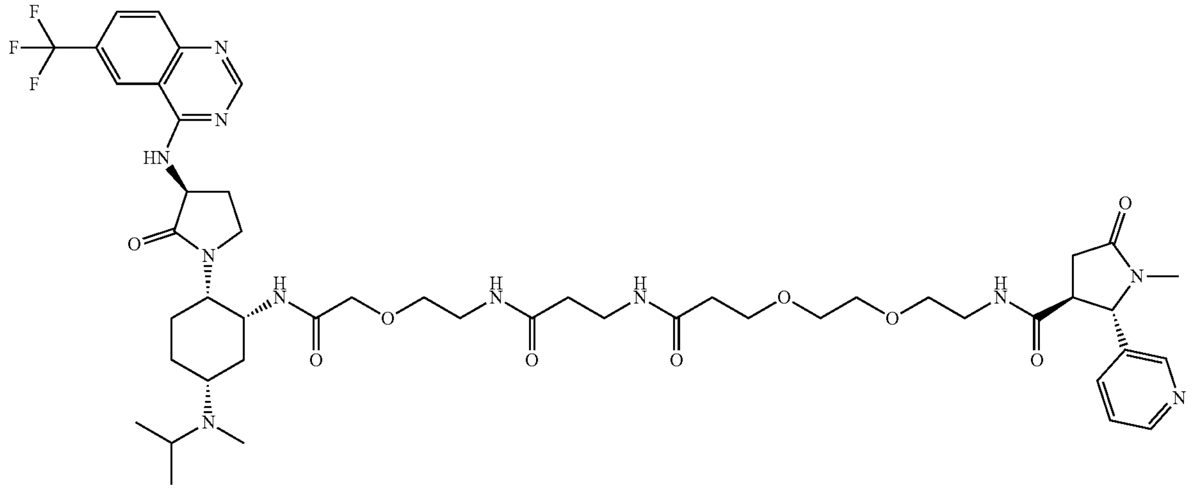 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)CCNC(=O)CCOCCOCCNC(=O)[C@H]2CC(=O)N(C)[C@@H]2c2cccnc2)C1]

To a solution of 1-((2S,3S)-1-methyl-5-oxo-2-(pyridin-3-yl)pyrrolidin-3-yl)-1,11,15-trioxo-5,8,19-trioxa-2,12,16-tri-azahenicosan-21-oic acid, hydrochloric acid salt (192 mg, 0.147 mmol) in dichloromethane (DCM) (1 mL) was added HOBt (18.02 mg, 0.118 mmol) and EDC (26.3 mg, 0.137 mmol) and the mixture was stirred for 30 min. (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (62 mg, 0.098 mmol) and DIPEA (0.034 mL, 0.196 mmol) were added, and the mixture was stirred overnight. The mixture was partitioned between saturated $NaHCO_3$ and dichloromethane (DCM). The aqueous layer was extracted with dichloromethane (DCM) (4×20 mL). The combined organic phases were washed with saturated NaCl, were dried over $Na_2SO_4$, and were concentrated onto silica. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as a white solid (83 mg, 0.082 mmol, 84% yield). LC-MS m/z 998.4 $(M+H)^+$. $^1H$ NMR (400 MHz, METHANOL-$d_4$) δ ppm 1.00 (d, J=6.4 Hz, 3H) 1.15 (d, J=6.4 Hz, 3H) 1.57-1.84 (m, 3H) 1.94-2.09 (m, 1H) 2.09-2.21 (m, 2H) 2.24 (s, 3H) 2.27-2.43 (m, 5H) 2.50-2.65 (m, 1H) 2.67 (s, 3H) 2.69-2.76 (m, 2H) 2.80-2.88 (m, 1H) 3.03-3.17 (m, 1H) 3.24-3.31 (m, 2H) 3.35-3.47 (m, 6H) 3.50 (ddd, J=6.2, 4.8, 2.2 Hz, 2H) 3.52-3.58 (m, 4H) 3.60-3.70 (m, 5H) 4.03-4.10 (m, 3H) 4.67 (br s, 1H) 4.80-4.84 (m, 2H) 5.27 (t, J=8.6 Hz, 1H) 7.53 (dd, J=7.8, 4.9 Hz, 1H) 7.80 (dt, J=8.3, 2.0 Hz, 1H) 7.90 (d, J=8.8 Hz, 1H) 8.05 (dd, J=8.8, 2.0 Hz, 1H) 8.51-8.54 (m, 1H) 8.57 (dd, J=4.9, 1.5 Hz, 1H) 8.59 (s, 1H) 8.78 (s, 1H).

Example 182

(2S,3S)-N-(3-((3-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl) carbamoyl)cyclohexyl)amino)-3-oxopropoxy)ethyl)amino)-3-oxopropyl)amino)-3-oxopropyl)-1-methyl-5-oxo-2-(pyridin-3-yl) pyrrolidine-3-carboxamide

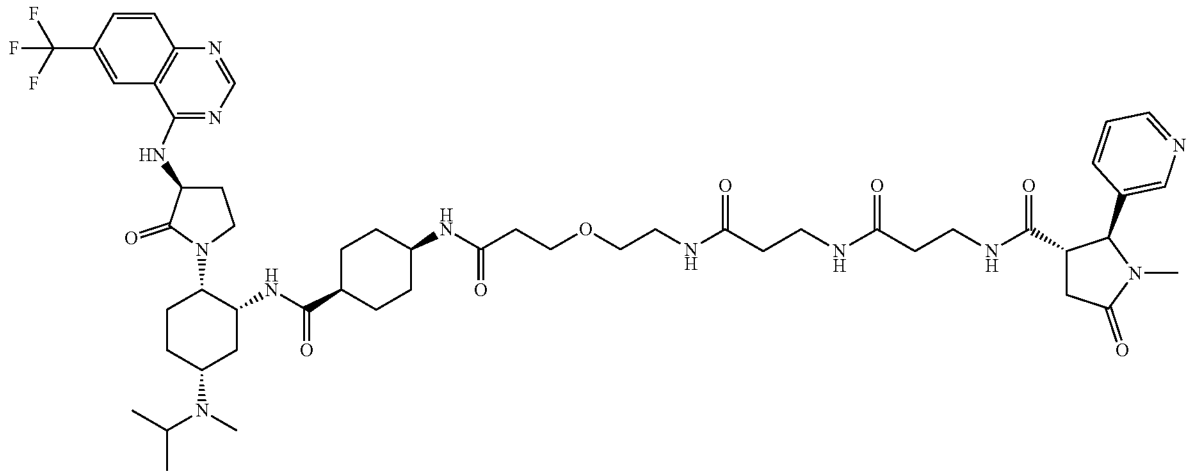 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCNC(=O)CCNC(=O)[C@H]3CC(=O)N(C)[C@@H]3c3cccnc3)CC2)C1]

Step 1 tert-Butyl (2-(3-(((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-3-oxopropoxy) ethyl)carbamate

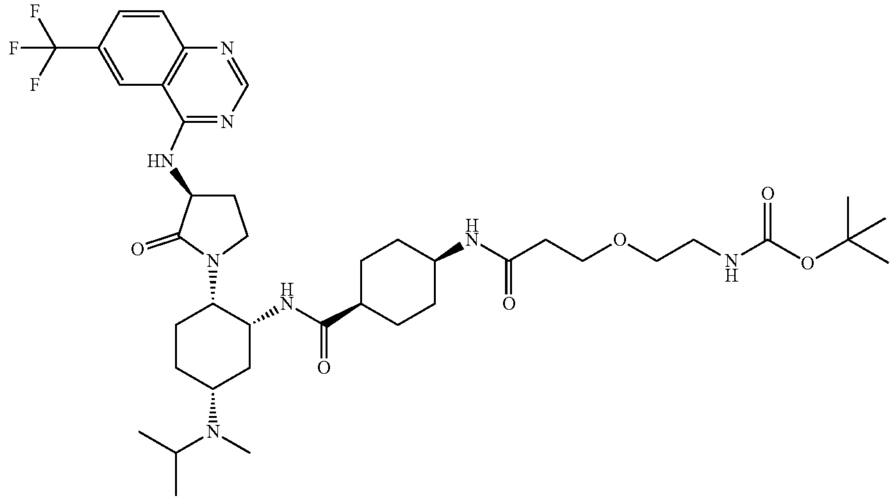 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)OC(C)(C)C)CC2)C1]

To a mixture of (1 s,4S)-4-amino-N-((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)cyclohexane-1-carboxamide, 2Hydrochloric acid salt (253 mg, 0.382 mmol) in dichloromethane (DCM) (5 mL) was added 3-(2-((tert-butoxycarbonyl)amino)ethoxy)propanoic acid (89 mg, 0.382 mmol), triethylamine (0.266 mL, 1.909 mmol) and HATU (174 mg, 0.458 mmol). The mixture was stirred at rt for 2 h and was concentrated. Purification by ISCO CombiFlash® chromatography (24 g RediSep Rf Gold® column, 35 mL/min) eluting with a gradient of 0 to 15% methanol containing ammonium hydroxide (10%) in dichloromethane (DCM) provided the title compound ((215 mg, 0.267 mmol, 70.0% yield). LC-MS m/z 636.3 $(M+H)^+$.

Step 2 tert-Butyl 3-((2S,3S)-1-methyl-5-oxo-2-(pyridin-3-yl)pyrrolidine-3-carboxamido) propanoate

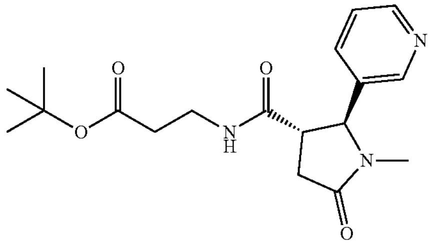 [SMILES: CN1C(=O)C[C@H](C(=O)NCCC(=O)OC(C)(C)C)[C@H]1c1cccnc1]

To a mixture of tert-butyl 3-aminopropanoate, hydrochloric acid salt (267 mg, 1.471 mmol) and (2S,3S)-1-methyl-5-oxo-2-(pyridin-3-yl)pyrrolidine-3-carboxylic acid (324 mg, 1.471 mmol) in dichloromethane (DCM) (3 mL) was added triethylamine (1.025 mL, 7.36 mmol) and HATU (671 mg, 1.765 mmol). The mixture was stirred at rt for 2 h and was partitioned between dichloromethane (DCM) and saturated $NaHCO_3$. The aqueous phase was extracted with dichloromethane (DCM) and the combined organic phases were washed with were dried over $Na_2SO_4$, were filtered, and the filtrate was concentrated. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (525 mg, 1.511 mmol, 103% yield). LC-MS m/z 348.1 $(M+H)^+$.

Step 3

3-((2S,3S)-1-Methyl-5-oxo-2-(pyridin-3-yl)pyrrolidine-3-carboxamido)propanoic acid, Hydrochloric acid salt

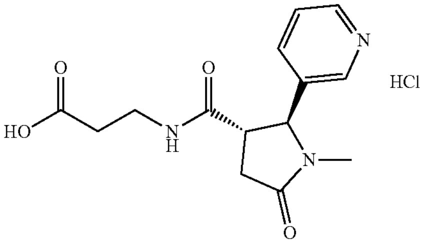 [SMILES: CN1C(=O)C[C@H](C(=O)NCCC(=O)O)[C@H]1c1cccnc1 ; Cl]

4 N HCl in 1,4-dioxane (3.02 mL, 12.09 mmol) was added to tert-butyl 3-((2S,3S)-1-methyl-5-oxo-2-(pyridin-3-yl) pyrrolidine-3-carboxamido)propanoate (525 mg, 1.511 mmol) in dichloromethane (DCM) (0.5 mL). The mixture was stirred at rt for 3 h and was concentrated to dryness to provide the title compound (560 mg, 1.537 mmol, 102% yield). LC-MS m/z 292.1 $(M+H)^+$.

Step 4 tert-Butyl (3-((2-(3-(((1S,4s)-4-(((1R,2S,5R)-5-(isopropyl(methyl)amino)-2-((S)-2-oxo-3-((6-(trifluoromethyl)quinazolin-4-yl)amino)pyrrolidin-1-yl) cyclohexyl)carbamoyl)cyclohexyl)amino)-3-oxopropoxy)ethyl)amino)-3-oxopropyl)carbamate

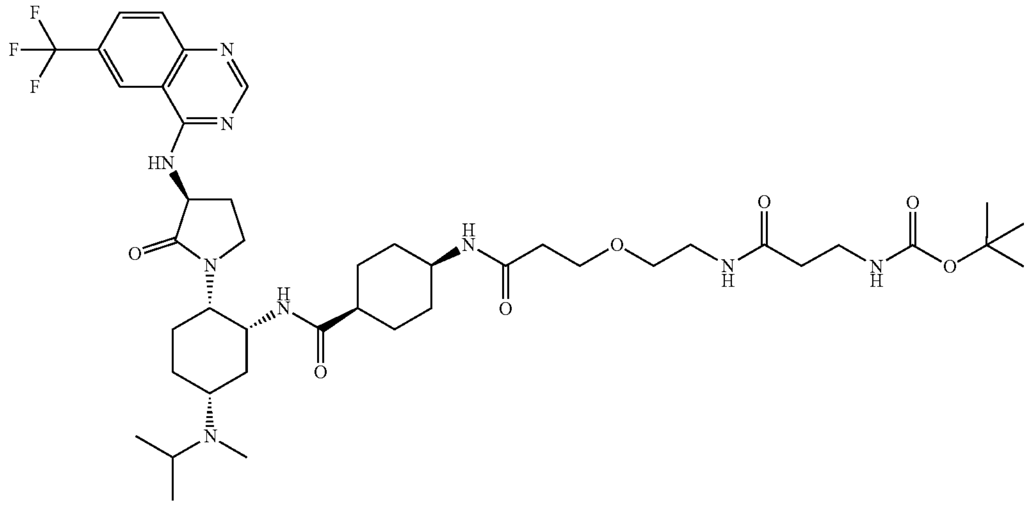 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCNC(=O)OC(C)(C)C)CC2)C1]

4 M HCl in 1,4-dioxane (0.534 mL, 2.137 mmol) was added to tert-butyl (2-(3-(((1S,4S)-4-(((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl)amino)-3-oxopropoxy)ethyl) carbamate (215 mg, 0.267 mmol) in dichloromethane (DCM) (0.1 mL). The mixture was stirred at rt overnight and was concentrated to dryness. To the residue in dichloromethane (DCM) (1 mL) was added 3-((tert-butoxycarbonyl)amino)propanoic acid (50.5 mg, 0.267 mmol), HATU (122 mg, 0.321 mmol), and triethylamine (0.298 mL, 2.137 mmol). The mixture was stirred at rt overnight. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (197 mg, 0.208 mmol, 78% yield). LC-MS m/z 876.1 $(M+H)^+$.

Step 5

(2S,3S)-N-(3-((3-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl) carbamoyl)cyclohexyl)amino)-3-oxopropoxy)ethyl)amino)-3-oxopropyl)amino)-3-oxopropyl)-1-methyl-5-oxo-2-(pyridin-3-yl) pyrrolidine-3-carboxamide

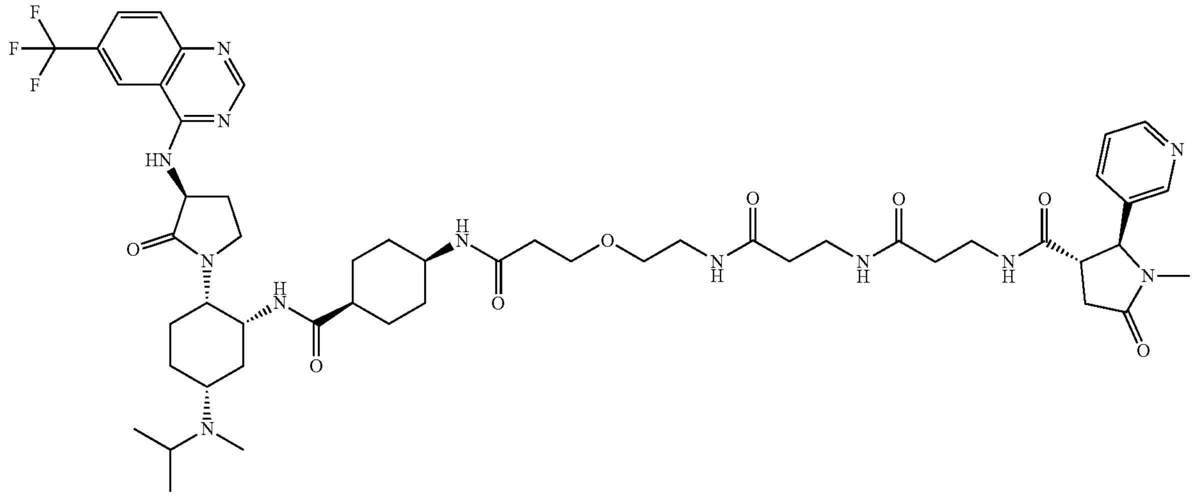 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCNC(=O)CCNC(=O)[C@H]3CC(=O)N(C)[C@@H]3c3cccnc3)CC2)C1]

4 M HCl in 1,4-dioxane (0.114 mL, 0.457 mmol) was added to tert-butyl (3-((2-(3-(((1S,4s)-4(((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)carbamoyl)cyclohexyl)amino)-3-oxopropoxy)ethyl)amino)-3-oxopropyl)carbamate (50 mg, 0.057 mmol) in dichloromethane (DCM) (0.1 mL). The mixture was stirred at rt for 2 h and was concentrated to dryness. The residue was placed in dichloromethane (DCM) (1 mL). 3-((2S,3S)-1-Methyl-5-oxo-2-(pyridin-3-yl)pyrrolidine-3-carboxamido)propanoic acid, hydrochloric acid salt (18.71 mg, 0.057 mmol), triethylamine (0.064 mL, 0.457 mmol), and HATU (26.0 mg, 0.068 mmol) were. The mixture was stirred at rt for 1 h and mixture was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as a white solid (40.1 mg, 0.038 mmol, 67.0% yield). LC-MS m/z 1049.9 $(M+H)^+$. $^1H$ NMR (400 MHz, METHANOL-$d_4$) δ ppm 1.05-1.17 (m, 3H) 1.23 (br d, J=6.4 Hz, 3H) 1.49-1.92 (m, 10H) 2.15-2.30 (m, 4H) 2.31-2.39 (m, 4H) 2.43 (br t, J=6.1 Hz, 4H) 2.52-2.65 (m, 1H) 2.65-2.67 (m, 3H) 2.67-2.73 (m, 1H) 2.79-2.94 (m, 1H) 2.94-3.15 (m, 2H) 3.29-3.35 (m, 9H) 3.49 (t, J=5.6 Hz, 2H) 3.55 (br s, 1H) 3.61-3.73 (m, 4H) 3.89 (br t, J=3.9 Hz, 1H) 4.05-4.13 (m, 1H) 4.49 (br s, 1H) 4.82-4.84 (m, 1H) 5.18 (br s, 1H) 7.52 (dd, J=7.8, 4.9 Hz, 1H) 7.79 (dt, J=7.8, 2.0 Hz, 1H) 7.92 (d, J=8.8 Hz, 1H) 8.07 (dd, J=8.8, 2.0 Hz, 1H) 8.50-8.53 (m, 1H) 8.54 (s, 1H) 8.57 (dd, J=4.9, 1.5 Hz, 1H) 8.60 (s, 1H) 8.71 (s, 1H).

Example 183

3-(4-(((1R,2S,5R)-5-(Isopropyl(methyl)amino)-2-((S)-2-oxo-3-((6-(trifluoromethyl) quinazolin-4-yl) amino)pyrrolidin-1-yl)cyclohexyl)amino)-4-oxobutyl)-N-(2-((2S,3S)-1-methyl-5-oxo-2-(pyridin-3-yl)pyrrolidine-3-carboxamido)ethyl)-3-azaspiro [5.5]undecane-9-carboxamide, 3 Formic acid salt

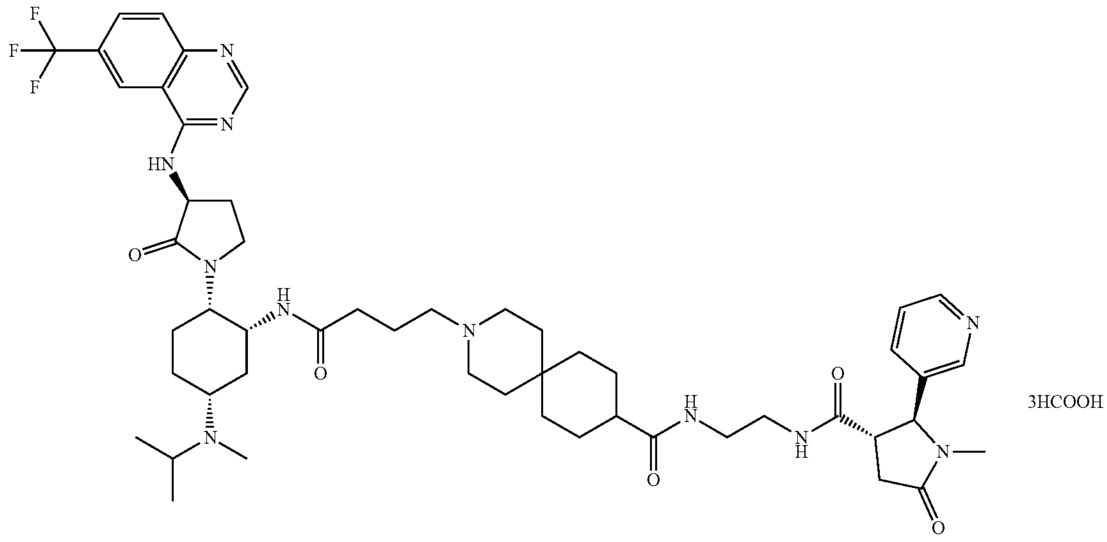 [SMILES: CC(C)N(C)[C@@H]1CC[C@H](N2CC[C@H](Nc3ncnc4ccc(C(F)(F)F)cc34)C2=O)[C@H](NC(=O)CCCN2CCC3(CCC(C(=O)NCCNC(=O)[C@H]4CC(=O)N(C)[C@@H]4c4cccnc4)CC3)CC2)C1]

Step 1 tert-Butyl (2-((2S,3S)-1-methyl-5-oxo-2-(pyridin-3-yl)pyrrolidine-3-carboxamido)ethyl) carbamate

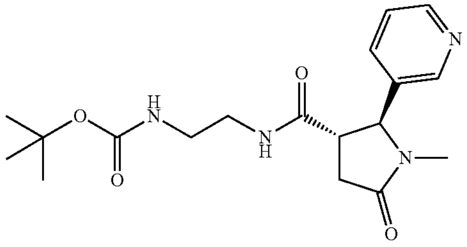 [SMILES: CN1C(=O)C[C@H](C(=O)NCCNC(=O)OC(C)(C)C)[C@H]1c1cccnc1]

To a mixture of tert-butyl (2-aminoethyl)carbamate (284 mg, 1.771 mmol) and (2S,3S)-1-methyl-5-oxo-2-(pyridin-3-yl)pyrrolidine-3-carboxylic acid (390 mg, 1.771 mmol) in dichloromethane (DCM) (5 mL) was added HATU (808 mg, 2.125 mmol) and triethylamine (0.741 mL, 5.31 mmol). The mixture was stirred at rt for 2 h. Purification by ISCO CombiFlash® chromatography (40 g RediSep Rf Gold® column, 40 mL/min) eluting with a gradient of 0 to 15% methanol containing ammonium hydroxide (10%) in dichloromethane (DCM) provided the title compound (517 mg, 1.426 mmol, 81% yield). LC-MS m/z 363.2 $(M+H)^+$.

Step 2

(2S,3S)-N-(2-Aminoethyl)-1-methyl-5-oxo-2-(pyridin-3-yl)pyrrolidine-3-carboxamide, 2Hydrochloric acid salt

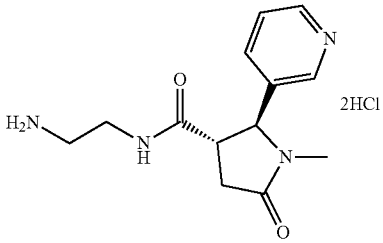 [SMILES: CN1C(=O)C[C@H](C(=O)NCCN)[C@H]1c1cccnc1]

4 M HCl in 1,4-dioxane (1.783 mL, 7.13 mmol) was added to tert-butyl (2-((2S,3S)-1-methyl-5-oxo-2-(pyridin-3-yl)pyrrolidine-3-carboxamido)ethyl)carbamate (517 mg, 1.426 mmol) in dichloromethane (DCM) (2 mL). The mixture was stirred at rt for 3 h and was concentrated to dryness to provide the title compound as a solid (500 mg, 1.491 mmol, 105% yield). LC-MS m/z 263.2 $(M+H)^+$.

Step 3 tert-Butyl 9-((2-((2S,3S)-1-methyl-5-oxo-2-(pyridin-3-yl)pyrrolidine-3-carboxamido) ethyl)carbamoyl)-3-azaspiro[5.5]undecane-3-carboxylate

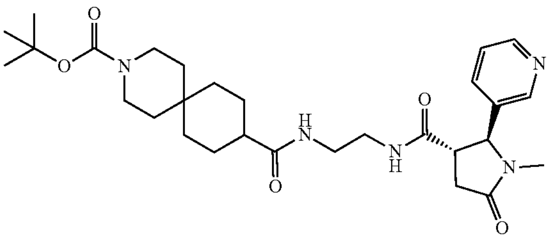 [SMILES: CN1C(=O)C[C@H](C(=O)NCCNC(=O)C2CCC3(CC2)CCN(C(=O)OC(C)(C)C)CC3)[C@H]1c1cccnc1]

To a mixture of 3-(tert-butoxycarbonyl)-3-azaspiro[5.5]undecane-9-carboxylic acid (104.5 mg, 0.351 mmol) and (2S,3S)-N-(2-aminoethyl)-1-methyl-5-oxo-2-(pyridin-3-yl) pyrrolidine-3-carboxamide, 2Hydrochloric acid salt (118 mg, 0.351 mmol) in dichloromethane (DCM) (0.5 mL) was added HATU (160 mg, 0.422 mmol) and triethylamine (0.294 mL, 2.108 mmol). The mixture was stirred at rt for 2 h. Purification by ISCO CombiFlash® chromatography (80 g RediSep Rf Gold® column, 60 mL/min) eluting with a gradient of 0 to 15% methanol containing ammonium hydroxide (10%) in dichloromethane (DCM) provided the title compound as a solid (105 mg, 0.194 mmol, 55.2% yield). LC-MS m/z 542.5 $(M+H)^+$.

Step 4

N-(2-((2S,3S)-1-Methyl-5-oxo-2-(pyrid i n-3-yl) pyrrolidine-3-carboxamido)ethyl)-3-azaspiro[5.5] undecane-9-carboxamide, 2Hydrochloric acid salt

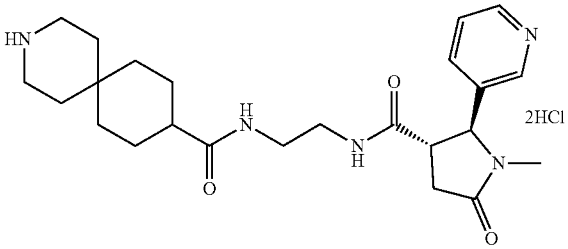 [SMILES: CN1C(=O)C[C@H](C(=O)NCCNC(=O)C2CCC3(CCNCC3)CC2)[C@H]1c1cccnc1]

4 M HCl in 1,4-dioxane (0.247 mL, 0.988 mmol) was added to tert-butyl 9-((2-((2S,3S)-1-methyl-5-oxo-2-(pyridin-3-yl)pyrrolidine-3-carboxamido)ethyl)carbamoyl)-3-azaspiro[5.5]undecane-3-carboxylate (107 mg, 0.198 mmol) in dichloromethane (DCM) (0.2 mL). The mixture was stirred at rt for 2 h and was concentrated to dryness to provide the title compound as a solid (122 mg, 0.237 mmol, 120% yield). LC-MS m/z 442.2 $(M+H)^+$.

Step 5 tert-Butyl 4-(9-((2-((2S,3S)-1-methyl-5-oxo-2-(pyridin-3-yl)pyrrolidine-3-carboxamido) ethyl)carbamoyl)-3-azaspiro[5.5]undecan-3-yl)butanoate

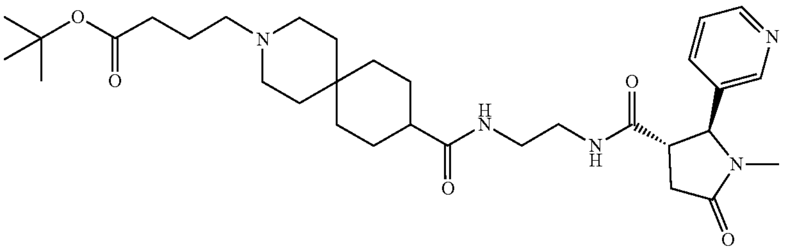 [SMILES: CN1C(=O)C[C@H](C(=O)NCCNC(=O)C2CCC3(CC2)CCN(CCCC(=O)OC(C)(C)C)CC3)[C@H]1c1cccnc1]

A mixture of N-(2-((2S,3S)-1-methyl-5-oxo-2-(pyridin-3-yl) pyrrolidine-3-carboxamido)ethyl)-3-azaspiro[5.5]undecane-9-carboxamide, 2hydrochloric acid salt (64 mg, 0.124 mmol), tert-butyl 4-bromobutanoate (27.8 mg, 0.124 mmol) and potassium carbonate (51.6 mg, 0.373 mmol) in acetonitrile (1 mL) was stirred at rt for 1.5 h and at 80° C. for 2 h. Saturated $NaHCO_3$ was added and the aqueous phase was extracted with dichloromethane (DCM). The combined organic phases were dried over $Na_2SO_4$, were filtered, and the filtrate was concentrated to dryness to provide the title compound (57 mg, 0.098 mmol, 78% yield). LC-MS m/z 584.4 $(M+H)^+$.

Step 6

3-(4-(((1R,2S,5R)-5-(Isopropyl(methyl)amino)-2-((S)-2-oxo-3-((6-(trifluoromethyl) quinazolin-4-yl) amino)pyrrolidin-1-yl)cyclohexyl)amino)-4-oxobutyl)-N-(2-((2S,3S)-1-methyl-5-oxo-2-(pyridin-3-yl)pyrrolidine-3-carboxamido)ethyl)-3-azaspiro [5.5]undecane-9-carboxamide, 3 Formic acid salt 4 N HCl in 1,4-dioxane (0.118 mL, 0.471 mmol) was added to tert-butyl 4-(9-((2-((2S,3S)-1-methyl-5-oxo-2-(pyridin-3-yl)pyrrolidine-3-carboxamido)ethyl)carbamoyl)-3-azaspiro[5.5]undecan-3-yl)butanoate (55 mg, 0.094 mmol) in dichloromethane (DCM) (1 mL). The mixture was stirred at rt for 2 h and was concentrated to dryness. To the residue in dichloromethane (DCM) (1 mL) was added (S)-1-((1S,2R,4R)-2-amino-4-(isopropyl(methyl)amino)cyclohexyl)-3-((6-(trifluoromethyl)quinazolin-4-yl)amino) pyrrolidin-2-one, 2Hydrochloric acid salt (50.6 mg, 0.094 mmol), triethylamine (0.105 mL, 0.754 mmol), and HATU (53.7 mg, 0.141 mmol). The mixture was stirred at rt for 3 h and was partitioned between saturated $NaHCO_3$ and dichloromethane (DCM). The aqueous phase was extracted with dichloromethane (DCM) and the combined organic phases were dried over $Na_2SO_4$, were filtered, and the filtrate was concentrated. Purification by ISCO Combi-Flash® chromatography (40 g RediSep Rf Gold® column, 40 mL/min) eluting with a gradient of 30 to 85% acetonitrile in water both containing formic acid (0.1%) provided the title compound (54 mg, 0.053 mmol, 56.4% yield). LC-MS m/z 974.4 $(M+H)^+$. $^1H$ NMR (400 MHz, METHANOL-$d_4$) δ ppm 0.97-1.06 (m, 4H) 1.13 (br d, J=6.3 Hz, 3H) 1.22-1.45 (m, 3H) 1.45-1.56 (m, 6H) 1.56-1.68 (m, 3H) 1.68-1.86 (m, 5H) 1.94-2.13 (m, 3H) 2.14-2.40 (m, 14H) 2.57 (dt d, J=12.4, 8.2, 8.2, 4.1 Hz, 1H) 2.66-2.67 (m, 3H) 2.67-2.79 (m, 2H) 2.82-2.90 (m, 1H) 2.98-3.04 (m, 1H) 3.20-3.31 (m, 4H) 3.38-3.51 (m, 1H) 3.56 (td, J=9.1, 3.9 Hz, 1H) 3.62-3.69 (m, 1H) 4.06 (dt, J=12.1, 3.9 Hz, 1H) 4.65 (br d, J=3.3 Hz, 1H) 4.84-4.88 (m, 1H) 5.22 (t, J=7.9 Hz, 1H) 7.51-7.55 (m, 1H) 7.80 (dt, J=8.0, 1.9 Hz, 1H) 7.92 (d, J=8.8 Hz, 1H) 8.07 (dd, J=8.8, 1.8 Hz, 1H) 8.53 (d, J=2.3 Hz, 1H) 8.58 (dd, J=4.9, 1.6 Hz, 1H) 8.60 (s, 1H) 8.83 (s, 1H).

The following compound was or could be prepared with procedures analogous to that described in Example 183:

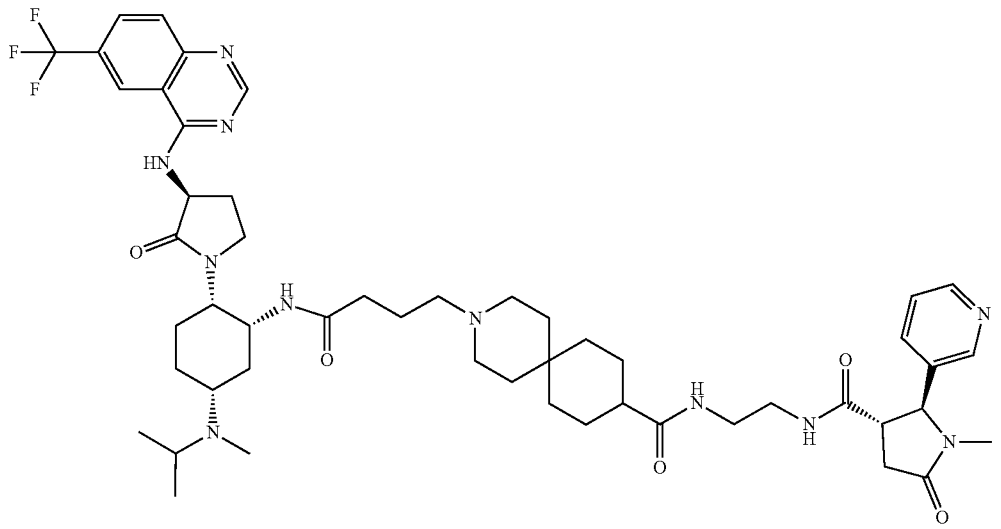

3HCOOH

| Ex. | Compound | LC-MS m/z | NMR |
| --- | --- | --- | --- |
| 184 | 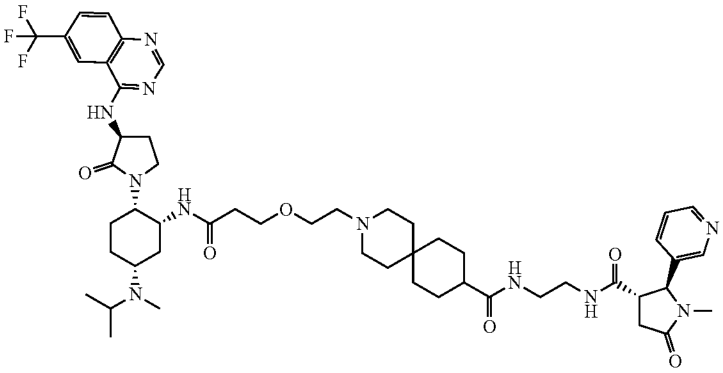 3HCOOH 3-(2-(3-(((1R,2S,5R)-5-(isopropyl(methyl)amino)-2-((S)-2-oxo-3-((6-(trifluoromethyl)quinazolin-4-yl)amino)450yridine450ne-1-yl)cyclohexyl)amino)-3-oxopropoxy)ethyl)-N-(2-((2S,3S)-1-methyl-5-oxo-2-(450yridine-3-yl)pyrrolidine-3-carboxamido)ethyl)-3-azaspiro[5.5]undecane-9-carboxamide, 3Formic acid salt. | 1004.3 (M + H)+ | $^1H$ NMR (400 MHz, METHANOL-$d_4$) δ ppm 1.05 (br d, J = 6.3 Hz, 4H) 1.13 (br d, J = 6.5 Hz, 3H) 1.25-1.41 (m, 2H) 1.49-1.61 (m, 6H) 1.62-1.84 (m, 5H) 1.90-2.01 (m, 1H) 2.02-2.17 (m, 2H) 2.23 (br dd, J = 15.1, 3.0 Hz, 1H) 2.27 (s, 3H) 2.30-2.41 (m, 5H) 2.43-2.60 (m, 5H) 2.67 (s, 3H) 2.68-2.79 (m, 2H) 2.80-2.91 (m, 1H) 2.96-3.06 (m, 1H) 3.22 (d, J = 5.3 Hz, 1H) 3.24-3.29 (m, 3H) 3.30 (s, 1H) 3.39-3.49 (m, 2H) 3.50-3.57 (m, 1H) 3.58-3.64 (m, 1H) 3.65-3.73 (m, 2H) 3.74-3.86 (m, 1H) 4.06 (dt, J = 12.4, 3.7 Hz, 1H) 4.67 (br d, J = 2.8 Hz, 1H) 4.85 (d, J = 6.0 Hz, 1H) 5.28 (t, J = 7.8 Hz, 1H) 7.47-7.57 (m, 1H) 7.80 (dt, J = 8.0, 1.9 Hz, 1H) 7.91 (d, J = 8.8 Hz, 1H) 8.07 (dd, J = 8.9, 1.9 Hz, 1H) 8.53 (d, J = 2.3 Hz, 1H) 8.58 (dd, J = 4.9, 1.6 Hz, 1H) 8.60 (s, 1H) 8.86 (s, 1H). |

Example 185

N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-1''-(4-((2S,3S)-1-methyl-5-oxo-2-(pyridin-3-yl)pyrrolidine-3-carboxamido)butyl)-[1,4':1',4''-terpiperidine]-4-carboxamide

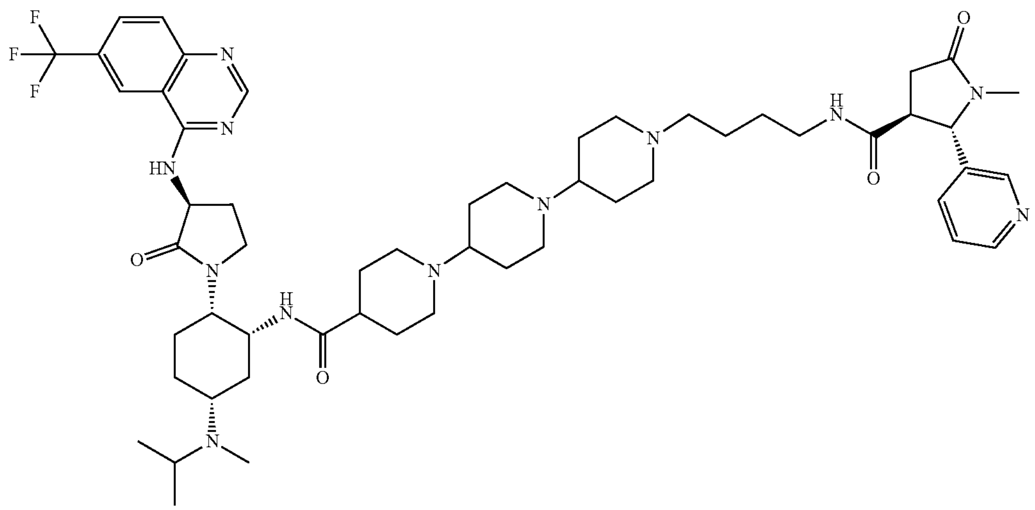 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C4CCN(CCCCNC(=O)[C@H]5CC(=O)N(C)[C@@H]5c5cccnc5)CC4)CC3)CC2)C1]

Step 1

1"Benzyl 4-ethyl[1,4':1',4"-terpiperidine]-1",4-dicarboxylate, 2Trifluroacetic acid salt

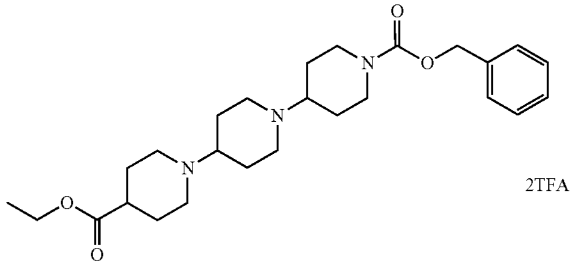 [SMILES: CCOC(=O)C1CCN(C2CCN(C3CCN(C(=O)OCc4ccccc4)CC3)CC2)CC1]

A mixture of ethyl[1,4'-bipiperidine]-4-carboxylate, 2hydrochloric acid salt (265 mg, 0.846 mmol) and triethylamine (0.248 mL, 1.776 mmol) in dichloromethane (DCM) (8 mL) was stirred at rt for 15 min. Benzyl 4-oxopiperidine-1-carboxylate (217 mg, 0.931 mmol) was added, with a few drops of acetic acid. The mixture was stirred for 30 min and sodium triacetoxyborohydride (269 mg, 1.269 mmol) was slowly added. The mixture was stirred at rt overnight and was concentrated. Purification by MDAP chromatography (XSelect™ CSH Prep C18 150 mm×30 mm 5 μm OBD column, 40 mL/min) eluting with a gradient of 15 to 55% acetonitrile in water both containing trifluoroacetic acid (0.1%) provided the title compound as a colorless film (2983 mg, 0.413 mmol, 48.8% yield). LC-MS m/z 458.2 $(M+H)^+$.

Step 2

1"-((Benzyloxy)carbonyl)-[1,4':1',4"-terpiperidine]-4-carboxylic acid

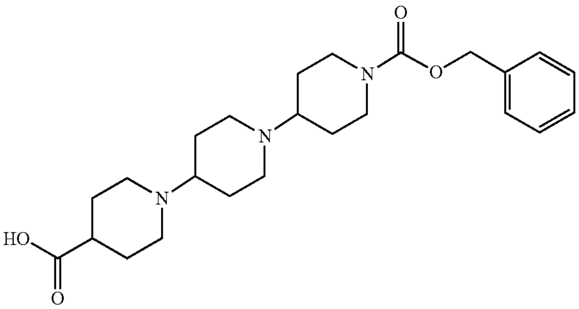 [SMILES: O=C(O)C1CCN(C2CCN(C3CCN(C(=O)OCc4ccccc4)CC3)CC2)CC1]

2 M Lithium hydroxide (0.869 mL, 1.738 mmol) was added to a solution of 1"-benzyl 4-ethyl[1,4':1',4"-terpiperidine]-1",4-dicarboxylate, 2trifluoroacetic acid salt (298 mg, 0.435 mmol) in tetrahydrofuran (THF) (2 mL) and ethanol (2 mL). The mixture was stirred at rt for 1 h and was concentrated under reduced pressure to remove the organic solvents. The pH of the aqueous residue was adjusted to 3 with 1 N HCl and was evaporated to dryness. The residue was suspended in methanol/dichloromethane (DCM) (2%) (30 mL), was stirred with sonification, and was filtered. The filtrate was concentrated under reduced pressure to provide the title compound as a white solid containing a large amount of inorganic salt. LC-MS m/z 430.2 $(M+H)^+$.

Step 3

Benzyl 4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)-[1,4':1',4"-terpiperidine]-1"-carboxylate, 3Trifluoroacetic acid salt

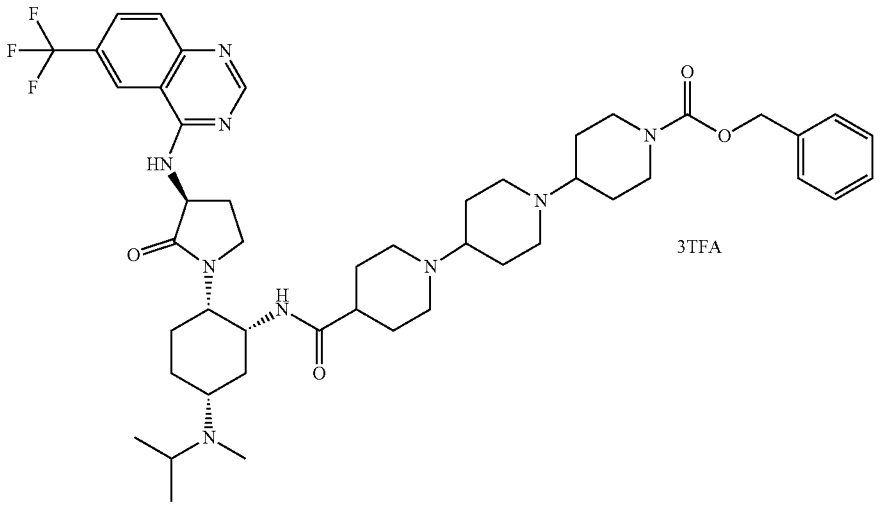 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C4CCN(C(=O)OCc5ccccc5)CC4)CC3)CC2)C1]

4 M HCl in 1,4-dioxane (1 mL, 4.00 mmol) was added to a solution of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (237 mg, 0.420 mmol) in dichloromethane (DCM) (2 mL). The mixture was stirred at rt for 30 min and was concentrated under reduced pressure. The residue was suspended in dichloromethane (DCM) (7 mL) and triethylamine (0.293 mL, 2.099 mmol), 1"-((benzyloxy)carbonyl)-[1,4':1',4"-terpiperidine]-4-carboxylic acid (321 mg, 0.411 mmol), and HATU (239 mg, 0.630 mmol) were added. The mixture was stirred at rt for 1 h, Water (1 mL) added and the mixture was concentrated under reduced pressure. Purification by MDAP chromatography (XSelect™ CSH Prep C18 150 mm×30 mm 5 μm OBD column, 40 mL/min) eluting with a gradient of 15 to 55% acetonitrile in water both containing trifluoroacetic acid (0.1%) provided the title compound as an off-white solid (313.9 mg, 0.253 mmol, 60.2% yield). LC-MS m/z 876.3 $(M+H)^+$.

Step 4

N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-[1,4':1',4"-terpiperidine]-4-carboxamide, 3Trifluoroacetic acid salt

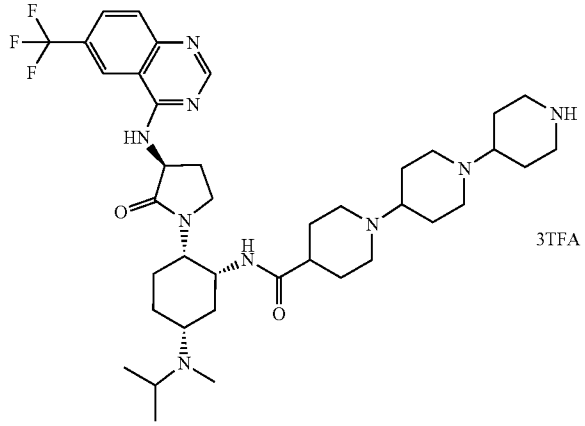 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C4CCNCC4)CC3)CC2)C1]

3TFA

To a solution of benzyl 4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)-[1,4':1',4"-terpiperidine]-1"-carboxylate, 3trifluoroacetic acid salt (313.9 mg, 0.258 mmol) in methanol (7 mL) was added 10% Pd/C (27.4 mg, 0.026 mmol). The mixture was vacuumed and was backfilled with hydrogen several times. The mixture was stirred under a balloon atmosphere of hydrogen at rt for 2 h, was filtered, and the filtrate was concentrated to provide the title compound as a white foam (290 mg, 0.243 mmol, 94% yield). LC-MS m/z 742.2 $(M+H)^+$.

Step 5

1"-(4-Azidobutyl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-[1,4':1',4"-terpiperidine]-4-carboxamide

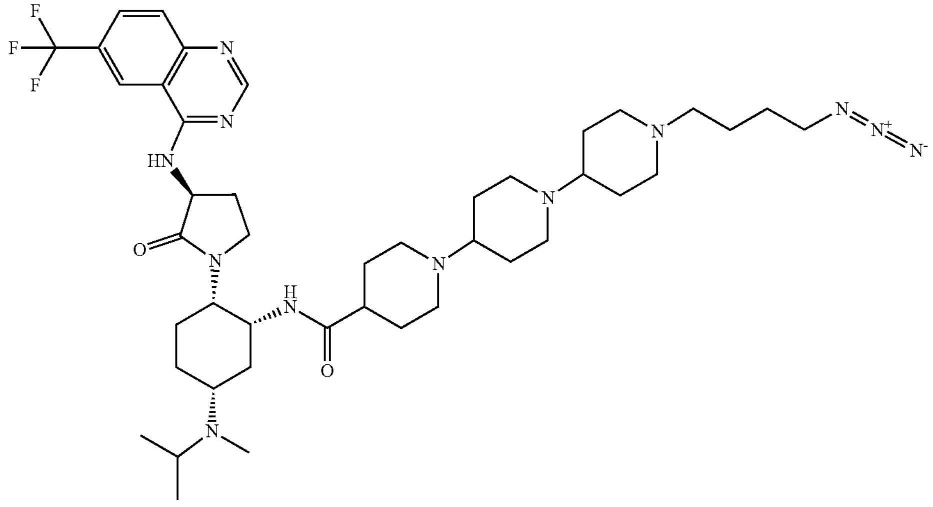 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C4CCN(CCCCN=[N+]=[N-])CC4)CC3)CC2)C1]

A mixture of N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-[1,4':1',4"-terpiperidine]-4-carboxamide, 3trifluoroacetic acid salt (90 mg, 0.083 mmol), 1-azido-4-iodobutane (35 mg, 0.156 mmol) and potassium carbonate (57.4 mg, 0.415 mmol) in acetonitrile (4 mL) was stirred at 75° C. for 2 h, was cooled, and was filtered. The filtrate was concentrated under reduced pressure. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a brown solid (44.2 mg, 0.051 mmol, 61.5% yield). LC-MS m/z 839.4 $(M+H)^+$.

Step 6

1"-(4-Aminobutyl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-[1,4':1',4"-terpiperidine]-4-carboxamide

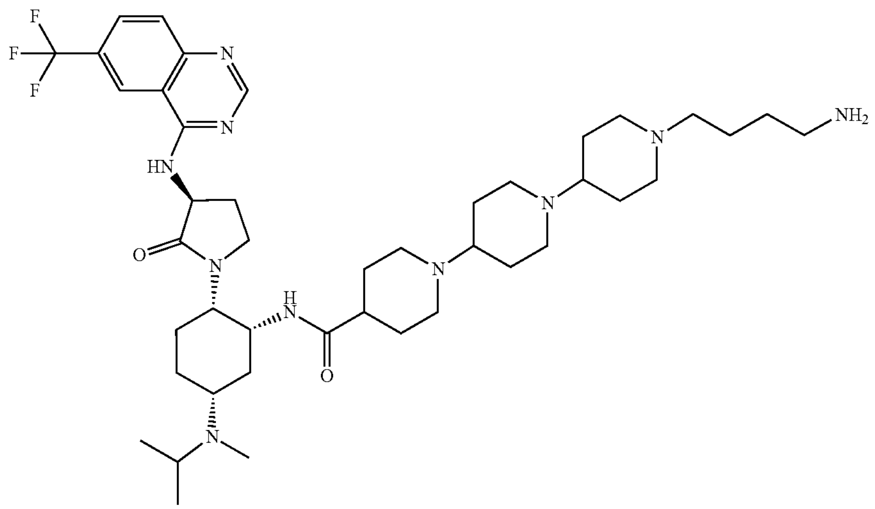 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C4CCN(CCCCN)CC4)CC3)CC2)C1]

To a solution of 1"-(4-azidobutyl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)-[1,4':1',4"-terpiperidine]-4-carboxamide (44 mg, 0.052 mmol) in methanol (7 mL) was added 10% Pd/C (5.58 mg, 5.24 μmol). The flask was vacuumed and was backfilled with hydrogen. The mixture was stirred under a balloon atmosphere of hydrogen at rt for 2 h and was filtered. The filtrate was concentrated to provide the title compound as a colorless film (36.5 mg, 0.044 mmol, 83% yield). LC-MS m/z 813.4 $(M+H)^+$.

Step 7

N-((1R,2S,5R)-5-(isopropyl(methyl)amino)-2-((S)-2-oxo-3-((6-(trifluoro methyl) quinazolin-4-yl) amino)pyrrolidin-1-yl)cyclohexyl)-1''-(4-((2S,3S)-1-methyl-5-oxo-2-(pyridin-3-yl)pyrrolidine-3-carboxamido)butyl)-[1,4':1',4''-terpiperidine]-4-carboxamide

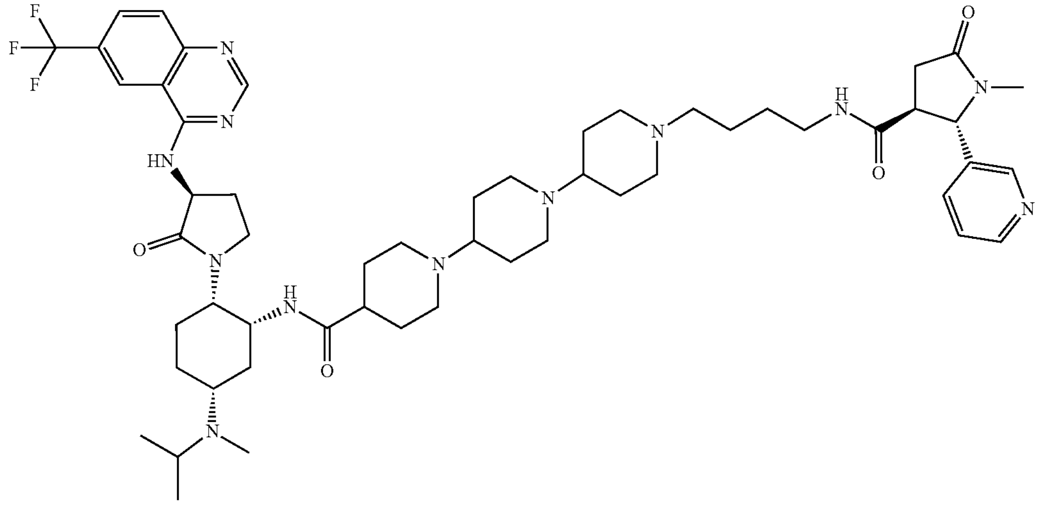 [SMILES: CC(C)N(C)[C@@H]1CC[C@H](N2CC[C@H](Nc3ncnc4ccc(C(F)(F)F)cc34)C2=O)[C@H](NC(=O)C2CCN(C3CCN(C4CCN(CCCCNC(=O)[C@H]5CC(=O)N(C)[C@@H]5c5cccnc5)CC4)CC3)CC2)C1]

To a solution of 1''-(4-aminobutyl)-N-((1R,2S,5R)-5-(isopropyl(methyl)amino)-2-((S)-2-oxo-3-((6-(trifluoromethyl) quinazolin-4-yl)amino)pyrrolidin-1-yl)cyclohexyl)-[1,4':1',4''-terpiperidine]-4-carboxamide (36.5 mg, 0.045 mmol), (2S,3S)-1-methyl-5-oxo-2-(pyridin-3-yl)pyrrolidine-3-carboxylic acid (15 mg, 0.068 mmol), and triethylamine (0.019 mL, 0.135 mmol) in dichloromethane (DCM) (3 mL) was added HATU (30 mg, 0.079 mmol). The mixture was stirred at rt overnight and was concentrated. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a white solid (23 mg, 0.022 mmol, 50.0% yield). LC-MS m/z 1015.3 $(M+H)^+$. $^1H$ NMR (400 MHz, METHANOL-$d_4$) δ ppm 1.01 (br d, J=6.3 Hz, 3H) 1.17 (br d, J=6.3 Hz, 3H) 1.43-1.64 (m, 8H) 1.64-1.82 (m, 4H) 1.82-2.09 (m, 10H) 2.09-2.36 (m, 15H) 2.49-2.63 (m, 1H) 2.67 (s, 3H) 2.68-2.70 (m, 1H) 2.73 (br d, J=7.6 Hz, 2H) 2.78-2.93 (m, 1H) 2.93-3.09 (m, 7H) 3.10-3.29 (m, 2H) 3.35-3.57 (m, 3H) 3.58-3.69 (m, 1H) 4.04 (dt, J=12.3, 3.7 Hz, 1H) 4.66 (br d, J=3.3 Hz, 1H) 4.82-4.88 (m, 1H) 5.30 (t, J=8.5 Hz, 1H) 7.82 (dt, J=8.0, 1.8 Hz, 1H) 7.92 (d, J=8.6 Hz, 1H) 8.07 (dd, J=8.9, 1.8 Hz, 1H) 8.52 (d, J=1.8 Hz, 1H) 8.57-8.61 (m, 2H) 8.78 (s, 1H).

Example 186

Step 6

(2S,3S)-N-(2-(2-((1S,3R)-3-(3-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)propanamido)cyclobutane-1-carboxamido)ethoxy)ethyl)-1-methyl-5-oxo-2-(pyridin-3-yl)pyrrolidine-3-carboxamide

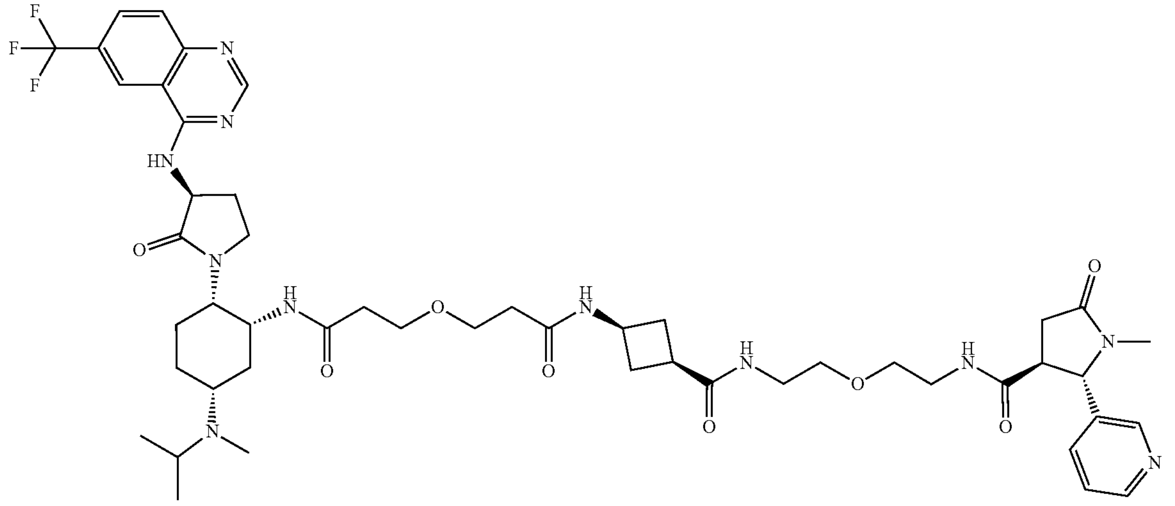 [SMILES: CC(C)N(C)[C@@H]1CC[C@H](N2CC[C@H](Nc3ncnc4ccc(C(F)(F)F)cc34)C2=O)[C@H](NC(=O)CCOCCC(=O)N[C@H]2C[C@@H](C(=O)NCCOCCNC(=O)[C@H]3CC(=O)N(C)[C@@H]3c3cccnc3)C2)C1]

Step 1 tert-Butyl (2-(2-((2S,3S)-1-methyl-5-oxo-2-(pyridin-3-yl)pyrrolidine-3-carboxamido) ethoxy)ethyl)carbamate

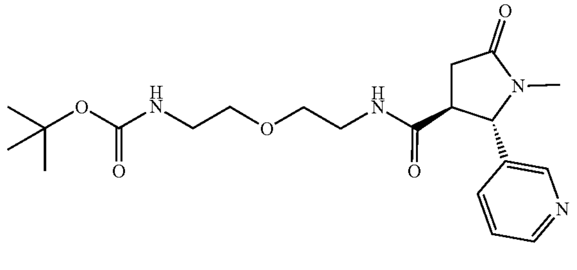 [SMILES: CN1C(=O)C[C@H](C(=O)NCCOCCNC(=O)OC(C)(C)C)[C@H]1c1cccnc1]

To a suspension of (2S,3S)-1-methyl-5-oxo-2-(pyridin-3-yl)pyrrolidine-3-carboxylic acid (250 mg, 1.135 mmol) in dichloromethane (DCM) (3 mL) was added CDI (244 mg, 1.476 mmol).

The mixture was stirred at rt for 30 min and a solution of tert-butyl (2-(2-aminoethoxy)ethyl)carbamate (308 mg, 1.476 mmol) in dichloromethane (DCM) (1 mL) was added. The mixture was stirred at rt overnight. Dichloromethane (DCM) (45 mL) was added and the organic phase was washed with saturated $NaHCO_3$. The aqueous phase was extracted with dichloromethane (DCM) (30 mL). The combined organic phases were washed with brine, were dried over $Na_2SO_4$, were filtered, and the filtrate was concentrated. Purification by CombiFlash® Rf chromatography (40 g silica column, 40 mL/min) eluting with a gradient of 0 to 15% methanol in dichloromethane (DCM) provided the title compound as a sticky, white foam 432 mg, 1.063 mmol, 94% yield). LC-MS m/z 407.2 $(M+H)^+$.

Step 2

(2S,3S)-N-(2-(2-Aminoethoxy)ethyl)-1-methyl-5-oxo-2-(pyridin-3-yl)pyrrolidine-3-carboxamide, 2Hydrochloric acid salt

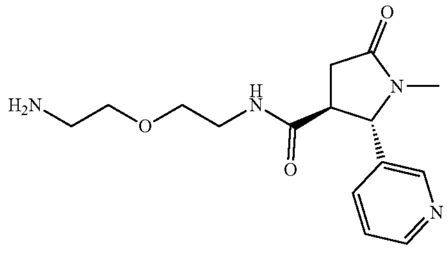

2HCl

4 M HCl in 1,4-dioxane (4 mL, 16.00 mmol) was added to a solution of tert-butyl (2-(2-((2S,3S)-1-methyl-5-oxo-2-(pyridin-3-yl)pyrrolidine-3-carboxamido)ethoxy)ethyl)carbamate (431 mg, 1.060 mmol) in dichloromethane (DCM) (4 mL). The mixture was stirred at rt overnight and was concentrated under reduced pressure. The residue was dried under high vacuum to provide the titled compound as a white solid (620 mg, 1.063 mmol, 100% yield). LC-MS m/z 307.1 $(M+H)^+$.

Step 3 tert-Butyl ((1R,3s)-3-((2-(2-((2S,3S)-1-methyl-5-oxo-2-(pyridin-3-yl)pyrrolidine-3-carboxamido)ethoxy)ethyl)carbamoyl)cyclobutyl)carbamate

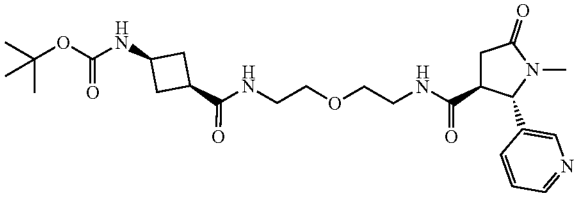 [SMILES: CN1C(=O)C[C@H](C(=O)NCCOCCNC(=O)[C@H]2C[C@@H](NC(=O)OC(C)(C)C)C2)[C@H]1c1cccnc1]

To a solution of (2S,3S)-N-(2-(2-aminoethoxy)ethyl)-1-methyl-5-oxo-2-(pyridin-3-yl)pyrrolidine-3-carboxamide 2hydrochloric acid salt (620 mg, 1.063 mmol) and (1 s,3s)-3-((tert-butoxycarbonyl)amino)cyclobutane-1-carboxylic acid (289 mg, 1.275 mmol) in dichloromethane (DCM) (4 mL) at RT was added triethylamine (0.740 mL, 5.31 mmol), followed by addition of HATU (536 mg, 1.381 mmol). The mixture was stirred at rt overnight. Dichloromethane (DCM) (45 mL) was added and the organic phase was washed with saturated $NaHCO_3$ and brine. The aqueous phase was extracted with dichloromethane (DCM) (30 mL). The combined organic phases were washed with saturated $NaHCO_3$, with brine, were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a white foam (502 mg, 0.947 mmol, 89% yield). LC-MS m/z 504.3 $(M+H)^+$.

Step 4

(2S,3S)-N-(2-(2-((1 s,3R)-3-Aminocyclobutane-1-carboxamido)ethoxy)ethyl)-1-methyl-5-oxo-2-(pyridin-3-yl)pyrrolidine-3-carboxamide, 2Hydrochloric acid salt

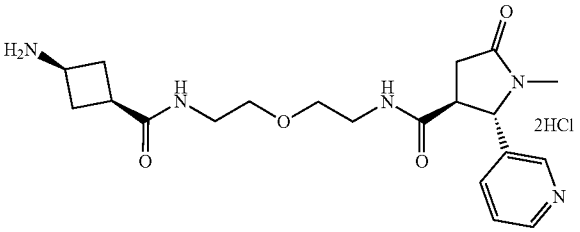 [SMILES: CN1C(=O)C[C@H](C(=O)NCCOCCNC(=O)[C@H]2C[C@@H](N)C2)[C@H]1c1cccnc1]

4 M HCl in 1,4-dioxane (4 mL, 16.00 mmol) was added to a solution of tert-butyl ((1R,3s)-3-((2-(2-((2S,3S)-1-methyl-5-oxo-2-(pyridin-3-yl)pyrrolidine-3-carboxamido)ethoxy)ethyl)carbamoyl)cyclobutyl)carbamate (500 mg, 0.943 mmol) in dichloromethane (DCM) (4 mL). The mixture was stirred for 6.5 h and was concentrated under reduced pressure. The residue was dried under high vacuum to provide the title compound as a white solid (815 mg, 0.941 mmol, 100% yield). LC-MS m/z 404.5 $(M+H)^+$.

Step 5 tert-Butyl 3-(3-(((1R,3s)-3-((2-(2-((2S,3S)-1-methyl-5-oxo-2-(pyridin-3-yl)pyrrolidine-3-carboxamido)ethoxy)ethyl)carbamoyl)cyclobutyl)amino)-3-oxopropoxy)propanoate

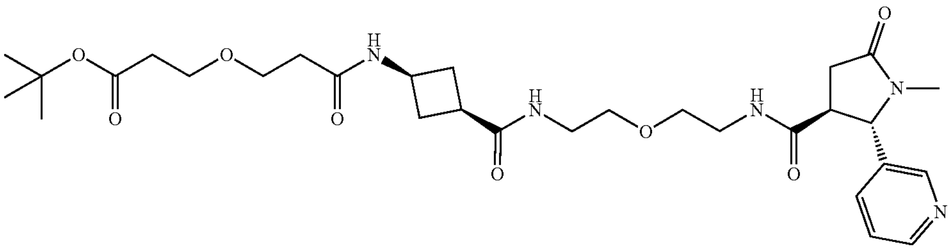 [SMILES: CN1C(=O)C[C@H](C(=O)NCCOCCNC(=O)[C@H]2C[C@@H](NC(=O)CCOCCC(=O)OC(C)(C)C)C2)[C@H]1c1cccnc1]

To a solution of (2S,3S)-N-(2-(2-((1 s, 3R)-3-aminocyclobutane-1-carboxamido)ethoxy)ethyl)-1-methyl-5-oxo-2-(pyridin-3-yl)pyrrolidine-3-carboxamide, 2hydrochloric acid salt (806 mg, 0.931 mmol) and 3-(3-(tert-butoxy)-3-oxopropoxy)propanoic acid (249 mg, 1.117 mmol) in dichloromethane (DCM) (6 mL) was added triethylamine (0.648 mL, 4.65 mmol), followed by addition of HATU (433 mg, 1.117 mmol). The reaction mixture was stirred at rt for overnight. Dichloromethane (DCM) (45 mL) was added and the organic phase was washed with saturated $NaHCO_3$ and brine. The aqueous phase was extracted with dichloromethane (DCM) (30 mL). The combined organic phases were washed with saturated $NaHCO_3$,with brine, were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a white foam (498 mg, 0.792 mmol, 85% yield). LC-MS m/z 604.5 $(M+H)^+$.

Step 6

(2S,3S)-N-(2-(2-((1S,3R)-3-(3-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)propanamido)cyclobutane-1-carboxamido)ethoxy)ethyl)-1-methyl-5-oxo-2-(pyridin-3-yl)pyrrolidine-3-carboxamide

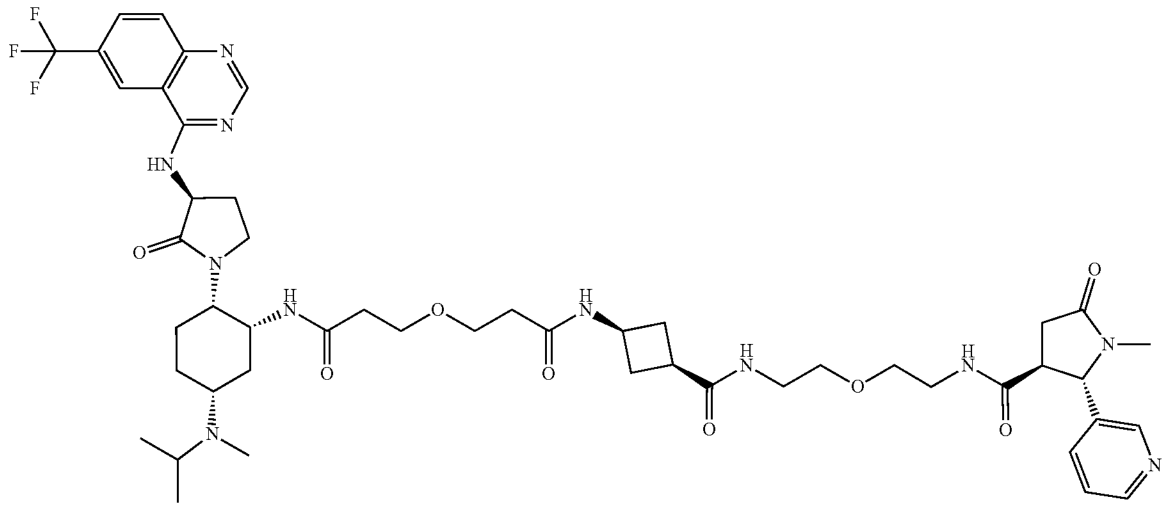 [SMILES: CC(C)N(C)[C@@H]1CC[C@H](N2CC[C@H](Nc3ncnc4ccc(C(F)(F)F)cc34)C2=O)[C@H](NC(=O)CCOCCC(=O)N[C@H]2C[C@@H](C(=O)NCCOCCNC(=O)[C@H]3CC(=O)N(C)[C@@H]3c3cccnc3)C2)C1]

4 M HCl in 1,4-dioxane (2 mL, 8.00 mmol) was added to a solution of tert-butyl 3-(3-(((1R,3s)-3-((2-(2-((2S,3S)-1-methyl-5-oxo-2-(pyridin-3-yl) pyrrolidine-3-carboxamido)ethoxy)ethyl) carbamoyl)cyclobutyl)amino)-3-oxopropoxy) propanoate (78 mg, 0.123 mmol) in dichloromethane (DCM) (2.0 mL). The mixture was stirred at rt for 2 h and was concentrated under reduced pressure. To residue was added dichloromethane (DCM) (2.0 mL), (S)-1 ((1S,2R,4R)-2-amino-4-(isopropyl(methyl)amino)cyclohexyl)-3-((6-(trifluoromethyl)quinazolin-4-yl)amino)pyrrolidin-2-one 2hydrochloric acid salt (65 mg, 0.103 mmol), and triethylamine (0.072 mL, 0.514 mmol), followed by HATU (47.9 mg, 0.123 mmol). The mixture was stirred at rt for 2 h. Dichloromethane (DCM) (45 mL) was added and the organic phase was washed with saturated $NaHCO_3$ and brine. The aqueous phase was extracted with dichloromethane (DCM) (30 mL). The combined organic phases were washed with saturated $NaHCO_3$,with brine, were dried over $Na_2SO_4$, were filtered, and the filtrate was concentrated. Purification by MDAP chromatography (XSelect™ CSH Prep C18 5 µm OBD column, 40 mL/min) eluting with a gradient of 30 to 85% acetonitrile in water containing ammonium bicarbonate (10 mM) and ammonium hydroxide (0.075%) provided the title compound as a white solid (80.2 mg, 0.080 mmol, 78% yield). LC-MS m/z 994.5 $(M+H)^+$. $^1H$ NMR (400 MHz, METHANOL-$d_4$) δ ppm 1.04 (d, J=6.11 Hz, 3H), 1.14 (d, J=6.60 Hz, 3H), 1.63-1.80 (m, 3H), 1.88-2.00 (m, 1H), 2.0-32.16 (m, 3H), 2.19-2.60 (m, 12H), 2.64-2.90 (m, 7H), 2.99-3.09 (m, 1H), 3.27-3.31 (m, 1H), 3.36-3.71 (m, 12H), 3.78 (dt, J=9.48, 6.14 Hz, 1H), 4.01-4.10 (m, 1H), 4.16-4.28 (m, 1H), 4.58-4.67 (m, 1H), 4.83 (d, J=6.60 Hz, 1H), 5.32 (t, J=8.19 Hz, 1H), 7.54 (dd, J=7.58, 4.89 Hz, 1H), 7.80 (dt, J=7.83, 1.96 Hz, 1H), 7.91 (d, J=8.80 Hz, 1H), 8.06 (dd, J=8.80, 1.71 Hz, 1H), 8.52 (d, J=1.71 Hz, 1H), 8.55-8.63 (m, 2H), 8.82 (s, 1H).

The following compounds were or could be prepared with procedures analogous to that described in Example 186:

| Ex. | Compound | LC-MS m/z | NMR |
|---|---|---|---|
| 187 | 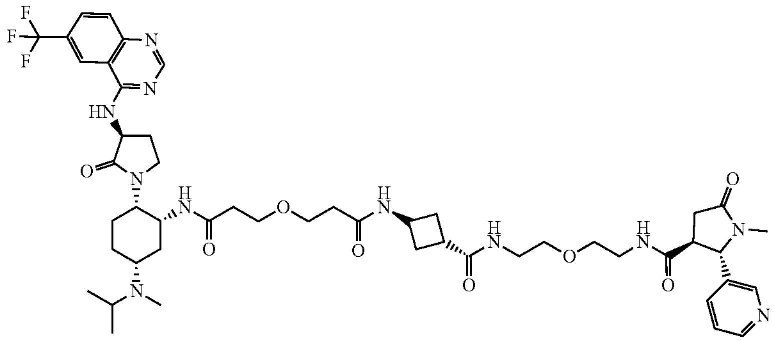 (2S,3S)-N-(2-(2-((1R,3S)-3-(3-(3-(((1R,2S,5R)-5-Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)propanamido)cyclobutane-1-carboxamido)ethoxy)ethyl)-1-methyl-5-oxo-2-(pyridin-3-yl)pyrrolidine-3-carboxamide. | 994.5 (M + H)+ | $^1$H NMR (400 MHz, METHANOL-$d_4$) δ ppm 1.19 (s, 9H) 1.67-1.80 (m, 2H) 1.83-2.02 (m, 4H) 2.11-2.31 (m, 3H) 2.38 (t, J = 6.4 Hz, 2H) 2.42-2.59 (m, 5H) 2.67 (s, 3H) 2.69-2.76 (m, 1H) 2.79-2.89 (m, 1H) 2.93-3.02 (m, 1H) 3.06 (ddd, J = 9.3, 8.1, 6.6 Hz, 1H) 3.24 (br s, 1H) 3.27-3.32 (m, 2H) 3.38 (dd, J = 6.1, 4.6 Hz, 2H) 3.45-3.53 (m, 4H) 3.53-3.59 (m, 1H) 3.60-3.72 (m, 3H) 3.72-3.85 (m, 2H) 4.01 (dt, J = 12.5, 3.8 Hz, 1H) 4.46 (quin, J = 7.5 Hz, 1H) 4.62 (br d, J = 2.9 Hz, 1H) 4.82 (d, J = 6.8 Hz, 1H) 5.33 (t, J = 8.3 Hz, 1H) 7.49-7.57 (m, 1H) 7.81 (dt, J = 7.8, 2.0 Hz, 1H) 7.91 (d, J = 8.8 Hz, 1H) 8.06 (dd, J = 8.8, 2.0 Hz, 1H) 8.52 (d, J = 1.5 Hz, 1H) 8.58 (dd, J = 4.9, 2.0 Hz, 1H) 8.59 (s, 1H) 8.82 (s, 1H). |
| 188 | 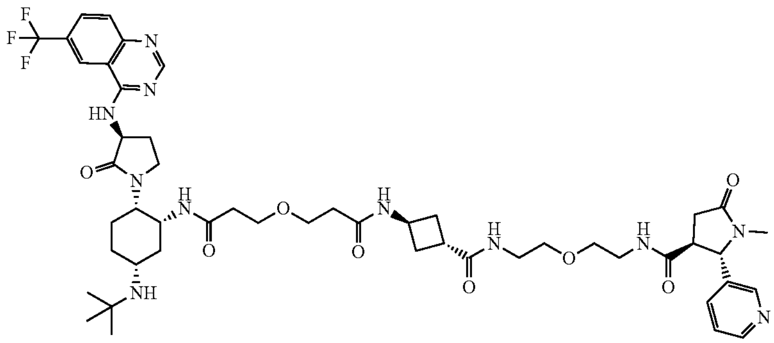 [SMILES: CN1C(=O)C[C@H](C(=O)NCCOCCNC(=O)[C@H]2C[C@H](NC(=O)CCOCCC(=O)N[C@@H]3C[C@H](NC(C)(C)C)CC[C@@H]3N3CC[C@H](Nc4ncnc5ccc(C(F)(F)F)cc45)C3=O)C2)[C@H]1c1cccnc1] (2S,3S)-N-(2-(2-((1R,3S)-3-(3-(3-(((1R,2S,5R)-5-(tert-butylamino)-2-((S)-2-oxo-3-((6-(trifluoromethyl)quinazolin-4-yl)amino)pyrrolidin-1-yl)cyclohexyl)amino)-3-oxopropoxy)propanamido)cyclobutane-1-carboxamido)ethoxy)ethyl)-1-methyl-5-oxo-2-(pyridin-3-yl)pyrrolidine-3-carboxamide. | 994.5 (M + H)+ | $^1$H NMR (400 MHz, METHANOL-$d_4$) δ ppm 1.04 (br d, J = 5.9 Hz, 3H) 1.14 (br d, J = 6.4 Hz, 3H) 1.68-1.78 (m, 2H) 1.91-2.01 (m, 1H) 2.10 (br d, J = 12.7 Hz, 1H) 2.15-2.21 (m, 2H) 2.27 (s, 3H) 2.37 (td, J = 6.2, 1.7 Hz, 2 H) 2.43-2.58 (m, 5H) 2.67 (s, 3H) 2.70-2.76 (m, 2H) 2.80-2.88 (m, 1H) 2.94-3.02 (m, 1H) 3.03-3.09 (m, 1H) 3.27-3.30 (m, 2H) 3.38 (td, J = 3.5, 2.2 Hz, 2H) 3.42-3.45 (m, 1H) 3.46-3.50 (m, 4H) 3.56-3.61 (m, 1H) 3.61-3.72 (m, 5H) 3.75-3.80 (m, 1H) 4.02-4.09 (m, 1H) 4.42-4.47 (m, 1H) 4.63 (br s, 1H) 4.80-4.84 (m, 2H) 4.90 (s, 1H) 5.31 (t, J = 8.3 Hz, 1H) 7.53 (dd, J = 7.8, 4.9 Hz, 1H) 7.80 (dt, J = 7.8, 2.0 Hz, 1H) 7.91 (d, J = 8.8 Hz, 1H) 8.06 (dd, J = 8.8, 2.0 Hz, 1H) 8.51 (d, J = 2.0 Hz, 1H) 8.57-8.59 (m, 1H) 8.59 (s, 1H) 8.81 (s, 1H). |

Example 189

(2S,3S)-N-(2-(2-(2-(4-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)piperidin-1-yl)ethoxy)ethoxy)ethyl)-1-methyl-5-oxo-2-(pyridin-3-yl)pyrrolidine-3-carboxamide

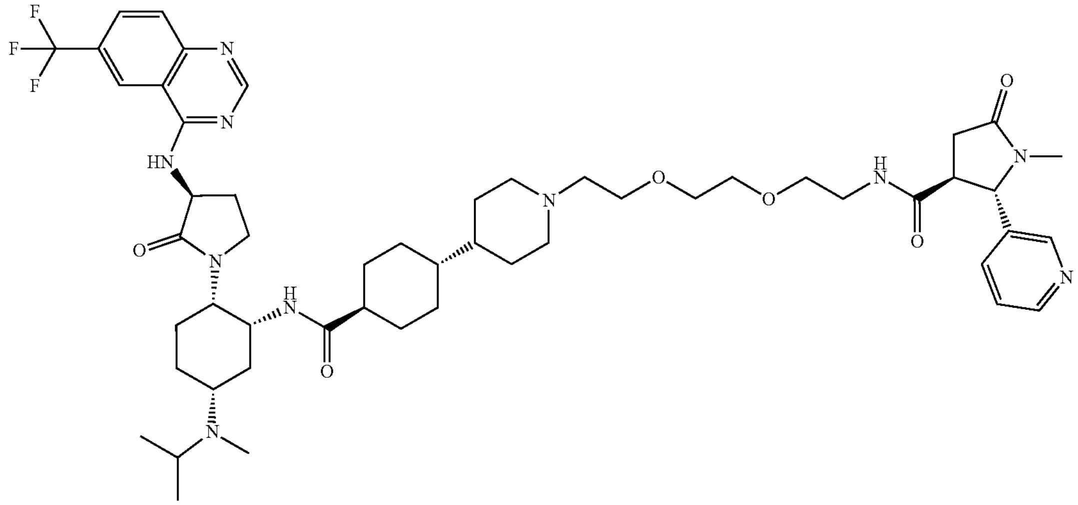 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](C3CCN(CCOCCOCCNC(=O)[C@H]4CC(=O)N(C)[C@@H]4c4cccnc4)CC3)CC2)C1]

Step 1 tert-Butyl 4-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohex-1-en-1-yl)-3,6-dihydropyridine-1(2H)-carboxylate, Formic acid salt

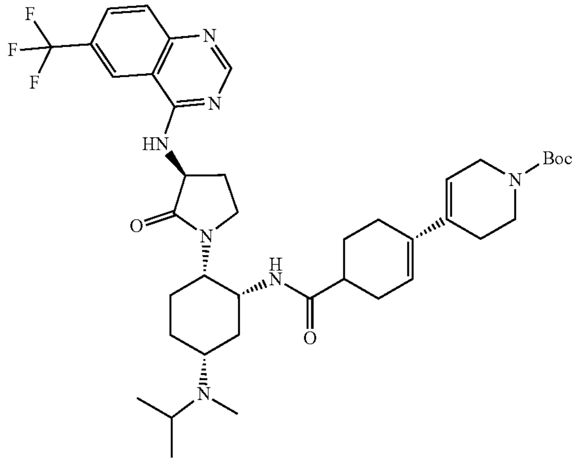

3 M HCl in cyclopentyl methyl ether (0.5 mL, 1.500 mmol) was added to a solution of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl) carbamate (78.5 mg, 0.139 mmol) in dichloromethane (DCM) (1 mL). The mixture was stirred at r t for 1 and was concentrated under reduced pressure. The residue was suspended in dichloromethane (DCM) (5 mL) and triethylamine (0.068 mL, 0.487 mmol), 4-(1-(tert-butoxycarbonyl)-1,2,3,6-tetrahydropyridin-4-yl)cyclohex-3-ene-1-carboxylic acid (49.4 mg, 0.161 mmol), and HATU (79 mg, 0.209 mmol) were added. The mixture was stirred at rt for 1 h and was concentrated under reduced pressure. Purification by MDAP chromatography (XSelect™ CSH Prep C18 150 mm×30 mm 5 μm OBD column, 40 mL/min) eluting with a gradient of 15 to 55% acetonitrile in water both containing formic acid (0.1%) provided the title compound as an off-white solid (105.2 mg, 0.133 mmol, 95% yield). LC-MS m/z 906.7 $(M+H)^+$.

Step 2

4-(1-(2-(2-(2-Azidoethoxy)ethoxy)ethyl)-1,2,3,6-tetrahydropyridin-4-yl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohex-3-ene-1-carboxamide

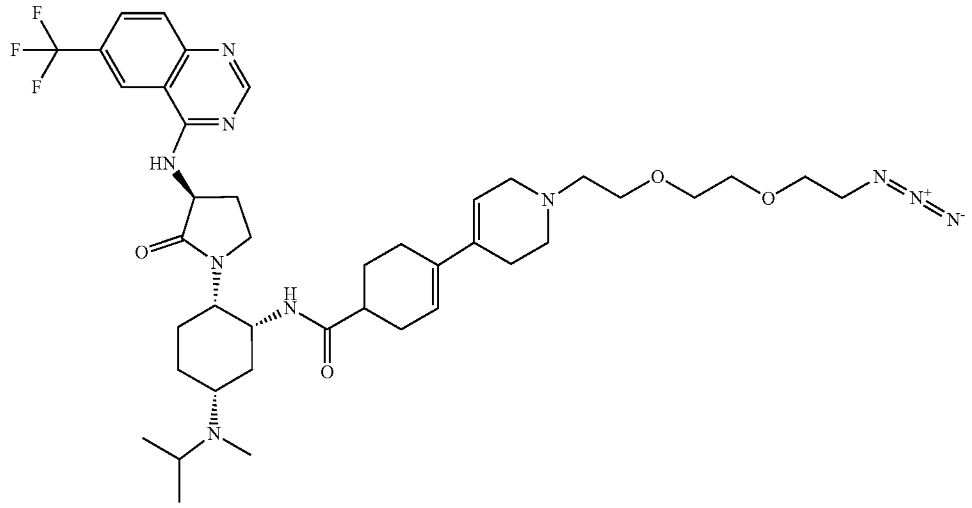 [SMILES: CC(C)N(C)[C@@H]1CC[C@H](N2CC[C@H](Nc3ncnc4ccc(C(F)(F)F)cc34)C2=O)[C@H](NC(=O)C2CC=C(C3=CCN(CCOCCOCCN=[N+]=[N-])CC3)CC2)C1]

A solution of tert-butyl 4-(4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohex-1-en-1-yl)-3,6-dihydropyridine-1(2H)-carboxylate (105 mg, 0.139 mmol) in dichloromethane (DCM) (2 mL) was treated with TFA (0.5 mL, 6.49 mmol) at rt overnight and was concentrated to dryness. The residue was suspended in acetonitrile (7.5 mL). Potassium carbonate (96 mg, 0.696 mmol) was added, followed by 2-(2-(2-azidoethoxy)ethoxy)ethyl methanesulfonate (52.9 mg, 0.209 mmol). The mixture was stirred at 85° C. for 5 h, was cooled, and was filtered. The filtrate was concentrated. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a pale-yellow film (71.5 mg, 0.088 mmol, 63.3% yield). LC-MS m/z 811.0 $(M+H)^+$.

Step 3

(1r,4R)-4-(1-(2-(2-(2-Aminoethoxy)ethoxy)ethyl)piperidin-4-yl)-N-((1R,2S,5R)-5-(isopropyl(methyl)amino)-2-((S)-2-oxo-3-((6-(trifluoromethyl)quinazolin-4-yl)amino) pyrrolidin-1-yl)cyclohexyl)cyclohexane-1-carboxamide, 3Trifluoroacetic acid salt To a solution of 4-(1-(2-(2-(2-azidoethoxy)ethoxy)ethyl)-1,2,3,6-tetrahydropyridin-4-yl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohex-3-ene-1-carboxamide (71.5 mg, 0.088 mmol) in methanol (5 mL) was added 10% Pd/C (9.38 mg, 8.82 μmol). The mixture was vacuumed and was backfilled with hydrogen several times. The mixture was stirred under a balloon atmosphere of hydrogen at rt for 24 h and was filtered through Celite®. The filtrate was concentrated. Purification by MDAP chromatography (XSelect™ CSH Prep C18 150 mm×30 mm 5 μm OBD column, 40 mL/min) eluting with a gradient of 5 to 35% acetonitrile in water both containing trifluoroacetic acid (0.1%) provided the title compound as colorless film (37.4 mg, 0.031 mmol, 35.6% yield). LC-MS m/z 789.4 $(M+H)^+$. $^1$H NMR (400 MHz, METHANOL-d4) δ ppm 0.81-0.92 (m, 1H) 0.95-1.07 (m, 1H) 1.10 (br d, J=6.8 Hz, 1H) 1.35 (br d, J=6.5 Hz, 3H) 1.44 (br d, J=6.5 Hz, 3H) 1.47-1.65 (m, 2H) 1.76-2.31 (m, 16H) 2.40-2.56 (m, 1H) 2.60-2.68 (m, 1H) 2.80-2.84 (m, 3H) 2.89-3.06 (m, 3H) 3.15 (t, J=5.0 Hz, 1H) 3.21-3.27 (m, 1H) 3.58-3.69 (m, 4H) 3.70-3.80 (m, 8H) 3.80-3.97 (m, 5H) 4.18-4.27 (m, 1H) 4.39 (br s, 1H) 8.03 (d, J=8.8 Hz, 1H) 8.33 (dd, J=8.8, 1.8 Hz, 1H) 8.89 (s, 1H) 9.11 (s, 1H).

The trans isomer was also isolated as a colorless film (46 mg, 0.039 mmol, 43.8% yield). LC-MS m/z 789.4 $(M+H)^+$.

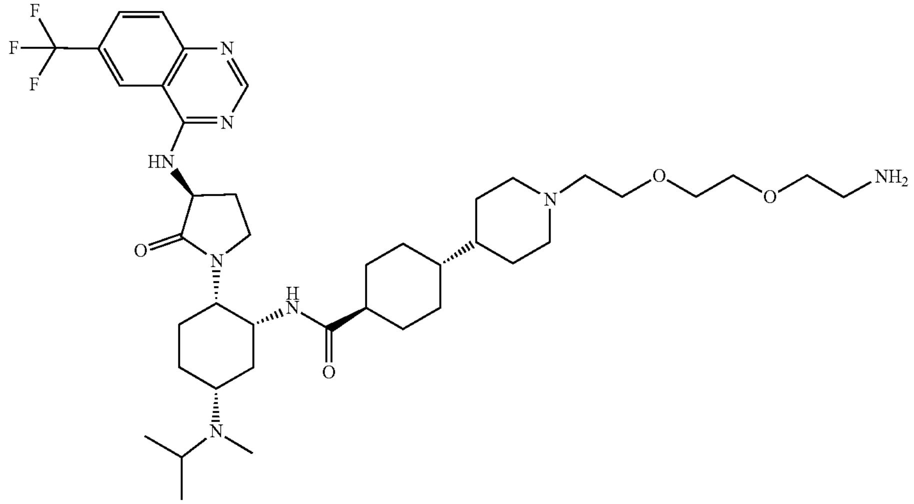

3TFA

Step 4

(2S,3S)-N-(2-(2-(2-(4-((1R,4r)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperidin-1-yl)ethoxy)ethoxy)ethyl)-1-methyl-5-oxo-2-(pyridin-3-yl)pyrrolidine-3-carboxamide

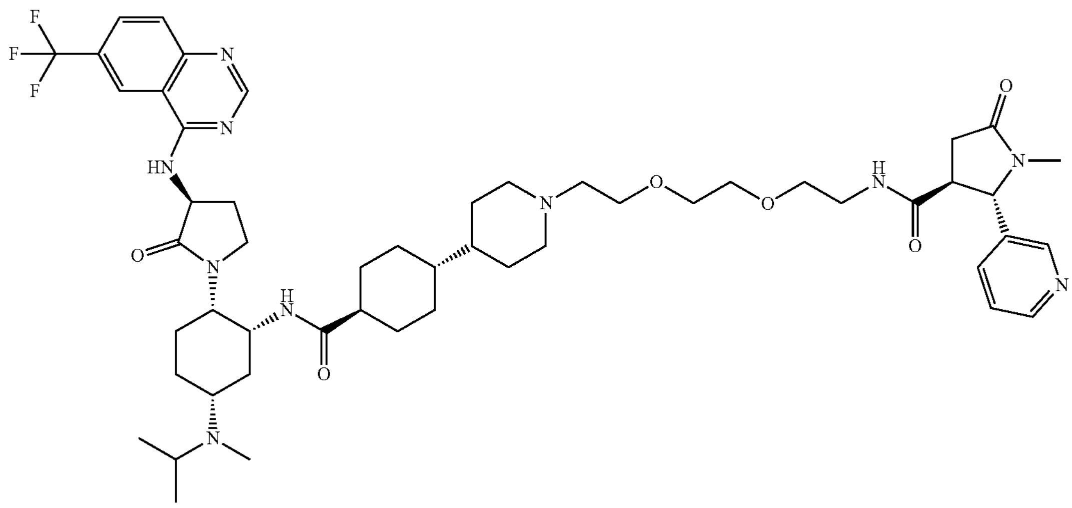 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](C3CCN(CCOCCOCCNC(=O)[C@H]4CC(=O)N(C)[C@@H]4c4cccnc4)CC3)CC2)C1]

To a solution of (1r,4R)-4-(1-(2-(2-(2-aminoethoxy)ethoxy)ethyl)piperidin-4-yl)-N-((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)cyclohexane-1-carboxamide (34 mg, 0.043 mmol) and (2S,3S)-1-methyl-5-oxo-2-(pyridin-3-yl)pyrrolidine-3-carboxylic acid (24 mg, 0.109 mmol) in dichloromethane (DCM) (3 mL) was added triethylamine (0.050 mL, 0.359 mmol) and HATU (33 mg, 0.087 mmol). The mixture was stirred at rt overnight and was concentrated. Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a white solid (10.2 mg, 9.88 μmol, 22.92% yield). LC-MS m/z 991.5 $(M+H)^+$. $^1H$ NMR (400 MHz, METHANOL-$d_4$) δ ppm 0.54-0.79 (m, 1H) 0.81-0.99 (m, 1H) 1.01-1.17 (m, 1H) 1.24-1.52 (m, 10H) 1.57-1.72 (m, 1H) 1.76-1.92 (m, 5H) 1.98-2.27 (m, 5H) 2.36-2.61 (m, 2H) 2.65-2.77 (m, 6H) 2.82-3.07 (m, 4H) 3.35-3.43 (m, 2H) 3.45-3.67 (m, 8H) 3.71-3.96 (m, 4H) 4.12-4.37 (m, 2H) 4.81-4.83 (m, 1H) 4.86-5.01 (m, 3H) 5.51 (s, 7H) 7.54 (dd, J=7.9, 4.9 Hz, 1H) 7.80 (dt, J=8.0, 1.9 Hz, 1H) 7.93 (d, J=8.6 Hz, 1H) 8.05-8.15 (m, 1H) 8.36 (br s, 2H) 8.44-8.57 (m, 1H) 8.63 (s, 1H) 8.73 (s, 1H).

The following compound was or could be prepared with procedures analogous to that described in Example 189:

| Ex. | Compound | LC-MS m/z | NMR |
|---|---|---|---|
| 190 | 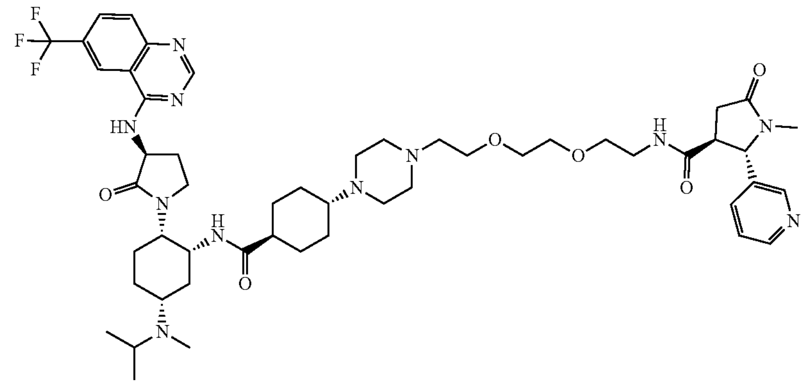 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](N3CCN(CCOCCOCCNC(=O)[C@H]4CC(=O)N(C)[C@@H]4c4cccnc4)CC3)CC2)C1] | 992.4 (M + H)+ | $^1H$ NMR (400 MHz, METHANOL-$d_4$) δ ppm 1.09-1.19 (m, 3H) 1.21-1.36 (m, 2H) 1.43-1.81 (m, 6H) 1.90-2.36 (m, 13H) 2.47-2.68 (m, 14H) 2.70-2.75 (m, 2H) 2.81 (d, J = 9.0 Hz, 1H) 3.05 (ddd, J = 9.4, 8.2, 6.8 Hz, 1H) 3.35-3.70 (m, 15H) 4.03 (dt, J = 12.5, 3.6 Hz, 1H) 4.66 (br d, J = 3.0 Hz, 1H) 4.80-4.85 (m, 1H) 5.26 (t, J = 7.8 Hz, 1H) 7.50-7.56 (m, 1H) 7.80 (dt, J = 8.0, 1.9 Hz, 1H) 7.91 (d, J = 8.8 Hz, 1H) 8.06 (dd, J = 9.0, 1.8 Hz, 1H) 8.52 (d, |

-continued

| Ex. | Compound | LC-MS m/z | NMR |
|---|---|---|---|
| | (2S,3S)-N-(2-(2-(2-(4-((1R,4r)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexyl)piperazin-1-yl)ethoxy)ethoxy)ethyl)-1-methyl-5-oxo-2-(pyridin-3-yl)pyrrolidine-3-carboxamide. | | J = 1.5 Hz, 1H) 8.58 (dd, J = 4.9, 1.6 Hz, 1H) 8.60 (s, 1H) 8.82 (d, J = 0.8 Hz, 1H). |

Example 191

(2S,3S)-N-(3-(9-(4-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-4-oxobutyl)-3,9-diazaspiro[5.5]undecan-3-yl)propyl)-1-methyl-5-oxo-2-(pyridin-3-yl) pyrrolidine-3-carboxamide

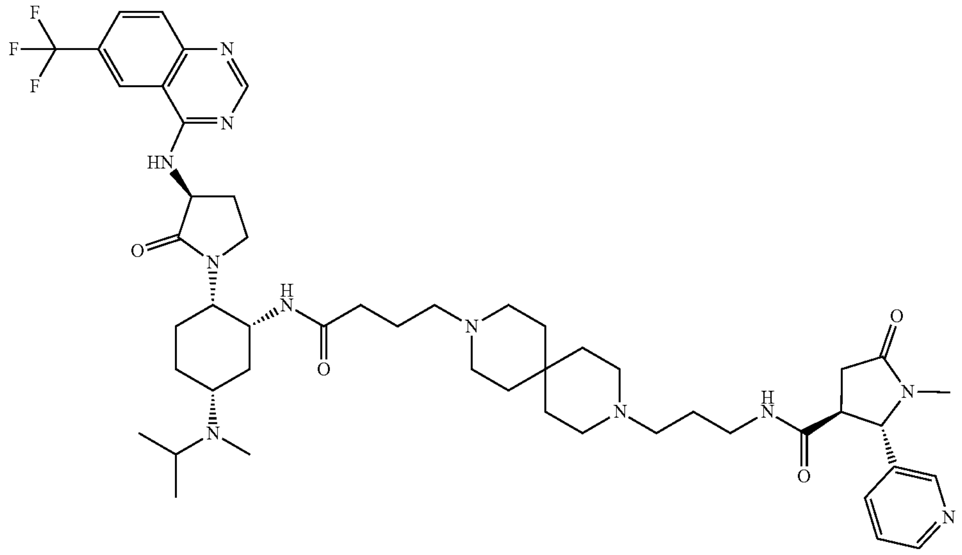 [SMILES: CC(C)N(C)[C@@H]1CC[C@H](N2CC[C@H](Nc3ncnc4ccc(C(F)(F)F)cc34)C2=O)[C@H](NC(=O)CCCN2CCC3(CCN(CCCNC(=O)[C@H]4CC(=O)N(C)[C@@H]4c4cccnc4)CC3)CC2)C1]

Step 1 tert-Butyl 9-(3-(1,3-dioxoisoindolin-2-yl)propyl)-3, 9-diazaspiro[5.5]undecane-3-carboxylate

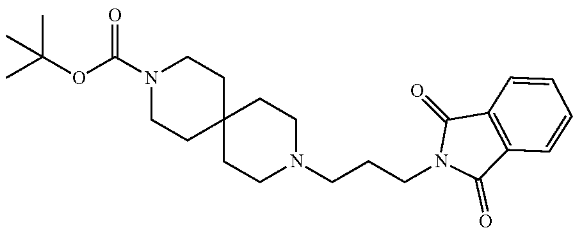 [SMILES: CC(C)(C)OC(=O)N1CCC2(CCN(CCCN3C(=O)c4ccccc4C3=O)CC2)CC1]

To a stirred solution of tert-butyl 3,9-diazaspiro[5.5]undecane-3-carboxylate (2.5 g, 9.83 mmol) in acetonitrile (20 mL) was added potassium carbonate (4.07 g, 29.5 mmol) and 2-(3-bromopropyl)isoindoline-1,3-dione (3.16 g, 11.79 mmol). The mixture was stirred at 80° C. for 8 h, was cooled to rt, and ice-cold water (40 mL) was added. The mixture was extracted with ethyl acetate (2×50 mL). The combined organic extracts were dried over $Na_2SO_4$, were filtered, and the filtrate was concentrated. Purification by normal-phase chromatography eluting with 80% ethyl acetate in hexanes provided the title compound as a pale-yellow liquid (2.0 g, 4.46 mmol, 45.3% yield). LC-MS m/z 442.3 $(M+H)^+$.

Step 2 tert-Butyl 9-(3-aminopropyl)-3,9-diazaspiro[5.5] undecane-3-carboxylate

To a stirred solution of tert-butyl 9-(3-(1,3-dioxoisoindolin-2-yl)propyl)-3,9-diazaspiro[5.5]undecane-3-carboxylate (2.0 g, 4.53 mmol) in ethanol (10 mL) was added slowly hydrazine hydrate (2.197 mL, 45.3 mmol). The mixture was stirred at 25° C. for 6 h and was concentrated to remove the ethanol. Ice cold water was added (40 mL) and the mixture was extracted with dichloromethane (DCM) (2×50 mL). The combined organic extracts were dried over $Na_2SO_4$, were filtered, and the filtrate was concentrated. Purification by normal-phase chromatography eluting with 80% ethyl acetate in hexanes provided the title compound as a pale-yellow liquid (1.5 g, 4.81 mmol, 106% yield). LC-MS m/z 312.3 $(M+H)^+$.

Step 3 tert-Butyl 9-(3-((2S,3S)-1-methyl-5-oxo-2-(pyridin-3-yl)pyrrolidine-3-carboxamido) propyl)-3,9-diazaspiro[5.5]undecane-3-carboxylate

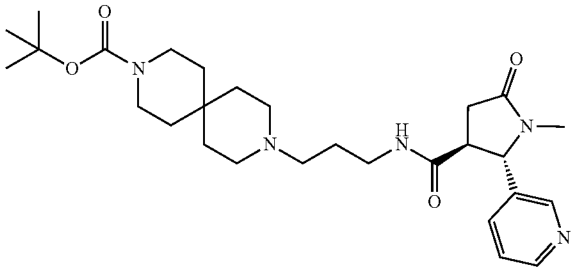 [SMILES: CN1C(=O)C[C@H](C(=O)NCCCN2CCC3(CC2)CCN(C(=O)OC(C)(C)C)CC3)[C@H]1c1cccnc1]

To a stirred solution of (2S,3S)-1-methyl-5-oxo-2-(pyridin-3-yl) pyrrolidine-3-carboxylic acid (1.155 g, 5.24 mmol) in pyridine (15 mL) were added EDC (1.371 g, 7.15 mmol) and tert-butyl 9-(3-aminopropyl)-3,9-diazaspiro[5.5]undecane-3-carboxylate (1.5 g, 4.47 mmol). The mixture was stirred at rt for 16 h. Ice cold water (40 mL) was added and the mixture was extracted with dichloromethane (DCM) (2×50 mL). The combined organic extracts were dried over $Na_2SO_4$, were filtered, and the filtrate was concentrated. Purification by normal-phase chromatography eluting with 10% methanol in dichloromethane (DCM) provided the title compound as a pale-yellow liquid (930 mg, 1.778 mmol, 37.3% yield). LC-MS m/z 514.3 $(M+H)^+$.

Step 4

(2S,3S)-N-(3-(3,9-Diazaspiro[5.5]undecan-3-yl) propyl)-1-methyl-5-oxo-2-(pyridin-3-yl) pyrrolidine-3-carboxamide, 3Trifluoroacetic acid salt

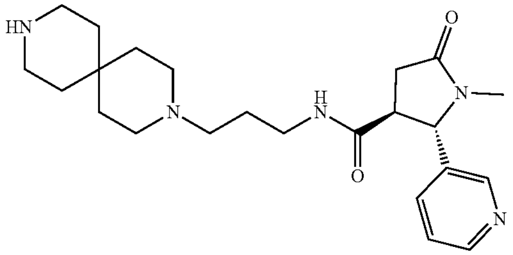

3TFA

Trifluoroacetic acid (1.125 mL, 14.60 mmol) was added to tert-butyl 9-(3-((2S,3S)-1-methyl-5-oxo-2-(pyridin-3-yl) pyrrolidine-3-carboxamido)propyl)-3,9-diazaspiro[5.5]undecane-3-carboxylate (150 mg, 0.292 mmol) in dichloromethane (DCM) (1.2 mL). The mixture was stirred overnight, and was concentrated under reduced pressure to provide the title compound (120 mg, 0.159 mmol, 54.5% yield). LC-MS m/z 414.3 $(M+H)^+$.

Step 5

Methyl 4-(9-(3-((2S,3S)-1-methyl-5-oxo-2-(pyridin-3-yl)pyrrolidine-3-carboxamido)propyl)-3,9-diazaspiro[5.5]undecan-3-yl)butanoate

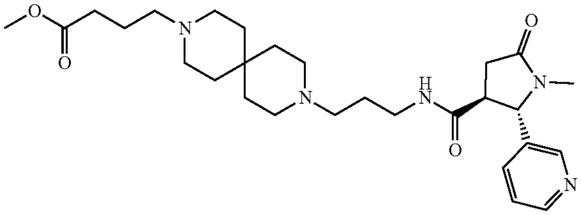

Potassium carbonate (468 mg, 3.39 mmol) was added to a solution of methyl 4-bromobutanoate (306 mg, 1.693 mmol) and (2S,3S)-N-(3-(3,9-diazaspiro[5.5]undecan-3-yl) propyl)-1-methyl-5-oxo-2-(pyridin-3-yl) pyrrolidine-3-carboxamide, 3trifluoroacetic acid salt (700 mg, 1.693 mmol) in acetonitrile (10 mL). The mixture was stirred at 70° C. for 18 h and was filtered. The filtrate was washed with ethyl acetate (20 mL). The combined liquids were evaporated under reduced pressure to provide the title compound (700 mg, 0.926 mmol, 54.7% yield). LC-MS m/z 514.2 $(M+H)^+$.

Step 6

4-(9-(3-((2S,3S)-1-Methyl-5-oxo-2-(pyridin-3-yl) pyrrolidine-3-carboxamido)propyl)-3,9-diazaspiro [5.5]undecan-3-yl)butanoic acid

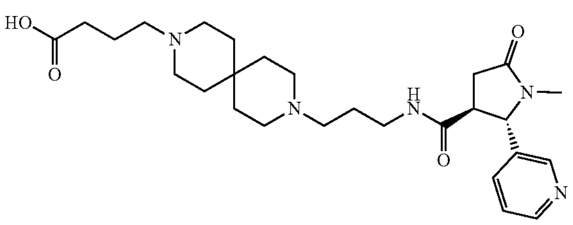 [SMILES: CN1C(=O)C[C@H](C(=O)NCCCN2CCC3(CC2)CCN(CCCC(=O)O)CC3)[C@H]1c1cccnc1]

Sodium hydroxide (1.217 mL, 4.87 mmol) was added to a solution of methyl 4-(9-(3-((2S,3S)-1-methyl-5-oxo-2-(pyridin-3-yl)pyrrolidine-3-carboxamido)propyl)-3,9-diazaspiro[5.5]undecan-3-yl)butanoate (500 mg, 0.973 mmol) in methanol (2 mL). The mixture was stirred at rt for 18 h and was concentrated. Purification by MDAP chromatography under acid conditions provided the title compound (100 mg, 0.200 mmol, 20.56% yield). LC-MS m/z 500.2 $(M+H)^+$.

Step 7

(2S,3S)-N-(3-(9-(4-(((1R,2S,5R)-5-(Isopropyl (methyl)amino)-2-((S)-2-oxo-3-((6-(trifluoromethyl) quinazolin-4-yl)amino)pyrrolidin-1-yl)cyclohexyl) amino)-4-oxobutyl)-3,9-diazaspiro[5.5]undecan-3-yl)propyl)-1-methyl-5-oxo-2-(pyridin-3-yl) pyrrolidine-3-carboxamide

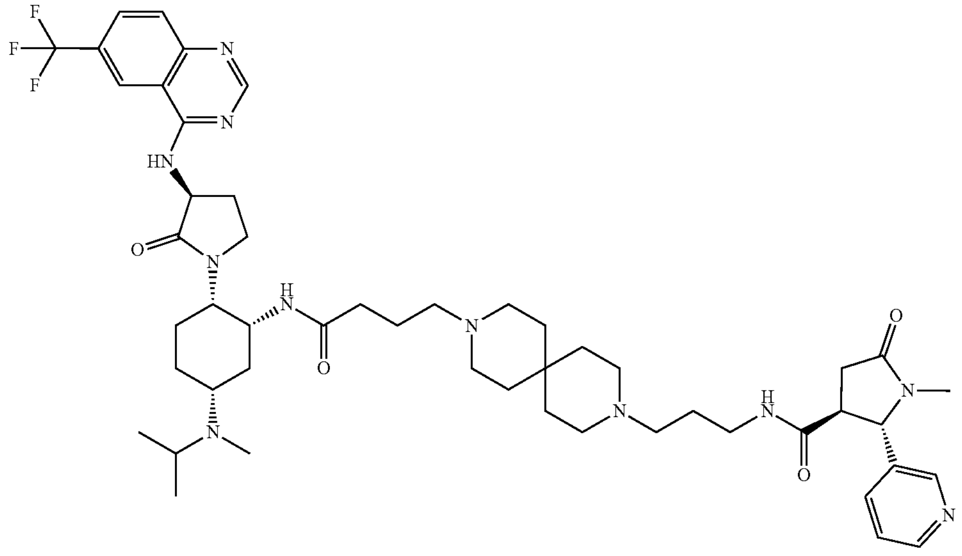 [SMILES: CC(C)N(C)[C@@H]1CC[C@H](N2CC[C@H](Nc3ncnc4ccc(C(F)(F)F)cc34)C2=O)[C@H](NC(=O)CCCN2CCC3(CCN(CCCNC(=O)[C@H]4CC(=O)N(C)[C@@H]4c4cccnc4)CC3)CC2)C1]

TFA (0.077 mL, 1.001 mmol) was added to a solution of tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (67.8 mg, 0.120 mmol) in dichloromethane (DCM) (2 mL). The mixture was stirred at rt for 1 h and was concentrated to dryness. To the residue in dichloromethane (DCM) (2 mL) was added 4-(9-(3-((2S,3S)-1-methyl-5-oxo-2-(pyridin-3-yl)pyrrolidine-3-carboxamido)propyl)-3,9-diazaspiro[5.5]undecan-3-yl)butanoic acid (50 mg, 0.100 mmol), HATU (57.1 mg, 0.150 mmol), and DIPEA (0.035 mL, 0.200 mmol). The resulting mixture was stirred at rt for 18 h. Dichloromethane (DCM) (10 mL) was added the mixture was washed with water. The organic phase was dried over $Na_2SO_4$ and was concentrated. Purification by MDAP chromatography (XSelect™ CSH Prep C18 5 μm OBD column, 40 mL/min) eluting with a gradient of 20 to 50% acetonitrile in water containing ammonium bicarbonate (10 mM) and ammonium hydroxide (0.075%) provided the title compound (30 mg, 0.029 mmol, 29.5% yield). LC-MS m/z 946.7 $(M+H)^+$. $^1H$ NMR (400 MHz, METHANOL-$d_4$) δ ppm 1.05 (br d, J=6.5 Hz, 3H) 1.13 (br d, J=6.3 Hz, 3H) 1.39 (br s, 8H) 1.59-1.88 (m, 7H) 1.91-2.05 (m, 1H) 2.15 (br dd, J=12.5, 2.5 Hz, 1H) 2.18-2.42 (m, 19H) 2.57 (dt d, J=12.3, 8.1, 8.1, 4.0 Hz, 1H) 2.66 (s, 3H) 2.69-2.78 (m, 2H) 2.80-2.91 (m, 1H) 2.96-3.06 (m, 1H) 3.11-3.29 (m, 2H) 3.38-3.48 (m, 1H) 3.51-3.60 (m, 1H) 3.61-3.72 (m, 1H) 4.06 (dt, J=12.1, 3.7 Hz, 1H) 4.65 (br d, J=3.3 Hz, 1H) 4.83 (d, J=6.8 Hz, 1H) 5.23 (t, J=7.9 Hz, 1H) 7.54 (dd, J=7.7, 4.6 Hz, 1H) 7.82 (dt, J=7.9, 1.8 Hz, 1H) 7.92 (d, J=8.8 Hz, 1H) 8.07 (dd, J=8.9, 1.9 Hz, 1H) 8.53 (d, J=2.0 Hz, 1H) 8.58 (dd, J=4.8, 1.5 Hz, 1H) 8.61 (s, 1H) 8.83 (s, 1H).

Example 192

(2S,3S)-N-(2-(((1R,4S)-4-(2-(2-(3-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-3-oxopropoxy)ethoxy)ethoxy)cyclohexyl)oxy)ethyl)-1-methyl-5-oxo-2-(pyridin-3-yl)pyrrolidine-3-carboxamide

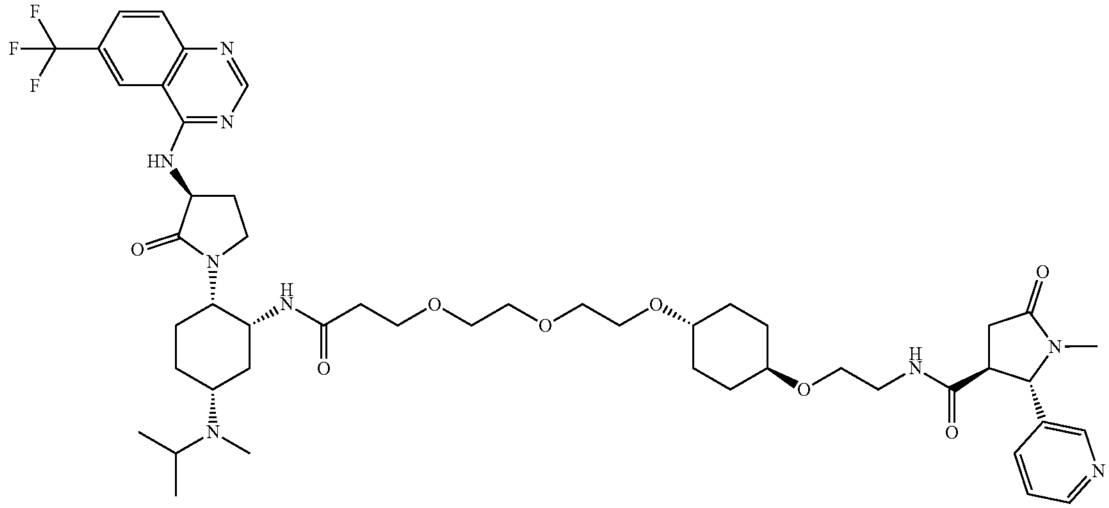 [SMILES: CC(C)N(C)[C@@H]1CC[C@H](N2CC[C@H](Nc3ncnc4ccc(C(F)(F)F)cc34)C2=O)[C@H](NC(=O)CCOCCOCCO[C@H]2CC[C@H](OCCNC(=O)[C@H]3CC(=O)N(C)[C@@H]3c3cccnc3)CC2)C1]

Step 1

N,N-Dibenzyl-2-(((1r,4r)-4-(vinyloxy)cyclohexyl)oxy)ethan-1-amine

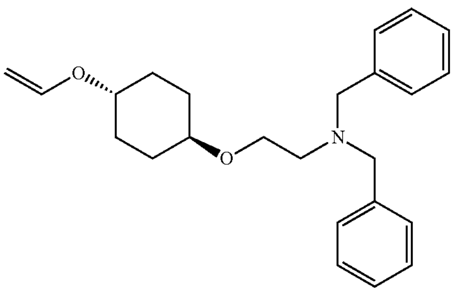 [SMILES: C=CO[C@H]1CC[C@H](OCCN(Cc2ccccc2)Cc2ccccc2)CC1]

To a mixture of palladium(II) trifluoroacetate (0.154 g, 0.464 mmol) and bathophenanthroline (0.154 g, 0.464 mmol) in ethyl vinyl ether (27.5 mL, 278 mmol) was added DIPEA (1.621 mL, 9.28 mmol) and (1r,4r)-4-(2-(dibenzylamino)ethoxy)cyclohexan-1-ol (Example 105, Step 2) (3.15 g, 9.28 mmol). The mixture was stirred at 75° C. for 3.5 h, was cooled to rt, and was concentrated under reduced pressure. Purification by ISCO CombiFlash® chromatography (80 g RediSep Gold® column, 60 mL/min) eluting with a gradient of 0 to 20% ethyl acetate in heptane provided the title compound (2.3956 g, 6.55 mmol, 70.6% yield). LC-MS m/z 366.4 $(M+H)^+$.

Step 2

2-(((1r,4r)-4-(2-(Dibenzylamino)ethoxy)cyclohexyl)oxy)ethan-1-ol

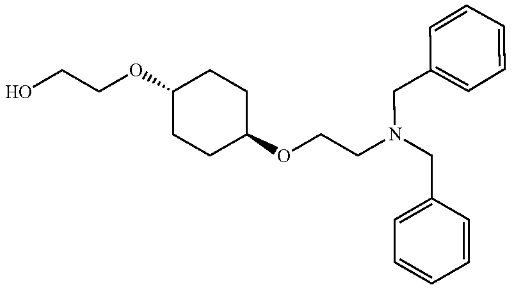 [SMILES: OCCO[C@H]1CC[C@H](OCCN(Cc2ccccc2)Cc2ccccc2)CC1]

To N,N-Dibenzyl-2-(((1r,4r)-4-(vinyloxy)cyclohexyl)oxy)ethan-1-amine (2.35 g, 6.43 mmol) in Tetrahydrofuran (THF) (50 mL) was added 1 M BH3 in tetrahydrofuran (THF) (9.64 mL, 9.64 mmol). The mixture was stirred at rt for 40 min. 5 N sodium hydroxide (12.86 mL, 64.3 mmol) and 30% hydrogen peroxide (13.13 mL, 129 mmol) were added and the mixture was stirred at rt for 23 h. The mixture was extracted with ethyl acetate (50 mL+2×30 mL). The combined organic extracts were washed with brine (30 mL), were dried over $MgSO_4$, were filtered, and the filtrate was concentrated under reduced pressure. Purification by ISCO CombiFlash® chromatography (40 g RediSep Gold® column, 40 mL/min) eluting with a gradient of 0 to 70% ethyl acetate in heptane provided the title compound (2.1723 g, 4.86 mmol, 76% yield). LC-MS m/z 384.4 $(M+H)^+$.

Step 3

N,N-dibenzyl-2-(((1r,4r)-4-(2-(2-(vinyloxy)ethoxy)ethoxy)cyclohexyl)oxy)ethan-1-amine

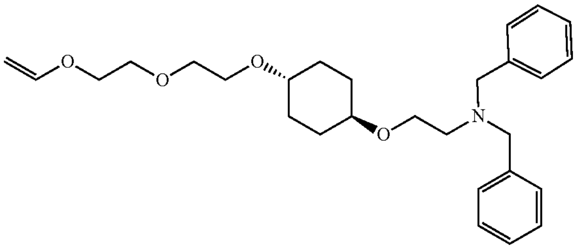 [SMILES: C=COCCOCCO[C@H]1CC[C@H](OCCN(Cc2ccccc2)Cc2ccccc2)CC1]

To a mixture of palladium(II) trifluoroacetate (0.081 g, 0.243 mmol) and bathophenanthroline (0.081 g, 0.243 mmol) in ethyl vinyl ether (14.39 ml, 146 mmol) was added DIPEA (0.848 ml, 4.85 mmol) and 2-(((1r,4r)-4-(2-(Dibenzylamino)ethoxy)cyclohexyl)oxy)ethan-1-ol (2.17 g, 4.85 mmol). The mixture was stirred at 75° C. for 4 h, was cooled to rt, was filtered, and was concentrated under reduced pressure. Purification by ISCO CombiFlash® chromatography (40 g RediSep Gold® column, 40 mL/min) eluting with a gradient of 0 to 30% ethyl acetate in heptane provided the title compound (1.9085 g, 3.79 mmol, 78% yield). LC-MS m/z 410.1 $(M+H)^+$.

Step 4

2-(2-(((1r,4r)-4-(2-(Dibenzylamino)ethoxy)cyclohexyl)oxy)ethoxy)ethan-1-ol

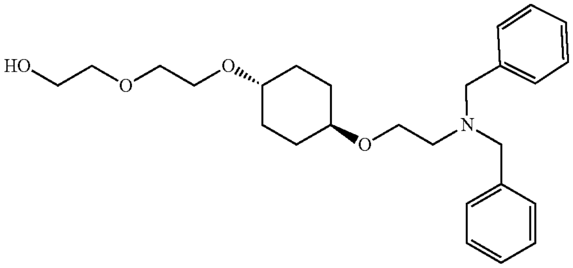 [SMILES: OCCOCCO[C@H]1CC[C@H](OCCN(Cc2ccccc2)Cc2ccccc2)CC1]

To N,N-dibenzyl-2-(((1r,4r)-4-(2-(2-(vinyloxy)ethoxy)ethoxy)cyclohexyl)oxy)ethan-1-amine (1.9 g, 3.78 mmol) in tetrahydrofuran (THF) (40 mL) was added 1 M BH3 in tetrahydrofuran (THF) (5.66 mL, 5.66 mmol). The mixture was stirred at rt for 30 min. 5 N sodium hydroxide (7.55 mL, 37.8 mmol) and 30% hydrogen peroxide (7.71 mL, 76 mmol) were added and the mixture was stirred at rt for 19 h. The mixture was extracted with ethyl acetate (50 mL+2× 30 mL). The combined organic extracts were washed with brine (30 mL), were dried over $MgSO_4$, were filtered, and the filtrate was concentrated under reduced pressure. Purification by ISCO CombiFlash® chromatography (40 g RediSep Gold® column, 40 mL/min) eluting with a gradient of 0 to 80% ethyl acetate in heptane provided the title compound (0.9820 g, 2.297 mmol, 60.8% yield). LC-MS m/z 428.4 $(M+H)^+$.

Step 5 tert-Butyl 3-(2-(2-(((1r,4r)-4-(2-(dibenzylamino)ethoxy)cyclohexyl)oxy)ethoxy)ethoxy)propanoate

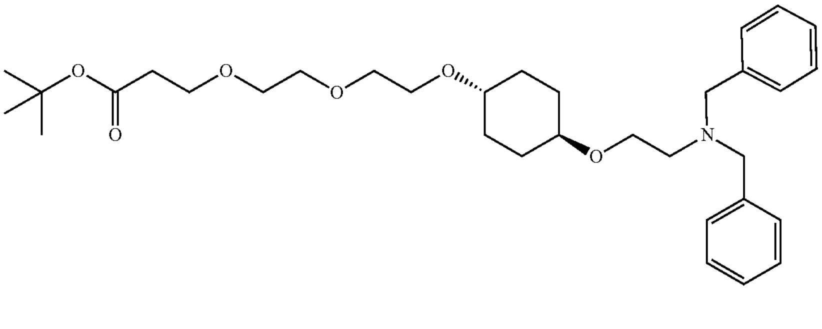 [SMILES: CC(C)(C)OC(=O)CCOCCOCCO[C@H]1CC[C@H](OCCN(Cc2ccccc2)Cc2ccccc2)CC1]

To a solution of 2-(2-(((1r,4r)-4-(2-(Dibenzylamino) ethoxy)cyclohexyl)oxy)ethoxy)ethan-1-ol (970 mg, 2.269 mmol) in dichloromethane (DCM) (16 mL) was added tert-butyl acrylate (0.665 mL, 4.54 mmol), tetrabutylammonium hydrogen sulfate (77 mg, 0.227 mmol), and 5 N sodium hydroxide (0.181 mL, 0.907 mmol). The mixture was stirred at rt for 21 h and was concentrated under reduced pressure. Water (0.181 mL) and dichloromethane (DCM) (3 mL) were added, the mixture was stirred at rt for 23 h and was concentrated under reduced pressure. Purification by ISCO CombiFlash® chromatography (24 g RediSep Gold® column, 30 mL/min) eluting with a stepwise gradient of 0 to 35% (15 min) and 35 to 80% (10 min) ethyl acetate in heptane provided the title compound (0.2283 g, 0.534 mmol, 23.54% yield). LC-MS m/z 556.6 $(M+H)^+$.

Step 6 tert-Butyl 3-(2-(2-(((1r,4r)-4-(2-aminoethoxy)cyclohexyl)oxy)ethoxy)ethoxy)propanoate

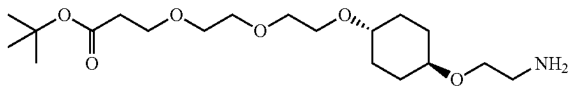 [SMILES: CC(C)(C)OC(=O)CCOCCOCCO[C@H]1CC[C@H](OCCN)CC1]

To a solution of tert-butyl 3-(2-(2-((trans-4-(2-(dibenzylamino)ethoxy)cyclohexyl)oxy)ethoxy)ethoxy)propanoate (850 mg, 1.529 mmol) in methanol (30 mL) was added 10% Pd/C (163 mg, 0.153 mmol). The mixture was stirred at rt under a hydrogen atmosphere for 4 h. The mixture was filtered through Celite® and the filtrate was concentrated under reduced pressure to provide the title compound (0.5599 g, 1.491 mmol, 97% yield). LC-MS m/z 376.4 $(M+H)^+$.

Step 7 tert-Butyl 3-(2-(2-(((1S,4r)-4-(2-((2S,3S)-1-methyl-5-oxo-2-(pyridin-3-yl)pyrrolidine-3-carboxamido)ethoxy)cyclohexyl)oxy)ethoxy)ethoxy)propanoate

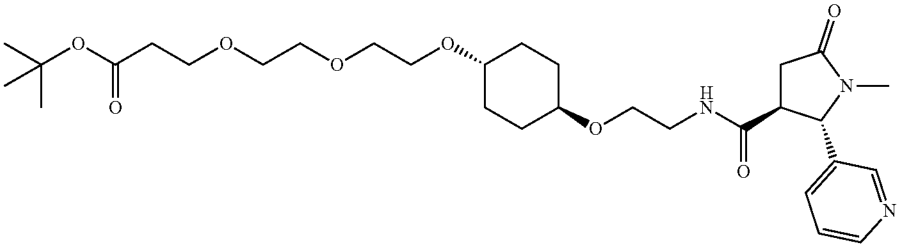 [SMILES: CN1C(=O)C[C@H](C(=O)NCCO[C@H]2CC[C@H](OCCOCCOCCC(=O)OC(C)(C)C)CC2)[C@H]1c1cccnc1]

To tert-butyl 3-(2-(2-(((1r,4r)-4-(2-aminoethoxy)cyclohexyl)oxy)ethoxy)ethoxy)propanoate (550 mg, 1.465 mmol) in dichloromethane (DCM) (10 mL) was added (2S,3S)-1-methyl-5-oxo-2-(pyridin-3-yl)pyrrolidine-3-carboxylic acid (323 mg, 1.465 mmol), DIPEA (0.767 mL, 4.39 mmol) and T3P (50% wt. in ethyl acetate) (1.308 mL, 2.197 mmol). The mixture was stirred at rt for 93 h. Saturated $NaHCO_3$(5 drops) was added and the mixture was concentrated under reduced pressure. reduced pressure. Purification by ISCO CombiFlash® chromatography (24 g RediSep Gold® column, 35 mL/min) eluting with a gradient of 0 to 55% ethyl acetate in heptane provided the title compound (0.9152 g, 1.381 mmol, 94% yield). LC-MS m/z 578.5 $(M+H)^+$.

Step 8

3-(2-(2-(((1S,4r)-4-(2-((2S,3S)-1-Methyl-5-oxo-2-(pyridin-3-yl)pyrrolidine-3-carboxamido)ethoxy) cyclohexyl)oxy)ethoxy)ethoxy)propanoic acid, Hydrochloric acid salt

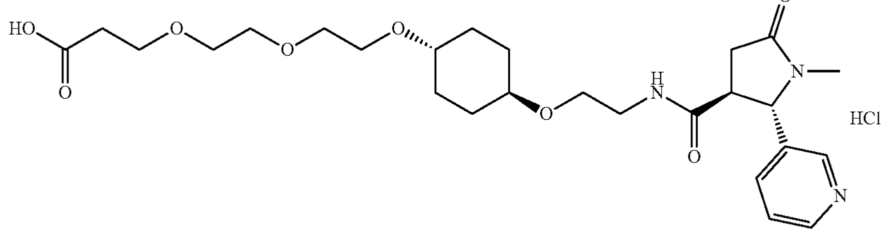

4 M HCl in 1,4-dioxane) (1.717 mL, 6.87 mmol) was added to tert-Butyl 3-(2-(2-(((1S,4r)-4-(2-((2S,3S)-1-methyl-5-oxo-2-(pyridin-3-yl) pyrrolidine-3-carboxamido) ethoxy)cyclohexyl) oxy)ethoxy)ethoxy)propanoate (0.910 g, 1.374 mmol) in 1,4-dioxane (2 mL). The mixture was stirred at rt for 18 h and was concentrated under reduced pressure to provide the title compound (0.8810 g, 1.085 mmol, 79% yield). LC-MS m/z 522.4 $(M+H)^+$.

Step 9

(2S,3S)-N-(2-(((1R,4S)-4-(2-(2-(3-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)amino)-3-oxopropoxy)ethoxy)ethoxy) cyclohexyl)oxy)ethyl)-1-methyl-5-oxo-2-(pyridin-3-yl)pyrrolidine-3-carboxamide

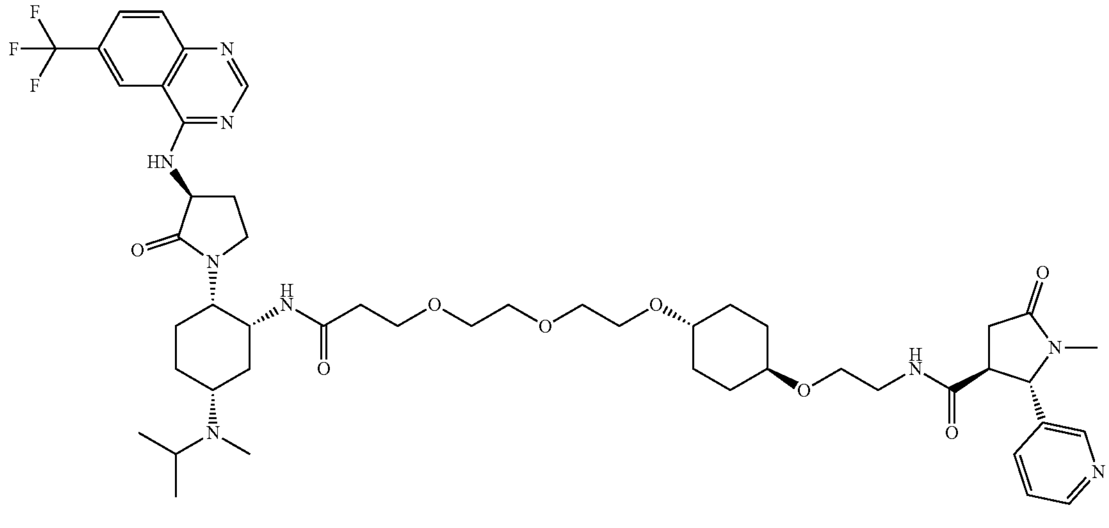 [SMILES: CC(C)N(C)[C@@H]1CC[C@H](N2CC[C@H](Nc3ncnc4ccc(C(F)(F)F)cc34)C2=O)[C@H](NC(=O)CCOCCOCCO[C@H]2CC[C@H](OCCNC(=O)[C@H]3CC(=O)N(C)[C@@H]3c3cccnc3)CC2)C1]

To (S)-1-((1S,2R,4R)-2-amino-4-(isopropyl(methyl)amino)cyclohexyl)-3-((6-(trifluoromethyl) quinazolin-4-yl)amino)pyrrolidin-2-one, 2Hydrochloride (50 mg, 0.093 mmol) in dichloromethane (DCM) (2 mL) was added 3-(2-(2-(((1S,4r)-4-(2-((2S,3S)-1-methyl-5-oxo-2-(pyridin-3-yl)pyrrolidine-3-carboxamido)ethoxy)cyclohexyl)oxy)ethoxy)ethoxy) propanoic acid, hydrochloric acid salt (76 mg, 0.093 mmol), DPIEA (0.097 mL, 0.558 mmol) and HATU (53.1 mg, 0.140 mmol). The mixture was stirred at ambient temperature for 18 h. Water (3 drops) was added and the mixture was concentrated under reduced pressure. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound (55.4 mg, 0.057 mmol, 61.5% yield). LC-MS m/z 968.4 $(M+H)^+$. $^1H$ NMR (400 MHz, METHANOL-$d_4$) δ ppm 1.05 (br d, J=6.4 Hz, 3H) 1.11-1.17 (m, 3H) 1.17-1.33 (m, 4H) 1.64-1.77 (m, 3H) 1.84-2.01 (m, 5H) 2.05-2.17 (m, 1H) 2.21-2.35 (m, 5H) 2.43-2.57 (m, 3H) 2.66 (s, 3H) 2.68-2.77 (m, 2H) 2.80-2.88 (m, 1H) 3.07 (ddd, J=9.5, 8.1, 6.8 Hz, 1H) 3.20-3.31 (m, 3H) 3.35-3.60 (m, 14H) 3.66-3.76 (m, 2H) 3.81-3.87 (m, 1H) 4.06 (dt, J=12.6, 3.5 Hz, 1H) 4.65 (br d, J=3.4 Hz, 1H) 4.83-4.88 (m, 1H) 5.31 (t, J=8.1 Hz, 1H) 7.54 (dd, J=7.8, 4.9 Hz, 1H) 7.81 (dt, J=7.8, 2.0 Hz, 1H) 7.91 (d, J=8.3 Hz, 1H) 8.07 (dd, J=8.8, 2.0 Hz, 1H) 8.52 (d, J=2.0 Hz, 1H) 8.55-8.62 (m, 2H) 8.84 (s, 1H).

Example 193

(2S,3S)-N-(3-(3-(4-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-4-oxobutoxy)propoxy)propyl)-1-methyl-5-oxo-2-(pyridin-3-yl)pyrrolidine-3-carboxamide

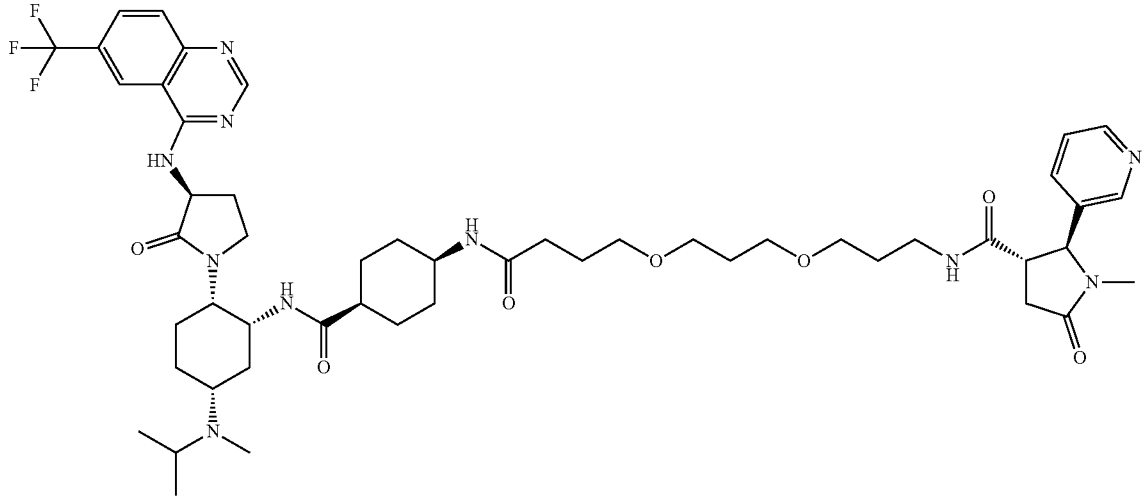 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCOCCCOCCCNC(=O)[C@H]3CC(=O)N(C)[C@@H]3c3cccnc3)CC2)C1]

Step 1

Benzyl (3-(3-hydroxypropoxy)propyl)carbamate

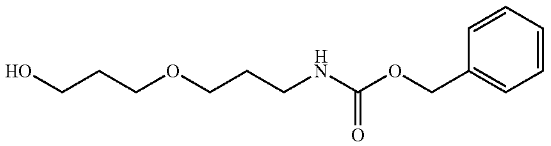 [SMILES: O=C(NCCCOCCCO)OCc1ccccc1]

4 M HCl in 1,4-dioxane (20.0 mL, 80 mmol) was added to a solution of tert-butyl 3-(3-(((benzyloxy)carbonyl)amino)propoxy)propanoate (Example 17, Step 1) (3.30 g, 9.78 mmol) in dichloromethane (DCM) (4.0 mL). The mixture was stirred overnight and was concentrated to dryness. To a solution of the residue in tetrahydrofuran (THF) (10.0 mL) at 0° C. was added slowly 1 M BH3 in tetrahydrofuran (THF) (24.45 mL, 24.45 mmol) and was stirred at rt 1 h. Saturated $NaHCO_3$ was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (80 g silica column, 60 mL/min) eluting with a gradient of 0 to 10% methanol in dichloromethane (DCM) provided the title compound as a colorless oil (2.02 g, 7.56 mmol, 77% yield). LC-MS m/z 268.1 $(M+H)^+$.

Step 2

Ethyl (E)-3-oxo-1-phenyl-2,8,12-trioxa-4-azahexadec-14-en-16-oate

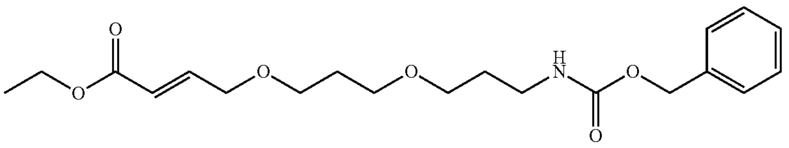 [SMILES: CCOC(=O)/C=C/COCCCOCCCNC(=O)OCc1ccccc1]

To a solution of benzyl (3-(3-hydroxypropoxy)propyl) carbamate (2.00 g, 7.48 mmol), triphenylphosphine (0.392 g, 1.496 mmol) and acetic acid (0.343 mL, 5.99 mmol) in toluene (30 mL) was added ethyl but-2-ynoate (1.304 mL, 11.22 mmol). The mixture was stirred at 110° C. overnight and was cooled to rt. Water was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (80 g silica column, 60 mL/min) eluting with a gradient of 0 to 50% ethyl acetate in heptane provided the title compound as a light-orange oil (2.82 g, 7.43 mmol, 99% yield). LC-MS m/z 380.1 $(M+H)^+$.

Step 3

Ethyl 4-(3-(3-aminopropoxy)propoxy)butanoate

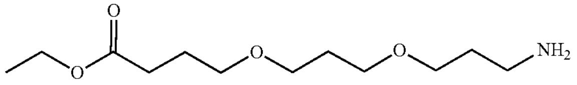 [SMILES: CCOC(=O)CCCOCCCOCCCN]

To a solution of ethyl (E)-3-oxo-1-phenyl-2,8,12-trioxa-4-azahexadec-14-en-16-oate (2.82 g, 7.43 mmol) in ethyl acetate (30.0 mL) under an atmosphere of nitrogen was added 10% Pd-C, Degussa type (0.316 g, 2.97 mmol). The mixture was vacuumed and was backfilled with hydrogen (3×) and was stirred under a balloon atmosphere of hydrogen overnight. The mixture was filtered through Celite® and the filtrate was concentrated to provide the title compound as a colorless oil (1.68 g, 6.79 mmol, 91% yield). LC-MS m/z 248.2 $(M+H)^+$.

Step 4

Ethyl 4-(3-(3-((2S,3S)-1-methyl-5-oxo-2-(pyridin-3-yl)pyrrolidine-3-carboxamido) propoxy)propoxy) butanoate

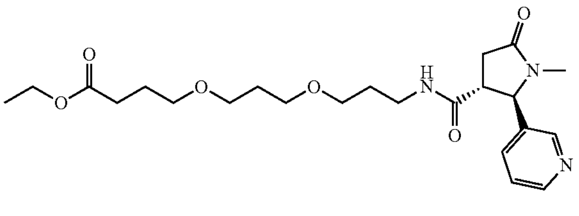 [SMILES: CCOC(=O)CCCOCCCOCCCNC(=O)[C@@H]1CC(=O)N(C)[C@H]1c1cccnc1]

To a solution of (2S,3S)-1-methyl-5-oxo-2-(pyridin-3-yl) pyrrolidine-3-carboxylic acid (300 mg, 1.362 mmol) in dichloromethane (DCM) (5.0 mL) was added ethyl 4-(3-(3-aminopropoxy)propoxy)butanoate (337 mg, 1.362 mmol), HOBt (250 mg, 1.635 mmol), and EDC (392 mg, 2.043 mmol) followed by DIPEA (0.714 mL, 4.09 mmol) and the mixture was stirred overnight. Water was added and the mixture was extracted with dichloromethane (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a light-colored wax (530 mg, 1.179 mmol, 87% yield). LC-MS m/z 450.1 $(M+H)^+$.

Step 5

4-(3-(3-((2S,3S)-1-Methyl-5-oxo-2-(pyridin-3-yl) pyrrolidine-3-carboxamido)propoxy) propoxy)butanoic acid

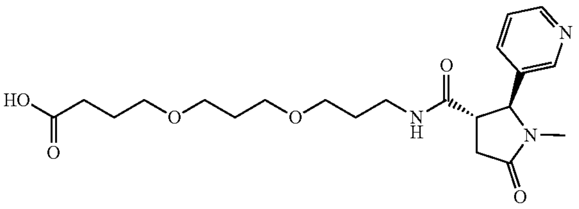 [SMILES: CN1C(=O)C[C@H](C(=O)NCCCOCCCOCCCC(=O)O)[C@H]1c1cccnc1]

To a solution of ethyl 4-(3-(3-((2S,3S)-1-methyl-5-oxo-2-(pyridin-3-yl) pyrrolidine-3-carboxamido)propoxy) propoxy)butanoate (530 mg, 1.179 mmol) in methanol (8.0 mL) and water (2.000 mL) was added lithium hydroxide monohydrate (198 mg, 4.72 mmol) and the mixture was stirred overnight. Water was added and the pH was adjusted to 4 with 1 N HCl. The methanol was removed under reduced pressure and the residue was extracted with methanol in dichloromethane (5%) (5×). The combined organic extracts were washed with brine (2×), were dried over $Na_2SO_4$, were filtered, and the filtrate was concentrated to provide the title compound as a light-colored wax (495 mg, 1.174 mmol, 100% yield). LC-MS m/z 422.1 $(M+H)^+$.

Step 6

(2S,3S)-N-(3-(3-(4-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl)cyclohexyl)amino)-4-oxobutoxy)propoxy)propyl)-1-methyl-5-oxo-2-(pyridin-3-yl)pyrrolidine-3-carboxamide

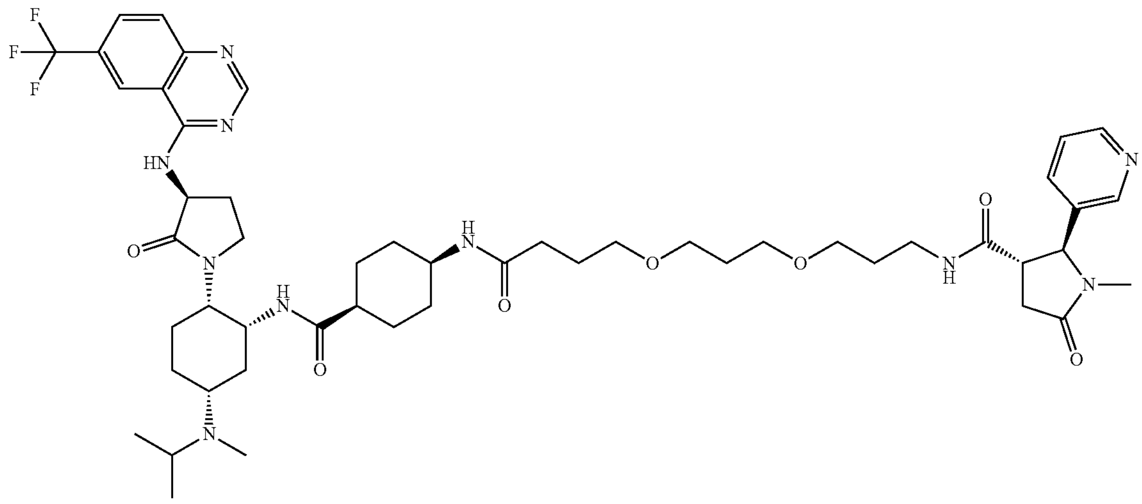 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCCOCCCOCCCNC(=O)[C@H]3CC(=O)N(C)[C@@H]3c3cccnc3)CC2)C1]

To a solution of 4-(3-(3-((2S,3S)-1-methyl-5-oxo-2-(pyridin-3-yl) pyrrolidine-3-carboxamido)propoxy)propoxy)butanoic acid (45.8 mg, 0.109 mmol), (1s,4S)-4-amino-N-((1R,2S,5R)-5-(isopropyl(methyl)amino)-2-((S)-2-oxo-3-((6-(trifluoromethyl)quinazolin-4-yl)amino)pyrrolidin-1-yl) cyclohexyl)cyclohexane-1-carboxamide, 2hydrochloric acid salt (60 mg, 0.091 mmol), HOBt (16.64 mg, 0.109 mmol), and DIPEA (0.079 mL, 0.453 mmol) in dichloromethane (DCM) (2.0 mL) was added EDC (26.0 mg, 0.136 mmol). The mixture was stirred at rt overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (49.9 mg, 0.048 mmol, 52.7% yield). LC-MS m/z 993.0 $(M+H)^+$. $^1H$ NMR (400 MHz, DMSO-$d_6$) b ppm 0.90 (d, J=6.4 Hz, 3H) 1.05 (d, J=6.8 Hz, 3H) 1.35-1.48 (m, 2H) 1.51-1.78 (m, 16H) 1.85-1.98 (m, 1H) 1.99-2.20 (m, 10H) 2.31-2.40 (m, 1H) 2.44 (dd, J=16.9, 7.6 Hz, 1H) 2.53 (br s, 1H) 2.59 (br s, 1H) 2.65-2.73 (m, 1H) 2.85-2.95 (m, 1H) 2.98-3.18 (m, 2H) 3.25-3.29 (m, 5H) 3.34 (t, J=6.6 Hz, 4H) 3.39-3.48 (m, 1H) 3.49-3.61 (m, 1H) 3.70 (br s, 1H) 3.83-3.96 (m, 1H) 4.45 (br d, J=4.9 Hz, 1H) 4.65 (d, J=6.4 Hz, 1H) 5.03 (q, J=7.8 Hz, 1H) 7.44 (dd, J=7.8, 4.9 Hz, 1H) 7.52 (d, J=6.4 Hz, 1H) 7.68 (dt, J=7.8, 2.0 Hz, 1H) 7.89 (d, J=8.3 Hz, 1H) 7.94 (br t, J=5.6 Hz, 1H) 8.06 (dd, J=8.8, 1.5 Hz, 1H) 8.47 (d, J=2.0 Hz, 1H) 8.56 (dd, J=4.6, 1.7 Hz, 1H) 8.59 (s, 1H) 8.63-8.74 (m, 2H) 8.89 (s, 1H).

Example 194

(1r,4R)-$N^1$-((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)-$N^4$-(3-(4-(3-((2S,3S)-1-methyl-5-oxo-2-(pyridin-3-yl)pyrrolidine-3-carboxamido)propoxy)butoxy) propyl) cyclohexane-1,4-dicarboxamide

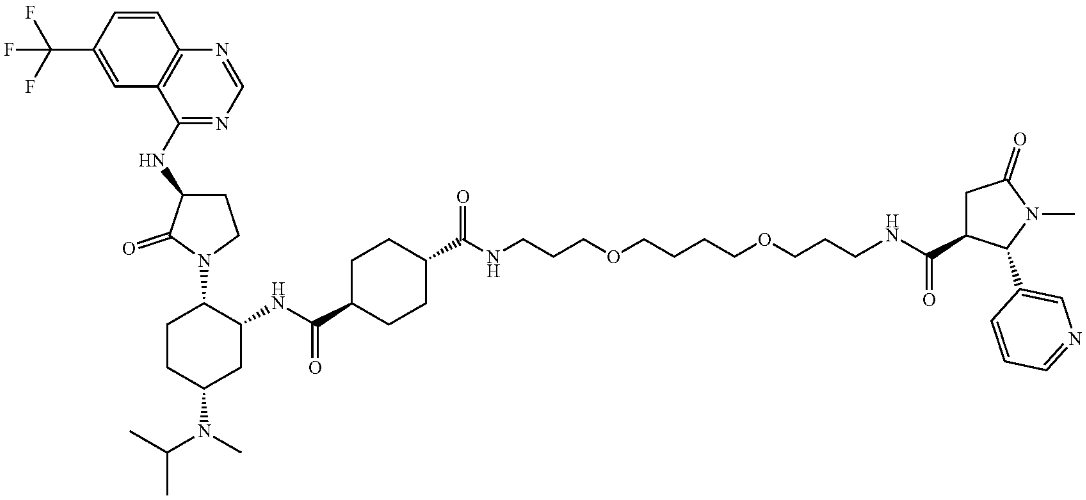 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](C(=O)NCCCOCCCCOCCCNC(=O)[C@H]3CC(=O)N(C)[C@@H]3c3cccnc3)CC2)C1]

Step 1

Methyl (1R,4r)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl) cyclohexane-1-carboxylate

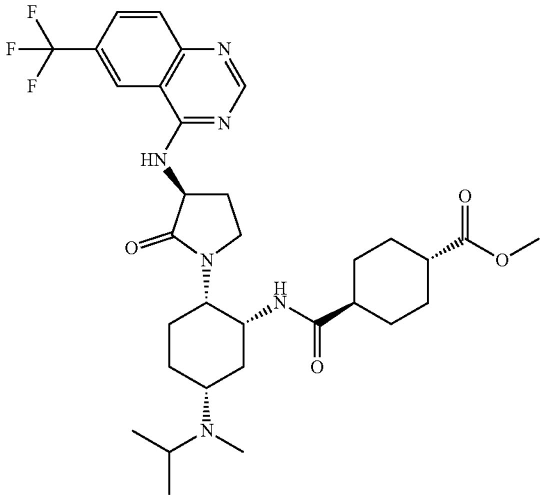 [SMILES: COC(=O)[C@H]1CC[C@H](C(=O)N[C@@H]2C[C@H](N(C)C(C)C)CC[C@@H]2N2CC[C@H](Nc3ncnc4ccc(C(F)(F)F)cc34)C2=O)CC1]

To a suspension of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2hydrochloric acid salt (117 mg, 0.218 mmol) in dichloromethane (DCM) (3 mL) was added triethylamine (0.152 mL, 1.088 mmol), followed (1r,4r)-4-(methoxycarbonyl)cyclohexane-1-carboxylic acid (48.6 mg, 0.261 mmol) and HATU (124 mg, 0.327 mmol). The mixture was stirred at rt for 2 h and was concentrated under reduced pressure to remove dichloromethane (DCM). Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a white solid (105 mg, 0.163 mmol, 74.7% yield). LC-MS m/z 905.8 $(M+H)^+$.

Step 2 tert-Butyl (3-(4-(3-((1R,4r)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl) cyclohexane-1-carboxamido)propoxy)butoxy)propyl)carbamate

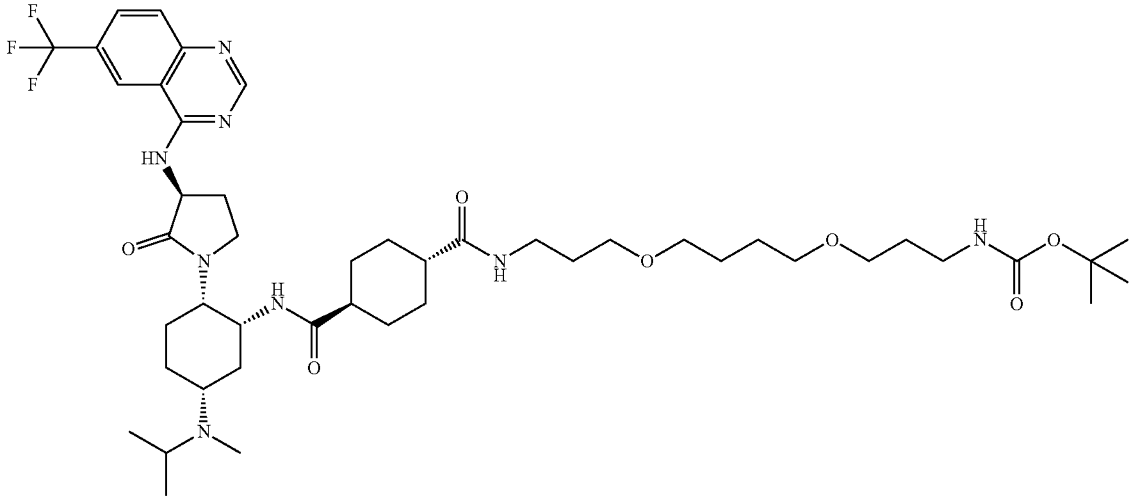 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](C(=O)NCCCOCCCCOCCCNC(=O)OC(C)(C)C)CC2)C1]

2 M HCl in water (2 mL, 4.00 mmol) was added to methyl (1R,4r)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexane-1-carboxylate (100 mg, 0.158 mmol). The mixture was stirred at 60° C. for 20 h and was concentrated under reduced pressure. The residue was dissolved in dichloromethane (DCM) (3 mL) and N,N-dimethylformamide (DMF) (1.5 mL). Triethylamine (0.110 mL, 0.790 mmol), tert-butyl (3-(4-(3-aminopropoxy)butoxy)propyl)carbamate (65 mg, 0.214 mmol) and HATU (90 mg, 0.237 mmol) were added sequentially. The mixture was stirred at rt for 1 h and was under reduced pressure to remove dichloromethane (DCM). Purification by MDAP chromatography (XSelect™ CSH Prep C18 5 μm OBD column, 40 mL/min) eluting with a gradient of 50 to 99% acetonitrile in water containing ammonium bicarbonate (10 mM) and the pH adjusted to 10 with ammonia provided the title compound as a white, foamy solid (51 mg, 0.055 mmol, 34.9% yield). LC-MS m/z 905.8 $(M+H)^+$.

Step 3

(1r,4R)-$N^1$-((1R,2S,5R)-5-(Isopropyl(methyl)amino)-2-((S)-2-oxo-3-((6-(trifluoromethyl) quinazolin-4-yl)amino)pyrrolidi n-1-yl)cyclohexyl)-$N^4$-(3-(4-(3-((2S,3S)-1-methyl-5-oxo-2-(pyridin-3-yl) pyrrolidine-3-carboxamido)propoxy)butoxy)propyl) cyclohexane-1,4-dicarboxamide

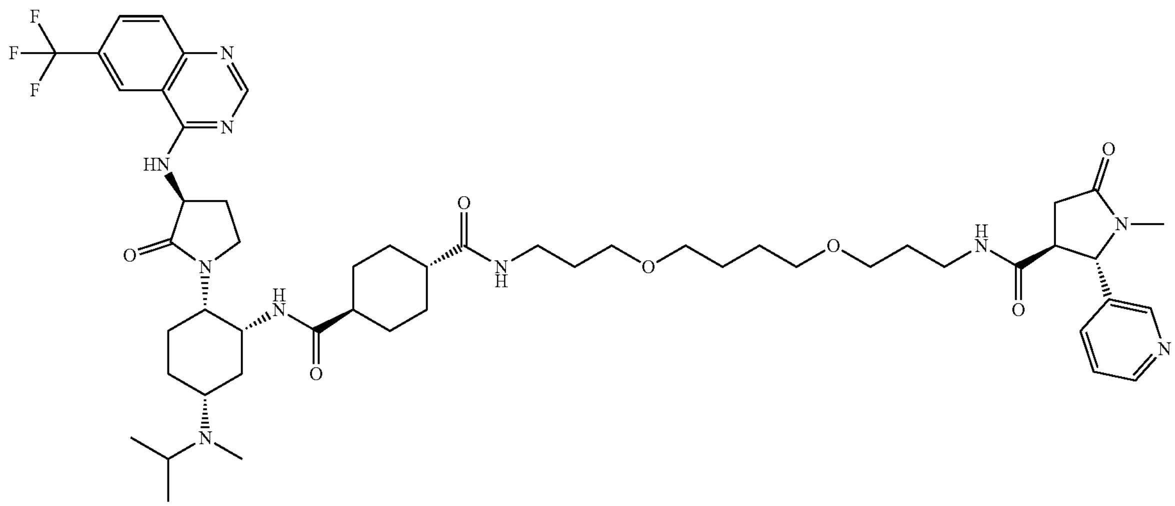 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@H](C(=O)NCCCOCCCCOCCCNC(=O)[C@H]3CC(=O)N(C)[C@@H]3c3cccnc3)CC2)C1]

3 M HCl in cyclopentyl methyl ether (0.5 mL, 1.500 mmol) was added to a solution of tert-butyl (3-(4-(3-((1R,4r)-4-(((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamoyl)cyclohexane-1-carboxamido)propoxy)butoxy)propyl)carbamate (49 mg, 0.054 mmol) in dichloromethane (DCM) (1 mL). The mixture was stirred at rt for 2 h and was concentrated. The residue was dissolved in dichloromethane (DCM) (2 mL) and with triethylamine (0.038 mL, 0.271 mmol), (2S,3S)-1-methyl-5-oxo-2-(pyridin-3-yl)pyrrolidine-3-carboxylic acid (14.31 mg, 0.065 mmol), and HATU (30.9 mg, 0.081 mmol) were added. The mixture was stirred at rt for 2 h and was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and the pH adjusted to 10 with ammonia provided the title compound as an off-white solid (50 mg, 0.047 mmol, 87% yield). LC-MS m/z 1007.7 $(M+H)^+$. $^1H$ NMR (400 MHz, METHANOL-$d_4$) δ ppm 0.99-1.06 (m, 3H) 1.12-1.19 (m, 3H) 1.48-1.57 (m, 4H) 1.57-1.62 (m, 4H) 1.65-1.78 (m, 7H) 1.81-2.03 (m, 5H) 2.09-2.23 (m, 4H) 2.25-2.28 (m, 3H) 2.30-2.36 (m, 1H) 2.50-2.59 (m, 1H) 2.64-2.68 (m, 3H) 2.71-2.75 (m, 2H) 2.78-2.88 (m, 1H) 2.96-3.06 (m, 1H) 3.19-3.30 (m, 4H) 3.32-3.34 (m, 2H) 3.35-3.40 (m, 3H) 3.42-3.47 (m, 4H) 3.49-3.54 (m, 1H) 3.58-3.69 (m, 1H) 3.98-4.07 (m, 1H) 4.59-4.68 (m, 1H) 4.79-4.85 (m, 1H) 5.25-5.34 (m, 1H) 7.50-7.56 (m, 1H) 7.77-7.83 (m, 1H) 7.88-7.93 (m, 1H) 8.03-8.10 (m, 1H) 8.50-8.53 (m, 1H) 8.56-8.61 (m, 2H) 8.79-8.82 (m, 1H).

Example 195

(2S,3S)-N-(24-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-24-oxo-3,6,9,12-tetraoxa-15-azatetracosyl)-1-methyl-5-oxo-2-(pyridin-3-yl)pyrrolidine-3-carboxamide, 3Trifluoroacetic acid salt

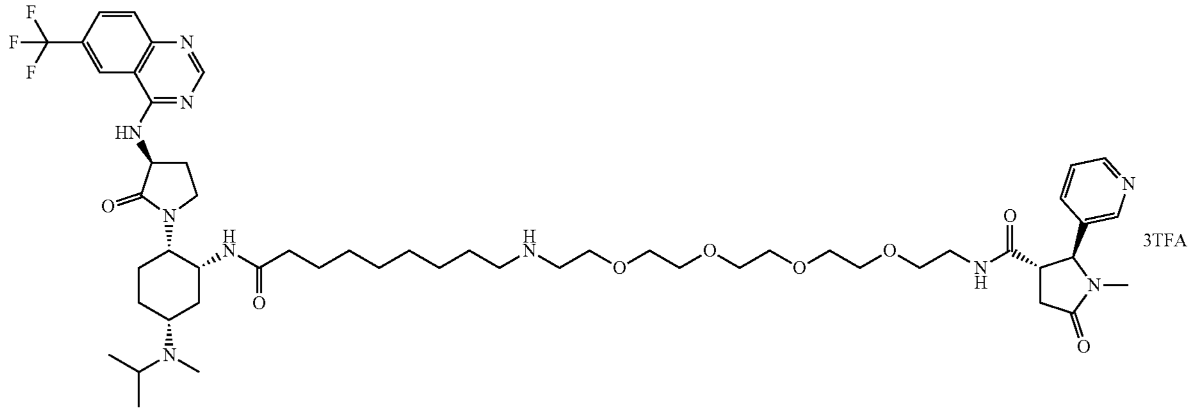 [SMILES: CC(C)N(C)[C@@H]1CC[C@H](N2CC[C@H](Nc3ncnc4ccc(C(F)(F)F)cc34)C2=O)[C@H](NC(=O)CCCCCCCCNCCOCCOCCOCCOCCNC(=O)[C@H]2CC(=O)N(C)[C@@H]2c2cccnc2)C1]

Step 1 tert-Butyl (1-((2S,3S)-1-methyl-5-oxo-2-(pyridin-3-yl)pyrrolidin-3-yl)-1-oxo-5,8,11,14-tetraoxa-2-azahexadecan-16-yl)carbamate

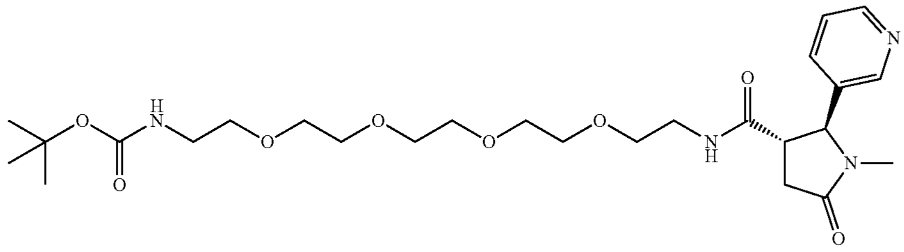 [SMILES: CN1C(=O)C[C@H](C(=O)NCCOCCOCCOCCOCCNC(=O)OC(C)(C)C)[C@H]1c1cccnc1]

To a solution of (2S,3S)-1-methyl-5-oxo-2-(pyridin-3-yl)pyrrolidine-3-carboxylic acid (100 mg, 0.454 mmol) in N,N-dimethylformamide (DMF) (5230 μL) was added HATU (207 mg, 0.545 mmol) and DIPEA (317 μL, 1.816 mmol), followed by tert-butyl (14-amino-3,6,9,12-tetraoxatetradecyl)carbamate (168 mg, 0.499 mmol). The mixture was stirred at rt and was concentrated under reduced pressure. Purification by MDAP chromatography (XBridge™ column) eluting with acetonitrile in water containing ammonium carbonate modifier provided the title compound as a yellow oil (238.8 mg, 0.341 mmol, 75% yield). LC-MS m/z 539.1 $(M+H)^+$.

Step 2

(2S,3S)-N-(14-Amino-3,6,9,12-tetraoxatetradecyl)-1-methyl-5-oxo-2-(pyridin-3-yl)pyrrolidine-3-carboxamide, 2Trifluroacetic acid salt

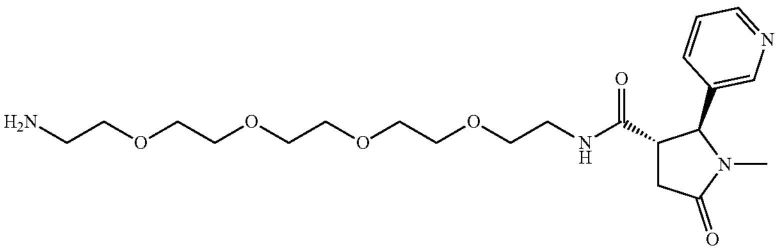

2TFA

TFA (997 μL, 12.95 mmol) was added to a solution of tert-butyl (1-((2S,3S)-1-methyl-5-oxo-2-(pyridin-3-yl)pyrrolidin-3-yl)-1-oxo-5,8,11,14-tetraoxa-2-azahexadecan-16-yl)carbamate (238.8 mg, 0.443 mmol) in dichloromethane (DCM) (997 μL). The mixture was stirred at rt and was azeotroped with dichloromethane (DCM) (3×) to provide the title compound as a yellow oil (586 mg, 0.369 mmol, 83% yield). LC-MS m/z 439.2 $(M+H)^+$.

Step 3

(S)-1-((1S,2R,4R)-2-Amino-4-(isopropyl(methyl)amino)cyclohexyl)-3-((6-(trifluoromethyl)quinazolin-4-yl)amino)pyrrolidin-2-one, 2Trifluroacetic acid salt

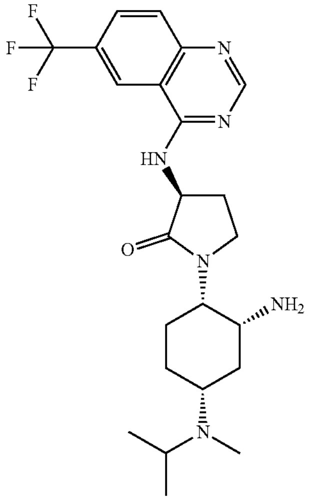

2TFA

TFA (1422 μL, 18.46 mmol) was added to tert-butyl ((1R,2S,5R)-5-(isopropyl(methyl)amino)-2-((S)-2-oxo-3-((6-(trifluoromethyl)quinazolin-4-yl)amino)pyrrolidin-1-yl)cyclohexyl)carbamate (695 mg, 1.231 mmol). The mixture was stirred at rt for 1.5 and was concentrated under reduced pressure. The residue was dried under hi vacuum to provide the title compound as a solid (1000 mg, 1.444 mmol, 117% yield). LC-MS m/z 465.2 $(M+H)^+$.

Step 4

9-(Tosyloxy)nonanoic acid

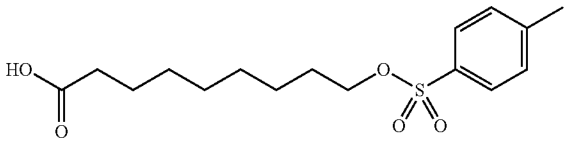 [SMILES: Cc1ccc(S(=O)(=O)OCCCCCCCCC(=O)O)cc1]

To a mixture of 9-hydroxynonanoic acid (318 mg, 1.825 mmol) in dichloromethane (DCM) (15 mL) was added 4-methylbenzenesulfonyl chloride (348 mg, 1.825 mmol), pyridine (0.177 mL, 2.190 mmol), and 4-dimethylaminopyridine (DMAP) (22.30 mg, 0.183 mmol). The mixture was stirred at rt overnight and was partitioned between dichloromethane (DCM) and 0.5 N HCl. The aqueous phase was extracted with dichloromethane (DCM). The combined organic extracts were dried over $Na_2SO_4$, were filtered, and the filtrate was concentrated. Purification by CombiFlash® chromatography (12 g RediSep Rf Gold® column, 30 mL/min) eluting with a gradient of 0 to 520% methanol/dichloromethane (DCM) (20/80) in dichloromethane (DCM) provided the title compound as a colorless oil (115 mg, 0.350 mmol, 19.19% yield). LC-MS m/z 329.0 $(M+H)^+$.

Step 5

9-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-9-oxononyl 4-methylbenzenesulfonate

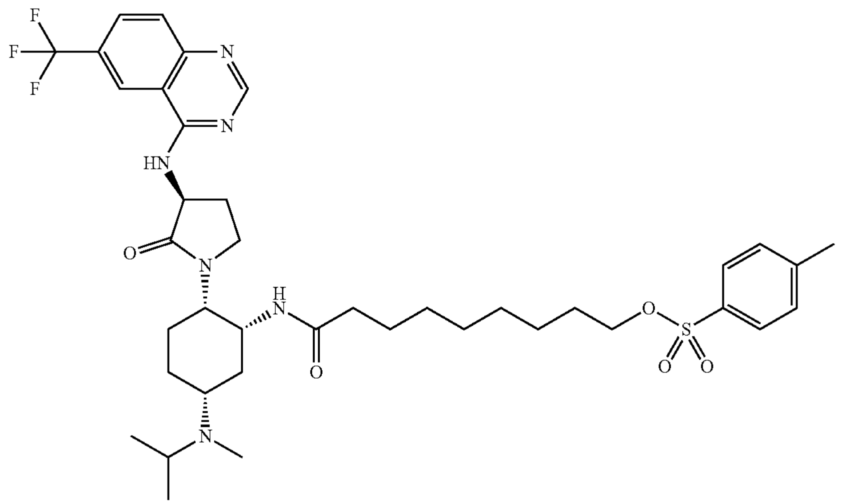 [SMILES: Cc1ccc(S(=O)(=O)OCCCCCCCCC(=O)N[C@@H]2C[C@H](N(C)C(C)C)CC[C@@H]2N2CC[C@H](Nc3ncnc4ccc(C(F)(F)F)cc34)C2=O)cc1]

To a mixture of (S)-1-((1S,2R,4R)-2-amino-4-(isopropyl(methyl)amino)cyclohexyl)-3-((6-(trifluoromethyl)quinazolin-4-yl)amino)pyrrolidin-2-one, 2trifluoroacetic acid salt (154 mg, 0.222 mmol) in dichloromethane (DCM) (1 mL) was added triethylamine (0.248 mL, 1.779 mmol) and the mixture was stirred at rt for 30 min. A mixture of 9-(tosyloxy)nonanoic acid (73.0 mg, 0.222 mmol) and HATU (101 mg, 0.267 mmol) in dichloromethane (DCM) (1 mL) was added and the mixture was stirred at rt for 15 min. The mixture was partitioned between dichloromethane (DCM) and saturated $NaHCO_3$ and the aqueous phase was extracted with dichloromethane (DCM). The combined organic phases were dried over $Na_2SO_4$, were filtered, and the filtrate was concentrated. Purification by CombiFlash® chromatography (12 g RediSep Rf Gold® column, 30 mL/min) eluting with a gradient of 0 to 50% methanol/dichloromethane (DCM) (80/20) in dichloromethane (DCM) provided the title compound as a light-yellow oil (120 mg, 0.155 mmol, 69.6% yield). LC-MS m/z 775.2 $(M+H)^+$.

Step 6

(2S,3S)-N-(24-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-24-oxo-3,6,9,12-tetraoxa-15-azatetracosyl)-1-methyl-5-oxo-2-(pyridin-3-yl)pyrrolidine-3-carboxamide, 3Trifluoroacetic acid salt

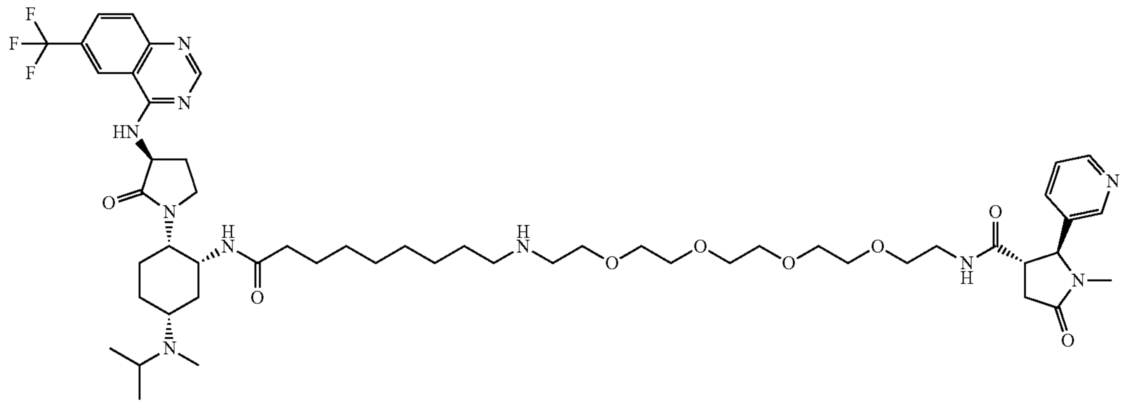

3TFA

To a mixture of 9-(((1R,2S,5R)-5-(isopropyl(methyl) amino)-2-((S)-2-oxo-3-((6-(trifluoromethyl)quinazolin-4-yl)amino)pyrrolidin-1-yl)cyclohexyl)amino)-9-oxononyl 4-methylbenzenesulfonate (40 mg, 0.052 mmol) and (2S, 3S)-N-(14-amino-3,6,9,12-tetraoxatetradecyl)-1-methyl-5-oxo-2-(pyridin-3-yl) pyrrolidine-3-carboxamide, 2trifluoroacetic acid salt (34.4 mg, 0.052 mmol) in N,N-dimethylformamide (DMF) (1 mL) was added potassium carbonate (49.9 mg, 0.361 mmol) and potassium iodide (10.28 mg, 0.062 mmol). The mixture was stirred at rt for 1 h and was stirred at 50° C. for 2 h. The mixture was partitioned between dichloromethane (DCM) and water and the aqueous phase was extracted with dichloromethane (DCM). The combined organic phases were dried over $Na_2SO_4$, were filtered, and the filtrate was concentrated. Purification by MDAP chromatography (XSelect™ CSH Prep C18 5 μm OBD column, 40 mL/min) eluting with a gradient of 15 to 55% acetonitrile in water both containing trifluoroacetic acid (0.1%) provided the title compound (6.4 mg, 4.62 μmol, 8.08% yield). LC-MS m/z 1042.3 $(M+H)^+$. $^1H$ NMR (400 MHz, METHANOL-$d_4$) δ ppm 1.20-1.39 (m, 13H) 1.45 (d, J=6.3 Hz, 3H) 1.56 (br d, J=6.6 Hz, 2H) 1.64-1.72 (m, 2H) 2.12-2.27 (m, 5H) 2.43-2.50 (m, 1H) 2.68 (s, 2H) 2.71 (s, 3H) 2.83 (s, 3H) 3.00-3.11 (m, 3H) 3.22-3.32 (m, 3H) 3.39 (t, J=5.3 Hz, 2H) 3.50-3.55 (m, 2H) 3.60-3.69 (m, 13H) 3.72-4.01 (m, 5H) 4.17-4.31 (m, 1H) 4.38 (br s, 1H) 4.94-5.02 (m, 2H) 5.65 (t, J=9.6 Hz, 1H) 7.91-7.95 (m, 1H) 8.02 (d, J=8.9 Hz, 1H) 8.29-8.37 (m, 2H) 8.77-8.82 (m, 2H) 8.91 (s, 1H) 9.05 (s, 1H).

The following compound was or could be prepared with procedures analogous to that described in Example 195:

| Ex. | Compound | LC-MS m/z | NMR |
|---|---|---|---|
| 196 | 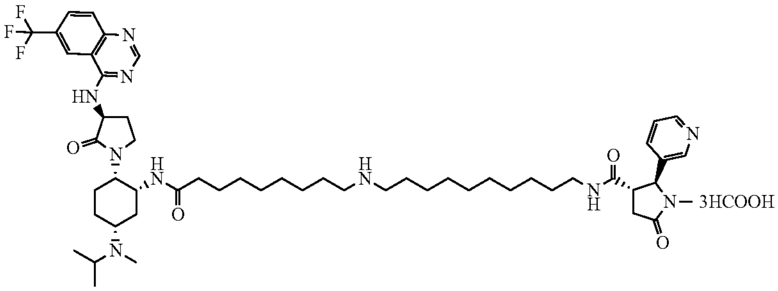 [SMILES: CC(C)N(C)[C@@H]1CC[C@H](N2CC[C@H](Nc3ncnc4ccc(C(F)(F)F)cc34)C2=O)[C@H](NC(=O)CCCCCCCCNCCCCCCCCCCNC(=O)[C@H]2CC(=O)N(C)[C@@H]2c2cccnc2)C1] (2S,3S)-N-(10-((9-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)amino)-9-oxononyl)amino)decyl)-1-methyl-5-oxo-2-(pyridin-3-yl)pyrrolidine-3-carboxamide, 3Formic acid salt. | 977.7 (M + H)+ | $^1H$ NMR (400 MHz, METHANOL-$d_4$) δ ppm 1.20-1.54 (m, 30 H) 1.58-1.72 (m, 4H) 1.95-2.05 (m, 2H) 2.09-2.17 (m, 3H) 2.21-2.29 (m, 2H) 2.43-2.62 (m, 2H) 2.65-2.73 (m, 4H) 2.79-2.86 (m, 4H) 2.91-3.06 (m, 5H) 3.10-3.24 (m, 2H) 3.60-3.69 (m, 1H) 3.72-3.81 (m, 1H) 3.84-3.98 (m, 2H) 4.17-4.28 (m, 1H) 4.33-4.40 (m, 1H) 4.81-4.86 (m, 1H) 5.16-5.33 (m, 1H) 7.53-7.62 (m, 1H) 7.81-7.88 (m, 1H) 7.92-7.99 (m, 1H) 8.06-8.12 (m, 1H) 8.15-8.21 (m, 1H) 8.49-8.65 (m, 2H) 8.72-8.75 (m, 1H) 8.81-8.88 (m, 1H) |

Example 197

(2S,3S)-N-(3-(3-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl)cyclohexyl)carbamoyl) cyclohexyl)amino)-3-oxopropoxy)propoxy)propyl)-1-methyl-5-oxo-2-(pyridin-3-yl)pyrrolidine-3-carboxamide

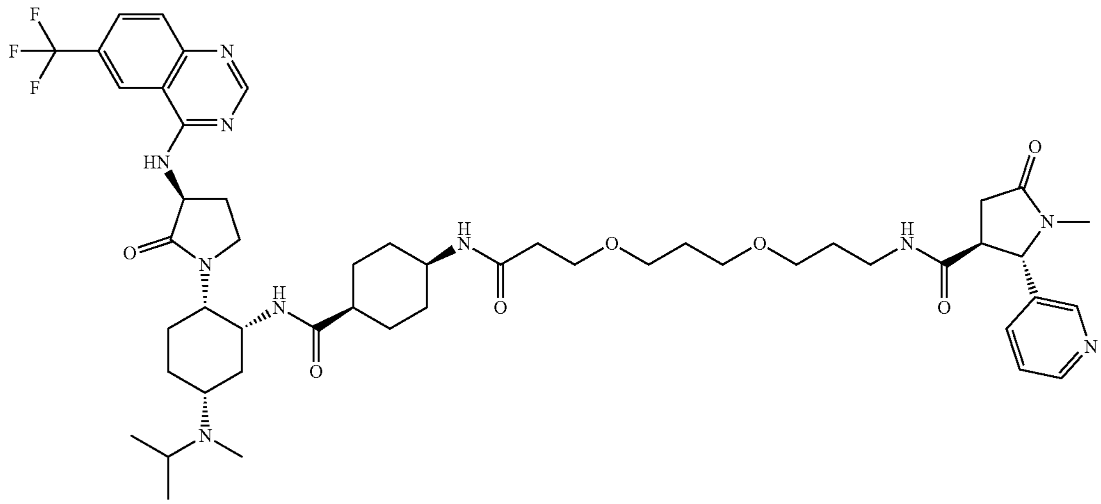 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCCOCCCNC(=O)[C@H]3CC(=O)N(C)[C@@H]3c3cccnc3)CC2)C1]

Step 1 Benzyl (3-(3-hydroxypropoxy)propyl)carbamate

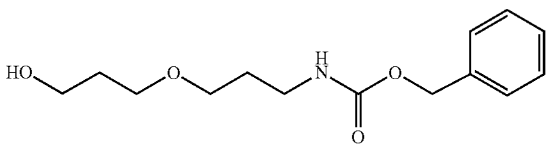 [SMILES: O=C(NCCCOCCCO)OCc1ccccc1]

4 M HCl in 1,4-dioxane (40.0 mL, 160 mmol) was added to a solution of tert-butyl 3-(3-(((benzyloxy)carbonyl)amino)propoxy)propanoate (Example 17, Step 1) (5.00 g, 14.82 mmol) in dichloromethane (DCM) (4.0 mL). The mixture was stirred for 5 h and was concentrated to dryness. The residue was dissolved in tetrahydrofuran (THF) (10.0 mL), was cooled to 0° C. and 1 M BH3 in tetrahydrofuran (THF) (44.5 mL, 44.5 mmol) was added slowly. The mixture was stirred at rt overnight. Saturated $NaHCO_3$ was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (80 g silica column, 60 mL/min) eluting with a gradient of 0 to 100% ethyl acetate in heptane provided the title compound as a colorless oil (1.1 g, 4.11 mmol, 27.8% yield). LC-MS m/z 268.1 $(M+H)^+$.

Step 2 tert-Butyl 3-oxo-1-phenyl-2,8,12-trioxa-4-azapentadecan-15-oate

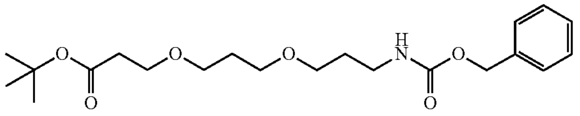 [SMILES: CC(C)(C)OC(=O)CCOCCCOCCCNC(=O)OCc1ccccc1]

To a solution of benzyl (3-(3-hydroxypropoxy)propyl)carbamate (1.10 g, 4.11 mmol) and tert-butyl acrylate (0.791 g, 6.17 mmol) in tetrahydrofuran (THF) (30.0 mL) was added a solution of 60% wt./wt. potassium hydroxide (0.231 g, 4.11 mmol) in water (0.22 mL). The mixture was stirred overnight. Water was added and the mixture was extracted with ethyl acetate (3×). The combined organic extracts were washed with brine (2×), were dried over $Na_2SO_4$, were filtered, and the filtrate was concentrated. Purification by CombiFlash® Rf chromatography (80 g silica column, 60 mL/min) eluting with a gradient of 0 to 50% ethyl acetate in heptane provided the title compound as a colorless oil (1.55 g, 3.92 mmol, 95% yield). LC-MS m/z 396.2 $(M+H)^+$.

Step 3 tert-Butyl 3-(3-(3-aminopropoxy)propoxy)propanoate

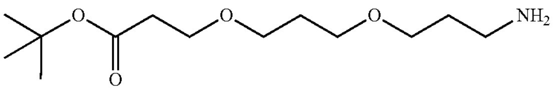 [SMILES: CC(C)(C)OC(=O)CCOCCCOCCCN]

To a solution of tert-butyl 3-oxo-1-phenyl-2,8,12-trioxa-4-azapentadecan-15-oate (1.55 g, 3.92 mmol) in ethyl acetate (5.0 mL) under an atmosphere of nitrogen was added 10% Pd—C, Degussa type (0.167 g, 1.568 mmol). The mixture was vacuumed and was backfilled with hydrogen (3×) and was stirred under a balloon atmosphere of hydrogen overnight. The mixture was filtered through Celite® and the filtrate was concentrated to provide the title compound as a colorless oil (1.00 g, 3.83 mmol, 98% yield). LC-MS m/z 262.2 $(M+H)^+$.

Step 4 tert-Butyl 3-(3-(3-((2S,3S)-1-methyl-5-oxo-2-(pyridin-3-yl)pyrrolidine-3-carboxamido) propoxy) propoxy)propanoate

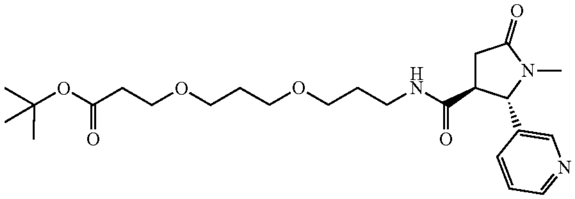 [SMILES: CN1C(=O)C[C@H](C(=O)NCCCOCCCOCCC(=O)OC(C)(C)C)[C@H]1c1cccnc1]

To a solution of (2S,3S)-1-methyl-5-oxo-2-(pyridin-3-yl) pyrrolidine-3-carboxylic acid (300 mg, 1.362 mmol) in dichloromethane (DCM) (5.0 mL) was added tert-butyl 3-(3-(3-aminopropoxy)propoxy)propanoate (356 mg, 1.362 mmol), HOBt (250 mg, 1.635 mmol), EDC (392 mg, 2.043 mmol), followed by DIPEA (0.714 mL, 4.09 mmol) and the mixture was stirred overnight. Water was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a light-colored wax (532 mg, 1.148 mmol, 84% yield). LC-MS m/z 464.1 $(M+H)^+$.

Step 5

(2S,3S)-N-(3-(3-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)amino)-3-oxopropoxy)propoxy)propyl)-1-methyl-5-oxo-2-(pyridin-3-yl)pyrrolidine-3-carboxamide

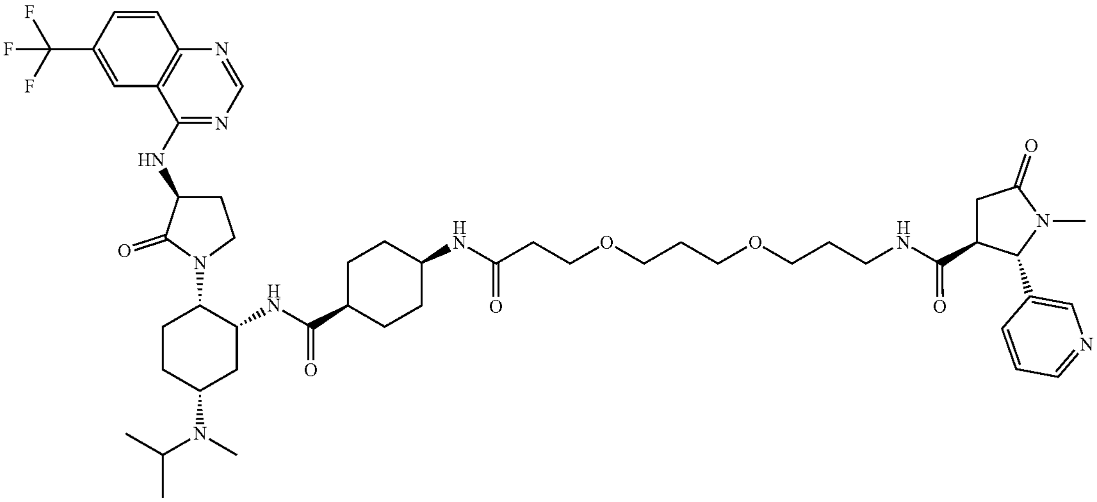 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCCOCCCNC(=O)[C@H]3CC(=O)N(C)[C@@H]3c3cccnc3)CC2)C1]

4 M HCl in 1,4-dioxane (4.0 mL, 16.00 mmol) was added to a solution of tert-butyl 3-(3-(3-((2S,3S)-1-methyl-5-oxo-2-(pyridin-3-yl) pyrrolidine-3-carboxamido) propoxy) propoxy) propanoate (58.8 mg, 0.127 mmol) in dichloromethane (DCM) (2.0 mL). The mixture was stirred for 1 h and was concentrated to dryness. To the residue in dichloromethane (DCM) (2.0 mL) was added Cis-4-amino-N-((1R,2S,5R)-5-(isopropyl(methyl)amino)-2-((S)-2-oxo-3-((6-(trifluoromethyl)quinazolin-4-yl)amino)pyrrolidin-1-yl) cyclohexyl)cyclohexane-1-carboxamide, 2 hydrochloric acid salt (60 mg, 0.091 mmol), HOBt (16.64 mg, 0.109 mmol) and DIPEA (0.079 mL, 0.453 mmol), followed by EDC (26.0 mg, 0.136 mmol). The mixture was stirred at rt overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (52.4 mg, 0.051 mmol, 56.1% yield). LC-MS m/z 979.6 $(M+H)^+$. $^1H$ NMR (400 MHz, DMSO-$d_6$) δ ppm 8.89 (s, 1H), 8.69 (d, J=7.8 Hz, 1H), 8.62-8.68 (m, 1H), 8.59 (s, 1H), 8.56 (dd, J=4.9, 1.5 Hz, 1H), 8.47 (d, J=2.0 Hz, 1H), 8.06 (dd, J=8.8, 1.5 Hz, 1H), 7.94 (t, J=5.4 Hz, 1H), 7.89 (d, J=8.8 Hz, 1H), 7.67 (dt, J=8.1, 2.1 Hz, 1H), 7.59 (d, J=6.8 Hz, 1H), 7.44 (dd, J=7.8, 4.9 Hz, 1H), 5.03 (q, J=8.0 Hz, 1H), 4.65 (d, J=6.4 Hz, 1H), 4.43 (br d, J=4.4 Hz, 1H), 3.85-3.96 (m, 1H), 3.67-3.77 (m, 1H), 3.47-3.61 (m, 3H), 3.42 (td, J=8.7, 3.7 Hz, 1H), 3.32-3.37 (m, 3H), 3.21-3.29 (m, 4H), 2.99-3.15 (m, 2H), 2.86-2.96 (m, 1H), 2.65-2.75 (m, 2H), 2.59 (m, 1H), 2.53-2.54 (m, 2H), 2.41-2.48 (m, 1H), 2.32-2.40 (m, 1H), 2.26 (t, J=6.6 Hz, 2H), 2.15 (s, 3H), 1.87-2.14 (m, 5H), 1.50-1.78 (m, 14H), 1.37-1.49 (m, 2H), 1.05 (d, J=6.4 Hz, 3H), 0.90 (d, J=6.4 Hz, 3H).

Example 198

(2S,3S)-N-(5-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl)cyclohexyl)amino)-3-oxopropoxy)ethyl)amino)-5-oxopentyl)-1-methyl-5-oxo-2-(pyridin-3-yl)pyrrolidine-3-carboxamide

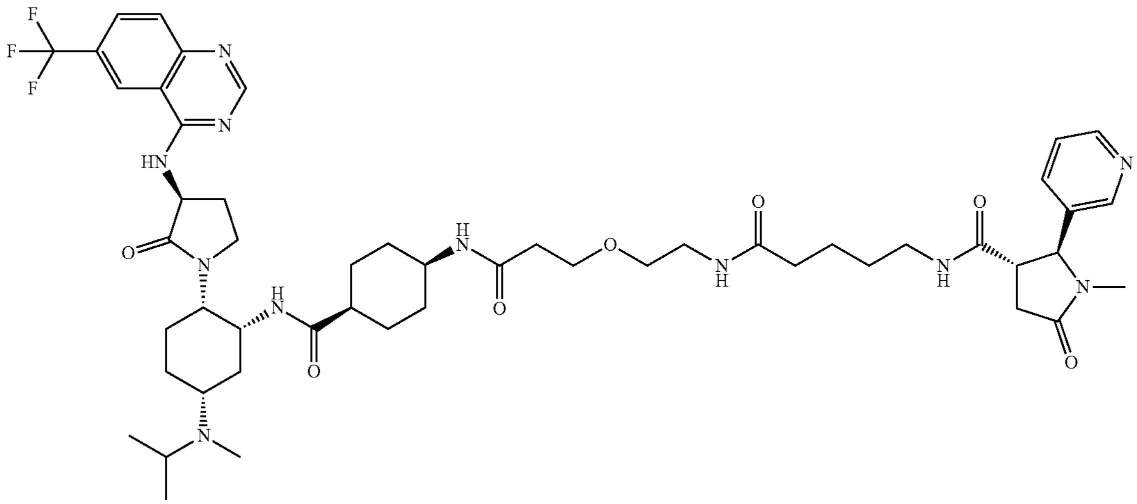 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCCCNC(=O)[C@H]3CC(=O)N(C)[C@@H]3c3cccnc3)CC2)C1]

Step 1 tert-Butyl 3,9-dioxo-1-phenyl-2,13-dioxa-4,10-diazahexadecan-16-oate

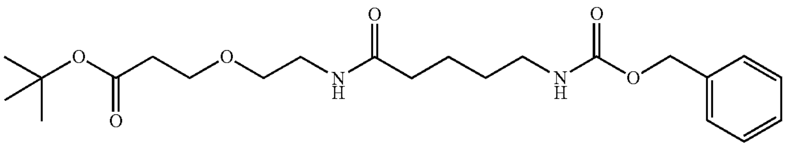 [SMILES: CC(C)(C)OC(=O)CCOCCNC(=O)CCCCNC(=O)OCc1ccccc1]

To a mixture of 5-(((benzyloxy)carbonyl)amino)pentanoic acid (494 mg, 1.966 mmol), tert-butyl 3-(2-aminoethoxy)propanoate (Example 167, Step 2) (310 mg, 1.638 mmol), DIPEA (1.430 mL, 8.19 mmol), and HOBt (301 mg, 1.966 mmol) in dichloromethane (DCM) (4.0 mL) was added EDC (471 mg, 2.457 mmol) and the mixture was stirred overnight. Water was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a colorless oil (588 mg, 1.392 mmol, 85% yield). LC-MS m/z 423.2 $(M+H)^+$.

Step 2 tert-Butyl 3-(2-(5-aminopentanamido)ethoxy)propanoate

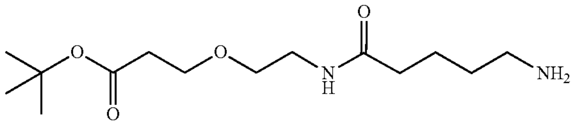 [SMILES: CC(C)(C)OC(=O)CCOCCNC(=O)CCCCN]

To a solution of tert-butyl 3,9-dioxo-1-phenyl-2,13-dioxa-4,10-diazahexadecan-16-oate (585 mg, 1.385 mmol) in ethyl acetate (5.0 mL) under an atmosphere of nitrogen was added 10% Pd—C, Degussa type (14.73 mg, 0.138 mmol). The mixture was vacuumed and was backfilled with hydrogen (3×) and was stirred under a balloon atmosphere of hydrogen overnight. The mixture was filtered through Celite® and the filtrate was concentrated to provide the title compound as a colorless oil (375 mg, 1.300 mmol, 94% yield). LC-MS m/z 289.2 $(M+H)^+$.

Step 3 tert-Butyl 3-(2-(5-((2S,3S)-1-methyl-5-oxo-2-(pyridin-3-yl)pyrrolidine-3-carboxamido) pentanamido) ethoxy)propanoate

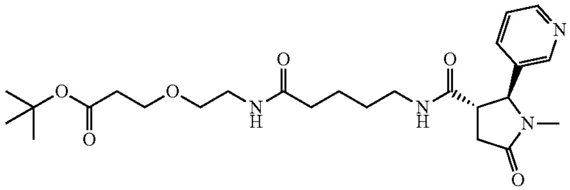 [SMILES: CN1C(=O)C[C@H](C(=O)NCCCCC(=O)NCCOCCC(=O)OC(C)(C)C)[C@H]1c1cccnc1]

To a solution of (2S,3S)-1-methyl-5-oxo-2-(pyridin-3-yl) pyrrolidine-3-carboxylic acid (230 mg, 1.044 mmol) in dichloromethane (DCM) (10.0 mL) was added tert-butyl 3-(2-(5-aminopentanamido)ethoxy)propanoate (361 mg, 1.253 mmol), HOBt (192 mg, 1.253 mmol), and EDC (300 mg, 1.567 mmol), followed by DIPEA (0.912 mL, 5.22 mmol) and the mixture was stirred overnight. Water was added and the mixture was extracted with dichloromethane (DCM) (3×). The combined organic extracts were washed with brine (2×), were dried over $Na_2SO_4$, were filtered, and the filtrate was concentrated. Purification by CombiFlash® Rf chromatography (40 g silica column, 40 mL/min) eluting with a gradient of 0 to 20% methanol in dichloromethane (DCM) provided the title compound as a light-colored wax (675 mg, 1.788 mmol, 98% yield). LC-MS m/z 378.3 $(M+H)^+$.

Step 4

(2S,3S)-N-(5-((2-(3-(((1S,4s)-4-(((1R,2S,5R)-5-(Isopropyl(methyl)amino)-2-((S)-2-oxo-3-((6-(trifluoromethyl)quinazolin-4-yl)amino)pyrrolidin-1-yl) cyclohexyl)carbamoyl) cyclohexyl)amino)-3-oxopropoxy)ethyl)amino)-5-oxopentyl)-1-methyl-5-oxo-2-(pyridin-3-yl)pyrrolidine-3-carboxamide

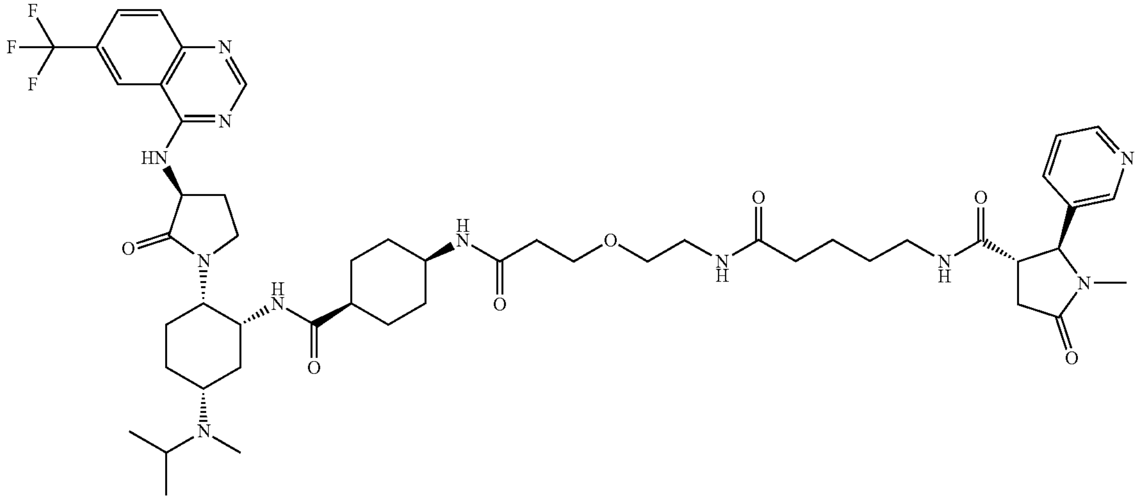 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCCCNC(=O)[C@H]3CC(=O)N(C)[C@@H]3c3cccnc3)CC2)C1]

4 M HCl in 1,4-dioxane (4.0 mL, 16.00 mmol) was added to a solution of tert-butyl 3-(2-(5-((2S,3S)-1-methyl-5-oxo-2-(pyridin-3-yl) pyrrolidine-3-carboxamido) pentanamido) ethoxy) propanoate (62.2 mg, 0.127 mmol) in dichloromethane (DCM) (2.0 mL). The mixture was stirred for 1 hour and was concentrated to dryness. To the residue in dichloromethane (DCM) (2.0 mL) was added (1 s,4S)-4-amino-N-((1R, 2S,5R)-5-(isopropyl(methyl)amino)-2-((S)-2-oxo-3-((6-(trifluoromethyl)quinazolin-4-yl)amino)pyrrolidin-1-yl) cyclohexyl)cyclohexane-1-carboxamide, 2hydrochloric acid salt (60 mg, 0.091 mmol), HOBt (16.64 mg, 0.109 mmol) and DIPEA (0.079 mL, 0.453 mmol), followed by EDC (26.0 mg, 0.136 mmol). The mixture was stirred at rt overnight. Saturated $NaHCO_3$ was added and the mixture was extracted with dichloromethane (DCM) (3×). The combined organic extracts were washed with brine (2×), were dried over $Na_2SO_4$, were filtered, and the filtrate was concentrated. Purification by MDAP chromatography (XSelect™ CSH Prep C18 5 μm OBD column, 40 mL/min) eluting with a gradient of 30 to 85% acetonitrile in water containing ammonium bicarbonate (10 mM) and ammonium hydroxide (0.075%) provided the title compound as an off-white solid (47.1 mg, 0.044 mmol, 49.1% yield). LC-MS m/z 1006.6 $(M+H)^+$. $^1H$ NMR (400 MHz, DMSO-$d_6$) δ ppm 0.90 (d, J=6.4 Hz, 3H) 1.05 (d, J=6.4 Hz, 3H) 1.26-1.36 (m, 2H) 1.37-1.49 (m, 4H) 1.50-1.64 (m, 6H) 1.64-1.78 (m, 3H) 1.94 (br dd, J=12.2, 7.3 Hz, 1H) 2.03 (br t, J=7.1 Hz, 3H) 2.06-2.18 (m, 6H) 2.29 (t, J=6.6 Hz, 2H) 2.32-2.39 (m, 1H) 2.40-2.48 (m, 1H) 2.52 (br s, 2H) 2.59 (br s, 1H) 2.65-2.75 (m, 1H) 2.85-2.94 (m, 1H) 2.95-3.09 (m, 2H) 3.15 (q, J=5.9 Hz, 2H) 3.22-3.30 (m, 1H) 3.33 (br d, J=5.9 Hz, 3H) 3.39-3.47 (m, 1H) 3.49-3.60 (m, 3H) 3.71 (br s, 1H) 3.82-3.99 (m, 1H) 4.36-4.50 (m, 1H) 4.64 (d, J=6.4 Hz, 1H) 5.03 (q, J=7.8 Hz, 1H) 7.44 (dd, J=7.8, 5.4 Hz, 1H) 7.62 (d, J=6.4 Hz, 1H) 7.67 (dt, J=7.9, 2.1 Hz, 1H) 7.75 (t, J=5.6 Hz, 1H) 7.89 (d, J=8.8 Hz, 1H) 7.95 (br t, J=5.6 Hz, 1H) 8.06 (dd, J=8.8, 2.0 Hz, 1H) 8.47 (d, J=2.0 Hz, 1H) 8.56 (dd, J=4.6, 1.7 Hz, 1H) 8.58 (s, 1H) 8.61-8.67 (m, 1H) 8.70 (br d, J=7.8 Hz, 1H) 8.89 (s, 1H).

BIOLOGICAL ASSAYS

Example Compounds 1-198 which are compounds of Formula (I) having a CCR2 binding moiety were tested in various biological assays as described in more detail below.

Example 199: Antibody Dependent Cellular Cytotoxicity Reporter Assay

An antibody dependent cellular cytoxocity reporter assay was conducted using the following four assay components: (i) ARM compound of Formula (I) targeting CCR2 (concentrations ranging from 1 μM to 10 μM) (ii) anti-cotinine antibody having a heavy chain sequence of SEQ ID NO: 11 and a light chain sequence of SEQ ID NO: 12 (rabbit variable region with human IgG1 Fc domain containing a DE mutation (S239D/1332E)) (concentrations ranging from 0.01 μg/mL to 200 μg/mL); (iii) target cells: CHOK1 cells engineered to overexpress either human CCR2 (typically 1000-20,000 cells per well) and (iv) reporter cells: Jurkat cells engineered to express FcγRIIIa with the reporter gene luciferase under the control of the NFAT promoter (typically 3000-75,000 cells per well). Reagents were combined in a final volume of 20 μL in a 384-well tissue culture treated plate. All four assay components were incubated together for about 12-18 hours. Thereafter, BioGlo Detection reagent (Promega) was added to the wells to lyse the cells and provide a substrate for the luciferase reporter protein. Luminescence signal was measured on a microplate reader and signal: background was calculated by dividing the signal of a test well by the signal obtained when no heterobivalent compound of Formula (I) was added. EC50 calculations were done using Graphpad Prism Software, specifically a nonlinear regression curve fit (Y=Bottom+(Top−Bottom)/(1+10A((LogEC50−X)*HillSlope))).

ARMs compounds of Formula (I) of the invention were tested for ADCC activity in the above assay in or more experimental runs and the results are shown in Table 3 below. Potency of the compounds of Formula (I) of the invention is reported as a pEC50 value. The pEC50 value is the negative log of the EC50 value, wherein the EC50 value is the half maximal effective concentration measured in molar (M). For compounds tested in more than one experimental run, the pEC50 value is reported as an average.

Example 200: PBMC Ex Vivo Depletion Assay

A human PBMC (peripheral blood mononuclear cells) monocyte depletion flow cytometry assay was developed to screen compounds in a 384-well plate format. This assay incorporated endogenous natural killer cells to deplete endogenous target monocytes.

To screen compounds in the human PBMC monocyte depletion flow cytometry assay, 11-point dose-response curves were made from 1 mM stocks in neat DMSO by serially diluting an ARM compound of Formula (I) four-fold into a 384-well plate row-wise. These serially diluted compounds were then stamped into a flat bottom polypropylene 384-well plate (Greiner Bio-One) at 100 nL/well. Fifty microliters of 30 μg/mL anti-cotinine antibody having a heavy chain sequence of SEQ ID NO: 11 and a light chain sequence of SEQ ID NO: 12 (rabbit variable region with human IgG1 Fc domain containing a DE mutation ($S_{239}$D/1332E)) that had been diluted in assay medium (RPMI 1640 (Gibco) containing 10% fetal bovine serum (Gibco), 1% Glutamax (Gibco) and 1% sodium pyruvate (Corning) was added to the wells of the plate. The plate was centrifuged for 1 min at 500 rpm (revolutions per minute) and then shaken for 5 min at room temperature. The plate was incubated for 15 minutes at 37° C./5% $CO_2$.

Frozen PBMC cells (HemaCare BioResearch) were thawed and centrifuged at 1,200 rpm for 4 minutes. The cells were diluted to a cell density of $2\times10^6$ cells/mL in assay medium. Fifty microliters of the diluted cells were added to the wells of the plate. The plate was centrifuged for 1 min at 500 rpm and incubated for 18-24 hours at 37° C./5% $CO_2$.

After 18-24 hours incubation, 2 μL of 6.25 μg human FC block (BD Pharmingen) that was diluted in assay medium was added to the wells of the plate. The plate was centrifuged for 1 minute at 500 rpm and then incubated at room temperature for 15 minutes. Five microliters of 750 nM Helix NP NIR (Biolegend) that had been diluted in assay medium was added to the wells of the plate. Nine microliters of antibody cocktail containing 1/5 diluted fluorescein isothiocyanate (FITC) labeled anti-CD45 antibody (Beckman Coulter), PC7 labeled anti-CD14 antibody (Beckman Coulter) and phyocoerythrin (PE) anti-CD4 antibody (Beckman Coulter) was then added to the wells of the plate. The plate was centrifuged for 1 min at 500 rpm and incubated for 30 minutes at 4-8° C. Samples from the plate were run on BD FACS Canto II flow cytometer and data was analyzed using FlowJo software.

ARMs compounds of Formula (I) of the invention were tested for the ability to deplete monocytes in the above assay in one or more experimental runs and the results are shown in Table 3 below. Potency of the compounds of the invention is reported as a pEC50 value. The pEC50 value is the negative log of the EC50 value, wherein the EC50 value is the half maximal effective concentration measured in molar (M). For compounds tested in more than one experimental run, the pEC50 value is reported as an average or as the individual values measured

TABLE 3

Results for ADCC Reporter Assay (Example 199) and PBMC Ex Vivo Depletion Assay (Example 200)

| Compound Example No. | ADCC Reporter Assay pEC50 | Ex Vivo Depletion Assay pEC50 |
|---|---|---|
| 1 | 8.488, 8.18 | 8.8 |
| 2 | 8.296 | 9.4 |
| 3 | 9.811, 9.548 | 9.3 |
| 4 | 8.201, 8.554, 8.311 | 9 |
| 5 | 9.5, 9.413 | 9.4 |
| 6 | 9.422 | 9.7 |
| 7 | 9.739 | 9.3 |
| 8 | 9.2 | n.d. |
| 9 | 7.6 | n.d. |
| 10 | 8.5 | n.d. |
| 11 | n.d.[1] | n.d. |
| 12 | n.d. | n.d. |
| 13 | n.d. | n.d. |
| 14 | n.d. | n.d. |
| 15 | n.d. | n.d. |
| 15A | n.d | n.d. |
| 16 | 9.034, 9.924 | 9.5 |
| 17 | 9.471, 9.183 | 9.2 |
| 18 | 9.171, 9.881 | 9.3 |
| 19 | 8.31 | 9.1 |
| 20 | 10.08 | 9.5 |
| 21 | 9.329 | 9.2 |
| 22 | 9, 9.3 | 9.2 |
| 23 | 8.95, 8.57, 9.247 | 8.7 |
| 24 | 8.836, 9.446 | 8.9 |
| 25 | 7.7 | 8.7 |
| 26 | n.d. | n.d. |
| 27 | 8.138 | 8 |
| 28 | 9.6 | 9 |
| 29 | 7.9 | 8.6 |
| 30 | 8.123 | 8.6 |
| 31 | 8.1 | 8.5 |
| 32 | 8.969, 9.227 | 9.4 |
| 33 | 8.343 | 9.5 |
| 34 | 9 | 8.8 |
| 35 | 8.6 | 9.2 |
| 36 | 8.4 | n.d. |
| 37 | 7.9 | 8.3 |
| 38 | 8.6 | 8.8 |
| 39 | 7.8 | 5.6 |
| 40 | 8.2 | 8.3 |
| 41 | 8.7 | 8.6 |
| 42 | 9.4 | 8.5 |
| 43 | 8.8 | 9 |
| 44 | 9.047 | 9.2 |
| 45 | 8.4 | 8.7 |
| 46 | 9.3 | 9.3 |
| 47 | 8.546 | 9.5 |
| 48 | 9.159, 9.168 | 8.7 |
| 49 | 9.073, 9.519 | 9.3 |
| 50 | 8.851 | 9.9 |
| 51 | 8.7 | 9.2 |
| 52 | 9.653, 9.532 | 9.7 |
| 53 | 8.119 | 9.2 |
| 54 | 9 | 9 |
| 55 | 9.424 | 9.9 |
| 56 | 9.184, 9.894 | n.d. |
| 57 | 8.792, 8.829, 8.295 | 8.8 |
| 58 | 7.3 | 8.1 |
| 59 | 6.6 | 8.8 |
| 60 | 11, 9.8 | 9.2 |
| 61 | 11, 9.7 | 9.5 |
| 62 | 9.062 | 9.3 |

TABLE 3-continued

Results for ADCC Reporter Assay (Example 199) and PBMC Ex Vivo Depletion Assay (Example 200)

| Compound Example No. | ADCC Reporter Assay pEC50 | Ex Vivo Depletion Assay pEC50 |
|---|---|---|
| 63 | 9.174, 9.508 | 9.2 |
| 64 | n.d. | n.d. |
| 65 | 8.853, 9.303 | 4 |
| 66 | 9.366 | 9.2 |
| 67 | 8.3 | 8.4 |
| 68 | 8 | 4 |
| 69 | 9.5 | 8.8 |
| 70 | 9.1 | 10 |
| 71 | 8 | 9.1 |
| 72 | 8.1 | 8.1 |
| 73 | 8.1 | 4 |
| 74 | 8.016 | 4 |
| 75 | 8.789 | 9 |
| 76 | 8.6 | 8.9 |
| 77 | 8.258 | 8.2 |
| 78 | 8.258 | 8.6 |
| 79 | 8.284 | 8.5 |
| 80 | 8.8 | 8.4 |
| 81 | 9.282 | n.d |
| 82 | 9.32 | 9.3 |
| 83 | 9.57 | n.d. |
| 84 | 9.672 | 9 |
| 85 | 8.084 | 8.7 |
| 86 | 8.1 | 9.8 |
| 87 | 8.4 | 9.4 |
| 88 | 8.6 | 8.1 |
| 89 | 8.2 | 7.6 |
| 90 | 8.7 | 8.8 |
| 91 | 8.7 | 9.1 |
| 92 | 8.2 | 7.6 |
| 93 | 8.4 | 6.9 |
| 94 | 8 | 8.7 |
| 95 | 8.2 | 6.2 |
| 96 | 8.2 | 9 |
| 97 | 8.2 | 10.2 |
| 98 | 9, 9.2 | 9.4 |
| 99 | 8.702 | 9.1 |
| 100 | 8.92 | 8.9 |
| 101 | 9.556 | 9.2 |
| 102 | 8.9 | 9.5 |
| 103 | 8.807, 9.239 | 4 |
| 104 | 8.643 | 9.2 |
| 105 | 9.1 | 9.4 |
| 106 | 9.253 | 9.1 |
| 107 | 9.8 | 9.7 |
| 108 | 10.3 | 9.4 |
| 109 | 9.77 | 9.2 |
| 110 | 9.776 | 10.3 |
| 111 | 8.2 | 8.3 |
| 112 | 9.4 | 9.1 |
| 113 | 8.317, 8.088 | 8.5 |
| 114 | 8.239 | 8.6 |
| 115 | 9.389, 9.515 | 9.8 |
| 116 | 8.3 | 10.4 |
| 117 | 9.5 | 8.4 |
| 118 | 8.4 | 7.8 |
| 119 | 8.8 | 8.8 |
| 120 | 8.263 | 8.9 |
| 121 | 8.277 | 8.9 |
| 122 | 9 | 9.1 |
| 123 | 8.3 | 7.8 |
| 124 | 8.7 | 4 |
| 125 | 8.5 | 7.8 |
| 126 | 8.8 | 8.6 |
| 127 | 9 | 8.7 |
| 128 | 9 | 8.8 |
| 129 | 8.3 | 8.9 |
| 130 | 8.4 | 9.2 |
| 131 | 8.5 | 9.3 |
| 132 | 8.5 | 9.2 |
| 133 | 8.3 | 8.9 |
| 134 | 10.2 | 9.9 |
| 135 | 8.6 | 8.8 |
| 136 | 8.309 | 8 |

TABLE 3-continued

Results for ADCC Reporter Assay (Example 199) and PBMC Ex Vivo Depletion Assay (Example 200)

| Compound Example No. | ADCC Reporter Assay pEC50 | Ex Vivo Depletion Assay pEC50 |
|---|---|---|
| 137 | 8.778 | 8.7 |
| 138 | 8.4 | 9.8 |
| 139 | 8.4 | 8.3 |
| 140 | 8.5 | 9.4 |
| 141 | 8.7 | 8.2 |
| 142 | 9.3 | 9.4 |
| 143 | 8.49 | 8.6 |
| 144 | 8.5 | 9.3 |
| 145 | 8.8 | 8.9 |
| 146 | 9.6 | 9.5 |
| 147 | 8.9 | 9.2 |
| 148 | 8.5 | n.d. |
| 149 | 9.6 | 9.6 |
| 150 | 8.5 | 9 |
| 151 | 8.518 | 8.7 |
| 152 | 8.854 | 8.9 |
| 153 | 8.6 | 9.2 |
| 154 | 8.6 | 9.3 |
| 155 | 8.8 | 9.6 |
| 156 | 9.1 | 9.1 |
| 157 | 9.7 | 9.2 |
| 158 | 8.6 | 9.3 |
| 159 | 8.7 | n.d. |
| 160 | 8.7 | 7.5 |
| 16 | 8.8 | 9.1 |
| 162 | 8.8 | 8.8 |
| 163 | 9.2 | 9.06 |
| 164 | 8.871 | 9 |
| 165 | 8.9 | 9.2 |
| 166 | 9.3 | 8.9 |
| 167 | 8.9 | 8.8 |
| 168 | 9.101 | 9 |
| 169 | 8.979 | 9.6 |
| 170 | 9 | 9.4 |
| 171 | 9.096 | n.d. |
| 172 | 9.1 | 8.7 |
| 173 | 9.1 | 9.1 |
| 175 | 9.1, 9.4 | 9.2 |
| 176 | 9.1, 9.4 | 9.5 |
| 177 | 9.3, 9.5 | 9.6 |
| 178 | 9.3, 9.9 | 9.4 |
| 179 | 9.14 | 9.2 |
| 180 | 9.341 | 8.9 |
| 181 | 9.171 | 9.4 |
| 182 | 9.289, 9.719 | 9.8 |
| 183 | 9.3 | 9.6 |
| 184 | 9.4 | 9.6 |
| 185 | 9.3 | 10.2 |
| 186 | 9.82 | 9.5 |
| 187 | 9.489 | 9.6 |
| 188 | 9.3 | 9.5 |
| 189 | 8.2 | 8.1 |
| 190 | 8.6 | 8.5 |
| 191 | 9.373 | 9.3 |
| 192 | n.d. | n.d. |
| 193 | 9.4, 9.9 | 9.7 |
| 194 | 9.561 | 9.2 |
| 195 | 9.8 | 9.5 |
| 196 | 9.6 | 9.7 |
| 197 | 9.6 | 9 |
| 198 | 9.4, 9.5 | 9.3 |

[1]n.d. = not determined

Example 201: In Vivo Depletion Assay

Human CCR2 (hCCR2) knock-in mice (C57 background) were dosed intravenously with a PBS solution containing a compound of Formula (I) to measure depletion cfCCR2 expressing cells in peripheral blood. Peripheral blood from V dosed mice was also analyzed to determine PK properties of the ARM compounds of Formula (I).

Stock solution preparation. Stock solutions of compounds of Formula (I) were prepared at 20 mg/mL and 100 mg/mL in PK8S0 for PK/PD and dose tolerability studies respectively. Stock solutions were stored at −2° C. until further usage. on the day of experiment, the stock Solution of the compound of Formula (I) was removed from storage at −2° C. and thawed at room temperature. Anti-cotinine antibody having a heavy chain sequence of SEC ID NO: 13 and a light chain sequence of SEQ ID NO: 14 (rabbit variable region sequence with mouse IgG2a Fc domain), if required was removed from storage at −80° C. and thawed at room temperature. Antibody vials were immediately transferred into wet ice after thawing. Compounds of Formula (I) were further diluted in DMSO as per experimental requirements.

The formulation composition was Saline: DMSI: PBS.

Saline was added based on the quantity required and then stock solution of the compound of Formula (I) prepared in DMSO, followed by addition of antibody in PBS. Formulations were incubated at room temperature for 30 minutes before administration to the mouse. DMSO was used at 1 to % (v/v) in the final formulation.

Administration to Animal: Solution formulation of antibody and compound of Formula (I) was injected (bolus injection) to the restrained mouse in the right/left lateral tai vein. Animals were dosed with 0.1 milligram per kilogram (mpk) of the compound of Formula (I) and 10 mpk of the anti-cotinine antibody.

Collection of Blood for PK: Blood was collected at time points 0.25 hour, 2 hours, and 4 hours following administration (50 μL/time point) through retro-orbital bleeding under mild isoflurane anesthesia.

Terminal bleeding at end of experiment (48 hr): Approximately 250 μL of blood in $K_2$EDTA tube and approximately 250 μL of blood in SST (serum separation tube) was collected from each mouse through retro-orbital bleeding under deep isoflurane anesthesia. After bleeding, each mouse was sacrificed by cervical dislocation. The blood distribution at termination was determined as follows:

For PK: 50 μL of $K_2$EDTA blood was transferred to another tube for PK

Flow cytometry: Remaining blood (~200 μL) was used for flow cytometry analysis.

For serum collection: serum separator tubes (BD) were centrifuged at 4° C., 5000 rpm for 15 minutes. Approximately 100 μL serum was separated and stored at −80° C. for further usage.

Blood drug concentration: Samples collected at the various timepoints (0.25 hr, 2 hr, 24 and 48 hr) were analyzed to determine blood drug concentration.

Flow Cytometry Analysis:

CCR2 depletion in peripheral blood was determined by flow cytometry. Briefly, peripheral blood was collected from all animals at the end of study termination and processed. Blood samples were lysed using 1×RBC Lysis buffer and the resulting cell pellet was washed twice in FACS buffer (HBSS containing 5% FBS). Cells were subjected to Fc blocking using mouse Fc block from Biolegend (Trustain, anti-mouse CD16/32, Cat: 101319) to block non-specific binding followed by surface staining for immune markers (CD45, CD3, CD11 b, Ly6C, human CCR2). Surface staining was done for 30 minutes in ice and cells were washed twice to remove unbound antibodies. Cells were stained with 7AAD to determine viability and acquired on BD FACSVerse flow cytometer. Appropriate FMO controls and single-color controls were included in the experiment for gating and compensation respectively.

CCR2+ monocytes were gated as CD11 b+Ly6C+Hi, medium and Low populations and treatment induced reduction in CD11 b+Ly6c+Hi cells (i.e., cells with high CCR2 expression) was evaluated. Percent depletion of CD11 b+Ly6c+Hi cells and CCR2 expression for the different treatment groups was determined. The results are shown below in Table 4 and are reported as percent (%) depletion of CCR2 expressing cells.

Blood Drug Concentration Analysis:

Drug concentration in blood samples was determined by an LC-MS/MS-based bioanalytical method developed at Syngene. Samples were analyzed on Q-Trap. AP-5500 LC-MS/MS system coupled with Exion UHPLC system from SCIEX, USA operated in multiple reaction monitoring mode employing electrospray ionization technique in positive polarity. Analyte and internal standard peaks were resolved on Synergi Polar, 75×2.0 mm. 4µ column using mobile phase 10 mM Ammonium acetate in Milli-Q water as phase A and 0.1% Formic acid in acetonitrile as Phase B. Gradient elution was performed with initial composition 95% Phase A at 0.0 min, holding it for 0.2 minutes, ramping to 5% by 1.0 minute, keeping the same for next 0.5 minutes and coming back to 95% by 1.6 minutes. The total run time was 2 minutes.

Working dilutions for calibration curve and quality control standards were prepared by serially diluting 20 mg/mL stock solution with DMSO. Spiked concentrations for calibration curve in the whole blood ranged from 1 ng/mL to 1000 ng/mL. The working solution of internal standard (Verapamil, 25 ng/mL) was prepared in acetonitrile. 10 µL of the study sample and calibration curve, quality control, and blank whole blood samples were aliquoted in 96 deep well plates for processing. 10 µL of Milli-Q water was added to all the samples and briefly vortexed to initiate complete hemolysis. 10 µL of 20 mM dithiothreitol (DTT) was added to all the samples and incubated for 30 minutes at 37° C. The addition of DTT enhanced the recovery of ARM compounds of Formula (I) from the biological matrix. 300 µL of working internal standard solution was added to all samples except total blank and wash samples, where 300 µL of acetonitrile was added. All the samples were vortex mixed for 5 minutes, followed by centrifugation at 4DDD rpm for 1D minutes at 4° C. Supernatants were transferred to the loading plate and injected 3 µL to LC-MS/MG system for analysis. The results are shown below in Table 4 and are reported as compound exposure 48 hours post-dose

TABLE 4

Results for In Vivo Depletion Assay—% Depletion of CCR2 expressing cells and PK analysis of ARM compounds of Formula (I) after 48 hours exposure

| Compound Example No. | % Depletion of CCR2 expressing cells | Exposure of Compound of Formula (I) 48 hours post-dose (ng/mL) |
|---|---|---|
| 1 | 88.5 | 100.095 |
| 2 | 92.3 | 30.95 |
| 3 | 87 | 16.02 |
| 4 | 78.8 | 35.365 |
| 5 | 91.05 | 18.705 |
| 6 | 82 | 41.29 |
| 7 | 47 | 53.76 |
| 8 | 90.3 | 33.4 |
| 9 | n.d.[1] | n.d. |
| 10 | 94.9 | 45.35 |
| 11 | 91.57 | 19.57 |
| 13 | 96.07 | 5.44 |

TABLE 4-continued

Results for In Vivo Depletion Assay—% Depletion of CCR2 expressing cells and PK analysis of ARM compounds of Formula (I) after 48 hours exposure

| Compound Example No. | % Depletion of CCR2 expressing cells | Exposure of Compound of Formula (I) 48 hours post-dose (ng/mL) |
|---|---|---|
| 14 | 47.24 | 2.4 |
| 15 | 92.6 | 4.77 |
| 16 | 74 | 53.38 |
| 17 | 91 | 52.54 |
| 18 | 88 | 23.28 |
| 19 | 59 | 67.24 |
| 20 | 79 | 27.61 |
| 23 | 90.7 | 27.12666667 |
| 24 | 89.47 | 32.36 |
| 27 | 80 | 127.3 |
| 28 | 87.1 | 17.5 |
| 30 | 34.88 | 85.42 |
| 31 | 94.9 | 37.22 |
| 32 | 83 | 41.58 |
| 33 | 89 | 67.43 |
| 34 | 95 | 24.36 |
| 35 | 88.81 | 18.96 |
| 36 | 83.33333333 | 52.22 |
| 37 | 75 | 48.72 |
| 38 | 84.55 | 47.61 |
| 44 | 91 | 11.8 |
| 46 | 96 | 123.25 |
| 47 | 73 | 89.78 |
| 48 | 89 | 96.79 |
| 49 | 85.84 | 43.5 |
| 51 | 97.32 | 27.24 |
| 52 | 79.18 | 88.24 |
| 53 | 68.42 | 65.6 |
| 55 | 76.2 | 8.97 |
| 56 | 97 | 65.2 |
| 57 | 77 | 42.18 |
| 60 | 90 | 14.03 |
| 61 | 92 | 9.55 |
| 62 | 56 | 53.18 |
| 63 | 82 | 19.47 |
| 69 | 98.59 | 39.89 |
| 70 | 30.51 | 2.3 |
| 71 | 35.25 | 1 |
| 76 | 65 | 102.43 |
| 80 | 89 | 92.24 |
| 81 | 94 | 36.68 |
| 82 | 94 | 55.53 |
| 83 | 67 | 38.7 |
| 85 | 57 | 50.92 |
| 86 | 25.67 | 1.4 |
| 90 | 87.57 | 16.8 |
| 94 | 88.66 | 116.8 |
| 98 | 88 | 88.97 |
| 99 | 80 | 30.92 |
| 100 | 74 | 19.4 |
| 102 | 91 | 52.04 |
| 105 | 95 | 78.06 |
| 107 | 96 | 30.61 |
| 108 | 93 | 134.24 |
| 111 | 50 | 103.07 |
| 119 | 77 | 72.22 |
| 121 | 69 | 25.42 |
| 122 | 94 | 18.57 |
| 130 | 81.81 | 57.4 |
| 136 | 88 | 82.2 |
| 137 | 89 | 99.06 |
| 138 | 74.67 | 1.6 |
| 140 | 89.13 | 65.4 |
| 142 | 79.27 | 38 |
| 144 | 85.67 | 17.2 |
| 146 | 83.08 | 57.67 |
| 147 | 77 | 28.8 |
| 150 | 85.52 | 20.8 |
| 152 | 82 | 34.81 |
| 155 | 70 | 43.4 |
| 157 | 79 | 18.4 |

TABLE 4-continued

Results for In Vivo Depletion Assay—% Depletion of CCR2 expressing cells and PK analysis of ARM compounds of Formula (I) after 48 hours exposure

| Compound Example No. | % Depletion of CCR2 expressing cells | Exposure of Compound of Formula (I) 48 hours post-dose (ng/mL) |
|---|---|---|
| 161 | 76.67 | 45.4 |
| 162 | 66 | 16.4 |
| 163 | 89 | 107.2 |
| 164 | 86 | 50.79 |
| 169 | 87 | 21.2 |
| 170 | 94.75 | 19.3 |
| 172 | 80 | 16.4 |
| 173 | 91 | 62.35 |
| 179 | 89.5 | 39.605 |
| 182 | 97 | 73.3 |
| 184 | 85.99 | 115.66 |
| 186 | 96 | 78.7 |
| 187 | 92 | 78.9 |
| 188 | 91 | 73.01 |
| 191 | 69 | 47.5 |
| 192 | 84.8 | 10.67 |
| 194 | 96 | 85 |

[1]n.d. = not determined

Example 202: Binding of Anti-Cotinine Antibody to ARM Compounds of Formula (I) Measured by Surface Plasmon Resonance (SPR)

Anti-cotinine antibodies having a heavy chain sequence of SEQ ID NO: 11 and a light chain sequence of SEQ ID NO: 12 (rabbit variable region with human IgG1 Fc domain containing a DE mutation (S239D/1332E)) were captured on one or more flow cells of a protein A sensor chip (Cytiva) using a Biacore T200 while reserving flow cell 1 as a reference. Following capture, a 3000 second wait step was included to reduce drift during compound analysis. ARM compounds of Formula (I) were then injected at 100 μL/min with 200 and 2000 second association and dissociation times. The entire experiment was run at 37° C. with running buffer containing 10 mM HEPES pH 7.4, 150 mM NaCl, 0.005% P20 and 1% DMSO. ARM compounds of Formula (I) were titrated with a top concentration of 200 nM using a 3-fold 5-point dilution series and a corresponding 5-injection buffer cycle was run for blank subtraction. Data were double referenced by subtracting the response of the reference flow cell from that of the antibody-containing flow cell and subsequently subtracting the referenced blank sensorgrams. Following compound analysis, the surface was regenerated using a 30 second injection of pH 1.5 glycine at a flow rate of 30 μL/min after which antibody was recaptured. The experiment was run using Biacore T200 control software and evaluated using Biacore T200 Evaluation software. Curves were fit with a 1:1 kinetic binding model to obtain $k_{on}$ (1/Ms), $k_{off}$(1/s), $K_d$ (M) determined as $k_{off}/k_{on}$, and residence time determined as $1/k_{off}$ (s).

Anti-cotinine antibody was tested for binding to ARMs compounds of Formula (I) of the invention in the above assay in or more experimental runs and the results are shown in Table 5 below. Affinity is reported as a $pK_d$ value. The $pK_d$ value is the negative log of the $K_d$ value, wherein the $K_d$ value is the dissociation constant measured in molar (M) as noted above. For compounds tested in more than one experimental run, the $pK_d$ value is reported as an average

TABLE 5

Binding of Anti-Cotinine Antibody to ARM Compounds of Formula (I) Measured by SPR

| Compound Example No. | $pK_d$ of Antibody for ARM Compound of Formula (I) |
|---|---|
| 1 | 9.65385714 |
| 2 | 9.4775 |
| 3 | 9.2795 |
| 4 | 9.52633333 |
| 5 | 9.19 |
| 6 | 9.282 |
| 7 | 9.2515 |
| 10 | 9.19933333 |
| 13 | 10.511 |
| 16 | 9.287 |
| 18 | 9.0895 |
| 19 | 9.19 |
| 20 | 8.8705 |
| 22 | 9.2495 |
| 23 | 9.2166 |
| 24 | 9.4425 |
| 28 | 9.273 |
| 29 | 9.3345 |
| 30 | 9.3155 |
| 31 | 9.3015 |
| 32 | 9.1825 |
| 34 | 9.933 |
| 35 | 9.785 |
| 36 | 8.9915 |
| 37 | 9.7475 |
| 38 | 9.611 |
| 40 | 9.4525 |
| 41 | 9.3615 |
| 42 | 9.23 |
| 46 | 9.074 |
| 47 | 9.051 |
| 48 | 8.975 |
| 49 | 9.191 |
| 50 | 9.1485 |
| 52 | 9.2545 |
| 53 | 9.531 |
| 54 | 9.5515 |
| 55 | 9.4085 |
| 56 | 9.3185 |
| 57 | 9.685 |
| 60 | 9.4635 |
| 61 | 9.558 |
| 62 | 9.6305 |
| 63 | 8.674 |
| 65 | 8.648 |
| 66 | 8.649 |
| 69 | 9.321 |
| 72 | 9.8865 |
| 73 | 9.8185 |
| 74 | 9.091 |
| 75 | 9.103 |
| 76 | 9.1155 |
| 77 | 9.152 |
| 79 | 9.126 |
| 80 | 9.109 |
| 83 | 9.302 |
| 85 | 9.6885 |
| 98 | 9.0095 |
| 99 | 9.062 |
| 102 | 9.076 |
| 103 | 9.0985 |
| 104 | 9.051 |
| 105 | 9.0705 |
| 107 | 9.161 |
| 108 | 8.9855 |
| 109 | 8.951 |
| 110 | 8.9085 |
| 111 | 9.0855 |
| 112 | 9.343 |
| 113 | 9.767 |
| 115 | 9.363 |
| 119 | 9.1735 |
| 121 | 9.332 |
| 122 | 9.146 |

TABLE 5-continued

Binding of Anti-Cotinine Antibody to ARM Compounds of Formula (I) Measured by SPR

| Compound Example No. | $pK_d$ of Antibody for ARM Compound of Formula (I) |
|---|---|
| 137 | 9.336 |
| 138 | 9.0865 |
| 143 | 9.275 |
| 151 | 9.0755 |
| 152 | 9.111 |
| 157 | 10.135 |
| 163 | 9.07 |
| 164 | 9.3225 |
| 168 | 9.06 |
| 169 | 9.0085 |
| 171 | 8.7865 |
| 173 | 9.1415 |
| 175 | 9.244 |
| 179 | 9.24 |
| 180 | 9.249 |
| 181 | 9.1645 |
| 182 | 9.117 |
| 186 | 9.1435 |
| 187 | 9.104 |
| 188 | 8.975 |
| 191 | 9.68 |
| 194 | 9.5415 |
| 198 | 9.3835 |

Anti-cotinine antibodies having a heavy chain sequence of SEQ ID NO: 9 and a light chain sequence of SEQ ID NO: 10 (humanized version) or a heavy chain sequence of SEQ ID NO: 11 and a light chain sequence of SEQ ID NO: 12 (rabbit version) were captured via the Fc domain to a protein A or A/G surface on flow cell 2 of a CMS sensor chip using the Biacore 8k. Both antibodies used in this experiment had a human IgG1 Fc domain containing a DE mutation (S239D/1332E).

After antibody capture, a 1500 second wait step was included to reduce drift in the binding step. ARM compounds of Formula (I) were then flowed over the captured antibodies at varying top concentrations ranging from 250 nM to 4 μM (see Table 6 below for top concentration values). The top concentration was diluted 4-fold over 5 dilutions (with a 0 nM compound cycle included to blank subtract the data). Association and dissociation times of the ARMs compounds of Formula (I) varied between experiments as follows and indicated in Table 6 below: reference 1-association for 600 seconds and dissociation for 1200 seconds at 20 μl/min; reference 2-association for 240 seconds and dissociation for 300 seconds at 30 μl/min; reference 3-association for 360 seconds and dissociation for 600 seconds at 30 μl/min. Anti-cotinine antibody bound to the protein A or A/G surface was regenerated using 50 mM NaOH. Experiments were run at 25° C. at pH 7.4 using HBS-EP+ buffer using Biacore 8K control software and evaluated using Biacore Insight Evaluation software. Curves were fit with the 1:1 kinetic fit inherent to the software, utilising a local Rmax and local drift setting.

Anti-cotinine antibody was tested for binding to ARMs compounds of Formula (I) of the invention in the above assay in or more experimental runs and the results are shown in Table 6 below. Affinity is reported as a $pK_d$ value. The $pK_d$ value is the negative log of the $K_d$ value, wherein the $K_d$ value is the dissociation constant measured in molar (M) as noted above. For compounds tested in more than one experimental run, the $pK_d$ value is reported as an average.

TABLE 6

Binding of Anti-Cotinine Antibody to ARM Compounds of Formula (I) Measured by SPR

| Antibody Name | Compound Example Number | $pK_d$ | ka (1/Ms) | kd (1/s) | Association/ dissociation time reference | Top Concentration of Analyte(M) |
|---|---|---|---|---|---|---|
| Humanized | 36 | Poor fit | | | 1 | 2.50E−08 |
| Humanized | 1 | 8.49 | 2.01E+05 | 6.49E−04 | 1 | 2.50E−08 |
| Humanized | 36 | 8.22 | 1.24E+05 | 7.51E−04 | 1 | 2.50E−08 |
| Humanized | 1 | 8.16 | 6.63E+04 | 4.56E−04 | 1 | 2.50E−08 |
| Rabbit | 10 | Poor fit | | | 2 | 1.00E−06 |
| Rabbit | 10 | Poor fit | | | 2 | 4.00E−06 |
| Rabbit | 36 | 9.94 | 3.17E+06 | 3.65E−04 | 3 | 2.50E−08 |
| Rabbit | 1 | 10.55 | 5.57E+06 | 1.56E−04 | 3 | 6.25E−09 |
| Rabbit | 10 | kd outside limits of instrument | | | 3 | 6.25E−09 |
| Humanized | 36 | kd outside limits of instrument | | | 3 | 2.50E−08 |
| Humanized | 1 | 9.6 | 1.64E+06 | 4.14E−04 | 3 | 2.50E−08 |
| Humanized | 10 | 9.47 | 1.42E+06 | 4.84E−04 | 3 | 2.50E−08 |

Example 203: Nicotinic Acetylcholine Receptor Antagonism Assay

Cells expressing human alpha1 nicotinic acetylcholine (nACh) receptor (nAChR) were washed and dissociated using Trypsin containing buffer. Cells were then washed and seeded at a density of 3-5 million cells/mL and allowed to grow for 3 days. Then, 60-80 μL of cells were added to plates and incubated with dose response of an ARM compound of Formula (I) with a top concentration of either 10 μM or 100 μM. The receptor was then stimulated via addition of acetylcholine (ACh) and activation of the receptor was monitored via the IONFlux automated patch clamp system. IonFlux Data Analyzer software was utilized to perform leak subtraction and measure (min) peak current amplitude. These data were then exported to Excel.

Data processing: (1) Current values recorded for vehicle only applications in individual traps/patterns were subtracted from corresponding current amplitude values for control, test article and control+test article. (2) Control response was calculated as % of the average response of the 3rd out of total 3 ACh (10 mM) applications alone. In rare situations, if the 3rd ACh response was obscured due to technical artifacts, the 2nd and/or 1st ACh (10 mM) application was considered as control. The peak current amplitude generated in the presence of each test article concentration was then used to calculate the % inhibition as compared to control response (10 mM ACh alone). These estimates were further corrected for vehicle response and run down corrected by normalizing with time matched control responses (10 mM ACh alone). The corrected percentages were then fit with a non-linear function in GraphPad Prism 6 (or later versions) to determine the IC50.

Exclusion criteria: (i) any n's with poor recording quality, (ii) control current amplitude <500 pA or (iii) significant outliers, as determined by the Grubbs test.

ARMs compounds of Formula (I) of the invention were tested for antagonism of the nAChR in the above assay in or more experimental runs and the results are shown in Table 7 below. Antagonistic activity of the compounds of Formula (I) of the invention is reported as an IC50 value (half maximal inhibitory concentration) and the maximum percentage antagonism observed at the highest concentration of compound of Formula (I) tested, as indicated in Table 7. For compounds tested in more than one experimental run, the IC50 value is reported as an average

TABLE 7

Results of nAChR Antagonism Assay

| Compound Example No. | IC50 (μM) | Maximum Concentration of Compound Tested (μM) | Maximum Response (%) |
|---|---|---|---|
| 1 | 84.6 | 100 | 25.6 |
| 5 | 100 | 100 | 40.5 |
| 7 | 13.65 | 100 | 95 |
| 8 | 47.2 | 100 | 73.1 |
| 9 | 82 | 100 | 53.9 |
| 10 | 33.33 | 33.33 | 48 |
| 16 | 100 | 100 | 47.8 |
| 17 | 100 | 100 | 55.1 |
| 18 | 100 | 100 | 44.9 |
| 19 | 100 | 100 | 34.2 |
| 23 | 85.24 | 100 | 50.5 |
| 24 | 85.31 | 100 | 59.55 |
| 27 | 93.7 | 100 | 53.8 |
| 28 | 40.85 | 100 | 69.9 |
| 30 | 10 | 10 | 5.4 |
| 34 | 28.53 | 100 | 79.2 |
| 35 | 89.2 | 100 | 52.3 |
| 37 | 10 | 10 | 7.3 |
| 38 | 10 | 10 | -2.2 |
| 40 | 10 | 10 | 24.7 |
| 41 | 10 | 10 | 20.1 |
| 44 | 100 | 100 | 51.5 |
| 48 | 31.79 | 100 | 77 |
| 49 | 80.33 | 100 | 56.7 |
| 52 | 33.3 | 33.33 | 8.3 |
| 53 | 11.1 | 11.11 | 10 |
| 57 | 30 | 30 | 47.6 |
| 60 | 10 | 10 | 18.2 |
| 62 | 28.96 | 100 | 67.9 |
| 63 | 38.54 | 100 | 76.6 |
| 72 | 10 | 10 | 32.7 |
| 73 | 10 | 10 | 4.1 |
| 76 | 32.44 | 100 | 67.7 |
| 77 | 10 | 10 | 19.6 |
| 94 | 4.66 | 10 | 67.1 |
| 99 | 33.1 | 100 | 71.1 |
| 102 | 66.08 | 100 | 61.3 |
| 105 | 38.93 | 100 | 75.7 |
| 107 | 10 | 10 | 12.2 |
| 111 | 52.92 | 100 | 67.6 |
| 122 | 10 | 10 | 23 |
| 130 | 10 | 10 | 16.8 |
| 137 | 70 | 100 | 62 |
| 140 | 10 | 10 | 18.2 |
| 142 | 10 | 10 | 13.1 |
| 182 | 76.4 | 100 | 61.9 |
| 184 | 6.39 | 10 | 69.2 |
| 186 | 31.76 | 100 | 55.2 |
| 187 | 71.1 | 100 | 63.7 |
| 188 | 85.89 | 100 | 53.5 |
| 191 | 2.95 | 10 | 74 |
| 192 | 74.33 | 100 | 53 |
| 194 | 100 | 100 | 44.9 |

Example 204: Dosing and Analysis of Tumor Bearing Animals

MC38 cells were injected subcutaneously into the flank of human CCR2 knock-in $C_{57}$ mice. Tumor volume was measured using a digital Vernier caliper, and the length (I) and width (w) of the tumor was measured. Tumor volume was calculated using the following formula: Tumor Volume ($mm^3$)=L×W2/2, Where, L=Length (mm); W=Width (mm). Anti-cotinine antibody (rabbit variable region sequence with mouse IgG2a Fc domain having a heavy chain sequence of SEQ ID NO: 13 and a light chain sequence of SEQ ID NO: 14), and ARM compound of Formula (I) (Example 36) were diluted in saline and administered intravenously to give the final concentrations tested. Antibody was tested at concentrations of 10 milligrams per kilogram (mpk), 5 mpk, 2.5 mpk, or 1.25 mpk; and compound of Formula (I) was tested at 0.2 mpk, 0.1 mpk, 0.05 mpk, and 0.025 mpk. Tumor volume at the various concentrations of antibody/compound of Formula (I) tested is shown in FIG. 1A.

Figure 10A:
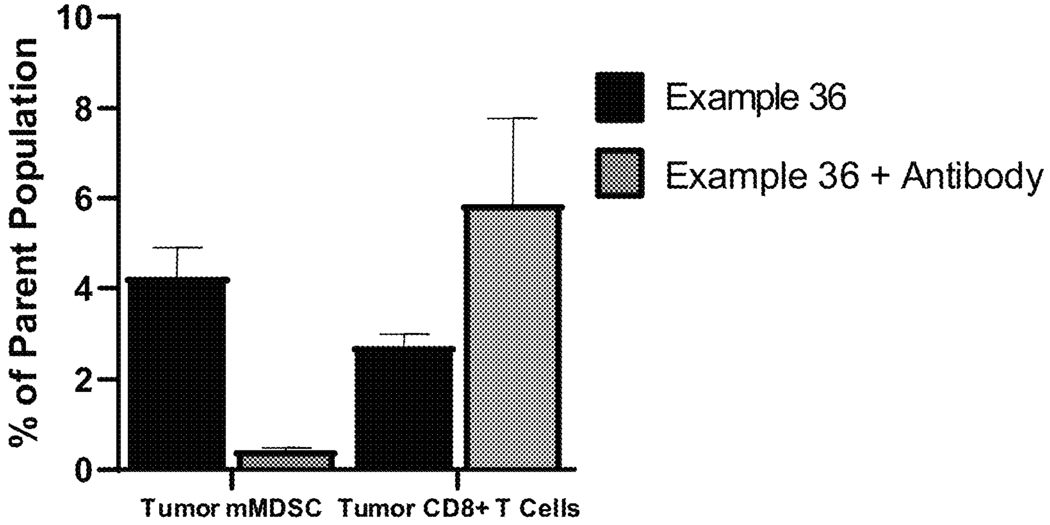
FIGS. 10A and 10B: Analysis of CD8 T cells, depletion of mMDSCs, and survival of mice upon treatment with anti-cotinine antibody and ARM compound (compound of Example 36) as described in Example 204.

Flow cytometry of peripheral blood collected from the tumor bearing mice and blood drug concentration analysis were conducted essentially as described in Example 201 above. For flow cytometry analysis of tumors, tumor isolation procedures were performed in laminar flow hood following sterile techniques. All dissection tools used during the procedure were sterilized. The tools were kept in 70% ethanol between usage. Mice bearing subcutaneous tumor were humanely euthanized using carbon dioxide asphyxiation, sprayed down with 70% ethanol and then wiped with Betadine to remove loose fur. The skin of the tumor site was lifted up using forceps and cut down with a dissection scissor to expose the subcutaneous tumor. The exposed tumor was cut and removed using a small dissection scissor. The tumor sample was placed in a 50 mL falcon tube adequately filled with RPMI 1640 serum free media and analyzed by flow cytometry. Antibody staining for flow cytometry analysis was conducted in the same manner as for the peripheral blood samples. The results demonstrate that the percentage of CD8+ T cells increased and the percentage of monocytic myeloid derived suppressor cells (mMDSCs) decreased upon treatment with ARM compound+antibody as compared to treatment with the ARM compound alone (FIG. 10A).

Figure 10B:
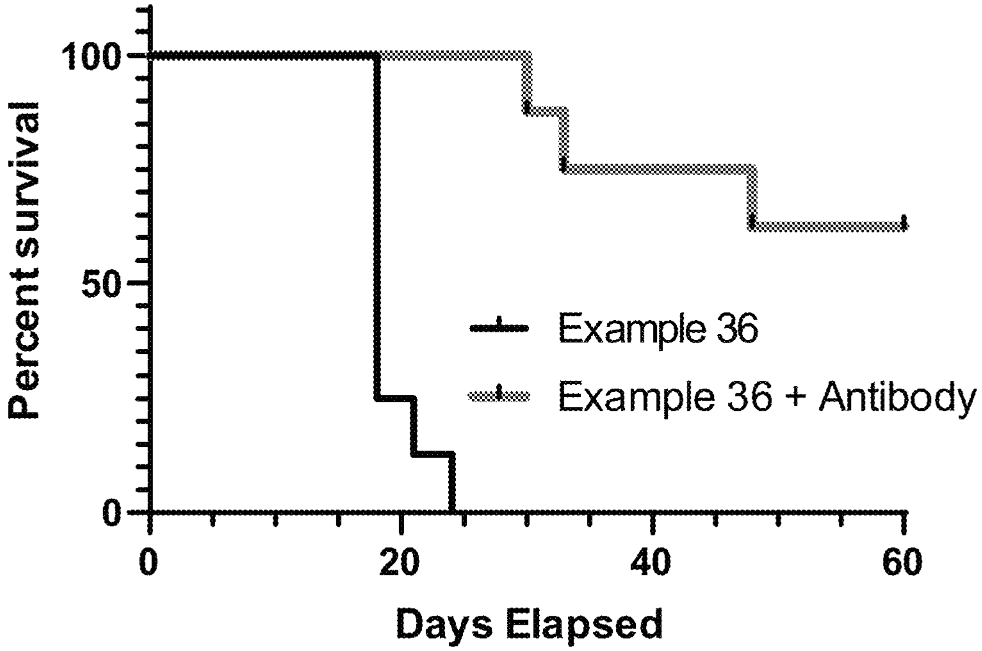

Survival analysis-Animals were humanely euthanized when tumors reached >1500 $mm^3$ or ulcerations of the tumor were visible. Percent survival of animals treated with the compound of Formula (I) alone, or in the presence of anti-cotinine antibody is shown in FIG. 10B.

Example 205: Ex Vivo Depletion and T-Cell Expansion Assay

Freshly collected human blood from healthy donors was provided by the GSK blood collection unit. Lymphoprep (15 mL) was added to Accuspin tube and centrifuged at 800 g for 1 minute. Room temperature blood (20 mL) was diluted to a final volume of 35 mL by addition of room temperature phosphate buffered saline (PBS) and this was layered on top of the 15 mL of centrifuged Lymphoprep solution. Tubes were centrifuged at 800 g for 20 minutes. The top layer (down to the PBMC interface) was aspirated. The PBMC interface was decanted into 50 mL Falcon tubes. PBS was added to a final volume of 50 mL and samples were centrifuged at 250 g for 10 minutes at room temperature. Supernatant was decanted and pellets were resuspended in PBS and centrifuged at 300 g for 6 minutes at room temperature. Supernatant was decanted and cell pellet was resuspended to a final concentration of 1 million cells/mL in PBS.

Cells were labeled with CFSE by addition of 1 μL of 0.25 mM Cell Trace CFSE dye per 1 mL of cells and incubated at 37° C. for 20 minutes. The cells were washed with 10 mL of RPMI+10% low IgG FBS. Cells were resuspended to 4 million cells/mL in RPMI+10% low IgG FBS.

Depletion of target cells was conducted in 100 μL final volume in 384-well plates. Cells were added to a final concentration of $1\times10^6$ cells/mL. Anti-cotinine antibody (rabbit variable region with human IgG1 Fc domain containing a DE mutation (S239D/1332E) having heavy chain sequence of SEQ ID NO: 11 and a light chain sequence of SEQ ID NO: 12) was added to a final concentration of 2.5 μg/mL and the compound of Example 36 was added to a final concentration of approximately 16 nM and CD3/CD28 beads were added at a concentration of $0.25\times10^6$ beads/mL. Samples were incubated at 37° C. overnight (about 16 hours).

Following the depletion step, samples were subjected to staining for flow cytometry. Samples were transferred to a 96-well round bottom polypropylene plate. Then, 100 μL of diluted (1:1000) Live/Dead dye was added to each sample. The plate was incubated in the dark for 15 minutes at room temperature. Then, 100 μL of HANK's buffer+1% BSA was added. The plate was centrifuged at 12000 rpm for 3 minutes and the supernatant was discarded. Fc Blocker (BD) was added with Hanks Buffer+1% BSA and antibody solution. Panel 1: (PerCP-Cy5.5-CD4-cat #560650, CD14-PC7-cat #A22331, CD45-BV421-cat #563879) Panel 2: (PerCP-Cy5.5-CD4-cat #560650, CD45-BV421-cat #563879, PE-CD8-cat #555635). Staining was conducted on ice for 20 minutes. Cells were washed with 200 μL of HANK's buffer+1% BSA and resuspended in 100 μL of Hank's buffer+1% BSA. Samples were analyzed on BD FACS Fortessa. Percent divided of the CD8+ T cell population was calculated by analyzing CFSE staining in the CD45+/CD8+ cell population.

Figure 8A:
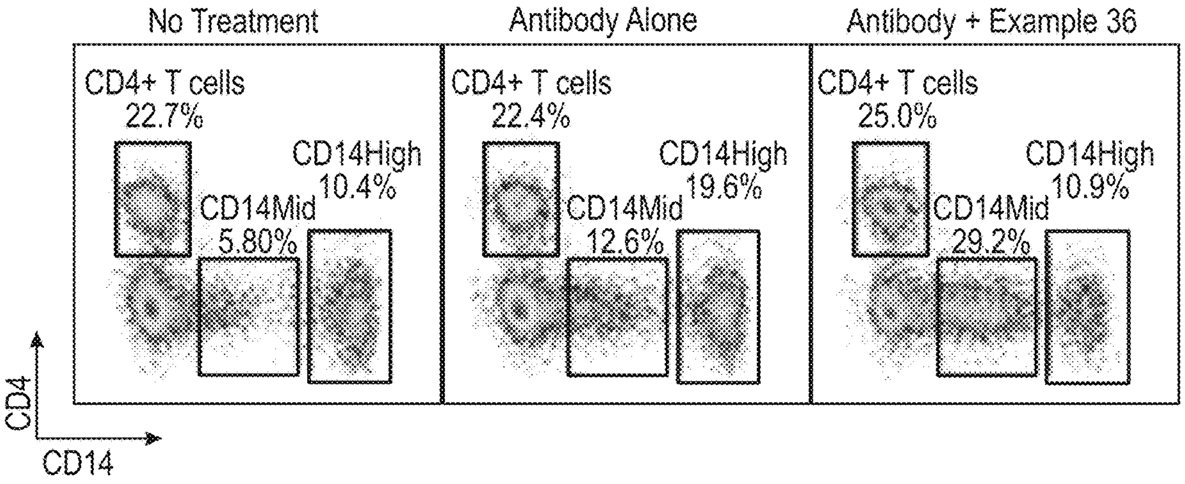
FIGS. 8A and 8B: Ex vivo T cell expansion following MDSC depletion as described in Example 205.
Figure 8B:
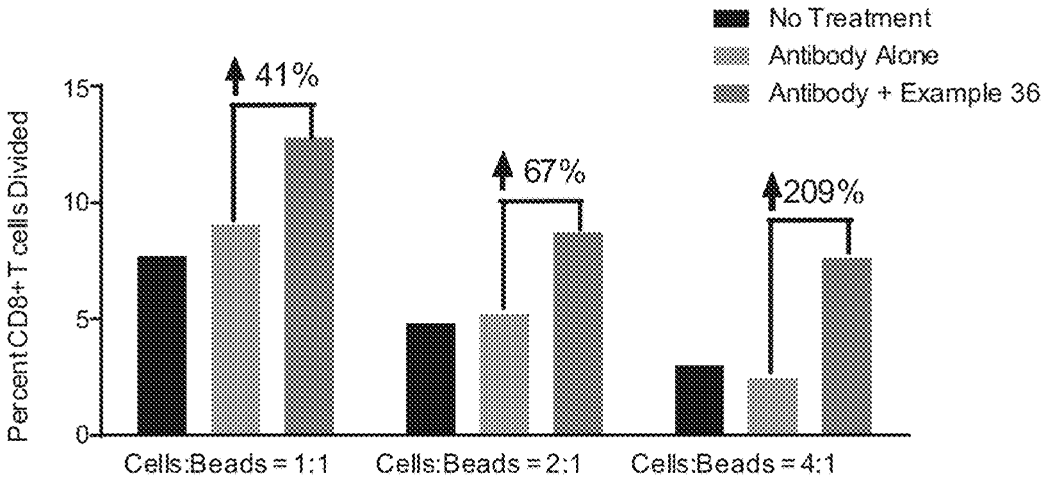

The results are shown in FIGS. 8A and 8B. The results show that CCR2+ cells are depleted upon treatment of ARM compound in the presence of anti-cotinine antibody. Additionally, CD8+ T cell expansion was observed in 2 of 3 donor samples in which robust CCR2+ cell depletion was observed.

Example 206: Exploration of Alternative In Vivo Dosing Strategies in Mice

Alternative strategies to intravenously dosing a pre-mixed solution of anti-cotinine antibody and small molecule ARM compound were explored. Experiments were conducted in human CCR2 knock-in mice (C57 background) and anti-cotinine antibody having a heavy chain sequence of SEQ ID NO: 13 and a light chain sequence of SEQ ID NO: 14 (rabbit variable region sequence with mouse IgG2a Fc domain). The results demonstrate that various alternative dosing strategies can be used for administration of the anti-cotinine antibody and small molecule ARM compound.

Figure 5:
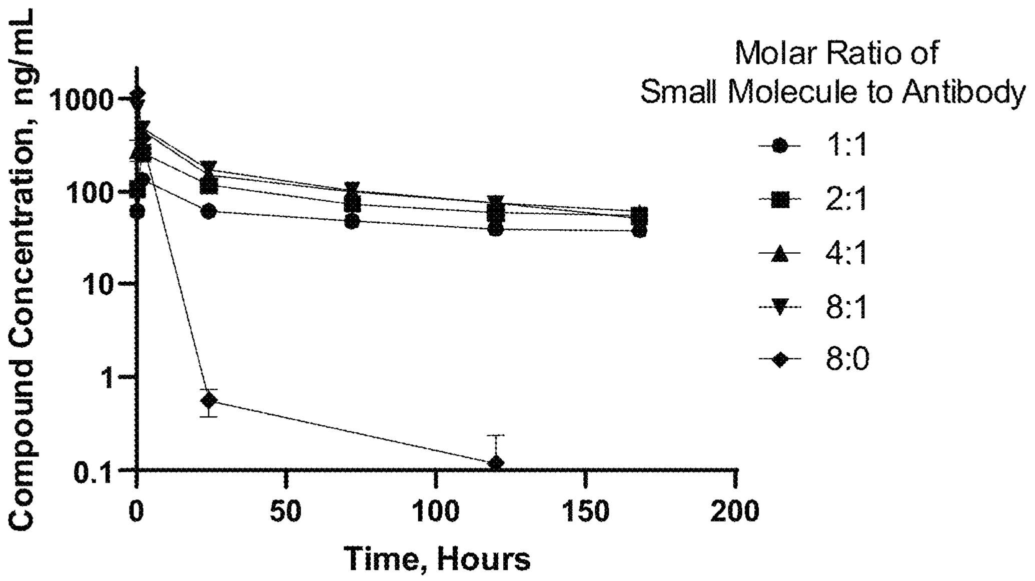
FIG. 5: Alternative dosing strategy of small molecule ARM compound to anti-cotinine antibody, as described in Example 206, with anti-cotinine antibody administered intravenously and ARM compound (Example 1) administered subcutaneously following a 2-hour delay from antibody dosing at various molar ratios of small molecule ARM: antibody; data shown is blood concentration of small molecule ARM compound at various timepoints following administration.

In some instances, a dosing strategy in which the anti-cotinine antibody was administered intravenously as described in the in vivo experiment of Example 204 and ARM compound of Formula (I) (Example 1) was administered subcutaneously following a 2-hour delay from antibody dosing was explored. Subcutaneous administrations of the ARM compound were made into the loose skin of mice over the interscapular. BD syringe (1 mL) with 26 G needle was used for the subcutaneous administration. The needle was inserted under the skin of the interscapular area tented by the thumb and forefinger and ARM compound was injected. Various molar ratios of small molecule ARM compound to anti-cotinine antibody were tested according to this dosing strategy (1:1, 2:1, 4:1, 8:1, 8:0). Blood concentration of the small molecule ARM compound at various timepoints following dosing was determined according to the methods described above in Example 201 and the results are shown in FIG. 5.

Figure 6A:
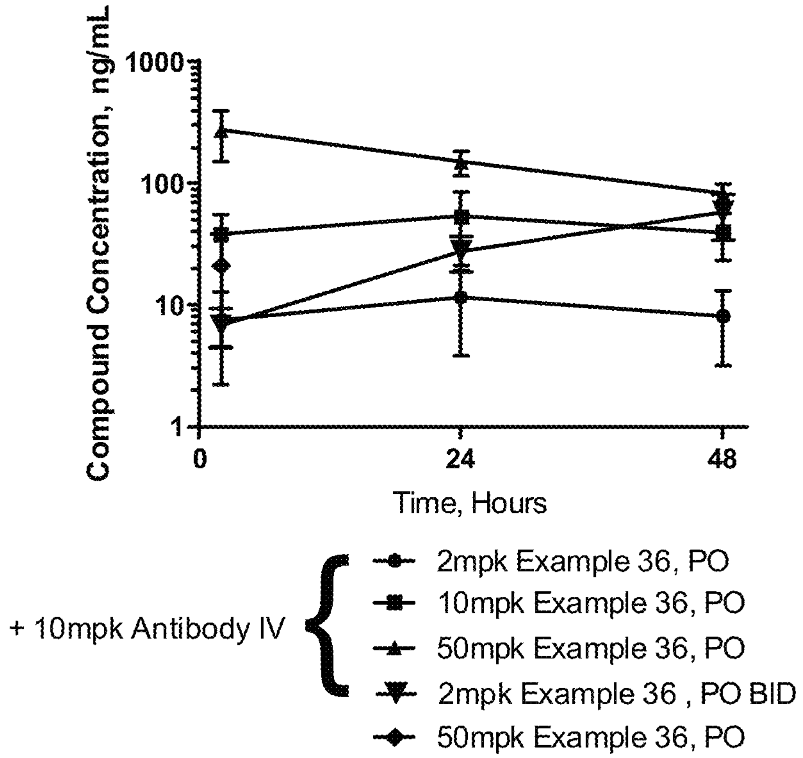
FIGS. 6A and 6B: Alternative dosing strategy of small molecule ARM compound to anti-cotinine antibody, as described in Example 206, with anti-cotinine antibody administered intravenously and ARM compound (Example 36) administered orally.
Figure 6B:
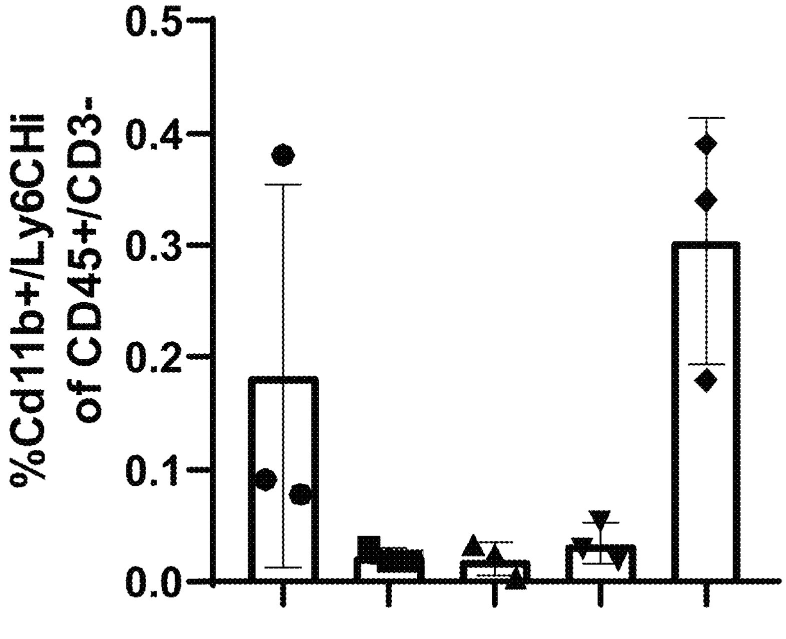

In other instances, anti-cotinine antibody was administered intravenously (10 mpk) and the small molecule ARM compound (compound of Example 36) was administered at various concentrations (2 mpk, 10 mpk, 50 mpk) via oral gavage after a brief delay (<30 minutes following antibody administration). Oral dosing utilized a ball tip 22G stainless steel needle and the ARM compound was administered slowly. Blood concentration of the small molecule ARM compound at various timepoints following dosing was measured and percent depletion of CCR2+ cells was determined by flow cytometry according to the methods described above in Example 201. Results are shown in FIGS. 6A and 6B.

Figure 3A:
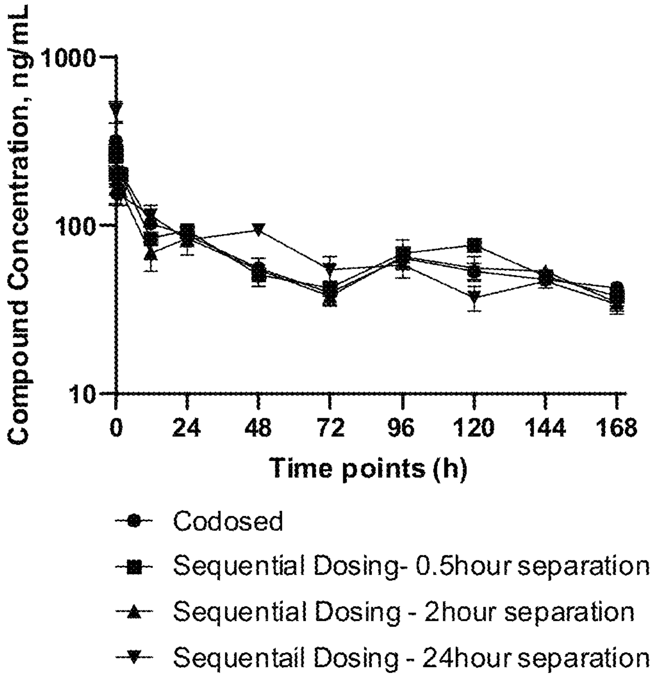
FIGS. 3A-3B: Alternative dosing strategy of small molecule ARM compound to anti-cotinine antibody, as described in Example 206, with anti-cotinine antibody and small molecule ARM compound (Example 1) co-dosed or sequentially dosed intravenously.
Figure 3B:
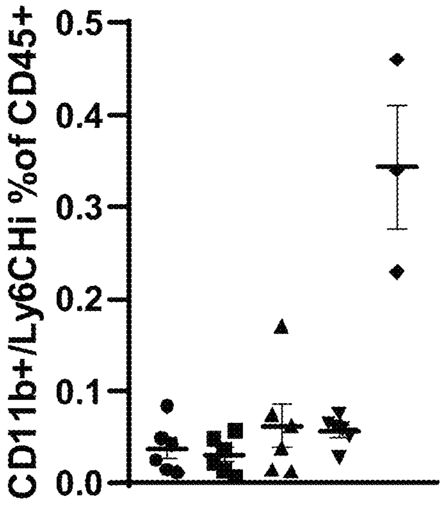
Figure 4:
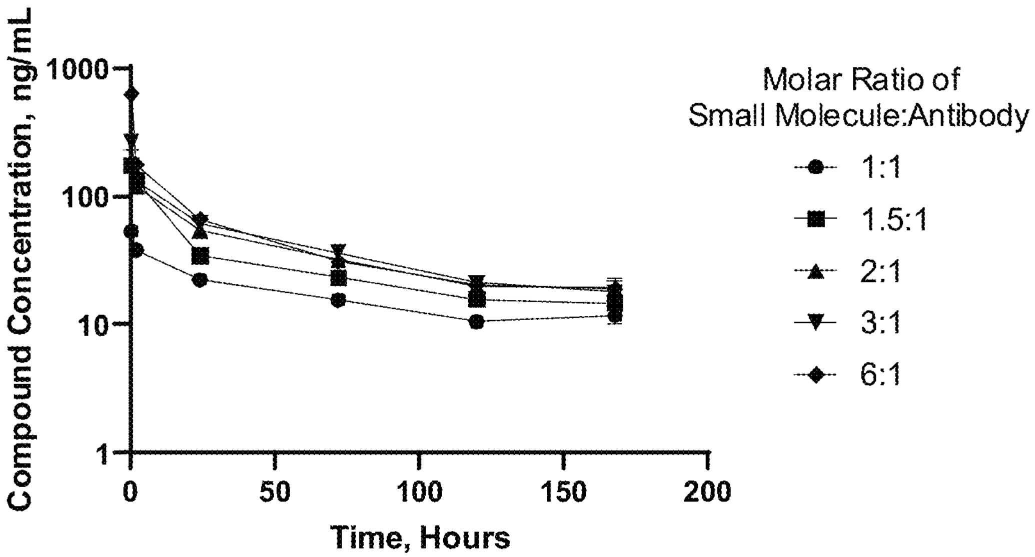
FIG. 4: Alternative dosing strategy of small molecule ARM compound to anti-cotinine antibody, as described in Example 206, with anti-cotinine antibody and small molecule ARM compound (Example 1) dosed sequentially intravenously; data is shown for sequential administration of antibody and small molecule ARM with a gap of 2 hours between small molecule ARM and antibody dosing; the results demonstrate that dosing at a 2:1 molar ratio of ARM to antibody is sufficient to saturate the antibody.

In other instances, anti-cotinine antibody was administered intravenously and the small molecule ARM compound (Example 1) was administered intravenously after a delay of 30 minutes, 2 hours or 24 hours. Antibody was administered at a concentration of 10 mpk and ARM compound was administered at a concentration of 0.2 mpk. Blood concentration of the small molecule ARM compound at various timepoints following dosing was measured as described in Example 201. Flow cytometry was used in some cases to determine the effect of treatment on the levels of CD11B+/Ly6cHi cells in the peripheral blood also as described in Example 201. The results are shown in FIGS. 3A, 3B and 4. In particular, FIG. 4 demonstrates that dosing the small molecule ARM compound and anti-cotinine antibody at a molar ratio of 2:1 is sufficient to saturate the anti-cotinine antibody (data shown for sequential administration of antibody and small molecule ARM with a gap of 2 hours between small molecule ARM and antibody dosing).

Example 207: Cynomolgus Monkey Dosing Study—Analysis of ARM Compound PK and Depletion of Target Expressing Cells Anti-cotinine antibody having a heavy chain sequence of SEQ ID NO: 9 and a light chain sequence of SEQ ID NO: 10 was supplied as a 125.86 mg/mL stock solution prepared in and diluted with in 20 mM Histidine, 180 mM Trehalose, 40 mM arginine, 8 mM Methionine, 0.05 mM EDTA, 0.02% PS80 [pH 5.89](pH range of diluted test formulations 5.77 to 5.91) and administered to monkeys at a dose volume of 2 mL/kg. The ARM compound of Example 1 was formulated as a solution (pH range of test formulations 7.26 to 7.43) in 2% Cavitron in 0.01 M phosphate buffered saline (PBS) [pH 7.37] and administered to monkeys at a dose volume of 2 mL/kg. Treatment groups and dosing schedule are shown below in Table 8 and are hereinafter referred to as Groups 1, 2, 3, and 4.

TABLE 8

Dosing Regimen for Cynomolgus Monkey Study

| Group # | Days of Dosing | Anti-Cotinine Antibody (mg/kg/dose) | Example 1 (mg/kg/dose) | Animal Number Male | Animal Number Female |
|---|---|---|---|---|---|
| 1 | Day 1 | 0 | 0 | 100 | 150 |
| 2 | Days 1 & 8 | 2 | 0.028 | 200 | 250 |
| 3 | Day 1 | 10 | 0.14 | 300 | 350 |
| 4 | Day 1 | 50 | 0.7 | 400 | 450 |

On Day 1, all monkeys in Groups 2 through 4 were dosed with small molecule ARM compound of Example 1 by slow IV bolus (approximately 2 minutes via tail vein and/or saphenous vein using a temporary IV catheter) followed by dosing with anti-cotinine antibody approximately 5 minutes after. Group 1 (Control) monkeys received the respective vehicles for anti-cotinine antibody and ARM compound of Example 1 according to the same dosing regimen. The catheters were flushed with −2 mL of sterile saline following administration of each formulation. On Day 8, only monkeys in Group 2 were dosed using the same regimen as Day 1 to determine if adding a second dose resulted in extended PD response.

Monkey plasma samples were analyzed for anti-cotinine antibody using an analytical method based on immunocapture/protein digestion followed by LC-MS/MS analysis. The LLQ for Example 1 was 1.00 μg/mL using a 10 μL aliquot of plasma.

Cynomolgus monkey blood/water (50/50, v/v) samples were analyzed for total amount of compound of Example 1 using an analytical method based on protein precipitation followed by UHPLC/MS/MS analysis. The lower limit of quantification (LLQ) for the compound of Example 1 was 1.00 ng/mL in blood using a 25 μL aliquot of monkey blood/water (50/50, v/v).

The computer systems that were used on this study to acquire and quantify data included: Analyst v. 1.7.1 and Watson v7.6.1 for cotinine antibody and Analyst vl.4.2 and Watson v7.6.1 for Example 1.

Peripheral blood samples were collected in potassium EDTA anti-coagulant prior to dosing on Day 1, and at 2 hours, 24 hours and 48 hours post-dose on Day 1, and Days 8, 15, and 22 from male and female monkeys in Groups 1, 3, and 4. Peripheral blood samples were collected in potassium EDTA anti-coagulant prior to dosing on Days 1 and 8, and at 2 hours, 24 hours, and 48 hours post-dose on Days 1 and 8, and Days 15 and 22 from male and female monkeys in Group 2. An additional sample was collected for immunophenotyping only from all monkeys prior to randomization at Screen (Day −6).

Whole blood was transferred to appropriate tubes for immunophenotyping analysis. Plasma was separated from remaining whole blood by centrifugation, aliquoted, and then stored in a freezer set to maintain −70° C. until cytokine analysis. Red blood cells were lysed using Lysis Buffer (eBioscience, San Diego, CA). After a wash, non-specific cell surface binding was blocked by pre-incubating cells (minimum of 5 minutes on wet ice) with human FC block (BD Biosciences, San Jose, CA), mouse IgG (Millipore Sigma, St. Louis, MO) and purified isotype-matched controls (BD Biosciences) at a minimum 2-fold excess. Monoclonal antibodies specific for human cell surface antigens (cross-reactive with cynomolgus monkey) were added to cells as a single panel and incubated for ~30 minutes on wet ice with protection from light:

Antibody Fluorochrome Clone Isotype Vendor
CD3 AF488 SP34-2 Mouse IgG1 BD Biosciences
CD4 PE-Cy5 L200 Mouse IgG1 BD Biosciences
CDS APC-Cv7 RPA-T8 Mouse IoG1 8D Biosciences
CD20 88700 2H7 Mouse IgG2b BD Biosciences
CD159a APC Z199 Mouse IgG2b Beckman Coulter
CD56 BUV805 NCAM 16.2 Mouse IoG2b 8D Biosciences
C069 BUV737 FN50 Mouse IgG1 BO Biosciences
C014 BV421 M5E2 Mouse IaG2a BO Biosciences
C016 BV4BO 3 GB Mouse IgG1 BO Biosciences
HLA-OR PE Immu-357 Mouse IgG2a BO Biosciences
C045 BV605 005B-12B3 Mouse IgG1 BO Biosciences Cells were washed and brought up in Stain Buffer (BD Biosciences), then analyzed the same day using the FACSymphony A3 flow cytometer with FACSDiva version 8.0.1 or version 9.1 software (BD Biosciences).

Figure 9A:
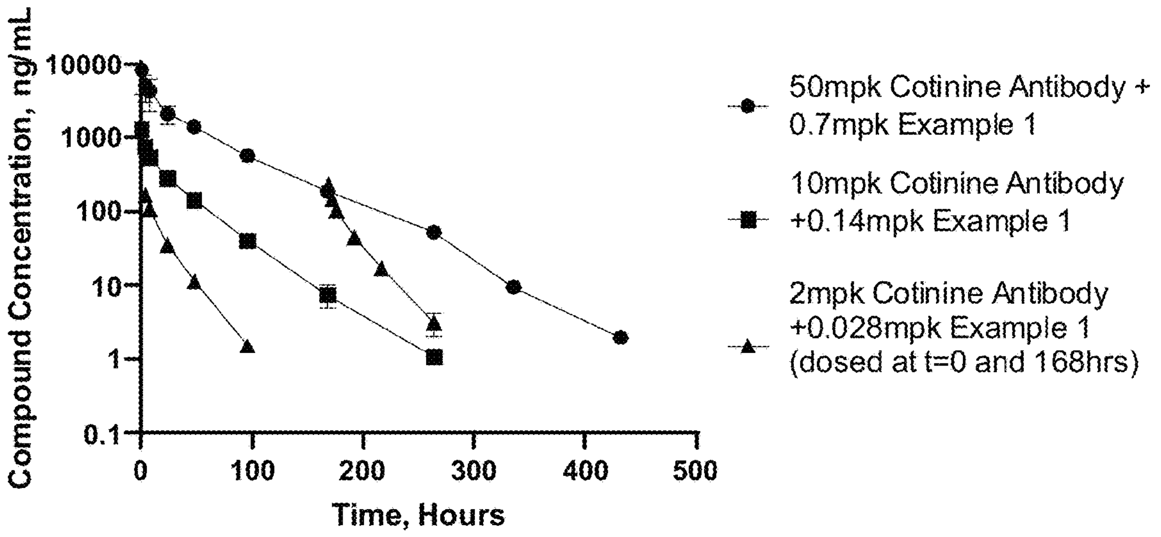
FIGS. 9A and 9B: Cynomolgus monkey study described in Example 207.
Figure 9B:
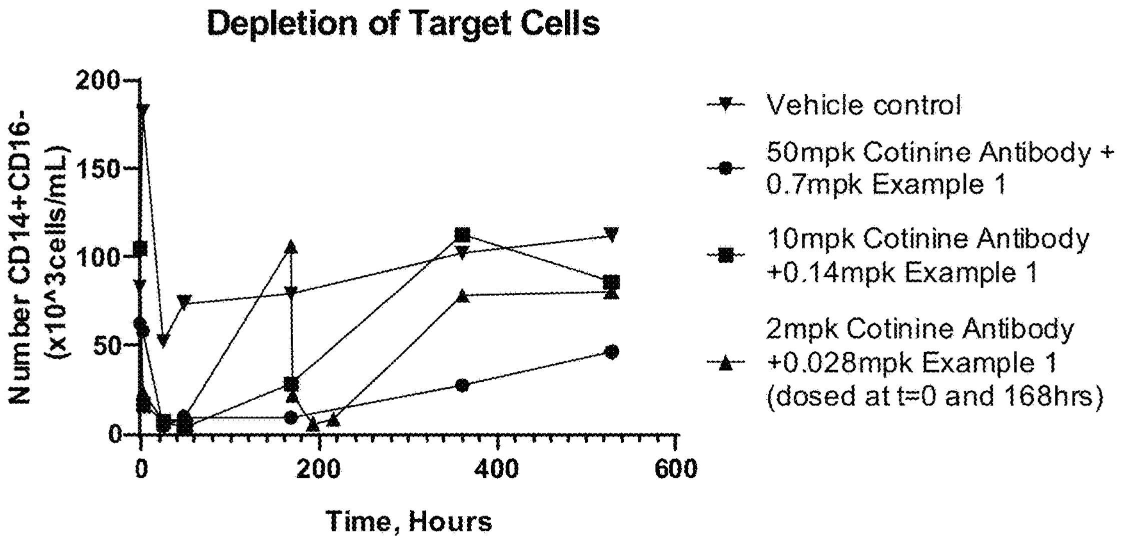

Lymphocytes and monocytes were gated from live, singlet cells based on side scatter light properties and CD45. Data are expressed as percent parent and/or grandparent and absolute numbers of lymphocyte and monocyte subsets, as calculated by multiplying the flow cytometric percentages by the absolute lymphocyte and monocyte counts determined by hematology measurements. The results are shown in FIGS. 9A and 9B.

Example 208: Cotinine Off-Switch Study

Figure 7A:
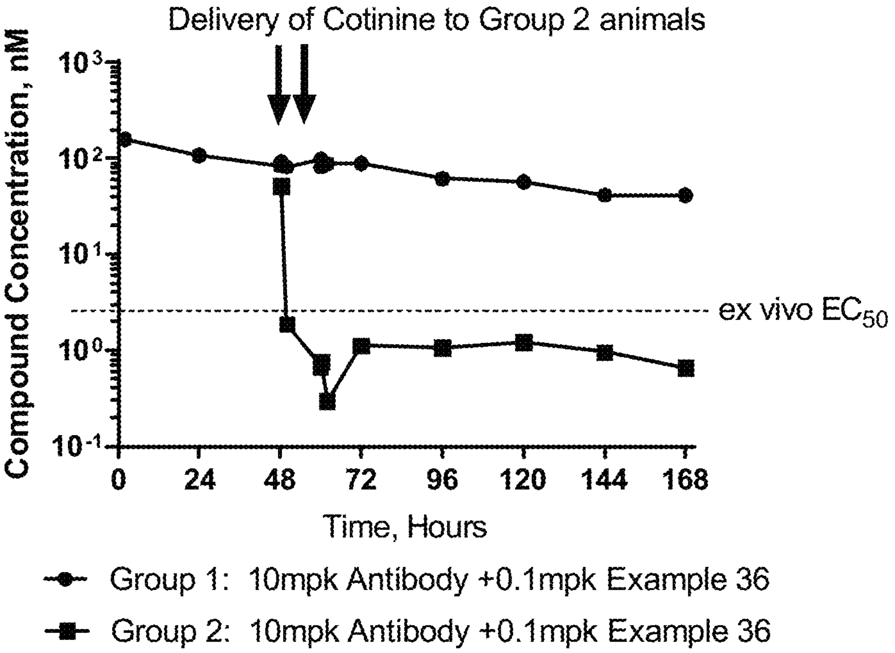
FIGS. 7A and 7B: Cotinine "off-switch" study described in Example 208.
Figure 7B:
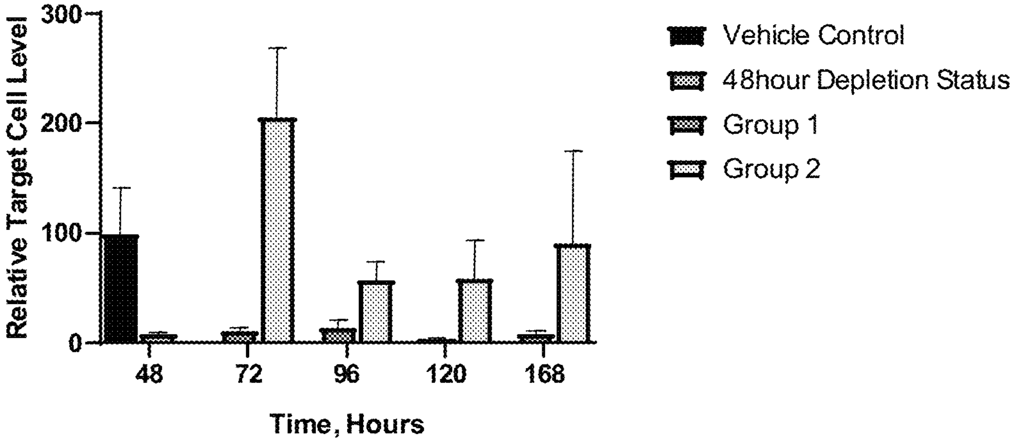

Human CCR2 Knock-in $C_{57}$ mice were dosed intravenously with anti-cotinine antibody having a heavy chain sequence of SEQ ID NO: 13 and a light chain sequence of SEQ ID NO: 14 (rabbit variable region sequence with mouse IgG2a Fc domain) and ARM compound of Example 36 (10 mpk antibody premixed with 0.1 mpk compound) intravenously. An additional three animals received only saline vehicle (vehicle control animals). After 48 hours, the vehicle control animals and 3 animals from the treated group were sacrificed and blood was collected by cardiac puncture for flow cytometry analysis. The remaining animals were split into two groups: Group 2 received 50 mpk (S)-cotinine (purchased from Sigma-Aldrich (Cat Number: C5923)) at 48 hours and again at 60 hours while Group 1 received no additional treatment. Blood was collected at 2, 24, 48, 48.25, 50, 60, 60.25, 62, 72, 96, 120, 144, and 168 hours post dosing of the anti-cotinine antibody and ARM compound. The blood was analyzed for concentration of the ARM compound as described in Example 201. At 72, 96, 120 and 168 hours, 3 animals were sacrificed from Groups 1 and 2 and blood was collected via cardiac puncture. The blood was processed and analyzed via flow cytometry as described in Example 201 for the levels of CD45+/CD3-/CD11 b+/Ly6Chi cells. The results are shown in FIGS. 7A and 7B.

Example 209: CD4/CD8 T Cell Depletion Study

Figure 2A:
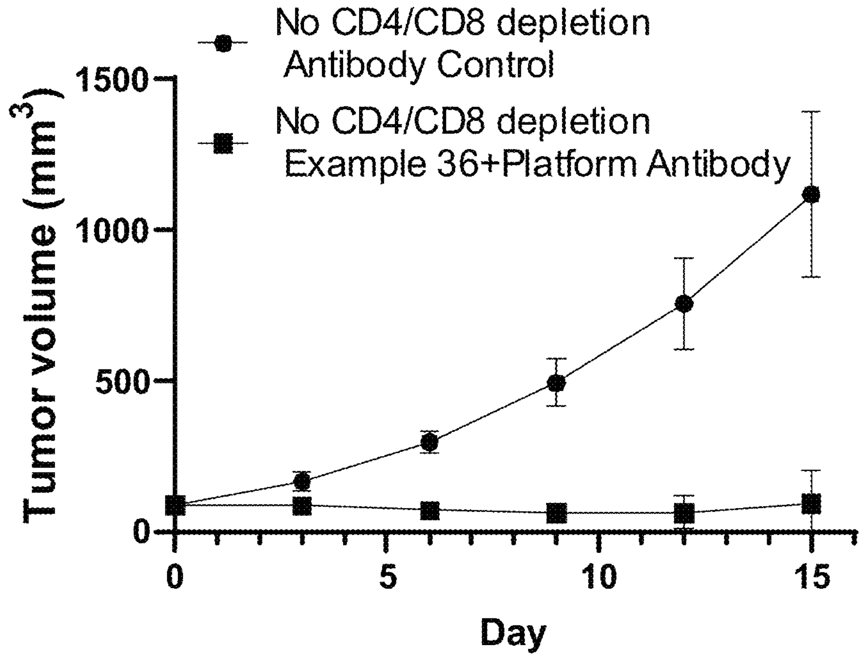
FIGS. 2A-2B: Tumor growth in human CCR2 knock-in mice inoculated with MC38 tumors dosed with anti-cotinine antibody and ARM compound (compound of Example 36) either with or without depletion of CD4 and CD8 T cells as described in Example 209.
Figure 2B:
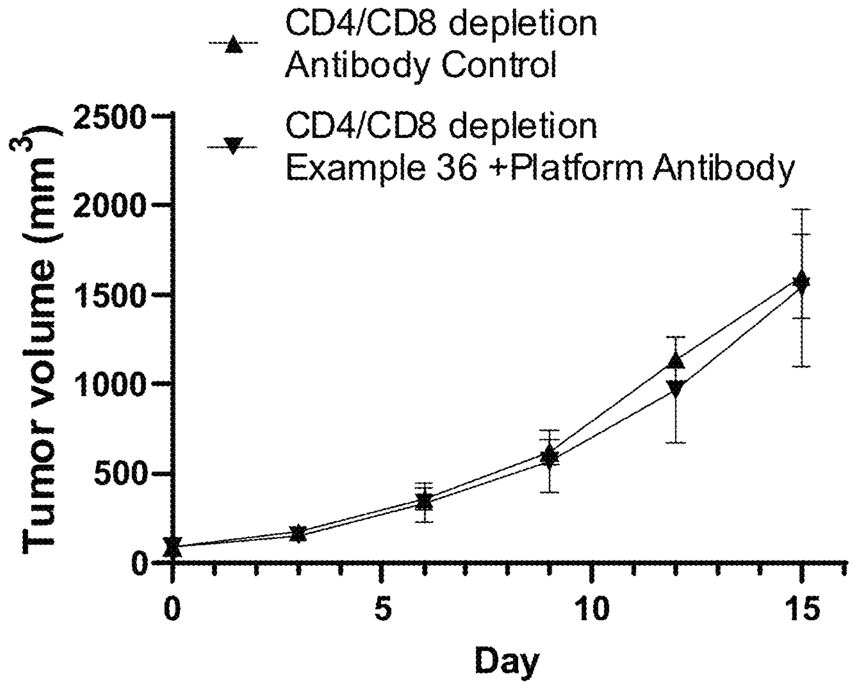

MC38 tumors were initiated by subcutaneous injection of $1.5\times10^6$ MC38 cells in the flank of human CCR2 knock-in mice. After 5 days, 200 μg of Anti-CD8 (clone 2.43) and 200 μg of Anti-CD4 (clone GK1.5) were injected intraperitoneally (the control groups received isotype control antibodies). After 2 additional days, animals were randomized and anti-cotinine antibody having a heavy chain sequence of SEQ ID NO: 13 and a light chain sequence of SEQ ID NO: 14 (rabbit variable region sequence with mouse IgG2a Fc domain) and ARM compound of Example 36 were dosed intravenously as a pre-mixed solution every 6 days. At the start of dosing and at 120 hours post-dosing flow cytometry was conducted on blood samples to confirm CD4/CD8 cell depletion (data not shown). Tumor volume was measured as described above in Example 204 and the results are shown in FIGS. 2A and 2B. The results demonstrate that tumor growth inhibition of the antibody/ARM compound is dependent upon the presence of CD4 and CD8 T cells.

Example 210: Mass Cytometry (CyTOF) Analysis of PBMCs from Healthy Donor vs. Cancer Patient Mass cytometry (CyTOF) was used to analyze depletion of CCR2 expressing cells in PBMCs isolated from healthy donor and cancer patient to determine whether a combination of anti-cotinine antibody and ARM compound of Formula (I) selectively depletes CCR2 expressing cells.

CyTOF Antibodies

Metal tagged antibodies were either purchased directly from Fluidigm or were prepared in house using MaxPar® antibody conjugation kits (Fluidigm). For in-house conjugation reactions, purified antibodies, in BSA-free buffer were coupled to isotopically purified metals following the manufacturer's instructions (Fluidigm) (Lou X, Angew Chem Int Ed Engl 2007; 46(32):6111-4). Following conjugation, the protein concentration of the metal labeled antibodies were measured on a NanoDrop ND-1000 (Thermo Fisher) at an absorbance of 280 nm and diluted to a final concentration of 0.5 mg/mL in Candor PBS Antibody Stabilization solution (Candor Bioscience). All antibodies, antibodies with associated metal conjugated kits and/or metal-tagged secondary antibodies utilized in the CyTOF experiments, are listed in Table 9:

TABLE 9

Mass Cytometry Staining Panel

| Metal Tag | Ab Target | Clone | Vendor | Catalog # | Metal kit | Vendor | Catalog # |
|---|---|---|---|---|---|---|---|
| 89Y | CD45 | HI30 | Fluidigm | 3089003B | | | |
| 111Cd | CD3 | UCHT1 | BioLegend | 300443 | 111Cd | Fluidigm | 201111A |
| 112Cd | HLA-DR | L243 | BioLegend | 307651 | 112Cd | Fluidigm | 201112A |
| 113Cd | CD4 | RPA-T4 | BioLegend | 300541 | 113Cd | Fluidigm | 201113A |
| 114Cd | CD11b | ICRF44 | BioLegend | 301337 | 114Cd | Fluidigm | 201114A |
| 116Cd | CD8a | RPA-T8 | BioLegend | 301053 | 116Cd | Fluidigm | 201116A |
| 141Pr | EpCAM | 9C4 | Fluidigm | 3141006B | | | |
| 142Nd | CD57 | HNK-1 | Fluidigm | 3142007B | | | |
| 143Nd | CD127 | A019D5 | Fluidigm | 3143012B | | | |
| 144Nd | CD15 | W6D3 | Fluidigm | 3144019B | | | |
| 145Nd | TCF1 | 7F11A10 | BioLegend | 655202 | 145Nd | Fluidigm | 201145A |
| 146Nd | CD11c | 3.9 | Fluidigm | 3146014B | | | |
| 147Nd | CD182 | CXCR2 | Fluidigm | 3147010B | | | |
| 148Nd | PD-L1 | 29E.2A3 | Fluidigm | 3148017B | | | |
| 149Sm | CCR1 | 53504.0 | R&D Systems | MAB145-100 | 149Sm | Fluidigm | 201149A |
| 150Nd | Biotin | 1D4C5 | Fluidigm | 3150008B | | | |
| | IL-10 (biotin) | JES3-12G8 | BioLegend | 501502 | | | |
| 151Eu | CD14 | M5E2 | Fluidigm | 3151009B | | | |
| 152Sm | FoxP3 | PCH101 | eBioscience | 14-4776-82 | 152Sm | Fluidigm | 201152A |
| 153Eu | CD192 (CCR2) | KO36C2 | Fluidigm | 3153023B | | | |
| 154Sm | TIM-3 | F38-2E2 | Fluidigm | 3154010B | | | |
| 155Gd | CD56 | B159 | Fluidigm | 3155008B | | | |
| 156Gd | IFNg | 4S.B4 | eBioscience | 14-7319-81 | 1526Gd | Fluidigm | 201156A |
| 159Tb | CCR7 | G043H7 | Fluidigm | 3159003A | | | |
| 160Gd | FITC | FIT22 | Fluidigm | 3160011B | | | |
| | IL-35 (FITC) | FIT22 | LS Bio | LS-C693362-500 | | | |

TABLE 9-continued

| Mass Cytometry Staining Panel | | | | | | | |
|---|---|---|---|---|---|---|---|
| Metal Tag | Ab Target | Clone | Vendor | Catalog # | Metal kit | Vendor | Catalog # |
| 161Gd | Tbet | 4B10 | Fluidigm | 3161014B | | | |
| 162Dy | CD27 | L128 | Fluidigm | 3162009B | | | |
| 163Dy | CCR8 | L263G8 | BioLegend | 360602 | 163Dy | Fluidigm | 201163A |
| 164Dy | ARG-1 | 14D2C43 | Fluidigm | 3164030B | | | |
| 165Ho | CD19 | HIB19 | Fluidigm | 3165025B | | | |
| 166Er | CD314 | ON72 | Fluidigm | 3166016B | | | |
| 167Er | CD38 | HIT2 | Fluidigm | 3167001B | | | |
| 168Er | CD206 | 15-2 | Fluidigm | 3168008B | | | |
| 169Tm | CD25 | 2A3 | Fluidigm | 3169003B | | | |
| 170Er | CD45RA | HI100 | Fluidigm | 3170010B | | | |
| 171Yb | CD195 (CCR5) | NP-6G4 | Fluidigm | 3171017A | | | |
| 172Yb | CX3CR1 | 2A9-1 | Fluidigm | 3172017B | | | |
| 173Yb | Granzyme B | GB11 | Fluidigm | 3173006B | | | |
| 174Yb | CD49d | 9F10 | Fluidigm | 3174018B | | | |
| 175Lu | PD-1 | EH12.2H7 | Fluidigm | 3175008B | | | |
| 176Yb | ICOS | C398.4A | BioLegend | 313502I | 176Yb | Fluidigm | 201176A |
| 209Bi | CD16 | 3G8 | Fluidigm | 3209002B | | | |

Mass Cytometry (CyTOF)

A compound treatment plate for PBMC incubation was prepared using an HP Dispenser (HP). First, a 10 μM stock of ARM compound of Example 36 was obtained. Then, using the HP Dispenser, 200 nL of the compound was added to the wells of a 96-well plate (Corning, 3799). An equal volume of DMSO was added to control wells. Second, anti-cotinine antibody (heavy chain of SEQ ID NO: 11 and light chain of SEQ ID NO: 12) was diluted in AIM-V media (Gibco) and 2 μL of antibody was added to treatment wells or 2 μL of AIM-V media was added to control wells. Once the treatment plate was prepared, then PBMC samples were thawed.

Cryopreserved PBMC samples, from either a healthy donor (Hemacare) or a cancer patient (Discovery Life Sciences) were thawed in a 37° C. water bath. PBMC samples were then added to 8 mL warm AIM-V media (Gibco), pelleted by centrifugation and resuspended in 1 mL AIM-V media. Cells were counted on the ViCell (Beckman Coulter). Equal numbers of PBMCs were transferred to each treatment well in the previously prepared 96-well plate and incubated at 37° C. for 24 hours.

Following a 24 hour incubation period, Protein Transport Inhibitor Cocktail (500×) (Invitrogen/eBioscience) was added to all wells and incubated at 37° C. for 2 hours. Samples were then centrifuged and washed twice with MaxPar phosphate-buffered saline (PBS) (Fluidigm). Cells were then incubated with a viability reagent (200 nM cisplatin-198, Fluidigm) diluted in MaxPar PBS for 5 min at room temperature, then washed twice in MaxPar Cell Staining Buffer (Fluidigm). The resultant cell pellets were resuspended in MaxPar Cell Staining Buffer. Samples were then blocked for 10 minutes at room temperature in Human TruStain FcX (BioLegend). Immediately following, cells were stained with all cell surface markers, included in Table 9, for 20 minutes at room temperature. Following cell surface staining, samples were washed twice with MaxPar Cell Staining Buffer. Cells were then permeabilized using eBioscience FoxP3 fix/perm buffer (Thermo Fisher) for 45 min at 4° C. Samples were pelleted by centrifugation and washed twice in the fix/perm buffer from the eBioscience FoxP3 fix/perm kit (Thermo Fisher). Samples were resuspended in the same FoxP3 fix/perm buffer. All intracellular antibodies, listed in Table 9, were then added and incubated at room temperature for 30 minutes. Following intracellular staining, cells were then pelleted by centrifugation and washed twice in the fix/perm buffer from the eBioscience FoxP3 fix/perm kit (Thermo Fisher). Cells were again resuspended in the FoxP3 fix/perm buffer and then incubated with secondary antibodies, anti-biotin and anti-FITC, for 25 minutes at room temperature. Samples were pelleted by centrifugation and washed twice with MaxPar Cell Staining Buffer. Cells were then resuspended in MaxPar Barcode Perm Buffer (Fluidigm) and then washed twice with the MaxPar Barcode Perm Buffer. To enable cell identification during CyTOF2 acquisition, each sample was then resuspended in Cell ID DNA Intercalator Ir (Fluidigm) diluted in MaxPar Fix/Perm Buffer (Fluidigm). Finally, to enable sample pooling, each sample was given a unique palladium barcode from the Cell-ID 20-Plex Pd Barcoding Kit (Fluidigm). Samples were incubated with the DNA Intercalator and palladium barcode at 4° C. minimally overnight or until time of CyTOF2 acquisition.

On the day of CyTOF2 acquisition, all samples were washed twice in Cell Staining Buffer. Following the second wash, and resuspension in residual amount of Cell Staining Buffer, all samples were pooled into a single sample and washed twice with 2 mL MilliQ Water (18.2m)). The final sample was then resuspended in 1 mL MilliQ Water (18.2m)) and strained through a 40 μm porosity Flowmi Strainer (Bel-Art). The pooled sample was then counted on a ViCell and diluted to 400,000 cells/mL in MilliQ Water (18.2m)). Finally, a 1:10 ratio of EQ Beads (Fluidigm) was added to the sample and was able to proceed with CyTOF2 (Fluidigm) acquisition using the Supersampler (Victorian Airship & Scientific Apparatus). All samples were acquired with CyTOF software version 6.0.626.

CyTOF Data Analysis

Raw FCS files were normalized, concatenated and debarcoded with standalone software CyTOF version 6.7.1014. Debarcoded FCS files were uploaded onto GSK Cytobank Enterprise (cytobank.org). EQ reference bead signal was removed from all samples. Viable cells were then identified using a combination Cisplatin Pt198 and Ir131 DNA Intercalator gating, with viable cells being defined as Cisplatin Pt198 low and Ir131 high. Viable cells were then further gated into viable singles, with a combination of the event length channel and CD45-89Y staining. Viable singlets were defined as events lower than 60 with a CD45 metal intensity greater than 30. Unsupervised clustering of the viable singlets was then completed with the viSNE application embedded within Cytobank.

Figure 11A:
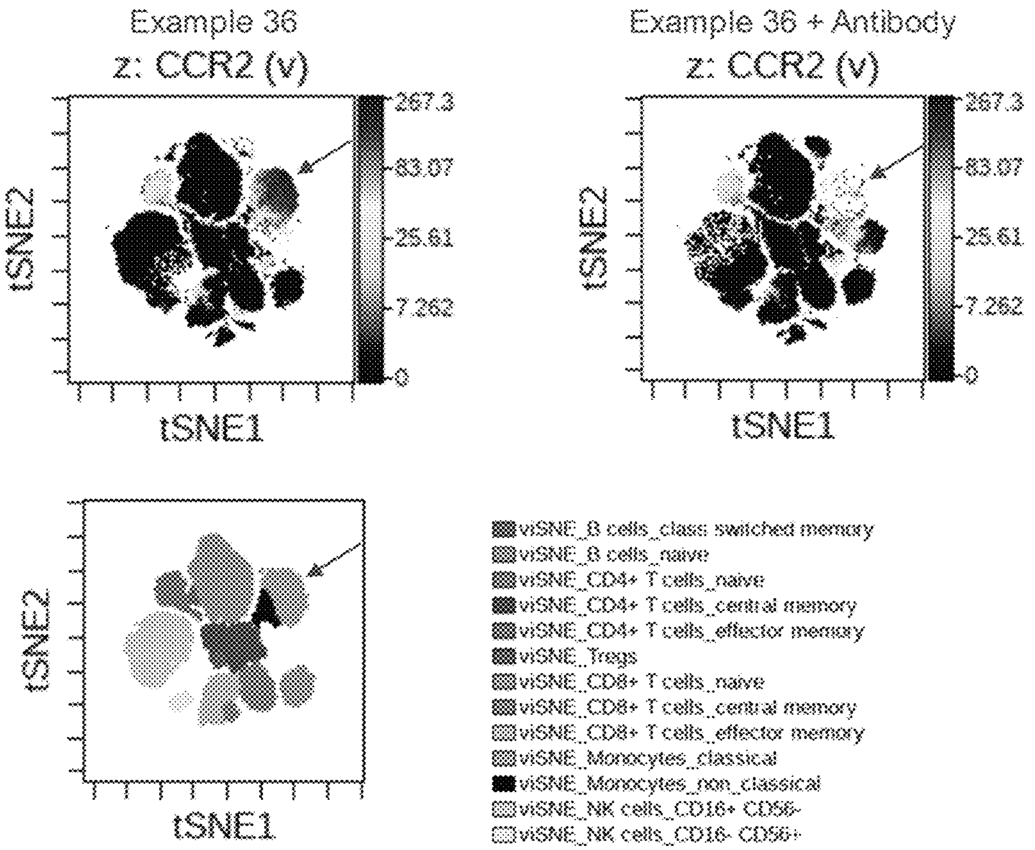
FIGS. 11A and 11B: Data from CyTOF analysis of depletion of CCR2 expressing cells in PBMCs isolated from a healthy donor and cancer patient as described in Example 210; the arrows indicate target cell populations expressing CCR2.
Figure 11B:
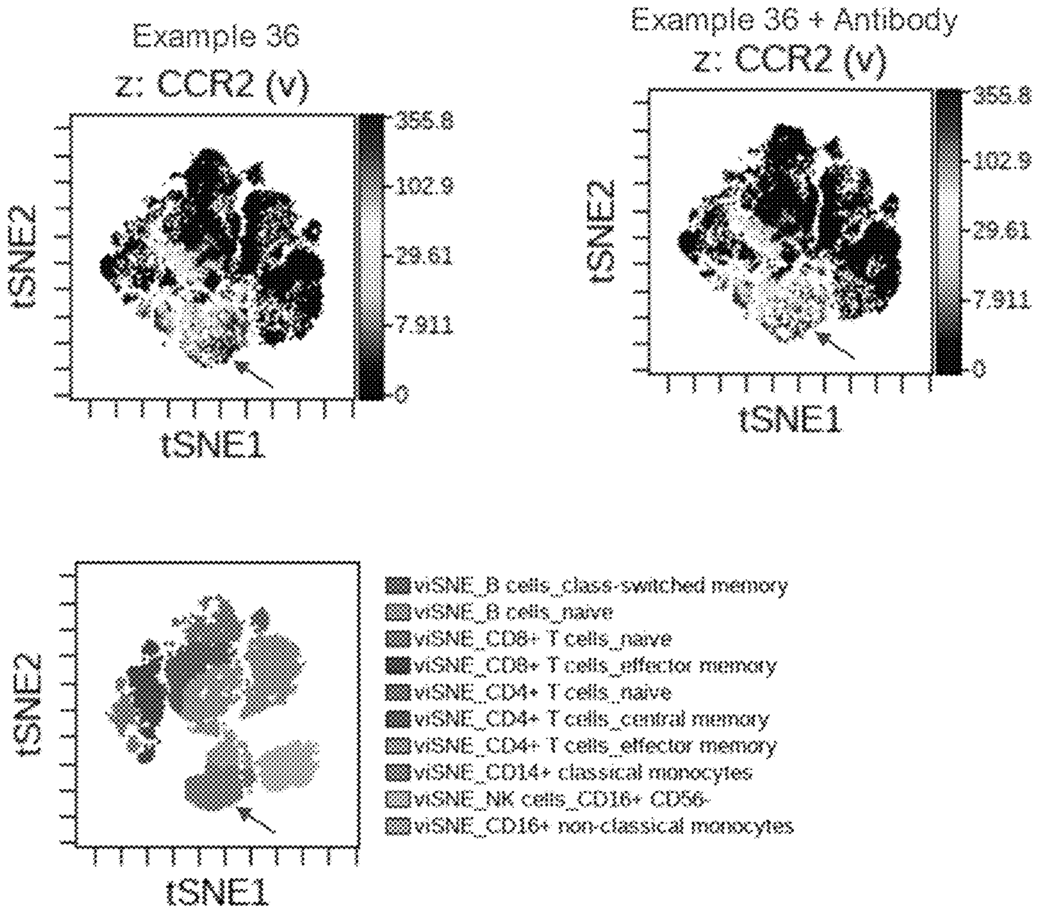
Figure 12:
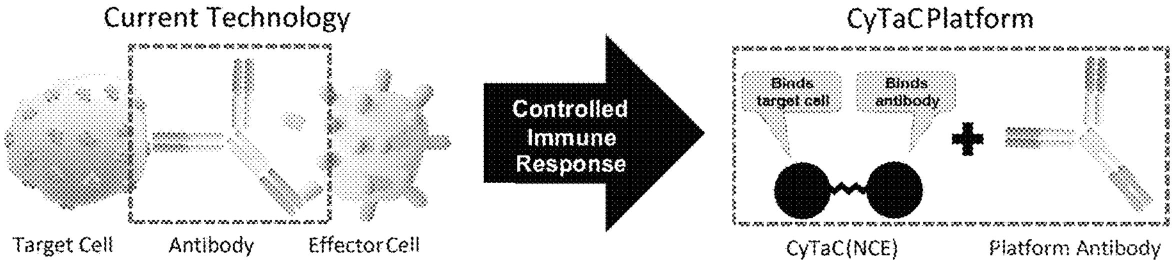
FIG. 12: Schematic representation of cytotoxicity targeting chimeras (CyTaCs) technology compared to current antibody technology.

Data is shown in FIGS. 11A and 11B. The results demonstrate that CCR2 expression is primarily restricted to target cells of interest for selective depletion (MDSCs) and that the CCR2 expressing target cells are selectively depleted in the presence of anti-cotinine antibody+ARM compound, but not in the presence of ARM compound alone.

The invention claimed is:

1. A compound of Formula (I):

(I)

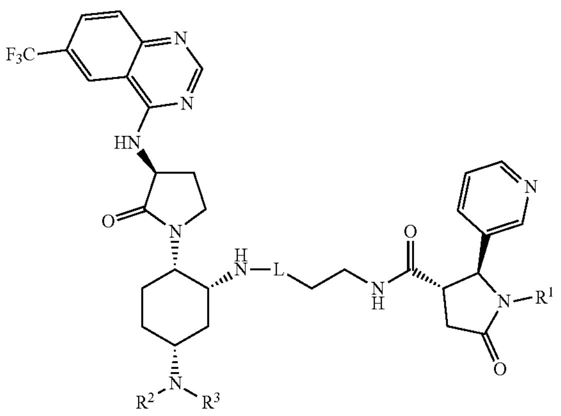

or a pharmaceutically acceptable salt thereof, wherein:

$R^1$ is $C_{1-4}$ alkyl or $C_{3-6}$ cycloalkyl;

$R^2$ is hydrogen or $C_{1-4}$ alkyl;

$R^3$ is hydrogen or $C_{1-4}$ alkyl;

L is a divalent linker of Formula (L-a), (L-b), (L-c), (L-f), (L-g), (L-h), (L-i), (L-j), (L-k), (L-m), (L-n-i), (L-n-ii), (L-n-iii), or (L-n-iv):

(L-a)

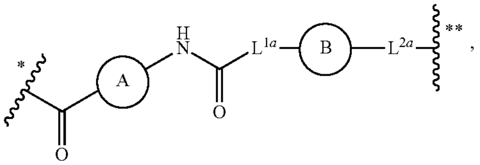

or a stereoisomer thereof, wherein:

Ring A and Ring B are each independently $C_{4-6}$ cycloalkylene;

$L^{1a}$ is $C_{3-5}$ linear alkylene, wherein 1 or 2 methylene units are replaced with —O— or —$NR^a$—;

each $R^a$ is independently hydrogen or $C_{1-3}$ alkyl; and $L^{2a}$ is —O—, —NHC(O)—, or —$CH_2$—O—;

(L-b)

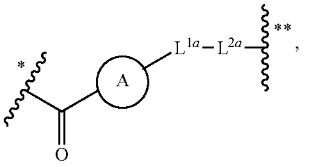

or a stereoisomer thereof, wherein:

Ring A is $C_{4-6}$ cycloalkylene or $C_{7-9}$ bridged bicyclic cycloalkylene;

$L^{1b}$ is —$CH_2$—NH—C(O)—, —NHC(O)—, or —C(O)NH—;

$L^{2b}$ is $C_{6-12}$ linear alkylene, wherein 1, 2, 3, or 4 methylene units are replaced with —O—, —$NR^{1b}$—, —C(O)$NR^{1b}$—, or —$NR^{1b}$C(O)—; or $L^{2b}$ is

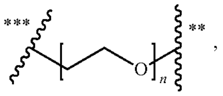

wherein n is 1, 2, 3, or 4, and

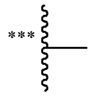

represents a covalent bond to $L^{1b}$; and each $R^{1b}$ is independently hydrogen or $C_{1-3}$ alkyl;

(L-c)

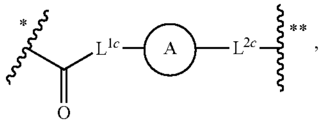

or a stereoisomer thereof, wherein:

$L^{1c}$ is $C_{2-10}$ linear alkylene, wherein 1, 2, or 3 methylene units are replaced with —O—, —NH—, —NHC(O)—, or —C(O)NH—;

Ring A is $C_{4-6}$ cycloalkylene or $C_{7-9}$ bridged bicyclic cycloalkylene; and $L^{2c}$ is —O— or a saturated $C_{2-10}$ linear alkylene, wherein 1, 2, or 3 methylene units are replaced with —O—, —NH—, —NHC(O)—, or —C(O)NH—;

(L-f)

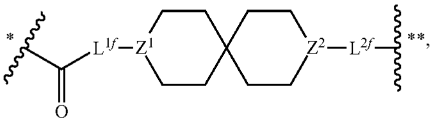

or a stereoisomer thereof, wherein:

$L^{1f}$ is a bond; $C_{1-6}$ linear alkylene, wherein 0, 1, or 2 methylene units are replaced with —O—, —NH—, or —C(O)—; or —($C_{3-6}$ cycloalkylene)-NHC(O)—;

$L^{2f}$ is a bond, —NHC(O)—, —C(O)NH—, or a $C_{1-6}$ linear alkylene, wherein 0, 1, or 2 methylene units are replaced with —O—; and each of $Z^1$ and $Z^2$ is independently N or CH;

(L-g)

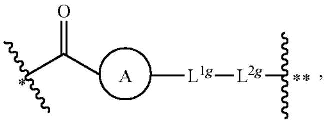

wherein:

Ring A is a 5 to 6 membered heteroarylene having 1 or 2 nitrogen ring atoms;

$L^{1g}$ is a bond, —$CH_2$—, —NH—, or —O—; and $L^{2g}$ is

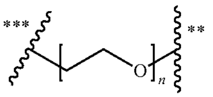

wherein n is 1, 2, 3, 4, or 5, and

represents a covalent bond to L1g;

(L-h)

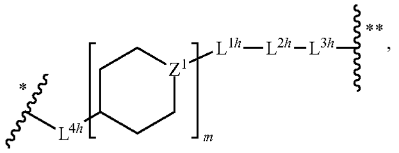

or a stereoisomer thereof, wherein:

each $Z^1$ is independently N or CH;

$L^{1h}$ is a bond, —C(O)—, —C(O)—NH—, or —NHC(O)—;

$L^{2h}$ is $C_{2-10}$ linear alkylene or

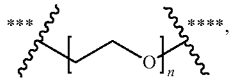

wherein n is 1, 2, 3, or 4, and

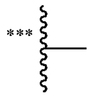

represents a covalent bond to $L^{1h}$ and

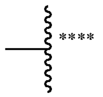

represents a covalent bond to $L^{3h}$;

$L^{3h}$ is a bond, —C(O) $CH_2$—, —O—($C_{3-6}$ cycloalkylene)-O—, or —C(O)NH$(CH_2)_3OCH_2$—;

$L^{4h}$ is a bond, —C(O)—, —$CH_2C(O)$—, or —C(O) $CH_2$—; and m is 1, 2, or 3;

(L-i)

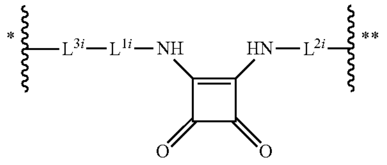

wherein:

$L^{1i}$ is a bond, $C_{1-12}$ linear alkylene, or

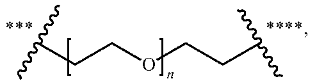

wherein n is 1, 2, 3, 4, or 5, and

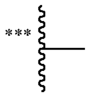

represents a covalent bond to $L^{3i}$ and

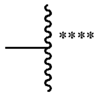

represents a covalent bond to NH;

$L^{2i}$ is a bond, $C_{1-12}$ linear alkylene, or

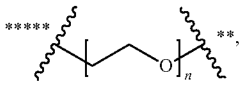

wherein n is 1, 2, 3, 4, or 5, and

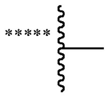

represents a covalent bond to HN; and $L^{3i}$ is a bond or —C(O)—;

(L-j)

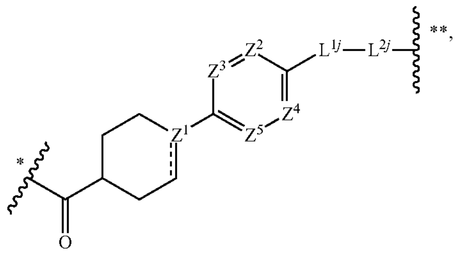

or a stereoisomer thereof, wherein:

$Z^1$ is C, CH, or N;

each of $Z^2$, $Z^3$, $Z^4$ and $Z^5$ is independently CH or N, provided that no more than two of $Z^2$, $Z^3$, $Z^4$ and $Z^5$ are N;

$L^{1j}$ is —NH—, —C(O)NH—, —NHC(O)—, or —O—;

$L^{2j}$ is $C_{1-6}$ linear alkylene or

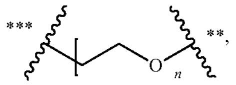

wherein n is 1 or 2, and

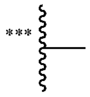

represents a covalent bond to $L^{1j}$; and represents a single bond or a double bond;

(L-k)

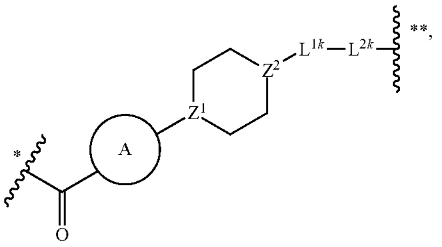

or a stereoisomer thereof, wherein:

Ring A is phenyl or a 5 or 6 membered heteroarylene having 1 or 2 nitrogen ring atoms;

each of $Z^1$ and $Z^2$ is independently CH or N;

$L^{1k}$ is a bond, —C(O)—, —C(O)NH— or —NHC(O)—; and $L^{2k}$ is a $C_{3-8}$ straight chain alkylene or

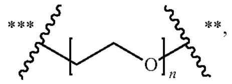

wherein n is 1, 2, or 3, and

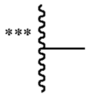

represents a covalent bond to $L^{1k}$;

(L-m)

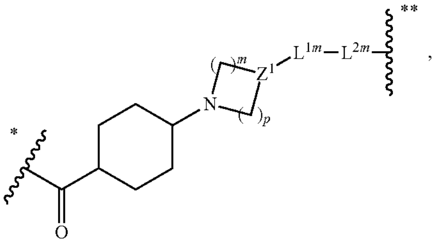

or a stereoisomer thereof, wherein:

$Z^1$ is CH or N;

m is 1 or 2;

p is 1 or 2;

0, 1, or 2 hydrogen atoms of

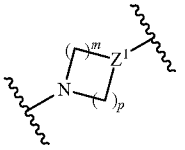

are replaced with F;

$L^{1m}$ is a bond, —C(O)—, —C(O)NH—, —NHC(O)—, —$S(O)_2NH$— or —$NHS(O)_2$—; and $L^{2m}$ is $C_{3-6}$ linear alkylene, $C_{3-6}$ cycloalkylene, or

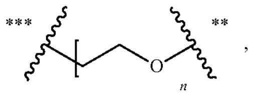

wherein n is 1 or 2, and

represents a covalent bond to $L^{1m}$;

(L-n-i)

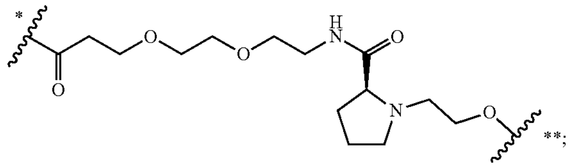

(L-n-ii)

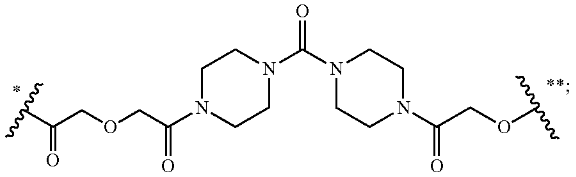

(L-n-iii)

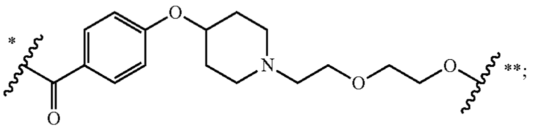

or (L-n-iv)

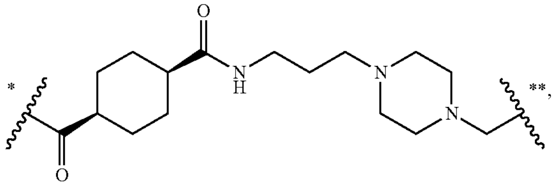

wherein each

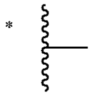

represents a covalent bond to the NH group of Formula (I), and each

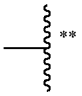

represents a covalent bond to the methylene group of Formula (I).

2. The compound of claim 1, or a pharmaceutically acceptable salt thereof, wherein $R^1$ is —$CH_3$.

3. The compound of claim 2, or a pharmaceutically acceptable salt thereof, wherein $R^2$ is isopropyl, and $R^3$ is methyl.

4. The compound of claim 1, or a pharmaceutically acceptable salt thereof, wherein L is a divalent linker of Formula (L-a-i):

(L-a-i)

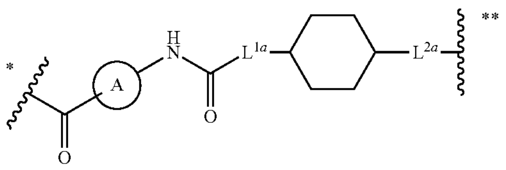

, or a stereoisomer thereof, wherein Ring A, $L^{1a}$, $L^{2a}$

, and

are as defined for Formula (L-a).

5. The compound of claim 1, or a pharmaceutically acceptable salt thereof, wherein L is a divalent linker of Formula (L-a-ii):

(L-a-ii)

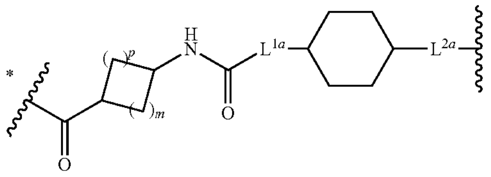

, or a stereoisomer thereof, wherein $L^{1a}$, $L^{2a}$,

, and

are as defined for Formula (L-a); p is 1 or 2; and m is 1 or 2.

6. The compound of claim 1, or a pharmaceutically acceptable salt thereof, wherein L is a divalent linker of Formula (L-a-iii):

(L-a-iii)

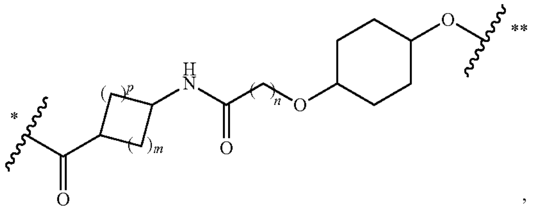

, or a stereoisomer thereof,
wherein p is 1 or 2; m is 1 or 2; n is 1, 2, or 3; and
and
are as defined for Formula (L-a).
7. The compound of claim 1, or a pharmaceutically acceptable salt thereof, wherein L is a divalent linker selected from the group consisting of:
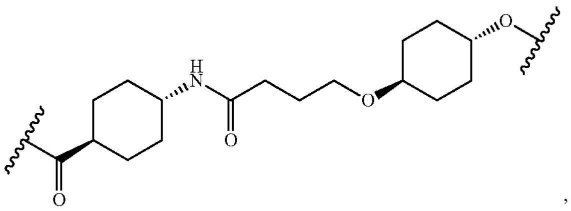
,
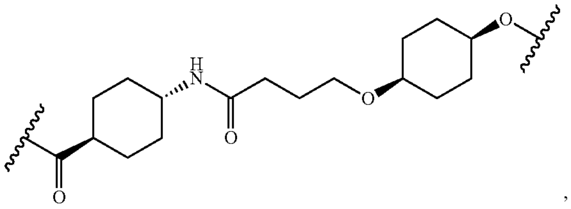
,
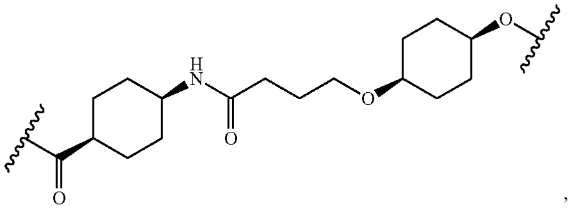
,
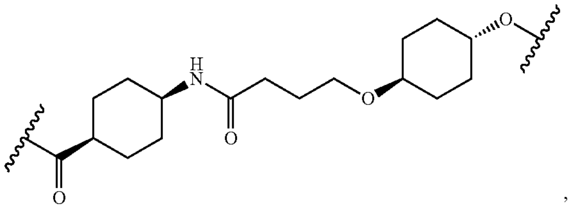
,
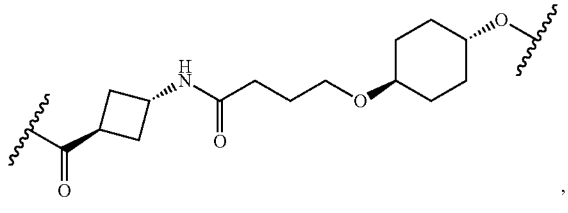
,
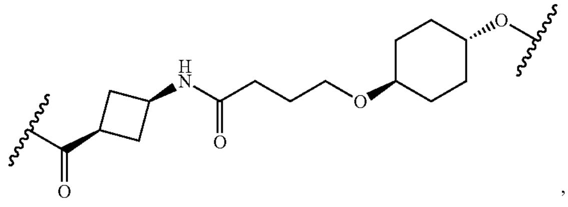
,
-continued
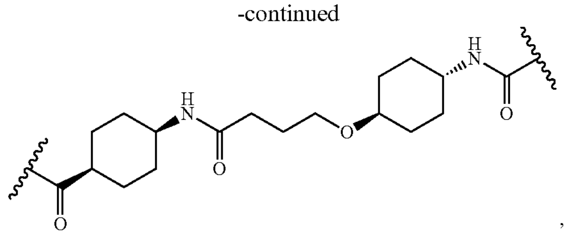
,
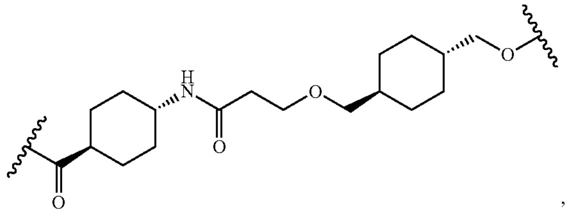
,
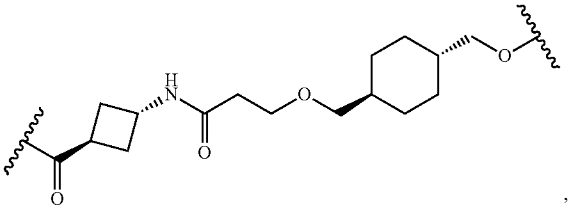
,
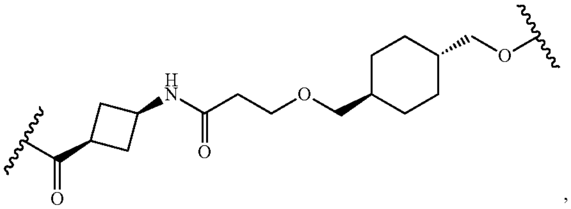
,
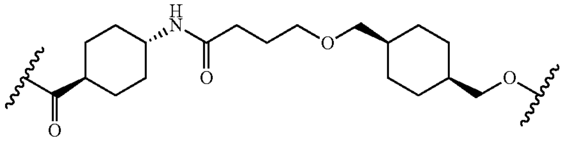
,
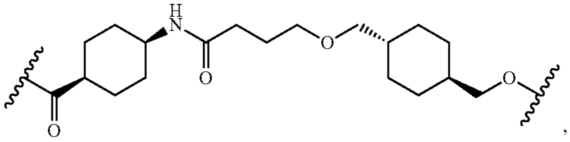
,
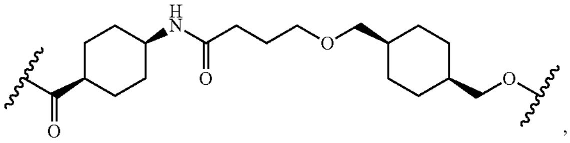
,
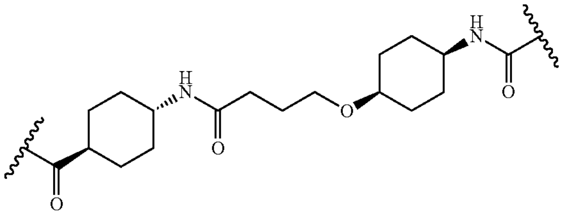
,
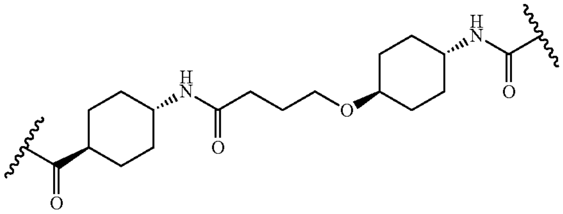
, -continued
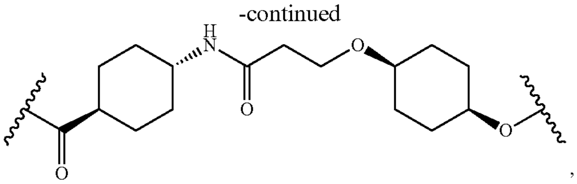
,
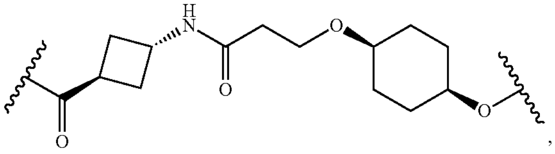
,
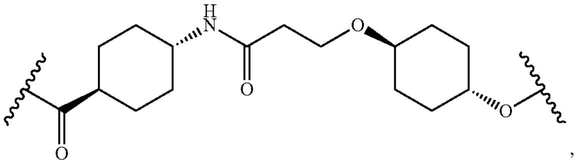
,
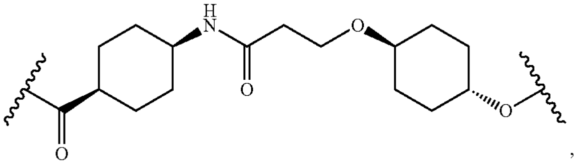
,
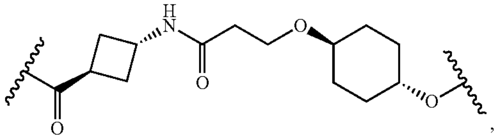
, and
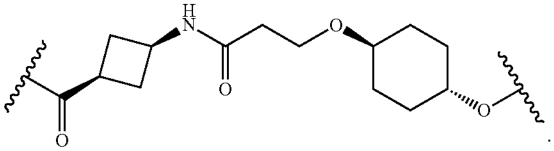
.
8. The compound of claim 1, or a pharmaceutically acceptable salt thereof, wherein L is a divalent linker selected from the group consisting of:
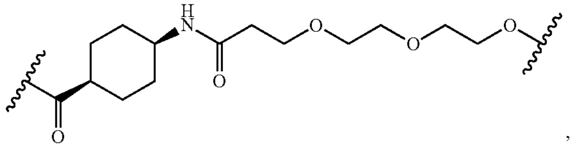
,
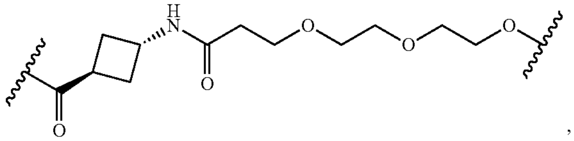
,
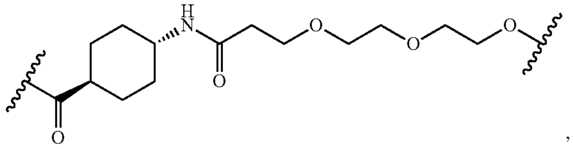
,
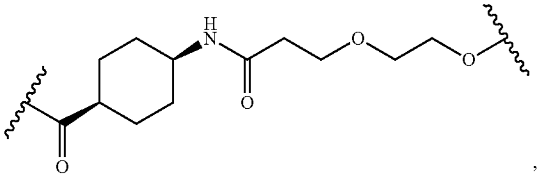
,
-continued
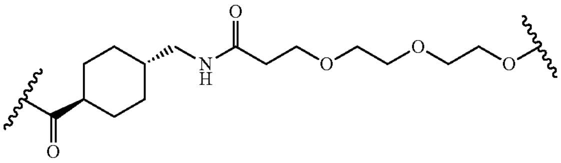
,
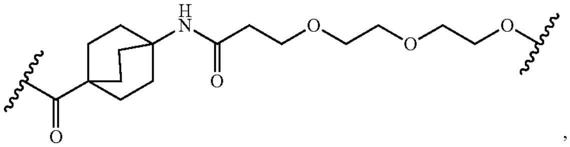
,
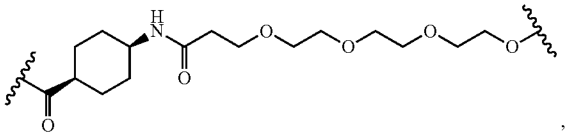
,
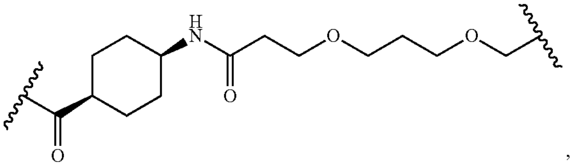
,
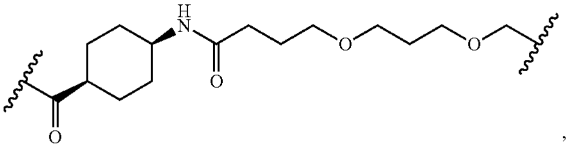
,
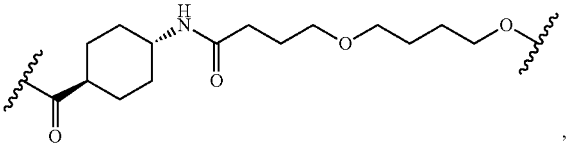
,
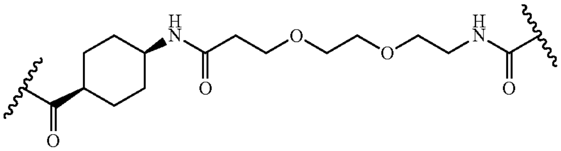
,
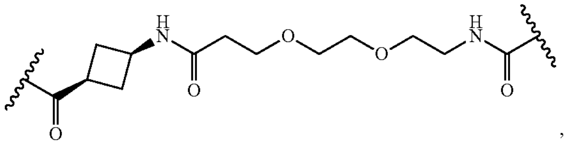
,
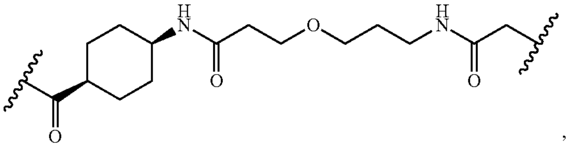
,
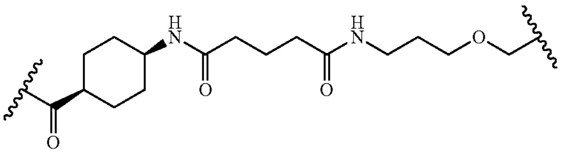
,
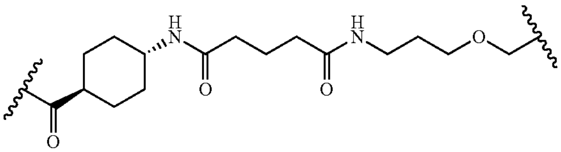
, -continued
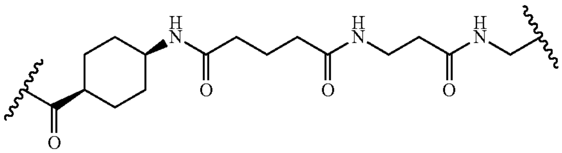
,
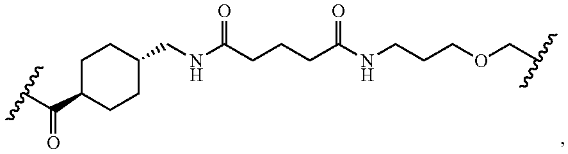
,
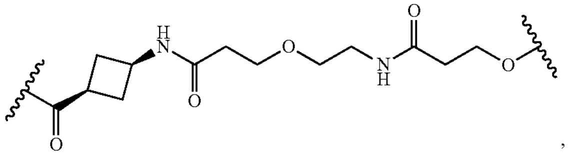
,
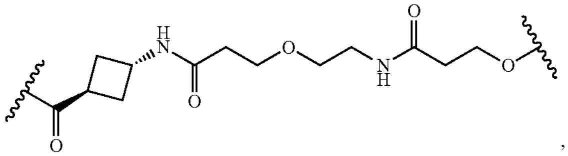
,
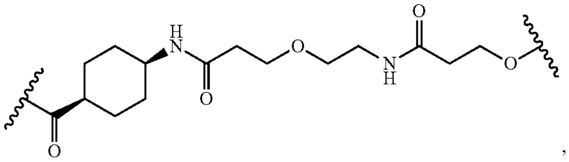
,
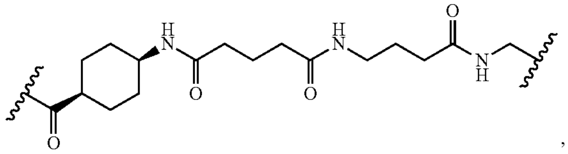
,
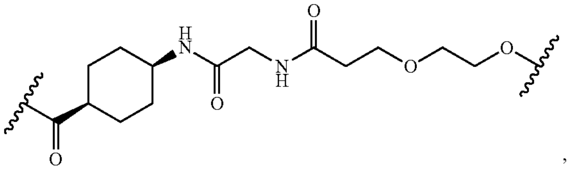
,
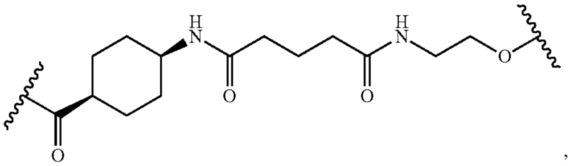
,
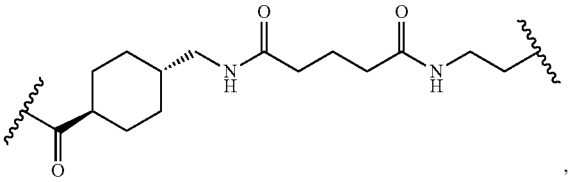
,
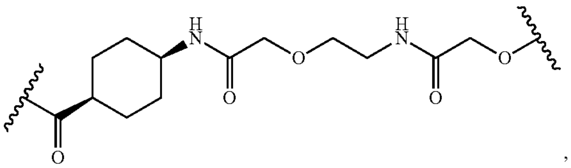
,
-continued
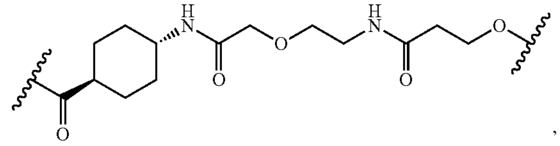
,
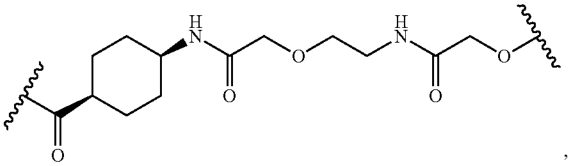
,
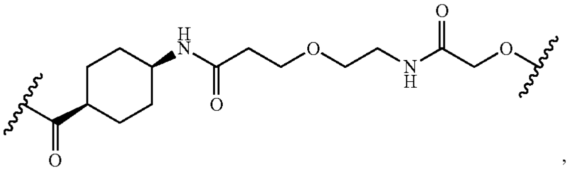
,
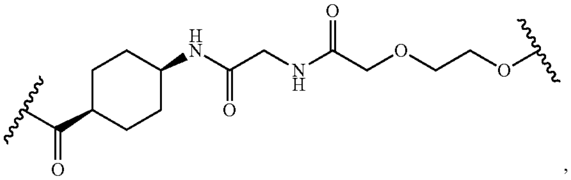
,
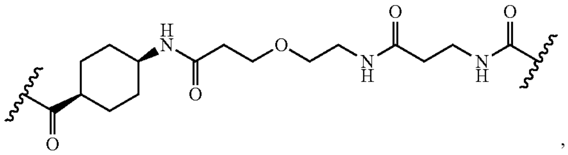
,
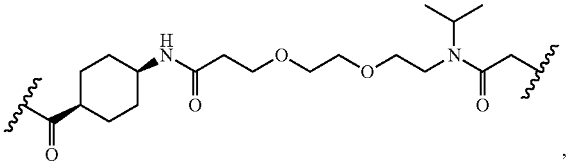
,
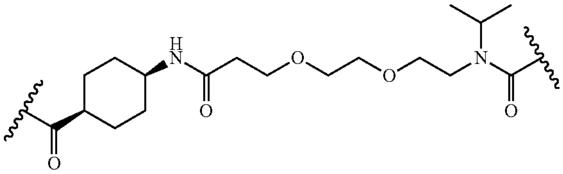
,
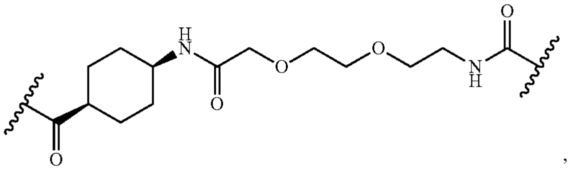
,
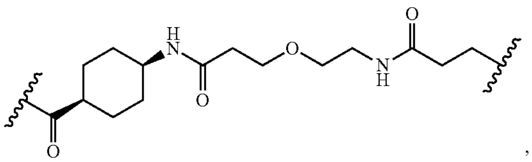
, and
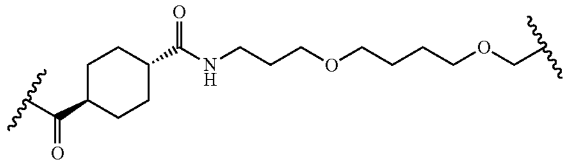
.

9. A compound in the following table or a pharmaceutically acceptable salt thereof:
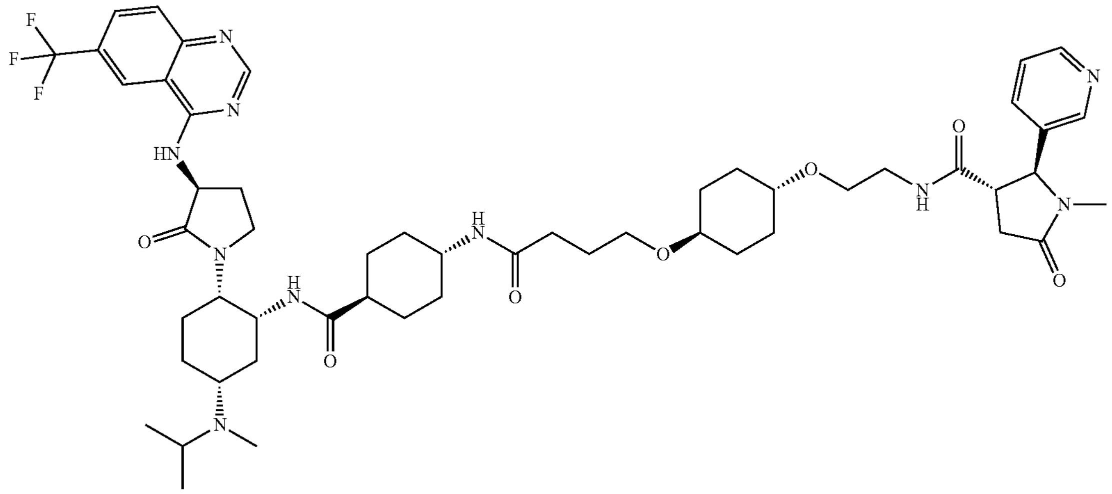
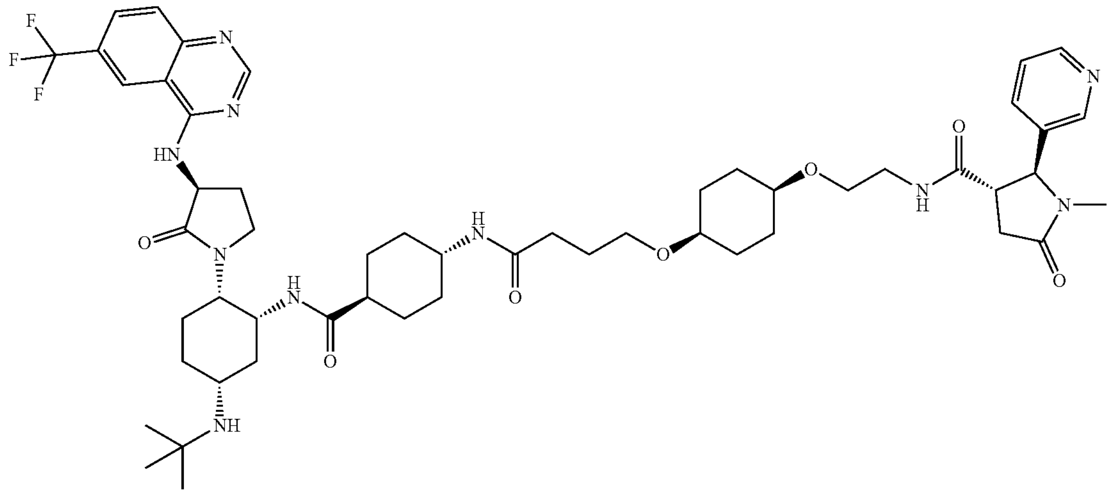
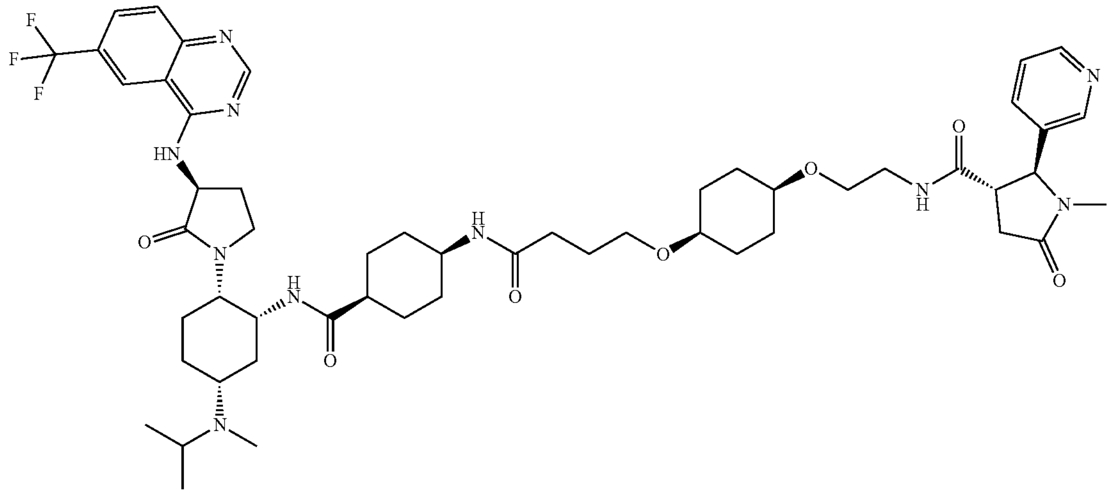

-continued
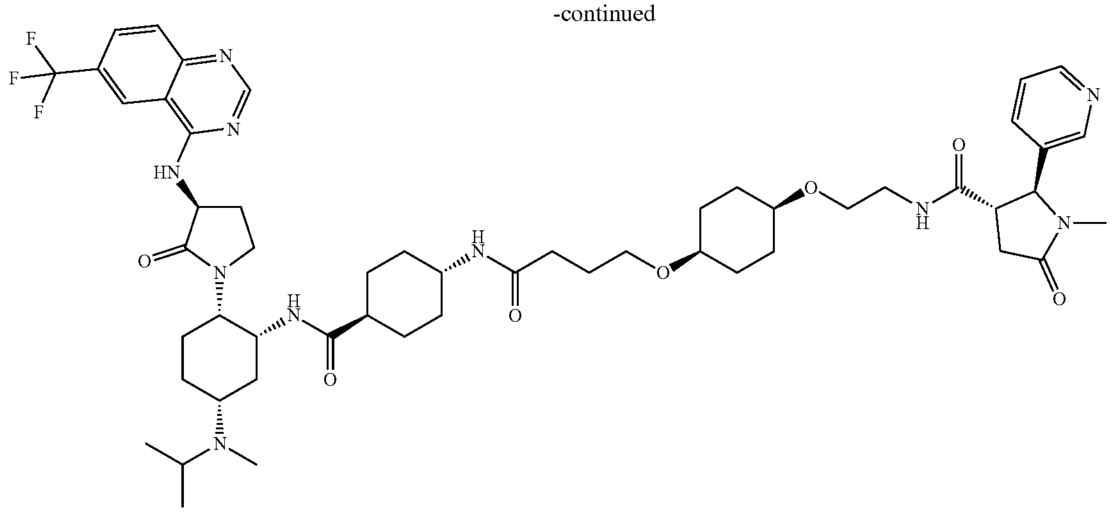
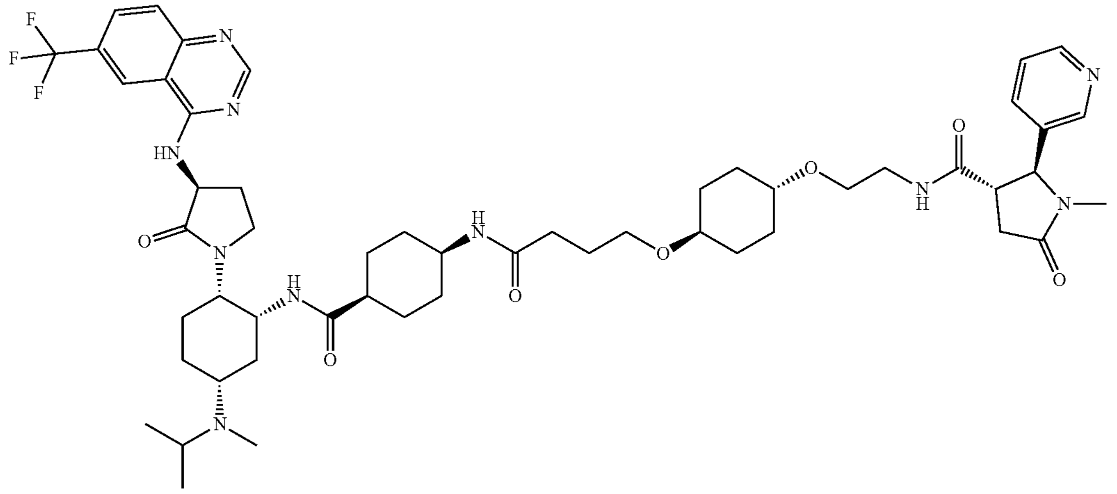
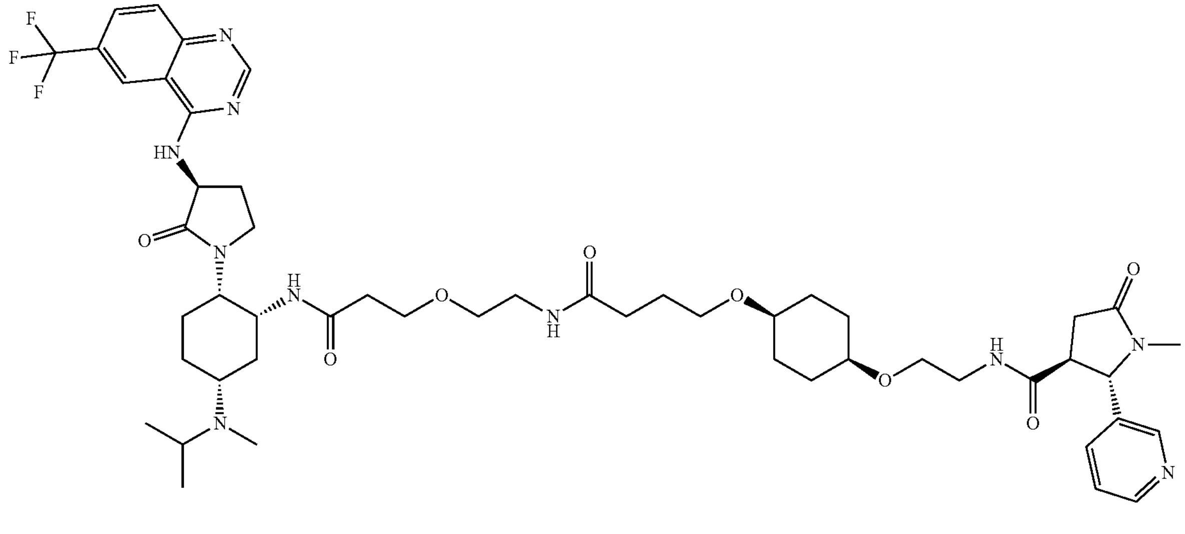

-continued
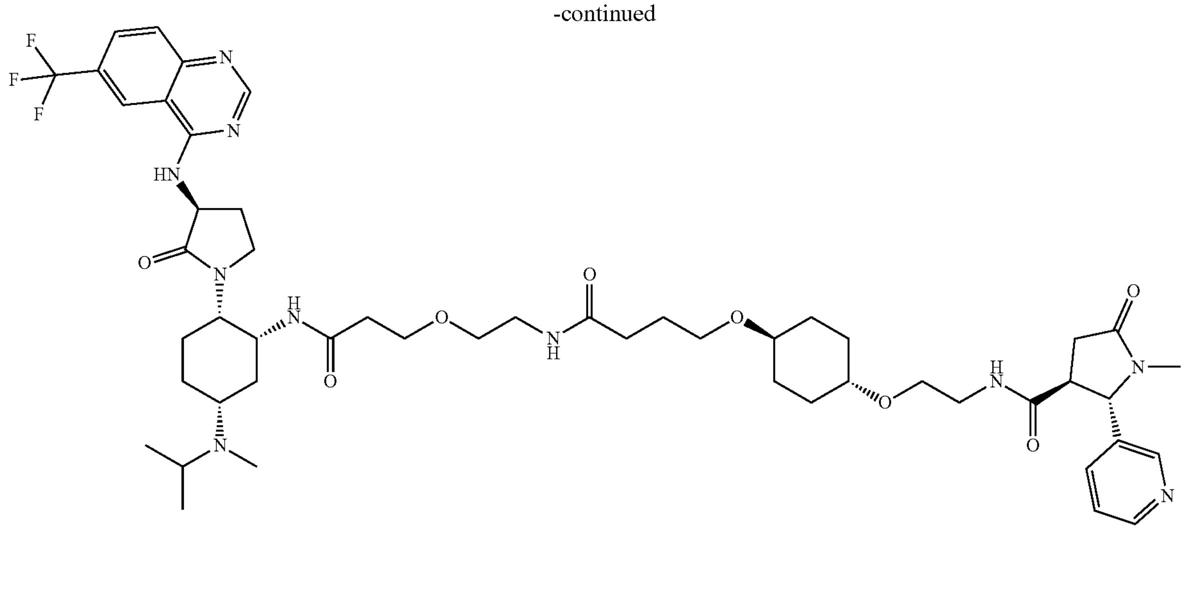
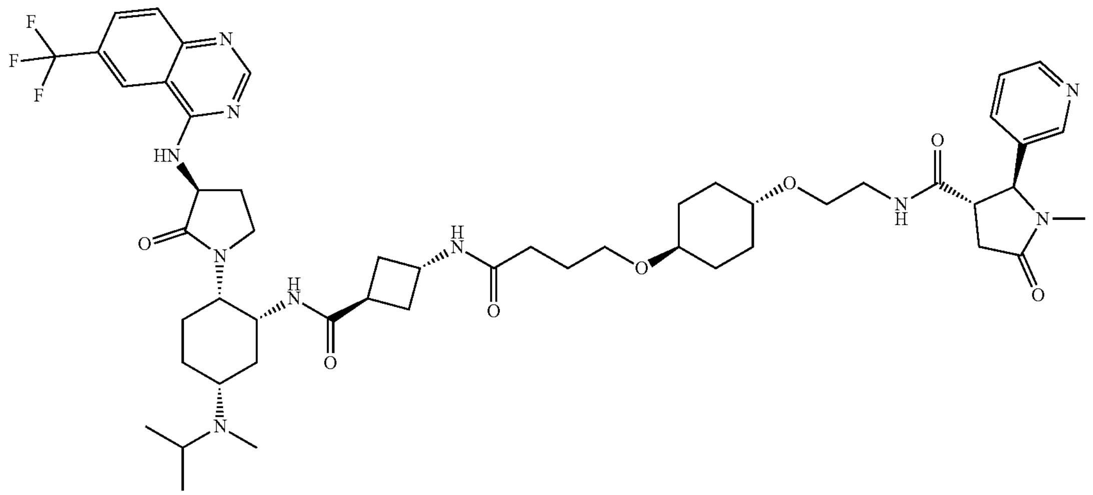
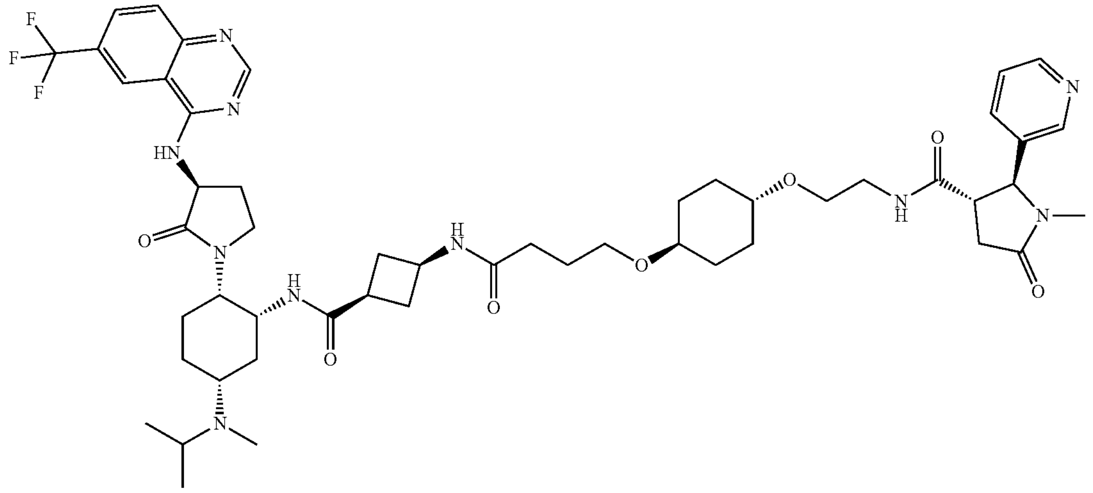

-continued
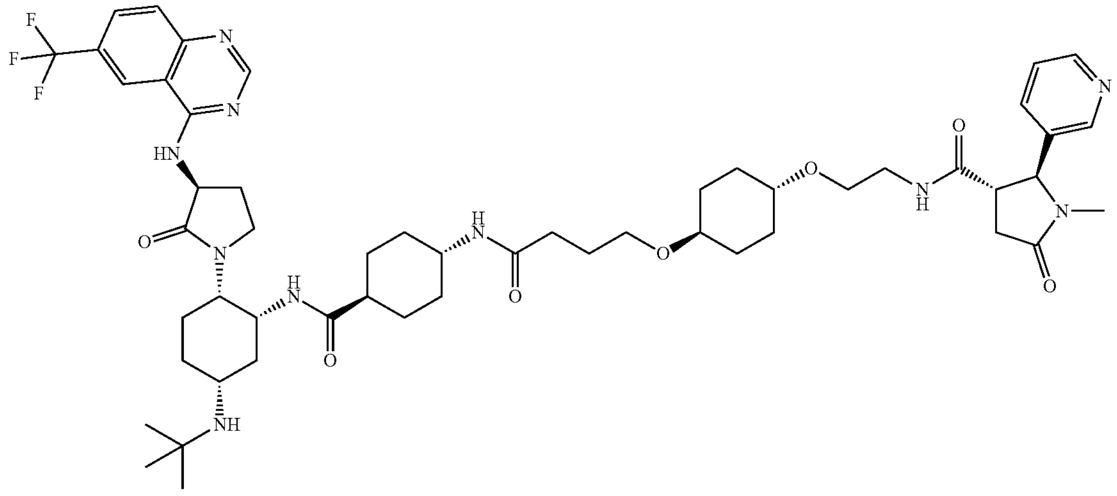
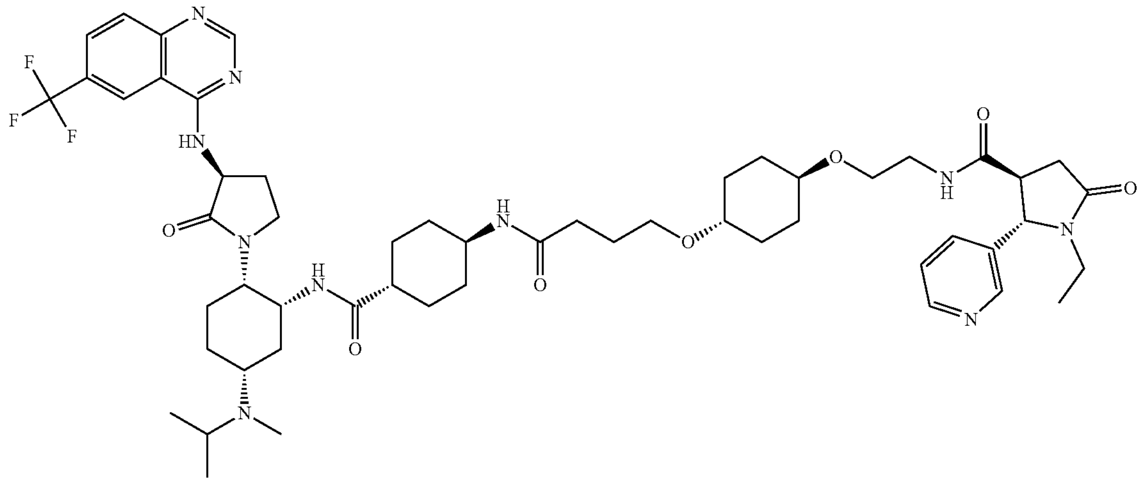
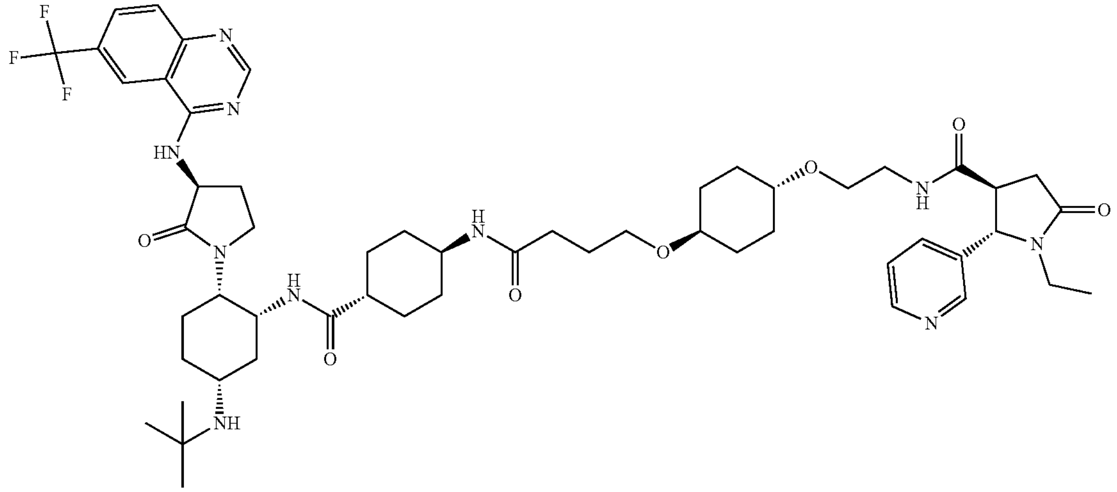

-continued
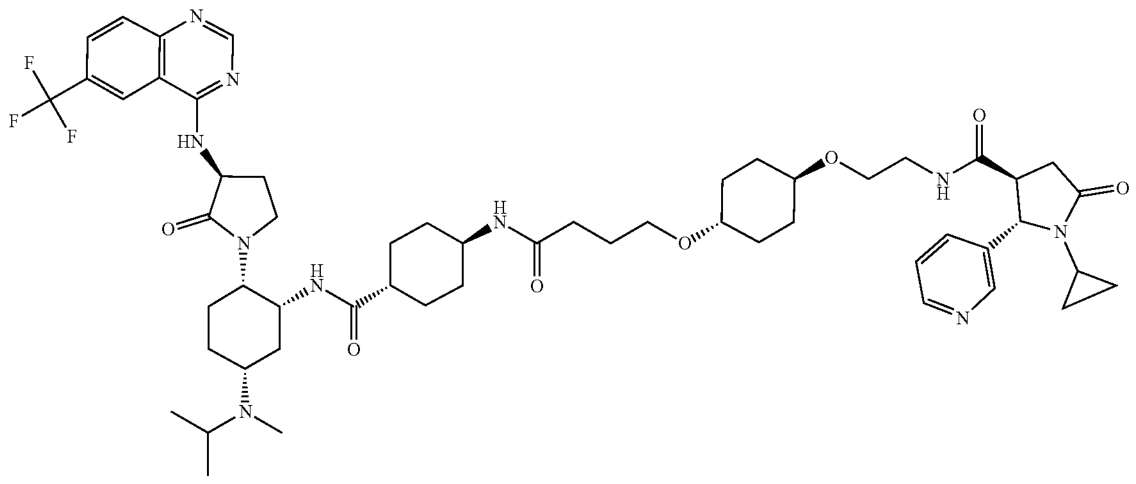
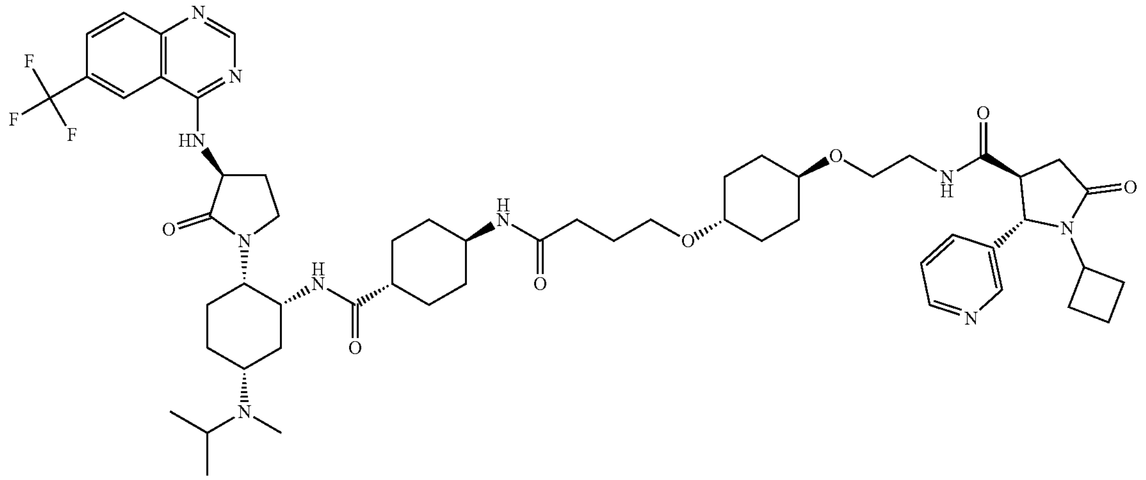
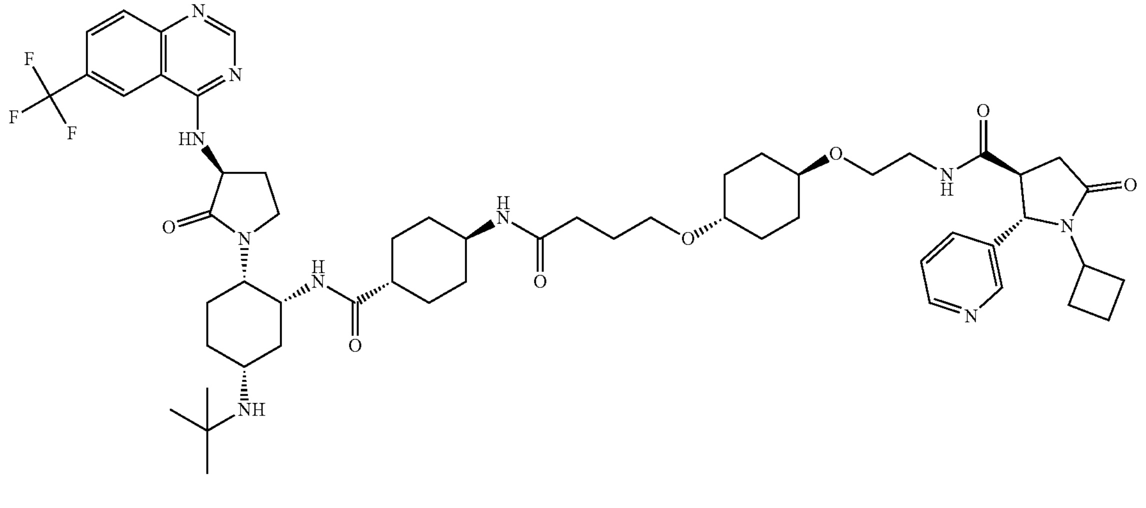

-continued
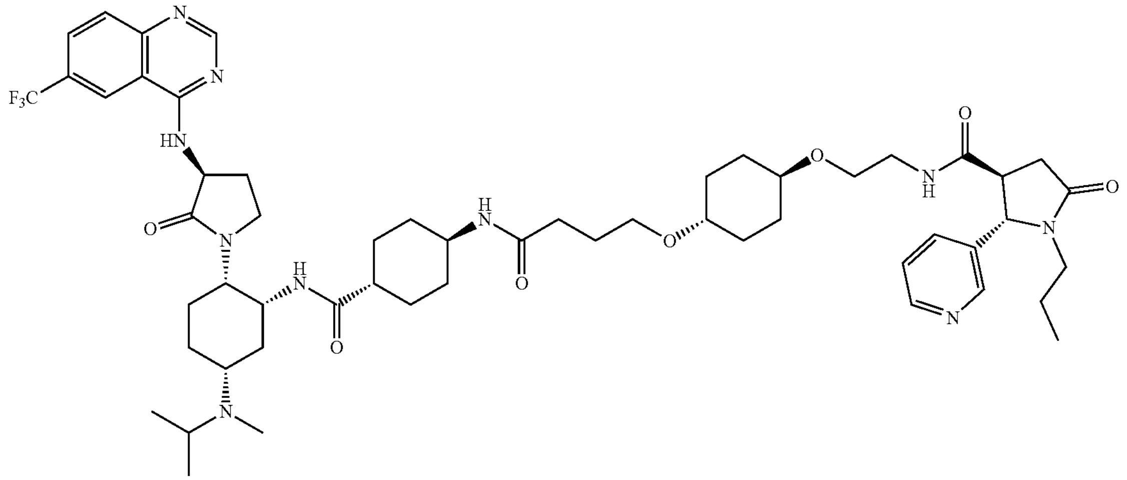
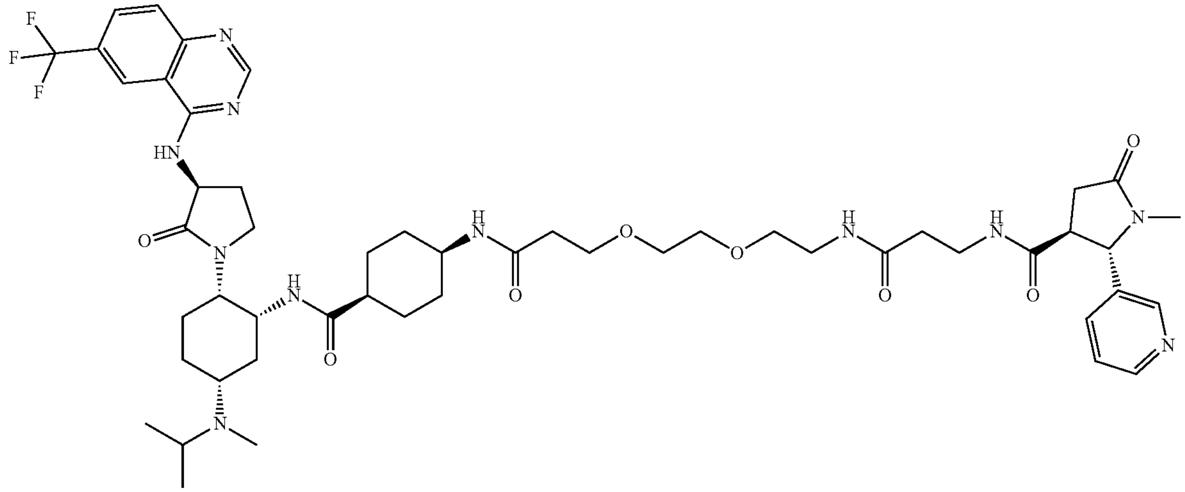
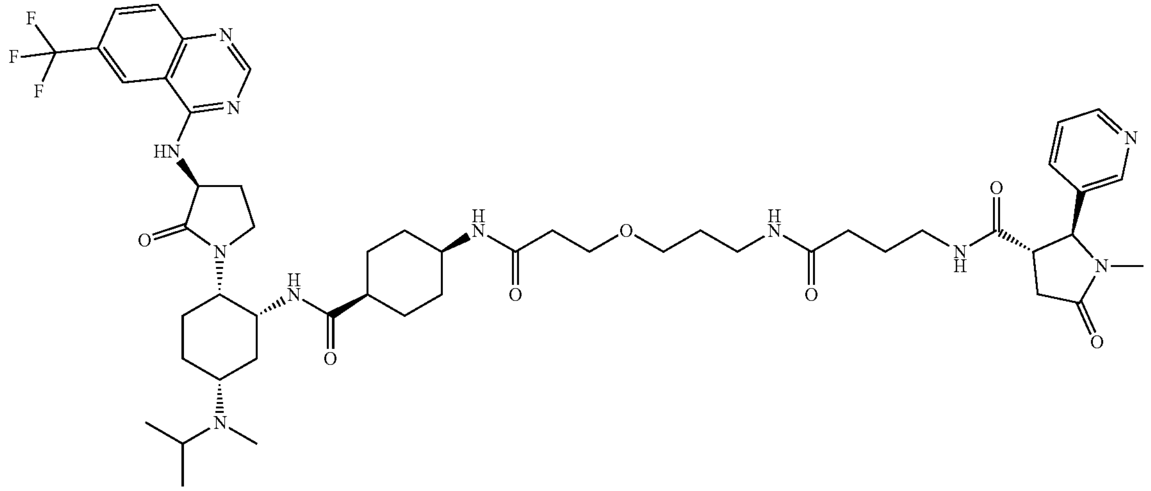

-continued
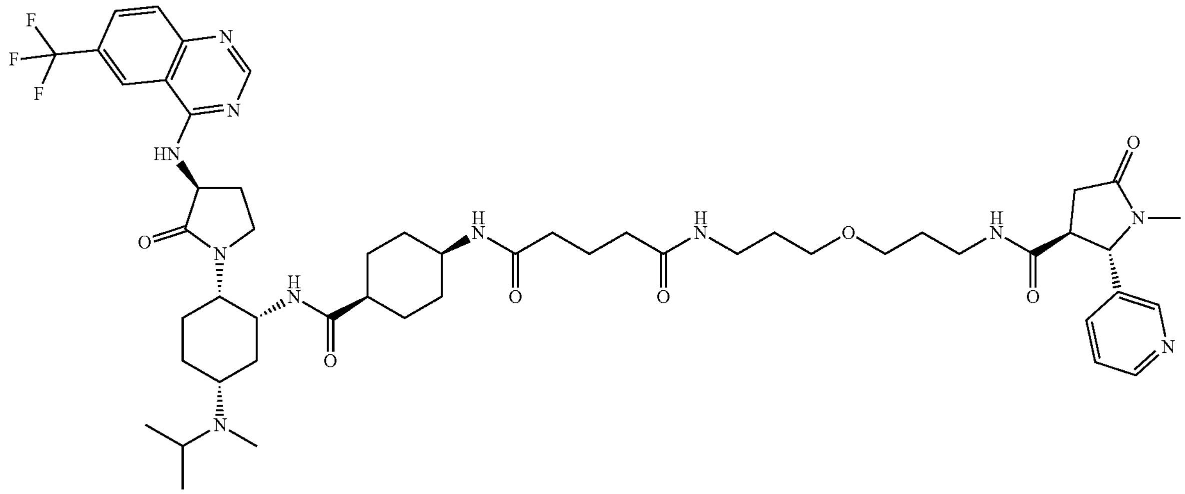
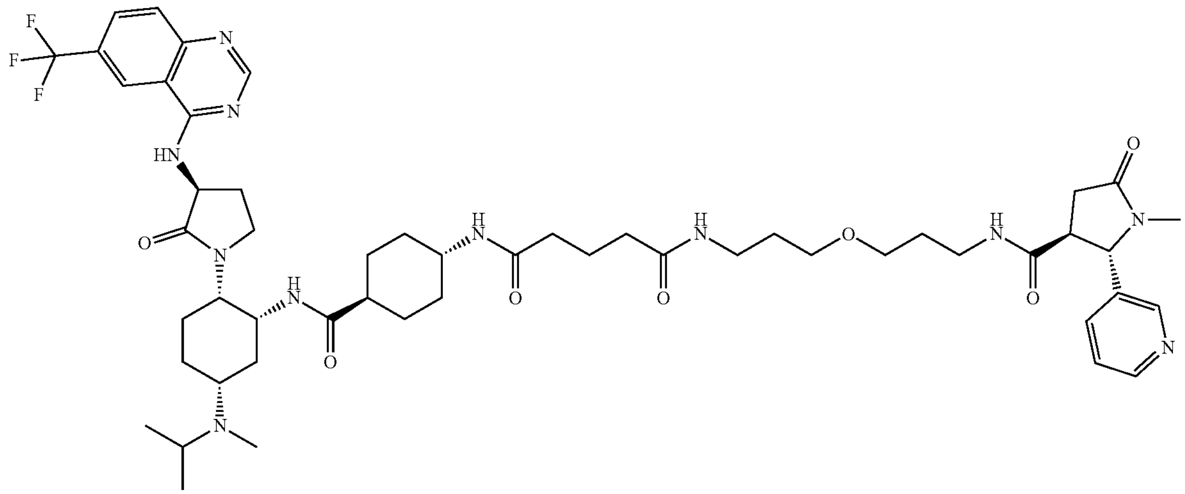
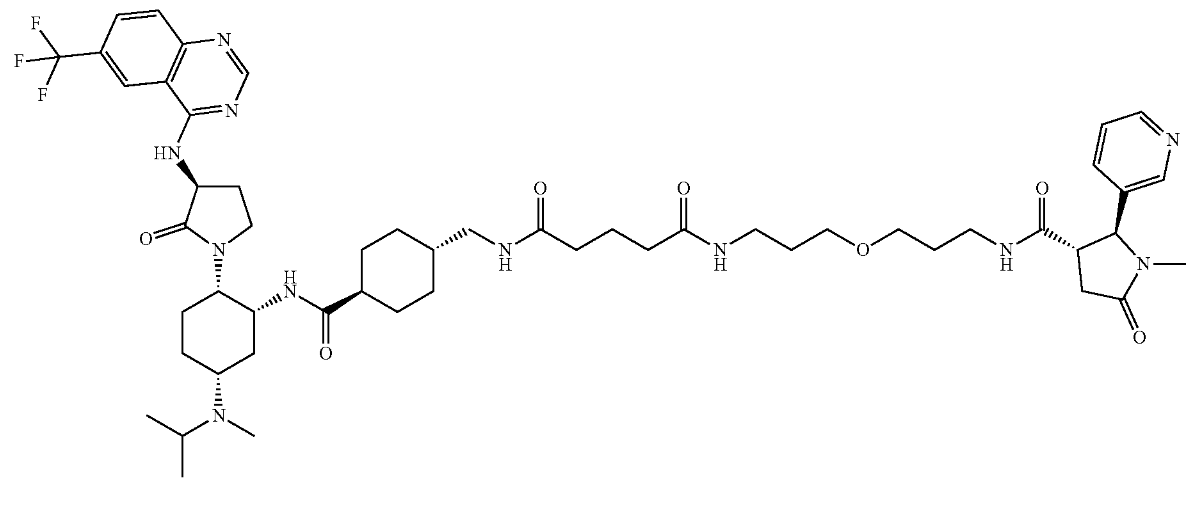

-continued
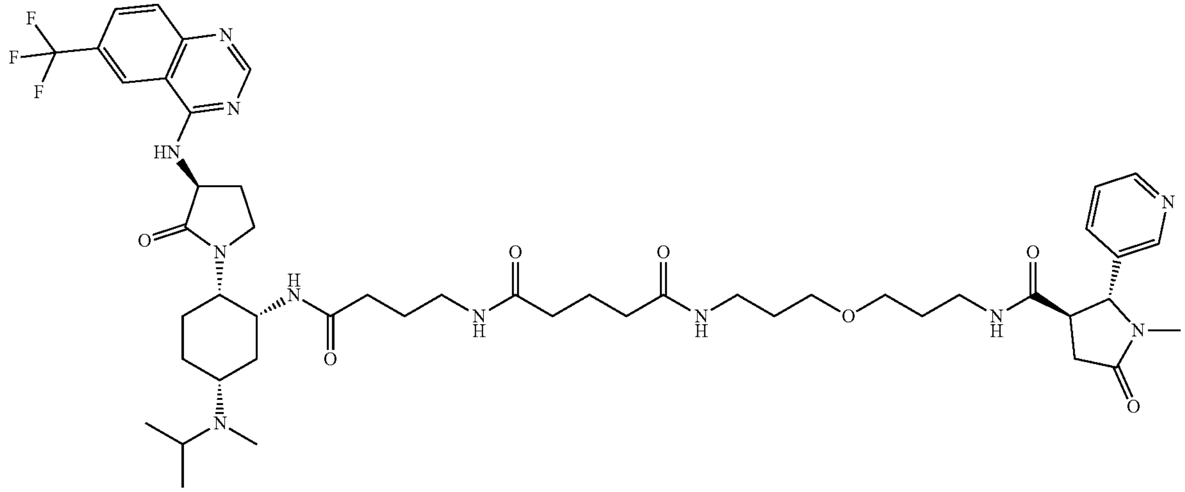
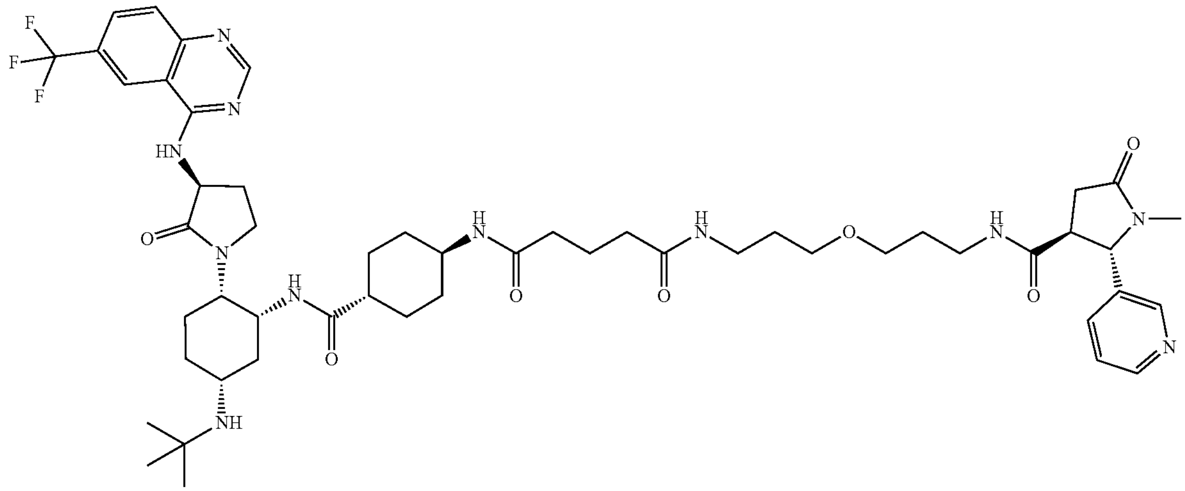
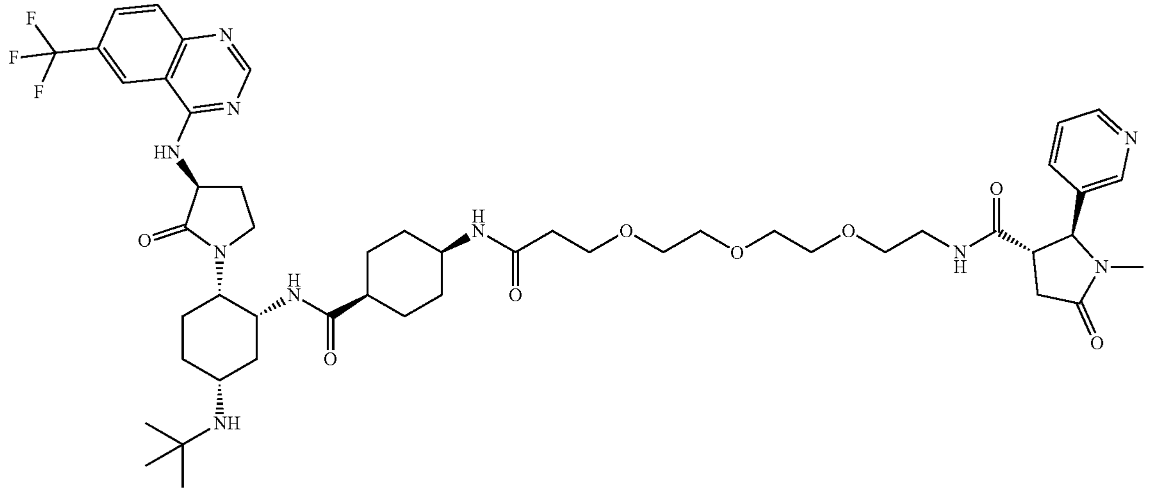

-continued
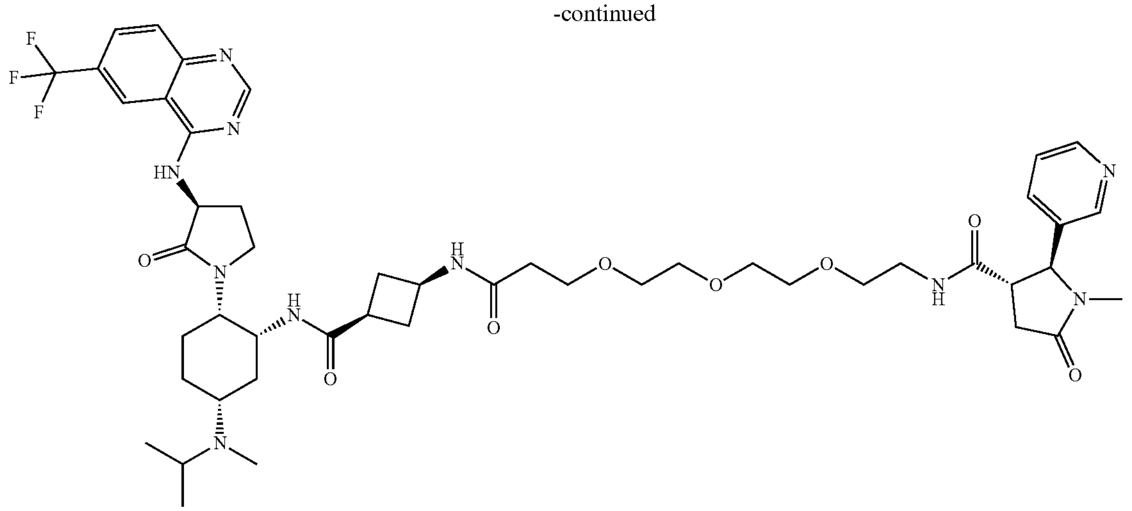
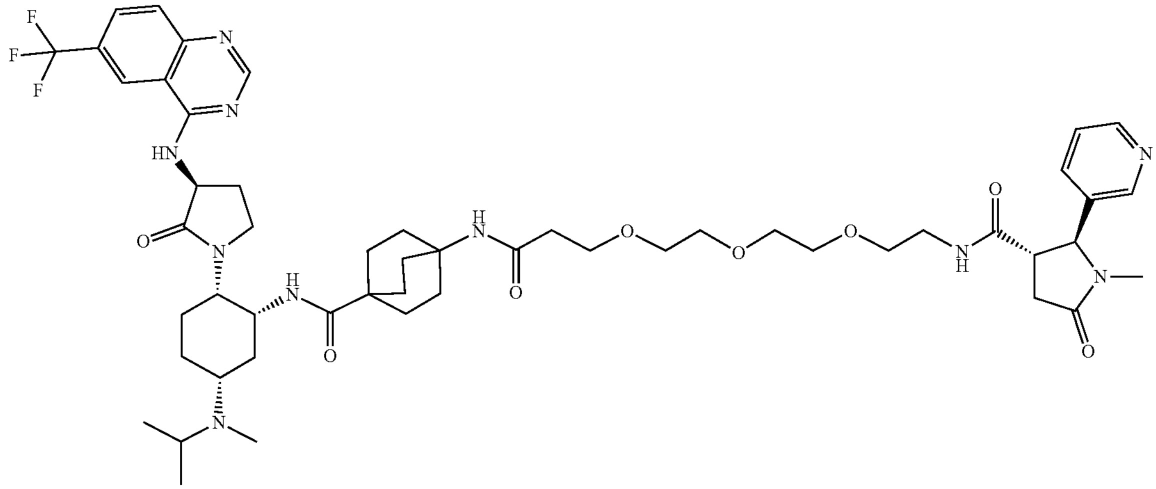
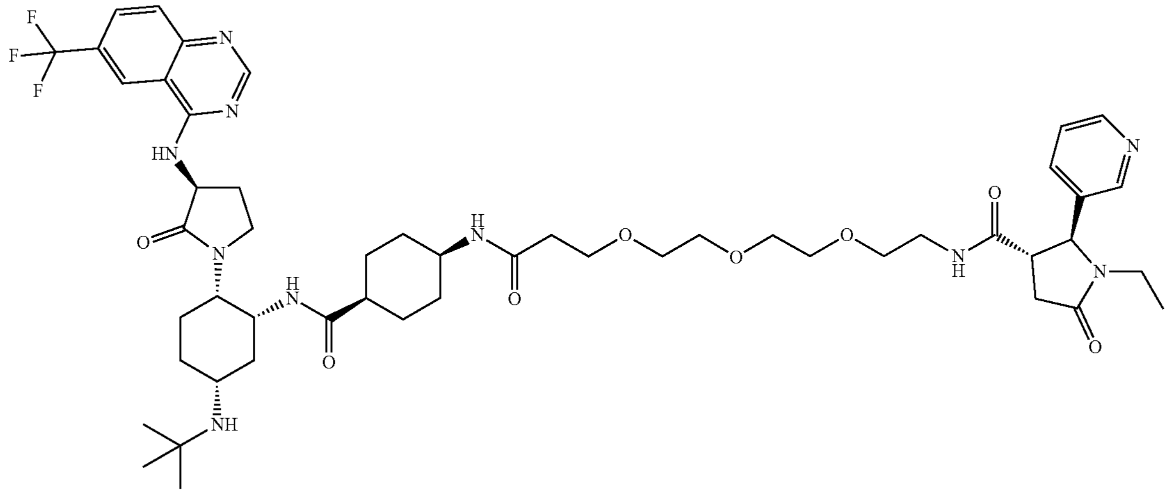

-continued
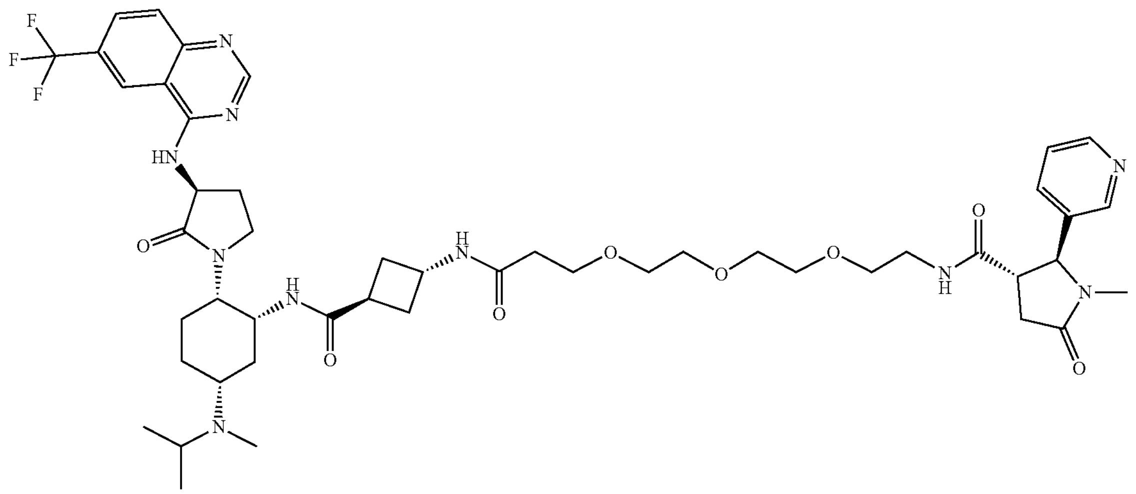
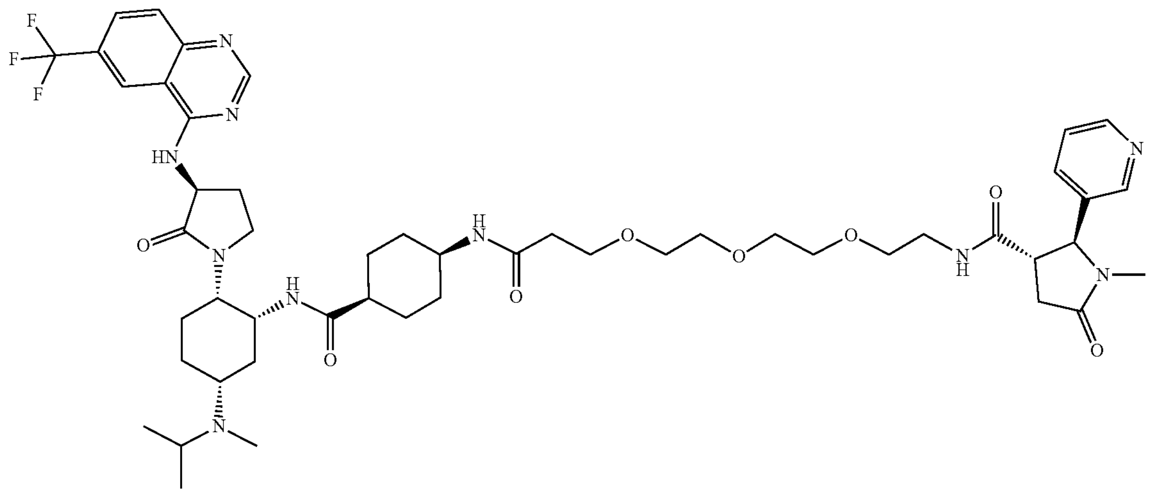
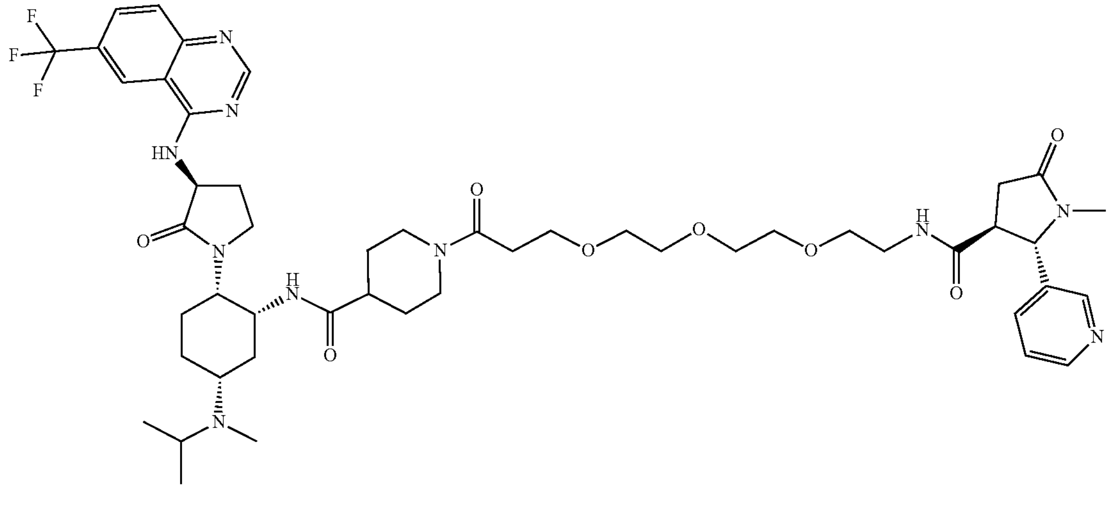

-continued
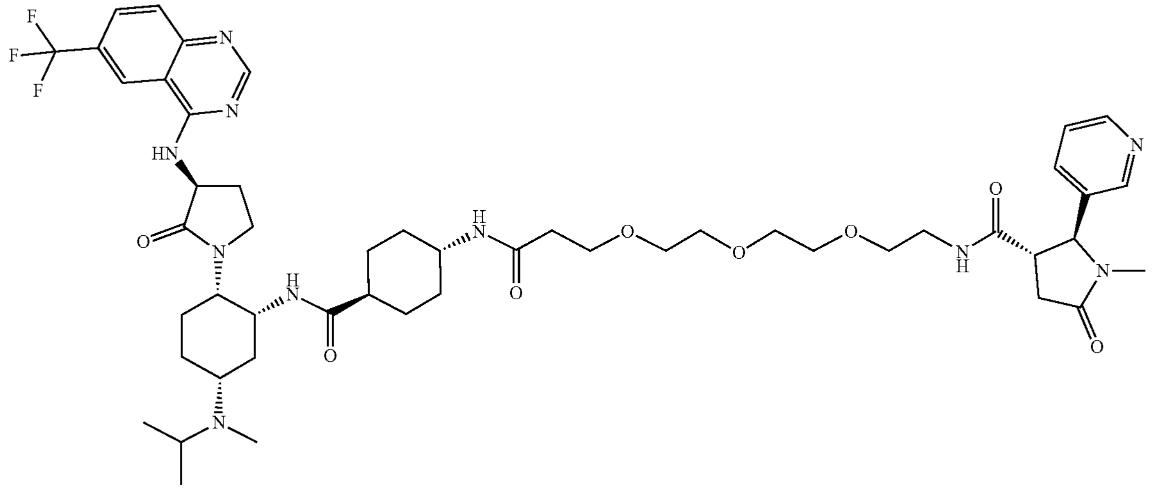
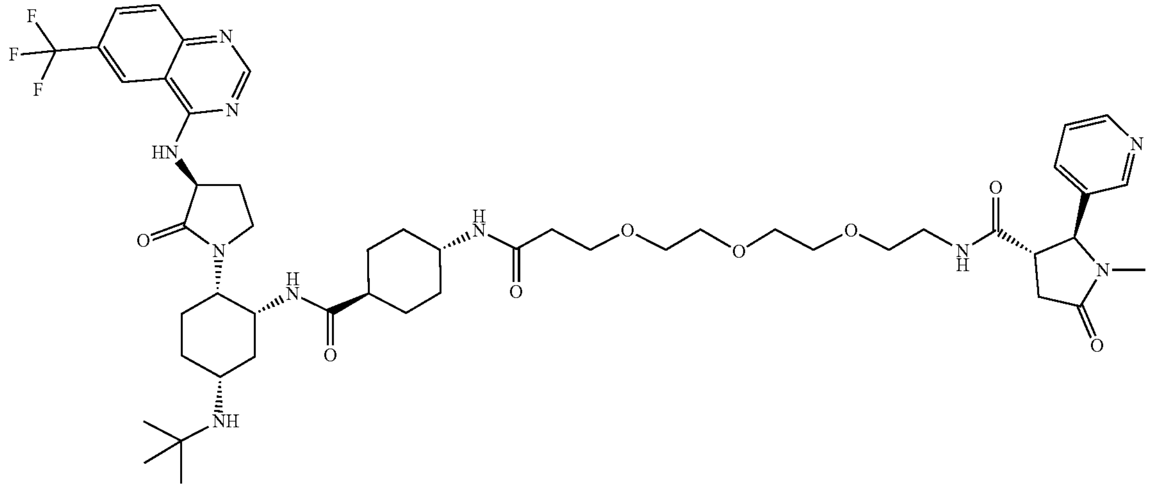
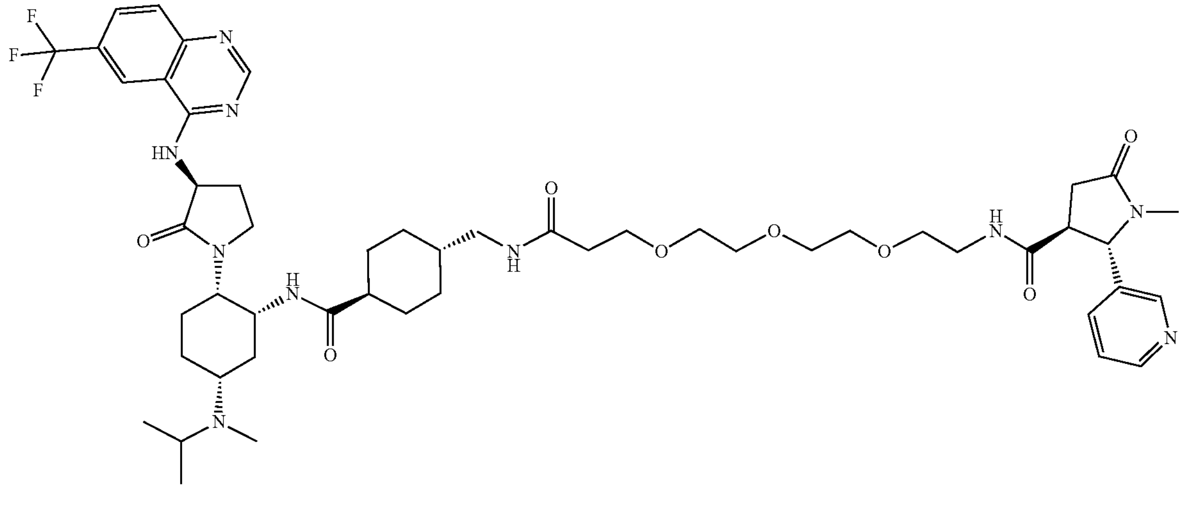

-continued
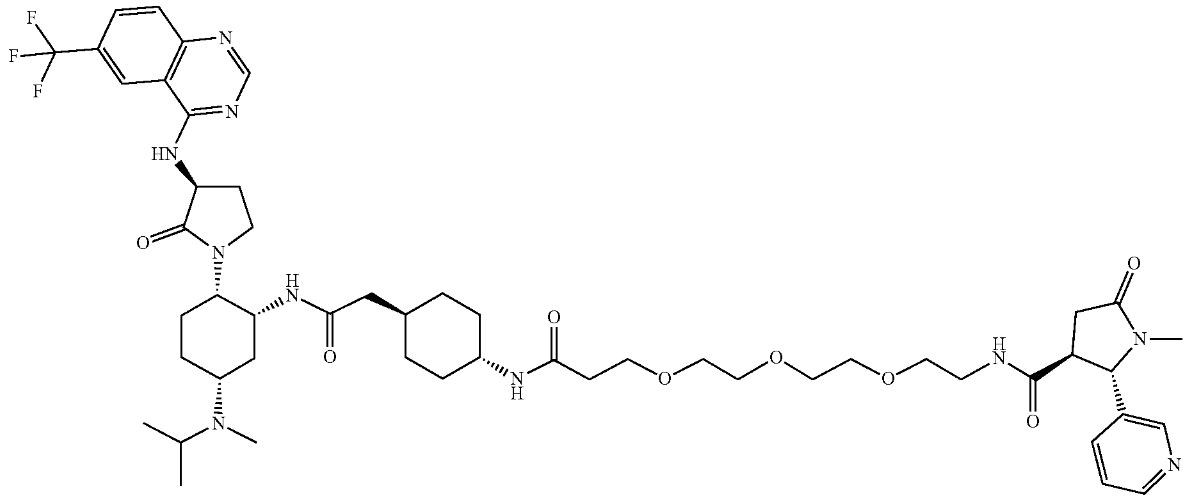
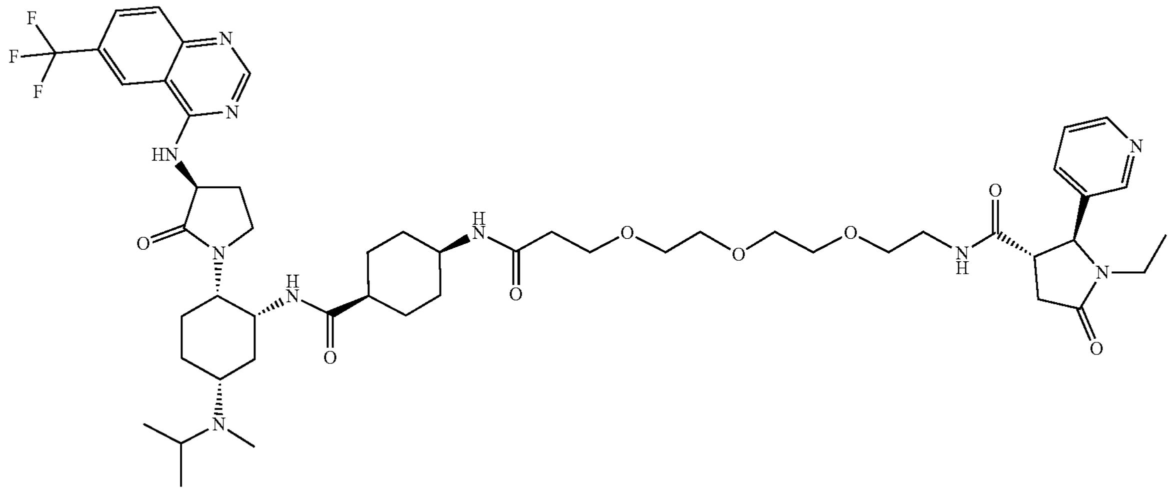
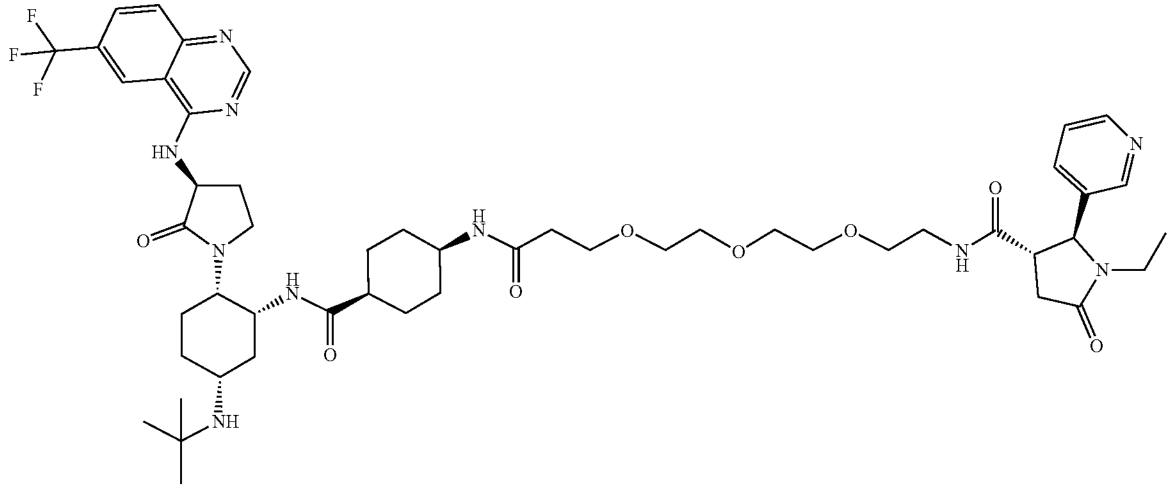

-continued
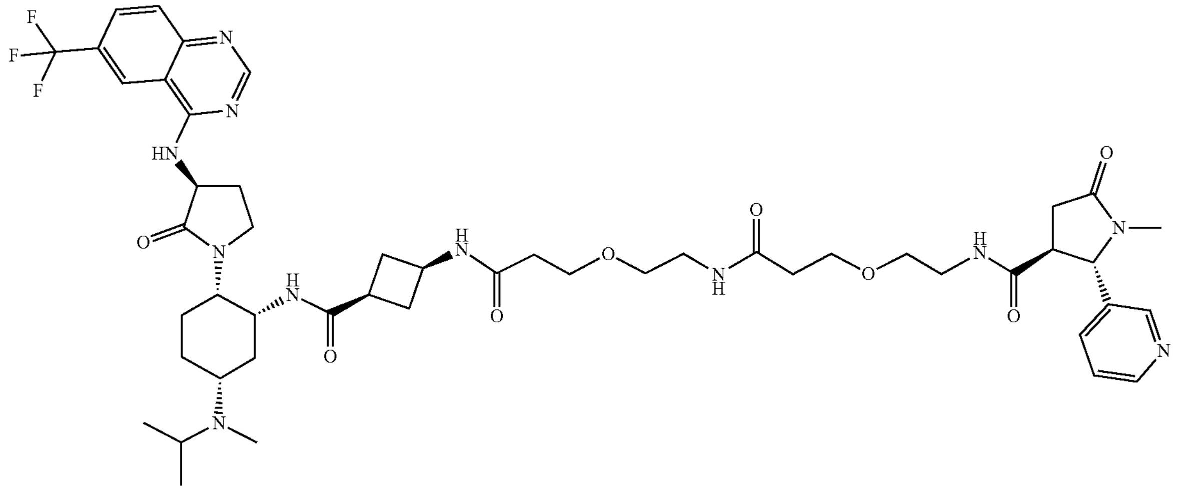
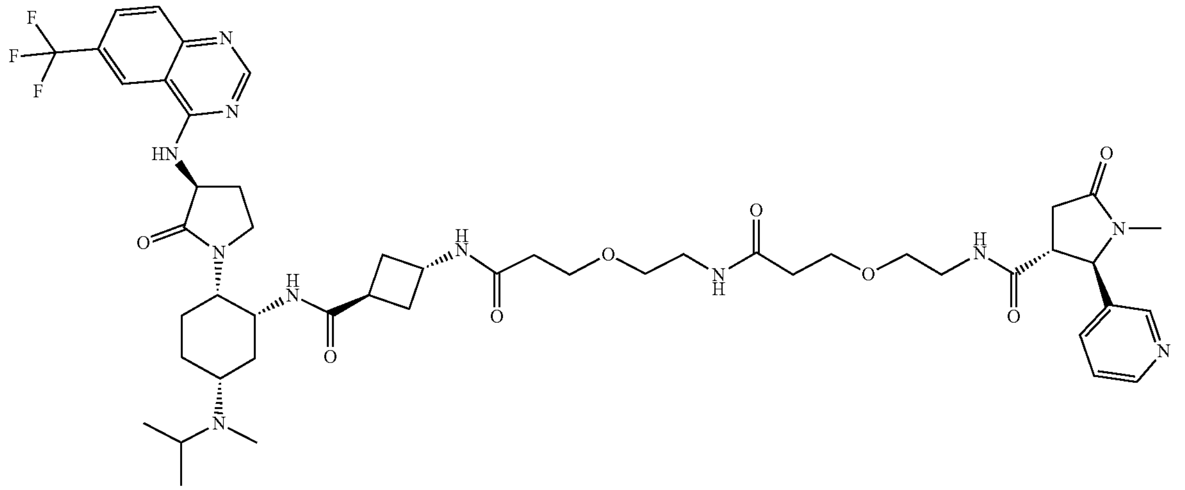
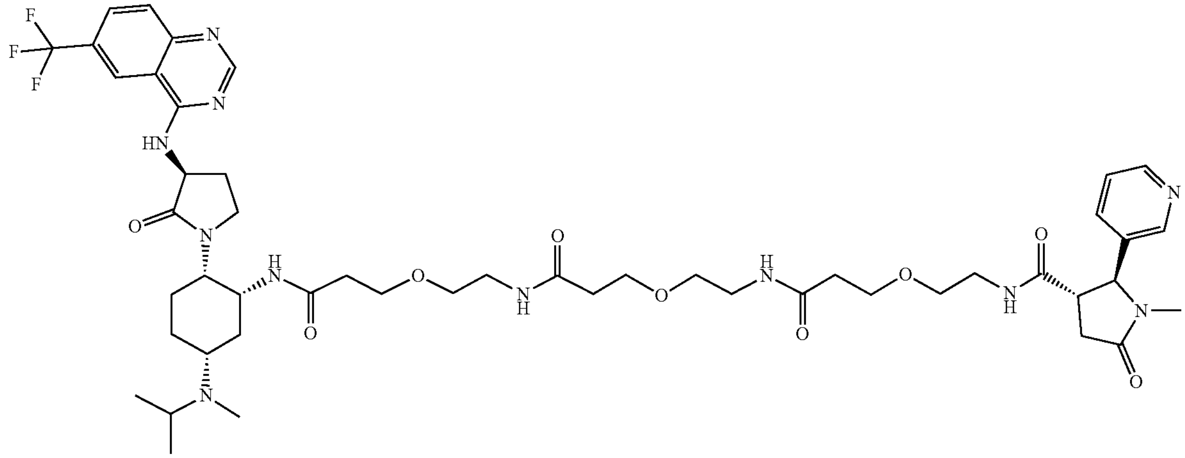

-continued
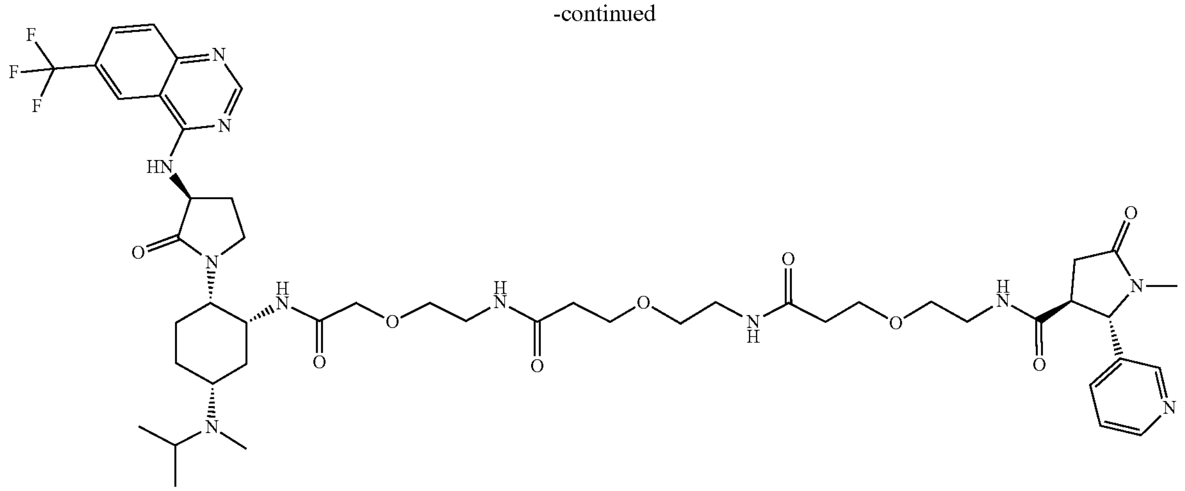
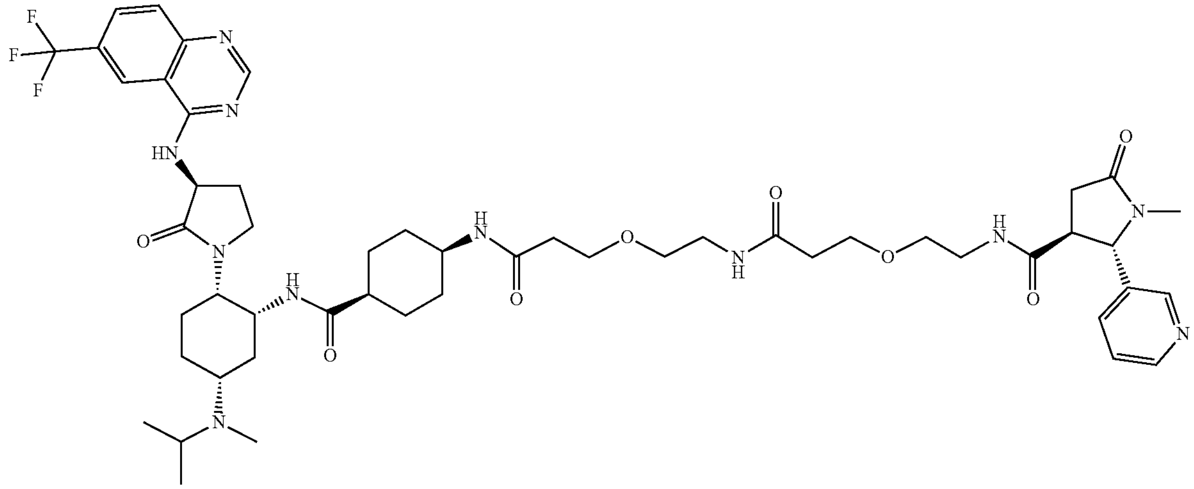 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)CCOCCNC(=O)CCOCCNC(=O)[C@H]3CC(=O)N(C)[C@@H]3c3cccnc3)CC2)C1]
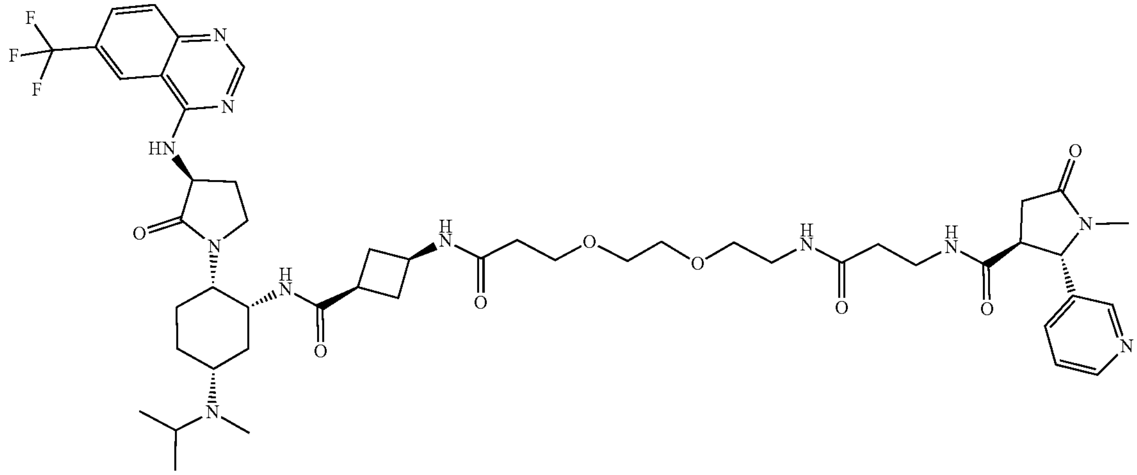

-continued
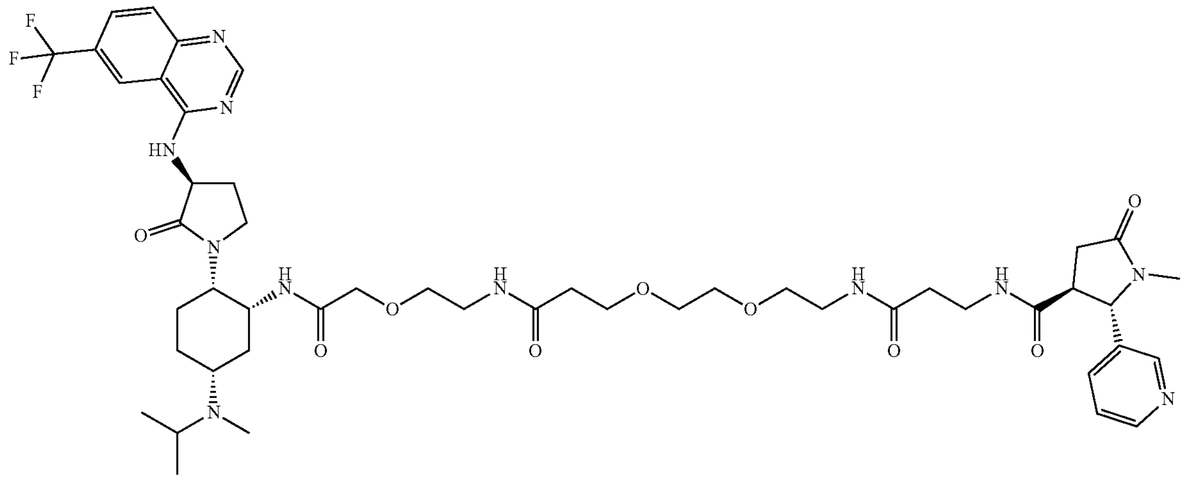
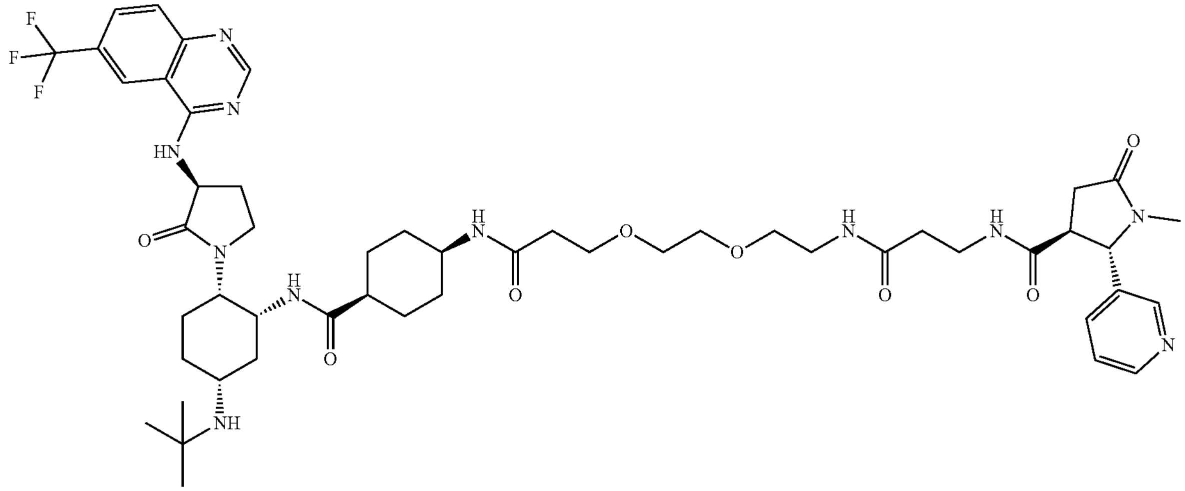
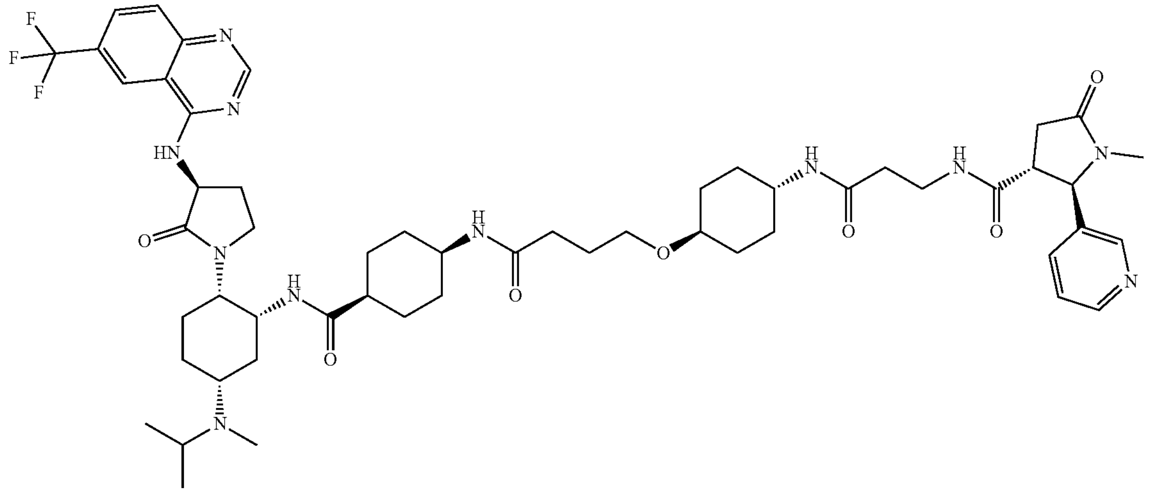

-continued
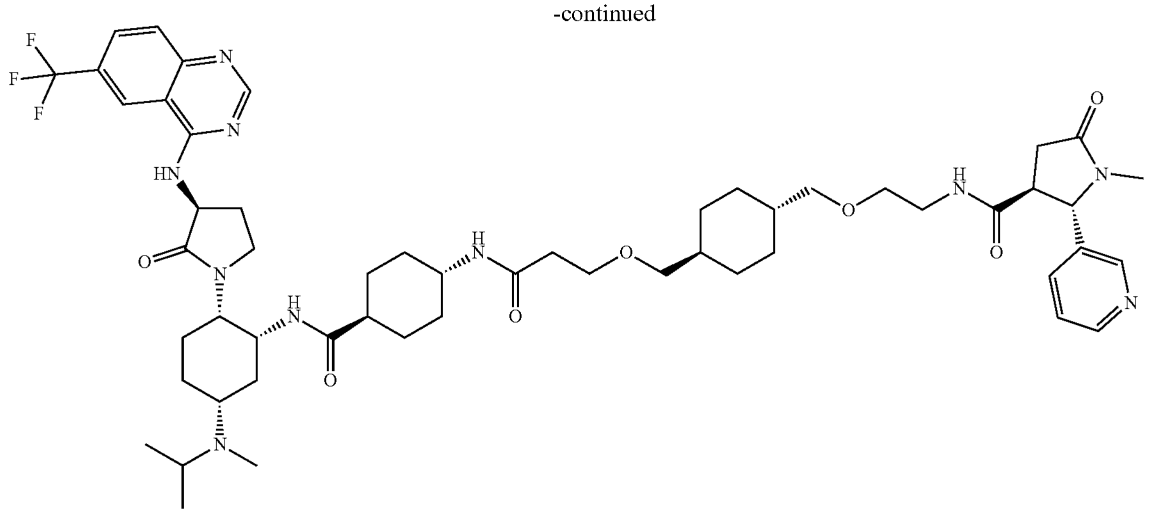
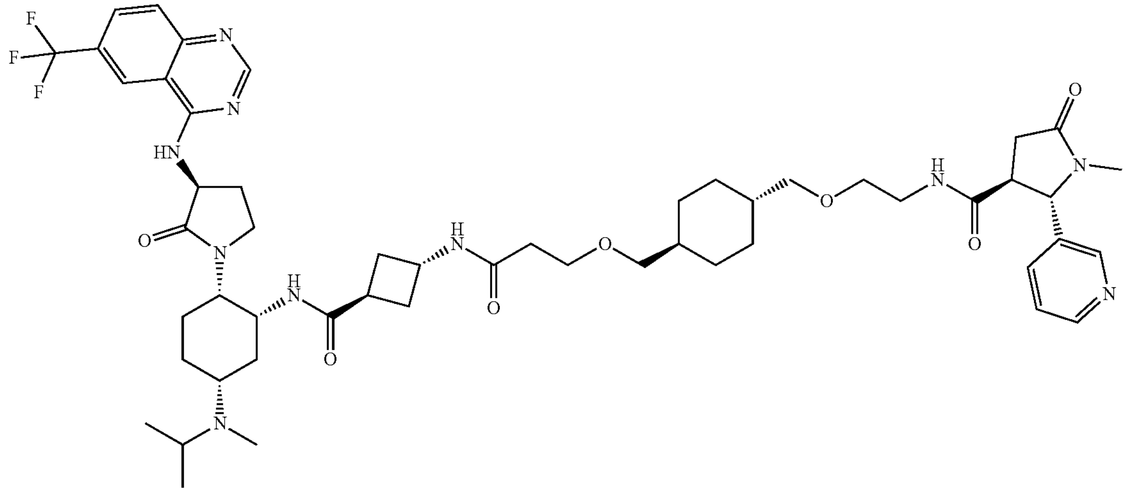
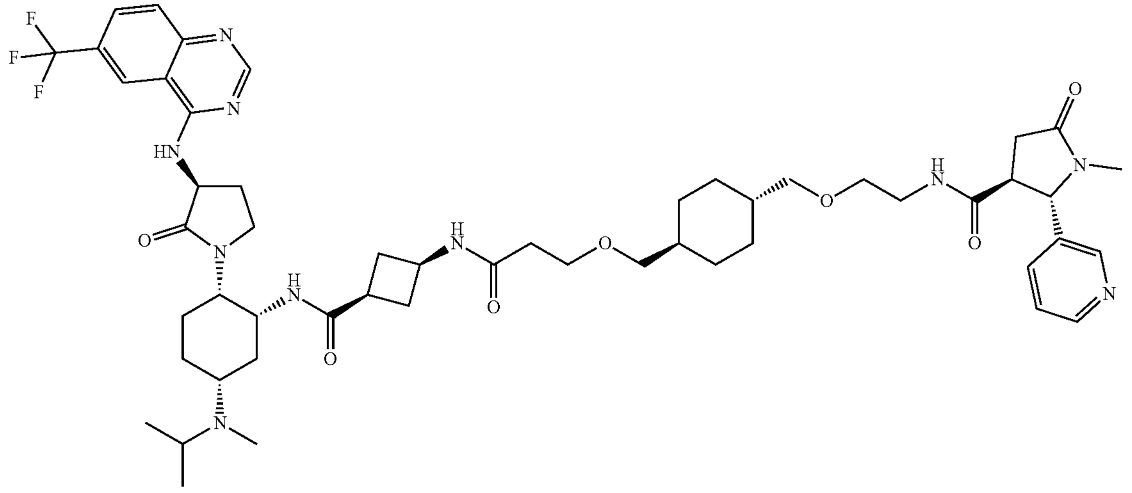

-continued
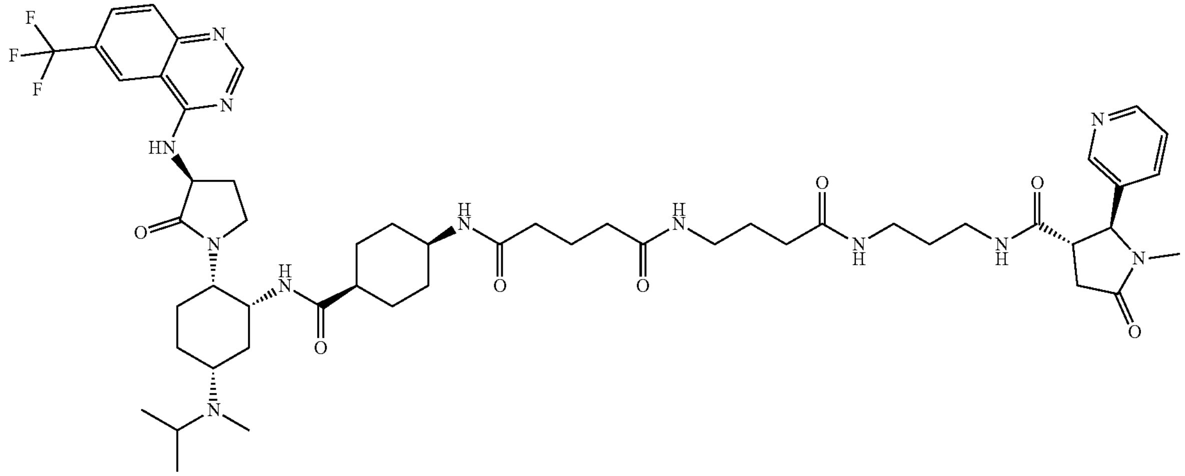
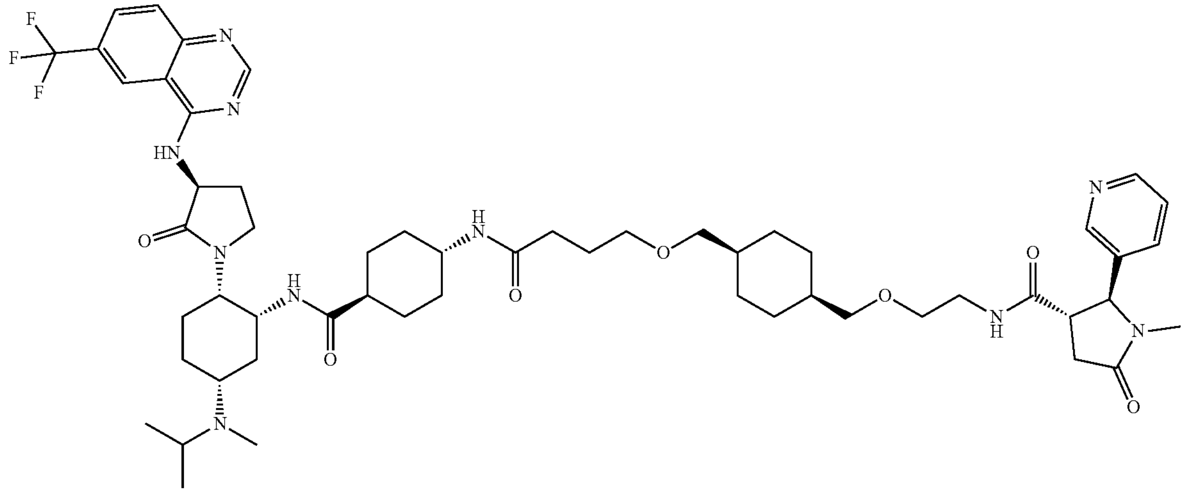
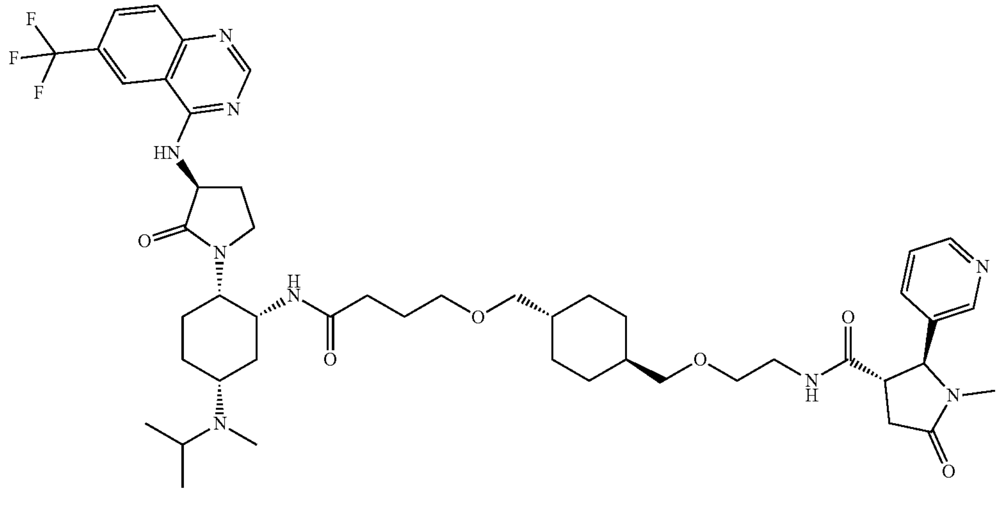

-continued
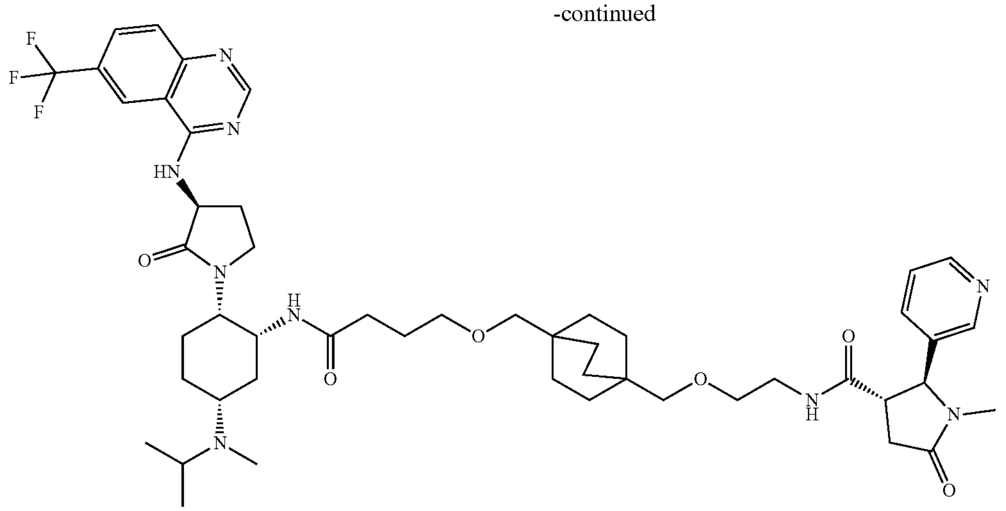
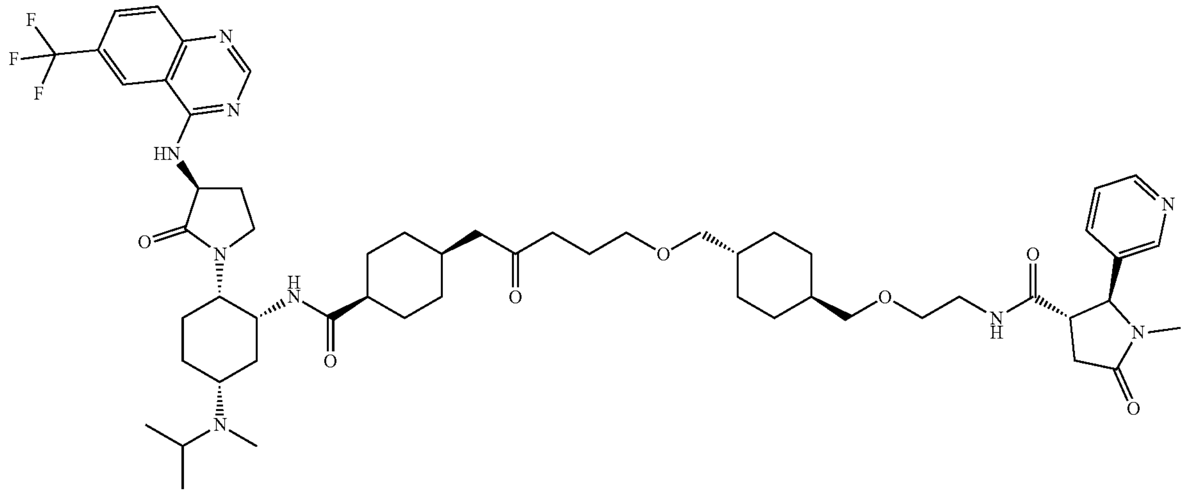
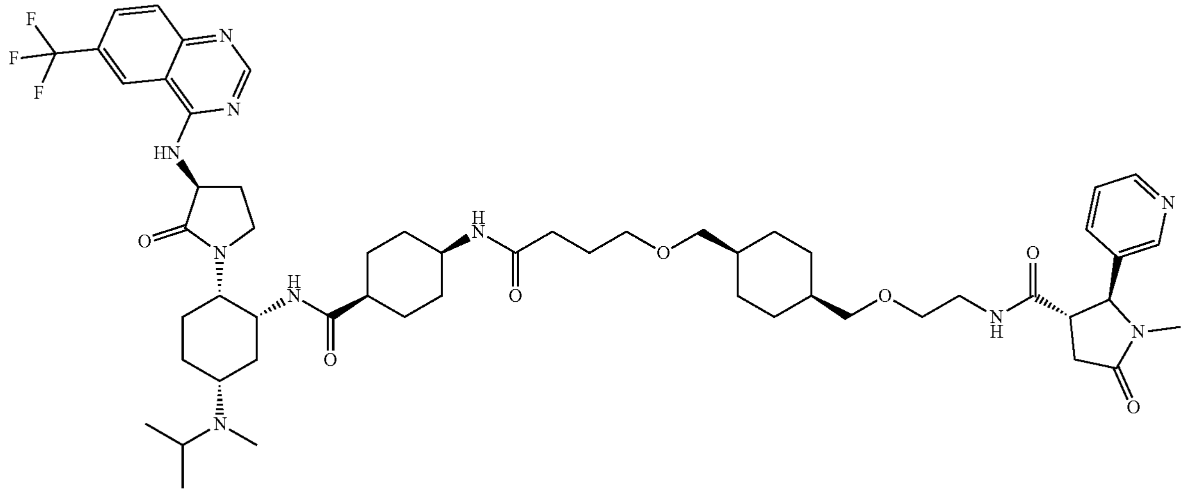

-continued
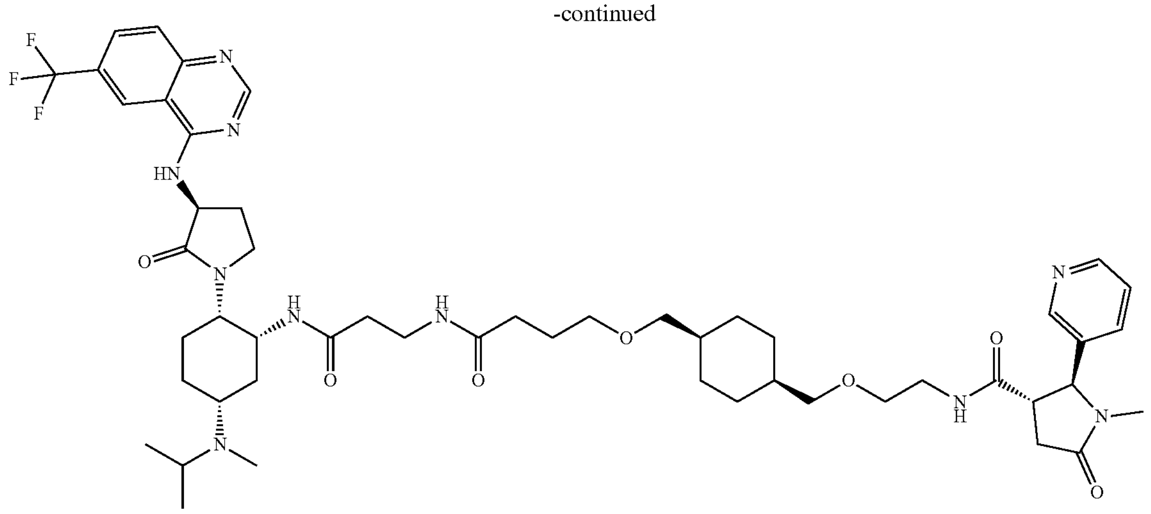
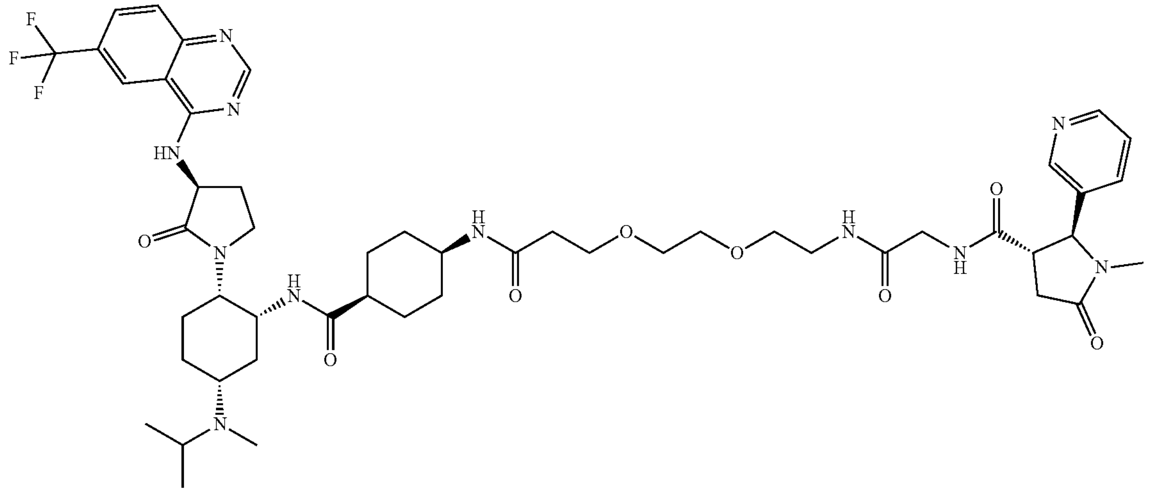
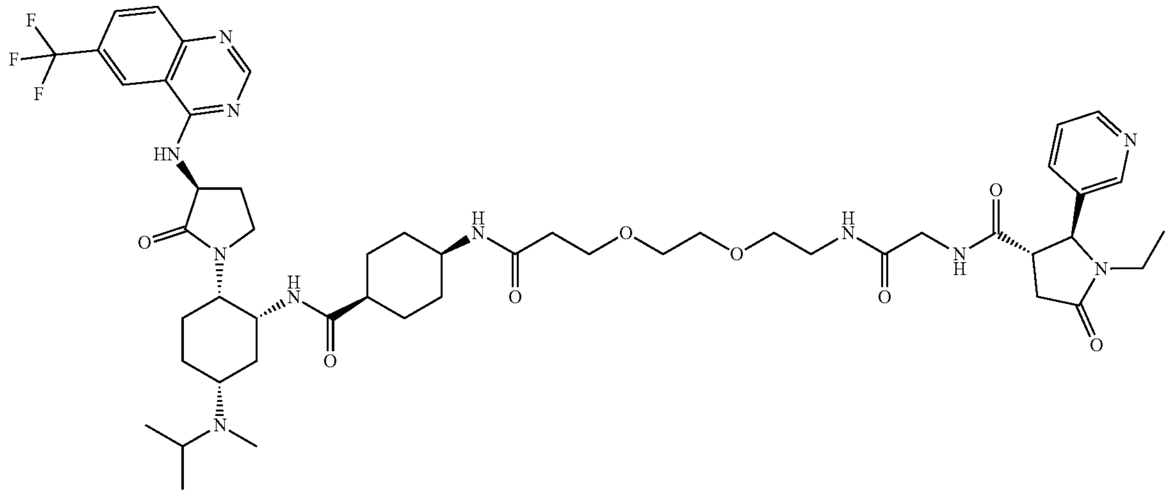

-continued
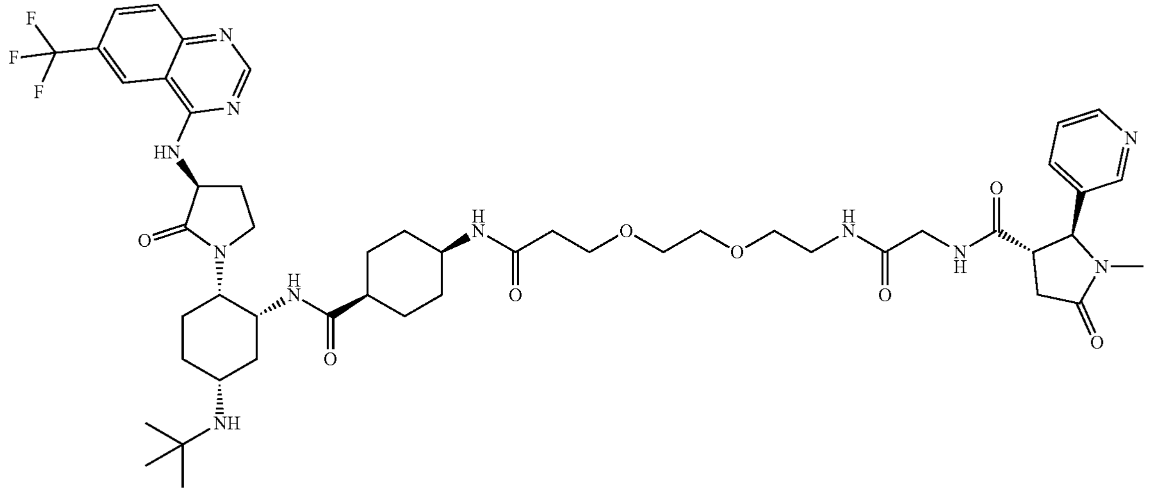
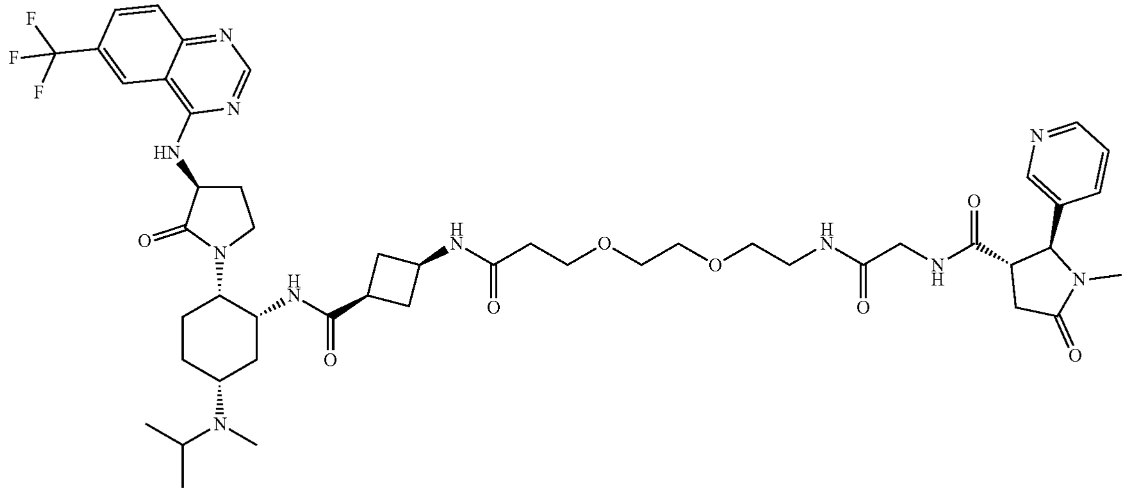
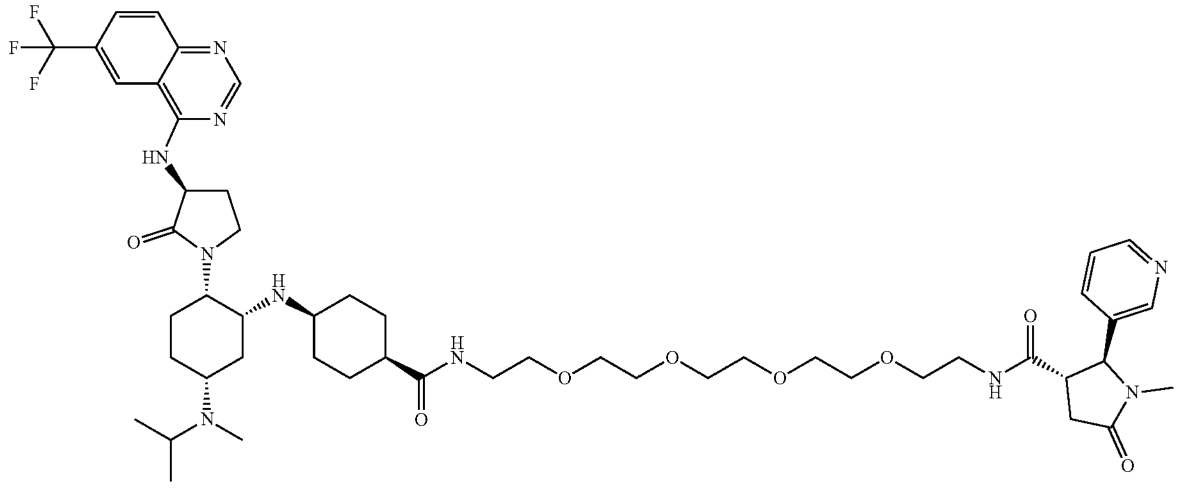

-continued
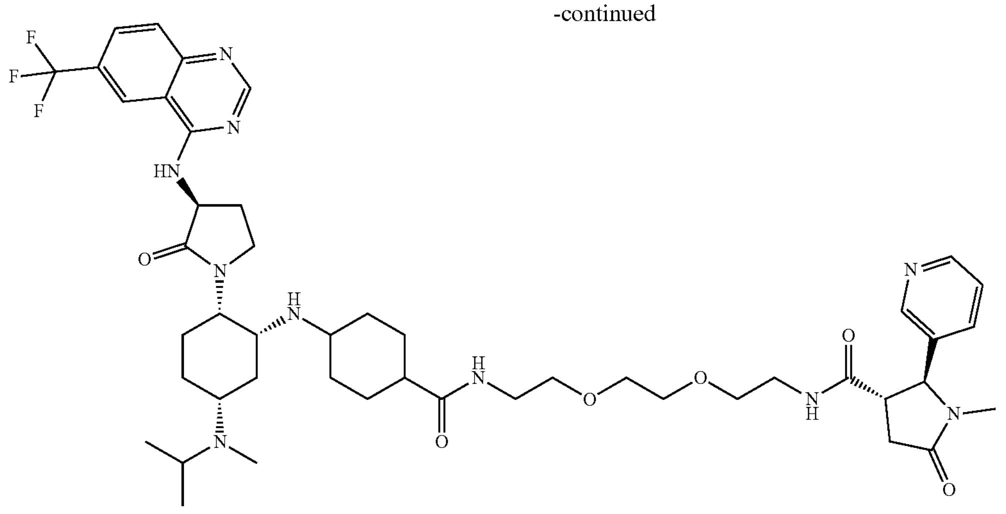
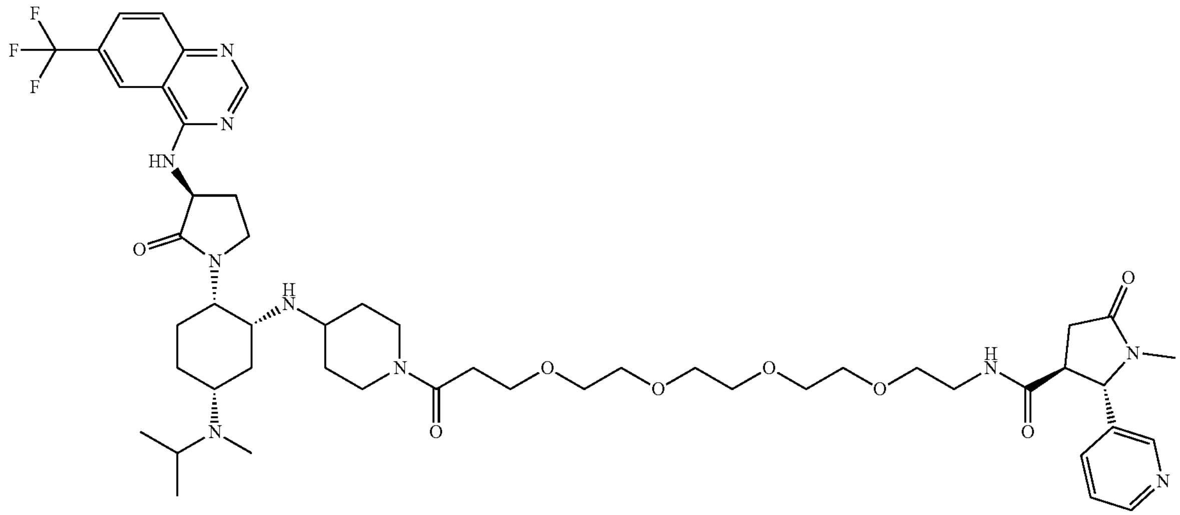
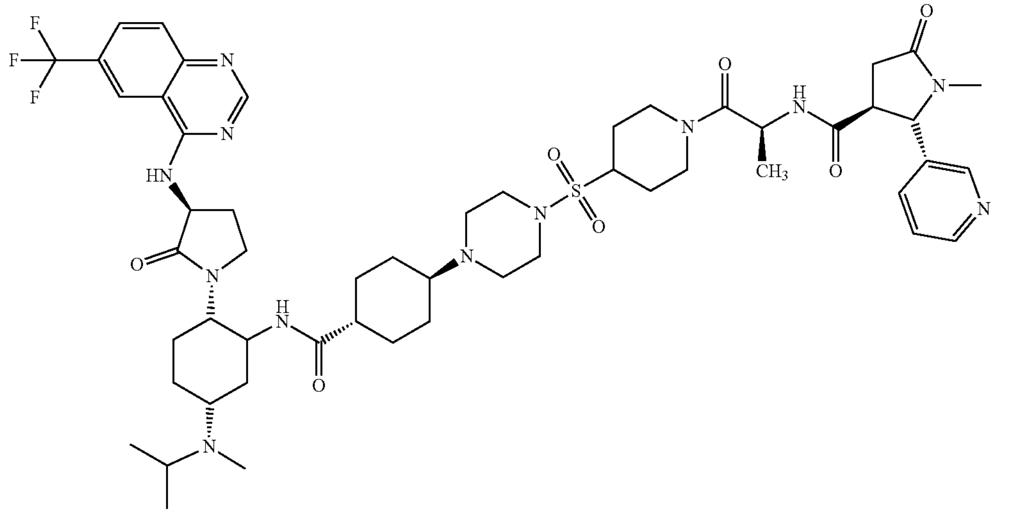

-continued
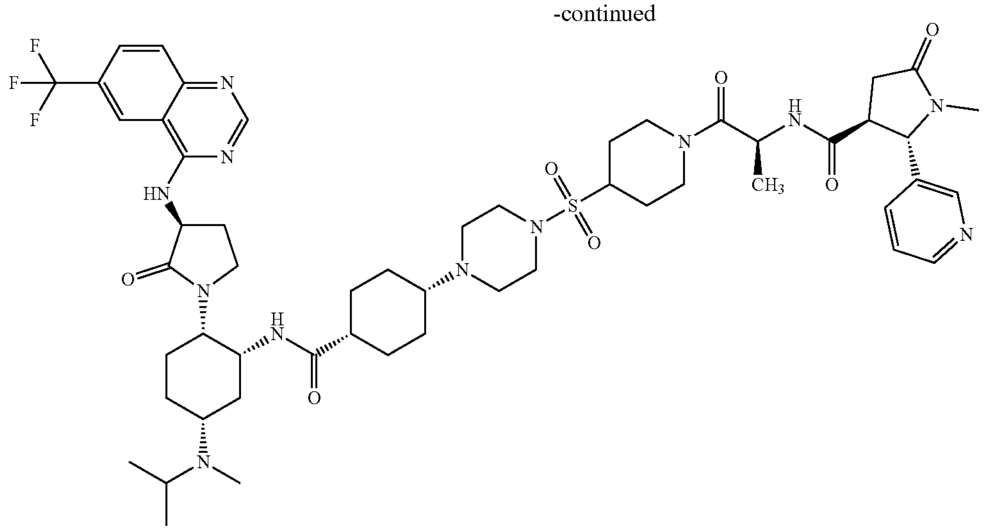
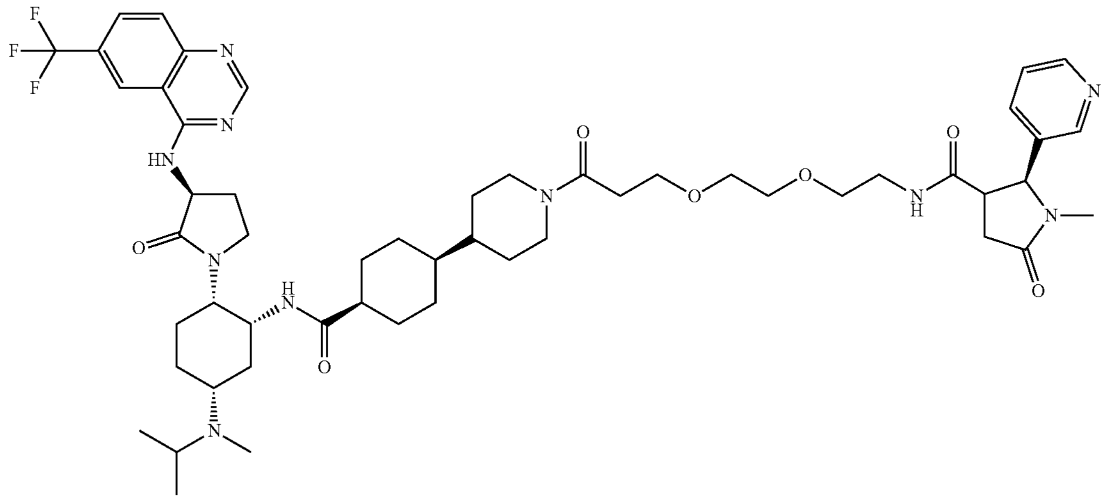
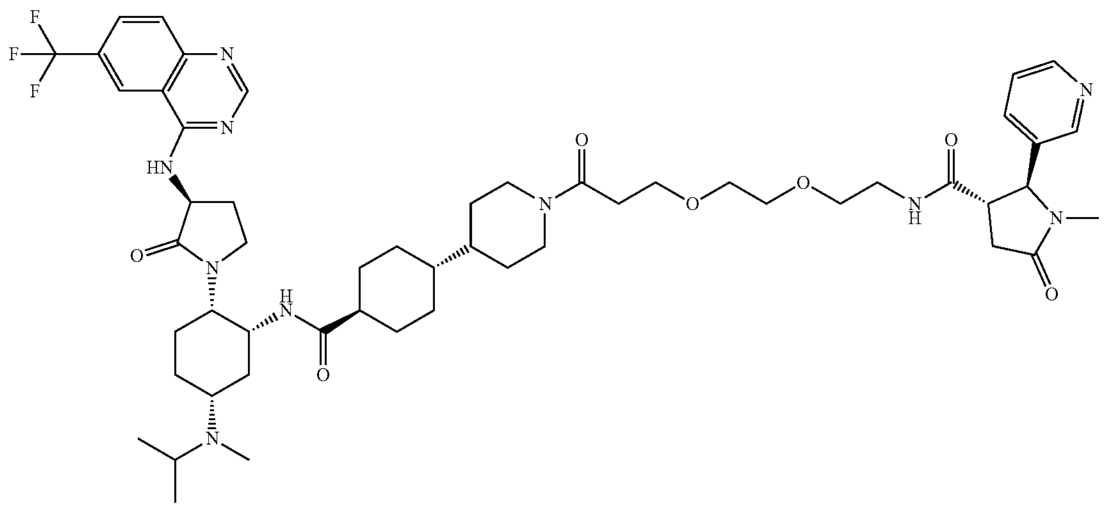

-continued
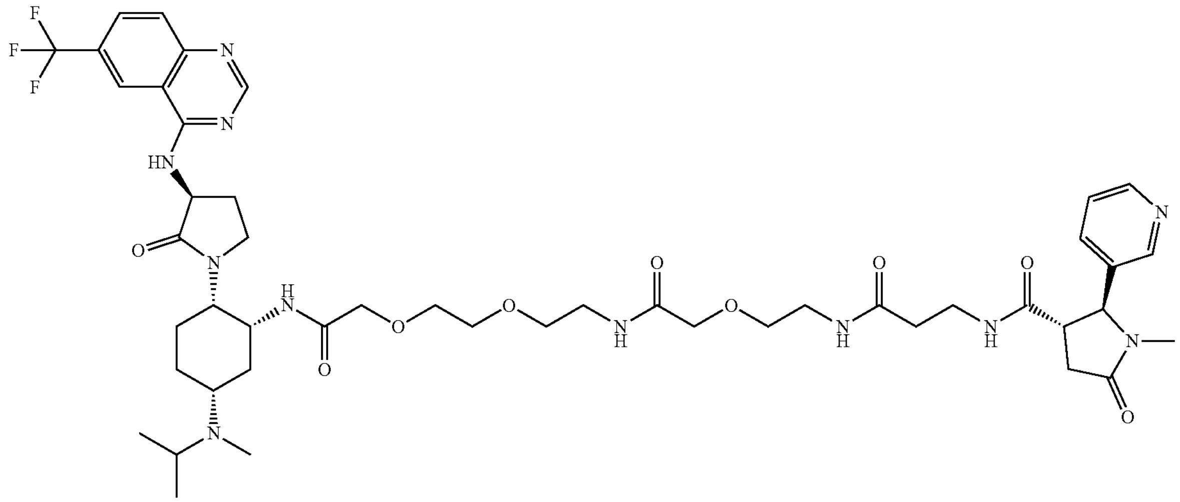
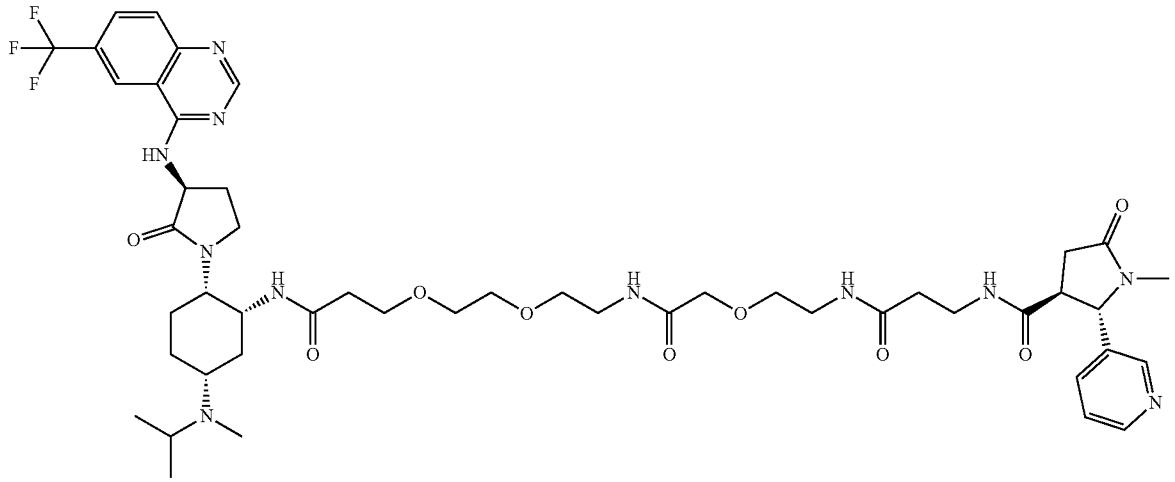
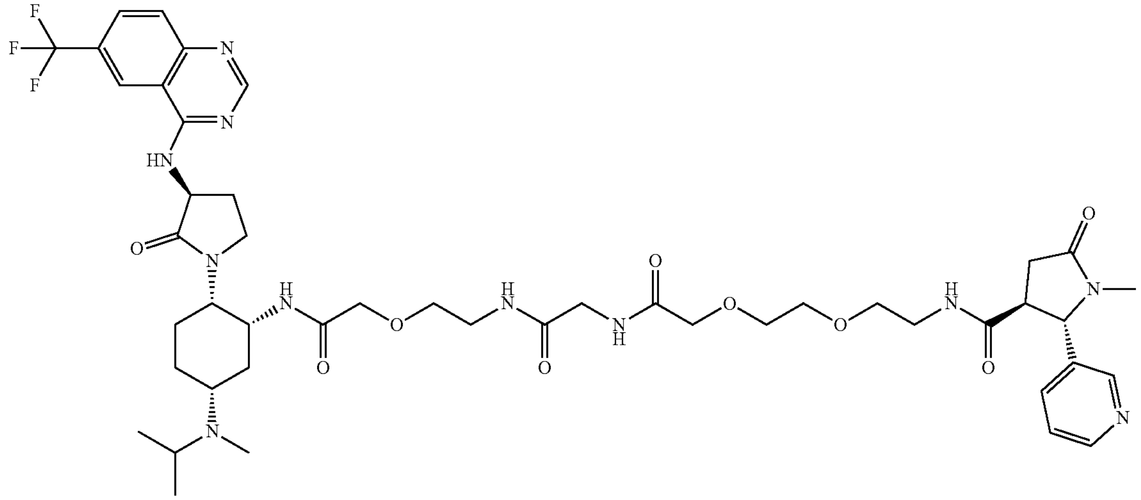

-continued
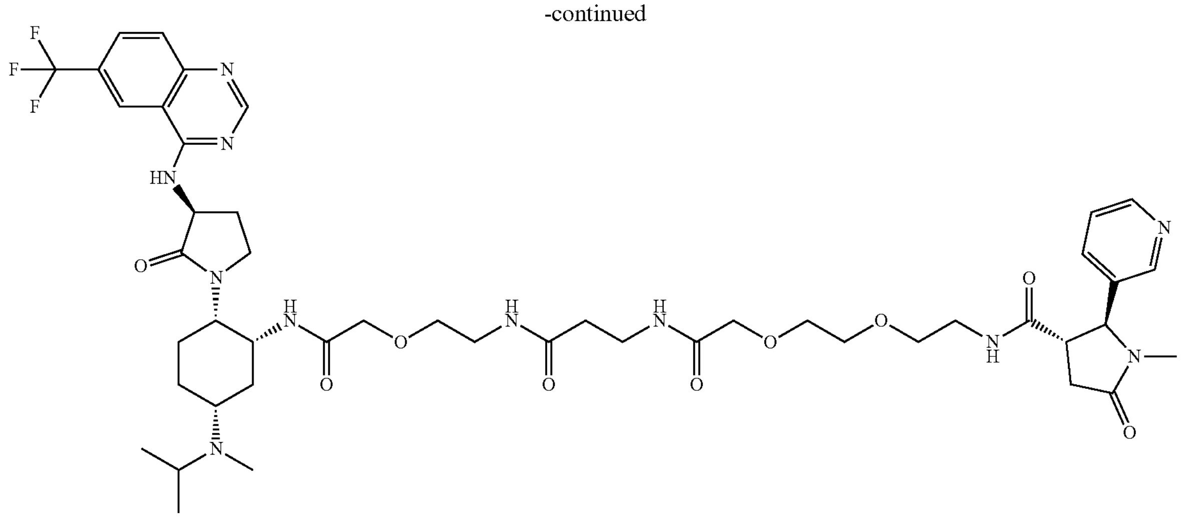
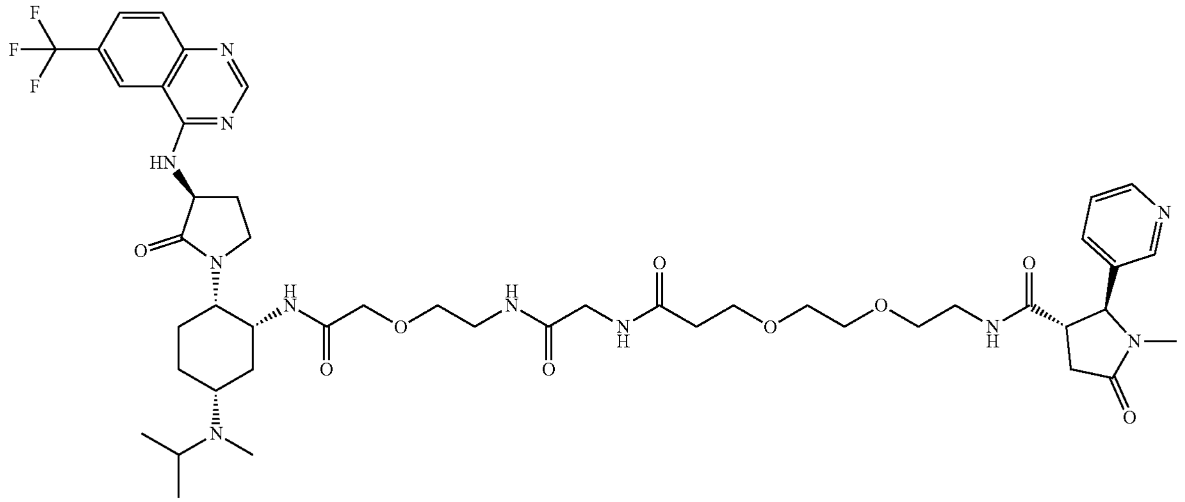
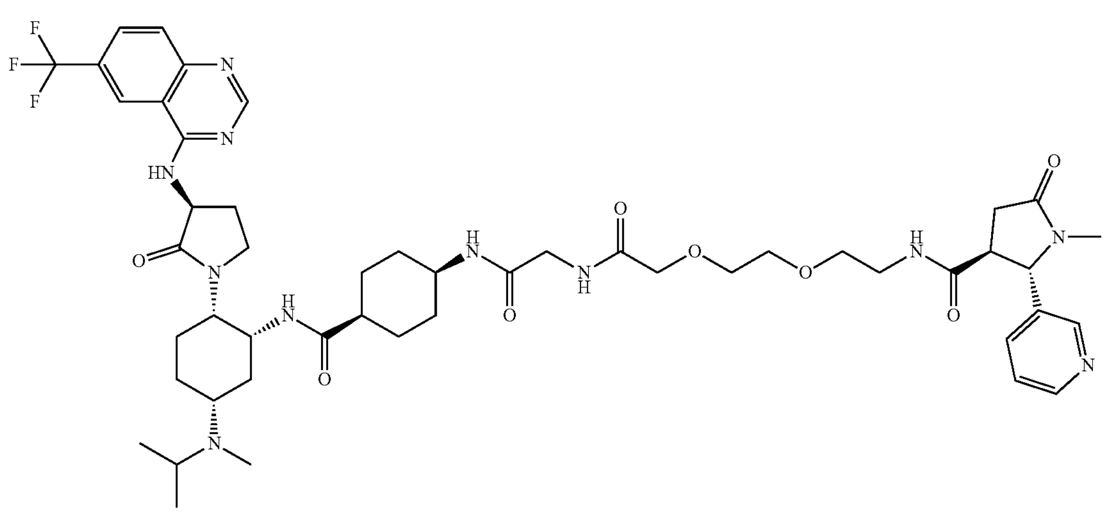

-continued
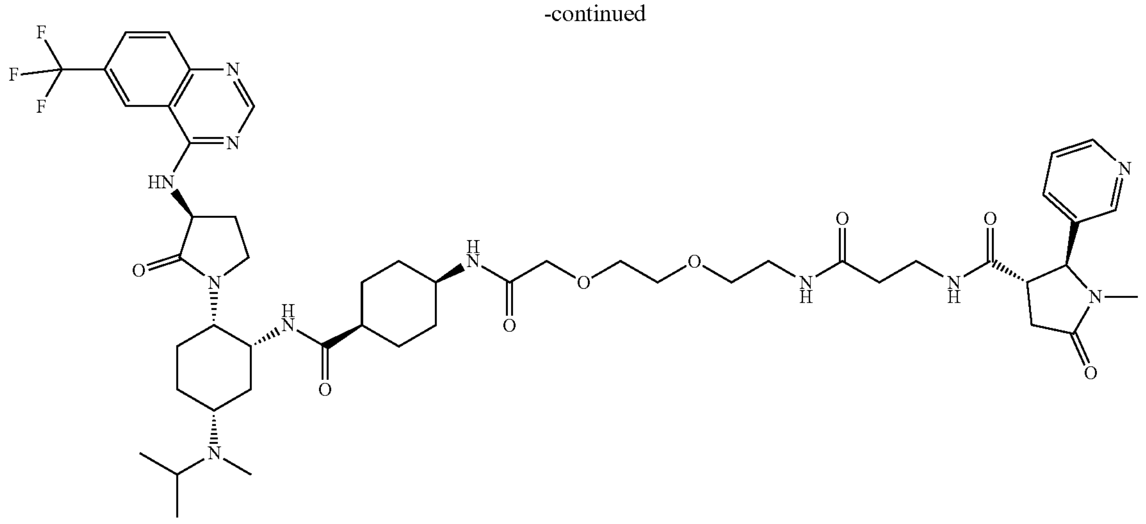
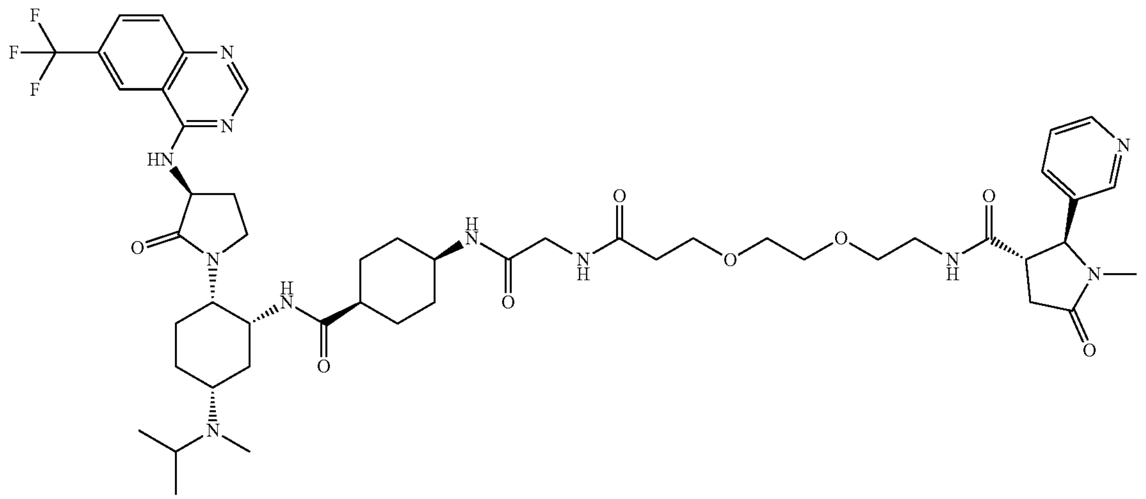
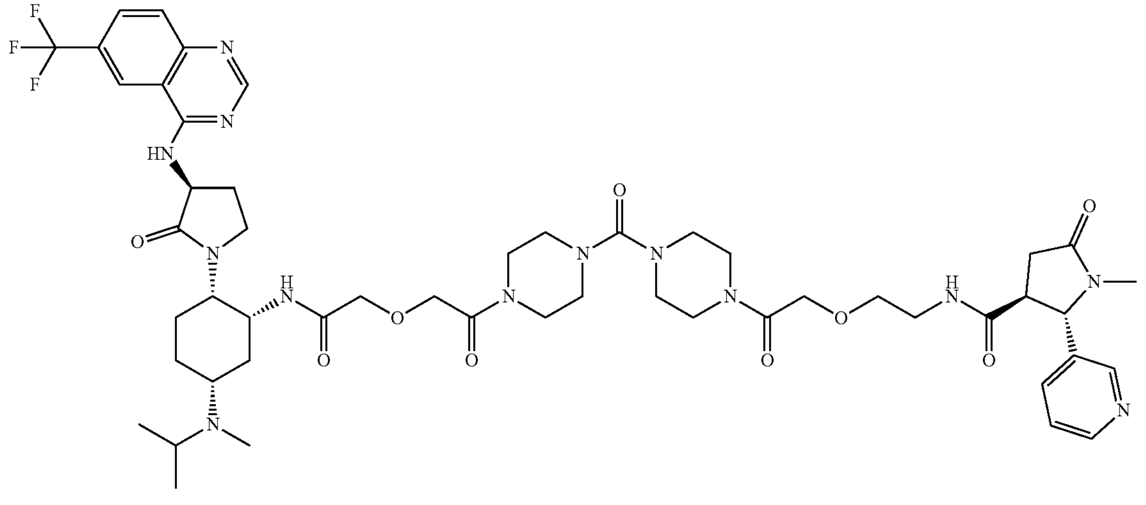

-continued
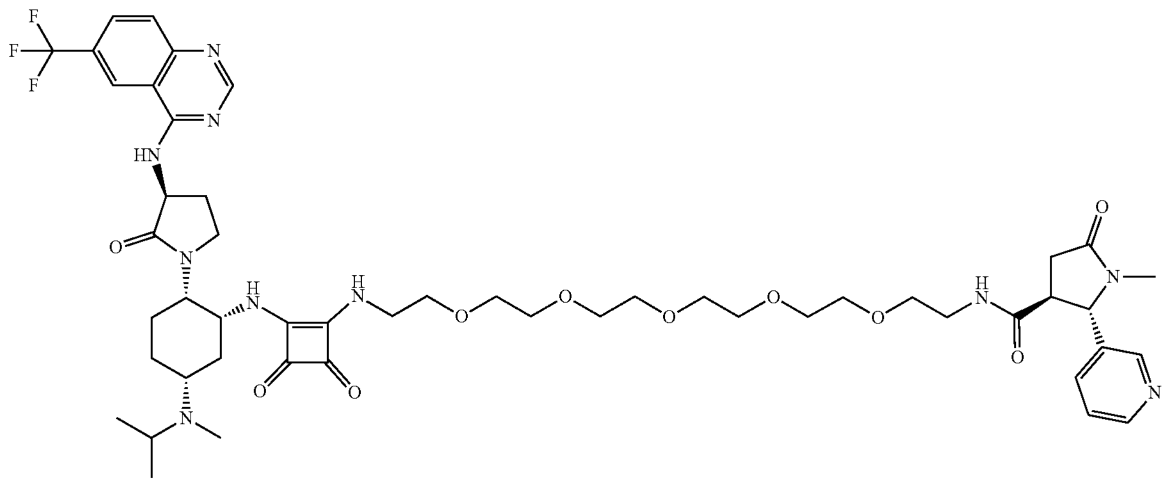
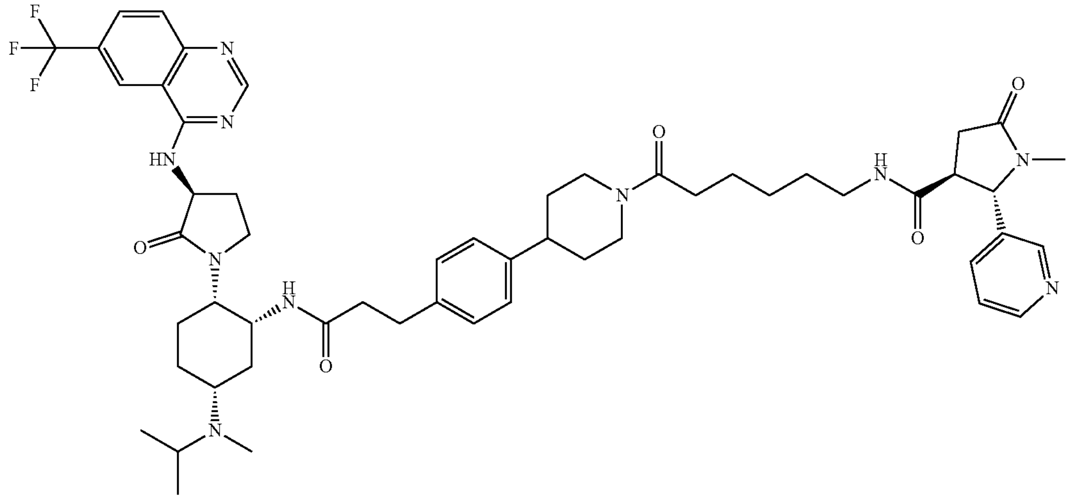
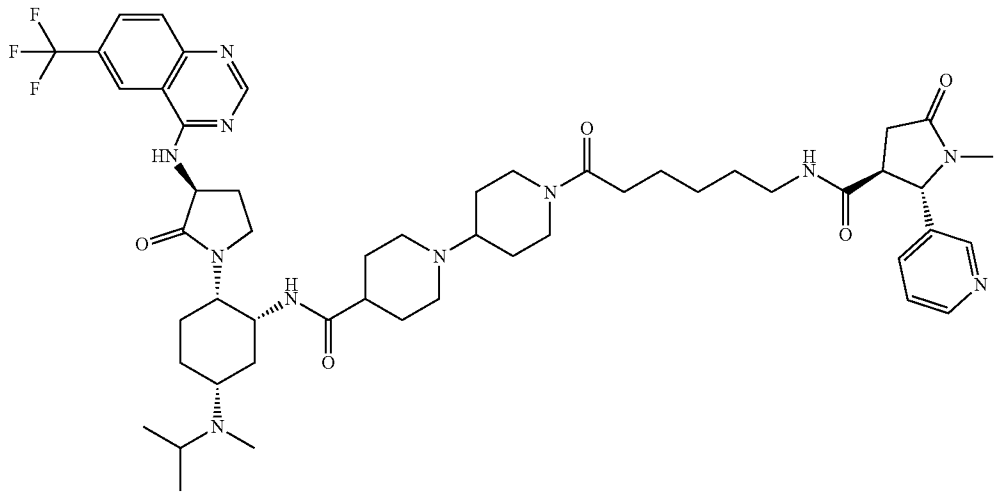

-continued
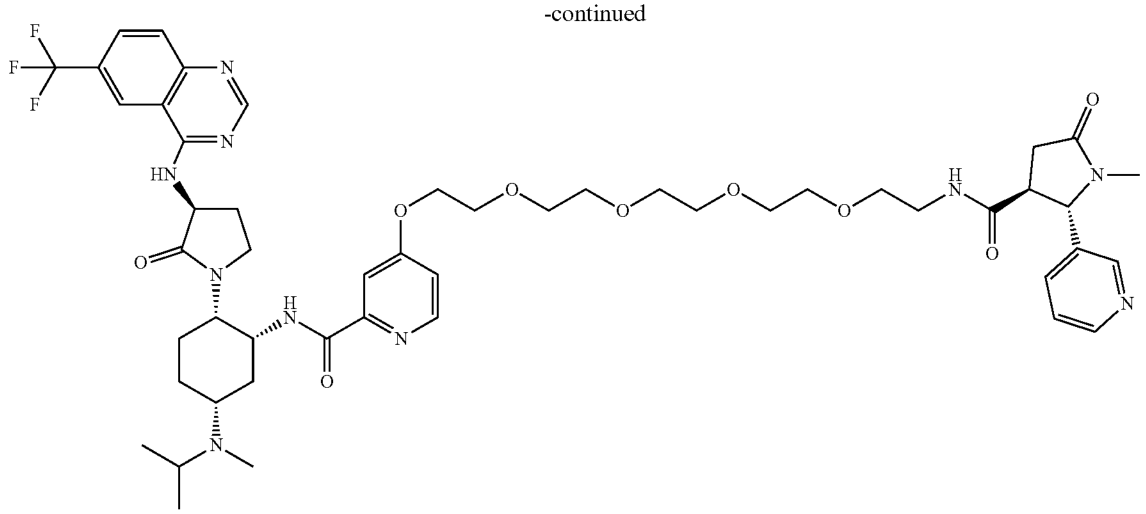
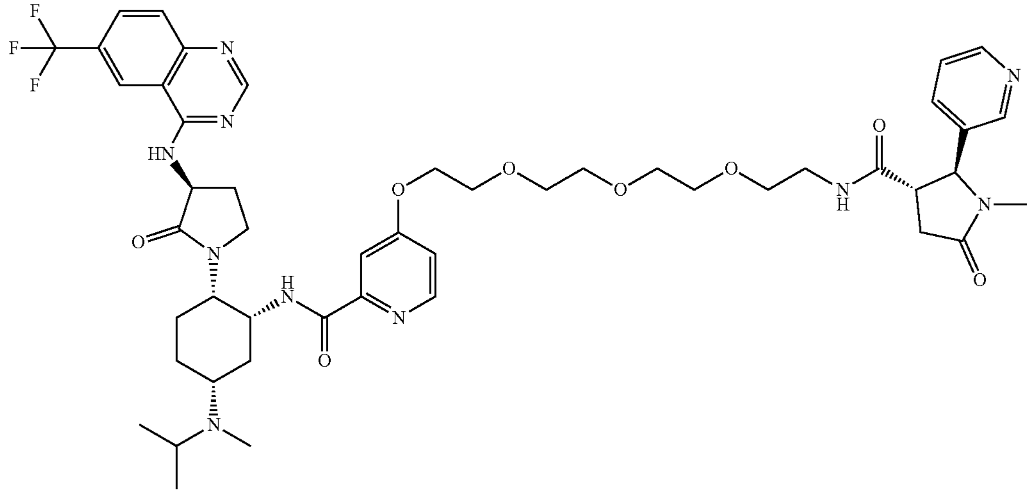
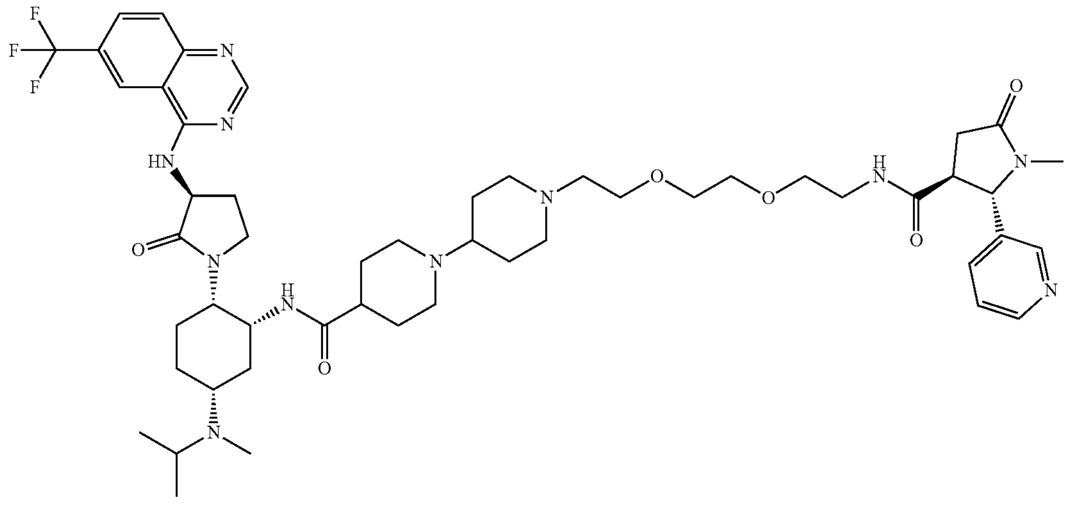

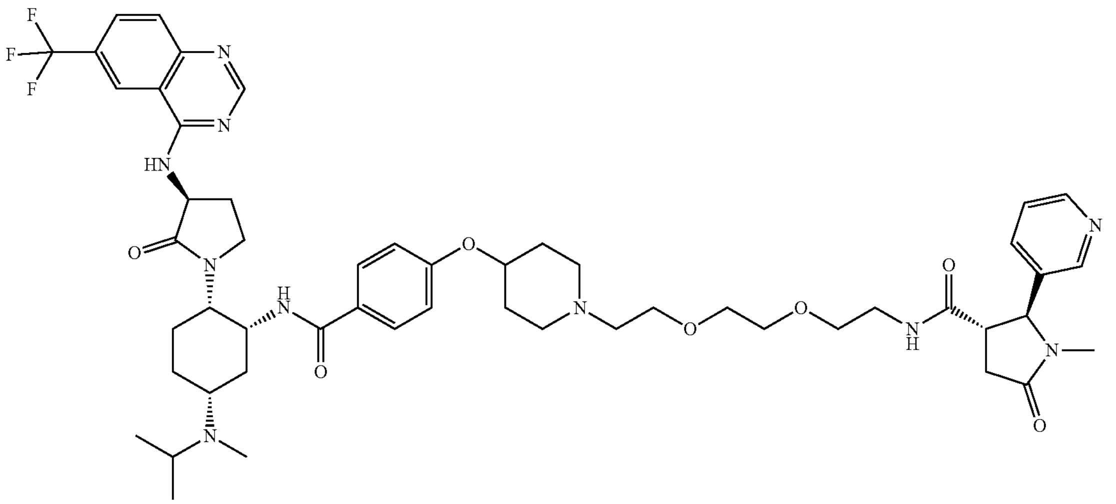
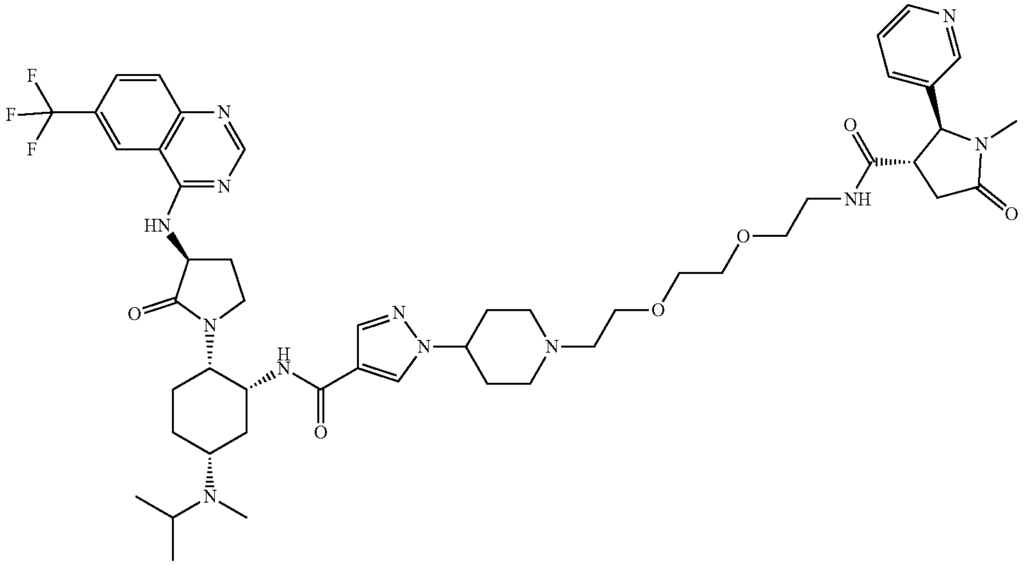
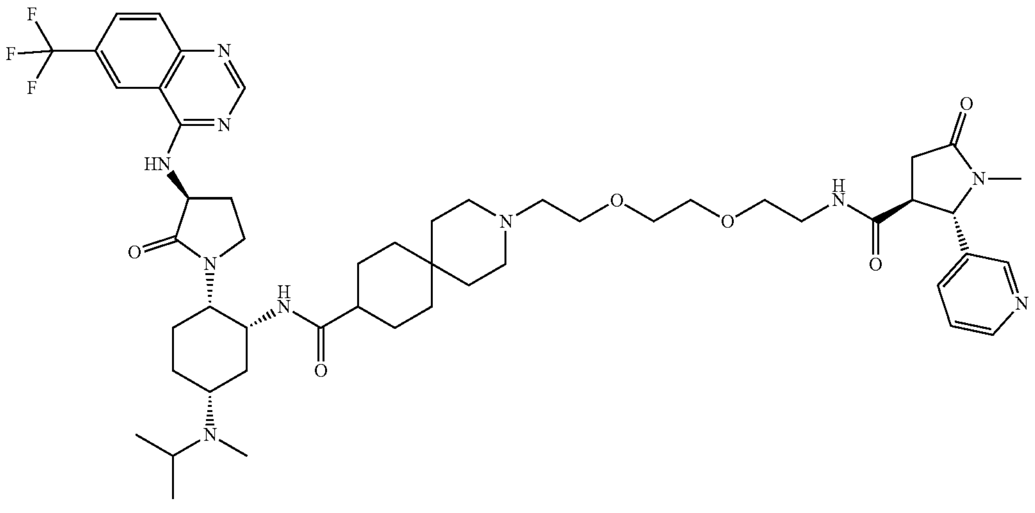

-continued
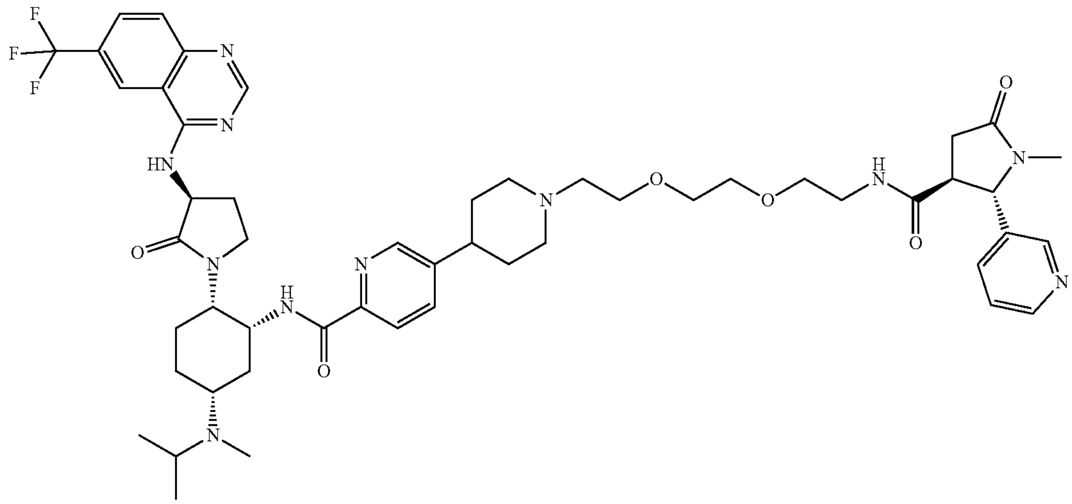
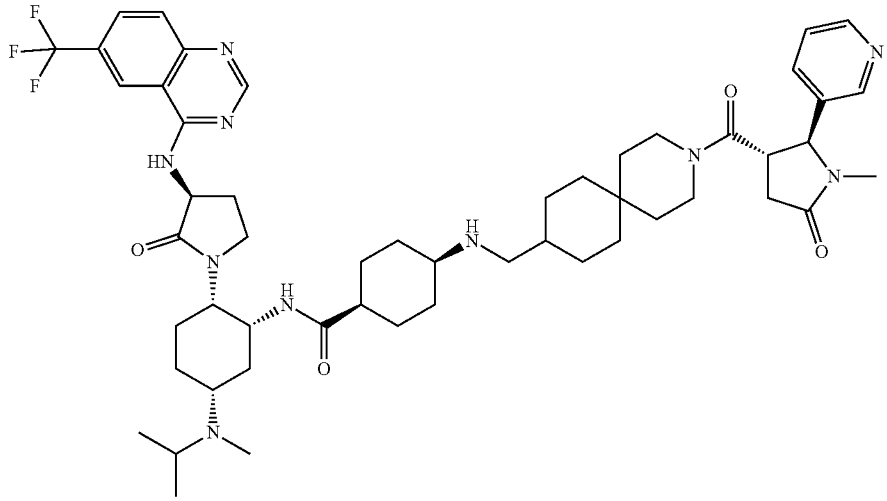
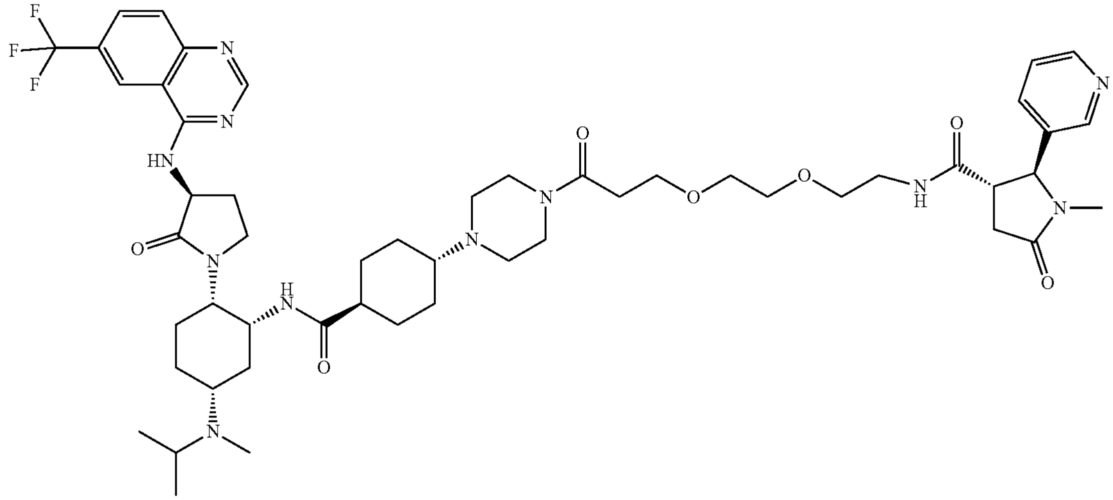

-continued
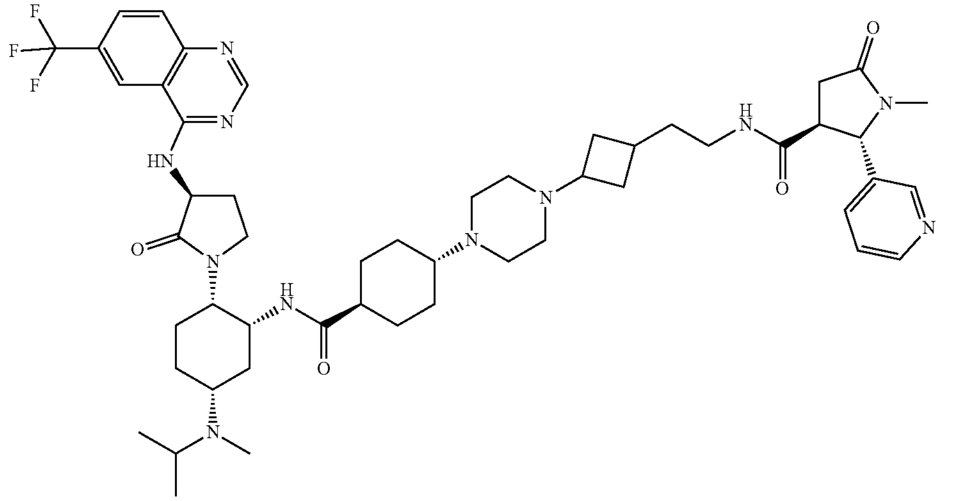
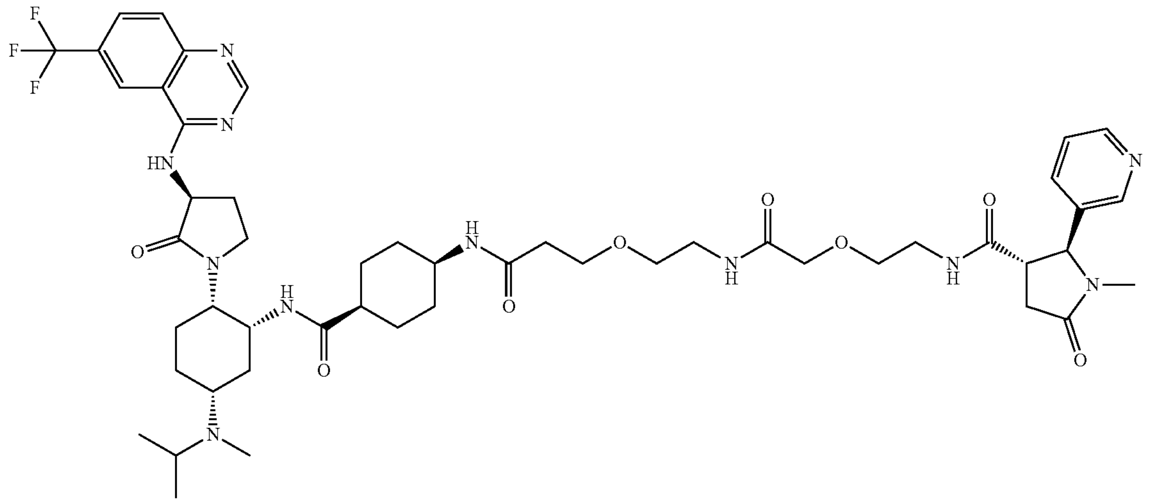
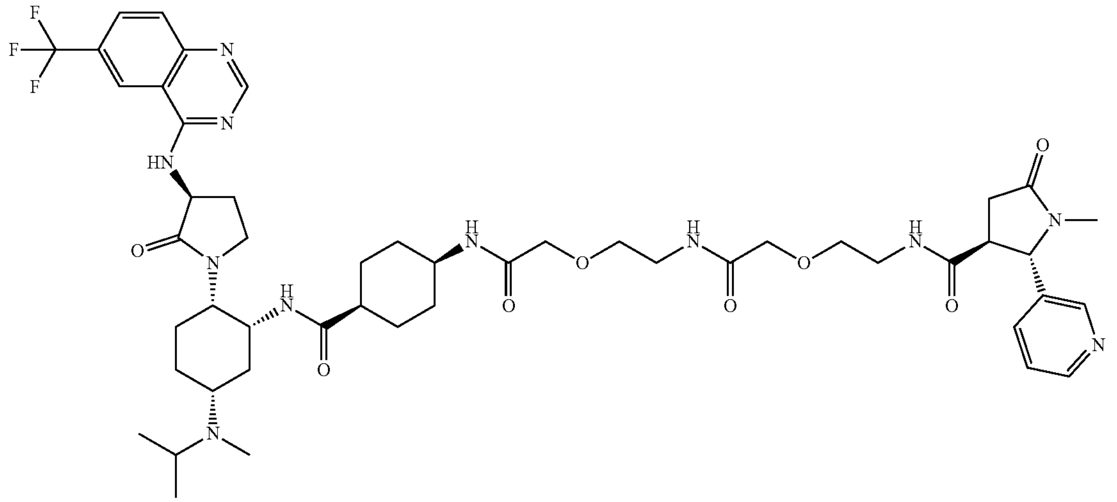

-continued
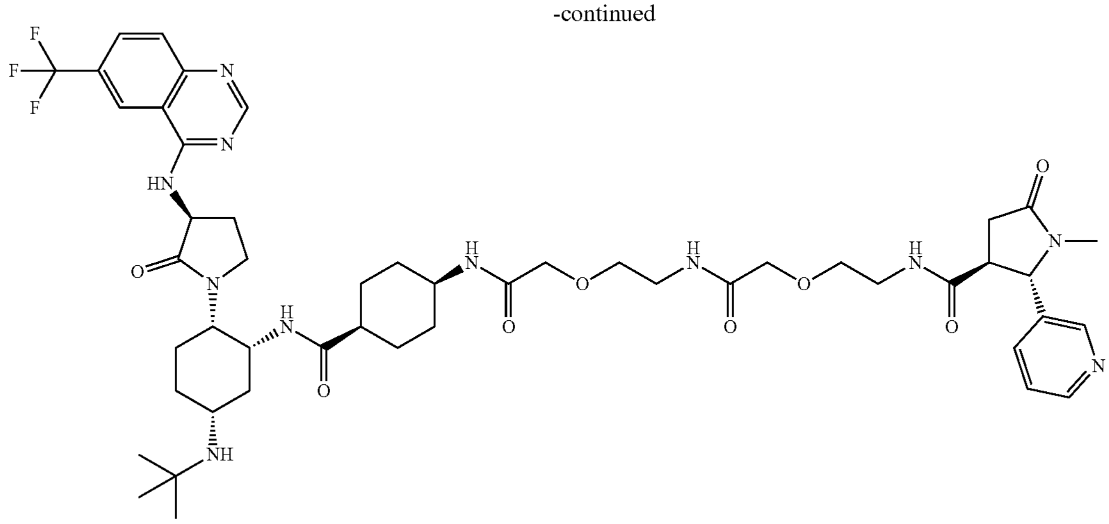
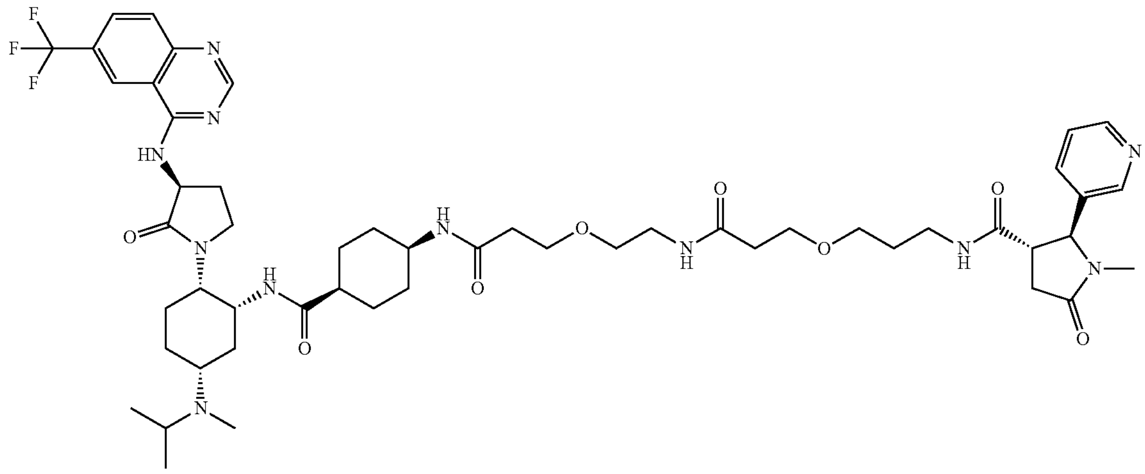
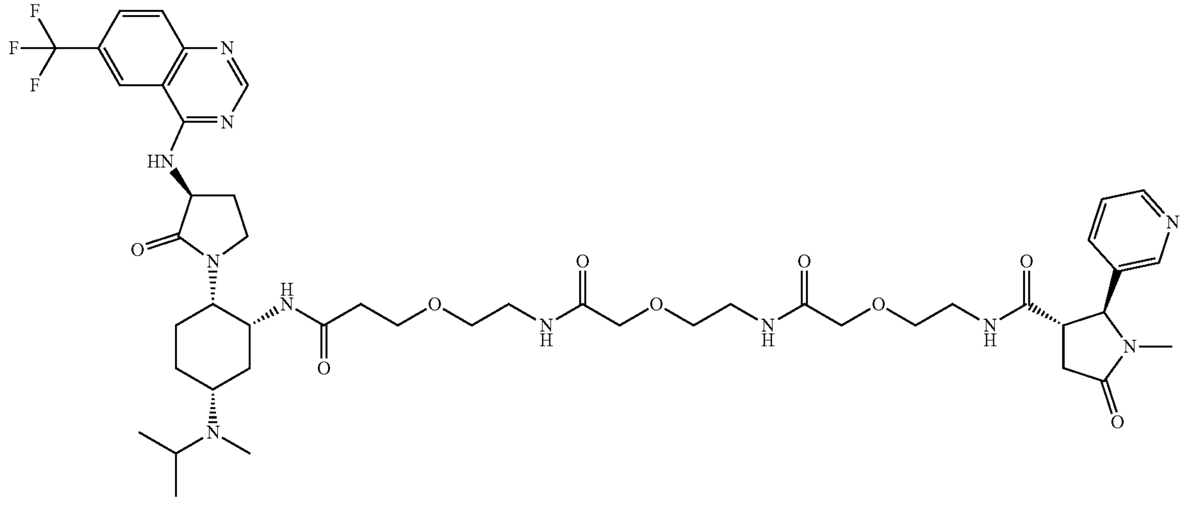

-continued
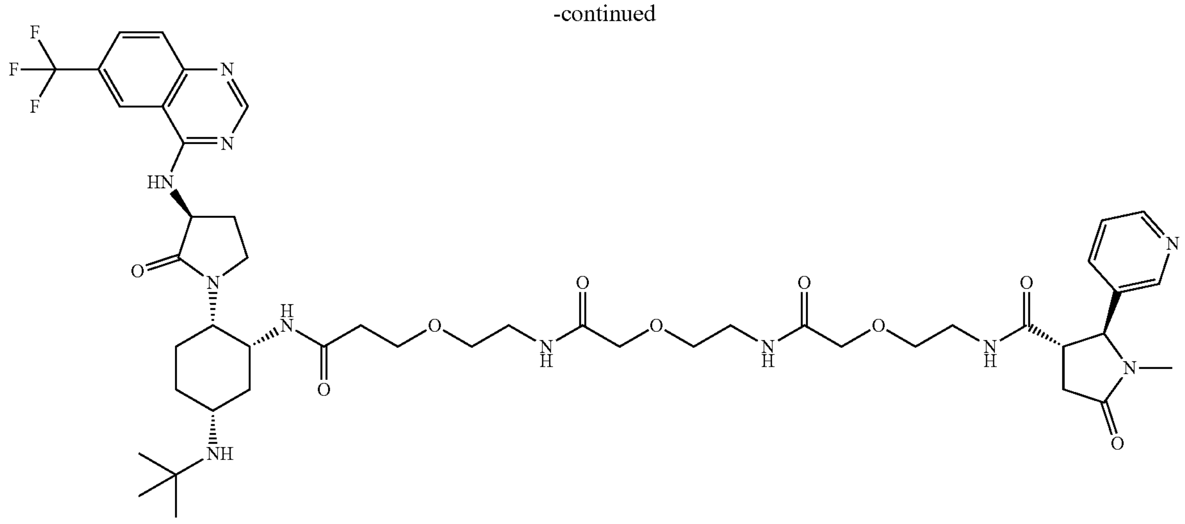
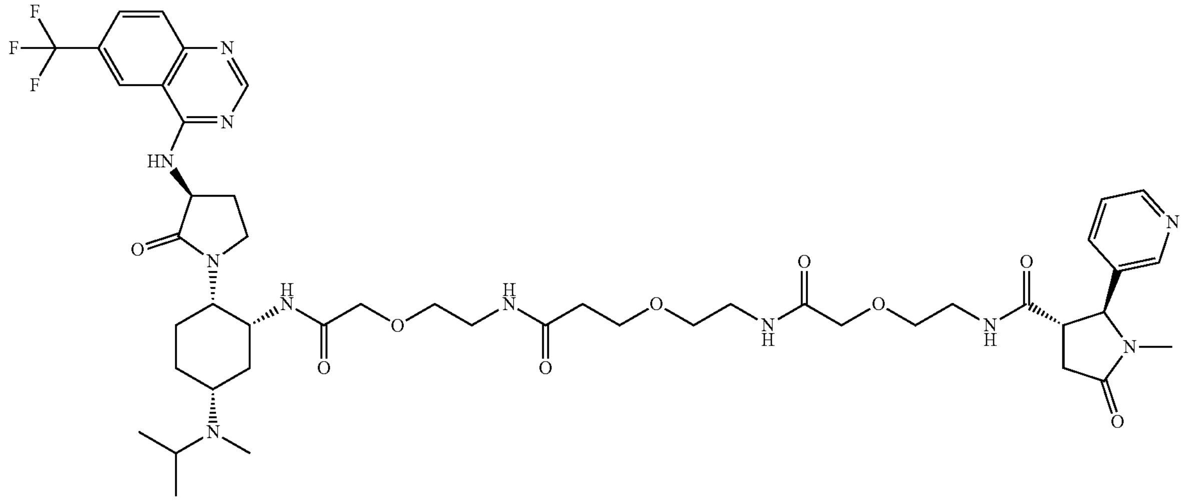
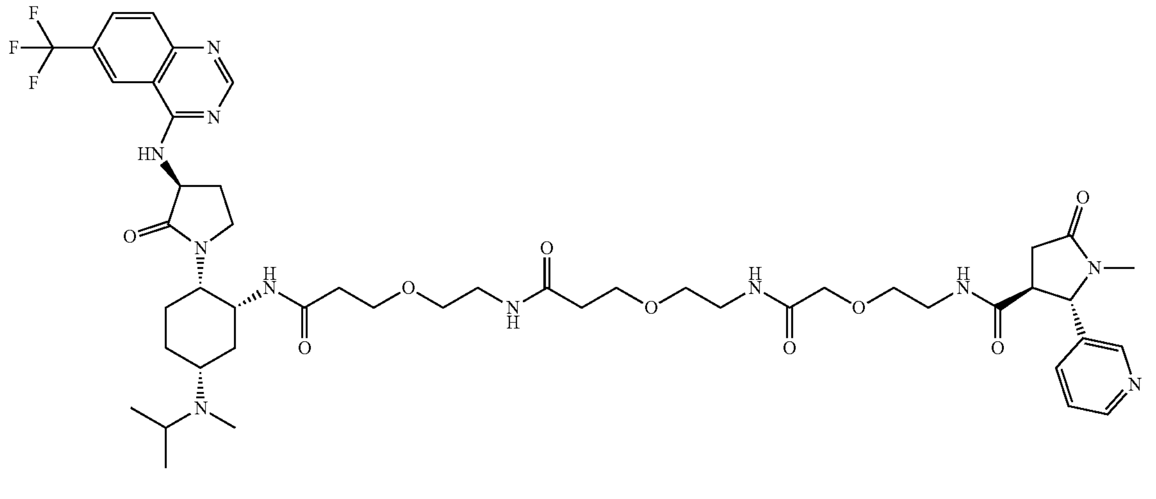

-continued
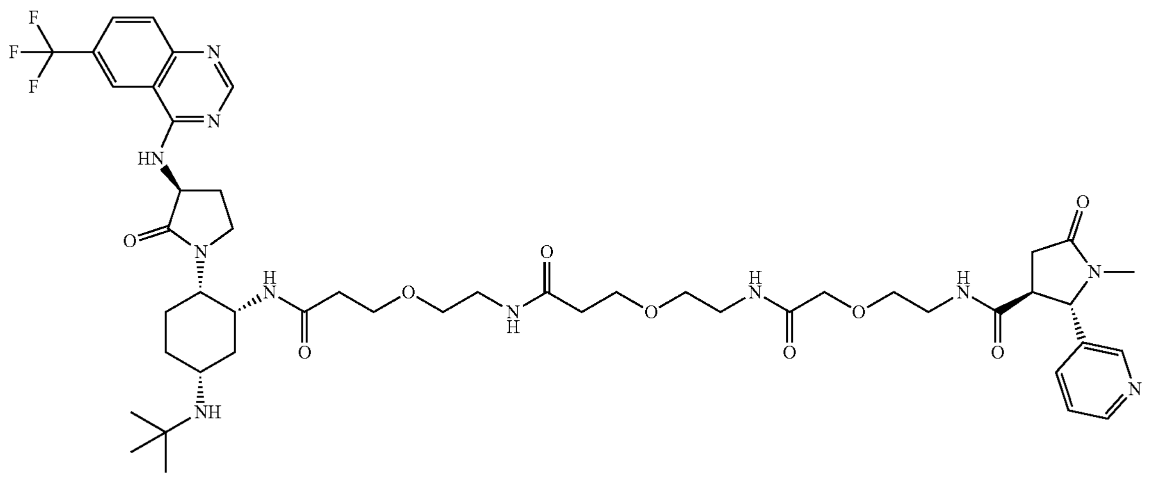
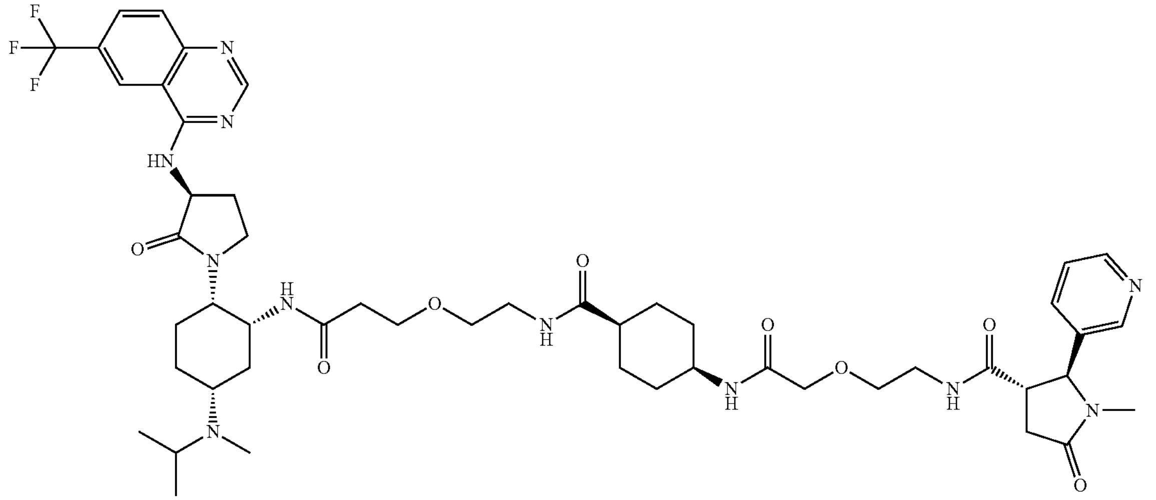
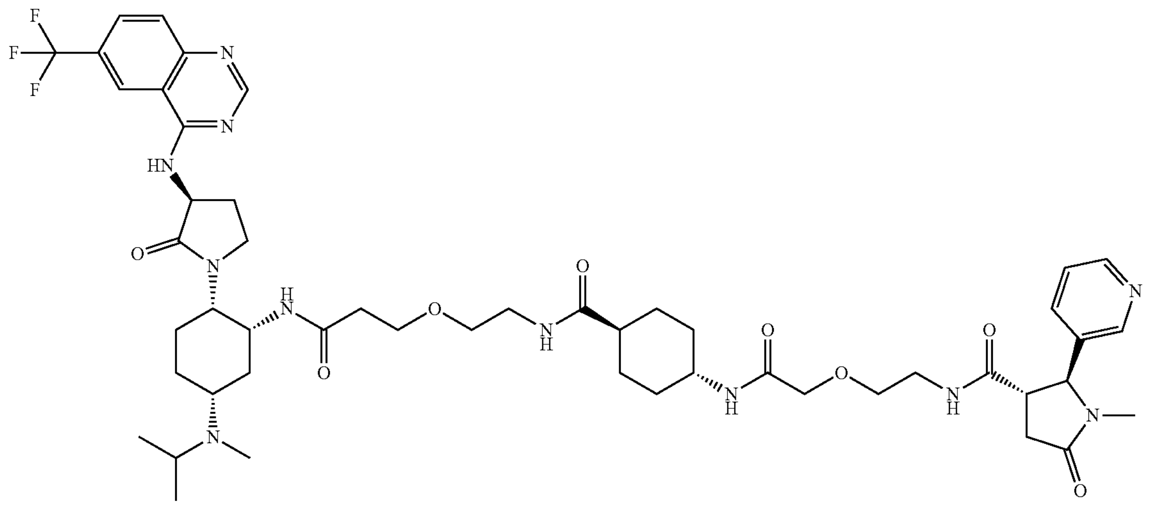

-continued
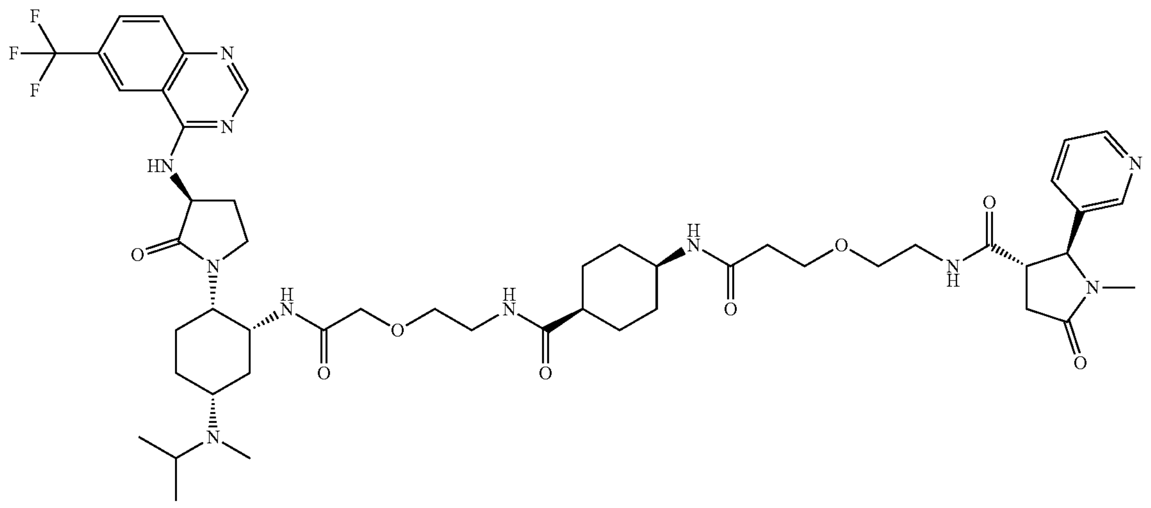 [SMILES: CC(C)N(C)[C@@H]1CC[C@H](N2CC[C@H](Nc3ncnc4ccc(C(F)(F)F)cc34)C2=O)[C@H](NC(=O)COCCNC(=O)[C@H]2CC[C@@H](NC(=O)CCOCCNC(=O)[C@H]3CC(=O)N(C)[C@@H]3c3cccnc3)CC2)C1]
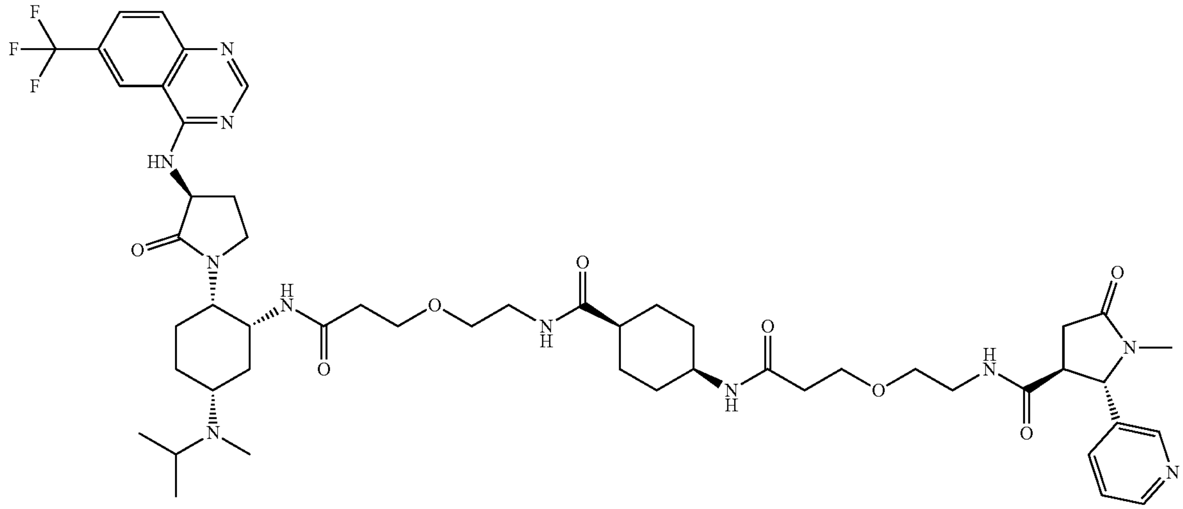
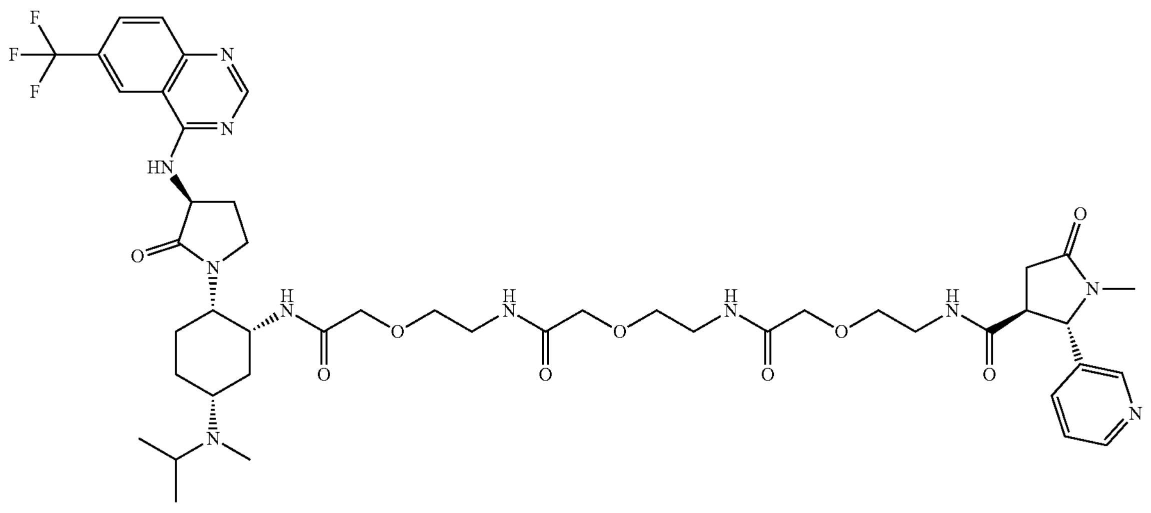

-continued
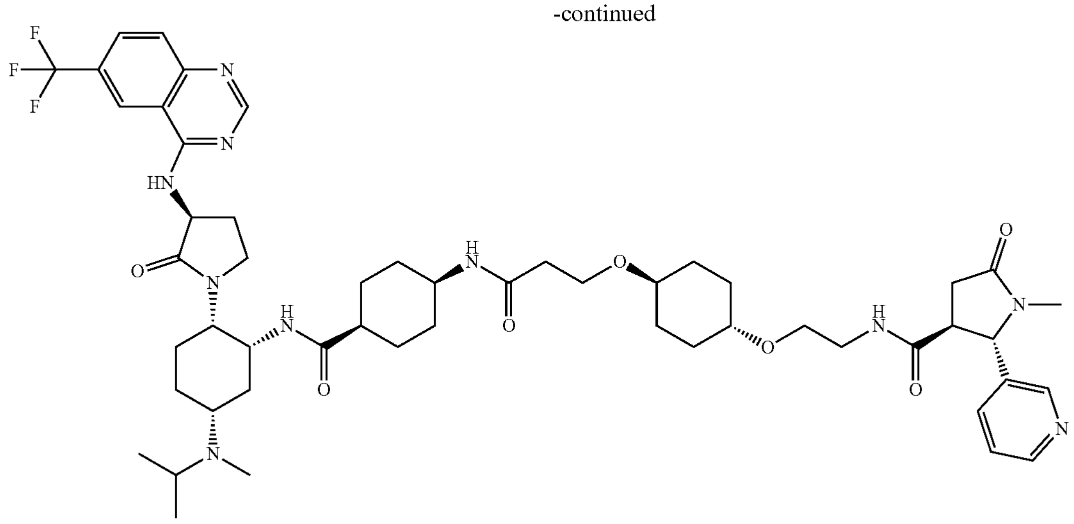
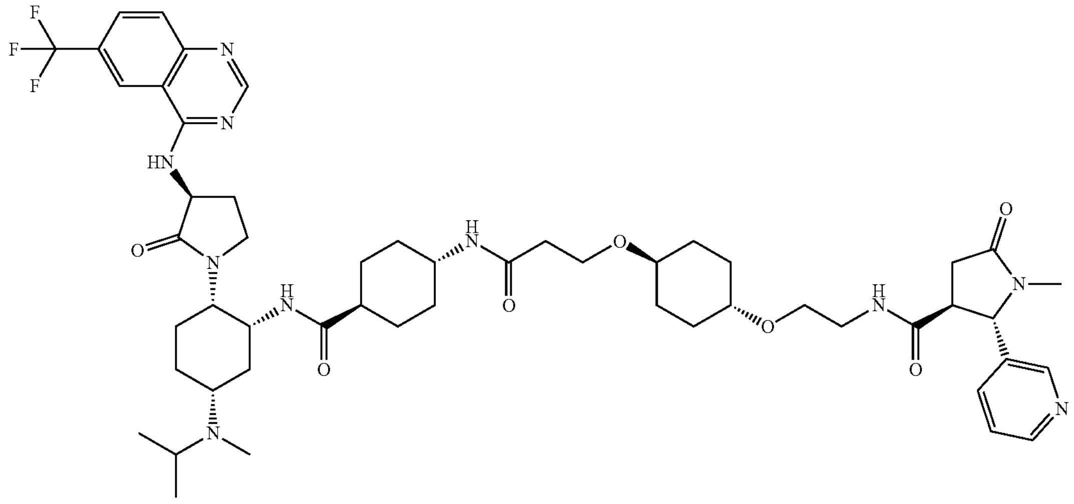
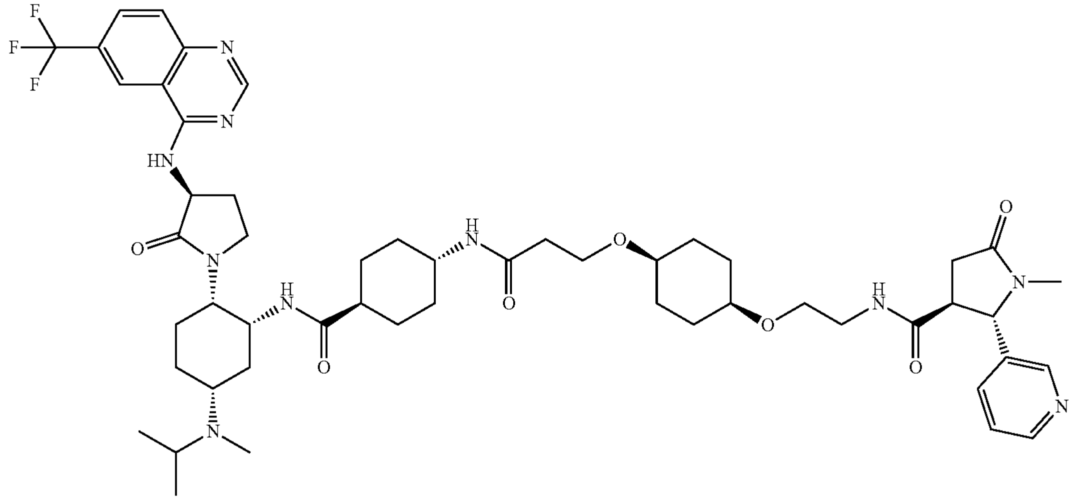

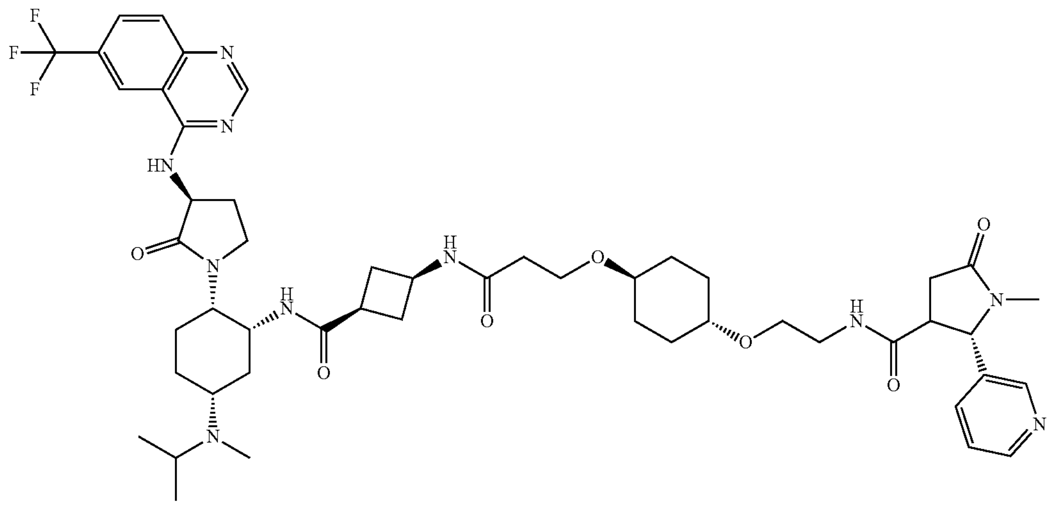
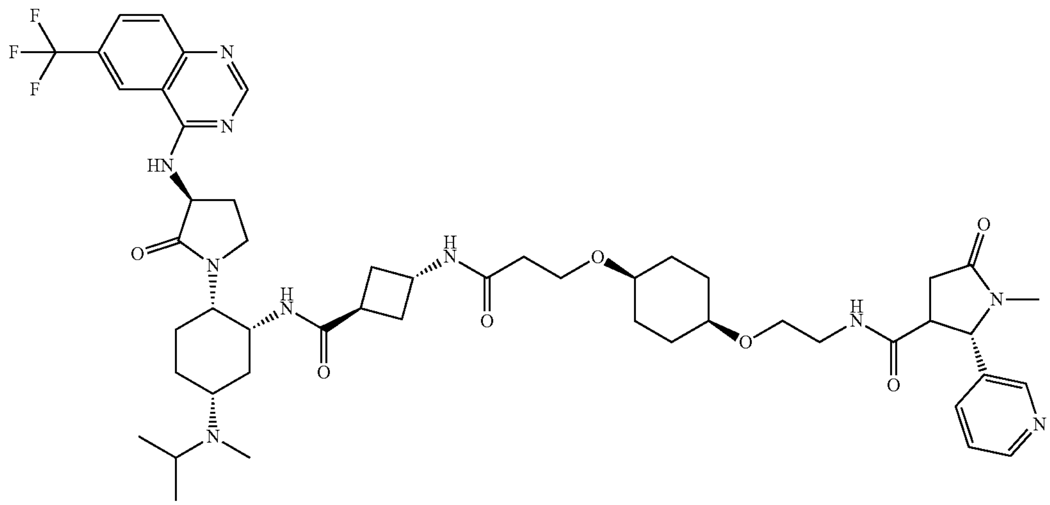
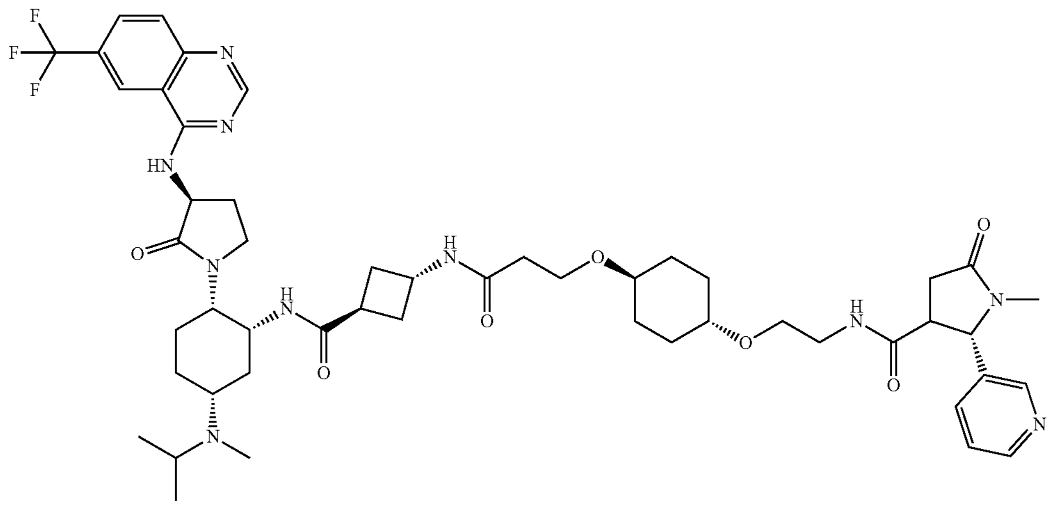

-continued
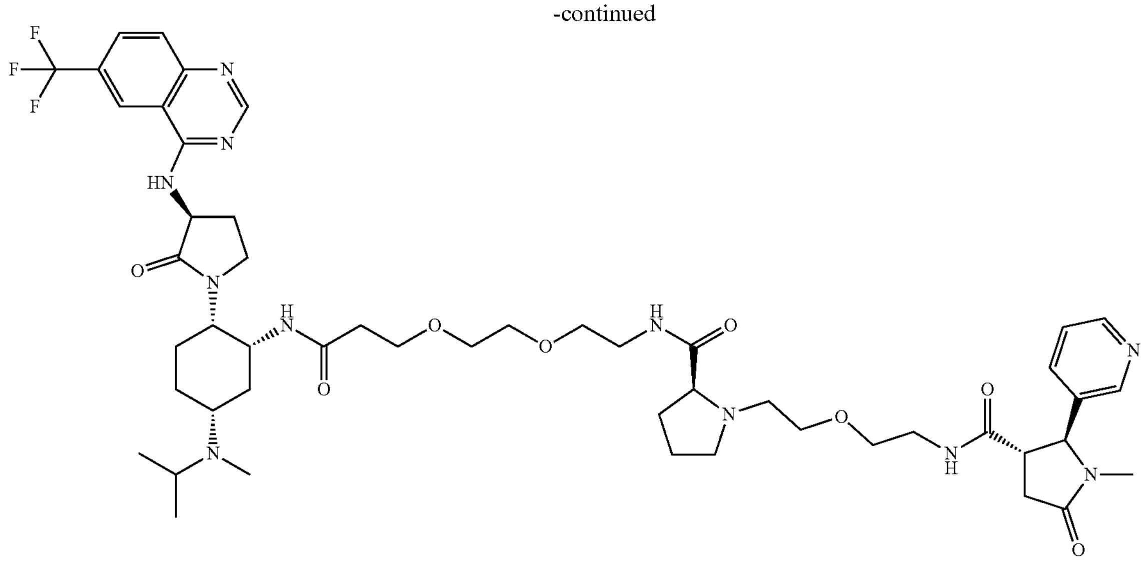
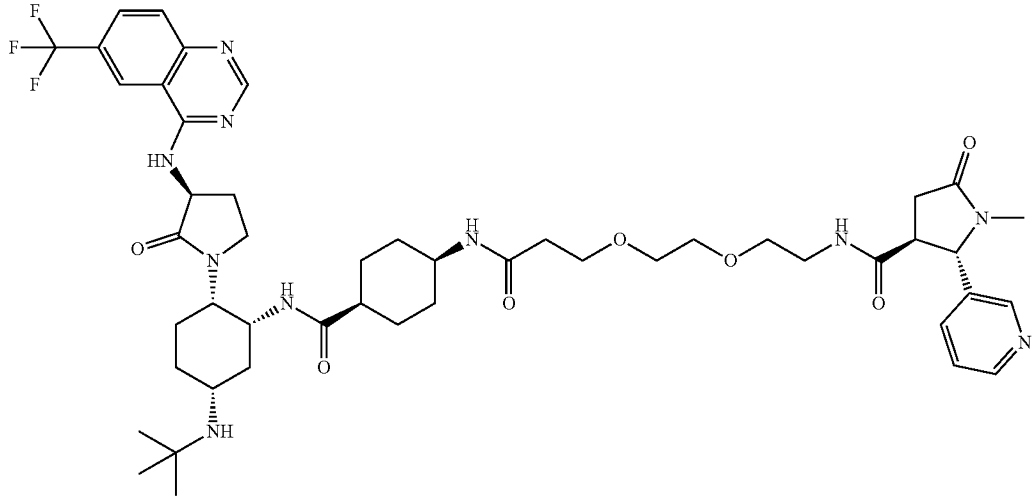
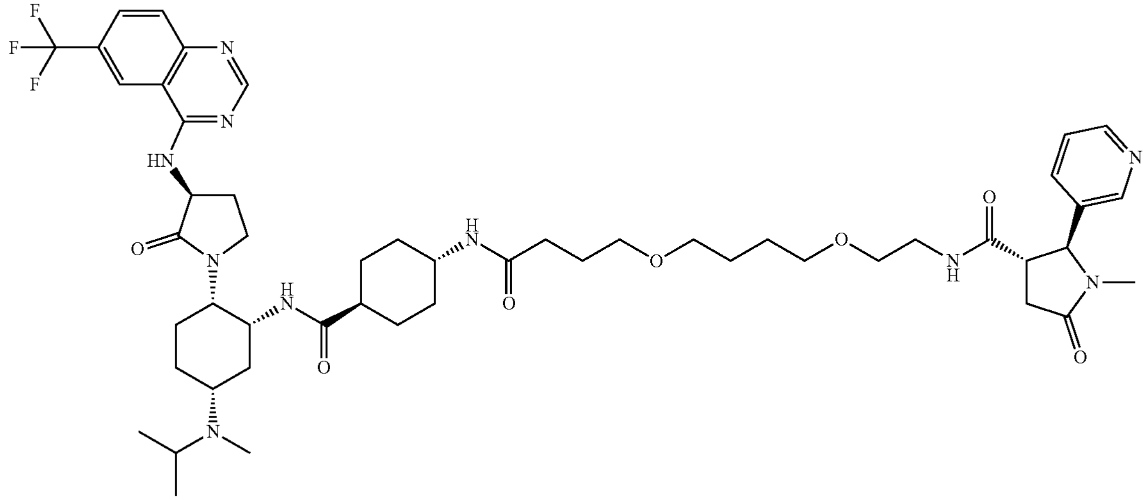

-continued
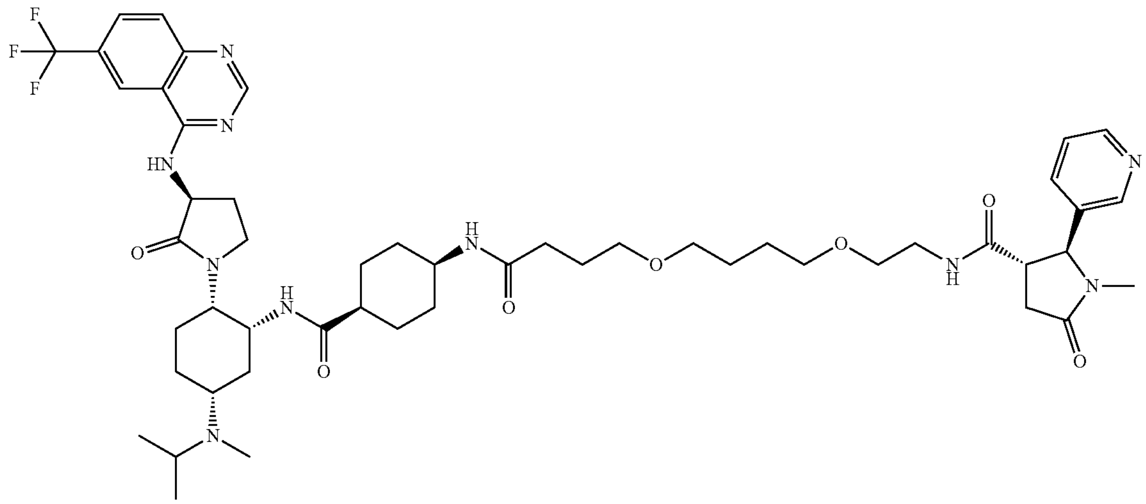
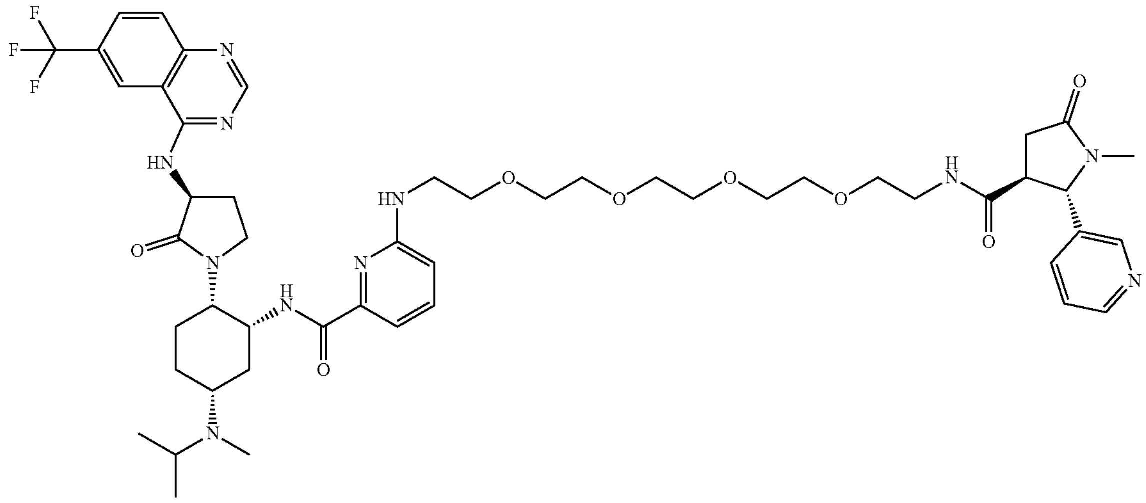
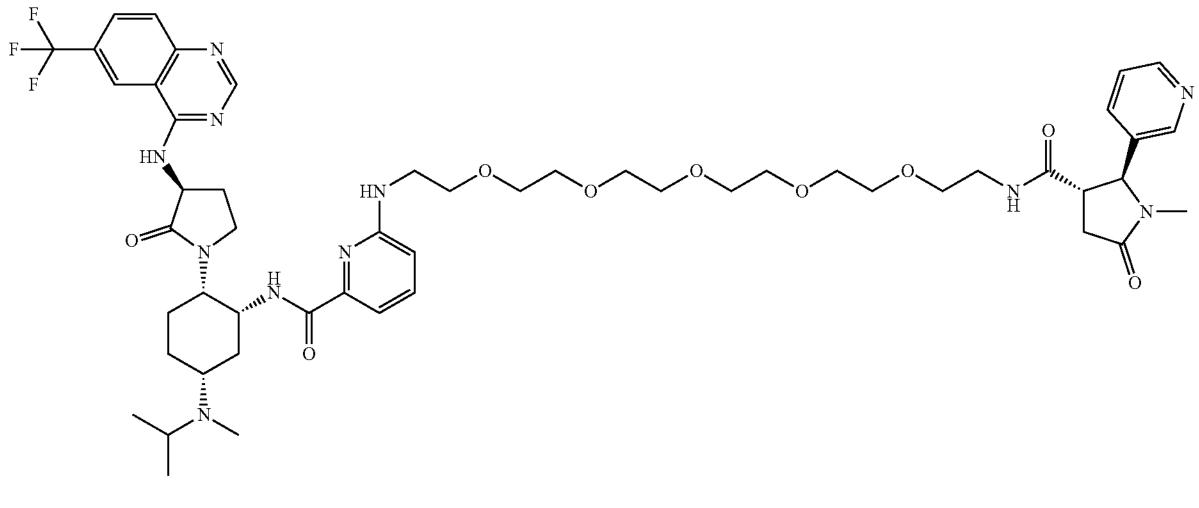

-continued
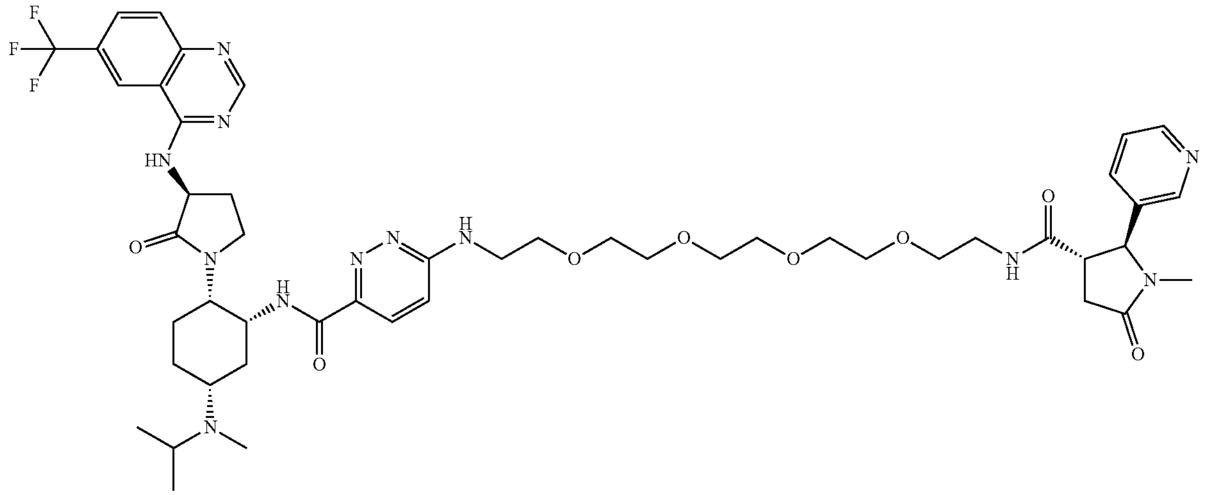
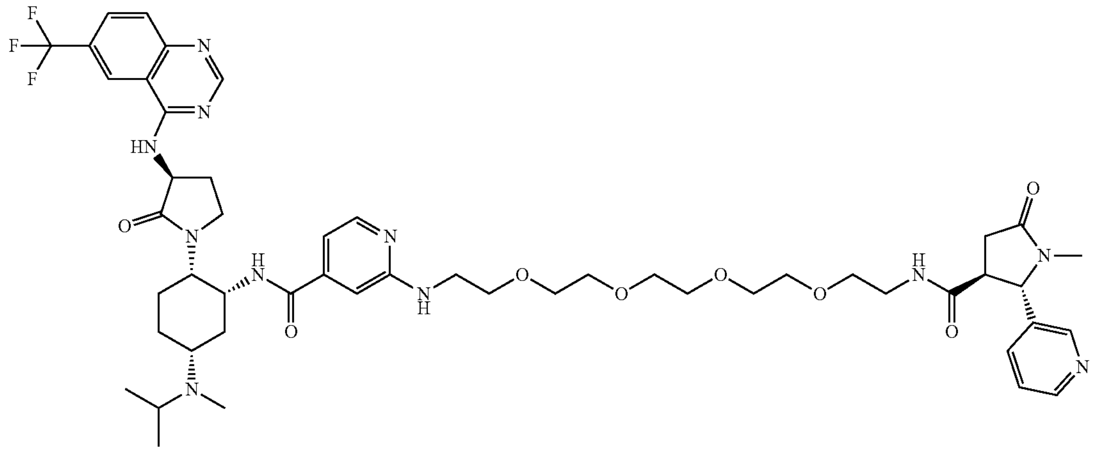
$3CF_3COOH$
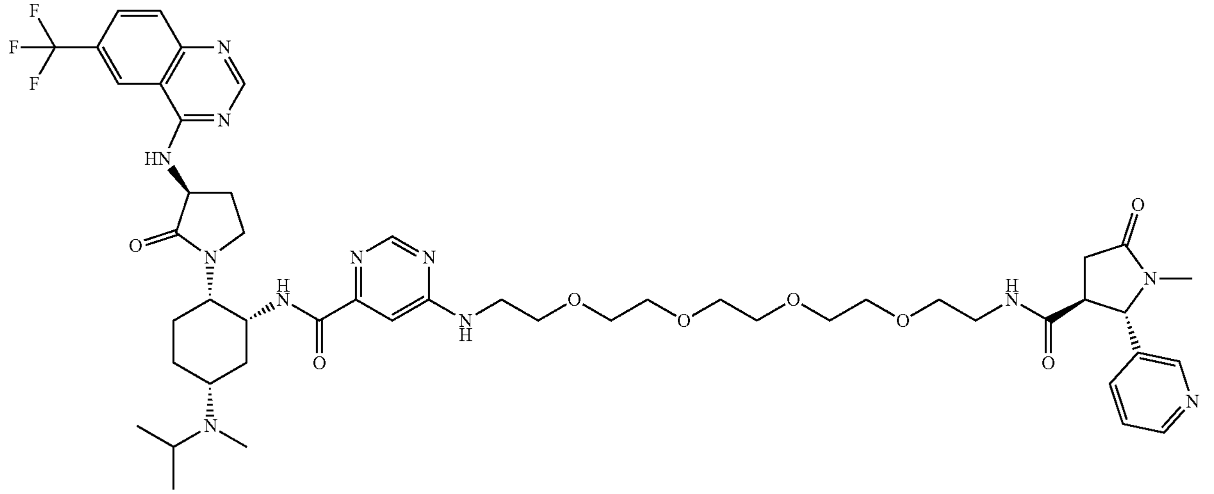

-continued
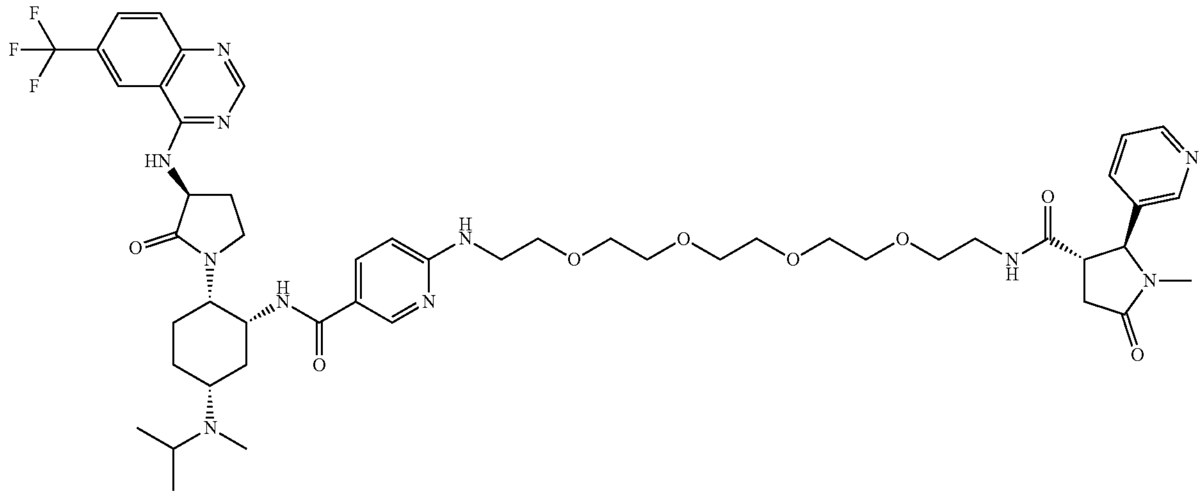
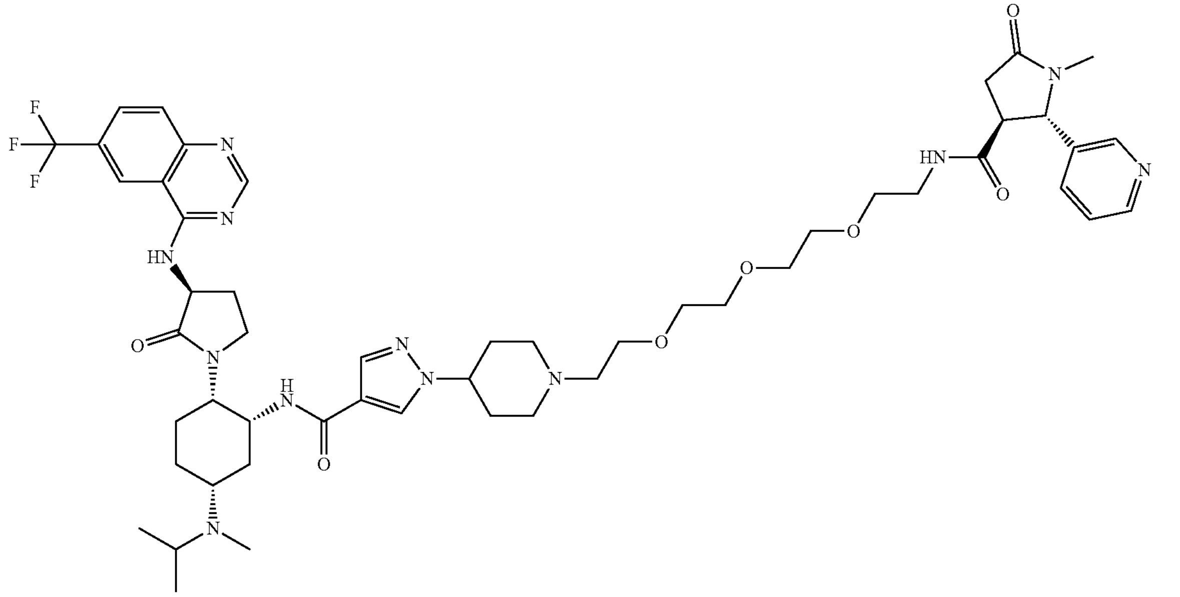
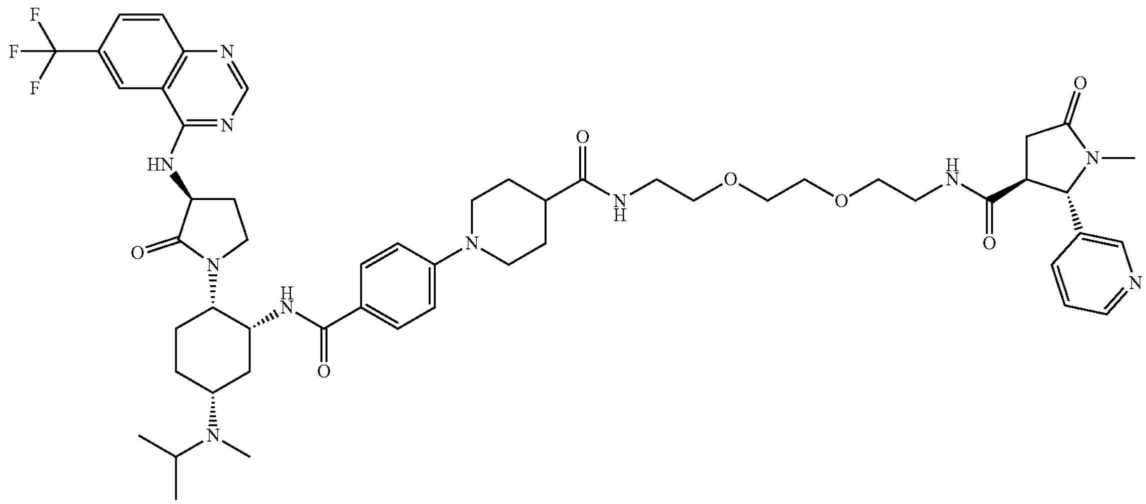

-continued
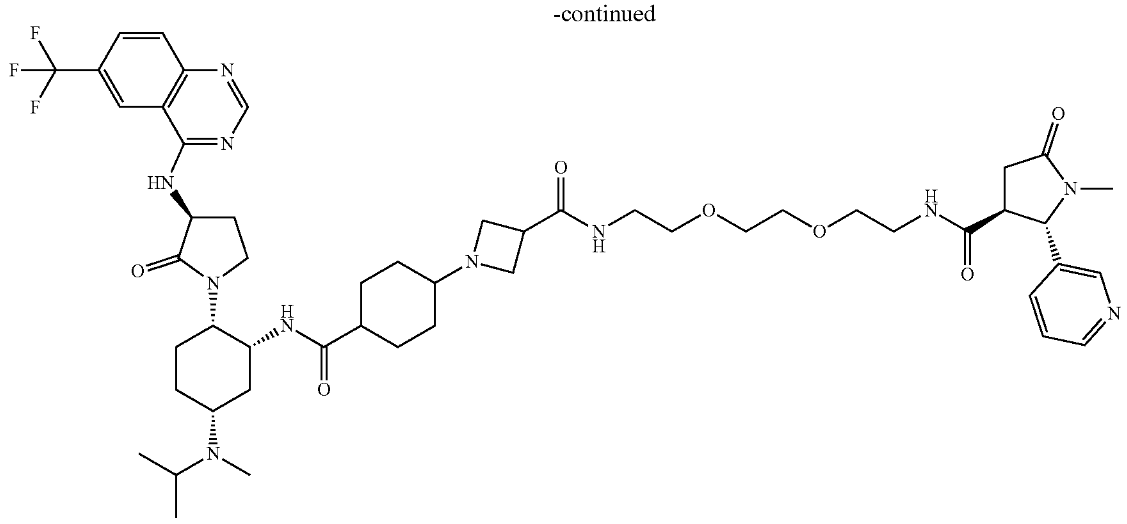
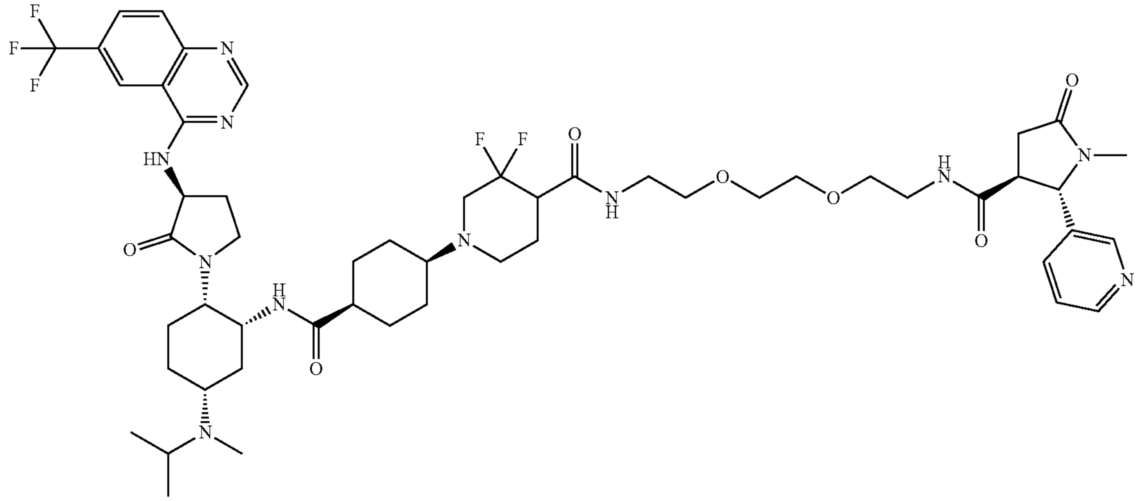
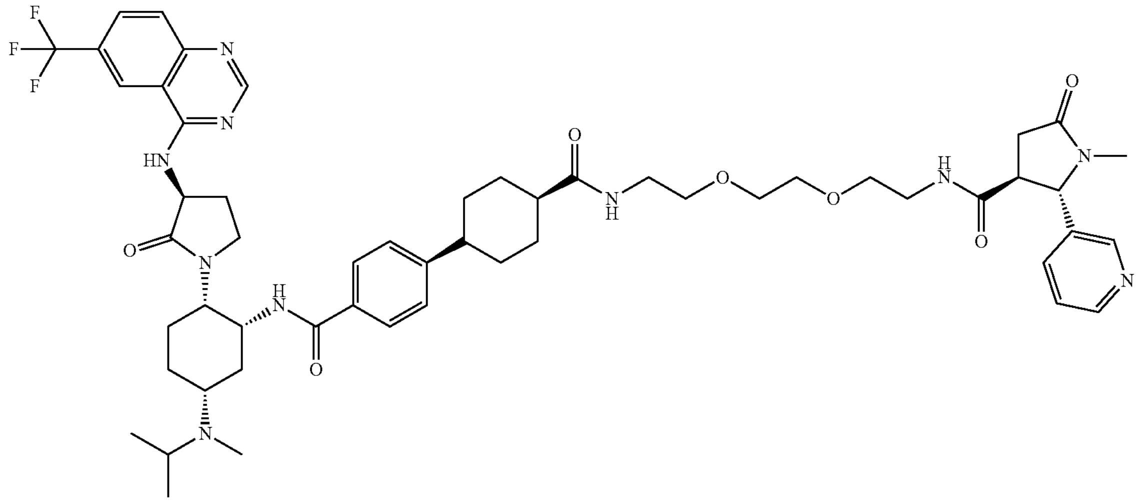

-continued
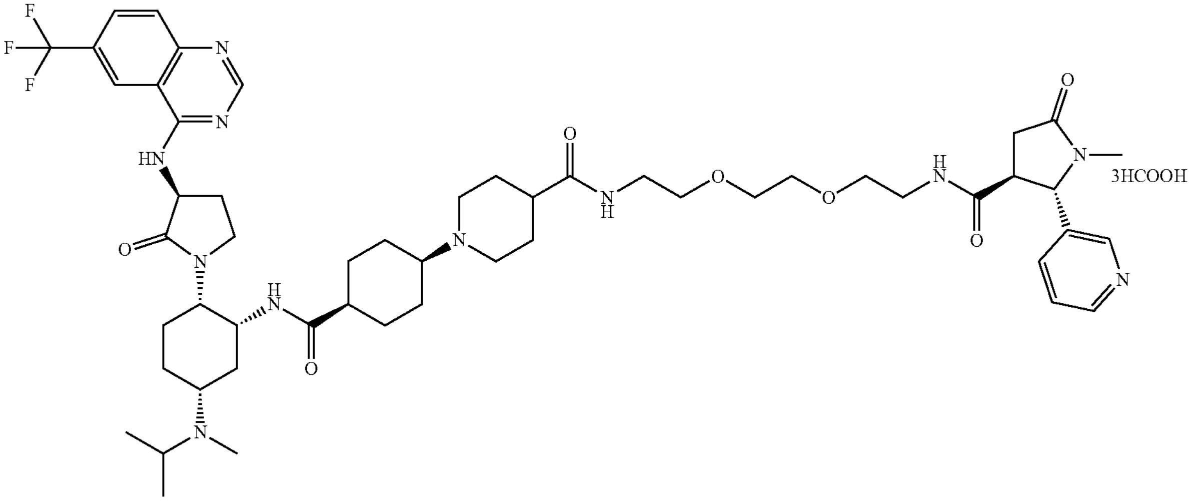
3HCOOH
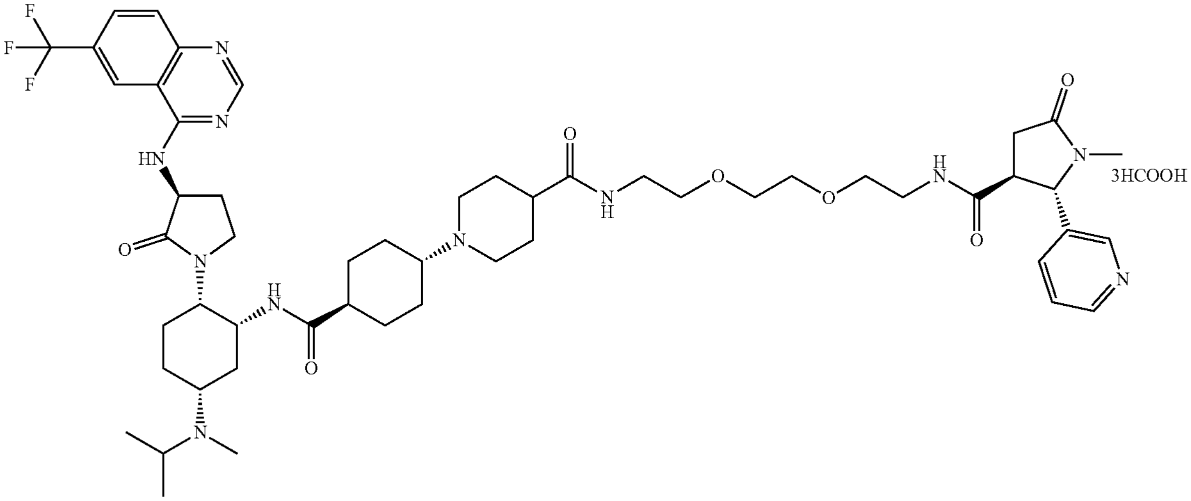
3HCOOH
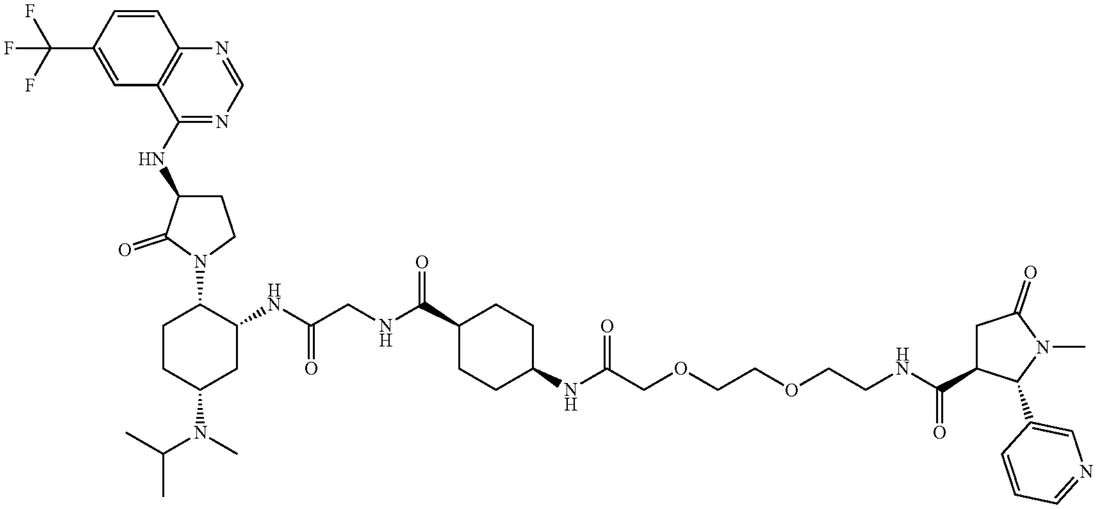

-continued
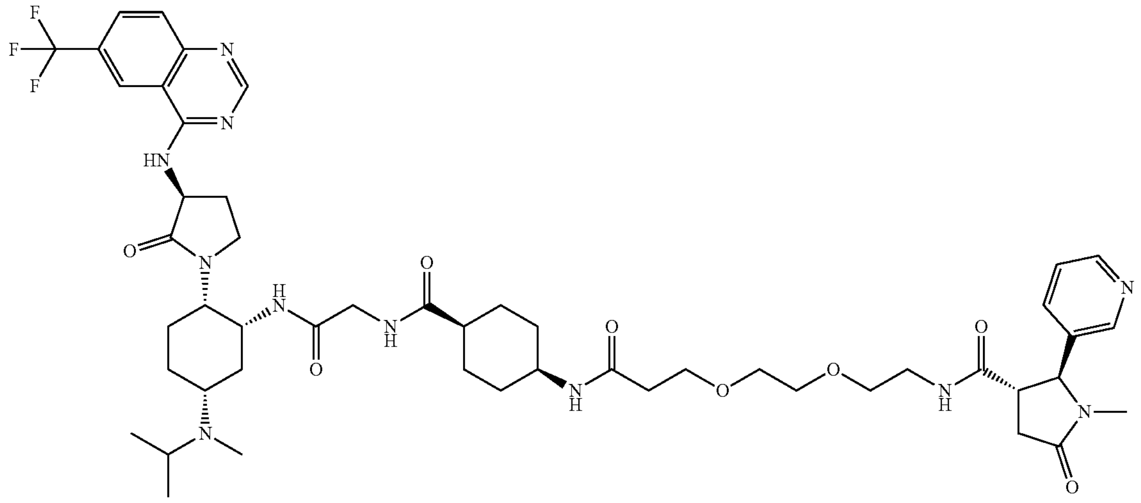
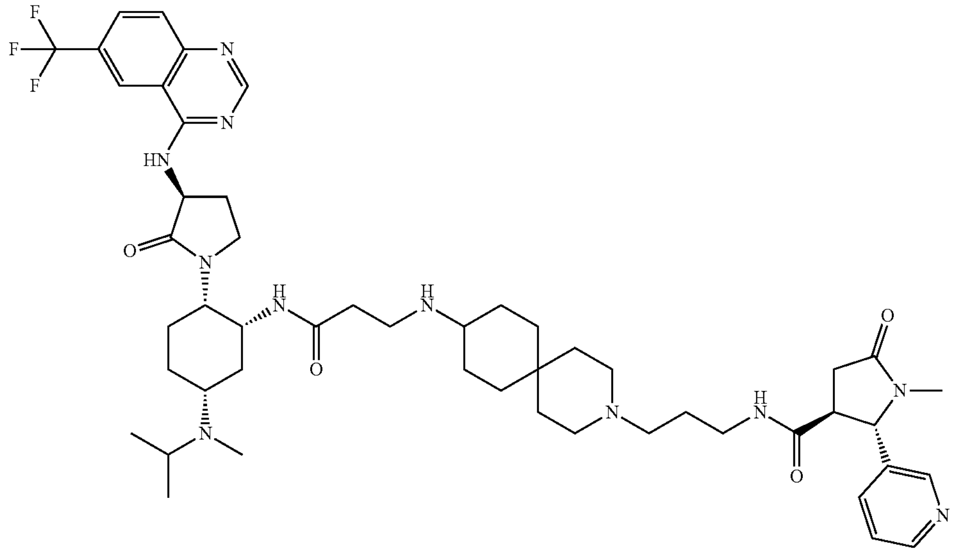
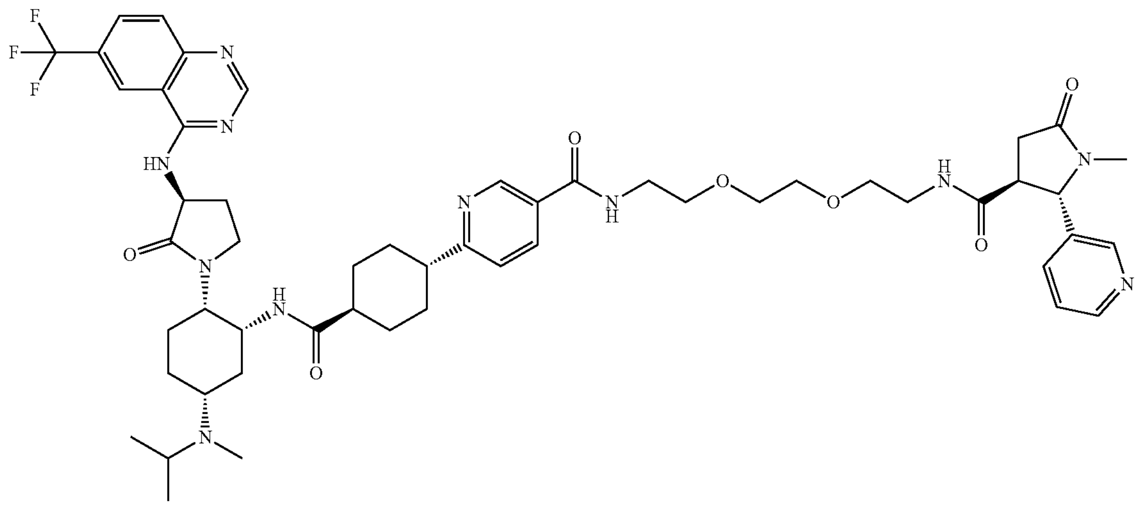

-continued
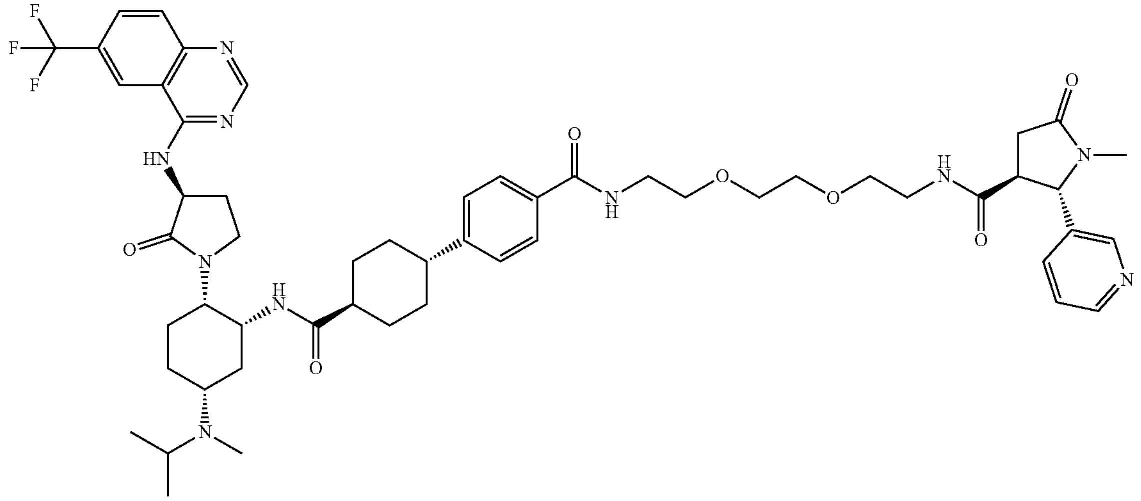
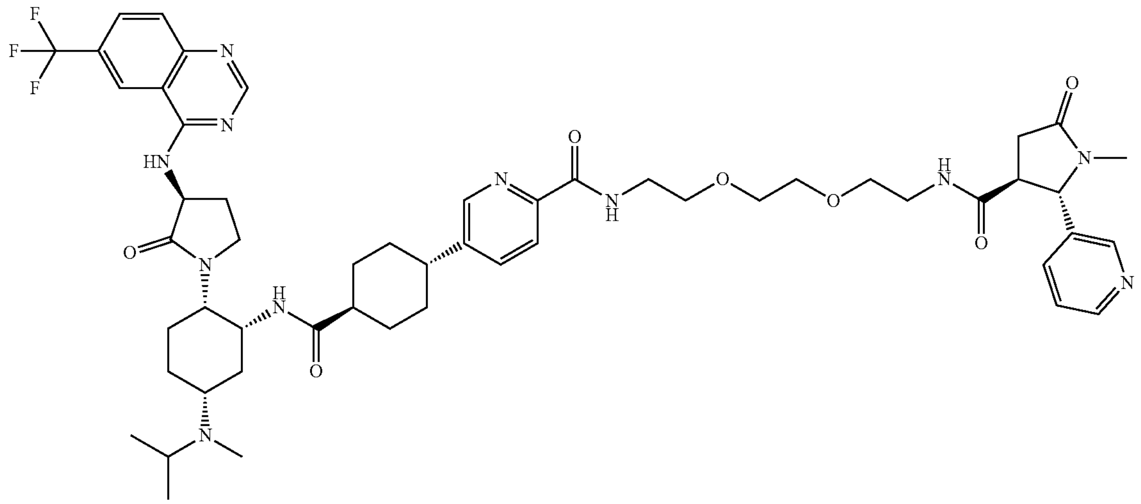
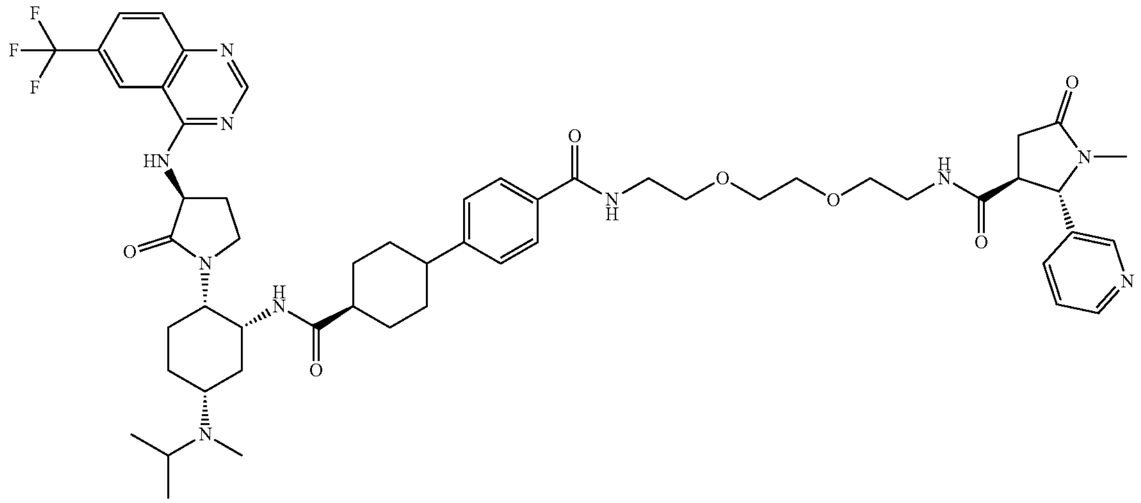

-continued
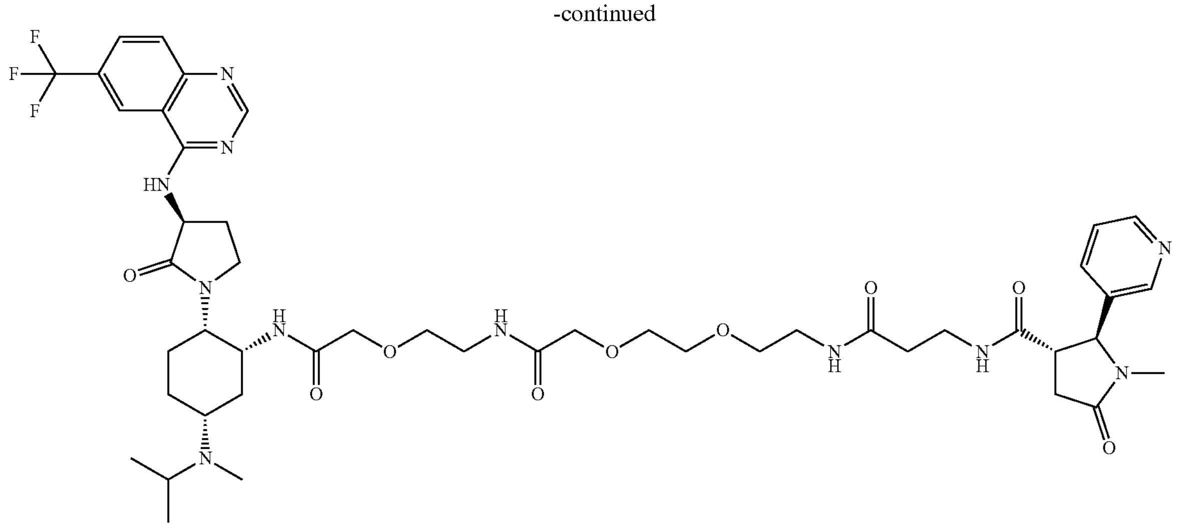
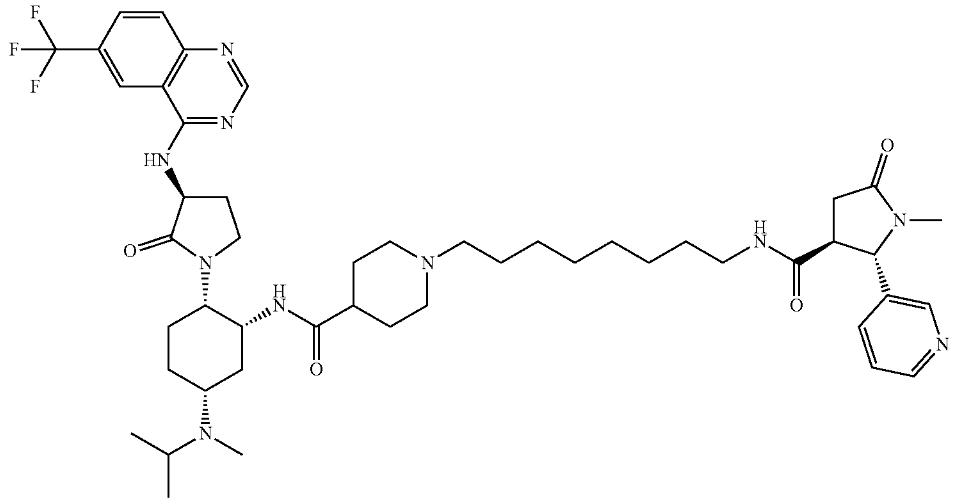
3HCOOH
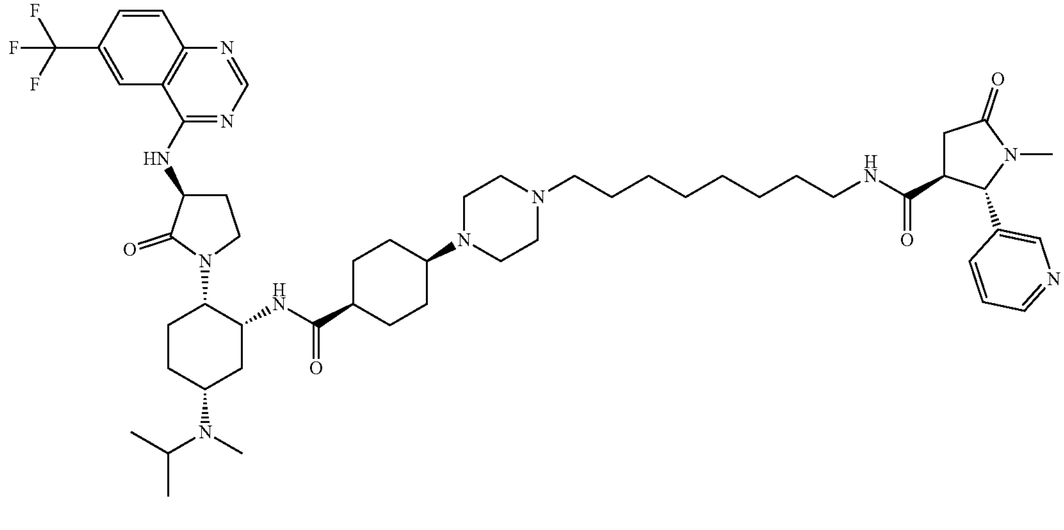

-continued
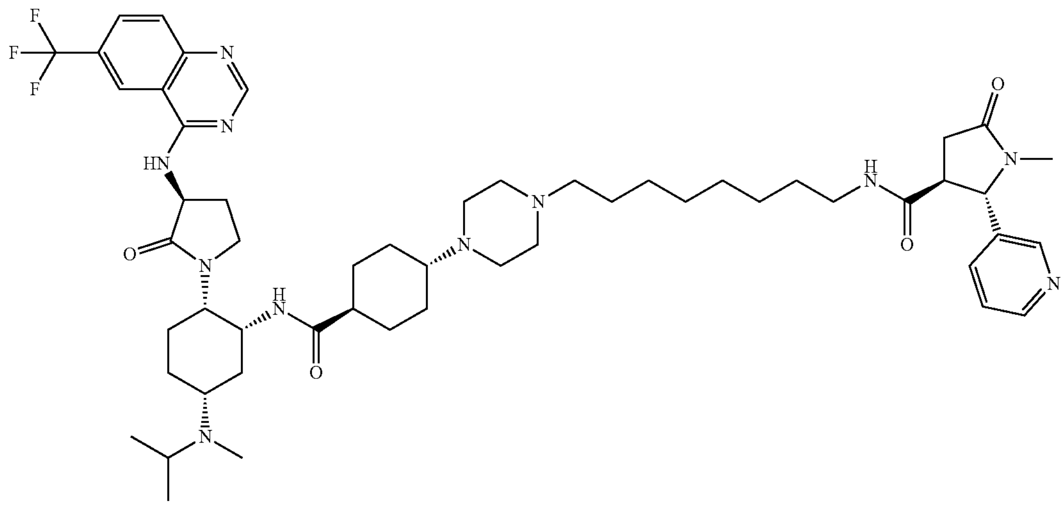
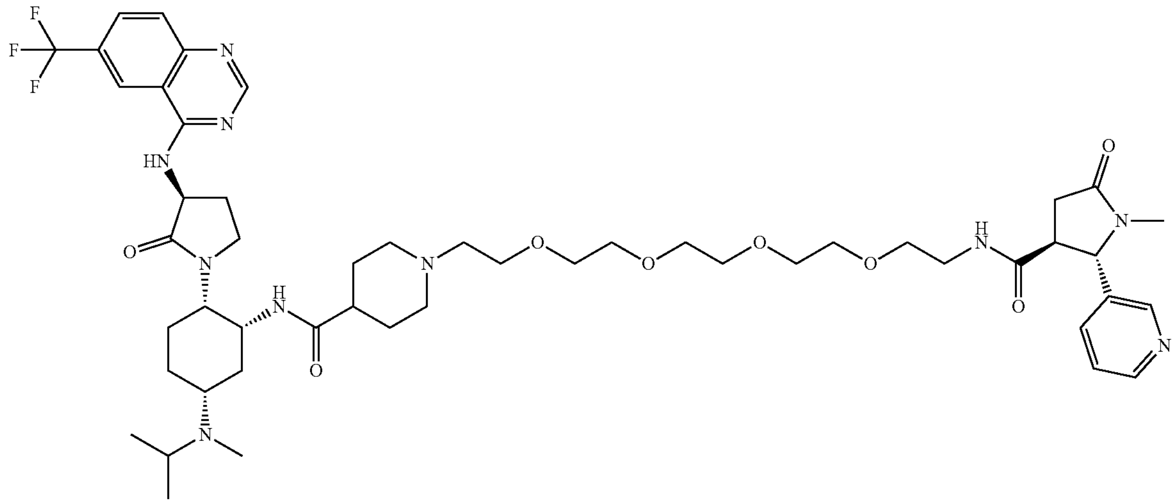
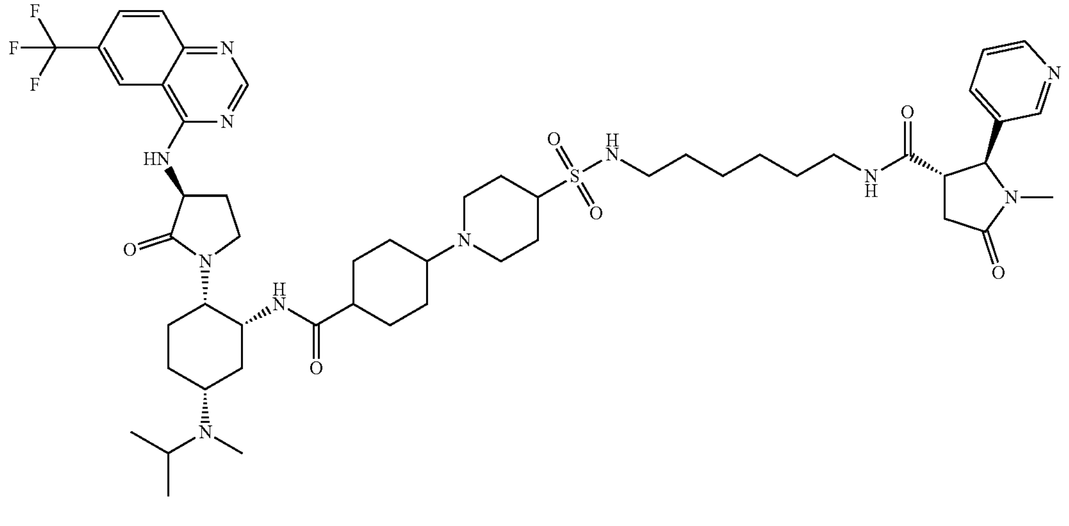

-continued
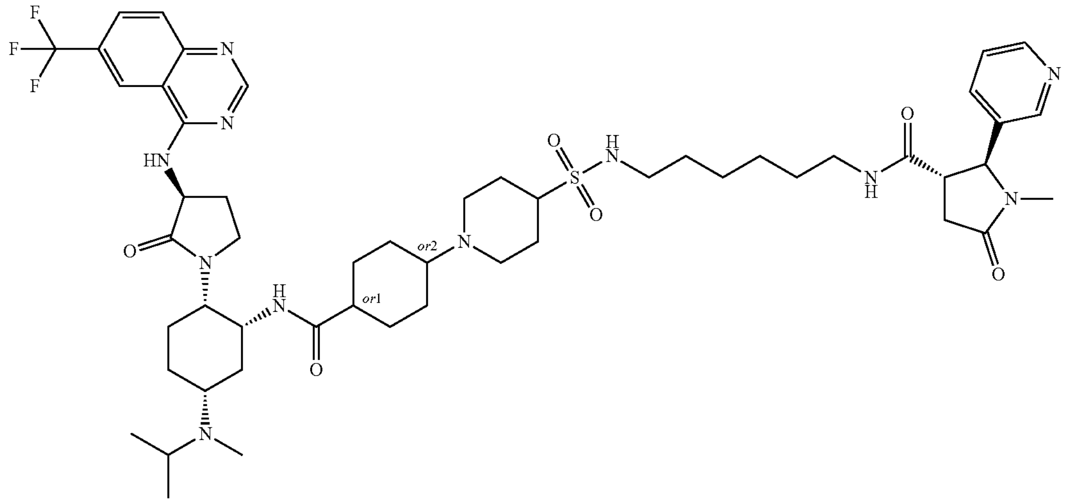
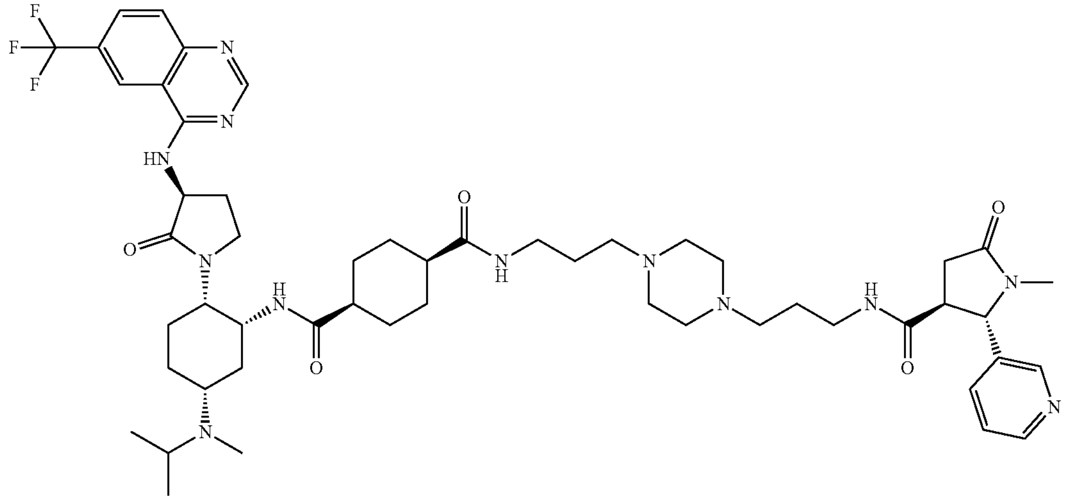
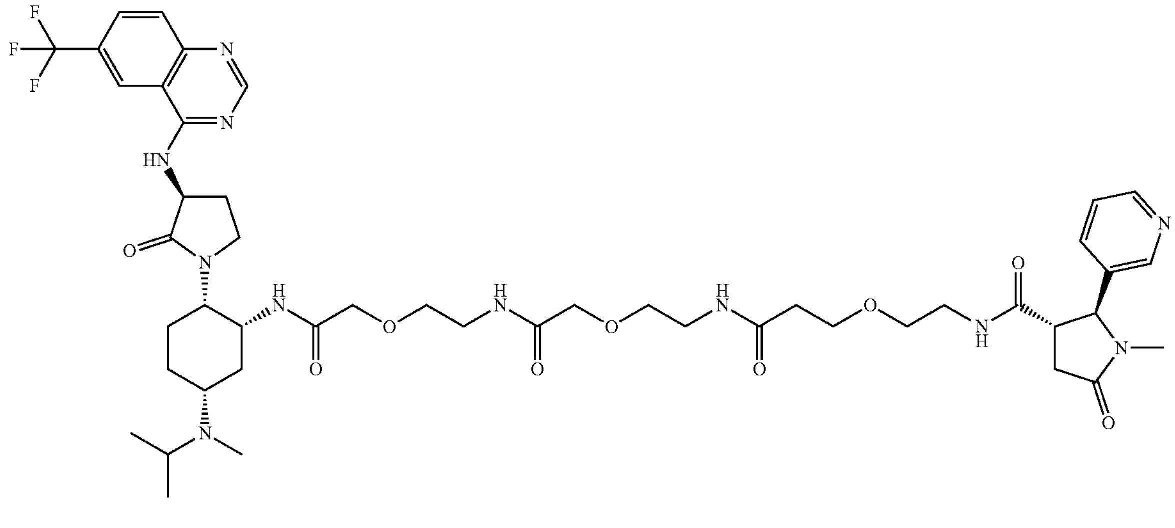

-continued
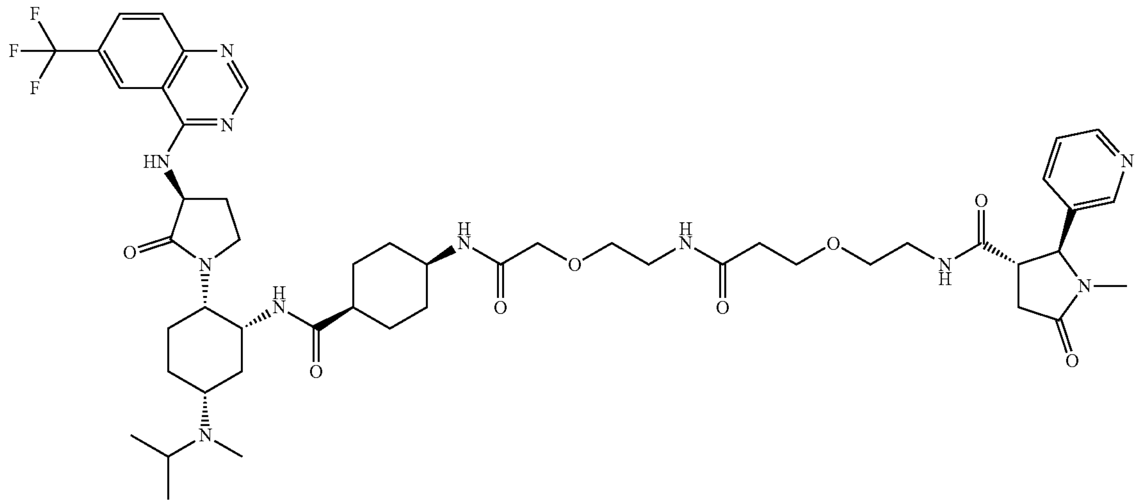
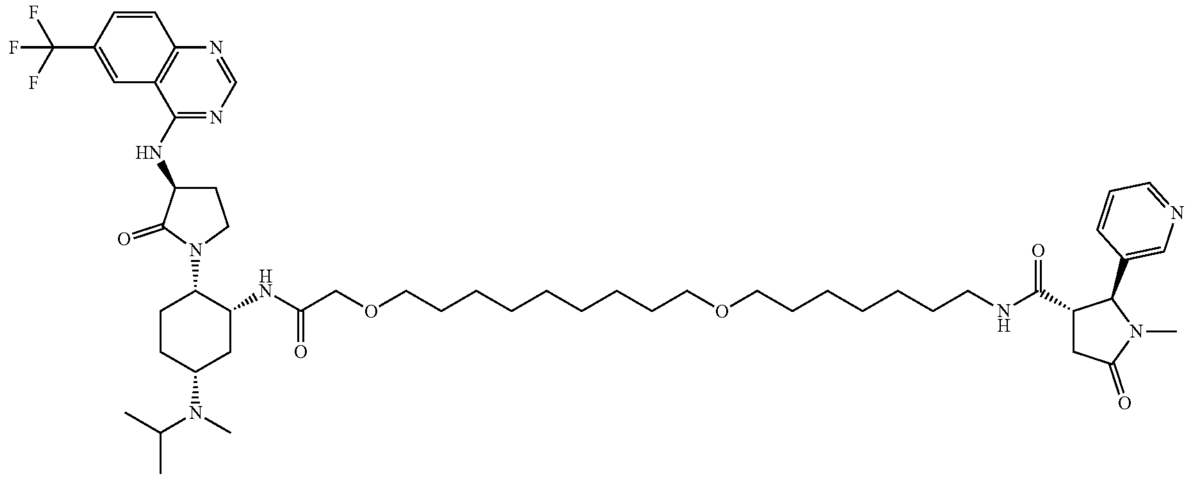
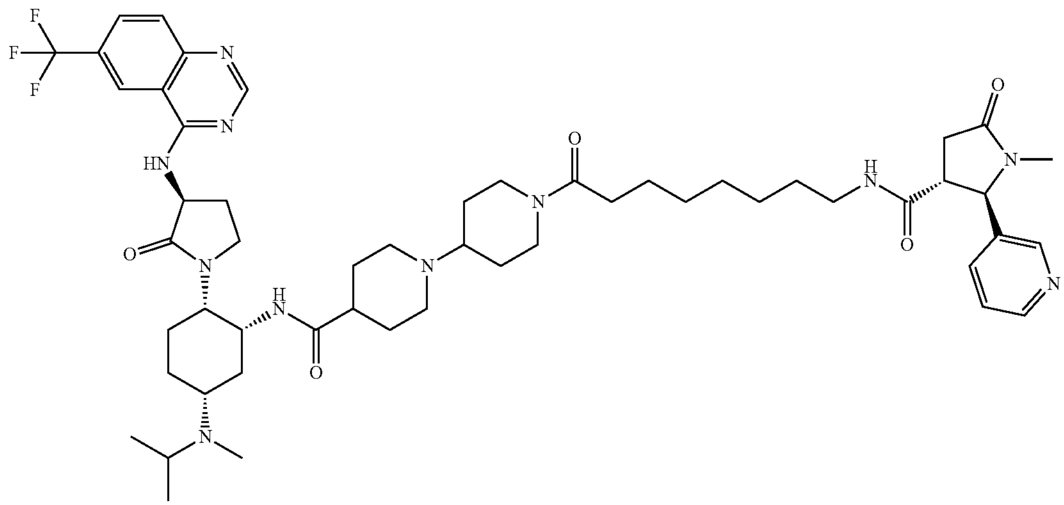

-continued
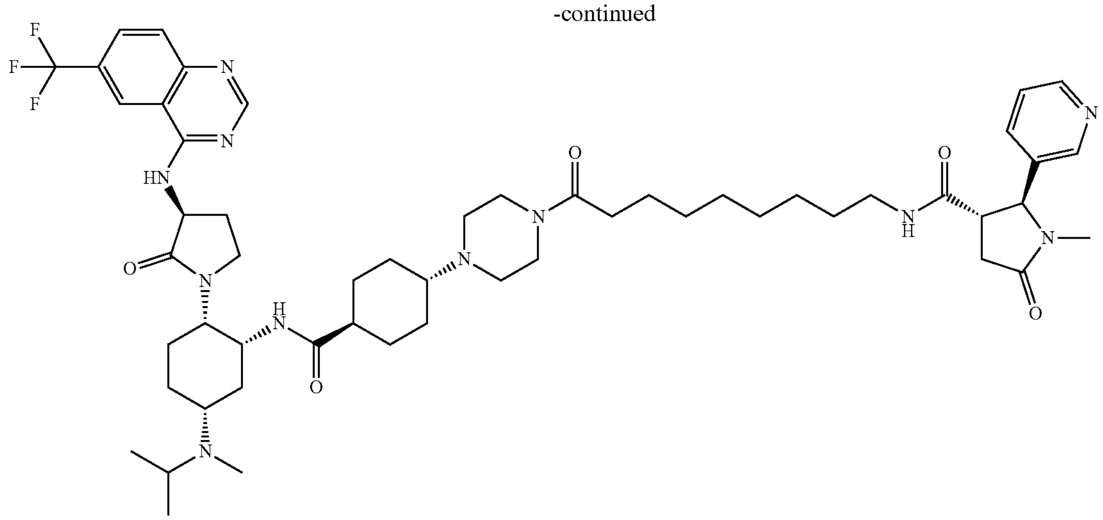
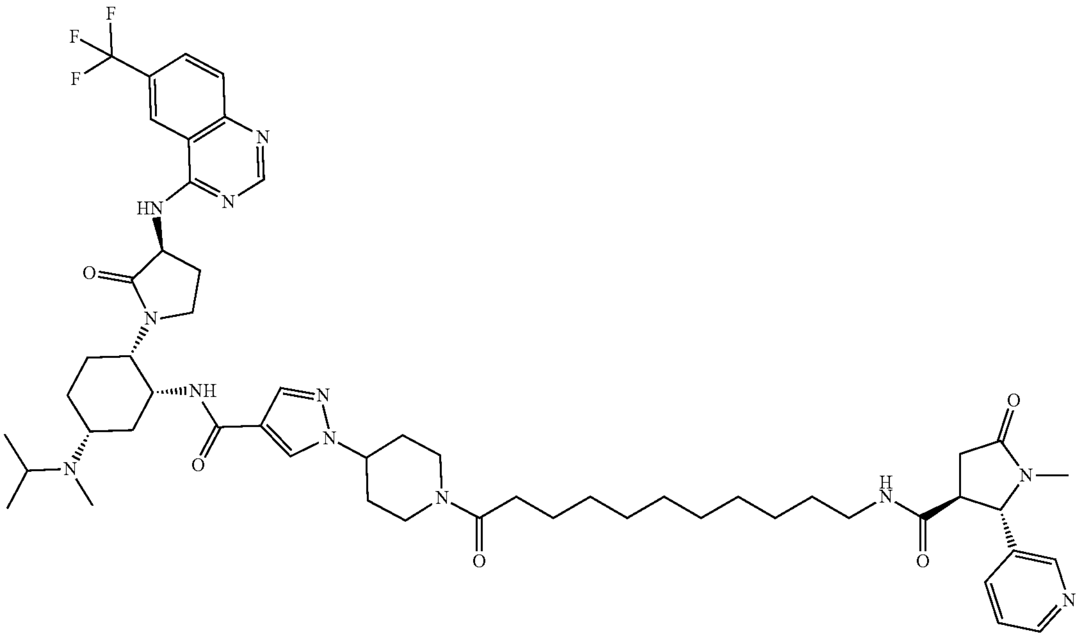

-continued
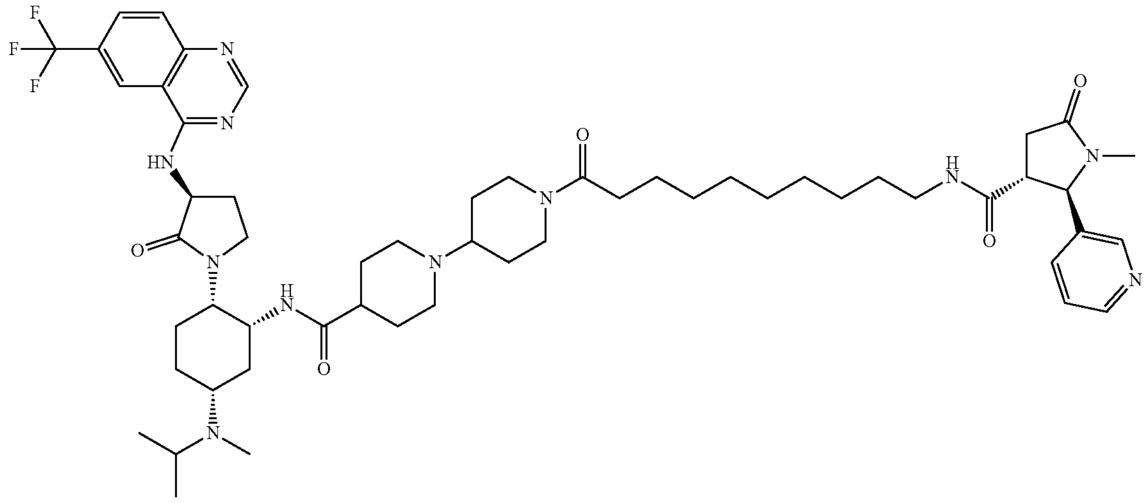
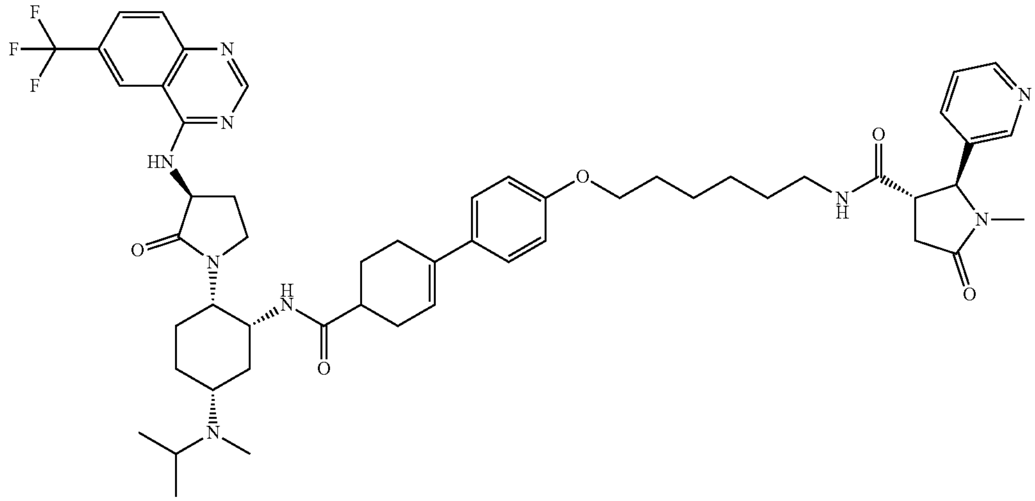
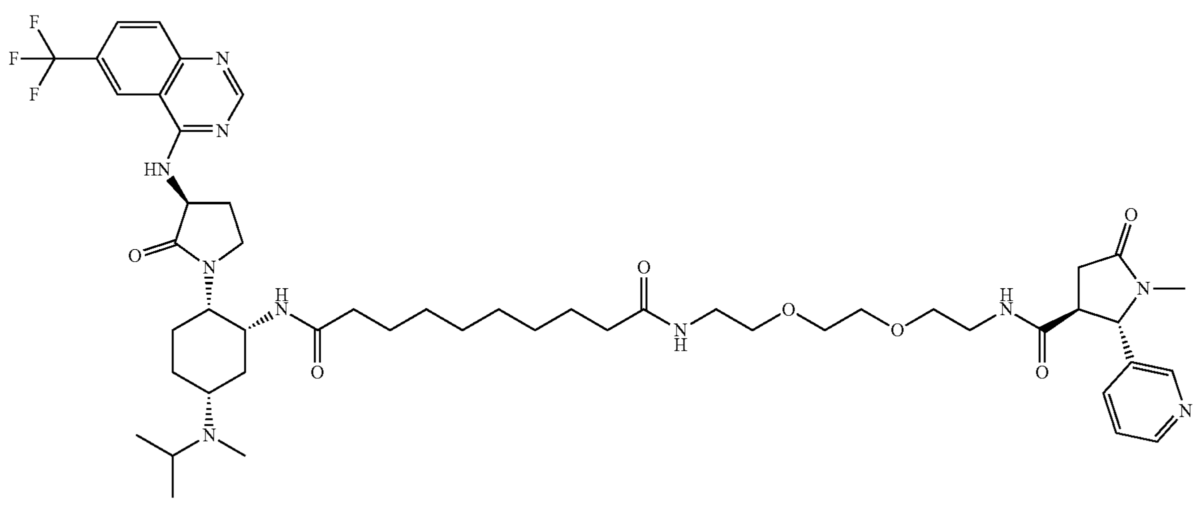

-continued
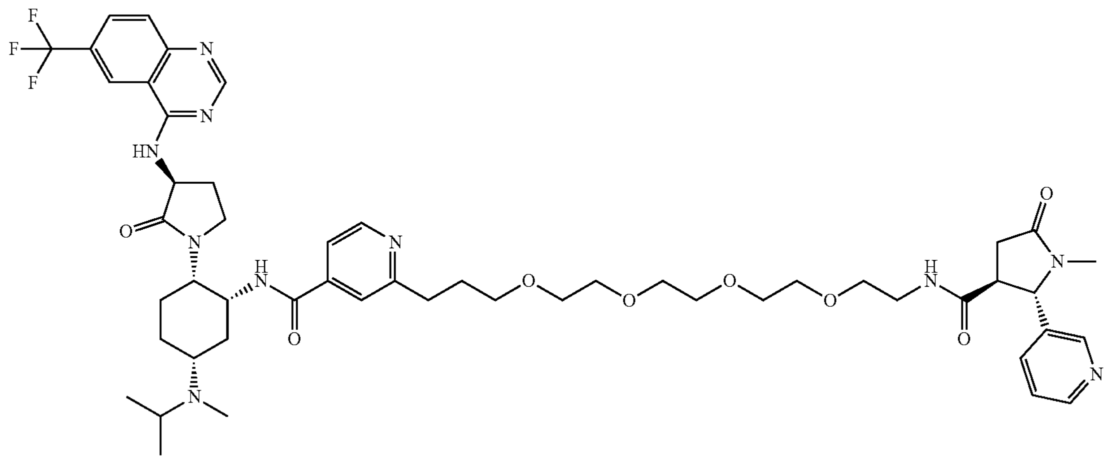
3HCOOH
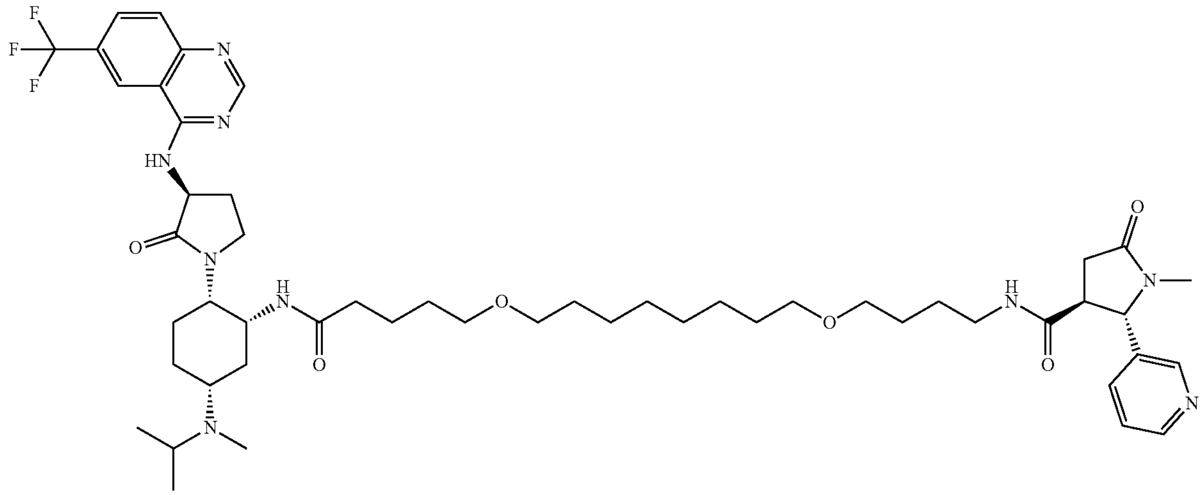
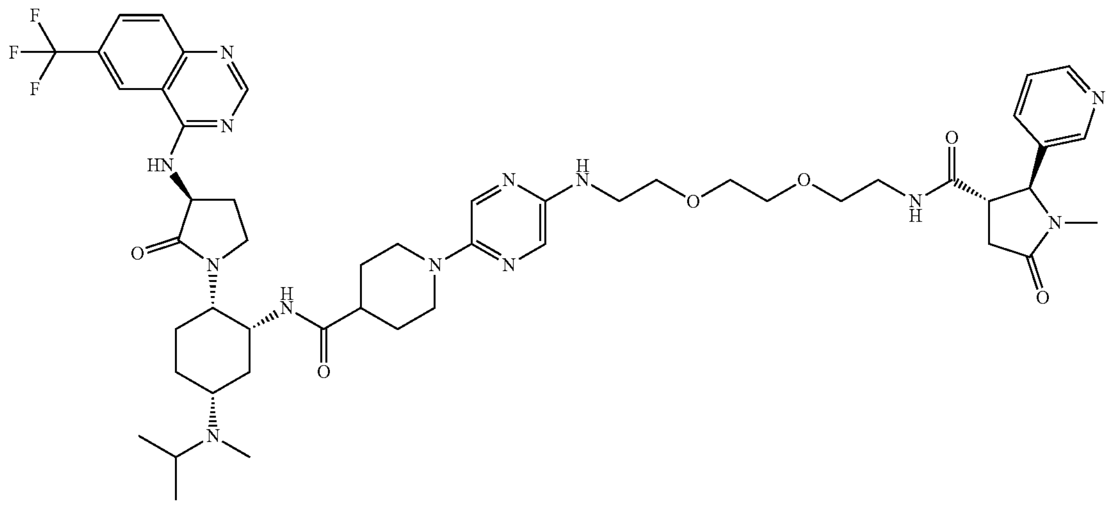

-continued
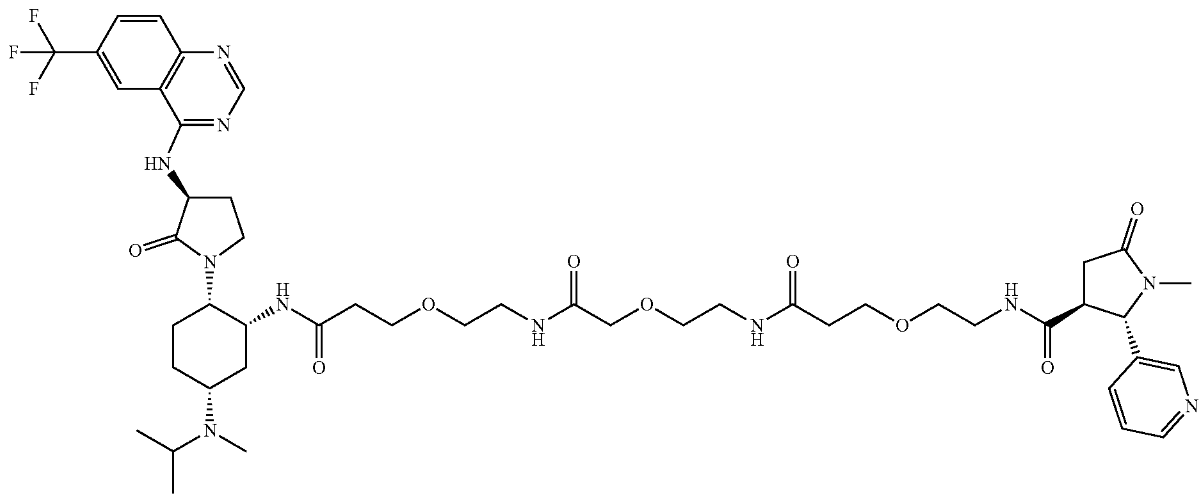
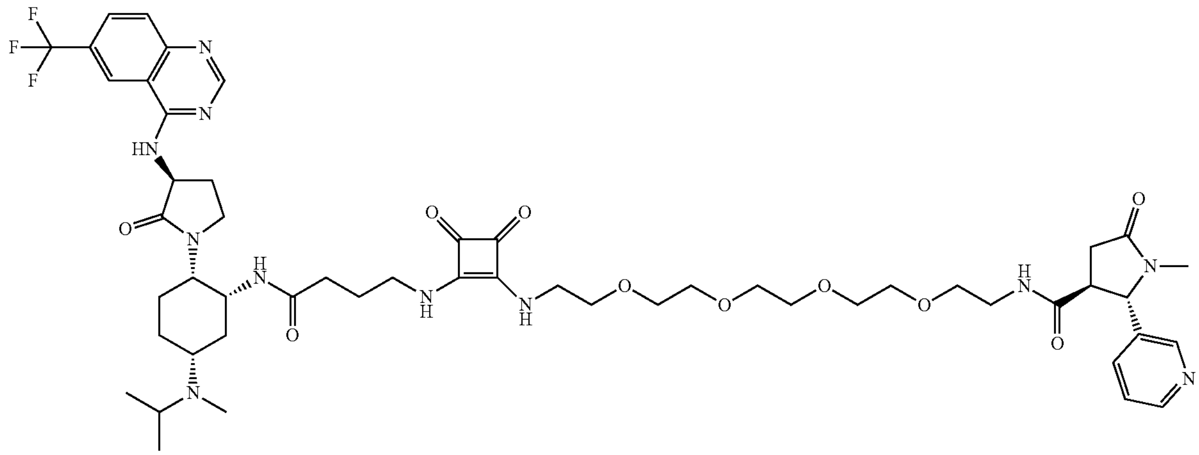
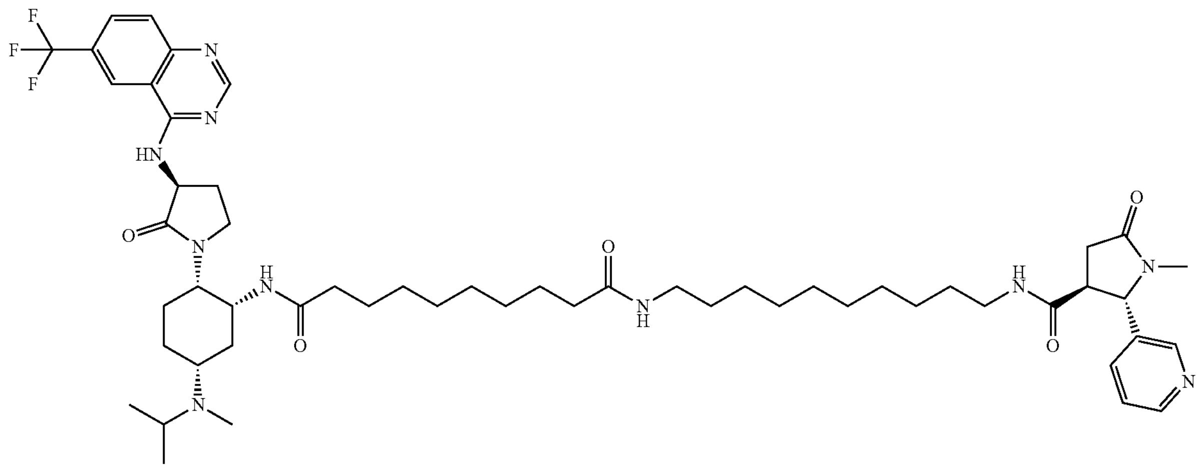

-continued
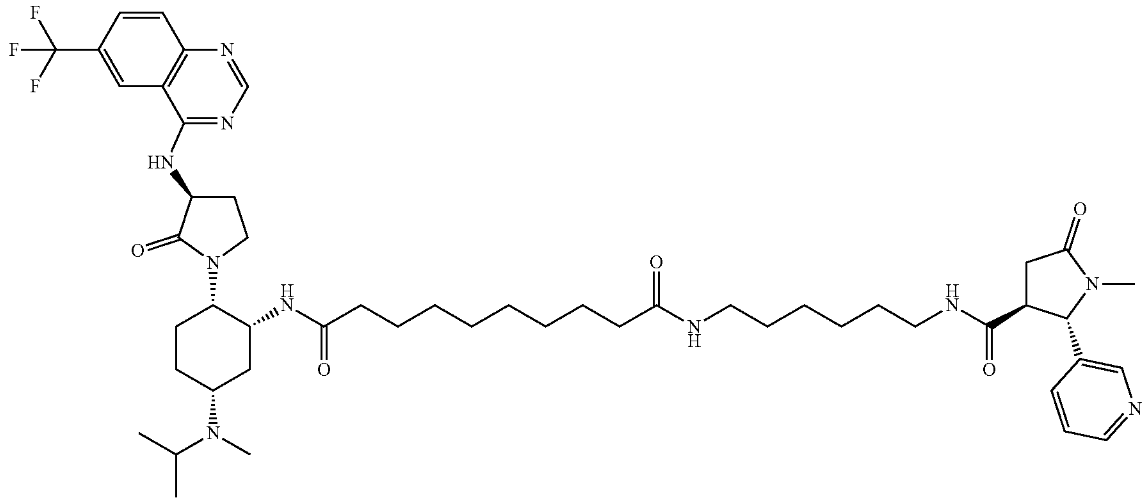
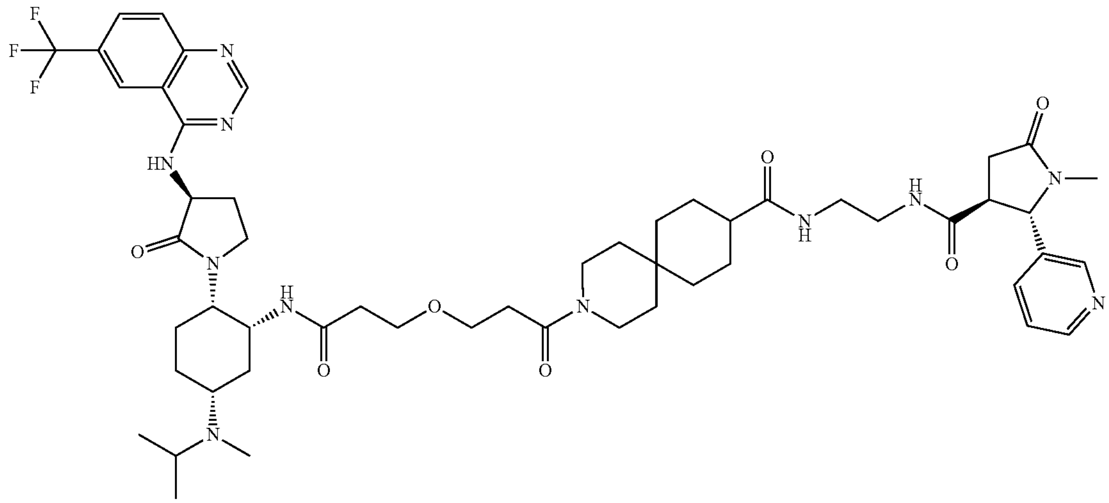
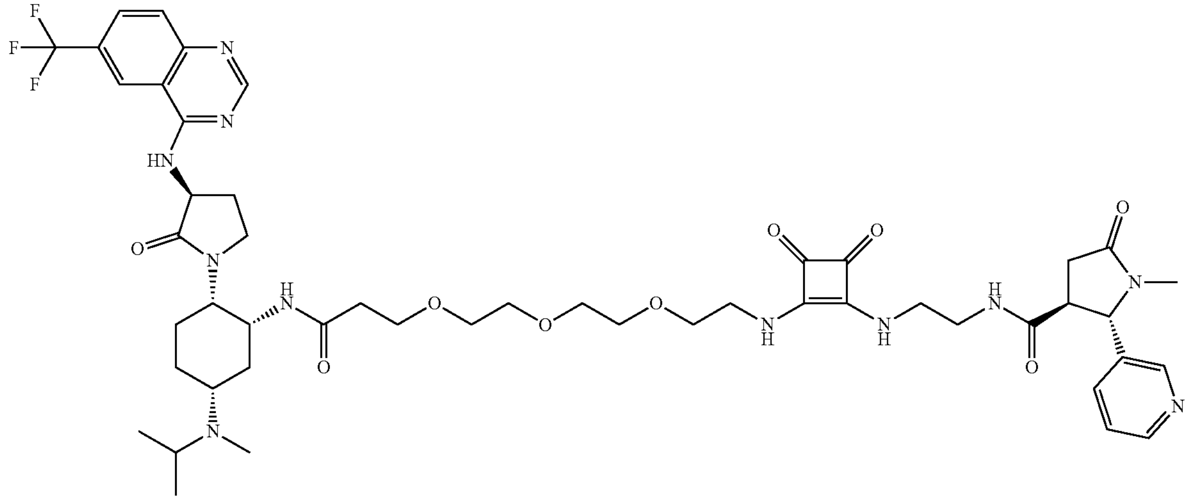

-continued
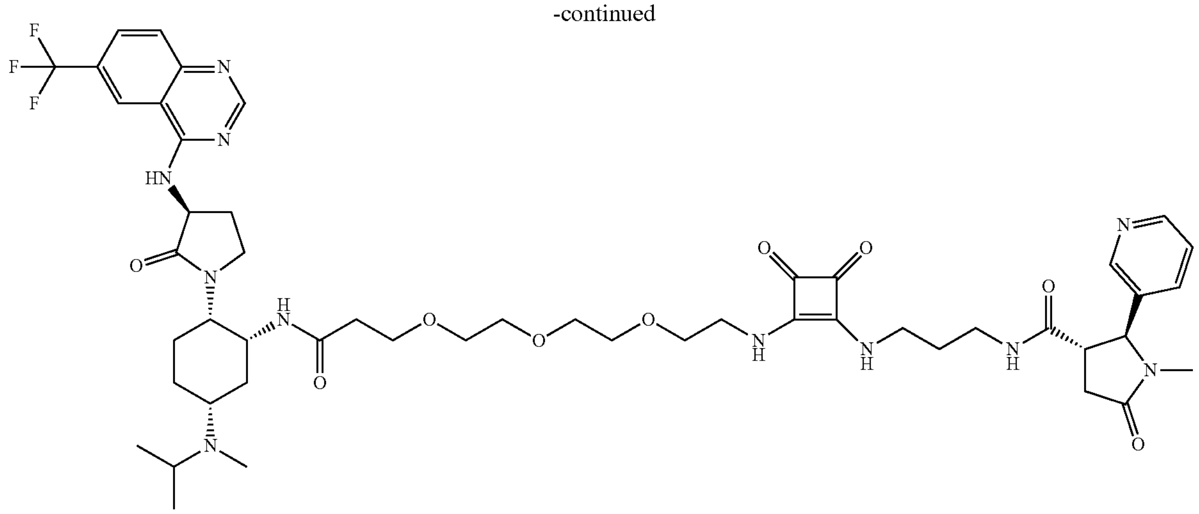
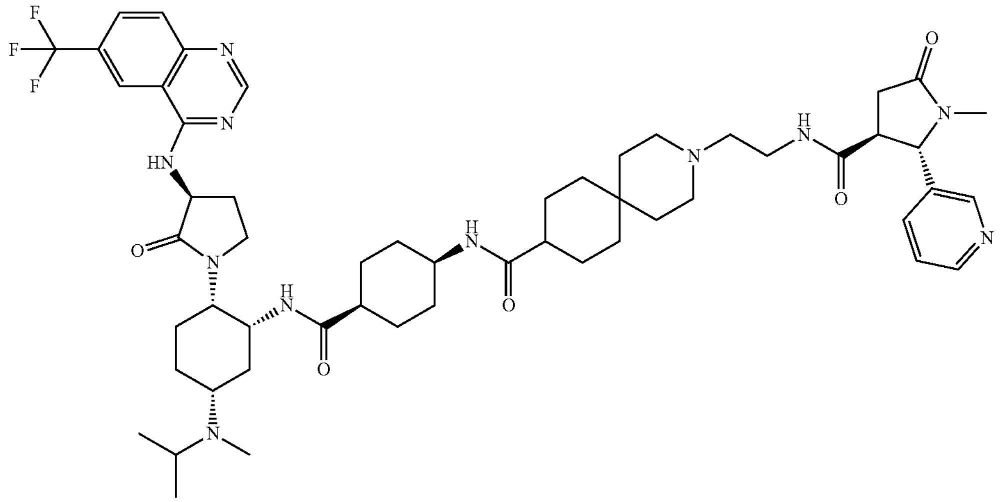
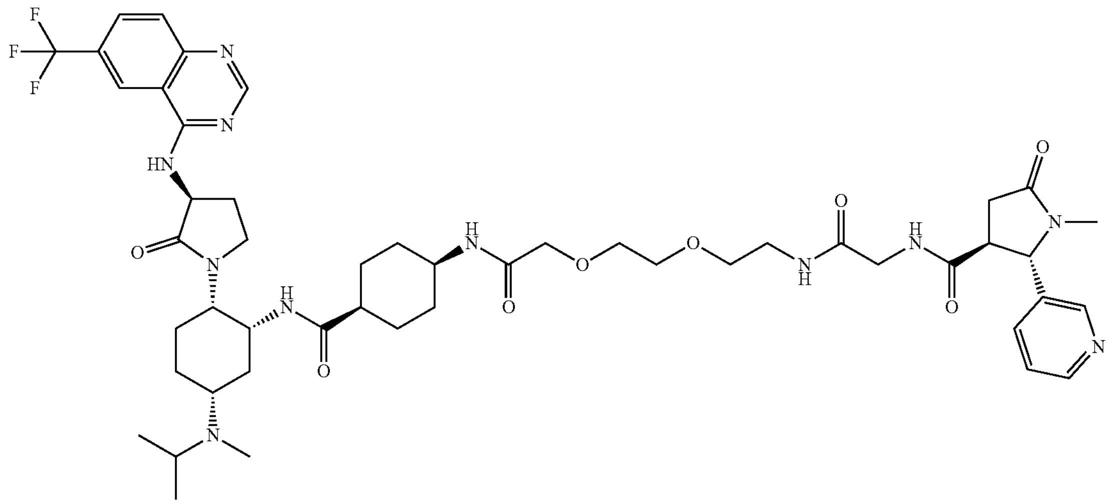 [SMILES: CC(C)N(C)[C@@H]1CC[C@H](N2CC[C@H](Nc3ncnc4ccc(C(F)(F)F)cc34)C2=O)[C@H](NC(=O)[C@H]2CC[C@@H](NC(=O)COCCOCCNC(=O)CNC(=O)[C@H]3CC(=O)N(C)[C@@H]3c3cccnc3)CC2)C1]

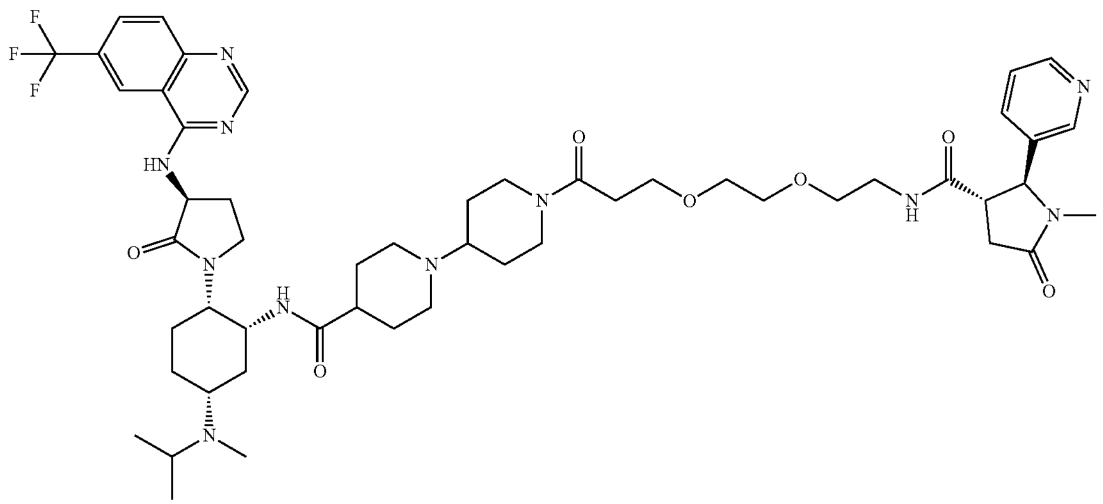
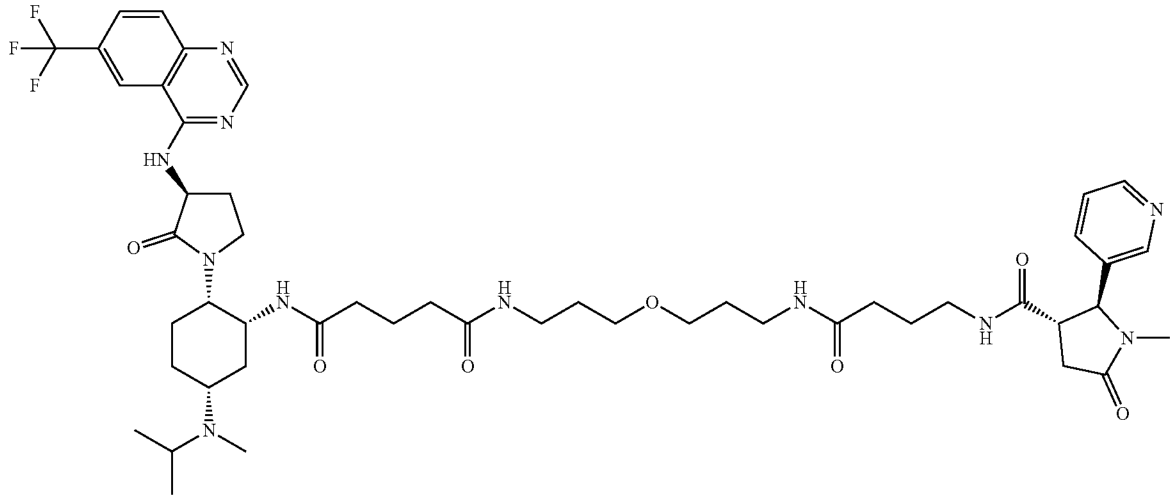
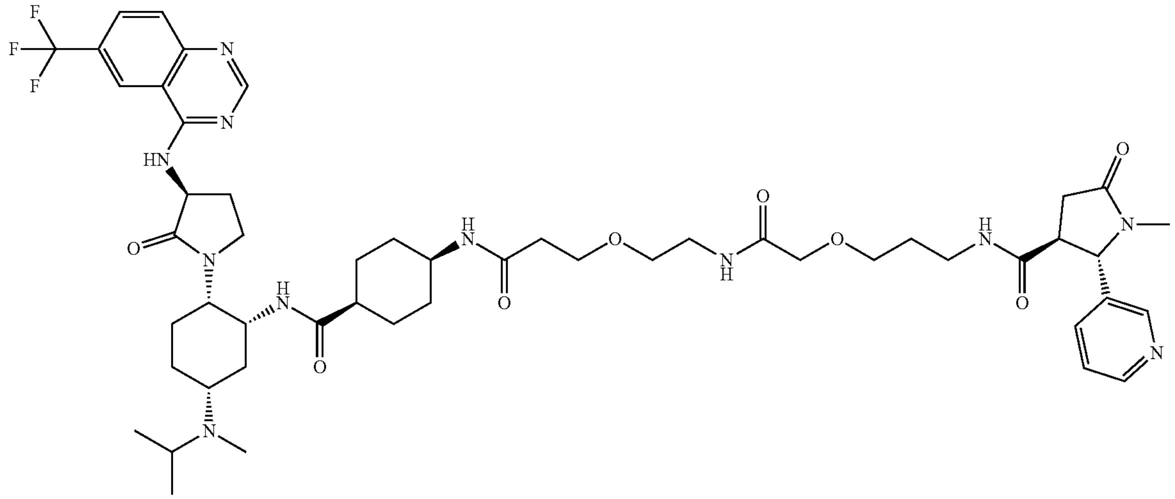

-continued
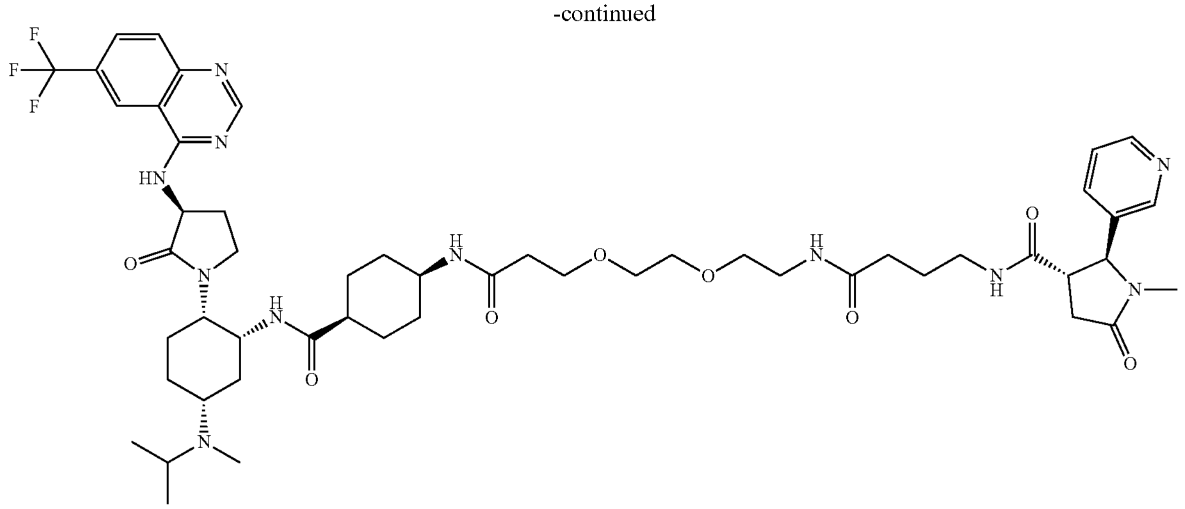
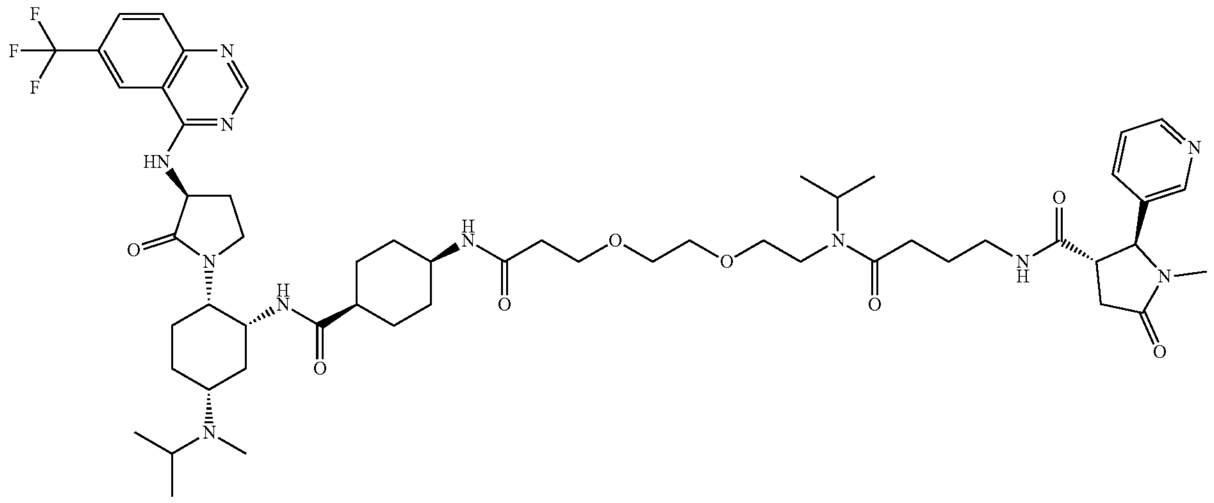
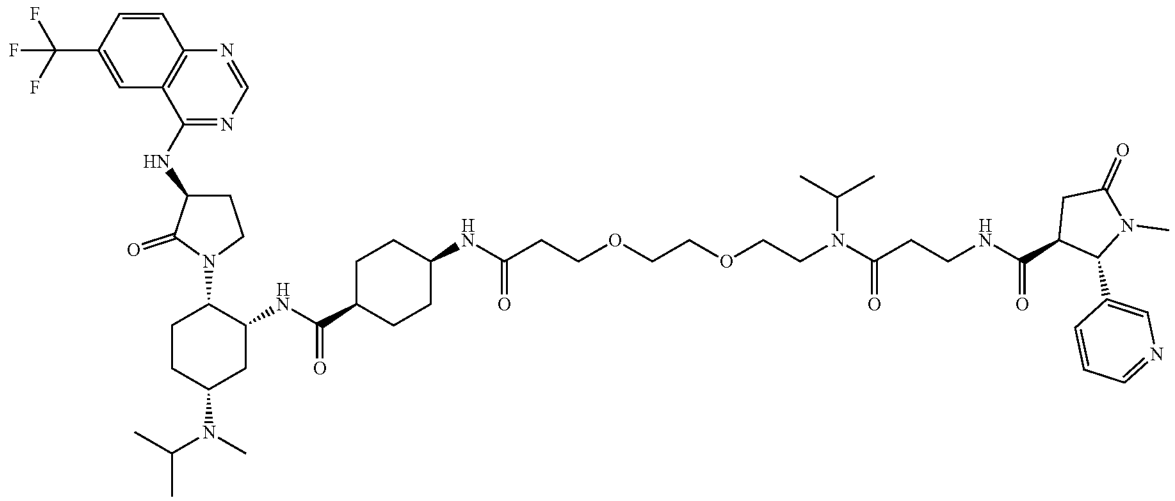

-continued
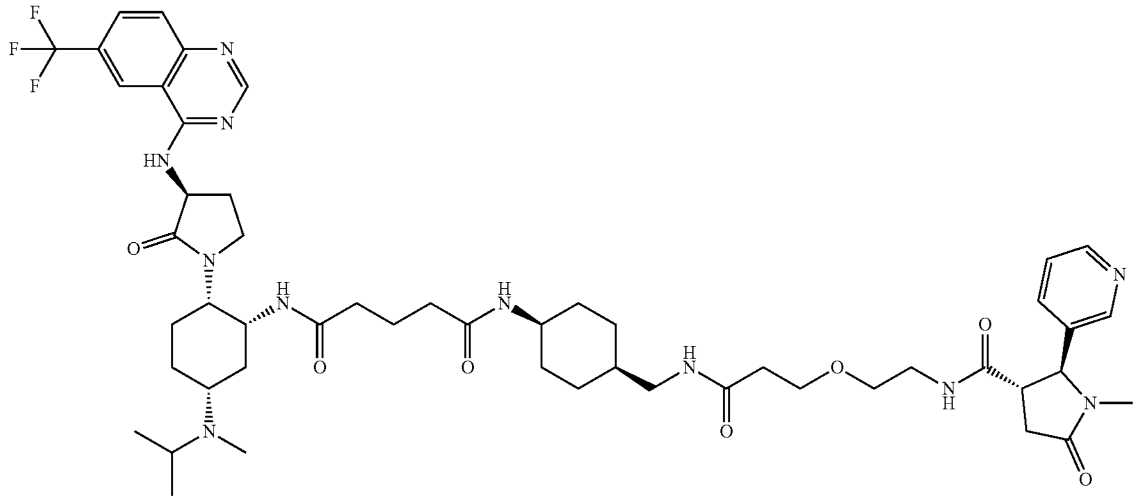
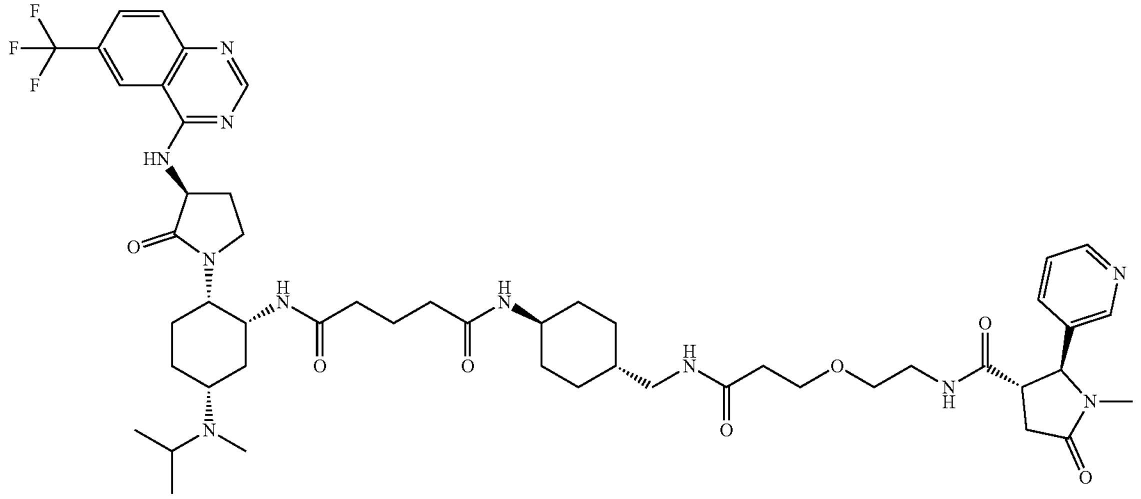
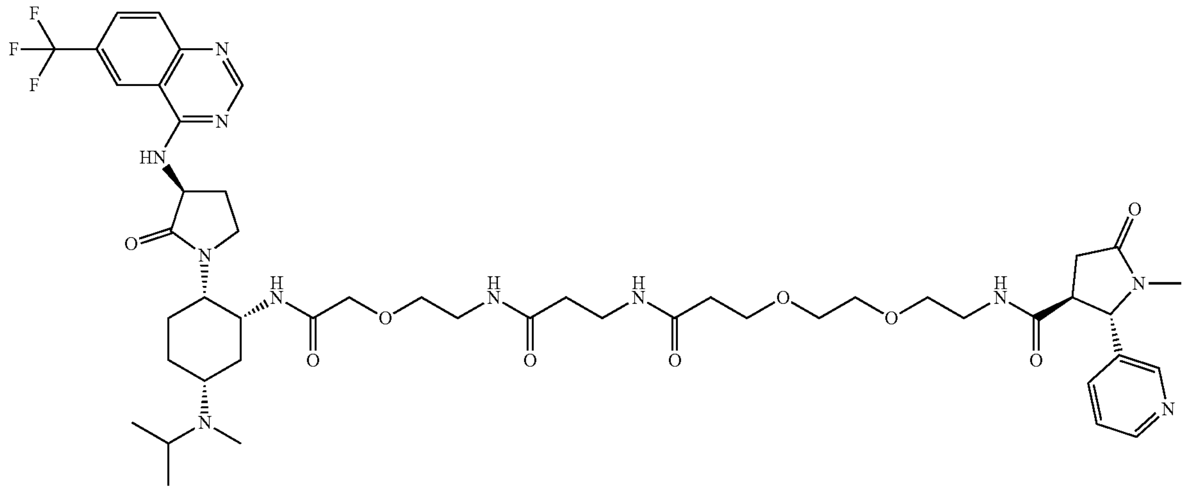

-continued
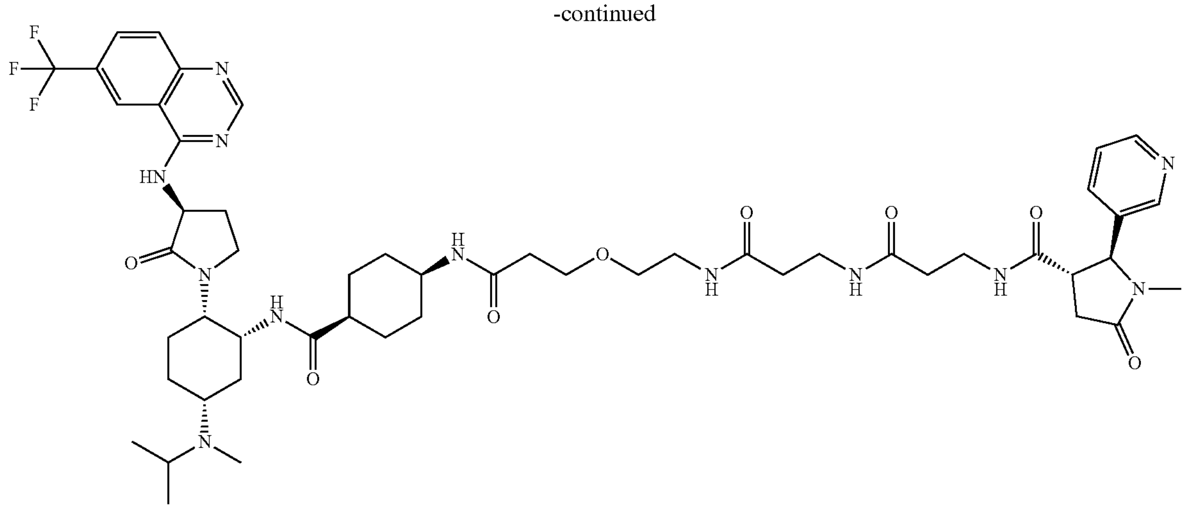
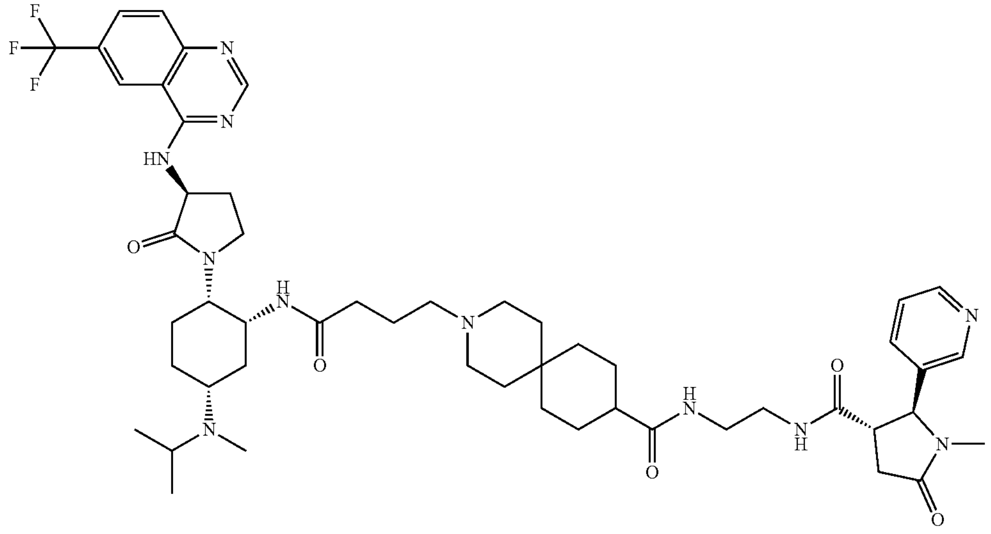
3HCOOH
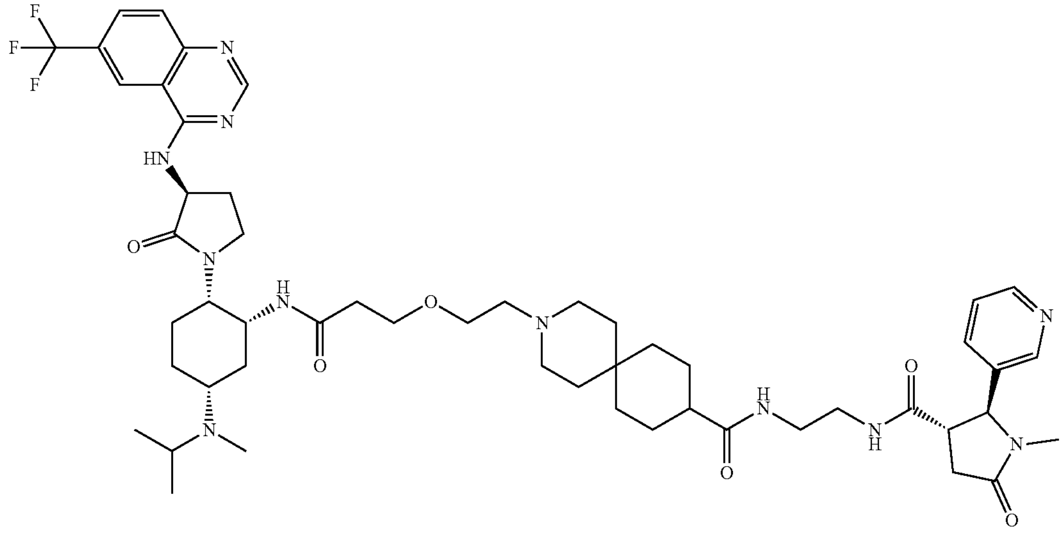
3HCOOH

-continued
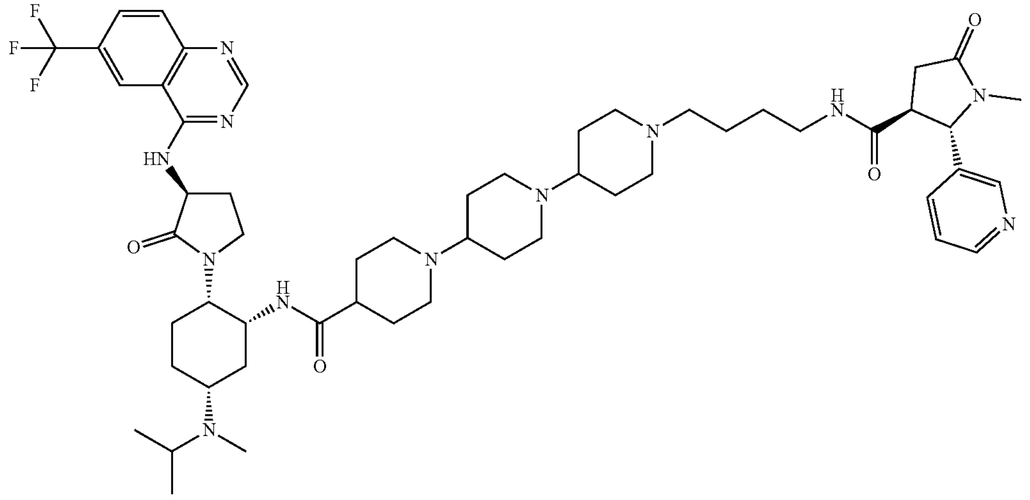
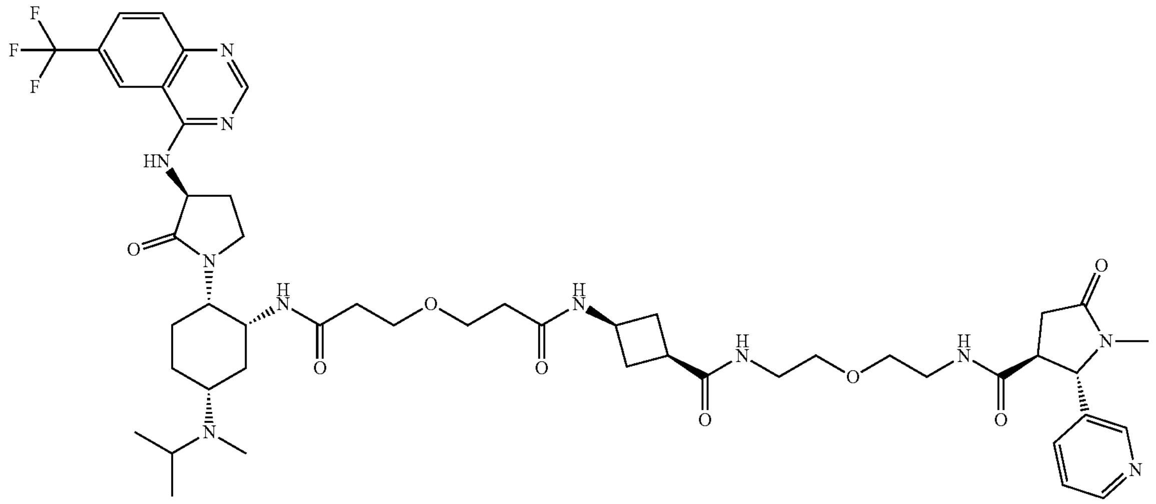
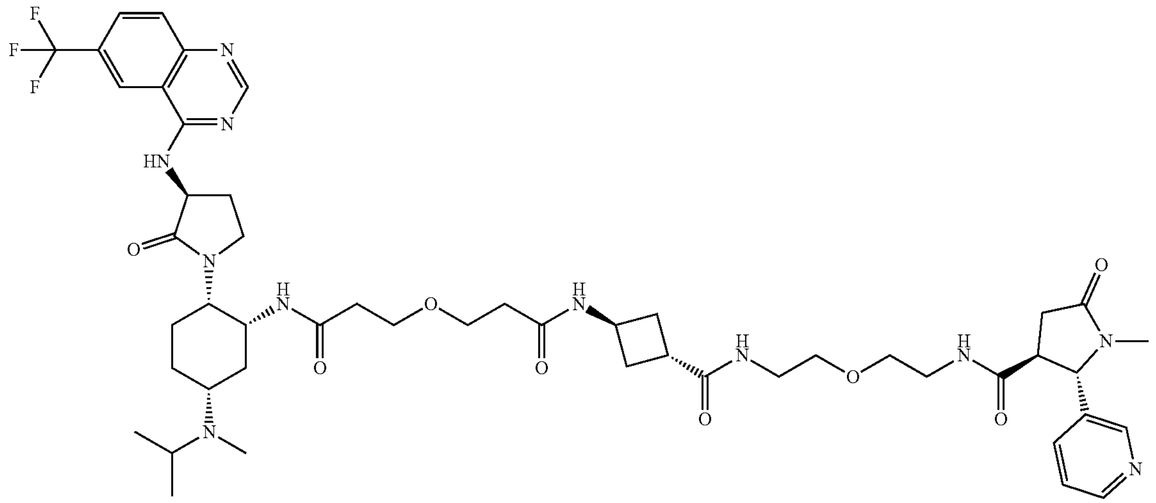

-continued
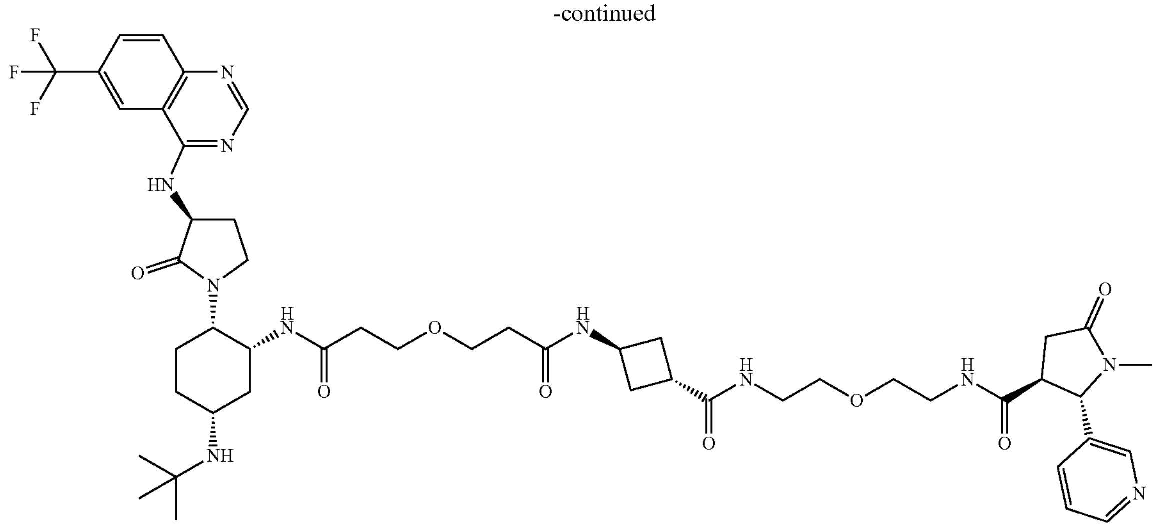
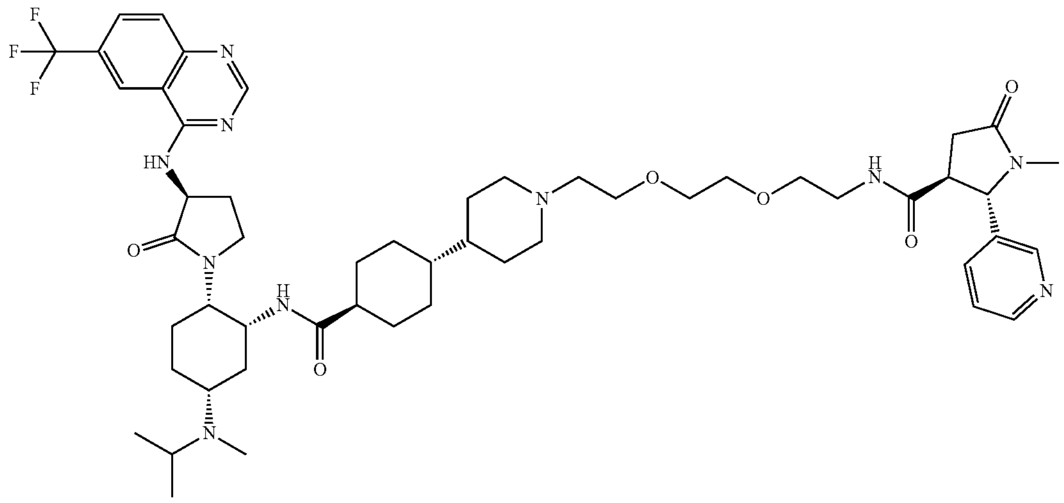
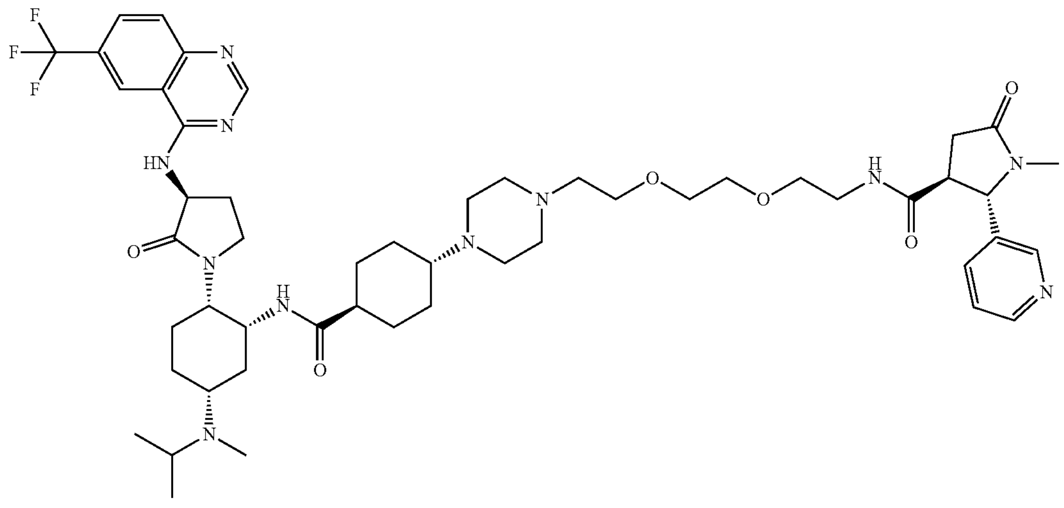

-continued
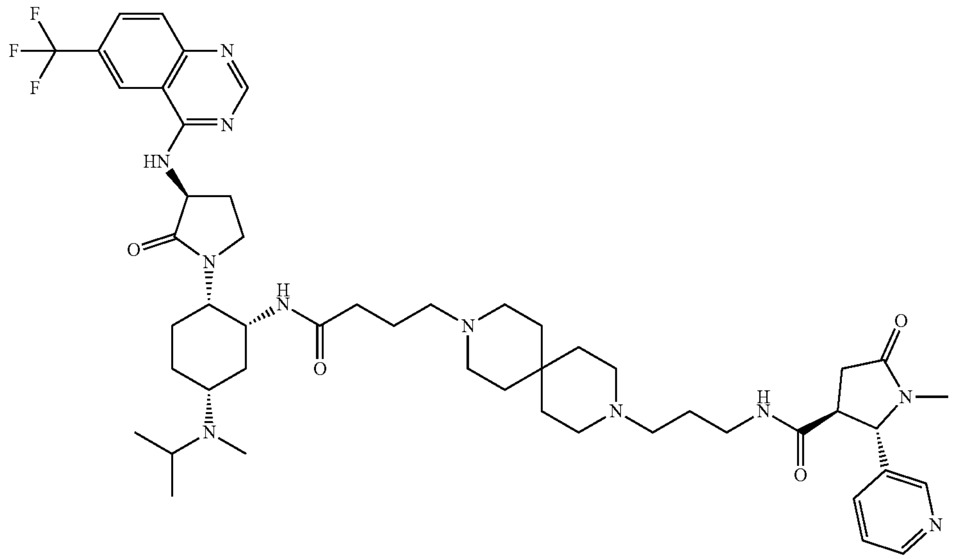
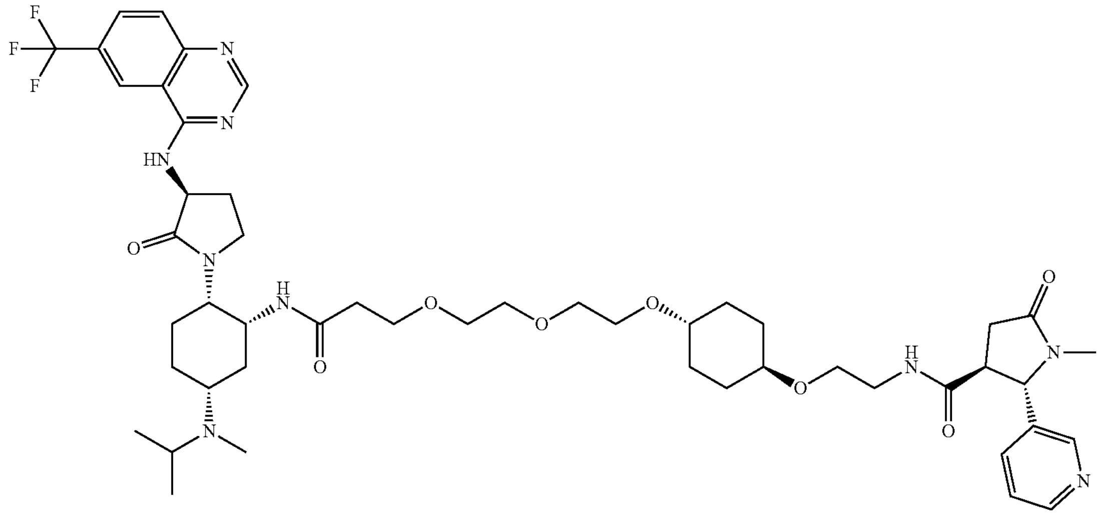
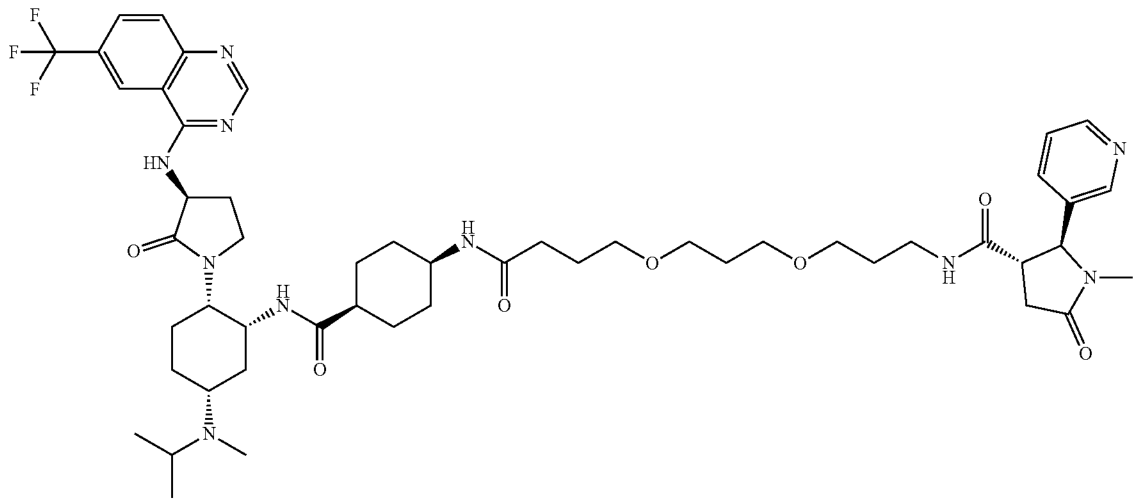

-continued
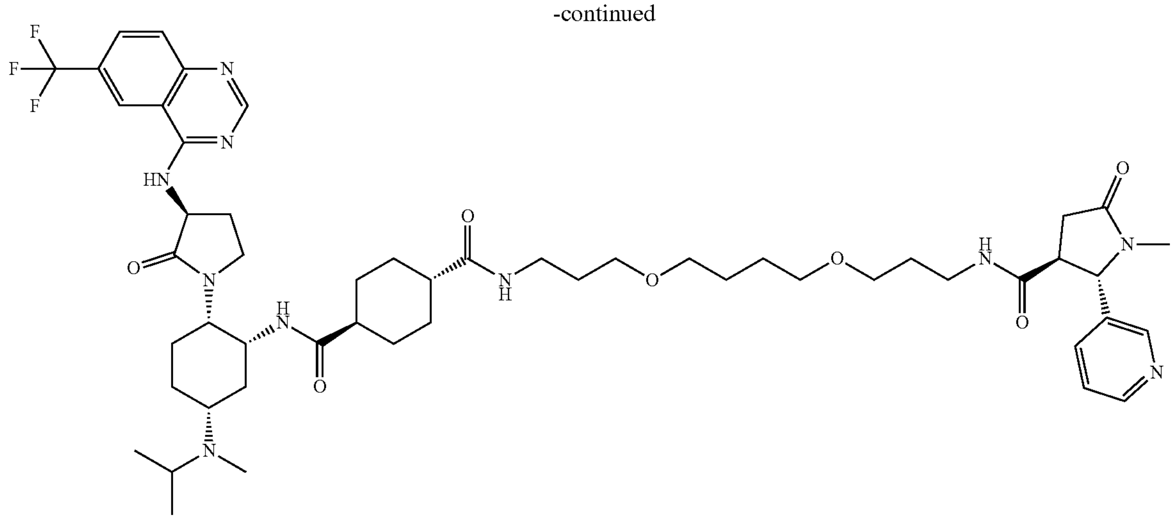
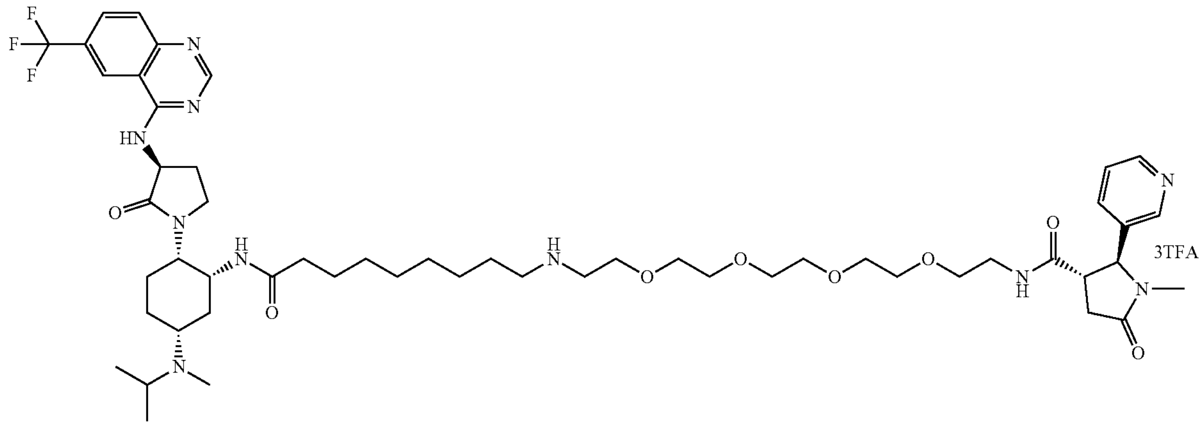
3TFA
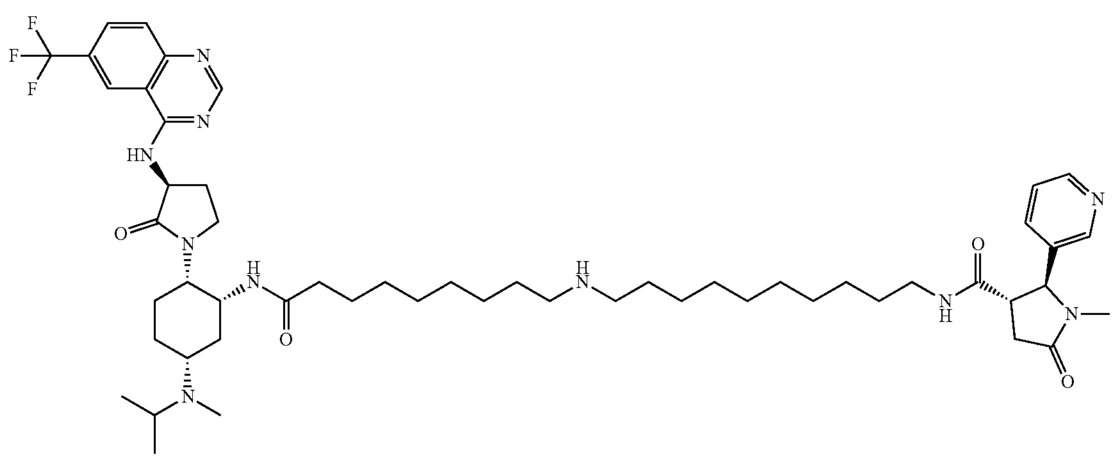
3HCOOH

-continued
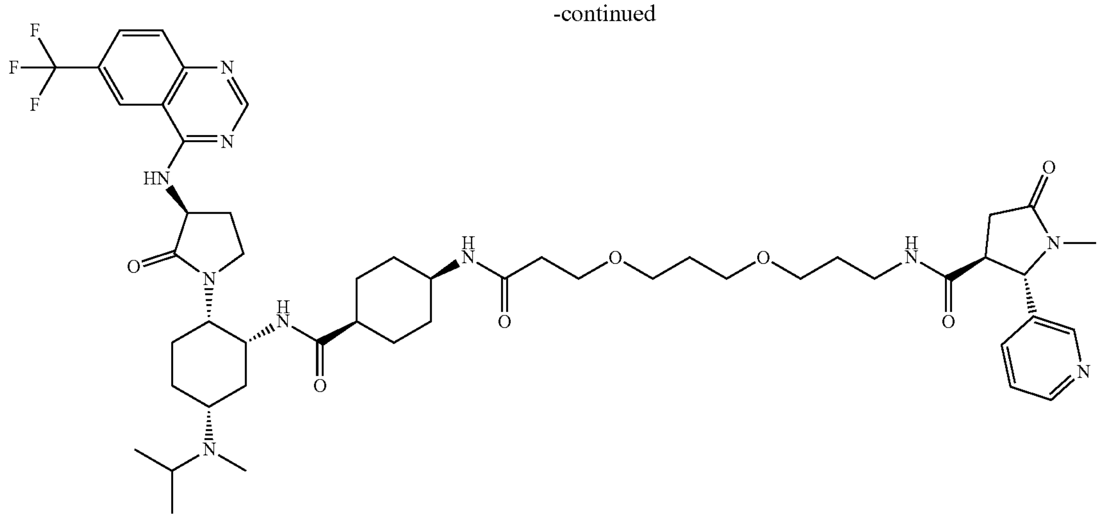
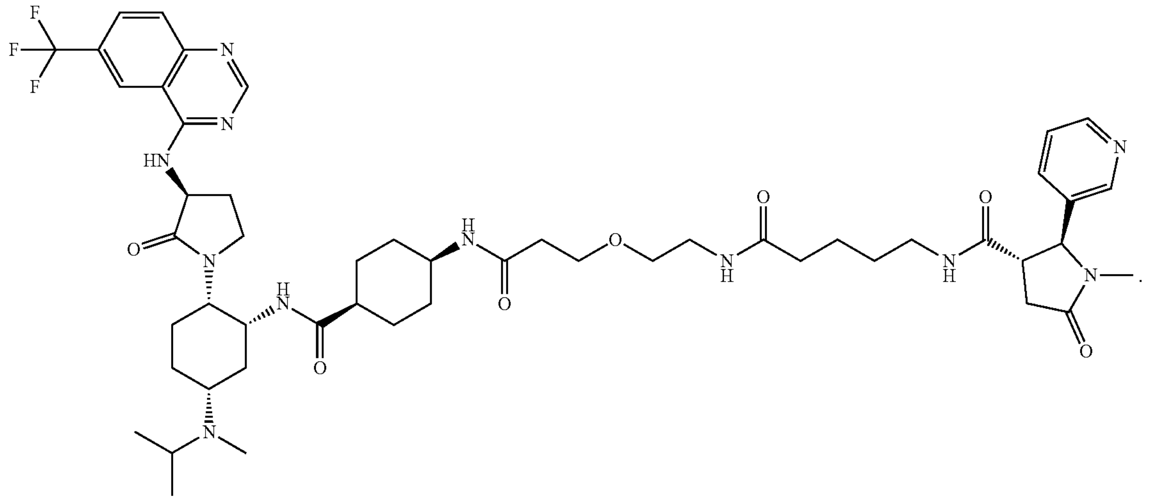
10. A compound represented by:
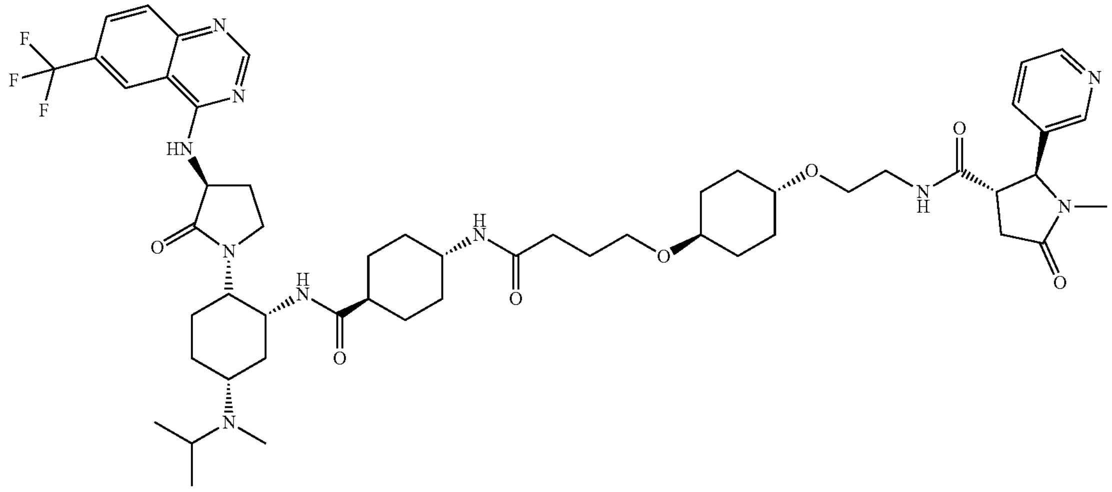
or a pharmaceutically acceptable salt thereof.

11. The compound of claim 10, wherein the compound is represented by:

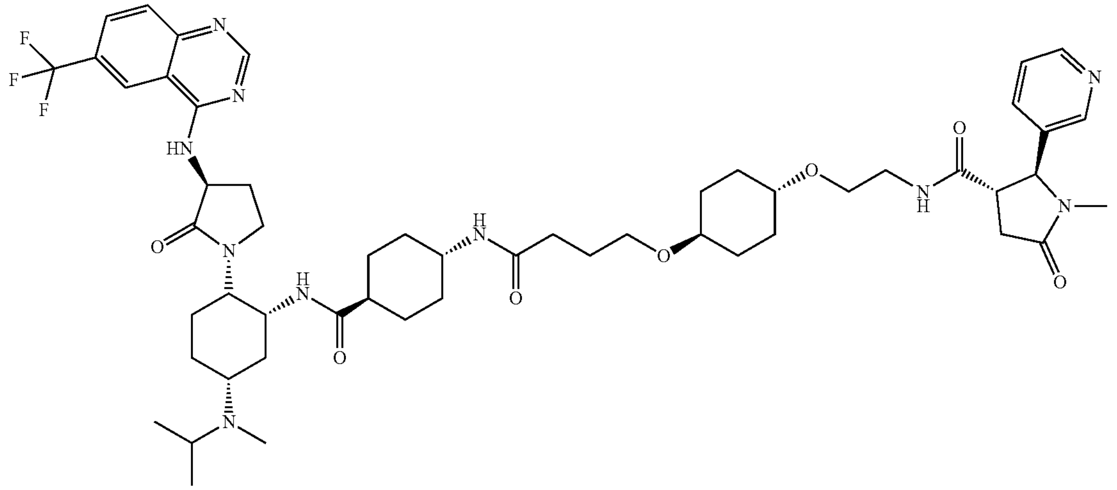

12. A pharmaceutical composition comprising (i) a compound of claim 1 or a pharmaceutically acceptable salt thereof, and (ii) a pharmaceutically acceptable excipient, carrier, or diluent.

13. A pharmaceutical composition comprising (i) a compound of claim 10 or a pharmaceutically acceptable salt thereof, and (ii) a pharmaceutically acceptable excipient, carrier, or diluent.

14. A pharmaceutical composition comprising a compound of claim 11 and a pharmaceutically acceptable excipient, carrier, or diluent.

15. A method of treating a disease or disorder mediated by chemokine receptor 2 (CCR2) and/or is associated with CCR2-positive pathogenic cells in a patient in need thereof, the method comprising: administering to the patient a therapeutically effective amount of the compound of claim 1 and an anti-cotinine antibody, or antigen-binding fragment thereof, wherein the disease or disorder is selected from a cancer, an inflammatory disease, an autoimmune disease, a viral infection, or a bacterial infection.

16. The method of claim 15, wherein the disease or disorder is mediated by chemokine receptor 2 (CCR2).

17. The method of claim 15, wherein the disease or disorder is a leukemia, lymphoma, myeloma, non-small cell lung cancer (NSCLC), hepatocellular carcinoma (HCC), colorectal cancer (CRC), cervical squamous cell carcinoma (CESC), head and neck squamous cell carcinoma (HNSC), pancreatic cancer, metastatic castration-resistant prostate cancer (mCRPC), ovarian cancer, bladder cancer, or breast cancer.

18. A method of treating cancer in a patient in need thereof, the method comprising: administering to the patient a therapeutically effective amount of the compound of claim 10 and an anti-cotinine antibody, or antigen-binding fragment thereof, wherein the cancer is a leukemia, lymphoma, myeloma, non-small cell lung cancer (NSCLC), hepatocellular carcinoma (HCC), colorectal cancer (CRC), cervical squamous cell carcinoma (CESC), head and neck squamous cell carcinoma (HNSC), pancreatic cancer, metastatic castration-resistant prostate cancer (mCRPC), ovarian cancer, bladder, or breast cancer.

19. The method of claim 18, wherein the cancer is a leukemia, lymphoma, myeloma, non-small cell lung cancer (NSCLC), hepatocellular carcinoma (HCC), colorectal cancer (CRC), head and neck squamous cell carcinoma (HNSC), pancreatic cancer, metastatic castration-resistant prostate cancer (mCRPC), ovarian cancer, or breast cancer.

20. The method of claim 18, wherein the cancer is leukemia.

21. A method of increasing antibody-dependent cell cytotoxicity (ADCC) of C-C motif chemokine receptor 2 (CCR2)-expressing cells, the method comprising: contacting the cells with an effective amount of the compound of claim 1 and an anti-cotinine antibody, or antigen-binding fragment thereof, wherein the CCR2-binding moiety of the compound binds the CCR2 expressed on the cells.

22. A method of increasing antibody-dependent cell cytotoxicity (ADCC) of C-C motif chemokine receptor 2 (CCR2)-expressing cells, the method comprising: contacting the cells with an effective amount of the compound of claim 10 and an anti-cotinine antibody, or antigen-binding fragment thereof, wherein the CCR2-binding moiety of the compound binds the CCR2 expressed on the cells.

23. The method of claim 22, wherein the CCR2-expressing cells are myeloid-derived suppressor cells (MDSCs), T regulatory cells (Tregs), neutrophils, macrophages, B regulatory cells (Bregs), CD8 regulatory cells, (CD8regs), exhausted T cells, or cancer-associated fibroblasts (CAFs).

24. A method of depleting C-C motif chemokine receptor 2 (CCR2)-expressing cells, the method comprising: contacting the cells with an effective amount of the compound of claim 1 and an anti-cotinine antibody, or antigen-binding fragment thereof, wherein the CCR2-binding moiety of the compound binds the CCR2 expressed on the cells.

25. The method of claim 20, wherein the anti-cotinine antibody has a heavy chain and a light chain, the heavy chain comprising a CDR1 having SEQ ID NO: 1, a CDR2 having SEQ ID NO: 2, and a CDR3 having SEQ ID NO: 3, and the light chain comprising a CDR1 having SEQ ID NO: 4, a CDR2 having SEQ ID NO: 5, and a CDR3 having SEQ ID NO: 6.

26. The method of claim 20, wherein the anti-cotinine antibody has a heavy chain and a light chain, the heavy chain comprising a heavy chain variable region (VH) having SEQ ID NO: 7, and the light chain comprising a light chain variable region (VL) having SEQ ID NO: 8.

27. The method of claim 20, wherein the anti-cotinine antibody has a heavy chain comprising SEQ ID NO: 9 and a light chain comprising SEQ ID NO: 10.

28. A combination comprising the compound of claim 1 and an anti-cotinine antibody, or antigen-binding fragment thereof.

29. A combination comprising the compound of claim 10 and an anti-cotinine antibody, or antigen-binding fragment thereof.

* * * * *

```
                              SEQUENCE LISTING


Sequence total quantity: 14
SEQ ID NO: 1           moltype = AA  length = 5
FEATURE                Location/Qualifiers
source                 1..5
                       mol_type = protein
                       organism = synthetic construct
SEQUENCE: 1
NYWMS                                                                5

SEQ ID NO: 2           moltype = AA  length = 17
FEATURE                Location/Qualifiers
source                 1..17
                       mol_type = protein
                       organism = synthetic construct
SEQUENCE: 2
DIHGNRGFNY HASWAKG                                                   17

SEQ ID NO: 3           moltype = AA  length = 9
FEATURE                Location/Qualifiers
source                 1..9
                       mol_type = protein
                       organism = synthetic construct
SEQUENCE: 3
ADDSGSHDI                                                            9

SEQ ID NO: 4           moltype = AA  length = 12
FEATURE                Location/Qualifiers
source                 1..12
                       mol_type = protein
                       organism = synthetic construct
SEQUENCE: 4
QSSQSVYSAK LS                                                        12

SEQ ID NO: 5           moltype = AA  length = 7
FEATURE                Location/Qualifiers
source                 1..7
                       mol_type = protein
                       organism = synthetic construct
SEQUENCE: 5
YGSTLAS                                                              7

SEQ ID NO: 6           moltype = AA  length = 12
FEATURE                Location/Qualifiers
source                 1..12
                       mol_type = protein
                       organism = synthetic construct
SEQUENCE: 6
QGTFYGPDWY FA                                                        12

SEQ ID NO: 7           moltype = AA  length = 116
FEATURE                Location/Qualifiers
source                 1..116
                       mol_type = protein
                       organism = synthetic construct
SEQUENCE: 7
EVQLVESGGG LVQPGGSLRL SCAASGFTFS NYWMSWVRQA PGKGLEWVGD IHGNRGFNYH    60
ASWAKGRFTV SRSKNTLYLQ MNSLRAEDTA VYYCAKADDS GSHDIWGQGT LVTVSS        116

SEQ ID NO: 8           moltype = AA  length = 111
FEATURE                Location/Qualifiers
source                 1..111
                       mol_type = protein
                       organism = synthetic construct
```

-continued

```
SEQUENCE: 8
DIQMTQSPSS LSASVGDRVT ITCQSSQSVY SAKLSWYQQK PGKAPKLLIY YGSTLASGVP  60
SRFSGSGSGT QFTLTISSLQ PEDFATYYCQ GTFYGPDWYF AFGGGTKVEI K           111

SEQ ID NO: 9            moltype = AA  length = 446
FEATURE                 Location/Qualifiers
source                  1..446
                        mol_type = protein
                        organism = synthetic construct
SEQUENCE: 9
EVQLVESGGG LVQPGGSLRL SCAASGFTFS NYWMSWVRQA PGKGLEWVGD IHGNRGFNYH  60
ASWAKGRFTV SRSKNTLYLQ MNSLRAEDTA VYYCAKADDS GSHDIWGQGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPDVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP EEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 10           moltype = AA  length = 218
FEATURE                 Location/Qualifiers
source                  1..218
                        mol_type = protein
                        organism = synthetic construct
SEQUENCE: 10
DIQMTQSPSS LSASVGDRVT ITCQSSQSVY SAKLSWYQQK PGKAPKLLIY YGSTLASGVP  60
SRFSGSGSGT QFTLTISSLQ PEDFATYYCQ GTFYGPDWYF AFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 11           moltype = AA  length = 446
FEATURE                 Location/Qualifiers
source                  1..446
                        mol_type = protein
                        organism = synthetic construct
SEQUENCE: 11
QQQLVESGGR LVTPGGSLTL TCTASGFSLN NYWMSWVRQA PGKGLEWIGD IHGNRGFNYH  60
ASWAKGRFTV SRTSTTVDLR MTSLTTEDTA IYFCARADDS GSHDIWGPGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKKVEPKSCD KTHTCPPCPA PELLGGPDVF  240
LFPPKPKDTL MISRTPEVTC VVVDVSHEDP EVKFNWYVDG VEVHNAKTKP REEQYNSTYR  300
VVSVLTVLHQ DWLNGKEYKC KVSNKALPAP EEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPGK                                      446

SEQ ID NO: 12           moltype = AA  length = 218
FEATURE                 Location/Qualifiers
source                  1..218
                        mol_type = protein
                        organism = synthetic construct
SEQUENCE: 12
ELDLTQTPSP VSAAVGDTVT INCQSSQSVY SAKLSWYQQK PGQPPKLLIY YGSTLASGVP  60
SRFKGSGSGT QFSLTISDVQ CADAATYYCQ GTYYGPDWYF AFGGGTEVVV KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 13           moltype = AA  length = 446
FEATURE                 Location/Qualifiers
source                  1..446
                        mol_type = protein
                        organism = synthetic construct
SEQUENCE: 13
QQQLVESGGR LVTPGGSLTL TCTASGFSLN NYWMSWVRQA PGKGLEWIGD IHGNRGFNYH  60
ASWAKGRFTV SRTSTTVDLR MTSLTTEDTA IYFCARADDS GSHDIWGPGT LVTVSSAKTT  120
APSVYPLAPV CGDTTGSSVT LGCLVKGYFP EPVTLTWNSG SLSSGVHTFP AVLQSDLYTL  180
SSSVTVTSST WPSQSITCNV AHPASSTKVD KKIEPRGPTI KPCPPCKCPA PNLLGGPSVF  240
IFPPKIKDVL MISLSPMVTC VVVDVSEDDP DVQISWFVNN VEVLTAQTQT HREDYNSTLR  300
VVSALPIQHQ DWMSGKEFKC KVNNKALPAP IERTISKPKG SVRAPQVYVL PPPEEEMTKK  360
QVTLTCMVTD FMPEDIYVEW TNNGKTELNY KNTEPVLDSD GSYFMYSKLR VEKKNWVERN  420
SYSCSVVHEG LHNHHTTKSF SRTPGK                                      446

SEQ ID NO: 14           moltype = AA  length = 218
FEATURE                 Location/Qualifiers
source                  1..218
                        mol_type = protein
                        organism = synthetic construct
SEQUENCE: 14
ELDLTQTPSP VSAAVGDTVT INCQSSQSVY SAKLSWYQQK PGQPPKLLIY YGSTLASGVP  60
SRFKGSGSGT QFSLTISDVQ CADAATYYCQ GTYYGPDWYF AFGGGTEVVV KRADAAPTVS  120
```

-continued

| | |
|---|---|
| IFPPSSEQLT SGGASVVCFL NNFYPKDINV KWKIDGSERQ NGVLNSWTDQ DSKDSTYSMS | 180 |
| STLTLTKDEY ERHNSYTCEA THKTSTSPIV KSFNRNEC | 218 |